US010900086B1

(12) United States Patent
Bowden et al.

(10) Patent No.: US 10,900,086 B1
(45) Date of Patent: Jan. 26, 2021

(54) COMPOSITIONS AND METHODS FOR DIAGNOSING PROSTATE CANCER USING A GENE EXPRESSION SIGNATURE

(71) Applicants: DANA-FARBER CANCER INSTITUTE, INC., Boston, MA (US); PRESIDENT AND FELLOWS OF HARVARD COLLEGE, Cambridge, MA (US)

(72) Inventors: Michaela Bowden, Arlington, MA (US); Svitlana Tyekucheva, Brighton, MA (US); Massimo Loda, Belmont, MA (US); Lorelei Mucci, Boston, MA (US)

(73) Assignees: DANA-FARBER CANCER INSTITUTE, INC., Boston, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 15/775,474

(22) PCT Filed: Nov. 11, 2016

(86) PCT No.: PCT/US2016/061519
§ 371 (c)(1),
(2) Date: May 11, 2018

(87) PCT Pub. No.: WO2017/083640
PCT Pub. Date: May 18, 2017

Related U.S. Application Data

(60) Provisional application No. 62/254,925, filed on Nov. 13, 2015.

(51) Int. Cl.
*C12Q 1/68* (2018.01)
*C12Q 1/6886* (2018.01)

(52) U.S. Cl.
CPC ...... *C12Q 1/6886* (2013.01); *C12Q 2600/112* (2013.01); *C12Q 2600/118* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 2009/0136945 A1 | 5/2009 | Loberg et al. | |
| 2013/0039917 A1* | 2/2013 | Rabbani | G01N 33/57484 424/139.1 |
| 2013/0244256 A1 | 9/2013 | Clarke et al. | |
| 2014/0193814 A1 | 7/2014 | Ting et al. | |
| 2014/0228233 A1* | 8/2014 | Pawlowski | C12Q 1/6886 506/9 |
| 2015/0309036 A1 | 10/2015 | Abate-Shen et al. | |

OTHER PUBLICATIONS

Enard et al. (Science 2002 vol. 296 p. 340) (Year: 2002).*
Cobb et al (Crit Care Med 2002 vol. 30 p. 2711) (Year: 2002).*

* cited by examiner

*Primary Examiner* — Katherine D Salmon
(74) *Attorney, Agent, or Firm* — Burns & Levinson, LLP; Daniel W. Clarke

(57) ABSTRACT

The present invention relates to compositions and methods and for the diagnosis, prognosis, and treatment of prostate cancer. The invention is based upon the identification of a gene expression signature that predicts the likelihood that prostate cancer will metastasize. Provided is a method of determining whether prostate cancer in a subject will metastasize. Also provided are compositions comprising a prostate cancer-associated gene. Also provided are kits comprising a package with a prostate cancer-associated gene.

16 Claims, 107 Drawing Sheets

Specification includes a Sequence Listing.

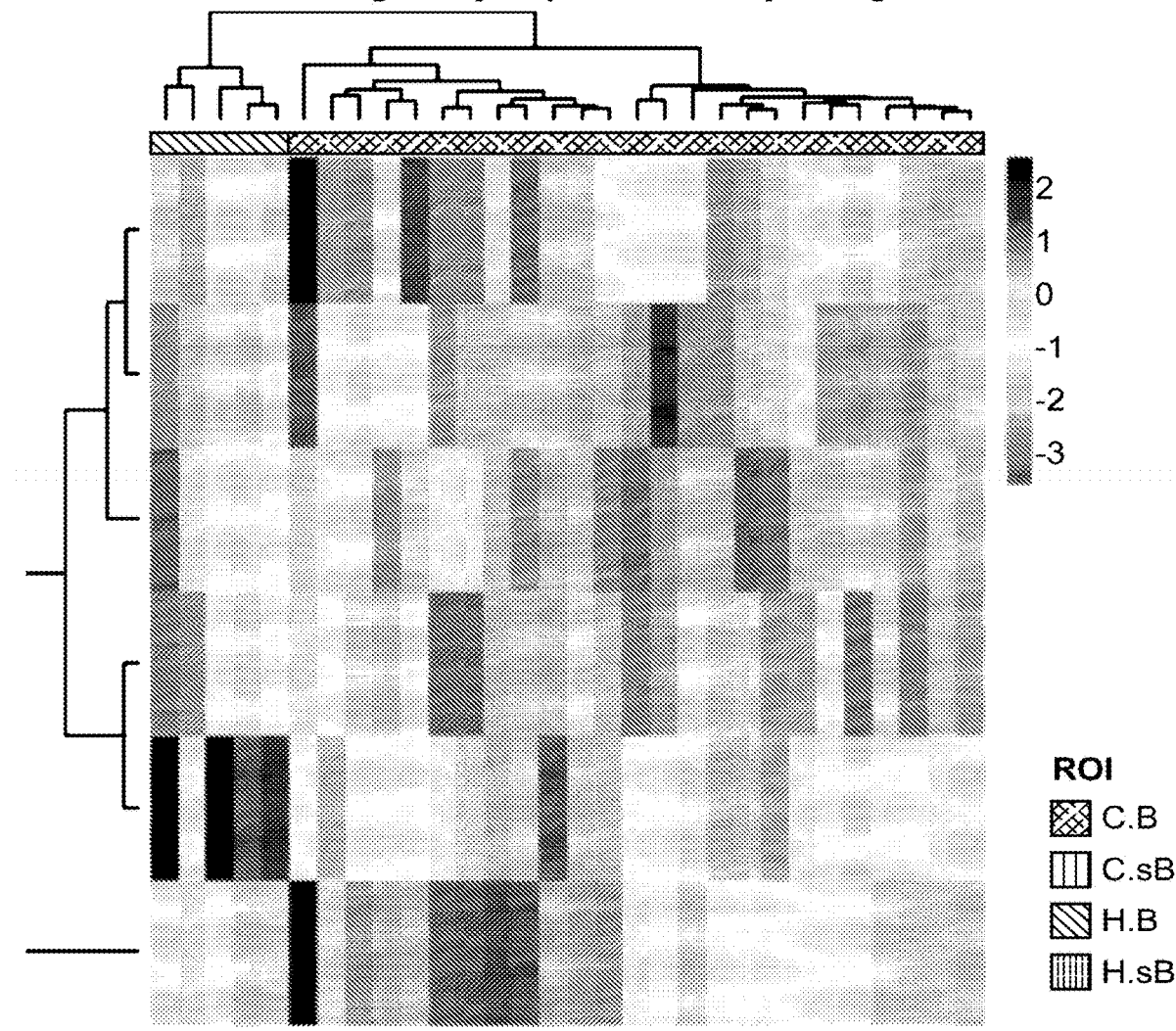

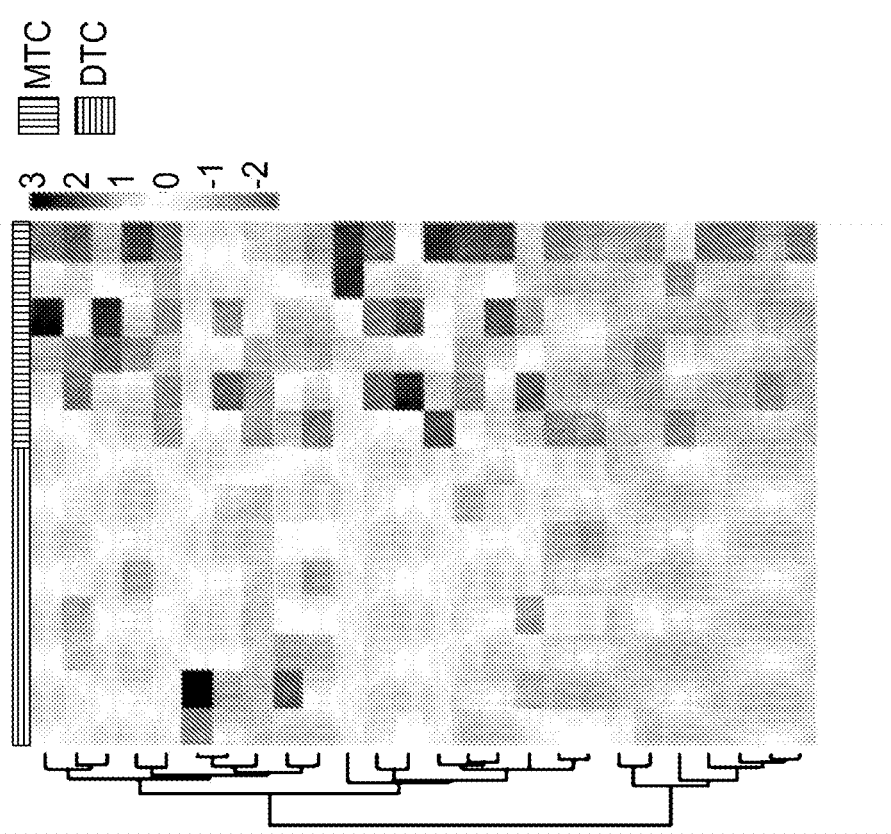

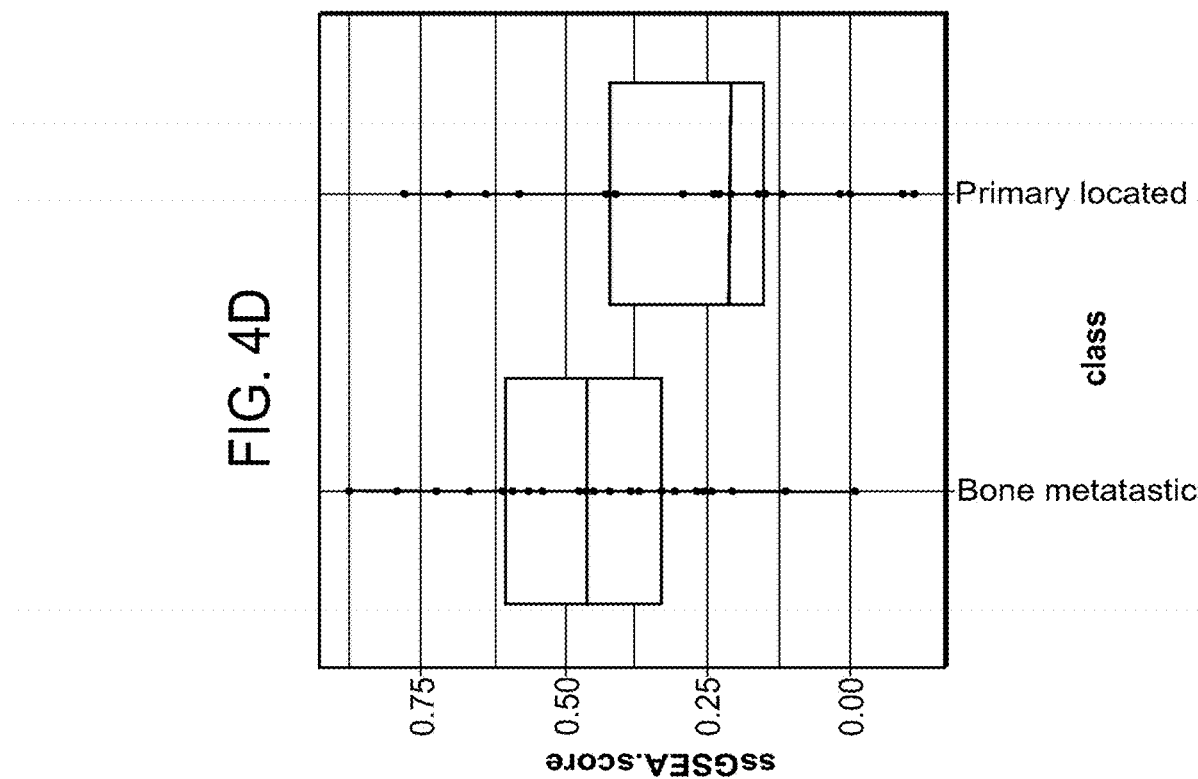
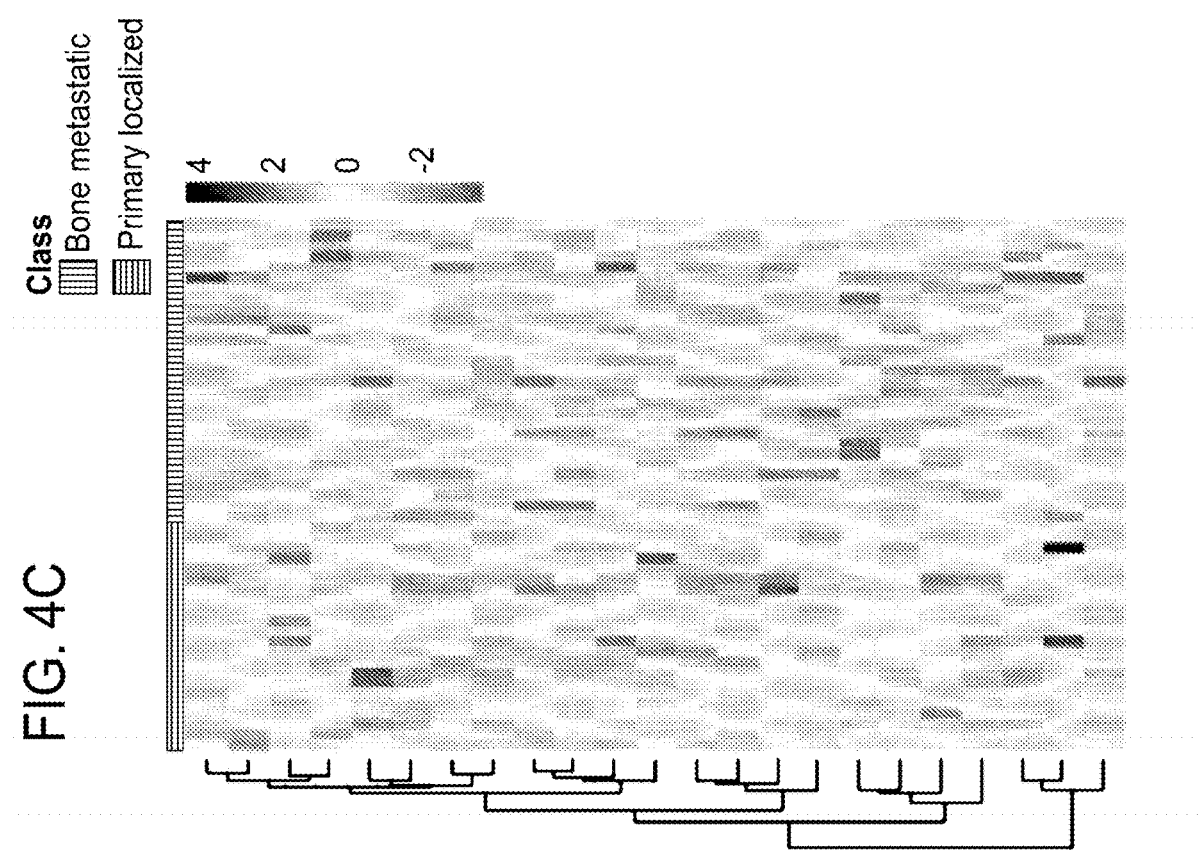

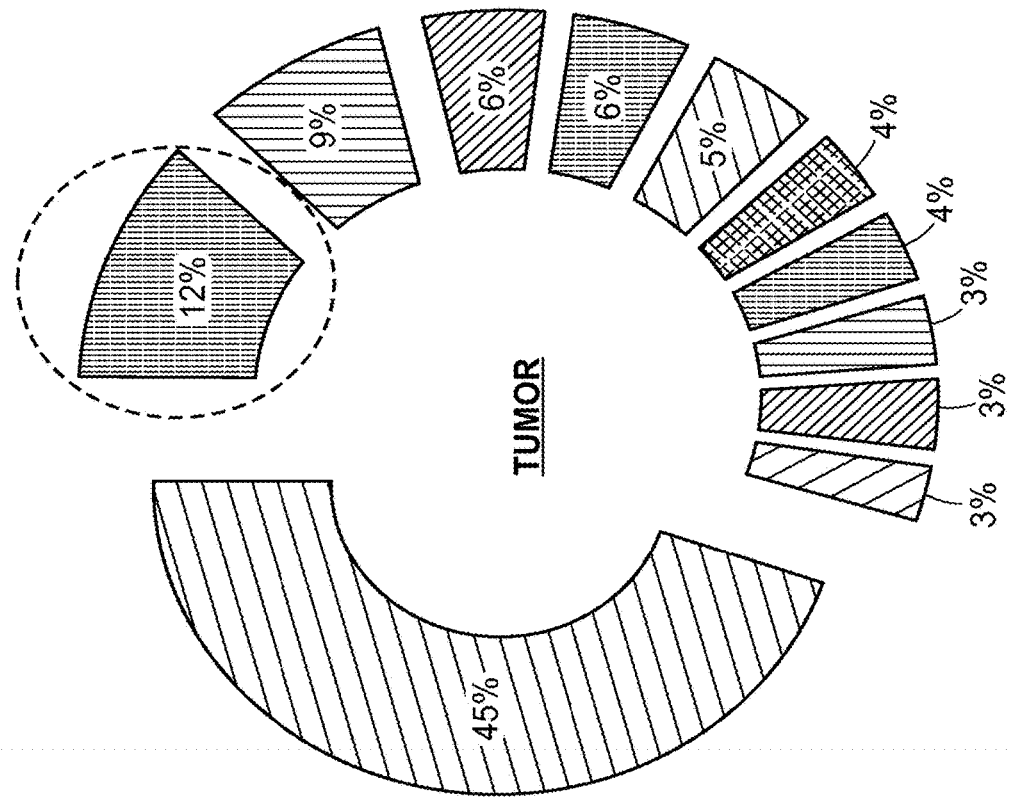
FIG. 5B ST6GAL1
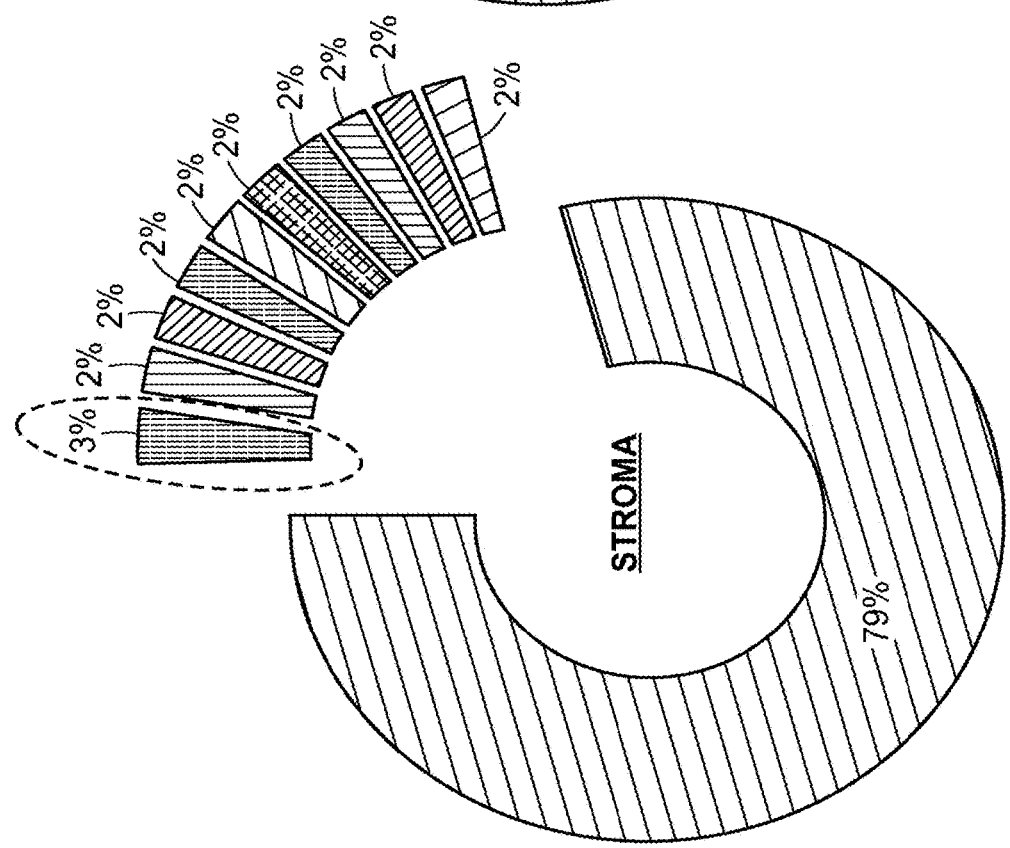
FIG. 5A NPNT

FIG. 7C

| Compartment | P-B | T-P | T-B |
|---|---|---|---|
| Epithelium | 52 (32 up/20 down) | 24 (3 up/21 down) | 234 (105 up/129 down) |
| Stroma | 2 (2 down) | 0 | 49 (36 up/13 down) |

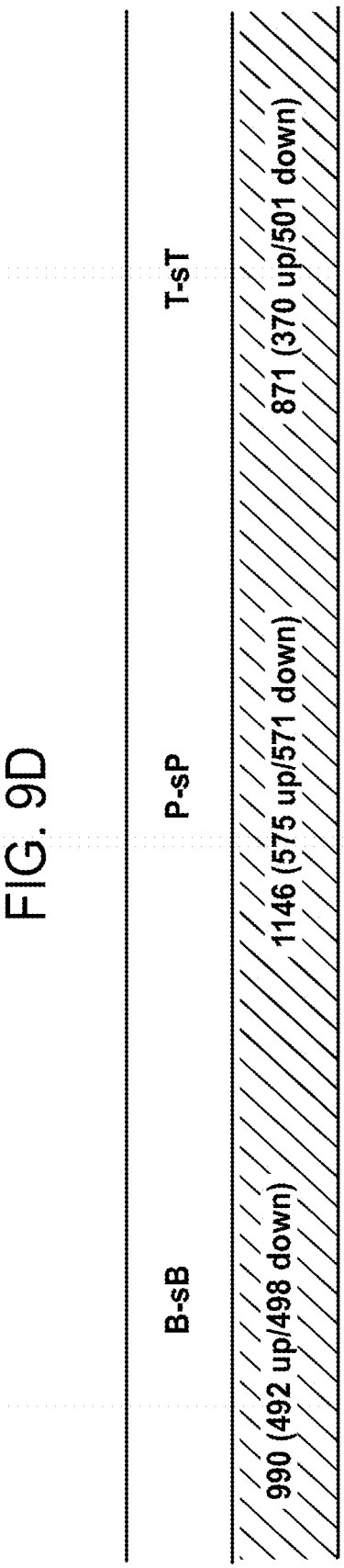

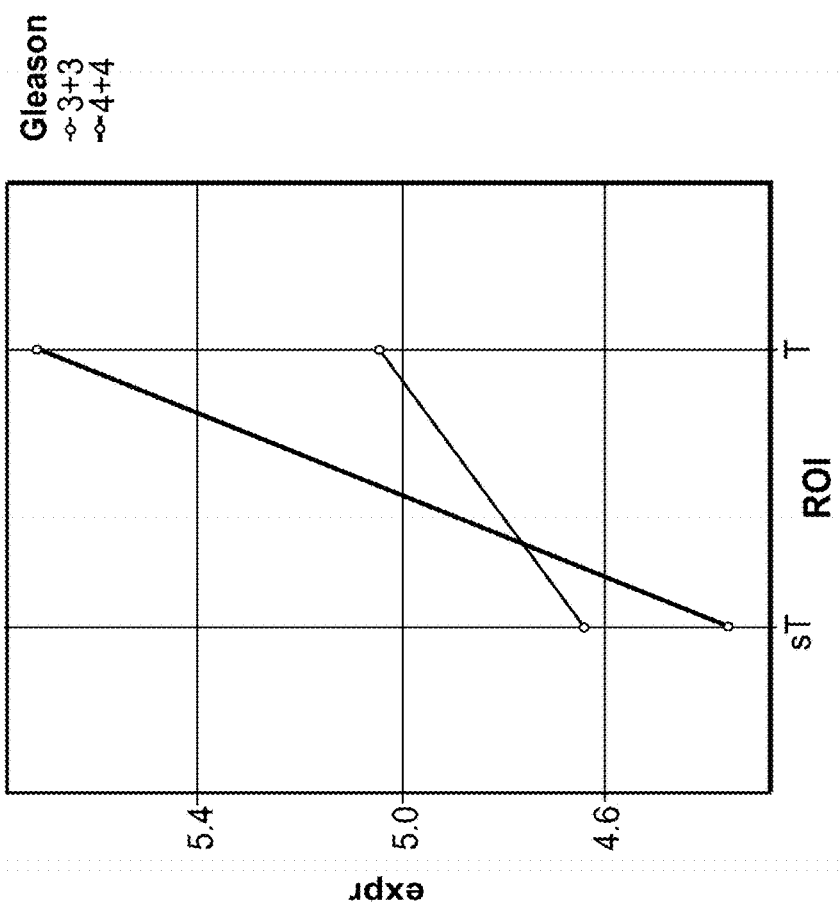
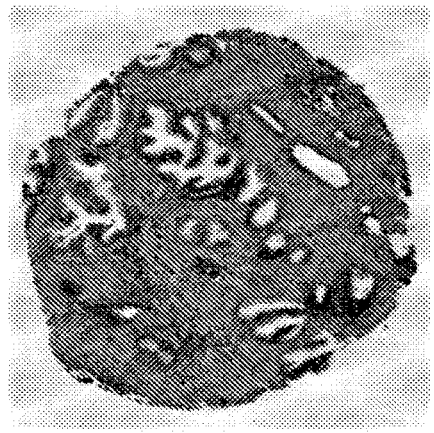
FIG. 13A
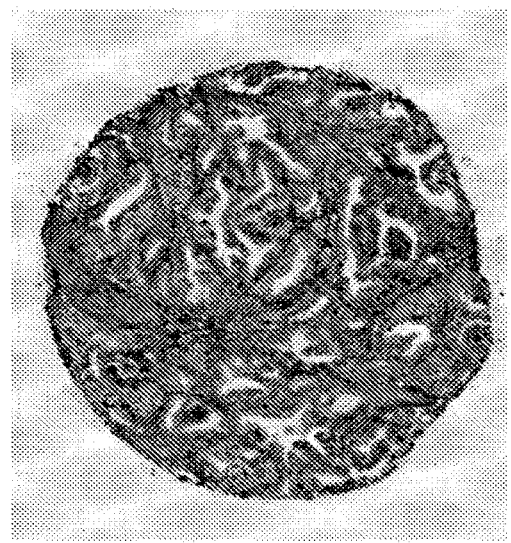
FIG. 13B

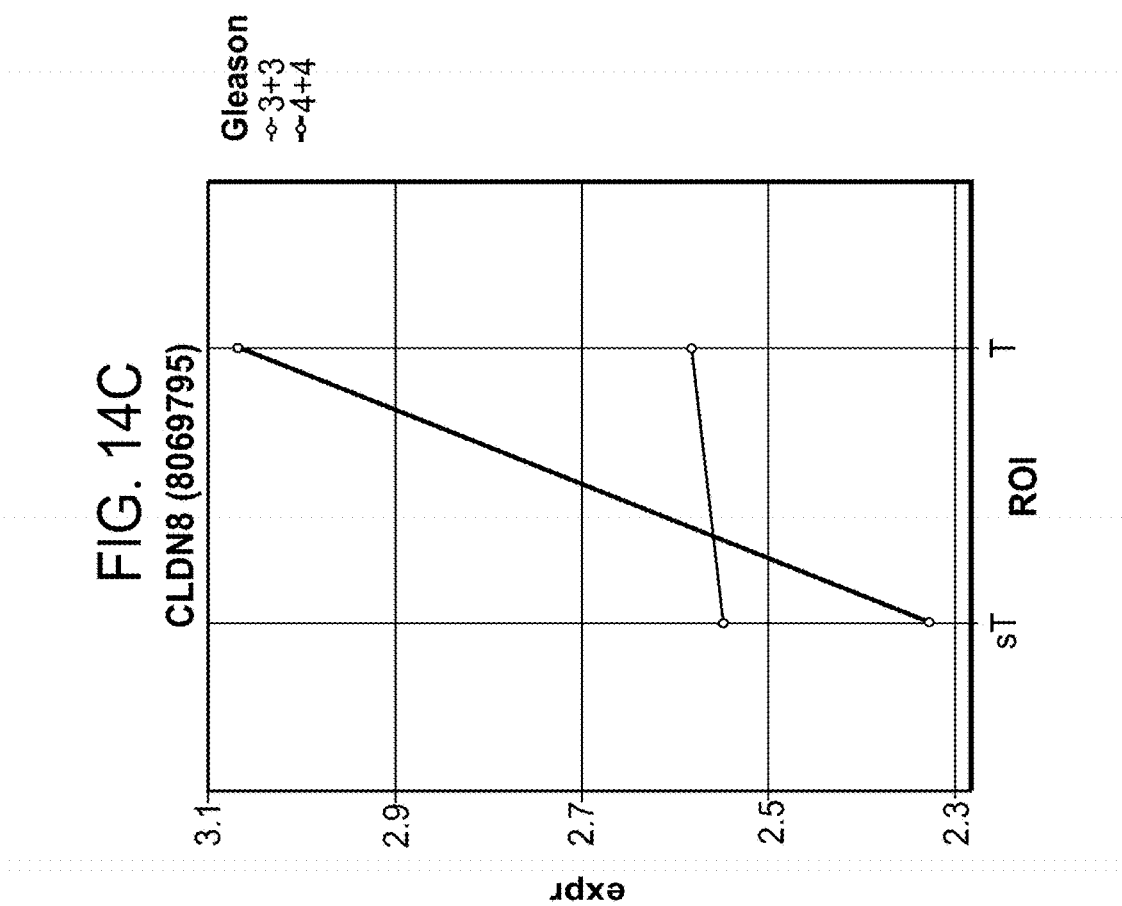
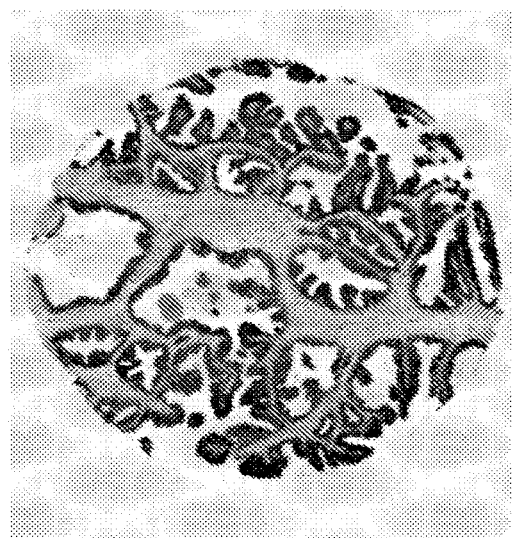
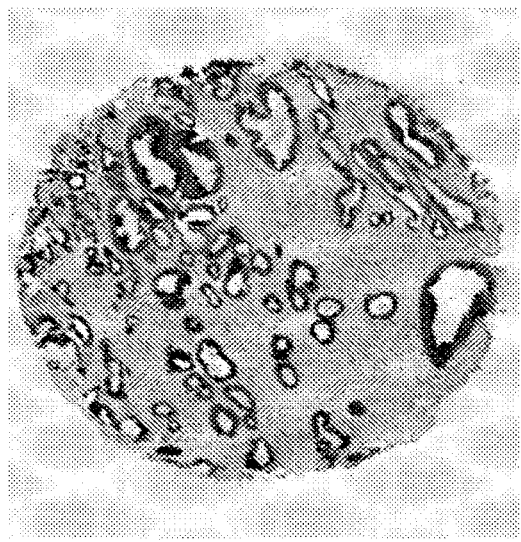

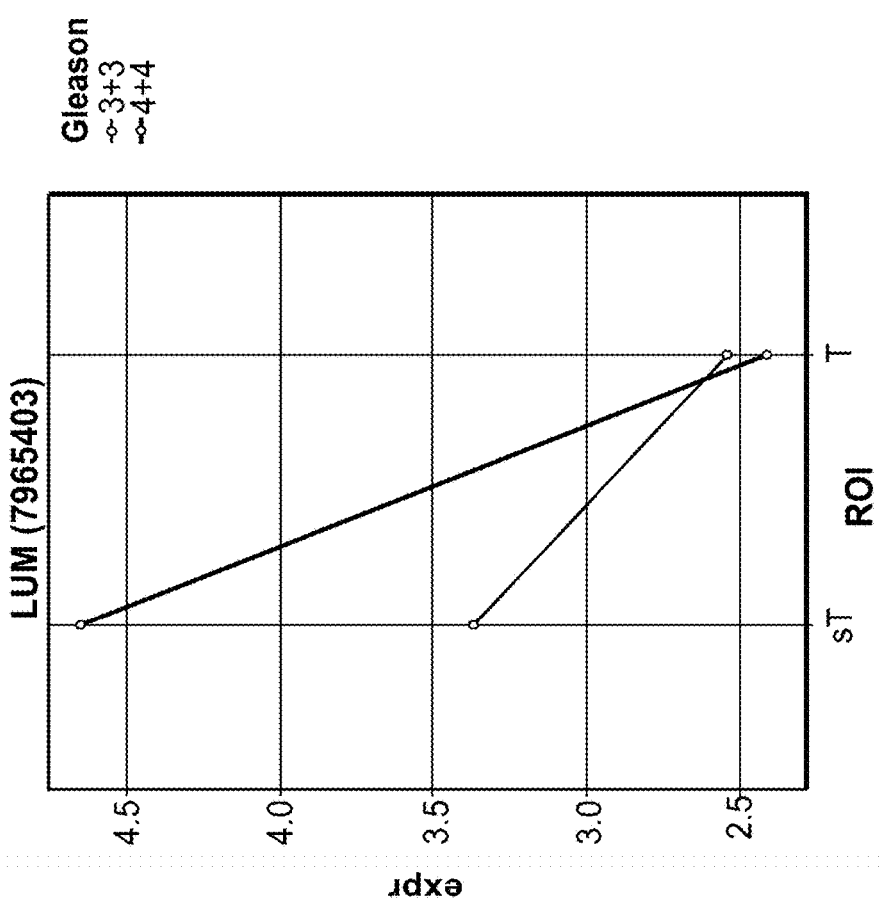
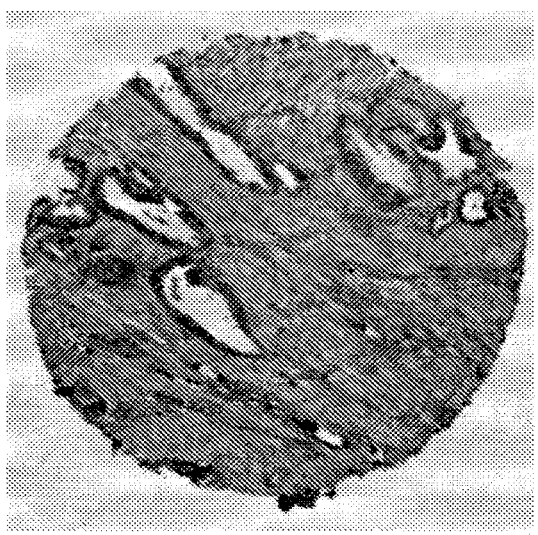
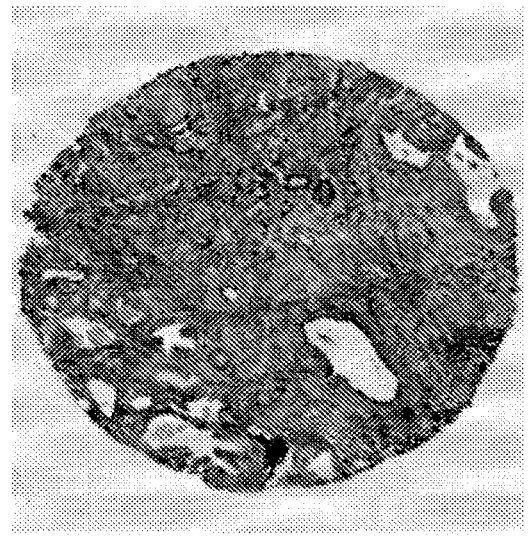
FIG. 17A
FIG. 17B

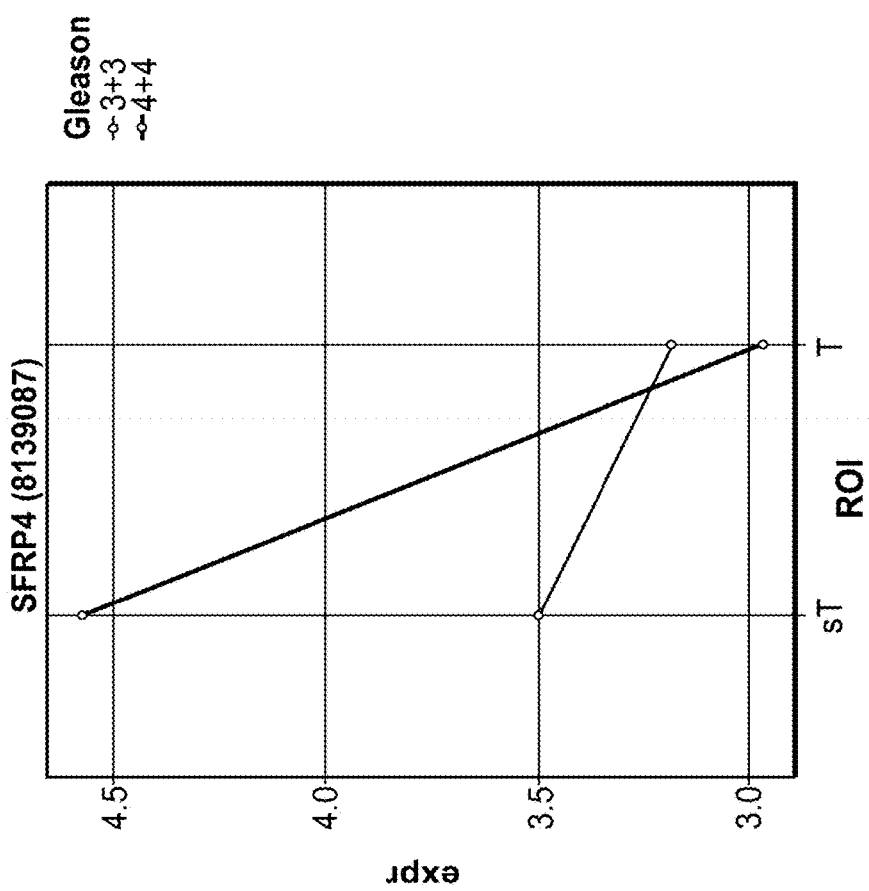
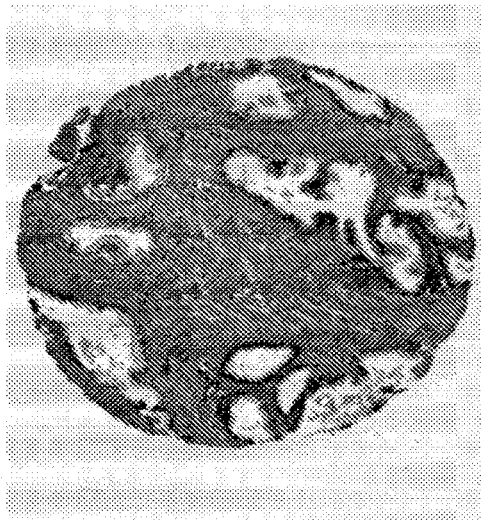
FIG. 19A
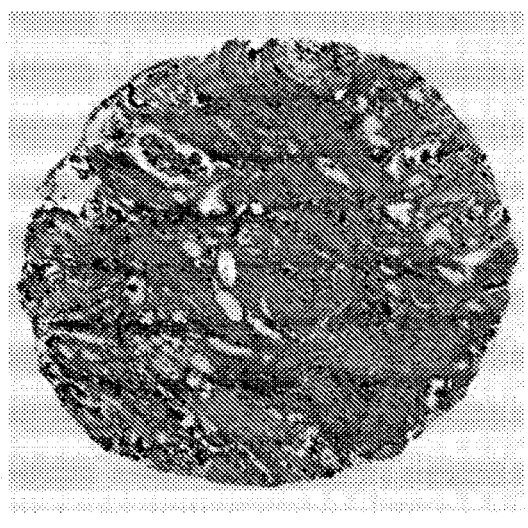
FIG. 19B

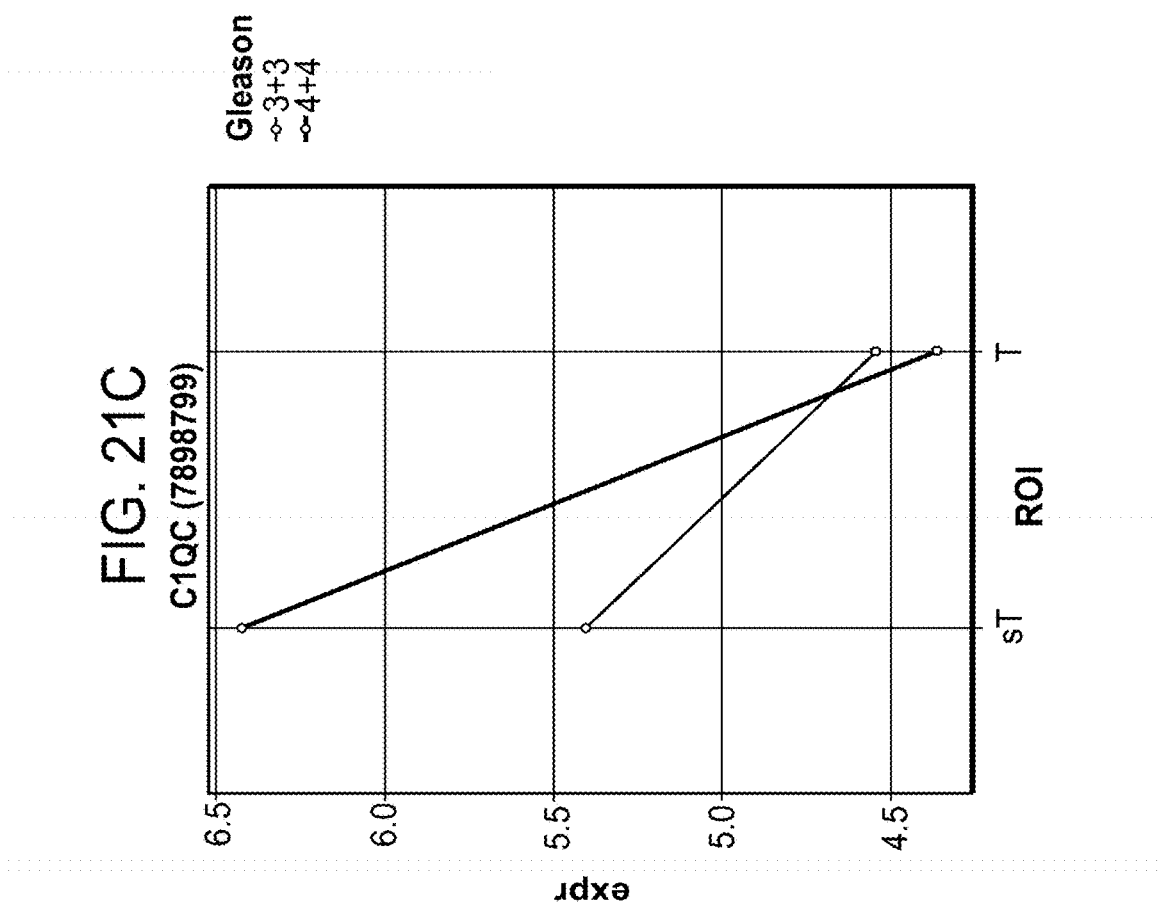
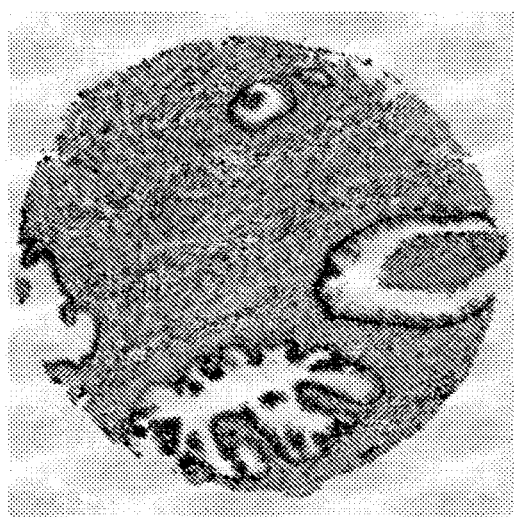
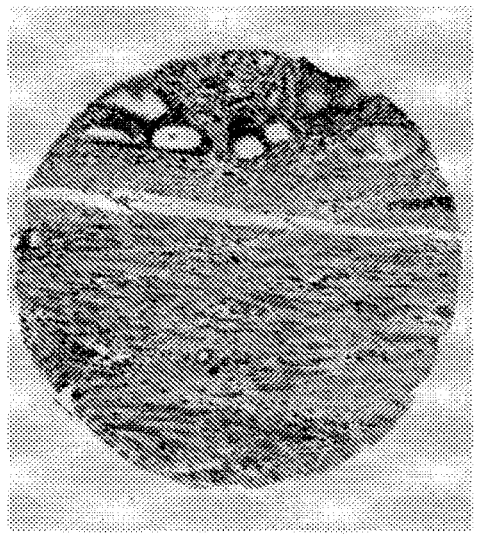
FIG. 21A
FIG. 21B

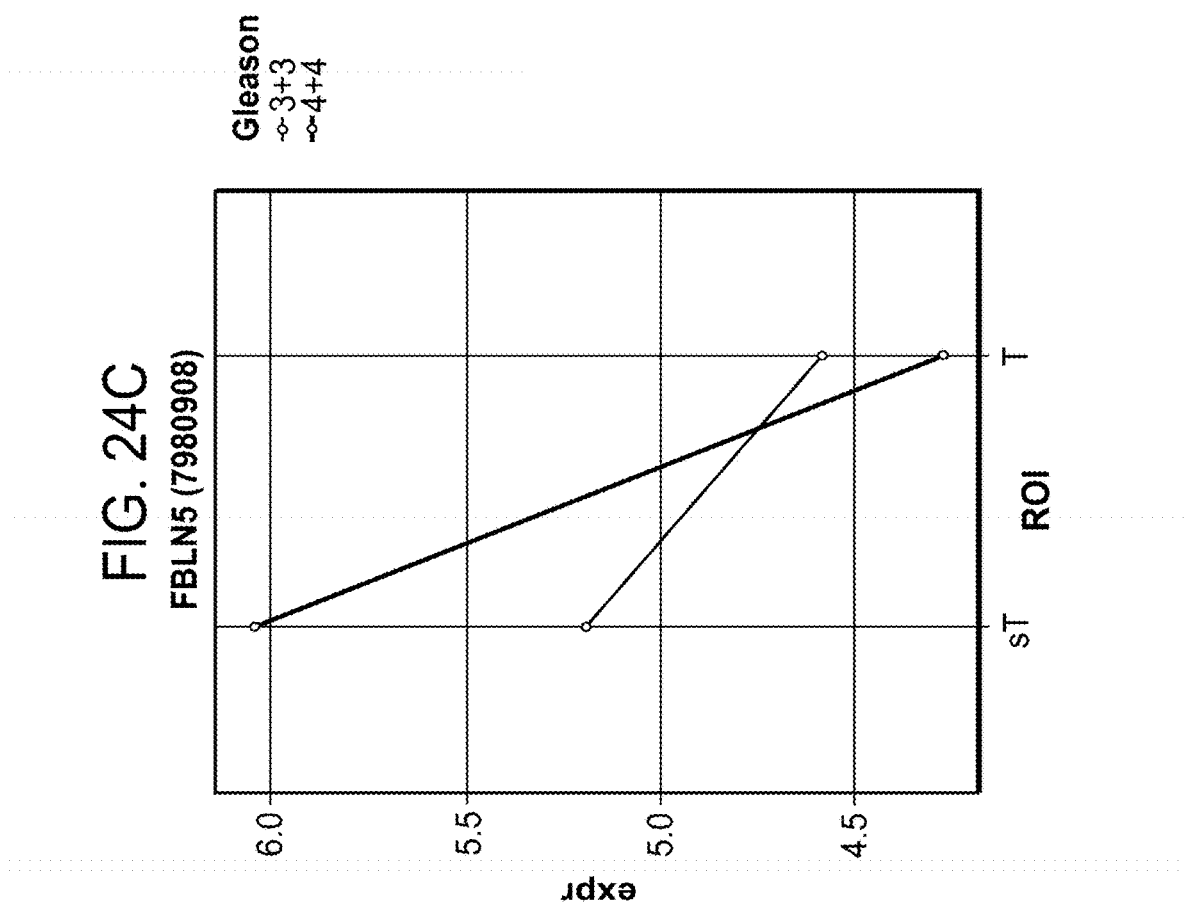
FIG. 24A
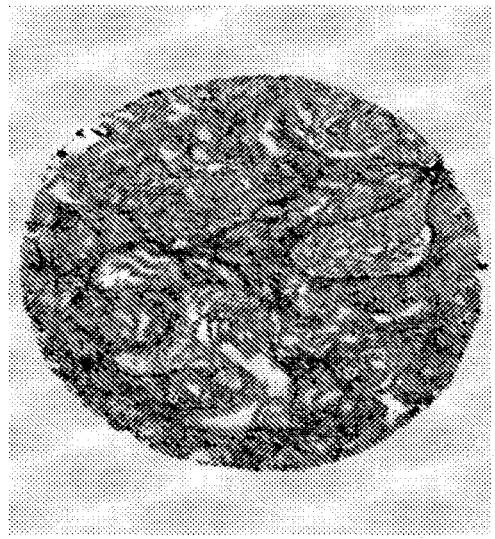
FIG. 24B

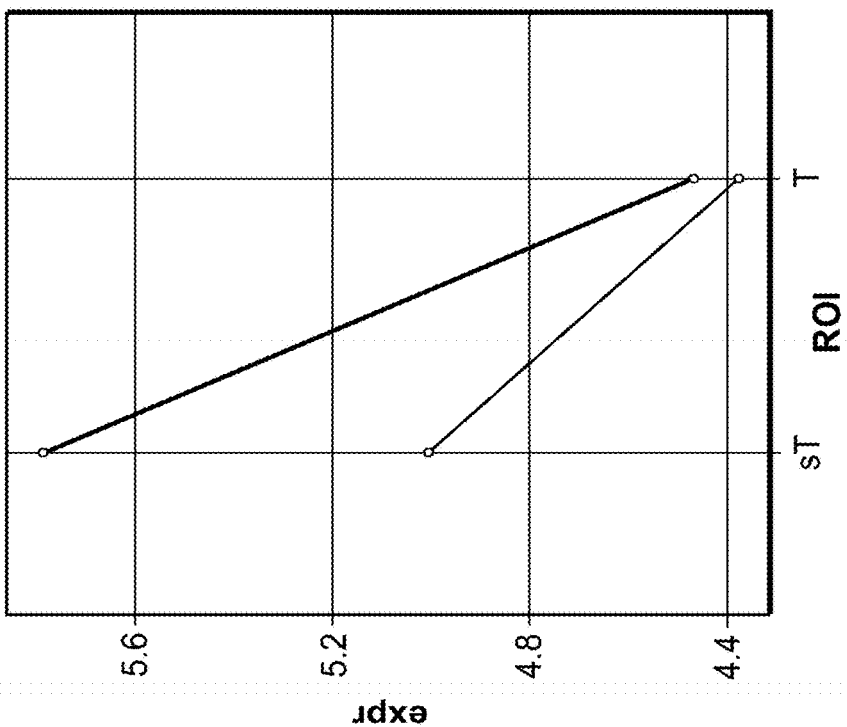
FIG. 25A
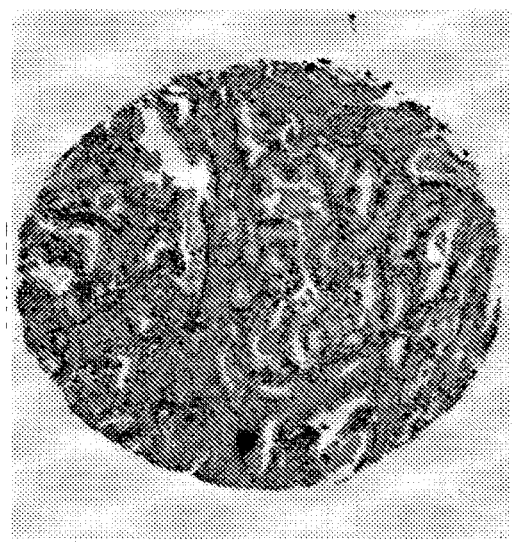
FIG. 25B

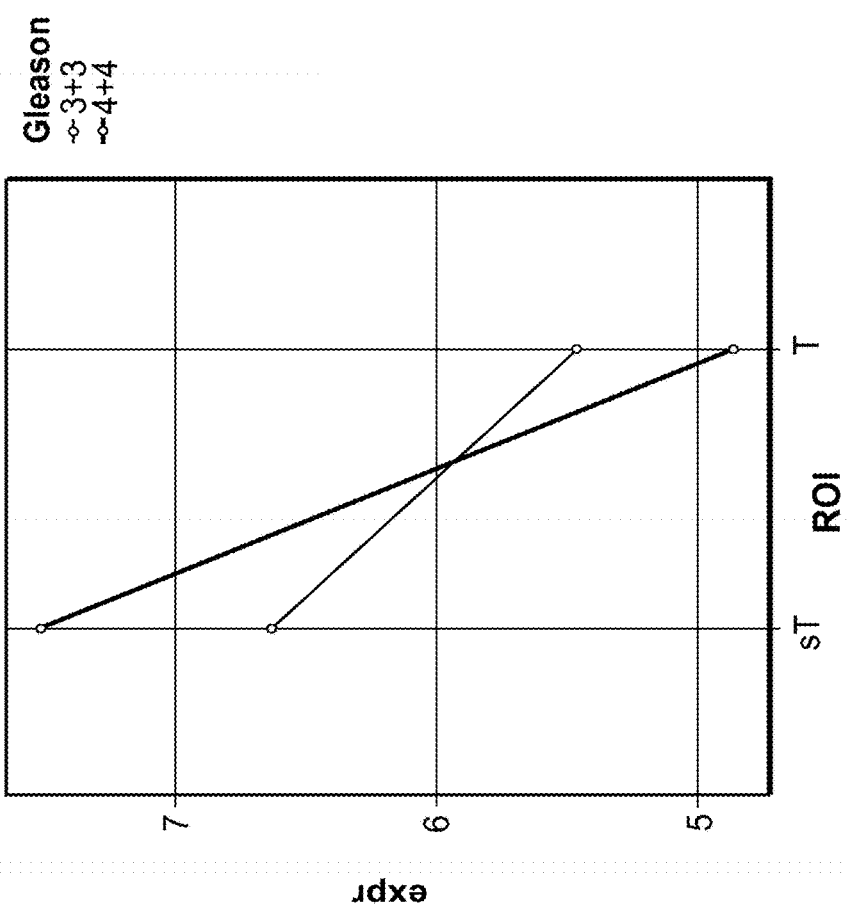
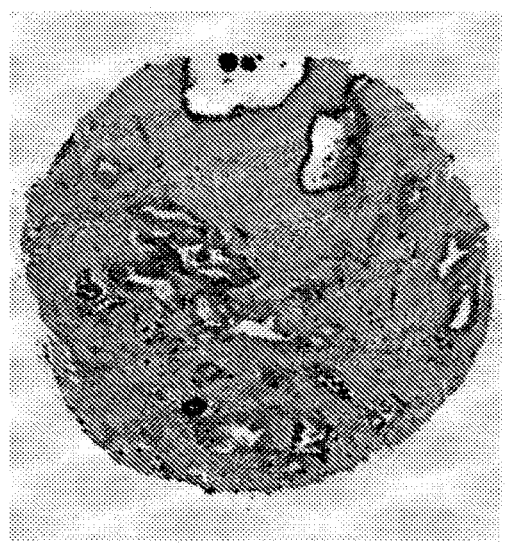
FIG. 31A
FIG. 31B
FIG. 31C

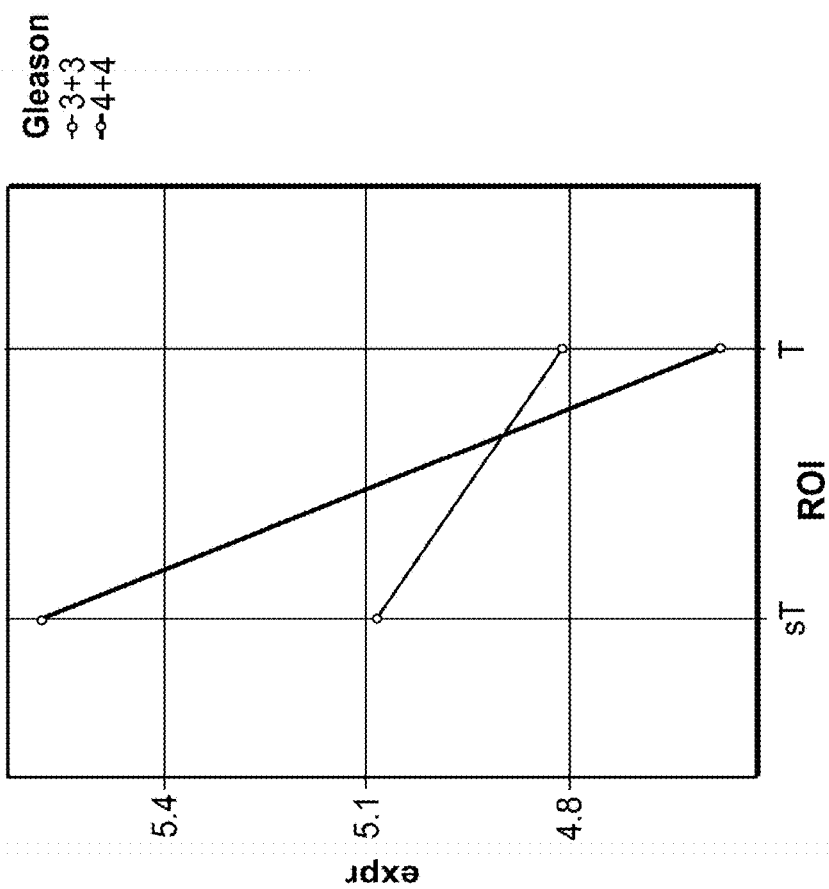
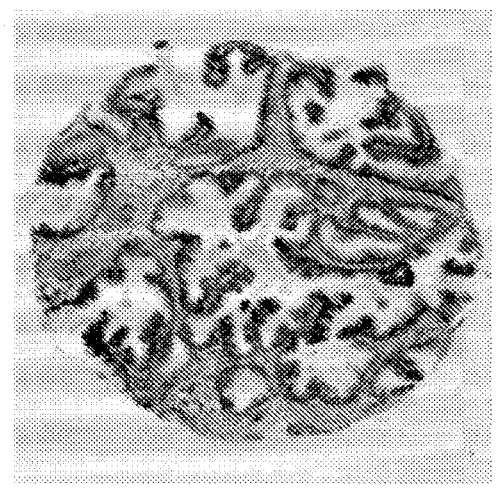
FIG. 33A
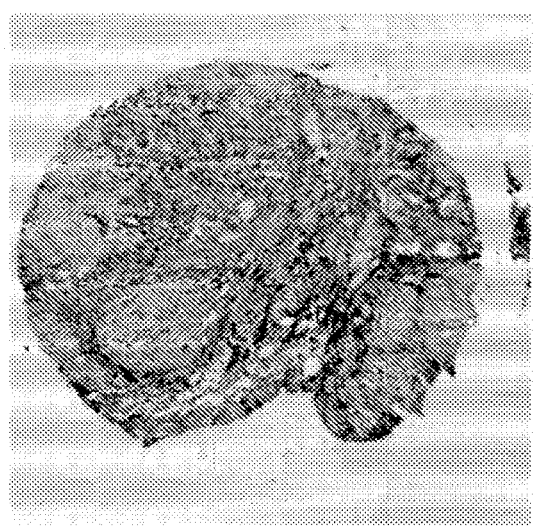
FIG. 33B

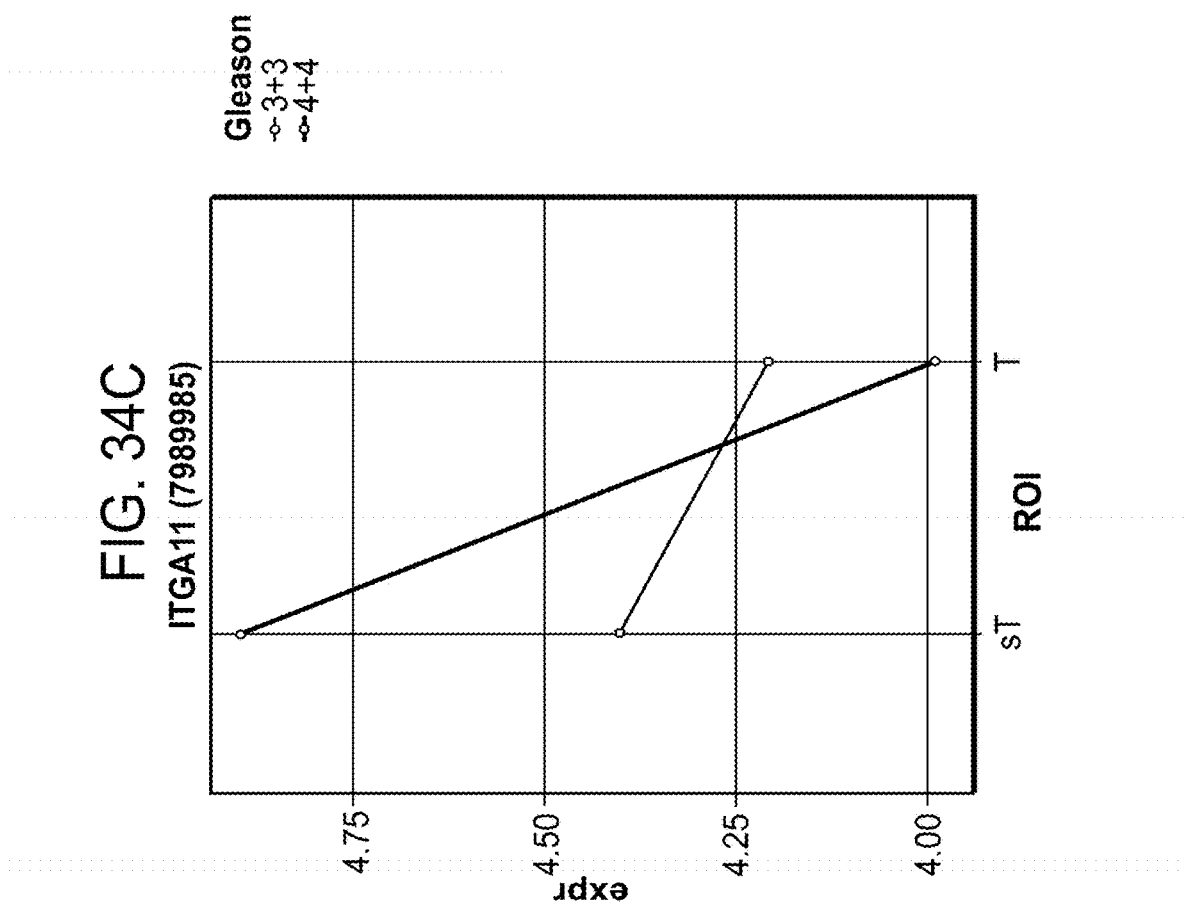
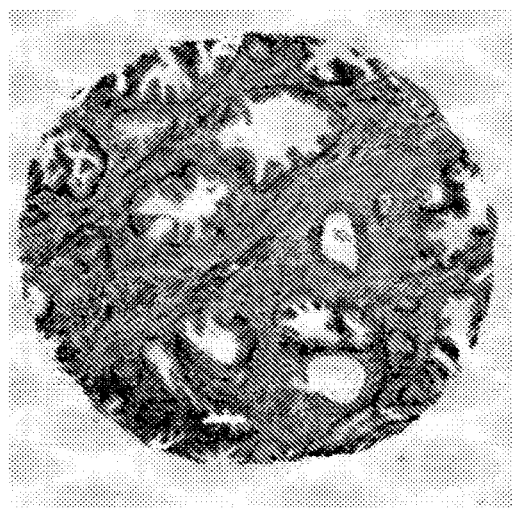
FIG. 34A
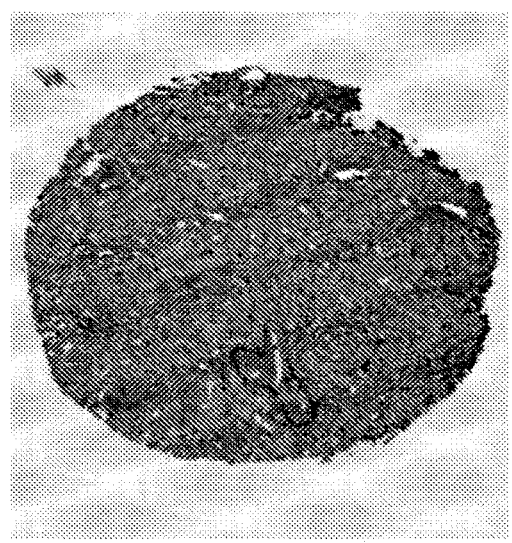
FIG. 34B

FIG. 38C

| UP IN EPITHELIUM | | | UP IN STROMA | | |
|---|---|---|---|---|---|
| Pathway Maps | p-value | FDR | Pathway Maps | p-value | FDR |
| Cell adhesion_Cadherin-mediated cell adhesion | 1.47E-05 | 1.54E-03 | Airway smooth muscle contraction in asthma | 3.32E-12 | 2.04E-10 |
| Cell adhesion_Endothelial cell contacts by junctional mechanisms | 1.47E-05 | 1.54E-03 | Cell adhesion_Chemokines and adhesion | 1.72E-16 | 5.28E-14 |
| Cell adhesion_Tight junctions | 7.65E-05 | 6.00E-03 | Cell adhesion_ECM remodeling | 2.73E-15 | 3.36E-13 |
| Cell cycle_Chromosome condensation in prometaphase | 2.13E-03 | 7.24E-02 | Cell adhesion_Histamine H1 receptor signaling in the interruption of cell barrier integrity | 8.96E-14 | 6.88E-12 |
| Cytoskeleton remodeling_Keratin filaments | 9.93E-04 | 4.55E-02 | Cell adhesion_integrin-mediated cell adhesion and migration | 5.77E-16 | 1.18E-13 |
| Regulation of lipid metabolism_Regulation of lipid metabolism via LXR_NF-Y and SREBP | 1.22E-03 | 4.79E-02 | Cytoskeleton remodeling_Cytoskeleton remodeling | 2.08E-17 | 1.28E-14 |
| Regulation of metabolism_Bile acids regulation of glucose and lipid metabolism via FXR | 5.60E-06 | 1.54E-03 | Cytoskeleton remodeling_TGF, WNT and cytoskeleton remodeling | 2.00E-15 | 3.07E-13 |
| Role of alpha-G/beta-4 integrins in carcinoma progression | 2.30E-03 | 7.24E-02 | Development_Regulation of epithelial-to-mesenchymal transition (EMT) | 8.10E-15 | 8.29E-13 |
| Unsaturated fatty acid biosynthesis | 1.01E-03 | 4.55E-02 | Development_TGF-beta-dependent induction of EMT via RhoA PL3K and ILK | 2.56E-12 | 1.75E-10 |
| wtCFTR and deltaF508 traffic / Membrane expression (normal and CF) | 2.52E-04 | 1.58E-02 | Immune response_Classical complement pathway | 5.47E-14 | 4.80E-12 |

FIG. 38C (cont.)

| Process Networks | p-value | FDR | Process Networks | p-value | FDR |
|---|---|---|---|---|---|
| Cell adhesion_Cell junctions | 1.12E-05 | 1.37E-03 | Cell adhesion_Cell-matrix interactions | 1.07E-20 | 7.68E-19 |
| Cytoskeleton_Intermediate filaments | 4.29E-03 | 1.32E-01 | Cell adhesion_Integrin-mediated cell-matrix adhesion | 5.97E-23 | 8.59E-21 |
| Inflammation_Kellikrein-kinin system | 2.45E-02 | 3.01E-01 | Cell adhesion_Platelet-endothelium-leucocyte interactions | 4.73E-10 | 8.52E-09 |
| Protein folding_Response to unfolded proteins | 9.84E-03 | 2.05E-01 | Cytoskeleton_Actin filaments | 3.54E-18 | 1.70E-16 |
| Proteolysis_Connective tissue degradation | 1.85E-03 | 9.06E-02 | Cytoskeleton_Regulation of cytoskeleton rearrangement | 2.22E-14 | 5.34E-13 |
| Regulation of metabolism_Bile acid regulation of lipid metabolism and negative FXR-depended regulation of bile acids concentration | 2.21E-03 | 9.06E-02 | Development_EMT_Regulation of epithelial-to mesenchymal transition | 3.71E-12 | 7.63E-11 |
| Reproduction_Male sex differentiation | 1.85E-02 | 2.54E-01 | Development_Regulation of angiogenesis | 3.70E-09 | 5.92E-08 |
| Reproduction_Spermatogenesis, motility and copulation | 1.18E-02 | 2.07E-01 | Development_Skeletal muscle development | 2.89E-16 | 8.33E-15 |
| Signal transduction_Androgen receptor nuclear signaling | 1.00E-02 | 2.05E-01 | Inflammation_Complement system | 4.78E-09 | 6.88E-08 |
| Transport_Manganese transport | 1.41E-02 | 2.17E-01 | Muscle contraction | 1.25E-17 | 4.50E-16 |

FIG. 38C (cont.)

| GO Processes | p-value | FDR | GO Processes | p-value | FDR |
|---|---|---|---|---|---|
| acylglycerol biosynthetic process | 3.23E-08 | 1.43E-05 | anatomical structure morphogenesis | 9.89E-57 | 9.82E-54 |
| establishment of localization | 9.32E-10 | 8.27E-07 | cardiovascular system development | 8.33E-59 | 9.92E-56 |
| fatty-acyl-CoA biosynthetic process | 6.35E-09 | 3.52E-06 | circulatory system development | 8.33E-59 | 9.92E-56 |
| localization | 1.84E-10 | 2.05E-07 | developmental process | 1.59E-53 | 9.48E-51 |
| long-chain fatty-acyl-CoA biosynthetic process | 2.67E-09 | 1.97E-06 | extracellular matrix organization | 2.08E-60 | 7.59E-57 |
| neutral lipid biosynthetic process | 3.23E-08 | 1.43E-05 | extracellular structure organization | 2.55E-60 | 7.59E-57 |
| regulation of biological quality | 1.85E-10 | 2.05E-07 | regulation of multicellular organismal process | 1.50E-53 | 9.48E-51 |
| single-organism localization | 3.57E-12 | 1.58E-08 | single-organism developmental process | 8.81E-54 | 6.56E-51 |
| single-organism transport | 1.79E-11 | 3.97E-08 | system development | 1.25E-59 | 2.49E-56 |
| transport | 4.36E-09 | 2.77E-06 | tissue development | 4.80E-56 | 4.09E-53 |

T - sT comp
P - sP comp
B - sB comp

Enrichment Analysis of DE genes at the intersection

B-sB: 975 DE genes

P-sP: 1124 DE genes

FIG. 39D
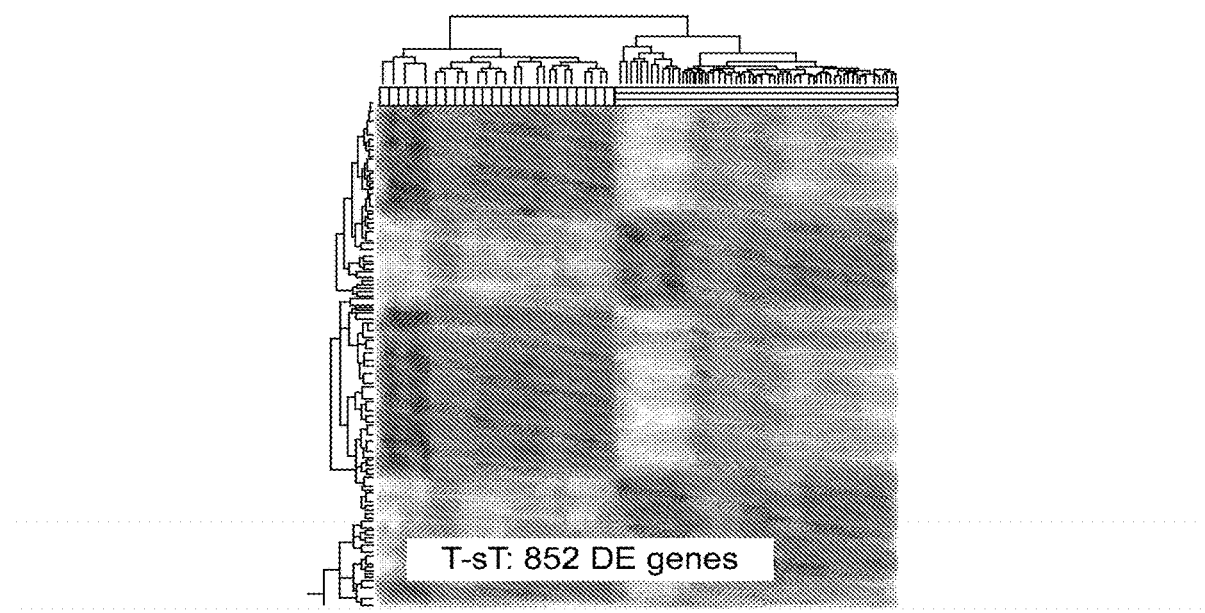
T-sT: 852 DE genes
FIG. 39E
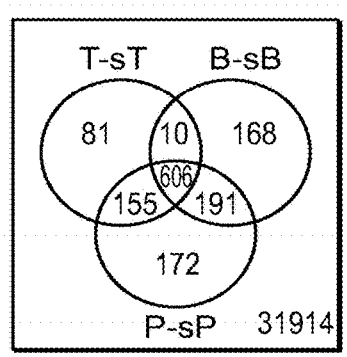
FIG. 39F
| Comparisons between Epithelium and Stroma | Number of differentially expressed genes |
|---|---|
| T - sT | 361 / 491 |
| P - sP | 560 / 564 |
| B - sB | 485 / 490 |

FIG. 42

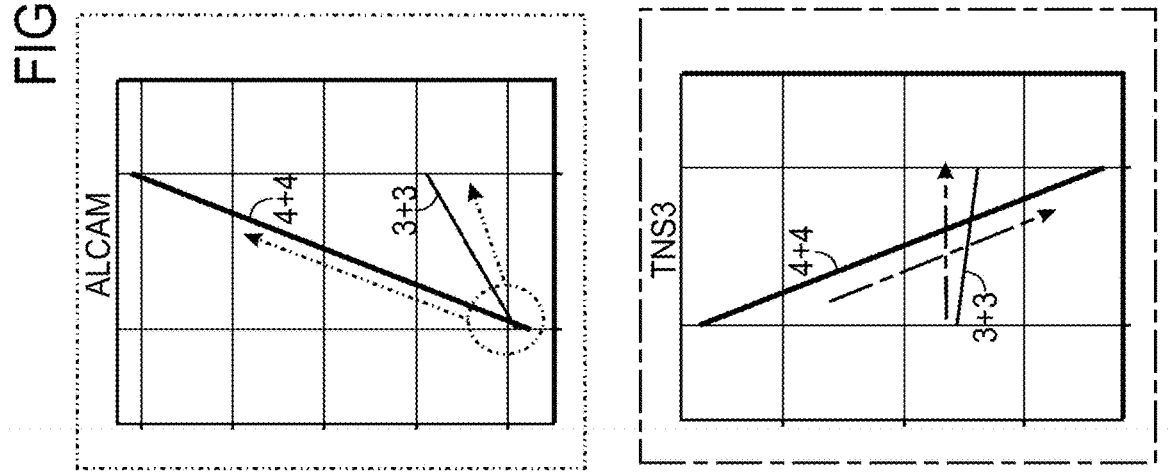

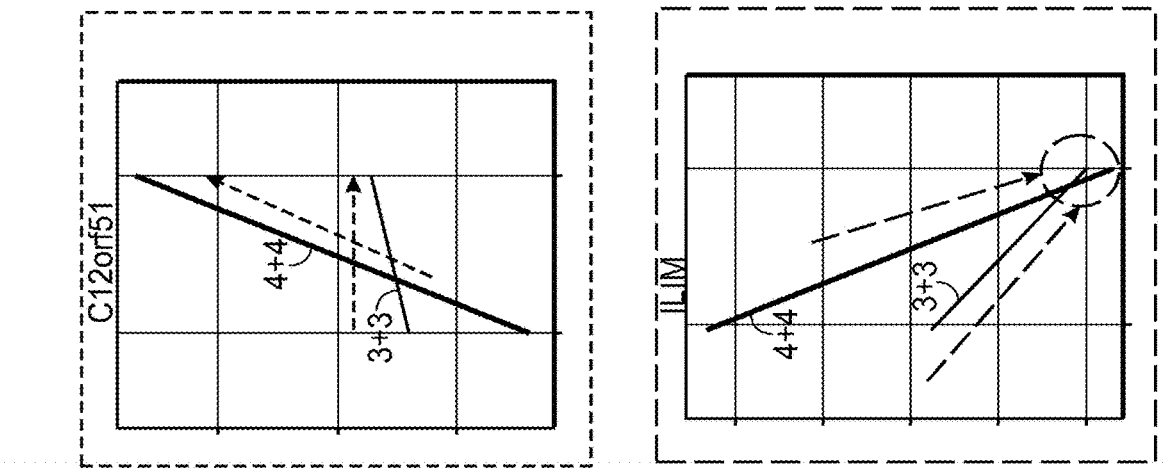

| | |
|---|---|
| CLDN8 | Epithelial |
| HSP9A | Epithelial |
| TMEM205 | Epithelial |
| PTPLAD1 | Epithelial |
| C12orf51 | Epithelial |
| TNS3 | Epithelial |
| ALCAM | Epithelial |
| MAI2 | Epithelial |
| C1QA | Stromal |
| C1QB | Stromal |
| C1QC | Stromal |
| FCGR2C | Stromal |
| C1S | Stromal |
| ILIM | Stromal |
| FBLN5 | Stromal |
| COL1A1 | Stromal |
| SFRP2 | Stromal |
| AEBP1 | Stromal |
| SFRP4 | Stromal |
| BGN | Stromal |
| HLA-DRB3 | Stromal |
| SULF1 | Stromal |
| PRELP | Stromal |
| CD52 | Stromal |
| THMBS2 | Stromal |
| LTBP2 | Stromal |
| SERPING1 | Stromal |
| ITGA11 | Stromal |
| MOXD1 | Stromal |

C12orf51 epithelial

PTPLAD1 epithelial

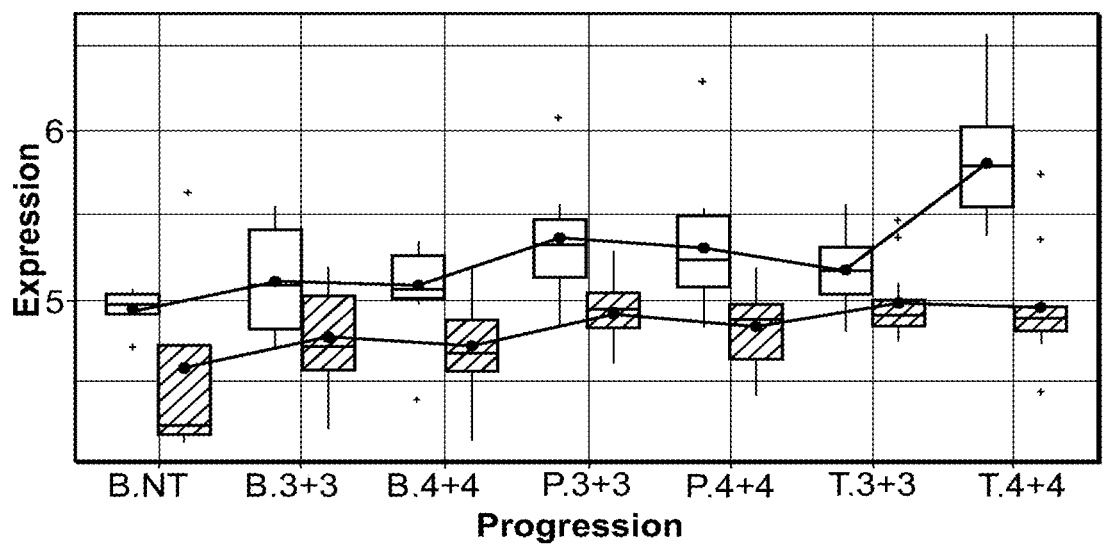
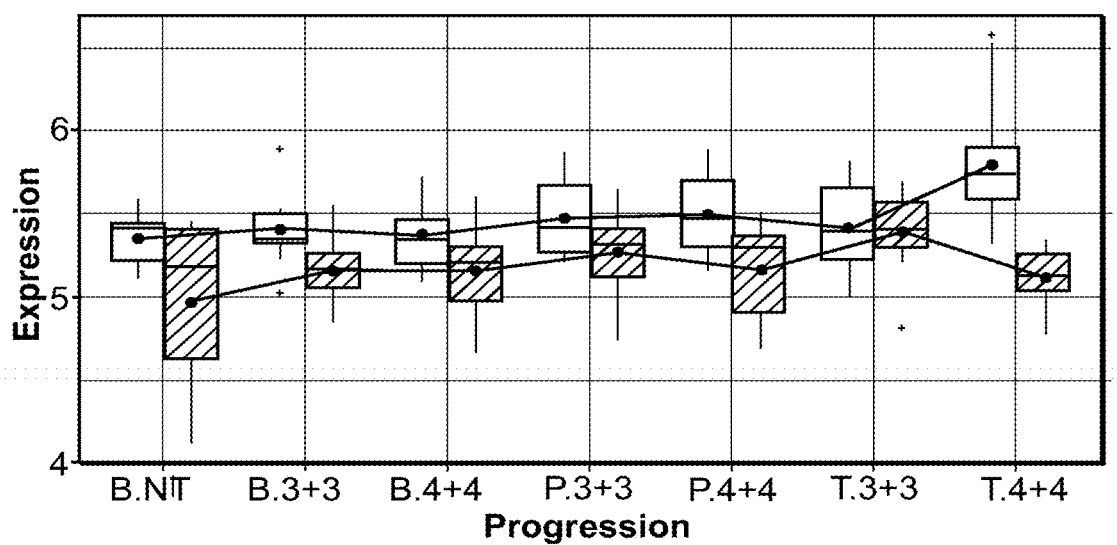

MAL2 epithelial

C1QA stroma

C1QA stroma

C1QB stroma

C1S stroma

LUM stroma

LTBP2 stroma

FBLN5 stroma

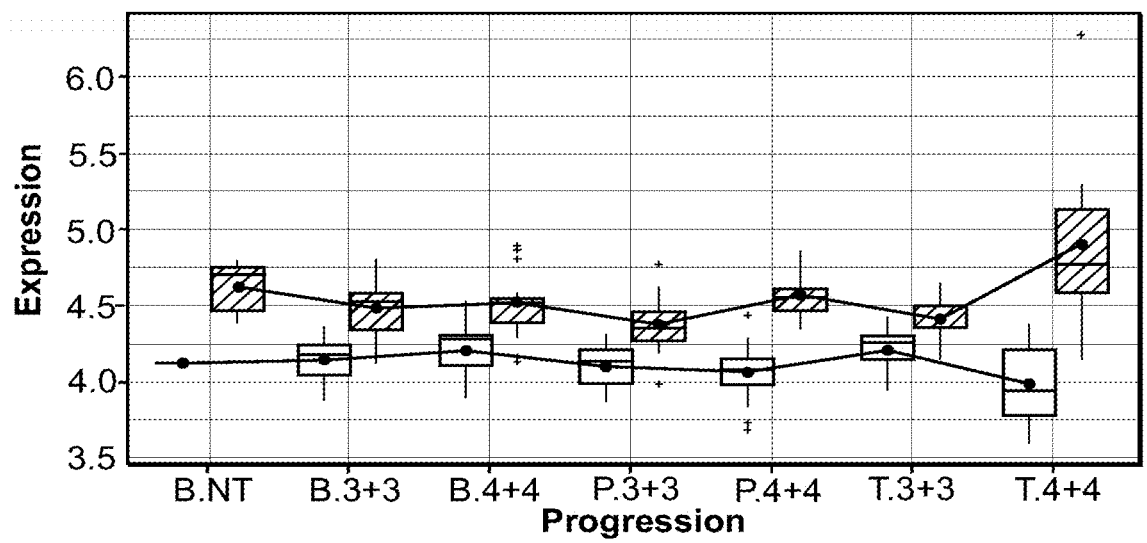
FIG. 63 ITGA11 stroma
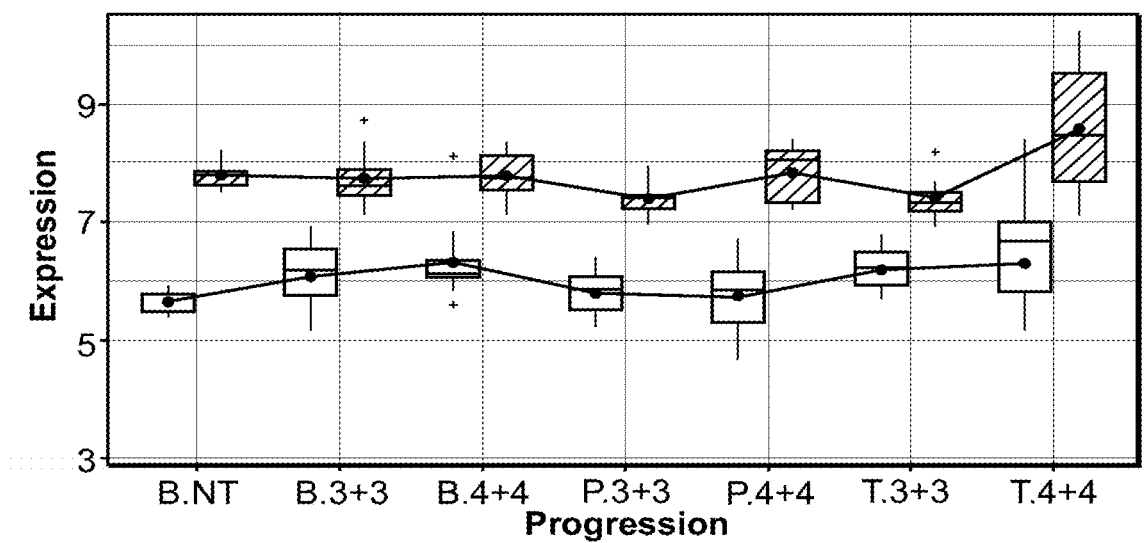
FIG. 64 COL1A1 stroma

SFRP2 stroma

MOXD1 stoma

THBS2 stroma

AEBP1 stroma

HLA-DRB3 stroma

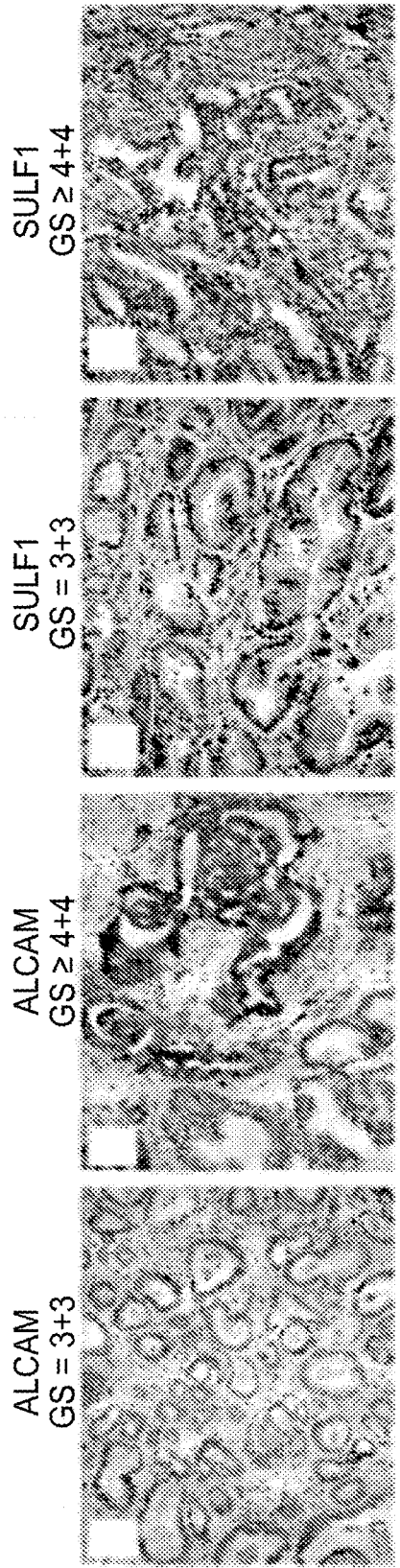
FIG. 78F ALCAM GS = 3+3
FIG. 78G ALCAM GS ≥ 4+4
FIG. 78H SULF1 GS = 3+3
FIG. 78I SULF1 GS ≥ 4+4

SEQUENCE LISTING

```
<160> NUMBER OF SEQ ID NOS: 76

<210> SEQ ID NO 1
<211> LENGTH: 583
<212> TYPE: PRT
<213> ORGANISM: Homo sapiens

<400> SEQUENCE: 1

Met Glu Ser Lys Gly Ala Ser Ser Cys Arg Leu Leu Phe Cys Leu Leu
1               5                   10                  15

Ile Ser Ala Thr Val Phe Arg Pro Gly Leu Gly Trp Tyr Thr Val Asn
            20                  25                  30

Ser Ala Tyr Gly Asp Thr Ile Ile Ile Pro Cys Arg Leu Asp Val Pro
        35                  40                  45

Gln Asn Leu Met Phe Gly Lys Trp Lys Tyr Glu Lys Pro Asp Gly Ser
    50                  55                  60

Pro Val Phe Ile Ala Phe Arg Ser Ser Thr Lys Lys Ser Val Gln Tyr
65                  70                  75                  80

Asp Asp Val Pro Glu Tyr Lys Asp Arg Leu Asn Leu Ser Glu Asn Tyr
                85                  90                  95

Thr Leu Ser Ile Ser Asn Ala Arg Ile Ser Asp Glu Lys Arg Phe Val
            100                 105                 110

Cys Met Leu Val Thr Glu Asp Asn Val Phe Glu Ala Pro Thr Ile Val
        115                 120                 125

Lys Val Phe Lys Gln Pro Ser Lys Pro Glu Ile Val Ser Lys Ala Leu
    130                 135                 140

Phe Leu Glu Thr Glu Gln Leu Lys Lys Leu Gly Asp Cys Ile Ser Glu
145                 150                 155                 160

Asp Ser Tyr Pro Asp Gly Asn Ile Thr Trp Tyr Arg Asn Gly Lys Val
                165                 170                 175
```

```
Leu His Pro Leu Glu Gly Ala Val Val Ile Ile Phe Lys Lys Glu Met
            180                 185                 190

Asp Pro Val Thr Gln Leu Tyr Thr Met Thr Ser Thr Leu Glu Tyr Lys
            195                 200                 205

Thr Thr Lys Ala Asp Ile Gln Met Pro Phe Thr Cys Ser Val Thr Tyr
            210                 215                 220

Tyr Gly Pro Ser Gly Gln Lys Thr Ile His Ser Glu Gln Ala Val Phe
225                     230                 235                 240

Asp Ile Tyr Tyr Pro Thr Glu Gln Val Thr Ile Gln Val Leu Pro Pro
                245                 250                 255

Lys Asn Ala Ile Lys Glu Gly Asp Asn Ile Thr Leu Lys Cys Leu Gly
            260                 265                 270

Asn Gly Asn Pro Pro Pro Glu Glu Phe Leu Phe Tyr Leu Pro Gly Gln
            275                 280                 285

Pro Glu Gly Ile Arg Ser Ser Asn Thr Tyr Thr Leu Thr Asp Val Arg
            290                 295                 300

Arg Asn Ala Thr Gly Asp Tyr Lys Cys Ser Leu Ile Asp Lys Lys Ser
305                     310                 315                 320

Met Ile Ala Ser Thr Ala Ile Thr Val His Tyr Leu Asp Leu Ser Leu
                325                 330                 335

Asn Pro Ser Gly Glu Val Thr Arg Gln Ile Gly Asp Ala Leu Pro Val
            340                 345                 350

Ser Cys Thr Ile Ser Ala Ser Arg Asn Ala Thr Val Val Trp Met Lys
            355                 360                 365

Asp Asn Ile Arg Leu Arg Ser Ser Pro Ser Phe Ser Ser Leu His Tyr
            370                 375                 380

Gln Asp Ala Gly Asn Tyr Val Cys Glu Thr Ala Leu Gln Glu Val Glu
385                     390                 395                 400

Gly Leu Lys Lys Arg Glu Ser Leu Thr Leu Ile Val Glu Gly Lys Pro
                405                 410                 415

Gln Ile Lys Met Thr Lys Lys Thr Asp Pro Ser Gly Leu Ser Lys Thr
            420                 425                 430

Ile Ile Cys His Val Glu Gly Phe Pro Lys Pro Ala Ile Gln Trp Thr
            435                 440                 445

Ile Thr Gly Ser Gly Ser Val Ile Asn Gln Thr Glu Glu Ser Pro Tyr
            450                 455                 460

Ile Asn Gly Arg Tyr Tyr Ser Lys Ile Ile Ile Ser Pro Glu Glu Asn
465                     470                 475                 480

Val Thr Leu Thr Cys Thr Ala Glu Asn Gln Leu Glu Arg Thr Val Asn
                485                 490                 495

Ser Leu Asn Val Ser Ala Ile Ser Ile Pro Glu His Asp Glu Ala Asp
            500                 505                 510

Glu Ile Ser Asp Glu Asn Arg Glu Lys Val Asn Asp Gln Ala Lys Leu
            515                 520                 525

Ile Val Gly Ile Val Val Gly Leu Leu Leu Ala Ala Leu Val Ala Gly
            530                 535                 540

Val Val Tyr Trp Leu Tyr Met Lys Lys Ser Lys Thr Ala Ser Lys His
545                     550                 555                 560

Val Asn Lys Asp Leu Gly Asn Met Glu Glu Asn Lys Lys Leu Glu Glu
                565                 570                 575

Asn Asn His Lys Thr Glu Ala
            580
```

<210> SEQ ID NO 2
<211> LENGTH: 2509
<212> TYPE: DNA
<213> ORGANISM: Homo sapiens

<400> SEQUENCE: 2

| | | | | | |
|---|---|---|---|---|---|
| tgtctgggag | aagacgctgc | ccctgcgtcg | ggacccgcca | gcgcgcgggc | accgcggggc | 60 |
| ccgggacgac | gccccctcct | gcggcgtgga | ctccgtcagt | ggcccaccaa | gaaggaggag | 120 |
| gaatatggaa | tccaaggggg | ccagttcctg | ccgtctgctc | ttctgcctct | tgatctccgc | 180 |
| caccgtcttc | aggccaggcc | ttggatggta | tactgtaaat | tcagcatatg | agataccat | 240 |
| tatcatacct | tgccgacttg | acgtacctca | gaatctcatg | tttggcaaat | ggaaatatga | 300 |
| aaagcccgat | ggctccccag | tatttattgc | cttcagatcc | tctacaaaga | aaagtgtgca | 360 |
| gtacgacgat | gtaccagaat | acaaagacag | attgaacctc | tcagaaaact | acactttgtc | 420 |
| tatcagtaat | gcaaggatca | gtgatgaaaa | gagatttgtg | tgcatgctag | taactgagga | 480 |
| caacgtgttt | gaggcaccta | caatagtcaa | ggtgttcaag | caaccatcta | aacctgaaat | 540 |
| tgtaagcaaa | gcactgtttc | tcgaaacaga | gcagctaaaa | aagttgggtg | actgcatttc | 600 |
| agaagacagt | tatccagatg | gcaatatcac | atggtacagg | aatggaaaag | tgctacatcc | 660 |
| ccttgaagga | gcggtggtca | taattttttaa | aaaggaaatg | gacccagtga | ctcagctcta | 720 |
| taccatgact | tccaccctgg | agtacaagac | aaccaaggct | gacatacaaa | tgccattcac | 780 |
| ctgctcggtg | acatattatg | gaccatctgg | ccagaaaaca | attcattctg | aacaggcagt | 840 |
| atttgatatt | tactatccta | cagagcaggt | gacaatacaa | gtgctgccac | caaaaaatgc | 900 |
| catcaaagaa | ggggataaca | tcactcttaa | atgcttaggg | aatggcaacc | ctccccaga | 960 |
| ggaattttg | ttttacttac | caggacagcc | cgaaggaata | gaagctcaa | atacttacac | 1020 |
| actaacggat | gtgaggcgca | atgcaacagg | agactacaag | tgttcctga | tagacaaaaa | 1080 |
| aagcatgatt | gcttcaacag | ccatcacagt | tcactatttg | gatttgtcct | taaacccaag | 1140 |
| tggagaagtg | actagacaga | ttggtgatgc | cctacccgtg | tcatgcacaa | tatctgctag | 1200 |
| caggaatgca | actgtggtat | ggatgaaaga | taacatcagg | cttcgatcta | gcccgtcatt | 1260 |
| ttctagtctt | cattatcagg | atgctggaaa | ctatgtctgc | gaaactgctc | tgcaggaggt | 1320 |
| tgaaggacta | agaaaagag | agtcattgac | tctcattgta | gaaggcaaac | tcaaataaa | 1380 |
| aatgacaaag | aaaactgatc | ccagtggact | atctaaaaca | ataatctgcc | atgtggaagg | 1440 |
| ttttccaaag | ccagccattc | aatggacaat | tactggcagt | ggaagcgtca | taaaccaaac | 1500 |
| agaggaatct | ccttatatta | atggcaggta | ttatagtaaa | attatcattt | ccctgaaga | 1560 |
| gaatgttaca | ttaacttgca | cagcagaaaa | ccaactggag | agaacagtaa | actccttgaa | 1620 |
| tgtctctgct | ataagtattc | cagaacacga | tgaggcagac | gagataagtg | atgaaaacag | 1680 |
| agaaaaggtg | aatgaccagg | caaaactaat | tgtgggaatc | gttgttggtc | tcctccttgc | 1740 |
| tgcccttgtt | gctggtgtcg | tctactggct | gtacatgaag | aagtcaaaga | ctgcatcaaa | 1800 |
| acatgtaaac | aaggacctcg | gtaatatgga | agaaaacaaa | agttagaag | aaaacaatca | 1860 |
| caaaactgaa | gcctaagaga | gaaactgtcc | tagttgtcca | gagataaaaa | tcatatagac | 1920 |
| caattgaagc | atgaacgtgg | attgtatta | agacataaac | aaagacattg | acagcaattc | 1980 |
| atggttcaag | tattaagcag | ttcattctac | caagctgtca | caggttttca | gagaattatc | 2040 |
| tcaagtaaaa | caaatgaaat | ttaattacaa | acaataagaa | caagttttgg | cagccatgat | 2100 |
| aataggtcat | atgttgtgtt | tggttcaatt | tttttttccgt | aaatgtctgc | actgaggatt | 2160 |

-continued

```
tcttttggt ttgccttta tgtaaattt ttacgtagct atttttatac actgtaagct    2220
ttgttctggg agttgctgtt aatctgatgt ataatgtaat gtttttattt caattgttta    2280
tatggataat ctgagcaggt acatttctga ttctgattgc tatcagcaat gccccaaact    2340
ttctcataag cacctaaaac ccaaaggtgg cagcttgtga agattgggga cactcatatt    2400
gccctaatta aaaactgtga tttttatcac aagggagggg aggccgagag tcagactgat    2460
agacaccata ggagccgact ctttgatatg ccaccagcga actctcaga                2509
```

<210> SEQ ID NO 3
<211> LENGTH: 338
<212> TYPE: PRT
<213> ORGANISM: Homo sapiens

<400> SEQUENCE: 3

```
Met Ser Leu Ser Ala Phe Thr Leu Phe Leu Ala Leu Ile Gly Gly Thr
1               5                   10                  15

Ser Gly Gln Tyr Tyr Asp Tyr Asp Phe Pro Leu Ser Ile Tyr Gly Gln
            20                  25                  30

Ser Ser Pro Asn Cys Ala Pro Glu Cys Asn Cys Pro Glu Ser Tyr Pro
        35                  40                  45

Ser Ala Met Tyr Cys Asp Glu Leu Lys Leu Lys Ser Val Pro Met Val
    50                  55                  60

Pro Pro Gly Ile Lys Tyr Leu Tyr Leu Arg Asn Asn Gln Ile Asp His
65                  70                  75                  80

Ile Asp Glu Lys Ala Phe Glu Asn Val Thr Asp Leu Gln Trp Leu Ile
                85                  90                  95

Leu Asp His Asn Leu Leu Glu Asn Ser Lys Ile Lys Gly Arg Val Phe
            100                 105                 110

Ser Lys Leu Lys Gln Leu Lys Lys Leu His Ile Asn His Asn Asn Leu
        115                 120                 125

Thr Glu Ser Val Gly Pro Leu Pro Lys Ser Leu Glu Asp Leu Gln Leu
    130                 135                 140

Thr His Asn Lys Ile Thr Lys Leu Gly Ser Phe Glu Gly Leu Val Asn
145                 150                 155                 160

Leu Thr Phe Ile His Leu Gln His Asn Arg Leu Lys Glu Asp Ala Val
                165                 170                 175

Ser Ala Ala Phe Lys Gly Leu Lys Ser Leu Glu Tyr Leu Asp Leu Ser
            180                 185                 190

Phe Asn Gln Ile Ala Arg Leu Pro Ser Gly Leu Pro Val Ser Leu Leu
        195                 200                 205

Thr Leu Tyr Leu Asp Asn Asn Lys Ile Ser Asn Ile Pro Asp Glu Tyr
    210                 215                 220

Phe Lys Arg Phe Asn Ala Leu Gln Tyr Leu Arg Leu Ser His Asn Glu
225                 230                 235                 240

Leu Ala Asp Ser Gly Ile Pro Gly Asn Ser Phe Asn Val Ser Ser Leu
                245                 250                 255

Val Glu Leu Asp Leu Ser Tyr Asn Lys Leu Lys Asn Ile Pro Thr Val
            260                 265                 270

Asn Glu Asn Leu Glu Asn Tyr Tyr Leu Glu Val Asn Gln Leu Glu Lys
        275                 280                 285

Phe Asp Ile Lys Ser Phe Cys Lys Ile Leu Gly Pro Leu Ser Tyr Ser
    290                 295                 300

Lys Ile Lys His Leu Arg Leu Asp Gly Asn Arg Ile Ser Glu Thr Ser
```

```
            305                 310                 315                 320
Leu Pro Pro Asp Met Tyr Glu Cys Leu Arg Val Ala Asn Glu Val Thr
                325                 330                 335
Leu Asn
```

<210> SEQ ID NO 4
<211> LENGTH: 2116
<212> TYPE: DNA
<213> ORGANISM: Homo sapiens

<400> SEQUENCE: 4

| | | | | | |
|---|---|---|---|---|---|
| acagtgagct | tccttatttg | aagcaggact | caattcttgg | ttaaaagcta | tggtatttga | 60 |
| gctagttaaa | cacatatctc | tctcccattc | catagggaat | gagctgggct | gtcctttctc | 120 |
| cccacgttca | cctgcacttc | gttagagagc | agtgttcaca | tgccacacca | caagatcccc | 180 |
| acaatgacat | aactccattc | agagactggc | gtgactgggc | tgggtctccc | cacccccctt | 240 |
| cagctcttgt | atcactcaga | atctggcagc | cagttccgtc | ctgacagagt | tcacagcata | 300 |
| tattggtgga | ttcttgtcca | tagtgcatct | gctttaagaa | ttaacgaaag | cagtgtcaag | 360 |
| acagtaagga | ttcaaaccat | tgccaaaaa | tgagtctaag | tgcatttact | ctcttcctgg | 420 |
| cattgattgg | tggtaccagt | ggccagtact | atgattatga | ttttccccta | tcaatttatg | 480 |
| ggcaatcatc | accaaactgt | gcaccagaat | gtaactgccc | tgaaagctac | ccaagtgcca | 540 |
| tgtactgtga | tgagctgaaa | ttgaaaagtg | taccaatggt | gcctcctgga | atcaagtatc | 600 |
| tttaccttag | gaataaccag | attgaccata | ttgatgaaaa | ggcctttgag | aatgtaactg | 660 |
| atctgcagtg | gctcattcta | gatcacaacc | ttctagaaaa | ctccaagata | aagggagag | 720 |
| ttttctctaa | attgaaacaa | ctgaagaagc | tgcatataaa | ccacaacaac | ctgacagagt | 780 |
| ctgtgggccc | acttcccaaa | tctctggagg | atctgcagct | tactcataac | aagatcacaa | 840 |
| agctgggctc | ttttgaagga | ttggtaaacc | tgaccttcat | ccatctccag | cacaatcggc | 900 |
| tgaaagagga | tgctgtttca | gctgctttta | aaggtcttaa | atcactcgaa | taccttgact | 960 |
| tgagcttcaa | tcagatagcc | agactgcctt | ctggtctccc | tgtctctctt | ctaactctct | 1020 |
| acttagacaa | caataagatc | agcaacatcc | ctgatgagta | tttcaagcgt | tttaatgcat | 1080 |
| tgcagtatct | gcgtttatct | cacaacgaac | tggctgatag | tggaatacct | ggaaattctt | 1140 |
| tcaatgtgtc | atccctggtt | gagctggatc | tgtcctataa | caagcttaaa | acataccaa | 1200 |
| ctgtcaatga | aaaccttgaa | actattacc | tggaggtcaa | tcaacttgag | aagtttgaca | 1260 |
| taaagagctt | ctgcaagatc | ctggggccat | tatcctactc | caagatcaag | catttgcgtt | 1320 |
| tggatggcaa | tcgcatctca | gaaaccagtc | ttccaccgga | tatgtatgaa | tgtctacgtg | 1380 |
| ttgctaacga | agtcactctt | aattaatatc | tgtatcctgg | aacaatattt | tatggttatg | 1440 |
| ttttctgtg | tgtcagtttt | catagtatcc | atattttatt | actgtttatt | acttccatga | 1500 |
| attttaaaat | ctgagggaaa | tgttttgtaa | acatttattt | ttttttaaaga | aaagatgaaa | 1560 |
| ggcaggccta | tttcatcaca | agaacacaca | catatacacg | aatagacatc | aaactcaatg | 1620 |
| ctttatttgt | aaatttagtg | ttttttttatt | tctactgtca | aatgatgtgc | aaaaccttt | 1680 |
| actggttgca | tggaaatcag | ccaagtttta | taatccttaa | atcttaatgt | tcctcaaagc | 1740 |
| ttggattaaa | tacatatgga | tgttactctc | ttgcaccaaa | ttatcttgat | acattcaaat | 1800 |
| ttgtctggtt | aaaaaatagg | tggtagatat | tgaggccaag | aatattgcaa | atacatgaa | 1860 |
| gcttcatgca | cttaaagaag | tattttttaga | ataagaattt | gcatacttac | ctagtgaaac | 1920 |

-continued

```
tttctagaa ttattttca ctctaagtca tgtatgtttc tctttgatta tttgcatgtt    1980
atgtttaata agctactagc aaaataaaac atagcaaatg gcatcactgt gtttgacttc    2040
ttgtgaaatt tctgtactt gtatataaaa tacataaaac aatagattag aaatcaaaag    2100
atatctctgg cctgca                                                    2116
```

<210> SEQ ID NO 5
<211> LENGTH: 1069
<212> TYPE: PRT
<213> ORGANISM: Homo sapiens

<400> SEQUENCE: 5

| | | | | | | | | | | | | | | |
|---|---|---|---|---|---|---|---|---|---|---|---|---|---|---|
| Met | Phe | Ser | Phe | Val | Asp | Leu | Arg | Leu | Leu | Leu | Leu | Ala | Ala | Thr |
| 1 | | | | 5 | | | | | 10 | | | | | 15 |
| Ala | Leu | Leu | Thr | His | Gly | Gln | Glu | Gly | Gln | Val | Glu | Gly | Gln | Asp |
| | | | 20 | | | | | 25 | | | | | 30 | |
| Glu | Asp | Ile | Pro | Pro | Ile | Thr | Cys | Val | Gln | Asn | Gly | Leu | Arg | Tyr | His |
| | | 35 | | | | | 40 | | | | | 45 | | |
| Asp | Arg | Asp | Val | Trp | Lys | Pro | Glu | Pro | Cys | Arg | Ile | Cys | Val | Cys | Asp |
| | 50 | | | | | 55 | | | | | 60 | | | | |
| Asn | Gly | Lys | Val | Leu | Cys | Asp | Asp | Val | Ile | Cys | Asp | Glu | Thr | Lys | Asn |
| 65 | | | | | 70 | | | | | 75 | | | | | 80 |
| Cys | Pro | Gly | Ala | Glu | Val | Pro | Glu | Gly | Glu | Cys | Cys | Pro | Val | Cys | Pro |
| | | | | 85 | | | | | 90 | | | | | 95 | |
| Asp | Gly | Ser | Glu | Ser | Pro | Thr | Asp | Gln | Glu | Thr | Thr | Gly | Val | Glu | Gly |
| | | | 100 | | | | | 105 | | | | | 110 | | |
| Pro | Lys | Gly | Asp | Thr | Gly | Pro | Arg | Gly | Pro | Arg | Gly | Pro | Ala | Gly | Pro |
| | | | 115 | | | | | 120 | | | | | 125 | | |
| Pro | Gly | Arg | Asp | Gly | Ile | Pro | Gly | Gln | Pro | Gly | Leu | Pro | Gly | Pro | Pro |
| | 130 | | | | | 135 | | | | | 140 | | | | |
| Gly | Pro | Pro | Gly | Pro | Pro | Gly | Pro | Pro | Gly | Leu | Gly | Gly | Asn | Phe | Ala |
| 145 | | | | | 150 | | | | | 155 | | | | | 160 |
| Pro | Gln | Leu | Ser | Tyr | Gly | Tyr | Asp | Glu | Lys | Ser | Thr | Gly | Gly | Ile | Ser |
| | | | | 165 | | | | | 170 | | | | | 175 | |
| Val | Pro | Gly | Pro | Met | Gly | Pro | Ser | Gly | Pro | Arg | Gly | Leu | Pro | Gly | Pro |
| | | | 180 | | | | | 185 | | | | | 190 | | |
| Pro | Gly | Ala | Pro | Gly | Pro | Gln | Gly | Phe | Gln | Gly | Pro | Pro | Gly | Glu | Pro |
| | | | 195 | | | | | 200 | | | | | 205 | | |
| Gly | Glu | Pro | Gly | Ala | Ser | Gly | Pro | Met | Gly | Pro | Arg | Gly | Pro | Pro | Gly |
| | 210 | | | | | 215 | | | | | 220 | | | | |
| Pro | Pro | Gly | Lys | Asn | Gly | Asp | Asp | Gly | Glu | Ala | Gly | Lys | Pro | Gly | Arg |
| 225 | | | | | 230 | | | | | 235 | | | | | 240 |
| Pro | Gly | Glu | Arg | Gly | Pro | Pro | Gly | Pro | Gln | Gly | Ala | Arg | Gly | Leu | Pro |
| | | | | 245 | | | | | 250 | | | | | 255 | |
| Gly | Thr | Ala | Gly | Leu | Pro | Gly | Met | Lys | Gly | His | Arg | Gly | Phe | Ser | Gly |
| | | | | 260 | | | | | 265 | | | | | 270 | |
| Leu | Asp | Gly | Ala | Lys | Gly | Asp | Ala | Gly | Pro | Ala | Gly | Pro | Lys | Gly | Glu |
| | | | 275 | | | | | 280 | | | | | 285 | | |
| Pro | Gly | Ser | Pro | Gly | Glu | Asn | Gly | Ala | Pro | Gly | Gln | Met | Gly | Pro | Arg |
| | | | 290 | | | | | 295 | | | | | 300 | | |
| Gly | Leu | Pro | Gly | Glu | Arg | Gly | Arg | Pro | Gly | Ala | Pro | Gly | Pro | Ala | Gly |
| 305 | | | | | 310 | | | | | 315 | | | | | 320 |
| Ala | Arg | Gly | Asn | Asp | Gly | Ala | Thr | Gly | Ala | Ala | Gly | Pro | Pro | Gly | Pro |
| | | | | 325 | | | | | 330 | | | | | 335 | |

```
Thr Gly Pro Ala Gly Pro Pro Gly Phe Pro Gly Ala Val Gly Ala Lys
            340                 345                 350

Gly Glu Ala Gly Pro Gln Gly Pro Arg Gly Ser Glu Gly Pro Gln Gly
        355                 360                 365

Val Arg Gly Glu Pro Gly Pro Pro Gly Pro Ala Gly Ala Ala Gly Pro
    370                 375                 380

Ala Gly Asn Pro Gly Ala Asp Gly Gln Pro Gly Ala Lys Gly Ala Asn
385                 390                 395                 400

Gly Ala Pro Gly Ile Ala Gly Ala Pro Gly Phe Pro Gly Ala Arg Gly
                405                 410                 415

Pro Ser Gly Pro Gln Gly Pro Gly Gly Pro Pro Gly Pro Lys Gly Asn
            420                 425                 430

Ser Gly Glu Pro Gly Ala Pro Gly Ser Lys Gly Asp Thr Gly Ala Lys
        435                 440                 445

Gly Glu Pro Gly Pro Val Gly Val Gln Gly Pro Pro Gly Pro Ala Gly
        450                 455                 460

Glu Glu Gly Lys Arg Gly Ala Arg Gly Glu Pro Gly Pro Thr Gly Leu
465                 470                 475                 480

Pro Gly Pro Pro Gly Glu Arg Gly Gly Pro Gly Ser Arg Gly Phe Pro
            485                 490                 495

Gly Ala Asp Gly Val Ala Gly Pro Lys Gly Pro Ala Gly Glu Arg Gly
            500                 505                 510

Ser Pro Gly Pro Ala Gly Pro Lys Gly Ser Pro Gly Glu Ala Gly Arg
            515                 520                 525

Pro Gly Glu Ala Gly Leu Pro Gly Ala Lys Gly Leu Thr Gly Ser Pro
        530                 535                 540

Gly Ser Pro Gly Pro Asp Gly Lys Thr Gly Pro Pro Gly Pro Ala Gly
545                 550                 555                 560

Gln Asp Gly Arg Pro Gly Pro Pro Gly Pro Pro Gly Ala Arg Gly Gln
            565                 570                 575

Ala Gly Val Met Gly Phe Pro Gly Pro Lys Gly Ala Ala Gly Glu Pro
            580                 585                 590

Gly Lys Ala Gly Glu Arg Gly Val Pro Gly Pro Pro Gly Ala Val Gly
        595                 600                 605

Pro Ala Gly Lys Asp Gly Glu Ala Gly Ala Gln Gly Pro Pro Gly Pro
    610                 615                 620

Ala Gly Pro Ala Gly Glu Arg Gly Glu Gln Gly Pro Ala Gly Ser Pro
625                 630                 635                 640

Gly Phe Gln Gly Leu Pro Gly Pro Ala Gly Pro Pro Gly Glu Ala Gly
            645                 650                 655

Lys Pro Gly Glu Gln Gly Val Pro Gly Asp Leu Gly Ala Pro Gly Pro
            660                 665                 670

Ser Gly Ala Arg Gly Glu Arg Gly Phe Pro Gly Glu Arg Gly Val Gln
            675                 680                 685

Gly Pro Pro Gly Pro Ala Gly Pro Arg Gly Ala Asn Gly Ala Pro Gly
        690                 695                 700

Asn Asp Gly Ala Lys Gly Asp Ala Gly Ala Pro Gly Ala Pro Gly Ser
705                 710                 715                 720

Gln Gly Ala Pro Gly Leu Gln Gly Met Pro Gly Glu Arg Gly Ala Ala
                725                 730                 735

Gly Leu Pro Gly Pro Lys Gly Asp Arg Gly Asp Ala Gly Pro Lys Gly
            740                 745                 750

Ala Asp Gly Ser Pro Gly Lys Asp Gly Val Arg Gly Leu Thr Gly Pro
```

|     |     |     |     | 755 |     |     |     | 760 |     |     |     | 765 |     |     |
| --- | --- | --- | --- | --- | --- | --- | --- | --- | --- | --- | --- | --- | --- | --- |

Ile Gly Pro Pro Gly Pro Ala Gly Ala Pro Gly Asp Lys Gly Glu Ser
770             775                 780

Gly Pro Ser Gly Pro Ala Gly Pro Thr Gly Ala Arg Gly Ala Pro Gly
785             790                 795                 800

Asp Arg Gly Glu Pro Gly Pro Pro Gly Pro Ala Gly Phe Ala Gly Pro
            805                 810                 815

Pro Gly Ala Asp Gly Gln Pro Gly Ala Lys Gly Glu Pro Gly Asp Ala
            820                 825                 830

Gly Ala Lys Gly Asp Ala Gly Pro Pro Gly Pro Ala Gly Pro Ala Gly
            835                 840                 845

Pro Pro Gly Pro Ile Gly Asn Val Gly Ala Pro Gly Ala Lys Gly Ala
850             855                 860

Arg Gly Ser Ala Gly Pro Pro Gly Ala Thr Gly Phe Pro Gly Ala Ala
865             870                 875                 880

Gly Arg Val Gly Pro Pro Gly Pro Ser Gly Asn Ala Gly Pro Pro Gly
            885                 890                 895

Pro Pro Gly Pro Ala Gly Lys Glu Gly Gly Lys Gly Pro Arg Gly Glu
            900                 905                 910

Thr Gly Pro Ala Gly Arg Pro Gly Glu Val Gly Pro Pro Gly Pro Pro
            915                 920                 925

Gly Pro Ala Gly Glu Lys Gly Ser Pro Gly Ala Asp Gly Pro Ala Gly
930             935                 940

Ala Pro Gly Thr Pro Gly Pro Gln Gly Ile Ala Gly Gln Arg Gly Val
945             950                 955                 960

Val Gly Leu Pro Gly Gln Arg Gly Glu Arg Gly Phe Pro Gly Leu Pro
            965                 970                 975

Gly Pro Ser Gly Glu Pro Gly Lys Gln Gly Pro Ser Gly Ala Ser Gly
            980                 985                 990

Glu Arg Gly Pro Pro Gly Pro Met Gly Pro Pro Gly Leu Ala Gly Pro
            995                 1000                1005

Pro Gly Glu Ser Gly Arg Glu Gly Ala Pro Gly Ala Glu Gly Ser
    1010                1015                1020

Pro Gly Arg Asp Gly Ser Pro Gly Ala Lys Gly Asp Arg Gly Glu
    1025                1030                1035

Thr Gly Pro Ala Gly Pro Pro Gly Ala Pro Gly Ala Pro Gly Ala
    1040                1045                1050

Pro Gly Pro Val Gly Pro Ala Gly Lys Ser Gly Asp Arg Gly Glu
    1055                1060                1065

Thr

<210> SEQ ID NO 6
<211> LENGTH: 16814
<212> TYPE: DNA
<213> ORGANISM: Homo sapiens

<400> SEQUENCE: 6
acatcttcag cctgggcacc cgccaagcgt tttaagtcga agagtggcag gggaggcctt    60
gagcctcagc tccatgccac gtgtaaagga tgcttggaaa ctgtctgcct cggcccctgg   120
gaggaaggcc tggaactgga cattggggtg gtggctgtca cacgccaggc acacaaaact   180
ccaaagccag ggatccccaa atatccttca gaacccagg cccatgatgt agcaaccccc   240
aattcacacc ttggaggttt caactcttct ttaagatggg cgtgggaaag cctggatggg   300

```
aaacatatgg ggaggggcgg ggagctgcag gcaggagccc ttcttactac gaaaacccaa    360
gaagcaagga agtggacagg tcactaaccc tcatactacc aagccctgcg gcaccctgcc    420
ctagaccacc actctaaatg tctgttccct ccaaaaacag gaccctgtc gcctattagg     480 gagggggtct cttggaactg acccacagta ggggcagga cttggtggg ttcaagaact      540 gccatctcag cacctcagcc ccctagtcct gccctgcagt cgctggcact aggcgggggc    600
agaccctggg ccacaagttg ctgccacatg gtcgggataa ttgatgaagg tccatccctc    660
cattgctgtc tccagccctg cctctctgga aactctatat tttcccttta attatagccc    720
ctgcagtctc cctctgctgc cccacccgca ccgctcatcc tggctgccca cggccagccg    780
gccagccgac gtggctccct cccttctgt tccttttttt tccccttgc cttcgttgca       840 caaaccagc tggggaggg cgtggagagg ggcgggggga ggcaatggaa tcttggatgg       900 tttggggag gcgggactcc ccgcttccac gtttgcagct ctggagcacc cggggtgggg     960
agctgcacag gagggagaga aatgaacagg gcactgcaag gagaccccca ggccttctct    1020
cagccctaca gagtttctca ggacgaggta gattgggtt gaggcagagc cttgttgggg    1080
gaatgggaca tggaggaaga aaggacgtgg agttctagag ccatcttcct tagatatagc    1140
ctgctgtcct tcgggtcccc agacccttc agagtgtaca gatgattctc tctggttcct    1200
aaggcataga gcaatgaccg ggattttcaa gaaagagatg aggcagtggg aagtagcccc    1260
taaaacaaag tcaatcatcc tctgcagccc atcccacacc cccaaggaa agtttcaccc    1320 agacacccaa aatatcccat acatccccaa cactgagtcc aggtacaact ggagaagggg    1380
ctttatgcag ctcccagaaa gacaccccct tagctaagtg ccctccctcc acccaggttc    1440
tctctggttt gactgtgctg ggaaggaggg tctctaagca gcccctggcc acagccatgg    1500
caaacaaaac tcttctctaa gtcaccaatg atcacaggcc tcccactaaa aatacttccc    1560
aactctgggg tggaagagtt tgggggatga attttagg gattgcaagc cccaatcccc     1620
acctctgtgt ccctagaatc cccccacccct accttggctg ctccatcacc caaccaccaa    1680
agctttcttc tgcagaggcc acctagtcat gtttctcacc ctgcacctca gcctccccac    1740
tccatctctc aatcatgcct agggtttgga ggaaggcatt tgattctgtt ctggagcaca    1800
gcagaagaat tgacatcctc aaaattaaaa ctcccttgcc tgcaccccctc cctcagatat    1860 ctgattctta atgtctagaa aggaatctgt aaattgttcc ccaaatattc ctaagctcca    1920
tcccctagcc acaccagaag acacccccaa acaggcacat cttttttaatt cccagcttcc    1980 tctgttttgg agaggtcctc agcatgcctc tttatgcccc tcccttagct cttgccagga    2040
tatcagaggg tgactggggc acagccagga ggaccccctc cccaacaccc ccaaccttc      2100 cacctttgga agtctcccca cccagctccc cagttcccca gttccacttc ttctagattg     2160
gaggtcccag gaagagagca gaggggcacc cctacccact ggttagccca cgccattctg    2220
aggacccagc tgcacccccta ccacagcacc tctgggcccag gctgggctgg ggggctgggg   2280
aggcagagct gcgaagaggg gagatgtggg gtggactccc ttccctcctc ctcccccttct    2340 ccattccaac tcccaaattg ggggccgggc caggcagctc tgattggctg gggcacgggc    2400
ggccggctcc ccctctccga ggggcagggt tcctccctgc tctccatcag gacagtataa    2460
aaggggcccg ggccagtcgt cggagcagac gggagtttct cctcggggtc ggagcaggag    2520
gcacgcggag tgtgaggcca cgcataagcg gacgctaacc ccctccccag ccacaaagag    2580
tctacatgtc tagggtctag acatgttcag cttttgtggac ctccggctcc tgctcctctt    2640
agcggccacc gccctcctga cgcacggcca agaggaaggc caagtcgagg gccaagacga    2700
```

-continued

```
agacagtaag tcccaaactt ttgggagtgc aaggatactc tatatcgcgc cttgcgcttg    2760
gtcccggggg ccgcggctta aaacgagacg tggatgatcc ggagactcgg gaatggaagg    2820
gagatgatga gggctcttcc tcggcgccct gagacaggag ggagctcacc ctggggcgag    2880 gttgggggttg aacgcgcccc gggagcggga ggtgagggtg gagcgcggcg tgagttggtg   2940
caagagagaa tcccgagcgc gcaaccgggg aagtggggat ctgggtgcag agtgaggaaa    3000
gcacgtcgaa gatgggatgg gggcgccgag cggggcattt gaagcccaag atgtagaagc    3060
aatcaggaag gccgtgggat gattcataag gaaagattgc cctctctgcg ggctagagtg    3120
ttgctggggc cgtgggggtg ctgggcagcc gcggaggggg tgcggagcgt gggcgggtgg    3180
aggatgagaa actttggcgc ggactcggcg gggcgggtc cttgcgcccc ctgctgaccg     3240
atgctgagca ctgcgtctcc cggtccaacg cttactgggg caggagccgg agcgggaaga    3300
cccgggttat tgctgggtgc ggacccccac ctctagatct ggaaagtaaa gccagggatg    3360
gggcagccca agcctcttaa agaggtagtc gggccggtga ggtcggcccc gccccggccc    3420
cattgcttag cgttgcccga cacctagtgg ccgtctgggg agccgctagc gcggtgggag    3480
tggttagcta acttctggac tatttgcgga ctttttggtt ctttggctaa aagtgacctg    3540
gaggcattgg ctggctttgg gggactgggg atggccccga gagcgggctt ttaagatgtc    3600
taggtgctgg aggttagggt gtctcctaat tttgaggtac atttcaagtc ttgggggggc    3660
gtcccttcca atcagccgct cccattctct tagccccgcc cccgccaccc cacatgccca    3720
gggaatgggg gcgggatgag ggatggacct cccttctctc ctccctcgcc ctcctcctgt    3780
ctctaccacg caagccactc cccacgagcc tgccctcccg atggggcccc tcctattctc    3840
cccccgccct ccccctctca ccctgtggtt ttatttcact tggcttcagc gccaatgggc    3900
tgaggttgga gttggaagcc accgcggact aaagctttgt ttaaattcct gagaactgga    3960
aagagttaca gcctcctgg ccaggcgcct cggcgctgtc accgcgctg atgaggagca     4020 ggcgagcttt taaggatttg aggaaagaag aacgggggga ggggcgggaa gtgaaaaatc    4080
caagtgtgcc tcttagaccc gggggaaagg tggttaagct gggggttgca gtcactactg    4140
acaacgcccc tcttccgcct gtcccagtcc caccaatcac ctgcgtacag aacgcctca    4200 ggtaccatga ccgagacgtg tggaaacccg agccctgccg gatctgcgtc tgcgacaacg    4260
gcaaggtgtt gtgcgatgac gtgatctgtg acgagaccaa gaactgcccc ggcgccgaag    4320
tccccgaggg cgagtgctgt cccgtctgcc ccgacggctc aggtgcgctg cgctcggcct    4380
ggggcctggg gctggggctg ggggtggtcg gcgctcgctg gccctccgtg ctggaggcct    4440
ctgccgacgg gagcagcatt agcaaacctt ggctctaacg ggcgtctctt cgtcccctag    4500
agtcacccac cgaccaagaa accaccgcg tcgaggtaat ctcctgccct cgaattttgc     4560
ccctgcgcgg cccgtgactc ctcacagtcc tcccttctct aacctggcct cttgtttctt    4620
ctcccccaat cccacaggga cccaaggag acactggccc ccgaggccca agggtaagcg     4680
ttgcactctg ggctgtgggg ggctgcaggt gggcatggct ctcggcccca cgctcacccc    4740
ggccccgccc tctcccccctg cagggacccg caggcccccc tggccgagat ggcatccctg   4800
gacagcctgg acttcccgga ccccccgac ccccggacc tccggaccc cctgcctcg       4860 gaggagtaag tggagaggcc ttgtgtgtcc actctcccct gttttgtttt tgtttttttgg   4920 cagatgacat aattttatac tttgaaataa tttcaaactt acagaaaagt tgcaagaatc    4980
ctacaggaaa ctctcacata cccttcacag tttgtgacat gtgctttatt agtctctgtt    5040
```

-continued

```
tatgtatatg tatctttttt tttctgaact gtttgagcaa gttgctaaca tcaggctctt    5100
ttgcgcctaa atacttaggt gtgttttcc taaaaacaag agcattctct taactgacct     5160
acacaatgat taaattcact ctctaatgtg cagtccgtac tcaaagttca ccgatgtccc    5220
gataatgtcc tttatagatt ccaccccca ccacccaat ctgggatcca gtccaggatt      5280
atgtattgca tttaatcatc atgtctctag tttccacaaa tgtagaacgt tcctcagact    5340
ttctttgtct ttagtggcac tgggagtttt gatgagtcca gttgttttgc agactgtccc    5400
tcaatttggg attgtctcat tagattagat gcagggatgc atctttggca ggaatgtctt    5460
aaaagcaatg ttattcttct cagcacatca caccaggaag tgcatgatgt cagtttcttc    5520
catcctcagt gccgtcttct gcctttcaat tcactgtcct cactctgact tctcttgttt    5580
gttctagaac tttgctcccc agctgtctta tggctatgat gagaaatcaa ccggaggaat    5640
ttccgtgcct ggcccccatgg tgagccagca ggggagcat ggatgacaga agagagaatg    5700
ggtatccaga ggatgtgggc atacgcggct ggtatacaca gcttgggagg tccatatcac    5760
cttttgggacc tcagagtcca gaaaggatgc aagacgactg ggtggtccca acaggcatga   5820
atgactacat ccacatgctt tcctacagag ggatcaccat gaccccccctt tcttctccct   5880
ctatagggtc cctctggtcc tcgtggtctc cctggccccc ctggtgcacc tgtgagtatc    5940
caggacgtct tcatatgcct ccttgggctt tggtcttttg gagggaagac tgggatgagg    6000
gcaggagaga tgctcagaga tctcttggta agattggaga aggttgacag ggacttgtct    6060
tctaacccat cttttccctt cttctcaagg gtccccaagg cttccaaggt cccctggtg     6120
agcctggcga gctggagct tcagtaagca ctctctatac agattcatac tccttctaca    6180
aacacacaga ctctcctata gaagaatccc aggcctgggg tcttccttac ctcttccctt   6240
caatcccagc cttccccttc tttttttctt atccatattc taaccacctc ttctatcttt   6300
tctagggtcc catgggtccc cgaggtcccc caggtcccc tggaaagaat ggagatgatg    6360
taagtatccc cagcaagaag ataccatctg accccatggc ctccatgggt tgggtcctgc   6420
aatttccact ccaccacatt tgggaacgat actcagagga aggagggcaa gtcctctctg   6480
atgcacggac tgcccggaa caatgatctt ttcgcttagt gagatgattc catgtcccca    6540
acaaagtgac tgttctcctc accccagcca ccttagagca atccccaacc ccatcccttt   6600
ggggaaattg gtgcgcagat ggtgaaatta aaatgctggt gacagaagta gacagaaatt   6660
cctttagagg cactcagatt tcaccaaacg aaggtttcac tgtagattta aactgagctc   6720
tagattcaaa gataagattc tgggccccca aacctgacct gcaacaatcc aaagaagact   6780
gagaccttct ccacttttcc agcccctagg cggtggtggg gaggcagagg catgatggtc   6840
ttttctctcc ctctcagggg gaagctggaa aacctggtcg tcctggtgag cgtgggcctc   6900
ctgggcctca ggtgagcagg gggctgtggc tgaacctggg cttcactgca cttgggcttc   6960
atttaggagc tgggtccaca gtgatgtgtt ctaatggccc ttccttgtct tcttcatctc   7020
tctccagggt gctcgaggat tgcccggaac agctggcctc cctggaatga agggacacag   7080
agtgagtcac ctttgagtca tttaagctcc ccaagtccct agcatacccc catccagtcc   7140
cagcctcttc cccaaaagat cctgagttgc atcatggtgg gtggcagcta cagaagtccc   7200
aagggacaga gagtggacat ccaaaagcac ctccctccat gggaaagcag tcccgattaa   7260
acgattgggt gagatctaga gccagttggg gtttagtcta gctcagaaac aaagggatgg   7320
cggtgatgac ctcccaaggc tctttctcag atctaggtgg atgtcaaggc tgttccaccc   7380
cctccacagg ttcttacctt ctacctcttt cctgctttag ggtttcagtg gtttggatgg   7440
```

```
tgccaaggga gatgctggtc ctgctggtcc taaggtaaga ggctgtctga acatcatggt   7500
cctccacatc cccagagtcc caccatgaat gaatttctca ctcattattc tctgatctac   7560
agggtgagcc tggcagccct ggtgaaaatg gagctcctgg tcagatggtg agtgtgccca   7620
gttccagagg gcagggatgg ggcaggaggc aggggcaaga tggaggcctg ggggaacaag   7680
gctgtctccc atctcatctg acttctcttg gtttggttgt cagggccccc gtggcctgcc   7740
tggtgagaga ggtcgccctg gagccccctgg ccctgctgta agtactcctg gcccctgggg   7800
ggatccctga gctctggaag gggctccccca ggaactctag ggactggcca gtgctcagtg   7860
gacttaacgg ggcttcccct ctcctgca gggtgctcgt ggaaatgatg gtgctactgg   7920
tgctgccggg cccctgtga gtgtggcctg taggcctcag ggcctgggag tggggagggg   7980
tctcagtgtc tgctcttggg gctgacaatg ggggcaggtt atgttggtct gaaccccagg   8040
acttcctctg tcccagggtg tgacttgcag ctgccatctc ttccttctcg ctgacatctc   8100
catttcattc acagggtccc accggccccg ctggtcctcc tggcttccct ggtgctgttg   8160
gtgctaaggt gagaccccccc actctcctct aagcatgacc ctcatgggcc aagggggttca   8220 tgtctccctt tccccaaac caaagggacc cagagtggca agagagcagc ccgttcacta   8280
acacctttgt cctggggtct ccgtctctga tcttagagtc ctgatcattg ctctcctgtc   8340
cctgtctccc cttcctcctg ccatcccgag aggcaaggtt gggtttccca gggtggcttc   8400
tgatatgtcc tttcttctga ttcagggtga agctggtccc caagggcccc gaggctctga   8460
aggtccccag ggtgtgcgtg gtgagcctgg ccccccctggc cctgctggtg ctgctggccc   8520
tgctgtaagt gtccccgact cagtgtccct ttgccacttt ctaacctcag agtccttgcc   8580
tgttgctgac actcctttct ctgtgccaca gggaaaccct ggtgctgatg acagcctgg   8640 tgctaaaggt gccaatgtaa gtatcctgcc aggcttcagt cccactcctg ccgcctgcag   8700
cctgcctgcc cctttccctc tgctcctagg ctcacgccct ggctgtctgc ctcccacagg   8760
gtgctcctgg tattgctggt gctcctggct tccctggtgc ccgaggcccc tctggaccccс   8820 agggccccgg cggccctcct ggtcccaagg gtaacagcgt gagtaccaaa ctctcccttc   8880
tgcccacccc atgcactggc tccagtgcgg ctctcatctg gggagcagga agacgcaggc   8940
caactgagcg cccccgactc tcagctcatc ctcttctccc cccttgcagg gtgaacctgg   9000
tgctcctggc agcaaaggag acactggtgc taagggagag cctgtaagtc tccccgccat   9060
ccttcttgca gccagcccca ccctgcccta ggagccccct gagggaaatc cagaaaggaa   9120
gaggagcccc tagtcttctg gggagtccct gccacacccc caggaacccc tgacactgga   9180
ggcccagcct cagccggctc tgaggctggc acaggatggc ccctcaccac aggccgcctc   9240
ctcctctcgg ccctctccag ggcctgttg tgttcaagg accccctggc cctgctggag   9300
aggaaggaaa gcgaggagct cgaggtgaac ccggacccac tggcctgccc ggaccccctg   9360
gcgagcgtgt aagtgtccct gcccgccccc tcccgctcca ccctcattgc ctggctggtg   9420
cctgtgtgtc gcggagttca ctggcctcct ctcctccttg cagggtggac ctggtagccg   9480
tggtttccct ggcgcagatg tgttgctgg tcccaaggta acctctcctt gcggccgggg   9540
ggctgaccct gccgctccct gggcatcttc ttcctctttt ggcccgtggc aaagagccac   9600
aaacttgaga ccctaactgt tcctgtgact tccccccaacc agggtcccgc tggtgaacgt   9660
ggttctcctg gccctgctgg ccccaaagga tctcctggtg aagctggtcg tcccggtgaa   9720
gctggtctgc ctggtgccaa ggtgaggccc caggctttca gcctggcttg gccaggccct   9780
```

```
gaccatcccg tgtagggtct gggatgaggc gttctggatc aggcccaagg gtctgccctc      9840
tggagtcctc ccccacctcc atcatgcttc tccccaagtc ccactcatac ctctctgcct      9900
ccctagggtc tgactggaag ccctggcagc cctggtcctg atggcaaaac tggcccccct      9960
gtaagtatca ctcccctga acccctgcc attgtcctgt ctgcctccct gctgtcctca     10020
ctgctgcttt cgtgcctccc atccttaggg tcccgccggt caagatggtc gccccggacc     10080
cccaggccca cctggtgccc gtggtcaggc tggtgtgatg ggattccctg gacctaaagg     10140
tgctgctgtg agtattaagt gaggatccat gaagagccag ggacaaacac acctgaagac     10200
ttgaaggagt cctgggctct gggctcagct gtgccgctga cctgccgtgt ggccactcac     10260
tctcactttc tggacctcag cctccctatc tgtaaaatga aagacttctc ggcggggcac     10320
ggtggctcat gcctgtaatc ccagcacttt gggaggccaa ggcgggcaga ccatgaggtc     10380
aggagtttga ccagtcggg ccaacatag tgaaaccacg tctctactaa aaatacaaaa     10440
gattagctgg gtgtggtggt gtgcacctgt aaccccagct agtcaggagg ctgaggcagg     10500
agaattgcat gaacccggga ggtggaggtt gcagtgagct gagatcacgc cattgcactc     10560
cagcctgggc aacagtgcga gattccatct caaaaaaaaa aaaaaagaa gaaagaaaga     10620 aagaaaaat gaaacacttc tccaggctcc atgaccactg ctctgtcctg gaataagtg     10680 ttgttggtgg ccctccaccc cgacacgtgg ggataggaca ggcctttgat atgataggca     10740
cccccagtct tggtggattc tttgaggtcc aaaaggagat agcagagaag atgaaagccc     10800
tttgcagtgc aggccacagc gggcatctaa cagggaaaag gcagaggagc ctggaagggc     10860
atcttgggag gagtgggctc agaaagggcc cagcaagaag cacctgcagg ggcattcccc     10920
gggggccaaa cagtctttg aaaagaaagt cccttaaaaa gtcccactca gagtaaatga     10980
gaggccccag gaggccctgg cttctcactt cagccccctc aaccctaact ccctttctcc     11040
acagggagag cccggcaagg ctggagagcg aggtgttccc ggacccctg gcgctgtcgt     11100 aagtatctcc tttccatccc tacctccttc ccattgctgc cccggcactt tctcctccct     11160
gcaggagggg tgctagaggc cacggtcctc agctgctcgg ggcctcctaa ccctgagttc     11220
ccctttgctc tctccctgca gggtcctgct ggcaaagatg gagaggctgg agctcaggga     11280 cccctggcc ctgctgtgag tgtccctgat ggggagatct ggggagcaga aaggggaga     11340 cacccctcagc ccctcgtctc ctcggcctcc ccgtgactgt agtgttctct ctgtgcaggg     11400
tcccgctggc gagagaggtg aacaaggccc tgctggctcc cccggattcc aggtgaggcc     11460
tcatggctgt caagatgctg ggaggtaggg gtaggaaaca cctcttttggt ctcttccaga     11520 ttctaaacct tccctcccctt cttccccac ttcccaccta cagggtctcc ctggtcctgc     11580
tggtcctcca ggtgaagcag gcaaacctgg tgaacaggta agagggagca gccgccagga     11640
ggggtgggag atgcagggaa tccagaggga caggcccccg ctcctagcta atcagacagc     11700
catcaactag agggattgag gttagacgcc ggaaagaact tcctcccatg aagggagcag     11760
cacagaggga agtgggggct gcatgattgc tagtctgggt gacttctttt aagagctgct     11820
ggaatatgct gtgactttcc ctcaaccctt ctattgataa atcttggtcc atagtttggg     11880
gaggggggaa gcctttgaca catccctagg aggaagagag gggctgtttg ggataatctc     11940
aattcagtgc tgagaagggg ttcctctcta atcacggcca gaccccagga ggaaggaccg     12000
tgctttccag cagagtggcc ccaggtgggt tttgctcact gtctgttcct ctctccctcc     12060
ccctcagggt gttcctggag accttggcgc cctggccccc tctggagcaa gagtaagtag     12120
gcctctctcg ctgcatccgt caaggtgcgt tgtacttggc cctatctcca gagcagcctt     12180
```

```
cacatgccct gtccttccct tctagggcga gagaggtttc cctggcgagc gtggtgtgca    12240 aggtcccccct ggtcctgctg gtccccgagg ggccaacggt gctcccggca acgatggtgc    12300
taaggtgagg gcagcgtgga aggggctctg gcaagtggcc cagggaccag gtctcacccc    12360
tcctgcagca ggggatggcg ggccatgacc aaagccatgg agatagggtg tggggtgggg    12420
ggaaaagacc acggcagggg cccacacaca gcctggagtc tgggctgtga gtcttttcat    12480
cttttctcaa ggcttgtcgt tggccttgga aacaagcctg ggagatacca agcgggctt    12540 agggctgtga cccactcttg ggccccagg cctcactcca gtcttcttgg ttgtcacata    12600
gggtgatgct ggtgccctg gagctcccgg tagccagggc gccctggcc ttcagggaat    12660 gcctggtgaa cgtggtgcag ctggtcttcc agggcctaag ggtgacagag taagttcaac    12720
cttccccctc ccctgagccc tacatggctc ccatctctgc ctgctttgaa tctctcagca    12780
tctctccttc tctctgggat ctgtccctct tctcgctaat cctcccctct tccccttttcc    12840 cctctggcct ttttgctgat gaatcctctc cctgtggtcc aggcccatct atccccatgg    12900
gttaccatgg tgatgagagg tggggcatc tccttggtgg aggctccctt attcatcccg    12960
ctacacaagt caggggcctc ttaacctcag ttccacctga gtctccagga aggcacccctt    13020 tttcctgaaa gaatctttga gtccttggcc caggtggagg cagggcagag ctgcagaggg    13080
cctctcagga aacccagaca caagcagaac actataggtc acctccttgc cccacactgg    13140
aaatctcaag cttatccatg tctttagggt gatgctggtc ccaaaggtgc tgatggctct    13200
cctggcaaag atggcgtccg tggtctgacc ggccccattg gtcctcctgg ccctgctggt    13260 gccctggtg acaaggtgag gtggccgcct ccccaccttc tgccctaaca catagcctcc    13320
tcagcaggcc tgggcacggt tccgtggggt tgcgttggga gagcaggtcc tgccaaactg    13380
agctgtcaac ctgggaacct ggagggacca gaaggagggg aggctctcct ggggtcatct    13440
actaggagta ttcaggggag gccctgaccc tgagcctctt gtcccttgct tcagggtga    13500 aagtggtccc agcggccctg ctggtcccac tggagctcgt ggtgcccccg taagtacaga    13560
agacctgtta agaccccata cttggcccctt cctcccttc acacagcacc cctggccctg    13620
tctgtgcctt caccccttgc ctctccctc accgcatccc cgccttccct cctgtcagcg    13680
catctctcca atctgactcc ttttcttcta gggagaccgt ggtgagcctg gtcccccgg    13740 ccctgctggc tttgctggcc cccctgtgag taccaagacc cccatcattt ttcatcaccg    13800
actgggacct gggacctcga gggacggaat gaggacaagg cgtcagccat cctcagggga    13860 gaaggggggga gacgggattg tttcccaccc aagcatcttc ctgcctccat tactgctcct    13920
cccccaggta gtggaaactc ctgcctcctt ccctccattc accgccctgc ttcctccccc    13980
agggtgctga cggccaacct ggtgctaaag gcgaacctgg tgatgctggt gctaaaggcg    14040
atgctggtcc ccctggccct gccggacccg ctggaccccc tggcccatt gtgagtggct    14100 tggccctctg tgcccacgag gctggtgggc tgggacccag gacgggtcca ggcttgatgc    14160
ctctgtgctc tcctacaggg taatgttggt gctcctggag ccaaaggtgc tcgcggcagc    14220
gctggtcccc ctgtgagtat caccgccctc tctgttgagc ctctcccctc tccccaggca    14280
gcggtggcag gtgagggcag ctgggtcgga tgagttggct gttctccctc tgactgttcc    14340
tatgttctct ccttccaggg tgctactggt ttccctggtg ctgctggccg agtcggtcct    14400
cctgccccct ctgtaagtct ctgcagcaga gtccactgct ctaggttggg ggtgctgggt    14460
gggggctgcc agaaggatgg tggggctgac tgaggaccca atgatgcacc agagcccct    14520
```

```
ggagtctgac agcccctcct atcctcatcc agggaaatgc tggaccccct ggccctcctg    14580
gtcctgctgg caaagaaggc ggcaaaggtc cccgtggtga gactggccct gctggacgtc    14640
ctggtgaagt tggtccccct ggtcccctg gccctgctgg cgagaaagga tccctggtg     14700
ctgatggtcc tgctgtaagt gccagctcag atctctgcag ctccggaggt gtgcagagct    14760
ggggaggggt ccctgtgctg ctgtctggca cctcaccct gtttgcctcc caagggtgc     14820
tcctggtact cccgggcctc aaggtattgc tggacagcgt ggtgtggtcg gcctgcctgg    14880
tcagagagga gagagaggct ccctggtct tcctggcccc tctgtaagtg cccccctcac    14940
cttgggggc cctgagaaaa accatcacag gacttggagt ggggcggagc caaggagaac     15000
agatttggta gagatgactc cagcggactc aagggtcctc ccagaccta tctctggcct     15060
gactctttct tctcccttag ggtgaacctg caaacaagg tccctctgga gcaagtggtg     15120
aacgtggtcc cctggtccc atgggccccc ctggattggc tggacccct ggtgaatctg      15180
gacgtgaggt gagcagtccc cagcccccat gccagtaccc tcagcatggc cattgtggcc    15240
ttgcctaagc cctcttcccc ggctgactct cacttctctc tctctctctc tgcagggggc    15300
tcctggtgcc gaaggttccc ctggacgaga cggttctcct ggcgccaagg taagatggca    15360
acactccatg accacagcct tgtctgctgc ttccctgccc catcctggcc cttcacccgg    15420
ggctgaccca tattcccctg ctctccccgc cagggtgacc gtggtgagac cggccccgct    15480
ggaccccctg gtgctcctgg tgctcctggt gccctggcc ccgttggccc tgctggcaag    15540
agtggtgatc gtggtgagac tgtaagtagc tgggctccag ttccctgtac ctggtcaggc    15600
cagggactct tcaggcctcc ttagaggcct ggggatgggt gtcggacttc acccaggcag    15660
ggggaggaaa ggagatcctg caagatgtca gggccttaat ccaaaaaact gagttaaagc    15720
tcagccccaa gtccctctc ccagacagga ccgcctctcc catgagttgg ccccagctcc     15780
cgtgaagatt gcagtgggga ggtttccctg ggagttggga gacctcttgc aggagcagag    15840
gctgagcggg agggtcccaa gagcaataaa gaaggggaat gctaggtggg aaacactggt    15900
tctaatggct tctgtggttt gccccgagag ggcttcttca aaggggttgg ttggctttgg    15960
cattcgatct aaataaggcc tgcgactctc aggcaggcag gctctgggag gcctcatcag    16020
cttcttcctc tgccagccac agacaacgcc cctggttgct tgggctgtg tgtcccttgg     16080
tgggaatggc aggcgggccg gggagtgtgt atctgtgtgt gtgtgctg ggcccaggag      16140
gagggtgggg ttcaagcccc tttgatctgc cagcctggtt gggagcagat cactcacctg    16200
gcctcacgct cgctcgtgcc cttcctacct gctgcagctg gcgctggggg cggggtcgga    16260
ggaggctgtt taccttggct cccacggctg gctttgcccc agctgcctcc tcgccacgcc    16320
ctcactctgc cagaaacccc gggcctgaga tcttgggaca gcttcttcag ggtgccaggc    16380
ctcctttccc atctctgaag tgagctgtcc acctggaggc ctgcggaacc tgtgcccagg    16440
aaaaccaggc tccgggcggc tcaccttccc ataccaagaa gagcctgtga ctcccaacag    16500
gtgctcatgc tcgtcatccc cagagcattg catcctggag ctgagcacgt gctgagtgtc    16560
cccccacccct cacccacccc cagccccgga agggccttgt aagcccacac ggcccaggct    16620
ctgccagtgt ggaggtaggg taccatttcc tgtggcccag cacaagggat aatgcaaagt    16680
cacgcactct ttcatgggca ggcagctctc cacccactcc ttgtcatcct caaaaatgtc    16740
ctgtgctgct ggccctgagc acgtgtgcca ctcgctgctg cccacaaagg agccatccgg    16800
aaagaattaa tgat                                                      16814
```

```
<210> SEQ ID NO 7
<211> LENGTH: 368
<212> TYPE: PRT
<213> ORGANISM: Homo sapiens

<400> SEQUENCE: 7

Met Trp Pro Leu Trp Arg Leu Val Ser Leu Ala Leu Ser Gln Ala
1               5                   10                  15

Leu Pro Phe Glu Gln Arg Gly Phe Trp Asp Phe Thr Leu Asp Asp Gly
            20                  25                  30

Pro Phe Met Met Asn Asp Glu Glu Ala Ser Gly Ala Asp Thr Ser Gly
                35                  40                  45

Val Leu Asp Pro Asp Ser Val Thr Pro Thr Tyr Ser Ala Met Cys Pro
50                  55                  60

Phe Gly Cys His Cys His Leu Arg Val Val Gln Cys Ser Asp Leu Gly
65                  70                  75                  80

Leu Lys Ser Val Pro Lys Glu Ile Ser Pro Asp Thr Thr Leu Leu Asp
                85                  90                  95

Leu Gln Asn Asn Asp Ile Ser Glu Leu Arg Lys Asp Asp Phe Lys Gly
            100                 105                 110

Leu Gln His Leu Tyr Ala Leu Val Leu Val Asn Asn Lys Ile Ser Lys
            115                 120                 125

Ile His Glu Lys Ala Phe Ser Pro Leu Arg Lys Leu Gln Lys Leu Tyr
130                 135                 140

Ile Ser Lys Asn His Leu Val Glu Ile Pro Pro Asn Leu Pro Ser Ser
145                 150                 155                 160

Leu Val Glu Leu Arg Ile His Asp Asn Arg Ile Arg Lys Val Pro Lys
                165                 170                 175

Gly Val Phe Ser Gly Leu Arg Asn Met Asn Cys Ile Glu Met Gly Gly
            180                 185                 190

Asn Pro Leu Glu Asn Ser Gly Phe Glu Pro Gly Ala Phe Asp Gly Leu
            195                 200                 205

Lys Leu Asn Tyr Leu Arg Ile Ser Glu Ala Lys Leu Thr Gly Ile Pro
210                 215                 220

Lys Asp Leu Pro Glu Thr Leu Asn Glu Leu His Leu Asp His Asn Lys
225                 230                 235                 240

Ile Gln Ala Ile Glu Leu Glu Asp Leu Leu Arg Tyr Ser Lys Leu Tyr
                245                 250                 255

Arg Leu Gly Leu Gly His Asn Gln Ile Arg Met Ile Glu Asn Gly Ser
            260                 265                 270

Leu Ser Phe Leu Pro Thr Leu Arg Glu Leu His Leu Asp Asn Asn Lys
            275                 280                 285

Leu Ala Arg Val Pro Ser Gly Leu Pro Asp Leu Lys Leu Leu Gln Val
290                 295                 300

Val Tyr Leu His Ser Asn Asn Ile Thr Lys Val Gly Val Asn Asp Phe
305                 310                 315                 320

Cys Pro Met Gly Phe Gly Val Lys Arg Ala Tyr Tyr Asn Gly Ile Ser
                325                 330                 335

Leu Phe Asn Asn Pro Val Pro Tyr Trp Glu Val Gln Pro Ala Thr Phe
            340                 345                 350

Arg Cys Val Thr Asp Arg Leu Ala Ile Gln Phe Gly Asn Tyr Lys Lys
            355                 360                 365

<210> SEQ ID NO 8
<211> LENGTH: 2465
```

```
<212> TYPE: DNA
<213> ORGANISM: Homo sapiens

<400> SEQUENCE: 8
cctttcctcc ctccccgccc tctcccgct  gtccctccc  cgtcggcccg cctgcccagc      60
ctttagcctc cgcccgccg  cctctgtctc cctctctcca caaactgccc aggagtgagt     120
agctgctttc ggtccgccgg acacaccgga cagatagacg tgcggacggc ccaccacccc     180
agcccgccaa ctagtcagcc tgcgcctggc gcctcccctc tccaggtcca tccgccatgt     240
ggcccctgtg gcgcctcgtg tctctgctgg ccctgagcca ggccctgccc tttgagcaga     300
gaggcttctg ggacttcacc ctggacgatg ggccattcat gatgaacgat gaggaagctt     360
cgggcgctga cacctcgggc gtcctggacc cggactctgt cacacccacc tacagcgcca     420
tgtgtccttt cggctgccac tgccacctgc gggtggttca gtgctccgac ctgggtctga     480
agtctgtgcc caaagagatc tcccctgaca ccacgctgct ggacctgcag aacaacgaca     540
tctccgagct ccgcaaggat gacttcaagg gtctccagca cctctacgcc ctcgtcctgg     600
tgaacaacaa gatctccaag atccatgaga aggccttcag cccactgcgg aagctgcaga     660
agctctacat ctccaagaac cacctggtgg agatcccgcc caacctaccc agctccctgg     720
tggagctccg catccacgac aaccgcatcc gcaaggtgcc caagggagtg ttcagcgggc     780
tccggaacat gaactgcatc gagatgggcg ggaacccact ggagaacagt ggctttgaac     840
ctggagcctt cgatggcctg aagctcaact acctgcgcat ctcagaggcc aagctgactg     900
gcatccccaa agacctccct gagaccctga atgaactcca cctagaccac aacaaaatcc     960
aggccatcga actggaggac ctgcttcgct actccaagct gtacaggctg ggcctaggcc    1020
acaaccagat caggatgatc gagaacggga gcctgagctt cctgcccacc ctccgggagc    1080
tccacttgga caacaacaag ttggccaggg tgccctcagg gctcccagac ctcaagctcc    1140
tccaggtggt ctatctgcac tccaacaaca tcaccaaagt gggtgtcaac gacttctgtc    1200
ccatgggctt cggggtgaag cgggcctact acaacggcat cagcctcttc aacaaccccg    1260
tgccctactg ggaggtgcag ccggccactt tccgctgcgt cactgaccgc ctggccatcc    1320
agtttggcaa ctacaaaaag tagaggcagc tgcagccacc gcggggcctc agtgggggtc    1380
tctggggaac acagccagac atcctgatgg ggaggcagag ccaggaagct aagccagggc    1440
ccagctgcgt ccaacccagc cccccacctc gggtccctga cccagctcg  atgcccatc     1500
accgcctctc cctggctccc aagggtgcag gtgggcgcaa ggcccggccc ccatcacatg    1560
ttcccttggc ctcagagctg cccctgctct cccaccacag ccaccagag  gcaccccatg    1620
aagctttttt ctcgttcact cccaaaccca agtgtccaag gctccagtcc taggagaaca    1680
gtccctgggc cagcagccag gaggcggtcc ataagaatgg ggacagtggg ctctgccagg    1740
gctgccgcac ctgtccagac acacatgttc tgttcctcct cctcatgcat ttccagcctt    1800
tcaaccctcc ccgactctgc ggctcccctc agccccttg  caagttcatg gcctgtccct    1860
cccagacccc tgctccactg gcccttcgac cagtcctccc ttctgttctc tctttccccg    1920
tccttcctct ctctctctct ctctctctct ctctctttct gtgtgtgtgt gtgtgtgtgt    1980
gtgtgtgtgt gtgtgtgtgt gtgtcttgtg cttcctcaga cctttctcgc ttctgagctt    2040
ggtggcctgt tccctccatc tctccgaacc tggcttcgcc tgtcccttc  actccacacc    2100
ctctggcctt ctgccttgag ctgggactgc tttctgtctg tccggcctgc acccagcccc    2160
tgcccacaaa accccaggga cagcagtctc cccagcctgc cctgctcagg ccttgccccc    2220
```

```
aaacctgtac tgtcccggag gaggttggga ggtggaggcc cagcatcccg cgcagatgac    2280
accatcaacc gccagagtcc cagacaccgg ttttcctaga agcccctcac ccccactggc    2340
ccactggtgg ctaggtctcc ccttatcctt ctggtccagc gcaaggaggg gctgcttctg    2400
aggtcggtgg ctgtctttcc attaaagaaa caccgtgcaa cgtgaaaaaa aaaaaaaaa     2460 aaaaa                                                                2465
```

<210> SEQ ID NO 9
<211> LENGTH: 245
<212> TYPE: PRT
<213> ORGANISM: Homo sapiens

<400> SEQUENCE: 9

```
Met Asp Val Gly Pro Ser Ser Leu Pro His Leu Gly Leu Lys Leu Leu
1               5                   10                  15

Leu Leu Leu Leu Leu Leu Pro Leu Arg Gly Gln Ala Asn Thr Gly Cys
            20                  25                  30

Tyr Gly Ile Pro Gly Met Pro Gly Leu Pro Gly Ala Pro Gly Lys Asp
        35                  40                  45

Gly Tyr Asp Gly Leu Pro Gly Pro Lys Gly Glu Pro Gly Ile Pro Ala
    50                  55                  60

Ile Pro Gly Ile Arg Gly Pro Lys Gly Gln Lys Gly Glu Pro Gly Leu
65                  70                  75                  80

Pro Gly His Pro Gly Lys Asn Gly Pro Met Gly Pro Pro Gly Met Pro
                85                  90                  95

Gly Val Pro Gly Pro Met Gly Ile Pro Gly Glu Pro Gly Glu Glu Gly
            100                 105                 110

Arg Tyr Lys Gln Lys Phe Gln Ser Val Phe Thr Val Thr Arg Gln Thr
        115                 120                 125

His Gln Pro Pro Ala Pro Asn Ser Leu Ile Arg Phe Asn Ala Val Leu
    130                 135                 140

Thr Asn Pro Gln Gly Asp Tyr Asp Thr Ser Thr Gly Lys Phe Thr Cys
145                 150                 155                 160

Lys Val Pro Gly Leu Tyr Tyr Phe Val Tyr His Ala Ser His Thr Ala
                165                 170                 175

Asn Leu Cys Val Leu Leu Tyr Arg Ser Gly Val Lys Val Val Thr Phe
            180                 185                 190

Cys Gly His Thr Ser Lys Thr Asn Gln Val Asn Ser Gly Gly Val Leu
        195                 200                 205

Leu Arg Leu Gln Val Gly Glu Glu Val Trp Leu Ala Val Asn Asp Tyr
    210                 215                 220

Tyr Asp Met Val Gly Ile Gln Gly Ser Asp Ser Val Phe Ser Gly Phe
225                 230                 235                 240

Leu Leu Phe Pro Asp
                245
```

<210> SEQ ID NO 10
<211> LENGTH: 1147
<212> TYPE: DNA
<213> ORGANISM: Homo sapiens

<400> SEQUENCE: 10

```
ggggaagcag atctgaggac atctctgtgc caggccagaa accgccacc tgcagttcct     60 tctccgggat ggacgtgggg cccagctccc tgccccacct tgggctgaag ctgctgctgc    120
tcctgctgct gctgcccctc aggggccaag ccaacacagg ctgctacggg atcccaggga    180
```

```
tgcccggcct gcctggggca ccagggaagg atgggtacga cggactgccg gggcccaagg    240
gggagccagg aatcccagcc attcccggga tccgaggacc caaagggcag aagggagaac    300
ccggcttacc cggccatcct gggaaaaatg gccccatggg accccctggg atgccagggg    360
tgcccggccc catgggcatc cctggagagc caggtgagga gggcagatac aagcagaaat    420
tccagtcagt gttcacggtc actcggcaga cccaccagcc ccctgcaccc aacagcctga    480
tcagattcaa cgcggtcctc accaacccgc agggagatta tgacacgagc actggcaagt    540
tcacctgcaa agtccccggc ctctactact ttgtctacca cgcgtcgcat acagccaacc    600
tgtgcgtgct gctgtaccgc agcggcgtca aagtggtcac cttctgtggc cacacgtcca    660
aaaccaatca ggtcaactcg gcgcgtgtgc tgctgaggtt gcaggtgggc gaggaggtgt    720
ggctggctgt caatgactac tacgacatgg tgggcatcca gggctctgac agcgtcttct    780
ccggcttcct gctcttcccc gactagggcg ggcagatgcg ctcgagaccc acgggccttc    840
cacctccctc agcttcctgc atggaccac cttactggcc agtctgcatc cttgcctaga    900
ccattctccc ctccagggag cccaccctga cccaccccca ctgcacccc tccccatggg    960 ttctctcctt cctctgaact tctttaggag tcactgcttg tgtggttcct gggacactta   1020
accaatgcct tctggtactg ccattctttt tttttttttt tcaagtattg aaggggtgg    1080 ggagatatat aaataaatca tgaaatcaat acataaaaaa aaaaaaaaaa aaaaaaaaa   1140 aaaaaaa                                                            1147
```

<210> SEQ ID NO 11
<211> LENGTH: 688
<212> TYPE: PRT
<213> ORGANISM: Homo sapiens

<400> SEQUENCE: 11

```
Met Trp Cys Ile Val Leu Phe Ser Leu Leu Ala Trp Val Tyr Ala Glu
1               5                   10                  15

Pro Thr Met Tyr Gly Glu Ile Leu Ser Pro Asn Tyr Pro Gln Ala Tyr
            20                  25                  30

Pro Ser Glu Val Glu Lys Ser Trp Asp Ile Glu Val Pro Glu Gly Tyr
        35                  40                  45

Gly Ile His Leu Tyr Phe Thr His Leu Asp Ile Glu Leu Ser Glu Asn
    50                  55                  60

Cys Ala Tyr Asp Ser Val Gln Ile Ile Ser Gly Asp Thr Glu Glu Gly
65                  70                  75                  80

Arg Leu Cys Gly Gln Arg Ser Ser Asn Asn Pro His Ser Pro Ile Val
                85                  90                  95

Glu Glu Phe Gln Val Pro Tyr Asn Lys Leu Gln Val Ile Phe Lys Ser
            100                 105                 110

Asp Phe Ser Asn Glu Glu Arg Phe Thr Gly Phe Ala Ala Tyr Tyr Val
        115                 120                 125

Ala Thr Asp Ile Asn Glu Cys Thr Asp Phe Val Asp Val Pro Cys Ser
    130                 135                 140

His Phe Cys Asn Asn Phe Ile Gly Gly Tyr Phe Cys Ser Cys Pro Pro
145                 150                 155                 160

Glu Tyr Phe Leu His Asp Asp Met Lys Asn Cys Gly Val Asn Cys Ser
                165                 170                 175

Gly Asp Val Phe Thr Ala Leu Ile Gly Glu Ile Ala Ser Pro Asn Tyr
            180                 185                 190
```

-continued

```
Pro Lys Pro Tyr Pro Glu Asn Ser Arg Cys Glu Tyr Gln Ile Arg Leu
        195                 200                 205

Glu Lys Gly Phe Gln Val Val Thr Leu Arg Arg Glu Asp Phe Asp
210                 215                 220

Val Glu Ala Ala Asp Ser Ala Gly Asn Cys Leu Asp Ser Leu Val Phe
225                 230                 235                 240

Val Ala Gly Asp Arg Gln Phe Gly Pro Tyr Cys Gly His Gly Phe Pro
                245                 250                 255

Gly Pro Leu Asn Ile Glu Thr Lys Ser Asn Ala Leu Asp Ile Ile Phe
                260                 265                 270

Gln Thr Asp Leu Thr Gly Gln Lys Lys Gly Trp Lys Leu Arg Tyr His
            275                 280                 285

Gly Asp Pro Met Pro Cys Pro Lys Glu Asp Thr Pro Asn Ser Val Trp
        290                 295                 300

Glu Pro Ala Lys Ala Lys Tyr Val Phe Arg Asp Val Val Gln Ile Thr
305                 310                 315                 320

Cys Leu Asp Gly Phe Glu Val Val Glu Gly Arg Val Gly Ala Thr Ser
                325                 330                 335

Phe Tyr Ser Thr Cys Gln Ser Asn Gly Lys Trp Ser Asn Ser Lys Leu
                340                 345                 350

Lys Cys Gln Pro Val Asp Cys Gly Ile Pro Glu Ser Ile Glu Asn Gly
            355                 360                 365

Lys Val Glu Asp Pro Glu Ser Thr Leu Phe Gly Ser Val Ile Arg Tyr
        370                 375                 380

Thr Cys Glu Glu Pro Tyr Tyr Tyr Met Glu Asn Gly Gly Gly Glu
385                 390                 395                 400

Tyr His Cys Ala Gly Asn Gly Ser Trp Val Asn Glu Val Leu Gly Pro
                405                 410                 415

Glu Leu Pro Lys Cys Val Pro Val Cys Gly Val Pro Arg Glu Pro Phe
                420                 425                 430

Glu Glu Lys Gln Arg Ile Ile Gly Gly Ser Asp Ala Asp Ile Lys Asn
            435                 440                 445

Phe Pro Trp Gln Val Phe Phe Asp Asn Pro Trp Ala Gly Gly Ala Leu
450                 455                 460

Ile Asn Glu Tyr Trp Val Leu Thr Ala Ala His Val Val Glu Gly Asn
465                 470                 475                 480

Arg Glu Pro Thr Met Tyr Val Gly Ser Thr Ser Val Gln Thr Ser Arg
                485                 490                 495

Leu Ala Lys Ser Lys Met Leu Thr Pro Glu His Val Phe Ile His Pro
            500                 505                 510

Gly Trp Lys Leu Leu Glu Val Pro Glu Gly Arg Thr Asn Phe Asp Asn
        515                 520                 525

Asp Ile Ala Leu Val Arg Leu Lys Asp Pro Val Lys Met Gly Pro Thr
        530                 535                 540

Val Ser Pro Ile Cys Leu Pro Gly Thr Ser Ser Asp Tyr Asn Leu Met
545                 550                 555                 560

Asp Gly Asp Leu Gly Leu Ile Ser Gly Trp Gly Arg Thr Glu Lys Arg
                565                 570                 575

Asp Arg Ala Val Arg Leu Lys Ala Arg Leu Pro Val Ala Pro Leu
                580                 585                 590

Arg Lys Cys Lys Glu Val Lys Val Glu Lys Pro Thr Ala Asp Ala Glu
            595                 600                 605

Ala Tyr Val Phe Thr Pro Asn Met Ile Cys Ala Gly Gly Glu Lys Gly
```

|     |     |     |     |     |     |     |     |     |     |
| --- | --- | --- | --- | --- | --- | --- | --- | --- | --- |
|     | 610 |     |     | 615 |     |     | 620 |     |     |
| Met | Asp | Ser | Cys | Lys | Gly | Asp | Ser | Gly | Gly |
| Ala | Phe | Ala | Val | Gln | Asp |     |     |     |     |
| 625 |     |     |     | 630 |     |     | 635 |     | 640 |
| Pro | Asn | Asp | Lys | Thr | Lys | Phe | Tyr | Ala | Ala |
|     |     |     | 645 |     |     |     | 650 |     |     |
| Gly | Leu | Val | Ser | Trp | Gly |     |     |     |     |
|     |     |     | 655 |     |     |     |     |     |     |
| Pro | Gln | Cys | Gly | Thr | Tyr | Gly | Leu | Tyr | Thr |
|     |     |     | 660 |     |     |     | 665 |     |     |
| Arg | Val | Lys | Asn | Tyr | Val |     |     |     |     |
|     |     |     | 670 |     |     |     |     |     |     |
| Asp | Trp | Ile | Met | Lys | Thr | Met | Gln | Glu | Asn |
|     |     |     | 675 |     |     |     | 680 |     |     |
| Ser | Thr | Pro | Arg | Glu | Asp |     |     |     |     |
|     |     |     | 685 |     |     |     |     |     |     |

<210> SEQ ID NO 12
<211> LENGTH: 2790
<212> TYPE: DNA
<213> ORGANISM: Homo sapiens

<400> SEQUENCE: 12

| | | | | | |
|---|---|---|---|---|---|
| ggacagggag | gctggccgga | ggttcctgca | gagggagcgt | caaggccctg | tgctgctgtc | 60 |
| cctgggggcc | agggggttg | cccagcatgc | ccactggcag | gagagaggga | actgaccccac | 120 |
| ttgctcctac | cagcttctga | aggtgacact | gagccccagg | tgacgccgca | ccaccaaaga | 180 |
| aggtgcttgt | gtttgtcaga | caaatacagc | caggcctgcc | accccttagg | ctccaaagtc | 240 |
| cggaggtgca | gaaagccagg | accaagagac | aggcagctca | ccagggtgga | caaatcgcca | 300 |
| gagatgtggt | gcattgtcct | gttttcactt | ttggcatggg | tttatgctga | gcctaccatg | 360 |
| tatggggaga | tcctgtcccc | taactatcct | caggcatatc | ccagtgaggt | agagaaatct | 420 |
| tgggacatag | aagttcctga | agggtatggg | attcacctct | acttcaccca | tctggacatt | 480 |
| gagctgtcag | agaactgtgc | gtatgactca | gtgcagataa | tctcaggaga | cactgaagaa | 540 |
| gggaggctct | gtggacagag | gagcagtaac | aatcccact | ctccaattgt | ggaagagttc | 600 |
| caagtcccat | acaacaaact | ccaggtgatc | tttaagtcag | acttttccaa | tgaagagcgt | 660 |
| tttacggggt | ttgctgcata | ctatgttgcc | acagacataa | atgaatgcac | agattttgta | 720 |
| gatgtccctt | gtagccactt | ctgcaacaat | ttcattggtg | gttacttctg | ctcctgcccc | 780 |
| ccggaatatt | tcctccatga | tgacatgaag | aattgcggag | ttaattgcag | tggggatgta | 840 |
| ttcactgcac | tgattgggga | gattgcaagt | cccaattatc | ccaaaccata | tccagagaac | 900 |
| tcaaggtgtg | aataccagat | ccggttggag | aaagggttcc | aagtggtggt | gaccttgcgg | 960 |
| agagaagatt | ttgatgtgga | agcagctgac | tcagcgggaa | actgccttga | cagtttagtt | 1020 |
| tttgttgcag | gagatcggca | atttggtcct | tactgtggtc | atggattccc | tgggcctcta | 1080 |
| aatattgaaa | ccaagagtaa | tgctcttgat | atcatcttcc | aaactgatct | aacagggcaa | 1140 |
| aaaaagggct | ggaaacttcg | ctatcatgga | gatccaatgc | cctgccctaa | ggaagacact | 1200 |
| cccaattctg | tttgggagcc | tgcgaaggca | aaatatgtct | ttagagatgt | ggtgcagata | 1260 |
| acctgtctgg | atgggtttga | agttgtggag | ggacgtgttg | gtgcaacatc | tttctattcg | 1320 |
| acttgtcaaa | gcaatggaaa | gtggagtaat | tccaaactga | aatgtcaacc | tgtggactgt | 1380 |
| ggcattcctg | aatccattga | gaatggtaaa | gttgaagacc | cagagagcac | tttgtttggt | 1440 |
| tctgtcatcc | gctacacttg | tgaggagcca | tattactaca | tggaaaatgg | aggaggtggg | 1500 |
| gagtatcact | gtgctggtaa | cgggagctgg | gtgaatgagg | tgctgggccc | ggagctgccg | 1560 |
| aaatgtgttc | cagtctgtgg | agtccccaga | gaaccctttg | aagaaaaaca | gaggataatt | 1620 |
| ggaggatccg | atgcagatat | taaaaacttc | ccctggcaag | tcttctttga | caacccatgg | 1680 |
| gctggtggag | cgctcattaa | tgagtactgg | gtgctgacgg | ctgctcatgt | tgtgggaga | 1740 |

-continued

```
aacagggagc caacaatgta tgttgggtcc acctcagtgc agacctcacg gctggcaaaa    1800
tccaagatgc tcactcctga gcatgtgttt attcatccgg gatggaagct gctggaagtc    1860
ccagaaggac gaaccaattt tgataatgac attgcactgg tgcggctgaa agacccagtg    1920
aaaatgggac ccaccgtctc tcccatctgc ctaccaggca cctcttccga ctacaacctc    1980
atggatgggg acctgggact gatctcaggc tggggccgaa cagagaagag agatcgtgct    2040
gttcgcctca aggcggcaag gttacctgta gctcctttaa gaaaatgcaa agaagtgaaa    2100
gtggagaaac ccacagcaga tgcagaggcc tatgttttca ctcctaacat gatctgtgct    2160
ggaggagaga agggcatgga tagctgtaaa ggggacagtg gtggggcctt gctgtacag     2220 gatcccaatg acaagaccaa attctacgca gctggcctgg tgtcctgggg ccccagtgt     2280 gggacctatg gctctacac acgggtaaag aactatgttg actggataat gaagactatg     2340
caggaaaata gcaccccccg tgaggactaa tccagataca tccaccagc ctctccaagg     2400 gtggtgacca atgcattacc ttctgttcct tatgatattc tcattatttc atcatgactg    2460
aaagaagaca cgagcgaatg atttaaatag aacttgattg ttgagacgcc ttgctagagg    2520
tagagtttga tcatagaatt gtgctggtca tacatttgtg gtctgactcc ttggggtcct    2580
ttccccggag tacctattgt agataacact atgggtgggg cactccttc ttgcactatt     2640 ccacagggat accttaattc tttgtttcct ctttacctgt tcaaaattcc atttacttga    2700
tcattctcag tatccactgt ctatgtacaa taaaggatgt ttataagcaa aaaaaaaaa     2760 aaaaaaaaa aaaaaaaaa aaaaaaaaa                                        2790
```

<210> SEQ ID NO 13
<211> LENGTH: 194
<212> TYPE: PRT
<213> ORGANISM: Homo sapiens

<400> SEQUENCE: 13

```
Ile Gln Lys His Lys Thr Leu Pro Lys Met Ser Gly Gly Trp Glu Leu
 1               5                  10                  15

Glu Leu Asn Gly Thr Glu Ala Lys Leu Val Arg Lys Val Ala Gly Glu
            20                  25                  30

Lys Ile Thr Val Thr Phe Asn Ile Asn Asn Ser Ile Pro Pro Thr Phe
        35                  40                  45

Asp Gly Glu Glu Glu Pro Ser Gln Gly Gln Lys Val Glu Glu Gln Glu
    50                  55                  60

Pro Glu Leu Thr Ser Thr Pro Asn Phe Val Val Glu Val Ile Lys Asn
65                  70                  75                  80

Asp Asp Gly Lys Lys Ala Leu Val Leu Asp Cys His Tyr Pro Glu Asp
                85                  90                  95

Glu Val Gly Gln Glu Asp Glu Ala Glu Ser Asp Ile Phe Ser Ile Arg
            100                 105                 110

Glu Val Ser Phe Gln Ser Thr Gly Glu Ser Glu Trp Lys Asp Thr Asn
        115                 120                 125

Tyr Thr Leu Asn Thr Asp Ser Leu Asp Trp Ala Leu Tyr Asp His Leu
    130                 135                 140

Met Asp Phe Leu Ala Asp Arg Gly Val Asp Asn Thr Phe Ala Asp Glu
145                 150                 155                 160

Leu Val Glu Leu Ser Thr Ala Leu Glu His Gln Glu Tyr Ile Thr Phe
                165                 170                 175

Leu Glu Asp Leu Lys Ser Phe Val Lys Ser Gln Ala His His His His
```

```
            180                 185                 190
His His

<210> SEQ ID NO 14
<211> LENGTH: 1044
<212> TYPE: DNA
<213> ORGANISM: Homo sapiens

<400> SEQUENCE: 14
gcccttcccg cctctgggga agggaacttc cgcttcggac cgagggcagt aggctctcgg      60
ctcctggtcc cactgctgct cagcccagtg gcctcacagg acaccagctt cccaggaggc     120
gtctgacaca gtatgatgat gaagatccca tggggcagca tcccagtact gatgttgctc     180
ctgctcctgg gcctaatcga tatctcccag gcccagctca gctgcaccgg gcccccagcc     240
atccctggca tcccgggtat ccctgggaca cctggccccg atggccaacc tgggacccca     300
gggataaaag gagagaaagg gcttccaggg ctggctggag accatggtga gttcggagag     360
aagggagacc cagggattcc tgggaatcca ggaaaagtcg gccccaaggg ccccatgggc     420
cctaaaggtg gcccagggc ccctggagcc ccaggcccca aggtgaatc gggagactac       480
aaggccaccc agaaaatcgc cttctctgcc acaagaacca tcaacgtccc cctgcgccgg     540
gaccagacca tccgcttcga ccacgtgatc accaacatga acaacaatta tgagccccgc     600
agtggcaagt tcacctgcaa ggtgcccggt ctctactact tcacctacca cgccagctct     660
cgagggaacc tgtgcgtgaa cctcatgcgt ggccgggagc gtgcacagaa ggtggtcacc     720
ttctgtgact atgcctacaa caccttccag gtcaccaccg gtggcatggt cctcaagctg     780
gagcagggg agaacgtctt cctgcaggcc accgacaaga actcactact gggcatggag     840
ggtgccaaca gcatcttttc cgggttcctg ctctttccag atatggaggc ctgacctgtg     900
ggctgcttca catccacccc ggctcccct gccagcaacg ctcactctac ccccaacacc      960
acccccttgcc caaccaatgc acacagtagg gcttggtgaa tgctgctgag tgaatgagta    1020
aataaactct tcaaggccaa ggga                                            1044

<210> SEQ ID NO 15
<211> LENGTH: 266
<212> TYPE: PRT
<213> ORGANISM: Homo sapiens

<400> SEQUENCE: 15

Met Val Cys Leu Lys Leu Pro Gly Gly Ser Ser Leu Ala Ala Leu Thr
1               5                   10                  15

Val Thr Leu Met Val Leu Ser Ser Arg Leu Ala Phe Ala Gly Asp Thr
            20                  25                  30

Arg Pro Arg Phe Leu Glu Leu Arg Lys Ser Glu Cys His Phe Phe Asn
        35                  40                  45

Gly Thr Glu Arg Val Arg Tyr Leu Asp Arg Tyr Phe His Asn Gln Glu
    50                  55                  60

Glu Phe Leu Arg Phe Asp Ser Asp Val Gly Glu Tyr Arg Ala Val Thr
65                  70                  75                  80

Glu Leu Gly Arg Pro Val Ala Glu Ser Trp Asn Ser Gln Lys Asp Leu
                85                  90                  95

Leu Glu Gln Lys Arg Gly Arg Val Asp Asn Tyr Cys Arg His Asn Tyr
            100                 105                 110

Gly Val Gly Glu Ser Phe Thr Val Gln Arg Arg Val His Pro Gln Val
        115                 120                 125
```

```
Thr Val Tyr Pro Ala Lys Thr Gln Pro Leu Gln His His Asn Leu Leu
    130                 135                 140

Val Cys Ser Val Ser Gly Phe Tyr Pro Gly Ser Ile Glu Val Arg Trp
145                 150                 155                 160

Phe Arg Asn Gly Gln Glu Glu Lys Ala Gly Val Val Ser Thr Gly Leu
                165                 170                 175

Ile Gln Asn Gly Asp Trp Thr Phe Gln Thr Leu Val Met Leu Glu Thr
            180                 185                 190

Val Pro Arg Ser Gly Glu Val Tyr Thr Cys Gln Val Glu His Pro Ser
        195                 200                 205

Val Thr Ser Ala Leu Thr Val Glu Trp Arg Ala Arg Ser Glu Ser Ala
    210                 215                 220

Gln Ser Lys Met Leu Ser Gly Val Gly Gly Phe Val Leu Gly Leu Leu
225                 230                 235                 240

Phe Leu Gly Ala Gly Leu Phe Ile Tyr Phe Arg Asn Gln Lys Gly His
                245                 250                 255

Ser Gly Leu Gln Pro Thr Gly Phe Leu Ser
            260                 265

<210> SEQ ID NO 16
<211> LENGTH: 1158
<212> TYPE: DNA
<213> ORGANISM: Homo sapiens

<400> SEQUENCE: 16
gcctgctgct ctggcccctg gtcctgtcct cttctccagc atggtgtgtc tgaagctccc      60
tggaggctcc agcttggcag cgttgacagt gacactgatg gtgctgagct cccgactggc     120
tttcgctggg gacaccccgac cacgtttctt ggagctgcgt aagtctgagt gtcatttctt     180
caatgggacg gagcgggtgc ggtacctgga cagatacttc cataaccagg aggagttcct     240
gcgcttcgac agcgacgtgg gggagtaccg ggcggtgacg gagctggggc ggcctgtcgc     300
cgagtcctgg aacagccaga aggacctcct ggagcagaag cggggccggg tggacaatta     360
ctgcagacac aactacgggg ttggtgagag cttcacagtg cagcggcgag tccatcctca     420
ggtgactgtg tatcctgcaa agacccagcc cctgcagcac acaacctcc tggtctgctc      480
tgtgagtggg ttctatccag gcagcattga agtcaggtgg ttccggaacg gccaggaaga     540
gaaggctggg gtggtgtcca cgggcctgat ccagaatgga gactggacct tccagaccct     600
ggtgatgcta gaaacagttc ctcggagtgg agaggtttac acttgccaag tggagcaccc     660
aagcgtaacg agcgctctca cagtggaatg gagagcacgg tctgaatctg cacagagcaa     720
gatgctgagt ggagtcgggg gctttgtgct gggcctgctc ttccttgggg ccgggctgtt     780
catctacttc aggaatcaga aggacactc tggacttcag ccaacaggat tcctgagctg      840
aagtgcagat gacaatttaa ggaagaatct tctgccccag ctttgcagga tgaaaagctt     900
tcccgcctgg ctgttattct tccacgagag agggctttct caggacctag ttgctactgg     960
ttcagcaact gcagaaaatg tcctcccttg tggcttcctc agttcctgcc cttggcctga    1020
agtcccagca ttgatggcag cgcctcatct tcaactttg tgctccccct tgcctaaacc     1080
ctatggcctc ctgtgcatct gtactcaccc tgtaccacaa acacattaca ttattaaatg    1140
tttctcaaag atggagtt                                                  1158

<210> SEQ ID NO 17
<211> LENGTH: 1172
```

```
<212> TYPE: PRT
<213> ORGANISM: Homo sapiens

<400> SEQUENCE: 17

Pro Pro Ala Pro Ser Pro Glu Pro Pro Ala Arg Ala Ala Met Ala
1               5                   10                  15

Ala Val Arg Gly Ala Pro Leu Leu Ser Cys Leu Leu Ala Leu Ala
                20                  25                  30

Leu Cys Pro Gly Gly Arg Pro Gln Thr Val Leu Thr Asp Asp Glu Ile
            35                  40                  45

Glu Glu Phe Leu Glu Gly Phe Leu Ser Glu Leu Glu Pro Glu Pro Arg
    50                  55                  60

Glu Asp Asp Val Glu Ala Pro Pro Pro Glu Pro Thr Pro Arg Val
65                  70                  75                  80

Arg Lys Ala Gln Ala Gly Gly Lys Pro Gly Lys Arg Pro Gly Thr Ala
                85                  90                  95

Ala Glu Val Pro Pro Glu Lys Thr Lys Asp Lys Gly Lys Lys Gly Lys
                100                 105                 110

Lys Asp Lys Gly Pro Lys Val Pro Lys Glu Ser Leu Glu Gly Ser Pro
            115                 120                 125

Arg Pro Pro Lys Lys Gly Lys Glu Lys Pro Pro Lys Ala Thr Lys Lys
    130                 135                 140

Pro Lys Glu Lys Pro Lys Ala Thr Lys Lys Pro Lys Glu Lys Pro
145                 150                 155                 160

Pro Lys Ala Thr Lys Lys Pro Lys Glu Lys Pro Lys Ala Thr Lys
                165                 170                 175

Lys Pro Pro Ser Gly Lys Arg Pro Pro Ile Leu Ala Pro Ser Glu Thr
                180                 185                 190

Leu Glu Trp Pro Leu Pro Pro Pro Ser Pro Gly Pro Glu Glu Leu
    195                 200                 205

Pro Gln Glu Gly Gly Ala Pro Leu Ser Asn Asn Trp Gln Asn Pro Gly
    210                 215                 220

Glu Glu Thr His Val Glu Ala Arg Glu His Gln Pro Glu Pro Glu Glu
225                 230                 235                 240

Glu Thr Glu Gln Pro Thr Leu Asp Tyr Asn Asp Gln Ile Glu Arg Glu
                245                 250                 255

Asp Tyr Glu Asp Phe Glu Tyr Ile Arg Arg Gln Lys Gln Pro Arg Pro
            260                 265                 270

Pro Pro Ser Arg Arg Arg Arg Pro Glu Arg Val Trp Pro Glu Pro Pro
    275                 280                 285

Glu Glu Lys Ala Pro Ala Pro Ala Pro Glu Glu Arg Ile Glu Pro Pro
    290                 295                 300

Val Lys Pro Leu Leu Pro Leu Pro Pro Asp Tyr Gly Asp Gly Tyr
305                 310                 315                 320

Val Ile Pro Asn Tyr Asp Asp Met Asp Tyr Tyr Phe Gly Pro Pro
                325                 330                 335

Pro Gln Lys Pro Asp Ala Glu Arg Gln Thr Asp Glu Glu Lys Glu Glu
            340                 345                 350

Leu Lys Lys Pro Lys Lys Glu Asp Ser Ser Pro Lys Glu Glu Thr Asp
    355                 360                 365

Lys Trp Ala Val Glu Lys Gly Lys Asp His Lys Glu Pro Arg Lys Gly
    370                 375                 380

Glu Glu Leu Glu Glu Glu Trp Thr Pro Thr Glu Lys Val Lys Cys Pro
385                 390                 395                 400
```

-continued

```
Pro Ile Gly Met Glu Ser His Arg Ile Glu Asp Asn Gln Ile Arg Ala
            405                 410                 415

Ser Ser Met Leu Arg His Gly Leu Gly Ala Gln Arg Gly Arg Leu Asn
        420                 425                 430

Met Gln Thr Gly Ala Thr Glu Asp Asp Tyr Tyr Asp Gly Ala Trp Cys
            435                 440                 445

Ala Glu Asp Asp Ala Arg Thr Gln Trp Ile Glu Val Asp Thr Arg Arg
        450                 455                 460

Thr Thr Arg Phe Thr Gly Val Ile Thr Gln Gly Arg Asp Ser Ser Ile
465                 470                 475                 480

His Asp Asp Phe Val Thr Thr Phe Phe Val Gly Phe Ser Asn Asp Ser
            485                 490                 495

Gln Thr Trp Val Met Tyr Thr Asn Gly Tyr Glu Glu Met Thr Phe His
        500                 505                 510

Gly Asn Val Asp Lys Asp Thr Pro Val Leu Ser Glu Leu Pro Glu Pro
            515                 520                 525

Val Val Ala Arg Phe Ile Arg Ile Tyr Pro Leu Thr Trp Asn Gly Ser
        530                 535                 540

Leu Cys Met Arg Leu Glu Val Leu Gly Cys Ser Val Ala Pro Val Tyr
545                 550                 555                 560

Ser Tyr Tyr Ala Gln Asn Glu Val Val Ala Thr Asp Asp Leu Asp Phe
            565                 570                 575

Arg His His Ser Tyr Lys Asp Met Arg Gln Leu Met Lys Val Val Asn
        580                 585                 590

Glu Glu Cys Pro Thr Ile Thr Arg Thr Tyr Ser Leu Gly Lys Ser Ser
            595                 600                 605

Arg Gly Leu Lys Ile Tyr Ala Met Glu Ile Ser Asp Asn Pro Gly Glu
        610                 615                 620

His Glu Leu Gly Glu Pro Glu Phe Arg Tyr Thr Ala Gly Ile His Gly
625                 630                 635                 640

Asn Glu Val Leu Gly Arg Glu Leu Leu Leu Leu Met Gln Tyr Leu
            645                 650                 655

Cys Arg Glu Tyr Arg Asp Gly Asn Pro Arg Val Arg Ser Leu Val Gln
        660                 665                 670

Asp Thr Arg Ile His Leu Val Pro Ser Leu Asn Pro Asp Gly Tyr Glu
        675                 680                 685

Val Ala Ala Gln Met Gly Ser Glu Phe Gly Asn Trp Ala Leu Gly Leu
        690                 695                 700

Trp Thr Glu Glu Gly Phe Asp Ile Phe Glu Asp Phe Pro Asp Leu Asn
705                 710                 715                 720

Ser Val Leu Trp Gly Ala Glu Glu Arg Lys Trp Val Pro Tyr Arg Val
            725                 730                 735

Pro Asn Asn Asn Leu Pro Ile Pro Glu Arg Tyr Leu Ser Pro Asp Ala
            740                 745                 750

Thr Val Ser Thr Glu Val Arg Ala Ile Ile Ala Trp Met Glu Lys Asn
        755                 760                 765

Pro Phe Val Leu Gly Ala Asn Leu Asn Gly Gly Glu Arg Leu Val Ser
        770                 775                 780

Tyr Pro Tyr Asp Met Ala Arg Thr Pro Thr Gln Glu Gln Leu Leu Ala
785                 790                 795                 800

Ala Ala Met Ala Ala Ala Arg Gly Glu Asp Glu Asp Glu Val Ser Glu
            805                 810                 815
```

```
Ala Gln Glu Thr Pro Asp His Ala Ile Phe Arg Trp Leu Ala Ile Ser
                820                 825                 830

Phe Ala Ser Ala His Leu Thr Leu Thr Glu Pro Tyr Arg Gly Gly Cys
        835                 840                 845

Gln Ala Gln Asp Tyr Thr Gly Gly Met Gly Ile Val Asn Gly Ala Lys
    850                 855                 860

Trp Asn Pro Arg Thr Gly Thr Ile Asn Asp Phe Ser Tyr Leu His Thr
865                 870                 875                 880

Asn Cys Leu Glu Leu Ser Phe Tyr Leu Gly Cys Asp Lys Phe Pro His
                885                 890                 895

Glu Ser Glu Leu Pro Arg Glu Trp Glu Asn Asn Lys Glu Ala Leu Leu
            900                 905                 910

Thr Phe Met Glu Gln Val His Arg Gly Ile Lys Gly Val Val Thr Asp
        915                 920                 925

Glu Gln Gly Ile Pro Ile Ala Asn Ala Thr Ile Ser Val Ser Gly Ile
    930                 935                 940

Asn His Gly Val Lys Thr Ala Ser Gly Gly Asp Tyr Trp Arg Ile Leu
945                 950                 955                 960

Asn Pro Gly Glu Tyr Arg Val Thr Ala His Ala Glu Gly Tyr Thr Pro
                965                 970                 975

Ser Ala Lys Thr Cys Asn Val Asp Tyr Asp Ile Gly Ala Thr Gln Cys
            980                 985                 990

Asn Phe Ile Leu Ala Arg Ser Asn  Trp Lys Arg Ile Arg  Glu Ile Met
        995                 1000                1005

Ala Met Asn Gly Asn Arg Pro  Ile Pro His Ile Asp  Pro Ser Arg
        1010                1015                1020

Pro Met Thr Pro Gln Gln Arg  Arg Leu Gln Gln Arg  Arg Leu Gln
        1025                1030                1035

His Arg Leu Arg Leu Arg Ala  Gln Met Arg Leu Arg  Arg Leu Asn
        1040                1045                1050

Ala Thr Thr Thr Leu Gly Pro  His Thr Val Pro Pro  Thr Leu Pro
        1055                1060                1065

Pro Ala Pro Ala Thr Thr Leu  Ser Thr Thr Ile Glu  Pro Trp Gly
        1070                1075                1080

Leu Ile Pro Pro Thr Thr Ala  Gly Trp Gly Glu Ser  Glu Thr Glu
        1085                1090                1095

Thr Tyr Thr Glu Val Val Thr  Glu Phe Gly Thr Glu  Val Glu Pro
        1100                1105                1110

Glu Phe Gly Thr Lys Val Glu  Pro Glu Phe Glu Thr  Gln Leu Glu
        1115                1120                1125

Pro Glu Phe Glu Thr Gln Leu  Glu Pro Glu Phe Glu  Glu Glu Glu
        1130                1135                1140

Glu Glu Glu Glu Glu Glu Glu  Ile Ala Thr Gly Gln  Ala Phe Pro
        1145                1150                1155

Phe Thr Thr Val Glu Thr Tyr  Thr Val Asn Phe Gly  Asp Phe
        1160                1165                1170

<210> SEQ ID NO 18
<211> LENGTH: 4038
<212> TYPE: DNA
<213> ORGANISM: Homo sapiens

<400> SEQUENCE: 18
agccgccagg  acctcggagc  gccccgacca  cccctgagcc  cctctggctt  cggagccccc    60
```

-continued

```
cagcacccct tcccgggtcc cctcgcccac cctaatccac tctccctccc tttcccggat   120
tccctcgctc accccatcct ctctcccgcc ccttcctgga ttccctcacc cgtctcgatc   180
ccctctccgc cctttgccag agacccagag ccctgaccc cccgcgccct ccccggagcc    240
ccccgcgcgt gccgcggcca tggcggccgt gcgcggggcg ccctgctca gctgcctcct    300 ggcgttgctg gccctgtgcc ctggagggcg cccgcagacg gtgctgaccg acgacgagat   360
cgaggagttc ctcgagggct tcctgtcaga gctagaacct gagccccggg aggacgacgt   420
ggaggccccg ccgcctcccg agcccacccc gcgggtccga aaagcccagg cgggggggcaa  480 gccaggaag cggccaggga cggccgcaga agtgcctccg gaaagaccaa agacaaagg     540 gaagaaaggc aagaaagaca aaggccccaa ggtgcccaag gagtccttgg aggggtcccc   600
caggccgccc aagaagggga aggagaagcc acccaaggcc accaagaagc ccaaggagaa   660
gccacctaag gccaccaaga agcccaagga gaagccaccc aaggccacca agaagcccaa   720
agagaagcca cccaaggcca ccaagaagcc ccgtcaggg aagaggcccc ccattctggc    780
tccctcagaa accctggagt ggccactgcc cccaccccc agccctggcc ccgaggagct    840
accccaggag ggaggggcgc ccctctcaaa taactggcag aatccaggag aggagaccca   900
tgtggaggca cgggagcacc agcctgagcc ggaggaggag accgagcaac ccacactgga   960
ctacaatgac cagatcgaga gggaggacta tgaggacttt gagtacattc ggcgccagaa  1020
gcaacccagg ccaccccaa gcagaaggag gaggcccgag cgggtctggc cagagccccc  1080
tgaggagaag gccccggccc cagccccgga ggagaggatt gagcctcctg tgaagcctct  1140
gctgcccccg ctgcccccctg actatggtga tggttacgtg atccccaact acgatgacat  1200
ggactattac tttgggcctc ctccgcccca gaagcccgat gctgagcgcc agacggacga  1260
agagaaggag gagctgaaga aacccaaaaa ggaggacagc agcccaagg aggagaccga   1320 caagtgggca gtggagaagg gcaaggacca caaagagccc cgaaagggcg aggagttgga   1380
ggaggagtgg acgcctacgg agaaagtcaa gtgtcccccc attgggatgg agtcacaccg   1440
tattgaggac aaccagatcc gagcctcctc catgctgcgc cacggcctgg ggcacagcg    1500 cggccggctc aacatgcaga ccggtgccac tgaggacgac tactatgatg gtgcgtggtg   1560
tgccgaggac gatgccagga cccagtggat agaggtggac accaggagga ctacccggtt   1620
cacaggcgtc atcacccagg gcagagactc cagcatccat gacgattttg tgaccacctt   1680
cttcgtgggc ttcagcaatg acagccagac atgggtgatg tacaccaacg gctatgagga   1740
aatgaccttt catgggaacg tggacaagga cacacccgtg ctgagtgagc tcccagagcc   1800
ggtggtggct cgtttcatcc gcatctaccc actcacctgg aatggcagcc tgtgcatgcg   1860
cctggaggtg ctggggtgct ctgtggcccc tgtctacagc tactacgcac agaatgaggt   1920
ggtggccacc gatgacctgg atttccggca ccacagctac aaggacatgc gccagctcat   1980
gaaggtggtg aacagggagt gccccaccat caccgcact tacagcctgg caagagctc     2040 acgaggcctc aagatctatg ccatggagat ctcagacaac cctggggagc atgaactggg   2100
ggagcccgag ttccgctaca ctgctgggat ccatggcaac gaggtgctgg ccgagagct    2160 gttgctgctg ctcatgcagt acctgtgccg agagtaccgc gatgggaacc acgtgtgcg    2220 cagcctggtg caggacacac gcatccacct ggtgccctca ctgaaccctg atggctacga   2280
ggtggcagcg cagatgggct cagagttttg gaactgggcg ctgggactgt ggactgagga   2340
gggctttgac atctttgaag atttcccgga tctcaactct gtgctctggg agctgaggga   2400
gaggaaatgg gtcccctacc gggtccccaa caataacttg cccatccctg aacgctacct   2460
```

```
ttcgccagat gccacggtat ccacggaggt ccgggccatc attgcctgga tggagaagaa    2520
cccttcgtg  ctgggagcaa atctgaacgg cggcgagcgg ctagtatcct accctacga    2580
tatggcccgc acgcctaccc aggagcagct gctggccgca gccatggcag cagcccgggg    2640
ggaggatgag gacgaggtct ccgaggccca ggagactcca gaccacgcca tcttccggtg    2700
gcttgccatc tccttcgcct ccgcacacct caccttgacc gagccctacc gcggaggctg    2760
ccaagcccag gactacaccg gcggcatggg catcgtcaac ggggccaagt ggaaccccg    2820
gaccgggact atcaatgact tcagttacct gcataccaac tgcctggagc tctccttcta    2880
cctgggctgt gacaagttcc ctcatgagag tgagctgccc cgcgagtggg agaacaacaa    2940
ggaggcgctg ctcaccttca tggagcaggt gcaccgcggc attaaggggg tggtgacgga    3000
cgagcaaggc atcccattg  ccaacgccac catctctgtg agtggcatta atcacggcgt    3060
gaagacagcc agtggtggtg attactggcg aatcttgaac ccgggtgagt accgcgtgac    3120
agcccacgcg gagggctaca ccccgagcgc caagacctgc aatgttgact atgacatcgg    3180
ggccactcag tgcaacttca tcctggctcg ctccaactgg aagcgcatcc gggagatcat    3240
ggccatgaac gggaaccggc ctatcccaca catagaccca tcgcgcccta tgaccccca    3300
acagcgacgc ctgcagcagc gacgcctaca acaccgcctg cggcttcggg cacagatgcg    3360
gctgcggcgc ctcaacgcca ccaccaccct aggcccccac actgtgcctc ccacgctgcc    3420
ccctgcccct gccaccaccc tgagcactac catagagccc tggggcctca taccgccaac    3480
caccgctggc tggggggagt cggagactga gacctacaca gaggtggtga cagagtttgg    3540
gaccgaggtg gagcccgagt ttgggaccaa ggtggagccc gagtttgaga cccagttgga    3600
gcctgagttt gagacccagc tggaacccga gtttgaggaa gaggaggagg aggaggaaga    3660
ggaggagata gccactggcc aggcattccc cttcacaaca gtagagacct acacagtgaa    3720
cttttgggac ttctgagatc agcgtcctac caagacccca gcccaactca agctacagca    3780
gcagcacttc ccaagcctgc tgaccacagt cacatcaccc atcagcacat ggaaggcccc    3840
tggtatggac actgaaagga agggctggtc ctgcccctt  gagggggtgc aaacatgact    3900
gggacctaag agccagaggc tgtgtagagg ctcctgctcc acctgccagt ctcgtaagag    3960
atggggttgc tgcagtgttg gagtaggggc agagggaggg agccaaggtc actccaataa    4020
aacaagctca tggcacgg                                                  4038
```

<210> SEQ ID NO 19
<211> LENGTH: 368
<212> TYPE: PRT
<213> ORGANISM: Homo sapiens

<400> SEQUENCE: 19

Met Arg Val Ala Gly Arg Glu Gly Arg Phe Leu Ser Ala Gly Val Ala
1               5                   10                  15

Ala Arg Glu Gly Ser Ala Met Phe Leu Ser Ile Leu Val Ala Leu Cys
            20                  25                  30

Leu Trp Leu His Leu Ala Leu Gly Val Arg Gly Ala Pro Cys Glu Ala
        35                  40                  45

Val Arg Ile Pro Met Cys Arg His Met Pro Trp Asn Ile Thr Arg Met
    50                  55                  60

Pro Asn His Leu His His Ser Thr Gln Glu Asn Ala Ile Leu Ala Ile
65                  70                  75                  80

Glu Gln Tyr Glu Glu Leu Val Asp Val Asn Cys Ser Ala Val Leu Arg 85                  90                  95
Phe Phe Leu Cys Ala Met Tyr Ala Pro Ile Cys Thr Leu Glu Phe Leu
            100                 105                 110

His Asp Pro Ile Lys Pro Cys Lys Ser Val Cys Gln Arg Ala Arg Asp
        115                 120                 125

Asp Cys Glu Pro Leu Met Lys Met Tyr Asn His Ser Trp Pro Glu Ser
    130                 135                 140

Leu Ala Cys Asp Glu Leu Pro Val Tyr Asp Arg Gly Val Cys Ile Ser
145                 150                 155                 160

Pro Glu Ala Ile Val Thr Asp Leu Pro Glu Asp Val Lys Trp Ile Asp
                165                 170                 175

Ile Thr Pro Asp Met Met Val Gln Glu Arg Pro Leu Asp Val Asp Cys
            180                 185                 190

Lys Arg Leu Ser Pro Asp Arg Cys Lys Cys Lys Val Lys Pro Thr
        195                 200                 205

Leu Ala Thr Tyr Leu Ser Lys Asn Tyr Ser Tyr Val Ile His Ala Lys
    210                 215                 220

Ile Lys Ala Val Gln Arg Ser Gly Cys Asn Glu Val Thr Thr Val Val
225                 230                 235                 240

Asp Val Lys Glu Ile Phe Lys Ser Ser Pro Ile Pro Arg Thr Gln
                245                 250                 255

Val Pro Leu Ile Thr Asn Ser Ser Cys Gln Cys Pro His Ile Leu Pro
            260                 265                 270

His Gln Asp Val Leu Ile Met Cys Tyr Glu Trp Arg Ser Arg Met Met
        275                 280                 285

Leu Leu Glu Asn Cys Leu Val Glu Lys Trp Arg Asp Gln Leu Ser Lys
    290                 295                 300

Arg Ser Ile Gln Trp Glu Glu Arg Leu Gln Glu Gln Arg Thr Val
305                 310                 315                 320

Gln Asp Lys Lys Lys Thr Ala Gly Arg Thr Ser Arg Ser Asn Pro Pro
                325                 330                 335

Lys Pro Lys Gly Lys Thr Pro Ala Pro Lys Pro Ala Ser Pro Lys Lys
            340                 345                 350

Asn Ile Lys Thr Arg Ser Ala Gln Lys Arg Thr Asn Pro Lys Arg Val
        355                 360                 365

<210> SEQ ID NO 20
<211> LENGTH: 2974
<212> TYPE: DNA
<213> ORGANISM: Homo sapiens

<400> SEQUENCE: 20
gcggccgagg gggagcccgc gccgcggctg cagctgccaa gggagcgttc cgagcccacg    60 tcagggagg tgtcgggata aatagggtcc cgcaatggcc gtggctggct gcgctccgag   120
ctgcggagtc cgggactgga gctgcccggg cgggttcgcg ccccgaaggc tgagagctgg   180
cgctgctcgt gccctgtgtg ccagacggcg gagctccgcg gccggacccc gcggccccgc   240
tttgctgccg actggagttt gggggaagaa actctcctgc gccccagagg atttcttcct   300
cggcgaaggg acagcgaaag atgagggtgg caggaagaga agggcgcttt ctgtctgccg   360
gggtcgcagc gcgagagggc agtgccatgt tcctctccat cctagtggcg ctgtgcctgt   420
ggctgcacct ggcgctgggc gtgcgcgcg cgccctgcga ggcggtgcgc atccctatgt   480
gccggcacat gcccctggaa catcacgcgga tgcccaacca cctgcaccac agcacgcagg   540

```
agaacgccat cctggccatc gagcagtacg aggagctggt ggacgtgaac tgcagcgccg    600
tgctgcgctt cttcctctgt gccatgtacg cgcccatttg caccctggag ttcctgcacg    660
accctatcaa gccgtgcaag tcggtgtgcc aacgcgcgcg cgacgactgc gagcccctca    720
tgaagatgta caaccacagc tggcccgaaa gcctggcctg cgacgagctg cctgtctatg    780
accgtggcgt gtgcatctcg cctgaagcca tcgtcacgga cctcccggag gatgttaagt    840
ggatagacat cacaccagac atgatggtac aggaaaggcc tcttgatgtt gactgtaaac    900
gcctaagccc cgatcggtgc aagtgtaaaa aggtgaagcc aactttggca acgtatctca    960
gcaaaaacta cagctatgtt attcatgcca aataaaagc tgtgcagagg agtggctgca    1020
atgaggtcac aacggtggtg gatgtaaaag agatcttcaa gtcctcatca cccatccctc    1080
gaactcaagt cccgctcatt acaaattctt cttgccagtg tccacacatc ctgccccatc    1140
aagatgttct catcatgtgt tacgagtggc gctcaaggat gatgcttctt gaaaattgct    1200
tagttgaaaa atggagagat cagcttagta aagatccat acagtgggaa gagaggctgc    1260
aggaacagcg gagaacagtt caggacaaga agaaaacagc cgggcgcacc agtcgtagta    1320 atcccccaa accaagggga agcctcctg ctcccaaacc agccagtccc aagaagaaca    1380
ttaaaactag gagtgcccag aagagaacaa acccgaaaag agtgtgagct aactagtttc    1440
caaagcggag acttccgact tccttacagg atgaggctgg gcattgcctg ggacagccta    1500
tgtaaggcca tgtgcccctt gccctaacaa ctcactgcag tgctcttcat agacacatct    1560
tgcagcattt ttcttaaggc tatgcttcag ttttcttg taagccatca caagccatag    1620
tggtaggttt gcccttggt acagaaggtg agttaaagct ggtggaaaag cttattgca    1680 ttgcattcag agtaacctgt gtgcatactc tagaagagta gggaaaataa tgcttgttac    1740
aattcgacct aatatgtgca ttgtaaaata atgccatat ttcaaacaaa acacgtaatt    1800 ttttacagt atgtttttatt accttttgat atctgttgtt gcaatgttag tgatgtttta    1860
aaatgtgatc gaaatataa tgcttctaag aaggaacagt agtggaatga atgtctaaaa    1920
gatctttatg tgtttatggt ctgcagaagg atttttgtga tgaaggggga tttttgaaa    1980 aatctagaga agtagcatat ggaaaactat aatgtgtctt ttttacaatg acttcagctc    2040
tgtttttagc tagaaactct aaaaacaaaa ataataataa agaaaaataa ataaaagga    2100 gaggcagaca atgtctggat tcctgttttt tggttacctg atttcatgat catgatgctt    2160
cttgtcaaca ccctcttaag cagcaccaga acagtgagt ttgtctgtac cattaggagt    2220
taggtactaa ttagttggct aatgctcaag tattttatac ccacaagaga ggtatgtcac    2280
tcatcttact tcccaggaca tccaccctga gaataatttg acaagcttaa aaatggcctt    2340
catgtgagtg ccaaattttg ttttcttcat ttaaatattt tctttgccta atacatgtg    2400 agaggagtta aatataaatg tacagagagg aaagttgagg ttccacctct gaaatgagaa    2460
ttacttgaca gttgggatac tttaatcaga aaaaagaac ttatcttgca gcatttatc    2520 aacaaatttc ataattgtgg acaattggag gcatttattt taaaaacaa ttttattggc    2580 cttttgctaa cacagtaagc atgtattctc tataaggcat tcaataaatg cacaacgccc    2640
aaaggaaata aaatcctatc taatcctact ctccactaca cagaggtaat cactattagt    2700
attttggcat attattctcc aggtgtttct tatgcactta taaaatgatt tgaacaaata    2760
aaactaggaa cctgctatac atgtgtttca taacctgcct cctttgcttg gccctttatt    2820
gagataagtt ttcctgtcaa gaaagcagaa accatctcat ttctaacagc tgtgttatat    2880
tccatagtat gcattactca acaaactgtt gtgctattgg atacttaggt ggtttcttca    2940
```
ctgacaatac tgaataaaca tctcaatagt caaa 2974

<210> SEQ ID NO 21
<211> LENGTH: 448
<212> TYPE: PRT
<213> ORGANISM: Homo sapiens

<400> SEQUENCE: 21

Met Pro Gly Ile Lys Arg Ile Leu Thr Val Thr Ile Leu Ala Leu Cys
1               5                   10                  15

Leu Pro Ser Pro Gly Asn Ala Gln Ala Gln Cys Thr Asn Gly Phe Asp
                20                  25                  30

Leu Asp Arg Gln Ser Gly Gln Cys Leu Asp Ile Asp Glu Cys Arg Thr
            35                  40                  45

Ile Pro Glu Ala Cys Arg Gly Asp Met Met Cys Val Asn Gln Asn Gly
        50                  55                  60

Gly Tyr Leu Cys Ile Pro Arg Thr Asn Pro Val Tyr Arg Gly Pro Tyr
65                  70                  75                  80

Ser Asn Pro Tyr Ser Thr Pro Tyr Ser Gly Pro Tyr Pro Ala Ala Ala
                85                  90                  95

Pro Pro Leu Ser Ala Pro Asn Tyr Pro Thr Ile Ser Arg Pro Leu Ile
                100                 105                 110

Cys Arg Phe Gly Tyr Gln Met Asp Glu Ser Asn Gln Cys Val Asp Val
            115                 120                 125

Asp Glu Cys Ala Thr Asp Ser His Gln Cys Asn Pro Thr Gln Ile Cys
        130                 135                 140

Ile Asn Thr Glu Gly Gly Tyr Thr Cys Ser Cys Thr Asp Gly Tyr Trp
145                 150                 155                 160

Leu Leu Glu Gly Gln Cys Leu Asp Ile Asp Glu Cys Arg Tyr Gly Tyr
                165                 170                 175

Cys Gln Gln Leu Cys Ala Asn Val Pro Gly Ser Tyr Ser Cys Thr Cys
            180                 185                 190

Asn Pro Gly Phe Thr Leu Asn Glu Asp Gly Arg Ser Cys Gln Asp Val
        195                 200                 205

Asn Glu Cys Ala Thr Glu Asn Pro Cys Val Gln Thr Cys Val Asn Thr
    210                 215                 220

Tyr Gly Ser Phe Ile Cys Arg Cys Asp Pro Gly Tyr Glu Leu Glu Glu
225                 230                 235                 240

Asp Gly Val His Cys Ser Asp Met Asp Glu Cys Ser Phe Ser Glu Phe
                245                 250                 255

Leu Cys Gln His Glu Cys Val Asn Gln Pro Gly Thr Tyr Phe Cys Ser
            260                 265                 270

Cys Pro Pro Gly Tyr Ile Leu Leu Asp Asp Asn Arg Ser Cys Gln Asp
        275                 280                 285

Ile Asn Glu Cys Glu His Arg Asn His Thr Cys Asn Leu Gln Gln Thr
    290                 295                 300

Cys Tyr Asn Leu Gln Gly Gly Phe Lys Cys Ile Asp Pro Ile Arg Cys
305                 310                 315                 320

Glu Glu Pro Tyr Leu Arg Ile Ser Asp Asn Arg Cys Met Cys Pro Ala
                325                 330                 335

Glu Asn Pro Gly Cys Arg Asp Gln Pro Phe Thr Ile Leu Tyr Arg Asp
            340                 345                 350

Met Asp Val Val Ser Gly Arg Ser Val Pro Ala Asp Ile Phe Gln Met
        355                 360                 365

```
Gln Ala Thr Thr Arg Tyr Pro Gly Ala Tyr Tyr Ile Phe Gln Ile Lys
        370                 375                 380

Ser Gly Asn Glu Gly Arg Glu Phe Tyr Met Arg Gln Thr Gly Pro Ile
385                 390                 395                 400

Ser Ala Thr Leu Val Met Thr Arg Pro Ile Lys Gly Pro Arg Glu Ile
                405                 410                 415

Gln Leu Asp Leu Glu Met Ile Thr Val Asn Thr Val Ile Asn Phe Arg
                420                 425                 430

Gly Ser Ser Val Ile Arg Leu Arg Ile Tyr Val Ser Gln Tyr Pro Phe
            435                 440                 445

<210> SEQ ID NO 22
<211> LENGTH: 2367
<212> TYPE: DNA
<213> ORGANISM: Homo sapiens

<400> SEQUENCE: 22
```

| | | | | |
|---|---|---|---|---|
| gcagtggctg ggaggacccc ggcgctctcc ccgtgtcctc tccacgactc gctcggcccc | 60 |
| tctggaataa aacacccgcg agccccgagg gcccagagga ggccgacgtg cccgagctcc | 120 |
| tccggggggtc ccgcccgcga gctttcttct cgccttcgca tctcctcctc gcgcgtcttg | 180 |
| gacatgccag gaataaaaag gatactcact gttaccattc tggctctctg tcttccaagc | 240 |
| cctgggaatg cacaggcaca gtgcacgaat ggctttgacc tggatcgcca gtcaggacag | 300 |
| tgtttagata ttgatgaatg ccgaaccatc cccgaggcct gccgaggaga catgatgtgt | 360 |
| gttaaccaaa atggcgggta tttatgcatt ccccggacaa accctgtgta tcgagggccc | 420 |
| tactcgaacc cctactcgac cccctactca ggtccgtacc cagcagctgc cccaccactc | 480 |
| tcagctccaa actatcccac gatctccagg cctcttatat gccgctttgg ataccagatg | 540 |
| gatgaaagca ccaatgtgt ggatgtggac gagtgtgcaa cagattccca ccagtgcaac | 600 |
| cccacccaga tctgcatcaa tactgaaggc gggtacacct gctcctgcac cgacggatat | 660 |
| tggcttctgg aaggccagtg cttagacatt gatgaatgtc gctatggtta ctgccagcag | 720 |
| ctctgtgcga atgttcctgg atcctattct tgtacatgca accctggttt tacccctcaat | 780 |
| gaggatggaa ggtcttgcca agatgtgaac gagtgtgcca ccgagaaccc ctgcgtgcaa | 840 |
| acctgcgtca acacctacgg ctctttcatc tgccgctgtg acccaggata tgaacttgag | 900 |
| gaagatggcg ttcattgcag tgatatggac gagtgcagct ctctgagtt cctctgccaa | 960 |
| catgagtgtg tgaaccagcc cggcacatac ttctgctcct gccctccagg ctacatcctg | 1020 |
| ctggatgaca accgaagctg ccaagacatc aacgaatgtg agcacaggaa ccacacgtgc | 1080 |
| aacctgcagc agacgtgcta caatttacaa gggggcttca atgcatcga ccccatccgc | 1140 |
| tgtgaggagc cttatctgag gatcagtgat aaccgctgta tgtgtcctgc tgagaaccct | 1200 |
| ggctgcagag accagccctt taccatcttg taccgggaca tggacgtggt gtcaggacgc | 1260 |
| tccgttcccg ctgacatctt ccaaatgcaa gccacgaccc gctacctgg ggcctattac | 1320 |
| attttccaga tcaaatctgg gaatgagggc agagaattt acatgcggca acgggcccc | 1380 |
| atcagtgcca ccctggtgat gacacgcccc atcaaaggc cccgggaaat ccagctggac | 1440 |
| ttggaaatga tcactgtcaa cactgtcatc aacttcagag gcagctccgt gatccgactg | 1500 |
| cggatatatg tgtcgcagta cccattctga gcctcgggct ggagcctccg acgctgcctc | 1560 |
| tcattggcac caagggacag gagaagagag gaaataacag agagaatgag agcgacacag | 1620 |
| acgttaggca tttcctgctg aacgtttccc cgaagagtca gccccgactt cctgactctc | 1680 |

```
acctgtacta ttgcagacct gtcaccctgc aggacttgcc acccccagtt cctatgacac    1740
agttatcaaa aagtattatc attgctcccc tgatagaaga ttgttggtga attttcaagg    1800
ccttcagttt atttccacta ttttcaaaga aaatagatta ggtttgcggg ggtctgagtc    1860
tatgttcaaa gactgtgaac agcttgctgt cacttcttca cctcttccac tccttctctc    1920
actgtgttac tgctttgcaa agacccggga gctggcgggg aaccctggga gtagctagtt    1980 tgcttttttgc gtacacagag aaggctatgt aaacaaacca cagcaggatc gaagggtttt    2040
tagagaatgt gtttcaaaac catgcctggt attttcaacc ataaaagaag tttcagttgt    2100
ccttaaattt gtataacggt ttaattctgt cttgttcatt ttgagtattt ttaaaaaata    2160
tgtcgtagaa ttccttcgaa aggccttcag acacatgcta tgttctgtct tcccaaaccc    2220
agtctcctct ccatttttagc ccagtgtttt ctttgaggac cccttaatct tgctttcttt    2280 agaatttta cccaattgga ttggaatgca gaggtctcca aactgattaa atatttgaaa    2340
aaaaaaaaaa aaaaaaaaaa aaaaaaa                                       2367
```

<210> SEQ ID NO 23
<211> LENGTH: 323
<212> TYPE: PRT
<213> ORGANISM: Homo sapiens

<400> SEQUENCE: 23

```
Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro
        35                  40                  45

Lys Ala Val Leu Lys Leu Glu Pro Gln Trp Ile Asn Val Leu Gln Glu
    50                  55                  60

Asp Ser Val Thr Leu Thr Cys Arg Gly Thr His Ser Pro Glu Ser Asp
65                  70                  75                  80

Ser Ile Pro Trp Phe His Asn Gly Asn Leu Ile Pro Thr His Thr Gln
                85                  90                  95

Pro Ser Tyr Arg Phe Lys Ala Asn Asn Asn Asp Ser Gly Glu Tyr Thr
            100                 105                 110

Cys Gln Thr Gly Gln Thr Ser Leu Ser Asp Pro Val His Leu Thr Val
        115                 120                 125

Leu Ser Glu Trp Leu Val Leu Gln Thr Pro His Leu Glu Phe Gln Glu
    130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Phe Ser Arg
                165                 170                 175

Ser Asp Pro Asn Phe Ser Ile Pro Gln Ala Asn His Ser His Ser Gly
            180                 185                 190

Asp Tyr His Cys Thr Gly Asn Ile Gly Tyr Thr Leu Tyr Ser Ser Lys
        195                 200                 205

Pro Val Thr Ile Thr Val Gln Ala Pro Ser Ser Pro Met Gly Ile
    210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Asn Ser
```

|  |  | 245 |  |  |  | 250 |  |  |  | 255 |  |
|---|---|---|---|---|---|---|---|---|---|---|---|

Thr Asp Pro Val Lys Ala Ala Gln Phe Glu Pro Pro Gly Arg Gln Met
            260                      265                    270

Ile Ala Ile Arg Lys Arg Gln Pro Glu Glu Thr Asn Asn Asp Tyr Glu
        275                    280                    285

Thr Ala Asp Gly Gly Tyr Met Thr Leu Asn Pro Arg Ala Pro Thr Asp
            290                    295                  300

Asp Asp Lys Asn Ile Tyr Leu Thr Leu Pro Pro Asn Asp His Val Asn
305                    310                    315                  320

Ser Asn Asn

<210> SEQ ID NO 24
<211> LENGTH: 2488
<212> TYPE: DNA
<213> ORGANISM: Homo sapiens

<400> SEQUENCE: 24

```
agactccaga atttgtttgc cctctagggt agaatccgcc aagctttgag agaaggctgt      60
gactgctgtg ctctgggcgc cagctcgctc cagggagtga tgggaatcct gtcattctta     120
cctgtccttg ccactgagag tgactgggct gactgcaagt ccccccagcc ttggggtcat     180
atgcttctgt ggacagctgt gctattcctg gctcctgttg ctgggacacc tgcagctccc     240
ccaaaggctg tgctgaaact cgagcccag tggatcaacg tgctccaaga ggactctgtg      300
actctgacat gccggggggac tcacagccct gagagcgact ccattccgtg gttccacaat     360
gggaatctca ttcccaccca cacgcagccc agctacaggt tcaaggccaa caacaatgac     420
agcggggagt acacgtgcca gactggccag accagcctca cgcgaccctgt gcatctgact     480
gtgctttctg agtggctggt gctccagacc cctcacctgg agttccagga gggagaaacc     540
atcgtgctga ggtgccacag ctggaaggac aagcctctgg tcaaggtcac attcttccag     600
aatggaaaat ccaagaaatt tcccgttcg atcccaact tctccatccc acaagcaaac      660
cacagtcaca gtggtgatta ccactgcaca ggaaacatag gctacacgct gtactcatcc     720
aagcctgtga ccatcactgt ccaagctccc agctcttcac cgatggggat cattgtggct     780
gtggtcactg ggattgctgt agcggccatt gttgctgctg tagtggcctt gatctactgc     840
aggaaaaagc ggatttcagc caattccact gatcctgtga aggctgccca atttgagcca     900
cctggacgtc aaatgattgc catcagaaag agacaacctg aagaaccaa caatgactat     960
gaaacagctg acggcggcta catgactctg aaccccaggg cacctactga cgatgataaa    1020
aacatctacc tgactcttcc tcccaacgac catgtcaaca gtaataacta agagtaacg    1080
ttatgccatg tggtcacact ctcagcttgc tgagtggatg acaaaaagag gggaattgtt    1140
aaaggaaaat ttaaatggag actggaaaaa ttcctgagca acaaaaccca cctggccctt    1200
agaaatagct ttaactttgc ttaaaactaca aacacaagca aaacttcacg gggtcatact    1260
acatacaagc ataagcaaaa cttaacttgg atgatttctg gtaaatgctt atgttagaaa    1320
taagacaacc ccagccaatc acaagcagcc tactaacata taattaggtg actagggact    1380
ttctaagaag atacctaccc ccaaaaaaca attatgtaat tgaaacccca tcgattgcct    1440
ttattttgct tccacatttt cccaataaat acttgcctgt gacattttgc cactggaaca    1500
ctaaacttca tgaattgcgc ctcagatttt cctttaaca tctttttttt ttgacagtct    1560
caatctgtta cccaggctgg agtgtagtgg tgctatcttg gctcactgca aacccgcctc    1620
ccaggtttaa gcgattctca tgcctcagcc tcccagtagc tgggattaca ggcatgtgcc    1680
```

-continued

```
gtcataacca gctaattttt gtattttta ttttttttt tagtagagac ggggtttcgc      1740
aatgttggcc aggccgatct cgaacttctg gcctctagcg atctgcccgc ctcggcctcc      1800
caaagtgctg ggatgaccag catcagcccc aatgcccagc ctctttaaca tcttctttcc      1860
tatgccctct ctgtggatcc ctactgctgg tttctgcctt ctccatgctg agaacaaaat      1920
cacctattca ctgcttatgc agtcggaagc tccagaagaa caaagagccc aattaccaga      1980
accacattaa gtctccattg ttttgccttg ggatttgaga agagaattag agaggtgagg      2040
atctggtatt tcctggtcta aattcccctt gaggaagacg aagggatgct gcagttccaa      2100
aagagaagga ctcttccaga gtcatctacc tgagtcccga tgctccctgt cctgaaaacc      2160
acagacaata tggtcccaaa tgactgactg caccttctgt gcctcagcca ttcttgacat      2220
caagaatctt ctgttccaca tccacacagc caatacaatt aatcaaacca ctgttatgaa      2280
aagatgtagc aacatgagaa atgcttatgt tacaggttac atgagaacaa tcatgtaagt      2340
ctatatgact tcagaaatgt taaaatagac taacctctaa caacaaatta aaagtgattg      2400
tttcaaggtg atgcaattat tgatgaccta ttttatttt ctataatgat catatattac      2460
ctttgtaata aaacattata accaaaac                                         2488
```

<210> SEQ ID NO 25
<211> LENGTH: 245
<212> TYPE: PRT
<213> ORGANISM: Homo sapiens

<400> SEQUENCE: 25

```
Met Glu Gly Pro Arg Gly Trp Leu Val Leu Cys Val Leu Ala Ile Ser
1               5                   10                  15

Leu Ala Ser Met Val Thr Glu Asp Leu Cys Arg Ala Pro Asp Gly Lys
            20                  25                  30

Lys Gly Glu Ala Gly Arg Pro Gly Arg Arg Gly Arg Pro Gly Leu Lys
        35                  40                  45

Gly Glu Gln Gly Glu Pro Gly Ala Pro Gly Ile Arg Thr Gly Ile Gln
    50                  55                  60

Gly Leu Lys Gly Asp Gln Gly Glu Pro Gly Pro Ser Gly Asn Pro Gly
65                  70                  75                  80

Lys Val Gly Tyr Pro Gly Pro Ser Gly Pro Leu Gly Ala Arg Gly Ile
                85                  90                  95

Pro Gly Ile Lys Gly Thr Lys Gly Ser Pro Gly Asn Ile Lys Asp Gln
            100                 105                 110

Pro Arg Pro Ala Phe Ser Ala Ile Arg Arg Asn Pro Pro Met Gly Gly
        115                 120                 125

Asn Val Val Ile Phe Asp Thr Val Ile Thr Asn Gln Glu Glu Pro Tyr
    130                 135                 140

Gln Asn His Ser Gly Arg Phe Val Cys Thr Val Pro Gly Tyr Tyr Tyr
145                 150                 155                 160

Phe Thr Phe Gln Val Leu Ser Gln Trp Glu Ile Cys Leu Ser Ile Val
                165                 170                 175

Ser Ser Ser Arg Gly Gln Val Arg Arg Ser Leu Gly Phe Cys Asp Thr
            180                 185                 190

Thr Asn Lys Gly Leu Phe Gln Val Val Ser Gly Gly Met Val Leu Gln
        195                 200                 205

Leu Gln Gln Gly Asp Gln Val Trp Val Glu Lys Asp Pro Lys Lys Gly
    210                 215                 220
```

His Ile Tyr Gln Gly Ser Glu Ala Asp Ser Val Phe Ser Gly Phe Leu
225                 230                 235                 240

Ile Phe Pro Ser Ala
            245

<210> SEQ ID NO 26
<211> LENGTH: 1098
<212> TYPE: DNA
<213> ORGANISM: Homo sapiens

<400> SEQUENCE: 26

```
gccactcctg ctgggcagcc cacagggtcc ctgggcggag ggcaggagca tccagttgga    60
gttgacaaca ggaggcagag gcatcatgga gggtccccgg ggatggctgg tgctctgtgt   120
gctggccata tcgctggcct ctatggtgac cgaggacttg tgccgagcac cagacgggaa   180
gaaaggggag gcaggaagac ctggcagacg ggggcggcca ggcctcaagg gggagcaagg   240
ggagccgggg gcccctggca tccgacagg catccaaggc cttaaaggag accaggggga   300
acctgggccc tctggaaacc ccggcaaggt gggctaccca gggcccagcg gccccctcgg   360
agcccgtggc atcccgggaa ttaaaggcac caagggcagc ccaggaaaca tcaaggacca   420
gccgaggcca gccttctccg ccattcggcg gaaccccca atggggggca acgtggtcat   480
cttcgacacg gtcatcacca accaggaaga accgtaccag aaccactccg gccgattcgt   540
ctgcactgta cccggctact actacttcac cttccaggtg ctgtcccagt gggaaatctg   600
cctgtccatc gtctcctcct caaggggcca ggtccgacgc tccctgggct tctgtgacac   660
caccaacaag gggctcttcc aggtggtgtc aggggggcatg gtgcttcagc tgcagcaggg   720
tgaccaggtc tgggttgaaa agacccccaa aaagggtcac atttaccagg ctctgaggc   780
cgacagcgtc ttcagcggct tcctcatctt cccatctgcc tgagccaggg aaggacccccc   840
tcccccaccc acctctctgg cttccatgct ccgcctgtaa aatggggggcg ctattgcttc   900
agctgctgaa gggagggggc tggctctgag agccccagga ctggctgccc cgtgacacat   960
gctctaagaa gctcgttct tagacctctt cctggaataa acatctgtgt ctgtgtctgc  1020
tgaacatgag cttcagttgc tactcggagc attgagaggg aggcctaaga ataataacaa  1080
tccagtgctt aagagtca                                                1098
```

<210> SEQ ID NO 27
<211> LENGTH: 295
<212> TYPE: PRT
<213> ORGANISM: Homo sapiens

<400> SEQUENCE: 27

Met Leu Gln Gly Pro Gly Ser Leu Leu Leu Leu Phe Leu Ala Ser His
1               5                   10                  15

Cys Cys Leu Gly Ser Ala Arg Gly Leu Phe Leu Phe Gly Gln Pro Asp
                20                  25                  30

Phe Ser Tyr Lys Arg Ser Asn Cys Lys Pro Ile Pro Ala Asn Leu Gln
            35                  40                  45

Leu Cys His Gly Ile Glu Tyr Gln Asn Met Arg Leu Pro Asn Leu Leu
        50                  55                  60

Gly His Glu Thr Met Lys Glu Val Leu Glu Gln Ala Gly Ala Trp Ile
65                  70                  75                  80

Pro Leu Val Met Lys Gln Cys His Pro Asp Thr Lys Lys Phe Leu Cys
                85                  90                  95

Ser Leu Phe Ala Pro Val Cys Leu Asp Asp Leu Asp Glu Thr Ile Gln

```
              100                 105                 110
Pro Cys His Ser Leu Cys Val Gln Val Lys Asp Arg Cys Ala Pro Val
            115                 120                 125

Met Ser Ala Phe Gly Phe Pro Trp Pro Asp Met Leu Glu Cys Asp Arg
130                 135                 140

Phe Pro Gln Asp Asn Asp Leu Cys Ile Pro Leu Ala Ser Ser Asp His
145                 150                 155                 160

Leu Leu Pro Ala Thr Glu Glu Ala Pro Lys Val Cys Glu Ala Cys Lys
                165                 170                 175

Asn Lys Asn Asp Asp Asp Asn Asp Ile Met Glu Thr Leu Cys Lys Asn
            180                 185                 190

Asp Phe Ala Leu Lys Ile Lys Val Lys Glu Ile Thr Tyr Ile Asn Arg
        195                 200                 205

Asp Thr Lys Ile Ile Leu Glu Thr Lys Ser Lys Thr Ile Tyr Lys Leu
    210                 215                 220

Asn Gly Val Ser Glu Arg Asp Leu Lys Lys Ser Val Leu Trp Leu Lys
225                 230                 235                 240

Asp Ser Leu Gln Cys Thr Cys Glu Glu Met Asn Asp Ile Asn Ala Pro
                245                 250                 255

Tyr Leu Val Met Gly Gln Lys Gln Gly Gly Glu Leu Val Ile Thr Ser
            260                 265                 270

Val Lys Arg Trp Gln Lys Gly Gln Arg Glu Phe Lys Arg Ile Ser Arg
        275                 280                 285

Ser Ile Arg Lys Leu Gln Cys
    290                 295

<210> SEQ ID NO 28
<211> LENGTH: 2005
<212> TYPE: DNA
<213> ORGANISM: Homo sapiens

<400> SEQUENCE: 28
caacggctca ttctgctccc ccgggtcgga gcccccggga gctgcgcgcg ggcttgcagc     60
gcctcgcccg cgctgtcctc ccggtgtccc gcttctccgc gccccagccg ccggctgcca    120
gcttttcggg gccccgagtc gcacccagcg aagagagcgg gcccgggaca agctcgaact    180
ccggccgcct cgcccttccc cggctccgct ccctctgccc cctcggggtc gcgcgcccac    240
gatgctgcag ggccctggct cgctgctgct gctcttcctc gcctcgcact gctgcctggg    300
ctcggcgcgc gggctcttcc tctttggcca gcccgacttc tcctacaagc gcagcaattg    360
caagcccatc cctgccaacc tgcagctgtg ccacggcatc gaataccaga acatgcggct    420
gcccaacctg ctgggccacg agaccatgaa ggaggtgctg gagcaggccg cgcttggat     480 cccgctggtc atgaagcagt gccaccccgga caccaagaag ttcctgtgct cgctcttcgc    540
ccccgtctgc ctcgatgacc tagacgagac catccagcca tgccactcgc tctgcgtgca    600
ggtgaaggac cgctgcgccc cggtcatgtc cgccttcggc ttcccctggc ccgacatgct    660
tgagtgcgac cgtttccccc aggacaacga cctttgcatc ccctcgcta gcagcgacca    720 cctcctgcca gccaccgagg aagctccaaa ggtatgtgaa gcctgcaaaa ataaaaatga    780
tgatgacaac gacataatgg aaacgctttg taaaaatgat tttgcactga aaataaaagt    840
gaaggagata acctacatca accgagatac caaaatcatc ctggagacca agagcaagac    900
catttacaag ctgaacggtg tgtccgaaag ggacctgaag aaatcggtgc tgtggctcaa    960
agacagcttg cagtgcacct gtgaggagat gaacgacatc aacgcgccct atctggtcat   1020
```

-continued

```
gggacagaaa cagggtgggg agctggtgat cacctcggtg aagcggtggc agaaggggca    1080
gagagagttc aagcgcatct cccgcagcat ccgcaagctg cagtgctagt cccggcatcc    1140
tgatggctcc gacaggcctg ctccagagca cggctgacca tttctgctcc gggatctcag    1200
ctcccgttcc ccaagcacac tcctagctgc tccagtctca gctgggcag cttcccctg      1260 ccttttgcac gtttgcatcc ccagcatttc ctgagttata aggccacagg agtggatagc    1320
tgttttcacc taaaggaaaa gcccacccga atcttgtaga atattcaaa ctaataaaat     1380 catgaatatt tttatgaagt ttaaaaatag ctcactttaa agctagtttt gaataggtgc    1440
aactgtgact tgggtctggt tggttgttgt ttgttgtttt gagtcagctg attttcactt    1500
cccactgagg ttgtcataac atgcaaattg cttcaatttt ctctgtggcc caaacttgtg    1560
ggtcacaaac cctgttgaga taaagctggc tgttatctca acatcttcat cagctccaga    1620
ctgagactca gtgtctaagt cttacaacaa ttcatcattt tataccttca atgggaactt    1680
aaactgttac atgtatcaca ttccagctac aatacttcca tttattagaa gcacattaac    1740
catttctata gcatgatttc ttcaagtaaa aggcaaaaga tataaatttt ataattgact    1800
tgagtacttt aagccttgtt taaaacattt cttacttaac ttttgcaaat taaacccatt    1860
gtagcttacc tgtaatatac atagtagttt acctttaaaa gttgtaaaaa tattgcttta    1920
accaacactg taaatatttc agataaacat tatattcttg tatataaact ttacatcctg    1980
ttttacctat aaaaaaaaaa aaaaa                                          2005
```

<210> SEQ ID NO 29
<211> LENGTH: 644
<212> TYPE: PRT
<213> ORGANISM: Homo sapiens

<400> SEQUENCE: 29

```
Met Cys Tyr Gly Thr Pro Ser Tyr Asn Tyr Ala Pro Asn Met Asp Lys
1               5                   10                  15

His Trp Ile Met Gln Tyr Thr Gly Pro Met Leu Pro Ile His Met Glu
            20                  25                  30

Phe Thr Asn Ile Leu Gln Arg Lys Arg Leu Gln Thr Leu Met Ser Val
        35                  40                  45

Asp Asp Ser Val Glu Arg Leu Tyr Asn Met Leu Val Glu Thr Gly Glu
    50                  55                  60

Leu Glu Asn Thr Tyr Ile Ile Tyr Thr Ala Asp His Gly Tyr His Ile
65                  70                  75                  80

Gly Gln Phe Gly Leu Val Lys Gly Lys Ser Met Pro Tyr Asp Phe Asp
                85                  90                  95

Ile Arg Val Pro Phe Phe Ile Arg Gly Pro Ser Val Glu Pro Gly Ser
            100                 105                 110

Ile Val Pro Gln Ile Val Leu Asn Ile Asp Leu Ala Pro Thr Ile Leu
        115                 120                 125

Asp Ile Ala Gly Leu Asp Thr Pro Pro Asp Val Asp Gly Lys Ser Val
    130                 135                 140

Leu Lys Leu Leu Asp Pro Glu Lys Pro Gly Asn Arg Phe Arg Thr Asn
145                 150                 155                 160

Lys Lys Ala Lys Ile Trp Arg Asp Thr Phe Leu Val Glu Arg Gly Lys
                165                 170                 175

Phe Leu Arg Lys Lys Glu Glu Ser Ser Lys Asn Ile Gln Gln Ser Asn
            180                 185                 190
```

-continued

His Leu Pro Lys Tyr Glu Arg Val Lys Glu Leu Cys Gln Gln Ala Arg
            195                 200                 205

Tyr Gln Thr Ala Cys Glu Gln Pro Gly Gln Lys Trp Gln Cys Ile Glu
    210                 215                 220

Asp Thr Ser Gly Lys Leu Arg Ile His Lys Cys Lys Gly Pro Ser Asp
225                 230                 235                 240

Leu Leu Thr Val Arg Gln Ser Thr Arg Asn Leu Tyr Ala Arg Gly Phe
                245                 250                 255

His Asp Lys Asp Lys Glu Cys Ser Cys Arg Glu Ser Gly Tyr Arg Ala
            260                 265                 270

Ser Arg Ser Gln Arg Lys Ser Gln Arg Gln Phe Leu Arg Asn Gln Gly
    275                 280                 285

Thr Pro Lys Tyr Lys Pro Arg Phe Val His Thr Arg Gln Thr Arg Ser
    290                 295                 300

Leu Pro Val Glu Phe Glu Gly Glu Ile Tyr Asp Ile Asn Leu Glu Glu
305                 310                 315                 320

Glu Glu Glu Leu Gln Val Leu Gln Pro Arg Asn Ile Ala Lys Arg His
                325                 330                 335

Asp Glu Gly His Lys Gly Pro Arg Asp Leu Gln Ala Ser Ser Gly Gly
            340                 345                 350

Asn Arg Gly Arg Met Leu Ala Asp Ser Ser Asn Ala Val Gly Pro Pro
    355                 360                 365

Thr Thr Val Arg Val Thr His Lys Cys Phe Ile Leu Pro Asn Asp Ser
    370                 375                 380

Ile His Cys Glu Arg Glu Leu Tyr Gln Ser Ala Arg Ala Trp Lys Asp
385                 390                 395                 400

His Lys Ala Tyr Ile Asp Lys Glu Ile Glu Ala Leu Gln Asp Lys Ile
                405                 410                 415

Lys Asn Leu Arg Glu Val Arg Gly His Leu Lys Arg Arg Lys Pro Glu
            420                 425                 430

Glu Cys Ser Cys Ser Lys Gln Ser Tyr Tyr Asn Lys Glu Lys Gly Val
    435                 440                 445

Lys Lys Gln Glu Lys Leu Lys Ser His Leu His Pro Phe Lys Glu Ala
    450                 455                 460

Ala Gln Glu Val Asp Ser Lys Leu Gln Leu Phe Lys Glu Asn Asn Arg
465                 470                 475                 480

Arg Arg Lys Lys Glu Arg Lys Glu Lys Arg Gln Arg Lys Gly Glu
                485                 490                 495

Glu Cys Ser Leu Pro Gly Leu Thr Cys Phe Thr His Asp Asn Asn His
            500                 505                 510

Trp Gln Thr Ala Pro Phe Trp Asn Leu Gly Ser Phe Cys Ala Cys Thr
    515                 520                 525

Ser Ser Asn Asn Asn Thr Tyr Trp Cys Leu Arg Thr Val Asn Glu Thr
530                 535                 540

His Asn Phe Leu Phe Cys Glu Phe Ala Thr Gly Phe Leu Glu Tyr Phe
545                 550                 555                 560

Asp Met Asn Thr Asp Pro Tyr Gln Leu Thr Asn Thr Val His Thr Val
                565                 570                 575

Glu Arg Gly Ile Leu Asn Gln Leu His Val Gln Leu Met Glu Leu Arg
            580                 585                 590

Ser Cys Gln Gly Tyr Lys Gln Cys Asn Pro Arg Pro Lys Asn Leu Asp
    595                 600                 605

Val Gly Asn Lys Asp Gly Gly Ser Tyr Asp Leu His Arg Met Leu Leu 610                 615                 620
Phe Leu Val Pro Cys Ser Ala Pro Leu Thr Ser Arg Ala Met Val Ser
625                 630                 635                 640

Asp Ala Ser Phe

<210> SEQ ID NO 30
<211> LENGTH: 3019
<212> TYPE: DNA
<213> ORGANISM: Homo sapiens

<400> SEQUENCE: 30

| | | | | | |
|---|---|---|---|---|---|
| attccaatgg | aacagacagg | gtaaggacca | atctggactg | tgttatcttt | tccaggtgca | 60 |
| agtatgtgct | atggaactcc | tagttataac | tatgcaccaa | atatggataa | acactggatt | 120 |
| atgcagtaca | caggaccaat | gctgcccatc | cacatggaat | ttacaaacat | tctacagcgc | 180 |
| aaaaggctcc | agactttgat | gtcagtggat | gattctgtgg | agaggctgta | taacatgctc | 240 |
| gtggagacgg | gggagctgga | gaatacttac | atcatttaca | ccgccgacca | tggttaccat | 300 |
| attgggcagt | ttggactggt | caaggggaaa | tccatgccat | atgactttga | tattcgtgtg | 360 |
| cctttttta | ttcgtggtcc | aagtgtagaa | ccaggatcaa | tagtcccaca | gatcgttctc | 420 |
| aacattgact | tggcccccac | gatcctggat | attgctgggc | tcgacacacc | tcctgatgtg | 480 |
| gacggcaagt | ctgtcctcaa | acttctggac | ccagaaaagc | caggtaacag | gtttcgaaca | 540 |
| aacaagaagg | ccaaaatttg | gcgtgataca | ttcctagtgg | aaagaggcaa | atttctacgt | 600 |
| aagaaggaag | aatccagcaa | gaatatccaa | cagtcaaatc | acttgcccaa | atatgaacgg | 660 |
| gtcaaagaac | tatgccagca | ggccaggtac | cagacagcct | gtgaacaacc | ggggcagaag | 720 |
| tggcaatgca | ttgaggatac | atctggcaag | cttcgaattc | acaagtgtaa | aggacccagt | 780 |
| gacctgctca | cagtccggca | gagcacgcgg | aacctctacg | ctcgcggctt | ccatgacaaa | 840 |
| gacaaagagt | gcagttgtag | ggagtctggt | taccgtgcca | gcagaagcca | agaaagagt | 900 |
| caacggcaat | tcttgagaaa | ccaggggact | ccaaagtaca | agcccagatt | tgtccatact | 960 |
| cggcagacac | gttccttgcc | cgtcgaattt | gaaggtgaaa | tatatgacat | aaatctggaa | 1020 |
| gaagaagaag | aattgcaagt | gttgcaacca | agaaacattg | ctaagcgtca | tgatgaaggc | 1080 |
| cacaaggggc | caagagatct | ccaggcttcc | agtggtggca | acaggggcag | gatgctggca | 1140 |
| gatagcagca | acgccgtggg | cccacctacc | actgtccgag | tgacacacaa | gtgttttatt | 1200 |
| cttcccaatg | actctatcca | ttgtgagaga | gaactgtacc | aatcggccag | agcgtggaag | 1260 |
| gaccataagg | catacattga | caaagagatt | gaagctctgc | aagataaaat | taagaattta | 1320 |
| agagaagtga | gaggacatct | gaagagaagg | aagcctgagg | aatgtagctg | cagtaaacaa | 1380 |
| agctattaca | ataaagagaa | aggtgtaaaa | aagcaagaga | aattaaagag | ccatcttcac | 1440 |
| ccattcaagg | aggctgctca | ggaagtagat | agcaaactgc | aacttttcaa | ggagaacaac | 1500 |
| cgtaggagga | agaaggagag | gaaggagaag | agacggcaga | ggaaggggga | agagtgcagc | 1560 |
| ctgcctggcc | tcacttgctt | cacgcatgac | aacaaccact | ggcagacagc | cccgttctgg | 1620 |
| aacctgggat | ctttctgtgc | ttgcacgagt | tctaacaata | cacctactg | gtgtttgcgt | 1680 |
| acagttaatg | agacgcataa | ttttcttttc | tgtgagtttg | ctactggctt | tttggagtat | 1740 |
| tttgatatga | atacagatcc | ttatcagctc | acaaatacag | tgcacacggt | agaacgaggc | 1800 |
| attttgaatc | agctacacgt | acaactaatg | gagctcagaa | gctgtcaagg | atataagcag | 1860 |
| tgcaacccaa | gacctaagaa | tcttgatgtt | ggaaataaag | atggaggaag | ctatgaccta | 1920 |

```
cacagaatgt tgctgttcct ggtaccctgt tcggcccctc taacctccag agctatggtc    1980
tcagatgctt cctttagag agaaggtcat tagtccacca agaagccaaa tgacaacagg     2040
aaaggtgatg ggaagatgaa aacaaaggaa ggtggacttt tgggtatatg ttatagccat    2100
aggacagtta tgggatggat gggaaggtta atcagccccg tctcactgca gacatcaact    2160
ggcaaggcct agaggagcta cacagtgtga atgaaaacat ctatgagtac agacaaaact    2220
acagacttag tctggtggac tggactaatt acttgaagga tttagataga gtatttgcac    2280
tgctgaagag tcactatgag caaataaaa caaataagac tcaaactgct caaagtgacg     2340
ggttcttggt tgtctctgct gagcacgctg tgtcaatgga gatggcctct gctgactcag    2400
atgaagaccc aaggcataag gttgggaaaa cacctcattt gaccttgcca gctgaccttc    2460
aaaccctgca tttgaaccga ccaacattaa gtccagagag taaacttgaa tggaataacg    2520
acattccaga agttaatcat ttgaattctg aacactggag aaaaaccgaa aaatggacgg    2580
ggcatgaaga gactaatcat ctggaaaccg atttcagtgg cgatggcatg acagagctag    2640
agctcgggcc cagccccagg ctgcagccca ttcgcaggca cccgaaagaa cttccccagt    2700
atggtggtcc tggaaaggac attttgaag atcaactata tcttcctgtg cattccgatg     2760
gaatttcagt tcatcagatg ttcaccatgg ccaccgcaga acaccgaagt aattccagca    2820
tagcggggaa gatgttgacc aaggtggaga agaatcacga aaggagaag tcacagcacc     2880 tagaaggcag cgcctcctct tcactctcct ctgattagat gaaactgtta ccttacccta    2940
aacacagtat ttctttttaa ctttttatt tgtaaactaa taaaggtaat cacagccacc     3000
aacaaaaaaa aaaaaaaaa                                                 3019
```

<210> SEQ ID NO 31
<211> LENGTH: 1172
<212> TYPE: PRT
<213> ORGANISM: Homo sapiens
<400> SEQUENCE: 31

```
Met Ala Trp Arg Leu Val Leu Ala Leu Trp Val Trp Pro Ser Thr
 1               5                  10                  15

Gln Ala Gly His Gln Asp Lys Asp Thr Thr Phe Asp Leu Phe Ser Ile
            20                  25                  30

Ser Asn Ile Asn Arg Lys Thr Ile Gly Ala Lys Gln Phe Arg Gly Pro
        35                  40                  45

Asp Pro Gly Val Pro Ala Tyr Arg Phe Val Arg Phe Asp Tyr Ile Pro
    50                  55                  60

Pro Val Asn Ala Asp Asp Leu Ser Lys Ile Thr Lys Ile Met Arg Gln
65                  70                  75                  80

Lys Glu Gly Phe Phe Leu Thr Ala Gln Leu Lys Gln Asp Gly Lys Ser
                85                  90                  95

Arg Gly Thr Leu Leu Ala Leu Glu Gly Pro Gly Leu Ser Gln Arg Gln
            100                 105                 110

Phe Glu Ile Val Ser Asn Gly Pro Ala Asp Thr Leu Asp Leu Thr Tyr
        115                 120                 125

Trp Ile Asp Gly Thr Arg His Val Val Ser Leu Glu Asp Val Gly Leu
    130                 135                 140

Ala Asp Ser Gln Trp Lys Asn Val Thr Val Gln Val Ala Gly Glu Thr
145                 150                 155                 160

Tyr Ser Leu His Val Gly Cys Asp Leu Ile Asp Ser Phe Ala Leu Asp
                165                 170                 175
```

-continued

```
Glu Pro Phe Tyr Glu His Leu Gln Ala Glu Lys Ser Arg Met Tyr Val
            180                 185                 190
Ala Lys Gly Ser Ala Arg Glu Ser His Phe Arg Gly Leu Leu Gln Asn
        195                 200                 205
Val His Leu Val Phe Glu Asn Ser Val Glu Asp Ile Leu Ser Lys Lys
    210                 215                 220
Gly Cys Gln Gln Gly Gln Gly Ala Glu Ile Asn Ala Ile Ser Glu Asn
225                 230                 235                 240
Thr Glu Thr Leu Arg Leu Gly Pro His Val Thr Thr Glu Tyr Val Gly
                245                 250                 255
Pro Ser Ser Glu Arg Arg Pro Glu Val Cys Glu Arg Ser Cys Glu Glu
            260                 265                 270
Leu Gly Asn Met Val Gln Glu Leu Ser Gly Leu His Val Leu Val Asn
        275                 280                 285
Gln Leu Ser Glu Asn Leu Lys Arg Val Ser Asn Asp Asn Gln Phe Leu
    290                 295                 300
Trp Glu Leu Ile Gly Gly Pro Lys Thr Arg Asn Met Ser Ala Cys
305                 310                 315                 320
Trp Gln Asp Gly Arg Phe Phe Ala Glu Asn Glu Thr Trp Val Val Asp
                325                 330                 335
Ser Cys Thr Thr Cys Thr Cys Lys Lys Phe Lys Thr Ile Cys His Gln
            340                 345                 350
Ile Thr Cys Pro Pro Ala Thr Cys Ala Ser Pro Ser Phe Val Glu Gly
        355                 360                 365
Glu Cys Cys Pro Ser Cys Leu His Ser Val Asp Gly Glu Gly Trp
370                 375                 380
Ser Pro Trp Ala Glu Trp Thr Gln Cys Ser Val Thr Cys Gly Ser Gly
385                 390                 395                 400
Thr Gln Gln Arg Gly Arg Ser Cys Asp Val Thr Ser Asn Thr Cys Leu
                405                 410                 415
Gly Pro Ser Ile Gln Thr Arg Ala Cys Ser Leu Ser Lys Cys Asp Thr
            420                 425                 430
Arg Ile Arg Gln Asp Gly Gly Trp Ser His Trp Ser Pro Trp Ser Ser
        435                 440                 445
Cys Ser Val Thr Cys Gly Val Gly Asn Ile Thr Arg Ile Arg Leu Cys
    450                 455                 460
Asn Ser Pro Val Pro Gln Met Gly Gly Lys Asn Cys Lys Gly Ser Gly
465                 470                 475                 480
Arg Glu Thr Lys Ala Cys Gln Gly Ala Pro Cys Pro Ile Asp Gly Arg
                485                 490                 495
Trp Ser Pro Trp Ser Pro Trp Ser Ala Cys Thr Val Thr Cys Ala Gly
            500                 505                 510
Gly Ile Arg Glu Arg Thr Arg Val Cys Asn Ser Pro Glu Pro Gln Tyr
        515                 520                 525
Gly Gly Lys Ala Cys Val Gly Asp Val Gln Glu Arg Gln Met Cys Asn
    530                 535                 540
Lys Arg Ser Cys Pro Val Asp Gly Cys Leu Ser Asn Pro Cys Phe Pro
545                 550                 555                 560
Gly Ala Gln Cys Ser Ser Phe Pro Asp Gly Ser Trp Ser Cys Gly Ser
                565                 570                 575
Cys Pro Val Gly Phe Leu Gly Asn Gly Thr His Cys Glu Asp Leu Asp
            580                 585                 590
Glu Cys Ala Leu Val Pro Asp Ile Cys Phe Ser Thr Ser Lys Val Pro
```

```
                595                 600                 605
Arg Cys Val Asn Thr Gln Pro Gly Phe His Cys Leu Pro Cys Pro Pro
610                     615                 620
Arg Tyr Arg Gly Asn Gln Pro Val Gly Val Gly Leu Glu Ala Ala Lys
625                 630                  635                 640
Thr Glu Lys Gln Val Cys Glu Pro Glu Asn Pro Cys Lys Asp Lys Thr
                    645                 650                 655
His Asn Cys His Lys His Ala Glu Cys Ile Tyr Leu Gly His Phe Ser
                660                 665                 670
Asp Pro Met Tyr Lys Cys Glu Cys Gln Thr Gly Tyr Ala Gly Asp Gly
            675                 680                 685
Leu Ile Cys Gly Glu Asp Ser Asp Leu Asp Gly Trp Pro Asn Leu Asn
690                 695                 700
Leu Val Cys Ala Thr Asn Ala Thr Tyr His Cys Ile Lys Asp Asn Cys
705                     710                 715                 720
Pro His Leu Pro Asn Ser Gly Gln Glu Asp Phe Asp Lys Asp Gly Ile
                    725                 730                 735
Gly Asp Ala Cys Asp Asp Asp Asp Asn Asp Gly Val Thr Asp Glu
                740                 745                 750
Lys Asp Asn Cys Gln Leu Leu Phe Asn Pro Arg Gln Ala Asp Tyr Asp
                755                 760                 765
Lys Asp Glu Val Gly Asp Arg Cys Asp Asn Cys Pro Tyr Val His Asn
770                     775                 780
Pro Ala Gln Ile Asp Thr Asp Asn Asn Gly Glu Gly Asp Ala Cys Ser
785                 790                 795                 800
Val Asp Ile Asp Gly Asp Val Phe Asn Glu Arg Asp Asn Cys Pro
            805                 810                 815
Tyr Val Tyr Asn Thr Asp Gln Arg Asp Thr Gly Asp Gly Val Gly
                820                 825                 830
Asp His Cys Asp Asn Cys Pro Leu Val His Asn Pro Asp Gln Thr Asp
                835                 840                 845
Val Asp Asn Asp Leu Val Gly Asp Gln Cys Asp Asn Asn Glu Asp Ile
850                 855                 860
Asp Asp Asp Gly His Gln Asn Asn Gln Asp Asn Cys Pro Tyr Ile Ser
865                     870                 875                 880
Asn Ala Asn Gln Ala Asp His Asp Arg Asp Gly Gln Gly Asp Ala Cys
                    885                 890                 895
Asp Pro Asp Asp Asp Asn Asp Gly Val Pro Asp Asp Arg Asp Asn Cys
                900                 905                 910
Arg Leu Val Phe Asn Pro Asp Gln Glu Asp Leu Asp Gly Asp Gly Arg
            915                 920                 925
Gly Asp Ile Cys Lys Asp Asp Phe Asp Asn Asp Ile Pro Asp Ile
            930                 935                 940
Asp Asp Val Cys Pro Glu Asn Asn Ala Ile Ser Glu Thr Asp Phe Arg
945                     950                 955                 960
Asn Phe Gln Met Val Pro Leu Asp Pro Lys Gly Thr Thr Gln Ile Asp
                    965                 970                 975
Pro Asn Trp Val Ile Arg His Gln Gly Lys Glu Leu Val Gln Thr Ala
                980                 985                 990
Asn Ser Asp Pro Gly Ile Ala Val  Gly Phe Asp Glu Phe  Gly Ser Val
            995                 1000                1005
Asp Phe  Ser Gly Thr Phe Tyr  Val Asn Thr Asp Arg  Asp Asp Asp
    1010                1015                1020
```

| Tyr | Ala | Gly | Phe | Val | Phe | Gly | Tyr | Gln | Ser | Ser | Ser | Arg | Phe | Tyr |
| | 1025 | | | | 1030 | | | | 1035 | | | | | |

| Val | Val | Met | Trp | Lys | Gln | Val | Thr | Gln | Thr | Tyr | Trp | Glu | Asp | Gln |
| | 1040 | | | | 1045 | | | | 1050 | | | | | |

| Pro | Thr | Arg | Ala | Tyr | Gly | Tyr | Ser | Gly | Val | Ser | Leu | Lys | Val | Val |
| | 1055 | | | | 1060 | | | | 1065 | | | | | |

| Asn | Ser | Thr | Thr | Gly | Thr | Gly | Glu | His | Leu | Arg | Asn | Ala | Leu | Trp |
| | 1070 | | | | 1075 | | | | 1080 | | | | | |

| His | Thr | Gly | Asn | Thr | Pro | Gly | Gln | Val | Arg | Thr | Leu | Trp | His | Asp |
| | 1085 | | | | 1090 | | | | 1095 | | | | | |

| Pro | Arg | Asn | Ile | Gly | Trp | Lys | Asp | Tyr | Thr | Ala | Tyr | Arg | Trp | His |
| | 1100 | | | | 1105 | | | | 1110 | | | | | |

| Leu | Thr | His | Arg | Pro | Lys | Thr | Gly | Tyr | Ile | Arg | Val | Leu | Val | His |
| | 1115 | | | | 1120 | | | | 1125 | | | | | |

| Glu | Gly | Lys | Gln | Val | Met | Ala | Asp | Ser | Gly | Pro | Ile | Tyr | Asp | Gln |
| | 1130 | | | | 1135 | | | | 1140 | | | | | |

| Thr | Tyr | Ala | Gly | Gly | Arg | Leu | Gly | Leu | Phe | Val | Phe | Ser | Gln | Glu |
| | 1145 | | | | 1150 | | | | 1155 | | | | | |

| Met | Val | Tyr | Phe | Ser | Asp | Leu | Lys | Tyr | Glu | Cys | Arg | Asp | Ile | |
| | 1160 | | | | 1165 | | | | 1170 | | | | | |

<210> SEQ ID NO 32
<211> LENGTH: 5314
<212> TYPE: DNA
<213> ORGANISM: Homo sapiens

<400> SEQUENCE: 32

```
gagcatcctg cactgcaggg ccggtctctc gctccagcag agcctgcgcc tttctgactc      60
ggtccggaac actgaaacca gtcatcactg catcttttg gcaaaccagg agctcagctg     120
caggaggcag gatggcctgg aggctggtcc tgctggctct gtgggtgtgg cccagcacgc     180
aagctggtca ccaggacaaa gacacgacct tcgacctttt cagtatcagc aacatcaacc     240
gcaagaccat tggcgccaag cagttccgcg ggcccgaccc cggcgtgccg gcttaccgct     300
tcgtgcgctt tgactacatc ccaccggtga acgcagatga cctcagcaag atcaccaaga     360
tcatgcggca aaggagggc ttcttcctca cggcccagct caagcaggac ggcaagtcca     420
ggggcacgct gttggctctg gagggccccg tctctcccca gaggcagttc gagatcgtct     480
ccaacggccc cgcggacacg ctggatctca cctactggat tgacggcacc cggcatgtgg     540
tctccctgga ggacgtcggc ctggctgact cgcagtggaa gaacgtcacc gtgcaggtgg     600
ctggcgagac ctacagcttg cacgtgggct gcgacctcat agacagcttc gctctggacg     660
agcccttcta cgagcacctg caggcggaaa agagccggat gtacgtggcc aaaggctctg     720
ccagagagag tcacttcagg ggtttgcttc agaacgtcca cctagtgttt gaaaactctg     780
tggaagatat tctaagcaag aagggttgcc agcaaggcca gggagctgag atcaacgcca     840
tcagtgagaa cacagagacg ctgcgcctgg gtccgcatgt caccaccgag tacgtgggcc     900
ccagctcgga ggaggcccc gaggtgtgcg aacgctcgtg cgaggagctg gaaacatgg     960
tccaggagct ctcggggctc cacgtcctcg tgaaccagct cagcgagaac ctcaagagag    1020
tgtcgaatga taaccagttt ctctgggagc tcattggtgg ccctcctaag acaaggaaca    1080
tgtcagcttg ctgcaggat ggccggttct ttgcggaaaa tgaacgtgg gtggtggaca    1140
gctgcaccac gtgtacctgc aagaaattta aaaccatttg ccaccaaatc acctgcccgc    1200
```

```
ctgcaacctg cgccagtcca tcctttgtgg aaggcgaatg ctgcccttcc tgcctccact    1260
cggtggacgg tgaggagggc tggtctccgt gggcagagtg gacccagtgc tccgtgacgt    1320
gtggctctgg gacccagcag agaggccggt cctgtgacgt caccagcaac acctgcttgg    1380
ggccctccat ccagacacgg gcttgcagtc tgagcaagtg tgacacccgc atccggcagg    1440
acggcggctg gagccactgg tcaccttggt cttcatgctc tgtgacctgt ggagttggca    1500
atatcacacg catccgtctc tgcaactccc cagtgcccca gatgggggc aagaattgca    1560 aagggagtgg ccgggagacc aaagcctgcc agggcgcccc atgcccaatc gatggccgct    1620 ggagccctg gtccccgtgg tcggcctgca ctgtcacctg tgccggtggg atccgggagc    1680
gcacccgggt ctgcaacagc cctgagcctc agtacggagg aaggcctgc gtggggatg    1740 tgcaggagcg tcagatgtgc aacaagagga gctgccccgt ggatggctgt ttatccaacc    1800
cctgcttccc gggagcccag tgcagcagct tccccgatgg gtcctggtca tgcggctcct    1860
gccctgtggg cttcttgggc aatggcaccc actgtgagga cctggacgag tgtgccctgg    1920
tccccgacat ctgcttctcc accagcaagg tgcctcgctg tgtcaacact cagcctggct    1980
tccactgcct gccctgcccg ccccgataca gagggaacca gccgtcgggg tcggcctgg    2040 aagcagccaa gacggaaaag caagtgtgtg agcccgaaaa cccatgcaag acaagacac    2100 acaactgcca caagcacgcg gagtgcatct acctgggcca cttcagcgac cccatgtaca    2160
agtgcgagtg ccagacaggc tacgcggcg acgggctcat ctgcggggag gactcggacc    2220
tggacggctg gcccaacctc aatctggtct gcgccaccaa cgccacctac cactgcatca    2280
aggataactg cccccatctg ccaaattctg ggcaggaaga ctttgacaag acgggattg    2340 gcgatgcctg tgatgatgac gatgacaatg acggtgtgac cgatgagaag gacaactgcc    2400
agctcctctt caatccccgc caggctgact atgacaagga tgaggttggg gaccgctgtg    2460
acaactgccc ttacgtgcac aaccctgccc agatcgacac agacaacaat ggagagggtg    2520
acgcctgctc cgtggacatt gatggggacg atgtcttcaa tgaacgagac aattgtccct    2580
acgtctacaa cactgaccag agggacacgg atggtgacgg tgtgggggat cactgtgaca    2640
actgccccct ggtgcacaac cctgaccaga ccgacgtgga caatgacctt gttggggacc    2700
agtgtgacaa caacgaggac atagatgacg acggccacca gaacaaccag gacaactgcc    2760
cctacatctc caacgccaac caggctgacc atgacagaga cggccagggc gacgcctgtg    2820
accctgatga tgacaacgat ggcgtccccg atgacaggga caactgccgg cttgtgttca    2880
acccagacca ggaggacttg gacggtgatg gacggggtga tatttgtaaa gatgattttg    2940
acaatgacaa catcccagat attgatgatg tgtgtcctga aaacaatgcc atcagtgaga    3000
cagacttcag gaacttccag atggtcccct tggatcccaa agggaccacc caaattgatc    3060
ccaactgggt cattcgccat caaggcaagg agctggttca gacagccaac tcggaccccg    3120
gcatcgctgt aggttttgac gagtttgggt ctgtggactt cagtggcaca ttctacgtaa    3180
acactgaccg ggacgacgac tatgccggct tcgtctttgg ttaccagtca gcagccgct    3240 tctatgtggt gatgtggaag caggtgacgc agacctactg ggaggaccag cccacgcggg    3300
cctatggcta ctccggcgtg tccctcaagg tggtgaactc caccacgggg acgggcgagc    3360
acctgaggaa cgcgctgtgg cacacgggga acacgccggg gcaggtgcga accttatggc    3420
acgaccccag gaacattggc tggaaggact acacggccta taggtggcac ctgactcaca    3480
ggcccaagac tggctacatc agagtcttag tgcatgaagg aaaacaggtc atggcagact    3540
caggacctat ctatgaccaa acctacgctg gcgggcggct gggtctattt gtcttctctc    3600
```

```
aagaaatggt ctatttctca gacctcaagt acgaatgcag agatatttaa acaagatttg   3660
ctgcatttcc ggcaatgccc tgtgcatgcc atggtcccta cacacctcag ttcattgtgg   3720
tccttgtggc ttctctctct agcagcacct cctgtcccct gaccttaact ctgatggttc   3780
ttcacctcct gccagcaacc ccaaacccaa gtgccttcag aggataaata tcaatggaac   3840
tcagagatga acatctaacc cactagagga aaccagtttg gtgatatatg agactttatg   3900
tggagtgaaa attgggcatg ccattacatt gcttttttctt gtttgtttaa aaagaatgac   3960
gtttacatat aaaatgtaat tacttattgt atttatgtgt atatggagtt aagggaata    4020 ctgtgcataa gccattatga taaattaagc atgaaaaata ttgctgaact acttttggtg   4080
cttaaagttg tcactattct tgaattagag ttgctctaca atgacacaca aatcccatta   4140
aataaattat aaacaagggt caattcaaat ttgaagtaat gttttagtaa ggagagatta   4200
gaagacaaca ggcatagcaa atgacataag ctaccgatta actaatcgga acatgtaaaa   4260
cagttacaaa aataaacgaa ctctcctctt gtcctacaat gaaagccctc atgtgcagta   4320
gagatgcagt ttcatcaaag aacaaacatc cttgcaaatg ggtgtgacgc ggttccagat   4380
gtggatttgg caaaacctca tttaagtaaa aggttagcag agcaaagtgc ggtgctttag   4440
ctgctgcttg tgccgctgtg gcgtcgggga ggctcctgcc tgagcttcct tccccagctt   4500
tgctgcctga gaggaaccag agcagacgca caggccggaa aaggcgcatc taacgcgtat   4560
ctaggctttg gtaactgcgg acaagttgct tttacctgat ttgatgatac atttcattaa   4620
ggttccagtt ataaatattt tgttaatatt tattaagtga ctatagaatg caactccatt   4680
taccagtaac ttatttttaaa tatgcctagt aacacatatg tagtataatt tctagaaaca   4740
aacatctaat aagtatataa tcctgtgaaa atatgaggct tgataatatt aggttgtcac   4800
gatgaagcat gctagaagct gtaacagaat acatagagaa taatgaggag tttatgatgg   4860
aaccttaaat atataatgtt gccagcgatt ttagttcaat atttgttact gttatctatc   4920
tgctgtatat ggaattcttt taattcaaac gctgaaaaga atcagcatt agtcttgcca    4980 ggcacaccca ataatcagtc atgtgtaata tgcacaagtt tgttttttgtt tttgttttttt   5040 ttgttggttg gtttgttttt ttgctttaag ttgcatgatc tttctgcagg aaatagtcac   5100
tcatcccact ccacataagg ggtttagtaa gagaagtctg tctgtctgat gatgggatagg   5160 gggcaaatct ttttcccctt tctgttaata gtcatcacat ttctatgcca aacaggaaca   5220
atccataact ttagtcttaa tgtacacatt gcattttgat aaaattaatt ttgttgtttc   5280
aaaaaaaaaa aaaaaaaaaa aaaaaaaaaa aaaa   5314
```

<210> SEQ ID NO 33
<211> LENGTH: 613
<212> TYPE: PRT
<213> ORGANISM: Homo sapiens

<400> SEQUENCE: 33

Met Cys Cys Trp Pro Leu Leu Leu Trp Gly Leu Leu Pro Gly Thr
1               5                   10                  15

Ala Ala Gly Gly Ser Gly Arg Thr Tyr Pro His Arg Thr Leu Leu Asp
            20                  25                  30

Ser Glu Gly Lys Tyr Trp Leu Gly Trp Ser Gln Arg Gly Ser Gln Ile
        35                  40                  45

Ala Phe Arg Leu Gln Val Arg Thr Ala Gly Tyr Val Gly Phe Gly Phe
    50                  55                  60

```
Ser Pro Thr Gly Ala Met Ala Ser Ala Asp Ile Val Val Gly Gly Val
 65                  70                  75                  80

Ala His Gly Arg Pro Tyr Leu Gln Asp Tyr Phe Thr Asn Ala Asn Arg
                 85                  90                  95

Glu Leu Lys Lys Asp Ala Gln Gln Asp Tyr His Leu Glu Tyr Ala Met
            100                 105                 110

Glu Asn Ser Thr His Thr Ile Ile Glu Phe Thr Arg Glu Leu His Thr
            115                 120                 125

Cys Asp Ile Asn Asp Lys Ser Ile Thr Asp Ser Thr Val Arg Val Ile
130                 135                 140

Trp Ala Tyr His His Glu Asp Ala Gly Glu Ala Gly Pro Lys Tyr His
145                 150                 155                 160

Asp Ser Asn Arg Gly Thr Lys Ser Leu Arg Leu Leu Asn Pro Glu Lys
                165                 170                 175

Thr Ser Val Leu Ser Thr Ala Leu Pro Tyr Phe Asp Leu Val Asn Gln
            180                 185                 190

Asp Val Pro Ile Pro Asn Lys Asp Thr Thr Tyr Trp Cys Gln Met Phe
            195                 200                 205

Lys Ile Pro Val Phe Gln Glu Lys His His Val Ile Lys Val Glu Pro
210                 215                 220

Val Ile Gln Arg Gly His Glu Ser Leu Val His His Ile Leu Leu Tyr
225                 230                 235                 240

Gln Cys Ser Asn Asn Phe Asn Asp Ser Val Leu Glu Ser Gly His Glu
                245                 250                 255

Cys Tyr His Pro Asn Met Pro Asp Ala Phe Leu Thr Cys Glu Thr Val
                260                 265                 270

Ile Phe Ala Trp Ala Ile Gly Gly Glu Gly Phe Ser Tyr Pro Pro His
            275                 280                 285

Val Gly Leu Ser Leu Gly Thr Pro Leu Asp Pro His Tyr Val Leu Leu
            290                 295                 300

Glu Val His Tyr Asp Asn Pro Thr Tyr Glu Glu Gly Leu Ile Asp Asn
305                 310                 315                 320

Ser Gly Leu Arg Leu Phe Tyr Thr Met Asp Ile Arg Lys Tyr Asp Ala
                325                 330                 335

Gly Val Ile Glu Ala Gly Leu Trp Val Ser Leu Phe His Thr Ile Pro
            340                 345                 350

Pro Gly Met Pro Glu Phe Gln Ser Glu Gly His Cys Thr Leu Glu Cys
            355                 360                 365

Leu Glu Glu Ala Leu Glu Ala Glu Lys Pro Ser Gly Ile His Val Phe
370                 375                 380

Ala Val Leu Leu His Ala His Leu Ala Gly Arg Gly Ile Arg Leu Arg
385                 390                 395                 400

His Phe Arg Lys Gly Lys Glu Met Lys Leu Leu Ala Tyr Asp Asp Asp
                405                 410                 415

Phe Asp Phe Asn Phe Gln Glu Phe Gln Tyr Leu Lys Glu Glu Gln Thr
            420                 425                 430

Ile Leu Pro Gly Asp Asn Leu Ile Thr Glu Cys Arg Tyr Asn Thr Lys
            435                 440                 445

Asp Arg Ala Glu Met Thr Trp Gly Gly Leu Ser Thr Arg Ser Glu Met
450                 455                 460

Cys Leu Ser Tyr Leu Leu Tyr Tyr Pro Arg Ile Asn Leu Thr Arg Cys
465                 470                 475                 480

Ala Ser Ile Pro Asp Ile Met Glu Gln Leu Gln Phe Ile Gly Val Lys
```

|     |     |     | 485 |     |     |     | 490 |     |     |     | 495 |     |
| --- | --- | --- | --- | --- | --- | --- | --- | --- | --- | --- | --- | --- |
| Glu | Ile | Tyr | Arg | Pro | Val | Thr | Thr | Trp | Pro | Phe | Ile | Ile | Lys | Ser | Pro |
|     |     |     | 500 |     |     |     | 505 |     |     |     | 510 |     |

Lys Gln Tyr Lys Asn Leu Ser Phe Met Asp Ala Met Asn Lys Phe Lys
             515                 520                 525

Trp Thr Lys Lys Glu Gly Leu Ser Phe Asn Glu Leu Val Leu Ser Leu
    530                 535                 540

Pro Val Asn Val Arg Cys Ser Lys Thr Asp Asn Ala Glu Trp Ser Ile
545                 550                 555                 560

Gln Gly Met Thr Ala Leu Pro Pro Asp Ile Glu Arg Pro Tyr Lys Ala
                565                 570                 575

Glu Pro Leu Val Cys Gly Thr Ser Ser Ser Ser Leu His Arg Asp
                580                 585                 590

Phe Ser Ile Asn Leu Leu Val Cys Leu Leu Leu Ser Cys Thr Leu
            595                 600                 605

Ser Thr Lys Ser Leu
    610

<210> SEQ ID NO 34
<211> LENGTH: 2188
<212> TYPE: DNA
<213> ORGANISM: Homo sapiens

<400> SEQUENCE: 34

```
ctcctcgttc tgctcctcac tccccagcgg ctggaggccg gtaccggcgg gcaggaggcg      60
cccgaggatg tgctgctggc cgctgctcct gctgtggggg ctgctccccg ggacggcggc     120 gggggggctcg ggccgaacct atccgcaccg accctcctg gactcggagg gcaagtactg     180
gctgggctgg agccagcggg gcagccagat cgccttccgc ctccaggtgc gcactgcagg     240
ctacgtgggc ttcggcttct cgcccaccgg ggccatggcg tccgccgaca tcgtcgtggg     300
cggggtggcc cacgggcggc cctacctcca ggattatttt acaaatgcaa atagagagtt     360
gaaaaaagat gctcagcaag attaccatct agaatatgcc atggaaaata gcacacacac     420
aataattgaa tttaccagag agctgcatac atgtgacata atgacaaga gtataacgga     480 tagcactgtg agagtgatct gggcctacca ccatgaagat gcaggagaag ctggtcccaa     540
gtaccatgac tccaataggg gcaccaagag tttgcggtta ttgaatcctg agaaaactag     600
tgtgctatct acagccttac catactttga tctggtaaat caggacgtcc ccatcccaaa     660
caaagataca acatattggt gccaaatgtt taagattcct gtgttccaag aaaagcatca     720
tgtaataaag gttgagccag tgatacagag aggccatgag agtctggtgc accacatcct     780
gctctatcag tgcagcaaca actttaacga cagcgttctg gagtccggcc acgagtgcta     840
tcaccccaac atgcccgatg cattcctcac ctgtgaaact gtgattttg cctgggctat     900 tggtggagag ggcttttctt atccacctca tgttggatta tcccttggca ctccattaga     960
tccgcattat gtgctcctag aagtccatta tgataatccc acttatgagg aaggcttaat    1020
agataattct ggactgaggt tattttacac aatggatata aggaaatatg atgctgggt     1080 gattgaggct ggcctctggg tgagcctctt ccataccatc cctccaggga tgcctgagtt    1140
ccagtctgag ggtcactgca ctttggagtg cctggaagag gctctggaag ccgaaaagcc    1200
aagtggaatt catgtgtttg ctgttcttct ccatgctcac ctggctggca gaggcatcag    1260
gctgcgtcat tttcgaaaag ggaaggaaat gaaattactt gcctatgatg atgattttga    1320
cttcaatttc caggagtttc agtatctaaa ggaagaacaa acaatcttac caggagataa    1380
```

```
cctaattact gagtgtcgct acaacacgaa agatagagct gagatgactt ggggaggact    1440
aagcaccagg agtgaaatgt gtctctcata ccttctttat tacccaagaa ttaatcttac    1500
tcgatgtgca agtattccag acattatgga acaacttcag ttcattgggg ttaaggagat    1560
ctacagacca gtcacgacct ggcctttcat tatcaaaagt cccaagcaat ataaaaacct    1620
ttctttcatg gatgctatga ataagtttaa atggactaaa aaggaaggtc tctccttcaa    1680
cgagctggtc ctcagcctgc cagtgaatgt gagatgttcc aagacagaca atgctgagtg    1740
gtcgattcaa ggaatgacag cattacctcc agatatagaa agaccctata aagcagaacc    1800
tttggtgtgt ggcacgtctt cttcctcttc cctgcacaga gatttctcca tcaacttgct    1860
tgtttgcctt ctgctactca gctgcacgct gagcaccaag agcttgtgat caaaattctg    1920
ttggacttga caatgttttc tatgatctga acctgtcatt tgaagtacag gttaaagact    1980
gtgtccactt tgggcatgaa gagtgtggag acttttcttc cccatttttcc ctccctcctt    2040 tttcctttcc atgttacatg agagacatca atcaggttct cttctctttc ttagaaatat    2100
ctgatgttat atatacatgg tcaataaaat aaaactggcc tgacttaaga taaccatttt    2160
aaaaaaaaaa aaaaaaaaaa aaaaaaaa                                       2188

<210> SEQ ID NO 35
<211> LENGTH: 500
<212> TYPE: PRT
<213> ORGANISM: Homo sapiens

<400> SEQUENCE: 35

Met Ala Ser Arg Leu Thr Leu Leu Thr Leu Leu Leu Leu Leu Leu Ala
1               5                   10                  15

Gly Asp Arg Ala Ser Ser Asn Pro Asn Ala Thr Ser Ser Ser Ser Gln
            20                  25                  30

Asp Pro Glu Ser Leu Gln Asp Arg Gly Glu Gly Lys Val Ala Thr Thr
        35                  40                  45

Val Ile Ser Lys Met Leu Phe Val Glu Pro Ile Leu Glu Val Ser Ser
    50                  55                  60

Leu Pro Thr Thr Asn Ser Thr Asn Ser Ala Thr Lys Ile Thr Ala
65                  70                  75                  80

Asn Thr Thr Asp Glu Pro Thr Thr Gln Pro Thr Thr Glu Pro Thr Thr
                85                  90                  95

Gln Pro Thr Ile Gln Pro Thr Gln Pro Thr Thr Gln Leu Pro Thr Asp
            100                 105                 110

Ser Pro Thr Gln Pro Thr Thr Gly Ser Phe Cys Pro Gly Pro Val Thr
        115                 120                 125

Leu Cys Ser Asp Leu Glu Ser His Ser Thr Glu Ala Val Leu Gly Asp
    130                 135                 140

Ala Leu Val Asp Phe Ser Leu Lys Leu Tyr His Ala Phe Ser Ala Met
145                 150                 155                 160

Lys Lys Val Glu Thr Asn Met Ala Phe Ser Pro Phe Ser Ile Ala Ser
                165                 170                 175

Leu Leu Thr Gln Val Leu Leu Gly Ala Gly Glu Asn Thr Lys Thr Asn
            180                 185                 190

Leu Glu Ser Ile Leu Ser Tyr Pro Lys Asp Phe Thr Cys Val His Gln
        195                 200                 205

Ala Leu Lys Gly Phe Thr Thr Lys Gly Val Thr Ser Val Ser Gln Ile
    210                 215                 220
```

```
Phe His Ser Pro Asp Leu Ala Ile Arg Asp Thr Phe Val Asn Ala Ser
225                 230                 235                 240

Arg Thr Leu Tyr Ser Ser Pro Arg Val Leu Ser Asn Asn Ser Asp
            245                 250                 255

Ala Asn Leu Glu Leu Ile Asn Thr Trp Val Ala Lys Asn Thr Asn Asn
            260                 265                 270

Lys Ile Ser Arg Leu Leu Asp Ser Leu Pro Ser Asp Thr Arg Leu Val
            275                 280                 285

Leu Leu Asn Ala Ile Tyr Leu Ser Ala Lys Trp Lys Thr Thr Phe Asp
            290                 295                 300

Pro Lys Lys Thr Arg Met Glu Pro Phe His Phe Lys Asn Ser Val Ile
305                 310                 315                 320

Lys Val Pro Met Met Asn Ser Lys Lys Tyr Pro Val Ala His Phe Ile
                325                 330                 335

Asp Gln Thr Leu Lys Ala Lys Val Gly Gln Leu Gln Leu Ser His Asn
            340                 345                 350

Leu Ser Leu Val Ile Leu Val Pro Gln Asn Leu Lys His Arg Leu Glu
            355                 360                 365

Asp Met Glu Gln Ala Leu Ser Pro Ser Val Phe Lys Ala Ile Met Glu
370                 375                 380

Lys Leu Glu Met Ser Lys Phe Gln Pro Thr Leu Leu Thr Leu Pro Arg
385                 390                 395                 400

Ile Lys Val Thr Thr Ser Gln Asp Met Leu Ser Ile Met Glu Lys Leu
                405                 410                 415

Glu Phe Phe Asp Phe Ser Tyr Asp Leu Asn Leu Cys Gly Leu Thr Glu
            420                 425                 430

Asp Pro Asp Leu Gln Val Ser Ala Met Gln His Gln Thr Val Leu Glu
            435                 440                 445

Leu Thr Glu Thr Gly Val Glu Ala Ala Ala Ser Ala Ile Ser Val
450                 455                 460

Ala Arg Thr Leu Leu Val Phe Glu Val Gln Gln Pro Phe Leu Phe Val
465                 470                 475                 480

Leu Trp Asp Gln Gln His Lys Phe Pro Val Phe Met Gly Arg Val Tyr
            485                 490                 495

Asp Pro Arg Ala
            500

<210> SEQ ID NO 36
<211> LENGTH: 1832
<212> TYPE: DNA
<213> ORGANISM: Homo sapiens

<400> SEQUENCE: 36
gctggctggc tccgcaggtc cgctgacgtc gccgcccaga tggcctccag gctgaccctg      60
ctgaccctcc tgctgctgct gctggctggg gatagagcct cctcaaatcc aaatgctacc     120
agctccagct cccaggatcc agagagtttg caagacagag cgaagggaa ggtcgcaaca      180 acagttatct ccaagatgct attcgttgaa cccatcctgg aggtttccag cttgccgaca     240
accaactcaa caaccaattc agccaccaaa ataacagcta ataccactga tgaacccacc     300
acacaaccca ccacagagcc caccacccaa cccaccatcc aacccaccca accaactacc     360
cagctcccaa cagattctcc tacccagccc actactgggt ccttctgccc aggacctgtt     420
actctctgct ctgacttgga gagtcattca acagaggccg tgttgggga tgctttggta      480 gatttctccc tgaagctcta ccacgccttc tcagcaatga agaaggtgga gaccaacatg     540
```

```
gccttttccc cattcagcat cgccagcctc cttacccagg tcctgctcgg ggctggggag      600
aacaccaaaa caaacctgga gagcatcctc tcttacccca aggacttcac ctgtgtccac      660
caggccctga agggcttcac gaccaaaggt gtcacctcag tctctcagat cttccacagc      720
ccagacctgg ccataaggga cacctttgtg aatgcctctc ggaccctgta cagcagcagc      780
cccagagtcc taagcaacaa cagtgacgcc aacttggagc tcatcaacac ctgggtggcc      840
aagaacacca caacaagat cagccggctg ctagacagtc tgccctccga tacccgcctt       900
gtcctcctca atgctatcta cctgagtgcc aagtggaaga caacatttga tcccaagaaa      960
accagaatgg aaccctttca cttcaaaaac tcagttataa agtgcccat gatgaatagc      1020 aagaagtacc ctgtggccca tttcattgac caaactttga agccaaggt ggggcagctg       1080 cagctctccc acaatctgag tttggtgatc ctggtacccc agaacctgaa acatcgtctt      1140
gaagacatgg aacaggctct cagcccttct gttttcaagg ccatcatgga gaaactggag      1200
atgtccaagt ccagcccac ctcctaaca ctaccccgca tcaaagtgac gaccagccag        1260
gatatgctct caatcatgga gaaattggaa ttcttcgatt tttcttatga ccttaacctg      1320
tgtgggctga cagaggaccc agatcttcag gtttctgcga tgcagcacca gacagtgctg      1380
gaactgacag agactggggt ggaggcggct gcagcctccg ccatctctgt ggcccgcacc      1440
ctgctggtct ttgaagtgca gcagcccttc ctcttcgtgc tctgggacca gcagcacaag      1500
ttccctgtct tcatggggcg agtatatgac cccagggcct gagacctgca ggatcaggtt      1560
agggcgagcg ctacctctcc agcctcagct ctcagttgca gccctgctgc tgcctgcctg      1620
gacttggccc ctgccacctc ctgcctcagg tgtccgctat ccaccaaaag ggctccctga      1680
gggtctgggc aagggacctg cttctattag cccttctcca tggccctgcc atgtctccca      1740
aaccactttt tgcagctttc tctagttcaa gttcaccaga ctctataaat aaaacctgac      1800
agaccatgac tttcaaaaaa aaaaaaaaaa aa                                    1832
```

<210> SEQ ID NO 37
<211> LENGTH: 500
<212> TYPE: PRT
<213> ORGANISM: Homo sapiens

<400> SEQUENCE: 37

```
Met Ala Ser Arg Leu Thr Leu Leu Thr Leu Leu Leu Leu Leu Leu Ala
1               5                   10                  15

Gly Asp Arg Ala Ser Ser Asn Pro Asn Ala Thr Ser Ser Ser Ser Gln
            20                  25                  30

Asp Pro Glu Ser Leu Gln Asp Arg Gly Glu Gly Lys Val Ala Thr Thr
        35                  40                  45

Val Ile Ser Lys Met Leu Phe Val Glu Pro Ile Leu Glu Val Ser Ser
    50                  55                  60

Leu Pro Thr Thr Asn Ser Thr Thr Asn Ser Ala Thr Lys Ile Thr Ala
65                  70                  75                  80

Asn Thr Thr Asp Glu Pro Thr Thr Gln Pro Thr Thr Glu Pro Thr Thr
                85                  90                  95

Gln Pro Thr Ile Gln Pro Thr Gln Pro Thr Thr Gln Leu Pro Thr Asp
            100                 105                 110

Ser Pro Thr Gln Pro Thr Thr Gly Ser Phe Cys Pro Gly Pro Val Thr
        115                 120                 125

Leu Cys Ser Asp Leu Glu Ser His Ser Thr Glu Ala Val Leu Gly Asp
    130                 135                 140
```

```
Ala Leu Val Asp Phe Ser Leu Lys Leu Tyr His Ala Phe Ser Ala Met
145                 150                 155                 160

Lys Lys Val Glu Thr Asn Met Ala Phe Ser Pro Phe Ser Ile Ala Ser
                165                 170                 175

Leu Leu Thr Gln Val Leu Leu Gly Ala Gly Glu Asn Thr Lys Thr Asn
            180                 185                 190

Leu Glu Ser Ile Leu Ser Tyr Pro Lys Asp Phe Thr Cys Val His Gln
        195                 200                 205

Ala Leu Lys Gly Phe Thr Thr Lys Gly Val Thr Ser Val Ser Gln Ile
    210                 215                 220

Phe His Ser Pro Asp Leu Ala Ile Arg Asp Thr Phe Val Asn Ala Ser
225                 230                 235                 240

Arg Thr Leu Tyr Ser Ser Pro Arg Val Leu Ser Asn Asn Ser Asp
                245                 250                 255

Ala Asn Leu Glu Leu Ile Asn Thr Trp Val Ala Lys Asn Thr Asn Asn
            260                 265                 270

Lys Ile Ser Arg Leu Leu Asp Ser Leu Pro Ser Asp Thr Arg Leu Val
        275                 280                 285

Leu Leu Asn Ala Ile Tyr Leu Ser Ala Lys Trp Lys Thr Thr Phe Asp
    290                 295                 300

Pro Lys Lys Thr Arg Met Glu Pro Phe His Phe Lys Asn Ser Val Ile
305                 310                 315                 320

Lys Val Pro Met Met Asn Ser Lys Lys Tyr Pro Val Ala His Phe Ile
                325                 330                 335

Asp Gln Thr Leu Lys Ala Lys Val Gly Gln Leu Gln Leu Ser His Asn
            340                 345                 350

Leu Ser Leu Val Ile Leu Val Pro Gln Asn Leu Lys His Arg Leu Glu
        355                 360                 365

Asp Met Glu Gln Ala Leu Ser Pro Ser Val Phe Lys Ala Ile Met Glu
    370                 375                 380

Lys Leu Glu Met Ser Lys Phe Gln Pro Thr Leu Leu Thr Leu Pro Arg
385                 390                 395                 400

Ile Lys Val Thr Thr Ser Gln Asp Met Leu Ser Ile Met Glu Lys Leu
                405                 410                 415

Glu Phe Phe Asp Phe Ser Tyr Asp Leu Asn Leu Cys Gly Leu Thr Glu
            420                 425                 430

Asp Pro Asp Leu Gln Val Ser Ala Met Gln His Gln Thr Val Leu Glu
        435                 440                 445

Leu Thr Glu Thr Gly Val Glu Ala Ala Ala Ala Ser Ala Ile Ser Val
    450                 455                 460

Ala Arg Thr Leu Leu Val Phe Glu Val Gln Gln Pro Phe Leu Phe Val
465                 470                 475                 480

Leu Trp Asp Gln Gln His Lys Phe Pro Val Phe Met Gly Arg Val Tyr
                485                 490                 495

Asp Pro Arg Ala
        500

<210> SEQ ID NO 38
<211> LENGTH: 1149
<212> TYPE: DNA
<213> ORGANISM: Homo sapiens

<400> SEQUENCE: 38
atgaggtcac ccctctgctg gctcctccca cttctcatct tggcctcagt ggcccaaggc    60
```

```
cagccaacaa gacgaccaag acccgggact gggcccgggc gcagacccag gcccaggccc      120
aggcccacac ccagctttcc tcagcctgat gaaccagcag agccaacaga cctgcctcct      180
cccctccctc caggccctcc atctatcttc cctgactgtc ccgcgaatg ctactgcccc      240 cctgatttcc catctgccct ctactgtgat agccgcaacc tgcgaaaggt ccctgtcatc      300
ccgccccgca tccattacct ctatctccag aacaacttca tcactgagct cccggtggag      360
tccttccaga atgccacagg cctgcgatgg attaacctgg acaacaaccg aatccgcaag      420
atagaccaga gggtgctgga gaaactgccc ggcctggtgt tcctctacat ggagaagaac      480
cagttggaag aggtcccctc ggccctgccc cggaacctgg agcagctgag gctgagccag      540
aaccacatct ccagaatccc gcctggtgtc ttcagcaagc tggagaacct gctgctcctg      600
gatctccagc acaacaggct gagcgacggc gtcttcaagc ccgacacctt ccatggcctc      660
aagaacctca tgcagctcaa cctggcccac aacatcctga aaagatgcc gcccagggtc      720 cccaccgcca ttcaccagct ctacctggac agtaacaaga ttgagaccat ccctaacgga      780
tacttcaaga gctttcccaa tcttgccttc attcggctta actacaacaa gctgacagac      840
aggggactcc ccaagaactc ctttaatatc tccaacctgc ttgtgctcca cctgtcccac      900
aacaggatca gcagtgtgcc cgccatcaac aacaggctgg aacacctgta cctcaacaac      960
aatagcatcg agaaaatcaa cggaacccag atttgcccca cgacctagt ggcgttccat     1020 gacttctcct cggacctgga gaacgtgcca cacctgcgct acctgcggct ggatggaaac     1080
tacttgaagc cgcccatccc gctggacctc atgatgtgct ccgcctcct gcagtccgtg     1140 gtcatctag                                                             1149
```

<210> SEQ ID NO 39
<211> LENGTH: 61
<212> TYPE: PRT
<213> ORGANISM: Homo sapiens

<400> SEQUENCE: 39

Met Lys Arg Phe Leu Phe Leu Leu Thr Ile Ser Leu Leu Val Met
1               5                   10                  15

Val Gln Ile Gln Thr Gly Leu Ser Gly Gln Asn Asp Thr Ser Gln Thr
            20                  25                  30

Ser Ser Pro Ser Ala Ser Ser Ser Met Ser Gly Gly Ile Phe Leu Phe
        35                  40                  45

Phe Val Ala Asn Ala Ile Ile His Leu Phe Cys Phe Ser
    50                  55                  60

<210> SEQ ID NO 40
<211> LENGTH: 467
<212> TYPE: DNA
<213> ORGANISM: Homo sapiens

<400> SEQUENCE: 40

```
ctaaaaagct gctaccaaga cagccacgaa gatcctacca aaatgaagcg cttcctcttc       60
ctcctactca ccatcagcct cctggttatg gtacagatac aaactggact ctcaggacaa      120
aacgacacca gccaaaccag cagcccctca gcatccagca gcatgagcgg aggcattttc      180 ctttctcttcg tggccaatgc cataatccac ctcttctgct tcagttgagg tgacacgtct      240
cagccttagc cctgtgcccc ctgaaacagc tgccaccatc actcgcaaga gaatcccctc      300
catctttggg aggggttgat gccagacatc accaggttgt agaagttgac aggcagtgcc      360
```

-continued

```
atgggggcaa cagccaaaat aggggggtaa tgatgtaggg gccaagcagt gcccagctgg      420
gggtcaataa agttacccct tgtacttgcaa aaaaaaaaaa aaaaaaa                  467
```

<210> SEQ ID NO 41
<211> LENGTH: 1821
<212> TYPE: PRT
<213> ORGANISM: Homo sapiens

<400> SEQUENCE: 41

```
Met Arg Pro Arg Thr Lys Ala Arg Ser Pro Gly Arg Ala Leu Arg Asn
1               5                   10                  15

Pro Trp Arg Gly Phe Leu Pro Leu Thr Leu Ala Leu Phe Val Gly Ala
            20                  25                  30

Gly His Ala Gln Arg Asp Pro Val Gly Arg Tyr Glu Pro Ala Gly Gly
        35                  40                  45

Asp Ala Asn Arg Leu Arg Arg Pro Gly Gly Ser Tyr Pro Ala Ala Ala
    50                  55                  60

Ala Ala Lys Val Tyr Ser Leu Phe Arg Glu Gln Asp Ala Pro Val Ala
65                  70                  75                  80

Gly Leu Gln Pro Val Glu Arg Ala Gln Pro Gly Trp Gly Ser Pro Arg
                85                  90                  95

Arg Pro Thr Glu Ala Glu Ala Arg Arg Pro Ser Arg Ala Gln Gln Ser
            100                 105                 110

Arg Arg Val Gln Pro Pro Ala Gln Thr Arg Arg Ser Thr Pro Leu Gly
        115                 120                 125

Gln Gln Gln Pro Ala Pro Arg Thr Arg Ala Ala Pro Ala Leu Pro Arg
    130                 135                 140

Leu Gly Thr Pro Gln Arg Ser Gly Ala Ala Pro Pro Thr Pro Pro Arg
145                 150                 155                 160

Gly Arg Leu Thr Gly Arg Asn Val Cys Gly Gly Gln Cys Cys Pro Gly
                165                 170                 175

Trp Thr Thr Ala Asn Ser Thr Asn His Cys Ile Lys Pro Val Cys Glu
            180                 185                 190

Pro Pro Cys Gln Asn Arg Gly Ser Cys Ser Arg Pro Gln Leu Cys Val
        195                 200                 205

Cys Arg Ser Gly Phe Arg Gly Ala Arg Cys Glu Glu Val Ile Pro Asp
    210                 215                 220

Glu Glu Phe Asp Pro Gln Asn Ser Arg Leu Ala Pro Arg Arg Trp Ala
225                 230                 235                 240

Glu Arg Ser Pro Asn Leu Arg Arg Ser Ser Ala Ala Gly Glu Gly Thr
                245                 250                 255

Leu Ala Arg Ala Gln Pro Pro Ala Pro Gln Ser Pro Pro Ala Pro Gln
            260                 265                 270

Ser Pro Pro Ala Gly Thr Leu Ser Gly Leu Ser Gln Thr His Pro Ser
        275                 280                 285

Gln Gln His Val Gly Leu Ser Arg Thr Val Arg Leu His Pro Thr Ala
    290                 295                 300

Thr Ala Ser Ser Gln Leu Ser Ser Asn Ala Leu Pro Pro Gly Pro Gly
305                 310                 315                 320

Leu Glu Gln Arg Asp Gly Thr Gln Gln Ala Val Pro Leu Glu His Pro
                325                 330                 335

Ser Ser Pro Trp Gly Leu Asn Leu Thr Glu Lys Ile Lys Lys Ile Lys
            340                 345                 350

Ile Val Phe Thr Pro Thr Ile Cys Lys Gln Thr Cys Ala Arg Gly His
```

-continued

```
              355                 360                 365
Cys Ala Asn Ser Cys Glu Arg Gly Asp Thr Thr Leu Tyr Ser Gln
            370                 375                 380
Gly Gly His Gly His Asp Pro Lys Ser Gly Phe Arg Ile Tyr Phe Cys
385                 390                 395                 400
Gln Ile Pro Cys Leu Asn Gly Arg Cys Ile Gly Arg Asp Glu Cys
                405                 410                 415
Trp Cys Pro Ala Asn Ser Thr Gly Lys Phe Cys His Leu Pro Ile Pro
                420                 425                 430
Gln Pro Asp Arg Glu Pro Pro Gly Arg Gly Ser Arg Pro Arg Ala Leu
            435                 440                 445
Leu Glu Ala Pro Leu Lys Gln Ser Thr Phe Thr Leu Pro Leu Ser Asn
        450                 455                 460
Gln Leu Ala Ser Val Asn Pro Ser Leu Val Lys Val His Ile His His
465                 470                 475                 480
Pro Pro Glu Ala Ser Val Gln Ile His Gln Val Ala Gln Val Arg Gly
                485                 490                 495
Gly Val Glu Glu Ala Leu Val Glu Asn Ser Val Glu Thr Arg Pro Pro
            500                 505                 510
Pro Trp Leu Pro Ala Ser Pro Gly His Ser Leu Trp Asp Ser Asn Asn
        515                 520                 525
Ile Pro Ala Arg Ser Gly Glu Pro Arg Pro Leu Pro Pro Ala Ala
530                 535                 540
Pro Arg Pro Arg Gly Leu Leu Gly Arg Cys Tyr Leu Asn Thr Val Asn
545                 550                 555                 560
Gly Gln Cys Ala Asn Pro Leu Leu Glu Leu Thr Thr Gln Glu Asp Cys
                565                 570                 575
Cys Gly Ser Val Gly Ala Phe Trp Gly Val Thr Leu Cys Ala Pro Cys
                580                 585                 590
Pro Pro Arg Pro Ala Ser Pro Val Ile Glu Asn Gly Gln Leu Glu Cys
                595                 600                 605
Pro Gln Gly Tyr Lys Arg Leu Asn Leu Thr His Cys Gln Asp Ile Asn
            610                 615                 620
Glu Cys Leu Thr Leu Gly Leu Cys Lys Asp Ala Glu Cys Val Asn Thr
625                 630                 635                 640
Arg Gly Ser Tyr Leu Cys Thr Cys Arg Pro Gly Leu Met Leu Asp Pro
                645                 650                 655
Ser Arg Ser Arg Cys Val Ser Asp Lys Ala Ile Ser Met Leu Gln Gly
                660                 665                 670
Leu Cys Tyr Arg Ser Leu Gly Pro Gly Thr Cys Thr Leu Pro Leu Ala
            675                 680                 685
Gln Arg Ile Thr Lys Gln Ile Cys Cys Cys Ser Arg Val Gly Lys Ala
        690                 695                 700
Trp Gly Ser Glu Cys Glu Lys Cys Pro Leu Pro Gly Thr Glu Ala Phe
705                 710                 715                 720
Arg Glu Ile Cys Pro Ala Gly His Gly Tyr Thr Tyr Ala Ser Ser Asp
                725                 730                 735
Ile Arg Leu Ser Met Arg Lys Ala Glu Glu Glu Leu Ala Arg Pro
            740                 745                 750
Pro Arg Glu Gln Gly Gln Arg Ser Ser Gly Ala Leu Pro Gly Pro Ala
        755                 760                 765
Glu Arg Gln Pro Leu Arg Val Val Thr Asp Thr Trp Leu Glu Ala Gly
            770                 775                 780
```

-continued

Thr Ile Pro Asp Lys Gly Asp Ser Gln Ala Gly Gln Val Thr Thr Ser
785                 790                 795                 800

Val Thr His Ala Pro Ala Trp Val Thr Gly Asn Ala Thr Pro Pro
        805                 810                 815

Met Pro Glu Gln Gly Ile Ala Glu Ile Gln Glu Glu Val Thr Pro
        820                 825                 830

Ser Thr Asp Val Leu Val Thr Leu Ser Thr Pro Gly Ile Asp Arg Cys
        835                 840                 845

Ala Ala Gly Ala Thr Asn Val Cys Gly Pro Gly Thr Cys Val Asn Leu
        850                 855                 860

Pro Asp Gly Tyr Arg Cys Val Cys Ser Pro Gly Tyr Gln Leu His Pro
865                 870                 875                 880

Ser Gln Ala Tyr Cys Thr Asp Asp Asn Glu Cys Leu Arg Asp Pro Cys
                885                 890                 895

Lys Gly Lys Gly Arg Cys Ile Asn Arg Val Gly Ser Tyr Ser Cys Phe
                900                 905                 910

Cys Tyr Pro Gly Tyr Thr Leu Ala Thr Ser Gly Ala Thr Gln Glu Cys
            915                 920                 925

Gln Asp Ile Asn Glu Cys Glu Gln Pro Gly Val Cys Ser Gly Gly Gln
930                 935                 940

Cys Thr Asn Thr Glu Gly Ser Tyr His Cys Glu Cys Asp Gln Gly Tyr
945                 950                 955                 960

Ile Met Val Arg Lys Gly His Cys Gln Asp Ile Asn Glu Cys Arg His
                965                 970                 975

Pro Gly Thr Cys Pro Asp Gly Arg Cys Val Asn Ser Pro Gly Ser Tyr
            980                 985                 990

Thr Cys Leu Ala Cys Glu Glu Gly Tyr Arg Gly Gln Ser  Gly Ser Cys
        995                 1000                1005

Val Asp Val Asn Glu Cys Leu Thr Pro Gly Val Cys  Ala His Gly
    1010                1015                1020

Lys Cys Thr Asn Leu Glu Gly Ser Phe Arg Cys Ser  Cys Glu Gln
    1025                1030                1035

Gly Tyr Glu Val Thr Ser Asp Glu Lys Gly Cys Gln  Asp Val Asp
    1040                1045                1050

Glu Cys Ala Ser Arg Ala Ser Cys Pro Thr Gly Leu  Cys Leu Asn
    1055                1060                1065

Thr Glu Gly Ser Phe Ala Cys Ser Ala Cys Glu Asn  Gly Tyr Trp
    1070                1075                1080

Val Asn Glu Asp Gly Thr Ala Cys Glu Asp Leu Asp  Glu Cys Ala
    1085                1090                1095

Phe Pro Gly Val Cys Pro Ser Gly Val Cys Thr Asn  Thr Ala Gly
    1100                1105                1110

Ser Phe Ser Cys Lys Asp Cys Asp Gly Gly Tyr Arg  Pro Ser Pro
    1115                1120                1125

Leu Gly Asp Ser Cys Glu Asp Val Asp Glu Cys Glu  Asp Pro Gln
    1130                1135                1140

Ser Ser Cys Leu Gly Gly Glu Cys Lys Asn Thr Val  Gly Ser Tyr
    1145                1150                1155

Gln Cys Leu Cys Pro Gln Gly Phe Gln Leu Ala Asn  Gly Thr Val
    1160                1165                1170

Cys Glu Asp Val Asn Glu Cys Met Gly Glu Glu His  Cys Ala Pro
    1175                1180                1185

-continued

His Gly Glu Cys Leu Asn Ser His Gly Ser Phe Phe Cys Leu Cys
1190                1195                1200

Ala Pro Gly Phe Val Ser Ala Glu Gly Gly Thr Ser Cys Gln Asp
1205                1210                1215

Val Asp Glu Cys Ala Thr Thr Asp Pro Cys Val Gly Gly His Cys
1220                1225                1230

Val Asn Thr Glu Gly Ser Phe Asn Cys Leu Cys Glu Thr Gly Phe
1235                1240                1245

Gln Pro Ser Pro Glu Ser Gly Glu Cys Val Asp Ile Asp Glu Cys
1250                1255                1260

Glu Asp Tyr Gly Asp Pro Val Cys Gly Thr Trp Lys Cys Glu Asn
1265                1270                1275

Ser Pro Gly Ser Tyr Arg Cys Val Leu Gly Cys Gln Pro Gly Phe
1280                1285                1290

His Met Ala Pro Asn Gly Asp Cys Ile Asp Ile Asp Glu Cys Ala
1295                1300                1305

Asn Asp Thr Met Cys Gly Ser His Gly Phe Cys Asp Asn Thr Asp
1310                1315                1320

Gly Ser Phe Arg Cys Leu Cys Asp Gln Gly Phe Glu Ile Ser Pro
1325                1330                1335

Ser Gly Trp Asp Cys Val Asp Val Asn Glu Cys Glu Leu Met Leu
1340                1345                1350

Ala Val Cys Gly Ala Ala Leu Cys Glu Asn Val Glu Gly Ser Phe
1355                1360                1365

Leu Cys Leu Cys Ala Ser Asp Leu Glu Glu Tyr Asp Ala Gln Glu
1370                1375                1380

Gly His Cys Arg Pro Arg Gly Ala Gly Gly Gln Ser Met Ser Glu
1385                1390                1395

Ala Pro Thr Gly Asp His Ala Pro Ala Pro Thr Arg Met Asp Cys
1400                1405                1410

Tyr Ser Gly Gln Lys Gly His Ala Pro Cys Ser Ser Val Leu Gly
1415                1420                1425

Arg Asn Thr Thr Gln Ala Glu Cys Cys Cys Thr Gln Gly Ala Ser
1430                1435                1440

Trp Gly Asp Ala Cys Asp Leu Cys Pro Ser Glu Asp Ser Ala Glu
1445                1450                1455

Phe Ser Glu Ile Cys Pro Ser Gly Lys Gly Tyr Ile Pro Val Glu
1460                1465                1470

Gly Ala Trp Thr Phe Gly Gln Thr Met Tyr Thr Asp Ala Asp Glu
1475                1480                1485

Cys Val Ile Phe Gly Pro Gly Leu Cys Pro Asn Gly Arg Cys Leu
1490                1495                1500

Asn Thr Val Pro Gly Tyr Val Cys Leu Cys Asn Pro Gly Phe His
1505                1510                1515

Tyr Asp Ala Ser His Lys Lys Cys Glu Asp His Asp Glu Cys Gln
1520                1525                1530

Asp Leu Ala Cys Glu Asn Gly Glu Cys Val Asn Thr Glu Gly Ser
1535                1540                1545

Phe His Cys Phe Cys Ser Pro Pro Leu Thr Leu Asp Leu Ser Gln
1550                1555                1560

Gln Arg Cys Met Asn Ser Thr Ser Ser Thr Glu Asp Leu Pro Asp
1565                1570                1575

His Asp Ile His Met Asp Ile Cys Trp Lys Lys Val Thr Asn Asp

```
                1580                1585                1590
Val Cys Ser Glu Pro Leu Arg Gly His Arg Thr Thr Tyr Thr Glu
    1595                1600                1605

Cys Cys Cys Gln Asp Gly Glu Ala Trp Ser Gln Gln Cys Ala Leu
    1610                1615                1620

Cys Pro Pro Arg Ser Ser Glu Val Tyr Ala Gln Leu Cys Asn Val
    1625                1630                1635

Ala Arg Ile Glu Ala Glu Arg Glu Ala Gly Val His Phe Arg Pro
    1640                1645                1650

Gly Tyr Glu Tyr Gly Pro Gly Pro Asp Asp Leu His Tyr Ser Ile
    1655                1660                1665

Tyr Gly Pro Asp Gly Ala Pro Phe Tyr Asn Tyr Leu Gly Pro Glu
    1670                1675                1680

Asp Thr Val Pro Asp Pro Ala Phe Pro Asn Thr Ala Gly His Ser
    1685                1690                1695

Ala Asp Arg Thr Pro Ile Leu Glu Ser Pro Leu Gln Pro Ser Glu
    1700                1705                1710

Leu Gln Pro His Tyr Val Ala Ser His Pro Glu Pro Pro Ala Gly
    1715                1720                1725

Phe Glu Gly Leu Gln Ala Glu Glu Cys Gly Ile Leu Asn Gly Cys
    1730                1735                1740

Glu Asn Gly Arg Cys Val Arg Val Arg Glu Gly Tyr Thr Cys Asp
    1745                1750                1755

Cys Phe Glu Gly Phe Gln Leu Asp Ala Ala His Met Ala Cys Val
    1760                1765                1770

Asp Val Asn Glu Cys Asp Asp Leu Asn Gly Pro Ala Val Leu Cys
    1775                1780                1785

Val His Gly Tyr Cys Glu Asn Thr Glu Gly Ser Tyr Arg Cys His
    1790                1795                1800

Cys Ser Pro Gly Tyr Val Ala Glu Ala Gly Pro Pro His Cys Thr
    1805                1810                1815

Ala Lys Glu
    1820

<210> SEQ ID NO 42
<211> LENGTH: 6901
<212> TYPE: DNA
<213> ORGANISM: Homo sapiens

<400> SEQUENCE: 42
ccaaaaataa aaccgtccgg gtccccttca gacggctgca ggcacaggga ggaggcgcga    60
aggtgcagca gccgtgcgag cccagctgga gtaggagcgc ggactcgagg ctcggggcgc   120
gcagccctcg ttccgccgag agccgggccc ccagtcggcc gcttcagggc cccctagact   180
cagagaagct ggccgccggg cggggccggg agaacagccc gcgggcgtcc agcgtgccga   240
ccacaaagct cttcgcggtg cccgcgcgca ccactctcca gccgccccgc gccatgaggc   300
cgcggaccaa agcccgcagc ccggggcgcg ccctgcggaa cccctggaga ggcttcctgc   360
cgctcaccct ggctctcttc gtgggcgcgg gtcatgccca aagggacccc gtagggagat   420
acgagccggc tggtggagac gcgaatcgac tgcggcgccc tggggcagc tacccggcag   480 cggctgcagc caaggtgtac agtctgttcc gggagcagga cgcgcctgtc gcgggcttgc   540
agcccgtgga gcgggcccag ccgggctggg ggagccccag gaggcccacc gaggcggagg   600
ccaggaggcc gtcccgcgcg cagcagtcgc ggcgtgtcca gccacctgcg cagacccgga   660
```

-continued

```
gaagcactcc cctgggccag cagcaaccag cacccggac ccgggccgcg ccggctctcc      720
cacgcctggg gaccccacag cggtctgggg ctgcgccccc aacccgccg cgagggcgac      780 tcacggggag gaacgtctgc gggggacagt gctgcccagg atggacaaca gcaaacagca    840
ccaaccactg tatcaaaccc gtttgcgagc cgccgtgcca gaaccgggc tcctgcagcc     900 gcccgcagct ctgtgtctgc cgctctggtt tccgtggagc ccgctgcgag gaggtcattc    960
ccgatgagga atttgacccc cagaactcca ggctggcacc tcgacgctgg gccgagcgtt   1020
cacccaacct gcgcaggagc agtgcggctg gagagggcac cttggccaga gcacagccgc   1080
cagcaccaca gtcgccgccc gcaccacagt cgccaccagc tgggaccctg agtggcctca   1140
gccagaccca cccttcccag cagcacgtgg ggttgtcccg cactgtccga cttcacccga   1200
ctgccacggc cagtagccag ctctcttcca acgccctgcc cccgggacca ggccttgagc   1260
agagagatgg cacccaacag gcggtacctc tggagcaccc ctcatccccc tgggggctga   1320
acctcacgga gaaaatcaag aagatcaaga tcgtcttcac tcccaccatc tgcaagcaga   1380
cctgtgcccg tggacactgt gccaacagct gtgagagggg cgacaccacc accctgtaca   1440
gccagggcgg ccatgggcac gatcccaagt ctggcttccg catctatttc tgccagatcc   1500
cctgcctgaa cggaggccgc tgcatcggca gggacgaatg ctggtgcccc gccaactcca   1560
ccgggaagtt ctgccacctg cctatcccgc agcggacag ggagcctcca gggaggggt    1620 cccgcccag ggccttgctg gaagcccac tgaagcagtc cactttcaca ctgccgctct    1680
ccaaccagct ggcctccgtg aaccctccc tggtgaaggt gcacattcac cacccacccg   1740
aggcctcagt gcagatccac caggtggccc aggtgcgggg cggggtggag gaggccctag   1800
tggagaacag cgtggagacc agaccccgc cctggctgcc tgccagccct ggccacagcc   1860
tctgggacag caacaacatc cctgctcggt ctggagagcc cctcggcca ctgccccag    1920 cagcacccag gcctcgagga ctgctgggcc ggtgttacct gaacactgtg aacggacagt   1980
gtgccaaccc tctgctggag ctgactaccc aggaggactg ctgtggcagt gtgggagcct   2040 tctgggggt gactttgtgt gccccatgcc cacccagacc agcctccccg gtgattgaga   2100
atggccagct ggagtgtcct cagggtaca agagactgaa cctcactcac tgccaagata   2160
tcaacgagtg cttgaccctg ggcctgtgca aggacgcgga gtgtgtgaat accaggggca   2220
gctacctgtg cacatgcaga cctggcctca tgctggatcc atcgcggagc cgctgtgtgt   2280
cggacaaggc aatctccatg ctgcaggac tgtgctaccg gtcgctgggg cccggcacct   2340
gcaccctgcc tttggcccag cggatcacca agcagatatg ctgctgcagc cgcgtgggca   2400
aagcatgggg cagcgagtgt gagaaatgcc ctctgcctgg cacagaggcc ttcagagaga   2460
tctgccctgc cggccacggc tacacctacg cgagctccga catccgcctg tccatgagga   2520
aagccgagga ggaggaactg gcaaggcccc caagggagca agggcagagg agcagcgggg   2580
cactgccggg gccagcagag aggcagcccc tccgggtcgt cacggacacc tggcttgagg   2640
ccgggaccat ccctgacaag ggtgactctc aggctggcca ggtcacgacc agtgtcactc   2700
atgcacctgc ctgggtcaca gggaatgcca caaccccacc aatgcctgaa caggggattg   2760
cagagataca ggaagaacaa gtgaccccct ccaccgatgt gctggtgacc ctgagcaccc   2820
caggcattga cagatgcgct gctggagcca ccaacgtctg tggccctgga acctgcgtga   2880
acctccccga tggatacaga tgtgtctgca gccctggcta ccagctgcac cccagccagg   2940
cctactgcac agatgacaac gagtgtctga gggacccctg caagggaaaa gggcgctgca   3000
```

```
tcaaccgcgt ggggtcctac tcctgcttct gctaccctgg ctacactctg gccacctcag    3060
gggcgacaca ggagtgtcaa gatatcaatg agtgtgagca gccagggttg tgcagcgggg    3120
ggcagtgcac caacaccgag ggctcgtacc actgcgagtg tgatcagggc tacatcatgg    3180
tcaggaaagg acactgccaa gatatcaacg aatgccgtca ccccggtacc tgccctgatg    3240
ggagatgcgt caattcccct ggctcctaca cttgtctggc ctgtgaggag ggctaccggg    3300
gccagagtgg gagctgtgta gatgtgaatg agtgtctgac tcccggggtc tgtgcccatg    3360
gaaagtgcac caacctagaa ggctccttca gatgctcttg tgagcagggc tatgaggtca    3420
cctcagatga aagggctgc caagatgtgg atgagtgtgc cagccgggcc tcatgcccca    3480
caggcctctg cctcaacacg gagggctcct tcgcctgctc tgcctgtgag aacgggtact    3540
gggtgaatga agacggcact gcctgtgaag acctagatga gtgtgccttc ccggagtct    3600 gcccctccgg agtctgcacc aacacggctg gctccttctc ctgcaaggac tgcgatgggg    3660
gctaccggcc cagcccctg gtgactcct gtgaagatgt ggatgaatgt gaagaccccc    3720
agagcagctg cctgggaggc gagtgcaaga acactgtggg ctcctaccag tgcctctgtc    3780
cccagggctt ccagctggcc aatggcaccg tgtgtgagga tgtgaatgag tgcatggggg    3840
aggagcactg cgcaccacac ggcgagtgcc tcaacagcca cggtctttc ttctgtctgt    3900 gcgcgcctgg cttcgtcagc gcagagggg gcaccagctg ccaggatgtg gacgagtgtg    3960
ccaccacaga cccgtgtgtg ggagggcact gtgtcaacac cgagggctcc ttcaactgtc    4020
tatgtgagac tggcttccag ccctcccag agagtggaga gtgtgtggat attgacgagt    4080
gtgaggacta tggagacccg gtgtgtggca cctggaagtg tgaaaacagc cctggctcct    4140
accgctgtgt tctgggctgc cagcctggct tccacatggc cccgaacgga gactgcattg    4200
acatagacga gtgcgccaac gacaccatgt gtggcagcca cggcttctgt gacaacactg    4260
atggctcctt ccgctgcctc tgtgaccagg gcttcgagat ctctccctca ggctgggact    4320
gtgtggatgt gaacgagtgt gagcttatgc tggcggtatg tggggccgcg ctctgtgaga    4380
acgtggaggg ctccttcctg tgcctctgtg ccagtgacct ggaggagtac gatgcccagg    4440
aggggcactg ccgcccacgg gggggctgag gtcagagtat gtctgaggcc caacggggg    4500 accatgcccc ggcccccacc cgcatggact gctactccgg gcagaaggc catgcgccct    4560 gctccagtgt cctgggccgg aacaccacac aggctgaatg ctgctgcacc cagggcgcta    4620
gctggggaga tgcctgtgac ctctgcccgt ctgaggactc agctgaattc agcgagatct    4680
gccctagtgt aaaaggctac attcctgtgg aaggagcctg gacgttggga cagaccatgt    4740
acacagatgc ggatgagtgt gtgatattcg ggcctggtct ctgcccgaac ggccggtgcc    4800
tcaacaccgt gcctggttat gtctgcctgt gcaatcccgg cttccactac gatgcttccc    4860
acaagaagtg tgaggatcac gatgagtgcc aggacctggc ctgtgagaat ggcgagtgcg    4920
tcaacacgga gggctccttc cactgcttct gcagccccccc gctcaccctg acctcagcc    4980 agcagcgctg catgaacagc accagcagca cggaggacct ccctgaccac gacatccaca    5040
tggacatctg ctggaaaaaa gtcaccaatg atgtgtgcag cgaacccctg cgtgggcacc    5100
gcaccaccta cacggaatgc tgctgccagg acggcgagcc ctggagccag cagtgtgctc    5160
tgtgtccccc gaggagctct gaggtctatg ctcagctgtg caacgtggct cgcattgagg    5220
cagagcggga ggccgggtc cacttccggc caggctatga gtatggcccc gggcccgatg    5280
acctgcacta cagcatctat ggcccagatg ggggcccctt ctacaactac ctgggccccg    5340
aggacaccgt ccctgatcct gccttcccca acacagccgg tcactcagcg gaccgcacac    5400
```

-continued

```
ccatccttga gtctcctttg cagccctcag aactccagcc ccactacgtg gccagccatc    5460
cagagccccc agccggcttc gaagggcttc aggcggagga gtgcggcatc ctgaacggct    5520
gtgagaatgg ccgctgtgtg cgcgtgcggg agggctacac ctgtgactgt tttgagggct    5580
tccagctgga tgcggcccac atggcctgcg tagatgtgaa tgagtgtgat gacttgaacg    5640
ggcctgctgt gctctgtgtc catggttact gcgagaacac agagggctcc taccgctgcc    5700
actgctcccc gggatatgtg gctgaggcag gccccccca ctgcactgcc aaggagtagc    5760
agtcaggggt cagtgtggca actacctgga aatggcctcc agtcacaggc aggggccttg    5820
aggatgattt cctagctggg aagacaccgt gacatcaggc cagaggtttc caatcagcct    5880
tgcctgcttt catctctccc agcttagcct ctggctgtaa gcttcggtca ttgcctccat    5940
gcccttgctt ggctcaagca ccaccaatcg ctttaatgct tcagccaccg catgaggccc    6000
tgtccaccac ctttcctggc cttgctatgg gatgcttacc aaaggatggc cctcatccac    6060
cctcccaagc tgtgcgagca tgcaaggccc atggcctca cactgcagac accccttcc    6120 agccacaatc caccatcatc ctgacgatcc cacaactggg acagaggcta catctgccct    6180
agggaggtcc ttcagaatct gtggagcaag aaaggatttg gggaagcttg gggactgact    6240
ccagagcccc ctcctaagaa ccatcaccac cactcagcca atctgttctg ggccctgatt    6300
ttgccacacc tccatcctgt agcccattct ctgaccccaa ggagtggcag aagatccctt    6360
cactcagaga agcaaggctg atattagctt gttgaatgta agagacacaa atgaagaaga    6420
acaaagagcc tgagaaagca gcaagaggac atgatgaaaa atacgtggag ttgatgagaa    6480
aggggagcca aggctttata cgtctaaaga aaatattcag tagctgaatc cgcccagtga    6540
tagcctgtgg gcaccagcag caagggctgc catgggatac agcacccatc tacaaagacc    6600
tctattacat aaacactgct tcttacagga aacaaacctc ttctgggatc tccttttgtg    6660
aaaaccagtt tgatgtgcta aaagtaaaag tctattttcc agtgtggtct tgttcagaag    6720
cagccagatt tccaatgttg ttttttcccct ccactcagaa acccctgccc tttcccttca    6780
gaaaacgatg gcaggcattc ctctgagttt acaagcagag actcactcca acccaaacta    6840
gctgggagtt cagaaccatg gtggaataaa gaaatgtgca tctagaaaaa aaaaaaaaa    6900 a                                                                    6901
```

<210> SEQ ID NO 43
<211> LENGTH: 1188
<212> TYPE: PRT
<213> ORGANISM: Homo sapiens

<400> SEQUENCE: 43

```
Met Asp Leu Pro Arg Gly Leu Val Val Ala Trp Ala Leu Ser Leu Trp
 1               5                  10                  15

Pro Gly Phe Thr Asp Thr Phe Asn Met Asp Thr Arg Lys Pro Arg Val
                20                  25                  30

Ile Pro Gly Ser Arg Thr Ala Phe Phe Gly Tyr Thr Val Gln Gln His
            35                  40                  45

Asp Ile Ser Gly Asn Lys Trp Leu Val Val Gly Ala Pro Leu Glu Thr
        50                  55                  60

Asn Gly Tyr Gln Lys Thr Gly Asp Val Tyr Lys Cys Pro Val Ile His
 65                  70                  75                  80

Gly Asn Cys Thr Lys Leu Asn Leu Gly Arg Val Thr Leu Ser Asn Val
                85                  90                  95
```

-continued

```
Ser Glu Arg Lys Asp Asn Met Arg Leu Gly Leu Ser Leu Ala Thr Asn
                100                 105                 110

Pro Lys Asp Asn Ser Phe Leu Ala Cys Ser Pro Leu Trp Ser His Glu
        115                 120                 125

Cys Gly Ser Ser Tyr Tyr Thr Thr Gly Met Cys Ser Arg Val Asn Ser
    130                 135                 140

Asn Phe Arg Phe Ser Lys Thr Val Ala Pro Ala Leu Gln Arg Cys Gln
145                 150                 155                 160

Thr Tyr Met Asp Ile Val Ile Val Leu Asp Gly Ser Asn Ser Ile Tyr
                165                 170                 175

Pro Trp Val Glu Val Gln His Phe Leu Ile Asn Ile Leu Lys Lys Phe
            180                 185                 190

Tyr Ile Gly Pro Gly Gln Ile Gln Val Gly Val Val Gln Tyr Gly Glu
        195                 200                 205

Asp Val Val His Glu Phe His Leu Asn Asp Tyr Arg Ser Val Lys Asp
    210                 215                 220

Val Val Glu Ala Ala Ser His Ile Glu Gln Arg Gly Gly Thr Glu Thr
225                 230                 235                 240

Arg Thr Ala Phe Gly Ile Glu Phe Ala Arg Ser Glu Ala Phe Gln Lys
                245                 250                 255

Gly Gly Arg Lys Gly Ala Lys Lys Val Met Ile Val Ile Thr Asp Gly
            260                 265                 270

Glu Ser His Asp Ser Pro Asp Leu Glu Lys Val Ile Gln Gln Ser Glu
        275                 280                 285

Arg Asp Asn Val Thr Arg Tyr Ala Val Ala Val Leu Gly Tyr Tyr Asn
    290                 295                 300

Arg Arg Gly Ile Asn Pro Glu Thr Phe Leu Asn Glu Ile Lys Tyr Ile
305                 310                 315                 320

Ala Ser Asp Pro Asp Lys His Phe Phe Asn Val Thr Asp Glu Ala
                325                 330                 335

Ala Leu Lys Asp Ile Val Asp Ala Leu Gly Asp Arg Ile Phe Ser Leu
            340                 345                 350

Glu Gly Thr Asn Lys Asn Glu Thr Ser Phe Gly Leu Glu Met Ser Gln
        355                 360                 365

Thr Gly Phe Ser Ser His Val Val Glu Asp Gly Val Leu Leu Gly Ala
    370                 375                 380

Val Gly Ala Tyr Asp Trp Asn Gly Ala Val Leu Lys Glu Thr Ser Ala
385                 390                 395                 400

Gly Lys Val Ile Pro Leu Arg Glu Ser Tyr Leu Lys Glu Phe Pro Glu
                405                 410                 415

Glu Leu Lys Asn His Gly Ala Tyr Leu Gly Tyr Thr Val Thr Ser Val
            420                 425                 430

Val Ser Ser Arg Gln Gly Arg Val Tyr Val Ala Gly Ala Pro Arg Phe
        435                 440                 445

Asn His Thr Gly Lys Val Ile Leu Phe Thr Met His Asn Asn Arg Ser
    450                 455                 460

Leu Thr Ile His Gln Ala Met Arg Gly Gln Gln Ile Gly Ser Tyr Phe
465                 470                 475                 480

Gly Ser Glu Ile Thr Ser Val Asp Ile Asp Gly Asp Gly Val Thr Asp
                485                 490                 495

Val Leu Leu Val Gly Ala Pro Met Tyr Phe Asn Glu Gly Arg Glu Arg
            500                 505                 510

Gly Lys Val Tyr Val Tyr Glu Leu Arg Gln Asn Arg Phe Val Tyr Asn
```

```
                515                 520                 525
Gly Thr Leu Lys Asp Ser His Ser Tyr Gln Asn Ala Arg Phe Gly Ser
530                 535                 540

Ser Ile Ala Ser Val Arg Asp Leu Asn Gln Asp Ser Tyr Asn Asp Val
545                 550                 555                 560

Val Val Gly Ala Pro Leu Glu Asp Asn His Ala Gly Ala Ile Tyr Ile
                565                 570                 575

Phe His Gly Phe Arg Gly Ser Ile Leu Lys Thr Pro Lys Gln Arg Ile
                580                 585                 590

Thr Ala Ser Glu Leu Ala Thr Gly Leu Gln Tyr Phe Gly Cys Ser Ile
                595                 600                 605

His Gly Gln Leu Asp Leu Asn Glu Asp Gly Leu Ile Asp Leu Ala Val
            610                 615                 620

Gly Ala Leu Gly Asn Ala Val Ile Leu Trp Ser Arg Pro Val Val Gln
625                 630                 635                 640

Ile Asn Ala Ser Leu His Phe Glu Pro Ser Lys Ile Asn Ile Phe His
                645                 650                 655

Arg Asp Cys Lys Arg Ser Gly Arg Asp Ala Thr Cys Leu Ala Ala Phe
            660                 665                 670

Leu Cys Phe Thr Pro Ile Phe Leu Ala Pro His Phe Gln Thr Thr Thr
            675                 680                 685

Val Gly Ile Arg Tyr Asn Ala Thr Met Asp Glu Arg Arg Tyr Thr Pro
690                 695                 700

Arg Ala His Leu Asp Glu Gly Gly Asp Arg Phe Thr Asn Arg Ala Val
705                 710                 715                 720

Leu Leu Ser Ser Gly Gln Glu Leu Cys Glu Arg Ile Asn Phe His Val
                725                 730                 735

Leu Asp Thr Ala Asp Tyr Val Lys Pro Val Thr Phe Ser Val Glu Tyr
                740                 745                 750

Ser Leu Glu Asp Pro Asp His Gly Pro Met Leu Asp Asp Gly Trp Pro
            755                 760                 765

Thr Thr Leu Arg Val Ser Val Pro Phe Trp Asn Gly Cys Asn Glu Asp
    770                 775                 780

Glu His Cys Val Pro Asp Leu Val Leu Asp Ala Arg Ser Asp Leu Pro
785                 790                 795                 800

Thr Ala Met Glu Tyr Cys Gln Arg Val Leu Arg Lys Pro Ala Gln Asp
                805                 810                 815

Cys Ser Ala Tyr Thr Leu Ser Phe Asp Thr Thr Val Phe Ile Ile Glu
                820                 825                 830

Ser Thr Arg Gln Arg Val Ala Val Glu Ala Thr Leu Glu Asn Arg Gly
            835                 840                 845

Glu Asn Ala Tyr Ser Thr Val Leu Asn Ile Ser Gln Ser Ala Asn Leu
            850                 855                 860

Gln Phe Ala Ser Leu Ile Gln Lys Glu Asp Ser Asp Gly Ser Ile Glu
865                 870                 875                 880

Cys Val Asn Glu Glu Arg Arg Leu Gln Lys Gln Val Cys Asn Val Ser
                885                 890                 895

Tyr Pro Phe Phe Arg Ala Lys Ala Lys Val Ala Phe Arg Leu Asp Phe
            900                 905                 910

Glu Phe Ser Lys Ser Ile Phe Leu His His Leu Glu Ile Glu Leu Ala
            915                 920                 925

Ala Gly Ser Asp Ser Asn Glu Arg Asp Ser Thr Lys Glu Asp Asn Val
            930                 935                 940
```

```
Ala Pro Leu Arg Phe His Leu Lys Tyr Glu Ala Asp Val Leu Phe Thr
945                 950                 955                 960

Arg Ser Ser Ser Leu Ser His Tyr Glu Val Lys Leu Asn Ser Ser Leu
                965                 970                 975

Glu Arg Tyr Asp Gly Ile Gly Pro Pro Phe Ser Cys Ile Phe Arg Ile
            980                 985                 990

Gln Asn Leu Gly Leu Phe Pro Ile His Gly Met Met Met Lys Ile Thr
        995                 1000                1005

Ile Pro Ile Ala Thr Arg Ser Gly Asn Arg Leu Leu Lys Leu Arg
    1010                1015                1020

Asp Phe Leu Thr Asp Glu Ala Asn Thr Ser Cys Asn Ile Trp Gly
    1025                1030                1035

Asn Ser Thr Glu Tyr Arg Pro Thr Pro Val Glu Glu Asp Leu Arg
    1040                1045                1050

Arg Ala Pro Gln Leu Asn His Ser Asn Ser Asp Val Val Ser Ile
    1055                1060                1065

Asn Cys Asn Ile Arg Leu Val Pro Asn Gln Glu Ile Asn Phe His
    1070                1075                1080

Leu Leu Gly Asn Leu Trp Leu Arg Ser Leu Lys Ala Leu Lys Tyr
    1085                1090                1095

Lys Ser Met Lys Ile Met Val Asn Ala Ala Leu Gln Arg Gln Phe
    1100                1105                1110

His Ser Pro Phe Ile Phe Arg Glu Glu Asp Pro Ser Arg Gln Ile
    1115                1120                1125

Val Phe Glu Ile Ser Lys Gln Glu Asp Trp Gln Val Pro Ile Trp
    1130                1135                1140

Ile Ile Val Gly Ser Thr Leu Gly Gly Leu Leu Leu Ala Leu
    1145                1150                1155

Leu Val Leu Ala Leu Trp Lys Leu Gly Phe Phe Arg Ser Ala Arg
    1160                1165                1170

Arg Arg Arg Glu Pro Gly Leu Asp Pro Thr Pro Lys Val Leu Glu
    1175                1180                1185

<210> SEQ ID NO 44
<211> LENGTH: 3983
<212> TYPE: DNA
<213> ORGANISM: Homo sapiens

<400> SEQUENCE: 44
ggcacgaggc cgcgccgagg aggctgccgc tctggcttgc cagtcccccg ccgccgctgc      60
acaccggacc cagccgccgt gccgcgggcc atggacctgc caggggcct ggtggtggcc     120 tgggcgctca gcctgtggcc agggttcacg acaccttca acatggacac caggaagccc     180
cgggtcatcc ctggctccag gaccgccttc tttggctaca cagtgcagca gcacgacatc     240
agtggcaata gtggctggt cgtgggcgcc ccactgaaa ccaatggcta ccagaagacg     300
ggagacgtgt acaagtgtcc agtgatccac gggaactgca ccaaactcaa cctgggaagg     360
gtcaccctgt ccaacgtgtc cgagcggaaa gacaacatgc gcctcggcct tagtctcgcc     420
accaacccca aggacaacag cttcctggcc tgcagcccc tctggtctca tgagtgtggg     480
agctcctact acaccacagg gatgtgttca agagtcaact ccaacttcag gttctccaag     540
accgtggccc cagctctcca aaggtgccag acctacatgg acatcgtcat tgtcctggat     600
ggctccaaca gcatctaccc ctgggtggag gttcagcact tcctcatcaa catcctgaaa     660
```

-continued

```
aagttttaca ttggcccagg gcagatccag gttggagttg tgcagtatgg cgaagatgtg    720
gtgcatgagt ttcacctcaa cgactacagg tctgtaaaag atgtggtgga agctgccagc    780
cacattgagc agagaggagg aacagagacc cggacggcat ttggcattga atttgcacgc    840
tcagaggctt tccagaaggg tggaaggaaa ggagccaaga aggtgatgat tgtcatcaca    900
gatggggagt cccacgacag cccagacctg gagaaggtga tccagcaaag cgaaagagac    960
aacgtaacaa gatatgcggt ggccgtcctg ggctactaca accgcagggg gatcaatcca   1020 gaaactttc taaatgaaat caaatacatc gccagtgacc ctgatgacaa gcacttcttc   1080
aatgtcactg atgaggctgc cttgaaggac attgtcgatg ccctggggga cagaatcttc   1140
agcctggaag gcaccaacaa gaacgagacc tcctttgggc tggagatgtc acagacgggc   1200
ttttcctcgc acgtggtgga ggatgggggtt ctgctgggag ccgtcggtgc ctatgactgg   1260
aatggagctg tgctaaagga gacgagtgcc gggaaggtca ttcctctccg cgagtcctac   1320
ctgaaagagt tcccccgagga gctcaagaac catggtgcat acctggggta cacagtcaca   1380
tcggtcgtgt cctccaggca ggggcgagtg tacgtggccg gagcccccg gttcaaccac   1440 acgggcaagg tcatcctgtt caccatgcac aacaaccgga gcctcaccat ccaccaggct   1500
atgcggggcc agcagatagg ctcttacttt gggagtgaaa tcacctcggt ggacatcgac   1560
ggcgacggcg tgactgatgt cctgctggtg ggcgcaccca tgtacttcaa cgagggccgt   1620
gagcgaggca aggtgtacgt ctatgagctg agacagaacc ggtttgttta acggaacg    1680 ctaaaggatt cacacagtta ccagaatgcc cgatttgggt cctccattgc ctcagttcga   1740
gacctcaacc aggattccta caatgacgtg gtggtgggag cccccctgga ggacaaccac   1800
gcaggagcca tctacatctt ccacggcttc cgaggcagca tcctgaagac acctaagcag   1860
agaatcacag cctcagagct ggctaccggc ctccagtatt ttggctgcag catccacggg   1920
caattggacc tcaatgagga tgggctcatc gacctggcag tgggagccct tggcaacgct   1980
gtgattctgt ggtcccgccc agtggttcag atcaatgcca gcctccactt tgagccatcc   2040
aagatcaaca tcttccacag agactgcaag cgcagtggca gggatgccac ctgcctggcc   2100
gccttcctct gcttcacgcc catcttcctg gcaccccatt tccaaacaac aactgttggc   2160
atcagataca acgccaccat ggatgagagg cggtatacac cgagggccca cctggacgag   2220 ggcgggggacc gattcaccaa cagagccgta ctgctctcct ccggccagga gctctgtgag   2280
cggatcaact tccatgtcct ggacactgct gactacgtga agccagtgac cttctcagtc   2340
gagtattccc tggaggaccc tgaccatggc cccatgctgg acgacggctg gcccaccact   2400
ctcagagtct cggtgccctt ctggaacggc tgcaatgagg atgagcactg tgtccctgac   2460
cttgtgttgg atgcccggag tgacctgccc acggccatgg agtactgcca gagggtgctg   2520
aggaagcctg cgcaggactg ctccgcatac acgctgtcct tcgacaccac agtcttcatc   2580
atagagagca cacgccagcg agtggcggtg gaggccacac tggagaacag gggcgagaac   2640
gcctacagta cggtcctaaa tatctcgcag tcagcaaacc tgcagtttgc cagcttgatc   2700
cagaaggagg actcagacgg tagcattgag tgtgtgaacg aggagaggag gctccagaag   2760
caagtctgca acgtcagcta tcccttcttc cgggccaagg ccaaggtggc tttccgtctt   2820
gattttgagt tcagcaaatc catcttccta caccacctgg agatcgagct cgctgcaggc   2880
agtgacagta atgagcggga cagcaccaag gaagacaacg tggccccctt acgcttccac   2940
ctcaaatacg aggctgacgt cctcttcacc aggagcagca gcctgagcca ctacgaggtc   3000
aagctcaaca gctcgctgga gagatacgat ggtatcgggc ctcccttcag ctgcatcttc   3060
```

```
aggatccaga acttgggctt gttccccatc cacgggatga tgatgaagat caccattccc    3120
atcgccacca ggagcggcaa ccgcctactg aagctgaggg acttcctcac ggacgaggcg    3180
aacacgtcct gtaacatctg gggcaatagc actgagtacc ggcccacccc agtggaggaa    3240
gacttgcgtc gtgctccaca gctgaatcac agcaactctg atgtcgtctc catcaactgc    3300
aatatacggc tggtccccaa ccaggaaatc aatttccatc tactggggaa cctgtggttg    3360
aggtccctaa aagcactcaa gtacaaatcc atgaaaatca tggtcaacgc agccttgcag    3420
aggcagttcc acagcccctt catcttccgt gaggaggatc ccagccgcca gatcgtgttt    3480
gagatctcca gcaagagga ctggcaggtc cccatctgga tcattgtagg cagcaccctg    3540
gggggcctcc tactgctggc cctgctggtc ctggcactgt ggaagctcgg cttctttaga    3600
agtgccaggc gcaggaggga gcctggtctg accccacccc caaagtgct ggagtgaggc    3660 tccagaggag actttgagtt gatggggcc aggacaccag tccaggtagt gttgagaccc    3720
aggcctgtgg ccccaccgag ctggagcgga gaggaagcca gctggctttg cacttgacct    3780
catctcccga gcaatggcgc ctgctccctc cagaatggaa ctcaagctgg ttttaagtgg    3840
aactgcctac tgggagactg ggacaccttt acacagaccc ctagggattt aaagggacac    3900
ccctacacac acccaggccc acgccaaggc ctccctcagg ctctgtggag ggcatttgct    3960
gccccagcta ctaaggtgct agg                                             3983
```

<210> SEQ ID NO 45
<211> LENGTH: 1445
<212> TYPE: PRT
<213> ORGANISM: Homo sapiens

<400> SEQUENCE: 45

```
Met Glu Glu Gly His Gly Leu Asp Leu Thr Tyr Ile Thr Glu Arg Ile
1               5                   10                  15

Ile Ala Val Ser Phe Pro Ala Gly Cys Ser Glu Glu Ser Tyr Pro His
            20                  25                  30

Asn Leu Gln Glu Val Thr Arg Met Leu Lys Ser Lys His Gly Asp Asn
        35                  40                  45

Tyr Leu Val Leu Asn Leu Ser Glu Lys Arg Tyr Asp Leu Thr Lys Leu
    50                  55                  60

Asn Pro Lys Ile Met Asp Val Gly Trp Pro Glu Leu His Ala Pro Pro
65                  70                  75                  80

Leu Asp Lys Met Cys Thr Ile Cys Lys Ala Gln Glu Ser Trp Leu Asn
                85                  90                  95

Ser Asn Leu Gln His Val Val Ile His Cys Arg Gly Gly Lys Gly
            100                 105                 110

Arg Ile Gly Val Val Ile Ser Ser Tyr Met His Phe Thr Asn Val Ser
        115                 120                 125

Ala Ser Ala Asp Gln Ala Leu Asp Arg Phe Ala Met Lys Lys Phe Tyr
    130                 135                 140

Asp Asp Lys Val Ser Ala Leu Met Gln Pro Ser Gln Lys Arg Tyr Val
145                 150                 155                 160

Gln Phe Leu Ser Gly Leu Leu Ser Gly Ser Val Lys Met Asn Ala Ser
                165                 170                 175

Pro Leu Phe Leu His Phe Val Ile Leu His Gly Thr Pro Asn Phe Asp
            180                 185                 190

Thr Gly Gly Val Cys Arg Pro Phe Leu Lys Leu Tyr Gln Ala Met Gln
        195                 200                 205
```

```
Pro Val Tyr Thr Ser Gly Ile Tyr Asn Val Gly Pro Glu Asn Pro Ser
        210                 215                 220

Arg Ile Cys Ile Val Ile Glu Pro Ala Gln Leu Leu Lys Gly Asp Val
225                 230                 235                 240

Met Val Lys Cys Tyr His Lys Lys Tyr Arg Ser Ala Thr Arg Asp Val
                245                 250                 255

Ile Phe Arg Leu Gln Phe His Thr Gly Ala Val Gln Gly Tyr Gly Leu
            260                 265                 270

Val Phe Gly Lys Glu Asp Leu Asp Asn Ala Ser Lys Asp Asp Arg Phe
        275                 280                 285

Pro Asp Tyr Gly Lys Val Glu Leu Val Phe Ser Ala Thr Pro Glu Lys
    290                 295                 300

Ile Gln Gly Ser Glu His Leu Tyr Asn Asp His Gly Val Ile Val Asp
305                 310                 315                 320

Tyr Asn Thr Thr Asp Pro Leu Ile Arg Trp Asp Ser Tyr Glu Asn Leu
                325                 330                 335

Ser Ala Asp Gly Glu Val Leu His Thr Gln Gly Pro Val Asp Gly Ser
            340                 345                 350

Leu Tyr Ala Lys Val Arg Lys Lys Ser Ser Asp Pro Gly Ile Pro
        355                 360                 365

Gly Gly Pro Gln Ala Ile Pro Ala Thr Asn Ser Pro Asp His Ser Asp
    370                 375                 380

His Thr Leu Ser Val Ser Ser Asp Ser Gly His Ser Thr Ala Ser Ala
385                 390                 395                 400

Arg Thr Asp Lys Thr Glu Glu Arg Leu Ala Pro Gly Thr Arg Arg Gly
                405                 410                 415

Leu Ser Ala Gln Glu Lys Ala Glu Leu Asp Gln Leu Leu Ser Gly Phe
            420                 425                 430

Gly Leu Glu Asp Pro Gly Ser Ser Leu Lys Glu Met Thr Asp Ala Arg
        435                 440                 445

Ser Lys Tyr Ser Gly Thr Arg His Val Val Pro Ala Gln Val His Val
    450                 455                 460

Asn Gly Asp Ala Ala Leu Lys Asp Arg Glu Thr Asp Ile Leu Asp Asp
465                 470                 475                 480

Glu Met Pro His His Asp Leu His Ser Val Asp Ser Leu Gly Thr Leu
                485                 490                 495

Ser Ser Ser Glu Gly Pro Gln Ser Val His Leu Gly Pro Phe Thr Cys
            500                 505                 510

His Lys Ser Ser Gln Asn Ser Leu Leu Ser Asp Gly Phe Gly Ser Asn
        515                 520                 525

Val Gly Glu Asp Pro Gln Gly Thr Leu Val Pro Asp Leu Gly Leu Gly
    530                 535                 540

Met Asp Gly Pro Tyr Glu Arg Glu Arg Thr Phe Gly Ser Arg Glu Pro
545                 550                 555                 560

Lys Gln Pro Gln Pro Leu Leu Arg Lys Pro Ser Val Ser Ala Gln Met
                565                 570                 575

Gln Ala Tyr Gly Gln Ser Ser Tyr Ser Thr Gln Thr Trp Val Arg Gln
            580                 585                 590

Gln Gln Met Val Val Ala His Gln Tyr Ser Phe Ala Pro Asp Gly Glu
        595                 600                 605

Ala Arg Leu Val Ser Arg Cys Pro Ala Asp Asn Pro Gly Leu Val Gln
    610                 615                 620
```

```
Ala Gln Pro Arg Val Pro Leu Thr Pro Thr Arg Gly Thr Ser Ser Arg
625                 630                 635                 640

Val Ala Val Gln Arg Gly Val Gly Ser Gly Pro His Pro Pro Asp Thr
            645                 650                 655

Gln Gln Pro Ser Pro Ser Lys Ala Phe Lys Pro Arg Phe Pro Gly Asp
            660                 665                 670

Gln Val Val Asn Gly Ala Gly Pro Glu Leu Ser Thr Gly Pro Ser Pro
            675                 680                 685

Gly Ser Pro Thr Leu Asp Ile Asp Gln Ser Ile Glu Gln Leu Asn Arg
690                 695                 700

Leu Ile Leu Glu Leu Asp Pro Thr Phe Glu Pro Ile Pro Thr His Met
705                 710                 715                 720

Asn Ala Leu Gly Ser Gln Ala Asn Gly Ser Val Ser Pro Asp Ser Val
            725                 730                 735

Gly Gly Gly Leu Arg Ala Ser Ser Arg Leu Pro Asp Thr Gly Glu Gly
            740                 745                 750

Pro Ser Arg Ala Thr Gly Arg Gln Gly Ser Ser Ala Glu Gln Pro Leu
            755                 760                 765

Gly Gly Arg Leu Arg Lys Leu Ser Leu Gly Gln Tyr Asp Asn Asp Ala
770                 775                 780

Gly Gly Gln Leu Pro Phe Ser Lys Cys Ala Trp Gly Lys Ala Gly Val
785                 790                 795                 800

Asp Tyr Ala Pro Asn Leu Pro Phe Pro Ser Pro Ala Asp Val Lys
            805                 810                 815

Glu Thr Met Thr Pro Gly Tyr Pro Gln Asp Leu Asp Ile Ile Asp Gly
            820                 825                 830

Arg Ile Leu Ser Ser Lys Glu Ser Met Cys Ser Thr Pro Ala Phe Pro
835                 840                 845

Val Ser Pro Glu Thr Pro Tyr Val Lys Thr Ala Leu Arg His Pro Pro
850                 855                 860

Phe Ser Pro Pro Glu Pro Pro Leu Ser Ser Pro Ala Ser Gln His Lys
865                 870                 875                 880

Gly Gly Arg Glu Pro Arg Ser Cys Pro Glu Thr Leu Thr His Ala Val
            885                 890                 895

Gly Met Ser Glu Ser Pro Ile Gly Pro Lys Ser Thr Met Leu Arg Ala
            900                 905                 910

Asp Ala Ser Ser Thr Pro Ser Phe Gln Gln Ala Phe Ala Ser Ser Cys
            915                 920                 925

Thr Ile Ser Ser Asn Gly Pro Gly Gln Arg Arg Glu Ser Ser Ser Ser
930                 935                 940

Ala Glu Arg Gln Trp Val Glu Ser Ser Pro Lys Pro Met Val Ser Leu
945                 950                 955                 960

Leu Gly Ser Gly Arg Pro Thr Gly Ser Pro Leu Ser Ala Glu Phe Ser
            965                 970                 975

Gly Thr Arg Lys Asp Ser Pro Val Leu Ser Cys Phe Pro Pro Ser Glu
            980                 985                 990

Leu Gln Ala Pro Phe His Ser His Glu Leu Ser Leu Ala Glu Pro Pro
            995                 1000                1005

Asp Ser Leu Ala Pro Pro Ser Ser Gln Ala Phe Leu Gly Phe Gly
    1010                1015                1020

Thr Ala Pro Val Gly Ser Gly Leu Pro Pro Glu Glu Asp Leu Gly
    1025                1030                1035

Ala Leu Leu Ala Asn Ser His Gly Ala Ser Pro Thr Pro Ser Ile
```

-continued

|   |   |   |   |   | 1040 |   |   |   | 1045 |   |   |   | 1050 |   |
|---|---|---|---|---|---|---|---|---|---|---|---|---|---|---|

Pro Leu Thr Ala Thr Gly Ala Ala Asp Asn Gly Phe Leu Ser His
1055              1060              1065

Asn Phe Leu Thr Val Ala Pro Gly His Ser Ser His His Ser Pro
1070              1075              1080

Gly Leu Gln Gly Gln Gly Val Thr Leu Pro Gly Gln Pro Pro Leu
1085              1090              1095

Pro Glu Lys Lys Arg Ala Ser Glu Gly Asp Arg Ser Leu Gly Ser
1100              1105              1110

Val Ser Pro Ser Ser Gly Phe Ser Ser Pro His Ser Gly Ser
1115              1120              1125

Thr Ile Ser Ile Pro Phe Pro Asn Val Leu Pro Asp Phe Ser Lys
1130              1135              1140

Ala Ser Glu Ala Ala Ser Pro Leu Pro Asp Ser Pro Gly Asp Lys
1145              1150              1155

Leu Val Ile Val Lys Phe Val Gln Asp Thr Ser Lys Phe Trp Tyr
1160              1165              1170

Lys Ala Asp Ile Ser Arg Glu Gln Ala Ile Ala Met Leu Lys Asp
1175              1180              1185

Lys Glu Pro Gly Ser Phe Ile Val Arg Asp Ser His Ser Phe Arg
1190              1195              1200

Gly Ala Tyr Gly Leu Ala Met Lys Val Ala Thr Pro Pro Pro Ser
1205              1210              1215

Val Leu Gln Leu Asn Lys Lys Ala Gly Asp Leu Ala Asn Glu Leu
1220              1225              1230

Val Arg His Phe Leu Ile Glu Cys Thr Pro Lys Gly Val Arg Leu
1235              1240              1245

Lys Gly Cys Ser Asn Glu Pro Tyr Phe Gly Ser Leu Thr Ala Leu
1250              1255              1260

Val Cys Gln His Ser Ile Thr Pro Leu Ala Leu Pro Cys Lys Leu
1265              1270              1275

Leu Ile Pro Glu Arg Asp Pro Leu Glu Glu Ile Ala Glu Ser Ser
1280              1285              1290

Pro Gln Thr Ala Ala Asn Ser Ala Ala Glu Leu Leu Lys Gln Gly
1295              1300              1305

Ala Ala Cys Asn Val Trp Tyr Leu Asn Ser Val Glu Met Glu Ser
1310              1315              1320

Leu Thr Gly His Gln Ala Ile Gln Lys Ala Leu Ser Ile Thr Leu
1325              1330              1335

Val Gln Glu Pro Pro Pro Val Ser Thr Val Val His Phe Lys Val
1340              1345              1350

Ser Ala Gln Gly Ile Thr Leu Thr Asp Asn Gln Arg Lys Leu Phe
1355              1360              1365

Phe Arg Arg His Tyr Pro Val Asn Ser Val Ile Phe Cys Ala Leu
1370              1375              1380

Asp Pro Gln Asp Arg Lys Trp Ile Lys Asp Gly Pro Ser Ser Lys
1385              1390              1395

Val Phe Gly Phe Val Ala Arg Lys Gln Gly Ser Ala Thr Asp Asn
1400              1405              1410

Val Cys His Leu Phe Ala Glu His Asp Pro Glu Gln Pro Ala Ser
1415              1420              1425

Ala Ile Val Asn Phe Val Ser Lys Val Met Ile Gly Ser Pro Lys
1430              1435              1440

Lys Val
       1445

<210> SEQ ID NO 46
<211> LENGTH: 4388
<212> TYPE: DNA
<213> ORGANISM: Homo sapiens

<400> SEQUENCE: 46

```
gcccttacca tggaggaggg ccatgggctg gacctcactt acatcacgga gcgcatcatc      60
gctgtgtcct tccctgccgg ctgctctgag gagtcctacc cgcacaacct acaggaggtc     120
acgcgcatgc tcaagtccaa gcacgggac  aactacctgg tattaaacct ttcagaaaag     180
agatatgacc ttacgaagct taacccaaag atcatggatg tgggctggcc agagctccac     240
gcaccgcccc tggataagat gtgtaccata tgcaaggcgc aggagtcctg gctgaacagc     300
aacctccagc atgtggtcgt cattcactgc aggggcggga aggacgcat  aggagtggtc     360
atatcatcct acatgcattt caccaacgtc tcagccagcg ccgaccaggc ccttgacagg     420
tttgcaatga gaagttttta tgatgacaaa gtttcagctt taatgcagcc ttcccaaaaa     480
cggtatgttc agttcctcag tgggctcctg tccggatcgg tgaaaatgaa tgcctctccc     540
ctgttcctgc attttgtcat cctccacggc accccaact  tcgacacagg tggagtgtgc     600
cggccctttc tgaagctcta ccaagccatg cagcctgtgt acacctccgg gatctacaac     660
gttggcccag aaaacccag  caggatctgc atcgtcatcg agccggccca gcttctgaag     720
ggagatgtca tggtgaaatg ctaccacaag aaataccgct cggccacccg tgacgtcatt     780
ttccgcctgc agtttcacac tggggctgtg cagggctacg gctggtgtt  tgggaaggag     840
gatctggaca tgccagcaa  agatgaccgt tttcctgact atgggaaggt tgaattagtc     900
ttctctgcca cgcctgagaa gattcaaggg tccgaacact tgtacaacga ccacggtgtg     960
attgtggact acaacacaac agacccactg atacgctggg actcgtacga gaacctcagt    1020
gcagatggag aagtgctaca cacgcagggc cctgtcgatg cagcctttta cgcgaaggtg    1080
aggaagaaaa gctcctcgga tcctggcatc ccaggtggcc cccaggcaat cccggccacc    1140
aacagcccag accacagtga ccacaccttg tctgtcagca gtgactccgg ccactctaca    1200
gcctctgcca ggacggataa gacggaagag cgcctggccc caggaaccag gaggggcctg    1260
agtgcccagg agaaggctga gttggaccag ctgctcagtg gctttggcct ggaagatcct    1320
ggaagctccc tcaaggaaat gactgatgct cgaagcaagt acagtgggac ccgccacgtg    1380
gtgccagccc aggttcacgt gaatggagac gctgctctga aggatcggga gacagacatt    1440
ctggatgacg agatgcccca ccacgacctg cacagtgtgg acagccttgg gcccctgtcc    1500
tcctcggaag ggcctcagtc ggtccacctg ggtccttca  cctgccacaa gagcagccag    1560
aactcactcc tatctgacgg ttttggcagc aacgttggtg aagatccgca gggcaccctc    1620
gttccggacc tgggccttgg catggacggc ccctatgagc gggagcggac ttttgggagt    1680
cgagagccca gcagccccca gccctgctg  agaaagccct cagtgtccgc ccagatgcag    1740
gcctatgggc agagcagcta ctccacacag acctgggtgc cccagcagca gatggttgta    1800
gctcaccagt atagcttcgc cccagatggg gaggcccggc tggtgagccg ctgccctgca    1860
gacaatcctg gcctcgtcca ggcccagccc agagtgccac tcaccccac  ccgagggacc    1920
agcagtaggg tggctgtcca gaggggtgta ggcagtgggc acatccccc  tgacacacag    1980
cagccctctc ccagcaaagc gttcaaaccc aggtttccag gagaccaggt tgtgaatgga    2040
```

```
gccggcccag agctgagcac aggcccctcc ccaggctcgc ccaccctgga catcgaccag    2100
tccatcgagc agctcaacag gctgatcctg gagctggatc ccaccttcga gcccatccct    2160
acccacatga acgccctcgg tagccaggcc aatggctctg tgtctccaga cagcgtggga    2220
ggtgggctcc gggcaagcag caggctgcct gacacaggag agggcccag cagggccacc     2280 gggcggcaag ctcctctgc tgaacagccc ctgggcggga gactcaggaa gctgagcctg     2340
gggcagtacg caacgatgc tgggggcag ctgcccttct ccaaatgtgc atggggaaag      2400
gctggtgtgg actatgcccc aaacctgccg ccattcccct caccagcgga cgtcaaagag    2460
acgatgaccc ctggctatcc ccaggacctc gatattatcg atggcagaat tttaagtagc    2520
aaggagtcca tgtgttcaac tccagcattt cctgtgtctc cagagacacc gtatgtgaaa   2580
acagcgctgc gccatcctcc gttcagccca cctgagcccc cgctgagcag cccagccagt    2640
cagcacaaag gaggacgtga accacgaagc tgccctgaga cgctcactca cgctgtgggg    2700
atgtcagaga gccccatcgg acccaaatcc acgatgctcc gggctgatgc gtcctcgacg    2760
ccctcctttc agcaggcttt tgcttcttcc tgcaccattt ccagcaacgg ccctgggcag    2820
aggagagaga gctcctcttc tgcagaacgc cagtgggtgg agagcagccc caagcccatg    2880
gtttccctgc tggggagcgg ccggcccacc ggaagtcccc tcagcgctga gttctccggt    2940
accaggaagg actccccagt gctgtcctgc ttcccgccgt cagagctcca ggctcctttc    3000
cacagccatg agctgtccct agcagagcca ccggactccc tggcgcctcc cagcagccag    3060
gccttcctgg gcttcggcac cgccccagtg ggaagtggcc ttccgcccga ggaggacctg    3120
ggggccttgc tggccaattc tcatggagcg tcaccgaccc ccagcatccc gctgacagcg    3180
acaggggctg ccgacaatgg cttcctgtcc cacaactttc tcacggtggc gcctggacac    3240
agcagccacc acagtccagg cctgcaggc cagggtgtga cctgcccgg gcagccaccc      3300 ctccctgaga gaagcgggc ctcggagggg atcgttctt tgggctcagt ctctcctcc       3360 tccagtggct tctccagccc gcacagcggg agcaccatca gtatcccctt cccaaatgtc    3420
cttcccgact tttccaaggc ttcagaagcg gcctcacctc tgccagatag tccaggtgat   3480
aaacttgtga tcgtgaaatt tgttcaagac acttccaagt tctggtacaa ggcggatatt    3540
tcaagagaac aagccatcgc catgttgaag acaaggagc cgggctcatt cattgttcga     3600
gacagccatt ccttccgagg ggcctatggc ctggccatga aggtggccac gcccccacct    3660
tcagtcctgc agctgaacaa gaaagctgga gatttggcca tgaactcgt ccggcacttt     3720 ttgatcgagt gtaccccgaa gggagtgcgg ttgaaagggt gctcgaatga accatatttc    3780
gggagcctga cggccttggt gtgccagcat tccatcacgc ccttggcctt gccgtgcaag    3840
ctgcttatcc cagagagaga tccattggag gaaatagcaa aaagttctcc ccagacggca    3900
gccaattcag cagctgagct gttgaagcag ggggcagcct gcaatgtgtg gtacttgaac    3960
tctgtggaga tggagtccct caccggccac caggcgatcc agaaggccct gagcatcacc    4020
ctggtccagg agcctccacc tgtgtccaca gttgtgcact tcaaggtgtc agcccagggc    4080
atcaccctga cagacaatca gaggaagctc ttcttccgga ggcattaccc cgtgaacagt    4140
gtgattttct gtgccttgga cccacaagac aggaagtgga tcaaagatgg cccttcctca    4200
aaagtctttg gatttgtggc ccggaagcag ggcagtgcca cggataatgt gtgccacctg    4260
tttgcagagc atgaccctga gcagcctgcc agtgccattg tcaacttcgt atcaaaggtc    4320
atgattggtt ccccaaagaa ggtctgagaa ctcccctccc tccctggacc caccgatgcc    4380
``` tctcgaag                                                                    4388

<210> SEQ ID NO 47
<211> LENGTH: 653
<212> TYPE: PRT
<213> ORGANISM: Homo sapiens

<400> SEQUENCE: 47

Met Cys Ile His Gln Leu Asn Leu Ala Thr Asn Pro Asn Leu Pro
1               5                   10                  15

Ile Thr Ser Val Leu Gly Lys Gln His Pro Ile Glu Ala His His Leu
            20                  25                  30

Ser Ser Ile Cys Asp Ile Met Glu Lys Ala Met Val Asn Gly Asp Thr
        35                  40                  45

Cys Ile Ile Arg Cys Ile Leu Val Val Phe Gln Val Val Phe Lys Phe
    50                  55                  60

Phe Phe Ser Pro Gln Thr Glu Arg Asn Arg Asp Ile Ile Arg Arg Ser
65                  70                  75                  80

Gly Leu Leu Leu Trp Gln Leu Leu Met Ala Pro Lys Asp Gln Ile Cys
                85                  90                  95

Pro Glu Ile Gln Lys Glu Val Cys Leu Ala Ile Ser Ser Gly Leu Asn
            100                 105                 110

Ile Leu Tyr Pro Gly Glu Thr Glu Ile Asn Asn Leu Leu Lys Leu Val
        115                 120                 125

Leu Thr Glu Gly Glu Arg Asn Ser Gly Leu Ser Gln Leu Arg Asp Val
    130                 135                 140

Ile Leu Thr Asn Leu Ala Glu Gln Leu Gln Asn Asn Arg Phe Gly Ser
145                 150                 155                 160

Asp Glu Asp Asp His Tyr Arg Leu Asn Asp Glu Leu Leu His Tyr Ile
                165                 170                 175

Leu Lys Ile Val Val Arg Glu Ser Cys Ile Leu Ile Thr Lys Cys Gln
            180                 185                 190

Thr Val Ser Lys Asp Asp Phe Gln Lys Leu Leu Ser Thr Val Pro Ala
        195                 200                 205

Ala Ser Ser Cys Leu Arg Tyr Leu Met Ala Val Gln Asn His Leu Leu
    210                 215                 220

Ser Asn Thr Ile Leu Ile Lys Pro Asp Glu Asn Asp Asp Ser Asp Ser
225                 230                 235                 240

Ser Leu Gln Gly Glu Thr Leu Lys Glu Leu Lys Val Ser Ile Leu Ala
                245                 250                 255

Leu Ala Thr Gln Ile Leu Thr Gly Cys Asp Glu Val Leu Glu Met Leu
            260                 265                 270

Gln Gln Val Thr Thr Ala Leu Ile Asn Ser Asp Ile Ala Asp Arg Glu
        275                 280                 285

Gln Arg Leu Lys Gly Leu Glu Gln Val Thr Lys Ala Thr Met Leu Gly
    290                 295                 300

His Leu Leu Pro Val Leu Leu Thr Ser Leu Met His Pro Asn Leu Gln
305                 310                 315                 320

Thr Leu Ile Met Ala Asp Ala Leu Met Pro Gln Leu Val Gln Leu Val
                325                 330                 335

Leu Tyr Thr Ser Gln Thr Ala Leu Leu Leu Lys Thr Gln Cys Pro Val
            340                 345                 350

Phe Ala Glu Val Gly Cys Ser Pro Cys Gly Ala Pro Asp Gln Lys Cys
        355                 360                 365

```
Arg Leu Phe Pro Asp Glu Arg Met Leu Glu Glu Lys Glu Glu Pro Gly
        370                 375                 380
Phe Leu Thr Gly Leu Lys Ile Pro Ala Pro Trp Ala Ala Gly Lys Thr
385                 390                 395                 400
Val Glu Thr Val His Pro Val Arg Asp Asn Tyr Lys Phe Lys Glu Thr
                405                 410                 415
Val His Ile Pro Gly Ala Arg Cys Leu Tyr Leu Arg Phe Asp Ser Arg
            420                 425                 430
Cys Ser Ser Gln Tyr Asp Tyr Asp Lys Leu Val Ile Tyr Ala Gly Pro
        435                 440                 445
Asn Thr Asn Ser Arg Lys Val Ala Glu Tyr Gly Gly Asn Thr Leu Gly
    450                 455                 460
Tyr Gly Ser Arg Ser Val Leu Gly Thr Gly Trp Pro Lys Asp Leu Val
465                 470                 475                 480
Lys Val Glu Gly Asp Thr Val Thr Phe Ser Phe Glu Met Arg Ser Gly
                485                 490                 495
Arg Glu His Asn Thr Pro Asp Lys Ala Met Trp Gly Phe Ala Cys Thr
            500                 505                 510
Val Arg Ala Gln Glu Ser Ser Glu Asp Val Ser Gly Gly Leu Pro Phe
        515                 520                 525
Leu Val Asp Leu Ala Leu Gly Leu Ser Val Leu Ala Cys Ser Met Leu
    530                 535                 540
Arg Ile Leu Tyr Asn Gly Pro Glu Ile Thr Lys Glu Glu Glu Ala Cys
545                 550                 555                 560
Gln Glu Leu Leu Arg Ser Lys Leu Leu Gln Arg Cys Gln Trp Gln Val
                565                 570                 575
Glu Ala Asn Gly Val Ile Ser Pro Ala Leu Thr Pro Ser Pro Ser Pro
            580                 585                 590
Leu Pro Leu Thr Ile Glu Glu Asp Arg Glu Phe Thr Tyr Pro Ser Asp
        595                 600                 605
Val Leu Val Pro Pro Val Gly Asn Tyr Phe Asp Leu Pro Arg Ile Arg
    610                 615                 620
Leu Pro Pro Gly Ile Met Ile Lys Leu Arg Glu Ile Ser Gly Arg Ala
625                 630                 635                 640
Arg Pro Gln Phe Arg Pro Ser Ile Lys Tyr Val Ala Val
                645                 650

<210> SEQ ID NO 48
<211> LENGTH: 2100
<212> TYPE: DNA
<213> ORGANISM: Homo sapiens

<400> SEQUENCE: 48
tcactgagcc caaagaagag gctataacca cgaatgaggt tataaaccaa ttattgcacc      60
acgttggtgc gatgtgcata caccaactca atcttcttgc caccaacccc aatcttccaa     120
tcacaagtgt cttgggcaag cagcatccaa ttgaagcaca tcatcttagc agtatttgtg     180
acattatgga gaaggccatg gttaatggag atacctgtat tatacgctgc attctcgttg     240
tctttcaggt ggtatttaaa ttttttcttca gcccacaaac tgaaaggaat cgagacatca     300
ttcgacggtc gggattgctt ctttggcagt tgttgatggc tccaaaagat caaatttgcc     360
ctgaaattca gaaggaagtc tgccttgcca tcagctctgg tttaaatatc ttgtacccag     420
gtgaaactga aatcaataac ttacttaaac tggtcttaac agaaggagag agaaacagtg     480
gactctccca gctacgggat gtgatcctaa ccaacctggc tgaacagctc caaaacaacc     540
```

-continued

```
gatttggcag tgatgaggat gatcattaca gactaaatga tgaacttta cactacattc      600
tgaagattgt tgtacgagaa tcctgtatct taatcaccaa gtgccaaact gtctctaaag      660
atgattttca aaagctcctt tcaactgtgc ctgctgcatc ctcctgcctg cgctatctga      720
tggcagttca gaatcacctt ctcagtaaca ctattttgat taaacctgat gagaatgatg      780
acagtgacag ctccttgcag ggagagacat tgaaggagct aaaagtcagt attttggctc      840
ttgccaccca atcctgact ggatgtgatg aagtgttgga aatgctacag caggtcacaa      900
ctgccctcat aaatagtgac atagcagacc gtgagcagag gttaaaaggc ttggaacaag      960
ttactaaggc tactatgctt ggtcaccttc ttccagtgtt actgacctcc ttgatgcatc     1020
caaatttaca gactctgatc atggcggatg ccctgatgcc tcagctagtg cagctggtac     1080
tctataccag ccagacggcg ttgctgctta aacccagtg tccggttttt gctgaggtgg     1140
gctgttcccc gtgtggtgca ccagaccaga agtgcaggct gttccctgat gagagaatgt     1200
tagaagagaa ggaagagcca ggatttctca ctggtttaaa gattcctgcc ccatgggctg     1260
ctggaaagac tgtggaaaca gtccacccg tcagagacaa ctataaattt aaagaaacgg     1320
tccatatccc aggagctcgc tgcctgtacc ttagatttga tagcagatgc tcttcgcaat     1380
atgactatga caaattggtg atatatgcgg ggcctaacac aaacagtagg aaggttgctg     1440
aatatggagg caacacactg ggatatggca gccgtagtgt cttaggaact ggttggccga     1500
aagacttggt gaaggtggaa ggagatacag tcaccttctc ctttgaaatg agaagtggcc     1560
gtgaacacaa cactcctgat aaagccatgt ggggctttgc ttgcacagtt cgcgctcagg     1620
agtcttcgga ggatgtctca ggaggcttgc cctttctggt agacctggct ttaggtctgt     1680
ctgtgttagc ttgttccatg ttaagaatcc tgtacaatgg accagaaatt accaaagaag     1740
aagaagcctg tcaggagcta ttgcggtcca aactttaca aaggtgccag tggcaggtgg     1800
aggccaatgg cgtgatctcc cctgcccta ctccgagccc ctctccactg cctctgacca     1860
tagaggaaga cagagaattc acctaccct ctgatgtcct cgtgcctcct gttggaaact     1920
actttgatct gcctcggatc agactgcctc caggaatcat gataaagctc agggaaattt     1980
ctgggcgtgc tagacctcaa tttagaccaa gtataaagta tgttgctgtg tagtgtttta     2040
cttttcccaa tgggaaaaaa aagtttaaac aattgaaatg ggtatatttc ttctgtggtc     2100
```

<210> SEQ ID NO 49
<211> LENGTH: 189
<212> TYPE: PRT
<213> ORGANISM: Homo sapiens

<400> SEQUENCE: 49

```
Met Glu Glu Gly Gly Asn Leu Gly Gly Leu Ile Lys Met Val His Leu
1               5                   10                  15

Leu Val Leu Ser Gly Ala Trp Gly Met Gln Met Trp Val Thr Phe Val
            20                  25                  30

Ser Gly Phe Leu Leu Phe Arg Ser Leu Pro Arg His Thr Phe Gly Leu
        35                  40                  45

Val Gln Ser Lys Leu Phe Pro Phe Tyr Phe His Ile Ser Met Gly Cys
    50                  55                  60

Ala Phe Ile Asn Leu Cys Ile Leu Ala Ser Gln His Ala Trp Ala Gln
65                  70                  75                  80

Leu Thr Phe Trp Glu Ala Ser Gln Leu Tyr Leu Leu Phe Leu Ser Leu
                85                  90                  95
```

```
Thr Leu Ala Thr Val Asn Ala Arg Trp Leu Glu Pro Arg Thr Thr Ala
                100                 105                 110

Ala Met Trp Ala Leu Gln Thr Val Glu Lys Glu Arg Gly Leu Gly Gly
        115                 120                 125

Glu Val Pro Gly Ser His Gln Gly Pro Asp Pro Tyr Arg Gln Leu Arg
    130                 135                 140

Glu Lys Asp Pro Lys Tyr Ser Ala Leu Arg Gln Asn Phe Phe Arg Tyr
145                 150                 155                 160

His Gly Leu Ser Ser Leu Cys Asn Leu Gly Cys Val Leu Ser Asn Gly
                165                 170                 175

Leu Cys Leu Ala Gly Leu Ala Leu Glu Ile Arg Ser Leu
            180                 185
```

<210> SEQ ID NO 50
<211> LENGTH: 1311
<212> TYPE: DNA
<213> ORGANISM: Homo sapiens

<400> SEQUENCE: 50

```
ggctcagctg ggaggcggga cgaattattg gttggggaa  acccacgagg ggacgcggcc    60
gaggagggtc gctgtccacc cggggggcgtg ggagtgaggt accagattca gcccatttgg   120
ccccgacgcc tctgttctcg gaatccgggt gctgcggatt gaggtcccgg ttcctaacgg   180
tgggatcggt gtcctcggga tgagatttgg cgtttcctcg gggctttggt gggatcggtg   240
tcctcaggat gagatttagg gtttcctcgg ggctttcggg atcttcacct aatatccggt   300
attattttat gagaggagtg gtcttggctg tcagaactgg atccctgggg tgatatttgg   360
gaattagtgg agtgatctct gaagacctag gctatgatc  tggagctgct gtggctgaaa   420
tttgggcct  ctgaagtggc atggagattg aggtccagag agcctgagat cttgagggct   480
gacatttgga gagatggggt cgagggttgt cttttgggcct tgactgcttt gggccttttct  540
cactctcatt cccgggatgc tttgccagaa tctctgctgg attggccgta acccctgtccc   600
cgagcgggct cacagggtct gaaggccacg catgaggcaa aggtaaagtt ctgagccacc   660
cggtgcctcc ttcccaggac tgcaagatgg aggaaggcgg gaacctagga ggcctgatta   720
agatggtcca tctactggtc ttgtcaggtg cctggggcat gcaaatgtgg gtgaccttcg   780
tctcaggctt cctgcttttc cgaagccttc cccgacatac cttcggacta gtgcagagca   840
aactcttccc cttctacttc cacatctcca tgggctgtgc cttcatcaac ctctgcatct   900
tggcttcaca gcatgcttgg gctcagctca cattctggga ggccagccag ctttacctgc   960
tgttcctgag ccttacgctg ccactgtca  acgcccgctg gctggaaccc cgcaccacag  1020
ctgccatgtg ggccctgcaa accgtggaga aggagcgagg cctgggtggg gaggtaccag  1080
gcagccacca gggtcccgat ccctaccgcc agctgcgaga aaggacccc  aagtacagtg  1140
ctctccgcca gaatttcttc cgctaccatg ggctgtcctc tctttgcaat ctgggctgcg  1200
tcctgagcaa tgggctctgt ctcgctggcc ttgccctgga aataaggagc ctctagcatg  1260
ggccctgcat gctaataaat gcttcttcag aaatgaaaaa aaaaaaaaaa a           1311
```

<210> SEQ ID NO 51
<211> LENGTH: 679
<212> TYPE: PRT
<213> ORGANISM: Homo sapiens

<400> SEQUENCE: 51

Met Ile Ser Ala Ser Arg Ala Ala Ala Ala Arg Leu Val Gly Ala Ala

-continued

```
1               5                    10                   15
Ala Ser Arg Gly Pro Thr Ala Ala Arg His Gln Asp Ser Trp Asn Gly
            20                  25                  30
Leu Ser His Glu Ala Phe Arg Leu Val Ser Arg Asp Tyr Ala Ser
            35              40                  45
Glu Ala Ile Lys Gly Ala Val Gly Ile Asp Leu Gly Thr Thr Asn
 50                  55                  60
Ser Cys Val Ala Val Met Glu Gly Lys Arg Ala Lys Val Leu Glu Asn
 65                  70                  75                  80
Ala Glu Gly Ala Arg Thr Thr Pro Ser Val Val Ala Phe Thr Ala Asp
                85                  90                  95
Gly Glu Arg Leu Val Gly Met Pro Ala Lys Arg Gln Ala Val Thr Asn
            100                 105                 110
Pro Asn Asn Thr Phe Tyr Ala Thr Lys Arg Leu Ile Gly Arg Arg Tyr
            115                 120                 125
Asp Asp Pro Glu Val Gln Lys Asp Ile Lys Asn Val Pro Phe Lys Ile
            130                 135                 140
Val Arg Ala Ser Asn Gly Asp Ala Trp Val Glu Ala His Gly Lys Leu
145                 150                 155                 160
Tyr Ser Pro Ser Gln Ile Gly Ala Phe Val Leu Met Lys Met Lys Glu
                165                 170                 175
Thr Ala Glu Asn Tyr Leu Gly Arg Thr Ala Lys Asn Ala Val Ile Thr
            180                 185                 190
Val Pro Ala Tyr Phe Asn Asp Ser Gln Arg Gln Ala Thr Lys Asp Ala
            195                 200                 205
Gly Gln Ile Ser Gly Leu Asn Val Leu Arg Val Ile Asn Glu Pro Thr
            210                 215                 220
Ala Ala Ala Leu Ala Tyr Gly Leu Asp Lys Ser Glu Asp Lys Val Ile
225                 230                 235                 240
Ala Val Tyr Asp Leu Gly Gly Gly Thr Phe Asp Ile Ser Ile Leu Glu
                245                 250                 255
Ile Gln Lys Gly Val Phe Glu Val Lys Ser Thr Asn Gly Asp Thr Phe
            260                 265                 270
Leu Gly Gly Glu Asp Phe Asp Gln Ala Leu Leu Arg His Ile Val Lys
            275                 280                 285
Glu Phe Lys Arg Glu Thr Gly Val Asp Leu Thr Lys Asp Asn Met Ala
            290                 295                 300
Leu Gln Arg Val Arg Glu Ala Ala Glu Lys Ala Lys Cys Glu Leu Ser
305                 310                 315                 320
Ser Ser Val Gln Thr Asp Ile Asn Leu Pro Tyr Leu Thr Met Asp Ser
                325                 330                 335
Ser Gly Pro Lys His Leu Asn Met Lys Leu Thr Arg Ala Gln Phe Glu
            340                 345                 350
Gly Ile Val Thr Asp Leu Ile Arg Arg Thr Ile Ala Pro Cys Gln Lys
            355                 360                 365
Ala Met Gln Asp Ala Glu Val Ser Lys Ser Asp Ile Gly Glu Val Ile
            370                 375                 380
Leu Val Gly Gly Met Thr Arg Met Pro Lys Val Gln Gln Thr Val Gln
385                 390                 395                 400
Asp Leu Phe Gly Arg Ala Pro Ser Lys Ala Val Asn Pro Asp Glu Ala
                405                 410                 415
Val Ala Ile Gly Ala Ala Ile Gln Gly Gly Val Leu Ala Gly Asp Val
            420                 425                 430
```

```
Thr Asp Val Leu Leu Asp Val Thr Pro Leu Ser Leu Gly Ile Glu
        435                 440                 445
Thr Leu Gly Gly Val Phe Thr Lys Leu Ile Asn Arg Asn Thr Thr Ile
    450                 455                 460
Pro Thr Lys Lys Ser Gln Val Phe Ser Thr Ala Ala Asp Gly Gln Thr
465                 470                 475                 480
Gln Val Glu Ile Lys Val Cys Gln Gly Glu Arg Glu Met Ala Gly Asp
                485                 490                 495
Asn Lys Leu Leu Gly Gln Phe Thr Leu Ile Gly Ile Pro Pro Ala Pro
            500                 505                 510
Arg Gly Val Pro Gln Ile Glu Val Thr Phe Asp Ile Asp Ala Asn Gly
        515                 520                 525
Ile Val His Val Ser Ala Lys Asp Lys Gly Thr Gly Arg Glu Gln Gln
    530                 535                 540
Ile Val Ile Gln Ser Ser Gly Gly Leu Ser Lys Asp Asp Ile Glu Asn
545                 550                 555                 560
Met Val Lys Asn Ala Glu Lys Tyr Ala Glu Glu Asp Arg Arg Lys Lys
                565                 570                 575
Glu Arg Val Glu Ala Val Asn Met Ala Glu Gly Ile Ile His Asp Thr
            580                 585                 590
Glu Thr Lys Met Glu Glu Phe Lys Asp Gln Leu Pro Ala Asp Glu Cys
        595                 600                 605
Asn Lys Leu Lys Glu Glu Ile Ser Lys Met Arg Glu Leu Leu Ala Arg
    610                 615                 620
Lys Asp Ser Glu Thr Gly Glu Asn Ile Arg Gln Ala Ala Ser Ser Leu
625                 630                 635                 640
Gln Gln Ala Ser Leu Lys Leu Phe Glu Met Ala Tyr Lys Lys Met Ala
                645                 650                 655
Ser Glu Arg Glu Gly Ser Gly Ser Ser Gly Thr Gly Glu Gln Lys Glu
            660                 665                 670
Asp Gln Lys Glu Glu Lys Gln
        675

<210> SEQ ID NO 52
<211> LENGTH: 2802
<212> TYPE: DNA
<213> ORGANISM: Homo sapiens

<400> SEQUENCE: 52
ggagcgcttg tttgctgcct cgtactcctc catttatccg ccatgataag tgccagccga      60
gctgcagcag cccgtctcgt gggcgccgca gcctcccggg ccctacggc cgcccgccac     120 caggatagct ggaatggcct tagtcatgag gcttttagac ttgtttcaag gcgggattat     180
gcatcagaag caatcaaggg agcagttgtt ggtattgatt gggtactac caactcctgc     240 gtggcagtta tggaaggtaa acgagcaaag gtgctggaga atgccgaagg tgccagaacc     300
accccttcag ttgtggcctt tacagcagat ggtgagcgac ttgttggaat gccggccaag     360
cgacaggctg tcaccaaccc aaacaataca ttttatgcta ccaagcgtct cattggccgg     420
cgatatgatg atcctgaagt acagaaagac attaaaaatg ttcccttttaa aattgtccgt     480 gcctccaatg gtgatgcctg ggttgaggct catgggaaat tgtattctcc gagtcagatt     540
ggagcatttg tgttgatgaa gatgaaagag actgcagaaa attacttggg gcgcacagca     600
aaaaatgctg tgatcacagt cccagcttat ttcaatgact cgcagagaca ggccactaaa     660
```

```
gatgctggcc agatatctgg actgaatgtg cttcgggtga ttaatgagcc cacagctgct    720
gctcttgcct atggtctaga caaatcagaa gacaaagtca ttgctgtata tgatttaggt    780
ggtggaactt ttgatatttc tatcctggaa attcagaaag gagtatttga ggtgaaatcc    840
acaaatgggg ataccttctt aggtggggaa gactttgacc aggccttgct acggcacatt    900
gtgaaggagt tcaagagaga gacaggggtt gatttgacta agacaacat ggcacttcag     960
agggtacggg aagctgctga aaaggctaag tgtgaactct cctcatctgt gcagactgac   1020
atcaatttgc cctatcttac aatggattct tctggaccca agcatttgaa tatgaagttg   1080
acccgtgctc aatttgaagg gattgtcact gatctaatca aaggactat cgctccatgc    1140
caaaaagcta tgcaagatgc agaagtcagc aagagtgaca taggagaagt gattcttgtg   1200
ggtggcatga ctaggatgcc caaggttcag cagactgtac aggatctttt tggcagagcc   1260
ccaagtaaag ctgtcaatcc tgatgaggct gtggccattg gagctgccat tcagggaggt   1320
gtgttggccg cgatgtcac ggatgtgctg ctccttgatg tcactcccct gtctctgggt    1380
attgaaactc taggaggtgt ctttaccaaa cttattaata ggaataccac tattccaacc   1440
aagaagagcc aggtattctc tactgccgct gatggtcaaa cgcaagtgga aattaaagtg   1500
tgtcagggtg aaagagagat ggctggagac aacaaactcc ttggacagtt tactttgatt   1560
ggaattccac cagcccctcg tggagttcct cagattgaag ttacatttga cattgatgcc   1620
aatgggatag tacatgtttc tgctaaagat aaaggcacag acgtgagca gcagattgta    1680
atccagtctt ctggtggatt aagcaaagat gatattgaaa atatggttaa aaatgcagag   1740
aaatatgctg aagaagaccg gcgaaagaag gaacgagttg aagcagttaa tatggctgaa   1800
ggaatcattc acgacacaga aaccaagatg gaagaattca aggaccaatt acctgctgat   1860
gagtgcaaca gctgaaaga agagatttcc aaaatgaggg agctcctggc tagaaaagac    1920
agcgaaacag gagaaaatat tagacaggca gcatcctctc ttcagcaggc atcattgaag   1980
ctgttcgaaa tggcatacaa aaagatggca tctgagcgag aaggctctgg aagttctggc   2040
actggggaac aaaaggaaga tcaaaaggag gaaaaacagt aataatagca gaaattttga   2100
agccagaagg acaacatatg aagcttagga gtgaagagac ttcctgagca gaaatgggcg   2160
aacttcagtc tttttactgt gttttttgcag tattctatat ataatttcct taatttgtaa   2220
atttagtgac cattagctag tgatcatttta atggacagtg attctaacag tataaagttc   2280
acaatattct atgtccctag cctgtcattt ttcagctgca tgtaaaagga ggtaggatga   2340
attgatcatt ataaagattt aactatttta tgctgaagtg accatatttt caaggggtga   2400
aaccatctcg cacacagcaa tgaaggtagt catccataga cttgaaatga gaccacatat   2460
ggggatgaga tccttctagt tagcctagta ctgctgtact ggcctgtatg tacatggggt   2520
ccttcaactg aggccttgca agtcaagctg gctgtgccat gtttgtagat ggggcagagg   2580
aatctagaac aatgggaaac ttagctattt atattaggta cagctattaa aacaaggtag   2640
gaatgaggct agacctttaa cttccctaag gcatactttt ctagctacct tctgccctgt   2700
gtctggcacc tacatccttg atgattgttc tcttacccat tctggaattt ttttttttt    2760
taaataaata cagaaagcat cttgaaaaaa aaaaaaaaa aa                       2802
```

<210> SEQ ID NO 53
<211> LENGTH: 225
<212> TYPE: PRT
<213> ORGANISM: Homo sapiens

<400> SEQUENCE: 53

```
Met Ala Thr His Ala Leu Glu Ile Ala Gly Leu Phe Leu Gly Gly Val
1               5                   10                  15

Gly Met Val Gly Thr Val Ala Val Thr Val Met Pro Gln Trp Arg Val
            20                  25                  30

Ser Ala Phe Ile Glu Asn Asn Ile Val Val Phe Glu Asn Phe Trp Glu
        35                  40                  45

Gly Leu Trp Met Asn Cys Val Arg Gln Ala Asn Ile Arg Met Gln Cys
    50                  55                  60

Lys Ile Tyr Asp Ser Leu Leu Ala Leu Ser Pro Asp Leu Gln Ala Ala
65                  70                  75                  80

Arg Gly Leu Met Cys Ala Ala Ser Val Met Ser Phe Leu Ala Phe Met
                85                  90                  95

Met Ala Ile Leu Gly Met Lys Cys Thr Arg Cys Thr Gly Asp Asn Glu
            100                 105                 110

Lys Val Lys Ala His Ile Leu Leu Thr Ala Gly Ile Ile Phe Ile Ile
        115                 120                 125

Thr Gly Met Val Val Leu Ile Pro Val Ser Trp Val Ala Asn Ala Ile
    130                 135                 140

Ile Arg Asp Phe Tyr Asn Ser Ile Val Asn Val Ala Gln Lys Arg Glu
145                 150                 155                 160

Leu Gly Glu Ala Leu Tyr Leu Gly Trp Thr Thr Ala Leu Val Leu Ile
                165                 170                 175

Val Gly Gly Ala Leu Phe Cys Cys Val Phe Cys Cys Asn Glu Lys Ser
            180                 185                 190

Ser Ser Tyr Arg Tyr Ser Ile Pro Ser His Arg Thr Thr Gln Lys Ser
        195                 200                 205

Tyr His Thr Gly Lys Lys Ser Pro Ser Val Tyr Ser Arg Ser Gln Tyr
    210                 215                 220

Val
225

<210> SEQ ID NO 54
<211> LENGTH: 2147
<212> TYPE: DNA
<213> ORGANISM: Homo sapiens

<400> SEQUENCE: 54
gatttgtaag tttacctgtt gcagccaata gcagggccat ctcagccagc cagcactgga    60
tactatctgg ccagaagtag caaagcagct cttatttgaa aaaccactgg gttccgagtt   120
cattactaca ggaaaaactg ttctcttctg tggcacagag aaccctgctt caaagcagaa   180
gtagcagttc cggagtccag ctggctaaaa ctcatcccag aggataatgg caacccatgc   240
cttagaaatc gctgggctgt tcttggtgg tgttggaatg gtgggcacag tggctgtcac   300
tgtcatgcct cagtggagag tgtcggcctt cattgaaaac aacatcgtgg ttttgaaaa   360 cttctgggaa ggactgtgga tgaattgcgt gaggcaggct aacatcagga tgcagtgcaa   420
aatctatgat ccctgctgg ctctttctcc ggacctacag gcagccagag gactgatgtg   480
tgctgcttcc gtgatgtcct tcttggcttt catgatggcc atccttggca tgaaatgcac   540
caggtgcacg ggggacaatg agaaggtgaa ggctcacatt ctgctgacgg ctggaatcat   600
cttcatcatc acgggcatgg tggtgctcat ccctgtgagc tgggttgcca atgccatcat   660
cagagatttc tataactcaa tagtgaatgt tgcccaaaaa cgtgagcttg gagaagctct   720
ctacttagga tggaccacgg cactggtgct gattgttgga ggagctctgt tctgctgcgt   780
```

```
tttttgttgc aacgaaaaga gcagtagcta cagatactcg ataccttccc atcgcacaac      840
ccaaaaaagt tatcacaccg gaaagaagtc accgagcgtc tactccagaa gtcagtatgt      900
gtagttgtgt atgttttttt aactttacta taaagccatg caaatgacaa aaatctatat      960
tactttctca aaatggaccc caaagaaact ttgatttact gttcttaact gcctaatctt     1020
aattacagga actgtgcatc agctatttat gattctataa gctatttcag cagaatgaga     1080
tattaaaccc aatgctttga ttgttctaga agtatagta atttgttttc taaggtggtt      1140
caagcatcta ctctttttat catttacttc aaaatgacat tgctaaagac tgcattattt     1200
tactactgta atttctccac gacatagcat tatgtacata gatgagtgta acatttatat     1260
ctcacataga gacatgctta tatggttttta tttaaaatga aatgccagtc cattacactg     1320
aataaataga actcaactat tgcttttcag ggaaatcatg gataggggttg aagaaggtta     1380 ctattaattg tttaaaaaca gcttagggat taatgtcctc catttataat gaagattaaa     1440
atgaaggctt taatcagcat tgtaaaggaa attgaatggc tttctgatat gctgtttttt     1500
agcctaggag ttagaaatcc taacttcttt atcctcttct cccagaggct ttttttttct     1560
tgtgtattaa attaacattt ttaaaaagca gatattttgt caagggggctt tgcattcaaa     1620 ctgcttttcc agggctatac tcagaagaaa gataaaagtg tgatctaaga aaaagtgatg     1680
gttttaggaa agtgaaaata ttttttgttt tgtatttgaa gaagaatgat gcattttgac     1740
aagaaatcat atatgtatgg atatatttta ataagtattt gagtacagac tttgaggttt     1800
catcaatata aataaaagag cagaaaaata tgtcttggtt ttcatttgct taccaaaaaa     1860
acaacaacaa aaaagttgt cctttgagaa cttcacctgc tcctatgtgg gtacctgagt      1920
caaaattgtc atttttgttc tgtgaaaaat aaatttcctt cttgtaccat ttctgtttag     1980
ttttactaaa atctgtaaat actgtatttt tctgtttatt ccaaatttga tgaaactgac     2040
aatccaattt gaaagtttgt gtcgacgtct gtctagctta aatgaatgtg ttctatttgc     2100
tttatacatt tatattaata aattgtacat ttttctaatt atttgaa                   2147
```

<210> SEQ ID NO 55
<211> LENGTH: 361
<212> TYPE: PRT
<213> ORGANISM: Homo sapiens

<400> SEQUENCE: 55

```
Met Glu Asn Gln Val Leu Thr Pro His Val Tyr Trp Ala Gln Arg His
1               5                   10                  15

Arg Glu Leu Tyr Leu Arg Val Glu Leu Ser Asp Val Gln Asn Pro Ala
            20                  25                  30

Ile Ser Ile Thr Glu Asn Val Leu His Phe Lys Ala Gln Gly His Gly
        35                  40                  45

Ala Lys Gly Asp Asn Val Tyr Glu Phe His Leu Glu Phe Leu Asp Leu
    50                  55                  60

Val Lys Pro Glu Pro Val Tyr Lys Leu Thr Gln Arg Gln Val Asn Ile
65                  70                  75                  80

Thr Val Gln Lys Lys Val Ser Gln Trp Trp Glu Arg Leu Thr Lys Gln
                85                  90                  95

Glu Lys Arg Pro Leu Phe Leu Ala Pro Asp Phe Asp Arg Trp Leu Asp
            100                 105                 110

Glu Ser Asp Ala Glu Met Glu Leu Arg Ala Lys Glu Glu Arg Leu
        115                 120                 125
```

Asn Lys Leu Arg Leu Glu Ser Glu Gly Ser Pro Glu Thr Leu Thr Asn
    130                 135                 140

Leu Arg Lys Gly Tyr Leu Phe Met Tyr Asn Leu Val Gln Phe Leu Gly
145                 150                 155                 160

Phe Ser Trp Ile Phe Val Asn Leu Thr Val Arg Phe Cys Ile Leu Gly
                165                 170                 175

Lys Glu Ser Phe Tyr Asp Thr Phe His Thr Val Ala Asp Met Met Tyr
            180                 185                 190

Phe Cys Gln Met Leu Ala Val Glu Thr Ile Asn Ala Ala Ile Gly
        195                 200                 205

Val Thr Thr Ser Pro Val Leu Pro Ser Leu Ile Gln Leu Leu Gly Arg
210                 215                 220

Asn Phe Ile Leu Phe Ile Ile Phe Gly Thr Met Glu Glu Met Gln Asn
225                 230                 235                 240

Lys Ala Val Val Phe Val Phe Tyr Leu Trp Ser Ala Ile Glu Ile
                245                 250                 255

Phe Arg Tyr Ser Phe Tyr Met Leu Thr Cys Ile Asp Met Asp Trp Lys
            260                 265                 270

Val Leu Thr Trp Leu Arg Tyr Thr Leu Gly Ile Pro Leu Tyr Pro Leu
275                 280                 285

Gly Cys Leu Ala Glu Ala Val Ser Val Ile Gln Ser Ile Pro Ile Phe
290                 295                 300

Asn Glu Thr Gly Arg Phe Ser Phe Thr Leu Pro Tyr Pro Val Lys Ile
305                 310                 315                 320

Lys Val Arg Phe Ser Phe Phe Leu Gln Ile Tyr Leu Ile Met Ile Phe
                325                 330                 335

Leu Gly Leu Tyr Ile Asn Phe Arg His Leu Tyr Lys Gln Arg Arg Arg
            340                 345                 350

Arg Tyr Gly Gln Lys Lys Lys Lys
            355                 360

<210> SEQ ID NO 56
<211> LENGTH: 1231
<212> TYPE: DNA
<213> ORGANISM: Homo sapiens

<400> SEQUENCE: 56
ggcaacgagg ggtatctcga ggtgccgggt tgcaggcgct caggagcgct agggtttgag      60
gcctgctttc tgctcgcgcc agcagagcac tacctgaggc agcgaggcgc agcgagccta     120
gcctccccgc gccctgggca gtgtggccat ggagaatcag gtgttgacgc cgcatgtcta     180
ctgggctcag cgacaccgcg agctatatct gcgcgtggag ctgagtgacg tacagaaccc     240
tgccatcagc atcactgaaa acgtgctgca tttcaaagct caaggacatg gtgccaaagg     300
agacaatgtc tatgaatttc acctggagtt cttagacctt gtgaaaccag agcctgttta     360
caaactgacc cagaggcagg taaacattac agtacagaag aaagtgagtc agtggtggga     420
gagactcaca aagcaggaaa agcgaccact gttttttggct cctgactttg atcgttggct     480
ggatgaatct gatgcggaaa tggagctcag agctaaggaa gaagagcgcc taaataaact     540
ccgactggaa agcgaaggct ctcctgaaac tcttacaaac ttaaggaaag gatacctgtt     600
tatgtataat cttgtgcaat tcttgggatt ctcctggatc tttgtcaacc tgactgtgcg     660
attctgtatc ttgggaaaag agtccttta tgacacattc catactgtgg ctgacatgat     720
gtatttctgc cagatgctgg cagttgtgga aactatcaat gcagcaattg gagtcactac     780

```
gtcaccggtg ctgccttctc tgatccagct tcttggaaga aatttttattt tgtttatcat    840 ctttggcacc atggaagaaa tgcagaacaa agctgtggtt ttctttgtgt tttatttgtg    900
gagtgcaatt gaaattttca ggtactcttt ctacatgctg acgtgcattg acatggattg    960
gaaggtgctc acatggcttc gttacactct ggggattccc ttatatccac tgggatgttt   1020
ggcggaagct gtctcagtga ttcagtccat tccaatattc aatgagaccg gacgattcag   1080
tttcacattg ccatatccag tgaaaatcaa agttagattt tcctttttc ttcagattta    1140 tcttataatg atatttttag gtttatacat aaattttcgt cacctttata aacagcgcag   1200
acggcgctat ggacaaaaaa aaaaaaaaaa a                                   1231
```

<210> SEQ ID NO 57
<211> LENGTH: 176
<212> TYPE: PRT
<213> ORGANISM: Homo sapiens

<400> SEQUENCE: 57

```
Met Ser Ala Gly Gly Ala Ser Val Pro Pro Pro Asn Pro Ala Val
1               5                   10                  15

Ser Phe Pro Pro Arg Val Thr Leu Pro Ala Gly Pro Asp Ile Leu
            20                  25                  30

Arg Thr Tyr Ser Gly Ala Phe Val Cys Leu Glu Ile Leu Phe Gly Gly
        35                  40                  45

Leu Val Trp Ile Leu Val Ala Ser Ser Asn Val Pro Leu Pro Leu Leu
    50                  55                  60

Gln Gly Trp Val Met Phe Val Ser Val Thr Ala Phe Phe Phe Ser Leu
65                  70                  75                  80

Leu Phe Leu Gly Met Phe Leu Ser Gly Met Val Ala Gln Ile Asp Ala
                85                  90                  95

Asn Trp Asn Phe Leu Asp Phe Ala Tyr His Phe Thr Val Phe Val Phe
            100                 105                 110

Tyr Phe Gly Ala Phe Leu Leu Glu Ala Ala Ala Thr Ser Leu His Asp
        115                 120                 125

Leu His Cys Asn Thr Thr Ile Thr Gly Gln Pro Leu Leu Ser Asp Asn
    130                 135                 140

Gln Tyr Asn Ile Asn Val Ala Ala Ser Ile Phe Ala Phe Met Thr Thr
145                 150                 155                 160

Ala Cys Tyr Gly Cys Ser Leu Gly Leu Ala Leu Arg Arg Trp Arg Pro
                165                 170                 175
```

<210> SEQ ID NO 58
<211> LENGTH: 2831
<212> TYPE: DNA
<213> ORGANISM: Homo sapiens

<400> SEQUENCE: 58

```
agcccgcgga gctgagcggc ggcggcggcg gcggcaggag cccgggaggc ggaggcggga     60
ggcggcggcg gcgcgcggag acgcagcagc ggcagcggca gcatgtcggc cggcggagcg    120
tcagtcccgc cgcccccgaa ccccgccgtg tccttcccgc cgccccgggt cacccctgccc   180 gccggccccg acatcctgcg gacctactcg ggcgccttcg tctgcctgga gattctgttc    240
gggggtcttg tctggatttt ggttgcctcc tccaatgttc ctctacctct actacaagga    300
tgggtcatgt ttgtgtccgt gacagcgttt ttcttttcgc tcctctttct gggcatgttc    360
ctctctggca tggtggctca aattgatgct aactggaact tcctggattt tgcctaccat    420
```

```
tttacagtat ttgtcttcta tttttggagcc tttttattgg aagcagcagc cacatccctg    480
catgatttgc attgcaatac aaccataacc gggcagccac tcctgagtga taaccagtat    540
aacataaacg tagcagcctc aattttttgcc tttatgacga cagcttgtta tggttgcagt   600
ttgggtctgg ctttacgaag atggcgaccg taacactcct tagaaactgg cagtcgtatg    660
ttagtttcac ttgtctactt tatatgtctg atcaatttgg ataccatttt gtccagatgc    720
aaaaacattc caaagtaat gtgtttagta gagagagact ctaagctcaa gttctggttt     780
atttcatgga tggaatgtta attttattat gatattaaag aaatggcctt ttattttaca    840
tctctcccct ttttcccttt ccccctttat tttcctcctt ttctttctga aagtttcctt    900
ttatgtccat aaaatacaaa tatattgttc ataaaaaatt agtatcccct ttgtttggtt    960
gctgagtcac ctgaacctta attttaattg gtaattacag cccctaaaaa aaacacattt    1020
caaataggct tcccactaaa ctctatattt tagtgtaaac caggaattgg cacactttt     1080 ttagaatggg ccagatggta aatatttatg cttcacggtc catacagtct ctgtcacaac    1140
tattcagttc tgctagtata gcgtgaaagc agctatacac aatacagaaa tgaatgagtg    1200
tggttatgtt ctaataaaac ttatttataa aaacaagggg aggctgggtt tagcctgtgg    1260
gccatagttt gtcaaccact ggtgtaaaac cttagttata tatgatctgc attttcttga    1320
actgatcatt gaaaacttat aaacctaaca gaaaagccac ataatattta gtgtcattat    1380
gcaataatca cattgccttt gtgttaatag tcaaatactt acctttggag aatacttacc    1440
tttggaggaa tgtataaaat ttctcaggca gagtcctgga tataggaaaa agtaatttat    1500
gaagtaaact tcagttgctt aatcaaacta atgatagtct aacaactgag caagatcctc    1560
atctgagagt gcttaaaatg ggatccccag agaccattaa ccaatactgg aactggtatc    1620
tagctactga tgtcttactt tgagtttatt tatgcttcag aatacagttg tttgccctgt    1680
gcatgaatat acccatattt gtgtgtggat atgtgaagct tttccaaata gagctctcag    1740
aagaattaag ttttttacttc taattatttt gcattacttt gagttaaatt tgaatagagt    1800
attaaatata aagttgtaga ttcttatgtg tttttgtatt agcccagaca tctgtaatgt    1860
ttttgcactg gtgacagaca aaatctgttt taaaatcata tccagcacaa aaactatttc    1920
tggctgaata gcacagaaaa gtattttaac ctacctgtag agatcctcgt catggaaagg    1980
tgccaaactg ttttgaatgg aaggacaagt aagagtgagg ccacagttcc caccacacga    2040
gggcttttgt attgttctac tttttcagcc ctttactttc tggctgaagc atccccttgg    2100
agtgccatgt ataagttggg ctattagagt tcatggaaca tagaacaacc atgaatgagt    2160
ggcatgatcc gtgcttaatg atcaagtgtt acttatctaa taatcctcta gaaagaaccc    2220
tgttagatct tggtttgtga taaaaatata aagacagaag acatgaggaa aaacaaaagg    2280
tttgaggaaa tcaggcatat gactttatac ttaacatcag atcttttcta taatatccta    2340
ctactttggt tttcctagct ccataccaca cacctaaacc tgtattatga attacatatt    2400
acaaagtcat aaatgtgcca tatggatata cagtacattc tagttggaat cgtttactct    2460
gctagaattt aggtgtgaga tttttttgttt cccaggtata gcaggcttat gtttggtggc    2520
attaaattgg tttctttaaa atgctttggt ggcacttttg taaacagatt gcttctagat    2580
tgttacaaac caagcctaag acacatctgt gaatacttag atttgtagct taatcacatt    2640
ctagacttgt gagttgaatg acaaagcagt tgaacaaaaa ttatggcatt taagaattta    2700
acatgtctta gctgtaaaaa tgagaaagtg ttggttggtt ttaaaatctg gtaactccat    2760
gatgaaaaga aatttatttt atacgtgtta tgtctctaat aaagtattca tttgataaaa    2820
```

```
aaaaaaaaaa a                                                        2831
```

<210> SEQ ID NO 59
<211> LENGTH: 1667
<212> TYPE: DNA
<213> ORGANISM: Homo sapiens

<400> SEQUENCE: 59

```
atcatattta aaatctggga caaagaaccg tcgggacgga actccttcca ttgcaaaagc     60
tcggcgcggc ctcgggagct gcccggcggc cccggaccga ggcagccctc ccctttaaaa   120
gaagcggagg acaggattgg gatccttgaa acccgaaacc cagaaacagc atcggagcgg   180
aaaccagagg ggaaaccttg aactcctcca gacaattgct tccggggagt tgcgagggag   240
cgaggggaa taaaggaccc gcgaggaagg gcccgcggat ggcgcgtccc tgagggtcgt    300
ggcgagttcg cggagcgtgg gaaggagcgg accctgctct ccccgggctg cgggccatgg   360
ccacggcgga gcgagagcc ctcggcatcg gcttccagtg gctctctttg gccactctgg    420
tgctcatctg cgccgggcaa ggggacgca gggaggatgg gggtccagcc tgctacggcg    480
gatttgacct gtacttcatt ttggacaaat caggaagtgt gctgcaccac tggaatgaaa   540
tctattactt tgtggaacag ttggctcaca aattcatcag cccacagttg agaatgtcct   600
ttattgtttt ctccacccga ggaacaacct aatgaaact gacagaagac agagaacaaa    660
tccgtcaagg cctagaagaa ctccagaaag ttctgccagg aggagacact tacatgcatg   720
aaggatttga aagggccagt gagcagattt attatgaaaa cagacaaggg tacaggacag   780
ccagcgtcat cattgctttg actgatggag aactccatga agatctcttt ttctattcag   840
agagggaggc taataggtct cgagatcttg gtgcaattgt ttactgtgtt ggtgtgaaag   900
atttcaatga gacacagctg gcccggattg cggacagtaa ggatcatgtg tttcccgtga   960
atgacggctt tcaggctctg caaggcatca tccactcaat tttgaagaag tcctgcatcg  1020
aaattctagc agctgaacca tccaccatat gtgcaggaga gtcatttcaa gttgtcgtga  1080
gaggaaacgg cttccgacat gccgcaacg tggacagggt cctctgcagc ttcaagatca   1140
atgactcggt cacactcaat gagaagccct ttctgtgga agatacttat ttactgtgtc   1200
cagcgcctat cttaaaagaa gttggcatga agctgcact ccaggtcagc atgaacgatg    1260
gcctctcttt tatctccagt tctgtcatca tcaccaccac acactgttct gacggttcca  1320
tcctggccat cgccctgctg atcctgttcc tgctcctagc cctggctctc ctctggtggt  1380
tctggccct ctgctgcact gtgattatca aggaggtccc tccaccccct gccgaggaga    1440
gtgaggaaaa taaaataaaa taacaagaag aagaaagaaa gaaatcccac agaaacagat  1500
aacctaacac agcccgtgca acgtattta tacaatgctc tgaaaatcat agtctcaatc   1560
tagacagtct tttcctctag ttccctgtat tcaaatccca gtgtctaaca ttcaataaat  1620
agctatatga aatcaaaaaa aaaaaaaaaa aaaaaaaaa aaaaaa               1667
```

<210> SEQ ID NO 60
<211> LENGTH: 333
<212> TYPE: PRT
<213> ORGANISM: Homo sapiens

<400> SEQUENCE: 60

```
Met Ala Thr Ala Glu Arg Arg Ala Leu Gly Ile Gly Phe Gln Trp Leu
1               5                   10                  15

Ser Leu Ala Thr Leu Val Leu Ile Cys Ala Gly Gln Gly Gly Arg Arg
```

```
                 20                  25                  30
Glu Asp Gly Gly Pro Ala Cys Tyr Gly Gly Phe Asp Leu Tyr Phe Ile
             35                  40                  45
Leu Asp Lys Ser Gly Ser Val Leu His His Trp Asn Glu Ile Tyr Tyr
 50                  55                  60
Phe Val Glu Gln Leu Ala His Lys Phe Ile Ser Pro Gln Leu Arg Met
 65                  70                  75                  80
Ser Phe Ile Val Phe Ser Thr Arg Gly Thr Thr Leu Met Lys Leu Thr
                 85                  90                  95
Glu Asp Arg Glu Gln Ile Arg Gln Gly Leu Glu Glu Leu Gln Lys Val
            100                 105                 110
Leu Pro Gly Gly Asp Thr Tyr Met His Glu Gly Phe Glu Arg Ala Ser
            115                 120                 125
Glu Gln Ile Tyr Tyr Glu Asn Arg Gln Gly Tyr Arg Thr Ala Ser Val
            130                 135                 140
Ile Ile Ala Leu Thr Asp Gly Glu Leu His Glu Asp Leu Phe Phe Tyr
145                 150                 155                 160
Ser Glu Arg Glu Ala Asn Arg Ser Arg Asp Leu Gly Ala Ile Val Tyr
                165                 170                 175
Cys Val Gly Val Lys Asp Phe Asn Glu Thr Gln Leu Ala Arg Ile Ala
            180                 185                 190
Asp Ser Lys Asp His Val Phe Pro Val Asn Asp Gly Phe Gln Ala Leu
            195                 200                 205
Gln Gly Ile Ile His Ser Ile Leu Lys Lys Ser Cys Ile Glu Ile Leu
        210                 215                 220
Ala Ala Glu Pro Ser Thr Ile Cys Ala Gly Glu Ser Phe Gln Val Val
225                 230                 235                 240
Val Arg Gly Asn Gly Phe Arg His Ala Arg Asn Val Asp Arg Val Leu
                245                 250                 255
Cys Ser Phe Lys Ile Asn Asp Ser Val Thr Leu Asn Glu Lys Pro Phe
            260                 265                 270
Ser Val Glu Asp Thr Tyr Leu Leu Cys Pro Ala Pro Ile Leu Lys Glu
            275                 280                 285
Val Gly Met Lys Ala Ala Leu Gln Val Ser Met Asn Asp Gly Leu Ser
        290                 295                 300
Phe Ile Ser Ser Ser Val Ile Ile Thr Thr Thr His Cys Ser Leu His
305                 310                 315                 320
Lys Ile Ala Ser Gly Pro Thr Thr Ala Ala Cys Met Glu
                325                 330

<210> SEQ ID NO 61
<211> LENGTH: 2526
<212> TYPE: DNA
<213> ORGANISM: Homo sapiens

<400> SEQUENCE: 61
gcacacagtg cacgaagacg ctgtcgggag agcccaggat tcaacacggg ccttgagaaa      60
tgtggctctt gtacctcctg gtgccggccc tgttctgcag ggcaggaggc tccattccca     120
tccctcagaa gttatttggg gaggtgactt cccctctgtt ccccaagcct taccccaaca     180
actttgaaac aaccactgtg atcacagtcc cacgggata cagggtgaag ctcgtcttcc      240
agcagtttga cctggagcct tctgaaggct gcttctatga ttatgtcaag atctctgctg     300
ataagaaaag cctggggagg ttctgtgggc aactgggttc tccactgggc aaccccccgg     360
```

-continued

```
gaaagaagga atttatgtcc caagggaaca agatgctgct gaccttccac acagacttct       420
ccaacgagga gaatgggacc atcatgttct acaagggctt cctggcctac taccaagctg       480
tggaccttga tgaatgtgct tcccggagca aattagggga ggaggatccc cagccccagt       540
gccagcacct gtgtcacaac tacgttggag gctacttctg ttcctgccgt ccaggctatg       600
agcttcagga agacaggcat tcctgccagg ctgagtgcag cagcgagctg tacacggagg       660
catcaggcta catctccagc ctggagtacc ctcggtccta ccccctgac ctgcgctgca        720 actacagcat ccgggtggag cggggcctca ccctgcacct caagttcctg agccttttg        780 atattgatga ccaccagcaa gtacactgcc cctatgacca gctacagatc tatgccaacg       840
ggaagaacat tggcgagttc tgtgggaagc aaaggccccc cgacctcgac accagcagca      900
atgctgtgga tctgctgttc ttcacagatg agtcggggga cagccgggc tggaagctgc        960 gctacaccac cgagatcatc aagtgccccc agcccaagac cctagacgag ttcaccatca      1020
tccagaacct gcagcctcag taccagttcc gtgactactt cattgctacc tgcaagcaag     1080
gctaccagct catagagggg aaccaggtgc tgcattcctt cacagctgtc tgccaggatg     1140
atggcacgtg gcatcgtgcc atgcccagat gcaagatcaa ggactgtggg cagccccgaa     1200
acctgcctaa tggtgacttc cgttacacca ccacaatggg agtgaacacc tacaaggccc     1260
gtatccagta ctactgccat gagccatatt acaagatgca gaccagagct ggcagcaggg     1320
agtctgagca aggggtgtac acctgcacag cacagggcat ttggaagaat gaacagaagg     1380
gagagaagat tcctcggtgc ttgccagtgt gtgggaagcc cgtgaacccc gtggaacaga     1440
ggcagcgcat catcggaggg caaaaagcca agatgggcaa cttcccctgg caggtgttca     1500
ccaacatcca cgggcgcggg ggcgggggcc tgctgggcga ccgctggatc ctcacagctg     1560
cccacaccct gtatcccaag gaacacgaag cgcaaagcaa cgcctctttg gatgtgttcc     1620
tgggccacac aaatgtggaa gagctcatga agctaggaaa tcaccccatc cgcagggtca     1680
gcgtccaccc ggactaccgt caggatgagt cctacaattt tgaggggggac atcgccctgc     1740 tggagctgga aaatagtgtc accctgggtc ccaacctcct ccccatctgc ctccctgaca     1800
acgatacctt ctacgacctg ggcttgatgg gctatgtcag tggcttcggg gtcatggagg     1860
agaagattgc tcatgacctc aggtttgtcc gtctgccgt agctaatcca caggcctgtg     1920
agaactggct ccggggaaag aataggatgg atgtgttctc tcaaaacatg ttctgtgctg     1980
gacacccatc tctaaagcag gacgcctgcc aggggggatag tgggggcgtt tttgcagtaa     2040
gggacccgaa cactgatcgc tgggtggcca cgggcatcgt gtcctgggggc atcgggtgca     2100 gcagggcta tggcttctac accaaagtgc tcaactacgt ggactggatc aagaaagaga     2160
tggaggagga ggactgagcc cagaattcac taggttcgaa tccagagagc agtgtggaaa     2220 aaaaaaaca aaaaacaact gaccagttgt tgataaccac taagagtctc tattaaaatt     2280
actgatgcag aaagaccgtg tgtgaaattc tctttcctgt agtcccattg atgtactta     2340 cctgaaacaa cccaaagggc cccttctctt cttctgagga ttgcagagga tatagttatc     2400
aatctctagt tgtcactttc ctcttccact ttgataccat tgggtcattg aatataactt     2460
tttccaaata aagtttatg agaaatgcca gtgtgcaaaa aaaaaaaaaa aaaaaaaaa       2520 aaaaaa                                                                    2526
```

<210> SEQ ID NO 62
<211> LENGTH: 705
<212> TYPE: PRT
<213> ORGANISM: Homo sapiens

<400> SEQUENCE: 62

```
Met Trp Leu Leu Tyr Leu Leu Val Pro Ala Leu Phe Cys Arg Ala Gly
1               5                   10                  15

Gly Ser Ile Pro Ile Pro Gln Lys Leu Phe Gly Glu Val Thr Ser Pro
            20                  25                  30

Leu Phe Pro Lys Pro Tyr Pro Asn Asn Phe Glu Thr Thr Thr Val Ile
        35                  40                  45

Thr Val Pro Thr Gly Tyr Arg Val Lys Leu Val Phe Gln Gln Phe Asp
    50                  55                  60

Leu Glu Pro Ser Glu Gly Cys Phe Tyr Asp Tyr Val Lys Ile Ser Ala
65                  70                  75                  80

Asp Lys Lys Ser Leu Gly Arg Phe Cys Gly Gln Leu Gly Ser Pro Leu
                85                  90                  95

Gly Asn Pro Pro Gly Lys Lys Glu Phe Met Ser Gln Gly Asn Lys Met
            100                 105                 110

Leu Leu Thr Phe His Thr Asp Phe Ser Asn Glu Asn Gly Thr Ile
        115                 120                 125

Met Phe Tyr Lys Gly Phe Leu Ala Tyr Gln Ala Val Asp Leu Asp
    130                 135                 140

Glu Cys Ala Ser Arg Ser Lys Ser Gly Glu Glu Asp Pro Gln Pro Gln
145                 150                 155                 160

Cys Gln His Leu Cys His Asn Tyr Val Gly Gly Tyr Phe Cys Ser Cys
                165                 170                 175

Arg Pro Gly Tyr Glu Leu Gln Glu Asp Arg His Ser Cys Gln Ala Glu
            180                 185                 190

Cys Ser Ser Glu Leu Tyr Thr Glu Ala Ser Gly Tyr Ile Ser Ser Leu
        195                 200                 205

Glu Tyr Pro Arg Ser Tyr Pro Pro Asp Leu Arg Cys Asn Tyr Ser Ile
    210                 215                 220

Arg Val Glu Arg Gly Leu Thr Leu His Leu Lys Phe Leu Glu Pro Phe
225                 230                 235                 240

Asp Ile Asp Asp His Gln Val His Cys Pro Tyr Asp Gln Leu Gln
                245                 250                 255

Ile Tyr Ala Asn Gly Lys Asn Ile Gly Glu Phe Cys Gly Lys Gln Arg
            260                 265                 270

Pro Pro Asp Leu Asp Thr Ser Ser Asn Ala Val Asp Leu Leu Phe Phe
        275                 280                 285

Thr Asp Glu Ser Gly Asp Ser Arg Gly Trp Lys Leu Arg Tyr Thr Thr
    290                 295                 300

Glu Ile Ile Lys Cys Pro Gln Pro Lys Thr Leu Asp Glu Phe Thr Ile
305                 310                 315                 320

Ile Gln Asn Leu Gln Pro Gln Tyr Gln Phe Arg Asp Tyr Phe Ile Ala
                325                 330                 335

Thr Cys Lys Gln Gly Tyr Gln Leu Ile Glu Gly Asn Gln Val Leu His
            340                 345                 350

Ser Phe Thr Ala Val Cys Gln Asp Asp Gly Thr Trp His Arg Ala Met
        355                 360                 365

Pro Arg Cys Lys Ile Lys Asp Cys Gly Gln Pro Arg Asn Leu Pro Asn
    370                 375                 380

Gly Asp Phe Arg Tyr Thr Thr Thr Met Gly Val Asn Thr Tyr Lys Ala
385                 390                 395                 400

Arg Ile Gln Tyr Tyr Cys His Glu Pro Tyr Tyr Lys Met Gln Thr Arg
```

```
                405                410                415
Ala Gly Ser Arg Glu Ser Glu Gln Gly Val Tyr Thr Cys Thr Ala Gln
            420                425                430

Gly Ile Trp Lys Asn Glu Gln Lys Gly Glu Lys Ile Pro Arg Cys Leu
435                440                445

Pro Val Cys Gly Lys Pro Val Asn Pro Val Glu Gln Arg Gln Arg Ile
    450                455                460

Ile Gly Gly Gln Lys Ala Lys Met Gly Asn Phe Pro Trp Gln Val Phe
465                470                475                480

Thr Asn Ile His Gly Arg Gly Gly Ala Leu Leu Gly Asp Arg Trp
            485                490                495

Ile Leu Thr Ala Ala His Thr Leu Tyr Pro Lys Glu His Glu Ala Gln
            500                505                510

Ser Asn Ala Ser Leu Asp Val Phe Leu Gly His Thr Asn Val Glu Glu
            515                520                525

Leu Met Lys Leu Gly Asn His Pro Ile Arg Arg Val Ser Val His Pro
        530                535                540

Asp Tyr Arg Gln Asp Glu Ser Tyr Asn Phe Glu Gly Asp Ile Ala Leu
545                550                555                560

Leu Glu Leu Glu Asn Ser Val Thr Leu Gly Pro Asn Leu Leu Pro Ile
                565                570                575

Cys Leu Pro Asp Asn Asp Thr Phe Tyr Asp Leu Gly Leu Met Gly Tyr
            580                585                590

Val Ser Gly Phe Gly Val Met Glu Glu Lys Ile Ala His Asp Leu Arg
            595                600                605

Phe Val Arg Leu Pro Val Ala Asn Pro Gln Ala Cys Glu Asn Trp Leu
    610                615                620

Arg Gly Lys Asn Arg Met Asp Val Phe Ser Gln Asn Met Phe Cys Ala
625                630                635                640

Gly His Pro Ser Leu Lys Gln Asp Ala Cys Gln Gly Asp Ser Gly Gly
                645                650                655

Val Phe Ala Val Arg Asp Pro Asn Thr Asp Arg Trp Val Ala Thr Gly
            660                665                670

Ile Val Ser Trp Gly Ile Gly Cys Ser Arg Gly Tyr Gly Phe Tyr Thr
            675                680                685

Lys Val Leu Asn Tyr Val Asp Trp Ile Lys Lys Glu Met Glu Glu Glu
        690                695                700

Asp
705

<210> SEQ ID NO 63
<211> LENGTH: 6810
<212> TYPE: DNA
<213> ORGANISM: Homo sapiens

<400> SEQUENCE: 63
cgccccgcac ccgcctgccc gcccgccacc tcccccggt ttctcattcc tgccactagc    60
gcgctcggcg gctcattccg cggccgccgc cagctgaggg gagcgtcgcg ggccgaggag   120
cagatgccgc gggggccgct cgcagccgcc gctgacttgt gaatgggacc gggactgggg   180
ccgggactga caccgcagcg cttgccctgc gccagggact ggcggctcgg aggttgcgtc   240
caccctcaag ggccccagaa atcactgtgt tttcagctca gcggcccttg ac attcctt    300 cgtgttgtca tttgttgagt gaccaatcag atgggtggag tgtgttacag aaattggcag   360
```

```
caagtatcca atgggtgaag aagaagctaa ctggggacgt gggcagccct gacgtgatga        420
gctcaaccag cagagacatt ccatcccaag agaggtctgc gtgacgcgtc cgggaggcca        480
ccctcagcaa gaccaccgta cagttggtgg aagggggtgac agctgcattc tcctgtgcct       540
accacgtaac caaaaatgaa ggagaactac tgtttacaag ccgccctggt gtgcctgggc        600
atgctgtgcc acagccatgc ctttgcccca gagcggcggg ggcacctgcg gccctccttc       660
catgggcacc atgagaaggg caaggagggg caggtgctac agcgctccaa gcgtggctgg        720
gtctggaacc agttcttcgt gatagaggag tacaccgggc ctgaccccgt gcttgtgggc        780
aggcttcatt cagatattga ctctggtgat gggaacatta atacattct ctcaggggaa        840 ggagctggaa ccattttttgt gattgatgac aaatcaggga acattcatgc caccaagacg       900
ttggatcgag aagagagagc ccagtacacg ttgatggctc aggcggtgga cagggacacc        960
aatcggccac tggagccacc gtcggaattc attgtcaagg tccaggacat taatgacaac       1020
cctccggagt tcctgcacga gacctatcat gccaacgtgc ctgagaggtc caatgtggga       1080
acgtcagtaa tccaggtgac agcttcagat gcagatgacc ccacttatgg aaatagcgcc       1140
aagttagtgt acagtatcct cgaaggacaa ccctatttttt cggtggaagc acagacaggt       1200
atcatcagaa cagccctacc caacatggac agggaggcca aggaggagta ccacgtggtg      1260
atccaggcca aggacatggg tggacatatg ggcggactct cagggacaac caaagtgacg      1320
atcacactga ccgatgtcaa tgacaaccca ccaaagtttc gcagagcgt ataccagatg       1380 tctgtgtcag aagcagccgt ccctggggag gaagtaggaa gagtgaaagc taaagatcca       1440
gacattggag aaaatggctt agtcacatac aatattgttg atggagatgg tatggaatcg      1500
tttgaaatca aacggacta tgaaacacag gagggggtga taaagctgaa aaagcctgta      1560
gattttgaaa ccaaaagagc ctatagcttg aaggtagagg cagccaacgt gcacatcgac       1620
ccgaagttta tcagcaatgg ccctttcaag gacactgtga ccgtcaagat ctcagtagaa      1680
gatgctgatg agccccctat gttcttggcc ccaagttaca tccacgaagt ccaagaaaat      1740
gcagctgctg gcaccgtggt tgggagagtg catgccaaag accctgatgc tgccaacagc      1800
ccgataaggt attccatcga tcgtcacact gacctcgaca gattttttcac tattaatcca      1860 gaggatggtt ttattaaaac tacaaaacct ctggatagag aggaaacagc ctggctcaac      1920
atcactgtct ttgcagcaga aatccacaat cggcatcagg aagccaaagt cccagtggcc      1980
attagggtcc ttgatgtcaa cgataatgct cccaagtttg ctgcccctta tgaaggtttc      2040
atctgtgaga gtgatcagac caagccactt tccaaccagc caattgttac aattagtgca      2100
gatgacaagg atgacacggc caatggacca agatttatct tcagcctacc ccctgaaatc      2160
attcacaatc caaatttcac agtcagagac aaccgagata cacagcagg cgtgtacgcc      2220 cggcgtggag ggttcagtcg gcagaagcag gacttgtacc ttctgcccat agtgatcagc      2280
gatggcggca tcccgcccat gagtagcacc aacacccctca ccatcaaagt ctgcgggtgc      2340
gacgtgaacg gggcactgct ctcctgcaac gcagaggcct acattctgaa cgccggcctg      2400
agcacaggcg ccctgatcgc catcctcgcc tgcatcgtca ttctcctggt cattgtagta      2460
ttgtttgtga ccctgagaag gcaaaagaaa gaaccactca ttgtctttga ggaagaagat      2520
gtccgtgaga acatcattac ttatgatgat gaagggggtg gggaagaaga cacagaagcc      2580
tttgatattg ccaccctcca gaatcctgat ggtatcaatg gatttatccc ccgcaaagac      2640
atcaaacctg agtatcagta catgcctaga cctgggctcc ggccagcgcc caacagcgtg      2700
gatgtcgatg acttcatcaa cacgagaata caggaggcag acaatgaccc cacggctcct      2760
```

```
ccttatgact ccattcaaat ctacggttat gaaggcaggg gctcagtggc cgggtccctg    2820
agctccctag agtcggccac cacagattca gacttggact atgattatct acagaactgg    2880
ggacctcgtt ttaagaaact agcagatttg tatggttcca aagacacttt tgatgacgat    2940
tcttaacaat aacgatacaa atttggcctt aagaactgtg tctggcgttc tcaagaatct    3000
agaagatgtg taaacaggta ttttttttaaa tcaaggaaag gctcatttaa aacaggcaaa    3060
gttttacaga gaggatacat ttaataaaac tgcgaggaca tcaaagtggt aaatactgtg    3120 aaatacctttt tctcacaaaa aggcaaatat tgaagttgtt tatcaacttc gctagaaaaa    3180
aaaaacactt ggcatacaaa atatttaagt gaaggagaag tctaacgctg aactgacaat    3240
gaagggaaat tgtttatgtg ttatgaacat ccaagtcttt cttcttttt aagttgtcaa    3300 agaagcttcc acaaaattag aaaggacaac agttctgagc tgtaatttcg ccttaaactc    3360
tggacactct atatgtagtg catttttaaa cttgaaatat ataatattca gccagcttaa    3420
acccatacaa tgtatgtaca atacaatgta caattatgtc tcttgagcat caatcttgtt    3480
actgctgatt cttgtaaatc ttttgcttc tactttcatc ttaaactaat acgtgccaga    3540
tataactgtc ttgtttcagt gagagacgcc ctatttctat gtcatttta atgtatctat    3600 ttgtacaatt ttaaagttct tattttagta tacgtataaa tatcagtatt ctgacatgta    3660
agaaaatgtt acggcatcac acttatattt tatgaacatt gtactgttgc tttaatatga    3720
gcttcaatat aagaagcaat cttttgaaata aaaaaagatt ttttttaat tctgggtttg    3780 attcttaaca ttgaaacaaa cgttaagtat ttctaatgat ccatttatat ttctaattta    3840
attgtgatct tttaataacc ctatttatga tctgttgttg tctgtctgct gcttttattg    3900
tttatttaaa atcaaatatg ttttacaaat gttttttcag acaagattct gtaacatcat    3960
gtaaagcttt tttgtacatt cttggtgtta acctcctggc ttctcttcac acacatcttc    4020
taaaaaagaa ggatgtgaaa gaactaggtc agtctatgac tttgcaatat gtgttatata    4080
gtatgcattt atcttgtata tcagtaattt gatggttatg agagatgaat ccatgaggga    4140
atggagctat cagaactcta atgttccagg tatacattct atgccccaca ctgagcactg    4200
gggaactggg ggactagagt caaaaatata aatttgccca gactctaatg ttattctatt    4260
ttttcttctg ttgaacttac caggctattg taagactctt gatagttgaa actgcttatt    4320
tttcctcctg taatttttaac taattgtaaa atgatgtggc attttatgtt ttaatgagaa    4380
tgggcgattc atttaaaaaa gctttgttta gaatatgctt ggggccgtaa gctcagaatg    4440
agggcaggga ccattttgga ttctgagagt cgatgccatt tggtccagga gtgtgtctac    4500
agtcccctgc attccagcta gtttcttggg gattgaaact tatgtgaagg gcatttcacc    4560
tgttcagttg ggccaaaggt caaaacgtag caatacttgg ggaaagacca cataaagtca    4620
cactgcaagt gctttccctc tttccccta cacacagggc acgtgctttt tcttggattg    4680
cagacaattt ttacagtttt tttctgactt tattgtgaaa gtttgtttca agcatttctt    4740
gatatcatgt tatgtactat ttttatgatt tagtcaacat gcatacaaag aaatgttttt    4800
tatgaagtgc tcacttccat tttactttgc attgaaatca aattgggctg aacacttcaa    4860
tggaatacat tttgtggaca atgtcacttt agaatcttc atctcagtga aggattacac    4920
attctcaata cttccataat tgcaggttgt gttcattttt ttatatagtt tttgtaatcc    4980
aaagaatatt ttgctagatt tgcacagatc tccaattgaa tttgcaatga agaaataact    5040
caaaaggaat atgaatagca tttaaataag tatacagctg taagtaaccc tgtcaccatg    5100
```

| | |
|---|---|
| gatgatcctt ttctctagga atgtatttgg attagagatg acaactacat tttcgcattt | 5160 |
| ttatgttgaa gtctttttta aaaaggctgt ttacttttca gtagttaaga atacttgttt | 5220 |
| ttcttttttct tttttttttt tttttttacc ttttatttttt tcgttaagcc tctattgttt | 5280 |
| gtagaacact cttagaaact tggaaataaa atgtctttcc caactagtgg agtccttttt | 5340 |
| catttggagc acattgcctt aaaagaagtc ttaatttaaa cggtccttcc ttattctaaa | 5400 |
| gtaatcactg ttttatacca tctatgcagc taaaagaagg aacatgcttc tgttcttttc | 5460 |
| ctcaagtaat ggttattgtt tctagtcatc attcattcat tgattcattc attaattcat | 5520 |
| caaaatctta ttttataaac cctgttccac ttactggagg attcagaatg aatcttacta | 5580 |
| cctttctga catcttttga taattcagcc ctgtaccaaa gtatccacct tgttgtctta | 5640 |
| taatcaccta tttacctatt tgccctccta gaaaatgcaa gaagatattt tctctccttc | 5700 |
| caaattgaag gaagaacata aagatataa caggaaggag atggtgagat atagagtgtg | 5760 |
| agcggaaatt aggccagctg tggcaattct ggacagatct tgggtttagc taagttattt | 5820 |
| cttttaggcc tgggtttctg ggggtgacag ggaagataaa agagtagttt atttgcacct | 5880 |
| cttggagaat tgcttaaaaa tatagagatc atggctctgt atgtcaggtg gaaccaggtc | 5940 |
| aggagtattt gaaactgctc ctgggtcatt gtgcatatc cttcacatct ttttgagaaa | 6000 |
| ctttataaga caatgggggt gaatgggggc tgggcagttg gagtctctga gcagaagagg | 6060 |
| ggcaaaattt atttggcagg cagtgtggag gacagattag gagcatataa acccagaggt | 6120 |
| gtgccccagg agggcttttg caaaggtcaa tatgagatag aatgagggcc tgaaataatt | 6180 |
| cagtaatttg gagatggaga agaggaaaga cttctctgct cttgcactgc catcagcctg | 6240 |
| gtctgggcca tggtcatctc tgacccggaa gactgacccc acctcttggc tcaccctctg | 6300 |
| cctcccaacc tcctcttcac aaagaagcca gagggatact tttaacacac aacccagatc | 6360 |
| acatgacttc gtaacttaaa cctcttcact ggcttcccaa agacttaaaa tgaattctga | 6420 |
| tgcctttatt ttattgcttt acatgaacag ggccctgcga acctctccag tgtcattcca | 6480 |
| ctccatcctc ctttcagtgc acgatgctcc agccacactg gccatctttc ggttcctgat | 6540 |
| acaaaaaaaa acacgttcct tttccatgga aagcaggtca cccttgttat tttgtatcga | 6600 |
| tgacaactct ttaaacttat tttgctttttt ggctttatgt atgtgtgtgg gtgggtggga | 6660 |
| ctgactgccc cactagaatg taagctccat gagggcaggg aatcttgctt tcttgtttac | 6720 |
| cattgtatac tcagttcttt acacagtgcc tgaaacataa caggtacaca ataaatatct | 6780 |
| attgaatgaa agcaaaaaaa aaaaaaaaaa | 6810 |

<210> SEQ ID NO 64
<211> LENGTH: 670
<212> TYPE: PRT
<213> ORGANISM: Homo sapiens

<400> SEQUENCE: 64

Met Ala Gln Ala Val Asp Arg Asp Thr Asn Arg Pro Leu Glu Pro Pro
1               5                   10                  15

Ser Glu Phe Ile Val Lys Val Gln Asp Ile Asn Asp Asn Pro Pro Glu
            20                  25                  30

Phe Leu His Glu Thr Tyr His Ala Asn Val Pro Glu Arg Ser Asn Val
        35                  40                  45

Gly Thr Ser Val Ile Gln Val Thr Ala Ser Asp Ala Asp Asp Pro Thr
    50                  55                  60

Tyr Gly Asn Ser Ala Lys Leu Val Tyr Ser Ile Leu Glu Gly Gln Pro

-continued

```
            65                  70                  75                  80
Tyr Phe Ser Val Glu Ala Gln Thr Gly Ile Ile Arg Thr Ala Leu Pro
                85                  90                  95

Asn Met Asp Arg Glu Ala Lys Glu Tyr His Val Val Ile Gln Ala
            100                 105                 110

Lys Asp Met Gly Gly His Met Gly Gly Leu Ser Gly Thr Thr Lys Val
            115                 120                 125

Thr Ile Thr Leu Thr Asp Val Asn Asp Asn Pro Pro Lys Phe Pro Gln
130                 135                 140

Ser Val Tyr Gln Met Ser Val Ser Glu Ala Ala Val Pro Gly Glu Glu
145                 150                 155                 160

Val Gly Arg Val Lys Ala Lys Asp Pro Asp Ile Gly Glu Asn Gly Leu
                165                 170                 175

Val Thr Tyr Asn Ile Val Asp Gly Asp Gly Met Glu Ser Phe Glu Ile
                180                 185                 190

Thr Thr Asp Tyr Glu Thr Gln Glu Gly Val Ile Lys Leu Lys Lys Pro
            195                 200                 205

Val Asp Phe Glu Thr Lys Arg Ala Tyr Ser Leu Lys Val Glu Ala Ala
210                 215                 220

Asn Val His Ile Asp Pro Lys Phe Ile Ser Asn Gly Pro Phe Lys Asp
225                 230                 235                 240

Thr Val Thr Val Lys Ile Ser Val Glu Asp Ala Asp Glu Pro Pro Met
                245                 250                 255

Phe Leu Ala Pro Ser Tyr Ile His Glu Val Gln Glu Asn Ala Ala Ala
                260                 265                 270

Gly Thr Val Val Gly Arg Val His Ala Lys Asp Pro Asp Ala Ala Asn
            275                 280                 285

Ser Pro Ile Arg Tyr Ser Ile Asp Arg His Thr Asp Leu Asp Arg Phe
            290                 295                 300

Phe Thr Ile Asn Pro Glu Asp Gly Phe Ile Lys Thr Thr Lys Pro Leu
305                 310                 315                 320

Asp Arg Glu Glu Thr Ala Trp Leu Asn Ile Thr Val Phe Ala Ala Glu
                325                 330                 335

Ile His Asn Arg His Gln Glu Ala Lys Val Pro Val Ala Ile Arg Val
            340                 345                 350

Leu Asp Val Asn Asp Asn Ala Pro Lys Phe Ala Ala Pro Tyr Glu Gly
            355                 360                 365

Phe Ile Cys Glu Ser Asp Gln Thr Lys Pro Leu Ser Asn Gln Pro Ile
            370                 375                 380

Val Thr Ile Ser Ala Asp Asp Lys Asp Asp Thr Ala Asn Gly Pro Arg
385                 390                 395                 400

Phe Ile Phe Ser Leu Pro Pro Glu Ile Ile His Asn Pro Asn Phe Thr
                405                 410                 415

Val Arg Asp Asn Arg Asp Asn Thr Ala Gly Val Tyr Ala Arg Arg Gly
            420                 425                 430

Gly Phe Ser Arg Gln Lys Gln Asp Leu Tyr Leu Pro Ile Val Ile
            435                 440                 445

Ser Asp Gly Gly Ile Pro Pro Met Ser Ser Thr Asn Thr Leu Thr Ile
450                 455                 460

Lys Val Cys Gly Cys Asp Val Asn Gly Ala Leu Leu Ser Cys Asn Ala
465                 470                 475                 480

Glu Ala Tyr Ile Leu Asn Ala Gly Leu Ser Thr Gly Ala Leu Ile Ala
                485                 490                 495
```

```
Ile Leu Ala Cys Ile Val Ile Leu Leu Val Ile Val Val Leu Phe Val
                500                 505                 510
Thr Leu Arg Arg Gln Lys Lys Glu Pro Leu Ile Val Phe Glu Glu Glu
            515                 520                 525
Asp Val Arg Glu Asn Ile Ile Thr Tyr Asp Asp Glu Gly Gly Gly Glu
    530                 535                 540
Glu Asp Thr Glu Ala Phe Asp Ile Ala Thr Leu Gln Asn Pro Asp Gly
545                 550                 555                 560
Ile Asn Gly Phe Ile Pro Arg Lys Asp Ile Lys Pro Glu Tyr Gln Tyr
                565                 570                 575
Met Pro Arg Pro Gly Leu Arg Pro Ala Pro Asn Ser Val Asp Val Asp
            580                 585                 590
Asp Phe Ile Asn Thr Arg Ile Gln Glu Ala Asp Asn Asp Pro Thr Ala
    595                 600                 605
Pro Pro Tyr Asp Ser Ile Gln Ile Tyr Gly Tyr Glu Gly Arg Gly Ser
610                 615                 620
Val Ala Gly Ser Leu Ser Ser Leu Glu Ser Ala Thr Thr Asp Ser Asp
625                 630                 635                 640
Leu Asp Tyr Asp Tyr Leu Gln Asn Trp Gly Pro Arg Phe Lys Lys Leu
                645                 650                 655
Ala Asp Leu Tyr Gly Ser Lys Asp Thr Phe Asp Asp Ser
            660                 665                 670

<210> SEQ ID NO 65
<211> LENGTH: 5490
<212> TYPE: DNA
<213> ORGANISM: Homo sapiens

<400> SEQUENCE: 65
ggctgagttt tatgacgggc cggtgctga agggcaggga caacttgat ggtgctactt      60
tgaactgctt ttctttttctc cttttttgcac aaagagtctc atgtctgata tttagacatg   120
atgagctttg tgcaaaaggg gagctggcta cttctcgctc tgcttcatcc cactattatt     180
ttggcacaac aggaagctgt tgaaggagga tgttcccatc ttggtcagtc ctatgcggat    240
agagatgtct ggaagccaga accatgccaa atatgtgtct gtgactcagg atccgttctc     300
tgcgatgaca taatatgtga cgatcaagaa ttagactgcc caacccaga aattccattt     360
ggagaatgtt gtgcagtttg cccacagcct ccaactgctc ctactcgccc tcctaatggt     420
caaggacctc aaggccccaa gggagatcca ggccctcctg gtattcctgg agaaatggt     480
gaccctggta ttccaggaca accagggtcc cctggttctc ctggcccccc tggaatctgt    540
gaatcatgcc ctactggtcc tcagaactat tctccccagt atgattcata tgatgtcaag    600
tctggagtag cagtaggagg actcgcaggc tatcctggac cagctggccc cccaggccct    660
cccggtcccc ctggtacatc tggtcatcct ggttcccctg gatctccagg ataccaagga    720
cccctggtg aacctgggca agctggtcct tcaggccctc caggacctcc tggtgctata    780
ggtccatctg gtcctgctgg aaaagatgga gaatcaggta gacccggacg acctggagag    840
cgaggattgc ctggacctcc aggtatcaaa ggtccagctg gataccctgg attccctggt    900
atgaaaggac acagaggctt cgatggacga aatggagaaa agggtgaaac aggtgctcct    960
ggattaaagg gtgaaaatgg tcttccaggc gaaaatggag ctcctggacc catgggtcca   1020
agagggctc ctggtgagcg aggacggcca ggacttcctg gggctgcagg tgctcggggt   1080
aatgacggtg ctcgaggcag tgatggtcaa ccaggcccctc ctggtcctcc tggaactgcc   1140
```

-continued

```
ggattccctg gatcccctgg tgctaagggt gaagttggac ctgcagggtc tcctggttca    1200
aatggtgccc ctggacaaag aggagaacct ggacctcagg gacacgctgg tgctcaaggt    1260
cctcctggcc ctcctgggat taatggtagt cctggtggta aaggcgaaat gggtcccgct    1320
ggcattcctg gagctcctgg actgatggga gcccggggtc ctccaggacc agccggtgct    1380
aatggtgctc ctggactgcg aggtggtgca ggtgagcctg gtaagaatgg tgccaaagga    1440
gagcccggac cacgtggtga acgcggtgag gctggtattc aggtgttcc aggagctaaa     1500
ggcgaagatg gcaaggatgg atcacctgga gaacctggtg caaatgggct tccaggagct    1560
gcaggagaaa ggggtgcccc tgggttccga ggacctgctg gaccaaatgg catcccagga    1620
gaaaagggtc ctgctggaga gcgtggtgct ccaggccctg cagggcccag aggagctgct    1680
ggagaacctg gcagagatgg cgtcctgga gtccaggaa tgaggggcat gcccggaagt      1740
ccaggaggac caggaagtga tgggaaacca gggcctcccg gaagtcaagg agaaagtggt    1800
cgaccaggtc ctcctgggcc atctggtccc cgaggtcagc ctggtgtcat ggcttcccc    1860
ggtcctaaag gaatgatgg tgctcctggt aagaatggag aacgaggtgg ccctggagga    1920
cctggccctc agggtcctcc tggaaagaat ggtgaaactg gacctcaggg accccaggg    1980
cctactgggc ctggtggtga caaaggagac acaggacccc ctggtccaca aggattacaa   2040
ggcttgcctg gtacaggtgg tcctccagga gaaaatggaa aacctgggga accaggtcca    2100
aagggtgatg ccggtgcacc tggagctcca ggaggcaagg gtgatgctgg tgcccctggt    2160
gaacgtggac ctcctggatt ggcagggggcc ccaggactta gaggtggagc tggtcccccct   2220
ggtcccgaag gaggaaaggg tgctgctggt cctcctgggc cacctggtgc tgctggtact    2280
cctggtctgc aaggaatgcc tggagaaaga ggaggtcttg gaagtcctgg tccaaagggt    2340
gacaagggtg aaccaggcgg tccaggtgct gatggtgtcc cagggaaaga tggcccaagg    2400
ggtcctactg gtcctattgg tcctcctggc ccagctggcc agcctggaga taagggtgaa    2460
ggtggtgccc ccggacttcc aggtatagct ggacctcgtg gtagccctgg tgagagaggt    2520
gaaactggcc ctccaggacc tgctggtttc cctggtgctc ctggacagaa tggtgaacct    2580
ggtggtaaag gagaaagagg ggctccgggt gagaaaggtg aaggaggccc tcctggagtt    2640
gcaggaccc ctggaggttc tggacctgct ggtcctcctg gtccccaagg tgtcaaaggt    2700
gaacgtggca gtcctggtgg acctggtgct gctggcttcc ctggtgctcg tggtcttcct    2760
ggtcctcctg gtagtaatgg taacccagga ccccaggtc ccagcggttc tccaggcaag    2820
gatgggcccc aggtcctgc gggtaacact ggtgctcctg gcagccctgg agtgtctgga    2880
ccaaaaggtg atgctggcca accaggagag aagggatcgc tggtgcccaa gggccaccca    2940
ggagctccag gcccacttgg gattgctggg atcactggag cacggggtct gcaggacca    3000
ccaggcatgc caggtcctag gggaagccct ggccctcagg gtgtcaaggg tgaaagtggg    3060
aaaccaggag ctaacggtct cagtggagaa cgtggtcccc ctggacccca gggtcttcct    3120
ggtctggctg gtacagctgg tgaacctgga agagatggaa accctggatc agatggtctt    3180
ccaggccgag atggatctcc tggtggcaag ggtgatcgtg gtgaaaatgg ctctcctggt    3240
gcccctggcg ctcctggtca tccaggccca cctggtcctg tcggtccagc tggaaagagt    3300
ggtgacagag gagaaagtgg ccctgctggc cctgctggtg ctcccggtcc tgctggttcc    3360
cgaggtgctc ctggtcctca aggcccacgt ggtgacaaag gtgaaacagg tgaacgtgga    3420
gctgctggca tcaaaggaca tcgaggattc cctggtaatc caggtgcccc aggttctcca    3480
```

```
ggccctgctg gtcagcaggg tgcaatcggc agtccaggac ctgcaggccc cagaggacct      3540
gttggaccca gtggacctcc tggcaaagat ggaaccagtg gacatccagg tcccattgga      3600
ccaccagggc ctcgaggtaa cagaggtgaa agaggatctg agggctcccc aggccaccca      3660
gggcaaccag gccctcctgg acctcctggt gcccctggtc cttgctgtgg tggtgttgga      3720
gccgctgcca ttgctgggat tggaggtgaa aaagctggcg gttttgcccc gtattatgga      3780
gatgaaccaa tggatttcaa atcaacacc gatgagatta tgacttcact caagtctgtt      3840
aatggacaaa tagaaagcct cattagtcct gatggttctc gtaaaaaccc cgctagaaac      3900
tgcagagacc tgaaattctg ccatcctgaa ctcaagagtg gagaatactg ggttgaccct      3960
aaccaaggat gcaaattgga tgctatcaag gtattctgta atatggaaac tggggaaaca      4020
tgcataagtg ccaatccttt gaatgttcca cggaaacact ggtggacaga ttctagtgct      4080
gagaagaaac acgtttggtt tggagagtcc atggatggtg gttttcagtt tagctacggc      4140
aatcctgaac ttcctgaaga tgtccttgat gtgcagctgg cattccttcg acttctctcc      4200
agccgagctt cccagaacat cacatatcac tgcaaaaata gcattgcata catggatcag      4260
gccagtggaa atgtaaagaa ggccctgaag ctgatggggt caaatgaagg tgaattcaag      4320
gctgaaggaa atagcaaatt cacctacaca gttctgagg atggttgcac gaaacacact      4380
ggggaatgga gcaaaacagt ctttgaatat cgaacacgca aggctgtgag actacctatt      4440
gtagatattg cacctatga cattggtggt cctgatcaag aatttggtgt ggacgttggc      4500
cctgtttgct ttttataaac caaactctat ctgaaatccc aacaaaaaaa atttaactcc      4560
atatgtgttc ctcttgttct aatcttgtca accagtgcaa gtgaccgaca aaattccagt      4620
tattttattc caaatgtttt ggaaacagta aatttgaca agaaaaatg atacttctct      4680 tttttgctg ttccaccaaa tacaattcaa atgcttttg ttttattttt ttaccaattc      4740
caatttcaaa atgtctcaat ggtgctataa taaataaact tcaacactct ttatgataac      4800
aacactgtgt tatattcttt gaatcctagc ccatctgcag agcaatgact gtgctcacca      4860
gtaaaagata acctttcttt ctgaaatagt caaatacgaa attagaaaag ccctccctat      4920
tttaactacc tcaactggtc agaaacacag attgtattct atgagtccca gaagatgaaa      4980 aaaatttat acgttgataa aacttataaa tttcattgat taatctcctg gaagattggt      5040 ttaaaagaa aagtgtaatg caagaattta agaaatatt tttaaagcca caattatttt      5100
aatattggat atcaactgct tgtaaaggtg ctcctctttt ttcttgtcat tgctggtcaa      5160
gattactaat atttgggaag gctttaaaga cgcatgttat ggtgctaatg tactttcact      5220
tttaaactct agatcagaat tgttgacttg cattcagaac ataaatgcac aaaatctgta      5280
catgtctccc atcagaaaga ttcattggca tgccacaggg gattctcctc cttcatcctg      5340
taaaggtcaa caataaaaac caaattatgg ggctgctttt gtcacactag catagagaat      5400
gtgttgaaat ttaactttgt aagcttgtat gtggttgttg atcttttttt tccttacaga      5460
cacccataat aaaatatcat attaaaattc                                        5490
```

<210> SEQ ID NO 66
<211> LENGTH: 1163
<212> TYPE: PRT
<213> ORGANISM: Homo sapiens

<400> SEQUENCE: 66

```
Met Met Ser Phe Val Gln Lys Gly Ser Trp Leu Leu Leu Ala Leu Leu
1               5                   10                  15
```

```
His Pro Thr Ile Ile Leu Ala Gln Gln Glu Ala Val Glu Gly Gly Cys
                20                  25                  30

Ser His Leu Gly Gln Ser Tyr Ala Asp Arg Asp Val Trp Lys Pro Glu
            35                  40                  45

Pro Cys Gln Ile Cys Val Cys Asp Ser Gly Ser Val Leu Cys Asp Asp
        50                  55                  60

Ile Ile Cys Asp Asp Gln Glu Leu Asp Cys Pro Asn Pro Glu Ile Pro
65                  70                  75                  80

Phe Gly Glu Cys Cys Ala Val Cys Pro Gln Pro Thr Ala Pro Thr
                85                  90                  95

Arg Pro Pro Asn Gly Gln Gly Pro Gln Gly Pro Lys Gly Asp Pro Gly
            100                 105                 110

Pro Pro Gly Ile Pro Gly Arg Asn Gly Asp Pro Gly Ile Pro Gly Gln
        115                 120                 125

Pro Gly Ser Pro Gly Ser Pro Gly Pro Pro Gly Ile Cys Glu Ser Cys
    130                 135                 140

Pro Thr Gly Pro Gln Asn Tyr Ser Pro Gln Tyr Asp Ser Tyr Asp Val
145                 150                 155                 160

Lys Ser Gly Val Ala Val Gly Gly Leu Ala Gly Tyr Pro Gly Pro Ala
                165                 170                 175

Gly Pro Pro Gly Pro Pro Gly Pro Gly Thr Ser Gly His Pro Gly
            180                 185                 190

Ser Pro Gly Ser Pro Gly Tyr Gln Gly Pro Pro Gly Glu Pro Gly Gln
        195                 200                 205

Ala Gly Pro Ser Gly Pro Pro Gly Pro Pro Gly Ala Ile Gly Pro Ser
    210                 215                 220

Gly Pro Ala Gly Lys Asp Gly Glu Ser Gly Arg Pro Gly Arg Pro Gly
225                 230                 235                 240

Glu Arg Gly Leu Pro Gly Pro Pro Gly Ile Lys Gly Pro Ala Gly Ile
                245                 250                 255

Pro Gly Phe Pro Gly Met Lys Gly His Arg Gly Phe Asp Gly Arg Asn
            260                 265                 270

Gly Glu Lys Gly Glu Thr Gly Ala Pro Gly Leu Lys Gly Glu Asn Gly
        275                 280                 285

Leu Pro Gly Glu Asn Gly Ala Pro Gly Pro Met Gly Pro Arg Gly Ala
    290                 295                 300

Pro Gly Glu Arg Gly Arg Pro Gly Leu Pro Gly Ala Ala Gly Ala Arg
305                 310                 315                 320

Gly Asn Asp Gly Ala Arg Gly Ser Asp Gly Gln Pro Gly Pro Pro Gly
                325                 330                 335

Pro Pro Gly Thr Ala Gly Phe Pro Gly Ser Pro Gly Ala Lys Gly Glu
            340                 345                 350

Val Gly Pro Ala Gly Ser Pro Gly Ser Asn Gly Ala Pro Gly Gln Arg
        355                 360                 365

Gly Glu Pro Gly Pro Gln Gly His Ala Gly Ala Gln Gly Pro Pro Gly
    370                 375                 380

Pro Pro Gly Ile Asn Gly Ser Pro Gly Gly Lys Gly Glu Met Gly Pro
385                 390                 395                 400

Ala Gly Ile Pro Gly Ala Pro Gly Leu Met Gly Ala Arg Gly Pro Pro
                405                 410                 415

Gly Pro Ala Gly Ala Asn Gly Ala Pro Gly Leu Arg Gly Gly Ala Gly
            420                 425                 430

Glu Pro Gly Lys Asn Gly Ala Lys Gly Glu Pro Gly Pro Arg Gly Glu
```

```
              435                 440                 445
Arg Gly Glu Ala Gly Ile Pro Gly Val Pro Gly Ala Lys Gly Glu Asp
450                 455                 460
Gly Lys Asp Gly Ser Pro Gly Glu Pro Gly Ala Asn Gly Leu Pro Gly
465                 470                 475                 480
Ala Ala Gly Glu Arg Gly Ala Pro Gly Phe Arg Gly Pro Ala Gly Pro
                485                 490                 495
Asn Gly Ile Pro Gly Glu Lys Gly Pro Ala Gly Glu Arg Gly Ala Pro
                500                 505                 510
Gly Pro Ala Gly Pro Arg Gly Ala Gly Glu Pro Gly Arg Asp Gly
            515                 520                 525
Val Pro Gly Gly Pro Gly Met Arg Gly Met Pro Gly Ser Pro Gly Gly
530                 535                 540
Pro Gly Ser Asp Gly Lys Pro Gly Pro Gly Ser Gln Gly Glu Ser
545                 550                 555                 560
Gly Arg Pro Gly Pro Pro Gly Pro Ser Gly Pro Arg Gly Gln Pro Gly
                565                 570                 575
Val Met Gly Phe Pro Gly Pro Lys Gly Asn Asp Gly Ala Pro Gly Lys
                580                 585                 590
Asn Gly Glu Arg Gly Gly Pro Gly Gly Pro Gly Pro Gln Gly Pro Pro
                595                 600                 605
Gly Lys Asn Gly Glu Thr Gly Pro Gln Gly Pro Pro Gly Pro Thr Gly
                610                 615                 620
Pro Gly Gly Asp Lys Gly Asp Thr Gly Pro Pro Gly Pro Gln Gly Leu
625                 630                 635                 640
Gln Gly Leu Pro Gly Thr Gly Gly Pro Pro Gly Glu Asn Gly Lys Pro
                645                 650                 655
Gly Glu Pro Gly Pro Lys Gly Asp Ala Gly Ala Pro Gly Ala Pro Gly
                660                 665                 670
Gly Lys Gly Asp Ala Gly Ala Pro Gly Glu Arg Gly Pro Pro Gly Leu
                675                 680                 685
Ala Gly Ala Pro Gly Leu Arg Gly Gly Ala Gly Pro Pro Gly Pro Glu
                690                 695                 700
Gly Gly Lys Gly Ala Ala Gly Pro Pro Gly Pro Pro Gly Ala Ala Gly
705                 710                 715                 720
Thr Pro Gly Leu Gln Gly Met Pro Gly Glu Arg Gly Gly Leu Gly Ser
                725                 730                 735
Pro Gly Pro Lys Gly Asp Lys Gly Glu Pro Gly Gly Pro Gly Ala Asp
                740                 745                 750
Gly Val Pro Gly Lys Asp Gly Pro Arg Gly Pro Thr Gly Pro Ile Gly
                755                 760                 765
Pro Pro Gly Pro Ala Gly Gln Pro Gly Asp Lys Gly Glu Gly Gly Ala
                770                 775                 780
Pro Gly Leu Pro Gly Ile Ala Gly Pro Arg Gly Ser Pro Gly Glu Arg
785                 790                 795                 800
Gly Glu Thr Gly Pro Pro Gly Pro Ala Gly Phe Pro Gly Ala Pro Gly
                805                 810                 815
Gln Asn Gly Glu Pro Gly Gly Lys Gly Glu Arg Gly Ala Pro Gly Glu
                820                 825                 830
Lys Gly Glu Gly Gly Pro Pro Gly Val Ala Gly Pro Pro Gly Lys Asp
            835                 840                 845
Gly Thr Ser Gly His Pro Gly Pro Ile Gly Pro Pro Gly Pro Arg Gly
            850                 855                 860
```

Asn Arg Gly Glu Arg Gly Ser Glu Gly Ser Pro Gly His Pro Gly Gln
865                 870                 875                 880

Pro Gly Pro Pro Gly Pro Gly Ala Pro Gly Pro Cys Cys Gly Gly
            885                 890                 895

Val Gly Ala Ala Ala Ile Ala Gly Ile Gly Gly Glu Lys Ala Gly Gly
        900                 905                 910

Phe Ala Pro Tyr Tyr Gly Asp Glu Pro Met Asp Phe Lys Ile Asn Thr
        915                 920                 925

Asp Glu Ile Met Thr Ser Leu Lys Ser Val Asn Gly Gln Ile Glu Ser
    930                 935                 940

Leu Ile Ser Pro Asp Gly Ser Arg Lys Asn Pro Ala Arg Asn Cys Arg
945                 950                 955                 960

Asp Leu Lys Phe Cys His Pro Glu Leu Lys Ser Gly Glu Tyr Trp Val
            965                 970                 975

Asp Pro Asn Gln Gly Cys Lys Leu Asp Ala Ile Lys Val Phe Cys Asn
        980                 985                 990

Met Glu Thr Gly Glu Thr Cys Ile Ser Ala Asn Pro Leu Asn Val Pro
        995                 1000                1005

Arg Lys His Trp Trp Thr Asp Ser Ser Ala Glu Lys Lys His Val
    1010                1015                1020

Trp Phe Gly Glu Ser Met Asp Gly Gly Phe Gln Phe Ser Tyr Gly
    1025                1030                1035

Asn Pro Glu Leu Pro Glu Asp Val Leu Asp Val Gln Leu Ala Phe
    1040                1045                1050

Leu Arg Leu Leu Ser Ser Arg Ala Ser Gln Asn Ile Thr Tyr His
    1055                1060                1065

Cys Lys Asn Ser Ile Ala Tyr Met Asp Gln Ala Ser Gly Asn Val
    1070                1075                1080

Lys Lys Ala Leu Lys Leu Met Gly Ser Asn Glu Gly Glu Phe Lys
    1085                1090                1095

Ala Glu Gly Asn Ser Lys Phe Thr Tyr Thr Val Leu Glu Asp Gly
    1100                1105                1110

Cys Thr Lys His Thr Gly Glu Trp Ser Lys Thr Val Phe Glu Tyr
    1115                1120                1125

Arg Thr Arg Lys Ala Val Arg Leu Pro Ile Val Asp Ile Ala Pro
    1130                1135                1140

Tyr Asp Ile Gly Gly Pro Asp Gln Glu Phe Gly Val Asp Val Gly
    1145                1150                1155

Pro Val Cys Phe Leu
    1160

<210> SEQ ID NO 67
<211> LENGTH: 2174
<212> TYPE: DNA
<213> ORGANISM: Homo sapiens

<400> SEQUENCE: 67
agaacatttc tttttcactt cccctttcag actccagaat tgtttgccc tctagggtag      60 aatccgccaa gctttgagag aaggctgtga ctgctgtgct ctgggcgcca gctcgctcca    120
gggagtgatg ggaatcctgt cattcttacc tgtccttgcc actgagagtg actgggctga    180
ctgcaagtcc cccagccctt gggtcatat gcttctgtgg acagctgtgc tattcctggc    240
tcctgttgct gggacacctg cagctccccc aaaggctgtg ctgaaactcg agccccagtg    300

|   |   |
|---|---|
| gatcaacgtg ctccaggagg actctgtgac tctgacatgc cggggactc acagccctga | 360 |
| gagcgactcc attcagtggt tccacaatgg aatctcatt cccacccaca cgcagcccag | 420 |
| ctacaggttc aaggccaaca caatgacag cggggagtac acgtgccaga ctggccagac | 480 |
| cagcctcagc gaccctgtgc atctgactgt gctttctgag tggctggtgc tccagaccc | 540 |
| tcacctggag ttcaggagg agaaaccat cgtgctgagg tgccacagct ggaaggacaa | 600 |
| gcctctggtc aaggtcacat tcttccagaa tggaaaatcc aagaaatttt cccgttcgga | 660 |
| tcccaacttc tccatcccac aagcaaacca cagtcacagt ggtgattacc actgcacagg | 720 |
| aaacataggc tacacgctgt actcatccaa gcctgtgacc atcactgtcc aagctcccag | 780 |
| ctcttcaccg atggggatca ttgtggctgt ggtcactggg attgctgtag cggccattgt | 840 |
| tgctgctgta gtggccttga tctactgcag gaaaaagcgg atttcagctc tcccaggata | 900 |
| ccctgagtgc agggaaatgg gagagaccct ccctgagaaa ccagccaatc ccactaatcc | 960 |
| tgatgaggct gacaaagttg gggctgagaa cacaatcacc tattcacttc tcatgcaccc | 1020 |
| ggatgctctg gaagagcctg atgaccagaa ccgtatttag tctccattgt cttgcattgg | 1080 |
| gatttgagaa gaaaatcaga gagggaagat ctggtatttc ctggcctaaa ttccccttgg | 1140 |
| ggaggacagg gagatgctgc agttccaaaa gagaaggttt cttccagagt catctacctg | 1200 |
| agtcctgaag ctccctgtcc tgaaagccac agacaatatg gtcccaaata accgactgca | 1260 |
| ccttctgtgc ttcagctctt cttgacatca aggctcttcc gttccacatc cacacagcca | 1320 |
| atccaattaa tcaaaccact gttattaaca gataatagca acttgggaaa tgcttatgtt | 1380 |
| acaggttacg tgagaacaat catgtaaatc tatatgattt cagaaatgtt aaaatagact | 1440 |
| aacctctacc agcacattaa aagtgattgt ttctgggtga taaaattatt gatgattttt | 1500 |
| attttctttta tttttctata aagatcatat attactttta taataaaaca ttataaaaac | 1560 |
| aacattctgt ttacctttc aaggctgtat tggttggagt gtagactgaa ctgcctgggg | 1620 |
| tctgtttctc ttcagtgatg agactcttag gaaggcagga atggatagga taggggagg | 1680 |
| agaggagaga tggggattta gaatgtagag tgagtgcccc ttttcttaaa actgaataca | 1740 |
| gtcacgcacc acataatgat gtttagttca caacagact gcatatatga tggtgatccc | 1800 |
| ataaaattat aataccatat ttctattgta cctttctat tcctatgttt agatatatga | 1860 |
| gtacttacca ttgtgttaca attgcctaaa gtattcagta cagtagcatg ctgtacaggt | 1920 |
| ttgtagccta ggggcaatag gctatacgct acagcctagg tgtgtagtag gccacaccat | 1980 |
| ttaggtttgt ataagtacct gctatgatgt tcacacaaca aaattgcctg catttctcaa | 2040 |
| aatgtatccc catatttcaa caatgcatga ctgtactctt ctgccaatga ccttgtattc | 2100 |
| ttgtttccat gtcttcttct ctttcctcct atggcaaata aaacactgtt ttgcaacaca | 2160 |
| aaaaaaaaaa aaaa | 2174 |

<210> SEQ ID NO 68
<211> LENGTH: 291
<212> TYPE: PRT
<213> ORGANISM: Homo sapiens

<400> SEQUENCE: 68

Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro

```
                 35                  40                  45
Lys Ala Val Leu Lys Leu Glu Pro Gln Trp Ile Asn Val Leu Gln Glu
             50                  55                  60

Asp Ser Val Thr Leu Thr Cys Arg Gly Thr His Ser Pro Glu Ser Asp
 65                  70                  75                  80

Ser Ile Gln Trp Phe His Asn Gly Asn Leu Ile Pro Thr His Thr Gln
                 85                  90                  95

Pro Ser Tyr Arg Phe Lys Ala Asn Asn Asn Asp Ser Gly Glu Tyr Thr
            100                 105                 110

Cys Gln Thr Gly Gln Thr Ser Leu Ser Asp Pro Val His Leu Thr Val
            115                 120                 125

Leu Ser Glu Trp Leu Val Leu Gln Thr Pro His Leu Glu Phe Gln Glu
            130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Phe Ser Arg
                165                 170                 175

Ser Asp Pro Asn Phe Ser Ile Pro Gln Ala Asn His Ser His Ser Gly
            180                 185                 190

Asp Tyr His Cys Thr Gly Asn Ile Gly Tyr Thr Leu Tyr Ser Ser Lys
            195                 200                 205

Pro Val Thr Ile Thr Val Gln Ala Pro Ser Ser Ser Pro Met Gly Ile
210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Asn Pro
                245                 250                 255

Thr Asn Pro Asp Glu Ala Asp Lys Val Gly Ala Glu Asn Thr Ile Thr
            260                 265                 270

Tyr Ser Leu Leu Met His Pro Asp Ala Leu Glu Glu Pro Asp Asp Gln
            275                 280                 285

Asn Arg Ile
    290

<210> SEQ ID NO 69
<211> LENGTH: 1233
<212> TYPE: DNA
<213> ORGANISM: Homo sapiens

<400> SEQUENCE: 69
cctataactt ggaatgtggg tggaggggtt catagttctc cctgagtgag acttgcctgc      60
tgctctggcc cctggtcctg tcctgttctc cagcatggtg tgtctgaggc tccctggagg     120
ctcctgcatg gcagttctga cagtgacact gatggtgctg agctccccac tggctttggc     180
tggggacacc agaccacgtt tcttggagta ctctacgtct gagtgtcatt tcttcaatgg     240
gacggagcgg gtgcggtacc tggacagata cttccataac caggaggaga acgtgcgctt     300
cgacagcgac gtgggggagt tccgggcggt gacggagctg gggcggcctg atgccgagta     360
ctggaacagc cagaaggacc tcctggagca gaagcgggcc cggtggacaa actactgcag     420
acacaactac ggggttgtgg agagcttcac agtgcagcgg cgagtccatc ctaaggtgac     480
tgtgtatcct tcaaagaccc agcccctgca gcaccataac ctcctggtct gttctgtgag     540
tggtttctat ccaggcagca ttgaagtcag gtggttccgg aatggccagg aagagaagac     600
tggggtggtg tccacaggcc tgatccacaa tggagactgg accttccaga ccctggtgat     660
```

-continued

```
gctggaaaca gttcctcgga gtggagaggt ttacacctgc caagtggagc acccaagcgt    720
gacaagccct ctcacagtgg aatggagagc acgtctgaa tctgcacaga gcaagatgct     780
gagtggagtc gggggctttg tgctgggcct gctcttcctt ggggccgggc tgttcatcta    840
cttcaggaat cagaaggac actctggact tcagccaaga ggattcctga gctgaagtgc     900
agatgacaca ttcaaagaag aactttctgc cccagctttg caggatgaaa agctttccct    960
cctggctgtt attcttccac aagagagggc tttctcagga cctggttgct actggttcag    1020
caactgcaga aaatgtcctc ccttgtggct tcctcagctc ctgttcttgg cctgaagccc    1080
cacagctttg atggcagtgc ctcatcttca actttttgtgc tcccctttgc ctaaaccca    1140 tggcctcctg tgcatctgta ctcaccctgt accacaaaca cattacatta ttaaatgttt    1200
ctcaaagatg gagttaaaaa aaaaaaaaaa aaa                                 1233
```

<210> SEQ ID NO 70
<211> LENGTH: 266
<212> TYPE: PRT
<213> ORGANISM: Homo sapiens

<400> SEQUENCE: 70

```
Met Val Cys Leu Lys Leu Pro Gly Gly Ser Cys Met Thr Ala Leu Thr
1               5                   10                  15

Val Thr Leu Met Val Leu Ser Ser Pro Leu Ala Leu Ser Gly Asp Thr
            20                  25                  30

Arg Pro Arg Phe Leu Trp Gln Pro Lys Arg Glu Cys His Phe Phe Asn
        35                  40                  45

Gly Thr Glu Arg Val Arg Phe Leu Asp Arg Tyr Phe Tyr Asn Gln Glu
    50                  55                  60

Glu Ser Val Arg Phe Asp Ser Asp Val Gly Glu Phe Arg Ala Val Thr
65                  70                  75                  80

Glu Leu Gly Arg Pro Asp Ala Glu Tyr Trp Asn Ser Gln Lys Asp Ile
                85                  90                  95

Leu Glu Gln Ala Arg Ala Ala Val Asp Thr Tyr Cys Arg His Asn Tyr
            100                 105                 110

Gly Val Gly Glu Ser Phe Thr Val Gln Arg Arg Val Gln Pro Lys Val
        115                 120                 125

Thr Val Tyr Pro Ser Lys Thr Gln Pro Leu Gln His His Asn Leu Leu
    130                 135                 140

Val Cys Ser Val Ser Gly Phe Tyr Pro Gly Ser Ile Glu Val Arg Trp
145                 150                 155                 160

Phe Leu Asn Gly Gln Glu Glu Lys Ala Gly Met Val Ser Thr Gly Leu
                165                 170                 175

Ile Gln Asn Gly Asp Trp Thr Phe Gln Thr Leu Val Met Leu Glu Thr
            180                 185                 190

Val Pro Arg Ser Gly Glu Val Tyr Thr Cys Gln Val Glu His Pro Ser
        195                 200                 205

Val Thr Ser Pro Leu Thr Val Glu Trp Arg Ala Arg Ser Glu Ser Ala
    210                 215                 220

Gln Ser Lys Met Leu Ser Gly Val Gly Gly Phe Val Leu Gly Leu Leu
225                 230                 235                 240

Phe Leu Gly Ala Gly Leu Phe Ile Tyr Phe Arg Asn Gln Lys Gly His
                245                 250                 255

Ser Gly Leu Gln Pro Thr Gly Phe Leu Ser
            260                 265
```

<210> SEQ ID NO 71
<211> LENGTH: 903
<212> TYPE: DNA
<213> ORGANISM: Homo sapiens

<400> SEQUENCE: 71

```
gtataaggtc cacaccccgg gagctgagtg attgcagaaa ctggccttcc atctctctca      60
gacaccaagc tgcagatcca ggtcactttg taggtcacca cctagagggg aggaagacct     120
cgctttggag agtgggaata aaacgctcgt ggaaagggt  acacgctttt ctgggaaagt     180
gaggccacca tggctctgga gaagtctctt gtccggctcc ttctgcttgt cctgatactg     240
ctggtgctgg gctgggtcca gccttccctg gcaaggaat  cccgggccaa gaaattccag     300
cggcagcata tggactcaga cagttccccc agcagcagct ccacctactg taaccaaatg     360
atgaggcgcc ggaatatgac acaggggcgg tgcaaaccag tgaacacctt gtgcacgag      420
cccctggtag atgtccagaa tgtctgtttc caggaaaagg tcacctgcaa gaacgggcag     480
ggcaactgct acaagagcaa ctccagcatg cacatcacag actgccgcct gacaaacggc     540
tccaggtacc ccaactgtgc ataccggacc agcccgaagg agagacacat cattgtggcc     600
tgtgaaggga gcccatatgt gccagtccac tttgatgctt ctgtggagga ctctacctaa     660
ggtcagagca gcgagatacc ccactcccct caacctcatc ctctccacag ctgcctcttc     720
cctcttcctt ccctgctgtg aaagaagtaa ctacagttag ggctcctatt caacacacac     780
atgcttccct ttcctgagtc ccatccctgc gtgattttgg gggtgaagag tgggttgtga     840
ggtgggcccc atgttaaccc ctccactctt tctttcaata aaacgcagtt gcaaacacct     900
gaa                                                                   903
```

<210> SEQ ID NO 72
<211> LENGTH: 156
<212> TYPE: PRT
<213> ORGANISM: Homo sapiens

<400> SEQUENCE: 72

```
Met Ala Leu Glu Lys Ser Leu Val Arg Leu Leu Leu Leu Val Leu Ile
1               5                   10                  15

Leu Leu Val Leu Gly Trp Val Gln Pro Ser Leu Gly Lys Glu Ser Arg
                20                  25                  30

Ala Lys Lys Phe Gln Arg Gln His Met Asp Ser Asp Ser Ser Pro Ser
            35                  40                  45

Ser Ser Ser Thr Tyr Cys Asn Gln Met Met Arg Arg Arg Asn Met Thr
        50                  55                  60

Gln Gly Arg Cys Lys Pro Val Asn Thr Phe Val His Glu Pro Leu Val
65                  70                  75                  80

Asp Val Gln Asn Val Cys Phe Gln Glu Lys Val Thr Cys Lys Asn Gly
                85                  90                  95

Gln Gly Asn Cys Tyr Lys Ser Asn Ser Ser Met His Ile Thr Asp Cys
            100                 105                 110

Arg Leu Thr Asn Gly Ser Arg Tyr Pro Asn Cys Ala Tyr Arg Thr Ser
        115                 120                 125

Pro Lys Glu Arg His Ile Ile Val Ala Cys Glu Gly Ser Pro Tyr Val
    130                 135                 140

Pro Val His Phe Asp Ala Ser Val Glu Asp Ser Thr
145                 150                 155
```

<210> SEQ ID NO 73
<211> LENGTH: 3008
<212> TYPE: DNA
<213> ORGANISM: Homo sapiens

<400> SEQUENCE: 73

| | |
|---|---|
| actaggcagg gatgagcaag aggaatggct caccettgag agctggggtc catagcccag | 60 |
| gtcagttctc cagctctccc acttaccagc caagacagga ggtgaggatt gagatgggat | 120 |
| gaacccagca ggcggccatg ggttaaaggt cgccatgaat gtaatgtgcc cagcacagtg | 180 |
| cctgctaaaa ggcaacactc ccttcctggt ctgaagacca acaagcaga ctgtactcag | 240 |
| gaaagccaga agaaccttcc agctgtctgg accagaaggt gccagcccag gggctgaaga | 300 |
| agacgtaatg cccagagcaa aaagcgcctg cagcccctg aagggctggg tgctctggaa | 360 |
| tagatgaggg ggcgaaatgg ggctggggac cagggacgga cagggtgggt ccagcacctg | 420 |
| cctcgcttcc gaagggctgc tccaacactg aaaaacaccc aaccagcttc ctttcagaaa | 480 |
| gactggaata ttccaaaact tctcactgga ggctccggag gaggtgggct ccagctgaaa | 540 |
| aggaaatgtg gaggcgtggg cgctcccggc ctgcatcctg cacctcttac actttggttt | 600 |
| tcccacagac tcctgaagaa taggtcagaa gaaagggtta aagccttaaa aggggaacaa | 660 |
| ccattgcggg gctcagggag gaggataatg ttctttgggc tgccgcaccc tgatccccgg | 720 |
| ggtcccgaac cctcccgtcc ctggccaggc ctgccagcca cagggtgagg gccccttcc | 780 |
| gccgcaacct gccactctca caccaatgcg ggaccgcctt ctcttccttc ccaccccccc | 840 |
| accccaccct gccgtccttt ctcccccaat ctccgcctct gattggctga gccccggct | 900 |
| ccccgctccc cctctcctcc atcccggtg aaaactgcgg gctccgagct gggtgcagca | 960 |
| accggaggcg gcgcgcgtc tggaggaggc tgcagcagcg gaagacccca gtccagatcc | 1020 |
| aggactgaga tcccagaacc atgaacctgg ccatcagcat cgctctcctg ctaacagtct | 1080 |
| tgcaggtctc ccgagggcag aaggtgacca gcctaacggc ctgcctagtg accagagcc | 1140 |
| ttcgtctgga ctgccgccat gagaatacca gcagttcacc catccagtac gagttcagcc | 1200 |
| tgacccgtga gacaaagaag cacgtgctct ttggcactgt gggggtgcct gagcacacat | 1260 |
| accgctcccg aaccaacttc accagcaaat acaacatgaa ggtcctctac ttatccgcct | 1320 |
| tcactagcaa ggacgagggc acctacacgt gtgcactcca ccactctggc cattccccac | 1380 |
| ccatctcctc ccagaacgtc acagtgctca gagacaaact ggtcaagtgt gagggcatca | 1440 |
| gcctgctggc tcagaacacc tcgtggctgc tgctgctcct gctctccctc tccctcctcc | 1500 |
| aggccacgga tttcatgtcc ctgtgactgg tggggcccat ggaggagaca ggaagcctca | 1560 |
| agttccagtg cagagatcct acttctctga gtcagctgac cccctccccc caatccctca | 1620 |
| aaccttgagg agaagtgggg accccacccc tcatcaggag ttccagtgct gcatgcgatt | 1680 |
| atctacccac gtccacgcgg ccacctcacc ctctccgcac acctctggct gtcttttgt | 1740 |
| acttttgtt ccagagctgc ttctgtctgg tttatttagg tttatccctt ccttttctttt | 1800 |
| gagagttcgt gaagagggaa gccaggattg ggacctgat ggagagtgag agcatgtgag | 1860 |
| gggtagtggg atggtggggt accagccact ggaggggtca tccttgccca tcggaccag | 1920 |
| aaacctggga gagacttgga tgaggagtgg ttgggctgtg cctgggccta gcacggacat | 1980 |
| ggtctgtcct gacagcactc ctcggcaggc atggctggtg cctgaagacc ccagatgtga | 2040 |
| gggcaccacc aagaatttgt ggcctacctt gtgagggaga gaactgagca tctccagcat | 2100 |
| tctcagccac aaccaaaaaa aaataaaaag ggcagccctc cttaccactg tggaagtccc | 2160 |

```
tcagaggcct tggggcatga cccagtgaag atgcaggttt gaccaggaaa gcagcgctag    2220
tggagggttg gagaaggagg taaaggatga gggttcatca tccctccctg cctaaggaag    2280
ctaaaagcat ggccctgctg cccctccctg cctccaccca cagtggagag ggctacaaag    2340
gaggacaaga ccctctcagg ctgtcccaag ctcccaagag cttccagagc tctgaccccac   2400 agcctccaag tcaggtgggg tggagtccca gagctgcaca gggtttggcc caagtttcta    2460
agggaggcac ttcctcccct cgcccatcag tgccagcccc tgctggctgg tgcctgagcc    2520
cctcagacag ccccctgccc cgcaggcctg ccttctcagg gacttctgcg gggcctgagg    2580
caagccatgg agtgagaccc aggagccgga cacttctcag gaaatggctt ttcccaaccc    2640
ccagccccca cccggtggtt cttcctgttc tgtgactgtg tatagtgcca ccacagctta    2700
tggcatctca ttgaggacaa agaaaactgc acaataaaac caagcctctg gaatctgtcc    2760
tcgtgtccac ctggccttcg ctcctccagc agtgcctgcc tgcccccgct cgctggggt     2820 ctccacgggt gaggctgggg aacgccacct cttcctcttc cctgacttct ccccaaccac    2880
ttagtagcaa cgctacccca ggggctaatg actgcacact gggcttcttt tcagaatgac    2940
cctaacgaga cacatttgcc caaataaacg aacatcccat gtctgctgac tcaaaaaaaa    3000
aaaaaaaa                                                             3008
```

<210> SEQ ID NO 74
<211> LENGTH: 161
<212> TYPE: PRT
<213> ORGANISM: Homo sapiens

<400> SEQUENCE: 74

```
Met Asn Leu Ala Ile Ser Ile Ala Leu Leu Leu Thr Val Leu Gln Val
1               5                   10                  15

Ser Arg Gly Gln Lys Val Thr Ser Leu Thr Ala Cys Leu Val Asp Gln
                20                  25                  30

Ser Leu Arg Leu Asp Cys Arg His Glu Asn Thr Ser Ser Ser Pro Ile
            35                  40                  45

Gln Tyr Glu Phe Ser Leu Thr Arg Glu Thr Lys Lys His Val Leu Phe
        50                  55                  60

Gly Thr Val Gly Val Pro Glu His Thr Tyr Arg Ser Arg Thr Asn Phe
65                  70                  75                  80

Thr Ser Lys Tyr His Met Lys Val Leu Tyr Leu Ser Ala Phe Thr Ser
                85                  90                  95

Lys Asp Glu Gly Thr Tyr Thr Cys Ala Leu His His Ser Gly His Ser
                100                 105                 110

Pro Pro Ile Ser Ser Gln Asn Val Thr Val Leu Arg Asp Lys Leu Val
            115                 120                 125

Lys Cys Glu Gly Ile Ser Leu Leu Ala Gln Asn Thr Ser Trp Leu Leu
        130                 135                 140

Leu Leu Leu Leu Ser Leu Ser Leu Leu Gln Ala Thr Asp Phe Met Ser
145                 150                 155                 160

Leu
```

<210> SEQ ID NO 75
<211> LENGTH: 657
<212> TYPE: DNA
<213> ORGANISM: Homo sapiens

<400> SEQUENCE: 75

```
gacaactcgg tggtggccac tgcgcagacc agacttcgct cgtactcgtg cgcctcgctt        60
cgcttttcct ccgcaaccat gtctgacaaa cccgatatgg ctgagatcga gaaattcgat       120
aagtcgaaac tgaagaagac agagacgcaa gagaaaaatc cactgccttc caaagaaacg       180
attgaacagg agaagcaagc aggcgaatcg taatgaggcg tgcgccgcca atatgcactg       240
tacattccac aagcattgcc ttcttatttt acttctttta gctgtttaac tttgtaagat       300
gcaaagaggt tggatcaagt ttaaatgact gtgctgcccc tttcacatca aagaactact       360
gacaacgaag gccgcgcctg cctttcccat ctgtctatct atctggctgg cagggaagga       420
aagaacttgc atgttggtga aggaagaagt ggggtggaag aagtggggtg ggacgacagt       480
gaaatctaga gtaaaaccaa gctggcccaa ggtgtcctgc aggctgtaat gcagtttaat       540
cagagtgcca ttttttttt tgttcaaatg attttaatta ttggaatgca caattttttt       600
aatatgcaaa taaaaagttt aaaaacttaa aaaaaaaaa aaaaaaaaa aaaaaaa           657

<210> SEQ ID NO 76
<211> LENGTH: 44
<212> TYPE: PRT
<213> ORGANISM: Homo sapiens

<400> SEQUENCE: 76

Met Ser Asp Lys Pro Asp Met Ala Glu Ile Glu Lys Phe Asp Lys Ser
1               5                   10                  15

Lys Leu Lys Lys Thr Glu Thr Gln Glu Lys Asn Pro Leu Pro Ser Lys
            20                  25                  30

Glu Thr Ile Glu Gln Lys Gln Ala Gly Glu Ser
        35                  40
```

COMPOSITIONS AND METHODS FOR DIAGNOSING PROSTATE CANCER USING A GENE EXPRESSION SIGNATURE

RELATED APPLICATIONS

This application is a national stage application, filed under 35 U.S.C. § 371, of International Application No. PCT/US2016/061519, filed on Nov. 11, 2016, which claims the benefit of priority under 35 U.S.C. § 119(e) to U.S. Provisional Application No. 62/254,925, filed Nov. 13, 2015, each of which is incorporated herein by reference in its entirety.

GOVERNMENT LICENSE RIGHTS

This invention was made with government support under grant number R01CA131945 awarded by the National Institutes of Health, under grant number R01CA187918, awarded by the National Institutes of Health, under grant number DoD PC130716, awarded by the National Institutes of Health, under grant number P50 CA90381, awarded by the National Institutes of Health, and under grant number R01CA174206, awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Dec. 8, 2016, is named 48289-528001WO1 ST25.txt and is 328,192 bytes in size.

BACKGROUND OF THE INVENTION

Prostate cancer, also known as carcinoma of the prostate, is the development of cancer in the prostate, a gland in the male reproductive system. Prostate cancer cells may also metastasize from the prostate to other parts of the body, e.g., the bones and/or lymph nodes. Prior to the invention described herein, studies within human prostate cancer cohorts were challenging due to the complexity in characterizing genomic changes in epithelium separately from the surrounding microenvironment (i.e., stroma) and the lack of statistical tools to assess and quantify cross-talk across the epithelial and stromal compartments. As such, there is a pressing need to identify more effective diagnostic, prognostic, and treatment methods for prostate cancer.

SUMMARY OF THE INVENTION

The invention is based upon the identification of a gene expression signature (i.e., a "bone homing signature") that predicts the likelihood that prostate cancer will metastasize, e.g., to bone. In some aspects, the invention relates to methods, arrays and kits for diagnosing and monitoring prostate cancer and cancer metastases.

Provided is a method of determining whether prostate cancer in a subject, e.g., a human subject, will metastasize, e.g., to bone, comprising obtaining a test sample from a subject having or at risk of developing prostate cancer; determining the expression level of at least one prostate cancer-associated gene in the test sample; comparing the expression level of the prostate cancer-associated gene in the test sample with the expression level of the prostate cancer-associated gene in a reference sample; and determining that the prostate cancer in the subject will metastasize if the expression level of the prostate cancer-associated gene in the test sample is differentially expressed as compared to the level of the prostate cancer-associated gene in the reference sample.

Alternatively, the expression level of the prostate cancer-associated gene in the test sample is compared with a threshold expression level of the prostate cancer-associated gene (e.g., a "cut-off level"). The method involves determining whether prostate cancer in the subject will metastasize, e.g., to the bone, if the expression level of the prostate cancer-associated gene in the test sample is differentially expressed as compared to the threshold expression level of the prostate cancer-associated gene. In some cases, the threshold expression level of each gene is determined and compared individually. Alternatively, the threshold expression level is a combined score computed from the expression of each gene in the "bone homing signature."

In another case, the expression level of the prostate cancer-associated gene in the test sample is compared with an expression level of a housekeeping gene within the test sample. The method involves determining whether prostate cancer in the subject will metastasize, e.g., to the bone, if the expression level of the prostate cancer-associated gene in the test sample is differentially expressed as compared to the expression level of the housekeeping gene. A suitable housekeeping genes includes glyceraldehyde 3-phosphate dehydrogenase (GAPDH). In some cases, the expression level of a housekeeping gene is utilized for normalization purposes.

The expression level of the prostate cancer-associated gene in the test sample is differentially expressed as compared to the level of the prostate cancer-associated gene in the reference sample, the threshold expression level, or the expression level of a housekeeping gene. For example, the expression level of the prostate cancer-associated gene in the test sample is upregulated (i.e., increased) by at least 2 fold, at least 3 fold, at least 4 fold, at least 5 fold, at least 6 fold, at least 7 fold, at least 8 fold, at least 9 fold, at least 10 fold, at least 15 fold, at least 20 fold, at least 25 fold, at least 30 fold, at least 35 fold, at least 40 fold, at least 45 fold, at least 50 fold, at least 60 fold, at least 70 fold, at least 80 fold, at least 90 fold, at least 100 fold, at least 125 fold, at least 150 fold, at least 175 fold, at least 200 fold, at least 250 fold, at least 300 fold, at least 350 fold, at least 400 fold, at least 500 fold, at least 600 fold, at least 700 fold or at least 800 fold as compared to the level of the prostate cancer-associated gene in the reference sample, the threshold expression level, or the expression level of a housekeeping gene.

Alternatively, the expression level of the prostate cancer-associated gene in the test sample is downregulated (i.e., decreased) by at least 2 fold, at least 3 fold, at least 4 fold, at least 5 fold, at least 6 fold, at least 7 fold, at least 8 fold, at least 9 fold, at least 10 fold, at least 15 fold, at least 20 fold, at least 25 fold, at least 30 fold, at least 35 fold, at least 40 fold, at least 45 fold, at least 50 fold, at least 60 fold, at least 70 fold, at least 80 fold, at least 90 fold, at least 100 fold, at least 125 fold, at least 150 fold, at least 175 fold, at least 200 fold, at least 250 fold, at least 300 fold, at least 350 fold, at least 400 fold, at least 500 fold, at least 600 fold, at least 700 fold or at least 800 fold as compared to the level of the prostate cancer-associated gene in the reference sample, the threshold expression level, or the expression level of a housekeeping gene.

For example, the prostate cancer-associated gene comprises adipocyte enhancer-binding protein 1 (AEBP1), anthrax toxin receptor 1 (ANTXR1), biglycan (BGN), complement component 1, q subcomponent, A chain (C1QA), complement component 1, q subcomponent, B chain (C1QB), complement component 1, q subcomponent, C chain (C1QC), complement component 1, R subcomponent (C1R), complement component 1, s subcomponent (C1S), cadherin 11 (CDH11), collagen type I (COL1A1), collagen type III alpha 1 chain (COL3A1), fibulin 5 (FBLN5), Fc Fragment of IgG Receptor IIb (receptor for CD32; FCGR2B), major histocompatibility complex, class II, DR Beta 1 (HLA-DRB1), lumican (LUM), monooxygenase, DBH-like 1 (MOXD1), proline/arginine-rich end leucine-rich repeat protein (PRELP), ribonuclease 1 (RNASE1), secreted frizzled related protein 2 (SFRP2), secreted frizzled related protein 4 (SFRP4), sulfatase 1 (SULF1), thrombospondin 2 (THBS2), Thy-1 cell surface antigen (THY1), or Thymosin Beta 4, X-Linked (TMSB4X); and it is determined that the prostate cancer in the subject will metastasize if the expression level of the prostate cancer-associated gene in the test sample is higher than the level of the prostate cancer-associated gene in the reference sample.

In another example, the prostate cancer-associated gene comprises activated leukocyte cell adhesion molecule (ALCAM), lumican (LUM), collagen type I alpha 1 chain (COL1A1), biglycan (BGN), complement component 1, q subcomponent, C chain (C1QC), complement component 1, s subcomponent (C1S), complement component 1, q subcomponent, B chain (C1QB), histocompatibility leukocyte antigen-DRB3 (HLA-DRB3), adipocyte enhancer-binding protein 1 (AEBP1), secreted frizzled related protein 4 (SFRP4), fibulin 5 (FBLN5), Fc fragment of IgG, low affinity IIC, receptor for CD32 (FCGR2C), complement component 1, q subcomponent, A chain (C1QA), secreted frizzled related protein 2 (SFRP2), sulfatase 1 (SULF1), thrombospondin 2 (THBS2), monooxygenase, DBH-like 1 (MOXD1), serpin peptidase inhibitor, Glade G (C1 inhibitor), member 1 (SERPING1), proline/arginine-rich end leucine-rich repeat protein (PRELP), cluster of differentiation 52 (CD52), latent transforming growth factor beta binding protein 2 (LTBP2), integrin, alpha 11 (ITGA11), or tensin 3 (TNS3); and it is determined that the prostate cancer in the subject will metastasize if the expression level of the prostate cancer-associated gene in the test sample is higher than the level of the prostate cancer-associated gene in the reference sample.

In some cases, the prostate cancer-associated gene comprises protein tyrosine phosphatase-like A domain containing 1 (PTPLAD1) or myelin and lymphocyte protein, T-cell differentiation protein 2 (MAL2); and it is determined that the prostate cancer in the subject will metastasize if the expression level of the prostate cancer-associated gene in the test sample is higher than the level of the prostate cancer-associated gene in the reference sample.

Alternatively, the prostate cancer-associated gene comprises chromosome 12 open reading frame 51 (C12orf51), transmembrane protein 205 (TMEM205), heat shock 70 kDa protein 9 (HSPA9), claudin 8 (CLDN8); and it is determined that the prostate cancer in the subject will metastasize if the expression level of the prostate cancer-associated gene in the test sample is higher than the level of the prostate cancer-associated gene in the reference sample.

Alternatively, the genes described herein are associated with an immune response. For example, an immune response gene panel includes C1S, C1QA, C1QB, C1QC, SERPING1, FCGR2C, CD52, and HLA-DRB3.

In another example, the genes described herein are associated with the extracellular matrix. For example, the extracellular matrix gene panel includes SFRP2, SULF1, COL1A1, ITGA11, Biglycan, LTBP3, Fibulin-5, Biglycan proteoglycan and Lumacin.

In some examples, the genes include a bone-related subset of genes. For example, the bone-related subset of genes includes PRELP, LTBP2, FBLN5, ITGA11, COL1A1, ALCAM, SFRP2, TNS3, SULF1, BGN, and THBS2.

In another example, the prostate cancer-associated gene comprises ALCAM, LUM, COL1A1, BGN, C1QC, C1S, C1QB, HLA-DRB3, AEBP1, SFRP4, FBLN5, FCGR2C, C1QA, SFRP2, SULF1, THBS2, MOXD1, SERPING1, PRELP, CD52, LTBP2, ITGA11, TNS3, C12orf51, TMEM205, HSPA9, CLDN8, PTPLAD1, and MAL2; and it is determined that the prostate cancer in the subject will metastasize if the expression level of ALCAM, LUM, COL1A1, BGN, C1QC, C1S, C1QB, HLA-DRB3, AEBP1, SFRP4, FBLN5, FCGR2C, C1QA, SFRP2, SULF1, THBS2, MOXD1, SERPING1, PRELP, CD52, LTBP2, ITGA11, TNS3 in the test sample is higher than the level of the prostate cancer-associated gene in the reference sample, and if the expression level of C12orf51, TMEM205, HSPA9, CLDN8, PTPLAD1, and MAL2 in the test sample is higher than the level of the prostate cancer-associated gene in the reference sample.

In some aspects, the number of predictive prostate cancer-associated genes comprises 29 genes, i.e., 29 of the genes described herein. In other aspects, the number of predictive genes is at least 1 gene; e.g., at least 2 genes, at least 3 genes, at least 4 genes, at least 5 genes, at least 6 genes, at least 7 genes, at least 8 genes, at least 9 genes, at least 10 genes, at least 11 genes, at least 12 genes, at least 13 genes, at least 14 genes, at least 15 genes, at least 16 genes, at least 17 genes, at least 18 genes, at least 19 genes, at least 20 genes, at least 21 genes, at least 22 genes, at least 23 genes, at least 24 genes, at least 25 genes, at least 26 genes, at least 27 genes, or at least 28 genes of the genes described herein.

For example, the expression level of the prostate cancer-associated gene is detected via an Affymetrix Gene Array hybridization chip for transcriptome analysis. Alternatively, a real time reverse transcriptase polymerase chain reaction (real time RT-PCR) assay may be used to validate the genes in other tissues. In another aspect, the expression level of the prostate cancer-associate gene is detected via next-generation sequencing, ribonucleic acid sequencing (RNA-seq), immunohistochemistry, or immunofluorescence.

In one aspect, the subject is identified as having Gleason 6 grade prostate cancer or Gleason 8 or higher grade prostate cancer with the methods described herein. For example, the subject is identified as having Gleason grade 9 prostate cancer, or Gleason grade 10 prostate cancer. In some cases, the subject is identified as having Gleason grade 7 prostate cancer.

In some cases, the test sample is obtained from prostate stromal (benign, high grade PIN (hgPIN), or tumor) tissue, prostate gland (benign, hgPIN, or tumor) tissue from patients having undergone radical prostatectomy or from patients who have not had radical prostatectomy. Preferably, the sample comprises ribonucleic acid (RNA) or deoxyribonucleic acid (DNA). Suitable reference samples were obtained from healthy normal control prostate stromal tissue, benign prostate stromal tissue from patients having undergone cystoprostatectomy and were confirmed not to have prostate cancer. Other suitable types of samples include a plasma sample and a blood sample.

In one aspect, the subject has relapsed with prostate cancer or is at risk of relapsing with prostate cancer. Identifying a relapsed subject who is likely to develop prostate cancer metasteses will enable timely prevention/treatment strategies.

Optionally, the subject has undergone a radical prostatectomy. In other cases, the methods further comprise performing a radical prostatectomy on the subject after determining whether the prostate cancer will metastasize, e.g., to bone. In another example, the subject is treated with a chemotherapeutic agent, radiation therapy, cryotherapy, or hormone therapy after determining whether the prostate cancer will metastasize. Exemplary chemotherapeutic agents include doceaxel, cabazitaxel, mitoxantrone, estramustine, doxorubicin, etoposide and paclitaxel.

In some cases, the corresponding polypeptide level of the prostate-cancer associated gene in the test sample is compared with the polypeptide level of the prostate cancer-associated gene in the reference sample, a threshold polypeptide level, or a housekeeping gene polypeptide level. It is determined that the prostate cancer in the subject will metastasize if the corresponding polypeptide level of the prostate cancer-associated gene in the test sample is higher than the polypeptide level of the prostate cancer-associated gene in the reference sample, a threshold polypeptide level, or a housekeeping gene polypeptide level.

The methods described herein involve monitoring whether prostate cancer in a subject will metastasize, e.g., to bone, over time. For example, the methods described herein are repeated over time, wherein an alteration in the level of the prostate cancer-associated gene over time indicates a corresponding alteration in the aggressiveness of the prostate cancer. Preferably, in this case, a radical prostatectomy is not performed so the cancer may be evaluated over time.

In some cases, the subject is treated if it is determined that the subject has prostate cancer that is likely to metastasize. For example, an inhibitor of the prostate cancer gene with a higher level of expression compared to the level of the prostate cancer-associated gene in the reference sample is administered to the subject, thereby treating the prostate cancer. Exemplary inhibitors include a small molecule inhibitor, RNA interference (RNAi), an antibody, or any combination thereof. Alternatively, the methods further comprise administering an agonist of the prostate cancer gene with a lower level of expression compared to the level of the prostate cancer-associated gene in the reference sample, thereby treating the prostate cancer.

Also provided are compositions comprising a prostate cancer-associated gene, wherein the prostate cancer-associated gene comprises ALCAM, LUM, COL1A1, BGN, C1QC, C1S, C1QB, HLA-DRB3, AEBP1, SFRP4, FBLN5, FCGR2C, C1QA, SFRP2, SULF1, THBS2, MOXD1, SERPING1, PRELP, CD52, LTBP2, ITGA11, TNS3, C12orf51, TMEM205, HSPA9, CLDN8, PTPLAD1, or MAL2 synthesized complementary deoxyribonucleic acid (cDNA).

Alternatively, the genes described herein are associated with an immune response. For example, an immune response gene panel includes C1S, C1QA, C1QB, C1QC, SERPING1, FCGR2C, CD52, and/or HLA-DRB3 synthesized complementary deoxyribonucleic acid (cDNA).

In another example, the genes described herein are associated with an extracellular matrix. For example, an extracellular matrix gene panel includes SFRP2, SULF1, COL1A1, ITGA11, Biglycan, LTBP3, Fibulin-5, Biglycan proteoglycan and/or Lumacin synthesized complementary deoxyribonucleic acid (cDNA).

In some examples, the genes include a bone-related subset of genes. For example the bone-related subset of genes includes PRELP, LTBP2, FBLN5, ITGA11, COL1A1, ALCAM, SFRP2, TNS3, SULF1, BGN, and/or THBS2 synthesized complementary deoxyribonucleic acid (cDNA).

Additional compositions include a composition comprising a prostate cancer-associated gene, wherein the prostate cancer-associated gene comprises AEBP1, ANTXR1, BGN, C1QA, C1QB, C1QC, C1R, C1S, CDH11, COL1A1, COL3A1, FBLN5, FCGR2B, HLA-DRB1, LUM, MOXD1, PRELP, RNASE1, SFRP2, SFRP4, SULF1, THBS2, THY1, or TMSB4X synthesized complementary deoxyribonucleic acid (cDNA).

Preferably, the prostate cancer-associated gene is immobilized on a solid support. In one aspect, the prostate cancer-associated gene is linked to a detectable label. Suitable detectable labels include a fluorescent label, a luminescent label, a chemiluminescent label, a radiolabel, a SYBR Green label, or a Cy3-label.

Also provided are kits comprising a package with a prostate cancer-associated gene, wherein the prostate cancer-associated gene comprises ALCAM, LUM, COL1A1, BGN, C1QC, C1S, C1QB, HLA-DRB3, AEBP1, SFRP4, FBLN5, FCGR2C, C1QA, SFRP2, SULF1, THBS2, MOXD1, SERPING1, PRELP, CD52, LTBP2, ITGA11, TNS3, C12orf51, TMEM205, HSPA9, CLDN8, PTPLAD1, or MAL2 and instructions for use thereof in the evaluation of prostate cancer progression and metastasis.

Provided is a kit comprising a package with a prostate cancer-associated gene, wherein the prostate cancer-associated gene comprises AEBP1, ANTXR1, BGN, C1QA, C1QB, C1QC, C1R, C1S, CDH11, COL1A1, COL3A1, FBLN5, FCGR2B, HLA-DRB1, LUM, MOXD1, PRELP, RNASE1, SFRP2, SFRP4, SULF1, THBS2, THY1, or TMSB4X and instructions for use thereof in the evaluation of prostate cancer progression and metastasis.

As described herein, a 24-gene signature reflecting bone remodeling and immune-related pathways was upregulated in high compared to low Gleason score cases and comprises a "bone homing signature" (Table 24).

As described in detail below, a 29-gene signature was defined herein (7 epithelial and 22 stromal genes), which distinguishes Gleason 6 from Gleason 8, which comprise a "bone homing signature" (Table 1).

TABLE 1

29-gene signature which distinguishes Gleason 6 from Gleason 8

| Gene | Comparison | Fold Change | p-value | adj p-value | Gene Description | Ref |
| --- | --- | --- | --- | --- | --- | --- |
| ALCAM | T, I* | 0.6342 | 1.15E−07 | 3.83E−03 | activated leukocyte cell adhesion molecule, CD166 | Hansen [1] |
| LUM | S | 1.2741 | 4.32E−05 | 3.68E−02 | Lumican | Klein [4], Coulson-Thomas [5] |
| COL1A1 | S | 1.1494 | 1.50E−05 | 2.26E−02 | Collagen Type I | Klein [4], Nakajima [6] |
| BGN | S | 1.0586 | 1.46E−05 | 2.26E−02 | Byglycan | Klein [4], Berendsen [v7] |
| C1QC | S | 1.0141 | 9.55E−06 | 1.99E−02 | Complement component 1, q subcomponent, C chain | Nayak [8], Teo [9] |

TABLE 1-continued 29-gene signature which distinguishes Gleason 6 from Gleason 8

| Gene | Comparison | Fold Change | p-value | adj p-value | Gene Description | Ref |
|---|---|---|---|---|---|---|
| C1S | S | 1.0054 | 3.02E−05 | 3.03E−02 | Complement component 1, s subcomponent | Ghebrehiwet [10] |
| C1QB | S | 0.7856 | 9.57E−06 | 1.99E−02 | Complement component 1, q subcomponent, B chain | Nayak [8], Luo [11] |
| HLA-DRB3 | S | 0.9441 | 6.75E−05 | 4.71E−02 | Major histocompatibility complex, class II, DR beta 3 | Li [12] |
| AEBP1 | S | 0.9868 | 6.35E−06 | 1.99E−02 | Stromal adipocyte enhancer-binding protein | Holloway [13], Yamashita [14], Cheon [15] |
| SFRP4 | S,I* | 1.0741 | 2.49E−07 | 4.15E−03 | Secreted frizzled related protein 4 | Hassan [16], Pohl [17] |
| FBLN5 | S,I* | 0.8493 | 4.17E−05 | 3.65E−02 | Fibulin 5 | Bing [18], Moller [19] |
| FCGR2C | S,I* | 0.7472 | 1.49E−07 | 4.15E−03 | Fc fragment of IgG, low affinity IIc, receptor for (CD32)(gene/pseudogene) | Li [12] |
| C1QA | S,I* | 0.7469 | 1.27E−06 | 7.05E−03 | Complement component 1, q subcomponent, A chain | Nayak [8] |
| SFRP2 | S,I* | 0.7266 | 8.73E−07 | 6.32E−03 | Secreted frizzled related protein 2 | Hassan [20], Perry [21] |
| SULF1 | S,I* | 0.7205 | 1.08E−05 | 1.99E−02 | Sulfatase 1 | Jiang [22], Buono [23] |
| THBS2 | S,I* | 0.6785 | 1.27E−05 | 2.12E−02 | Thrombospondin 2 | Slavin [24] |
| MOXD1 | S,I* | 0.6074 | 2.56E−05 | 2.78E−02 | Monooxygenase, DBH-like 1 | |
| SERPING1 | I | 1.4925 | 2.68E−05 | 3.67E−02 | Serpin peptidase inhibitor, clade G (C1 inhibitor), member 1 | Kiflemariam [25] |
| PRELP | I | 1.1871 | 2.15E−05 | 3.67E−02 | Proline/arginine-rich end leucine-rich repeat protein | Rucci [26] |
| CD52 | I | 1.0080 | 4.31E−05 | 4.49E−02 | cluster of differentiation 52 | Gupta [27], Hameed [28] |
| LTBP2 | I | 0.7318 | 1.11E−06 | 1.16E−02 | Latent transforming growth factor beta binding protein 2 | Cheung [29] |
| ITGA11 | I | 0.7135 | 1.47E−07 | 4.89E−03 | Integrin, alpha 11 | Kaltz [30] |
| TNS3 | I | 0.6221 | 2.15E−06 | 1.19E−02 | Tensin 3 | Qian [31] |
| C12orf51 | I | −0.6032 | 6.91E−06 | 2.28E−02 | HECT domain containing E3 ubiquitin protein ligase 4, HECTD4 | Heo [32] |
| TMEM205 | I | −0.6430 | 3.85E−05 | 4.43E−02 | Transmembrane protein 205 | Shen [33], Gottesman [34] |
| HSPA9 | I | −0.6460 | 1.33E−06 | 1.16E−02 | Heat shock 70 kDa protein 9 (mortalin) | Walter [35] |
| CLDN8 | I | −0.7098 | 2.80E−05 | 3.67E−02 | Claudin 8 | McMillan [36] |
| PTPLAD1 | I | −0.7476 | 2.90E−05 | 3.67E−02 | Protein tyrosine phosphatase-like A domain containing 1 | Courilleau [37] |
| MAL2 | I | −0.9724 | 2.81E−05 | 3.67E−02 | T-cell differentiation protein 2 | Marazuela [38], Llorente [39] | where T is Tumor, S is Stroma and I is Interaction; T: [T8-T6], S: [sT8-sT6], I: [sT8-T8]-[sT6-T6]
Also found in Interaction, values not tabulated (see Supplemental)

TABLE 19

29-gene signature references

| Gene | Reference |
|---|---|
| ALCAM | Hansen AG, et al., *Cancer Res.* 74, 1404-15 (2014) |
| LUM | Klein EA, et al., *Eur Urol*, 2011. 66: p. 672-84; Coulson-Thomas VJ, et al., *Exp Cell Res*, 319: p. 967-81 (2013) |
| COL1A1 | Klein EA, et al., *Eur Urol*, 2011. 66: p. 672-84; Nakajima K, *Neoplasia*. 16, 939-49 (2014). |
| BGN | Klein EA, et al., *Eur Urol*, 2011. 66: p. 672-84; Berendsen AD, et al., *Matrix Biol*. 35, 223-31 (2014) |
| C1QC | Nayak A, et al., *Immunol Lett.* 131, 139-50 (2010); Teo BH, et al., *Biochem J.* 447, 229-37 (2012) |
| C1S | Ghebrehiwet B, et al., *Front Immunol*. 3, 52 (2012) |
| C1QB | Nayak A, et al., *Immunol Lett.* 131, 139-50 (2010); Luo Y et al., *PLoS One*. 6, e20971 (2011) |
| HLA-DRB3 | Li X, W.J. et al., *Sci Transl Med*. 5, 216 (2013) |
| AEBP1 | Holloway RW, et al,. *J Biol Chem*. 287, 39171-81 (2012); Yamashita S, et al., *Cancer Res.* 68, 2112-21 (2008); Cheon DJ, et al., *Clin Cancer Res.* 20, 711-23 (2014) |
| SFRP4 | Hassan MQ, M.Y. et al., *J Biol Chem.* 287, 42084-92 (2012); Pohl S, Scott R, et al., *Tumour Biol.* 36, 143-52 (2015) |
| FBLN5 | Bing Z, et al., *Mol Biol Rep*. 39, 6077-85 (2012); Møller HD, et al., *Mol Cancer Res.* 9, 553-63 (2011) |
| FCGR2C | Li X, W.J. et al., *Sci Transl Med*. 5, 216 (2013) |
| C1QA | |
| SFRP2 | Hassan MQ, M.Y et al., *J Biol Chem.* 287, 42084-92 (2012); Perry AS, et al., *Int J Cancer*. 132, 1771-80 (2013) |
| SULF1 | Jiang SS, et al., *Aging*. 3, 672-84 (2011); Buono M, et al., *J Exp Med*. 207, 1647-60 (2011) |
| THBS2 | Slavin S, et al., *Carcinogenesis*. 35, 1301-9 (2014) |
| MOXD1 | |
| SERPING1 | Kiflemariam S, et al., *Am J Pathol*. 185, 1600-9 (2015) |
| PRELP | Rucci N, R.A. et al., *J Cell Biol*. 187, 669-83 (2009) |
| CD52 | Gupta R. et al., Am J Clin Pathol, 132, 728-32 (2009); Hameed A. et al., *Cancer Growth Metastasis*. 7, 33-42 (2014) |
| LTBP2 | Cheung CL. et al., *J Clin Endocrinol Metab*. 93, 4448-55 (2008) |
| ITGA11 | Kaltz N. et al., *Exp Cell Res*. 316, 2609-17 (2010) |
| TNS3 | Qian X. et al., *Cancer Cell*. 16, 246-58 (2009) |
| C12orf51 | Heo SG, Hwang JY, Uhmn S, Go MJ, Oh B, Lee JY, Park JW |
| TMEM205 | Shen DW. et al., *J Cell Physiol*. 225, 822-8 (2010) |
| HSPA9 | Chen TH et al., *Blood*. 117, 1530-9 (2011) |
| CLDN8 | McMillan M. et al., *Reprod Fertil Dev*. 26, 633-44 (2014) |
| PTPLAD1 | Courilleau D. et al., *J Biol Chem*. 275, 17344-8 (2000) |
| MAL2 | Marazuela M. et al., *J Histochem Cytochem*. 52, 243-52 (2004); Llorente A. et al., *J Cell Sci*, 117, 5343-81 (2004) |

Definitions

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term "about."

The term "antineoplastic agent" is used herein to refer to agents that have the functional property of inhibiting a development or progression of a neoplasm in a human, e.g., a prostate cancer. Inhibition of metastasis is frequently a property of antineoplastic agents.

By "agent" is meant any small compound, antibody, nucleic acid molecule, or polypeptide, or fragments thereof.

By "alteration" is meant a change (increase or decrease) in the expression levels or activity of a gene or polypeptide as detected by standard art-known methods such as those described herein. As used herein, an alteration includes at least a 1% change in expression levels, e.g., at least a 2%, 3%, 4%, 5%, 6%, 7%, 8%, 9%, 10%, 20%, 30%, 40%, 50%, 60%, 70%, 80%, 90%, or 100% change in expression levels. For example, an alteration includes at least a 5%-10% change in expression levels, preferably a 25% change, more preferably a 40% change, and most preferably a 50% or greater change in expression levels.

By "ameliorate" is meant decrease, suppress, attenuate, diminish, arrest, or stabilize the development or progression of a disease.

The term "antibody" (Ab) as used herein includes monoclonal antibodies, polyclonal antibodies, multispecific antibodies (e.g., bispecific antibodies), and antibody fragments, so long as they exhibit the desired biological activity. The term "immunoglobulin" (Ig) is used interchangeably with "antibody" herein.

By "binding to" a molecule is meant having a physicochemical affinity for that molecule. By "control" or "reference" is meant a standard of comparison. As used herein, "changed as compared to a control" sample or subject is understood as having a level that is statistically different than a sample from a normal, untreated, or control sample. Control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., an antibody, a protein) or a substance produced by a reporter construct (e.g, β-galactosidase or luciferase). Depending on the method used for detection, the amount and measurement of the change can vary. Determination of statistical significance is within the ability of those skilled in the art, e.g., the number of standard deviations from the mean that constitute a positive result.

"Cystoprostatectomy" (CP) refers to a surgical procedure wherein the bladder and prostate are simultaneously removed.

"Detect" refers to identifying the presence, absence, or amount of the agent (e.g., a nucleic acid molecule, for example deoxyribonucleic acid (DNA) or ribonucleic acid (RNA)) to be detected.

By "detectable label" is meant a composition that when linked (e.g., joined—directly or indirectly) to a molecule of interest renders the latter detectable, via, for example, spectroscopic, photochemical, biochemical, immunochemical, or chemical means. Direct labeling can occur through bonds or interactions that link the label to the molecule, and indirect labeling can occur through the use of a linker or bridging moiety which is either directly or indirectly labeled. Bridging moieties may amplify a detectable signal. For example, useful labels may include radioactive isotopes, magnetic beads, metallic beads, colloidal particles, fluorescent labeling compounds, electron-dense reagents, enzymes (for example, as commonly used in an enzyme-linked immunosorbent assay (ELISA)), biotin, digoxigenin, or haptens. When the fluorescently labeled molecule is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, p-phthaldehyde and fluorescamine. The molecule can also be detectably labeled using fluorescence emitting metals such as 152 Eu, or others of the lanthanide series. These metals can be attached to the molecule using such metal chelating groups as diethylenetriaminepentacetic acid (DTPA) or ethylenediaminetetraacetic acid (EDTA). The molecule also can be detectably labeled by coupling it to a chemiluminescent compound. The presence of the chemiluminescent-tagged molecule is then determined by detecting the presence of luminescence that arises during the course of chemical reaction. Examples of particularly useful chemiluminescent labeling compounds are luminol, isoluminol, theromatic acridinium ester, imidazole, acridinium salt and oxalate ester.

A "detection step" may use any of a variety of known methods to detect the presence of nucleic acid. The types of detection methods in which probes can be used include Western blots, Southern blots, dot or slot blots, and Northern blots.

As used herein, the term "diagnosing" refers to classifying pathology or a symptom, determining a severity of the pathology (e.g., grade or stage), monitoring pathology progression, forecasting an outcome of pathology, and/or determining prospects of recovery.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to ameliorate the symptoms of a disease, e.g., prostate cancer, relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term "expression profile" is used broadly to include a genomic expression profile. Profiles may be generated by any convenient means for determining a level of a nucleic acid sequence, e.g., quantitative hybridization of microRNA, labeled microRNA, amplified microRNA, complementary/synthetic DNA (cDNA), etc., quantitative polymerase chain reaction (PCR), and ELISA for quantitation, and allow the analysis of differential gene expression between two samples. A subject or patient tumor sample is assayed. Samples are collected by any convenient method, as known in the art. According to some embodiments, the term "expression profile" means measuring the relative abundance of the nucleic acid sequences in the measured samples.

By "FDR" is meant False Discovery Rate. When performing multiple statistical tests, for example, in comparing the signal of two groups in multiple data features, there is an increasingly high probability of obtaining false positive results, by random differences between the groups that can reach levels that would otherwise be considered statistically significant. In some cases, in order to limit the proportion of such false discoveries, statistical significance is defined only for data features in which the differences reached a p-value (by two-sided t-test) below a threshold, which is dependent on the number of tests performed and the distribution of p-values obtained in these tests.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. For example, a fragment may contain 10, 20, 30, 40, 50, 60, 70, 80, 90, or 100, 200, 300, 400, 500, 600, 700, 800, 900, or 1000 nucleotides or amino acids. However, the invention also comprises polypeptides and nucleic acid fragments, so long as they exhibit the desired biological activity of the full length polypeptides and nucleic acid, respectively. A nucleic acid fragment of almost any length is employed. For example, illustrative polynucleotide segments with total lengths of about 10,000, about 5000, about 3000, about 2,000, about 1,000, about 500, about 200, about 100, about 50 base pairs in length (including all intermediate lengths) are included in many implementations of this invention. Similarly, a polypeptide fragment of almost any length is employed. For example, illustrative polypeptide segments with total lengths of about 10,000, about 5,000, about 3,000, about 2,000, about 1,000, about 5,000, about 1,000, about 500, about 200, about 100, or about 50 amino acids in length (including all intermediate lengths) are included in many implementations of this invention.

A "Gleason score" or "Gleason grade" evaluates the prognosis of men with prostate cancer using samples from a prostate biopsy. Prostate cancer cells in biopsy samples are given a Gleason grade. The grade describes the aggressiveness of the cancer, and its likelihood to grow and spread outside the prostate. The system describes a score between 2 and 10, with 2 being the least aggressive and being 10 the most aggressive. When cancer cells are seen under the microscope, they have different patterns, depending on how quickly they're likely to grow. The pattern is given a grade from 1 to 5, based on how much the arrangement of cancer cells mimics normal prostate cells from glands. This is called the Gleason grade. If a grade is given, it will usually be 3 or higher, as grades 1 and 2 are not cancerous. To be counted, a pattern (grade) needs to occupy more than 5% of the biopsy specimen. The scoring system requires biopsy material (core biopsy or operative specimens) in order to be accurate (cytological preparations cannot be used).

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152: 507).

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation.

A "purified" or "biologically pure" gene or protein is sufficiently free of other materials such that any impurities do not materially affect the biological properties of the gene or protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

By "isolated nucleic acid" is meant a nucleic acid that is free of the genes which flank it in the naturally-occurring genome of the organism from which the nucleic acid is derived. The term covers, for example (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a synthetic cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide. Isolated nucleic acid molecules also include messenger ribonucleic acid (mRNA) molecules.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

The term "immobilized" or "attached" refers to a probe (e.g., nucleic acid or protein) and a solid support in which the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule to the support and the non-covalent binding of a biotinylated probe to the molecule Immobilization may also involve a combination of covalent and non-covalent interactions.

"Laser capture microdissection" or "LCM" is a method for isolating specific cells from microscopic regions of tissues, cells or organisms. LCM is a method to procure subpopulations of tissue cells under direct microscopic visualization. LCM technology can harvest the cells of interest directly or it can isolate specific cells by cutting away unwanted cells to give histologically pure enriched cell populations.

By "marker" is meant any protein or polynucleotide having an alteration in expression level or activity that is associated with a disease or disorder, e.g., prostate cancer.

By "modulate" is meant alter (increase or decrease). Such alterations are detected by standard art-known methods such as those described herein.

The term, "normal amount" refers to a normal amount of a complex in an individual known not to be diagnosed with prostate cancer. The amount of the molecule can be measured in a test sample and compared to the "normal control level," utilizing techniques such as reference limits, discrimination limits, or risk defining thresholds to define cutoff points and abnormal values (e.g., for prostate cancer). The "normal control level" means the level of one or more proteins (or nucleic acids) or combined protein indices (or combined nucleic acid indices) typically found in a subject known not to be suffering from prostate cancer. Such normal control levels and cutoff points may vary based on whether a molecule is used alone or in a formula combining other proteins into an index. Alternatively, the normal control level can be a database of protein patterns from previously tested subjects who did not convert to prostate cancer over a clinically relevant time horizon.

The level that is determined may be the same as a control level or a cut off level or a threshold level, or may be increased or decreased relative to a control level or a cut off level or a threshold level. In some aspects, the control subject is a matched control of the same species, gender, ethnicity, age group, smoking status, body mass index (BMI), current therapeutic regimen status, medical history, or a combination thereof, but differs from the subject being diagnosed in that the control does not suffer from the disease in question or is not at risk for the disease.

Relative to a control level, the level that is determined may be an increased level. As used herein, the term "increased" with respect to level (e.g., expression level, biological activity level, etc.) refers to any % increase above a control level. The increased level may be at least or about a 1% increase, at least or about a 5% increase, at least or about a 10% increase, at least or about a 15% increase, at least or about a 20% increase, at least or about a 25% increase, at least or about a 30% increase, at least or about a 35% increase, at least or about a 40% increase, at least or about a 45% increase, at least or about a 50% increase, at least or about a 55% increase, at least or about a 60% increase, at least or about a 65% increase, at least or about a 70% increase, at least or about a 75% increase, at least or about a 80% increase, at least or about a 85% increase, at least or about a 90% increase, or at least or about a 95% increase, relative to a control level.

Relative to a control level, the level that is determined may be a decreased level. As used herein, the term "decreased" with respect to level (e.g., expression level, biological activity level, etc.) refers to any % decrease below a control level. The decreased level may be at least or about a 1% decrease, at least or about a 5% decrease, at least or about a 10% decrease, at least or about a 15% decrease, at least or about a 20% decrease, at least or about a 25% decrease, at least or about a 30% decrease, at least or about a 35% decrease, at least or about a 40% decrease, at least or about a 45% decrease, at least or about a 50% decrease, at least or about a 55% decrease, at least or about a 60% decrease, at least or about a 65% decrease, at least or about a 70% decrease, at least or about a 75% decrease, at least or about a 80% decrease, at least or about a 85% decrease, at least or about a 90% decrease, or at least or about a 95% decrease, relative to a control level.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule.

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "neoplasia" is meant a disease or disorder characterized by excess proliferation or reduced apoptosis. Illustrative neoplasms for which the invention can be used include, but are not limited to pancreatic cancer, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

As used herein, "obtaining" as in "obtaining an agent" includes synthesizing, purchasing, or otherwise acquiring the agent.

By "Ontology Enrichment Analysis," is meant as a technique for interpreting sets of genes making use of the Gene Ontology (GO) system of classification, in which genes are assigned to a set of predefined bins depending on their functional characteristics. Researchers performing high-throughput experiments that yield sets of genes often want to retrieve a functional profile of that gene set, in order to better understand the underlying biological processes. This can be done by comparing the input gene set each of the bins (terms) in the GO, and a statistical test can be performed for each bin to see if it is enriched for the input genes. The output of the analysis is typically a ranked list of GO terms, each associated with a p-value.

Unless specifically stated or obvious from context, as used herein, the term "or" is understood to be inclusive. Unless specifically stated or obvious from context, as used herein, the terms "a", "an", and "the" are understood to be singular or plural.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

By "protein" or "polypeptide" or "peptide" is meant any chain of more than two natural or unnatural amino acids, regardless of post-translational modification (e.g., glycosylation or phosphorylation), constituting all or part of a naturally-occurring or non-naturally occurring polypeptide or peptide, as is described herein.

By "PIN" is meant a prostatic intraepithelial neoplasia. PIN is a condition in which some prostate cells have begun to look and behave abnormally.

The terms "preventing" and "prevention" refer to the administration of an agent or composition to a clinically asymptomatic individual who is at risk of developing, susceptible, or predisposed to a particular adverse condition, disorder, or disease, and thus relates to the prevention of the occurrence of symptoms and/or their underlying cause.

The term "prognosis," "staging," and "determination of aggressiveness" are defined herein as the prediction of the degree of severity of the neoplasia, e.g., prostate cancer, and of its evolution as well as the prospect of recovery as anticipated from usual course of the disease. Once the aggressiveness (e.g. the Gleason score) has been determined, appropriate methods of treatments are chosen.

"Radical prostatectomy" (RP) refers to an operation to remove (completely or partially) the prostate gland and some of the tissue surrounding it to treat prostate cancer or benign prostatic hyperplasia.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "reduces" is meant a negative alteration of at least 10%, 25%, 50%, 75%, or 100%.

A "reference sequence" is a defined sequence used as a basis for sequence comparison or a gene expression comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 40 nucleotides, preferably at least about 60 nucleotides, more preferably at least about 75 nucleotides, and even more preferably about 100 nucleotides or about 300 or about 500 nucleotides or any integer thereabout or there between.

The term "sample" as used herein refers to a biological sample obtained for the purpose of evaluation in vitro. Exemplary tissue samples for the methods described herein include tissue samples from prostate tumors or the surrounding microenvironment (i.e., the stroma). With regard to the methods disclosed herein, the sample or patient sample preferably may comprise any body fluid or tissue. In some embodiments, the bodily fluid includes, but is not limited to, blood, plasma, serum, lymph, breast milk, saliva, mucous, semen, vaginal secretions, cellular extracts, inflammatory fluids, cerebrospinal fluid, feces, vitreous humor, or urine obtained from the subject. In some aspects, the sample is a composite panel of at least two of a blood sample, a plasma sample, a serum sample, and a urine sample. In exemplary aspects, the sample comprises blood or a fraction thereof (e.g., plasma, serum, fraction obtained via leukopheresis). Preferred samples are whole blood, serum, plasma, or urine. A sample can also be a partially purified fraction of a tissue or bodily fluid.

A reference sample can be a "normal" sample, from a donor not having the disease or condition fluid, or from a normal tissue in a subject having the disease or condition. A reference sample can also be from an untreated donor or cell culture not treated with an active agent (e.g., no treatment or administration of vehicle only). A reference sample can also be taken at a "zero time point" prior to contacting the cell or subject with the agent or therapeutic intervention to be tested or at the start of a prospective study.

A "solid support" describes a strip, a polymer, a bead, or a nanoparticle. The strip may be a nucleic acid-probe (or protein) coated porous or non-porous solid support strip comprising linking a nucleic acid probe to a carrier to prepare a conjugate and immobilizing the conjugate on a porous solid support. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to a binding agent (e.g., an antibody or nucleic acid molecule). Thus, the support configuration may be spherical, as in a bead, or cylindrical, as in the inside surface of a test tube, or the external surface of a rod. Alternatively, the surface may be flat such as a sheet, or test strip, etc. For example, the supports include polystyrene beads. Those skilled in the art will know many other suitable carriers for binding antibody or antigen, or will be able to ascertain the same by use of routine experimentation. In other aspects, the solid support comprises a polymer, to which an agent is chemically bound, immobilized, dispersed, or associated. A polymer support may be a network of polymers, and may be prepared in bead form (e.g., by suspension polymerization). The location of active sites introduced into a polymer support depends on the type of polymer support. For example, in a swollen-gel-bead polymer support the active sites are distributed uniformly throughout the beads, whereas in a macroporous-bead polymer support they are predominantly on the internal surfaces of the macropores. The solid support, e.g., a device contains a binding agent alone or together with a binding agent for at least one, two, three or more other molecules.

By "specifically binds" is meant a compound or antibody that recognizes and binds a polypeptide of the invention, but which does not substantially recognize and bind other molecules in a sample, for example, a biological sample, which naturally includes a polypeptide of the invention.

A "specific binding agent" describes agents having greater than 10-fold, preferably greater than 100-fold, and most preferably, greater than 1000-fold affinity for the target molecule as compared to another molecule. As the skilled artisan will appreciate the term specific is used to indicate that other biomolecules present in the sample do not significantly bind to the binding agent specific for the target molecule. Preferably, the level of binding to a biomolecule other than the target molecule results in a binding affinity which is at most only 10% or less, only 5% or less only 2% or less or only 1% or less of the affinity to the target molecule, respectively. A preferred specific binding agent will fulfill both the above minimum criteria for affinity as well as for specificity. For example, an antibody has a binding affinity in the low micromolar ($10^{-6}$), nanomolar ($10^{-7}$-$10^{-9}$), with high affinity antibodies in the low nanomolar ($10^{-9}$) or pico molar ($10^{-12}$) range for its specific target molecule.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

The term "subject" as used herein includes all members of the animal kingdom prone to suffering from the indicated disorder. In some aspects, the subject is a mammal, and in some aspects, the subject is a human. The methods are also applicable to companion animals such as dogs and cats as well as livestock such as cows, horses, sheep, goats, pigs, and other domesticated and wild animals.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition, or syndrome. Methods for identification of subjects suffering from or suspected of suffering from conditions associated with cancer (e.g., prostate cancer) is within the ability of those in the art. Subjects suffering from, and suspected of suffering from, a specific disease, condition, or syndrome are not necessarily two distinct groups.

As used herein, "susceptible to" or "prone to" or "predisposed to" or "at risk of developing" a specific disease or condition refers to an individual who based on genetic, environmental, health, and/or other risk factors is more likely to develop a disease or condition than the general population. An increase in likelihood of developing a disease may be an increase of about 10%, 20%, 50%, 100%, 150%, 200%, or more.

"Primer set" means a set of oligonucleotides that may be used, for example, for PCR. A primer set would consist of at least 2, 4, 6, 8, 10, 12, 14, 16, 18, 20, 30, 40, 50, 60, 80, 100, 200, 250, 300, 400, 500, 600, or more primers.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. It will be appreciated that, although not precluded, treating a disorder or condition does not require that the disorder, condition or symptoms associated therewith be completely eliminated.

In some cases, a composition of the invention is administered orally or systemically. Other modes of administration include rectal, topical, intraocular, buccal, intravaginal, intracisternal, intracerebroventricular, intratracheal, nasal, transdermal, within/on implants, or parenteral routes. The term "parenteral" includes subcutaneous, intrathecal, intravenous, intramuscular, intraperitoneal, or infusion. Intravenous or intramuscular routes are not particularly suitable for long-term therapy and prophylaxis. They could, however, be preferred in emergency situations. Compositions comprising a composition of the invention can be added to a physiological fluid, such as blood. Oral administration can be preferred for prophylactic treatment because of the convenience to the patient as well as the dosing schedule. Parenteral modalities (subcutaneous or intravenous) may be preferable for more acute illness, or for therapy in patients that are unable to tolerate enteral administration due to gastrointestinal intolerance, ileus, or other concomitants of critical illness. Inhaled therapy may be most appropriate for pulmonary vascular diseases (e.g., pulmonary hypertension).

Pharmaceutical compositions may be assembled into kits or pharmaceutical systems for use in arresting cell cycle in rapidly dividing cells, e.g., cancer cells. Kits or pharmaceutical systems according to this aspect of the invention comprise a carrier means, such as a box, carton, tube, having in close confinement therein one or more container means, such as vials, tubes, ampoules, bottles, syringes, or bags. The kits or pharmaceutical systems of the invention may also comprise associated instructions for using the kit.

Any compositions or methods provided herein can be combined with one or more of any of the other compositions and methods provided herein.

Any compositions or methods provided herein can be combined with one or more of any of the other compositions and methods provided herein.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 4A is a heatmap showing the 29-gene signature assessed in a breast metastasis study.

FIG. 4B is a PCA (principal component analysis) plot showing the 29-gene signature assessed in a breast metastasis study.

FIG. 4C is an ssGSEA (single sample gene set enrichment analysis) score of the 29-gene signature assessed in a breast metastasis study.

FIG. 4D is a heatmap showing the 29-gene signature assessed in a prostate bone metastasis study.

FIG. 5A is a pie chart showing the top 10 genes that were over-represented in statistically significant GAP-SUB crosstalk interactions in the stromal compartment that differentiates Gleason 6 from Gleason 8.

FIG. 5B is a pie chart showing the top 10 genes that were over-represented in statistically significant GAP-SUB crosstalk interactions in the epithelial compartment that differentiates Gleason 6 from Gleason 8.

FIG. 7C is a chart showing the number of differentially expressed genes for each of the comparisons within the epithelium and within the stroma.

FIG. 9D is a chart showing the comparisons across the compartments, bracketed numbers indicated up- or down-regulation of the gene.

FIG. 13A is an IHC image showing of MAL2 (T-cell differentiation protein 2) expression in normal tissue ([sT8-T8]-[sT6-T6]). Negative staining was observed in the epithelium was observed.

FIG. 13B is an IHC image showing of MAL2 expression in a tumor. Negative in the epithelium stroma was observed.

FIG. 13C is a graph showing the ROI versus MAL2 (8148040) expression in a Gleason 3+3 and Gleason 4+4 patient.

FIG. 14A is an IHC image showing of CLDN8 (claudin 8) expression in normal tissue ([sT8-T8]-[sT6-T6]). Strong cytoplasmic/membranous staining was observed in epithelium stroma.

FIG. 14B is an IHC image showing of CLDN8 expression in a tumor. Moderate cytoplasmic/membranous staining was observed in epithelium stroma.

FIG. 14C is a graph showing the ROI versus CLDN8 (8069795) expression in a Gleason 3+3 and Gleason 4+4 patient.

FIG. 17A is an image IHC showing of LUM (lumacin) expression in normal tissue ([sT8-sT6]). Moderate cytoplasmic/membranous staining was observed in epithelium stroma.

FIG. 17B is an IHC image showing of LUM expression in a tumor. Negative cytoplasmic/membranous staining was observed in epithelium stroma.

FIG. 17C is a graph showing the ROI versus LUM (7965403) expression in a Gleason 3+3 and Gleason 4+4 patient.

FIG. 19A is an IHC image showing of SFRP4 (secreted frizzled related protein 4) expression in normal tissue ([sT8-sT6]). Negative staining was observed in epithelium stroma.

FIG. 19B is an IHC image showing of SFRP4 expression in a tumor. Negative staining was observed in epithelium stroma.

FIG. 19C is a graph showing the ROI versus SFRP4 (8139087) expression in a Gleason 3+3 and Gleason 4+4 patient.

FIG. 21A is an IHC image showing of C1QC (complement component 1, q subcomponent, C chain) expression in normal tissue ([sT8-sT6]). Negative staining was observed in epithelium stroma.

FIG. 21B is an IHC image showing of C1QC expression in a tumor. Negative staining was observed in epithelium stroma.

FIG. 21C is a graph showing the ROI versus C1QC (7898799) expression in a Gleason 3+3 and Gleason 4+4 patient.

FIG. 24A is an IHC image showing of FBLN5 (fibulin 5) expression in normal tissue ([sT8-sT6]). Negative staining was observed in epithelium stroma.

FIG. 24B is an IHC image showing of FBLN5 expression in a tumor. Negative staining was observed in epithelium stroma.

FIG. 24C is a graph showing the ROI versus FBLN5 (7980908) expression in a Gleason 3+3 and Gleason 4+4 patient.

FIG. 25A is an IHC image showing of C1QB (complement component 1, q subcomponent, B chain) expression in normal tissue ([sT8-sT6]). Negative staining was observed in epithelium stroma.

FIG. 25B is an IHC image showing of C1QB expression in a tumor. Negative staining was observed in epithelium stroma.

FIG. 25C is a graph showing the ROI versus C1QB (7898805) expression in a Gleason 3+3 and Gleason 4+4 patient.

FIG. 31A is an IHC image showing of SERPING1 (serpin peptidase inhibitor, Glade G (C1 inhibitor), member 1) expression in normal tissue ([sT8-T8]-[sT6-T6]). Weak staining was observed in epithelium stroma.

FIG. 31B is an IHC image showing of SERPING1 expression in a tumor. Moderate staining was observed in epithelium stroma.

FIG. 31C is a graph showing the ROI versus SERPING1 (7940028) expression in a Gleason 3+3 and Gleason 4+4 patient.

FIG. 33A is an IHC image showing of LTBP2 (latent transforming growth factor beta binding protein 2) expression in normal tissue ([sT8-T8]-[sT6-T6]). Moderate staining was observed in epithelium stroma.

FIG. 33B is an IHC image showing of LTBP2 expression in a tumor. Moderate staining was observed in epithelium stroma.

FIG. 33C is a graph showing the ROI versus LTBP2 (7980152) expression in a Gleason 3+3 and Gleason 4+4 patient.

FIG. 34A is an IHC image showing of ITGA11 (integrin, alpha 11) expression in normal tissue ([sT8-T8]-[sT6-T6]). Weak staining was observed in epithelium stroma.

FIG. 34B is an IHC image showing of ITGA11 expression in a tumor. Weak staining was observed in epithelium stroma.

FIG. 34C is a graph showing the ROI versus ITGA11 (7989985) expression in a Gleason 3+3 and Gleason 4+4 patient.

FIG. 38C is a chart showing the 2 separate enrichment analyses representing genes upregulated in the epithelium or stromal compartment, the top 10 statistically significant pathways, process networks and GO processes for each data set were tabulated side-by-side.

FIG. 39C is a heatmap of each epithelial ROI relative to its associated adjacent stromal ROI, namely P-sP and T-sT (D). Upregulated genes are shown in red and downregulated genes in blue, where expression levels are plotted as Log (Fold Change).

FIG. 39D is a heatmap of each epithelial ROI relative to its associated adjacent stromal ROI, namely T-sT. Upregulated genes are shown in red and downregulated genes in blue, where expression levels are plotted as Log(Fold Change).

FIG. 39E is a Venn diagram showing gene associations from the 3 epithelial-stroma comparisons between the three morphologically distinction regions.

FIG. 39F is a chart showing the number of differentially expressed gene for each comparison indicating which are upregulated or downregulated.

FIG. 40 is a schematic showing the laser capture microdissection complete workflow.

FIG. 41 are plots showing ERG target genes, CACNA1D, PLA1A, TDRD1 and HLA-DMB, showing the same trending profile as ERG within the epithelium compartment, namely increasing expression from benign through PIN with the highest expression observed in the tumor samples.

FIG. 42 are representative interaction plots showing Gleason 4 Tumor (no change Gleason 3), Gleason 4 and 3 Tumor divergence, Gleason 4 and 3 Stroma convergence, Gleason 4 Stroma (no change in Gleason 3), where genes highlighted in blue and red are epithelial and purple and green are stromal.

Figure 43A:
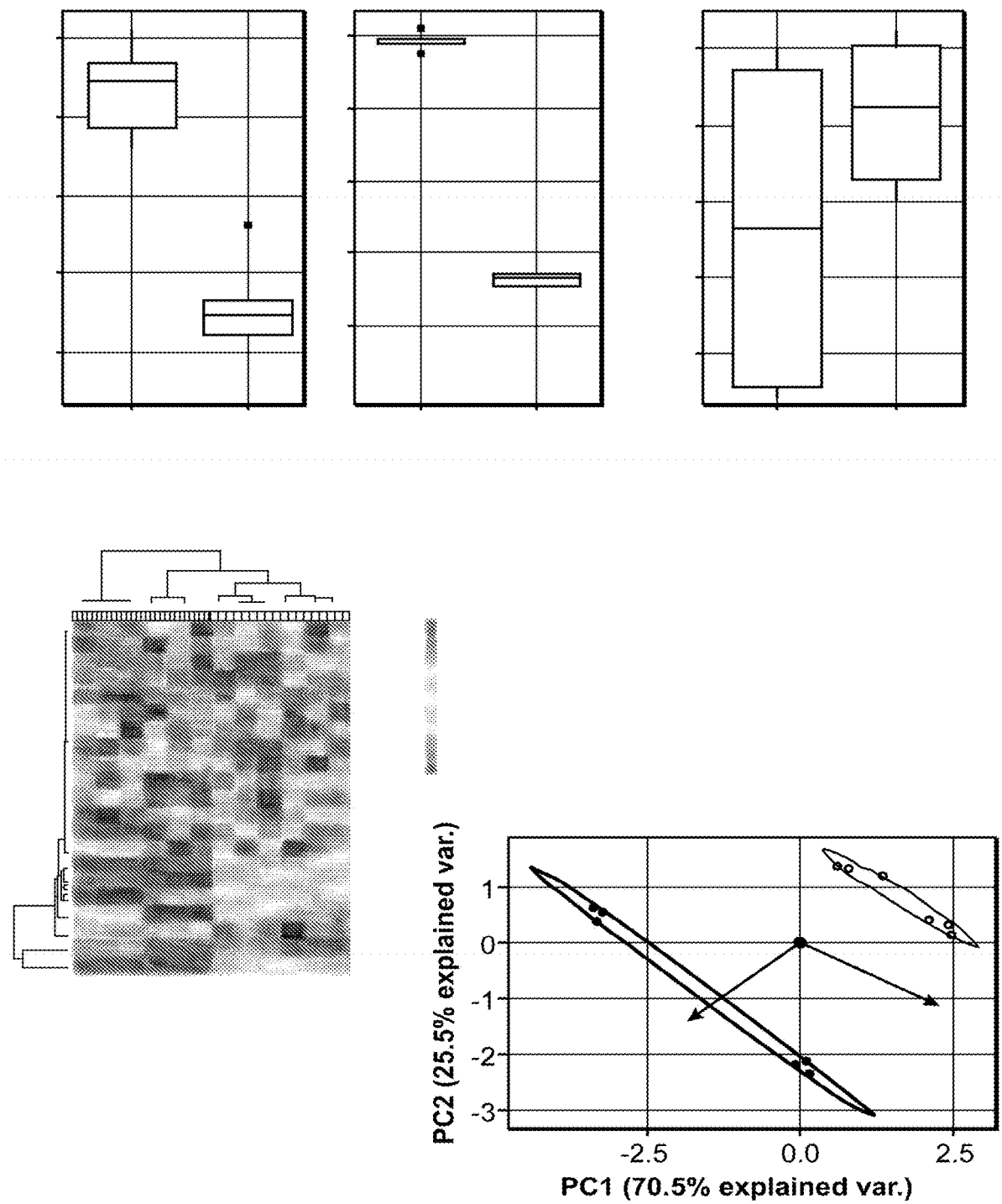

FIG. 43A describes the Xiao study comparing osteosarcoma primary cells to metastatic cells, where our 29-gene signature looks like the osteosarcoma cell lines.

Figures 1, 43B:
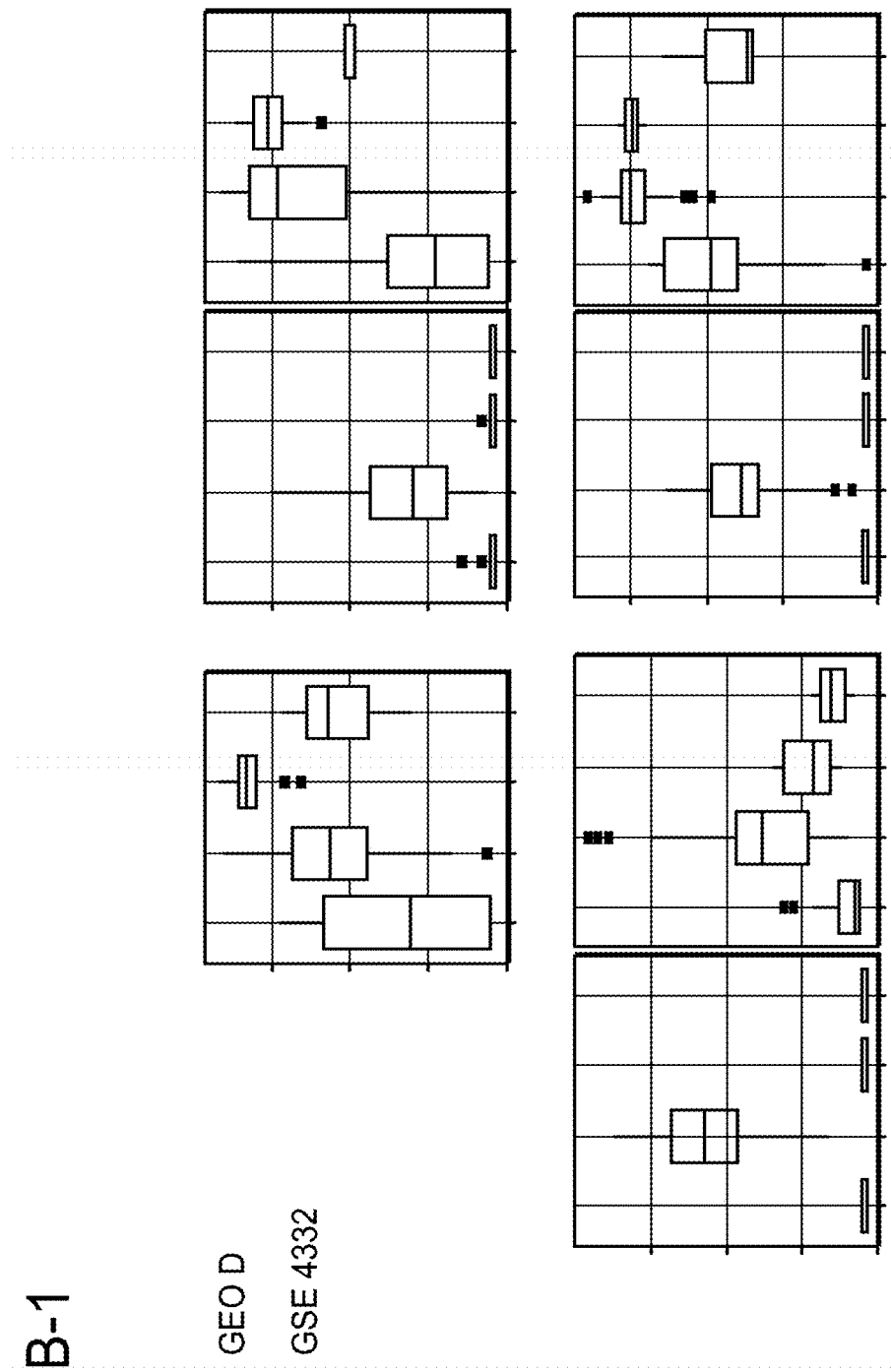
FIG. 1A is an image of hierarchical clustering represented by a heatmap, showing the epithelium comparison between cystoprostatectomy and benign radical prostatectomy [HB-B].
Figure 43B:
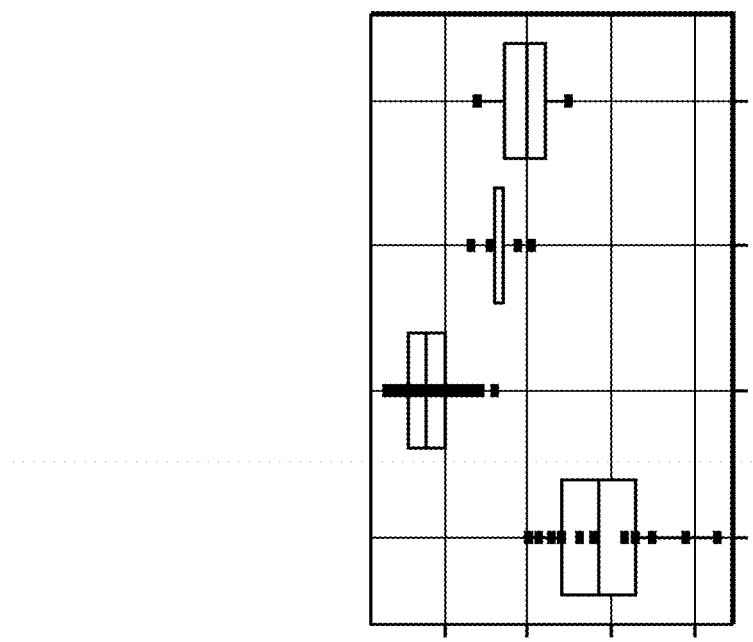
Figure 2:
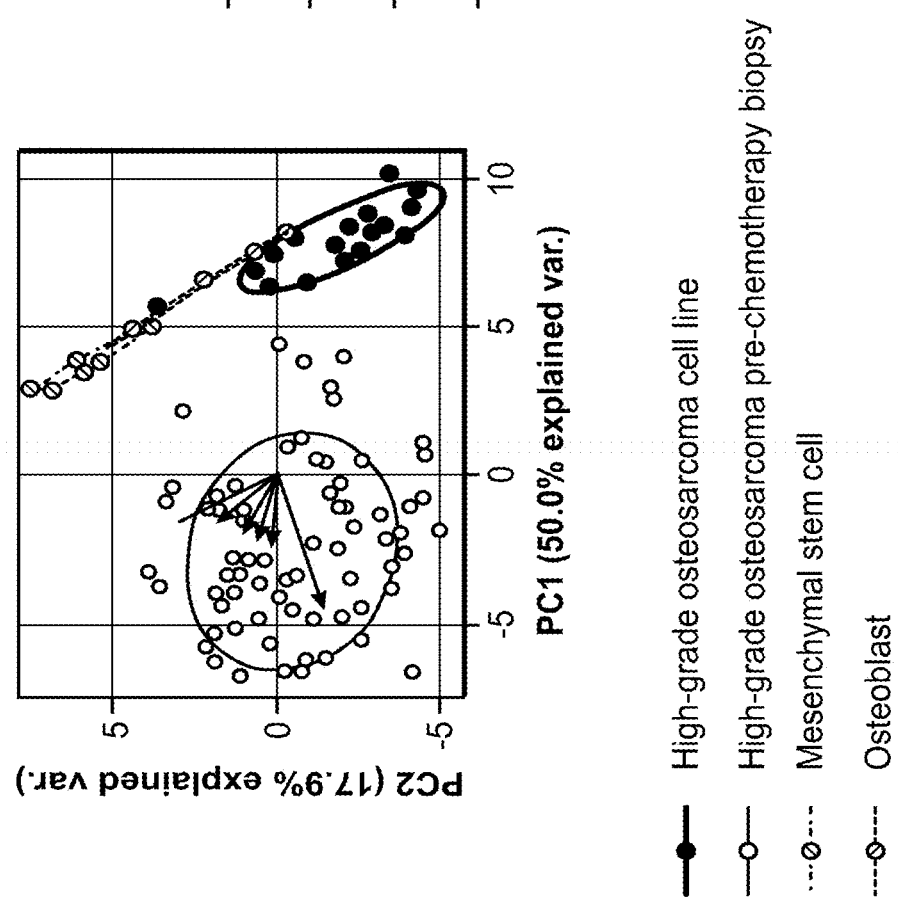

FIG. 43B describes the Cleton-Janson study comparing pre-chemotherapy osteosarcoma biopsies to a high grade osteosarcoma cell line, mesenchymal stem cells and osteoblasts, where out 29-gene signature is overexpressed in the latter three sample sets relative to the pre-chemotherapy biopsies.

Figure 44A:
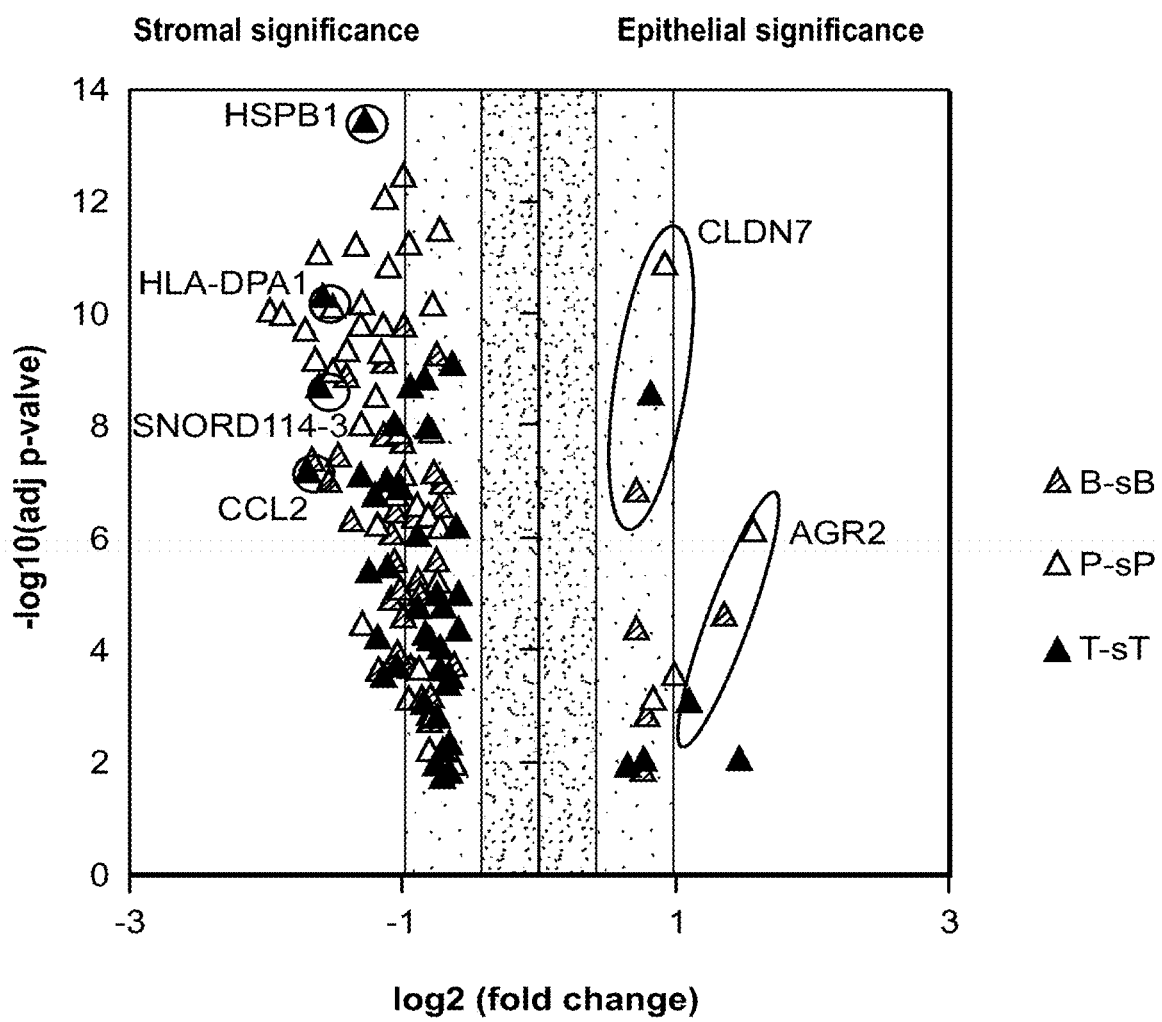

FIG. 44A is a volcano plot for common cancer genes differentially expressed between epithelium (B, P, T) and stroma (sB, sP, sT), exclusive of genes differentially expressed between healthy epithelium and stroma showing FDR –[$\log_{10}$] versus fold change [$\log_2$]. The gray shaded area represents all differentially expressed genes that were found in the HB-HsB.

Figure 44B:
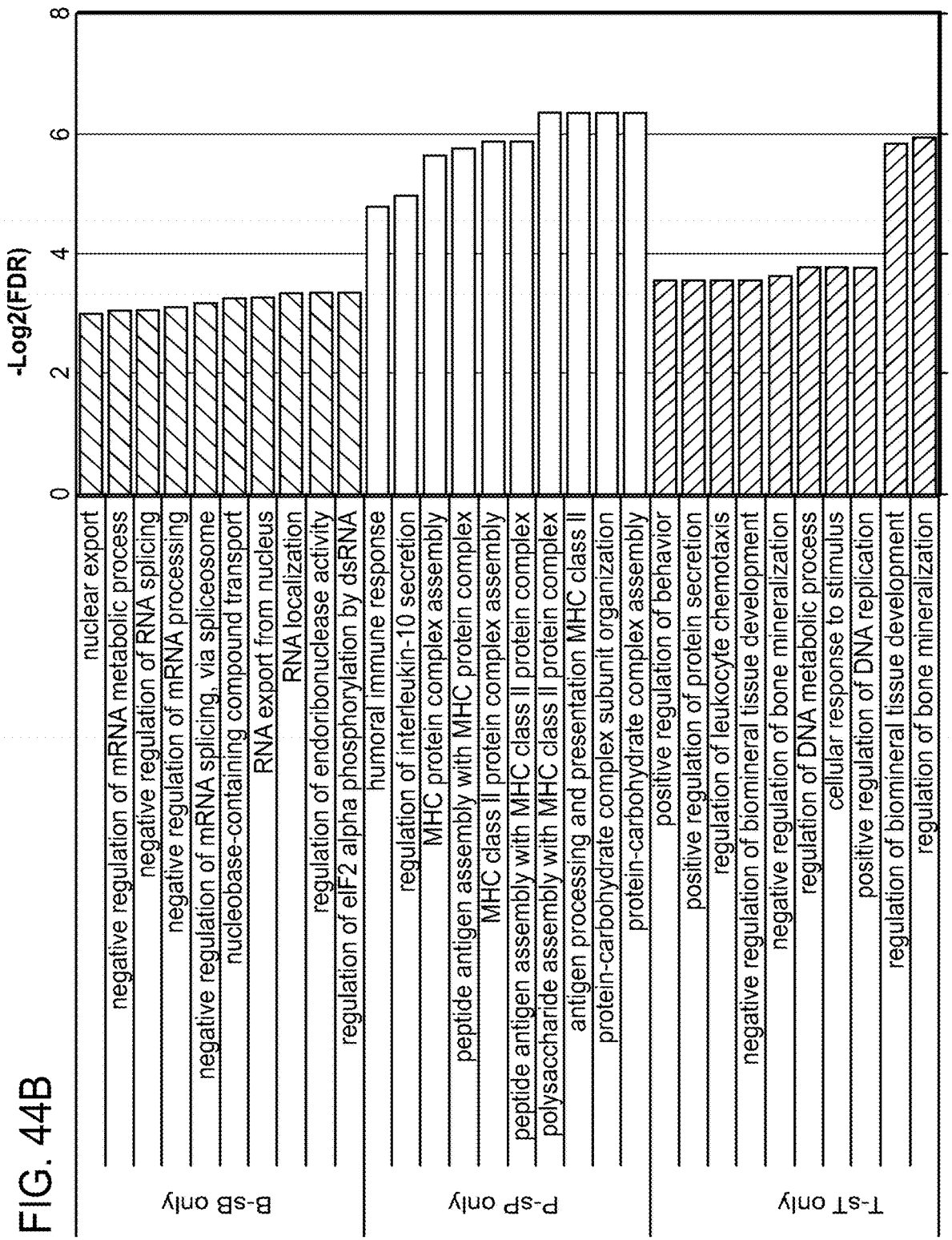

FIG. 44B is a chart showing GeneGo Metacore analysis to generate statistically significant GO cellular processes for the differentially expressed genes that were found exclusively for each of the individual comparisons, B-sB, P-sP and T-sT, respectively. Top 10 GO processes for each comparison were plotted as –[$\log_{10}$] FDR.

Figure 44C:
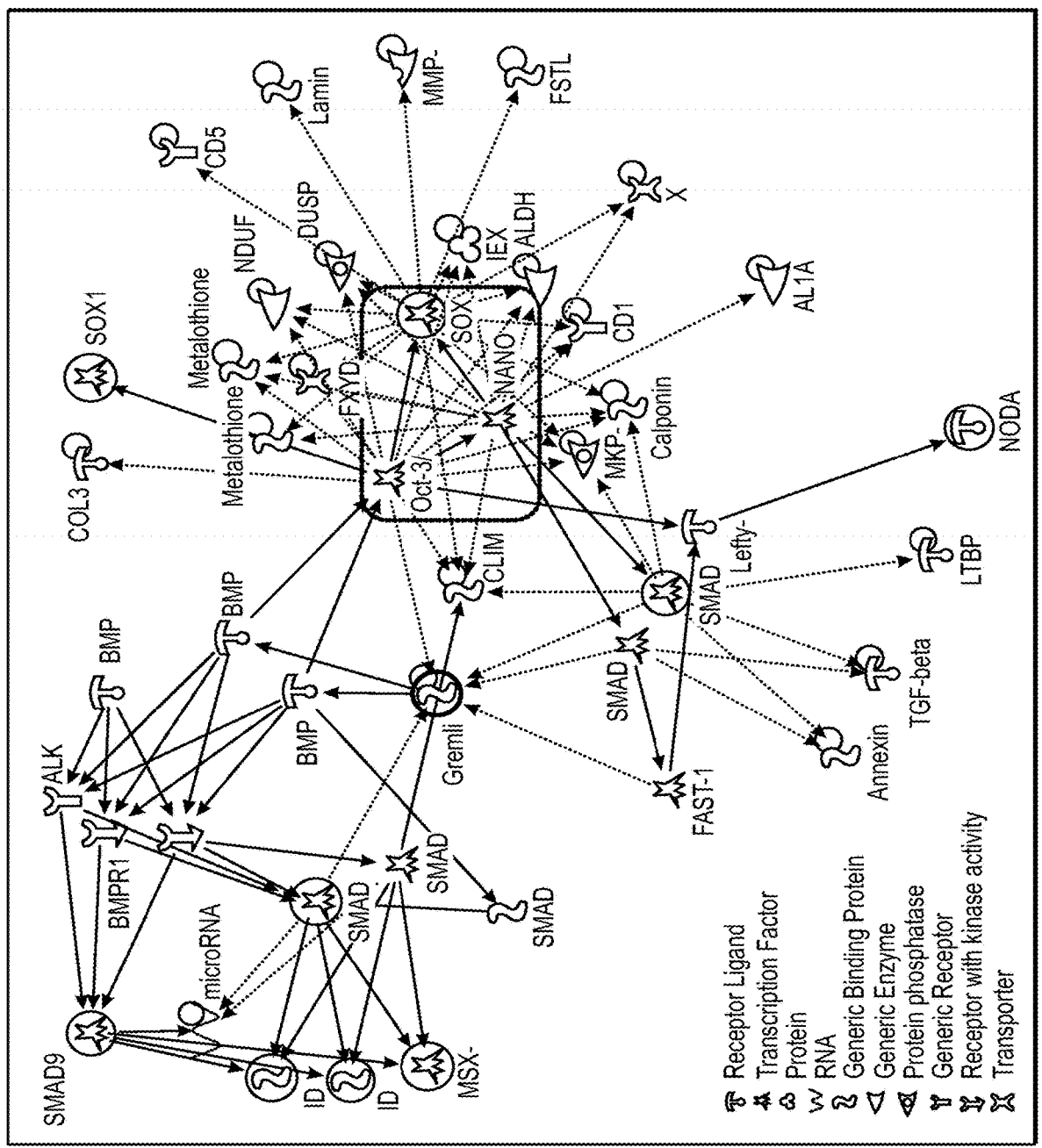

FIG. 44C is a chart showing that GeneGo Metacore was also used to generate a biological network using canonical pathways of the most direct connections amongst the differentially expressed genes that are upregulated in the stroma of the T-sT comparison.

Figure 45:
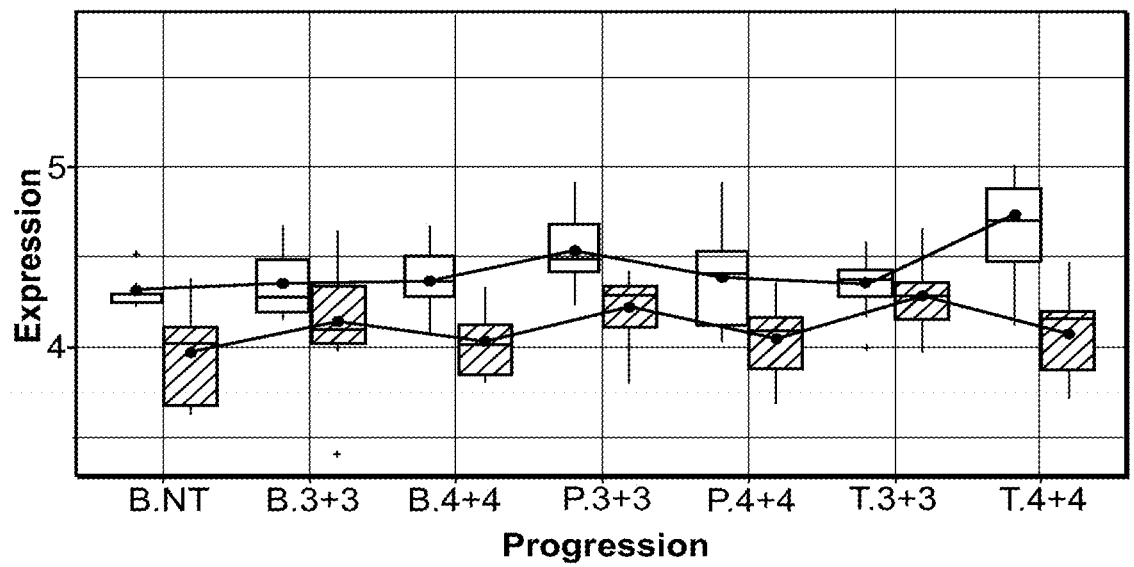

FIG. 45 is a plot showing trends across benign to PIN to tumor samples for the C12or51 gene.

Figure 46:
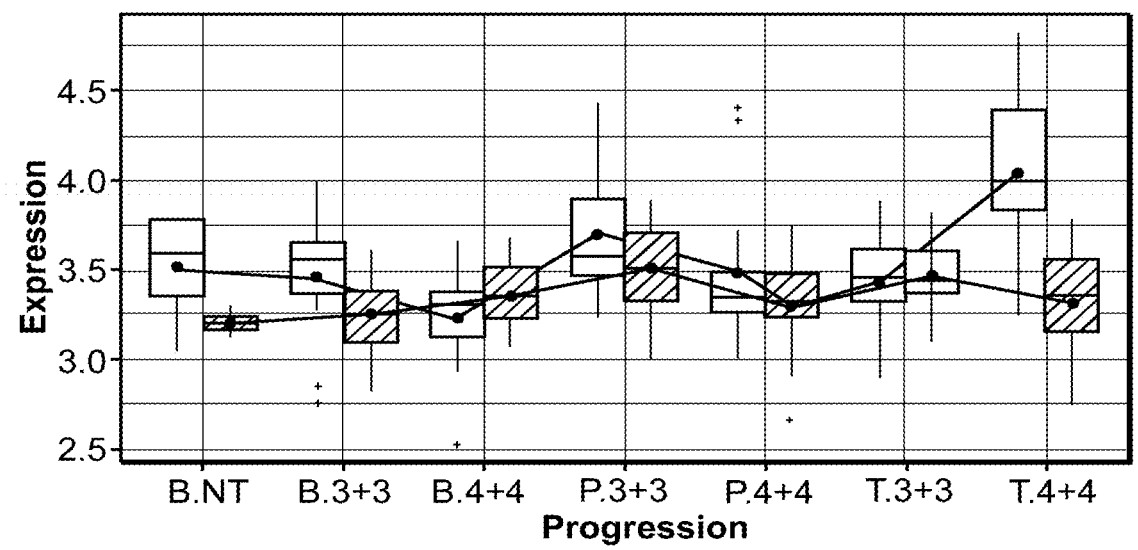

FIG. 46 is a plot showing trends across benign to PIN to tumor samples for the PTPLAD1 gene.

Figure 47:
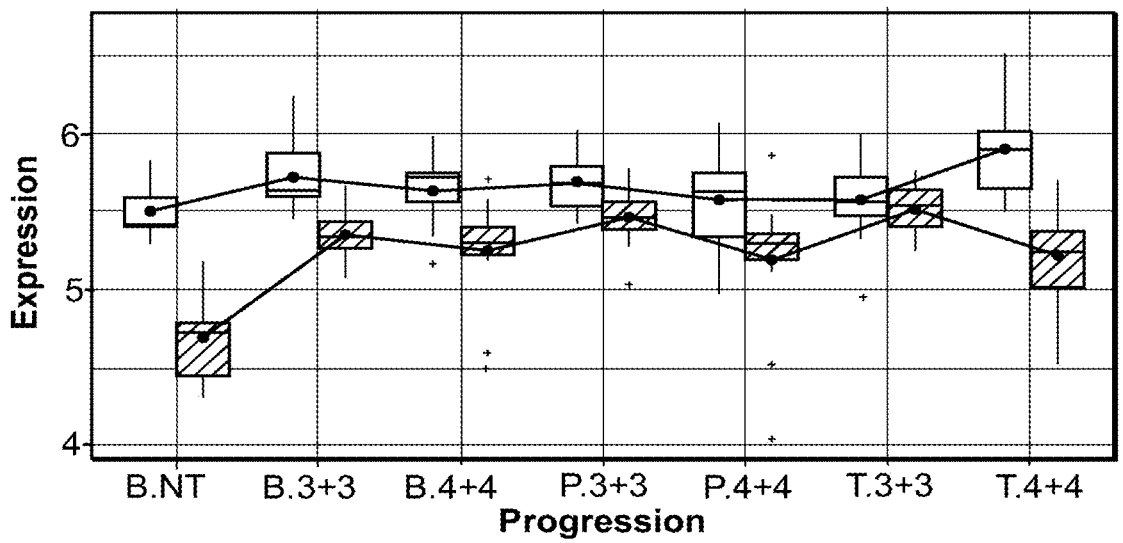

FIG. 47 is a plot showing trends across benign to PIN to tumor samples for the TMEM205 gene.

Figure 48:
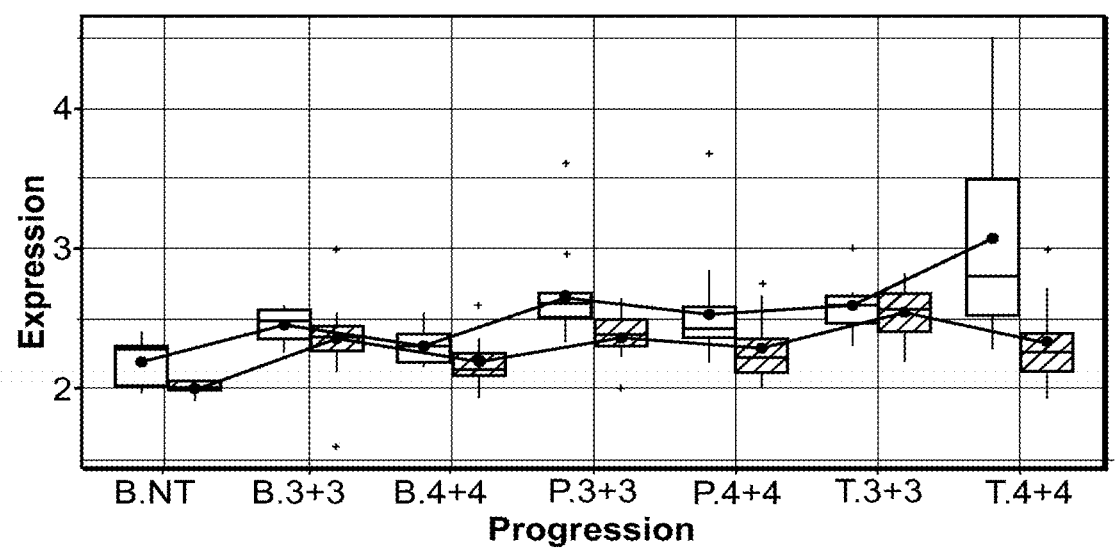

FIG. 48 is a plot showing trends across benign to PIN to tumor samples for the CLDN8 gene.

FIG. 49 is a plot showing trends across benign to PIN to tumor samples for the ALCAM gene.

FIG. 50 is a plot showing trends across benign to PIN to tumor samples for the HSPA9 gene.

Figure 51:
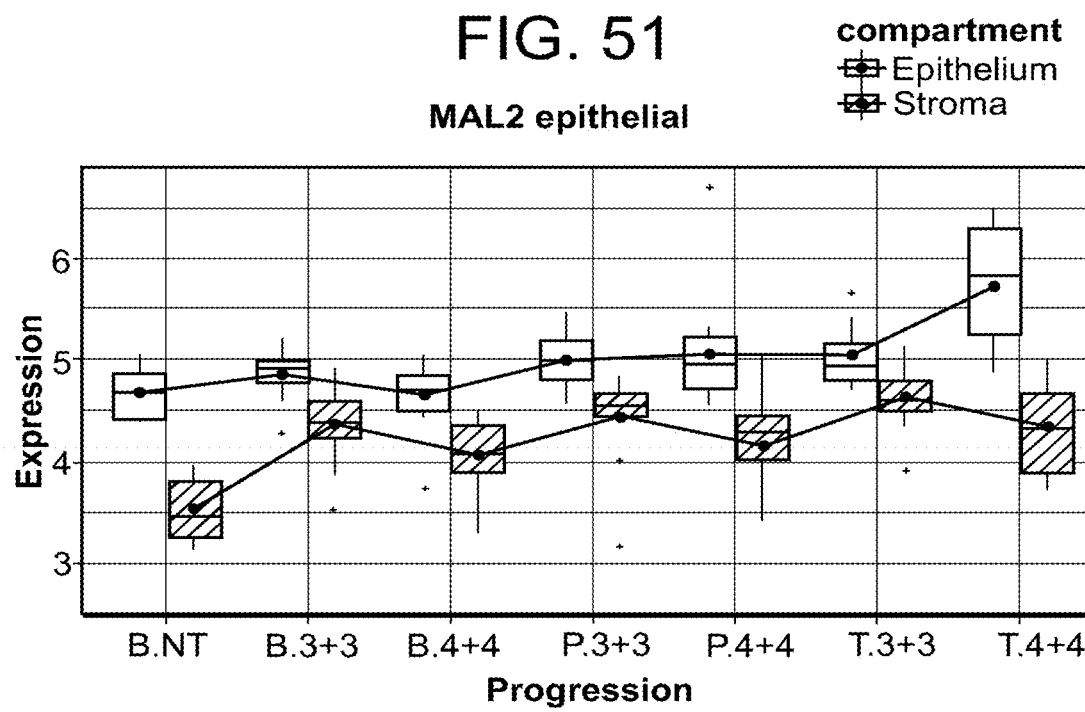

FIG. 51 is a plot showing trends across benign to PIN to tumor samples for the MAL2 gene.

Figure 52:
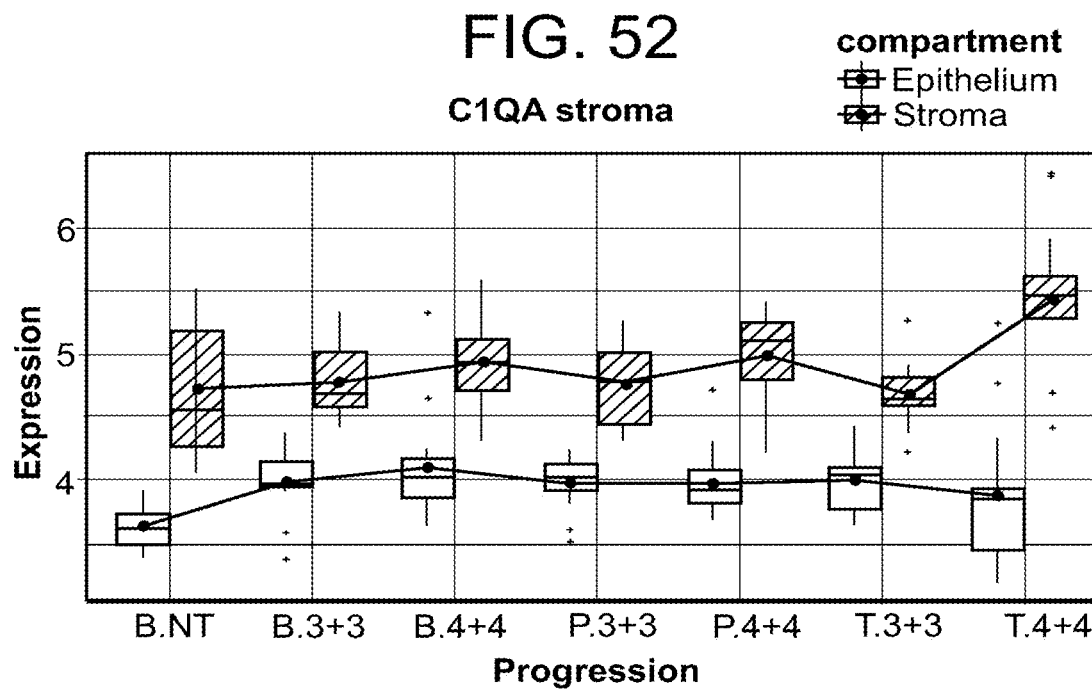

FIG. 52 is a plot showing trends across benign to PIN to tumor samples for the C1QA gene.

Figure 53:
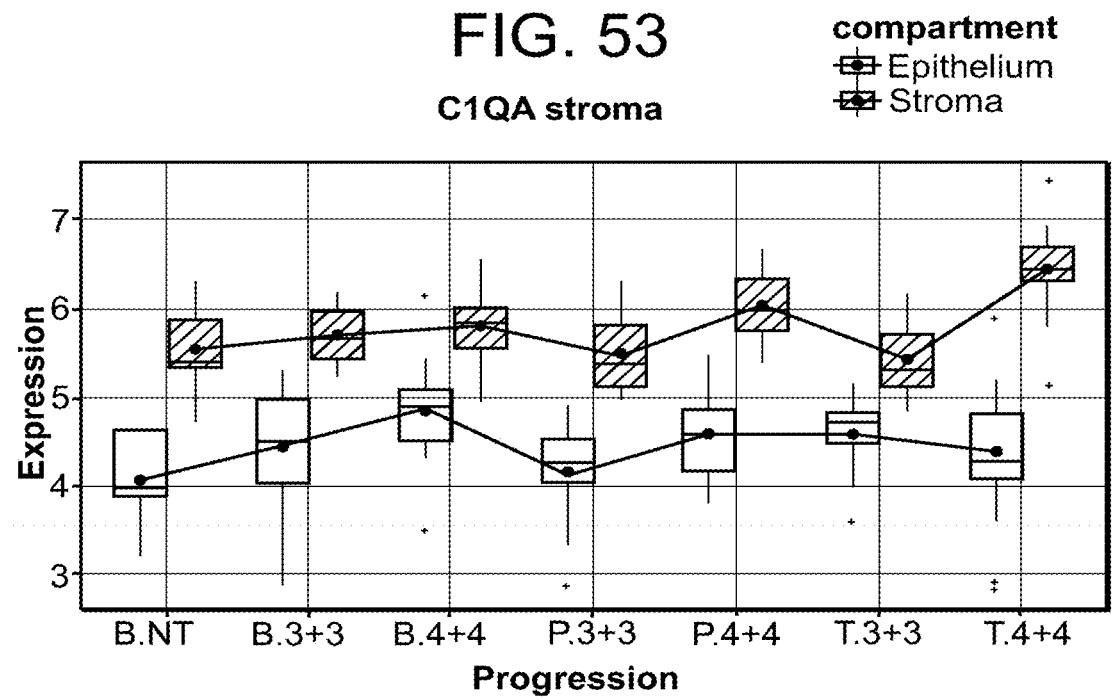

FIG. 53 is a plot showing trends across benign to PIN to tumor samples for the C1QC gene.

Figure 54:
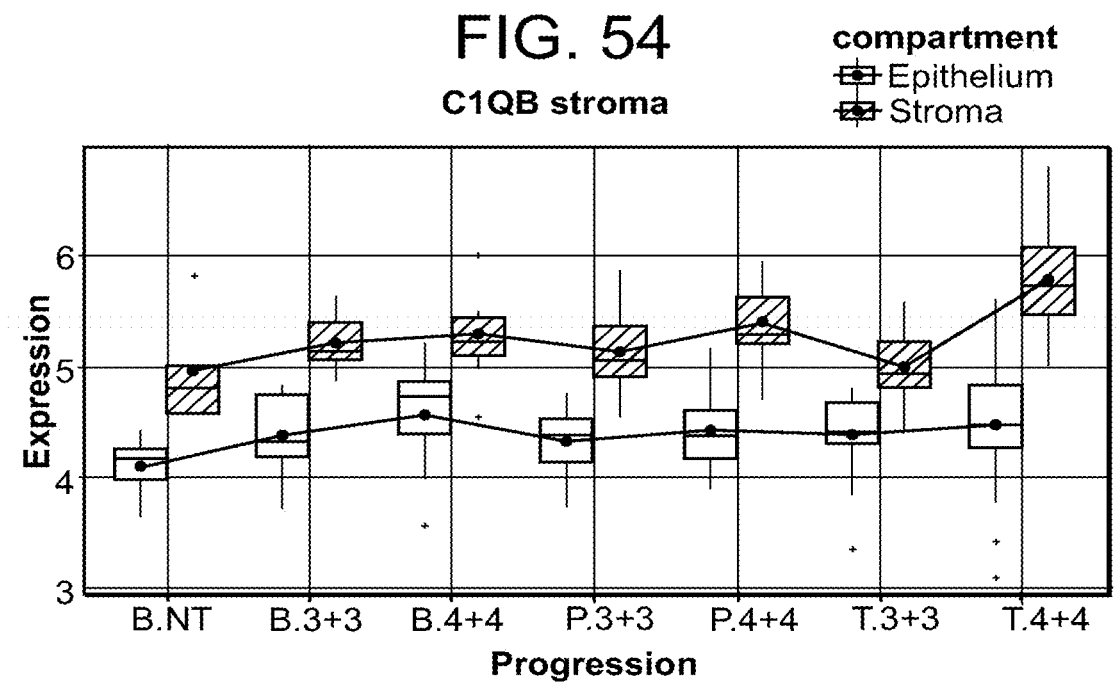

FIG. 54 is a plot showing trends across benign to PIN to tumor samples for the C1QB gene.

Figure 55:
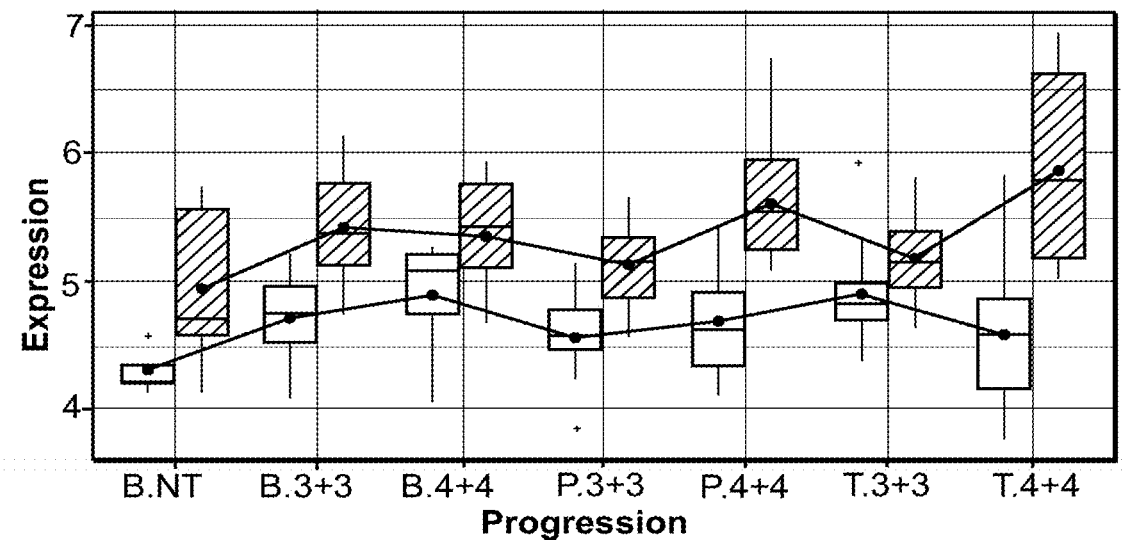

FIG. 55 is a plot showing trends across benign to PIN to tumor samples for the CD52 gene.

Figure 56:
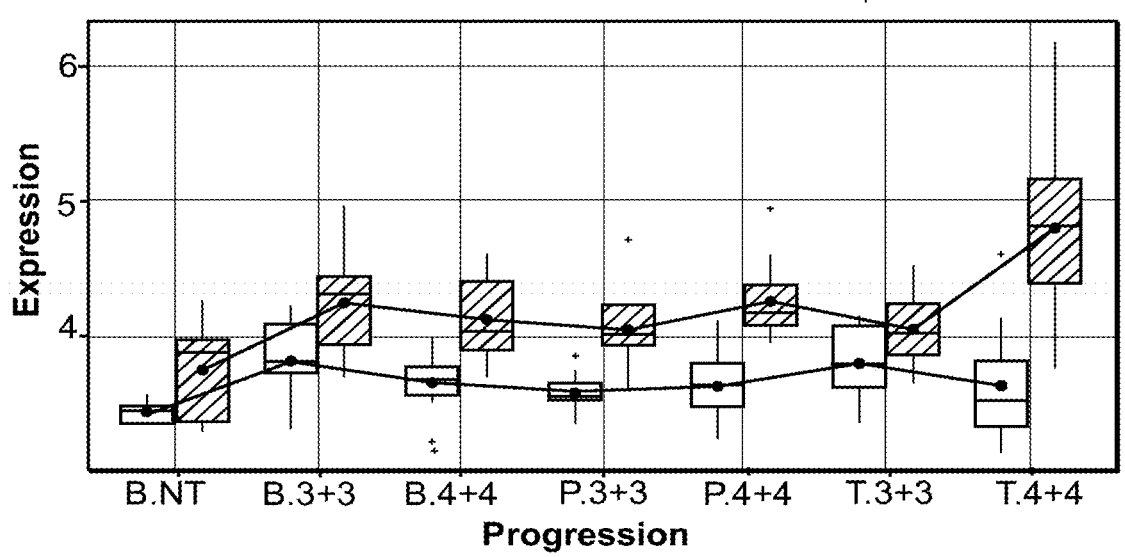

FIG. 56 is a plot showing trends across benign to PIN to tumor samples for the FCGR2C gene.

Figure 57:
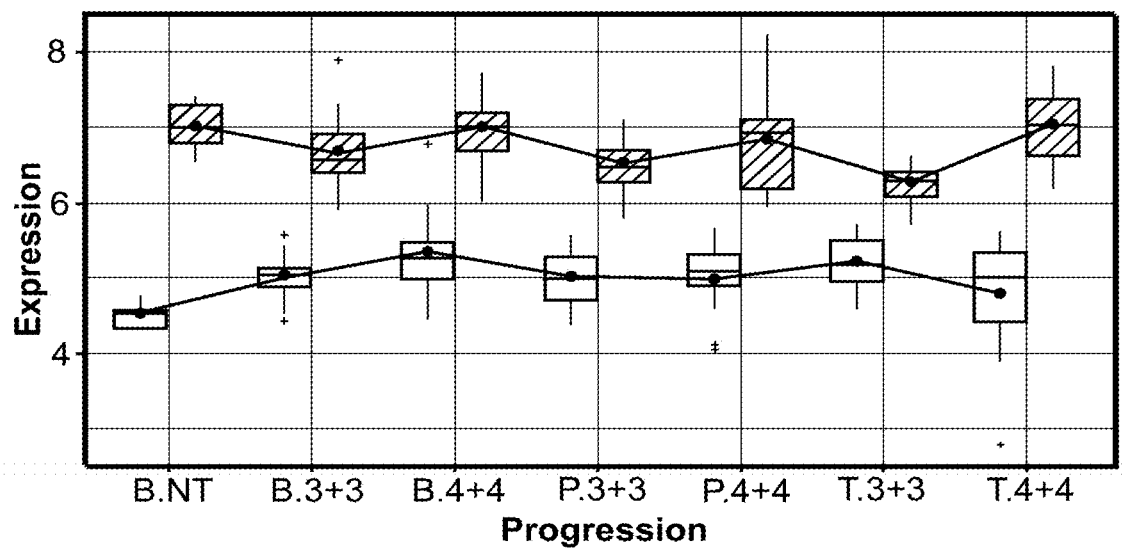

FIG. 57 is a plot showing trends across benign to PIN to tumor samples for the PRELP gene.

Figure 58:
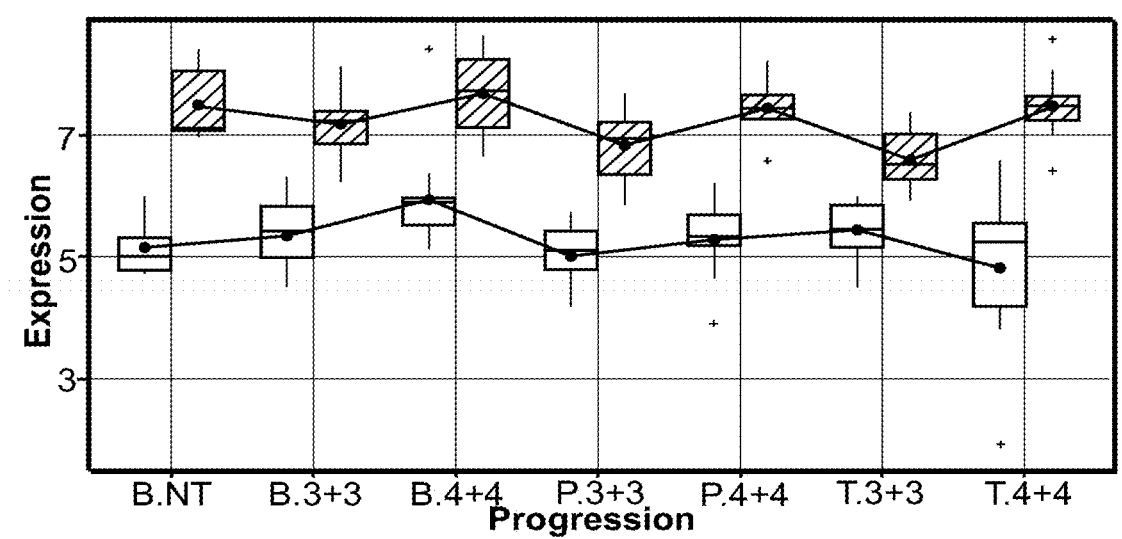

FIG. 58 is a plot showing trends across benign to PIN to tumor samples for the SERPING1 gene.

Figure 59:
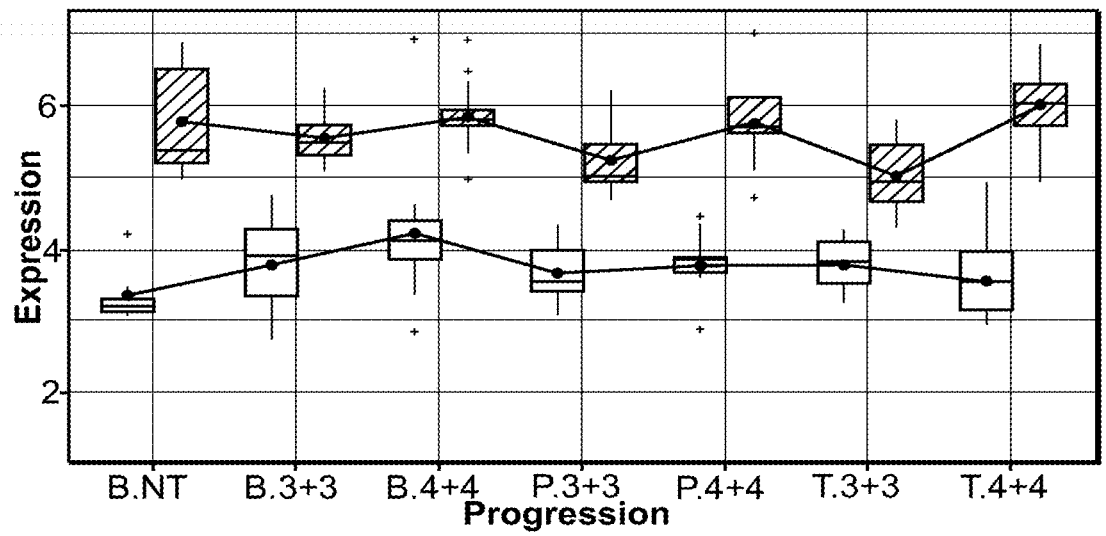

FIG. 59 is a plot showing trends across benign to PIN to tumor samples for the C1S gene.

Figure 60:
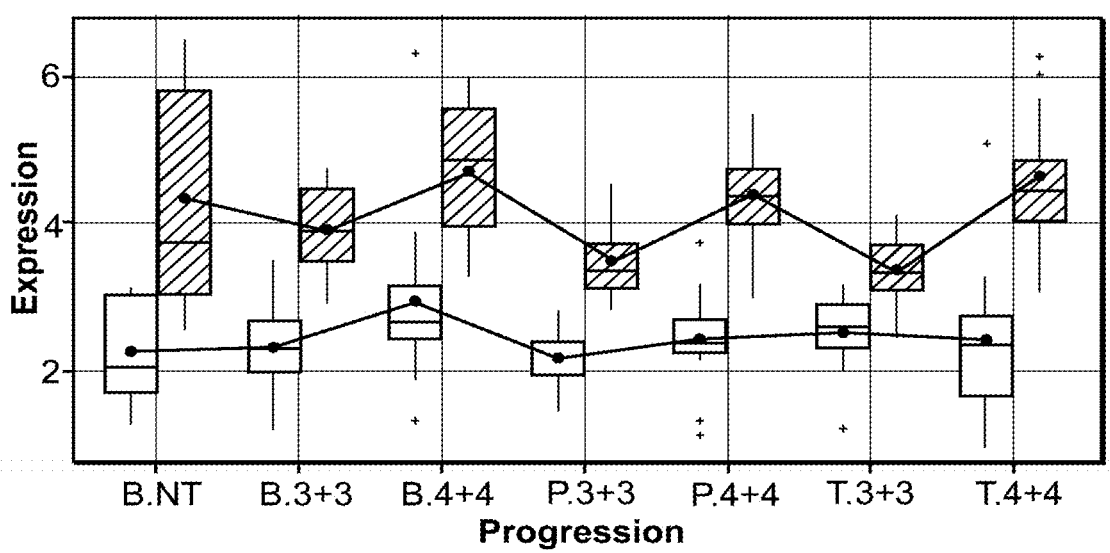

FIG. 60 is a plot showing trends across benign to PIN to tumor samples for the LUM gene.

Figure 61:
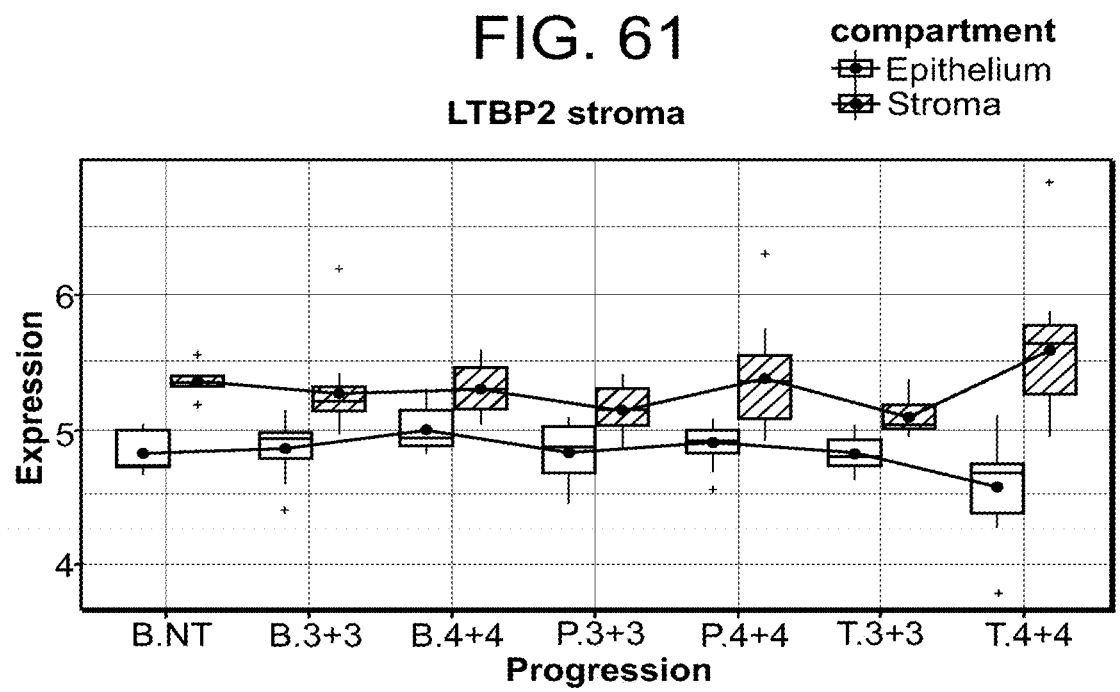

FIG. 61 is a plot showing trends across benign to PIN to tumor samples for the LTBP2 gene.

Figure 62:
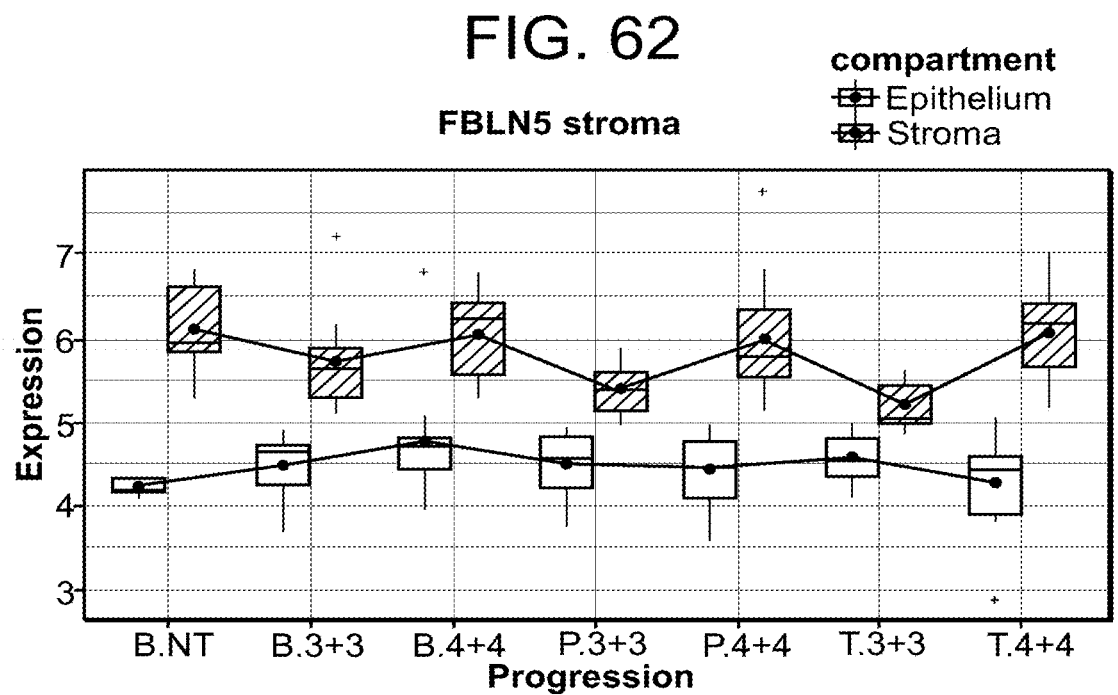

FIG. 62 is a plot showing trends across benign to PIN to tumor samples for the FBLN5 gene.

FIG. 63 is a plot showing trends across benign to PIN to tumor samples for the ITGA11 gene.

FIG. 64 is a plot showing trends across benign to PIN to tumor samples for the COL1A1 gene.

Figure 65:
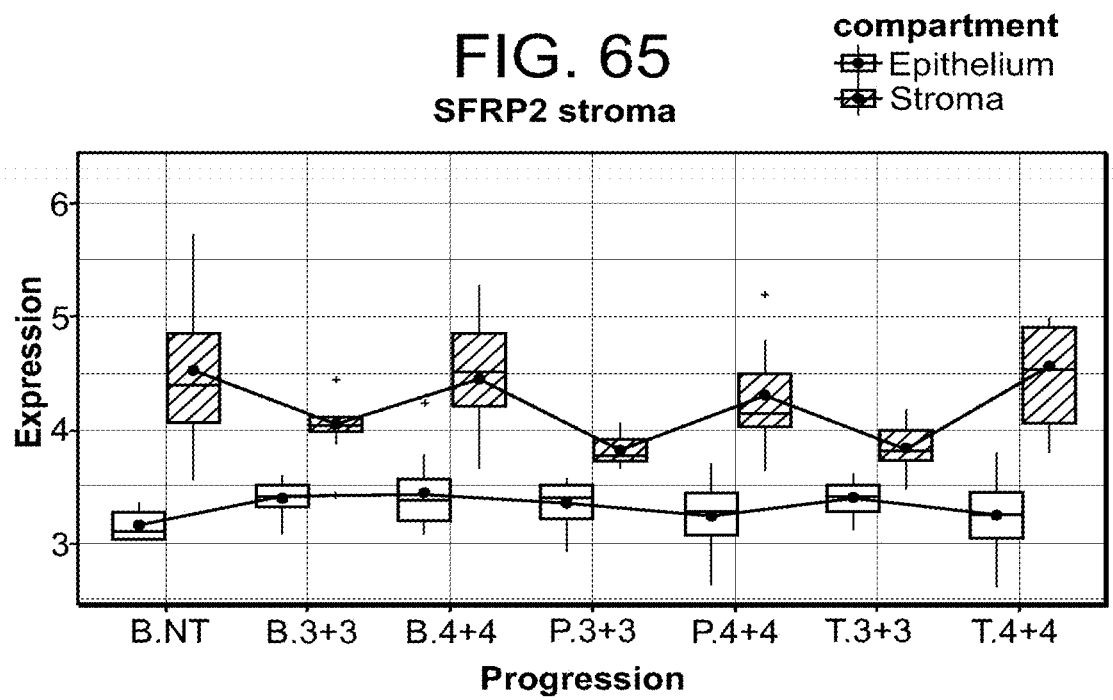

FIG. 65 is a plot showing trends across benign to PIN to tumor samples for the SFRP2 gene.

Figure 66:
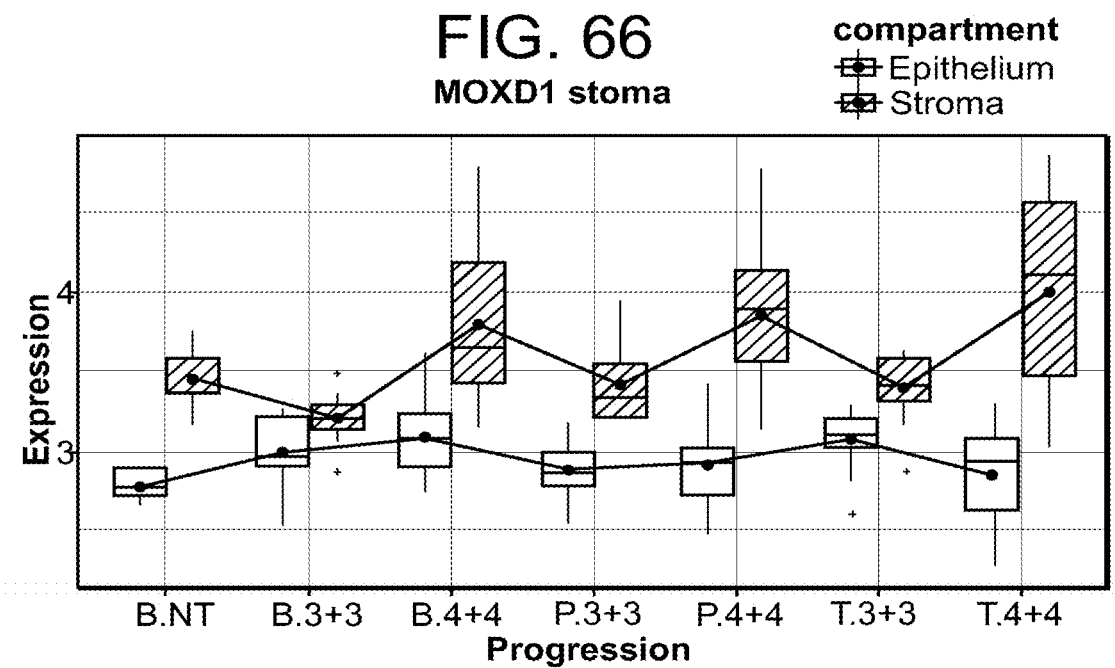

FIG. 66 is a plot showing trends across benign to PIN to tumor samples for the MOXD1 gene.

Figure 67:
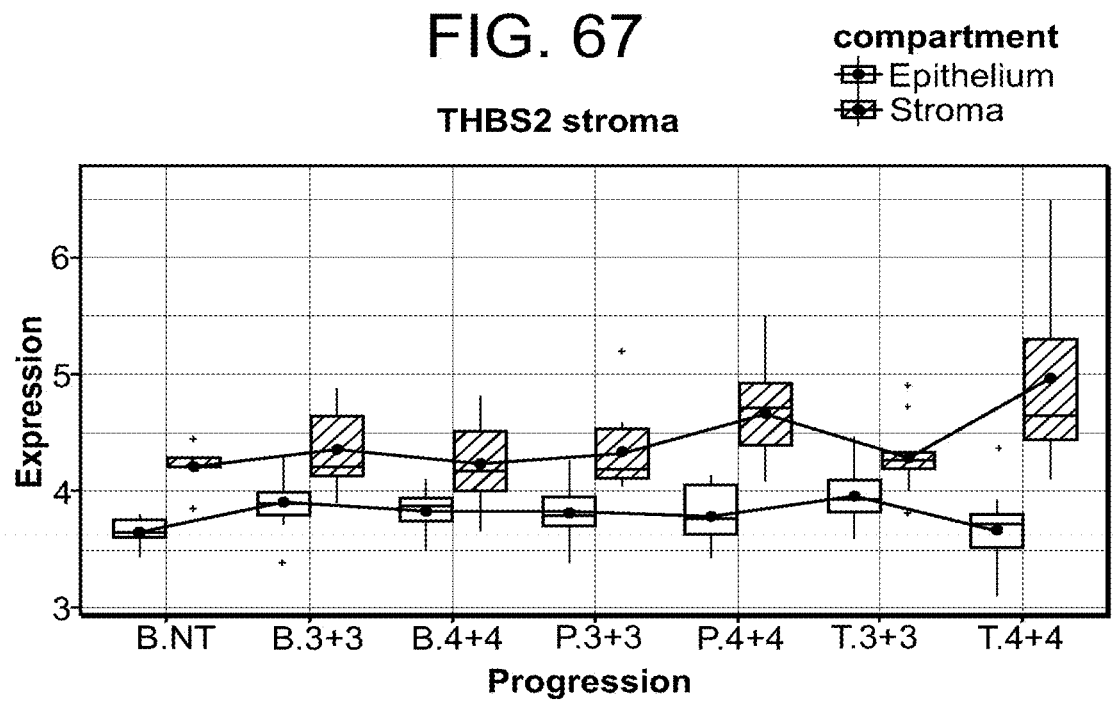

FIG. 67 is a plot showing trends across benign to PIN to tumor samples for the THBS2 gene.

Figure 68:
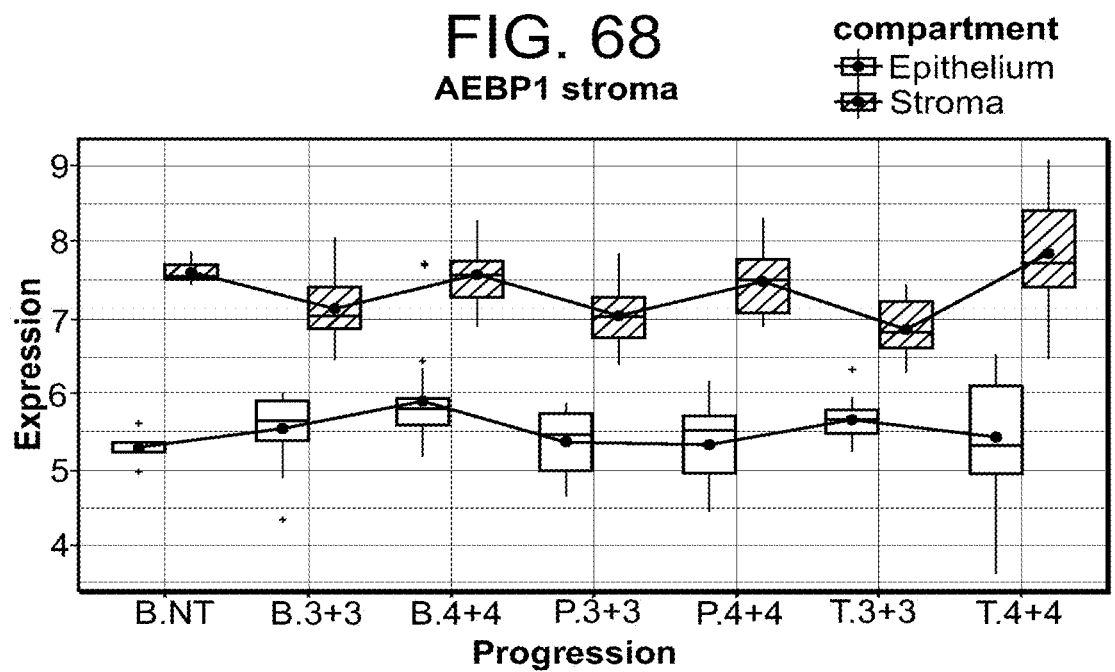

FIG. 68 is a plot showing trends across benign to PIN to tumor samples for the AEBP1 gene.

Figure 69:
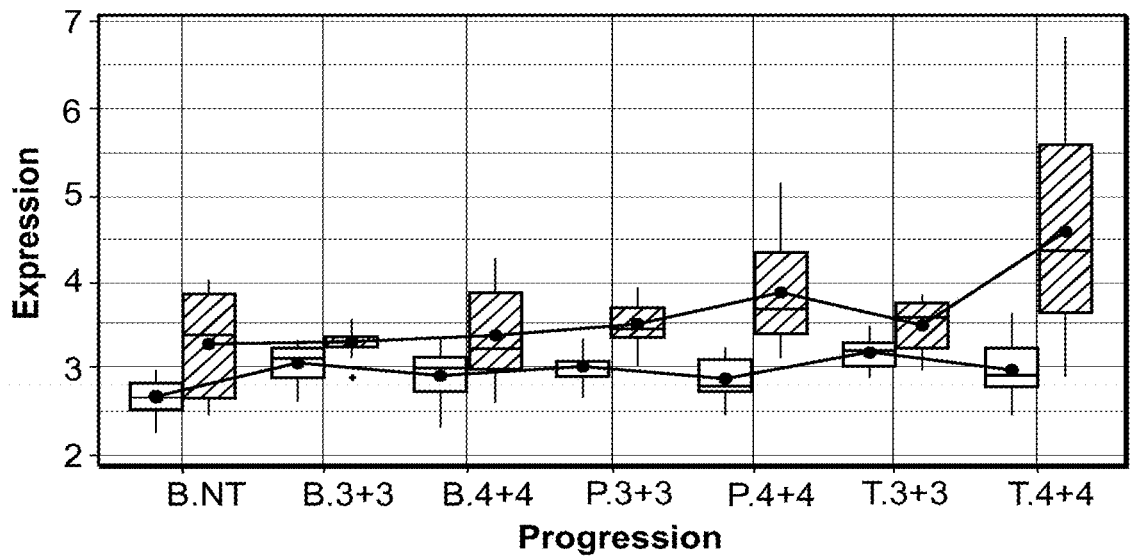

FIG. 69 is a plot showing trends across benign to PIN to tumor samples for the SFRP4 gene.

Figure 70:
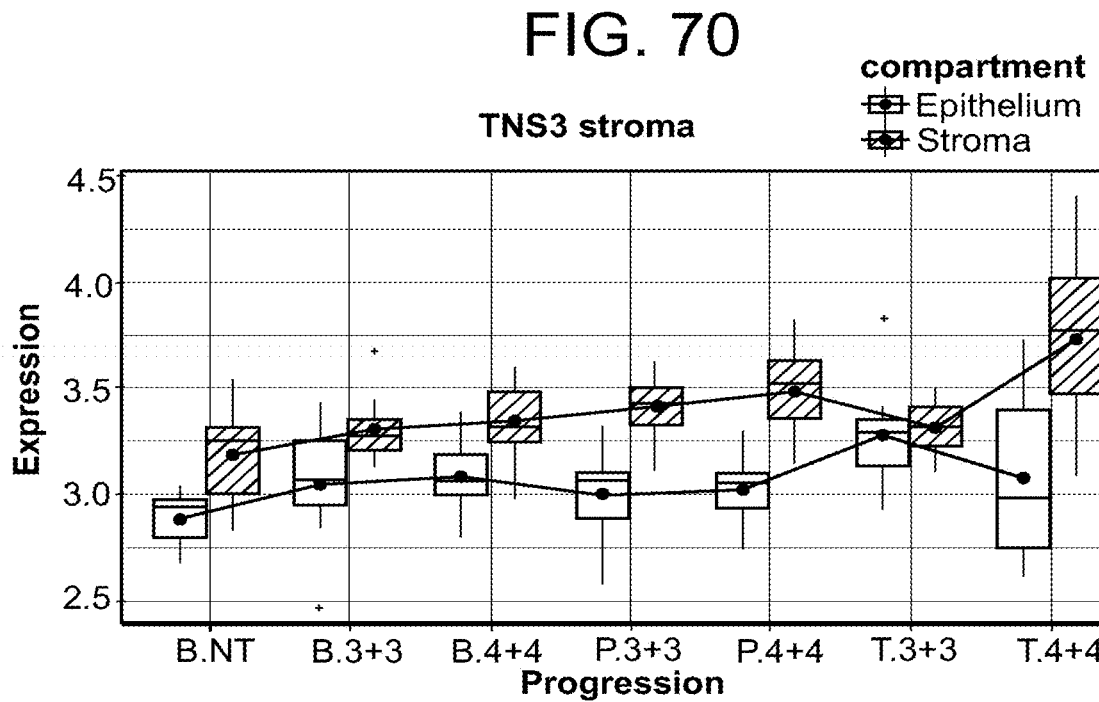

FIG. 70 is a plot showing trends across benign to PIN to tumor samples for the TNS3 gene.

Figure 71:
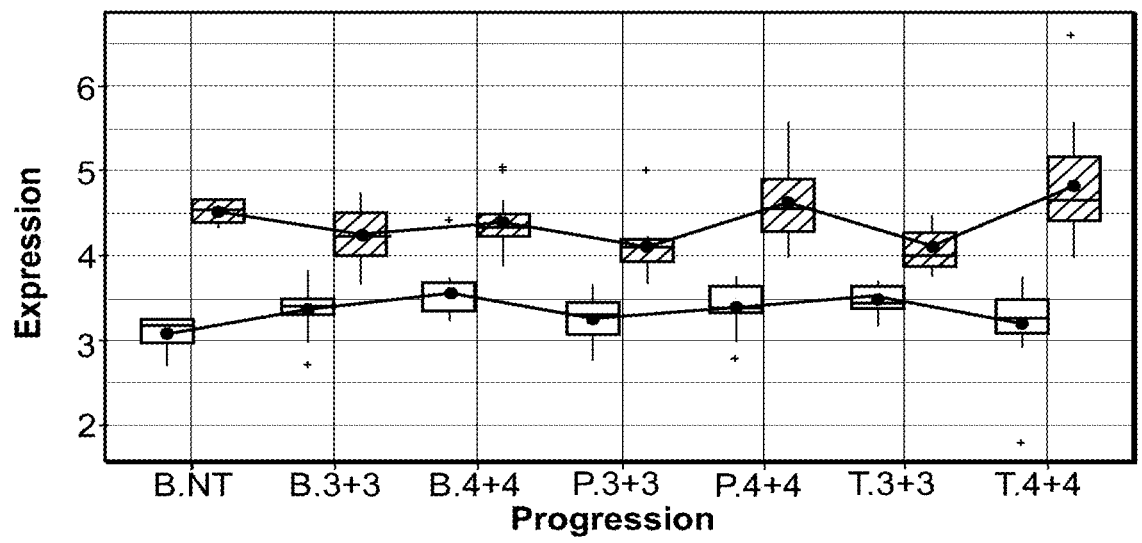

FIG. 71 is a plot showing trends across benign to PIN to tumor samples for the SULF1 gene.

Figure 72:
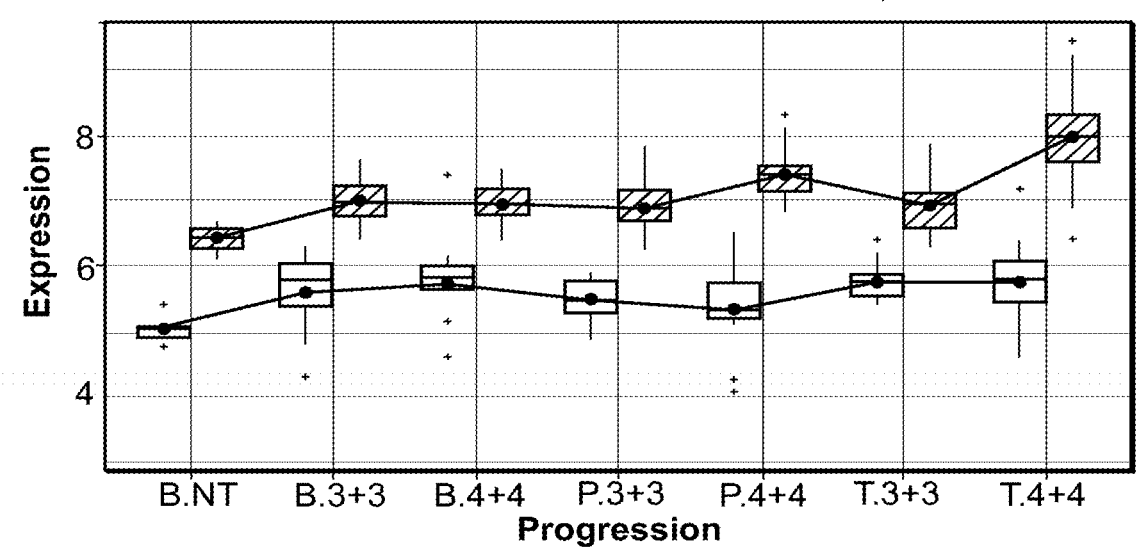

FIG. 72 is a plot showing trends across benign to PIN to tumor samples for the BGN gene.

Figure 73:
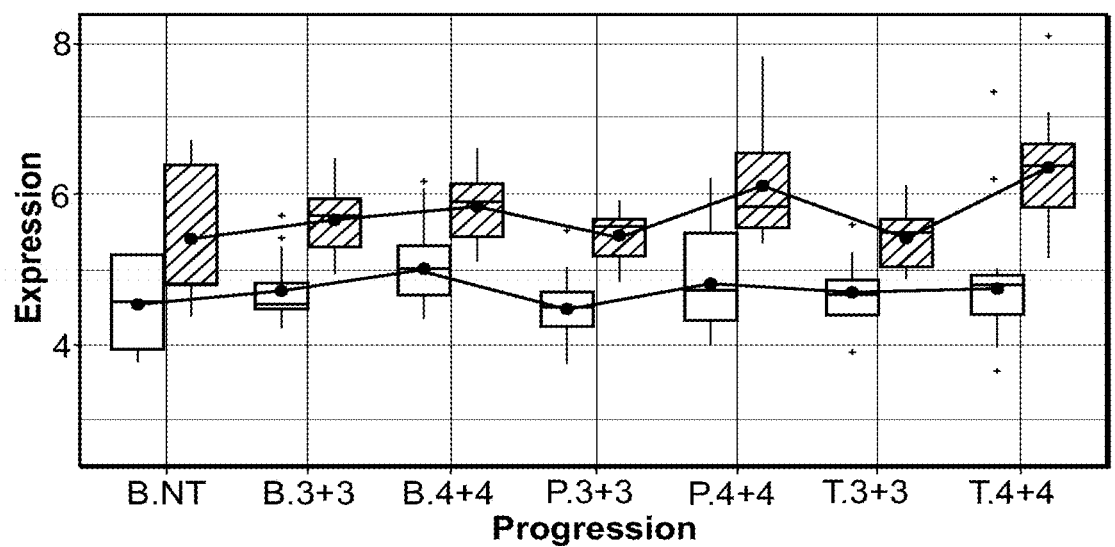

FIG. 73 is a plot showing trends across benign to PIN to tumor samples for the HLA-DRB3 gene.

Figure 74:
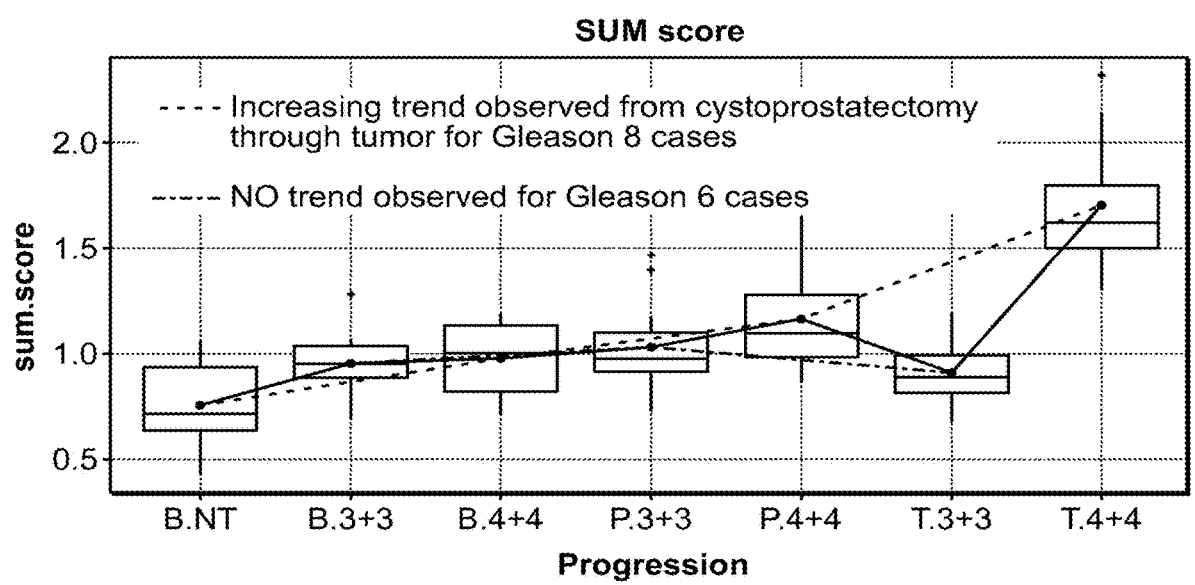

FIG. 74 is a plot showing combined scores of the 29-gene signature.

Figure 75A:
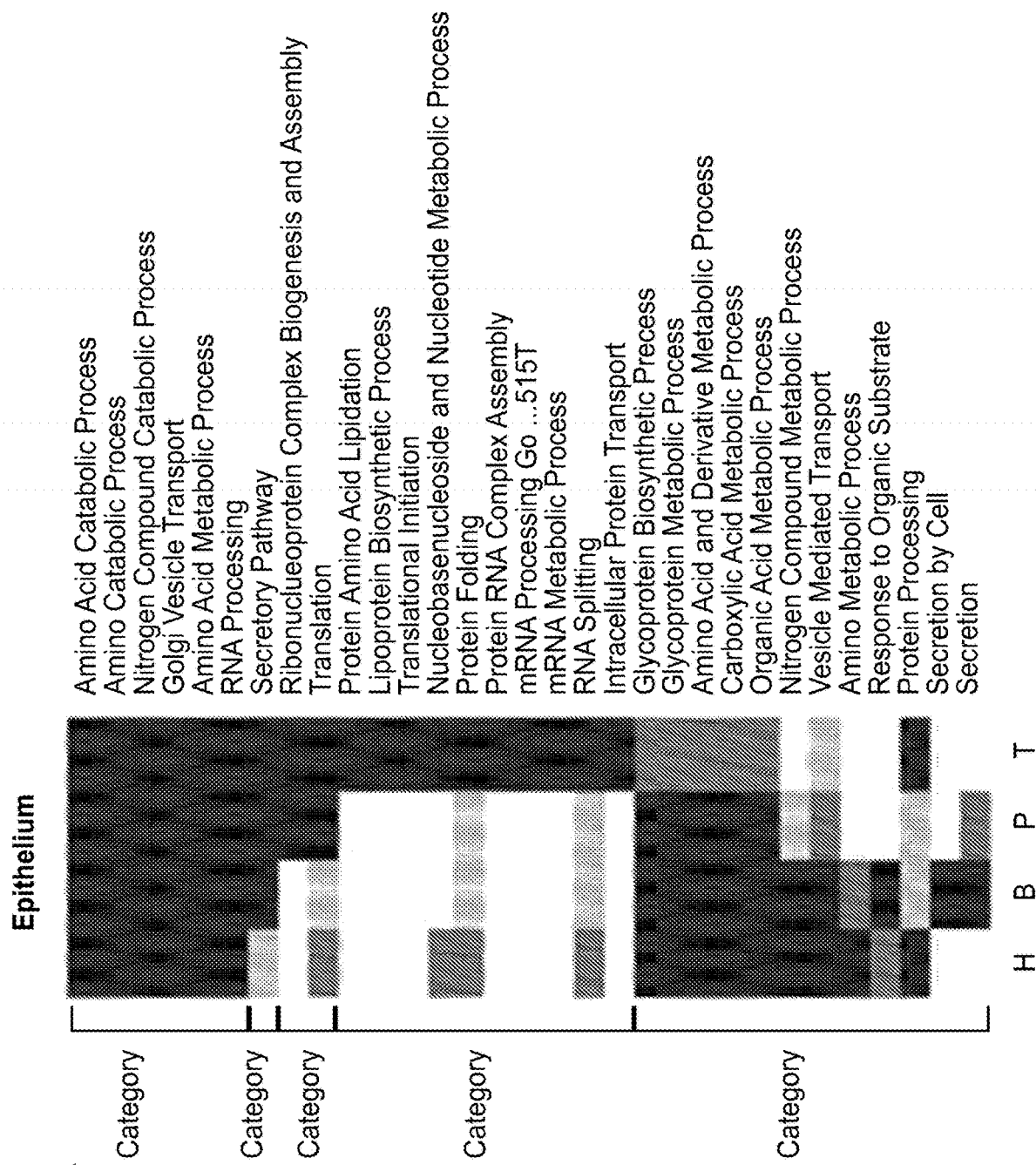
Figure 75B:
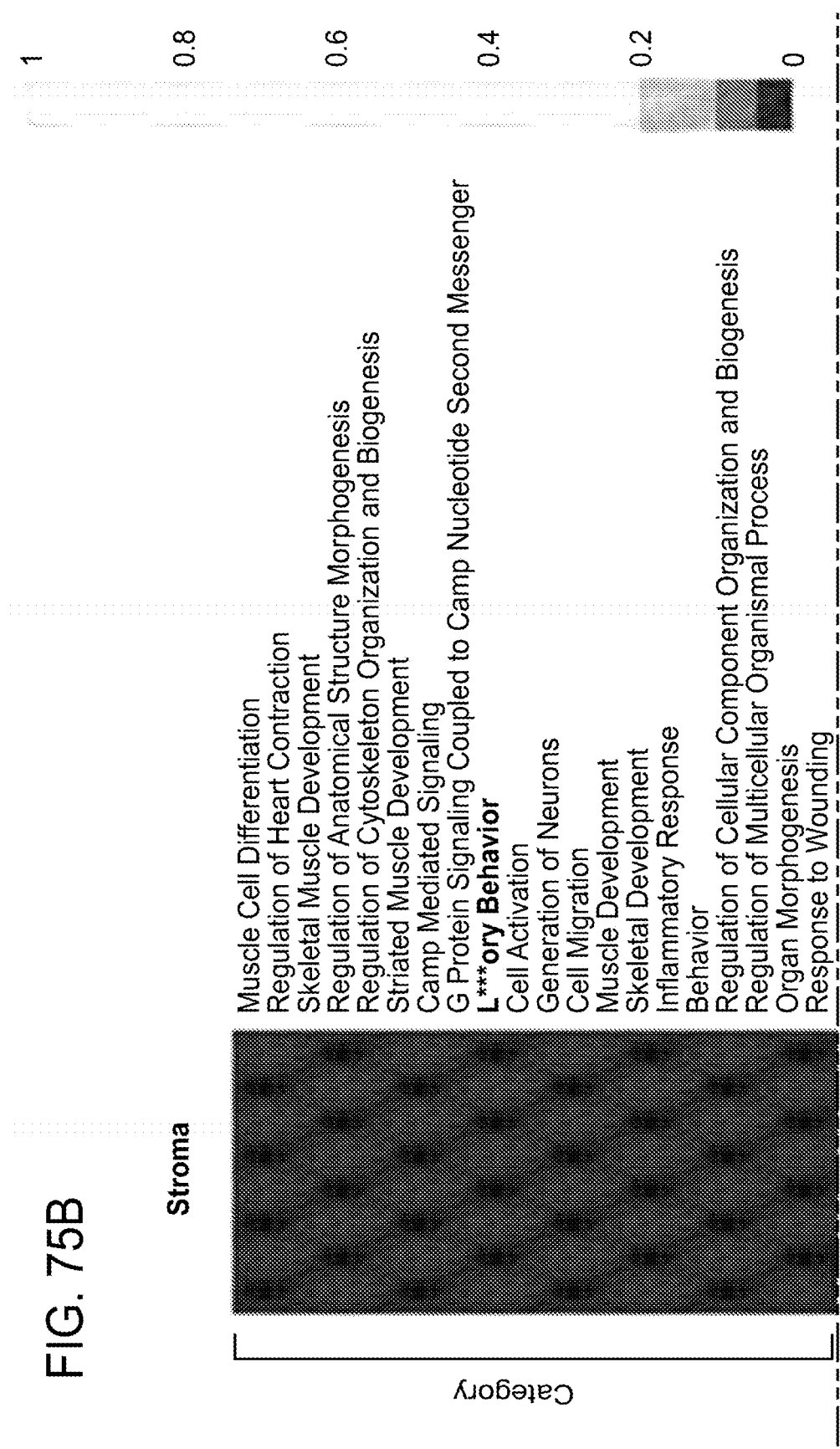
Figure 75B:
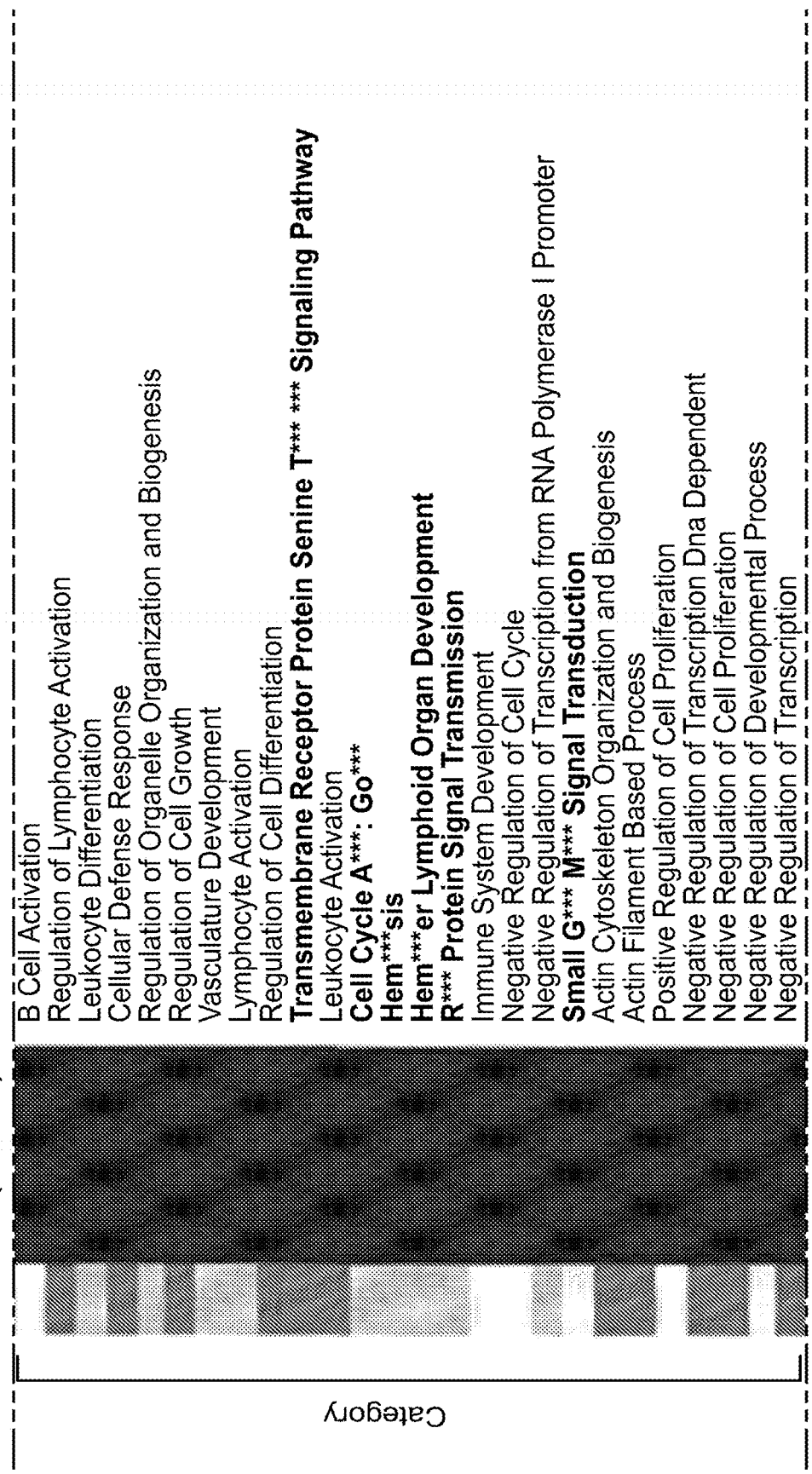
Figure 75B:
Figure 75B:
Figure 75B:
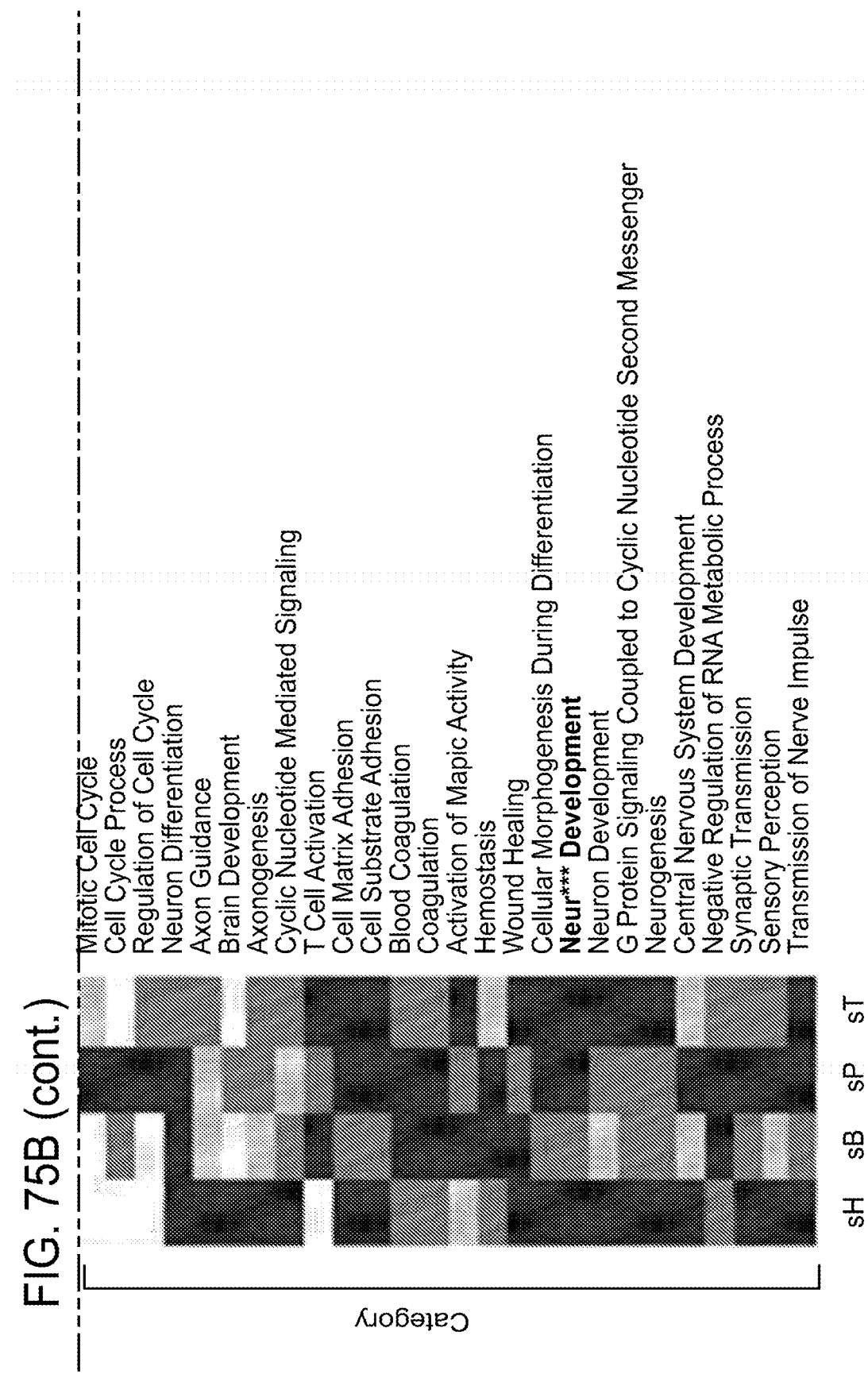
Figure 76A:
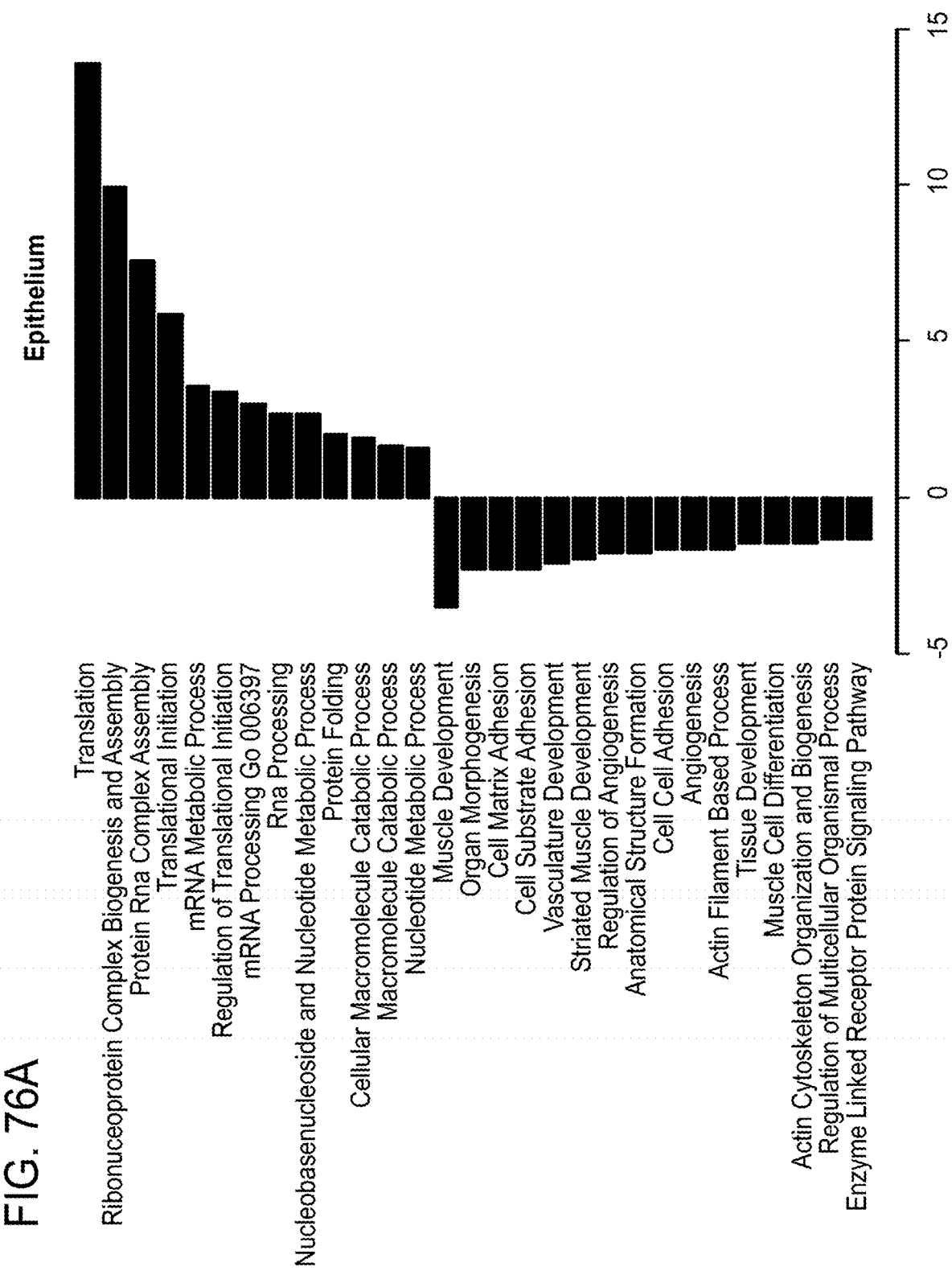
Figure 76B:
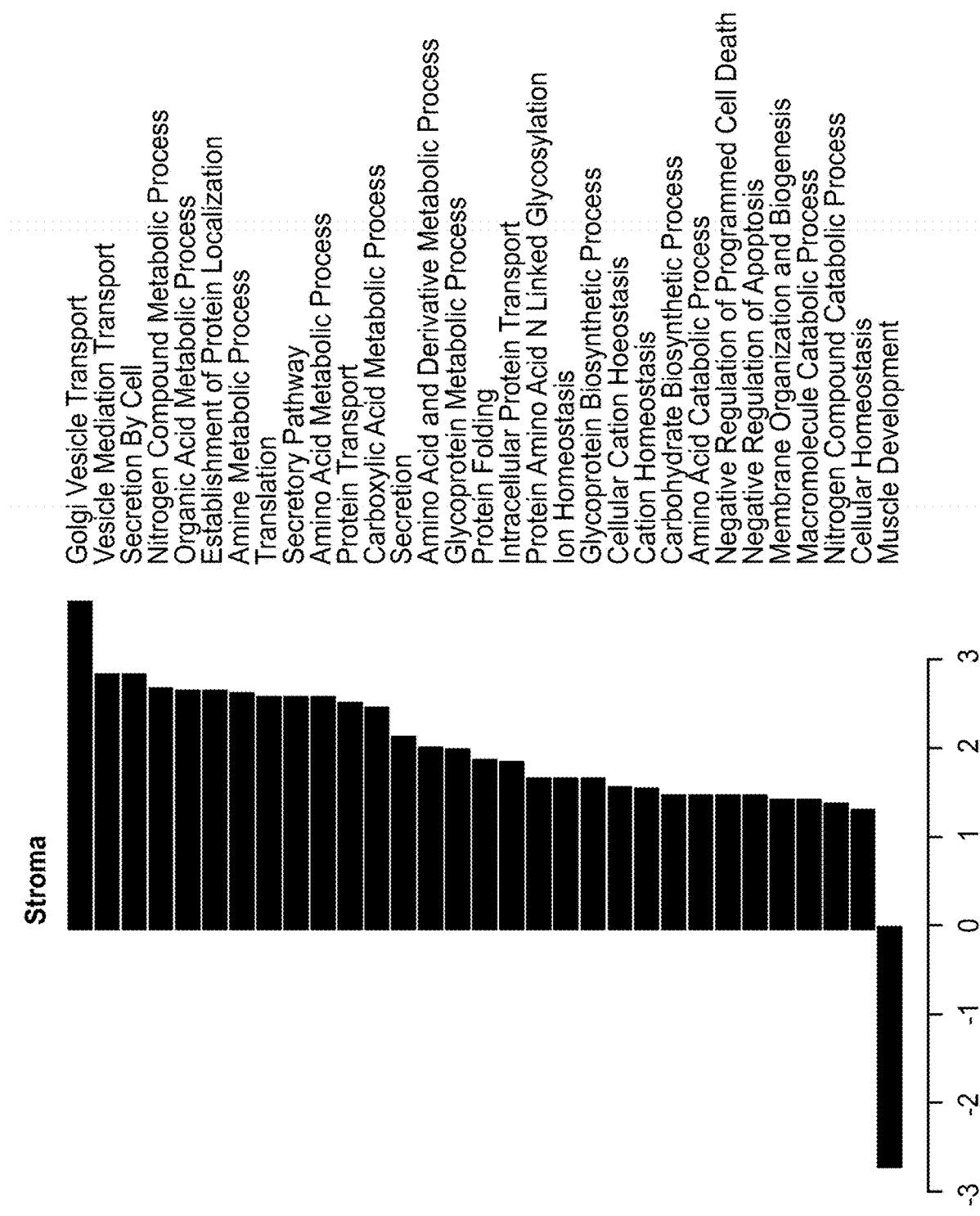

FIG. 75A-FIG. 75B is a series of heatmaps of the GO biological processes differentially enriched in (FIG. 75A) epithelial and (FIG. 75B) stromal compartments across stages of prostate cancer progression. H denotes comparisons obtained from cystoprostatectomy data. The cells in the heatmaps are colored according to the FDR of the process in the gene set analysis. Dark blue color corresponds to significance at 0.05 level and yellow to FDR>0.2. Categories across compartments show conserved to unique processes from H to B to P to T and most relevant pathways are summarized in categories as outlined below:

Category 1 (top) epithelial amino acid metabolism
Category 2 epithelial: secretory pathway
Category 3 epithelial: RNA synthesis
Category 4 epithelial: RNA, protein and lipid synthesis
Category 5 epithelial: miscellaneous
Category 1 (top) stromal: muscle development and localization
Category 2 stromal immune regulation, angiogenesis and cell proliferation
Category 3 stromal: signal transduction, cell migration and angiogenesis
Category 4 stromal: TGF beta, signal transduction and bone remodeling
Category 5 stromal: miscellaneous FIG. 76A-FIG. 76B are bar charts showing GO biological processes differentially enriched between (FIG. 76A) Benign and tumor epithelium; (FIG. 76B) Benign and tumor adjacent stroma. Length of the bars are equal to −log 10(FDR) values from the gene set analysis. Negative values indicate enrichment in benign epithelium or stroma respectively, positive values indicate enrichment in the tumor or tumor adjacent stroma.

Figure 77A:
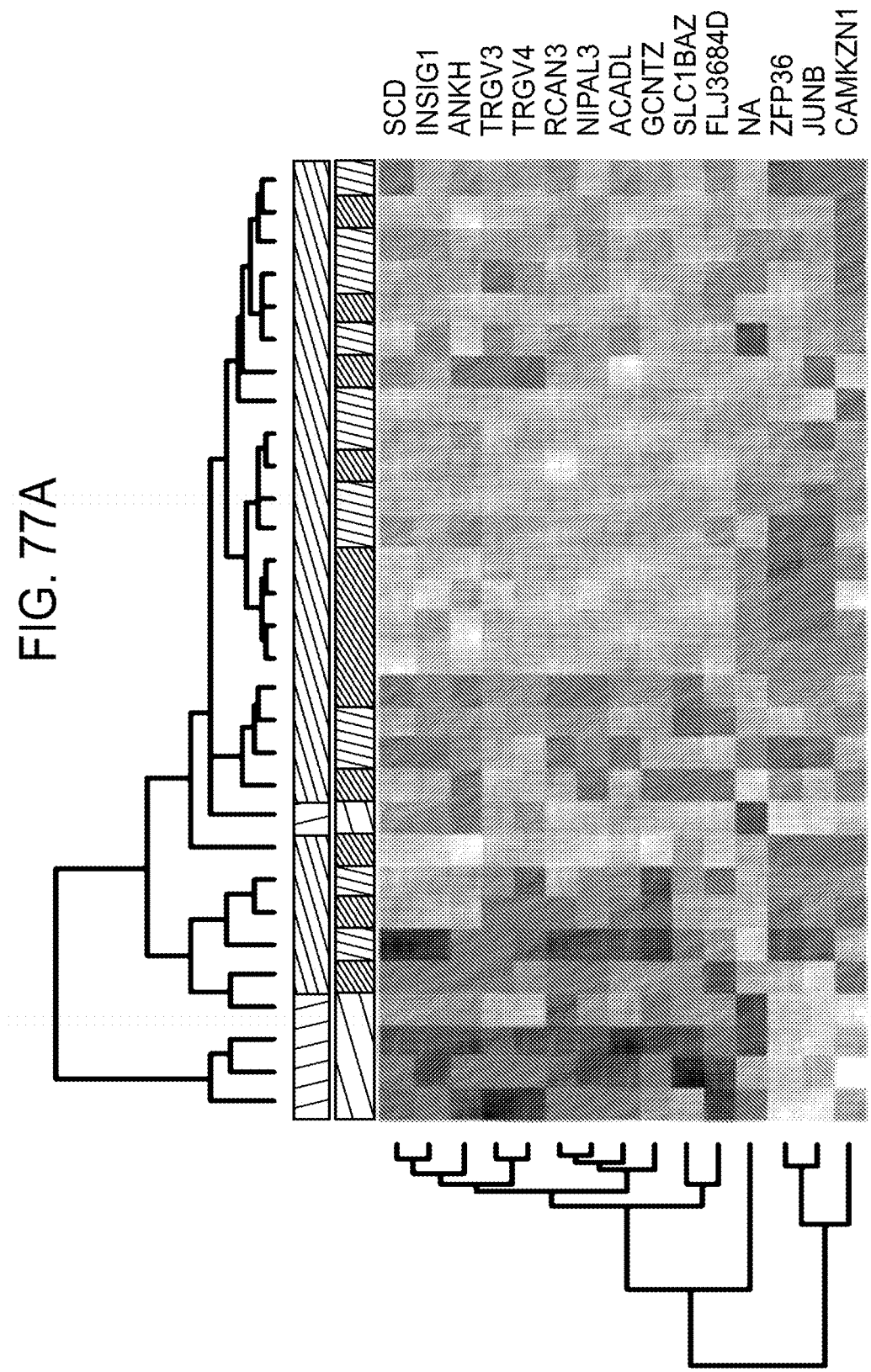
Figure 77B:
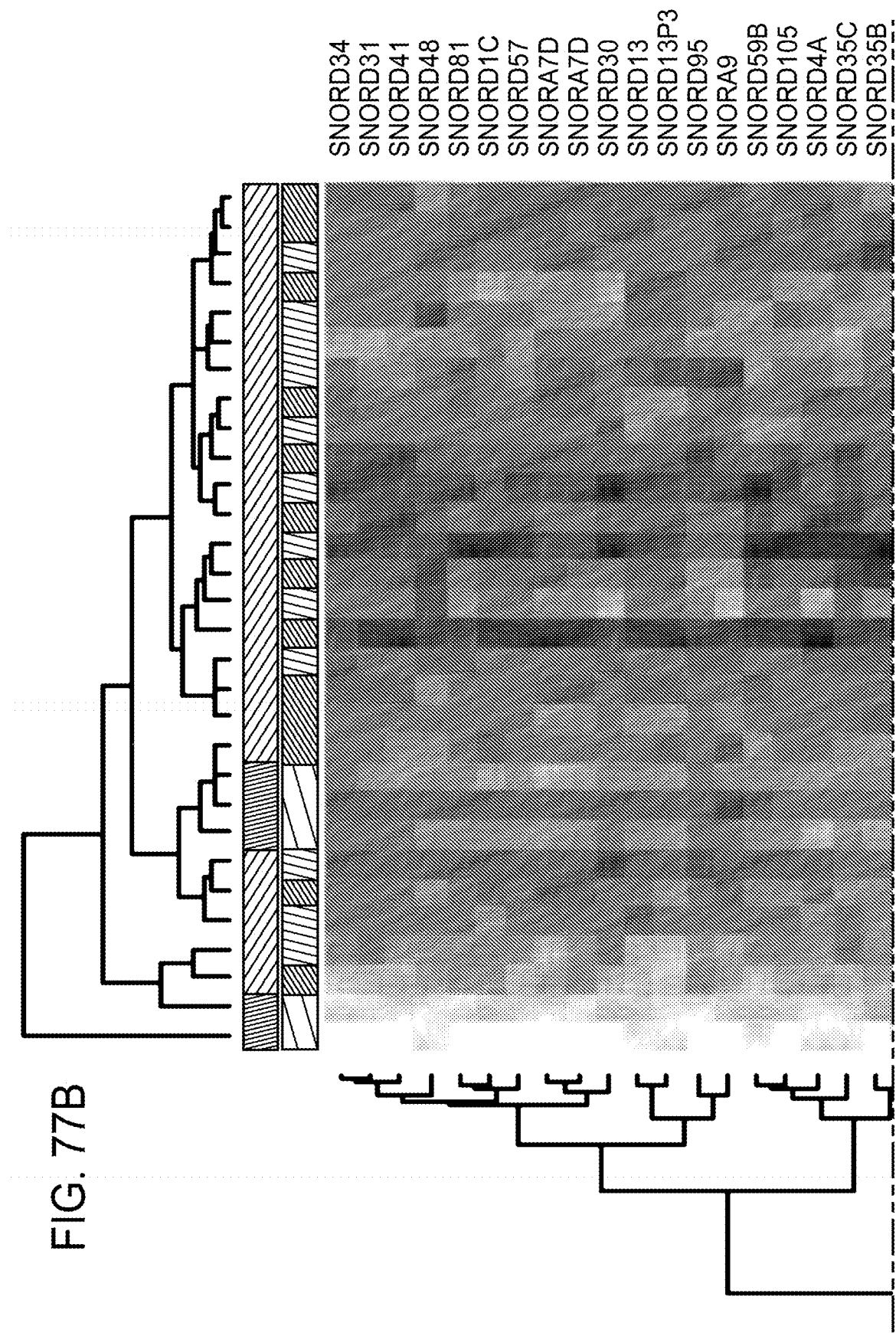
Figure 77B:
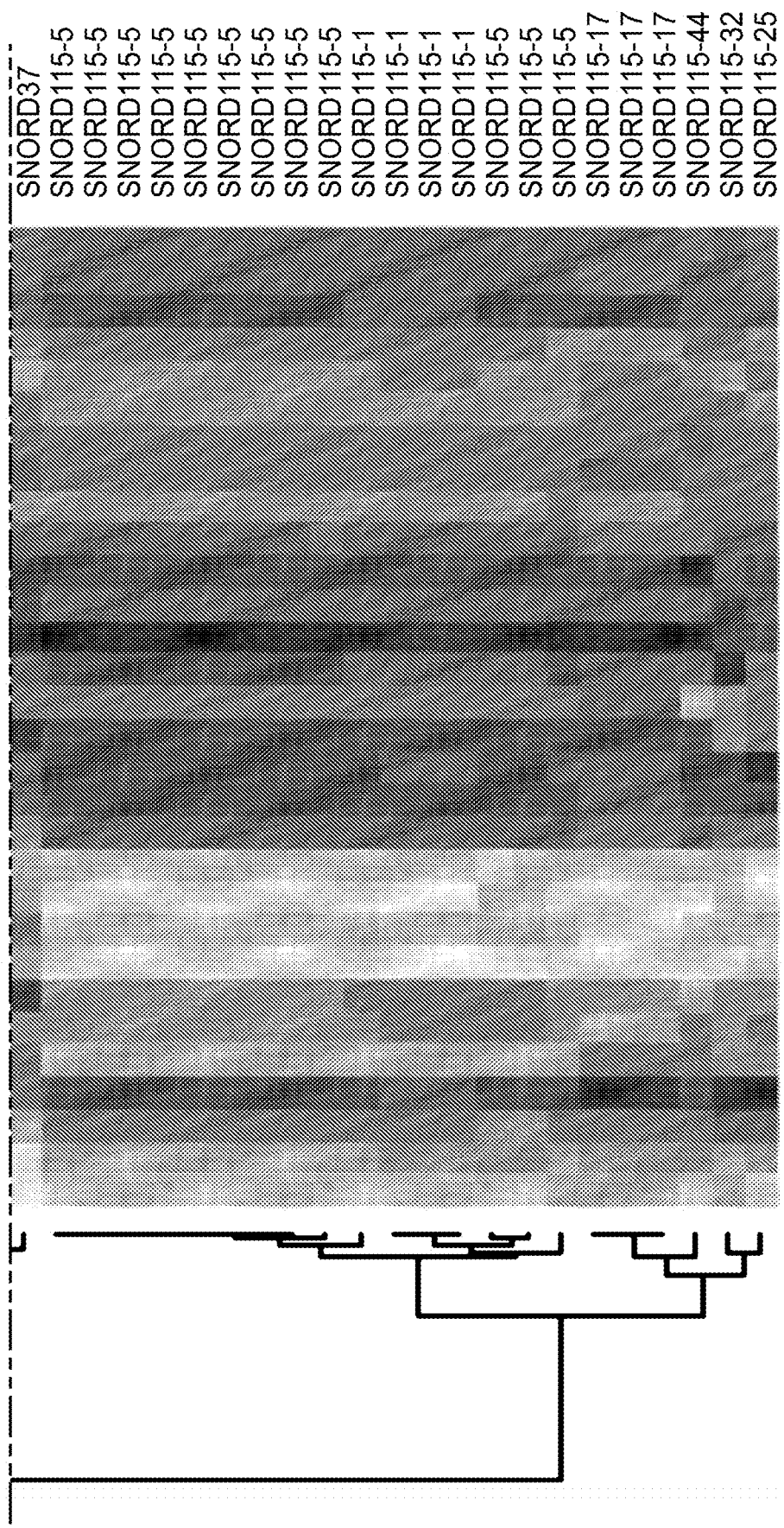
Figure 77C:
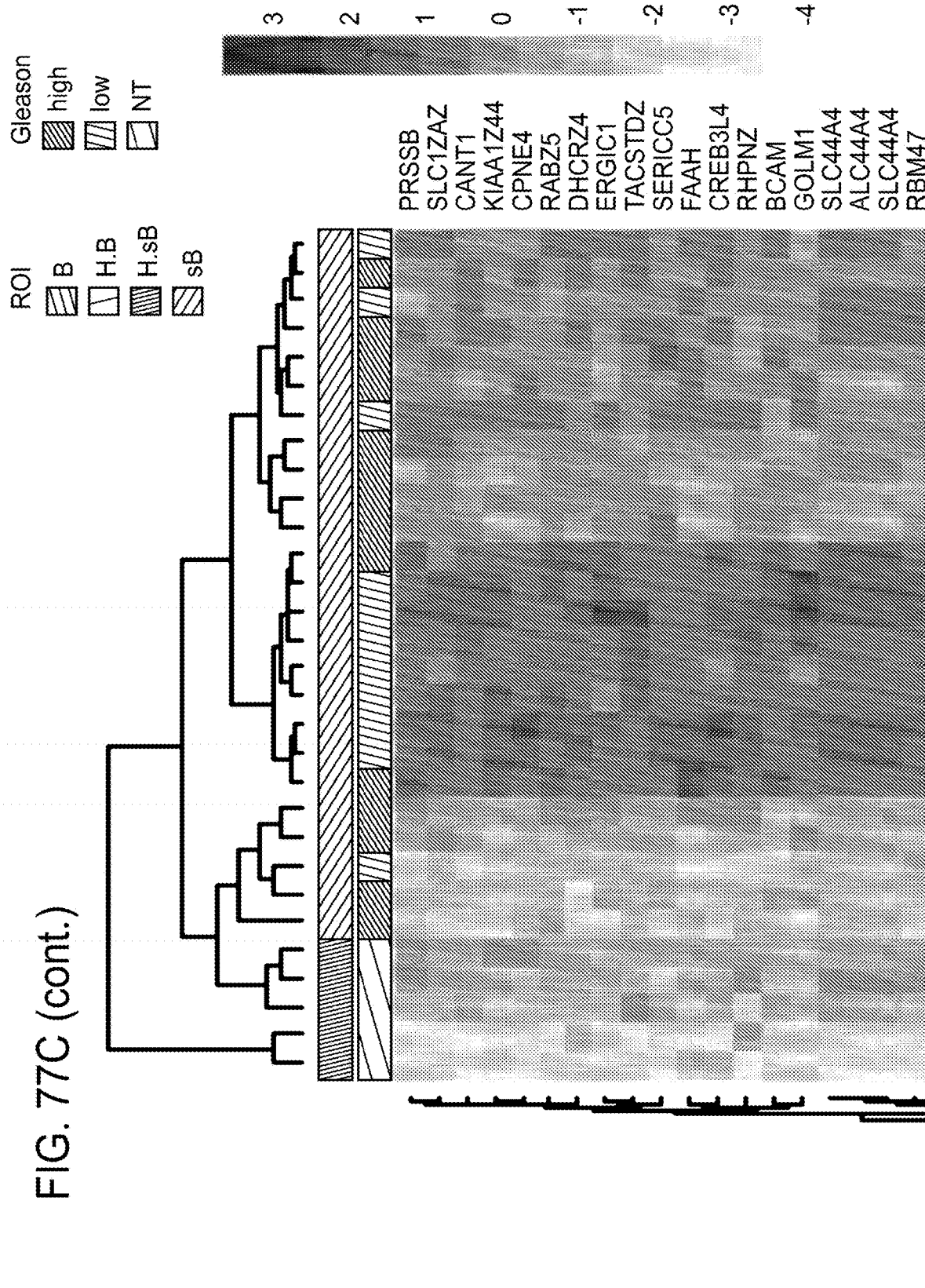
Figure 77C:
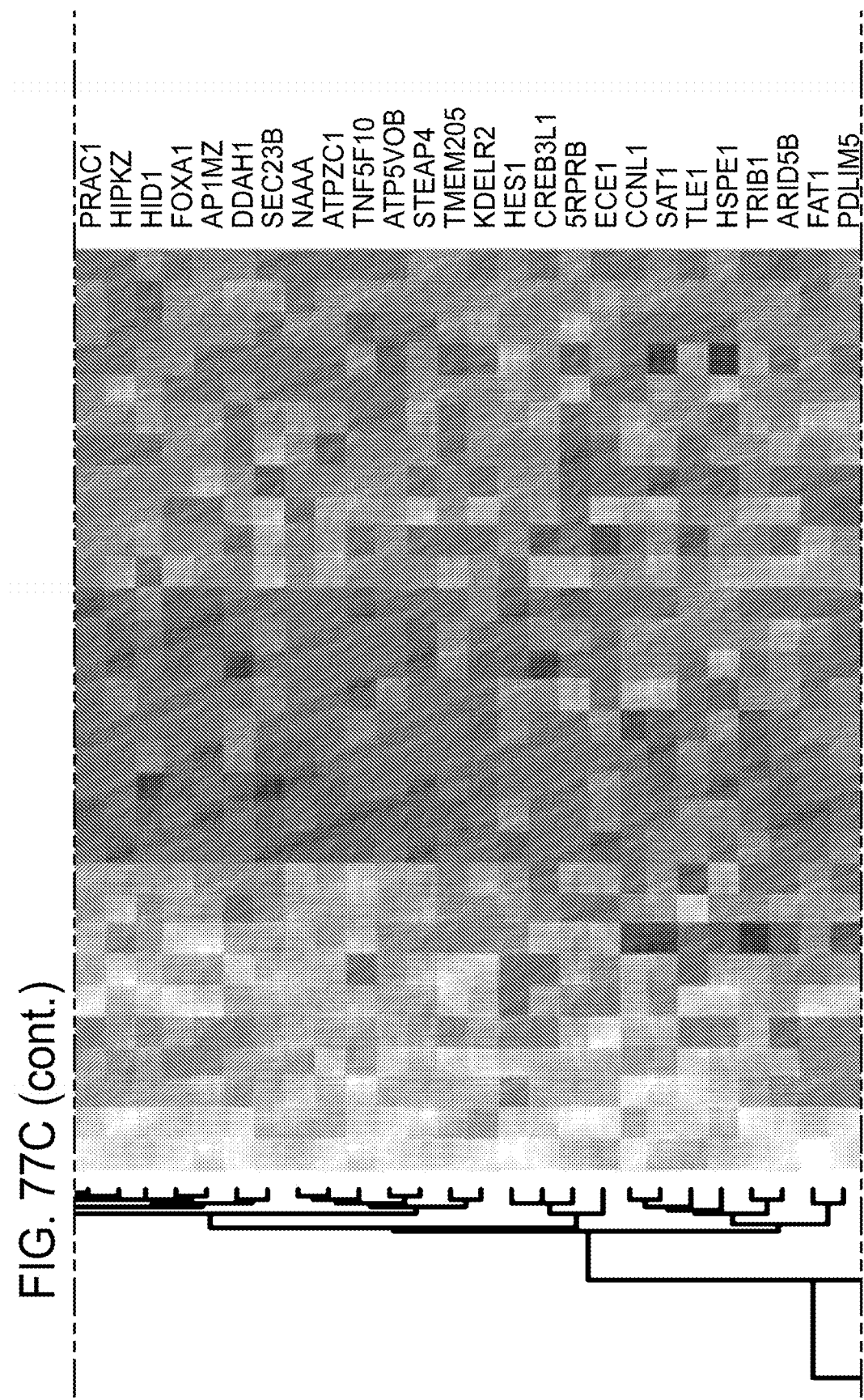
Figure 77C:
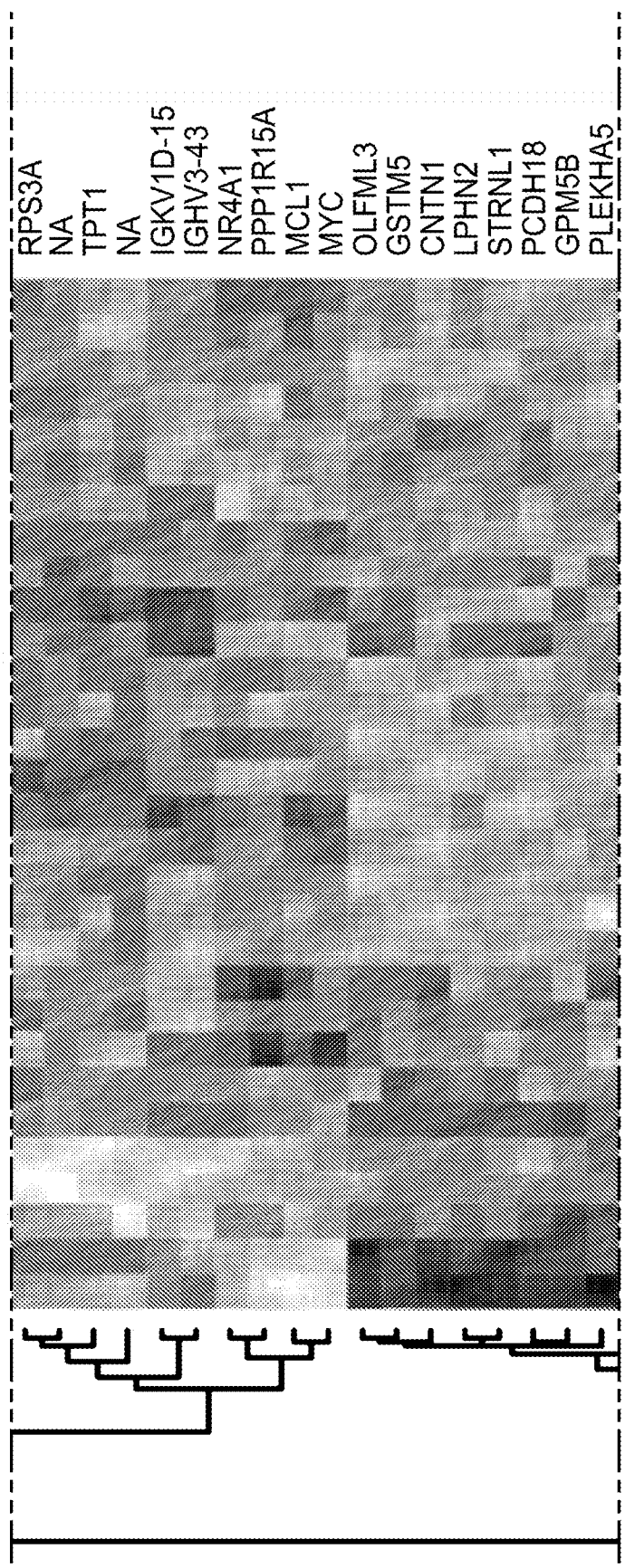
Figure 77C:
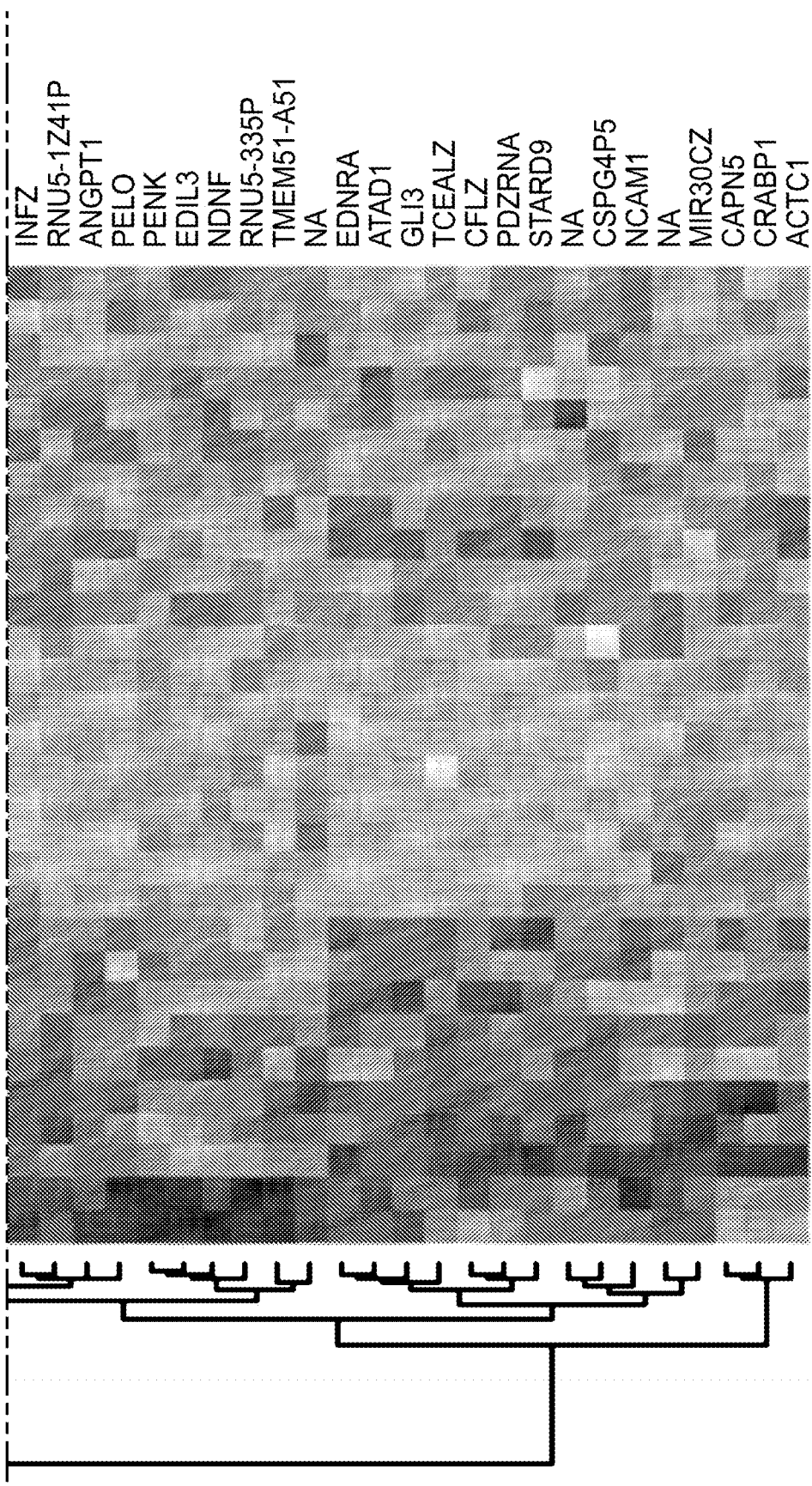
Figure 77D:
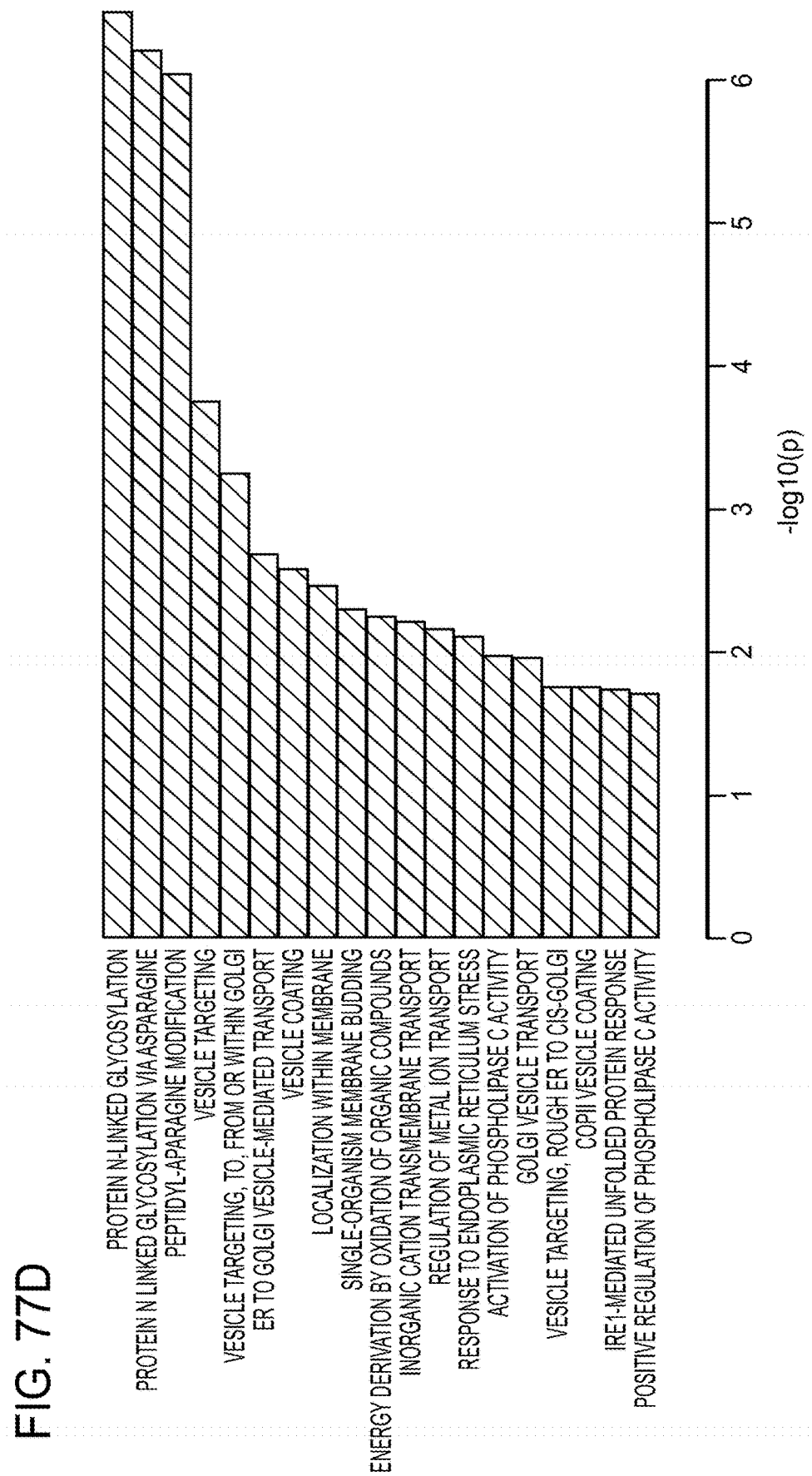
Figure 77D:
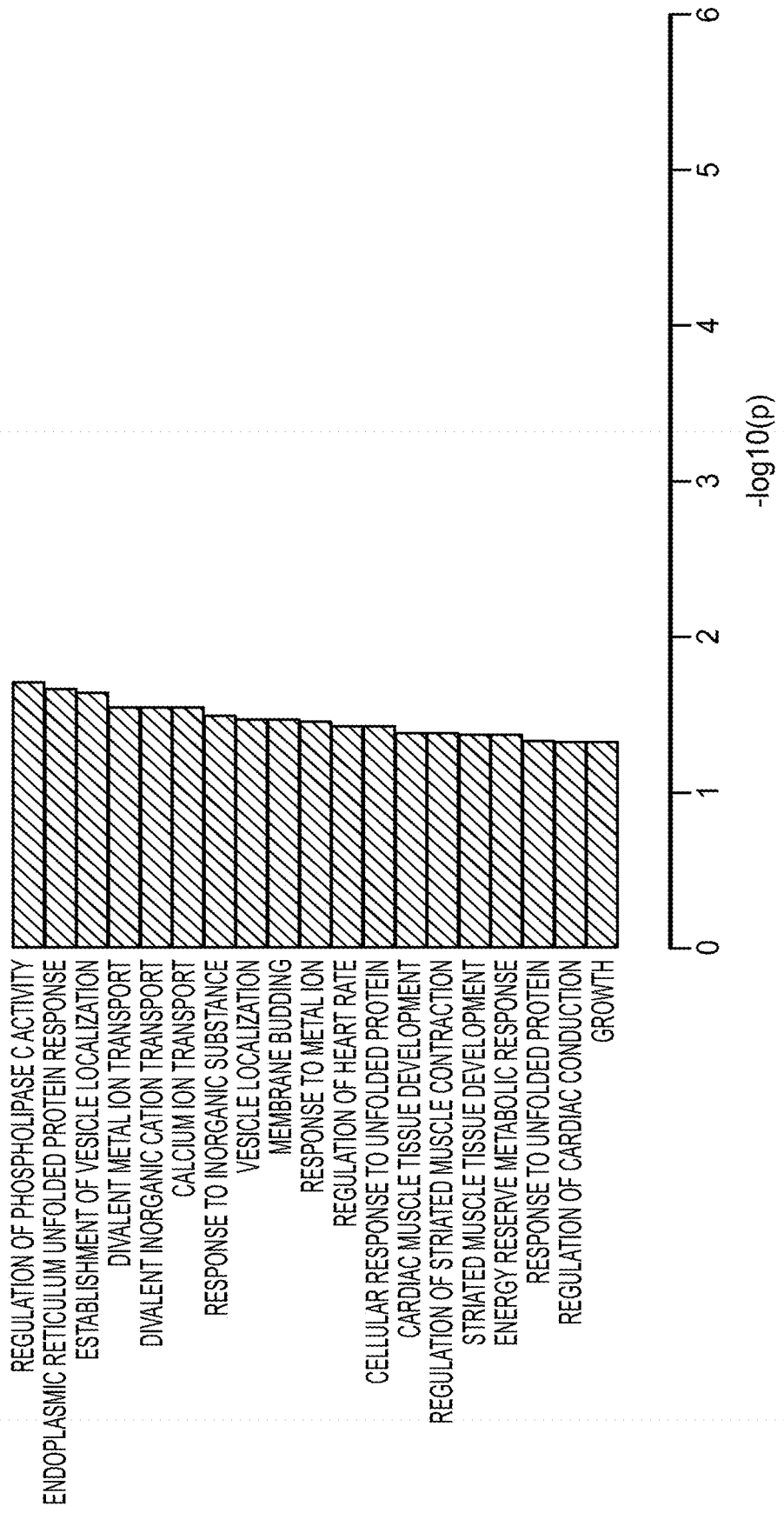

FIG. 77A-FIG. 77C is a series of heatmaps showing genes and pathways differentially expressed in benign tissue between cystoprostatectomy and RP specimens. FIG. 77A is a heatmap of genes differentially expressed in benign epithelium of prostate cancer patients and cystoprostatectomy patients without prostate cancer. Gleason grade corresponds to the grade of the prostate tumor present in the same block and NT (no tumor) denotes cystoprostatectomy cases. FIG. 77B and FIG. 77C are a heatmaps of genes differentially expressed stroma surrounding benign glands from prostate cancer patients and cystoprostatectomy patients without prostate cancer. FIG. 77B shows small nucleolar RNA's, while FIG. 77C shows the remainder of genes, i.e., "regular genes". FIG. 77D is a bar chart showing −Log 10 FDR-values from the pathways analysis of the genes differentially expressed in benign stroma using GO biological processes annotations.

Figures 78A, 78B, 78C:
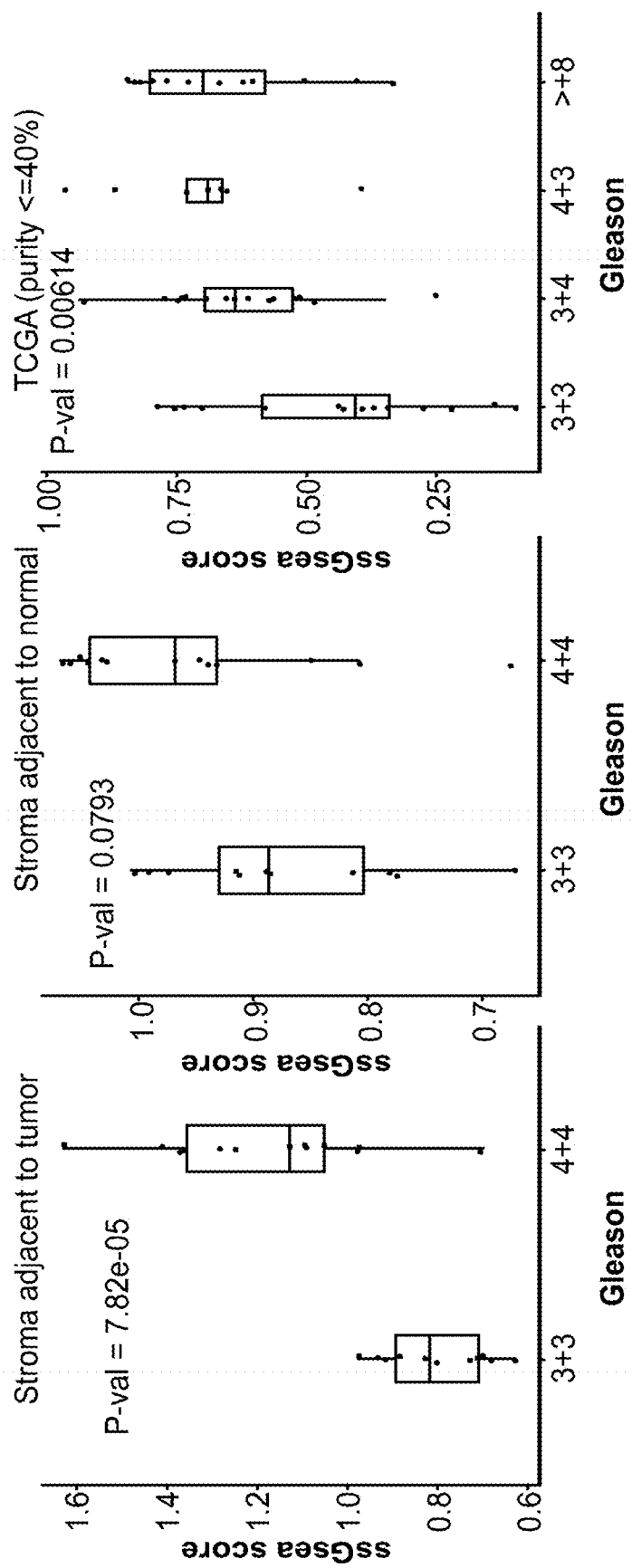
Figure 78E:
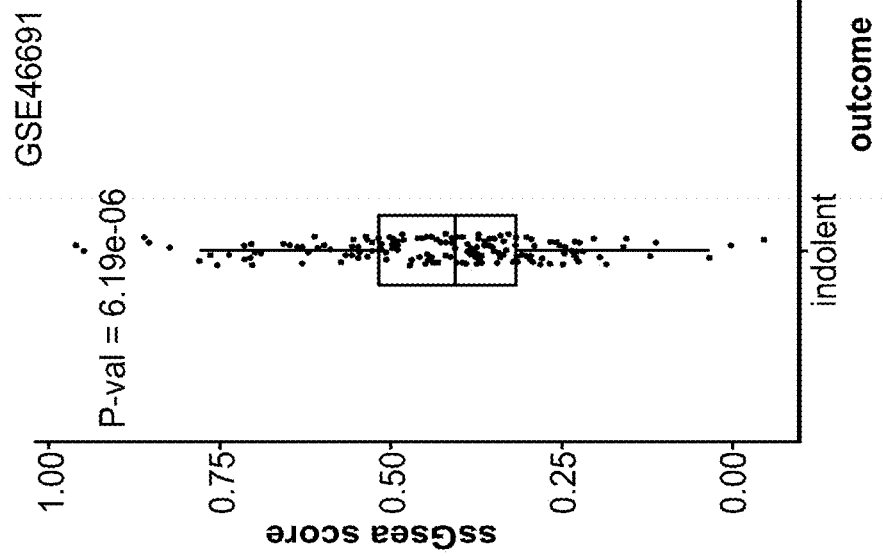
Figure 78D:
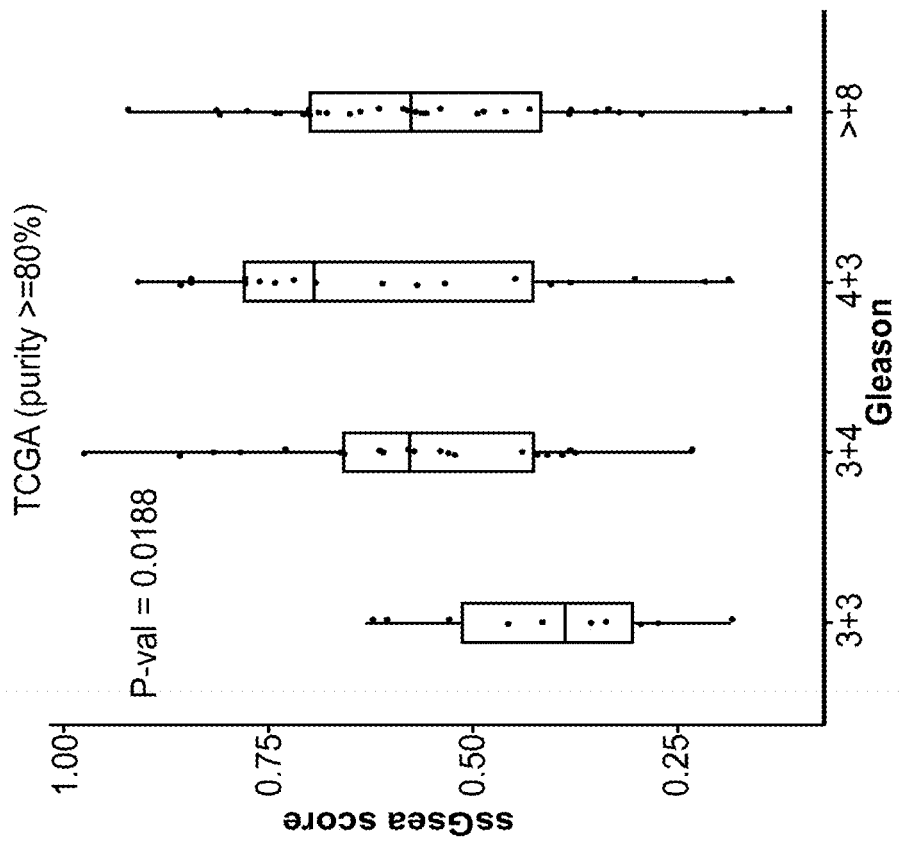

FIG. 78A-FIG. 78H is a series of graphs and photomicrographs showing genes differentially expressed in stroma surrounding high and low Gleason grade prostate tumors. FIG. 78A is a graph showing ssGSEA score of the stromal signature in tumor-adjacent stroma. FIG. 78B is a graph showing ssGSEA score of the stromal signature in benign-adjacent stroma. FIG. 78C is a graph showing ssGSEA score of the stromal signature in low cellularity TCGA samples. FIG. 78D is a graph showing ssGSEA score of the stromal signature in high cellularity TCGA samples. FIG. 78E is a graph showing ssGSEA score of the stromal signature between indolent and lethal cases from GSE46691 cohort. FIG. 78F is a photomicrograph showing immunohistochemical staining of epithelial ALCAM in Gleason 3+3 case. FIG. 78G is a photomicrograph showing immunohistochemical staining of epithelial gene ALCAM in Gleason 4+4 case. FIG. 78H is a photomicrograph showing immunohistochemical staining of stromal SULF1 in Gleason 3+3 case. FIG. 78I is a photomicrograph showing immunohistochemical staining of stromal SULF1 in Gleason 3+3 case.

Figure 79A:
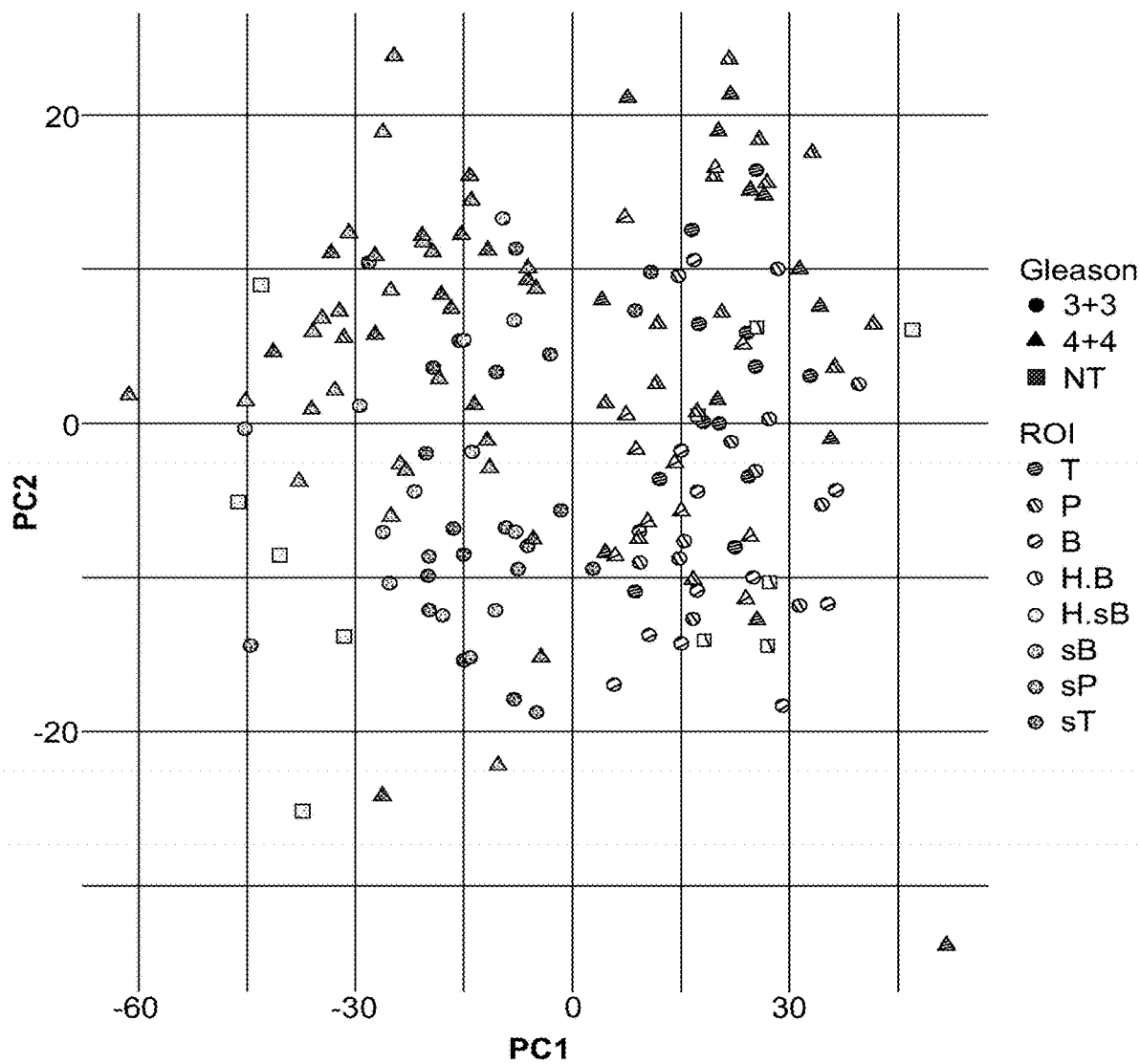
Figure 79B:
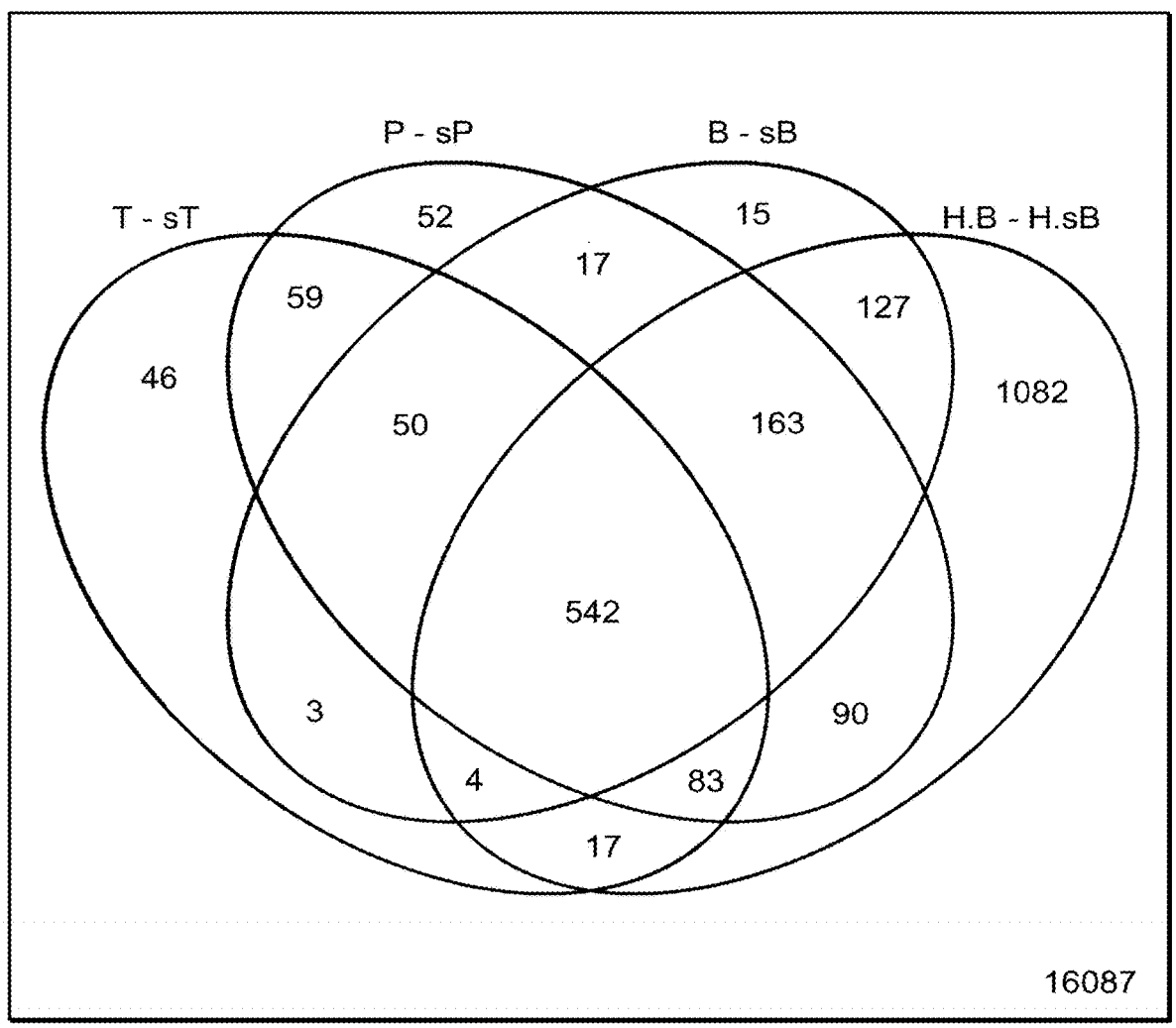

FIG. 79A is a principal components plot showing clear separation of the epithelial and stromal compartment on the first principal component. FIG. 79B is a Venn diagram showing gene associations from the 4 epithelial-stroma comparisons between the three morphologically distinction regions.

DETAILED DESCRIPTION OF THE INVENTION

In prostate cancer, approximately 80% of metastatic sites are found in the bone. The invention is based, at least in part, upon the identification of a gene expression signature (i.e., a "bone homing signature") that predicts the likelihood that prostate cancer will metastasize, e.g., to bone. In some aspects, the invention relates to methods, arrays and kits for diagnosing and monitoring prostate cancer and cancer metastases.

The present invention relates to the pathological progression of prostate cancer to metastatic sites. For example, as described in detail below, the surrounding tumor microenvironment, i.e., the stroma, is modified to appear more bone-like, which is an indication that prostate tumor cells have or will metastizie to metastatic sites, e.g., to bone. That is, when the tumor microenvironment looks like bone and contains structures that act and behave like bone, the likelihood that prostate cancer cells will metastasize to the bone is high.

Stromal cells are connective tissue cells of any organ, e.g., in the uterine mucosa (endometrium), prostate, bone marrow, and the ovary. Stromal cells are cells that support the function of the parenchymal cells of that organ. Fibroblasts and pericytes are among the most common types of stromal cells. As described in detail below, the stroma is involved in human prostate cancer initiation and in a progressive evolution towards a microenvironment similar to that of bone, the prototypic destination of end-stage prostate cancer. As described herein, molecular manipulation of the surrounding tumor microenvironment by the tumor influences prostate cancer initiation, maintenance, and metastatic progression.

As described in detail below, a 29-gene signature was defined herein (7 epithelial and 22 stromal genes), which distinguishes Gleason 6 from Gleason 8, which comprise the "bone homing signature" (Table 1).

In another case, the "bone homing signature" is described in Table 24, which provides a 24 gene signature that distinguishes low grade from high grade Gleason score.

Prostate Cancer

After skin cancer, prostate cancer is the most common cancer in American men, and is the second leading cause of cancer death in American men (only behind lung cancer). As of year 2015, 220,800 new cases were diagnosed, and about 27,540 deaths were due to prostate cancer. About 1 man in 7 will be diagnosed with prostate cancer during his lifetime, and about 1 man in 38 will die of prostate cancer. Rates of prostate cancer vary widely across the world. Prostate cancer is least common among Asian men and most common among black men, with figures for white men in between.

Prostate cancer develops primarily in men over fifty. Although the disease is typically diagnosed during the later years of men, its impact is still significant in that the average life span of a man who dies from prostate cancer is reduced by 9-10 years. The disease is slowly fatal once the tumor spreads outside the prostate. Thus, early detection and accurate staging are of great importance for the accurate choice of therapy, and should improve the success rate of treatments and reduce the mortality rate associated with prostate cancer. Patients diagnosed with a locally confined tumor can be cured by radical prostatectomy or by radiation therapy. No curative treatment is currently available for patients with distantly spread disease. More than 80% of men will develop prostate cancer by the age of 80. However, in the majority of cases, it will be slow-growing and harmless. In such men, diagnosing prostate cancer is over-diagnosis, the needless identification of a technically aberrant condition that will never harm the patient, and treatment in such men exposes them to all of the adverse effects, with no possibility of extending their lives.

In vivo pre-clinical models have shown that while progression from normal prostatic epithelium to invasive cancer is driven by molecular alterations, tumor cells and cells in the cancer microenvironment co-exist, are co-dependent and co-evolve. In addition, stromal cells may acquire the ability to mimic other cell types, e.g., bone cells. Whereas benign epithelium in prostates with and without tumor is similar in gene expression space, stroma away from the tumor is very different from that in cystoprostatectomies.

Prostate Cancer Treatment

Treatment of prostate cancer varies depending on individual situations; however, some treatment options include expectant management or active surveillance, surgery, radiation therapy, cryosurgery (cryotherapy), hormone therapy, chemotherapy, vaccine treatment or bone-directed treatment. The treatments are generally used one at a time, although they may be combined in certain situations.

Active surveillance monitors the cancer closely with regular prostate-specific antigen (PSA) blood tests, digital rectal exams, and ultrasounds. Often, the tests are performed about every 3-6 months. Men with slow-growing cancers often opt for active surveillance because it is not yet known whether treating the cancer with surgery or radiation will increase the patient's life expectancy.

Surgery is often a commonly elected treatment for prostate cancer if the cancer is thought not to have spread outside the glands. The main type of surgery for prostate cancer treatment is called radical prostatectomy. Often, the surgeon removes the entire prostate (or part of it) plus some of the tissue around it, including the seminal vesicles. The surgery may be done by open surgery or through laparoscopic surgery (through small incisions).

Radiation therapy may be used in prostate cancer as the first treatment for low-grade cancer that is sequestered to the prostate gland. Additionally, radiation therapy can be used in a patient as part of the first treatment for cancers that have spread outside of the prostate gland and into adjacent tissues. Radiation therapy is an option in situations in which the cancer recurs or was not completely removed, or in advanced-stage cancer. The therapy may be used to reduce the size of the tumor and to provide relief from symptoms for the patient.

Cryosurgery is a method used to treat early-stage prostate cancer (or if the cancer has recurred after other treatments). This approach involves freezing the cancer by passing cold gasses through hollow probes which are inserted into the prostate. The cold gases create ice balls that destroy the prostate.

The goal of hormone therapy is to reduce the level of male hormones, androgens testosterone and dihydrotestoterone (DHT), and to stop them from affecting prostate cancer cells, by either shrinking prostate cancer cells, or decreasing prostate cancer cell growth rate. Hormone therapy alone often does not cure prostate cancer. Situations in which hormone therapy may be used include: if the cancer has spread enough such that surgery and radiation are not viable options, if the cancer remains or recurs with other treatments, in combination with radiation as an initial treatment, or before radiation to try to shrink the cancer and make the radiation treatment more effective.

Chemotherapy may be used to treat prostate cancer in situations in which the cancer has spread outside the prostate gland. Exemplary chemo drugs include doceaxel, cabazitaxel, mitoxantrone, estramustine, doxorubicin, etoposide and paclitaxel. Alternatively, a vaccine (e.g., sipuleucel-T) may be used to treat advanced prostate cancer that is no longer responding to other treatments. If the cancer has spread outside the prostate, preventing the spread of the cancer to the bones is a major goal of treatment. Bisphosphonates can help relieve pain that has spread to the bones.

In one embodiment, the active compounds are administered in combination therapy, i.e., combined with other agents, e.g., therapeutic agents, that are useful for treating pathological conditions or disorders, such as various forms of cancer, autoimmune disorders and inflammatory diseases. The term "in combination" in this context means that the agents are given substantially contemporaneously, either simultaneously or sequentially. If given sequentially, at the onset of administration of the second compound, the first of the two compounds is preferably still detectable at effective concentrations at the site of treatment.

Prostatic Intraepithelial Neoplasia

PIN (prostatic intraepithelial neoplasia) is a condition in which some prostate cells have begun to look and behave abnormally. The abnormal cells are located in two areas: the lining of tiny sacs known as acini, which give the prostate its sponge-like composition and produce fluid that is added to sperm to create semen; and the lining of the ducts that carry this fluid to the main ejaculatory duct that reaches the penis. When PIN develops, the epithelial cells lining the acini and ducts become abnormal, but the lining itself remains intact. In contrast, when prostate cancer develops, the epithelial lining is ruptured and the malignant cells penetrate into the tissue of the prostate gland itself. To further complicate matters, a related condition known as proliferative inflammatory atrophy (PIA) may also develop in the same area of the prostate, and may also increase cancer risk.

In high-grade PIN, the degree of cellular abnormality is more pronounced than in low-grade PIN. Several pieces of evidence also indicate that high-grade PIN is more likely to lead to the development of prostate cancer. First, high-grade PIN tends to arise in the peripheral zone of the prostate, which is where most cases of prostate cancer develop. Second, an autopsy study has shown that 82% of prostate specimens with cancer also had areas of high-grade PIN, while only 43% of those without prostate cancer had areas of high-grade PIN. Third, most studies that have compared outcomes have found that men with high-grade PIN have an increased risk of being diagnosed with prostate cancer during a follow-up biopsy, when compared with men whose initial biopsies revealed low-grade PIN or normal tissue.

High-grade PIN is characterized by cells that share many genetic and molecular similarities with cancer cells. In high-grade PIN, the cell nucleus, which contains genetic material, is often enlarged, and particular components of the nucleus become abnormal, all of which may contribute to increasingly atypical behavior that can push the cells further down the path to malignancy. Over time, the abnormal cells may begin to proliferate excessively while becoming resistant to the programmed cell death that normally makes room for new cells by eliminating old ones. Malignant tumors grow partly because abnormal cells proliferate more than normal, but also because these cells somehow resist apoptosis. The result may be the out-of-control cell growth characteristic of cancer. High-grade PIN does not always progress to full-fledged invasive prostate cancer.

Prostate Cancer Diagnosis

Prostate cancer is diagnosed by biopsy—the removal of small pieces of the prostate for microscopic examination.

Medical imaging may then be done to determine if the cancer has spread to other parts of the body. However, prior to a biopsy, less invasive testing can be conducted. There are also several other tests that can be used to gather more information about the prostate and the urinary tract. For example, a digital rectal examination (DRE) may allow a doctor to detect prostate abnormalities. Also, cystoscopy shows the urinary tract from inside the bladder, using a thin, flexible camera tube inserted down the urethra. Transrectal ultrasonography creates a picture of the prostate using sound waves from a probe in the rectum.

Gleason Score

A "Gleason score" or "Gleason grade" evaluates the prognosis of men with prostate cancer using samples from a prostate biopsy. Prostate cancer cells in biopsy samples are given a Gleason grade. The grade describes the aggressiveness of the cancer, and its likelihood to grow and spread outside the prostate. The system describes a score between 2 and 10, with 2 being the least aggressive and being 10 the most aggressive. When cancer cells are seen under the microscope, they have different patterns, depending on how quickly they're likely to grow. The pattern is given a grade from 1 to 5, based on how much the arrangement of cancer cells mimics normal prostate cells from glands. This is called the Gleason grade. If a grade is given, it will usually be 3 or higher, as grades 1 and 2 are not cancerous. To be counted, a pattern (grade) needs to occupy more than 5% of the biopsy specimen. The scoring system requires biopsy material (core biopsy or operative specimens) in order to be accurate (cytological preparations cannot be used).

The "Gleason Grade" is a commonly used prostate cancer grading system. There may be more than one grade of cancer in the biopsy sample. An overall Gleason score adds together two Gleason grades. The first (primary grade) is the most common grade in all the samples, and has to be greater than 50% of the total pattern observed). The second (secondary grade) is the highest grade of what's left, and has to be less than 50%, but at least 5% of the pattern of the total pattern observed). When these two grades are added together, the total is called the Gleason score. The higher the Gleason score, the more aggressive the cancer, and the more likely it is to spread. The Gleason system is based exclusively on the architectural pattern of the glands of the prostate tumor. It evaluates how effectively the cells of any particular cancer are able to structure themselves into glands resembling those of normal prostate. The ability of a tumor to mimic normal gland architecture is called its differentiation, and a tumor whose structure is nearly normal (well differentiated) will probably have a biological behavior relatively close to normal (e.g., not very aggressively malignant).

A Gleason grading from very well differentiated (grade 1) to very poorly differentiated (grade 5) is usually done for the most part by viewing the low magnification microscopic image of the cancer. There are important additional details which require higher magnification, and an ability to accurately grade any tumor is achieved only through much training and experience in pathology.

Gleason Grades 1 and 2: These two grades closely resemble normal prostate. These grades seldom occur in the general population confer a prognostic benefit which is only slightly better than grade 3. The glands are round to oval shaped and proportionally large (as compared to a Gleason pattern of 3), and are approximately equal in size and shape to one another. Both of these grades are composed by mass; in grade 2 they are more loosely aggregated, and some glands wander (invade) into the surrounding muscle (stroma).

Gleason Grade 3: This is the most common grade and is also considered well differentiated (like grades 1 and 2). This is because all three grades have a normal "gland unit" like that of a normal prostate; that is, every cell is part of a circular row which forms the lining of a central space (the lumen). The lumen contains prostatic secretion like normal prostate, and each gland unit is surrounded by prostate muscle which keeps the gland units apart. In contrast to grade 2, wandering of glands (invading) into the stroma (muscle) is very prominent and is the main defining feature. The cells are dark rather than pale and the glands often have more variable shapes, and are often long and/or angular. The glands are usually small/micro-glandular in comparison to Gleason 1 or 2 grades.

Gleason Grade 4: This is a fairly common grade and is often (but not always) associated with a poor patient prognosis. Grade 4 is associated with a loss of architecture. For the first time, disruption and loss of the normal gland unit is observed. In fact, grade 4 is identified almost entirely by loss of the ability to form individual, separate gland units, each with its separate lumen (secretory space). Much experience is required for this diagnosis.

Gleason Grade 5: Gleason grade 5 is an important grade because it usually predicts another significant step towards poor prognosis. Grade 5 is less common than grade 4, and it is seldom seen in men whose prostate cancer is diagnosed early in its development. This grade shows a variety of patterns, all of which demonstrate no evidence of any attempt to form gland units. This grade is often called undifferentiated, because its features are not significantly distinguishing to make it look any different from undifferentiated cancers which occur in other organs.

When a pathologist looks at prostate cancer specimens under the microscope and gives them a Gleason grade, an attempt to identify two architectural patterns and assign a Gleason grade to each one is made. There may be a primary or most common pattern and then a secondary or second most common pattern and then a secondary or second most common pattern which the pathologist will seek to describe for each specimen; alternatively there may often be only a single pure grade.

The combined Gleason sums or scores may be determined as follows:

2 (1+1): The lowest possible Gleason score is 2, where both the primary and secondary patterns have a Gleason grade of 1.

5 (2+3): The primary pattern has a Gleason grade of 2 and the secondary pattern has grade 3.

6 (3+3): a pure Gleason pattern. The lowest Gleason score of a cancer is found on a prostate biopsy is a 6. All of the cancer cells found in the biopsy look likely to grow slowly. These cancers may be called well-differentiated or low-grade and are less aggressive.

(7) 3+4: Most of the cancer cells found in the biopsy look likely to grow slowly. There are some cancer cells that look more likely to grow at a more moderate rate.

(7) 4+3: Most of the cancer cells found in the biopsy look likely to grow at a moderate rate; there are some cancer cells that look likely to grow slowly.

(8) 4+4—All of the cancer cells found in the biopsy look likely to grow at a moderately quick rate; these cancers tend to be aggressive.

(9) 4+5—Most of the cancer cells found in the biopsy look likely to grow at a moderately quick rate, and there are some cancer cells that are likely to grow more quickly.

(9) 5+4—Most of the cancer cells found in the biopsy look likely to grow quickly.

(10) 5+5—All of the cancer cells found in the biopsy look likely to grow quickly.

Tumors with Gleason scores of 8-10 tend to be advanced neoplasms that are unlikely to be cured. Although prostate cancers may become more aggressive over time, most often, the Gleason score remains stable for several years.

Gene Expression Profiling

Gene expression profiling (GEP) in the tumor-adjacent stroma is strongly associated with Gleason grade. In general, methods of gene expression profiling can be divided into two large groups: methods based on hybridization analysis of polynucleotides, and methods based on sequencing of polynucleotides. Methods known in the art for the quantification of mRNA expression in a sample include northern blotting and in situ hybridization, RNAse protection assays, and reverse transcription polymerase chain reaction (RT-PCR). Alternatively, antibodies are employed that recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS). For example, RT-PCR is used to compare mRNA levels in different sample populations, in normal and tumor tissues, with or without drug treatment, to characterize patterns of gene expression, to discriminate between closely related mRNAs, and/or to analyze RNA structure.

In some cases, a first step in gene expression profiling by RT-PCR is the reverse transcription of the RNA template into cDNA, followed by amplification in a PCR reaction. For example, extracted RNA is reverse-transcribed using a GeneAmp RNA PCR kit (Perkin Elmer, Calif., USA), following the manufacturer's instructions. The cDNA is then used as template in a subsequent PCR amplification and quantitative analysis using, for example, a TaqMan® (Life Technologies, Inc., Grand Island, N.Y.) assay.

Microarrays

Differential gene expression can also be identified, or confirmed using a microarray technique. In these methods, polynucleotide sequences of interest (including cDNAs and oligonucleotides) are plated, or arrayed, on a microchip substrate. The arrayed sequences are then hybridized with specific DNA probes from cells or tissues of interest. Just as in the RT-PCR method, the source of mRNA typically is total RNA isolated from human tumors or tumor cell lines and corresponding normal tissues or cell lines. Thus, RNA is isolated from a variety of primary tumors or tumor cell lines. If the source of mRNA is a primary tumor, mRNA is extracted from frozen or archived tissue samples.

In the microarray technique, PCR-amplified inserts of cDNA clones are applied to a substrate in a dense array. The microarrayed genes, immobilized on the microchip, are suitable for hybridization under stringent conditions.

In some cases, fluorescently labeled cDNA probes are generated through incorporation of fluorescent nucleotides by reverse transcription of RNA extracted from tissues of interest (e.g., prostate tissue). Labeled cDNA probes applied to the chip hybridize with specificity to loci of DNA on the array. After washing to remove non-specifically bound probes, the chip is scanned by confocal laser microscopy or by another detection method, such as a charge-coupled device (CCD) camera. Quantification of hybridization of each arrayed element allows for assessment of corresponding mRNA abundance.

In some configurations, dual color fluorescence is used. With dual color fluorescence, separately labeled cDNA probes generated from two sources of RNA are hybridized pairwise to the array. The relative abundance of the transcripts from the two sources corresponding to each specified gene is thus determined simultaneously. In various configurations, the miniaturized scale of the hybridization can afford a convenient and rapid evaluation of the expression pattern for large numbers of genes. In various configurations, such methods can have sensitivity required to detect rare transcripts, which are expressed at fewer than 1000, fewer than 100, or fewer than 10 copies per cell. In various configurations, such methods can detect at least approximately two-fold differences in expression levels (Schena et al., Proc. Natl. Acad. Sci. USA 93(2): 106-149 (1996)). In various configurations, microarray analysis is performed by commercially available equipment, following manufacturer's protocols, such as by using the Affymetrix GenChip technology, or Incyte's microarray technology.

RNA-Seq

RNA sequencing (RNA-seq), also called whole transcriptome shotgun sequencing (WTSS), uses next-generation sequencing (NGS) to reveal the presence and quantity of RNA in a biological sample at a given moment in time.

RNA-Seq is used to analyze the continually changing cellular transcriptome. See, e.g., Wang et al., 2009 Nat Rev Genet, 10(1): 57-63, incorporated herein by reference. Specifically, RNA-Seq facilitates the ability to look at alternative gene spliced transcripts, post-transcriptional modifications, gene fusion, mutations/SNPs and changes in gene expression. In addition to mRNA transcripts, RNA-Seq can look at different populations of RNA to include total RNA, small RNA, such as miRNA, tRNA, and ribosomal profiling. RNA-Seq can also be used to determine exon/intron boundaries and verify or amend previously annotated 5' and 3' gene boundaries.

Prior to RNA-Seq, gene expression studies were done with hybridization-based microarrays. Issues with microarrays include cross-hybridization artifacts, poor quantification of lowly and highly expressed genes, and needing to know the sequence of interest. Because of these technical issues, transcriptomics transitioned to sequencing-based methods. These progressed from Sanger sequencing of Expressed Sequence Tag libraries, to chemical tag-based methods (e.g., serial analysis of gene expression), and finally to the current technology, NGS of cDNA (notably RNA-Seq).

Gene Set Enrichment Analysis

By "ssGSEA" is meant single-sample Gene Set Enrichment Analysis. When analyzing genome-wide transcription profiles from microarray data, a typical goal is to find genes significantly differentially correlated with distinct sample classes defined by a particular phenotype (e.g., tumor vs. normal). These findings can be used to provide insights into the underlying biological mechanisms or to classify (predict the phenotype of) a new sample. Gene Set Enrichment Analysis (GSEA) evaluates whether a priori defined sets of genes, associated with particular biological processes (such as pathways), chromosomal locations, or experimental results are enriched at either the top or bottom of a list of differentially expressed genes ranked by some measure of differences in a gene's expression across sample classes. Examples of ranking metrics are fold change for categorical phenotypes (e.g., tumor vs. normal) and Pearson correlation for continuous phenotypes (e.g., age). Enrichment provides evidence for the coordinate up- or down-regulation of a gene set's members and the activation or repression of some corresponding biological process.

Where GSEA generates a gene set's enrichment score with respect to phenotypic differences across a collection of samples within a dataset, ssGSEA calculates a separate enrichment score for each pairing of sample and gene set, independent of phenotype labeling. In this manner, ssGSEA transforms a single sample's gene expression profile to a gene set enrichment profile. A gene set's enrichment score represents the activity level of the biological process in which the gene set's members are coordinately up- or down-regulated. This transformation allows researchers to characterize cell state in terms of the activity levels of biological processes and pathways rather than through the expression levels of individual genes.

In working with the transformed data, the goal is to find biological processes that are differentially active across the phenotype of interest and to use these measures of process activity to characterize the phenotype. Thus, the benefit here is that the ssGSEA projection transforms the data to a higher-level (pathways instead of genes) space representing a more biologically interpretable set of features on which analytic methods can be applied.

Bone Homing Signature

As described in Table 1, a 29-gene signature was defined herein (7 epithelial and 22 stromal genes), which distinguishes Gleason 6 from Gleason 8, which comprise the "bone homing signature."

In another case, the "bone homing signature" is described in Table 24, which provides a 24 gene signature that distinguishes low grade from high grade Gleason score.

Exemplary distinguishing genes are provided below.

An exemplary human ALCAM amino acid sequence is set forth the below (SEQ ID NO: 1; GenBank Accession No: AAI37097, Version 1 (GI: 187951595), incorporated herein by reference):

```
  1 meskgasscr llfcllisat vfrpglgwyt vnsaygdtii iper-
    ldvpqn lmfgkwkyek 61 pdgspvfiaf rsstkksvqy ddvpeykdrl nlsenytlsi snarisdekr fvcmlvt-
    edn 121 vfeaptivkv fkqpskpeiv skalfleteq lkklgdcise dsypdg-
    nitw yrngkvlhpl 181 egavviifkk emdpvtqlyt mtstleyktt kadiqmpftc svtyygpsgq ktihse-
    qavf 241 diyypteqvt iqvlppknai kegdnitlkc lgngnpppee flfylpgqpe girssn-
    tytl 301 tdvrrnatgd ykcslidkks miastaitvh yldlslnpsg evtrqigdal pvscti-
    sasr 361 natvvwmkdn irlrsspsfs slhygdagny vcetalqeve glkkreslt1 iveg-
    kpqikm 421 tkktdpsgls ktiichvegf pkpaiqwtit gsgsvinqte espyingryy skiiis-
    peen 481 vtltctaenq lertvnslnv saisipehde adeisdenre kvndqakliv givvgll-
    laa 541 lvagvvywly mkksktaskh vnkdlgnmee nkkleennhk tea
```

Exemplary regions or fragments of ALCAM include residues 38-113 (immunoglobulin V-type region), 260-330 (immunoglobulin V-type region), 334-412 (immunoglobulin V-type region), and 339-393 (immunoglobulin V-type region).

An exemplary human ALCAM nucleotide sequence (the start and stop codons for the coding sequences are bold and underlined) is set forth below (SEQ ID NO: 2; GenBank Accession No. BC137096, Version 1 (GI: 187951594), incorporated herein by reference):

```
  1 tgtctgg-
    gag aagacgctgc ccctgcgtcg ggacccgcca gcgcgcgggc accgcggggc 61 ccgggacgac gccccctcct gcggcgtgga ctccgtcagt ggcccaccaa gaaggag-
    gag 121 gaat
    atggaa tccaaggggg ccagttcctg ccgtctgctc ttctgcctct tgatctccgc 181 caccgtcttc aggccaggcc ttggatggta tactgtaaat tcagcatatg gagatac-
    cat 241 tatcataccct tgccgacttg acgtacctca gaatct-
    catg tttggcaaat ggaaatatga 301 aaagcccgat ggctccccag tatttattgc cttcagatcc tcta-
    caaaga aaagtgtgca
```

-continued

```
 361 gtacgacgat gtaccagaat acaaagacag att-
     gaacctc tcagaaaact acactttgtc 421 tatcagtaat gcaaggatca gtgatgaaaa gagatttgtg tgcatgctag taact-
     gagga 481 caacgtgttt gaggcaccta caatagtcaa ggtgttcaag caaccatcta aacct-
     gaaat 541 tgtaagcaaa gcactgtttc tcgaaacaga gcagctaaaa aagttgggtg actgcat-
     ttc 601 agaagacagt tatccagatg gcaatatcac atggtacagg aatggaaaag tgcta-
     catcc 661 ccttgaagga gcggtggtca taatttt-
     taa aaaggaaatg gacccagtga ctcagctcta 721 taccatgact tccaccctgg agtacaagac aaccaaggct gacatacaaa tgccatt-
     cac 781 ctgctcggtg acatattatg gaccatctgg ccagaaaaca attcat-
     tctg aacaggcagt 841 atttgatatt tactatccta cagagcaggt gacaatacaa gtgctgc-
     cac caaaaaatgc 901 catcaaagaa ggggataaca tcactcttaa atgct-
     taggg aatggcaacc ctcccccaga 961 ggaattttttg ttttacttac caggacagcc cgaaggaata agaagctcaa atactta-
     cac 1021 actaacggat gtgaggcgca atgcaacagg agacta-
     caag tgttccctga tagacaaaaa 1081 aagcatgatt gcttcaacag ccatcacagt tcactatttg gatttgtcct taaacc-
     caag 1141 tggagaagtg actagacaga ttggt-
     gatgc cctacccgtg tcatgcacaa tatctgctag 1201 caggaatgca actgtggtat ggatgaaaga taacatcagg cttcgatcta gcccgt-
     catt 1261 ttctagtctt cattatcagg atgctggaaa ctatgtctgc gaaactgctc tgcag-
     gaggt 1321 tgaaggacta agaaaagag agtcattgac tctcat-
     tgta gaaggcaaac ctcaaataaa 1381 aatgacaaag aaaactgatc ccagtggact atctaaaaca ataatctgcc atgtg-
     gaagg 1441 tttttccaaag ccagccattc aatggacaat tactggcagt ggaagcgtca taaac-
     caaac 1501 agaggaatct ccttatatta atggcaggta ttatagtaaa attatcatttt ccccct-
     gaaga 1561 gaatgttaca ttaacttgca cagcagaaaa ccaactggag agaacagtaa actcctt-
     gaa 1621 tgtctctgct ataagtattc cagaacacga tgaggcagac gaga-
     taagtg atgaaaacag 1681 agaaaaggtg aatgaccagg caaaactaat tgtgg-
     gaatc gttgttggtc tcctccttgc 1741 tgcccttgtt gctggtgtcg tctactggct gtacatgaag aagtcaaaga ctgcat-
     caaa 1801 acatgtaaac aaggacctcg gtaatatgga agaaaacaaa aagt-
     tagaag aaaacaatca 1861 caaaactgaa gcc
     taagaga gaaactgtcc tagttgtcca gagataaaaa tcatatagac 1921 caattgaagc atgaacgtgg attgtattta agacataaac aaaga-
     cattg acagcaattc 1981 atggttcaag tattaagcag ttcattctac caagctgtca caggttttca gagaat-
     tatc
```

-continued

```
2041 tcaagtaaaa caaatgaaat ttaattacaa acaataagaa caagttttgg cagccat-
     gat 2101 aataggtcat atgttgtgtt tggttcaatt ttttttccgt aaatgtctgc actgag-
     gatt 2161 tcttttggt ttgcctttta tgtaaatttt ttacgtagct atttt-
     tatac actgtaagct 2221 ttgttctggg agttgctgtt aatctgatgt ataatgtaat gttttattt caat-
     tgttta 2281 tatggataat ctgagcaggt acatttctga ttctgattgc tatcagcaat gccc-
     caaact 2341 ttctcataag cacctaaaac ccaaaggtgg cagcttgtga agattgggga cactcat-
     att 2401 gccctaatta aaaactgtga tttttatcac aagggagggg aggccgagag tcagact-
     gat 2461 agacaccata ggagccgact ctttgatatg ccaccagcga actctcaga
```

Exemplary regions or fragments of ALCAM include bases 125-1876 (activated leukocyte cell adhesion molecule).

An exemplary human LUM amino acid sequence is set forth below (SEQ ID NO: 3; GenBank Accession No. NP_002336, Version 1 (GI: 4505047), incorporated herein by reference):

```
  1  mslsaftlfl aliggtsgqy ydydfplsiy gqsspncape cncpe-
     sypsa mycdelklks 61  vpmvppgiky lylrnnqidh idekafenvt dlqwlildhn llenskikgr vfsk-
     lkqlkk 121  lhinhnnlte svgplpksle dlqlthnkit klgsfeglvn ltfihlqhnr lkeday-
     saaf 181  kglksleyld isfnqiarlp sglpvslltl yldnnkisni pdeyfkrfna lqylrlshne 241  ladsgipgns fnvssiveld lsynklknip tvnenlenyy levnglekfd iksfck-
     ilgp 301  lsyskikhlr ldgnrisets lppdmyeclr vanevtln
```

Exemplary regions or fragments of LUM include residues 1-18 (signal peptide), 37-71 (leucine rich repeats), 66-128 (leucine rich repeats), 75-260 (substrate binding site), and 161-185 (leucine rich repeats).

An exemplary human LUM nucleotide sequence (the start and stop codons for the coding sequences are bold and underlined) is set forth below (SEQ ID NO: 4; GenBank Accession No. NM_002345, Version 3 (GI: 61742794), incorporated herein by reference):

```
  1  acagtgagct tccttatttg aagcaggact caattcttgg ttaaaagcta tggtat-
     ttga 61  gctagttaaa cacatatctc tctcccattc catagg-
     gaat gagctgggct gtcctttctc 121  cccacgttca cctgcacttc gttagagagc agtgttcaca tgccacacca caa-
     gatcccc 181  acaatgacat aactccattc aga-
     gactggc gtgactgggc tgggtctccc caccccctt 241  cagctcttgt atcactcaga atctggcagc cagttccgtc ctgacagagt tcacag-
     cata 301  tattggtgga ttcttgtcca tagtgcatct gctttaagaa ttaacgaaag cagtgt-
     caag 361  acagtaagga ttcaaaccat ttgccaaaa
     a tgagtctaag tgcatttact ctcttcctgg
```

-continued

```
 421 cattgattgg tggtaccagt ggccagtact atgattatga ttttccccta tcaatttatg 481 ggcaatcatc accaaactgt gcaccagaat gtaactgccc tgaaagctac ccaagtgcca 541 tgtactgtga tgagctgaaa ttgaaaagtg taccaatggt gcctcctgga atcaagtatc 601 tttaccttag gaataaccag attgaccata ttgatgaaaa ggcctttgag aatgtaactg 661 atctgcagtg gctcattcta gatcacaacc ttctagaaaa ctccaagata aagggagag 721 ttttctctaa attgaaacaa ctgaagaagc tgcatataaa ccacaacaac ctgacagagt 781 ctgtgggccc acttcccaaa tctctggagg atctgcagct tactcataac aagatcacaa 841 agctgggctc ttttgaagga ttggtaaacc tgaccttcat ccatctccag cacaatcggc 901 tgaaagagga tgctgtttca gctgctttta aaggtcttaa atcactcgaa taccttgact 961 tgagcttcaa tcagatagcc agactgcctt ctggtctccc tgtctctctt ctaactctct 1021 acttagacaa caataagatc agcaacatcc ctgatgagta tttcaagcgt tttaatgcat 1081 tgcagtatct gcgtttatct cacaacgaac tggctgatag tggaatacct ggaaattctt 1141 tcaatgtgtc atccctggtt gagctggatc tgtcctataa caagcttaaa aacataccaa 1201 ctgtcaatga aaaccttgaa aactattacc tggaggtcaa tcaacttgag aagtttgaca 1261 taaagagctt ctgcaagatc ctggggccat atcctactc caagatcaag cattgcgtt 1321 tggatggcaa tcgcatctca gaaccagtc ttccaccgga tatgtatgaa tgtctacgtg 1381 ttgctaacga agtcactctt aatt
     aatatc tgtatcctgg aacaatattt tatggttatg 1441 tttttctgtg tgtcagtttt catagtatcc atattttatt actgtttatt acttccatga 1501 attttaaaat ctgagggaaa tgttttgtaa acatttattt tttttaaaga aaagatgaaa 1561 ggcaggccta tttcatcaca agaacacaca catatacacg aatagacatc aaactcaatg 1621 ctttatttgt aaatttagtg tttttttatt tctactgtca aatgatgtgc aaaaccttt 1681 actggttgca tggaaatcag ccaagtttta taatccttaa atcttaatgt tcctcaaagc 1741 ttggattaaa tacatatgga tgttactctc ttgcaccaaa ttatcttgat acattcaaat 1801 ttgtctggtt aaaaaatagg tggtagatat tgaggccaag aatattgcaa aatacatgaa 1861 gcttcatgca cttaaagaag tatttttaga ataagaattt gcatacttac ctagtgaaac 1921 ttttctagaa ttatttttca ctctaagtca tgtatgtttc tctttgatta tttgcatgtt 1981 atgtttaata agctactagc aaaataaaac atagcaaatg gcatcactgt gtttgacttc
```

```
2041 ttgtgaaatt tctgtacttt gtatataaaa tacataaaac aatagattag aaat-
     caaaag 2101 atatctctgg cctgca
```

Exemplary regions or fragments of LUM include bases 2003-2008 (polyA signal sequence), and 1302-1367.

An exemplary human COL1A1 amino acid sequence is set forth below (SEQ ID NO: 5; GenBank Accession No. CAA6726, Version 1 (GI: 1888409), incorporated herein by reference):

```
   1 mfsfvdlrll lllaatallt hgqeeggveg qdedippitc vqnglryhdr dvwk-
     peperi 61 cvcdngkvlc ddvicde-
     tkn cpgaevpege ccpvcpdgse sptdqettgv egpkgdtgpr 121 gprgpagppg rdgipgqpgl pgppgppgpp gppglggnfa pqlsygydek stg-
     gisvpgp 181 mgpsgprglp gpp-
     gapgpqg fqgppgepge pgasgpmgpr gppgppgkng ddgeagkpgr 241 pgergppgpq garglpgtag lpgmkghrgf sgldgakgda gpagpkgepg spgen-
     gapgq 301 mgprglpger grpgapgpag argndgatga agppgptgpa gppgfp-
     gavg akgeagpqgp 361 rgsegpqgvr gepgppgpag aagpagnpga dgqpgakgan gap-
     giagapg fpgargpsgp 421 qgpggppgpk gnsgepgapg skgdtgakge pgpvgvqgpp gpa-
     geegkrg argepgptgl 481 pgppgerggp gsrgfpgadg vagpkgpage rgspgpagpk gspgeagrpg eaglp-
     gakgl 541 tgspgspgpd gktgppgpag qdgrpgppgp pgargqagvm gfpgpkgaag epgk-
     agergv 601 pgppgavgpa gkdgea-
     gaqg ppgpagpage rgeqgpagsp gfqglpgpag ppgeagkpge 661 qgvpgdlgap gpsgargerg fpgergvqgp pgpagprgan gapgndgakg dagap-
     gapgs 721 qgapglqgmp gergaaglpg pkgdrgdagp kgadgspgkd gvrgltgpig ppgpa-
     gapgd 781 kgesgpsgpa gptgargapg drgepgppgp agfagppgad gqp-
     gakgepg dagakgdagp 841 pgpagpagpp gpignvgapg akgargsagp pgatgfp-
     gaa grvgppgpsg nagppgppgp 901 agkeggkgpr getgpagrpg evgppgppgp agekgspgad gpa-
     gapgtpg pqgiagqrgv 961 vglpgqrger gfpglpgpsg epgkqgpsga sgergppgpm gppglagppg esgre-
     gapga 1021 egspgrdgsp gakgdrgetg pagppgapga pgapgpvgpa gksgdrget
```

Exemplary regions or fragments of COL1A1 include residues 236-295 (triple helix repeat), 452-535 (triple helix repeat), and 701-759 (triple helix repeat).

An exemplary human COL1A1 nucleotide sequence (the start and stop codons for the coding sequences are bold and underlined) is set forth below (SEQ ID NO: 6; GenBank Accession No. X98705, Version 1 (GI: 1888408), incorporated herein by reference):

```
   1  acatcttcag cctgggcacc cgccaagcgt tttaagtcga agagtggcag gggaggcctt
  61  gagcctcagc tccatgccac gtgtaaagga tgcttgaaa ctgtctgcct cggccctgg
 121  gaggaaggcc tggaactgga catggggtg gtggctgtca cacgccaggc acacaaaact
 181  ccaaagccag ggatcccaa atatccttca gaaccccagg cccatgatgt agcaaccccc
 241  aattcacacc ttggaggttt caactcttct ttaagatggg cgtgggaaag cctgatggg
 301  aaacatatgg ggaggggcgg ggagctgcag gcaggagccc ttcttactac gaaaacccaa
 361  gaagcaagga agtggacagg tcactaaccc tcatactacc aagccctgcg gcaccctgcc
 421  ctagaccacc actctaaatg tctgttccct ccaaaaacag daccccctgtc gcctattagg
 481  gagggggtct cttggaactg acccacagta gggggcagga ctttggtggg ttcaagaact
 541  gccatctcag cacctcagcc ccctagtcct gccctgcagt cgctggcact aggcgggggc
 601  agaccctggg ccacaagttg ctgccacatg gtcgggataa ttgatgaagg tccatccctc
 661  cattgctgtc tccagccctg cctctctgga aactctatat tttccctttta attatagccc
 721  ctgcagtctc cctctgctgc cccacccgca ccgctcatcc tggctgccca cggccagccg
 781  gccagccgac gtggctccct ccccttctgt tccttttttt tcccctttgc cttcgttgca
 841  caaaaccagc tgggggaggg cgtggagagg ggcgggggga ggcaatggaa tcttgatgg
 901  tttgggggag gcgggactcc ccgcttccac gtttgcagct ctggagcacc cggggtgggg
 961  agctgcacag gagggagaga aatgaacagg gcactgcaag gagaccccca ggccttctct
1021  cagccctaca gagtttctca ggacgaggta gattgggggtt gaggcagagc cttgttgggg
1081  gaatgggaca tggaggaaga aaggacgtgg agttctagag ccatcttcct tagatatagc
1141  ctgctgtcct tcgggtcccc agaccctttc agagtgtaca gatgatctctc tctggttcct
1201  aaggcataga gcaatgaccg ggatttttcaa gaaagagatg aggcagtggg aagtagcccc
1261  taaaacaaag tcaatcatcc tctgcagccc atcccacacc cccaaaggaa agttccaccc
1321  agacacccaa aatatcccat acatcccaa cactgagtcc aggtacaact ggagaagggg
1381  ctttatgcag ctcccagaaa gacacccctt tagctaagtg ccctccctcc acccaggttc
1441  tctctggttt gactgtgctg ggaaggaggg tctctaagca gcccctggcc acagccatgg
1501  caaacaaaac tcttctctaa gtcaccaatg atcacaggcc tcccactaaa aatacttccc
1561  aactctgggg tggaagagtt tgggggatga atttttaggg gattgcaagc cccaatcccc
1621  acctctgtgt ccctagaatc ccccacccct accttggctg ctccatcacc caaccaccaa
1681  agctttcttc tgcagaggcc acctagtcat gtttctcacc ctgcacctca gcctccccac
```

-continued

```
1741 tccatctctc aatcatgcct agggtttgga ggaaggcatt tgattctgtt ctggagcaca 1801 gcagaagaat tgacatcctc aaaattaaaa ctcccttgcc tgcaccctc cctcagatat 1861 ctgattctta atgtctagaa aggaatctgt aaattgttcc ccaaatattc ctaagctcca 1921 tccctagcc acaccagaag acacccccaa acaggcacat cttttaatt cccagcttcc 1981 tctgttttgg agaggtcctc agcatgcctc tttatgcccc tccctagct cttgccagga 2041 tatcagaggg tgactggggc acagccagga ggaccccctc cccacaccc ccaaccttc 2101 caccttgga agtctcccca cccagctccc cagttcccca gttccacttc ttctagattg 2161 gaggtcccag gaagagagca gaggggcacc cctacccact ggttagccca cgccattctg 2221 aggacccagc tgcaccccta ccacagcacc tctggcccag gctgggctgg ggggctgggg 2281 aggcagagct gcgaagaggg gagatgtggg gtggactccc ttccctcctc ctcccctct 2341 ccattccaac tcccaaattg ggggccgggc caggcagctc tgattggctg gggcacgggc 2401 ggccggctcc ccctctccga ggggcagggt tcctccctgc tctccatcag gacagtataa 2461 aagggggccg gccagtcgt cggagcagac gggagtttct cctcgggtc ggagcaggag 2521 gcacgcggag tgtgaggcca cgcataagcg gacgctaacc ccctcccag ccacaaagag 2581 tctacatgtc tagggtctag ac
     atgttcag ctttgtggac ctccggctcc tgctcctctt 2641 agcggccacc gccctcctga cgcacggcca agaggaaggc caagtcgagg gccaagacga 2701 agacagtaag tcccaaactt ttgggagtgc aaggatactc tatatcgcgc cttgcgcttg 2761 gtcccggggg ccgcggctta aaacgagacg tggatgatcc ggagactcgg gaatggaagg 2821 gagatgatga gggctcttcc tcggcgccct gagacaggag ggagctcacc ctggggcgag 2881 gttggggttg aacgcgcccc gggagcggga ggtgagggtg gagcgcggcg tgagttggtg 2941 caagagagaa tcccgagcgc gcaaccgggg aagtggggat ctgggtgcag agtgaggaaa 3001 gcacgtcgaa gatgggatgg gggcgccgag cggggcattt gaagcccaag atgtagaagc 3061 aatcaggaag gccgtgggat gattcataag gaaagatgc cctctctgcg ggctagagtg 3121 ttgctggggc cgtggggtg ctgggcagcc gcggaggggg tgcggagcgt gggcgggtgg 3181 aggatgagaa actttggcgc ggactcggcg gggcggggtc cttgcgcccc ctgctgaccg 3241 atgctgagca ctgcgtctcc cggtccaacg cttactgggg caggagccgg agcggaaga 3301 cccgggttat tgctgggtgc ggaccccac ctctagatct ggaaagtaaa gccaggatg 3361 gggcagccca agcctcttaa agaggtagtc gggccggtga ggtcggcccc gccccggccc 3421 cattgcttag cgttgcccga cacctagtgg ccgtctgggg agccgctagc gcggtgggag
```

-continued

```
3481 tggttagcta acttctggac tat-
     tgcgga cttttggtt ctttggctaa aagtgacctg 3541 gaggcattgg ctggctttgg gggactgggg atgccccga gagcgggctt ttaa-
     gatgtc 3601 taggtgctgg aggttagggt gtctcctaat tttgaggtac attt-
     caagtc ttgggggggc 3661 gtcccttcca atcagccgct cccattctct tagccccgcc ccgc-
     caccc cacatgccca 3721 gggaatgggg gcgggat-
     gag ggatggacct cccttctctc ctccctcgcc ctcctcctgt 3781 ctctaccacg caagccactc cccacgagcc tgccctcccg atggggcccc tcctat-
     tctc 3841 cccccgccct cccctctca ccctgtggtt ttattt-
     cact tggcttcagc gccaatgggc 3901 tgaggttgga gttggaagcc accgcggact aaagctttgt ttaaat-
     tcct gagaactgga 3961 aagagttaca gcctccctgg ccaggcgcct cggcgctgtc acccgcgctg atgag-
     gagca 4021 ggcgagcttt taaggatttg aggaaagaag aacgggggga ggggcgg-
     gaa gtgaaaaatc 4081 caagtgtgcc tcttagaccc gggggaaagg tggttaagct gggggttgca gtcac-
     tactg 4141 acaacgcccc tcttccgcct gtcccagtcc caccaatcac ctgcgta-
     cag aacggcctca 4201 ggtaccatga ccga-
     gacgtg tggaaacccg agccctgccg gatctgcgtc tgcgacaacg 4261 gcaaggtgtt gtgcgatgac gtgatctgtg acgagac-
     caa gaactgcccc ggcgccgaag 4321 tccccgaggg cgagtgctgt cccgtctgcc ccgacggctc aggtgcgctg cgctcggcct 4381 ggggcctggg gctggggctg ggggtggtcg gcgctcgctg gccctccgtg ctg-
     gaggcct 4441 ctgccgacgg gagcag-
     catt agcaaacctt ggctctaacg ggcgtctctt cgtcccctag 4501 agtcaccac cgaccaagaa accaccggcg tcgaggtaat ctcctgccct cgaat-
     tttgc 4561 ccctgcgcgg cccgtgactc ctcacagtcc tcccttctct aacctggcct cttgtttctt 4621 ctcccccaat cccacaggga cccaagg-
     gag acactggccc ccgaggccca agggtaagcg 4681 ttgcactctg ggctgtgggg ggctgcaggt gggcatggct ctcggcccca cgct-
     cacccc 4741 ggccccgccc tctccccctg cagggacccg caggccccc tggccgagat ggcatccctg 4801 gacagcctgg acttcccgga ccccccggac ccccggacc tccggaccc cctggcctcg 4861 gag-
     gagtaag tggagaggcc ttgtgtgtcc actctcccct gttttgtttt tgttttttgg 4921 cagatgacat aattttatac tttgaaataa ttt-
     caaactt acagaaaagt tgcaagaatc 4981 ctacaggaaa ctctcacata cccttcacag tttgtgacat gtgctttt-
     att agtctctgtt 5041 tatgtatatg tatctttttt tttctgaact gttt-
     gagcaa gttgctaaca tcaggctctt 5101 ttgcgcctaa atacttaggt gtgttttttcc taaaaacaag agcat-
     tctct taactgacct 5161 acacaatgat taaatt-
     cact ctctaatgtg cagtccgtac tcaaagttca ccgatgtccc 5221 gataatgtcc tttatagatt ccaccccca ccacccccaat ctgggatcca gtccag-
     gatt
```

```
5281 atgtattgca tttaatcatc atgtctctag tttccacaaa tgtagaacgt tcctca-
     gact
5341 ttctttgtct ttagtggcac tgggagtttt gat-
     gagtcca gttgttttgc agactgtccc
5401 tcaatttggg attgtctcat tagattagat gcagg-
     gatgc atctttggca ggaatgtctt
5461 aaaagcaatg ttattcttct cagcacatca caccaggaag tgcat-
     gatgt cagtttcttc
5521 catcctcagt gccgtcttct gccttt-
     caat tcactgtcct cactctgact tctcttgttt
5581 gttctagaac tttgctcccc agctgtctta tggctatgat gagaaatcaa ccggag-
     gaat
5641 ttccgtgcct ggccccatgg tgagccagca gggggag-
     cat ggatgacaga agagagaatg
5701 ggtatccaga ggatgtgggc atacgcggct ggtatacaca gcttgggagg tccatat-
     cac
5761 ctttgggacc tcagagtcca gaaaggatgc aagacgactg ggtggtccca acagg-
     catga
5821 atgactacat ccacatgctt tcctacagag ggatcac-
     cat gacccccctt tcttctccct
5881 ctatagggtc cctctggtcc tcgtggtctc cctggccccc ctggtgcacc tgt-
     gagtatc
5941 caggacgtct tcatatgcct ccttgggctt tggtcttttg gagggaagac tgggat-
     gagg
6001 gcaggagaga tgctcagaga tctcttggta agattg-
     gaga aggttgacag ggacttgtct
6061 tctaacccat cttttccett cttctcaagg gtccccaagg cttc-
     caaggt cccctggtg
6121 agcctggcga gcctggagct tcagtaagca ctctctatac agattcatac tccttc-
     taca
6181 aacacacaga ctctcctata gaagaatccc aggcctgggg tcttcct-
     tac ctcttccctt
6241 caatcccagc cttcccttc tttttttctt atccatattc taaccacctc ttc-
     tatctttt
6301 tctagggtcc catgggtccc cgaggtcccc caggtccccc tggaaagaat ggagat-
     gatg
6361 taagtatccc cagcaagaag ataccatctg acccccatggc ctc-
     catgggt tgggtcctgc
6421 aatttccact ccaccacatt tgggaac-
     gat actcagagga aggagggcaa gtcctctctg
6481 atgcacggac tgccctggaa caatgatctt ttcgcttagt gagat-
     gattc catgtcccca
6541 acaaagtgac tgttctcctc accccagcca ccttagagca atccc-
     caacc ccatcccttt
6601 ggggaaattg gtgcgcagat ggt-
     gaaatta aaatgctggt gacagaagta gacagaaatt
6661 cctttagagg cactcagatt tcaccaaacg aaggtttcac tgtagattta aact-
     gagctc
6721 tagattcaaa gataagattc tgggccccca aacctgacct gcaacaatcc aaagaa-
     gact
6781 gagaccttct ccactttcc agcccctagg cggtggtggg gaggcagagg cat-
     gatggtc
6841 ttttctctcc ctctcagggg gaagctggaa aacctggtcg tcctggt-
     gag cgtgggcctc
6901 ctgggcctca ggtgagcagg gggctgtggc tgaacctggg ctt-
     cactgca cttgggcttc
```

```
6961 atttaggagc tgggtccaca gtgatgtgtt ctaatggccc ttccttgtct tctt-
     catctc 7021 tctccagggt gctcgaggat tgcccggaac agctggcctc cctg-
     gaatga agggacacag 7081 agtgagtcac ctttgagtca tttaagctcc ccaagtccct agcat-
     acccc catccagtcc 7141 cagcctcttc cccaaaagat cct-
     gagttgc atcatggtgg gtggcagcta cagaagtccc 7201 aagggacaga gagtggacat ccaaaagcac ctccctccat gggaaagcag tcccgat-
     taa 7261 acgattgggt gagatctaga gccagttggg gtttagtcta gctcagaaac aaagg-
     gatgg 7321 cggtgatgac ctcccaaggc tctttctcag atctaggtgg atgtcaaggc tgttc-
     caccc 7381 cctccacagg ttcttacctt ctacctcttt cctgctttag ggtttcagtg gtttg-
     gatgg 7441 tgccaaggga gatgctggtc ctgctggtcc taaggtaaga ggctgtctga acat-
     catggt 7501 cctccacatc cccagagtcc caccatgaat gaatttctca ctcattattc tctgatc-
     tac 7561 agggtgagcc tggcagccct ggtgaaaatg gagctcctgg tca-
     gatggtg agtgtgccca 7621 gttccagagg gcagggatgg ggcaggaggc aggggcaaga tggaggcctg ggg-
     gaacaag 7681 gctgtctccc atct-
     catctg acttctcttg gtttggttgt cagggccccc gtggcctgcc 7741 tggt-
     gagaga ggtcgccctg gagcccctgg ccctgctgta agtactcctg gccccttggg 7801 ggatccctga gctctg-
     gaag gggctcccca ggaactctag ggactggcca gtgctcagtg 7861 gacttaacgg ggcttcccct ctcctgca gggtgctcgt ggaaatgatg gtgc-
     tactgg 7921 tgctgccggg cccctgtga gtgtggcctg taggcctcag ggctgggag tggg-
     gagggg 7981 tctcagtgtc tgctcttggg gctgacaatg ggggcaggtt atgttggtct gaaccccagg 8041 acttcctctg tcccagggtg tgacttgcag ctgccatctc ttccttctcg ctga-
     catctc 8101 cattt-
     cattc acagggtccc accggcccg ctggtcctcc tggcttccct ggtgctgttg 8161 gtgctaaggt gagaccccc actctcctct aagcatgacc ctcatgggcc aaggggttca 8221 tgtctccctg ttccccaaac caaagggacc cagagtggca agagagcagc ccgtt-
     cacta 8281 acacctttgt cctgggtct ccgtctctga tcttagagtc ctgat-
     cattg ctctcctgtc 8341 cctgtctccc cttcctcctg ccatcccgag aggcaaggtt gggtttccca gggtggcttc 8401 tga-
     tatgtcc tttcttctga ttcagggtga agctggtccc caagggcccc gaggctctga 8461 aggtccccag ggtgtgcgtg gtgagcctgg cccccctggc cctgctggtg ctgctggccc 8521 tgctgtaagt gtccccgact cagtgtccct ttgc-
     cacttt ctaacctcag agtccttgcc 8581 tgttgctgac actcctttct ctgtgccaca gggaaaccct ggtgct-
     gatg gacagcctgg 8641 tgctaaaggt gccaatgtaa gtatcctgcc aggcttcagt cccactcctg ccgcctgcag 8701 cctgcctgcc cctttccctc tgctcctagg ctcacgccct ggctgtctgc ctcc-
     cacagg
```

```
-continued
 8761 gtgctcctgg tat-
      tgctggt gctcctggct tccctggtgc ccgaggcccc tctggacccc 8821 agggccccgg cggccctcct ggtcccaagg gtaacagcgt gagtac-
      caaa ctctcccttc 8881 tgcccacccc atgcactggc tccagtgcgg ctct-
      catctg gggagcagga agacgcaggc 8941 caactgagcg cccccgactc tcagct-
      catc ctcttctccc cccttgcagg gtgaacctgg 9001 tgctcctggc agcaaaggag acactggtgc taagggagag cctgtaagtc tccccgc-
      cat 9061 ccttcttgca gcccagccca ccctgcccta ggagccccct gagg-
      gaaatc cagaaaggaa 9121 gaggagcccc tagtcttctg gggagtccct gccacacccc cag-
      gaacccc tgacactgga 9181 ggcccagcct cagccggctc tgaggctggc acaggatggc ccctcac-
      cac aggccgcctc 9241 ctcctctcgg ccctctccag ggccctgttg gtgttcaagg accccctggc cctgctg-
      gag 9301 aggaaggaaa gcgaggagct cgaggtgaac ccggacc-
      cac tggcctgccc ggaccccctg 9361 gcgagcgtgt aagtgtccct gcccgccccc tcccgctcca ccctcat-
      tgc ctggctggtg 9421 cctgtgtgtc gcg-
      gagttca ctggcctcct ctcctccttg cagggtggac ctggtagccg 9481 tggtttccct ggcgcagatg gtgttgctgg tcc-
      caaggta acctctcctt gcggccgggg 9541 ggctgaccct ccgctccct gggcatcttc ttcctctttt ggcccgtggc aaagagc-
      cac 9601 aaacttgaga ccctaactgt tcctgtgact tcccccaacc agggtcccgc tggt-
      gaacgt 9661 ggttctcctg gccctgctgg ccccaaagga tctcctggtg aagctggtcg tcccggt-
      gaa 9721 gctggtctgc ctggtgccaa ggt-
      gaggccc caggctttca gcctggcttg gccaggccct 9781 gaccatcccg tgtagggtct gggatgaggc gttctggatc aggcc-
      caagg gtctgccctc 9841 tggagtcctc ccccacctcc atcatgcttc tccccaagtc ccact-
      catac ctctctgcct 9901 ccctagggtc tgactg-
      gaag ccctggcagc cctggtcctg atggcaaaac tggccccct 9961 gtaagtatca ctcccctga acccctgcc attgtcctgt ctgcctccct gctgtcctca 10021 ctgctgcttt cgtgcctccc atccttaggg tcccgccggt caa-
      gatggtc gccccggacc 10081 cccaggccca cctggtgccc gtggtcaggc tggtgtgatg ggat-
      tccctg gacctaaagg 10141 tgctgctgtg agtattaagt gaggatccat gaagagccag ggacaaacac acctgaa-
      gac 10201 ttgaaggagt cctgggctct gggctcagct gtgccgctga cctgccgtgt ggccact-
      cac 10261 tctcactttc tggacctcag cctccc-
      tatc tgtaaaatga aagacttctc ggcggggcac 10321 ggtggctcat gcctgtaatc ccagcacttt gggaggccaa ggcgggcaga ccat-
      gaggtc 10381 aggagtttga gaccagtcgg gccaacatag tgaaaccacg tctctactaa aaata-
      caaaa 10441 gattagctgg gtgtggtggt gtgcacctgt aaccccagct agtcag-
      gagg ctgaggcagg
```

-continued 10501 agaattgcat gaacccggga ggtggaggtt gcagtgagct gagatcacgc cattgcactc 10561 cagcctgggc aacagtgcga gattccatct caaaaaaaaa aaaaaaagaa gaaagaaaga 10621 aagaaaaaat gaaacacttc tccaggctcc atgaccactg ctctgtcctg gaaataagtg 10681 ttgttggtgg ccctccaccc cgacacgtgg ggataggaca ggcctttgat atgataggca 10741 cccccagtct tggtggattc tttgaggtcc aaaggagat agcagagaag atgaaagccc 10801 tttgcagtgc aggccacagc gggcatctaa cagggaaaag gcagaggagc ctggaagggc 10861 atcttgggag gagtgggctc agaaagggcc cagcaagaag cacctgcagg ggcattcccc 10921 gggggccaaa cagtcttttg aaaagaaagt cccttaaaaa gtcccactca gagtaaatga 10981 gaggcccag gaggccctgg cttctcactt cagccccctc aaccctaact cctttctcc 11041 acagggagag cccggcaagg ctggagagcg aggtgttccc ggacccctg gcgctgtcgt 11101 aagtatctcc tttccatccc tacctccttc ccattgctgc cccggcactt tctcctccct 11161 gcaggagggg tgctagaggc cacggtcctc agctgctcgg ggcctcctaa ccctgagttc 11221 cccctttgctc tctccctgca gggtcctgct ggcaaagatg gagaggctgg agctcaggga 11281 cccctggcc ctgctgtgag tgtccctgat gggagatct ggggagcaga aaggggaga 11341 caccctcagc ccctcgtctc ctcggcctcc ccgtgactgt agtgttctct ctgtgcaggg 11401 tcccgctggc gagagaggtg aacaaggccc tgctggctcc cccggattcc aggtgaggcc 11461 tcatggctgt caagatgctg ggaggtaggg gtaggaaaca cctcttggt ctcttccaga 11521 ttctaaacct tccctcccct cttcccccac ttcccaccta cagggtctcc ctggtcctgc 11581 tggtcctcca ggtgaagcag gcaaacctgg tgaacaggta agagggagca gccggccaga 11641 ggggtgggag atgcagggaa tccagaggga caggcccccg ctcctagcta atcagacagc 11701 catcaactag agggattgag gttagacgcc ggaaagaact tcctcccatg aaggagcag 11761 cacagaggga agtgggggct gcatgattgc tagtctgggt gacttctttt aagagctgct 11821 ggaatatgct gtgactttcc ctcaacccttc tattgataa atcttggtcc atagtttggg 11881 gaggggggaa gcctttgaca catccctagg aggaagagag gggctgtttg ggataatctc 11941 aattcagtgc tgagaagggg ttcctctcta atcacggcca gaccccagga ggaaggaccg 12001 tgctttccag cagagtggcc ccaggtgggt tttgctcact gtctgttcct ctctccctcc 12061 ccctcagggt gttcctggag accttggcgc ccctggcccc tctggagcaa gagtaagtag 12121 gcctctctcg ctgcatccgt caaggtgcgt tgtacttggc cctatctcca gagcagcctt -continued

```
12181 cacatgccct gtccttccct tctagggcga gagaggtttc cctggcgagc gtggtgtgca 12241 aggtccccct ggtcctgctg gtccccgagg ggccaacggt gctcccggca acgatggtgc 12301 taaggtgagg gcagcgtgga aggggctctg gcaagtggcc cagggaccag gtctcacccc 12361 tcctgcagca ggggatggcg ggccatgacc aaagccatgg agatagggtg tggggtgggg 12421 ggaaaagacc acggcagggg cccacacaca gcctggagtc tgggctgtga gtcttttcat 12481 cttttctcaa ggcttgtcgt tggccttgga aacaagcctg ggagatacca agcgggctt 12541 agggctgtga cccactcttg gggcccagg cctcactcca gtcttcttgg ttgtcacata 12601 gggtgatgct ggtgcccctg gagctcccgg tagccagggc gcccctggcc ttcagggaat 12661 gcctggtgaa cgtggtgcag ctggtcttcc agggcctaag ggtgacagag taagttcaac 12721 cttccccctc ccctgagccc tacatggctc ccatctctgc ctgctttgaa tctctcagca 12781 tctctccttc tctctgggat ctgtccctct tctcgctaat cctcccctct tcccctttcc 12841 cctctggcct ttttgctgat gaatcctctc cctgtggtcc aggcccatct atccccatgg 12901 gttaccatgg tgatgagagg tgggggcatc tccttggtgg aggctccctt attcatcccg 12961 ctacacaagt caggggcctc ttaacctcag ttccacctga gtctccagga aggcacccct 13021 tttcctgaaa gaatctttga gtccttggcc caggtggagg cagggcagag ctgcagaggg 13081 cctctcagga aacccagaca caagcagaac actataggtc acctccttgc cccacactgg 13141 aaatctcaag cttatccatg tctttagggt gatgctggtc ccaaaggtgc tgatggctct 13201 cctggcaaag atggcgtccg tggtctgacc ggcccattg gtcctcctgg ccctgctggt 13261 gcccctggtg acaaggtgag gtggccgcct ccccaccttc tgccctaaca catagcctcc 13321 tcagcaggcc tgggcacggt tccgtggggt gcgttggga gagcaggtcc tgccaaactg 13381 agctgtcaac ctgggaacct ggagggacca gaaggagggg aggctctcct ggggtcatct 13441 actaggagta ttcagggag gccctgaccc tgagcctctt gtcccttgct ctcagggtga 13501 aagtggtccc agcggccctg ctggtcccac tggagctcgt ggtgcccccg taagtacaga 13561 agacctgtta agacccata cttggcccett ccctcccttc acacagcacc cctggccctg 13621 tctgtgcctt cacccettgc ctctcccctc accgcatccc cgccttccct cctgtcagcg 13681 catctctcca atctgactcc tttcttcta gggagaccgt ggtgagcctg gtcccccgg 13741 ccctgctggc tttgctggcc cccctgtgag taccaagacc cccatcattt ttcatcaccg 13801 actgggacct gggacctcga gggacggaat gaggacaagg cgtcagccat cctcagggga 13861 gaaggggga gacgggattg tttcccaccc aagcatcttc ctgcctccat tactgctcct
```

```
13921  cccccaggta gtggaaactc ctgcctcctt ccctc-
       cattc accgccctgc ttcctccccc 13981  agggtgctga cggc-
       caacct ggtgctaaag gcgaacctgg tgatgctggt gctaaaggcg 14041  atgctggtcc ccctggccct gccggacccg ctgaccccc tggccc-
       catt gtgagtggct 14101  tggccctctg tgcccacgag gctggtgggc tgggacccag gacgggtcca ggctt-
       gatgc 14161  ctctgtgctc tcctacaggg taatgttggt gctcctg-
       gag ccaaaggtgc tcgcggcagc 14221  gctggtcccc ctgtgagtat cacccgcctc tctgtt-
       gagc ctctcccctc tccccaggca 14281  gcggtggcag gtgagggcag ctgggtcgga tgagttggct gttctccctc tgactgttcc 14341  tatgttctct ccttccaggg tgc-
       tactggt ttccctggtg ctgctggccg agtcggtcct 14401  cctggcccct ctgtaagtct ctgcagcaga gtc-
       cactgct ctaggttggg ggtgctgggt 14461  ggggctgcc agaaggatgg tggggctgac tgaggaccca atgatgcacc agagccccct 14521  ggagtctgac agcccctcct atcctcatcc agg-
       gaaatgc tggaccccct ggccctcctg 14581  gtcctgctgg caaagaaggc ggcaaaggtc cccgtggtga gactggccct gctggacgtc 14641  ctggt-
       gaagt tggtccccct ggtcccctg gccctgctgg cgagaaagga tccctggtg 14701  ctgatggtcc tgctgtaagt gccagctcag atctctgcag ctccg-
       gaggt gtgcagagct 14761  ggggagggt ccctgtgctg ctgtctggca cct-
       cacccct gtttgcctcc caaagggtgc 14821  tcctggtact cccgggcctc aaggtat-
       tgc tggacagcgt ggtgtggtcg gcctgcctgg 14881  tcagagagga gagagaggct tccctggtct tcctggcccc tctgtaagtg cccccct-
       cac 14941  cttgggggc cctgagaaaa accatcacag gacttggagt ggggcg-
       gagc caaggagaac 15001  agatttggta gagatgactc cagcggactc aagggtcctc cca-
       gaccta tctctggcct 15061  gactcttct tctcccttag ggt-
       gaacctg gcaaacaagg tccctctgga gcaagtggtg 15121  aacgtggtcc ccctggtccc atgggccccc ctggattggc tggaccccct ggt-
       gaatctg 15181  gacgtgaggt gagcagtccc cagcccccat gccagtaccc tcagcatggc cat-
       tgtggcc 15241  ttgcctaagc cctcttcccc ggctgactct cacttctctc tctctctctc tgcaggggc 15301  tcctggtgcc gaaggttccc ctggacgaga cggttctcct ggcgccaagg taa-
       gatggca 15361  acactccatg accacagcct tgtctgctgc ttccctgccc catcctggcc ctt-
       cacccgg 15421  ggctgaccca tattccctg ctctccccgc cagggtgacc gtggtga-
       gac cggccccgct 15481  ggaccccctg gtgctcctgg tgctcctggt gccctggcc ccgttggccc tgctggcaag 15541  agtggtgatc gtggtgag
       ac tgtaagtagc tgggctccag ttccctgtac ctggtcaggc 15601  cagggactct tcaggcctcc ttagaggcct ggg-
       gatgggt gtcggacttc acccaggcag 15661  ggggaggaaa ggagatcctg caagatgtca gggccttaat ccaaaaaact gagt-
       taaagc
```

-continued

```
15721 tcagccccaa gtcccctctc ccagacagga ccgcctctcc cat-
      gagttgg ccccagctcc 15781 cgtgaa-
      gatt gcagtgggga ggtttccctg ggagttggga gacctcttgc aggagcagag 15841 gctgagcggg agggtcccaa gagcaataaa gaaggg-
      gaat gctaggtggg aaacactggt 15901 tctaatggct tctgtggttt gccccgagag ggcttcttca aggggttgg ttggctttgg 15961 cattcgatct aaataaggcc tgcgactctc aggcaggcag gctctgggag gcct-
      catcag 16021 cttcttcctc tgccagc-
      cac agacaacgcc cctggttgct tgggcctgtg tgtcccttgg 16081 tgggaatggc aggcgggccg gggagtgtgt atctgtgtgt gtgtgtgctg ggcccag-
      gag 16141 gagggtgggg ttcaagcccc tttgatctgc cagcctggtt gggagcagat cact-
      cacctg 16201 gcctcacgct cgctcgtgcc cttcc-
      tacct gctgcagctg gcgctggggg cggggtcgga 16261 ggaggctgtt taccttggct cccacggctg gctttgcccc agctgcctcc tcgc-
      cacgcc 16321 ctcactctgc cagaaacccc gggcct-
      gaga tcttgggaca gcttcttcag ggtgccaggc 16381 ctcctttccc atctctgaag tgagctgtcc acctggaggc ctgcg-
      gaacc tgtgcccagg 16441 aaaaccaggc tccggcggc tcaccttccc ataccaagaa gagcctgtga ctcc-
      caacag 16501 gtgctcatgc tcgtcatccc cagagcattg catcctggag ctgagcacgt gct-
      gagtgtc 16561 ccccaccct cacccacccc cagccccgga agggccttgt aagcc-
      cacac ggcccaggct 16621 ctgccagtgt ggaggtaggg taccatttcc tgtggcccag cacaagg-
      gat aatgcaaagt 16681 cacgcactct ttcatgggca ggcagctctc cacccactcc ttgt-
      catcct caaaaatgtc 16741 ctgtgctgct ggcctgagc acgtgtgcca ctcgctgctg cccacaaagg agc-
      catccgg 16801 aaagaattaa tgat
```

Exemplary regions or fragments of COL1A1 include bases 4168-4362, 4501-4535, 4638-4673, 7421-7474, 10309-10603 and 10608-10634.

An exemplary human BGN amino acid sequence is set forth below (SEQ ID NO: 7; GenBank Accession No. NP_001702, Version 1 (GI: 4502403), incorporated herein by reference):

```
  1 mwplwrlvsl lalsqalpfe qrgfwdftld dgpfmmndee asgadtsgvl dpdsvtp-
    tys 61 amcpfgchch lrvvqcsdlg lksvpkeisp dttlldlqnn diselrkddf kglqhly-
    alv 121 lvnnkiskih ekafsplrkl qklyisknhl veippnlpss lvel-
    rihdnr irkvpkgvfs 181 glrnmnciem ggnplensgf epgafdglkl nylriseakl tgipkdl-
    pet lnelhldhnk
```

-continued

```
241 iqaieledll rysk-
    lyrigl ghnqirmien gslsflptlr elhldnnkla rvpsglpdlk 301 llqvvylhsn nitkvgvndf cpmgfgvkra yyngislfnn pvpywevqpa tfrcvt-
    drla 361 iqfgnykk
```

Exemplary regions or fragments of BGN include residues 20-368, 62-94 (leucine rich repeat), 82-102, 92-115 (leucine rich repeat), 95-321, 279-295, and 313-342.

An exemplary human BGN nucleotide sequence (the start and stop codons for the coding sequences are bold and underlined) is set forth below (SEQ ID NO: 8; GenBank Accession No. NM_001711, Version 4 (GI: 268607602), incorporated herein by reference):

```
   1 cctttcctcc ctccccgccc tctccccgct gtccctccc cgtcggcccg cctgcccagc 61 ctttagcctc ccgcccgccg cctctgtctc cctctctcca caaactgccc aggagtgagt 121 agctgctttc ggtccgccgg acacaccgga cagatagacg tgcggacggc ccaccacccc 181 agcccgccaa ctagtcagcc tgcgcctggc gcctcccctc tccaggtcca tccgccatgt 241 ggccctgtg gcgcctcgtg tctctgctgg ccctgagcca ggccctgccc tttgagcaga 301 gaggcttctg ggacttcacc ctggacgatg gccattcat gatgaacgat gaggaagctt 361 cgggcgctga cacctcgggc gtcctggacc cggactctgt cacacccacc tacagcgcca 421 tgtgtccttt cggctgccac tgccacctgc gggtggttca gtgctccgac ctgggtctga 481 agtctgtgcc caaagagatc tcccctgaca ccacgctgct ggacctgcag aacaacgaca 541 tctccgagct ccgcaaggat gacttcaagg gtctccagca cctctacgcc ctcgtcctgg 601 tgaacaacaa gatctccaag atccatgaga aggccttcag cccactgcgg aagctgcaga 661 agctctacat ctccaagaac cacctggtgg agatcccgcc caacctaccc agctccctgg 721 tggagctccg catccacgac aaccgcatcc gcaaggtgcc caagggagtg ttcagcgggc 781 tccggaacat gaactgcatc gagatgggcg ggaacccact ggagaacagt ggctttgaac 841 ctggagcctt cgatggcctg aagctcaact acctgcgcat ctcagaggcc aagctgactg 901 gcatccccaa agacctccct gagaccctga atgaactcca cctagaccac aacaaaatcc 961 aggccatcga actggaggac ctgcttcgct actccaagct gtacaggctg ggcctaggcc 1021 acaaccagat caggatgatc gagaacggga gcctgagctt cctgcccacc ctccgggagc 1081 tccacttgga caacaacaag ttggccaggg tgccctcagg gctcccagac ctcaagctcc 1141 tccaggtggt ctatctgcac tccaacaaca tcaccaaagt gggtgtcaac gacttctgtc 1201 ccatgggctt cggggtgaag cgggcctact acaacggcat cagcctcttc aacaacccgg 1261 tgccctactg ggaggtgcag ccggccsctt tccgctgcgt cactgaccgc ctggccatcc 1321 agtttggcaa ctacaaaaag tagaggcagc tgcagccacc gcggggcctc agtggggggtc 1381 tctggggaac acagccagac atcctgatgg ggaggcagag ccaggaagct aagccagggc 1441 ccagctgcgt ccaacccagc cccccacctc gggtccctga ccccagctcg atgccccatc 1501 accgcctctc cctggctccc aagggtgcag gtgggcgcaa ggcccggccc ccatcacatg 1561 ttcccttggc ctcagagctg ccctgctct ccaccacag ccacccagag gcacccatg 1621 aagctttttt ctcgttcact cccaaaccca agtgtccaag gctccagtcc taggagaaca 1681 gtccctgggt cagcagccag gaggcggtcc ataagaatgg ggacagtggg ctctgccagg 1741 gctgccgcac ctgtccgac acacatgttc tgttcctcct cctcatgcat ttccagcctt 1801 tcaacccctcc ccgactctgc ggctcccctc agccccttg caagttcatg gcctgtccct
```

-continued

```
1861 cccagacccc tgctccactg gcccttcgac cagtcctccc ttctgttctc tctttccccg 1921 tccttcctct ctctctctct ctctctctct ctctctttct gtgtgtgtgt gtgtgtgtgt 1981 gtgtgtgtgt gtgtgtgtgt gtgtcttgtg cttcctcaga cctttctcgc ttct-
     gagctt 2041 ggtggcctgt tccctccatc tctccgaacc tggcttcgcc tgtcccttc actc-
     cacacc 2101 ctctggcctt ctgcctt-
     gag ctgggactgc tttctgtctg tccggcctgc acccagcccc 2161 tgcc-
     cacaaa accccaggga cagcagtctc cccagcctgc cctgctcagg ccttgccccc 2221 aaacctgtac tgtcccggag gaggttggga ggtggaggcc cagcatcccg cgca-
     gatgac 2281 accatcaacc gccagagtcc cagacaccgg ttttcctaga agcccctcac ccc-
     cactggc 2341 ccactggtgg ctaggtctcc cct-
     tatcctt ctggtccagc gcaaggaggg gctgcttctg 2401 aggtcggtgg ctgtctttcc attaaagaaa caccgtgcaa cgt-
     gaaaaaa aaaaaaaaa 2461 aaaaa
```

Exemplary regions or fragments of BGN include bases 348-1340 (mature protein), 543-614, 687-749, 1263-1340, 2421-2426 (regulatory site), and 244 (polyA site).

An exemplary human C1QC amino acid sequence is set forth below (SEQ ID NO: 9; GenBank Accession No. AAH09016, Version 1 (GI: 14290496), incorporated herein by reference):

```
  1 mdvgpsslph lglklllll llplrgqant gcy-
    gipgmpg lpgapgkdgy dglpgpkgep 61 gipaip-
    girg pkgqkgepgl pghpgkngpm gppgmpgvpg pmgipgepge egrykqkfqs 121 vftvtrqthq ppapnslirf navitnpqgd ydtstgkftc kvpglyyfvy hash-
    tanlcv 181 llyrsgvkvv tfcghtsktn qvnsggvllr lqv-
    geevwla vndyydmvgi qgsdsvfsgf 241 llfpd
```

Exemplary regions or fragments of C1QC include residues 43-87 (collagen triple helix repeat and 113-245 (complement component).

An exemplary human C1QC nucleotide sequence (the start and stop codons for the coding sequences are bold and underlined) is set forth below (SEQ ID NO: 10; GenBank Accession No. BC009016, Version 1 (GI: 14290495), incorporated herein by reference):

```
  1 ggggaagcag atctgaggac atctctgtgc caggccagaa accgcc-
    cacc tgcagttcct 61 tctccggg
    at ggacgtgggg cccagctccc tgccccacct tgggctgaag ctgctgctgc 121 tcctgctgct gctgcccctc aggggccaag ccaacacagg ctgc-
    tacggg atcccaggga 181 tgcccggcct gcctgggca ccagggaagg atgggtacga cggactgccg gggcc-
    caagg 241 gggagccagg aatcccagcc attcccggga tccgaggacc caaagggcag aagg-
    gagaac
```

-continued

```
 301 ccggcttacc cggccatcct gggaaaaatg gccc-
     catggg acccctggg atgccagggg 361 tgcccggccc catgggcatc cctggagagc caggtgagga gggcaga-
     tac aagcagaaat 421 tccagtcagt gtt-
     cacggtc actcggcaga cccaccagcc ccctgcaccc aacagcctga 481 tcagattcaa cgcggtcctc accaacccgc agg-
     gagatta tgacacgagc actggcaagt 541 tcacctgcaa gtccccggc ctctactact ttgtctacca cgcgtcgcat acagc-
     caacc 601 tgtgcgtgct gctgtaccgc agcggcgtca aagtggt-
     cac cttctgtggc cacacgtcca 661 aaaccaatca ggtcaactcg ggcggtgtgc tgctgaggtt gcaggtgggc gag-
     gaggtgt 721 ggctggctgt caatgactac tacgacatgg tggg-
     catcca gggctctgac agcgtcttct 781 ccggcttcct gctcttcccc gac
     tagggcg ggcagatgcg ctcgagaccc acgggccttc 841 cacctccctc agcttcctgc atggacccac cttactggcc agtctg-
     catc cttgcctaga 901 ccattctccc ctccagggag cccaccctga cccaccccca ctgcaccccc tccc-
     catggg 961 ttctctcctt cctctgaact tctttag-
     gag tcactgcttg tgtggttcct gggacactta 1021 accaatgcct tctggtactg ccattctttt tttttttttt tcaagt-
     attg gaagggtgg 1081 ggagatatat aaataaatca tgaaatcaat acat-
     aaaaaa aaaaaaaaaa aaaaaaaaaa 1141 aaaaaaa
```

Exemplary regions or fragments of C1QC include bases 194-827, 827-911, 1061-1062, and 116-1147.

An exemplary human C1S amino acid sequence is set forth below (SEQ ID NO: 11; GenBank Accession No. AAH56903, Version 1 (GI: 34785163), incorporated herein by reference):

```
  1 mwcivlfsll awvyaeptmy geilspnypq aypseveksw dievpegygi hlyfth-
    ldie 61 lsencaydsv qiisgdteeg ricgqrssnn phspiveefq vpynklqvif ksdfs-
    neerf 121 tgfaayyvat dine-
    ctdfvd vpcshfcnnf iggyfcscpp eyflhddmkn cgvncsgdvf 181 taligeiasp nypkpypens rceyqirlek gfqvvvtlrr edfdveaads agncld-
    slvf 241 vagdrqfgpy cghgfpgpln ietksnaldi ifqtdltgqk kgwkl-
    ryhgd pmpcpkedtp 301 nsvwepakak yvfrdvvqit cldgfe-
    vveg rvgatsfyst cqsngkwsns klkcqpvdcg 361 ipesiengkv edpestlfgs virytceepy yymengggge yhcagngswv nevlg-
    pelpk 421 cvpvcgvpre pfeekqriig gsdadiknfp wqvffdnpwa gga-
    lineywv ltaahvvegn 481 reptmyvgst svqtsrlaks kmlt-
    pehvfi hpgwkllevp egrtnfdndi alvrlkdpvk 541 mgptvspicl pgtssdynlm dgdig-
    lisgw grtekrdrav rlkaarlpva plrkckevkv
```

-continued
```
601 ekptadaeay vftpnmicag gekgmdsckg dsgga-
    favqd pndktkfyaa glvswgpqcg 661 tyglytrvkn yvdwimktmq enstpred
```

Exemplary regions or fragments of C1S include residues 18-129, 131-171, 175-287, 294-355 and 438-678.

An exemplary human C1S nucleotide sequence (the start and stop codons for the coding sequences are bold and underlined) is set forth below (SEQ ID NO: 12; GenBank Accession No. BC056903, Version 1 (GI: 34785162), incorporated herein by reference):

```
   1 ggacagggag gctggccgga ggttcctgca gagggagcgt caaggccctg tgctgctgtc 61 cctggggggcc agaggggttg cccagcatgc ccactggcag gagagaggga actgacccac 121 ttgctcctac cagcttctga aggtgacact gagccccagg tgacgccgca ccaccaaaga 181 aggtgcttgt gtttgtcaga caaatacagc caggcctgcc acccctaggg ctccaaagtc 241 cggaggtgca gaaagccagg accaagagac aggcagctca ccagggtgga caaatcgcca 301 gagatgtggt gcattgtcct gttttcactt ttggcatggg tttatgctga gcctaccatg 361 tatggggaga tcctgtcccc taactatcct caggcatatc ccagtgaggt agagaaatct 421 tgggacatag aagttcctga agggtatggg attcacctct acttcaccca tctggacatt 481 gagctgtcag agaactgtgc gtatgactca gtgcagataa tctcaggaga cactgaagaa 541 gggaggctct gtggacagag gagcagtaac aatccccact ctccaattgt ggaagagttc 601 caagtcccat acaacaaact ccaggtgatc tttaagtcag acttttccaa tgaagagcgt 661 tttacggggt tgctgcata ctatgttgcc acagacataa atgaatgcac agattttgta 721 gatgtccctt gtagccactt ctgcaacaat ttcattggtg gttacttctg ctcctgcccc 781 ccggaatatt tcctccatga tgacatgaag aattgcggag ttaattgcag tggggatgta 841 ttcactgcac tgattgggga gattgcaagt cccaattatc ccaaaccata tccagagaac 901 tcaaggtgtg aataccagat ccggttggag aaagggttcc aagtggtggt gaccttgcgg 961 agagaagatt ttgatgtgga agcagctgac tcagcgggaa actgccttga cagtttagtt 1021 tttgttgcag agatcggca atttggtcct tactgtggtc atggattccc tgggcctcta 1081 aatattgaaa ccaagagtaa tgctcttgat atcatcttcc aaactgatct aacagggcaa 1141 aaaaagggct ggaaacttcg ctatcatgga gatccaatgc cctgccctaa ggaagacact 1201 cccaattctg tttgggagcc tgcgaaggca aaatatgtct ttagagatgt ggtgcagata 1261 acctgtctgg atgggtttga agttgtggag ggacgtgttg gtgcaacatc tttctattcg 1321 acttgtcaaa gcaatggaaa gtggagtaat tccaaactga aatgtcaacc tgtggactgt 1381 ggcattcctg aatccattga gaatggtaaa gttgaagacc cagagagcac tttgtttggt 1441 tctgtcatcc gctacacttg tgaggagcca tattactaca tggaaaatgg aggaggtggg 1501 gagtatcact gtgctggtaa cgggagctgg gtgaatgagg tgctgggccc ggagctgccg 1561 aaatgtgttc cagtctgtgg agtccccaga gaaccctttg aagaaaaaca gaggataatt 1621 ggaggatccg atgcagatat taaaaacttc ccctggcaag tcttctttga caacccatgg 1681 gctggtggag cgctcattaa tgagtactgg gtgctgacgg ctgctcatgt tgtggaggga 1741 aacagggagc caacaatgta tgttgggtcc acctcagtgc agacctcacg gctggcaaaa 1801 tccaagatgc tcactcctga gcatgtgttt attcatccgg gatggaagct gctggaagtc 1861 ccagaaggac gaaccaattt tgataatgac attgcactgg tgcggctgaa agacccagtg 1921 aaaatgggac ccaccgtctc tcccatctgc ctaccaggca cctcttccga ctacaacctc
```

-continued

```
1981 atggatgggg acctgggact gatctcaggc tggggccgaa cagagaagag agatcgtgct 2041 gttcgcctca aggcggcaag gttacctgta gctcctttaa gaaaatgcaa agaagtgaaa 2101 gtggagaaac ccacagcaga tgcagaggcc tatgttttca ctcctaacat gatctgtgct 2161 ggaggagaga agggcatgga tagctgtaaa ggggacagtg gtggggcctt tgctgtacag 2221 gatcccaatg acaagaccaa attctacgca gctggcctgg tgtcctgggg gccccagtgt 2281 gggacctatg ggctctacac acgggtaaag aactatgttg actggataat gaagactatg 2341 caggaaaata gcaccccccg tgaggactaa tccagataca tcccaccagc ctctccaagg 2401 gtggtgacca atgcattacc ttctgttcct tatgatattc tcattatttc atcatgactg 2461 aaagaagaca cgagcgaatg atttaaatag aacttgattg ttgagacgcc ttgctagagg 2521 tagagtttga tcatagaatt gtgctggtca tacatttgtg gtctgactcc ttggggtcct 2581 ttccccggag tacctattgt agataacact atgggtgggg cactcctttc ttgcactatt 2641 ccacagggat accttaattc tttgtttcct ctttacctgt tcaaaattcc atttacttga 2701 tcattctcag tatccactgt ctatgtacaa taaaggatgt ttataagcaa aaaaaaaaaa 2761 aaaaaaaaaa aaaaaaaaaa aaaaaaaaaa
```

Exemplary regions or fragments of C1S include bases 2752-2790. An exemplary human C1QB amino acid sequence is set forth below (SEQ ID NO: 13; GenBank Accession No. 3RPX_B, Version 1 (GI: 332639950), incorporated herein by reference):

```
  1 iqkhktlpkm sggwelelng teaklvrkva gekitvtfni nnsipptfdg eeepsqgqkv 61 eeqepeltst pnfvvevikn ddgkkalvld chypedevgq edeaesdifs irevsfqstg 121 esewkdtnyt lntdsldwal ydhlmdflad rgvdntfade lvelstaleh qeyitfledl 181 ksfvksqahh hhhh
```

Exemplary regions or fragments of C1QB include residues 4-184, 13-20, 114-118, 138-151, and 155-184.

An exemplary human C1QB nucleotide sequence (the start and stop codons for the coding sequences are bold and underlined) is set forth below (SEQ ID NO: 14; GenBank Accession No. NM_00491, Version 3 (GI: 87298827), incorporated herein by reference):

```
  1 gcccttcccg cctctgggga agggaacttc cgcttcggac cgagggcagt aggctctcgg 61 ctcctggtcc cactgctgct cagcccagtg gcctcacagg acaccagctt cccaggaggc 121 gtctgacaca gtatgatgat gaagatccca tggggcagca tcccagtact gatgttgctc 181 ctgctcctgg gcctaatcga tatctcccag gcccagctca gctgcaccgg gcccccagcc 241 atccctggca tcccgggtat ccctgggaca cctggccccg atggccaacc tgggaccccca 301 gggataaaag gagagaaagg gcttccaggg ctggctggag accatggtga gttcggagag 361 aagggagacc cagggattcc tgggaatcca ggaaaagtcg gcccaaggg ccccatgggc 421 cctaaaggtg gcccagggc cctggagcc caggcccca aggtgaatc gggagactac 481 aaggccaccc agaaaatcgc cttctctgcc acaagaacca tcaacgtccc cctgcgccgg 541 gaccagacca tccgcttcga ccacgtgatc accaacatga acaacaatta tgagccccgc 601 agtggcaagt tcacctgcaa ggtgcccgt ctctactact tcacctacca cgccagctct 661 cgagggaacc tgtgcgtgaa cctcatgcgt ggccgggagc gtgcacagaa ggtggtcacc
```

-continued

```
 721 ttctgtgact atgcctacaa caccttccag gtcaccaccg gtggcatggt cctcaagctg 781 gagcagggggg agaacgtctt cctgcaggcc accgacaaga actcactact gggcatggag 841 ggtgccaaca gcatcttttc cggggttcctg ctctttccag atatggaggc ctgacctgtg 901 ggctgcttca catccacccc ggctcccccct gccagcaacg ctcactctac ccccaacacc 961 accccttgcc caaccaatgc acacagtagg gcttggtgaa tgctgctgag tgaatgagta 1021 aataaactct tcaaggccaa ggga
```

Exemplary regions or fragments of C1QB include bases 214-216, 334-526, 509-658 and 663-916.

An exemplary human HLA-DRB3 amino acid sequence is set forth below (SEQ ID NO: 15) GenBank Accession No. NP_072049, Version 2 (GI: 17986005), incorporated herein by reference:

```
  1 mvclklpggs slaaltvtlm vlssrlafag dtrprflelr ksechffngt ervryldryf 61 hnqeeflrfd sdvgeyravt elgrpvaesw nsqkdlleqk rgrvdnycrh nygvgesftv 121 qrrvhpqvtv ypaktqplqh hnllvcsysg fypgsievrw frngqeekag vvstgliqng 181 dwtfqtlvml etvprsgevy tcqvehpsvt saltvewrar sesaqskmls gvggfvlgll 241 flgaglfiyf rnqkghsglq ptgfls
```

Exemplary regions or fragments of HLA-DRB3 include residues 1-29, 30-266, 30-124, 42-116, and 125-227.

An exemplary human HLA-DRB3 nucleotide sequence (the start and stop codons for the coding sequences are bold and underlined) is set forth below (SEQ ID NO: 16; GenBank Accession No. NM_0022555, Version 3 (GI: 18641371), incorporated herein by reference):

```
   1 gcctgctgct ctggcccctg gtcctgtcct cttctccagc atggtgtgtc tgaagctccc 61 tggaggctcc agcttggcag cgttgacagt gacactgatg gtgctgagct cccgactggc 121 tttcgctggg gacacccgac cacgtttctt ggagctgcgt aagtctgagt gtcatttctt 181 caatgggacg gagcgggtgc ggtacctgga cagatacttc cataaccagg aggagttcct 241 gcgcttcgac agcgacgtgg gggagtaccg ggcggtgacg gagctggggc ggcctgtcgc 301 cgagtcctgg aacagccaga aggacctcct ggagcagaag cggggccggg tggacaatta 361 ctgcagacac aactacgggg ttggtgagag cttcacagtg cagcggcgag tccatcctca 421 ggtgactgtg tatcctgcaa agacccagcc cctgcagcac cacaacctcc tggtctgctc 481 tgtgagtggt ttctatccag gcagcattga agtcaggtgg ttccggaacg gccaggaaga 541 gaaggctggg gtggtgtcca cgggcctgat ccagaatgga gactggacct tccagaccct 601 ggtgatgcta gaaacagttc ctcggagtgg agaggtttac acttgccaag tggagcaccc 661 aagcgtaacg agcgctctca cagtggaatg gagagcacgg tctgaatctg cacagagcaa 721 gatgctgagt ggagtcgggg gctttgtgct gggcctgctc ttccttgggg ccgggctgtt 781 catctacttc aggaatcaga aaggacactc tggacttcag ccaacaggat tcctgagctg

841 aagtgcagat gacaatttaa ggaagaatct tctgccccag ctttgcagga tgaaaagctt 901 tcccgcctgg ctgttattct tccacgagag agggctttct caggacctag ttgctactgg 961 ttcagcaact gcagaaaatg tcctcccttg tggcttcctc agttcctgcc cttggcctga 1021 agtcccagca ttgatggcag cgcctcatct tcaactttttg tgctcccctt tgcctaaacc 1081 ctatggcctc ctgtgcatct gtactcaccc tgtaccacaa acacattaca ttattaaatg 1141 tttctcaaag atggagtt
```

Exemplary regions or fragments of HLA-DRB3 include bases 41-841, 41-127, 128-838, 128-412, 141-410, 176-407, 1133-1138 (regulatory site), and 1158 (polyA site).

An exemplary human AEBP1 amino acid sequence is set forth below (SEQ ID NO: 17; GenBank Accession No. BAD92981, Version 1 (GI: 62089074), incorporated herein by reference):

```
   1 ppapspeppa raaamaavrg apllscllal lalcpggrpq tvltddeiee flegflsele
  61 pepreddvea ppppeptpry rkagaggkpg krpgtaaevp pektkdkgkk gkkdkgpkvp
 121 keslegsprp pkkgkekppk atkkpkekpp katkkpkekp pkatkkpkek ppkatkkpps
 181 gkrppilaps etlewplppp pspgpeelpq eggaplsnnw qnpgeethve arehqpepee
 241 eteqptldyn dqieredyed feyirrqkqp rpppsrrrrp ervwpeppee kapapapeer
 301 ieppvkpllp plppdygdgy vipnyddmdy yfgppppqkp daerqtdeek eelkkpkked
 361 sspkeetdkw avekgkdhke prkgeeleee wtptekvkcp pigmeshrie dnqirassml
 421 rhglgaqrgr lnmqtgated dyydgawcae ddartqwiev dtrrttrftg vitqgrdssi
 481 hddfvttffv gfsndsqtwv mytngyeemt fhgnvdkdtp vlselpepvv arfiriyplt
 541 wngslcmrle vlgcsvapvy syyaqnevva tddldfrhhs ykdmrqlmkv vneecptitr
 601 tyslgkssrg lkiyameisd npgehelgep efrytagihg nevlgrelll llmqylcrey
 661 rdgnprvrsl vqdtrihlvp slnpdgyeva aqmgsefgnw alglwteegf difedfpdln
 721 svlwgaeerk wvpyrvpnnn lpiperylsp datvstevra iiawmeknpf vlganlngge
 781 rlvsypydma rtptqeclla aamaaarged edevseaqet pdhaifrwla isfasahltl
 841 tepyrggcqa qdytggmgiv ngakwnprtg tindfsylht nclelsfylg cdkfphesel
 901 prewennkea lltfmeqvhr gikgvvtdeq gipianatis vsginhgvkt asggdywril
 961 npgeyrvtah aegytpsakt cnvdydigat qcnfilarsn wkrireimam ngnrpiphid
1021 psrpmtpqqr rlqqrrlqhr lrlraqmrlr rlnatttlgp htvpptlppa pattlsttie
1081 pwglipptta gwgesetety tevvtefgte vepefgtkve pefetqlepe fetqlepefe
1141 eeeeeeeeee iatgqafpft tvetytvnfg df
```

Exemplary regions or fragments of AEBP1 include residues 400-553, 448-483, 574-917, 921-996, and 921-996.

An exemplary human AEBP1 nucleotide sequence (the start and stop codons for the coding sequences are bold and underlined) is set forth below (SEQ ID NO: 18; GenBank Accession No. AB209744, Version 1 (GI: 62089073), incorporated herein by reference):

```
   1 agccgccagg acctcggagc gccccgacca cccctgagcc cctctggctt cggagccccc
  61 cagcacccct tcccgggtcc cctcgcccac cctaatccac tctccctccc tttcccggat
 121 tccctcgctc accccatcct ctctcccgcc ccttcctgga ttccctcacc cgtctcgatc
 181 ccctctccgc cctttgccag agacccagag cccctgaccc cccgcgccct ccccggagcc
 241 ccccgcgcgt gccgcggcca tggcggccgt gcgcggggcg ccctgctca gctgcctcct
 301 ggcgttgctg gccctgtgcc ctggagggcg cccgcagacg gtgctgaccg acgacgagat
 361 cgaggagttc ctcgagggct tcctgtcaga gctagaacct gagccccggg aggacgacgt
 421 ggaggccccg ccgcctcccg agcccacccc gcgggtccga aaagcccagg cgggggggcaa
 481 gccagggaag cggccaggga cggccgcaga agtgcctccg gaaaagacca agacaaagg
 541 gaagaaaggc aagaaagaca aaggccccaa ggtgcccaag gagtccttgg aggggtcccc
```

-continued

```
 601 caggccgccc aagaagggga aggagaagcc acccaaggcc accaagaagc ccaaggagaa
 661 gccacctaag gccaccaaga agcccaagga gaagccaccc aaggccacca agaagcccaa
 721 agagaagcca cccaaggcca ccaagaagcc cccgtcaggg aagaggcccc ccattctggc
 781 tccctcagaa accctggagt ggccactgcc cccacccccc agccctggcc ccgaggagct
 841 accccaggag ggaggggcgc ccctctcaaa taactggcag aatccaggag aggagaccca
 901 tgtggaggca cgggagcacc agcctgagcc ggaggaggag accgagcaac ccacactgga
 961 ctacaatgac cagatcgaga gggaggacta tgaggacttt gagtacattc ggcgccagaa
1021 gcaacccagg ccaccccaa gcagaaggag gaggcccgag cgggtctggc cagagccccc
1081 tgaggagaag gccccggccc cagccccgga ggagaggatt gagcctcctg tgaagcctct
1141 gctgccccg ctgcccctg actatggtga tggttacgtg atccccaact acgatgacat
1201 ggactattac tttgggcctc ctccgcccca gaagcccgat gctgagcgcc agacggacga
1261 agagaaggag gagctgaaga aacccaaaaa ggaggacagc agccccaagg aggagaccga
1321 caagtgggca gtggagaagg gcaaggacca caaagagccc cgaaagggcg aggagttgga
1381 ggaggagtgg acgcctacgg agaaagtcaa gtgtcccccc attgggatgg agtcacaccg
1441 tattgaggac aaccagatcc gagcctcctc catgctgcgc cacggcctgg gggcacagcg
1501 cggccggctc aacatgcaga ccggtgccac tgaggacgac tactatgatg gtgcgtggtg
1561 tgccgaggac gatgccagga cccagtggat agaggtggac accaggagga ctacccggtt
1621 cacaggcgtc atcacccagg gcagagactc cagcatccat gacgattttg tgaccacctt
1681 cttcgtgggc ttcagcaatg acagccagac atgggtgatg tacaccaacg gctatgagga
1741 aatgaccttt catgggaacg tggacaagga cacacccgtg ctgagtgagc tcccagagcc
1801 ggtggtggct cgtttcatcc gcatctaccc actcacctgg aatggcagcc tgtgcatgcg
1861 cctggaggtg ctggggtgct ctgtggcccc tgtctacagc tactacgcac agaatgaggt
1921 ggtggccacc gatgacctgg atttccggca ccacagctac aaggacatgc gccagctcat
1981 gaaggtggtg aacgaggagt gccccaccat caccccgcact tacagcctgg gcaagagctc
2041 acgaggcctc aagatctatg ccatggagat ctcagacaac cctggggagc atgaactggg
2101 ggagcccgag ttccgctaca ctgctgggat ccatggcaac gaggtgctgg gccgagagct
2161 gttgctgctg ctcatgcagt acctgtgccg agagtaccgc gatgggaacc cacgtgtgcg
2221 cagcctggtg caggacacac gcatccacct ggtgccctca ctgaaccctg atggctacga
2281 ggtggcagcg cagatgggct cagagtttgg gaactgggcg ctggactgt ggactgagga
2341 gggctttgac atctttgaag atttcccgga tctcaactct gtgctctggg agctgagga
2401 gaggaaatgg gtcccctacc gggtccccaa caataacttg cccatccctg aacgctacct
2461 ttcgccagat gccacggtat ccacggaggt ccgggccatc attgcctgga tggagaagaa
2521 ccccttcgtg ctgggagcaa atctgaacgg cggcgagcgg ctagtatcct accctacga
2581 tatggcccgc acgcctaccc aggagcagct gctggccgca gccatggcag cagcccgggg
2641 ggaggatgag gacgaggtct ccgaggccca ggagactcca gaccacgcca tcttccggtg
2701 gcttgccatc tccttcgcct ccgcacacct caccttgacc gagccctacc gcggaggctg
2761 ccaagcccag gactacaccg gcggcatggg catcgtcaac ggggccaagt ggaaccccg
2821 gaccgggact atcaatgact tcagttacct gcataccaac tgcctggagc tctccttcta
2881 cctgggctgt gacaagttcc ctcatgagag tgagctgccc cgcgagtggg agaacaacaa
2941 ggaggcgctg ctcaccttca tggagcaggt gcaccgcggc attaaggggg tggtgacgga
3001 cgagcaaggc atccccattg ccaacgccac catctctgtg agtggcatta atcacggcgt
```

-continued

```
3061 gaagacagcc agtggtggtg attactggcg aatcttgaac ccgggtgagt accgcgtgac 3121 agcccacgcg gagggctaca ccccgagcgc caagacctgc aatgttgact atgacatcgg 3181 ggccactcag tgcaacttca tcctggctcg ctccaactgg aagcgcatcc gggagatcat 3241 ggccatgaac gggaaccggc ctatcccaca catagaccca tcgcgcccta tgacccccca 3301 acagcgacgc ctgcagcagc gacgcctaca acaccgcctg cggcttcggg cacagatgcg 3361 gctgcggcgc ctcaacgcca ccaccacccc aggcccccac actgtgcctc ccacgctgcc 3421 ccctgcccct gccaccaccc tgagcactac catagagccc tggggcctca taccgccaac 3481 caccgctggc tggggggagt cggagactga gacctacaca gaggtggtga cagagtttgg 3541 gaccgaggtg gagcccgagt ttgggaccaa ggtggagccc gagtttgaga cccagttgga 3601 gcctgagttt gagacccagc tggaacccga gtttgaggaa gaggaggagg aggaggaaga 3661 ggaggagata gccactggcc aggcattccc cttcacaaca gtagagacct acacagtgaa 3721 ctttggggac ttctgagatc agcgtcctac caagacccca gcccaactca agctacagca 3781 gcagcacttc ccaagcctgc tgaccacagt cacatcaccc atcagcacat ggaaggcccc 3841 tggtatggac actgaaagga agggctggtc ctgccccttt gagggggtgc aaacatgact 3901 gggacctaag agccagaggc tgtgtagagg ctcctgctcc acctgccagt ctcgtaagag 3961 atggggttgc tgcagtgttg gagtaggggc agagggaggg agccaaggtc actccaataa 4021 aacaagctca tggcacgg
```

Exemplary regions or fragments of AEBP1 include bases 218-3736.

An exemplary human SFRP4 amino acid sequence is set forth below (SEQ ID NO: 19; GenBank Accession No. EAW94085, Version 1 (GI: 119614491), incorporated herein by reference):

```
1   mrvagregrf lsagvaareg samflsilva lclwlhlalg vrgapceavr ipmcrhmpwn 61  itrmpnhlhh stqenailai eqyeelvdvn csavlrfflc amyapictle flhdpikpck 121 svcqrarddc eplmkmynhs wpeslacdel pvydrgvcis peaivtdlpe dvkwiditpd 181 mmvqerpldv dckrlspdrc kckkvkptla tylsknysyv ihakikavqr sgcnevttvv 241 dvkeifksss piprtqvpli tnsscqcphi lphqdvlimc yewrsrmmll enclvekwrd 301 qlskrsiqwe erlqeqrrtv qdkkktagrt srsnppkpkg ktpapkpasp kkniktrsaq 361 krtnpkry
```

Exemplary regions or fragments of SFRP4 include residues 42-168, 210-318, and 311-366.

An exemplary human SFRP4 nucleotide sequence (the start and stop codons for the coding sequences are bold and underlined) is set forth below (SEQ ID NO: 20; GenBank Accession No. NM_003014, Version 3 (GI: 170784837), incorporated herein by reference):

```
1   gcggccgagg gggagcccgc gccgcggctg cagctgccaa gggagcgttc cgagcccacg 61  tcaggggagg tgtcgggata aatagggtcc cgcaatggcc gtggctggct gcgctccgag 121 ctgcggagtc cgggactgga gctgcccggg cgggttcgcg ccccgaaggc tgagagctgg 181 cgctgctcgt gccctgtgtg ccagacgcg gagctccgcg gccggacccc gcggccccgc 241 tttgctgccg actggagttt gggggaagaa actctcctgc gccccagagg atttcttcct
```

-continued

```
 301 cggcgaaggg acagcgaaag atgagggtgg caggaagaga agggcgcttt ctgtctgccg
 361 gggtcgcagc gcgagagggc agtgccatgt tcctctccat cctagtggcg ctgtgcctgt
 421 ggctgcacct ggcgctgggc gtgcgcggcg cgccctgcga ggcggtgcgc atccctatgt
 481 gccggcacat gccctggaac atcacgcgga tgcccaacca cctgcaccac agcacgcagg
 541 agaacgccat cctggccatc gagcagtacg aggagctggt ggacgtgaac tgcagcgccg
 601 tgctgcgctt cttcctctgt gccatgtacg cgcccatttg cacctggag ttcctgcacg
 661 accctatcaa gccgtgcaag tcggtgtgcc aacgcgcgcg cgacgactgc gagcccctca
 721 tgaagatgta caaccacagc tggcccgaaa gcctggcctg cgacgagctg cctgtctatg
 781 accgtggcgt gtgcatctcg cctgaagcca tcgtcacgga cctcccggag gatgttaagt
 841 ggatagacat cacaccagac atgatggtac aggaaaggcc tcttgatgtt gactgtaaac
 901 gcctaagccc cgatcggtgc aagtgtaaaa aggtgaagcc aactttggca acgtatctca
 961 gcaaaaacta cagctatgtt attcatgcca aataaaagc tgtgcagagg agtggctgca
1021 atgaggtcac aacggtggtg gatgtaaaag agatcttcaa gtcctcatca cccatccctc
1081 gaactcaagt cccgctcatt acaaattctt cttgccagtg tccacacatc ctgccccatc
1141 aagatgttct catcatgtgt tacgagtggc gctcaaggat gatgcttctt gaaaattgct
1201 tagttgaaaa atggagagat cagcttagta aaagatccat acagtgggaa gagaggctgc
1261 aggaacagcg gagaacagtt caggacaaga agaaaacagc cgggcgcacc agtcgtagta
1321 atcccccaa accaaaggga agcctcctg ctcccaaacc agccagtccc aagaagaaca
1381 ttaaaactag gagtgcccag aagagaacaa acccgaaaag agtgtgagct aactagtttc
1441 caaagcggag acttccgact tccttacagg atgaggctgg gcattgcctg ggacagccta
1501 tgtaaggcca tgtgcccctt gccctaacaa ctcactgcag tgctcttcat agacacatct
1561 tgcagcattt ttcttaaggc tatgcttcag ttttctttg taagccatca caagccatag
1621 tggtaggttt gccctttggt acagaaggtg agttaaagct ggtggaaaag cttattgca
1681 ttgcattcag agtaacctgt gtgcatactc tagaagagta gggaaaataa tgcttgttac
1741 aattcgacct aatatgtgca ttgtaaaata atgccatat ttcaaacaaa acacgtaatt
1801 tttttacagt atgtttatt acctttgat atctgttgtt gcaatgttag tgatgtttta
1861 aaatgtgatc gaaatataaa tgcttctaag aaggaacagt agtggaatga atgtctaaaa
1921 gatctttatg tgtttatggt ctgcagaagg attttgtga tgaaagggga tttttgaaa
1981 aatctagaga agtagcatat ggaaaactat aatgtgtctt ttttacaatg acttcagctc
2041 tgttttagc tagaaactct aaaaacaaaa ataataataa agaaaaataa ataaaagga
2101 gaggcagaca atgtctggat tcctgttttt tggttacctg atttcatgat catgatgctt
2161 cttgtcaaca ccctcttaag cagcaccaga aacagtgagt ttgtctgtac cattaggagt
2221 taggtactaa ttagttggct aatgctcaag tattttatac ccacaagaga ggtatgtcac
2281 tcatcttact tcccaggaca tccaccctga gaataatttg acaagcttaa aaatggcctt
2341 catgtgagtg ccaaattttg ttttcttcat ttaaatattt tctttgccta aatacatgtg
2401 agaggagtta aatataaatg tacagagagg aaagttgagg ttccacctct gaatgagaa
2461 ttacttgaca gttgggatac tttaatcaga aaaaagaac ttatcttgca gcattttatc
2521 aacaaatttc ataattgtgg acaattggag gcatttattt taaaaaacaa ttttattggc
2581 cttttgctaa cacagtaagc atgtattctc tataaggcat tcaataaatg cacaacgccc
2641 aaaggaaata aaatcctatc taatcctact ctccactaca cagaggtaat cactattagt
2701 attttggcat attattctcc aggtgtttct tatgcactta taaaatgatt tgaacaaata
```

```
2761 aaactaggaa cctgctatac atgtgtttca taacctgcct cctttgcttg gccctttatt 2821 gagataagtt ttcctgtcaa gaaagcagaa accatctcat ttctaacagc tgtgttatat 2881 tccatagtat gcattactca acaaactgtt gtgctattgg atacttaggt ggtttcttca 2941 ctgacaatac tgaataaaca tctcaatagt caaa
```

Exemplary regions or fragments of SFRP4 include bases 387-1427, 387-440, 525-1024, 979-1177, and 1178-1241.

An exemplary human FBLN5 amino acid sequence is set forth below (SEQ ID NO: 21; GenBank Accession No. AAH22280, Version 1 (GI: 18490145), incorporated herein by reference):

```
  1 mpgikriltv tilalclpsp gnaqaqctng fdldrqsgqc ldidecrtip eacrgdmmcv 61 nqnggylcip rtnpvyrgpy snpystpysg pypaaappls apnyptisrp licrfgyqmd 121 esnqcvdvde catdshqcnp tqicintegg ytcsctdgyw llegqcldid ecrygycqql 181 canvpgsysc tcnpgftlne dgrscqdvne catenpcvqt cvntygsfic rcdpgyelee 241 dgvhcsdmde csfseflcqh ecvnqpgtyf cscppgyill ddnrscqdin ecehrnhtcn 301 lqqtcynlqg gfkcidpirc eepylrisdn rcmcpaenpg crdqpftily rdmdvvsgrs 361 vpadifqmqa ttrypgayyi fqiksgnegr efymrqtgpi satlvmtrpi kgpreiqldl 421 emitvntvin frgssvirlr iyvsqypf
```

Exemplary regions or fragments of FBLN5 include residues 125-165, 207-238 and 258-286.

An exemplary human FBLN5 nucleotide sequence (the start and stop codons for the coding sequences are bold and underlined) is set forth below (SEQ ID NO: 22; GenBank Accession No. BC022280, Version 1 (GI: 18490144), incorporated herein by reference):

```
  1 gcagtggctg ggaggacccc ggcgctctcc ccgtgtcctc tccacgactc gctcggcccc 61 tctggaataa aacacccgcg agccccgagg gcccagagga ggccgacgtg cccgagctcc 121 tccgggggtc ccgcccgcga gctttcttct cgccttcgca tctcctcctc gcgcgtcttg 181 gacatgccag gaataaaaag gatactcact gttaccattc tggctctctg tcttccaagc 241 cctgggaatg cacaggcaca gtgcacgaat ggctttgacc tggatcgcca gtcaggacag 301 tgtttagata ttgatgaatg ccgaaccatc cccgaggcct gccgaggaga catgatgtgt 361 gttaaccaaa atggcgggta tttatgcatt ccccggacaa accctgtgta tcgagggccc 421 tactcgaacc cctactcgac cccctactca ggtccgtacc cagcagctgc cccaccactc 481 tcagctccaa actatcccac gatctccagg cctcttatat gccgctttgg ataccagatg 541 gatgaaagca accaatgtgt ggatgtggac gagtgtgcaa cagattccca ccagtgcaac 601 cccacccaga tctgcatcaa tactgaaggc gggtacacct gctcctgcac cgacggatat 661 tggcttctgg aaggccagtg cttagacatt gatgaatgtc gctatggtta ctgccagcag 721 ctctgtgcga atgttcctgg atcctattct tgtacatgca accctggttt taccctcaat 781 gaggatggaa ggtcttgcca agatgtgaac gagtgtgcca ccgagaaccc ctgcgtgcaa 841 acctgcgtca acacctacgg ctctttcatc tgccgctgtg acccaggata tgaacttgag 901 gaagatggcg ttcattgcag tgatatggac gagtgcagct ctctgagtt cctctgccaa 961 catgagtgtg tgaaccagcc cggcacatac ttctgctcct gccctccagg ctacatcctg
```

-continued

```
1021 ctggatgaca accgaagctg ccaagacatc aacgaatgtg agcacaggaa ccacacgtgc 1081 aacctgcagc agacgtgcta caatttacaa gggggcttca aatgcatcga ccccatccgc 1141 tgtgaggagc cttatctgag gatcagtgat aaccgctgta tgtgtcctgc tgagaaccct 1201 ggctgcagag accagccctt taccatcttg taccgggaca tggacgtggt gtcaggacgc 1261 tccgttcccg ctgacatctt ccaaatgcaa gccacgaccc gctacctggg ggcctattac 1321 attttccaga tcaaatctgg gaatgagggc agagaatttt acatgcggca acgggcccc 1381 atcagtgcca ccctggtgat gacacgcccc atcaaagggc cccgggaaat ccagctggac 1441 ttggaaatga tcactgtcaa cactgtcatc aacttcagag gcagctccgt gatccgactg 1501 cggatatatg tgtcgcagta cccattctga gcctcgggct ggagcctccg acgctgcctc 1561 tcattggcac caagggacag gagaagagag gaaataacag agagaatgag agcgacacag 1621 acgttaggca tttcctgctg aacgtttccc cgaagagtca gccccgactt cctgactctc 1681 acctgtacta ttgcagacct gtcaccctgc aggacttgcc accccagtt cctatgacac 1741 agttatcaaa aagtattatc attgctcccc tgatagaaga ttgttggtga attttcaagg 1801 ccttcagttt atttccacta ttttcaaaga aaatagatta ggtttgcggg ggtctgagtc 1861 tatgttcaaa gactgtgaac agcttgctgt cacttcttca cctcttccac tccttctctc 1921 actgtgttac tgctttgcaa agacccggga gctggcgggg aaccctggga gtagctagtt 1981 tgcttttttgc gtacacagag aaggctatgt aaacaaacca cagcaggatc gaagggtttt 2041 tagagaatgt gtttcaaaac catgcctggt attttcaacc ataaagaag tttcagttgt 2101 ccttaaattt gtataacggt ttaattctgt cttgttcatt ttgagtattt ttaaaaaata 2161 tgtcgtagaa ttccttcgaa aggccttcag acacatgcta tgttctgtct tcccaaaccc 2221 agtctcctct ccattttagc ccagtgtttt ctttgaggac cccttaatct tgctttcttt 2281 agaattttta cccaattgga ttggaatgca gaggtctcca aactgattaa atatttgaaa 2341 aaaaaaaaa aaaaaaaaa aaaaaaa
```

Exemplary regions or fragments of FBLN5 include bases 184-1530 and 1128-1530.

An exemplary human FCGR2C amino acid sequence is set forth below ((SEQ ID NO: 23) GenBank Accession No. NP_963857, Version 3 (GI: 126116592), incorporated herein by reference):

```
  1 mgilsflpvl atesdwadck spqpwghmll wtavlflapv agtpaappka vlklepqwin 61 vlqedsvtlt crgthspesd sipwfhngnl ipthtqpsyr fkannndsge ytcqtgqtsl 121 sdpvhltvls ewlvlqtphl efgegetivl rchswkdkpl vkvtffqngk skkfsrsdpn 181 fsipqanhsh sgdyhctgni gytlysskpv titvqapsss pmgiivavvt giavaaivaa 241 vvaliycrkk risanstdpv kaaqfeppgr qmiairkrqp eetnndyeta dggymtlnpr 301 aptdddkniy ltlppndhvn snn
```

Exemplary regions or fragments of FCGR2C include residues 1-45 (signaling peptide), 43-323, 50-128, 56-128, 138-214, and 224-246.

An exemplary human FCGR2C nucleotide sequence (the start and stop codons for the coding sequences are bold and underlined) is set forth below (SEQ ID NO: 24; GenBank Accession No. NM_201563, Version 5 (GI: 586946409), incorporated herein by reference):

```
   1 agactccaga atttgtttgc cctctagggt agaatccgcc aagctttgag agaaggctgt
  61 gactgctgtg ctctgggcgc cagctcgctc cagggagtga tgggaatcct gtcattctta
 121 cctgtccttg ccactgagag tgactgggct gactgcaagt cccccagcc ttggggtcat
 181 atgcttctgt ggacagctgt gctattcctg gctcctgttg ctgggacacc tgcagctccc
 241 ccaaaggctg tgctgaaact cgagccccag tggatcaacg tgctccaaga ggactctgtg
 301 actctgacat gccggggac tcacagccct gagagcgact ccattccgtg gttccacaat
 361 gggaatctca ttcccaccca cacgcagccc agctacaggt tcaaggccaa caacaatgac
 421 agcggggagt acacgtgcca gactggccag accagcctca cgaccctgt gcatctgact
 481 gtgcttctg agtggctggt gctccagacc cctcacctgg agttccagga gggagaaacc
 541 atcgtgctga ggtgccacag ctggaaggac aagcctctgg tcaaggtcac attcttccag
 601 aatggaaaat ccaagaaatt ttcccgttcg atcccaact tctccatccc acaagcaaac
 661 cacagtcaca gtggtgatta ccactgcaca ggaaacatag gctacacgct gtactcatcc
 721 aagcctgtga ccatcactgt ccaagctccc agctcttcac cgatggggat cattgtggct
 781 gtggtcactg ggattgctgt agcggccatt gttgctgctg tagtggcctt gatctactgc
 841 aggaaaaagc ggatttcagc caattccact gatcctgtga aggctgccca atttgagcca
 901 cctggacgtc aaatgattgc catcagaaag agacaacctg aagaaccaa caatgactat
 961 gaaacagctg acggcggcta catgactctg aaccccaggg cacctactga cgatgataaa
1021 aacatctacc tgactcttcc tcccaacgac catgtcaaca gtaataacta aagagtaacg
1081 ttatgccatg tggtcacact ctcagcttgc tgagtggatg acaaaaagag gggaattgtt
1141 aaaggaaaat ttaaatggag actggaaaaa ttcctgagca aacaaaacca cctgcccctt
1201 agaaatagct ttaactttgc ttaaactaca aacacaagca aaacttcacg gggtcatact
1261 acatacaagc ataagcaaaa cttaacttgg atgatttctg gtaaatgctt atgttagaaa
1321 taagacaacc ccagccaatc acaagcagcc tactaacata taattaggtg actagggact
1381 ttctaagaag atacctaccc ccaaaaaaca attatgtaat tgaaaaccca tcgattgcct
1441 ttatttttgct tccacatttt cccaataaat acttgcctgt gacattttgc cactggaaca
1501 ctaaacttca tgaattgcgc ctcagatttt tcctttaaca tctttttttt ttgacagtct
1561 caatctgtta cccaggctgg agtgtagtgg tgctatcttg gctcactgca aacccgcctc
1621 ccaggtttaa gcgattctca tgcctcagcc tcccagtagc tgggattaca ggcatgtgcc
1681 gtcataacca gctaattttt gtatttttta tttttttttt tagtagagac ggggtttcgc
1741 aatgttggcc aggccgatct cgaacttctg gcctctagcg atctgcccgc ctcggcctcc
1801 caaagtgctg ggatgaccag catcagcccc aatgcccagc ctctttaaca tcttctttcc
1861 tatgccctct ctgtggatcc ctactgctgg tttctgcctt ctccatgctg agaacaaaat
1921 cacctattca ctgcttatgc agtcggaagc tccagaagaa caaagagccc aattaccaga
1981 accacattaa gtctccattg ttttgccttg ggatttgaga agagaattag agaggtgagg
2041 atctggtatt tcctggtcta aattcccctt gaggaagacg aagggatgct gcagttccaa
2101 aagagaagga ctcttccaga gtcatctacc tgagtcccga tgctccctgt cctgaaaacc
2161 acagacaata tggtcccaaa tgactgactg caccttctgt gcctcagcca ttcttgacat
2221 caagaatctt ctgttccaca tccacacagc caatacaatt aatcaaacca ctgttatgaa
2281 aagatgtagc aacatgagaa atgcttatgt tacaggttac atgagaacaa tcatgtaagt
```

-continued

```
2341 ctatatgact tcagaaatgt taaaatagac taacctctaa caacaaatta aaagtgattg 2401 tttcaaggtg atgcaattat tgatgaccta ttttattttt ctataatgat catatattac 2461 ctttgtaata aaacattata accaaaac
```

Exemplary regions or fragments of FCGR2C include bases 100-1071, 100-234, 226-1068, 769-837 and 979-981.

An exemplary human C1QA amino acid sequence is set forth below (SEQ ID NO: 25; GenBank Accession No. EAW95015, Version 1 (GI: 119615421), incorporated herein by reference):

```
  1 megprgwlvl cvlaislasm vtedlcrapd gkkgeagrpg rrgrpglkge qgepgapgir 61 tgiqglkgdq gepgpsgnpg kvgypgpsgp lgargipgik gtkgspgnik dqprpafsai 121 rrnppmggnv vifdtvitnq eepyqnhsgr fvctvpgyyy ftfqvlsqwe iclsivsssr 181 gqvrrslgfc dttnkglfqv vsggmvlqlq qgdqvwvekd pkkghiyqgs eadsvfsgfl 241 ifpsa
```

Exemplary regions or fragments of C1QA include residues 48-106, and 108-244.

An exemplary human C1QA nucleotide sequence (the start and stop codons for the coding sequences are bold and underlined) is set forth below (SEQ ID NO: 26; GenBank Accession No. NM_015991, Version 2 (GI: 87298824), incorporated herein by reference):

```
  1 gccactcctg ctgggcagcc cacagggtcc ctgggcggag ggcaggagca tccagttgga 61 gttgacaaca ggaggcagag gcatcatgga gggtccccgg ggatggctgg tgctctgtgt 121 gctggccata tcgctggcct ctatggtgac cgaggacttg tgccgagcac cagacgggaa 181 gaaagggagg gcaggaagac ctggcagacg ggggcggcca ggcctcaagg gggagcaagg 241 ggagccgggg gcccctggca tccggacagg catccaaggc cttaaaggag accaggggga 301 acctgggccc tctggaaacc ccggcaaggt gggctaccca gggccagcg gcccccctcgg 361 agcccgtggc atcccgggaa ttaaaggcac caagggcagc ccaggaaaca tcaaggacca 421 gccgaggcca gccttctccg ccattcggcg gaaccccca atgggggca acgtggtcat 481 cttcgacacg gtcatcacca accaggaaga accgtaccag aaccactccg gccgattcgt 541 ctgcactgta cccggctact actacttcac cttccaggtg ctgtcccagt gggaaatctg 601 cctgtccatc gtctcctcct caaggggcca ggtccgacgc tccctgggct tctgtgacac 661 caccaacaag gggctcttcc aggtggtgtc aggggggcatg gtgcttcagc tgcagcaggg 721 tgaccaggtc tgggttgaaa agacccccaa aaagggtcac atttaccagg gctctgaggc 781 cgacagcgtc ttcagcggct tcctcatctt cccatctgcc tgagccaggg aaggaccccc 841 tcccccaccc acctctctgg cttccatgct ccgcctgtaa aatgggggcg ctattgcttc 901 agctgctgaa gggagggggc tggctctgag agccccagga ctggctgccc cgtgacacat 961 gctctaagaa gctcgtttct tagacctctt cctggaataa acatctgtgt ctgtgtctgc
```

```
-continued
1021 tgaacatgag cttcagttgc tactcggagc attgagaggg aggcctaaga ataataacaa 1081 tccagtgctt aagagtca
```

Exemplary regions or fragments of C1QA include bases 86-151, 182-184, 200-202, 996-1001 and 249-1098.

An exemplary human SFRP2 amino acid sequence is set forth below (SEQ ID NO: 27; GenBank Accession No. NP_003004, Version 1 (GI: 48475052), incorporated herein by reference):

```
  1 mlqgpgslll lflashcclg sarglflfgq pdfsykrsnc kpipanlqlc hgieyqnmrl 61 pnllghetmk evleqagawi plvmkqchpd tkkflcslfa pvclddldet iqpchslcvq 121 vkdrcapvms afgfpwpdml ecdrfpqdnd lciplassdh llpateeapk vceacknknd 181 ddndimetlc kndfalkikv keityinrdt kiiletkskt iyklngvser dlkksvlwlk 241 dslqctceem ndinapylvm gqkqggelvi tsvkrwqkgq refkrisrsi rklqc
```

Exemplary regions or fragments of SFRP2 include residues 1-295, 20-295, 1-19, 36-163 and 169-295.

An exemplary human SFRP2 nucleotide sequence (the start and stop codons for the coding sequences are bold and underlined) is set forth below (SEQ ID NO: 28; GenBank Accession No. NM_003013, Version 2 (GI: 52630413), incorporated herein by reference):

```
   1 caacggctca ttctgctccc ccgggtcgga gcccccggga gctgcgcgcg ggcttgcagc 61 gcctcgcccg cgctgtcctc ccggtgtccc gcttctccgc gccccagccg ccggctgcca 121 gcttttcggg gccccgagtc gcacccagcg aagagagcgg gcccgggaca agctcgaact 181 ccggccgcct cgcccttccc cggctccgct ccctctgccc cctcggggtc gcgcgcccac 241 gaatgctgcag ggccctggct cgctgctgct gctcttcctc gcctcgcact gctgcctggg 301 ctcggcgcgc gggctcttcc tctttggcca gcccgacttc tcctacaagc gcagcaattg 361 caagcccatc cctgccaacc tgcagctgtg ccacggcatc gaataccaga acatgcggct 421 gcccaacctg ctgggccacg agaccatgaa ggaggtgctg gagcaggccg gcgcttggat 481 cccgctggtc atgaagcagt gccacccgga caccaagaag ttcctgtgct cgctcttcgc 541 ccccgtctgc ctcgatgacc tagacgagac catccagcca tgccactcgc tctgcgtgca 601 ggtgaaggac cgctgcgccc cggtcatgtc cgccttcggc ttccctggc ccgacatgct 661 tgagtgcgac cgtttccccc aggacaacga ccttttgcatc cccctcgcta gcagcgacca 721 cctcctgcca gccaccgagg aagctccaaa ggtatgtgaa gcctgcaaaa ataaaaatga 781 tgatgacaac gacataatgg aaacgctttg taaaaatgat tttgcactga aaataaaagt 841 gaaggagata acctacatca accgagatac caaaatcatc ctggagacca agagcaagac 901 catttacaag ctgaacggtg tgtccgaaag ggacctgaag aaatcggtgc tgtggctcaa 961 agacagcttg cagtgcacct gtgaggagat gaacgacatc aacgcgccct atctggtcat 1021 gggacagaaa cagggtgggg agctggtgat caccctcggtg aagcggtggc agaaggggca 1081 gagagagttc aagcgcatct cccgcagcat ccgcaagctg cagtgctagt cccggcatcc 1141 tgatggctcc gacaggcctg ctccagagca cggctgacca tttctgctcc gggatctcag 1201 ctcccgttcc ccaagcacac tcctagctgc tccagtctca gcctgggcag cttccccctg 1261 ccttttgcac gtttgcatcc ccagcatttc ctgagttata aggccacagg agtggatagc 1321 tgttttcacc taaaggaaaa gcccacccga atcttgtaga aatattcaaa ctaataaaat
```

-continued

```
1381 catgaatatt tttatgaagt ttaaaaatag ctcactttaa agctagtttt gaataggtgc 1441 aactgtgact tgggtctggt tggttgttgt ttgttgtttt gagtcagctg attttcactt 1501 cccactgagg ttgtcataac atgcaaattg cttcaatttt ctctgtggcc caaacttgtg 1561 ggtcacaaac cctgttgaga taaagctggc tgttatctca acatcttcat cagctccaga 1621 ctgagactca gtgtctaagt cttacaacaa ttcatcattt tataccttca atgggaactt 1681 aaactgttac atgtatcaca ttccagctac aatacttcca tttattagaa gcacattaac 1741 catttctata gcatgatttc ttcaagtaaa aggcaaaaga tataaatttt ataattgact 1801 tgagtacttt aagccttgtt taaaacattt cttacttaac ttttgcaaat taaacccatt 1861 gtagcttacc tgtaatatac atagtagttt acctttaaaa gttgtaaaaa tattgcttta 1921 accaacactg taaatatttc agataaacat tatattcttg tatataaact ttacatcctg 1981 ttttacctat aaaaaaaaaa aaaaa
```

Exemplary regions or fragments of SFRP2 include bases 1-743, 242-1129, 242-298 and 299-1126.

An exemplary human SULF1 amino acid sequence is set forth below (SEQ ID NO: 29; GenBank Accession No. AAH68565, Version 1 (GI: 46249932), incorporated herein by reference):

```
  1 mcygtpsyny apnmdkhwim gytgpmlpih meftnilqrk rlqtlmsvdd sverlynmlv 61 etgelentyi iytadhgyhi gqfglvkgks mpydfdirvp ffirgpsvep qsivpqivln 121 idlaptildi agldtppdvd gksvlklldp ekpgnrfrtn kkakiwrdtf lvergkflrk 181 keesskniqq snhlpkyerv kelcqqaryq taceqpgqkw qciedtsgkl rihkckgpsd 241 lltvrqstrn lyargfhdkd kecscresgy rasrsqrksq rqflrnqgtp kykprfvhtr 301 qtrslpvefe geiydinlee eeelqvlqpr niakrhdegh kgprdlqass ggnrgrmlad 361 ssnavgpptt vrvthkcfil pndsihcere lyqsarawkd hkayidkeie alqdkiknlr 421 evrghlkrrk peecscskqs yynkekgvkk qeklkshlhp fkeaaqevds klqlfkennr 481 rrkkerkekr rqrkgeecsl pgltcfthdn nhwqtapfwn lgsfcactss nnntywclrt 541 vnethnflfc efatgfleyf dmntdpyqlt ntvhtvergi lnqlhvqlme lrscqgykqc 601 nprpknldvg nkdggsydlh rmllflvpcs apltsramvs dasf
```

Exemplary regions or fragments of SULF1 include residues 1-644, 39-133, 122-147 and 292-439.

An exemplary human SULF1 nucleotide sequence (the start and stop codons for the coding sequences are bold and underlined) is set forth below (SEQ ID NO: 30; GenBank Accession No. BC068565, Version 1 (GI: 46249931), incorporated herein by reference):

```
  1 attccaatgg aacagacagg gtaaggacca atctggactg tgttatcttt tccaggtgca 61 agtatgtgct atggaactcc tagttataac tatgcaccaa atatggataa acactggatt 121 atgcagtaca caggaccaat gctgcccatc cacatggaat ttacaaacat tctacagcgc 181 aaaaggctcc agactttgat gtcagtggat gattctgtgg agaggctgta taacatgctc 241 gtggagacgg gggagctgga gaatacttac atcatttaca ccgccgacca tggttaccat 301 attgggcagt ttggactggt caaggggaaa tccatgccat atgactttga tattcgtgtg 361 ccttttttta ttcgtggtcc aagtgtagaa ccaggatcaa tagtcccaca gatcgttctc
```

-continued

```
 421 aacattgact tggcccccac gatcctggat attgctgggc tcgacacacc tcctgatgtg 481 gacggcaagt ctgtcctcaa acttctggac ccagaaaagc caggtaacag gtttcgaaca 541 aacaagaagg ccaaaatttg gcgtgataca ttcctagtgg aaagaggcaa atttctacgt 601 aagaaggaag aatccagcaa gaatatccaa cagtcaaatc acttgcccaa atatgaacgg 661 gtcaaagaac tatgccagca ggccaggtac cagacagcct gtgaacaacc ggggcagaag 721 tggcaatgca ttgaggatac atctggcaag cttcgaattc acaagtgtaa aggacccagt 781 gacctgctca cagtccggca gagcacgcgg aacctctacg ctcgcggctt ccatgacaaa 841 gacaaagagt gcagttgtag ggagtctggt taccgtgcca gcagaagcca agaaaagagt 901 caacggcaat tcttgagaaa ccaggggact ccaaagtaca agcccagatt tgtccatact 961 cggcagacac gttccttgcc cgtcgaattt gaaggtgaaa tatatgacat aaatctggaa 1021 gaagaagaag aattgcaagt gttgcaacca agaaacattg ctaagcgtca tgatgaaggc 1081 cacaaggggc caagagatct ccaggcttcc agtggtggca cagggggcag gatgctggca 1141 gatagcagca acgccgtggg cccacctacc actgtccgag tgacacacaa gtgttttatt 1201 cttcccaatg actctatcca ttgtgagaga gaactgtacc aatcggccag agcgtggaag 1261 gaccataagg catacattga caaagagatt gaagctctgc aagataaaat taagaattta 1321 agagaagtga gaggacatct gaagagaagg aagcctgagg aatgtagctg cagtaaacaa 1381 agctattaca ataaagagaa aggtgtaaaa agcaagagaa aattaaagag ccatcttcac 1441 ccattcaagg aggctgctca ggaagtagat agcaaactgc aacttttcaa ggagaacaac 1501 cgtaggagga gaaggagag gaaggagaag agacggcaga ggaaggggga agagtgcagc 1561 ctgcctggcc tcacttgctt cacgcatgac aacaaccact ggcagacagc cccgttctgg 1621 aacctgggat ctttctgtgc ttgcacgagt tctaacaata cacctactg gtgtttgcgt 1681 acagttaatg agacgcataa ttttcttttc tgtgagtttg ctactggctt tttggagtat 1741 tttgatatga atacagatcc ttatcagctc acaaatacag tgcacacggt agaacgaggc 1801 attttgaatc agctacacgt acaactaatg gagctcagaa gctgtcaagg atataagcag 1861 tgcaacccaa gacctaagaa tcttgatgtt ggaaataaag atggaggaag ctatgaccta 1921 cacagaatgt tgctgttcct ggtaccctgt tcggcccctc taacctccag agctatggtc 1981 tcagatgctt ccttttagag agaaggtcat tagtccacca agaagccaaa tgacaacagg 2041 aaaggtgatg ggaagatgaa aacaaaggaa ggtggacttt tgggtatatg ttatagccat 2101 aggacagtta tgggatggat gggaaggtta atcagccccg tctcactgca gacatcaact 2161 ggcaaggcct agaggagcta cacagtgtga atgaaaacat ctatgagtac agacaaaact 2221 acagacttag tctggtggac tggactaatt acttgaagga tttagataga gtatttgcac 2281 tgctgaagag tcactatgag caaaataaaa caaataagac tcaaactgct caaagtgacg 2341 ggttcttggt tgtctctgct gagcacgctg tgtcaatgga gatggcctct gctgactcag 2401 atgaagaccc aaggcataag gttgggaaaa cacctcattt gaccttgcca gctgaccttc 2461 aaacccctgca tttgaaccga ccaacattaa gtccagagag taaacttgaa tggaataacg 2521 acattccaga agttaatcat ttgaattctg aacactggaa aaaaccgaa aaatggacgg 2581 ggcatgaaga gactaatcat ctggaaaccg atttcagtgg cgatggcatg acagagctag 2641 agctcgggcc cagccccagg ctgcagccca ttcgcaggca cccgaaagaa cttcccccagt 2701 atggtggtcc tggaaaggac attttttgaag atcaactata tcttcctgtg cattccgatg 2761 gaatttcagt tcatcagatg ttcaccatgg ccaccgcaga acaccgaagt aattccagca 2821 tagcggggaa gatgttgacc aaggtggaga agaatcacga aaaggagaag tcacagcacc
```

```
2881 tagaaggcag cgcctcctct tcactctcct ctgattagat gaaactgtta ccttaccta 2941 aacacagtat ttcttttaa cttttttatt tgtaaactaa taaggtaat cacagccacc 3001 aacaaaaaaa aaaaaaaa
```

Exemplary regions or fragments of SULF1 include bases 1-3019, 64-1998 and 3005-3019.

An exemplary human THBS2 amino acid sequence is set forth below (SEQ ID NO: 31; GenBank Accession No. AAI50176, Version 1 (GI: 152012473), incorporated herein by reference):

```
   1 mawrivilal wvwpstqagh qdkdttfdlf sisninrkti gakqfrgpdp gvpayrfvrf 61 dyippvnadd lskitkimrq kegffltaql kqdgksrgtl lalegpgisq rqfeivsngp 121 adtldltywi dgtrhvvsle dvgladsqwk nvtvqvaget yslhvgcdli dsfaldepfy 181 ehlqaeksrm yvakgsares hfrgliqnvh lvfensvedi lskkgcqqgq gaeinaisen 241 tetirlgphv tteyvgpsse rrpevcersc eelgnmvqel sglhvivnql senikrvsnd 301 nqflweligg ppktrnmsac wqdgrffaen etwvvdsctt ctckkfktic hqitcppatc 361 aspsfvegec cpsclhsvdg eegwspwaew tqcsvtcgsg tqqrgrscdv tsntclgpsi 421 qtracsiskc dtrirqdggw shwspwsscs vtcgvgnitr irlonspvpq mggknckgsg 481 retkacqgap cpidgrwspw spwsactvtc aggirertry cnspepqygg kacvgdvqer 541 qmcnkrscpv dgclsnpcfp gaqcssfpdg swscgscpvg figngthced ldecalvpdi 601 cfstskvprc vntqpgfhcl pcppryrgnq pvgvgleaak tekqvcepen pckdkthnch 661 khaeciyigh fsdpmykcec qtgyagdgli cgedsdldgw pnlnlvcatn atyhcikdnc 721 phipnsgqed fdkdgigdac dddddndgvt dekdncqllf nprqadydkd evgdrcdncp 781 yvhnpaqidt dnngegdacs vdidgddvfn erdncpyvyn tdqrdtdgdg vgdhcdncpl 841 vhnpdqtdvd ndlvgdqcdn nedidddghq nnqdncpyis nanqadhdrd gqgdacdpdd 901 dndgvpddrd ncrlvfnpdq edldgdgrgd ickddfdndn ipdiddvcpe nnaisetdfr 961 nfqmvpldpk gttqidpnwv irhqgkelvq tansdpgiav gfdefgsvdf sgtfyvntdr 1021 dddyagfvfg yqsssrfyvv mwkqvtqtyw edqptraygy sgvslkvvns ttgtgehlrn 1081 alwhtgntpg qvrtlwhdpr nigwkdytay rwhlthrpkt gyirvivheg kqvmadsgpi 1141 ydqtyaggrl glfvfsqemv yfsdlkyecr di
```

Exemplary regions or fragments of THBS2 include residues 320-374, 440-492, 765-787, 789-823, 802-820, 886-897 and 899-917.

An exemplary human THBS2 nucleotide sequence (the start and stop codons for the coding sequences are bold and underlined) is set forth below (SEQ ID NO: 32; GenBank Accession No. BC150175, Version 1 (GI: 152012472), incorporated herein by reference):

```
   1 gagcatcctg cactgcaggg ccggtctctc gctccagcag agcctgcgcc tttctgactc 61 ggtccggaac actgaaacca gtcatcactg catcttttg gcaaaccagg agctcagctg 121 caggaggcag gatggcctgg aggctggtcc tgctggctct gtgggtgtgg cccagcacgc 181 aagctggtca ccaggacaaa gacacgacct tcgacctttt cagtatcagc aacatcaacc 241 gcaagaccat tggcgccaag cagttccgcg ggcccgaccc cggcgtgccg gcttaccgct 301 tcgtgcgctt tgactacatc ccaccggtga acgcagatga cctcagcaag atcaccaaga
```

-continued

```
 361 tcatgcggca aaggagggc ttcttcctca cggcccagct caagcaggac ggcaagtcca
 421 ggggcacgct gttggctctg gagggccccg gtctctccca gaggcagttc gagatcgtct
 481 ccaacggccc cgcggacacg ctggatctca cctactggat tgacggcacc cggcatgtgg
 541 tctccctgga ggacgtcggc ctggctgact cgcagtggaa aacgtcacc gtgcaggtgg
 601 ctggcgagac ctacagcttg cacgtgggct gcgacctcat agacagcttc gctctggacg
 661 agcccttcta cgagcacctg caggcggaaa agagccggat gtacgtggcc aaaggctctg
 721 ccagagagag tcacttcagg ggtttgcttc agaacgtcca cctagtgttt gaaaactctg
 781 tggaagatat tctaagcaag aagggttgcc agcaaggcca gggagctgag atcaacgcca
 841 tcagtgagaa cacagagacg ctgcgcctgg gtccgcatgt caccaccgag tacgtgggcc
 901 ccagctcgga gaggaggccc gaggtgtgcg aacgctcgtg cgaggagctg ggaaacatgg
 961 tccaggagct ctcggggctc cacgtcctcg tgaaccagct cagcgagaac ctcaagagag
1021 tgtcgaatga taaccagttt ctctgggagc tcattggtgg ccctcctaag acaaggaaca
1081 tgtcagcttg ctggcaggat ggccggttct ttgcggaaaa tgaaacgtgg gtggtggaca
1141 gctgcaccac gtgtacctgc aagaaattta aaccatttg ccaccaaatc acctgcccgc
1201 ctgcaacctg cgccagtcca tcctttgtgg aaggcgaatg ctgcccttcc tgcctccact
1261 cggtggacgg tgaggagggc tggtctccgt gggcagagtg gacccagtgc tccgtgacgt
1321 gtggctctgg gacccagcag agaggccggt cctgtgacgt caccagcaac acctgcttgg
1381 ggccctccat ccagacacgg gcttgcagtc tgagcaagtg tgacaccgc atccggcagg
1441 acggcggctg gagccactgg tcaccttggt cttcatgctc tgtgacctgt ggagttggca
1501 atatcacacg catccgtctc tgcaactccc cagtgcccca gatgggggc aagaattgca
1561 aagggagtgg ccgggagacc aaagcctgcc agggcgcccc atgcccaatc gatggccgct
1621 ggagcccctg gtccccgtgg tcggcctgca ctgtcacctg tgccggtggg atccgggagc
1681 gcacccgggt ctgcaacagc cctgagcctc agtacggagg gaaggcctgc gtggggatg
1741 tgcaggagcg tcagatgtgc aacaaggaga gctgccccgt ggatggctgt ttatccaacc
1801 cctgcttccc gggagcccag tgcagcagct tccccgatgg gtcctggtca tgcggctcct
1861 gccctgtggg cttcttgggc aatggcaccc actgtgagga cctggacgag tgtgccctgg
1921 tccccgacat ctgcttctcc accagcaagg tgcctcgctg tgtcaacact cagcctggct
1981 tccactgcct gccctgcccg ccccgataca gagggaacca gccgtcgggg tcggcctggg
2041 aagcagccaa gacggaaaag caagtgtgtg agcccgaaaa cccatgcaag gacaagacac
2101 acaactgcca caagcacgcg gagtgcatct acctgggcca cttcagcgac cccatgtaca
2161 agtgcgagtg ccagacaggc tacgcgggcg acgggctcat ctgcggggag gactcggacc
2221 tggacggctg gcccaacctc aatctggtct gcgccaccaa cgccacctac cactgcatca
2281 aggataactg ccccccatctg ccaaattctg ggcaggaaga cttttgacaag gacgggattg
2341 gcgatgcctg tgatgatgac gatgacaatg acggtgtgac cgatgagaag acaactgcc
2401 agctcctctt caatcccgc caggctgact atgacaagga tgaggttggg gaccgctgtg
2461 acaactgccc ttacgtgcac aaccctgccc agatcgacac agacaacaat ggagagggtg
2521 acgcctgctc cgtggacatt gatgggacg atgtcttcaa tgaacgagac aattgtccct
2581 acgtctacaa cactgaccag agggacacgg atggtgacgg tgtggggat cactgtgaca
2641 actgccccct ggtgcacaac cctgaccaga ccgacgtgga caatgacctt gttggggacc
2701 agtgtgacaa caacgaggac atagatgacg acggccacca gaacaaccag gacaactgcc
```

-continued

```
2761 cctacatctc caacgccaac caggctgacc atgacagaga cggccagggc gacgcctgtg
2821 accctgatga tgacaacgat ggcgtccccg atgacaggga caactgccgg cttgtgttca
2881 acccagacca ggaggacttg acggtgatg acggggtga tatttgtaaa gatgattttg
2941 acaatgacaa catcccagat attgatgatg tgtgtcctga aaacaatgcc atcagtgaga
3001 cagacttcag gaacttccag atggtcccct tggatcccaa agggaccacc caaattgatc
3061 ccaactgggt cattcgccat caaggcaagg agctggttca gacagccaac tcggaccccg
3121 gcatcgctgt aggttttgac gagtttgggt ctgtggactt cagtggcaca ttctacgtaa
3181 acactgaccg ggacgacgac tatgccggct tcgtctttgg ttaccagtca agcagccgct
3241 tctatgtggt gatgtggaag caggtgacgc agacctactg ggaggaccag cccacgcggg
3301 cctatggcta ctccggcgtg tccctcaagg tggtgaactc caccacgggg acgggcgagc
3361 acctgaggaa cgcgctgtgg cacacgggga acacgccggg gcaggtgcga accttatggc
3421 acgaccccag gaacattggc tggaaggact acacggccta taggtggcac ctgactcaca
3481 ggcccaagac tggctacatc agagtcttag tgcatgaagg aaaacaggtc atggcagact
3541 caggacctat ctatgaccaa acctacgctg gcgggcggct gggtctattt gtcttctctc
3601 aagaaatggt ctatttctca gacctcaagt acgaatgcag agatatttaa acaagatttg
3661 ctgcatttcc ggcaatgccc tgtgcatgcc atggtcccta gacacctcag ttcattgtgg
3721 tccttgtggc ttctctctct agcagcacct cctgtccctt gaccttaact ctgatggttc
3781 ttcacctcct gccagcaacc ccaaacccaa gtgccttcag aggataaata tcaatggaac
3841 tcagagatga acatctaacc cactagagga accagtttg gtgatatatg agactttatg
3901 tggagtgaaa attgggcatg ccattacatt gcttttctt gtttgtttaa aaagaatgac
3961 gtttacatat aaaatgtaat tacttattgt atttatgtgt atatggagtt gaagggaata
4021 ctgtgcataa gccattatga taaattaagc atgaaaaata ttgctgaact acttttggtg
4081 cttaaagttg tcactattct tgaattagag ttgctctaca atgacacaca aatcccatta
4141 aataaattat aaacaagggt caattcaaat ttgaagtaat gttttagtaa ggagagatta
4201 gaagacaaca ggcatagcaa atgacataag ctaccgatta actaatcgga acatgtaaaa
4261 cagttacaaa aataaacgaa ctctcctctt gtcctacaat gaaagccctc atgtgcagta
4321 gagatgcagt ttcatcaaag aacaaacatc cttgcaaatg ggtgtgacgc ggttccagat
4381 gtggatttgg caaaacctca tttaagtaaa aggttagcag agcaaagtgc ggtgctttag
4441 ctgctgcttg tgccgctgtg gcgtcgggga ggctcctgcc tgagcttcct tccccagctt
4501 tgctgcctga gaggaaccag agcagacgca caggccgaa aaggcgcatc taacgcgtat
4561 ctaggctttg gtaactgcgg acaagttgct tttacctgat ttgatgatac atttcattaa
4621 ggttccagtt ataaatattt tgttaatatt tattaagtga ctatagaatg caactccatt
4681 taccagtaac ttattttaaa tatgcctagt aacacatatg tagtataatt tctagaaaca
4741 aacatctaat aagtatataa tcctgtgaaa atatgaggct tgataatatt aggttgtcac
4801 gatgaagcat gctagaagct gtaacagaat acatagagaa taatgaggag tttatgatgg
4861 aaccttaaat atataatgtt gccagcgatt ttagttcaat atttgttact gttatctatc
4921 tgctgtatat ggaattcttt taattcaaac gctgaaaaga atcagcattt agtcttgcca
4981 ggcacaccca ataatcagtc atgtgtaata tgcacaagtt tgttttgtt tttgtttttt
5041 ttgttggttg gtttgttttt ttgctttaag ttgcatgatc tttctgcagg aaatagtcac
5101 tcatcccact ccacataagg ggtttagtaa gagaagtctg tctgtctgat gatggatagg
5161 gggcaaatct tttccccctt tctgttaata gtcatcacat ttctatgcca aacaggaaca
```

```
5221 atccataact ttagtcttaa tgtacacatt gcattttgat aaaattaatt ttgttgtttc 5281 aaaaaaaaaa aaaaaaaaaa aaaaaaaaaa aaaa
```

Exemplary regions or fragments of THBS2 include bases 1-5314, 132-3650 and 136-3650.

An exemplary human MOXD1 amino acid sequence is set forth below (SEQ ID NO: 33; GenBank Accession: AAH18756, Version 1 (GI: 17511810), incorporated herein by reference):

```
  1 mccwpllllw gllpgtaagg sgrtyphrtl ldsegkywlg wsqrgsqiaf rlqvrtagyv 61 gfgfsptgam asadivvggv ahgrpylqdy ftnanrelkk daqqdyhley amensthtii 121 eftrelhtcd indksitdst vrviwayhhe dageagpkyh dsnrgtkslr linpektsvl 181 stalpyfdlv nqdvpipnkd ttywcqmfki pvfqekhhvi kvepviqrgh eslvhhilly 241 qcsnnfndsv lesghecyhp nmpdafltce tvifawaigg egfsypphvg lslgtpldph 301 yvllevhydn ptyeeglidn sglrlfytmd irkydagvie aglwvslfht ippgmpefqs 361 eghctlecle ealeaekpsg ihvfavllha hlagrgirlr hfrkgkemkl laydddfdfn 421 fqefqylkee qtilpgdnli tecryntkdr aemtwgglst rsemclsyll yyprinltrc 481 asipdimeql qfigvkeiyr pvttwpfiik spkgyknisf mdamnkfkwt kkegisfnel 541 vlslpvnvrc sktdnaewsi qgmtalppdi erpykaeplv cgtssssslh rdfsinllvc 601 lllllsctlst ksl
```

Exemplary regions or fragments of MOXD1 include residues 29-165, 187-318, 333-485 and 1-613.

An exemplary human MOXD1 nucleotide sequence (the start and stop codons for the coding sequences are bold and underlined) is set forth below (SEQ ID NO: 34; GenBank Accession No. BC018756, Version 1 (GI: 17511809), incorporated herein by reference):

```
  1 ctcctcgttc tgctcctcac tccccagcgg ctggaggccg gtaccggcgg gcaggaggcg 61 cccgaggatg tgctgctggc cgctgctcct gctgtggggg ctgctccccg ggacggcggc 121 gggggctcg ggccgaacct atccgcaccg accctcctg gactcggagg gcaagtactg 181 gctgggctgg agccagcggg gcagccagat cgccttccgc ctccaggtgc gcactgcagg 241 ctacgtgggc ttcggcttct cgcccaccgg ggccatggcg tccgccgaca tcgtcgtggg 301 cggggtggcc cacgggcggc cctacctcca ggattatttt acaaatgcaa atagagagtt 361 gaaaaaagat gctcagcaag attaccatct agaatatgcc atggaaaata gcacacacac 421 aataattgaa tttaccagag agctgcatac atgtgacata aatgacaaga gtataacgga 481 tagcactgtg agagtgatct gggcctacca ccatgaagat gcaggagaag ctggtcccaa 541 gtaccatgac tccaataggg gcaccaagag tttgcggtta ttgaatcctg agaaaactag 601 tgtgctatct acagccttac catactttga tctggtaaat caggacgtcc ccatcccaaa 661 caaagataca acatattggt gccaaatgtt taagattcct gtgttccaag aaaagcatca 721 tgtaataaag gttgagccag tgatacagag aggccatgag agtctggtgc accacatcct 781 gctctatcag tgcagcaaca actttaacga cagcgttctg gagtccggcc acgagtgcta 841 tcacccccaac atgcccgatg cattcctcac ctgtgaaact gtgattttttg cctgggctat 901 tggtggagag ggcttttctt atccacctca tgttggatta tcccttggca ctccattaga
```

```
-continued
 961 tccgcattat gtgctcctag aagtccatta tgataatccc acttatgagg aaggcttaat 1021 agataattct ggactgaggt tattttacac aatggatata aggaaatatg atgctgggt 1081 gattgaggct ggcctctggg tgagcctctt ccataccatc cctccaggga tgcctgagtt 1141 ccagtctgag ggtcactgca ctttggagtg cctggaagag gctctggaag ccgaaaagcc 1201 aagtggaatt catgtgtttg ctgttcttct ccatgctcac ctggctggca gaggcatcag 1261 gctgcgtcat tttcgaaaag ggaaggaaat gaaattactt gcctatgatg atgattttga 1321 cttcaatttc caggagtttc agtatctaaa ggaagaacaa acaatcttac caggagataa 1381 cctaattact gagtgtcgct acaacacgaa agatagagct gagatgactt ggggaggact 1441 aagcaccagg agtgaaatgt gtctctcata ccttctttat tacccaagaa ttaatcttac 1501 tcgatgtgca agtattccag acattatgga acaacttcag ttcattgggg ttaaggagat 1561 ctacagacca gtcacgacct ggcctttcat tatcaaaagt cccaagcaat ataaaaacct 1621 ttctttcatg gatgctatga ataagtttaa atggactaaa aaggaaggtc tctccttcaa 1681 cgagctggtc ctcagcctgc cagtgaatgt gagatgttcc aagacagaca atgctgagtg 1741 gtcgattcaa ggaatgacag cattacctcc agatatagaa agaccctata aagcagaacc 1801 tttggtgtgt ggcacgtctt cttcctcttc cctgcacaga gatttctcca tcaacttgct 1861 tgtttgcctt ctgctactca gctgcacgct gagcaccaag agcttgtgat caaaattctg 1921 ttggacttga caatgttttc tatgatctga acctgtcatt tgaagtacag gttaaagact 1981 gtgtccactt tgggcatgaa gagtgtggag acttttcttc cccattttcc ctccctcctt 2041 tttcctttcc atgttacatg agagacatca atcaggttct cttctctttc ttagaaatat 2101 ctgatgttat atatacatgg tcaataaaat aaaactggcc tgacttaaga taaccatttt 2161 aaaaaaaaaa aaaaaaaaaa aaaaaaa
```

Exemplary regions or fragments of MOXD1 include bases 68-1909 and 2167-2188. An exemplary human SERPING1 amino acid sequence is set forth below (SEQ ID NO: 35; GenBank Accession No. NP_001027466, Version 1 (GI: 7385870), incorporated herein by reference):

```
  1 masrltlltl lllllagdra ssnpnatsss sqdpeslqdr gegkvattvi skmlfvepil
 61 evsslpttns ttnsatkita nttdepttqp ttepttqpti qptqpttqlp tdsptqpttg
121 sfcpgpvtlc sdleshstea vlgdalvdfs lklyhafsam kkvetnmafs pfsiaslltq
181 vllgagentk tnlesilsyp kdftcvhqal kgfttkgvts vsqifhspdl airdtfvnas
241 rtlyssspry lsnnsdanle lintwvaknt nnkisrllds lpsdtrlvll naiylsakwk
301 ttfdpkktrm epfhfknsvi kvpmmnskky pvahfidqtl kakvgqlqls hnlslvilvp
361 qnlkhrledm eqalspsvfk aimeklemsk fqptlltlpr ikvttsqdml simekleffd
421 fsydlnlcgl tedpdlqvsa mqhqtvlelt etgveaaaas aisvartllv fevqqpflfv
481 lwdqqhkfpv fmgrvydpra
```

Exemplary regions or fragments of SERPING1 include residues 1-22, 23-500, 85-119 and 453-476.

An exemplary human SERPING1 nucleotide sequence (the start and stop codons for the coding sequences are bold and underlined) is set forth below (SEQ ID NO: 36; GenBank Accession NM_001032295, Version 1 (GI: 73858569), incorporated herein by reference):

```
   1 gctggctggc tccgcaggtc cgctgacgtc gccgcccaga tggcctccag gctgaccctg
  61 ctgaccctcc tgctgctgct gctggctggg gatagagcct cctcaaatcc aaatgctacc
 121 agctccagct cccaggatcc agagagtttg caagacagag gcgaagggaa ggtcgcaaca
 181 acagttatct ccaagatgct attcgttgaa cccatcctgg aggtttccag cttgccgaca
 241 accaactcaa caaccaattc agccaccaaa ataacagcta ataccactga tgaacccacc
 301 acacaaccca ccacagagcc caccacccaa cccaccatcc aacccaccca accaactacc
 361 cagctcccaa cagattctcc tacccagccc actactgggt ccttctgccc aggacctgtt
 421 actctctgct ctgacttgga gagtcattca acagaggccg tgttggggga tgctttggta
 481 gatttctccc tgaagctcta ccacgccttc tcagcaatga agaaggtgga gaccaacatg
 541 gcctttttccc cattcagcat cgccagcctc cttacccagg tcctgctcgg ggctggggag
 601 aacaccaaaa caaacctgga gagcatcctc tcttacccca aggacttcac ctgtgtccac
 661 caggccctga agggcttcac gaccaaaggt gtcacctcag tctctcagat cttccacagc
 721 ccagacctgg ccataaggga cacctttgtg aatgcctctc ggaccctgta cagcagcagc
 781 cccagagtcc taagcaacaa cagtgacgcc aacttggagc tcatcaacac ctgggtggcc
 841 aagaaccacc acaacaagat cagccggctg ctagacagtc tgccctccga tacccgcctt
 901 gtcctcctca atgctatcta cctgagtgcc aagtggaaga caacatttga tcccaagaaa
 961 accagaatgg aaccctttca cttcaaaaac tcagttataa aagtgcccat gatgaatagc
1021 aagaagtacc ctgtggccca tttcattgac caaactttga agccaaggt ggggcagctg
1081 cagctctccc acaatctgag tttggtgatc ctggtacccc agaacctgaa acatcgtctt
1141 gaagacatgg aacaggctct cagcccttct gttttcaagg ccatcatgga gaaactggag
1201 atgtccaagt tccagcccac tctcctaaca ctaccccgca tcaaagtgac gaccagccag
1261 gatatgctct caatcatgga gaaattggaa ttcttcgatt tttcttatga ccttaacctg
1321 tgtgggctga cagaggaccc agatcttcag gtttctgcga tgcagcacca gacagtgctg
1381 gaactgacag agactggggt ggaggcggct gcagcctccg ccatctctgt ggcccgcacc
1441 ctgctggtct ttgaagtgca gcagcccttc ctcttcgtgc tctgggacca gcagcacaag
1501 ttccctgtct tcatggggcg agtatatgac cccagggcct gagacctgca ggatcaggtt
1561 agggcgagcg ctacctctcc agcctcagct ctcagttgca gccctgctgc tgcctgcctg
1621 gacttggccc ctgccacctc ctgcctcagg tgtccgctat ccaccaaaag ggctccctga
1681 gggtctgggc aagggacctg cttctattag cccttctcca tggccctgcc atgctctcca
1741 aaccactttt tgcagctttc tctagttcaa gttcaccaga ctctataaat aaaacctgac
1801 agaccatgac tttcaaaaaa aaaaaaaaaa aa
```

Exemplary regions or fragments of SERPING1 include bases 1435-1440, 1069-1288, 292-396 and 40-105.

An exemplary human PRELP amino acid sequence is set forth below (SEQ ID NO: 37; GenBank Accession No. NP_001027466, Version 1 (GI: 7382870), incorporated herein by reference):

```
  1 masrltlltl lllllagdra ssnpnatsss sqdpeslqdr gegkvattvi skmlfvepil
 61 evsslpttns ttnsatkita nttdepttqp ttepttqpti qptqpttqlp tdsptqpttg
121 sfcpgpvtlc sdleshstea vlgdalvdfs lklyhafsam kkvetnmafs pfsiaslltq
```

-continued

```
181 vllgagentk tnlesilsyp kdftcvhqal kgftttkgvts vsqifhspdl airdtfvnas 241 rtlyssspry lsnnsdanle lintwvaknt nnkisrllds lpsdtrlvll naiylsakwk 301 ttfdpkktrm epfhfknsvi kvpmmnskky pvahfidqtl kakvgqlqls hnlslvilvp 361 qnlkhrledm eqalspsvfk aimeklemsk fqptlltlpr ikvttsqdml simekleffd 421 fsydlnlcgl tedpdlqvsa mqhqtvlelt etgveaaaas aisvartllv fevqqpflfv 481 lwdqqhkfpv fmgrvydpra
```

Exemplary regions or fragments of PRELP include residues 85-119, 145-495, 453-476 and 466-500.

An exemplary human PRELP nucleotide sequence (the start and stop codons for the coding sequences are bold and underlined) is set forth below (SEQ ID NO: 38; GenBank Accession No. CR542270, Version 1 (GI: 49457533), incorporated herein by reference):

```
   1 atgaggtcac ccctctgctg gctcctccca cttctcatct tggcctcagt ggcccaaggc 61 cagccaacaa gacgaccaag acccgggact gggcccgggc gcagacccag gcccaggccc 121 aggcccacac ccagctttcc tcagcctgat gaaccagcag agccaacaga cctgcctcct 181 cccctccctc caggccctcc atctatcttc cctgactgtc cccgcgaatg ctactgcccc 241 cctgatttcc catctgccct ctactgtgat agccgcaacc tgcgaaaggt ccctgtcatc 301 ccgccccgca tccattacct ctatctccag aacaacttca tcactgagct cccggtggag 361 tccttccaga atgccacagg cctgcgatgg attaacctgg acaacaaccg aatccgcaag 421 atagaccaga gggtgctgga gaaactgccc ggcctggtgt cctctacat ggagaagaac 481 cagttggaag aggtcccctc ggccctgccc cggaacctgg agcagctgag gctgagccag 541 aaccacatct ccagaatccc gcctggtgtc ttcagcaagc tggagaacct gctgctcctg 601 gatctccagc acaacaggct gagcgacggc gtcttcaagc ccgacacctt ccatggcctc 661 aagaacctca tgcagctcaa cctggcccac aacatcctga gaaagatgcc gcccagggtc 721 cccaccgcca ttcaccagct ctacctggac agtaacaaga ttgagaccat ccctaacgga 781 tacttcaaga gctttcccaa tcttgccttc attcggctta actacaacaa gctgacagac 841 aggggactcc ccaagaactc ctttaatatc tccaacctgc ttgtgctcca cctgtcccac 901 aacaggatca gcagtgtgcc cgccatcaac aacaggctgg aacacctgta cctcaacaac 961 aatagcatcg agaaaatcaa cggaacccag atttgcccca cgacctagt ggcgttccat 1021 gacttctcct cggacctgga gaacgtgcca cacctgcgct acctgcggct ggatggaaac 1081 tacttgaagc cgcccatccc gctggacctc atgatgtgct tccgcctcct gcagtccgtg 1141 gtcatctag
```

Exemplary regions or fragments of PRELP include bases 1-1149.

An exemplary human CD52 amino acid sequence is set forth below (SEQ ID NO: 39; GenBank Accession No. NP_001794, Version 2 (GI: 68342030), incorporated herein by reference):

```
 1 mkrflflllt isllvmvgiq tglsgqndts qtsspsasss msggififfv anaiihlfcf 61 s
```

Exemplary regions or fragments of CD52 include residues 1-61 and 43-61.

An exemplary human CD52 nucleotide sequence (the start and stop codons for the coding sequences are bold and underlined) is set forth below (SEQ ID NO: 40; GenBank Accession No. BC000644, Version 2 (GI: 37588979), incorporated herein by reference):

```
  1 ctaaaaagct gctaccaaga cagccacgaa gatcctacca aaatgaagcg cttcctcttc 61 ctcctactca ccatcagcct cctggttatg gtacagatac aaactggact ctcaggacaa 121 aacgacacca gccaaaccag cagcccctca gcatccagca gcatgagcgg aggcattttc 181 cttttcttcg tggccaatgc cataatccac ctcttctgct tcagttgagg tgacacgtct 241 cagccttagc cctgtgcccc ctgaaacagc tgccaccatc actcgcaaga gaatccctc 301 catctttggg aggggttgat gccagacatc accaggttgt agaagttgac aggcagtgcc 361 atgggggcaa cagccaaaat aggggggtaa tgatgtaggg gccaagcagt gcccagctgg 421 gggtcaataa agttaccctt gtacttgcaa aaaaaaaaa aaaaaaa
```

Exemplary regions or fragments of CD52 include bases 1-467, 43-228 and 450-467.

An exemplary human LTBP2 amino acid sequence is set forth below (SEQ ID NO: 41; GenBank Accession No. AAH78659, Version 1 (GI: 50927279), incorporated herein by reference):

```
   1 mrprtkarsp gralrnpwrg flpitlalfv gaghaqrdpv gryepaggda nrirrpggsy 61 paaaaakvys lfreqdapva glqpveraqp gwgsprrpte aearrpsraq qsrrvqppaq 121 trrstplgqq qpaprtraap alprigtpqr sgaapptppr gritgrnvog gqccpgwtta 181 nstnhcikpv ceppcqnrgs csrpqlcvcr sgfrgarcee vipdeefdpq nsrlaprrwa 241 erspnirrss aagegtlara qppapqsppa pqsppagtls glscithpsqq hvglsrtvrl 301 hptatassql ssnalppgpg leqrdgtqqa vplehpsspw glnitekikk ikivftptic 361 kqtcarghca nscergdttt lysqgghghd pksgfriyfc qipcinggrc igrdecwcpa 421 nstgkfchlp ipqpdreppg rgsrpralle aplkqstftl plsnqlasvn pslvkvhihh 481 ppeasvqihq vaqvrggvee alvensvetr pppwlpaspg hslwdsnnip arsgepprpl 541 ppaaprprgl lgrcylntvn gqcanpllel ttqedccgsv gafwgvtica pcpprpaspv 601 iengqlecpq gykrlnlthc qdinecltlg lckdaecvnt rgsylctcrp glmldpsrsr 661 cvsdkaisml qglcyrslgp gtctlplaqr itkqicccsr vgkawgsece kcplpgteaf 721 reicpaghgy tyassdirls mrkaeeeela rppreqgqrs sgalpgpaer qplrvvtdtw 781 leagtipdkg dsqagqvtts vthapawvtg nattppmpeq giaeigeeqv tpstdvlvtl 841 stpgidrcaa gatnvcgpgt cvnlpdgyrc vcspgyqlhp sqayctddne clrdpckgkg 901 rcinrvgsys cfcypgytla tsgatqecqd ineceqpgvc sggqctnteg syhcecdqgy 961 imvrkghcqd inecrhpgtc pdgrcvnspg sytclaceeg yrgqsgscvd vnecltpgvc 1021 ahgkctnleg sfrosceqgy evtsdekgcq dvdecasras cptglclnte gsfacsacen 1081 gywvnedgta cedldecafp gvcpsgvctn tagsfsckdc dggyrpsplg dscedvdece 1141 dpqssclgge ckntvgsyqc lcpqgfqlan gtvcedvnec mgeehcaphg eclnshgsff 1201 clcapgfvsa eggtscqdvd ecattdpcvg ghcvntegsf nclcetgfqp spesgecvdi 1261 decedygdpv cgtwkcensp gsyrcvlgcq pgfhmapngd cididecand tmcgshgfcd 1321 ntdgsfrclc dqgfeispsg wdcvdvnece lmlavcgaal cenvegsflc lcasdleeyd
```

-continued

```
1381 ageghcrprg aggqsmseap tgdhapaptr mdcysgqkgh apcssvlgrn ttqaeccctq 1441 gaswgdacdl cpsedsaefs eicpsgkgyi pvegawtfgq tmytdadecv ifgpglcpng 1501 rclntvpgyv clcnpgfhyd ashkkcedhd ecqdlaceng ecvntegsfh cfcsppltld 1561 lsqqrcmnst sstedlpdhd ihmdicwkkv tndvcseplr ghrttytecc cqdgeawsqq 1621 calcpprsse vyaqlcnvar ieaereagvh frpgyeygpg pddlhyslyg pdgapfynyl 1681 gpedtvpdpa fpntaghsad rtpilesplq pselqphyva shpeppagfe glqaeecgil 1741 ngcengrcvr vregytcdcf egfqldaahm acvdvnecdd ingpavicvh gycentegsy 1801 rchcspgyva eagpphctak e
```

Exemplary regions or fragments of LTBP2 include residues 622-655, 681-723, 930-961, 970-1005, 1218-1249 and 1774-1808.

An exemplary human LTBP2 nucleotide sequence (the start and stop codons for the coding sequences are bold and underlined) is set forth below (SEQ ID NO: 42; GenBank Accession No. BC078659, Version 1 (GI: 50927278), incorporated herein by reference):

```
   1 ccaaaaataa aaccgtccgg gtccccttca gacggctgca ggcacaggga ggaggcgcga 61 aggtgcagca gccgtgcgag cccagctgga gtaggagcgc ggactcgagg ctcggggcgc 121 gcagccctcg ttccgccgag agccgggccc ccagtcggcc gcttcagggc cccctagact 181 cagagaagct ggccgccggg cggggccggg agaacagccc gcgggcgtcc agcgtgccga 241 ccacaaagct cttcgcggtg cccgcgcgca ccactctcca gccgccccgc gccatgaggc 301 cgcggaccaa agcccgcagc ccggggcgcg ccctgcggaa ccctggaga ggcttcctgc 361 cgctcaccct ggctctcttc gtgggcgcgg gtcatgccca aagggacccc gtagggagat 421 acgagccggc tggtggagac gcgaatcgac tgcggcgccc tggggcagc tacccggcag 481 cggctgcagc caaggtgtac agtctgttcc gggagcagga cgcgcctgtc gcgggcttgc 541 agcccgtgga gcgggcccag ccgggctggg ggagcccag gaggcccacc gaggcggagg 601 ccaggaggcc gtcccgcgcg cagcagtcgc ggcgtgtcca gccacctgcg cagacccgga 661 gaagcactcc cctgggccag cagcaaccag caccccggac ccgggccgcg ccggctctcc 721 cacgcctggg gaccccacag cggtctgggg ctgcgccccc aaccccgccg cgagggcgac 781 tcacggggag gaacgtctgc gggggacagt gctgcccagg atggacaaca gcaaacagca 841 ccaaccactg tatcaaaccc gtttgcgagc cgccgtgcca gaaccggggc tcctgcagcc 901 gcccgcagct ctgtgtctgc cgctctggtt tccgtggagc ccgctgcgag gaggtcattc 961 ccgatgagga atttgacccc cagaactcca ggctggcacc tcgacgctgg gccgagcgtt 1021 cacccaacct gcgcaggagc agtgcggctg gagagggcac cttggccaga gcacagccgc 1081 cagcaccaca gtcgccgccc gcaccacagt cgccaccagc tgggaccctg agtggcctca 1141 gccagaccca cccttcccag cagcacgtgg ggttgtcccg cactgtccga cttcacccga 1201 ctgccacggc cagtagccag ctctcttcca acgccctgcc cccgggacca ggccttgagc 1261 agagagatgg cacccaacag gcggtacctc tggagcaccc ctcatccccc tgggggctga 1321 acctcacgga gaaaatcaag aagatcaaga tcgtcttcac tcccaccatc tgcaagcaga 1381 cctgtgcccg tggacactgt gccaacagct gtgagagggg cgacaccacc accctgtaca 1441 gccaggcgcg ccatgggcac gatcccaagt ctggcttccg catctatttc tgccagatcc 1501 cctgcctgaa cggaggccgc tgcatcggca gggacgaatg ctggtgcccc gccaactcca
```

-continued

```
1561 ccgggaagtt ctgccacctg cctatcccgc agccggacag ggagcctcca gggaggggt
1621 cccgccccag ggccttgctg gaagcccac tgaagcagtc cactttcaca ctgccgctct
1681 ccaaccagct ggcctccgtg aacccctccc tggtgaaggt gcacattcac cacccacccg
1741 aggcctcagt gcagatccac caggtggccc aggtgcgggg cggggtggag gaggccctag
1801 tggagaacag cgtggagacc agaccccgc cctggctgcc tgccagccct ggccacagcc
1861 tctgggacag caacaacatc cctgctcggt ctggagagcc ccctcggcca ctgccccag
1921 cagcacccag gcctcgagga ctgctgggcc ggtgttacct gaacactgtg aacggacagt
1981 gtgccaaccc tctgctggag ctgactaccc aggaggactg ctgtggcagt gtgggagcct
2041 tctggggggt gactttgtgt gccccatgcc cacccagacc agcctccccg gtgattgaga
2101 atggccagct ggagtgtcct caggggtaca agagactgaa cctcactcac tgccaagata
2161 tcaacgagtg cttgacccctg gcctgtgca aggacgcgga gtgtgtgaat accaggggca
2221 gctacctgtg cacatgcaga cctggcctca tgctggatcc atcgcggagc cgctgtgtgt
2281 cggacaaggc aatctccatg ctgcagggac tgtgctaccg gtcgctgggg cccggcacct
2341 gcaccctgcc tttggcccag cggatcacca agcagatatg ctgctgcagc gcgtgggca
2401 aagcatgggg cagcgagtgt gagaaatgcc ctctgcctgg cacagaggcc ttcagagaga
2461 tctgccctgc cggccacggc tacacctacg cgagctccga catccgcctg tccatgagga
2521 aagccgagga ggaggaactg gcaaggcccc caagggagca agggcagagg agcagcgggg
2581 cactgcccgg gccagcagag aggcagcccc tccgggtcgt cacggacacc tggcttgagg
2641 ccgggaccat ccctgacaag ggtgactctc aggctggcca ggtcacgacc agtgtcactc
2701 atgcacctgc ctgggtcaca gggaatgcca caaccccacc aatgcctgaa caggggattg
2761 cagagataca ggaagaacaa gtgaccccct ccaccgatgt gctggtgacc ctgagcaccc
2821 caggcattga cagatgcgct gctggagcca ccaacgtctg tggccctgga acctgcgtga
2881 acctccccga tggatacaga tgtgtctgca gccctggcta ccagctgcac cccagccagg
2941 cctactgcac agatgacaac gagtgtctga gggacccctg caaggggaaaa gggcgctgca
3001 tcaaccgcgt ggggtcctac tcctgcttct gctaccctgg ctacactctg gccacctcag
3061 gggcgacaca ggagtgtcaa gatatcaatg agtgtgagca gccaggggtg tgcagcgggg
3121 ggcagtgcac caacaccgag ggctcgtacc actgcgagtg tgatcagggc tacatcatgg
3181 tcaggaaagg acactgccaa gatatcaacg aatgccgtca ccccggtacc tgccctgatg
3241 ggagatgcgt caattcccct ggctcctaca cttgtctggc ctgtgaggag ggctaccggg
3301 gccagagtgg gagctgtgta gatgtgaatg agtgtctgac tcccggggtc tgtgcccatg
3361 gaaagtgcac caacctagaa ggctccttca gatgctcttg tgagcagggc tatgaggtca
3421 cctcagatga aagggctgc aagatgtgg atgagtgtgc cagccgggcc tcatgcccca
3481 caggcctctg cctcaacacg gagggctcct tcgcctgctc tgcctgtgag aacgggtact
3541 gggtgaatga agacggcact gcctgtgaag acctagatga gtgtgccttc ccgggagtct
3601 gcccctccga agtctgcacc aacacggctg gctccttctc ctgcaaggac tgcgatgggg
3661 gctaccggcc cagcccctg ggtgactcct gtgaagatgt ggatgaatgt gaagaccccc
3721 agagcagctg cctgggaggc gagtgcaaga cactgtggg ctcctaccag tgcctctgtc
3781 cccagggctt ccagctggcc aatggcaccg tgtgtgagga tgtgaatgag tgcatggggg
3841 aggagcactc gcaccacac ggcgagtgcc tcaacagcca cggtctttc ttctgtctgt
3901 gcgcgcctgg cttcgtcagc gcagaggggg gcaccagctg ccaggatgtg gacgagtgtg
```

-continued

```
3961 ccaccacaga cccgtgtgtg ggagggcact gtgtcaacac cgagggctcc ttcaactgtc 4021 tatgtgagac tggcttccag ccctccccag agagtggaga gtgtgtggat attgacgagt 4081 gtgaggacta tggagacccg gtgtgtggca cctggaagtg tgaaaacagc cctggctcct 4141 accgctgtgt tctgggctgc cagcctggct tccacatggc cccgaacgga gactgcattg 4201 acatagacga gtgcgccaac gacaccatgt gtggcagcca cggcttctgt gacaacactg 4261 atggctcctt ccgctgcctc tgtgaccagg gcttcgagat ctctccctca ggctgggact 4321 gtgtggatgt gaacgagtgt gagcttatgc tggcggtatg tggggccgcg ctctgtgaga 4381 acgtggaggg ctccttcctg tgcctctgtg ccagtgacct ggaggagtac gatgccagg 4441 aggggcactg ccgcccacgg ggggctggag gtcagagtat gtctgaggcc caacggggg 4501 accatgcccc ggcccccacc cgcatggact gctactccgg gcagaagggc catgcgccct 4561 gctccagtgt cctgggccgg aacaccacac aggctgaatg ctgctgcacc cagggcgcta 4621 gctggggaga tgcctgtgac ctctgcccgt ctgaggactc agctgaattc agcgagatct 4681 gccctagtgg aaaaggctac attcctgtgg aaggagcctg gacgtttgga cagaccatgt 4741 acacagatgc ggatgagtgt gtgatattcg ggcctggtct ctgcccgaac ggccggtgcc 4801 tcaacaccgt gcctggttat gtctgcctgt gcaatcccgg cttccactac gatgcttccc 4861 acaagaagtg tgaggatcac gatgagtgcc aggacctggc ctgtgagaat ggcgagtgcg 4921 tcaacacgga gggctccttc cactgcttct gcagccccc gctcaccctg gacctcagcc 4981 agcagcgctg catgaacagc accagcagca cggaggacct ccctgaccac gacatccaca 5041 tggacatctg ctggaaaaaa gtcaccaatg atgtgtgcag cgaaccctg cgtgggcacc 5101 gcaccaccta cacggaatgc tgctgccagg acggcgaggc ctggagccag cagtgtgctc 5161 tgtgtccccc gaggagctct gaggtctatg ctcagctgtg caacgtggct cgcattgagg 5221 cagagcggga ggccggggtc cacttccggc caggctatga gtatggcccc gggcccgatg 5281 acctgcacta cagcatctat ggcccagatg ggccccctt ctacaactac ctgggccccg 5341 aggacaccgt ccctgatcct gccttcccca acacagccgg tcactcagcg gaccgcacac 5401 ccatccttga gtctccttg cagcccctag aactccagcc ccactacgtg ccagccatc 5461 cagagccccc agccggcttc gaagggcttc aggcggagga gtgcggcatc ctgaacggct 5521 gtgagaatgg ccgctgtgtg cgcgtgcggg agggctacac ctgtgactgt tttgagggct 5581 tccagctgga tgcggcccac atggcctgcg tagatgtgaa tgagtgtgat gacttgaacg 5641 ggcctgctgt gctctgtgtc catggttact gcgagaacac agagggctcc taccgctgcc 5701 actgctcccc gggatatgtg gctgaggcag gcccccccca ctgcactgcc aaggagtagc 5761 agtcaggggt cagtgtggca actacctgga aatggcctcc agtcacaggc aggggccttg 5821 aggatgattt cctagctggg aagacaccgt gacatcaggc cagaggtttc caatcagcct 5881 tgcctgcttt catctctccc agcttagcct ctggctgtaa gcttcggtca ttgcctccat 5941 gcccttgctt ggctcaagca ccaccaatcg ctttaatgct tcagccaccg catgaggccc 6001 tgtccaccac ctttcctggc cttgctatgg gatgcttacc aaaggatggc cctcatccac 6061 cctcccaagc tgtgcgagca tgcaaggccc catggcctca cactgcagac accccttcc 6121 agccacaatc caccatcatc ctgacgatcc cacaactggg acagaggcta catctgccct 6181 agggaggtcc ttcagaatct gtggagcaag aaaggatttg ggaagcttg gggactgact 6241 ccagagccc ctcctaagaa ccatcaccac cactcagcca atctgttctg ggccctgatt 6301 ttgccacacc tccatcctgt agcccattct ctgaccccaa ggagtggcag aagatccctt 6361 cactcagaga agcaaggctg atattagctt gttgaatgta agagacacaa atgaagaaga
```

-continued

```
6421 acaaagagcc tgagaaagca gcaagaggac atgatgaaaa atacgtggag ttgatgagaa 6481 aggggagcca aggctttata cgtctaaaga aaatattcag tagctgaatc cgcccagtga 6541 tagcctgtgg gcaccagcag caagggctgc catgggatac agcacccatc tacaaagacc 6601 tctattacat aaacactgct tcttacagga aacaaacctc ttctgggatc tccttttgtg 6661 aaaaccagtt tgatgtgcta aaagtaaaag tctattttcc agtgtggtct tgttcagaag 6721 cagccagatt tccaatgttg ttttccccct ccactcagaa accctgccc tttcccttca 6781 gaaaacgatg gcaggcattc ctctgagttt acaagcagag actcactcca acccaaacta 6841 gctgggagtt cagaaccatg gtggaataaa gaaatgtgca tctagaaaaa aaaaaaaaaa 6901 a
```

Exemplary regions or fragments of LTBP2 include bases 294-5759, 779-2795, 6689-6690, and 6886-6901.

An exemplary human ITGA11 amino acid sequence is set forth below (SEQ ID NO: 43; GenBank Accession No. AAD51919, Version 2 (GI: 5915662), incorporated herein by reference):

```
   1 mdlprglvva walslwpgft dtfnmdtrkp rvipgsrtaf fgytvqqhdi sgnkwlvvga 61 pletngyqkt gdvykcpvih gnotkinlgr vtlsnvserk dnmrlglsla tnpkdnsfla 121 csplwshecg ssyyttgmcs rvnsnfrfsk tvapalqrcq tymdivivld gsnsiypwve 181 vqhflinilk kfyigpgqiq vgvvqygedv vhefhlndyr svkdvveaas hieqrggtet 241 rtafgiefar seafqkggrk gakkvmivit dgeshdspdl ekviqqserd nvtryavavl 301 gyynrrginp etflneikyi asdpddkhff nvtdeaalkd ivdalgdrif slegtnknet 361 sfglemsqtg fsshvvedgv llgavgaydw ngavlketsa gkviplresy lkefpeelkn 421 hgaylgytvt svvssrqgry yvagaprfnh tgkvilftmh nnrsltihqa mrgqqigsyf 481 gseitsvdid gdgvtdvllv gapmyfnegr ergkvyvyel rqnrfvyngt lkdshsyqna 541 rfgssiasvr dlnqdsyndv vvgaplednh agaiyifhgf rgsilktpkg ritaselatg 601 lqyfgcsihg qldlnedgli dlavgalgna vilwsrpvvq inaslhfeps kinifhrdck 661 rsgrdatcla aficftpifl aphfqtttvg irynatmder rytprahlde ggdrftnrav 721 llssgqelce rinfhvldta dyvkpvtfsv eysledpdhg pmlddgwptt lrvsvpfwng 781 cnedehcvpd lvldarsdlp tameycqrvl rkpaqdcsay tlsfdttvfi iestrqrvav 841 eatlenrgen aystvlnisq sanlqfasli qkedsdgsie cvneerrlqk qvcnvsypff 901 rakakvafrl dfefsksifl hhleielaag sdsnerdstk ednvaplrfh lkyeadvlft 961 rssslshyev klnssleryd gigppfscif riqnlglfpi hgmmmkitip iatrsgnrll 1021 klrdfltdea ntscniwgns teyrptpvee dlrrapqlnh snsdvvsinc nirlvpnqei 1081 nfhllgnlwl rslkalkyks mkimvnaalq rqfhspfifr eedpsrqivf eiskqedwqv 1141 piwiivgstl ggllllallv lalwklgffr sarrrrepgl dptpkvle
```

Exemplary regions or fragments of ITGA11 include residues 163-341, 291-331, 358-449, 635-1070 ad 538-592.

An exemplary human ITGA11 nucleotide sequence (the start and stop codons for the coding sequences are bold and underlined) is set forth below (SEQ ID NO: 44; GenBank Accession No. AF137378, Version 2 (GI: 5915661), incorporated herein by reference):

```
   1 ggcacgaggc cgcgccgagg aggctgccgc tctggcttgc cagtccccccg ccgccgctgc
  61 acaccggacc cagccgccgt gccgcgggcc atggacctgc caggggcct ggtggtggcc
 121 tgggcgctca gcctgtggcc agggttcacg gacaccttca acatggacac caggaagccc
 181 cgggtcatcc ctggctccag gaccgccttc tttggctaca cagtgcagca gcacgacatc
 241 agtggcaata agtggctggt cgtgggcgcc ccactggaaa ccaatggcta ccagaagacg
 301 ggagacgtgt acaagtgtcc agtgatccac gggaactgca ccaaactcaa cctgggaagg
 361 gtcaccctgt ccaacgtgtc cgagcggaaa gacaacatgc gcctcggcct tagtctcgcc
 421 accaacccca aggacaacag cttcctggcc tgcagccccc tctggtctca tgagtgtggg
 481 agctcctact acaccacagg gatgtgttca agagtcaact ccaacttcag gttctccaag
 541 accgtggccc cagctctcca aggtgccag acctacatgg acatcgtcat tgtcctggat
 601 ggctccaaca gcatctaccc ctgggtggag gttcagcact tcctcatcaa catcctgaaa
 661 aagttttaca ttggcccagg gcagatccag gttggagttg tgcagtatgg cgaagatgtg
 721 gtgcatgagt ttcacctcaa cgactacagg tctgtaaaag atgtggtgga agctgccagc
 781 cacattgagc agagaggagg aacagagacc cggacggcat ttggcattga atttgcacgc
 841 tcagaggctt tccagaaggg tggaaggaaa ggagccaaga aggtgatgat tgtcatcaca
 901 gatgggagt cccacgacag cccagacctg agaaggtga tccagcaaag cgaaagagac
 961 aacgtaacaa gatatgcggt ggccgtcctg ggctactaca accgcagggg gatcaatcca
1021 gaaactttc taaatgaaat caaatacatc gccagtgacc ctgatgacaa gcacttcttc
1081 aatgtcactg atgaggctgc cttgaaggac attgtcgatg ccctggggga cagaatcttc
1141 agcctggaag gcaccaacaa gaacgagacc cctttgggc tggagatgtc acagacgggc
1201 ttttcctcgc acgtggtgga ggatgggtt ctgctgggag ccgtcggtgc ctatgactgg
1261 aatggagctg tgctaaagga cgagtgcc gggaaggtca ttcctctccg cgagtcctac
1321 ctgaaagagt tccccgagga gctcaagaac catggtgcat acctggggta cagtcaca
1381 tcggtcgtgt cctccaggca ggggcgagtg tacgtggccg gagccccccg gttcaaccac
1441 acgggcaagg tcatcctgtt caccatgcac aacaaccgga gcctcaccat ccaccaggct
1501 atgcggggcc agcagatagg ctcttacttt gggagtgaaa tcacctcggt ggacatcgac
1561 ggcgacggcg tgactgatgt cctgctggtg ggcgcaccca tgtacttcaa cgagggccgt
1621 gagcgaggca aggtgtacgt ctatgagctg agacagaacc ggtttgttta acggaacg
1681 ctaaaggatt cacacagtta ccagaatgcc cgatttgggt cctccattgc ctcagttcga
1741 gacctcaacc aggattccta caatgacgtg gtggtgggag ccccctgga ggacaaccac
1801 gcaggagcca tctacatctt ccacggcttc cgaggcagca tcctgaagac acctaagcag
1861 agaatcacag cctcagagct ggctaccggc ctccagtatt ttggctgcag catccacggg
1921 caattggacc tcaatgagga tgggctcatc gacctggcag tgggagccct tgcaacgct
1981 gtgattctgt ggtcccgccc agtggttcag atcaatgcca gcctccactt tgagccatcc
2041 aagatcaaca tcttccacag agactgcaag cgcagtggca gggatgccac ctgcctggcc
2101 gccttcctct gcttcacgcc catcttcctg gcacccccatt tccaaacaac aactgttggc
2161 atcagataca cgccaccat ggatgagagg cggtatacac cgagggccca cctggacgag
2221 ggcggggacc gattcaccaa cagagccgta ctgctctcct ccggcaggaa gctctgtgag
2281 cggatcaact tccatgtcct ggacactgct gactacgtga agccagtgac cttctcagtc
2341 gagtattccc tggaggaccc tgaccatggc cccatgctgg acgacggctg gcccaccact
2401 ctcagagtct cggtgcccctt ctggaacggc tgcaatgagg atgagcactg tgtccctgac
```

-continued

```
2461 cttgtgttgg atgcccggag tgacctgccc acggccatgg agtactgcca gagggtgctg 2521 aggaagcctg cgcaggactg ctccgcatac acgctgtcct tcgacaccac agtcttcatc 2581 atagagagca cacgccagcg agtggcggtg gaggccacac tggagaacag gggcgagaac 2641 gcctacagta cggtcctaaa tatctcgcag tcagcaaacc tgcagtttgc cagcttgatc 2701 cagaaggagg actcagacgg tagcattgag tgtgtgaacg aggagaggag gctccagaag 2761 caagtctgca acgtcagcta tcccttcttc cgggccaagg ccaaggtggc tttccgtctt 2821 gattttgagt tcagcaaatc catcttccta caccacctgg agatcgagct cgctgcaggc 2881 agtgacagta atgagcggga cagcaccaag gaagacaacg tggccccctt acgcttccac 2941 ctcaaatacg aggctgacgt cctcttcacc aggagcagca gcctgagcca ctacgaggtc 3001 aagctcaaca gctcgctgga gagatacgat ggtatcgggc ctcccttcag ctgcatcttc 3061 aggatccaga acttgggctt gttccccatc cacgggatga tgatgaagat caccattccc 3121 atcgccacca ggagcggcaa ccgcctactg aagctgaggg acttcctcac ggacgaggcg 3181 aacacgtcct gtaacatctg gggcaatagc actgagtacc ggcccacccc agtggaggaa 3241 gacttgcgtc gtgctccaca gctgaatcac agcaactctg atgtcgtctc catcaactgc 3301 aatatacggc tggtccccaa ccaggaaatc aatttccatc tactggggaa cctgtggttg 3421 aggcagttcc acagcccctt catcttccgt gaggaggatc ccagccgcca gatcgtgttt 3481 gagatctcca agcaagagga ctggcaggtc cccatctgga tcattgtagg cagcaccctg 3541 gggggcctcc tactgctggc cctgctggtc ctggcactgt ggaagctcgg cttctttaga 3601 agtgccaggc gcaggaggga gcctggtctg gaccccaccc ccaaagtgct ggagtgaggc 3661 tccagaggag actttgagtt gatgggggcc aggacaccag tccaggtagt gttgagaccc 3721 aggcctgtgg ccccaccgag ctggagcgga gaggaagcca gctggctttg cacttgacct 3781 catctcccga gcaatggcgc ctgctccctc cagaatggaa ctcaagctgg ttttaagtgg 3841 aactgcctac tgggagactg ggacaccttt acacagaccc ctagggattt aaagggacac 3901 ccctacacac acccaggccc acgccaaggc ctccctcagg ctctgtggag ggcatttgct 3961 gccccagcta ctaaggtgct agg
```

Exemplary regions or fragments of ITGA11 include bases 91-3657, 961-963, 1081-1083, 91-156, and 3265-3267.

An exemplary human TNS3 amino acid sequence is set forth below (SEQ ID NO: 45; GenBank Accession No. AAN32667, Version 1 (GI: 23451123), incorporated herein by reference):

```
  1 meeghgldlt yiteriiays fpagcseesy phnlqevtrm lkskhgdnyl vlnlsekryd 61 ltklnpkimd vgwpelhapp ldkmcticka qeswlnsnlq hvvvihcrgg kgrigvviss 121 ymhftnvsas adqaldrfam kkfyddkvsa lmqpsqkryv qflsgllsgs vkmnaspflf 181 hfvilhgtpn fdtggvcrpf lklyqamqpv ytsgiynvgp enpsricivi epaqllkgdv 241 mvkcyhkkyr satrdvifrl qfhtgavqgy glvfgkedld naskddrfpd ygkvelvfsa 301 tpekiqgseh lyndhgvivd ynttdplirw dsyenlsadg evlhtqgpvd gslyakvrkk 361 sssdpgipgg pqaipatnsp dhsdhtlsvs sdsghstasa rtdkteerla pgtrrglsaq 421 ekaeldqlls gfgledpgss lkemtdarsk ysgtrhvvpa qvhvngdaal kdretdildd 481 emphhdlhsv dslgtlssse gpqsvhlgpf tchkssqnsl lsdgfgsnvg edpqgtlvpd 541 lglgmdgpye rertfgsrep kqpqpllrkp sysaqmqayg qssystqtwv rqqqmvvahq
```

-continued

```
 601 ysfapdgear lvsrcpadnp glvqaqprvp ltptrgtssr vavqrgvgsg phppdtqqps 661 pskafkprfp gdqvvngagp elstgpspgs ptldidqsie qlnrlileld ptfepipthm 721 nalgsgangs vspdsvgggl rassrlpdtg egpsratgrq gssaeqplgg rlrklslgqy 781 dndaggqlpf skcawgkagv dyapnlppfp spadvketmt pgypqdldii dgrilsskes 841 mcstpafpvs petpyvktal rhppfsppep plsspasqhk ggreprscpe tlthavgmse 901 spigpkstml radasstpsf qqafassscti ssngpgqrre ssssaerqwv esspkpmvsl 961 lgsgrptgsp lsaefsgtrk dspvlscfpp selqapfhsh elslaeppds lappssqafl 1021 gfgtapvgsg lppeedlgal lanshgaspt psipltatga adngfishnf ltvapghssh 1081 hspglqgqgv tlpgqpplpe kkrasegdrs lgsyspsssg fssphsgsti sipfpnvlpd 1141 fskaseaasp lpdspgdklv ivkfvqdtsk fwykadisre qaiamlkdke pgsfivrdsh 1201 sfrgayglam kvatpppsvl qinkkagdla nelvrhflie ctpkgvrikg csnepyfgsl 1261 talvcqhsit plalpcklli perdpleeia esspqtaans aaellkqgaa cnvwylnsve 1321 mesitghqai qkalsitivq epppvstvvh fkvsaggitl tdnqrklffr rhypvnsvif 1381 caldpqdrkw ikdgpsskvf gfvarkqgsa tdnvchlfae hdpeqpasai vnfvskvmig 1441 spkkv
```

Exemplary regions or fragments of TNS3 include residues 72-186, 173-299, 1168-1284, and 1308-1439.

An exemplary human TNS3 nucleotide sequence (the start and stop codons for the coding sequences are bold and underlined) is set forth below (SEQ ID NO: 46; GenBank Accession No. AF417489, Version 1 (GI: 23451122), incorporated herein by reference):

```
   1 gcccttacca tggaggaggg ccatgggctg gacctcactt acatcacgga gcgcatcatc 61 gctgtgtcct tccctgccgg ctgctctgag gagtcctacc cgcacaacct acaggaggtc 121 acgcgcatgc tcaagtccaa gcacggggac aactacctgg tattaaacct ttcagaaaag 181 agatatgacc ttacgaagct taacccaaag atcatggatg tgggctggcc agagctccac 241 gcaccgcccc tggataagat gtgtaccata tgcaaggcgc aggagtcctg gctgaacagc 301 aacctccagc atgtggtcgt cattcactgc aggggcggga aggacgcat aggagtggtc 361 atatcatcct acatgcattt caccaacgtc tcagccagcg ccgaccaggc ccttgacagg 421 tttgcaatga agaagtttta tgatgacaaa gtttcagctt taatgcagcc ttcccaaaaa 481 cggtatgttc agttcctcag tgggctcctg tccggatcgg tgaaaatgaa tgcctctccc 541 ctgttcctgc attttgtcat cctccacggc accccaact tcgacacagg tggagtgtgc 601 cggcccttc tgaagctcta ccaagccatg cagcctgtgt acacctccgg gatctacaac 661 gttgcccag aaaacccag caggatctgc atcgtcatcg agccggccca gcttctgaag 721 ggagatgtca tggtgaaatg ctaccacaag aaataccgct cggccacccg tgacgtcatt 781 ttccgcctgc agtttcacac tggggctgtg cagggctacg ggctggtgtt tgggaaggag 841 gatctggaca atgccagcaa agatgaccgt tttcctgact atgggaaggt tgaattagtc 901 ttctctgcca cgcctgagaa gattcaaggg tccgaacact tgtacaacga ccacggtgtg 961 attgtggact acaacacaac agacccactg atacgctggg actcgtacga gaacctcagt 1021 gcagatggag aagtgctaca cacgcagggc cctgtcgatg gcagccttta cgcgaaggtg 1081 aggaagaaaa gctcctcgga tcctggcatc ccaggtggcc cccaggcaat cccggccacc 1141 aacagcccag accacagtga ccacaccttg tctgtcagca gtgactccgg ccactctaca
```

-continued

```
1201 gcctctgcca ggacggataa gacggaagag cgcctggccc caggaaccag gaggggcctg 1261 agtgcccagg agaaggctga gttggaccag ctgctcagtg gctttggcct ggaagatcct 1321 ggaagctccc tcaaggaaat gactgatgct cgaagcaagt acagtgggac ccgccacgtg 1381 gtgccagccc aggttcacgt gaatggagac gctgctctga aggatcggga gacagacatt 1441 ctggatgacg agatgcccca ccacgacctg cacagtgtgg acagccttgg accctgtcc 1501 tcctcggaag gcctcagtc ggtccacctg ggtcccttca cctgccacaa gagcagccag 1561 aactcactcc tatctgacgg ttttggcagc aacgttggtg aagatccgca gggcaccctc 1621 gttccggacc tgggccttgg catggacggc cctatgagc gggagcggac ttttgggagt 1681 cgagagccca agcagcccca gccctgctg agaaagccct cagtgtccgc ccagatgcag 1741 gcctatgggc agagcagcta ctccacacag acctgggtgc ccagcagca gatggttgta 1801 gctcaccagt atagcttcgc cccagatggg gaggcccggc tggtgagccg ctgccctgca 1861 gacaatcctg gcctcgtcca ggcccagccc agagtgccac tcacccccac ccgagggacc 1921 agcagtaggg tggctgtcca gagggtgta ggcagtgggc cacatccccc tgacacacag 1981 cagccctctc ccagcaaagc gttcaaaccc aggtttccag gagaccaggt tgtgaatgga 2041 gccggcccag agctgagcac aggcccctcc ccaggctcgc ccaccctgga catcgaccag 2101 tccatcgagc agctcaacag gctgatcctg gagctggatc ccaccttcga gcccatccct 2161 acccacatga acgccctcgg tagccaggcc aatggctctg tgtctccaga cagcgtggga 2221 ggtgggctcc gggcaagcag caggctgcct gacacaggag agggcccag cagggccacc 2281 gggcggcaag gctcctctgc tgaacagccc ctgggcggga gactcaggaa gctgagcctg 2341 gggcagtacg acaacgatgc tggggggcag ctgccctct ccaaatgtgc atggggaaag 2401 gctggtgtgg actatgcccc aaacctgccg ccattcccct caccagcgga cgtcaaagag 2461 acgatgaccc ctggctatcc ccaggacctc gatattatcg atggcagaat tttaagtagc 2521 aaggagtcca tgtgttcaac tccagcattt cctgtgtctc cagagacacc gtatgtgaaa 2581 acagcgctgc gccatcctcc gttcagccca cctgagcccc cgctgagcag cccagccagt 2641 cagcacaaag gaggacgtga accacgaagc tgccctgaga cgctcactca cgctgtgggg 2701 atgtcagaga gccccatcgg acccaaatcc acgatgctcc gggctgatgc gtcctcgacg 2761 ccctcctttc agcaggcttt tgcttcttcc tgcaccattt ccagcaacgg ccctgggcag 2821 aggagagaga gctcctcttc tgcagaacgc cagtgggtgg agagcagccc caagcccatg 2881 gtttccctgc tggggagcgg ccggcccacc ggaagtcccc tcagcgctga gttctccggt 2941 accaggaagg actccccagt gctgtcctgc ttccgccgt cagagctcca ggctcctttc 3001 cacagccatg agctgtccct agcagagcca ccggactccc tggcgcctcc cagcagccag 3061 gccttcctgg gcttcggcac cgccccagtg ggaagtggcc ttccgcccga ggaggacctg 3121 ggggccttgc tggccaattc tcatggagcg tcaccgaccc ccagcatccc gctgacagcg 3181 acagggctg ccgacaatgg cttcctgtcc acaactttc tcacggtggc gcctggacac 3241 agcagccacc acagtccagg cctgcaggc cagggtgtga ccctgcccgg gcagccaccc 3301 ctccctgaga agaagcgggc ctcggagggg atcgttctt tgggctcagt ctctccctcc 3361 tccagtgggct ctctccagccc gcacagcggg agcaccatca gtatcccctt cccaaatgtc 3421 cttcccgact tttccaaggc ttcagaagcg gcctcacctc tgccagatag tccaggtgat 3481 aaacttgtga tcgtgaaatt tgttcaagac acttccaagt tctggtacaa ggcggatatt 3541 tcaagagaac aagccatcgc catgttgaag gacaaggagc cgggctcatt cattgttcga
```

-continued

```
3601 gacagccatt ccttccgagg ggcctatggc ctggccatga aggtggccac gcccccacct 3661 tcagtcctgc agctgaacaa gaaagctgga gatttggcca atgaactcgt ccggcacttt 3721 ttgatcgagt gtaccccgaa gggagtgcgg ttgaaagggt gctcgaatga accatatttc 3781 gggagcctga cggccttggt gtgccagcat tccatcacgc ccttggcctt gccgtgcaag 3841 ctgcttatcc cagagagaga tccattggag gaaatagcag aaagttctcc ccagacggca 3901 gccaattcag cagctgagct gttgaagcag ggggcagcct gcaatgtgtg gtacttgaac 3961 tctgtggaga tggagtccct caccggccac caggcgatcc agaaggccct gagcatcacc 4021 ctggtccagg agcctccacc tgtgtccaca gttgtgcact tcaaggtgtc agcccagggc 4081 atcaccctga cagacaatca gaggaagctc ttcttccgga ggcattaccc cgtgaacagt 4141 gtgattttct gtgccttgga cccacaagac aggaagtgga tcaaagatgg cccttcctca 4201 aaagtctttg gatttgtggc ccggaagcag ggcagtgcca cggataatgt gtgccacctg 4261 tttgcagagc atgaccctga gcagcctgcc agtgccattg tcaacttcgt atcaaaggtc 4321 atgattggtt ccccaaagaa ggtctgagaa ctcccctccc tccctggacc caccgatgcc 4381 tctcgaag
```

Exemplary regions or fragments of TNS3 include bases 10-4347.

An exemplary human C12orf51 amino acid sequence is set forth below (SEQ ID NO: 47; GenBank Accession No. AAI43385, Version 1 (GI: 219521788), incorporated herein by reference):

```
  1 mcihqlnlla tnpnlpitsv lgkqhpieah hlssicdime kamvngdtci ircilvvfqv 61 vfkfffspqt ernrdiirrs glllwqllma pkdqicpeiq kevolaissg lnilypgete 121 innllklvlt egernsglsq lrdviltnla eqlqnnrfgs deddhyrlnd ellhyilkiv 181 vrescilitk cqtvskddfq kllstvpaas sclrylmavq nhllsntili kpdenddsds 241 slqgetlkel kvsilalatq iltgcdevle mlqqvttali nsdiadreqr lkgleqvtka 301 tmlghllpvl ltslmhpnlq tlimadalmp qlvqlvlyts qtalllktqc pvfaevgcsp 361 cgapdqkcrl fpdermleek eepgfltglk ipapwaagkt vetvhpvrdn ykfketvhip 421 garclylrfd srcssqydyd klviyagpnt nsrkvaeygg ntlgygsrsv lgtgwpkdlv 481 kvegdtvtfs femrsgrehn tpdkamwgfa ctvraqesse dvsgglpflv dlalglsvla 541 csmlrilyng peitkeeeac qellrskllq rcqwqveang vispaltpsp splpltieed 601 reftypsdvl vppvgnyfdl prirlppgim iklreisgra rpqfrpsiky vav
```

Exemplary regions or fragments of C12orf51 include residues 1-653.

An exemplary human C12orf51 nucleotide sequence (the start and stop codons for the coding sequences are bold and underlined) is set forth below (SEQ ID NO: 48; GenBank Accession No. BC143384, Version 1 (GI: 219521787), incorporated herein by reference):

```
  1 tcactgagcc caaagaagag gctataacca cgaatgaggt tataaaccaa ttattgcacc 61 acgttggtgc gatgtgcata caccaactca atcttcttgc caccaacccc aatcttccaa 121 tcacaagtgt cttgggcaag cagcatccaa ttgaagcaca tcatcttagc agtatttgtg 181 acattatgga gaaggccatg gttaatggag atacctgtat tatacgctgc attctcgttg 241 tctttcaggt ggtatttaaa ttttctctca gcccacaaac tgaaaggaat cgagacatca
```

-continued

```
 301 ttcgacggtc gggattgctt ctttggcagt tgttgatggc tccaaaagat caaatttgcc 361 ctgaaattca gaaggaagtc tgccttgcca tcagctctgg tttaaatatc ttgtacccag 421 gtgaaactga aatcaataac ttacttaaac tggtcttaac agaaggagag agaaacagtg 481 gactctccca gctacgggat gtgatcctaa ccaacctggc tgaacagctc caaaacaacc 541 gatttggcag tgatgaggat gatcattaca gactaaatga tgaacttta cactacattc 601 tgaagattgt tgtacgagaa tcctgtatct taatcaccaa gtgccaaact gtctctaaag 661 atgattttca aaagctcctt tcaactgtgc ctgctgcatc ctcctgcctg cgctatctga 721 tggcagttca gaatcacctt ctcagtaaca ctattttgat taaacctgat gagaatgatg 781 acagtgacag ctccttgcag ggagagacat tgaaggagct aaaagtcagt attttggctc 841 ttgccaccca aatcctgact ggatgtgatg aagtgttgga aatgctacag caggtcacaa 901 ctgccctcat aaatagtgac atagcagacc gtgagcagag gttaaaaggc ttggaacaag 961 ttactaaggc tactatgctt ggtcaccttc ttccagtgtt actgacctcc ttgatgcatc 1021 caaatttaca gactctgatc atggcggatg ccctgatgcc tcagctagtg cagctggtac 1081 tctataccag ccagacggcg ttgctgctta aacccagtg tccggttttt gctgaggtgg 1141 gctgttcccc gtgtggtgca ccagaccaga agtgcaggct gttccctgat gagagaatgt 1201 tagaagagaa ggaagagcca ggatttctca ctggtttaaa gattcctgcc ccatgggctg 1261 ctggaaagac tgtggaaaca gtccaccccg tcagagacaa ctataaattt aaagaaacgg 1321 tccatatccc aggagctcgc tgcctgtacc ttagatttga tagcagatgc tcttcgcaat 1381 atgactatga caaattggtg atatatgcgg ggcctaacac aaacagtagg aaggttgctg 1441 aaatatggagg caacacactg ggatatggca gccgtagtgt cttaggaact ggttggccga 1501 aagacttggt gaaggtggaa ggagatacag tcaccttctc ctttgaaatg agaagtggcc 1561 gtgaacacaa cactcctgat aaagccatgt ggggctttgc ttgcacagtt cgcgctcagg 1621 agtcttcgga ggatgtctca ggaggcttgc cctttctggt agacctggct ttaggtctgt 1681 ctgtgttagc ttgttccatg ttaagaatcc tgtacaatgg accagaaatt accaaagaag 1741 aagaagcctg tcaggagcta ttgcggtcca aacttttaca aaggtgccag tggcaggtgg 1801 aggccaatgg cgtgatctcc cctgcccttta ctccgagccc ctctccactg cctctgacca 1861 tagaggaaga cagagaattc acctaccct ctgatgtcct cgtgcctcct gttggaaact 1921 actttgatct gcctcggatc agactgcctc caggaatcat gataaagctc agggaaattt 1981 ctgggcgtgc tagacctcaa tttagaccaa gtataaagta tgttgctgtg tagtgtttta 2041 cttttcccaa tgggaaaaaa aagtttaaac aattgaaatg ggtatatttc ttctgtggtc
```

Exemplary regions or fragments of C12orf51 include bases 1-2100, and 72-2033.

An exemplary human TMEM205 amino acid sequence is set forth below (SEQ ID NO: 49) GenBank Accession No. NP_940938, Version 1 (GI: 63055043), incorporated herein by reference):

Exemplary regions or fragments of TMEM205 include residues 17-114, 18-38, 81-101, and 166-186.

An exemplary human TMEM205 nucleotide sequence (the start and stop codons for the coding sequences are bold and underlined) is set forth below (SEQ ID NO: 50; GenBank Accession NM_198536, Version 2 (GI: 224028276), incorporated herein by reference):

```
  1 meeggnlggl ikmvhllvls gawgmqmwvt fvsgfllfrs lprhtfglvq sklfpfyfhi 61 smgcafinlc ilasqhawaq ltfweasqly llflsltlat vnarwleprt taamwalqtv 121 ekergleggev pgshqgpdpy rqlrekdpky salrqnffry hglsslcnlg cvlsnglcla 181 glaleirsl
```

```
  1 ggctcagctg ggaggcggga cgaattattg gttgggggaa acccacgagg ggacgcggcc
 61 gaggagggtc gctgtccacc cggggcgtg ggagtgaggt accagattca gcccatttgg
121 ccccgacgcc tctgttctcg gaatccgggt gctgcggatt gaggtcccgg ttcctaacgg
181 tgggatcggt gtcctcggga tgagatttgg cgtttcctcg gggctttggt gggatcggtg
241 tcctcaggat gagatttagg gtttcctcgg ggctttcggg atcttcacct aatatccggt
301 attattttat gagaggagtg gtcttggctg tcagaactgg atccctgggg tgatatttgg
361 gaattagtgg agtgatctct gaagacctag ggctatgatc tggagctgct gtggctgaaa
421 tttggggcct ctgaagtggc atggagattg aggtccagag agcctgagat cttgagggct
481 gacatttgga gagatggggt cgagggttgt ctttgggcct tgactgcttt gggccttct
541 cactctcatt cccgggatgc tttgccagaa tctctgctgg attggccgta acctgtccc
601 cgagcgggct cacagggtct gaaggccacg catgaggcaa aggtaaagtt ctgagccacc
661 cggtgcctcc ttcccaggac tgcaagatgg aggaaggcgg gaacctagga ggcctgatta
721 agatggtcca tctactggtc ttgtcaggtg cctggggcat gcaaatgtgg gtgaccttcg
781 tctcaggctt cctgcttttc cgaagccttc cccgacatac cttcggacta gtgcagagca
841 aactcttccc cttctacttc cacatctcca tgggctgtgc cttcatcaac ctctgcatct
901 tggcttcaca gcatgcttgg gctcagctca cattctggga ggccagccag ctttacctgc
961 tgttcctgag ccttacgctg gccactgtca acgcccgctg gctggaaccc cgcaccacag
1021 ctgccatgtg ggccctgcaa accgtggaga aggagcgagg cctgggtggg gaggtaccag
1081 gcagccacca gggtcccgat ccctaccgcc agctgcgaga aaggacccc aagtacagtg
1141 ctctccgcca gaatttcttc cgctaccatg gctgtcctc tctttgcaat ctgggctgcg
1201 tcctgagcaa tgggctctgt ctcgctggcc ttgccctgga aataaggagc ctctagcatg
1261 ggccctgcat gctaataaat gcttcttcag aaatgaaaaa aaaaaaaaa a
```

Exemplary regions or fragments of TMEM205 include bases 633-635, 687-1256, 843-905 and 927-989.

An exemplary human HSPA9 amino acid sequence is set forth below (SEQ ID NO: 51; GenBank Accession No. AAH24034, Version 1 (GI: 18645123), incorporated herein by reference):

```
  1 misasraaaa rlvgaaasrg ptaarhqdsw nglsheafrl vsrrdyasea ikgavvgidl
 61 gttnscvavm egkrakvlen aegarttpsv vaftadgerl vgmpakrqav tnpnntfyat
121 krligrrydd pevqkdiknv pfkivrasng dawveahgkl yspsqigafv lmkmketaen
181 ylgrtaknav itvpayfnds qrqatkdagq lsglnvlrvi neptaaalay gldksedkvi
241 avydlgggtf disileiqkg vfevkstngd tflggedfdq allrhivkef kretgvdltk
301 dnmalqrvre aaekakcels ssvqtdinlp yltmdssgpk hlnmkltraq fegivtdlir
361 rtiapcqkam qdaevsksdi gevilvggmt rmpkvqqtvq dlfgrapska vnpdeavaig
421 aaiqggvlag dvtdvllldv tplslgietl ggvftklinr nttiptkksq vfstaadgqt
481 qveikvcqge remagdnkll gqftligipp aprgvpqiev tfdidangiv hvsakdkgtg
541 reqqiviqss gglskddien mvknaekyae edrrkkerve avnmaegiih dtetkmeefk
```

-continued

```
601 dqlpadecnk lkeelskmre llarkdsetg enirqaassl qqaslklfem aykkmasere
661 gsgssgtgeq kedqkeekq
```

Exemplary regions or fragments of HSPA9 include residues 52-673, 52-428, and 387-391.

An exemplary human HSPA9 nucleotide sequence (the start and stop codons for the coding sequences are bold and underlined) is set forth below (SEQ ID NO: 52; GenBank Accession No. BC024034, Version 2 (GI: 38196942), incorporated herein by reference):

```
   1 ggagcgcttg tttgctgcct cgtactcctc catttatccg cc atg ataag tgccagccga
  61 gctgcagcag cccgtctcgt gggcgccgca gcctcccggg gccctacggc cgcccgccac
 121 caggatagct ggaatggcct tagtcatgag gcttttagac ttgtttcaag gcgggattat
 181 gcatcagaag caatcaaggg agcagttgtt ggtattgatt gggtactac caactcctgc
 241 gtggcagtta tggaaggtaa acgagcaaag gtgctggaga atgccgaagg tgccagaacc
 301 acccccttcag ttgtggcctt tacagcagat ggtgagcgac ttgttggaat gccggccaag
 361 cgacaggctg tcaccaaccc aaacaataca ttttatgcta ccaagcgtct cattggccgg
 421 cgatatgatg atcctgaagt acagaaagac attaaaaatg ttccctttaa aattgtccgt
 481 gcctccaatg gtgatgcctg ggttgaggct catgggaaat tgtattctcc gagtcagatt
 541 ggagcatttg tgttgatgaa gatgaaagag actgcagaaa attacttggg gcgcacagca
 601 aaaaatgctg tgatcacagt cccagcttat ttcaatgact cgcagagaca ggccactaaa
 661 gatgctggcc agatatctgg actgaatgtg cttcgggtga ttaatgagcc cacagctgct
 721 gctcttgcct atggtctaga caaatcagaa gacaaagtca ttgctgtata tgatttaggt
 781 ggtggaactt ttgatatttc tatcctggaa attcagaaag gagtatttga ggtgaaatcc
 841 acaaatgggg ataccttctt aggtggggaa gactttgacc aggccttgct acggcacatt
 901 gtgaaggagt tcaagagaga gacagggggtt gatttgacta agacaacat ggcacttcag
 961 agggtacggg aagctgctga aaaggctaag tgtgaactct cctcatctgt gcagactgac
1021 atcaatttgc cctatcttac aatggattct tctggaccca agcatttgaa tatgaagttg
1081 acccgtgctc aatttgaagg gattgtcact gatctaatca gaaggactat cgctccatgc
1141 caaaaagcta tgcaagatgc agaagtcagc aagagtgaca taggagaagt gattcttgtg
1201 ggtggcatga ctaggatgcc caaggttcag cagactgtac aggatctttt tggcagagcc
1261 ccaagtaaag ctgtcaatcc tgatgaggct gtggccattg gagctgccat tcagggaggt
1321 gtgttggccg gcgatgtcac ggatgtgctg ctccttgatg tcactcccct gtctctgggt
1381 attgaaactc taggaggtgt ctttaccaaa cttattaata ggaataccac tattccaacc
1441 aagaagagcc aggtattctc tactgccgct gatggtcaaa cgcaagtgga aattaaagtg
1501 tgtcagggtg aaagagagat ggctggagac aacaaactcc ttggacagtt tactttgatt
1561 ggaattccac cagcccctcg tggagttcct cagattgaag ttacatttga cattgatgcc
1621 aatgggatag tacatgtttc tgctaaagat aaaggcacag gacgtgagca gcagattgta
1681 atccagtctt ctggtggatt aagcaaagat gatattgaaa atatggttaa aaatgcagag
1741 aaatatgctg aagaagaccg gcgaaagaag gaacgagttg aagcagttaa tatggctgaa
1801 ggaatcattc acgacacaga aaccaagatg gaagaattca ggaccaatt acctgctgat
1861 gagtgcaaca agctgaaaga agagatttcc aaaatgaggg agctcctggc tagaaaagac
1921 agcgaaacag gagaaaatat tagacaggca gcatcctctc ttcagcaggc atcattgaag
```

-continued

```
1981 ctgttcgaaa tggcatacaa aaagatggca tctgagcgag aaggctctgg aagttctggc 2041 actggggaac aaaaggaaga tcaaaaggag gaaaaacagt aataatagca gaaattttga 2101 agccagaagg acaacatatg aagcttagga gtgaagagac ttcctgagca gaaatgggcg 2161 aacttcagtc tttttactgt gtttttgcag tattctatat ataatttcct taatttgtaa 2221 atttagtgac cattagctag tgatcattta atggacagtg attctaacag tataaagttc 2281 acaatattct atgtccctag cctgtcattt ttcagctgca tgtaaaagga ggtaggatga 2341 attgatcatt ataaagattt aactatttta tgctgaagtg accatatttt caagggtga 2401 aaccatctcg cacacagcaa tgaaggtagt catccataga cttgaaatga gaccacatat 2461 ggggatgaga tccttctagt tagcctagta ctgctgtact ggcctgtatg tacatggggt 2521 ccttcaactg aggccttgca agtcaagctg gctgtgccat gtttgtagat ggggcagagg 2581 aatctagaac aatgggaaac ttagctattt atattaggta cagctattaa aacaaggtag 2641 gaatgaggct agacctttaa cttccctaag gcatactttt ctagctacct tctgccctgt 2701 gtctggcacc tacatccttg atgattgttc tcttacccat tctggaattt ttttttttt 2761 taaataaata cagaaagcat cttgaaaaaa aaaaaaaaa aa
```

Exemplary regions or fragments of HSPA9 include bases 43-2082, 263-900, and 2786-2802.

An exemplary human CLDN8 amino acid sequence is set forth below (SEQ ID NO: 53; GenBank Accession No. BAA95567, Version 1 (GI: 7768788), incorporated herein by reference):

```
  1 mathaleiag lflggvgmvg tvavtvmpqw rvsafienni vvfenfwegl wmnovrqani 61 rmqckiydsl lalspdlqaa rglmcaasvm sflafmmail gmkctrctgd nekvkahill 121 tagiifiitg mvvlipvswv anaiirdfyn sivnvaqkre lgealylgwt talvlivgga 181 lfccvfccne ksssyrysip shrttqksyh tgkkspsvys rsqyv
```

Exemplary regions or fragments of CLDN8 include residues 1-225 and 5-182.

An exemplary human CLDN8 nucleotide sequence (the start and stop codons for the coding sequences are bold and underlined) is set forth below (SEQ ID NO: 54; GenBank Accession No. NM_199328, Version 2 (GI: 297206863), incorporated herein by reference):

```
  1 gatttgtaag tttacctgtt gcagccaata gcagggccat ctcagccagc cagcactgga 61 tactatctgg ccagaagtag caaagcagct cttatttgaa aaaccactgg gttccgagtt 121 cattactaca ggaaaaactg ttctcttctg tggcacagaa aaccctgctt caaagcagaa 181 gtagcagttc cggagtccag ctggctaaaa ctcatcccag aggataatgg caacccatgc 241 cttagaaatc gctgggctgt tcttggtgg tgttggaatg gtgggcacag tggctgtcac 301 tgtcatgcct cagtggagag tgtcggcctt cattgaaaac aacatcgtgg tttttgaaaa 361 ctttctgggaa ggactgtgga tgaattgcgt gaggcaggct aacatcagga tgcagtgcaa 421 aatctatgat tccctgctgg ctctttctcc ggacctacag gcagccagag gactgatgtg 481 tgctgcttcc gtgatgtcct tcttggcttt catgatggcc atccttggca tgaaatgcac 541 caggtgcacg ggggacaatg agaaggtgaa ggctcacatt ctgctgacgg ctggaatcat 601 cttcatcatc acgggcatgg tggtgctcat ccctgtgagc tgggttgcca atgccatcat
```

-continued

```
 661 cagagatttc tataactcaa tagtgaatgt tgcccaaaaa cgtgagcttg gagaagctct 721 ctacttagga tggaccacgg cactggtgct gattgttgga ggagctctgt tctgctgcgt 781 tttttgttgc aacgaaaaga gcagtagcta cagatactcg ataccttccc atcgcacaac 841 ccaaaaaagt tatcacaccg gaaagaagtc accgagcgtc tactccagaa gtcagtatgt 901 gtagttgtgt atgtttttt aactttacta taaagccatg caaatgacaa aaatctatat 961 tactttctca aaatggaccc caaagaaact ttgatttact gttcttaact gcctaatctt 1021 aattacagga actgtgcatc agctatttat gattctataa gctatttcag cagaatgaga 1081 tattaaaccc aatgctttga ttgttctaga aagtatagta atttgttttc taaggtggtt 1141 caagcatcta ctcttttat catttacttc aaaatgacat tgctaaagac tgcattattt 1201 tactactgta atttctccac gacatagcat tatgtacata gatgagtgta acatttatat 1261 ctcacataga gacatgctta tatggtttta tttaaaatga aatgccagtc cattacactg 1321 aataaaataga actcaactat tgcttttcag ggaaatcatg gatagggttg aagaaggtta 1381 ctattaattg tttaaaaaca gcttagggat taatgtcctc catttataat gaagattaaa 1441 atgaaggctt taatcagcat tgtaaaggaa attgaatggc tttctgatat gctgttttt 1501 agcctaggag ttagaaatcc taacttcttt atcctcttct cccagaggct tttttttct 1561 tgtgtattaa attaacattt ttaaaaagca gatattttgt caaggggctt tgcattcaaa 1621 ctgcttttcc agggctatac tcagaagaaa gataaaagtg tgatctaaga aaaagtgatg 1681 gttttaggaa agtgaaaata ttttgtttt tgtatttgaa gaagaatgat gcattttgac 1741 aagaaatcat atatgtatgg atatatttta ataagtattt gagtacagac tttgaggttt 1801 catcaatata aataaaagag cagaaaaata tgtcttggtt ttcatttgct taccaaaaaa 1861 acaacaacaa aaaaagttgt cctttgagaa cttcacctgc tcctatgtgg gtacctgagt 1921 caaaattgtc atttttgttc tgtgaaaaat aaatttcctt cttgtaccat ttctgtttag 1981 ttttactaaa atctgtaaat actgtatttt tctgtttatt ccaaatttga tgaaactgac 2041 aatccaattt gaaagtttgt gtcgacgtct gtctagctta aatgaatgtg ttctatttgc 2101 tttatacatt tatattaata aattgtacat ttttctaatt atttgaa
```

Exemplary regions or fragments of CLDN8 include bases 206-208, 248-310, 470-532, 578-640 and 725-787.

An exemplary human PTPLAD1 amino acid sequence is set forth below (SEQ ID NO: 55; GenBank Accession No. AAH35508, Version 1 (GI: 27370575), incorporated herein by reference):

```
  1 menqvltphv ywaqrhrely lrvelsdvqn paisitenvl hfkagghgak gdnvyefhle 61 fldlvkpepv ykltqrqvni tvqkkvsqww erltkqekrp lflapdfdrw ldesdaemel 121 rakeeerlnk lrlesegspe tltnlrkgyl fmynlvqflg fswifvnltv rfcilgkesf 181 ydtfhtvadm myfcqmlavv etinaaigvt tspvlpsliq llgrnfilfi ifgtmeemqn 241 kavvffvfyl wsaieifrys fymltcidmd wkvltwlryt lgiplyplgc laeaysviqs 301 ipifnetgrf sftlpypvki kvrfsfflqi ylimiflgly infrhlykqr rrygqkkkk 361 k
```

Exemplary regions or fragments of PTPLAD1 include residues 8-115, and 195-358.

An exemplary human PTPLAD1 nucleotide sequence (the start and stop codons for the coding sequences are bold and underlined) is set forth below (SEQ ID NO: 56; GenBank Accession No. BC035508, Version 1 (GI: 23271044), incorporated herein by reference):

```
   1 ggcaacgagg ggtatctcga ggtgccgggt tgcaggcgct caggagcgct agggtttgag
  61 gcctgctttc tgctcgcgcc agcagagcac tacctgaggc agcgaggcgc agcgagccta
 121 gcctccccgc gccctgggca gtgtggccat ggagaatcag gtgttgacgc cgcatgtcta
 181 ctgggctcag cgacaccgcg agctatatct gcgcgtggag ctgagtgacg tacagaaccc
 241 tgccatcagc atcactgaaa acgtgctgca tttcaaagct caaggacatg gtgccaaagg
 301 agacaatgtc tatgaatttc acctggagtt cttagacctt gtgaaaccag agcctgttta
 361 caaactgacc cagaggcagg taaacattac agtacagaag aaagtgagtc agtggtggga
 421 gagactcaca aagcaggaaa agcgaccact gttttggct cctgactttg atcgttggct
 481 ggatgaatct gatgcggaaa tggagctcag agctaaggaa gaagagcgcc taaataaact
 541 ccgactggaa agcgaaggct ctcctgaaac tcttacaaac ttaaggaaag gatacctgtt
 601 tatgtataat cttgtgcaat tcttgggatt ctcctggatc tttgtcaacc tgactgtgcg
 661 attctgtatc ttgggaaaag agtccttta tgacacattc catactgtgg ctgacatgat
 721 gtatttctgc cagatgctgg cagttgtgga actatcaat gcagcaattg gagtcactac
 781 gtcaccggtg ctgccttctc tgatccagct tcttggaaga aatttatttt tgtttatcat
 841 ctttggcacc atggaagaaa tgcagaacaa agctgtggtt ttctttgtgt tttatttgtg
 901 gagtgcaatt gaaattttca ggtactcttt ctacatgctg acgtgcattg acatggattg
 961 gaaggtgctc acatggcttc gttacactct ggggattccc ttatatccac tgggatgttt
1021 ggcggaagct gtctcagtga ttcagtccat tccaatattc aatgagaccg gacgattcag
1081 tttcacattg ccatatccag tgaaaatcaa agttagattt tccttttttc ttcagattta
1141 tcttataatg atatttttag gtttatacat aaattttcgt caccttata aacagcgcag
1201 acggcgctat ggacaaaaaa aaaaaaaaa a
```

Exemplary regions or fragments of PTPLAD1 include bases 1-5, 149-1231 and 1222-1231.

An exemplary human MAL2 amino acid sequence is set forth below (SEQ ID NO: 57; GenBank Accession No. EAW91981, Version 1 (GI: 119612387), incorporated herein by reference):

```
  1 msaggasvpp ppnpaysfpp prvtlpagpd ilrtysgafv cleilfgglv wilvassnvp
 61 lpllqgwvmf vsvtafffsl lflgmflsgm vaqidanwnf ldfayhftvf vfyfgaflle
121 aaatslhdlh cnttitgqpl lsdnqyninv aasifafmtt acygcslgla lrrwrp
```

Exemplary regions or fragments of MAL2 include residues 1-176 and 32-169.

An exemplary human MAL2 nucleotide sequence (the start and stop codons for the coding sequences are bold and underlined) is set forth below (SEQ ID NO: 58; GenBank Accession No. NM_052886, Version 2 (GI: 109633023), incorporated herein by reference):

```
   1 agcccgcgga gctgagcggc ggcggcggcg gcggcaggag cccgggaggc ggaggcggga
  61 ggcggcggcg gcgcgcggag acgcagcagc ggcagcggca gcatgtcggc cggcggagcg
 121 tcagtcccgc cgcccccgaa ccccgccgtg tccttcccgc cgcccgggt cacccctgccc
 181 gccggccccg acatcctgcg gacctactcg ggcgccttcg tctgcctgga gattctgttc
 241 gggggtcttg tctggatttt ggttgcctcc tccaatgttc ctctacctct actacaagga
 301 tgggtcatgt ttgtgtccgt gacagcgttt ttcttttcgc tcctcttct gggcatgttc
 361 ctctctggca tggtggctca aattgatgct aactggaact tcctggattt tgcctaccat
 421 tttacagtat ttgtcttcta ttttggagcc ttttattgg aagcagcagc cacatccctg
 481 catgatttgc attgcaatac aaccataacc gggcagccac tcctgagtga taaccagtat
 541 aacataaacg tagcagcctc aatttttgcc tttatgacga cagcttgtta tggttgcagt
 601 ttgggtctgg ctttacgaag atggcgaccg taacactcct tagaaactgg cagtcgtatg
 661 ttagtttcac ttgtctactt tatatgtctg atcaatttgg ataccatttt gtccagatgc
 721 aaaaacattc caaaagtaat gtgttagta gagagagact ctaagctcaa gttctggttt
 781 atttcatgga tggaatgtta atttattat gatattaaag aaatggcctt ttatttaca
 841 tctctcccct ttttccctt cccctttat tttcctcctt ttctttctga agtttcctt
 901 ttatgtccat aaaatacaaa tatattgttc ataaaaatt agtatccctt ttgtttggtt
 961 gctgagtcac ctgaacctta atttaattg gtaattacag cccctaaaaa aaacacattt
1021 caaataggct tcccactaaa ctctatattt tagtgtaaac caggaattgg cacactttt
1081 ttagaatggg ccagatggta aatatttatg cttcacggtc catacagtct ctgtcacaac
1141 tattcagttc tgctagtata gcgtgaaagc agctatacac aatacagaaa tgaatgagtg
1201 tggttatgtt ctaataaaac ttatttataa aaacaagggg aggctgggtt tagcctgtgg
1261 gccatagttt gtcaaccact ggtgtaaaac cttagttata tatgatctgc attttcttga
1321 actgatcatt gaaaacttat aaacctaaca gaaaagccac ataatattta gtgtcattat
1381 gcaataatca cattgccttt gtgttaatag tcaaatactt acctttggag aatacttacc
1441 tttggaggaa tgtataaaat ttctcaggca gagtcctgga tataggaaaa agtaatttat
1501 gaagtaaact tcagttgctt aatcaaacta atgatagtct aacaactgag caagatcctc
1561 atctgagagt gcttaaaatg ggatccccag agaccattaa ccaatactgg aactggtatc
1621 tagctactga tgtcttactt tgagtttatt tatgcttcag aatacagttg tttgccctgt
1681 gcatgaaatat acccatattt gtgtgtggat atgtgaagct tttccaaata gagctctcag
1741 aagaattaag tttttacttc taattatttt gcattacttt gagttaaatt tgaatagagt
1801 attaaatata aagttgtaga ttcttatgtg tttttgtatt agcccagaca tctgtaatgt
1861 ttttgcactg gtgacagaca aaatctgttt taaaatcata tccagcacaa aaactatttc
1921 tggctgaata gcacagaaaa gtattttaac ctacctgtag atcctcgt catggaaagg
1981 tgccaaactg ttttgaatgg aaggacaagt aagagtgagg ccacagttcc caccacacga
2041 gggcttttgt attgttctac ttttcagcc ctttactttc tggctgaagc atcccttgg
2101 agtgccatgt ataagttggg ctattagagt tcatggaaca tagaacaacc atgaatgagt
2161 ggcatgatcc gtgcttaatg atcaagtgtt acttatctaa taatcctcta gaaagaaccc
2221 tgttagatct tggtttgtga taaaaatata aagacagaag acatgaggaa aaacaaaagg
2281 tttgaggaaa tcaggcatat gactttatac ttaacatcag atcttttcta taatatccta
2341 ctactttggt tttcctagct ccataccaca cacctaaacc tgtattatga attacatatt
2401 acaaagtcat aaatgtgcca tatggatata cagtacattc tagttggaat cgtttactct
```

-continued

```
2461 gctagaattt aggtgtgaga ttttttgttt cccaggtata gcaggcttat gtttggtggc 2521 attaaattgg tttctttaaa atgctttggt ggcacttttg taaacagatt gcttctagat 2581 tgttacaaac caagcctaag acacatctgt gaatacttag atttgtagct taatcacatt 2641 ctagacttgt gagttgaatg acaaagcagt tgaacaaaaa ttatggcatt taagaattta 2701 acatgtctta gctgtaaaaa tgagaaagtg ttggttggtt ttaaaatctg gtaactccat 2761 gatgaaaaga aatttatttt atacgtgtta tgtctctaat aaagtattca tttgataaaa 2821 aaaaaaaaa a
```

Exemplary regions or fragments of MAL2 include bases 1-234, 205-267, 301-363, 409-471, and 550-612.

An exemplary human ANTXR1 nucleotide sequence is set forth below (SEQ ID NO: 59; GenBank Accession No. NM_053034.2, Version 2, incorporated herein by reference):

```
   1 atcatattta aaatctggga caaagaaccg tcgggacgga actccttcca ttgcaaaagc 61 tcggcgcggc ctcgggagct gcccggcggc cccggaccga ggcagccctc cccttttaaaa 121 gaagcggagg acaggattgg gatccttgaa acccgaaacc cagaaacagc atcggagcgg 181 aaaccagagg ggaaaccttg aactcctcca gacaattgct tccggggagt tgcgagggag 241 cgaggggggaa taaaggaccc gcgaggaagg gcccgcggat ggcgcgtccc tgagggtcgt 301 ggcgagttcg cggagcgtgg gaaggagcgg accctgctct ccccgggctg cgggccatgg 361 ccacggcgga gcggagagcc ctcggcatcg gcttccagtg gctctctttg gccactctgg 421 tgctcatctg cgccgggcaa gggggacgca gggaggatgg gggtccagcc tgctacggcg 481 gatttgacct gtacttcatt ttggacaaat caggaagtgt gctgcaccac tggaatgaaa 541 tctattactt tgtggaacag ttggctcaca aattcatcag cccacagttg agaatgtcct 601 ttattgtttt ctccacccga ggaacaacct taatgaaact gacagaagac agagaacaaa 661 tccgtcaagg cctagaagaa ctccagaaag ttctgccagg aggagacact tacatgcatg 721 aaggatttga aagggccagt gagcagattt attatgaaaa cagacaaggg tacaggacag 781 ccagcgtcat cattgctttg actgatggag aactccatga agatctcttt ttctattcag 841 agagggaggc taataggtct cgagatcttg gtgcaattgt ttactgtgtt ggtgtgaaag 901 atttcaatga gacacagctg gcccggattg cggacagtaa ggatcatgtg tttcccgtga 961 atgacggctt tcaggctctg caaggcatca tccactcaat tttgaagaag tcctgcatcg 1021 aaattctagc agctgaacca tccaccatat gtgcaggaga gtcatttcaa gttgtcgtga 1081 gaggaaacgg cttccgacat gcccgcaacg tggacagggt cctctgcagc ttcaagatca 1141 atgactcggt cacactcaat gagaagccct tttctgtgga agatacttat ttactgtgtc 1201 cagcgcctat cttaaaagaa gttggcatga aagctgcact ccaggtcagc atgaacgatg 1261 gcctctcttt tatctccagt tctgtcatca tcaccaccac acactgttct gacggttcca 1321 tcctggccat cgccctgctg atcctgttcc tgctcctagc cctggctctc ctctggtggt 1381 tctggccct ctgctgcact gtgattatca aggaggtccc tccacccct gccgaggaga 1441 gtgaggaaaa taaataaaa taacaagaag aagaagaaa gaatcccac agaaacagat 1501 aacctaacac agcccgtgca acgtatttta tacaatgctc tgaaaatcat agtctcaatc 1561 tagacagtct tttcctctag ttccctgtat tcaaatccca gtgtctaaca ttcaataaat 1621 agctatatga aatcaaaaaa aaaaaaaaaa aaaaaaaaaa aaaaaaa
```

An exemplary human ANTXR1 amino acid sequence is set for the below (SEQ ID NO: 60; GenBank Accession No: AAH12074.1, Version 1, incorporated herein by reference):

```
  1 mataerralg igfqwlslat lvlicagqgg rredggpacy ggfdlyfild ksgsvlhhwn
 61 eiyyfvegla hkfispqlrm sfivfstrgt tlmkltedre qirqgleelq kvlpggdtym
121 hegferaseq iyyenrqgyr tasviialtd gelhedlffy sereanrsrd lgaivycvgv
181 kdfnetqlar iadskdhvfp vndgfqalqg iihsilkksc ieilaaepst icagesfqvv
241 vrgngfrhar nvdrvicsfk indsvtlnek pfsvedtyll cpapilkevg mkaalqvsmn
301 dglsfisssv iittthcslh kiasgpttaa cme
```

An exemplary human C1R nucleotide sequence is set forth below (SEQ ID NO: 61; GenBank Accession No. NM_001733.4, Version 4, incorporated herein by reference):

```
   1 gcacacagtg cacgaagacg ctgtcgggag agcccaggat tcaacacggg ccttgagaaa
  61 tgtggctctt gtacctcctg gtgccggccc tgttctgcag ggcaggaggc tccattccca
 121 tccctcagaa gttatttggg gaggtgactt ccctctgtt ccccaagcct taccccaaca
 181 actttgaaac aaccactgtg atcacagtcc ccacgggata cagggtgaag ctcgtcttcc
 241 agcagtttga cctggagcct tctgaaggct gcttctatga ttatgtcaag atctctgctg
 301 ataagaaaag cctggggagg ttctgtgggc aactgggttc tccactgggc aaccccccgg
 361 gaaagaagga atttatgtcc caagggaaca agatgctgct gaccttccac acagacttct
 421 ccaacgagga gaatgggacc atcatgttct acaagggctt cctggcctac taccaagctg
 481 tggaccttga tgaatgtgct tcccggagca aattagggga ggaggatccc cagcccccagt
 541 gccagcacct gtgtcacaac tacgttggag gctacttctg ttcctgccgt ccaggctatg
 601 agcttcagga agacaggcat tcctgccagg ctgagtgcag cagcgagctg tacacggagg
 661 catcaggcta catctccagc ctggagtacc ctcggtccta cccccctgac ctgcgctgca
 721 actacagcat ccgggtggag cggggcctca ccctgcacct caagttcctg gagccttttg
 781 atattgatga ccaccagcaa gtacactgcc cctatgacca gctacagatc tatgccaacg
 841 ggaagaacat tggcgagttc tgtgggaagc aaaggccccc cgacctcgac accagcagca
 901 atgctgtgga tctgctgttc ttcacagatg agtcggggga cagccggggc tggaagctgc
 961 gctacaccac cgagatcatc aagtgccccc agcccaagac cctagacgag ttcaccatca
1021 tccagaacct gcagcctcag taccagttcc gtgactactt cattgctacc tgcaagcaag
1081 gctaccagct catagagggg aaccaggtgc tgcattcctt cacagctgtc tgccaggatg
1141 atggcacgtg gcatcgtgcc atgcccagat gcaagatcaa ggactgtggg cagccccgaa
1201 acctgcctaa tggtgacttc cgttacacca ccacaatggg agtgaacacc tacaaggccc
1261 gtatccagta ctactgccat gagccatatt acaagatgca gaccagagct ggcagcaggg
1321 agtctgagca agggtgtac acctgcacag cacagggcat ttggaagaat gaacagaagg
1381 gagagaagat tcctcggtgc ttgccagtgt gtgggaagcc cgtgaaccc gtggaacaga
1441 ggcagcgcat catcggaggg caaaaagcca agatgggcaa cttcccctgg caggtgttca
1501 ccaacatcca cgggcgcggg ggcggggccc tgctgggcga ccgctggatc ctcacagctg
1561 cccacaccct gtatcccaag gaacacgaag cgcaaagcaa cgcctctttg gatgtgttcc
1621 tgggccacac aaatgtggaa gagctcatga gctaggaaa tcacccatc cgcagggtca
1681 gcgtccaccc ggactaccgt caggatgagt cctacaattt tgaggggac atcgccctgc
```

-continued

```
1741 tggagctgga aaatagtgtc accctgggtc ccaacctcct ccccatctgc ctccctgaca 1801 acgatacctt ctacgacctg ggcttgatgg gctatgtcag tggcttcggg gtcatggagg 1861 agaagattgc tcatgacctc aggtttgtcc gtctgcccgt agctaatcca caggcctgtg 1921 agaactggct ccggggaaag aataggatgg atgtgttctc tcaaaacatg ttctgtgctg 1981 gacacccatc tctaaagcag gacgcctgcc aggggatag tgggggcgtt tttgcagtaa 2041 gggacccgaa cactgatcgc tgggtggcca cgggcatcgt gtcctgggc atcgggtgca 2101 gcaggggcta tggcttctac accaaagtgc tcaactacgt ggactggatc aagaaagaga 2161 tggaggagga ggactgagcc cagaattcac taggttcgaa tccagagagc agtgtggaaa 2221 aaaaaaaaca aaaacaact gaccagttgt tgataaccac taagagtctc tattaaaatt 2281 actgatgcag aaagaccgtg tgtgaaattc tctttcctgt agtcccattg atgtacttta 2341 cctgaaacaa cccaaagggc cccttctttt cttctgagga ttgcagagga tatagttatc 2401 aatctctagt tgtcactttc ctcttccact ttgataccat tgggtcattg aatataactt 2461 tttccaaata aagttttatg agaaatgcca gtgtgcaaaa aaaaaaaaa aaaaaaaaa 2521 aaaaaa
```

An exemplary human C1R amino acid sequence is set forth below (SEQ ID NO: 62; GenBank Accession No: AAA51851.1, Version 1, incorporated herein by reference):

```
  1 mwllyllvpa lfcraggsip ipqklfgevt splfpkpypn nfetttvitv ptgyrvklvf 61 qqfdlepseg cfydyvkisa dkkslgrfcg qlgspignpp gkkefmsqgn kmlltfhtdf 121 sneengtimf ykgflayyqa vdldecasrs ksgeedpqpq cqhlchnyvg gyfcscrpgy 181 elqedrhscq aecsselyte asgyissley prsyppdlrc nysirvergl tlhlkflepf 241 diddhqqvhc pydqlqiyan gknigefcgk qrppdldtss navdlifftd esgdsrgwkl 301 rytteiikcp qpktldefti lqnlqpqyqf rdyfiatckq gygliegnqv lhsftavcqd 361 dgtwhrampr ckikdcgqpr nlpngdfryt ttmgvntyka riqyychepy ykmqtragsr 421 eseqgvytct aqgiwkneqk gekiprolpv cgkpvnpveq rqriiggqka kmgnfpwqvf 481 tnihgrggga llgdrwilta ahtlypkehe aqsnasldvf lghtnveelm kignhpirry 541 svhpdyrqde synfegdial lelensvtlg pnllpiclpd ndtfydlglm gyvsgfgvme 601 ekiandlrfv rlpvanpqac enwlrgknrm dvfsqnmfca ghpslkqdac qgdsggvfav 661 rdpntdrwva tgivswgigc srgygfytkv lnyvdwikke meeed
```

An exemplary human CDH11 nucleotide sequence is set forth below (SEQ ID NO: 63; GenBank Accession No. NM_001797.3, Version 3, incorporated herein by reference):

```
  1 cgccccgcac ccgcctgccc gcccgccacc tcccccggt ttctcattcc tgccactagc 61 gcgctcggcg gctcattccg cggccgccgc cagctgaggg gagcgtcgcg ggccgaggag 121 cagatgccgc ggggccgct cgcagccgcc gctgacttgt gaatgggacc gggactgggg 181 ccgggactga caccgcagcg cttgccctgc ccagggact ggcggctcgg aggttgcgtc 241 caccctcaag ggccccagaa atcactgtgt tttcagctca gcggccctgt gcattcctt 301 cgtgttgtca tttgttgagt gaccaatcag atgggtggag tgtgttacag aaattggcag 361 caagtatcca atgggtgaag aagaagctaa ctggggacgt gggcagccct gacgtgatga 421 gctcaaccag cagagacatt ccatcccaag agaggtctgc gtgacgcgtc cgggaggcca
```

```
 481 ccctcagcaa gaccaccgta cagttggtgg aagggtgac agctgcattc tcctgtgcct
 541 accacgtaac caaaaatgaa ggagaactac tgtttacaag ccgccctggt gtgcctgggc
 601 atgctgtgcc acagccatgc ctttgcccca gagcggcggg ggcacctgcg gccctccttc
 661 catgggcacc atgagaaggg caaggagggg caggtgctac agcgctccaa gcgtggctgg
 721 gtctggaacc agttcttcgt gatagaggag tacaccgggc ctgaccccgt gcttgtgggc
 781 aggcttcatt cagatattga ctctggtgat gggaacatta aatacattct ctcaggggaa
 841 ggagctggaa ccattttgt gattgatgac aaatcaggga acattcatgc caccaagacg
 901 ttggatcgag aagagagagc ccagtacacg ttgatggctc aggcggtgga cagggacacc
 961 aatcggccac tggagccacc gtcggaattc attgtcaagg tccaggacat taatgacaac
1021 cctccggagt tcctgcacga gacctatcat gccaacgtgc ctgagaggtc caatgtggga
1081 acgtcagtaa tccaggtgac agcttcagat gcagatgacc ccacttatgg aaatagcgcc
1141 aagttagtgt acagtatcct cgaaggacaa ccctattttt cggtggaagc acagacaggt
1201 atcatcagaa cagccctacc caacatggac agggaggcca aggaggagta ccacgtggtg
1261 atccaggcca aggacatggg tggacatatg ggcggactct cagggacaac caaagtgacg
1321 atcacactga ccgatgtcaa tgcaacccca ccaaagtttc cgcagagcgt ataccagatg
1381 tctgtgtcag aagcagccgt ccctggggag gaagtaggaa gagtgaaagc taaagatcca
1441 gacattggag aaaatggctt agtcacatac aatattgttg atggagatgg tatggaatcg
1501 tttgaaatca caacggacta tgaaacacag gagggggtga taagctgaa aaagcctgta
1561 gattttgaaa ccaaaagagc ctatagcttg aaggtagagg cagccaacgt gcacatcgac
1621 ccgaagttta tcagcaatgg cccttttcaag gacactgtga ccgtcaagat ctcagtagaa
1681 gatgctgatg agcccctat gttcttggcc ccaagttaca tccacgaagt ccagaaaat
1741 gcagctgctg gcaccgtggt tgggagagtg catgccaaag accctgatgc tgccaacagc
1801 ccgataaggt attccatcga tcgtcacact gacctcgaca gatttttcac tattaatcca
1861 gaggatggtt ttattaaaac tacaaaacct ctggatagag aggaaacagc ctggctcaac
1921 atcactgtct ttgcagcaga aatccacaat cggcatcagg aagccaaagt cccagtggcc
1981 attagggtcc ttgatgtcaa cgataatgct cccaagtttg ctgccccta tgaaggtttc
2041 atctgtgaga gtgatcagac caagccactt tccaaccagc caattgttac aattagtgca
2101 gatgacaagg atgacacggc caatggacca agatttatct tcagcctacc ccctgaaatc
2161 attcacaatc caaatttcac agtcagagac aaccgagata cacagcagg cgtgtacgcc
2221 cggcgtggag ggttcagtcg gcagaagcag gacttgtacc ttctgcccat agtgatcagc
2281 gatggcggca tcccgcccat gagtagcacc aacaccctca ccatcaaagt ctgcgggtgc
2341 gacgtgaacg gggcactgct ctcctgcaac gcagaggcct acattctgaa cgccggcctg
2401 agcacaggcg ccctgatcgc catcctcgcc tgcatcgtca ttctcctggt cattgtagta
2461 ttgtttgtga ccctgagaag gcaaaagaaa gaaccactca ttgtctttga ggaagaagat
2521 gtccgtgaga acatcattac ttatgatgat gaaggggtg gggaagaaga cacagaagcc
2581 tttgatattg ccaccctcca gaatcctgat ggtatcaatg gatttatccc ccgcaaagac
2641 atcaaacctg agtatcagta catgcctaga cctgggctcc ggccagcgcc aacagcgtg
2701 gatgtcgatg acttcatcaa cacgagaata caggaggcag acaatgaccc cacggctcct
2761 ccttatgact ccattcaaat ctacggttat gaaggcaggg gctcagtggc cgggtccctg
2821 agctcctag agtcggccac cacagattca gacttggact atgattatct acagaactgg
2881 ggacctcgtt ttaagaaact agcagatttg tatggttcca agacacttt tgatgacgat
```

-continued

```
2941  tcttaacaat aacgatacaa atttggcctt aagaactgtg tctggcgttc tcaagaatct
3001  agaagatgtg taaacaggta ttttttaaa tcaaggaaag gctcatttaa aacaggcaaa
3061  gttttacaga gaggatacat ttaataaaac tgcgaggaca tcaaagtggt aaatactgtg
3121  aaatacccttt tctcacaaaa aggcaaatat tgaagttgtt tatcaacttc gctagaaaaa
3181  aaaaacactt ggcatacaaa atatttaagt gaaggagaag tctaacgctg aactgacaat
3241  gaagggaaat tgtttatgtg ttatgaacat ccaagtcttt cttctttttt aagttgtcaa
3301  agaagcttcc acaaaattag aaaggacaac agttctgagc tgtaatttcg ccttaaactc
3361  tggacactct atatgtagtg cattttttaaa cttgaaatat ataatattca gccagcttaa
3421  acccatacaa tgtatgtaca atacaatgta caattatgtc tcttgagcat caatcttgtt
3481  actgctgatt cttgtaaatc ttttttgcttc tactttcatc ttaaactaat acgtgccaga
3541  tataactgtc ttgtttcagt gagagacgcc ctatttctat gtcatttta atgtatctat
3601  ttgtacaatt ttaaagttct tattttagta tacgtataaa tatcagtatt ctgacatgta
3661  agaaaatgtt acggcatcac acttatattt tatgaacatt gtactgttgc tttaatatga
3721  gcttcaatat aagaagcaat ctttgaaata aaaaaagatt tttttttaat tctgggtttg
3781  attcttaaca ttgaaacaaa cgttaagtat ttctaatgat ccatttatat ttctaattta
3841  attgtgatct tttaataacc ctatttatga tctgttgttg tctgtctgct gcttttattg
3901  tttatttaaa atcaaatatg ttttacaaat gttttttcag acaagattct gtaacatcat
3961  gtaaagcttt tttgtacatt cttggtgtta acctcctggc ttctcttcac acacatcttc
4021  taaaaaagaa ggatgtgaaa gaactaggtc agtctatgac tttgcaatat gtgttatata
4081  gtatgcattt atcttgtata tcagtaattt gatggttatg agagatgaat ccatgaggga
4141  atggagctat cagaactcta atgttccagg tatacattct atgccccaca ctgagcactg
4201  gggaactggg ggactagagt caaaaatata aatttgccca gactctaatg ttattctatt
4261  ttttcttctg ttgaacttac caggctattg taagactctt gatagttgaa actgcttatt
4321  tttcctcctg taattttaac taattgtaaa atgatgtggc attttatgtt ttaatgagaa
4381  tgggcgattc atttaaaaaa gctttgttta gaatatgctt ggggccgtaa gctcagaatg
4441  agggcaggga ccattttgga ttctgagagt cgatgccatt tggtccagga gtgtgtctac
4501  agtcccctgc attccagcta gtttcttggg gattgaaact tatgtgaagg gcatttcacc
4561  tgttcagttg ggccaaaggt caaaacgtag caatacttgg ggaaagacca cataaagtca
4621  cactgcaagt gctttccctc tttccccta cacacagggc acgtgctttt tcttggattg
4681  cagacaattt ttacagtttt tttctgactt tattgtgaaa gtttgtttca agcatttctt
4741  gatatcatgt tatgtactat ttttatgatt tagtcaacat gcatacaaag aaatgttttt
4801  tatgaagtgc tcacttccat tttactttgc attgaaatca aattgggctg aacacttcaa
4861  tggaatacat tttgtggaca atgtcacttt agaatctttc atctcagtga aggattacac
4921  attctcaata cttccataat tgcaggttgt gttcattttt ttatatagtt tttgtaatcc
4981  aaagaatatt tgctagatt tgcacagatc tccaattgaa tttgcaatga agaaataact
5041  caaaaggaat atgaatagca tttaaataag tatacagctg taagtaaccc tgtcaccatg
5101  gatgatcctt ttctctagga atgtatttgg attagagatg acaactacat tttcgcattt
5161  ttatgttgaa gtctttttta aaaaggctgt ttactttca gtagttaaga atacttgttt
5221  ttcttttct ttttttttt ttttttacc ttttattttt tcgttaagcc tctattgttt
5281  gtagaacact cttagaaact tggaaataaa atgtcttttcc caactagtgg agtccttttt
```

-continued

```
5341 catttggagc acattgcctt aaaagaagtc ttaatttaaa cggtccttcc ttattctaaa 5401 gtaatcactg ttttatacca tctatgcagc taaaagaagg aacatgcttc tgttctttc 5461 ctcaagtaat ggttattgtt tctagtcatc attcattcat tgattcattc attaattcat 5521 caaaatctta ttttataaac cctgttccac ttactggagg attcagaatg aatcttacta 5581 cctttctga catcttttga taattcagcc ctgtaccaaa gtatccacct tgttgtctta 5641 taatcaccta tttacctatt tgccctccta gaaaatgcaa gaagatattt tctctccttc 5701 caaattgaag gaagaacata aagatataa caggaaggag atggtgagat atagagtgtg 5761 agcggaaatt aggccagctg tggcaattct ggacagatct tgggtttagc taagttattt 5821 cttttaggcc tgggtttctg ggggtgacag ggaagataaa agagtagttt atttgcacct 5881 cttggagaat tgcttaaaaa tatagagatc atggctctgt atgtcaggtg gaaccaggtc 5941 aggagtattt gaaactgctc ctgggtcatt gtgacatatc cttcacatct ttttgagaaa 6001 ctttataaga caatgggggt gaatggggc tgggcagttg gagtctctga gcagaagagg 6061 ggcaaaattt atttggcagg cagtgtggag gacagattag gagcatataa acccagaggt 6121 gtgccccagg agggcttttg caaaggtcaa tatgagatag aatgagggcc tgaaataatt 6181 cagtaatttg gagatggaga agaggaaaga cttctctgct cttgcactgc catcagcctg 6241 gtctgggcca tggtcatctc tgacccggaa gactgacccc acctcttggc tcaccctctg 6301 cctcccaacc tcctcttcac aaagaagcca gagggatact tttaacacac aacccagatc 6361 acatgacttc gtaacttaaa cctcttcact ggcttcccaa agacttaaaa tgaattctga 6421 tgcctttatt ttattgcttt acatgaacag ggccctgcga acctctccag tgtcattcca 6481 ctccatcctc ctttcagtgc acgatgctcc agccacactg gccatctttc ggttcctgat 6541 acaaaaaaaa acacgttcct tttccatgga aagcaggtca cccttgttat tttgtatcga 6601 tgacaactct ttaaacttat tttgctttt ggctttatgt atgtgtgtgg gtgggtggga 6661 ctgactgccc cactagaatg taagctccat gagggcaggg aatcttgctt tcttgtttac 6721 cattgtatac tcagttcttt acacagtgcc tgaaacataa caggtacaca ataaatatct 6781 attgaatgaa agcaaaaaaa aaaaaaaaaa
```

An exemplary human CDH11 amino acid sequence is set for the below (SEQ ID NO: 64; GenBank Accession No: NP_001317505.1, Version 1, incorporated herein by reference):

```
  1 maqavdrdtn rpleppsefi vkvqdindnp peflhetyha nvpersnvgt sviqvtasda 61 ddptygnsak lvysilegqp yfsveaqtgi irtalpnmdr eakeeyhvvi qakdmgghmg 121 glsgttkvti tltdvndnpp kfpqsvyqms vseaavpgee vgrvkakdpd igenglvtyn 181 ivdgdgmesf eittdyetqe gviklkkpvd fetkrayslk veaanvhidp kfisngpfkd 241 tvtvkisved adeppmflap syihevqena aagtvvgrvh akdpdaansp irysidrhtd 301 ldrfftinpe dgfikttkpl dreetawlni tvfaaeihnr hqeakvpvai rvidvndnap 361 kfaapyegfi cesdqtkpls nqpivtisad dkddtangpr fifslppeii hnpnftvrdn 421 rdntagvyar rggfsrqkqd lyllpivisd ggippmsstn tltikvcgcd vngallscna 481 eayilnagls tgaliailac ivillvivvl fvtirrqkke plivfeeedv reniitydde 541 gggeedteaf diatlqnpdg ingfiprkdi kpeyqymprp glrpapnsvd vddfintriq 601 eadndptapp ydsiqiygye grgsvagsls slesattdsd ldydylqnwg prfkkladly 661 gskdtfddds
```

An exemplary human COL3A1 nucleotide sequence is set forth below (SEQ ID NO: 65; GenBank Accession No. NM_000090.3, Version 3, incorporated herein by reference):

```
   1 ggctgagttt tatgacgggc ccggtgctga agggcaggga acaacttgat ggtgctactt
  61 tgaactgctt ttcttttctc cttttttgcac aaagagtctc atgtctgata tttagacatg
 121 atgagctttg tgcaaaaggg gagctggcta cttctcgctc tgcttcatcc cactattatt
 181 ttggcacaac aggaagctgt tgaaggagga tgttcccatc ttggtcagtc ctatgcggat
 241 agagatgtct ggaagccaga accatgccaa atatgtgtct gtgactcagg atccgttctc
 301 tgcgatgaca taatatgtga cgatcaagaa ttagactgcc ccaacccaga aattccattt
 361 ggagaatgtt gtgcagtttg cccacagcct ccaactgctc ctactcgccc tcctaatggt
 421 caaggacctc aaggccccaa gggagatcca ggccctcctg gtattcctgg gagaaatggt
 481 gaccctggta ttccaggaca accagggtcc cctggttctc ctggcccccc tggaatctgt
 541 gaatcatgcc ctactggtcc tcagaactat tctccccagt atgattcata tgatgtcaag
 601 tctggagtag cagtaggagg actcgcaggc tatcctggac cagctggccc cccaggccct
 661 cccggtcccc ctggtacatc tggtcatcct ggttcccctg gatctccagg ataccaagga
 721 cccccctggtg aacctgggca agctggtcct tcaggccctc caggacctcc tggtgctata
 781 ggtccatctg gtcctgctgg aaaagatgga gaatcaggta gacccggacg acctggagag
 841 cgaggattgc ctggacctcc aggtatcaaa ggtccagctg ggatacctgg attccctggt
 901 atgaaaggac acagaggctt cgatggacga aatggagaaa agggtgaaac aggtgctcct
 961 ggattaaagg gtgaaaatgg tcttccaggc gaaaatggag ctcctggacc catgggtcca
1021 agagggctc ctggtgagcg aggacggcca ggacttcctg gggctgcagg tgctcggggt
1081 aatgacggtg ctcgaggcag tgatggtcaa ccaggccctc tggtcctcc tggaactgcc
1141 ggattccctg gatcccctgg tgctaagggt gaagttggac ctgcagggtc tcctggttca
1201 aatggtgccc ctggacaaag aggagaacct ggacctcagg gacacgctgg tgctcaaggt
1261 cctcctggcc ctcctgggat taatggtagt cctggtggta aaggcgaaat gggtcccgct
1321 ggcattcctg gagctcctgg actgatggga gcccggggtc ctccaggacc agccggtgct
1381 aatggtgctc ctggactgcg aggtggtgca ggtgagcctg gtaagaatgg tgccaaagga
1441 gagcccggac cacgtggtga acgcggtgag gctggtattc caggtgttcc aggagctaaa
1501 ggcgaagatg gcaaggatgg atcacctgga gaacctggtg caaatgggct tccaggagct
1561 gcaggagaaa ggggtgcccc tgggttccga ggacctgctg gaccaaatgg catcccagga
1621 gaaaagggtc ctgctggaga gcgtggtgct ccaggccctg cagggcccag aggagctgct
1681 ggagaacctg gcagagatgg cgtccctgga ggtccaggaa tgaggggcat gcccggaagt
1741 ccaggaggac caggaagtga tgggaaacca gggcctcccg gaagtcaagg agaaagtggt
1801 cgaccaggtc ctcctgggcc atctggtccc cgaggtcagc ctggtgtcat gggcttcccc
1861 ggtcctaaag gaaatgatgg tgctcctggt aagaatggag aacgaggtgg ccctggagga
1921 cctggccctc agggtcctcc tggaaagaat ggtgaaactg gacctcaggg acccccaggg
1981 cctactgggc ctggtggtga caaggagac acaggacccc ctggtccaca aggattacaa
2041 ggcttgcctg gtacaggtgg tcctccagga gaaaatggaa aacctggggaa accaggtcca
2101 aagggtgatg ccggtgcacc tggagctcca ggaggcaagg gtgatgctgg tgcccctggt
2161 gaacgtggac ctccggatt gcaggggcc ccaggactta gaggtggagc tggtccccct
2221 ggtccgaag gaggaaaggg tgctgctggt cctcctgggc cacctggtgc tgctggtact
```

-continued

```
2281 cctggtctgc aaggaatgcc tggagaaaga ggaggtcttg gaagtcctgg tccaaagggt 2341 gacaagggtg aaccaggcgg tccaggtgct gatggtgtcc cagggaaaga tggcccaagg 2401 ggtcctactg gtcctattgg tcctcctggc ccagctggcc agcctggaga taagggtgaa 2461 ggtggtgccc ccggacttcc aggtatagct ggacctcgtg gtagccctgg tgagagaggt 2521 gaaactggcc ctccaggacc tgctggtttc cctggtgctc ctggacagaa tggtgaacct 2581 ggtggtaaag gagaaagagg ggctccgggt gagaaggtg aaggaggccc tcctggagtt 2641 gcaggacccc ctggaggttc tggacctgct ggtcctcctg gtccccaagg tgtcaaaggt 2701 gaacgtggca gtcctggtgg acctggtgct gctggcttcc ctggtgctcg tggtcttcct 2761 ggtcctcctg gtagtaatgg taacccagga cccccaggtc ccagcggttc tccaggcaag 2821 gatgggcccc caggtcctgc gggtaacact ggtgctcctg gcagccctgg agtgtctgga 2881 ccaaaaggtg atgctggcca accaggagag aagggatcgc tggtgccca gggcccacca 2941 ggagctccag gcccacttgg gattgctggg atcactggag cacggggtct tgcaggacca 3001 ccaggcatgc caggtcctag gggaagccct ggccctcagg gtgtcaaggg tgaaagtggg 3061 aaaccaggag ctaacggtct cagtggagaa cgtggtcccc ctggacccca gggtcttcct 3121 ggtctggctg gtacagctgg tgaacctgga agagatgaa accctggatc agatggtctt 3181 ccaggccgag atggatctcc tggtggcaag ggtgatcgtg gtgaaaatgg ctctcctggt 3241 gcccctggcg ctcctggtca tccaggccca cctggtcctg tcggtccagc tggaaagagt 3301 ggtgacagag gagaaagtgg ccctgctggc cctgctggtg ctcccggtcc tgctggttcc 3361 cgaggtgctc ctggtcctca aggcccacgt ggtgacaaag gtgaaacagg tgaacgtgga 3421 gctgctggca tcaaaggaca tcgaggattc cctggtaatc caggtgcccc aggttctcca 3481 ggccctgctg gtcagcaggg tgcaatcggc agtccaggac ctgcaggccc cagaggacct 3541 gttggaccca gtggacctcc tggcaaagat ggaaccagtg gacatccagg tcccattgga 3601 ccaccagggc ctcgaggtaa cagaggtgaa agaggatctg agggctcccc aggccacccca 3661 gggcaaccag gccctcctgg acctcctggt gcccctggtc cttgctgtgg tggtgttgga 3721 gccgctgcca ttgctgggat tggaggtgaa aaagctggcg ttttgccc gtattatgga 3781 gatgaaccaa tggatttcaa aatcaacacc gatgagatta tgacttcact caagtctgtt 3841 aatggacaaa tagaaagcct cattagtcct gatggttctc gtaaaaaccc cgctagaaac 3901 tgcagagacc tgaaattctg ccatcctgaa ctcaagagtg gagaatactg ggttgaccct 3961 aaccaaggat gcaaattgga tgctatcaag gtattctgta atatggaaac tggggaaaca 4021 tgcataagtg ccaatccttt gaatgttcca cggaaacact ggtggacaga ttctagtgct 4081 gagaagaaac acgtttggtt tggagagtcc atggatggtg gtttcagtt tagctacggc 4141 aatcctgaac ttcctgaaga tgtccttgat gtgcagctgg cattccttcg acttctctcc 4201 agccgagctt cccagaacat cacatatcac tgcaaaaata gcattgcata catggatcag 4261 gccagtggaa atgtaaagaa ggccctgaag ctgatggggt caaatgaagg tgaattcaag 4321 gctgaaggaa atagcaaatt cacctacaca gttctggagg atggttgcac gaaacacact 4381 ggggaatgga gcaaaacagt ctttgaatat cgaacacgca aggctgtgag actacctatt 4441 gtagatattg caccctatga cattggtggt cctgatcaag aatttggtgt ggacgttggc 4501 cctgtttgct tttataaaac caaactctat ctgaaatccc aacaaaaaaa atttaactcc 4561 atatgtgttc ctcttgttct aatcttgtca accagtgcaa gtgaccgaca aaattccagt 4621 tatttatttc aaaatgtttt ggaaacagta taatttgaca agaaaaatg atacttctct 4681 ttttttgctg ttccaccaaa tacaattcaa atgcttttg ttttattttt ttaccaattc
```

-continued

```
4741  caatttcaaa  atgtctcaat  ggtgctataa  taaataaact  tcaacactct  ttatgataac 4801  aacactgtgt  tatattcttt  gaatcctagc  ccatctgcag  agcaatgact  gtgctcacca 4861  gtaaaagata  acctttcttt  ctgaaatagt  caaatacgaa  attagaaaag  ccctccctat 4921  tttaactacc  tcaactggtc  agaaacacag  attgtattct  atgagtccca  gaagatgaaa 4981  aaaattttat  acgttgataa  aacttataaa  tttcattgat  taatctcctg  gaagattggt 5041  ttaaaagaa   aagtgtaatg  caagaattta  aagaaatatt  tttaaagcca  caattatttt 5101  aatattggat  atcaactgct  tgtaaaggtg  ctcctctttt  ttcttgtcat  tgctggtcaa 5161  gattactaat  atttgggaag  gctttaaaga  cgcatgttat  ggtgctaatg  tactttcact 5221  tttaaactct  agatcagaat  tgttgacttg  cattcagaac  ataaatgcac  aaaatctgta 5281  catgtctccc  atcagaaaga  ttcattggca  tgccacaggg  gattctcctc  cttcatcctg 5341  taaaggtcaa  caataaaaac  caaattatgg  ggctgctttt  gtcacactag  catagagaat 5401  gtgttgaaat  ttaactttgt  aagcttgtat  gtggttgttg  atctttttt   tccttacaga 5461  cacccataat  aaaatatcat  attaaaattc
```

An exemplary human COL3A1 amino acid sequence is set for the below (SEQ ID NO: 66; GenBank Accession No: AAH28178.1, Version 1, incorporated herein by reference):

```
   1  mmsfvqkgsw  lllallhpti  ilaqqeaveg  gcshlgqsya  drdvwkpepc  qicvcdsgsv 61  lcddiicddq  eldcpnpeip  fgeccavcpq  pptaptrppn  gqgpqgpkgd  pgppgipgrn 121  gdpgipgqpg  spgspgppgi  cescptgpqn  yspqydsydv  ksgvavggla  gypgpagppg 181  ppgppgtsgh  pgspgspgyq  gppgepgqag  psgppgppga  igpsgpagkd  gesgrpgrpg 241  erglpgppgi  kgpagipgfp  gmkghrgfdg  rngekgetga  pglkgenglp  gengapgpmg 301  prgapgergr  pglpgaagar  gndgargsdg  qpgppgppgt  agfpgspgak  gevgpagspg 361  sngapgqrge  pgpqghagaq  gppgppging  spggkgemgp  agipgapglm  gargppgpag 421  angapglrgg  agepgkngak  gepgprgerg  eagipgvpga  kgedgkdgsp  gepganglpg 481  aagergapgf  rgpagpngip  gekgpagerg  apgpagprga  agepgrdgvp  ggpgmrgmpg 541  spggpgsdgk  pgppgsqges  grpgppgpsg  prgqpgvmgf  pgpkgndgap  gkngerggpg 601  gpgpqgppgk  ngetgpqgpp  gptgpggdkg  dtgppgpqgl  qglpgtggpp  gengkpgepg 661  pkgdagapga  pggkgdagap  gergppglag  apglrggagp  pgpeggkgaa  gppgppgaag 721  tpglqgmpge  rgglgspgpk  gdkgepggpg  adgvpgkdgp  rgptgpigpp  gpagqpgdkg 781  eggapglpgi  agprgspger  getgppgpag  fpgapgqnge  pggkgergap  gekgeggppg 841  vagppgkdgt  sghpgpigpp  gprgnrgerg  segspghpgq  pgppgppgap  gpccggvgaa 901  aiagiggeka  ggfapyygde  pmdfkintde  imtslksvng  qieslispdg  srknparncr 961  dlkfchpelk  sgeywvdpnq  gckldaikvf  cnmetgetci  sanplnvprk  hwwtdssaek 1021  khvwfgesmd  ggfqfsygnp  elpedvldvq  laflrlissr  asqnityhck  nsiaymdqas 1081  gnvkkalklm  gsnegefkae  gnskftytvl  edgctkhtge  wsktvfeyrt  rkavrlpivd 1141  iapydiggpd  qefgvdvgpv  cfl
```

An exemplary human FCGR2B nucleotide sequence is set forth below (SEQ ID NO: 67; GenBank Accession No. NM_004001.4, Version 4, incorporated herein by reference):

```
   1 agaacatttc tttttcactt cccctttcag actccagaat ttgtttgccc tctagggtag
  61 aatccgccaa gctttgagag aaggctgtga ctgctgtgct ctgggcgcca gctcgctcca
 121 gggagtgatg ggaatcctgt cattcttacc tgtccttgcc actgagagtg actgggctga
 181 ctgcaagtcc ccccagcctt ggggtcatat gcttctgtgg acagctgtgc tattcctggc
 241 tcctgttgct gggacacctg cagctccccc aaaggctgtg ctgaaactcg agcccagtg
 301 gatcaacgtg ctccaggagg actctgtgac tctgacatgc cgggggactc acagccctga
 361 gagcgactcc attcagtggt tccacaatgg gaatctcatt cccacccaca cgcagcccag
 421 ctacaggttc aaggccaaca acaatgacag cggggagtac acgtgccaga ctggccagac
 481 cagcctcagc gaccctgtgc atctgactgt gctttctgag tggctggtgc tccagacccc
 541 tcacctggag ttccaggagg agaaaccat cgtgctgagg tgccacagct ggaaggacaa
 601 gcctctggtc aaggtcacat tcttccagaa tggaaaatcc aagaatttt cccgttcgga
 661 tcccaacttc tccatcccac aagcaaacca cagtcacagt ggtgattacc actgcacagg
 721 aaacataggc tacacgctgt actcatccaa gcctgtgacc atcactgtcc aagctcccag
 781 ctcttcaccg atggggatca ttgtggctgt ggtcactggg attgctgtag cggccattgt
 841 tgctgctgta gtggccttga tctactgcag gaaaaagcgg atttcagctc tcccaggata
 901 ccctgagtgc agggaaatgg gagagaccct ccctgagaaa ccagccaatc ccactaatcc
 961 tgatgaggct gacaaagttg gggctgagaa cacaatcacc tattcacttc tcatgcaccc
1021 ggatgctctg gaagagcctg atgaccagaa ccgtatttag tctccattgt cttgcattgg
1081 gatttgagaa gaaaatcaga gagggaagat ctggtatttc ctggcctaaa ttccccttgg
1141 ggaggacagg gagatgctgc agttccaaaa gagaaggttt cttccagagt catctacctg
1201 agtcctgaag ctccctgtcc tgaaagccac agacaatatg gtcccaaata accgactgca
1261 ccttctgtgc ttcagctctt cttgacatca aggctcttcc gttccacatc cacacagcca
1321 atccaattaa tcaaaccact gttattaaca gataatagca acttgggaaa tgcttatgtt
1381 acaggttacg tgagaacaat catgtaaatc tatatgattt cagaaatgtt aaaatagact
1441 aacctctacc agcacattaa aagtgattgt ttctgggtga taaaattatt gatgattttt
1501 attttctttta tttttctata aagatcatat attactttta taataaaaca ttataaaaac
1561 aacattctgt ttacctttc aaggctgtat tggttggagt gtagactgaa ctgcctgggg
1621 tctgtttctc ttcagtgatg agactcttag gaaggcagga atggatagga taggggagg
1681 agaggagaga tggggattta aatgtagag tgagtgcccc ttttcttaaa actgaataca
1741 gtcacgcacc acataatgat gtttagttca acaacagact gcatatatga tggtgatccc
1801 ataaaattat aataccatat ttctattgta ccttttctat tcctatgttt agatatatga
1861 gtacttacca ttgtgttaca attgcctaaa gtattcagta cagtagcatg ctgtacaggt
1921 ttgtagccta ggggcaatag gctatacgct acagcctagg tgtgtagtag gccacaccat
1981 ttaggtttgt ataagtacct gctatgatgt tcacacaaca aaattgcctg catttctcaa
```

-continued

```
2041 aatgtatccc catatttcaa caatgcatga ctgtactctt ctgccaatga ccttgtattc 2101 ttgtttccat gtcttcttct ctttcctcct atggcaaata aaacactgtt ttgcaacaca 2161 aaaaaaaaaa aaaa
```

An exemplary human FCGR2B amino acid sequence is set for the below (SEQ ID NO: 68; GenBank Accession No: AAI46679.1, Version 1, incorporated herein by reference):

```
  1 mgilsflpvl atesdwadck spqpwghmll wtavlflapv agtpaappka viklepqwin 61 vlqedsvtlt crgthspesd slqwfhngnl ipthtqpsyr fkannndsge ytcqtgqtsl 121 sdpvhltvls ewlvlqtphl efgegetivl rchswkdkpl vkvtffqngk skkfsrsdpn 181 fsipqanhsh sgdyhctgni gytlysskpv titvqapsss pmgiivavvt giavaaivaa 241 vvaliycrkk risanptnpd eadkvgaent itysllmhpd aleepddqnr i
```

An exemplary human HLA-DRB1 nucleotide sequence is set forth below (SEQ ID NO: 69; GenBank Accession No. NM_001243965.1, Version 1, incorporated herein by reference):

```
   1 cctataactt ggaatgtggg tggaggggtt catagttctc cctgagtgag acttgcctgc 61 tgctctggcc cctggtcctg tcctgttctc cagcatggtg tgtctgaggc tccctggagg 121 ctcctgcatg gcagttctga cagtgacact gatggtgctg agctccccac tggctttggc 181 tggggacacc agaccacgtt tcttggagta ctctacgtct gagtgtcatt tcttcaatgg 241 gacggagcgg gtgcggtacc tggacagata cttccataac caggaggaga acgtgcgctt 301 cgacagcgac gtgggggagt tccgggcggt gacggagctg gggcggcctg atgccgagta 361 ctggaacagc cagaaggacc tcctggagca aagcgggcc cgggtggaca actactgcag 421 acacaactac ggggttgtgg agagcttcac agtgcagcgg cgagtccatc ctaaggtgac 481 tgtgtatcct tcaaagaccc agcccctgca gcaccataac ctcctggtct gttctgtgag 541 tggtttctat ccaggcagca ttgaagtcag gtggttccgg aatggccagg aagagaagac 601 tggggtggtg tccacaggcc tgatccacaa tggagactgg accttccaga ccctggtgat 661 gctggaaaca gttcctcgga gtggagaggt ttacacctgc caagtggagc acccaagcgt 721 gacaagccct ctcacagtgg aatggagagc acggtctgaa tctgcacaga gcaagatgct 781 gagtggagtc gggggctttg tgctgggcct gctcttcctt ggggccgggc tgttcatcta 841 cttcaggaat cagaaaggac actctggact tcagccaaga ggattcctga gctgaagtgc 901 agatgacaca ttcaaagaag aactttctgc cccagctttg caggatgaaa agctttccct 961 cctggctgtt attcttccac aagagagggc tttctcagga cctggttgct actggttcag 1021 caactgcaga aaatgtcctc ccttgtggct tcctcagctc ctgttcttgg cctgaagccc 1081 cacagctttg atggcagtgc ctcatcttca acttttgtgc tccctttgc ctaaaccta 1141 tggcctcctg tgcatctgta ctcaccctgt accacaaaca cattacatta ttaaatgttt 1201 ctcaaagatg gagttaaaaa aaaaaaaaaa aaa
```

An exemplary human HLA-DRB1 amino acid sequence is set for the below (SEQ ID NO: 70; GenBank Accession No: BAO73164.1, Version 1, incorporated herein by reference):

```
  1 mvclklpggs cmtaltvtlm vlssplalsg dtrprflwqp krechffngt ervrfldryf
 61 ynqeesvrfd sdvgefravt elgrpdaeyw nsqkdlleqa raavdtycrh nygvgesftv
121 qrrvqpkvtv ypsktqplqh hnllvcsysg fypgsievrw flngqeekag mvstgliqng
181 dwtfqtlvml etvprsgevy tcqvehpsvt spltvewrar sesaqskmls gvggfvlgll
241 flgaglflyf rnqkghsglq ptgfls
```

An exemplary human RNASE1 nucleotide sequence is set forth below (SEQ ID NO: 71; GenBank Accession No. NM_198235.2, Version 2, incorporated herein by reference):

```
  1 gtataaggtc cacacccgg gagctgagtg attgcagaaa ctggccttcc atctctctca
 61 gacaccaagc tgcagatcca ggtcactttg taggtcacca cctagagggg aggaagacct
121 cgctttggag agtgggaata aaacgctcgt ggaaaaggt acacgctttt ctgggaaagt
181 gaggccacca tggctctgga gaagtctctt gtccggctcc ttctgcttgt cctgatactg
241 ctggtgctgg gctgggtcca gccttccctg ggcaaggaat cccgggccaa gaaattccag
301 cggcagcata tggactcaga cagttccccc agcagcagct ccacctactg taaccaaatg
361 atgaggcgcc ggaatatgac acaggggcgg tgcaaaccag tgaacacctt tgtgcacgag
421 cccctggtag atgtccagaa tgtctgtttc caggaaaagg tcacctgcaa gaacgggcag
481 ggcaactgct acaagagcaa ctccagcatg cacatcacag actgccgcct gacaaacggc
541 tccaggtacc ccaactgtgc ataccggacc agcccgaagg agagacacat cattgtggcc
601 tgtgaaggga gcccatatgt gccagtccac tttgatgctt ctgtggagga ctctacctaa
661 ggtcagagca gcgagatacc ccacctccct caacctcatc ctctccacag ctgcctcttc
721 cctcttcctt ccctgctgtg aaagaagtaa ctacagttag ggctcctatt caacacacac
781 atgcttccct ttcctgagtc ccatccctgc gtgattttgg gggtgaagag tgggttgtga
841 ggtgggcccc atgttaaccc ctccactctt tctttcaata aaacgcagtt gcaaacacct
901 gaa
```

An exemplary human RNASE1 amino acid sequence is set for the below (SEQ ID NO: 72; GenBank Accession No: AAH22882.1, Version 1, incorporated herein by reference):

```
  1 maleksivrl lllvlillvl gwvqpslgke srakkfqrqh mdsdsspsss stycnqmmrr
 61 rnmtqgrckp vntfvheplv dvqnvcfqek vtckngqgnc yksnssmhit dcrltngsry
121 pncayrtspk erhiivaceg spyvpvhfda svedst
```

An exemplary human THY1 nucleotide sequence is set forth below (SEQ ID NO: 73; GenBank Accession No. NM_006288.4, Version 4, incorporated herein by reference):

```
  1 actaggcagg gatgagcaag aggaatggct caccttgag agctggggtc catagcccag
 61 gtcagttctc cagctctccc acttaccagc caagacagga ggtgaggatt gagatgggat
121 gaacccagca ggcggccatg ggttaaaggt cgccatgaat gtaatgtgcc cagcacagtg
181 cctgctaaaa ggcaacactc ccttcctggt ctgaagacca aacaagcaga ctgtactcag
241 gaaagccaga agaaccttcc agctgtctgg accagaaggt gccagcccag gggctgaaga
301 agacgtaatg cccagagcaa aaagcgcctg cagcccctg aagggctggg tgctctgaa
361 tagatgaggg ggcgaaatgg ggctggggac cagggacgga cagggtgggt ccagcacctg
```

-continued

```
 421 cctcgcttcc gaagggctgc tccaacactg aaaaacaccc aaccagcttc ctttcagaaa
 481 gactggaata ttccaaaact tctcactgga ggctccggag gaggtgggct ccagctgaaa
 541 aggaaatgtg gaggcgtggg cgctcccggc ctgcatcctg cacctcttac actttggttt
 601 tcccacagac tcctgaagaa taggtcagaa gaaagggtta aagccttaaa aggggaacaa
 661 ccattgcggg gctcagggag gaggataatg ttctttgggc tgccgcaccc tgatccccgg
 721 ggtcccgaac cctcccgtcc ctggccaggc ctgccagcca cagggtgagg gccccttcc
 781 gccgcaacct gccactctca caccaatgcg ggaccgcctt ctcttccttc cccaccccc
 841 accccaccct gccgtccttt ctcccccaat ctccgcctct gattggctga gccccggct
 901 ccccgctccc cctctcctcc atccccggtg aaaactgcgg gctccgagct gggtgcagca
 961 accggaggcg gcggcgcgtc tggaggaggc tgcagcagcg aagaccccca gtccagatcc
1021 aggactgaga tcccagaacc atgaacctgg ccatcagcat cgctctcctg ctaacagtct
1081 tgcaggtctc ccgagggcag aaggtgacca gcctaacggc ctgcctagtg gaccagagcc
1141 ttcgtctgga ctgccgccat gagaatacca gcagttcacc catccagtac gagttcagcc
1201 tgacccgtga gacaaagaag cacgtgctct ttggcactgt gggggtgcct gagcacacat
1261 accgctcccg aaccaacttc accagcaaat acaacatgaa ggtcctctac ttatccgcct
1321 tcactagcaa ggacgagggc acctacacgt gtgcactcca ccactctggc cattccccac
1381 ccatctcctc ccagaacgtc acagtgctca gagacaaact ggtcaagtgt gagggcatca
1441 gcctgctggc tcagaacacc tcgtggctgc tgctgctcct gtctcccctc tccctcctcc
1501 aggccacgga tttcatgtcc ctgtgactgg tggggcccat ggaggagaca ggaagcctca
1561 agttccagtg cagagatcct acttctctga gtcagctgac cccctccccc caatccctca
1621 aaccttgagg agaagtgggg accccacccc tcatcaggag ttccagtgct gcatgcgatt
1681 atctacccac gtccacgcgg ccacctcacc ctctccgcac acctctggct gtctttttgt
1741 acttttttgtt ccagagctgc ttctgtctgg tttatttagg ttttatcctt ccttttcttt
1801 gagagttcgt gaagagggaa gccaggattg gggacctgat ggagagtgag agcatgtgag
1861 gggtagtggg atggtggggt accagccact ggagggggtca tccttgccca tcgggaccag
1921 aaacctggga gagacttgga tgaggagtgg ttgggctgtg cctgggccta gcacggacat
1981 ggtctgtcct gacagcactc ctcggcaggc atggctggtg cctgaagacc ccagatgtga
2041 gggcaccacc aagaatttgt ggcctacctt gtgagggaga gaactgagca tctccagcat
2101 tctcagccac aaccaaaaaa aaataaaaag gcagccctc cttaccactg tggaagtccc
2161 tcagaggcct tggggcatga cccagtgaag atgcaggttt gaccaggaaa gcagcgctag
2221 tggagggttg gagaaggagg taaaggatga gggttcatca tccctccctg cctaaggaag
2281 ctaaaagcat ggccctgctg cccctccctg cctccaccca cagtggagag ggctacaaag
2341 gaggacaaga ccctctcagg ctgtcccaag ctcccaagag cttccagagc tctgacccac
2401 agcctccaag tcaggtgggg tggagtccca gagctgcaca gggtttggcc caagtttcta
2461 agggaggcac ttcctcccct cgcccatcag tgccagcccc tgctggctgg tgcctgagcc
2521 cctcagacag cccctgccc cgcaggcctg ccttctcagg gacttctgcg gggcctgagg
2581 caagccatgg agtgagaccc aggagccgga cacttctcag gaaatggctt ttcccaaccc
2641 ccagcccca cccggtggtt cttcctgttc tgtgactgtg tatagtgcca ccacagctta
2701 tggcatctca ttgaggacaa agaaaactgc acaataaaac caagcctctg gaatctgtcc
2761 tcgtgtccac ctggccttcg ctcctccagc agtgcctgcc tgccccgct tcgctggggt
```

```
                                   -continued
2821  ctccacgggt gaggctgggg aacgccacct cttcctcttc cctgacttct ccccaaccac 2881  ttagtagcaa cgctacccca ggggctaatg actgcacact gggcttcttt tcagaatgac 2941  cctaacgaga cacatttgcc caaataaacg aacatcccat gtctgctgac tcaaaaaaaa 3001  aaaaaaaa
```

An exemplary human THY1 amino acid sequence is set for the below (SEQ ID NO: 74; GenBank Accession No: AAA61180.1, Version 1, incorporated herein by reference):

```
  1  mnlaisiall ltvlqvsrgq kvtsltaclv dqslrldcrh entsssspiqy efsltretkk 61  hvlfgtvgvp ehtyrsrtnf tskyhmkvly lsaftskdeg tytcalhhsg hsppissqnv 121  tvlrdklvkc egisllaqnt swlllllls1 sllqatdfms l
```

An exemplary human TMSB4X nucleotide sequence is set forth below (SEQ ID NO: 75; GenBank Accession No. NM_021109.3, Version 3, incorporated herein by reference):

```
  1  gacaactcgg tggtggccac tgcgcagacc agacttcgct cgtactcgtg cgcctcgctt 61  cgcttttcct ccgcaaccat gtctgacaaa cccgatatgg ctgagatcga gaaattcgat 121  aagtcgaaac tgaagaagac agagacgcaa gagaaaaatc cactgccttc caaagaaacg 181  attgaacagg agaagcaagc aggcgaatcg taatgaggcg tgcgccgcca atatgcactg 241  tacattccac aagcattgcc ttcttatttt acttcttta gctgtttaac tttgtaagat 301  gcaaagaggt tggatcaagt ttaaatgact gtgctgcccc tttcacatca aagaactact 361  gacaacgaag gccgcgcctg cctttcccat ctgtctatct atctggctgg cagggaagga 421  aagaacttgc atgttggtga aggaagaagt ggggtggaag aagtggggtg ggacgacagt 481  gaaatctaga gtaaaaccaa gctggcccaa ggtgtcctgc aggctgtaat gcagtttaat 541  cagagtgcca ttttttttt tgttcaaatg atttttaatta ttggaatgca caattttttt 601  aatatgcaaa taaaaagttt aaaaacttaa aaaaaaaaa aaaaaaaaa aaaaaaa
```

An exemplary human TMSB4X amino acid sequence is set for the below (SEQ ID NO: 76; GenBank Accession No: AAI51216.1, Version 1, incorporated herein by reference):
1 msdkpdmaei ekfdksklkk tetqeknplp sketieqekq ages

The Role of Stromal Cells in Prostate Carcinogenesis

As described in detail below, due to the inherent heterogeneity of prostate cancer and the lack of single therapeutic agents that have wide ranging impact on prostate cancer progression, in particular advanced and/or metastatic disease, the interplay between the tumor gland and its surrounding microenvironment (adjacent stroma) provided evidence of how the tumor grows and metastasizes. It also raised implications as to whether monitoring the stromal environment has clinical utility in patients that could relapse or have relapsed. Relapsed patients almost always develop metastatic disease.

The genotype of prostate epithelial tumors is considered the most important determinant of prostate cancer growth and metastasis (Chung L W. et al., *J Urol.* 173, 10-20 (2005). However, the tumor microenvironment has garnered increasing amounts of attention as a critical driver and enhancer of prostate cancer progression (Ganguly S S, et al., *Front Oncol.* 2014 4:364). The environment that surrounds benign, PIN, and malignant epithelia is comprised of fibroblasts, myofibroblasts, as well as endothelial, nerve, immune and inflammatory cells (Niu Y N, et al., *Asian J Androl.* 11, 28-35 (2009)). The bidirectional signaling between epithelial cells and stromal constituents during normal prostate homeostasis is disrupted early in tumorigenesis (Tuxhorn J A, et al., *J Urol.* 166, 2472-83 (2001) and Tuxhorn J A et al., *Cancer Res.* 62, 6021-5 (2002)) when the stromal compartment becomes disorganized and normal fibroblasts begin to be replaced by cancer-associated fibroblasts (CAF's).

Xenografts and tissue recombination experiments have contributed to the definition of the role of stromal cells in prostate carcinogenesis. In fact, benign prostate epithelial cells undergo transformation when recombined with prostate cancer-derived CAFs (Hayward S W, et al., *Cancer Res.* 61, 8135-42 (2001)).

Signaling factors from the microenvironment influence epithelial cells to acquire properties such as increased motility, proliferation or migratory and invasive behavior (Thiery J P. et al., *Nat Rev Cancer.* 2, 442-54 (2002), Koeneman K S, et al., *Prostate.* 39, 246-61 (1999), and Leach D A, et al., *Oncotarget.* 2015 Apr. 19). TGFβ and Wnt signaling pathways play important regulatory roles in stromal-epithelial interactions in prostate development and prostatic carcinogenesis (Lee C, Jia Z, et al., *Biomed Res Int.* 2014; 2014: 502093. doi: 10.1155/2014/502093. Epub 2014 Jun. 25, Yang F, et al., *Oncotarget.* 5, 10854-69 (2014), and Macheda M L, et al., *Curr Cancer Drug Targets.* 8, 454-65 (2008)). A variety of growth factors, PDGF, VEGF, IGF, FGF and HGH are involved in angiogenesis (Bhomick N A, et al., Nature. 432, 332-7 (2004), Muir C, et al., *Clin Exp Metastasis.* 23, 75-86 (2006), Johansson A, et al., Prostate. 67, 1664-76 (2007), Ohlson N, et al., Prostate. 67, 32-40 (2007), and Knudsen B S, et al., *Adv Cancer Res.* 91, 31-67 (2004)) and soluble cytokine and chemokine factors strongly influence the interaction between the epithelial and stromal compartment during prostate cancer progression (Wang J, et al., *Cell Signal.* 17, 1578-92 (2005), and Ao M, et al., *Cancer Res.* 67, 4244-53 (2007)). Extracellular Matrix (ECM) and cell adhesion molecule (CAM) degradation mediated through integrin-binding is involved in cancer cell invasion and metastasis (Ingber D E *Differentiation.* 70, 547-60 (2002)).

Transcriptome analysis has revealed many dysregulated genes that impact prostate cancer progression (Singh D, et al., *Cancer Cell.* 1, 203-9 (2002), Lapointe J, et al., *Proc Natl Acad Sci.* 101, 811-16 (2004), Yu Y P, et al., *J Clin Oncol.* 22, 2790-9 (220040), Tomlins S A, *Nat Genet.* 39, 41-51 (2007), Wallace T A, et al., *Cancer Res.* 68, 927-36 (2008), Penney K L, et al., *J Clin Oncol.* 29, 2391-6 (2011) and Grasso C S, et al., *Nature.* 487, 239-43 (2012)). However, prior to the invention described herein, there was a lack of knowledge regarding the extent to which the stroma contributes to the overall expression signature.

Laser-capture microdissection (LCM) has facilitated the isolation and study of specific cellular populations within the prostate tumor microenvironment. This technology, however, is labor-intensive, limiting large-scale efforts being undertaken. To date, differences between the tumor and its adjacent stroma in prostate cancer (Gregg J L, et al., *BMC Cancer.* 10, 1-14 (2010)) between normal and reactive stroma (Dakhova O, et al., *Clin Cancer Res.* 15, 3979-89 (2009)), epithelial differences between benign and tumor epithelium (Tomlins S A, et al., *Nature Genetics* 39, 41-51 (2007), and Furusato B, et al., *Prostate Cancer Prostatic Dis.* 11, 194-7 (2008) have been addressed utilizing LCM, albeit on a small scale.

The Gregg study utilized laser capture microdissection and whole transcriptome hybridization arrays in a small number of radical prostatectomy cases to look at differentially expressed genes between the tumor gland and its surrounding stromal area. The Gregg signature of upregulated stromal genes was recapitulated on the data set described herein, when comparing the tumor and its adjacent stroma.

As described herein, the progression of normal prostate to PIN to invasive cancer driven by molecular alterations in both epithelium and stroma, and that changes in the microenvironment contribute to tumor initiation, maintenance and progression. Therefore, as described below, it was assessed whether, in gene expression space, 1) epithelium and stroma (benign and malignant) were different; 2) whether non transformed epithelial and stromal tissues differed in prostates with and without tumor, and finally 3) how the stromal genes behaved in prostate cancer progression.

Pharmaceutical Therapeutics

For therapeutic uses, the compositions or agents described herein may be administered systemically, for example, formulated in a pharmaceutically-acceptable buffer such as physiological saline. Preferable routes of administration include, for example, subcutaneous, intravenous, interperitoneally, intramuscular, or intradermal injections that provide continuous, sustained levels of the drug in the patient. Treatment of human patients or other animals will be carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia, i.e., the prostate cancer. Generally, amounts will be in the range of those used for other agents used in the treatment of other diseases associated with neoplasia, although in certain instances lower amounts will be needed because of the increased specificity of the compound. For example, a therapeutic compound is administered at a dosage that is cytotoxic to a neoplastic cell.

Formulation of Pharmaceutical Compositions

The administration of a compound or a combination of compounds for the treatment of a neoplasia, e.g., a prostate cancer, may be by any suitable means that results in a concentration of the therapeutic that, combined with other components, is effective in ameliorating, reducing, or stabilizing a neoplasia. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 µg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other cases, this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 mg/Kg body weight. In other aspects, it is envisaged that doses may be in the range of about 5 mg compound/Kg body to about 20 mg compound/Kg body. In other embodiments, the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with the thymus; (v) formulations that allow for convenient dosing, such that doses are administered, for example, once every one or two weeks; and (vi) formulations that target a neoplasia by using carriers or chemical derivatives to deliver the therapeutic agent to a particular cell type (e.g., neoplastic cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates a neoplasia, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in the form suitable for sterile injection. To prepare such a composition, the suitable active antineoplastic therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol.

Controlled Release Parenteral Compositions

Controlled release parenteral compositions may be in form of aqueous suspensions, microspheres, microcapsules, magnetic microspheres, oil solutions, oil suspensions, or emulsions. Alternatively, the active drug may be incorporated in biocompatible carriers, liposomes, nanoparticles, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutam-nine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly (glycolic acid) or poly(ortho esters) or combinations thereof).

Kits or Pharmaceutical Systems

The present compositions may be assembled into kits or pharmaceutical systems for use in ameliorating a neoplasia (e.g., prostate cancer). Kits or pharmaceutical systems according to this aspect of the invention comprise a carrier means, such as a box, carton, tube or the like, having in close confinement therein one or more container means, such as vials, tubes, ampoules, or bottles. The kits or pharmaceutical systems of the invention may also comprise associated instructions for using the agents of the invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Materials and Methods

Clinical Specimens 61 of the 135 enrolled patients fulfilled 3 primary selection criteria. Prostate cancer, PIN and normal or hyperplastic prostate tissue, all surrounded by significant intervening stroma were required to be present in the same histological block. Pure low grade (Gleason 6) or high grade (Gleason ≥8) prostate cancer in the whole prostate was pathologically defined. Cases with comprehensive Gleason 7 were excluded by definition. Enough material for micro-dissection and nucleic acid extraction in the epithelial and stromal compartments of at least one block was required.

135 prostate cancer patients who underwent radical prostatectomy were recruited from the various medical institutions. 5 prostates from cysto-prostatectomy cases, included in the PROPP-Study, were collected from patients with bladder cancer were also included in the study as normal controls. All cases with incidental prostate cancer or excessive inflammation in the stromal counterpart or atrophy in the epithelial counterpart were excluded.

Digi-Pathology

A pathology review of all the histological slides was centralized in Italy. The slides selected according to the stated criteria were scanned with an Aperio instrument in Bologna and put on a dedicated proprietary website protected by regulated access. Circling of the epithelial and stromal counterparts in cancer, PIN and normal tissue areas was performed on digitized H&Es (FIG. 7A), where red circling indicated tumor, blue hgPIN and green benign regions of interest for subsequent microdissection. Annotated pathological scans were remotely accessed for the laser capture microdissection.

Laser Capture Microdissection (LCM) and Formalin-Fixed, Paraffin-Embedded (FFPE) RNA Extraction The LCM workflow comprised preliminary ROI review by digital annotation, tissue block sectioning and staining, 2 hr of microdissection on the Arcturus platform (Life Technologies), overnight incubation in lysis buffer/Proteinase K and subsequent RNA extraction by AllPrep (Qiagen) and quantification by RiboGreen assay (Life Technology), a sample tracking and digital inventory, comprising over 450 RNA extracts and >1500 corresponding images (pre-, post- and cap). See, Yuan, et al., Nature Protocols, v. 7, no. 5, 2012; and Kelly et al., PLoS One, 6, 10, e25357, each of which is incorporated herein by reference.

Labeling and Gene Hybridization Array

To accommodate the low RNA concentration and yields associated with microdissected tissues, the SensationPlus FFPE method was adopted as a suitable labeling technique. 20 ng total RNA at a concentration of 2.5 ng/ul, reliably and reproducibly measured RNA expression across the whole transcriptome on the Affymetrix Gene Array STA 1.0.

Normalization and Differential Gene Expression Analysis

Normalization and rigorous quality control of the gene expression data was performed. A normalization method was developed that adjusted raw data at the probe level for technical variables, such as batches, overall median of the fluorescence intensities in each array prior to normalization using the RMA (robust multichip average) method. The QC did not identify any failing samples, and there were no extreme outliers. Thus, all assayed samples were retained and ROIs for further analysis. Because of a relatively large sample size, profiling was performed in two batches, a correction to minimize false positive findings due to potential batch effects and to increase the power of discovering true differential expression was implemented by adjusting the raw data as described above.

The random effects linear models approach was implemented to account for correlations between compartments within cases. Differentially expressed genes within the epithelial, within the stromal, and between the epithelial and stromal morphological regions of interest were expressed as log fold-changes. P-values for the tests were adjusted using the Benjamin-Hochberg method, thus controlling False Discovery Rate (FUR) in multiple comparisons. A FDR≤0.05 was considered significant. The data sets were filtered to exclude genes where the fold-changes did not exceed 1.5.

GEO Datasets

Publicly available data was downloaded as preprocessed from the original publications from GEO. Using microarray annotations as supplied in the GSE datasets available probesets were extracted that corresponded to the genes in the signature. These data were used to perform hierarchical clustering, principal component analysis, and to compute single sample gene set enrichment scores (ssGSEA).

Using single sample Gene Sets Enrichment Analysis (Barbie D A, et al. Nature. 2009; 462:108-112) algorithm, epithelial, stromal and combined scores were computed for the gene expression data from the Physicians' Health Study (PHS) (120 indolent, 30 lethal cases), and Health Professionals Follow-Up Study (HPFS) (171 indolent, 83 lethal cases) (i.e. cohorts where outcomes were known). An epithelial score was computed by applying ssGSEA to epithelial genes from the signature with epithelialy expressed genes as a reference. The stromal score was computed by applying ssGSEA to stromal genes from the signature with stromally expressed genes as a reference. The combined score was defined as the maximum between standardized epithelial and standardized stromal scores. The scores were studied for both a complete 29 gene signature and for a manually reduced set of only bone-related genes. As described above, an exemplary bone-related subset of genes includes PRELP, LTBP2, FBLN5, ITGA11, COL1A1, ALCAM, SFRP2, TNS3, SULF1, BGN, and/or THBS2. These scores predicted the outcomes (i.e. lethal or indolent disease). The areas under the ROC curves for these predictions are shown in Table 22.

TABLE 22

Area under the ROC curve for predicted outcomes in 29-gene signature and signature restricted to bone-related genes

| Cohort | Stromal Score | Epithelial Score | Max Score |
|---|---|---|---|
| 29-gene signature | | | |
| PHS | 0.59 | 0.69 | 0.69 |
| HPFS | 0.66 | 0.64 | .65 |
| Signature restricted to bone-related genes | | | |
| PHS | 0.63 | 0.68 | 0.72 |
| HPFS | 0.66 | 0.63 | 0.7 |

Enrichment and Pathway Assessment

Differentially expressed genes from the epithelial-stromal data sets of interest were mapped onto gene ID's of functional ontologies represented by pathway maps and networks derived from the MetaCore portal (portal.genego.com) and the public ontology, Gene Ontology (GO; geneontology.org). In MetaCore™, the enrichment analysis workflow tool was utilized to conduct the Ontology Enrichment (EO), by mapping gene IDs of the dataset of interest onto gene IDs in entities of built-in functional ontologies such as pathway maps, networks, diseases, etc. The terms in a given ontology were ranked based on "relevance" in the dataset. The statistical relevance procedure, a p-value of hypergeometric distribution, was calculated as the probability of a match to occur by chance, given the size of the ontology, the dataset and the particular entity. The lower the p-value, the higher is the "non-randomness" of finding the intersection between the dataset and the particular ontology term. That, in turn, translated into a higher ranking for the entity matched. The more genes/proteins belong to a process/pathway, the lower the p-value. In EA proprietary ontologies (canonical pathway maps, cellular processes, toxicities, disease biomarkers etc.) were used and public ontologies such as Gene Ontology (cellular processes, protein functions, localizations).

Molecular Signatures Database v5.0

The Molecular Signatures Database (MSigDB) is a collection of annotated gene sets for use with GSEA software, comprised of 8 major gene collections.

The Molecular Signatures Database (MSigDB) is a collection of annotated gene sets for use with GSEA software. MSigDB assists with investigating gene sets and computing overlaps.

When gene sets share genes, examination of how they overlap may highlight common processes, pathways, and underlying biological themes. This tool evaluates the overlap of a user provided gene set, and provides an estimate of the statistical significance, with as many MSigDB collections as chosen.

Due to the characteristics of the hypergeometric distribution there are limits to the size the user provided gene set may be to still produce meaningful significance estimates. At most 2940 genes will be allowed, anything larger will be rejected.

A list of gene identifiers is entered in the box provided, and a pull down menu below the box allows input of how the identifying genes are specified. Overlaps are computed using HUGO gene symbols and any required conversion is done automatically by the tool. The "compute overlaps" button displays the results, including:

Statistics:

The number of overlaps shown lists the number of overlapping gene sets displayed in the report.

By default, the report displays the 10 gene sets in the collection that best overlap with the gene set of interest. To compute overlaps from the Investigate Gene Sets page, the number of overlapping gene sets to display in the report is chosen. The number of gene sets in the collection lists the total number of gene sets being analyzed, the number of genes in comparison lists the number of genes in the gene set of interest, and the number of genes in the collection lists the number of unique genes in the gene sets being analyzed.

Descriptions of the overlapping gene sets, including: link to the gene set page, number of genes in the gene set, description of the gene set, number of genes in the overlap between this gene set and the gene set, P value from the hypergeometric distribution for (k−1, K, N−K, n) where k is the number of genes in the intersection of the query set with a set from MSigDB, K is the number of genes in the set from MSigDB, N is the total number of gene universe (all known human gene symbols), and n is the number of genes in the query set, FDR q-value. This is the false discovery rate analog of hypergeometric p-value after correction for multiple hypothesis testing according to Benjamini and Hochberg. Color bar shading from light green to black, where lighter colors indicate more significant q-values (<0.05) and black indicates less significant q-values (≥0.05). Overlap matrix showing the genes in the overlapping gene sets, rows list the genes in the gene set, with gene descriptions and links to gene annotations, and columns list the overlapping gene sets, with links to the gene set pages Example 2: Cohort Description A 25 case cohort was selected, comprising 12 pure 3+3 low grade and 13≥4+4 high grade radical prostatectomy (RP) specimens. In addition, 5 cystoprostatectomy (CP) specimens with no prostate cancer were used. Common clinical characteristics available from all sites were collected to include pre-operative PSA levels, age at diagnosis pathological disease stage, nodal status and patient follow-up. The mean age of patients in the study cohort was 63.7±1. The pre-operative PSA levels were significantly higher in the Gleason 4 case group, where p value <0.035 (Median PSA 10.2±1.9). Clinical characteristics are shown in Table 2. Laser capture microdissection of 165 regions of interest from normal prostate tissue, prostatic intraepithelial neoplasia and invasive tumor, each with its immediately surrounding stroma, were used for gene expression profiling (GEP). Regions of interest in each case comprised tumor (T), high-grade PIN (P) and benign (B) glands and adjacent (sT, sP, sB) stroma. Normal benign tissue and adjacent stroma samples from cystoprostatectomy cases were denoted as HB and HsB, respectively, where H stands for healthy. The differences between glands and stroma within and between the two cellular compartments were studied. Using these comparisons, the role of epithelial and stromal-expressing genes in prostate cancer initiation, progression and advanced disease and the complex interactions that arise at the epithelium-stroma interface were investigated.

| Sample # | Grade | Country | Grade | Chronic Inflammation | Age at procedure | Clinical stage | Pre-OP PSA [ng/ml] | Pathologic Tumor Stage | Nodal Status | Follow-up/ Outcome, where available? |
|---|---|---|---|---|---|---|---|---|---|---|
| 1 | 3 + 3 | Ireland | 3 + 3 | yes, mild | 58 | T2 | 8 | pT2c | Nx, Mx | Unknown |
| 3 | | Ireland | 3 + 3 | yes, moderate | 67 | T2 | 2.89 | pT2c | N0 | PSA 0.1 (12-11-2014) |
| 14 | | USA | 3 + 3 | no | 66 | T2 | 6.4 | pT2 | N0 | Non-prostrate cancer death |
| 15 | | USA | 3 + 3 | no | 77 | T2 | NA | pT2 | N0 | Lethal Prostate Cancer |
| 17 | | USA | 3 + 3 | yes, moderate | 64 | T1 | 7.8 | pT1 | N0 | PSA relapse |
| 18 | | USA | 3 + 3 | na | 70 | T2 | 9 | pT2 | N0 | Unknown |
| 19 | | USA | 3 + 3 | yes, mild | 57 | T2 | NA | pT2 | N0 | Non-prostrate cancer death |
| 21 | | UK | 3 + 3 | na | 64 | T2 | 4.3 | pT1 | N0 | Unknown |
| 26 | | UK | 3 + 3 | no | 64 | NA | 5.3 | pT2a | nodular tumour tissue on specimen | discharge - Psa unrecordable 2010 |
| 29 | | UK | 3 + 3 | no | 66 | T1c | 7.8 | pT2c | nodular tumour tissue on specimen | discharge |
| 30 | | UK | 3 + 3 | no | 60 | T2a | 6.6 | pT3a | no nodules found | discharge |
| 31 | | Ireland | 3 + 3 | no | 58 | NA | NA | pT2a | NA | Unknown |
| 2 | 4 + 4 | Ireland | 4 + 5 | yes, moderate | 59 | T2 | 4 | pT2c | perineural involvement | BCR 10-21-2010 (PSA 0.74), 04-05-2011 (PSA 1.7), Radiotherapy 109-17-2013 (PSA 0.01) |
| 4 | | Italy | 4 + 4 | yes, mild | 72 | T1 | 2.75 | pT2b | N0, Mx (R1), 0/13 | Lethal Prostate Cancer |
| 5 | | Italy | 4 + 5 | yes, mild | 54 | T2 | 35 | pT3b | N1, Mx (R1), 3/22 | Biochemical relapse. TAC negative |
| 6 | | Italy | 5 + 4 | no | 62 | T2 | 12.39 | pT3a | N0, Mx (R1), 0/20 | RT, no metastatic disease (until 03/14) |
| 12 | | Italy | 4 + 4 | yes, mild | 65 | T1 | 15.2 | pT3a | N1, MX (R1), 3/19 | Lethal Prostate Cancer |
| 13 | | Italy | 5 + 5 | yes, mild | 64 | T2 | 30 | pT3b | N0, Mx (R1), 0/20 | Lethal Prostate Cancer |
| 20 | | USA | 4 + 4 | no | 59 | M1 | | M1 | N0 or N1 | Lethal Prostate Cancer |
| 22 | | Italy | 4 + 5 | yes, mild | 74 | T2 | 6.78 | pT3b | N0 Mx (R0), 0/14 | RT and hormone therapy, no metastatic disease (until 5/14) |
| 23 | | Italy | 5 + 4 | yes, mild | 72 | T3 | 14.3 | pT3b | N1 Mx (R1), 4/18 | Bone Metastasis (5/11) |
| 24 | | Ireland | 5 + 4 | na | 59 | | | pT2c | Nx (likely N0) | Patient alive |
| 25 | | Ireland | 4 + 5 | yes | 57 | | | pT3a | Nx | Unknown |
| 27 | | UK | 4 + 4 | no | 63 | T2a | 9.8 | pT2c | nodular tumour tissue on specimen | discharge - Psa unrecordable 2009 |
| 28 | | UK | 4 + 4 | no | 66 | T2 | 5.8 | pT2c | no nodules found | discharge - Psa unrecordable 2011 |
| 7 | cystoprostatectomy | Sweden | no tumor | yes, mild | 77 | | | | | |
| 8 | | Sweden | no tumor | no | 42 | | | | | |
| 9 | | Sweden | no tumor | no | 75 | | | | | |
| 10 | | Sweden | no tumor | no | 53 | | | | | |
| 11 | | Sweden | no tumor | yes, mild | 67 | | | | | |

Figure 1B:
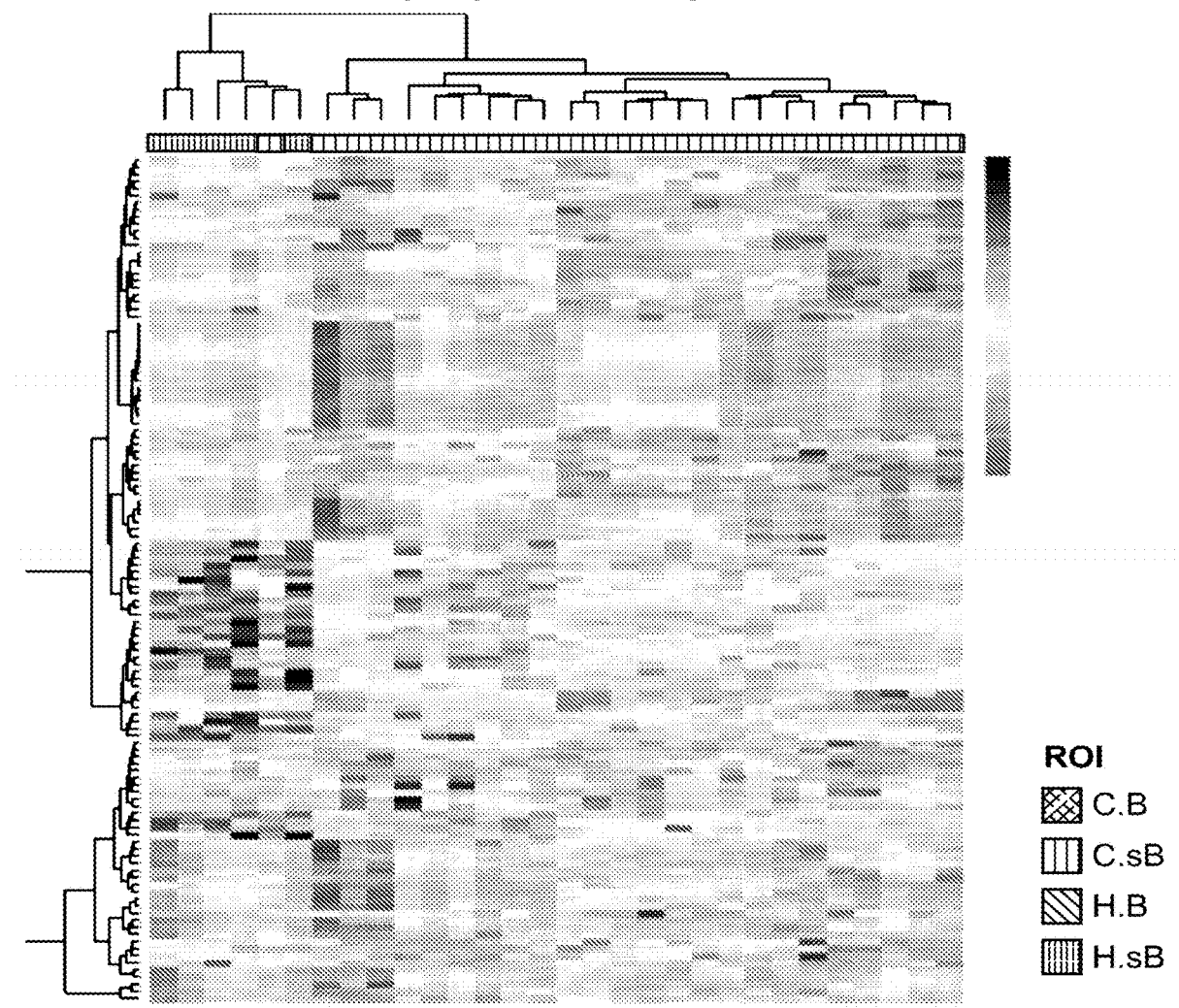
FIG. 1B is an image of hierarchical clustering represented by a heatmap, showing the comparison between cystoprostatectomy and benign radical prostatectomy adjacent stroma [HsB-sB], where H denotes "Healthy." s: Stroma; B: benign

Example 3: Stroma, not Epithelium, Away from the Tumor in RP was Different from Stroma in Cystoprostatectomies Direct comparison of benign epithelia from the Cystoprostatectomy (CP) and radical prostatectomy (RP) tissues (B-HB) HB found 6 differentially expressed genes (FIG. 1A). When performing the same comparison on the adjacent stroma from the CP and RP tissues (sB-HsB), a larger number of statistically significant genes were differently expressed (FIG. 1B). The differentially expressed genes found in the stromal comparison are tabulated in Table 3, where genes highlighted in orange or yellow indicate upregulated and downregulated gene expression for a given comparison, respectively. Initially, the GeneGo Enrichment analysis tool to assess the most significant GO processes, pathways and networks associated with the 90 genes were utilized. Apoptosis, bone regulation and immune response were statistically significant with FDR values <0.05 (Table 4). These findings further indicate that the transcriptome of the stroma was altered at an early stage during cancer initiation, and importantly, in areas not in close proximity to the invasive tumor. Changes occur in the cellular composition of the stroma at an early stage during cancer initiation. This stroma is comprised of components that are favorable for tumor invasion, which is additionally supported by significant enrichment of multiple cancer and inflammatory pathways from the GSEA Molecular Signature Database (MSigDB), where early estrogen response was also prevalent (Table 5). An FDR q-value of <0.05 was considered significant.

| Affymetrix id | Gene | logFC | adj.P.Val |
|---|---|---|---|
| 7982084 | SNORD115-11 | 2.138076 | 0.006879 |
| 7982070 | SNORD115-32 | 1.988756 | 0.020522 |
| 7982050 | SNORD115-11 | 1.921432 | 0.012826 |
| 7982028 | SNORD115-11 | 1.910864 | 0.011278 |
| 7982064 | SNORD115-11 | 1.910864 | 0.011278 |
| 7982078 | SNORD115-11 | 1.910864 | 0.011278 |
| 7982092 | SNORD115-11 | 1.910864 | 0.011278 |
| 7982016 | SNORD115-12 | 1.905817 | 0.011278 |
| 7982024 | SNORD115-12 | 1.905817 | 0.011278 |
| 7982030 | SNORD115-12 | 1.905817 | 0.011278 |
| 7982058 | SNORD115-26 | 1.900849 | 0.011278 |
| 8041170 | SNORD53 | 1.862117 | 0.016172 |
| 7982094 | SNORD115-44 | 1.71456 | 0.029182 |
| 7982008 | SNORD115-1 | 1.675323 | 0.006879 |
| 7982032 | SNORD115-1 | 1.675323 | 0.006879 |
| 7982038 | SNORD115-1 | 1.675323 | 0.006879 |
| 8032749 | SNORD37 | 1.639979 | 0.011278 |
| 7982046 | SNORD115-20 | 1.609413 | 0.035174 |
| 8118319 | SNORD48 | 1.537744 | 0.026177 |
| 7982090 | SNORD115-42 | 1.536964 | 0.02773 |
| 8010078 | SNORD1C | 1.479898 | 0.020075 |
| 7982018 | SNORD115-6 | 1.47845 | 0.033548 |
| 8148304 | TRIB1 | 1.475093 | 0.009004 |
| 7922418 | SNORD74 | 1.460443 | 0.015011 |
| 8158998 | SNORD36C | 1.440785 | 0.035974 |
| 8025498 | SNORA70 | 1.410315 | 0.006879 |
| 8162117 | GOLM1 | 1.386531 | 0.023341 |
| 8159006 | SNORD36B | 1.368625 | 0.025836 |
| 7964246 | SNORD59B | 1.365847 | 0.041563 |
| 8140840 | STEAP4 | 1.364313 | 0.002336 |
| 7982040 | SNORD115-17 | 1.328292 | 0.036714 |
| 7982042 | SNORD115-17 | 1.328292 | 0.036714 |
| 7982044 | SNORD115-17 | 1.328292 | 0.036714 |
| 8125149 | SLC44A4 | 1.319444 | 0.042885 |
| 8178653 | SLC44A4 | 1.319444 | 0.042885 |
| 8179861 | SLC44A4 | 1.319444 | 0.042885 |
| 8170863 | SNORA70 | 1.300163 | 0.012499 |
| 7894479 | NDUFA2 | 1.271016 | 0.009014 |
| 8116532 | SNORD95 | 1.250076 | 0.020218 |
| 8027002 | GDF15 | 1.24626 | 0.031238 |
| 8090690 | CPNE4 | 1.228446 | 0.034996 |
| 8005953 | SNORD4A | 1.162119 | 0.02773 |
| 8025584 | SNORD105 | 1.149028 | 0.011278 |
| 8001007 | PRSS8 | 1.142531 | 0.024831 |
| 7971373 | TPT1 | 1.131423 | 0.037097 |
| 8066258 | SNORA71A | 1.098432 | 0.026588 |
| 8112865 | SERINC5 | 0.986519 | 0.021305 |
| 8048116 | SNORA70 | 0.957688 | 0.031238 |
| 8166469 | SAT1 | 0.955272 | 0.017944 |
| 8060503 | SNORD57 | 0.947798 | 0.035974 |
| 8107769 | SLC12A2 | 0.922728 | 0.045785 |
| 8092169 | TNFSF10 | 0.911916 | 0.044703 |
| 8029489 | BCAM | 0.903686 | 0.024489 |
| 7894732 | RPS5 | 0.890314 | 0.026761 |
| 7906079 | RAB25 | 0.88773 | 0.011278 |
| 7951032 | SNORA1 | 0.872365 | 0.049907 |
| 7939642 | CREB3L1 | 0.867038 | 0.020111 |
| 8018982 | CANT1 | 0.862629 | 0.023341 |
| 8082607 | ATP2C1 | 0.844597 | 0.024868 |
| 7900922 | ATP6V0B | 0.837325 | 0.000315 |
| 8104079 | FAT1 | 0.836118 | 0.03119 |
| 7892856 | SNORA53 | 0.816169 | 0.028 |
| 8098328 | GALNT7 | 0.813794 | 0.03897 |
| 7895939 | EIF3D | 0.811534 | 0.036318 |
| 8097792 | SNORD73A | 0.808633 | 0.036714 |
| 8126784 | PLA2G7 | 0.799143 | 0.039942 |
| 8084880 | HES1 | 0.779594 | 0.012538 |
| 8041853 | EPCAM | 0.77872 | 0.030178 |
| 8161919 | TLE1 | 0.772504 | 0.017338 |
| 7895996 | EIF3D | 0.767289 | 0.031938 |
| 7919751 | MCL1 | 0.758355 | 0.02285 |
| 7892766 | TPP1 | 0.756182 | 0.011278 |
| 7971389 | SNORA31 | 0.753672 | 0.036318 |
| 7894306 | EIF3D | 0.749257 | 0.047277 |
| 8148317 | MYC | 0.730151 | 0.035974 |
| 8125530 | HLA-DMB | 0.727286 | 0.037097 |
| 8091658 | CCNL1 | 0.706273 | 0.006879 |
| 8034084 | AP1M2 | 0.688523 | 0.036714 |
| 8030128 | PPP1R15A | 0.688029 | 0.043994 |
| 8047780 | SNORA41 | 0.682967 | 0.04206 |
| 8148040 | MAL2 | 0.673755 | 0.031238 |
| 8109999 | ERGIC1 | 0.66576 | 0.037097 |
| 7901229 | FAAH | 0.649129 | 0.03897 |
| 7913357 | ECE1 | 0.614526 | 0.004048 |
| 8099897 | UGDH | 0.608742 | 0.042243 |
| 8034210 | TMEM205 | 0.605526 | 0.006879 |
| 7979906 | COX16 | 0.605428 | 0.032133 |
| 7893466 | EIF4G2 | 0.593179 | 0.044703 |
| 8082816 | SRPRB | 0.593091 | 0.008345 |
| 8138108 | KDELR2 | 0.590541 | 0.031451 |
| 7985560 | LOC440297 | −0.59063 | 0.042154 |
| 7954245 | PLEKHA5 | −0.6061 | 0.001696 |
| 8127498 | MIR30C2 | −0.60712 | 0.000484 |
| 7983143 | STARD9 | −0.61365 | 0.023341 |
| 7934870 | ATAD1 | −0.61775 | 0.02291 |
| 7902565 | LPHN2 | −0.61803 | 0.042243 |
| 8112018 | NA | −0.61823 | 0.001696 |
| 8139212 | GLI3 | −0.62931 | 0.029212 |
| 8162388 | OMD | −0.65733 | 0.002934 |
| 8077323 | CNTN4 | −0.68342 | 0.002158 |
| 8171359 | GPM6B | −0.70164 | 0.024844 |
| 7954926 | PDZRN4 | −0.71382 | 0.028 |
| 7895986 | NA | −0.71384 | 0.027396 |
| 8152297 | ANGPT1 | −0.71451 | 0.01214 |
| 8067839 | KGFLP1 | −0.71897 | 0.006879 |
| 8089293 | NA | −0.72176 | 0.049907 |
| 7985159 | CRABP1 | −0.72215 | 0.006879 |

-continued

| Affymetrix id | Gene | logFC | adj.P.Val |
|---|---|---|---|
| 8000480 | RNU6-1241P | −0.79991 | 0.006879 |
| 7943892 | NCAM 1 | −0.83126 | 0.020797 |
| 8150901 | PENK | −0.83296 | 0.036714 |
| 7977270 | LOC388022 | −0.88628 | 0.035974 |
| 7898112 | NA | −0.89781 | 0.000484 |
| 7930714 | ATRNL1 | −0.90288 | 0.01214 |
| 7978586 | CFL2 | −0.90318 | 0.032624 |
| 7896499 | KAT7 | −0.97386 | 0.039942 |
| 8097692 | EDNRA | −0.9937 | 0.030288 |
| 8115443 | AC016577.1 | −1.0244 | 0.02253 |

-continued

| Affymetrix id | Gene | logFC | adj.P.Val |
|---|---|---|---|
| 8168892 | TCEAL2 | −1.04081 | 0.030637 |
| 8149248 | RP11 | −1.16788 | 8.73E−05 |

Negative FC: LOC440297, PLEKHA5, MIR30C2, STARD9, ATAD1, LPHN2, GLI3, OMD, CNTN4, GPM6B, PDZRN4, ANGPT1, KGFLP1, CRABP1, RNU6-1241P, NCAM1, PENK, LOC388022, ATRNL1, CFL2, KAT7, EDNRA, AC016577.1, TCEAL2, and RP11.

Postive FC: SNORD115-11, SNORD115-32, SNORD115-11, SNORD115-12, SNORD115-26, SNORD53, SNORD115-44, SNORD115-1, SNORD37, SNORD115-20, SNORD48, SNORD115-42, SNORD1C, SNORD115-6, TRIB1, SNORD74, SNORD36C, SNORA70, GOLM1, SNORD36B, SNORD59B, STEAP4, SNORD115-17, SLC44A4, NDUFA2, SNORD95, GDF15, CPNE4, SNORD4A, SNORD105, PRSS8, TPT1, SNORA71A, SERINC5, SAT1, SNORD57, SLC12A2, TNFSF10, BCAM, RPS5, RAB25, SNORA1, CREB3L1, CANT1, ATP2C1, ATP6V0B, FAT1, SNORA53, GALNT7, EIF3D, SNORD73A, PLA2G7, HES1, EPCAM, TLE1, EIF3D, MCL1, TPP1, SNORA31, MYC, HLA-DMB, CCNL1, AP1M2, PPP1R15A, SNORA41, MAL2, ERGIC1, FAAH, ECE1, UGDH, TMEM205, COX16, EIF4G2, SRPRB, and KDELR2.

| | | | | C.sB-H.sB_GeneGo_genelist | | | |
|---|---|---|---|---|---|---|---|
| Enrichment by Pathway Maps | | | | | | | Network |
| # | Maps | Total | pValue | Min FDR | p-value | FDR | In Data | Objects from Active Data |
| 1 | Development_Delta- and kappa-type opioid receptors signaling via beta-arrestin | 23 | 3.582E−03 | 2.166E−01 | 3.582E−03 | 2.166E−01 | 2 | Metenkefalin, Leuenkephalin |
| 2 | Translation_Opioid receptors in regulation of translation | 24 | 3.898E−03 | 2.166E−01 | 3.898E−03 | 2.166E−01 | 2 | Metenkefalin, Leuenkephalin |
| 3 | Muscle contraction_Delta-type opioid receptor in smooth muscle contraction | 26 | 4.568E−03 | 2.166E−01 | 4.568E−03 | 2.166E−01 | 2 | Metenkefalin, Leuenkephalin |
| 4 | Immune response_IL-22 signaling pathway | 34 | 7.732E−03 | 2.166E−01 | 7.732E−03 | 2.166E−01 | 2 | c-Myc, Mcl-1 |
| 5 | Development_Regulation of telomere length and cellular immortalization | 35 | 8.180E−03 | 2.166E−01 | 8.180E−03 | 2.166E−01 | 2 | c-Myc, PTOP |
| 6 | Role of Endothelin-1 in inflammation and vasoconstriction in Sickle cell disease | 38 | 9.594E−03 | 2.166E−01 | 9.594E−03 | 2.166E−01 | 2 | EDNRA, EDNRB |
| 7 | Neurophysiological process_Delta-type opioid receptor in the nervous system | 40 | 1.059E−02 | 2.166E−01 | 1.059E−02 | 2.166E−01 | 2 | Metenkefalin, Leuenkephalin |
| 8 | Development_Notch Signaling Pathway | 43 | 1.217E−02 | 2.166E−01 | 1.217E−02 | 2.166E−01 | 2 | HES1, TLE |
| 9 | Development_Hedgehog signaling | 46 | 1.385E−02 | 2.166E−01 | 1.385E−02 | 2.166E−01 | 2 | GLI-3, GLI-3R |
| 10 | Development_GM-CSF signaling | 50 | 1.623E−02 | 2.166E−01 | 1.623E−02 | 2.166E−01 | 2 | c-Myc, Mcl-1 |

| | | | | C.sB-H.sB_GeneGo_genelist | | | |
|---|---|---|---|---|---|---|---|
| Enrichment by Process Networks | | | | | | | Network |
| # | Networks | Total | pValue | Min FDR | p-value | FDR | In Data | Objects from Active Data |
| 1 | Development_Regulation of angiogenesis | 223 | 1.364E−03 | 1.295E−01 | 1.364E−03 | 1.295E−01 | 6 | Angiopoietin 1, c-Myc, GLI-3, EDNRA, Galpha(q)-specific peptide GPCRs, EDNRB |
| 2 | Development_Blood vessel morphogenesis | 228 | 8.381E−03 | 3.981E−01 | 8.381E−03 | 3.981E−01 | 5 | Angiopoietin 1, c-Myc, EDNRA, Galpha(q)-specific peptide GPCRs, EDNRB |
| 3 | Apoptosis_Endoplasmic reticulum stress pathway | 89 | 1.324E−02 | 4.193E−01 | 1.324E−02 | 4.193E−01 | 3 | GADD34, OASIS, eIF3S7 |
| 4 | Cardiac development_FGF_ErbB signaling | 124 | 3.163E−02 | 6.219E−01 | 3.163E−02 | 6.219E−01 | 3 | GLI-3, EDNRA, GLI-3R |
| 5 | Development_Regulation of telomere length | 53 | 3.519E−02 | 6.219E−01 | 3.519E−02 | 6.219E−01 | 2 | c-Myc, PTOP |
| 6 | Cardiac development_Wnt_beta-catenin, Notch, VEGF, IP3 and integrin signaling | 150 | 5.093E−02 | 6.219E−01 | 5.093E−02 | 6.219E−01 | 3 | HES1, GLI-3, GLI-3R |

-continued

| # | Processes | Total | pValue | Min FDR | p-value | FDR | In Data | Network Objects from Active Data |
|---|---|---|---|---|---|---|---|---|
| 7 | Development_Hedgehog signaling | 254 | 5.241E−02 | 6.219E−01 | 5.241E−02 | 6.219E−01 | 4 | HES1, c-Myc, GLI-3, GLI-3R |
| 8 | Signal transduction_Neuropeptide signaling pathways | 155 | 5.517E−02 | 6.219E−01 | 5.517E−02 | 6.219E−01 | 3 | Galpha(q)-specific peptide GPCRs, LEC, Enkephalin A |
| 9 | Apoptosis_Apoptotic mitochondria | 77 | 6.875E−02 | 6.219E−01 | 6.875E−02 | 6.219E−01 | 2 | GADD34, Mcl-1 |
| 10 | Transport_Calcium transport | 192 | 9.154E−02 | 6.219E−01 | 9.154E−02 | 6.219E−01 | 3 | Soluble calcium-activated nucleotidase 1, ATP2C1, NOL3 |

C.sB-H.sB_GeneGo_genelist

Enrichment by GO Processes

| # | Processes | Total | pValue | Min FDR | p-value | FDR | In Data | Network Objects from Active Data |
|---|---|---|---|---|---|---|---|---|
| 1 | endothelin receptor signaling pathway | 3 | 5.757E−08 | 2.005E−04 | 5.757E−08 | 2.005E−04 | 3 | EDNRA, Galpha(q)-specific peptide GPCRs, EDNRB |
| 2 | positive regulation of monocyte chemotaxis | 17 | 4.971E−07 | 5.774E−04 | 4.971E−07 | 5.774E−04 | 4 | Galpha(q)-specific peptide GPCRs, PLA2, PLA2G7, ATF/CREB |
| 3 | smooth muscle cell proliferation | 5 | 5.725E−07 | 5.774E−04 | 5.725E−07 | 5.774E−04 | 3 | EDNRA, Galpha(q)-specific peptide GPCRs, NOL3 |
| 4 | endoplasmic reticulum unfolded protein response | 127 | 6.631E−07 | 5.774E−04 | 6.631E−07 | 5.774E−04 | 7 | GADD34, KDELR, OASIS, CLN2 (Tripeptidyl-peptidase I), Phosphatase regulator (inhibitor), ATF/CREB, SRP-beta receptor |
| 5 | cellular response to unfolded protein | 132 | 8.610E−07 | 5.997E−04 | 8.610E−07 | 5.997E−04 | 7 | GADD34, KDELR, OASIS, CLN2 (Tripeptidyl-peptidase I), Phosphatase regulator (inhibitor), ATF/CREB, SRP-beta receptor |
| 6 | ER-nucleus signaling pathway | 141 | 1.342E−06 | 7.048E−04 | 1.342E−06 | 7.048E−04 | 7 | GADD34, KDELR, OASIS, CLN2 (Tripeptidyl-peptidase I), Phosphatase regulator (inhibitor), ATF/CREB, SRP-beta receptor |
| 7 | regulation of monocyte chemotaxis | 22 | 1.505E−06 | 7.048E−04 | 1.505E−06 | 7.048E−04 | 4 | Galpha(q)-specific peptide GPCRs, PLA2, PLA2G7, ATF/CREB |
| 8 | cellular response to topologically incorrect protein | 145 | 1.619E−06 | 7.048E−04 | 1.619E−06 | 7.048E−04 | 7 | GADD34, KDELR, OASIS, CLN2 (Tripeptidyl-peptidase I), Phosphatase regulator (inhibitor), ATF/CREB, SRP-beta receptor |
| 9 | regulation of bone mineralization | 95 | 1.961E−06 | 7.587E−04 | 1.961E−06 | 7.587E−04 | 6 | OASIS, Osteomodulin, Galpha(q)-specific peptide GPCRs, PLA2, ATF/CREB, M6B |

-continued

| | | | | | | | |
|---|---|---|---|---|---|---|---|
| 10 | response to endoplasmic reticulum stress | 226 | 2.908E−06 | 1.013E−03 | 2.908E−06 | 1.013E−03 | 8 | GADD34, KDELR, OASIS, CLN2 (Tripeptidyl-peptidase I), PLA2, Phosphatase regulator (inhibitor), ATF/CREB, SRP-beta receptor |

| MSigDB Curated Data Sets | # Genes in Gene Set (K) | Description | # Genes in Overlap (k) | k/K | p-value | FDR q-value | Genes |
|---|---|---|---|---|---|---|---|
| Chemical and Genetic Pertubations | 96 | Genes up-regulated in prostate cancer samples. | 9 | 0.0938 | 1.49E−12 | 7.05E−10 | GDF15, TRIB1, GALNT7, BCAM CANT1, CREB3L1, EPCAM, GOLM1, SRPRB |
| Chemical and Genetic Pertubations | 176 | Genes up-regulated in MCF7 cells (breast cancer) after stimulation with NRG1 [GeneID = 3084]. | 7 | 0.0398 | 3.48E−08 | 8.23E−05 | GDF15, TRIB1, HES1, CCNL1, PPP1R15A, MCL1, MYC |
| Chemical and Genetic Pertubations | 701 | Genes down-regulated in basal subtype of breast cancer samles. | 11 | 0.0157 | 5.74E−08 | 9.05E−05 | GDF15, TRIB1, GALNT7, BCAM CANT1, CREB3L1, TNFSF10, UGDH, ATRNL1 OMD, SLC44A4 FAAH |
| Chemical and Genetic Pertubations | 222 | Class III of genes transiently induced by EGF [GeneID = 1950] in 184A1 cells (mammary | 7 | 0.0315 | 1.70E−07 | 1.35E−04 | TRIB1, GALNT7, EHS1, CCNL1, PPP1R15A, MCL1, STEAP4 |
| Chemical and Genetic Pertubations | 464 | Genes down-regulated in HMLE cells (immortalized nontransformed mammary epithelium) after E-cadhedrin (CDH1) [GeneID = 999] knockdown by RNA9. | 9 | 0.0195 | 1.71E−07 | 1.35E−04 | EPCAM, HES1, TSFSF10, PRSS8, RAB25, LPHN2, GPM6B, SERINC5, APIM2 |
| Chemical and Genetic Pertubations | 781 | Genes down-regulated in TMX2-28 cells (breast cancer) which do not express ESR1 [GeneID=2099]) compared to the parental MCF7 cells which do. | 11 | 0.0141 | 1.69E−07 | 1.35E−04 | GDF15, TNFS10, UGDH, ATRNL1, PRSS8, SAT1, SLC12A2, TLE1, PLEKHA5, FAT1, CPENE4 |
| Chemical and Genetic Pertubations | 482 | The 'group 5 set' of genes associated with acquired endocrine therapy resistance in breast tumors expressing ESR1 but not ERBB2 [GeneID = 2099; 2064]. | 9 | 0.0187 | 236E−07 | 1.59E−04 | GDF15, GALNT7, BCAM, UGDH, SAT1, SLC12A2, KDELR2, MAL2, CFL2 |
| Chemical and Genetic Pertubations | 265 | Genes up-regulated in mucinous ovarian carcinoma tumors of low malignant potential (LMP) compared to normal ovarian surface epithelium tissue. | 7 | 0.0264 | 5.60E−07 | 3.31E−04 | GALNT7, CANT1, EPCAM, TN FSF10, RAB25, KDELR2, TPT1 |
| Chemical and Genetic Pertubations | 720 | The 'group 3 set' of genes associated with acquired endocrine therapy resistance in breast tumors expressing ESR1 and ERBB2 [GeneID = 2099; 2064]. | 10 | 0.0139 | 728E−07 | 3.82E−04 | GDF15, TRIB1, BCAM, GOLM1, SAT1, SLC12A2, STEAP4, LPHN2, KDELR2, MAL2, ATP6VOB |
| Chemical and Genetic Pertubations | 425 | Genes up-regulated in cultured stromal stem cells from adipose tissue, compared to the freshly isolated cells. | 8 | 0.0188 | 1.08E−06 | 5.10E−04 | GDF15, TRIB1, CCNL1, PPP1R15A, MYC, TNFS10, OMD |

-continued

| MSigDB Curated Data Sets | # Genes in Gene Set (K) | Description | # Genes in Overlap (k) | k/K | p-value | FDR q-value | Genes |
|---|---|---|---|---|---|---|---|
| GO Biological Process | 1634 | Genes annotated by the GO term GO:0007165. The cascade of processes by which a signal interacts with a receptor, causing a change in the level or activity of a second messenger or other downstream target, and ultimately effecting a change in the functioning of the cell. | 12 | 0.0073 | 3.68E−05 | 3.04E−02 | ATP2C1, GLI3, TNFSF10, CANT1, EDNRA, MCL1, TLE1, CRABP1, GDF15, ANGPT1, BCAM, PENK |
| GO Biological Process | 1994 | Genes annotated by the GO term GO:0016020. Double layer of lipid molecules that encloses all cells, and, in eukaryotes, many organelles; may be a single or double lipid bilayer; also includes associated proteins. | 16 | 0.008 | 4.88E−07 | 1.14E−02 | SLC12A2, TNFSF10, GOLM1, BCAM, EDNRA, NCAM1, ECE1, KDELR2, LPHN2, ATP6V08B, ATP2C1, NDUFA2, MCL1, PRSS8, EPCAM, STEAP4 |
| GO Biological Process | 1670 | Genes annotated by the GO term GO:0044425. Any constituent part of a membrane, a double layer of lipid molecules that encloses all cells, and, in eukaryotes, many organelles; may be a single or double lipid bilayer; also includes associated proteins. | 13 | 0.0078 | 9.11E−06 | 1.06E−03 | SLC12A2, TNFSF10, GOLM1, BCAM, EDNRA, NCAM1, ECE1, KDELR2, LPHN2, ATP6V08, ATP2C1, NDUFA2, MCL1 |
| GO Biological Process | 1330 | Genes annotated by the GO term GO:0016021. Penetrating at least one phospholipid bilayer of a membrane. May also refer to the state of being buried in the bilayer with no exposure outside the bilayer. When used to describe a protein, indicates that all or part of the peptide sequence is embedded in the membrane. | 10 | 0.0075 | 1.43E−04 | 9.27E−03 | SLC12A2, TNFSF10, GOLM1, BCAM, EDNRA, NCAM1, ECE1, KDELR2, LPHN2, ATP6V0B |
| GO Cellular Component | 1348 | Genes annotated by the GO term GO:0031224. Located in a membrane such that some covalently attached portion of the gene product, for example part of a peptide sequence or some other covalently attached moiety such as a GPI anchor, spans or is embedded in one or both leaflets of the membrane. | 10 | 0.0074 | 159E−04 | 9.27E−03 | SLC12A2, TNFSF10, GOLM1, BCAM, EDNRA, NCAM1, ECE1, KDELR2, LPHN2, ATP6V08 |
| Hallmarks | 200 | Genes regulated by NF-kB in response to TNF [GeneID = 7124]. | 7 | 0.035 | 8.35E−08 | 4.18E−06 | MYC, SAT1, MLC1, HES1, PPP1R15A, TRIB1, CCNL1 |
| Hallmarks | 144 | Genes down-regulated in response to ultraviolet (UV) radiation. | 3 | 0.0208 | 2.30E−03 | 4.13E−02 | MYC, ATP2C1, LPHN2 |
| Hallmarks | 161 | Genes mediating programmed cell death (apoptosis) by activation of caspases. | 3 | 0.0186 | 3.16E−03 | 4.13E−02 | SAT1, MCL1, TNFSF10 |
| Hallmarks | 200 | Genes defining early response to estrogen. | 3 | 0.015 | 5.78E−03 | 4.13E−02 | MYC, HES1, CANT1 |
| Hallmarks | 200 | Genes up-regulated by STAT5 in response to IL2 stimulation. | 3 | 0.015 | 5.78E−03 | 4.13E−02 | MYCTNFSF10, PENK |
| Hallmarks | 200 | Genes defining inflammatory response. | 3 | 0.015 | 5.78E−03 | 4.13E−02 | MYC, ATP2C1, TNFSFIO |
|  |  | A subgroup of genes regulated by MYC - version 1 (vl). | 3 | 0.015 | 5.78E−03 | 4.13E−02 | MYC, EIF3D, RPS5 |
| Hallmarks | 200 | Genes down-regulated in comparison of unstimulated macrophage cells versus macrophage cells stimulated with LPS (TLR4 agonist) for 40 min. | 5 | 0.025 | 3.27E−05 | 1.04E−02 | CCNL1, PPP1R15A, MCL1, MYC, GDF15 |
| Hallmarks | 200 | Genes down-regulated in comparison of dendritic cells (DC) stimulated with Gardiquimod (TLR7 agonist) at 0.5 h versus those stimulated with Gardiquimod (TLR7 agonist) at 8 h. | 5 | 0.025 | 3.27E−05 | 1.04E−02 | CCNL1, ATP6V08B, SAT1, TNFSFIO, CFL2 |
| Immunologic Signatures | 200 | Genes down-regulated in comparison of control dendritic cells (DC) at 6 h versus those stimulated with CpG DNA (TLR9 agonist) at 6 h. | 5 | 0.025 | 3.27E−05 | 1.04E−02 | CCNL1, PPP1R15A, ATP6V0B, PENK, ATAD1 |
| Immunologic Signatures | 200 | Genes up-regulated in comparison of dendritic cells (DC) stimulated with IPS (TLR4 agonist) at 8 h versus DC cells stimulated with Pam3Csk4 (TLR1/2 agonist) at 8 h. | 5 | 0.025 | 3.27E−05 | 1.04E−02 | MCL1, SAT1, TNFSF10, ECE1, RAB25 |

| MSigDB Curated Data Sets | # Genes in Gene Set (K) | Description | # Genes in Overlap (k) | k/K | p-value | FDR q-value | Genes |
|---|---|---|---|---|---|---|---|
| Immunologic Signatures | 200 | Genes up-regulated in comparison of peripheral blood mononuclear cells (PBMC) from patients with type 1 diabetes at the time of the diagnosis versus those at 4 months later. | 5 | 0.025 | 3.27E−05 | 1.04E−02 | PPP1R15A, MCL1, SAT1, TRIB1, KDELR2 |
| Immunologic Signatures | 200 | Genes down-regulated in comparison of effector CD8 T cells at the peak expansion phase (day8) versus those at contraction (day 15) after LCMV-Armstrong infection in mice. | 5 | 0.025 | 3.27E−05 | 1.04E−02 | PPP1R15A, MYC, FAAH, RPS5, COX 16 |
| Immunologic Signatures | 200 | Genes down-regulated in regulatory T cell (Treg) treated with retinoic acid (tretinoin) (PubChem = 444795) versus conventional T cells. | 4 | 0.02 | 4.89E−04 | 2.67E−02 | GPM6B, GOLM1, CANT1, CRABP1 |
| Immunologic Signatures | 200 | Genes down-regulated in comparison of control microglia cells versus those 1 h after stimulation with IFNG |GeneID = 3458]. | 4 | 0.02 | 4.89E−04 | 2.67E−02 | CCNL1, TRIB1, UGDH, NDUFA2 |
| Immunologic Signatures | 200 | Genes down-regulated in comparison of regulatory T cell (Treg) from IL2RB [GeneID = 3560] deficient mice versus regulatory T cell (Treg) from wild type animals. | 4 | 0.02 | 4.89E−04 | 2.67E−02 | SAT1, PENK, OMD, EPCAM |
| Immunologic Signatures | 200 | Genes down-regulated in comparison of control CD4 [GeneID = 920] CD8 thymocytes versus those after stimulation with anti-Valpha2 antibodies. | 4 | 0.02 | 4.89E−04 | 2.67E−02 | GDF15, TNFS10, OMD, GLI3 |
| MIR | 64 | Targets of MicroRNA CTAGGAA/MIR-384 | 3 | 0.0469 | 2.19E−04 | 4.83E−02 | GPM6B, NCAM1, ATP2C1 |
| Oncogenic Signatures | 196 | Genes up-regulated in MCF-7 cells (breast cancer) positive for ESR1 [Gene ID = 2099] MCF-7 cells (breast cancer) stably over-expressing constitutively active MAP2K1 [Gene ID = 5604] gene. | 5 | 0.0255 | 2.97E−05 | 5.62E−03 | GDF15, SLC12A2, BCAM, LPHN2, GOLM1 |
| Oncogenic Signatures | 190 | Genes down-regulated in DLD1 cells (colon carcinoma) over-expressing LEF1 [Gene ID = 51176]. | 4 | 0.0211 | 4.03E−04 | 2.59E−02 | PRSS8, AP1M2, SLC44A4, RAB25 |
| Oncogenic Signatures | 191 | Genes up-regulated in MCF-7 cells (breast cancer) positive for ESR1 [Gene ID = 2099] and engineered to express ligand-activatable ERBB2 [Gene 10 = 2064]. | 4 | 0.0209 | 4.11E−04 | 2.59E−02 | GDF15, SLC12A2, BCAM, SAT1 |
| Oncogenic Signatures | 100 | Genes up-regulated in neurons. | 3 | 0.03 | 8.10E−04 | 3.83E−02 | PENK, MAL2, CPNE4 |
| Transcription Factor Targets | 234 | Genes with promoter regions [−2kb, 2kb] around transcription start site containing the motif HWAAATCAATAW which matches annotation for ONECUT1: one cut domain, family member 1 | 6 | 0.0256 | 4.45E−06 | 2.28E−03 | PDZRN4, TLE1, CNTN4, LPHN2, SLC12A2, TPP1 |
| Transcription Factor Targets | 256 | Genes with promoter regions [−2kb, 2kb] around transcription start site containing the motif GATTTAACATAA which matches annotation for CDC5L: CDC5 cell division cycle 5-like (S. pombe) | 6 | 0.0234 | 7.43E−06 | 2.28E−03 | PDZRN4, TLE1, ANGPT1, TNFSF10, SAT1, GLI3 |
| Transcription Factor Targets | 1296 | Genes with promoter regions [−2kb, 2kb] around transcription start site containing the motif TATAAA which matches annotation for TAF<br> TATA | 11 | 0.0085 | 2.17E−05 | 4.44E−03 | PDZRN4, CNTN4, ANGPT1, TNFSF10, MYC, GALNT7, PPP1R15A, CFL2, PENK, STEAP4, GDF15 |
| Transcription Factor Targets | 211 | Genes with promoter regions [−2kb, 2kb] around transcription start site containing the motif CNNTGACGTMA which matches annotation for CREB1: cAMP responsive element binding protein 1 | 5 | 0.0237 | 4.22E−05 | 5.19E−03 | PPP1R15A, TRIB1, GPM6B, RAB25, TPT1 |
| Transcription Factor Targets | 2485 | Genes with promoter regions [−2kb, 2kb] around transcription start site containing the motif CAGGTG which matches annotation for TCF3: transcription factor 3 (E2A immunoglobulin enhancer binding factors E12/E47) | 15 | 0.006 | 3.52E−05 | 5.19E−03 | TLE1, CNTN4, ANGPT1, MYC, GALNT7, TRIB1, GPM6B, RAB25, NCAM1, BCAM, ATP6V0B, UGDH, ERGIC1, EPCAM, APIM2 |
| Transcription Factor Targets | 1972 | Genes with promoter regions [−2kb, 2kb] around transcription start site containing the motif CTTTGT which matches annotation for LEF1: lymphoid enhancer-binding factor 1 | 8 | 0.0066 | 5.15E−05 | 5.28E−03 | PDZRN4, CNTN4, LPHN2, ANGPT1, TNFSF10, CFL2, |

-continued

| MSigDB Curated Data Sets | # Genes in Gene Set (K) | Description | # Genes in Overlap (k) | k/K | p-value | FDR q-value | Genes |
|---|---|---|---|---|---|---|---|
| Transcription Factor Targets | 231 | Genes with promoter regions [−2kb, 2kb] around transcription start site containing the motif CYYTGACGTCA which matches annotation for ATF1: activating transcription factor 1 | 5 | 0.0216 | 6.48E−05 | 5.70E−03 | TRIB1, GPM6B ANGPT1, CFL2, TRIB1, GPM6B, RAB25 |
| Transcription Factor Targets | 248 | Genes with promoter regions [−2kb, 2kb] around transcription start site containing the motif CBCTGACGTCANCS which matches annotation for ATF3: activating transcription factor 3 | 5 | 0.0202 | 9.06E−05 | 6.96E−03 | PPP1R15A, CFL2, TRIB1, GPM6B, RAB25 |
| Transcription Factor Targets | 258 | Genes with promoter regions [−2kb, 2kb] around transcription start site containing the motif CVTGACGYMABG which matches annotation for ATF4: activating transcription factor 4 (tax-responsive enhancer element B67) | 5 | 0.0194 | 1.09E−04 | 7.28E−03 | PPP1R15A, PENK, TRIB1, GPM6B, RAB25 |
| Transcription Factor Targets | 263 | Genes with promoter regions [−2kb, 2kb] around transcription start site containing the motif NSTGACGTAANN which matches annoation for CREB1: cAMP responsive element binding protein 1 | 5 | 0.019 | 1.19E−04 | 7.28E−03 | PPP1R15A, PENK, TRIB1 GPMGB, RAB25 |

TABLE 17

GeneGo Enrichment Analysis of the 29 gene signature

| GO | Enrichment Set | p-value | FDR | In Data | Network Objects from Active Data |
|---|---|---|---|---|---|
| Processes | humoral immune response mediated by circulating immunoglobulin | 7.58E−16 | 1.10E−12 | 10 | C1qa, C1qb, HLA-DRB3, HLA-DRB, MHC class II beta chain, HLA-DRB1, C1qc, C1s, C1q, C1 inhibitor |
| | immunoglobulin mediated immune response | 4.49E−14 | 2.60E−11 | | |
| | B cell mediated immunity | 5.39E−14 | 2.60E−11 | | |
| | lymphocyte mediated immunity | 1.03E−12 | 3.73E−10 | | |
| | adaptive immune response based on somatic recombination of immune receptors built from immunoglobulin superfamily domains | 1.89E−12 | 5.46E−10 | | |
| | humoral immune response | 4.05E−12 | 9.77E−10 | | |
| | leukocyte mediated immunity | 1.05E−11 | 1.90E−09 | | |
| | activation of immune response | 5.81E−09 | 8.41E−07 | | |
| | adaptive immune response | 1.05E−11 | 1.90E−09 | | |
| | complement activation, classical pathway | 5.53E−09 | 8.41E−07 | 6 | C1qa, C1qb, C1qc, C1s, C1q, C1 inhibitor |
| Molecular Functions | calcium ion binding | 1.09E−03 | 2.35E−02 | 6 | SULF1, LTBP2, Thrombospondin 2, LTBP3, C1s, Fibulin-5 |
| | extracellular matrix structural constituent | 6.27E−06 | 9.47E−04 | 4 | COL1A1, Biglycan, Lumican, Prolargin |
| | glycosaminoglycan binding | 3.80E−04 | 1.77E−02 | 4 | LTBP2, Biglycan, Thrombospondin 2, Prolargin |
| | growth factor binding | 5.51E−05 | 4.16E−03 | 4 | COL1A1, LTBP2, GRP75, LTBP3 |
| | heparin binding | 2.34E−03 | 4.41E−02 | 3 | LTBP2, Thrombospondin 2, Prolargin |
| | metalloenzyme activator activity | 2.92E−03 | 4.91E−02 | 1 | SFRP2 |
| | protein binding | 8.52E−04 | 2.35E−02 | 24 | SFRP4, C1qa, SFRP2, COL1A1, C1qb, LTBP2, ITGA11, B-ind1, AEBP1, HLA-DRB3, CD166, MAL2, GRP75, FCGR2C, Claudin-8, HLA-DRB1, Thrombospondin 2, LTBP3, C1qc, C1s, Fibulin-5, C1 inhibitor, Tensin 3, Lumican |
| | structural molecule activity | 4.06E−03 | 5.32E−02 | 5 | COL1A1, Biglycan, Claudin-8, Lumican, Prolargin |
| | Wnt-activated receptor activity | 4.69E−04 | 1.77E−02 | 2 | SFRP4, SFRP2 |
| | Wnt-protein binding | 9.36E−04 | 2.35E−02 | 2 | SFRP4, SFRP2 |
| Localizations | extracellular matrix | 1.92E−09 | 2.88E−07 | 10 | SFRP2, COL1A1, LTBP2, Biglycan, AEBP1, Thrombospondin 2, LTBP3, Fibulin-5, Lumican, Prolargin |
| | extracellular region part | 6.80E−09 | 5.10E−07 | 22 | SFRP4, C1qa, SFRP2, SULF1, COL1A1, C1qb, LTBP2, Tmem205, Biglycan, AEBP1, CD166, MAL2, GRP75, HLA-DRB1, Thrombospondin 2, LTBP3, C1qc, C1s, Fibulin-5, C1 inhibitor, Lumican, Prolargin |
| | extracellular region | 1.43E−08 | 7.16E−07 | 24 | SFRP4, C1qa, SFRP2, SULF1, COL1A1, C1qb, LTBP2, Tmem205, Biglycan, AEBP1, CD166, |

TABLE 17-continued

GeneGo Enrichment Analysis of the 29 gene signature

| GO | Enrichment Set | p-value | FDR | In Data | Network Objects from Active Data |
|---|---|---|---|---|---|
| | extracellular space | 2.85E−08 | 1.07E−06 | 14 | MAL2, GRP75, HLA-DRB1, Thrombospondin 2, LTBP3, C1qc, C1q, C1s, Biglycan proteoglycan, Fibulin-5, C1 inhibitor, Lumican, Prolargin SFRP4, C1qa, SFRP2, SULF1, COL1A1, C1qb, LTBP2, AEBP1, HLA-DRB1, C1qc, C1s, Fibulin-5, C1 inhibitor, Lumican |
| | extracellular vesicle | 2.89E−07 | 4.10E−06 | 17 | C1qa, C1qb, LTBP2, Tmem205, Biglycan, AEBP1, CD166, MAL2, GRP75, HLA-DRB1, LTBP3, C1qc, C1s, Fibulin-5, C1 inhibitor, Lumican, Prolargin |
| | extracellular vesicular exosome | 2.89E−07 | 4.10E−06 | | |
| | extracellular organelle | 3.00E−07 | 4.10E−06 | | |
| | membrane-bounded vesicle | 5.59E−08 | 1.68E−06 | 20 | C1qa, COL1A1, C1qb, LTBP2, Tmem205, Biglycan, AEBP1, HLA-DRB3, CD166, MAL2, GRP75, HLA-DRB1, Thrombospondin 2, LTBP3, C1qc, C1s, Fibulin-5, C1 inhibitor, Lumican, Prolargin |
| | vesicle | 1.01E−07 | 2.52E−06 | | |
| | proteinaceous extracellular matrix | 1.54E−07 | 3.30E−06 | 8 | COL1A1, LTBP2, Biglycan, Thrombospondin 2, LTBP3, Fibulin-5, Lumican, Prolargin |

TABLE 18

MSigDB characterization of the GO processes and functions of the 29 gene signature.

| Gene Set Name | MSigDB data sets | # Genes in Gene Set (K) | Description | # Genes in Overlap (k) | k/K | p-value | FDR q-value | Genes |
|---|---|---|---|---|---|---|---|---|
| BIOCARTA_COMP_PATHWAY | Biocarta | 19 | Complement Pathway | 4 | 0.2105 | 4.92E-10 | 5.34E-08 | C1QA, C1QB, C1QC, C1S |
| BIOCARTA_CLASSIC_PATHWAY | Biocarta | 14 | Classical Complement Pathway | 4 | 0.2857 | 1.27E-10 | 2.76E-08 | C1QA, C1QB, C1QC, C1S |
| NABA_MATRISOME_ASSOCIATED | Canonical Pathways | 753 | Ensemble of genes encoding ECM-associated proteins including ECM-affiliated proteins, ECM regulators and secreted factors | 7 | 0.0093 | 3.52E-07 | 4.68E-05 | C1QA, C1QB, C1QC, SERPING, SFRP4, SFRP2, SULF1 |
| NABA_MATRISOME | Canonical Pathways | 1028 | Ensemble of genes encoding extracellular matrix and extracellular matrix-associated proteins | 15 | 0.0146 | 9.20E-18 | 1.22E-14 | LUM, PRELP, BGN, THBS2, FBLN5, AEBP1, LTBP2, COL1A1, C1QA, C1QB, C1QC, SERPING, SFRP4, SFRP2, SULF1 |
| NABA_CORE_MATRISOME | Canonical Pathways | 275 | Ensemble of genes encoding core extracellular matrix including ECM glycoproteins, collagens and proteoglycans | 8 | 0.0291 | 5.72E-12 | 3.80E-09 | PRELP, BGN, THBS2, FBLN5, AEBP1, LTBP2, COL1A1 |
| KEGG_SYSTEMIC_LUPUS_ERYTHEMATOSUS | Canonical Pathways | 140 | Systemic lupus erythematosus | 6 | 0.0429 | 3.22E-10 | 7.13E-08 | C1QA, C1QB, C1QC, C1S, HLA-DRB3, FCGR2C |
| KEGG_COMPLEMENT_AND_COAGULATION_CASCADES | Canonical Pathways | 69 | Complement and coagulation cascades | 5 | 0.0725 | 7.60E-10 | 1.26E-07 | C1QA, C1QB, C1QC, |

TABLE 18-continued

MSigDB characterization of the GO processes and functions of the 29 gene signature.

| Gene Set Name | MSigDB data sets | # Genes in Gene Set (K) | Description | # Genes in Overlap (k) | k/K | p-value | FDR q-value | Genes |
|---|---|---|---|---|---|---|---|---|
| REACTOME_COMPLEMENT_CASCADE | Canonical Pathways | 32 | Genes involved in Complement cascade | 4 | 0.125 | 4.54E-09 | 6.71E-07 | SERPING1, C1S C1QA, C1QB, C1QC, C1S |
| BIOCARTA_COMP_PATHWAY | Canonical Pathways | 19 | Complement Pathway | 4 | 0.2105 | 4.92E-10 | 9.35E-08 | C1QA, C1QB, C1QC, C1S |
| REACTOME_INITIAL_TRIGGERING_OF_COMPLEMENT | Canonical Pathways | 16 | Genes involved in Initial triggering of complement | 4 | 0.25 | 2.31E-10 | 6.16E-08 | C1QA, C1QB, C1QC, C1S |
| BIOCARTA_CLASSIC_PATHWAY | Canonical Pathways | 14 | Classical Complement Pathway | 4 | 0.2857 | 1.27E-10 | 4.24E-08 | C1QA, C1QB, C1QC, C1S |
| REACTOME_CREATION_OF_C4_AND_C2_ACTIVATORS | Canonical Pathways | 10 | Genes involved in Creation of C4 and C2 activators | 4 | 0.4 | 2.68E-11 | 1.19E-08 | C1QA, C1QB, C1QC, C1S |
| SCHUETZ_BREAST_CANCER_DUCTAL_INVASIVE_UP | Chemical and Genetic Perturbations | 351 | Genes up-regulated in invasive ductal carcinoma (IDC) relative to ductal carcinoma in situ (DCIS, non-invasive) | 11 | 0.0313 | 1.35E-16 | 4.58E-13 | LUM, COL1A1, SULF1, AEBP1, THBS2, BGN, C1S, C1QA, C1QB, SERPING, TNS3 |
| BOQUEST_STEM_CELL_UP | Chemical and Genetic Perturbations | 260 | Genes up-regulated in freshly isolated CD31- [GeneID = 5175] (stromal stem cells from adipose tissue) versus the CD31+ (non-stem) counterparts. | 9 | 0.0346 | 4.69E-14 | 2.27E-11 | LUM, COL1A1, AEBP1, THBS2, C1S, SFRP4, PRELP, LTBP2, FBLN5 |
| RODWELL_AGING_KIDNEY_NO_BLOOD_UP | Chemical and Genetic Perturbations | 222 | Genes whose expression increases with age in normal kidney, excluding those with higher expression in blood. | 9 | 0.0405 | 1.12E-14 | 7.61E-12 | LUM, COL1A1, AEBP1, C1S, C1QA, C1QB, |

TABLE 18-continued

MSigDB characterization of the GO processes and functions of the 29 gene signature.

| Gene Set Name | MSigDB data sets | # Genes in Gene Set (K) | Description | # Genes in Overlap (k) | k/K | p-value | FDR q-value | Genes |
|---|---|---|---|---|---|---|---|---|
| PICCALUGA_ANGIOIMMUNOBLASTIC_LYMPHOMA_UP | Chemical and Genetic Perturbations | 205 | Up-regulated genes in angioimmunoblastic lymphoma (AILT) compared to normal T lymphocytes. | 9 | 0.0439 | 5.43E-15 | 6.15E-12 | SERPING, MOXD1, C1QC LUM, COL1A1, SULF1, C1S, C1QA, C1QB, SERPING, TNS3, C1QC |
| VECCHI_GASTRIC_CANCER_ADVANCED_VS_EARLY_UP | Chemical and Genetic Perturbations | 175 | Up-regulated genes distinguishing between two subtypes of gastric cancer: advanced (AGC) and early (EGC). | 8 | 0.0457 | 1.51E-13 | 6.40E-11 | SULF1, THBS2, BGN, MOXD1, SFRP4, PRELP, LTBP2, SFRP2 |
| CHIANG_LIVER_CANCER_SUBCLASS_CTNNB1_DN | Chemical and Genetic Perturbations | 170 | Top 200 marker genes down-regulated in the 'CTNNB1' subclass of hepatocellular carcinoma (HCC); characterized by activated CTNNB1 [GeneID = 1499]. | 9 | 0.0529 | 9.84E-16 | 1.67E-12 | COL1A1, SULF1, AEBP1, THBS2, BGN, MOXD1, CD52, MAL2 |
| TURASHVILI_BREAST_LOBULAR_CARCINOMA_VS_LOBULAR_NORMAL_DN | Chemical and Genetic Perturbations | 74 | Genes down-regulated in lobular carcinoma vs normal lobular breast cells. | 6 | 0.0811 | 6.53E-12 | 2.22E-09 | COL1A1, AEBP1, THBS2, BGN, SFRP4, SFRP2 |
| TURASHVILI_BREAST_LOBULAR_CARCINOMA_VS_DUCTAL_NORMAL_UP | Chemical and Genetic Perturbations | 69 | Genes up-regulated in lobular carcinoma vs normal ductal breast cells. | 6 | 0.087 | 4.24E-12 | 1.60E-09 | COL1A1, SULF1, AEBP1, THBS2, BGN, SFRP2 |
| NAKAYAMA_SOFT_TISSUE_TUMORS_PCA1_UP | Chemical and Genetic Perturbations | 76 | Top 100 probe sets contributing to the positive side of the 1st principal component; predominantly associated with spindle cell and | 7 | 0.0921 | 3.86E-14 | 2.18E-11 | LUM, THBS2, C1S, C1QA, C1QB, CD52, FCGR2C |

TABLE 18-continued

MSigDB characterization of the GO processes and functions of the 29 gene signature.

| Gene Set Name | MSigDB data sets | # Genes in Gene Set (K) | Description | # Genes in Overlap (k) | k/K | p-value | FDR q-value | Genes |
|---|---|---|---|---|---|---|---|---|
| ANASTASSIOU_CANCER_MESENCHYMAL_TRANSITION_SIGNATURE | Chemical and Genetic Perturbations | 64 | Genes in the 'mesenchymal transition signature' common to all invasive cancer types. pleomorphic sarcoma samples. | 7 | 0.1094 | 1.10E-14 | 7.61E-12 | LUM, COL1A1, SULF1, AEBP1, THBS2, BGN, SFRP4 |
| EXTRACELLULAR_SPACE | GO Cellular Component | 245 | Genes annotated by the GO term GO:0005615. That part of a multicellular organism outside the cells proper, usually taken to be outside the plasma membranes, and occupied by fluid. | 3 | 0.0122 | 4.94E-04 | 2.30E-02 | C1QA, C1QB, SFRP4 |
| EXTRACELLULAR_REGION | GO Cellular Component | 447 | Genes annotated by the GO term GO:0005576. The space external to the outermost structure of a cell. For cells without external protective or external encapsulating structures this refers to space outside of the plasma membrane. This term covers the host cell environment outside an intracellular parasite. | 7 | 0.0157 | 1.02E-08 | 1.19E-06 | FBLN5, LUM, LTBP2, PRELP, C1QA, C1QB, SFRP4 |
| EXTRACELLULAR_REGION_PART | GO Cellular Component | 338 | Genes annotated by the GO term GO:0044421. Any constituent part of the extracellular region, the space external to the outermost structure of a cell. For cells without external protective or external encapsulating structures this refers | 7 | 0.0207 | 1.49E-09 | 3.46E-07 | FBLN5, LUM, LTBP2, PRELP, C1QA, C1QB, SFRP4 |

TABLE 18-continued

MSigDB characterization of the GO processes and functions of the 29 gene signature.

| Gene Set Name | MSigDB data sets | # Genes in Gene Set (K) | Description | # Genes in Overlap (k) | k/K | p-value | FDR q-value | Genes |
|---|---|---|---|---|---|---|---|---|
| | | | to space outside of the plasma membrane. This term covers constituent parts of the host cell environment outside an intracellular parasite. | | | | | |
| CELL_SURFACE | GO Cellular Component | 79 | Genes annotated by the GO term GO:0009986. The external part of the cell wall and/or plasma membrane. | 2 | 0.0253 | 1.15E-03 | 4.46E-02 | HSPA9, SULF1 |
| EXTRACELLULAR_MATRIX | GO Cellular Component | 100 | Genes annotated by the GO term GO:0031012. A structure lying external to one or more cells, which provides structural support for cells or tissues; may be completely external to the cell (as in animals) or be part of the cell (as in plants). | 4 | 0.04 | 4.81E-07 | 2.80E-05 | FBLN5, LUM, LTBP2, PRELP |
| PROTEINACEOUS_EXTRACELLULAR_MATRIX | GO Cellular Component | 98 | Genes annotated by the GO term GO:0005578. A layer consisting mainly of proteins (especially collagen) and glycosaminoglycans (mostly as proteoglycans) that forms a sheet underlying or overlying cells such as endothelial and epithelial cells. The proteins are secreted by cells in the vicinity. | 4 | 0.0408 | 4.43E-07 | 2.80E-05 | FBLN5, LUM, LTBP2, PRELP |
| COLLAGEN_BINDING | GO Molecular Function | 14 | Genes annotated by the GO term GO:0005518. Interacting selectively with collagen, a group | 2 | 0.1429 | 3.48E-05 | 1.38E-02 | ITGA11, LUM |

TABLE 18-continued

MSigDB characterization of the GO processes and functions of the 29 gene signature.

| Gene Set Name | MSigDB data sets | # Genes in Gene Set (K) | Description | # Genes in Overlap (k) | k/K | p-value | FDR q-value | Genes |
|---|---|---|---|---|---|---|---|---|
| | | | of fibrous proteins of very high tensile strength that form the main component of connective tissue in animals. Collagen is highly enriched in glycine (some regions are 33% glycine) and proline, occurring predominantly as 3-hydroxyproline (about 20%). | | | | | |
| HALLMARK_INTERFERON_GAMMA_RESPONSE | Hallmark | 200 | Genes up-regulated in response to IFNG [GeneID = 3458]. | 2 | 0.01 | 7.08E-03 | 4.43E-02 | C1S, SERPING1 |
| HALLMARK_MYOGENESIS | Hallmark | 200 | Genes involved in development of skeletal muscle (myogenesis). | 2 | 0.01 | 7.08E-03 | 4.43E-02 | FBLN5, AEBP1 |
| HALLMARK_APOPTOSIS | Hallmark | 161 | Genes mediating programmed cell death (apoptosis) by activation of caspases. | 2 | 0.0124 | 4.65E-03 | 3.88E-02 | BGN, LUM |
| HALLMARK_UV_RESPONSE_DN | Hallmark | 144 | Genes down-regulated in response to ultraviolet (UV) radiation. | 2 | 0.0139 | 3.74E-03 | 3.74E-02 | COL1A1, GBLN5 |
| HALLMARK_COMPLEMENT | Hallmark | 200 | Genes encoding components of the complement system, which is part of the innate immune system. | 4 | 0.02 | 7.59E-06 | 1.90E-04 | C1S, SERPING, C1QA, C1QC |
| HALLMARK_COAGULATION | Hallmark | 138 | Genes encoding components of blood coagulation system; also up-regulated in platelets. | 3 | 0.0217 | 9.14E-05 | 1.52E-03 | C1S, SERPING, C1QA |
| HALLMARK_CHOLESTEROL_HOMEOSTASIS | Hallmark | 74 | Genes involved in cholesterol homeostasis. | 2 | 0.027 | 1.01E-03 | 1.26E-02 | ALCAM, MAL2 |
| HALLMARK_EPITHELIAL_MESENCHYMAL_TRANSITION | Hallmark | 200 | Genes defining epithelial-mesenchymal transition, as in wound healing, | 6 | 0.03 | 2.75E-09 | 1.38E-07 | COL1A1, FBLN5, BGN, LIM, SFRP4, |

TABLE 18-continued

MSigDB characterization of the GO processes and functions of the 29 gene signature.

| Gene Set Name | MSigDB data sets | # Genes in Gene Set (K) | Description | # Genes in Overlap (k) | k/K | p-value | FDR q-value | Genes |
|---|---|---|---|---|---|---|---|---|
| GSE10325_LUPUS_CD4_TCELL_VS_LUPUS_BCELL_DN | Immunologic Signatures | 200 | fibrosis and metastasis. Genes down-regulated in comparison of systemic lupus erythematosus CD4 [GeneID = 920] T cells versus systemic lupus erythematosus B cells. | 3 | 0.015 | 2.73E-04 | 2.74E-02 | THBS2 TNS3, FCGR2, ALCAM |
| GSE17721_0.5H_VS_24H_PAM3CSK4_BMDM_DN | Immunologic Signatures | 200 | Genes down-regulated in comparison of dendritic cells (DC) stimulated with Pam3Csk4 (TLR1/2 agonist) at 0.5 h versus those stimulated at 24 h. | 3 | 0.015 | 2.73E-04 | 2.74E-02 | C1S, ALCAM, HSPA9 |
| GSE17721_ALL_VS_24H_PAM3CSK4_BMDM_DN | Immunologic Signatures | 200 | Genes down-regulated in comparison of dendritic cells (DC) stimulated with Pam3Csk4 (TLR1/2 agonist) at all time points versus those stimulated with Pam3Csk4 (TLR1/2 agonist) at 24 h only. | 3 | 0.015 | 2.73E-04 | 2.74E-02 | C1S, CD52, PTPLAD1 |
| GSE20715_WT_VS_TLR4_KO_6H_OZONE_LUNG_DN | Immunologic Signatures | 200 | Genes down-regulated in comparison of lung tissue from wild type mice subjected to ozone for 6 h vs that from TLR4 [GeneId = 7099] deficient animal subjected to ozone for 6 h. | 3 | 0.015 | 2.73E-04 | 2.74E-02 | PTPLAD1, CLDN8, AEBP1 |
| GSE22886_DC_VS_MONOCYTE_UP | Immunologic Signatures | 200 | Genes up-regulated in comparison of dendritic cells (DC) versus monocytes. | 3 | 0.015 | 2.73E-04 | 2.74E-02 | C1QA, C1QB, PTPLAD1 |
| GSE24634_IL4_VS_CTRL_TREATED_NAIVE_CD4_TCELL_DAY10_DN | Immunologic Signatures | 200 | Genes down-regulated in | 3 | 0.015 | 2.73E-04 | 2.74E-02 | TNS3, FCGR2C, |

TABLE 18-continued

MSigDB characterization of the GO processes and functions of the 29 gene signature.

| Gene Set Name | MSigDB data sets | # Genes in Gene Set (K) | Description | # Genes in Overlap (k) | k/K | p-value | FDR q-value | Genes |
|---|---|---|---|---|---|---|---|---|
| | | | comparison of CD25-T cells treated with IL4 [GeneID = 3565] at day 10 versus untreated CD25- T cells at day 10. | | | | | SERPING1 |
| GSE24634_TEFF_VS_TCONV_DAY10_IN_CULTURE_DN | Immunologic Signatures | 200 | Genes down-regulated in comparison of untreated CD25+ T effector cells at day 10 versus untreated CD25- T cells at day 10. | 3 | 0.015 | 2.73E-04 | 2.74E-02 | C1QA, TNS3, FCGR2C |
| GSE13485_CTRL_VS_DAY3_YF17D_VACCINE_PBMC_DN | Immunologic Signatures | 200 | Genes down-regulated in comparison of unstimulated peripheral blood mononuclear cells (PBMC) versus PBMC 3 days after stimulation with YF17D vaccine. | 4 | 0.02 | 7.59E-06 | 4.83E-03 | C1QA, TNS3, C1QB, SERPING1 |
| GSE3982_DC_VS_TH1_UP | Immunologic Signatures | 200 | Genes up-regulated in comparison of dendritic cells (DC) versus Th1 cells. | 4 | 0.02 | 7.59E-06 | 4.83E-03 | C1QA, FCGR2, ALCAM, CD52 |
| GSE24634_TREG_VS_TCONV_POST_DAY10_IL4_CONVERSION_DN | Immunologic Signatures | 200 | Genes down-regulated in comparison of CD25+ regulatory T cell (Treg) treated with IL4 [GeneID = 3565] at day 10 versus CD25- T cells treated with IL4 [GeneID = 3565] at 10 h. | | | | | |
| KEGG_FOCAL_ADHESION | KEGG | 201 | Focal adhesion | 3 | 0.0149 | 2.77E-04 | 8.59E-03 | ITGA11, THBS2, COL1A1 |
| KEGG_CELL_ADHESION_MOLECULES_CAMS | KEGG | 134 | Cell adhesion molecules (CAMs) | 3 | 0.0224 | 8.38E-05 | 3.12E-03 | HLA-DRB3, CLDN8, ALCAM |
| KEGG_LEISHMANIA_INFECTION | KEGG | 72 | Leishmania infection | 2 | 0.0278 | 9.56E-04 | 2.54E-02 | HLA-DRB3, FCGR2C |

TABLE 18-continued

MSigDB characterization of the GO processes and functions of the 29 gene signature.

| Gene Set Name | MSigDB data sets | # Genes in Gene Set (K) | Description | # Genes in Overlap (k) | k/K | p-value | FDR q-value | Genes |
|---|---|---|---|---|---|---|---|---|
| KEGG_ECM_RECEPTOR_INTERACTION | KEGG | 84 | ECM-receptor interaction | 3 | 0.0357 | 2.08E-05 | 9.67E-04 | ITGA11, THBS2, COL1A1 |
| KEGG_SYSTEMIC_LUPUS_ERYTHEMATOSUS | KEGG | 140 | Systemic lupus erythematosus | 6 | 0.0429 | 3.22E-10 | 5.98E-08 | C1QA, C1QB, C1QC, C1S, HLA-DRB3, HCGR2C |
| KEGG_COMPLEMENT_AND_COAGULATION_CASCADES | KEGG | 69 | Complement and coagulation cascades | 5 | 0.0725 | 7.60E-10 | 7.07E-08 | C1QA, C1QB, C1QC, C1S, SERPING1 |
| KEGG_PRION_DISEASES | KEGG | 35 | Prion diseases | 3 | 0.0857 | 1.46E-06 | 9.04E-05 | C1QA, C1QB, C1QC |
| RB_P107_DN.V1_UP | Oncogenic Signatures | 140 | Genes up-regulated in primary keratinocytes from RB1 and RBL1 [Gene ID = 5925, 5933] skin specific knockout mice. | 3 | 0.0214 | 9.54E-05 | 4.51E-03 | FBLN5, COL1A1, BGN |
| SNF5_DN.V1_UP | Oncogenic Signatures | 177 | Genes up-regulated in MEF cells (embryonic fibroblasts) with knockout of SNF5 [Gene ID = 6598] gene. | 4 | 0.0226 | 4.69E-06 | 2.95E-04 | C1QC, C1S, SFRP2, CD52 |
| ESC_V6.5_UP_EARLY.V1_DN | Oncogenic Signatures | 172 | Genes down-regulated during early stages of differentiation of embryoid bodies from V6.5 embryonic stem cells. | 4 | 0.0233 | 4.18E-06 | 2.95E-04 | AEBP1, COL1A1, BGN, ALCAM |
| CAHOY_ASTROGLIAL | Oncogenic Signatures | 100 | Genes up-regulated in astroglia cells. | 4 | 0.04 | 4.81E-07 | 9.08E-05 | AEBP1, FBLN5, SERPING1, LTBP2 |
| REACTOME_IMMUNE_SYSTEM | Reactome | 933 | Genes involved in Immune System | 5 | 0.0054 | 2.70E-04 | 2.02E-02 | C1QA, C1QB, C1QC, C1S |
| REACTOME_METABOLISM_OF_CARBOHYDRATES | Reactome | 247 | Genes involved in Metabolism of carbohydrates | 3 | 0.0121 | 5.05E-04 | 3.41E-02 | LUM, PRELP, BGN |

TABLE 18-continued

MSigDB characterization of the GO processes and functions of the 29 gene signature.

| Gene Set Name | MSigDB data sets | # Genes in Gene Set (K) | Description | # Genes in Overlap (k) | k/K | p-value | FDR q-value | Genes |
|---|---|---|---|---|---|---|---|---|
| REACTOME_INNATE_IMMUNE_SYSTEM | Reactome | 279 | Genes involved in Innate Immune System | 4 | 0.0143 | 2.80E-05 | 3.78E-03 | C1QA, C1QB, C1QC, C1S |
| REACTOME_GLYCOSAMINOGLYCAN_METABOLISM | Reactome | 111 | Genes involved in Glycosaminoglycan metabolism | 3 | 0.027 | 4.79E-05 | 5.38E-03 | LUM, PRELP, BGN |
| REACTOME_KERATAN_SULFATE_KERATIN_METABOLISM | Reactome | 30 | Genes involved in Keratan sulfate/keratin metabolism | 2 | 0.0667 | 1.65E-04 | 1.39E-02 | LUM, PRELP |
| REACTOME_KERATAN_SULFATE_BIOSYNTHESIS | Reactome | 26 | Genes involved in Keratan sulfate biosynthesis | 2 | 0.0769 | 1.24E-04 | 1.19E-02 | LUM, PRELP |
| REACTOME_COMPLEMENT_CASCADE | Reactome | 32 | Genes involved in Complement cascade | 4 | 0.125 | 4.54E-09 | 1.02E-06 | C1QA, C1QB, C1QC, C1S |
| REACTOME_KERATAN_SULFATE_DEGRADATION | Reactome | 11 | Genes involved in Keratan sulfate degradation | 2 | 0.1818 | 2.11E-05 | 3.55E-03 | PRELP, BGN |
| REACTOME_INITIAL_TRIGGERING_OF_COMPLEMENT | Reactome | 16 | Genes involved in Initial triggering of complement | 4 | 0.25 | 2.31E-10 | 7.80E-08 | C1QA, C1QB, C1QC, C1S |
| REACTOME_CREATION_OF_C4_AND_C2_ACTIVATORS | Reactome | 10 | Genes involved in Creation of C4 and C2 activators | 4 | 0.4 | 2.68E-11 | 1.80E-08 | C1QA, C1QB, C1QC, C1S |
| GGGAGGRR_V$MAZ_Q6 | Transcription Factor Targets | 2274 | Genes with promoter regions [-2 kb, 2 kb] around transcription start site containing the motif GGGAGGRR which matches annotation for MAZ:MYC-associated zinc finger protein (purine-binding transcription factor) | 8 | 0.0035 | 5.98E-05 | 9.20E-03 | ITGA11, PRELP, COL1A1, C1QA, ALCAM, C1QC, SFRP2, FCGR2C |
| CAGGTG_V$E12_Q6 | Transcription Factor Targets | 2485 | Genes with promoter regions [-2 kb, 2 kb] around transcription start site containing the motif CAGGTG which matches annotation for TCF3: | 10 | 0.004 | 1.63E-06 | 1.00E-03 | ITGA11, SULF1, CLDN8, LTBP2, PRELP, COL1A1, C1QA, |

TABLE 18-continued

MSigDB characterization of the GO processes and functions of the 29 gene signature.

| Gene Set Name | MSigDB data sets | # Genes in Gene Set (K) | Description | # Genes in Overlap (k) | k/K | p-value | FDR q-value | Genes |
|---|---|---|---|---|---|---|---|---|
| | | | transcription factor 3 (E2A immunoglobulin enhancer binding factor E12/E47) | | | | | ALCAM, C1QC, LUM |
| TTANTCA_UNKNOWN | Transcription Factor Targets | 952 | Genes with promoter regions [−2 kb, 2 kb] around transcription start site containing motif TTANTCA. Motif does not match any known transcription factor | 6 | 0.0063 | 2.46E-05 | 5.04E-03 | ITGA11, SULF1, CLDN8, LTBP2, SFRP4, MAL2 |
| WTTGKCTG_UNKNOWN | Transcription Factor Targets | 516 | Genes with promoter regions [−2 kb, 2 kb] around transcription start site containing motif WTTGKCTG. Motif does not match any known transcription factor | 4 | 0.0078 | 2.99E-04 | 3.67E-02 | PRELP, COL1A1, SERPING, C1S |
| V$MYOD_01 | Transcription Factor Targets | 265 | Genes with promoter regions [−2 kb, 2 kb] around transcription start site containing the motif SRACAGGTGKYG which matches annotation for MYOD1: myogenic differentiation 1 | 3 | 0.0113 | 6.20E-04 | 3.81E-02 | PRELP, ALCAM, C1QC |
| V$CP2_01 | Transcription Factor Targets | 260 | Genes with promoter regions [−2 kb, 2 kb] around transcription start site containing the motif GCHCDAMCCAG which matches annotation for TFCP2: transcription factor CP2 | 3 | 0.0115 | 5.87E-04 | 3.81E-02 | PRELP, COL1A1, C12orf51 |
| V$CEBPB_02 | Transcription Factor Targets | 258 | Genes with promoter regions [−2 kb, 2 kb] around transcription start site containing the motif NKNTTGCNYAAYNN which matches annotation for CEBPB: | 3 | 0.0116 | 5.74E-04 | 3.81E-02 | ITGA11, SULF1, C12orf51 |

TABLE 18-continued

MSigDB characterization of the GO processes and functions of the 29 gene signature.

| Gene Set Name | MSigDB data sets | # Genes in Gene Set (K) | Description | # Genes in Overlap (k) | k/K | p-value | FDR q-value | Genes |
|---|---|---|---|---|---|---|---|---|
| V$SREBP_Q3 | Transcription Factor Targets | 258 | CCAAT/enhancer binding protein (C/EBP), beta Genes with promoter regions [−2 kb, 2 kb] around transcription start site containing motif VNNVTCACCCYA. Motif does not match any known transcription factor | 3 | 0.0116 | 5.74E-04 | 3.81E-02 | PRELP, LUM, HSPA9 |
| V$TAL1BETAE47_01 | Transcription Factor Targets | 248 | Genes with promoter regions [−2 kb, 2 kb] around transcription start site containing the motif NNNAACAGATGKTNNN which matches annotation for TAL1: T-cell acute lymphocytic leukemia 1<br> TCF3: transcription factor 3 (E2A immunoglobulin enhancer binding factors E12/E47) | 3 | 0.0121 | 5.11E-04 | 3.81E-02 | SULF1, C1QA, SERPING1 |
| V$CEBPA_01 | Transcription Factor Targets | 244 | Genes with promoter regions [−2 kb, 2 kb] around transcription start site containing the motif NNATTRCNNAANNN which matches annotation for CEBPA:CCAAT/ enhancer binding protein (C/EBP), alpha | 4 | 0.0164 | 1.66E-05 | 5.04E-03 | ITGA11, SULF1, CLDN8 |

Figure 6A:
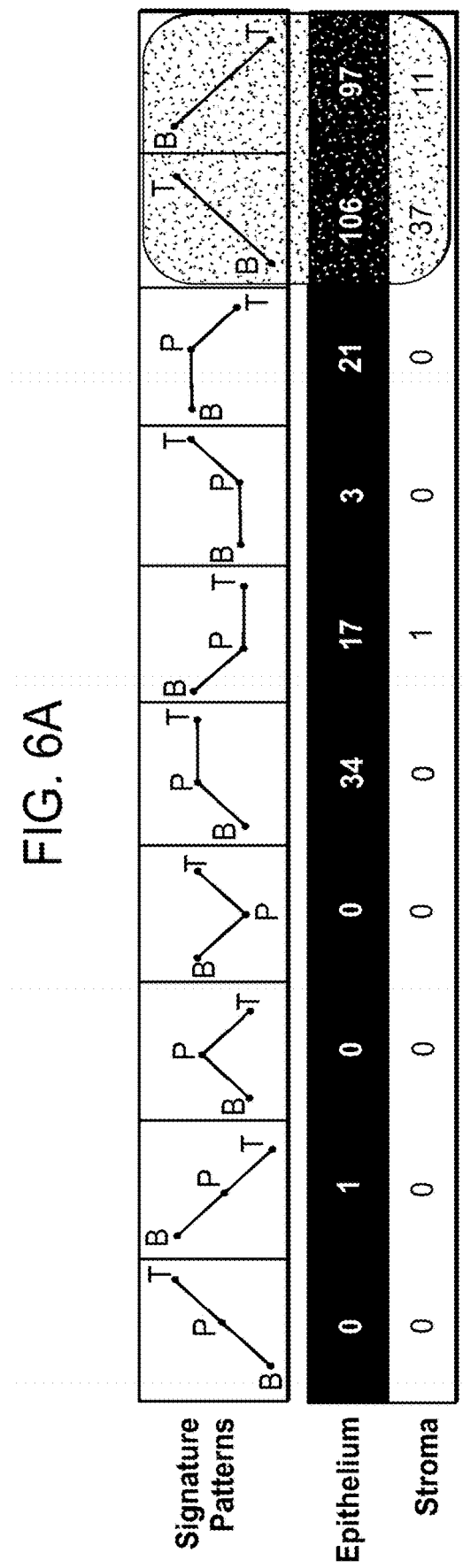
FIG. 6A is a diagram showing 10 profiling trends that are possible to observe within the epithelial and stromal compartment comparisons with tabulated numbers of those that passed 1.5 fold change criteria and had an adjusted p-value <0.05. Not all possible trends were observed. In particular a small number of genes trending through PIN within either the epithelium or the stromal compartment were observed. Interstromal differences were primarily observed between tumor adjacent stroma (sT) and benign adjacent stroma (sB). PIN adjacent stroma (sP) gene expression levels had high variance.

Example 4: Trends in Gene Expression During Transition from Benign to PIN to Tumor Initial attention was paid to the global expression profiling trends to explore differences between the epithelial and stromal compartments (FIG. 6A), and to establish how well conserved are known epithelial and stromal genes in the data. In assessing the overall global trends within each compartment, 10 potential profiles that could be observed were defined (FIG. 6A). The global trends reflect the differences in the mean expressions within the regions of epithelial and stromal origin across the 25 cases, corrected for correlations within each individual. P63 is a marker for normal basal cells of the prostate gland ontogeny. KRT5 also stains basal cells of the benign prostate gland. Alpha-methyl-acyl-CoA racemase (AMACR) is an enzyme that functions in peroxisomal beta oxidation of dietary branched chain fatty acids and C27 bile acid intermediates. Increased fatty acid synthesis and the use of branched fatty acids play an important role in development and progression of prostate cancer. AMACR is overexpressed in premalignant and malignant lesions of the prostate compared with the normal prostate (Hansen A G, et al., Cancer Res, 2014. 74:1404-15.

Figure 6B:
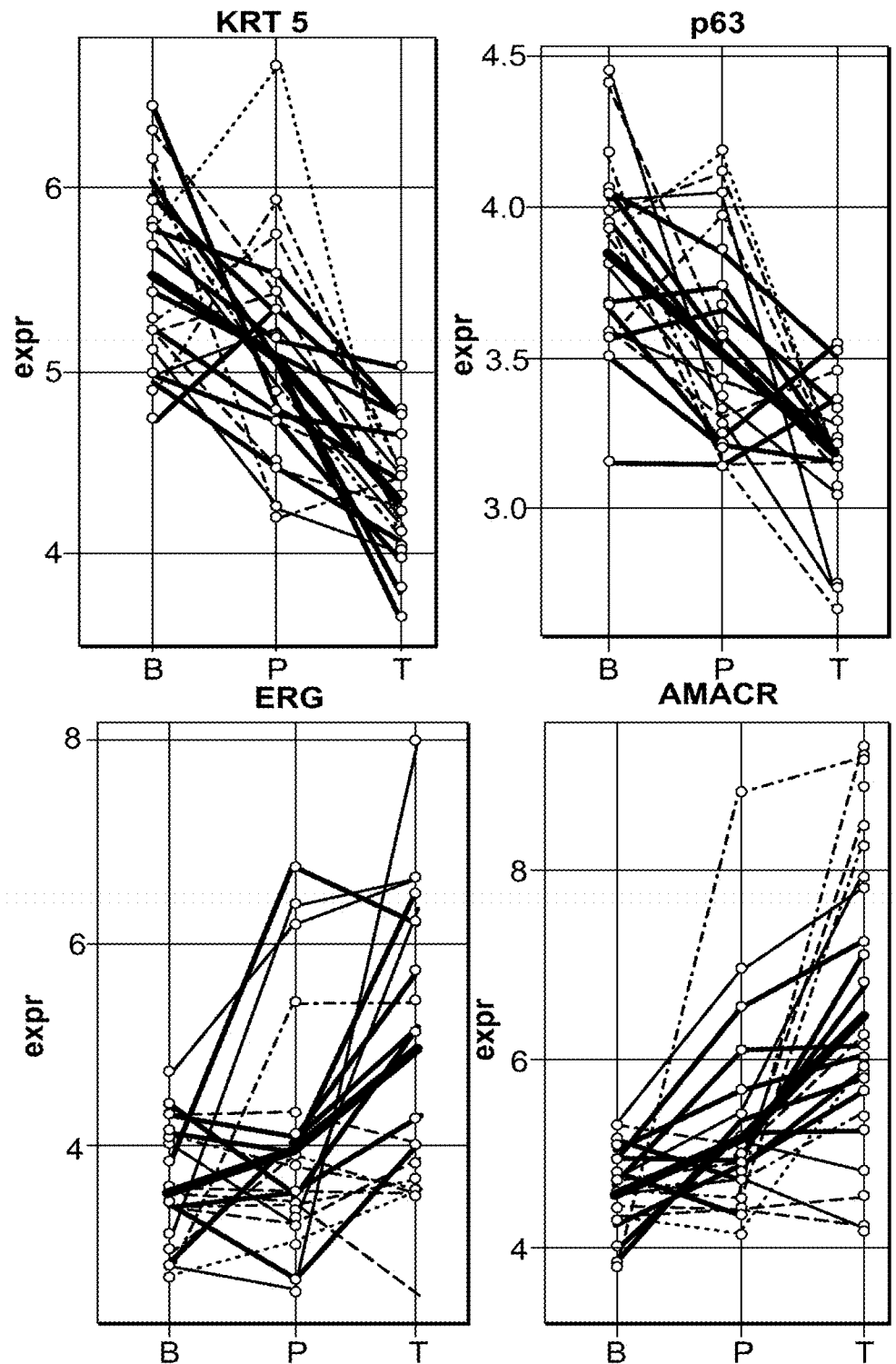
FIG. 6B is a plot showing the representative prostate-related genes plotted as epithelial trends, where the black line indicates the mean expression of an individual gene within a given region of interest across all 25 radical prostatectomy cases.
Figure 6C:
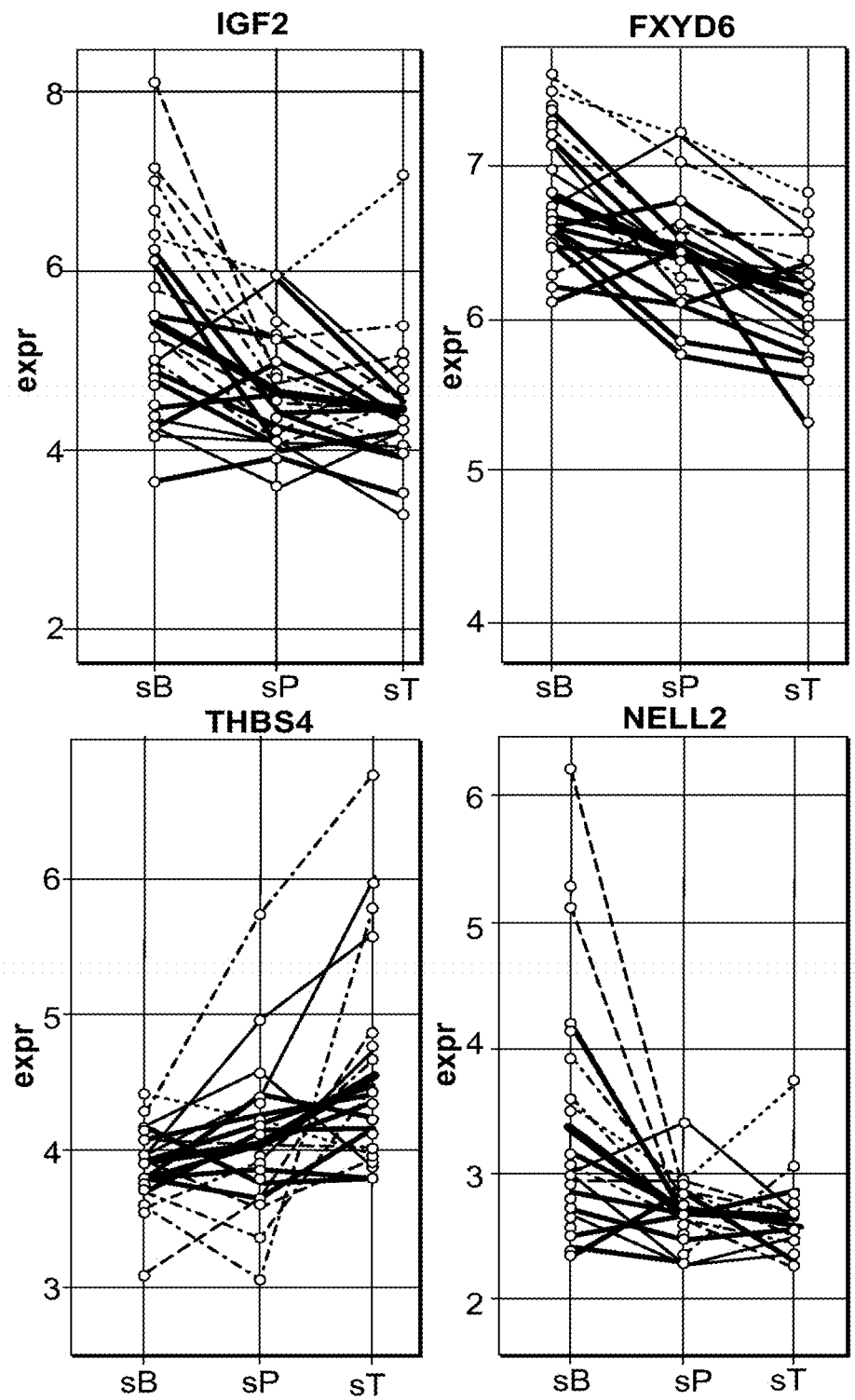
FIG. 6C is a plot showing the representative prostate-related genes plotted as stromal trends, where the black line indicates the mean expression of an individual gene within a given region of interest across all 25 radical prostatectomy cases.
Figure 41:
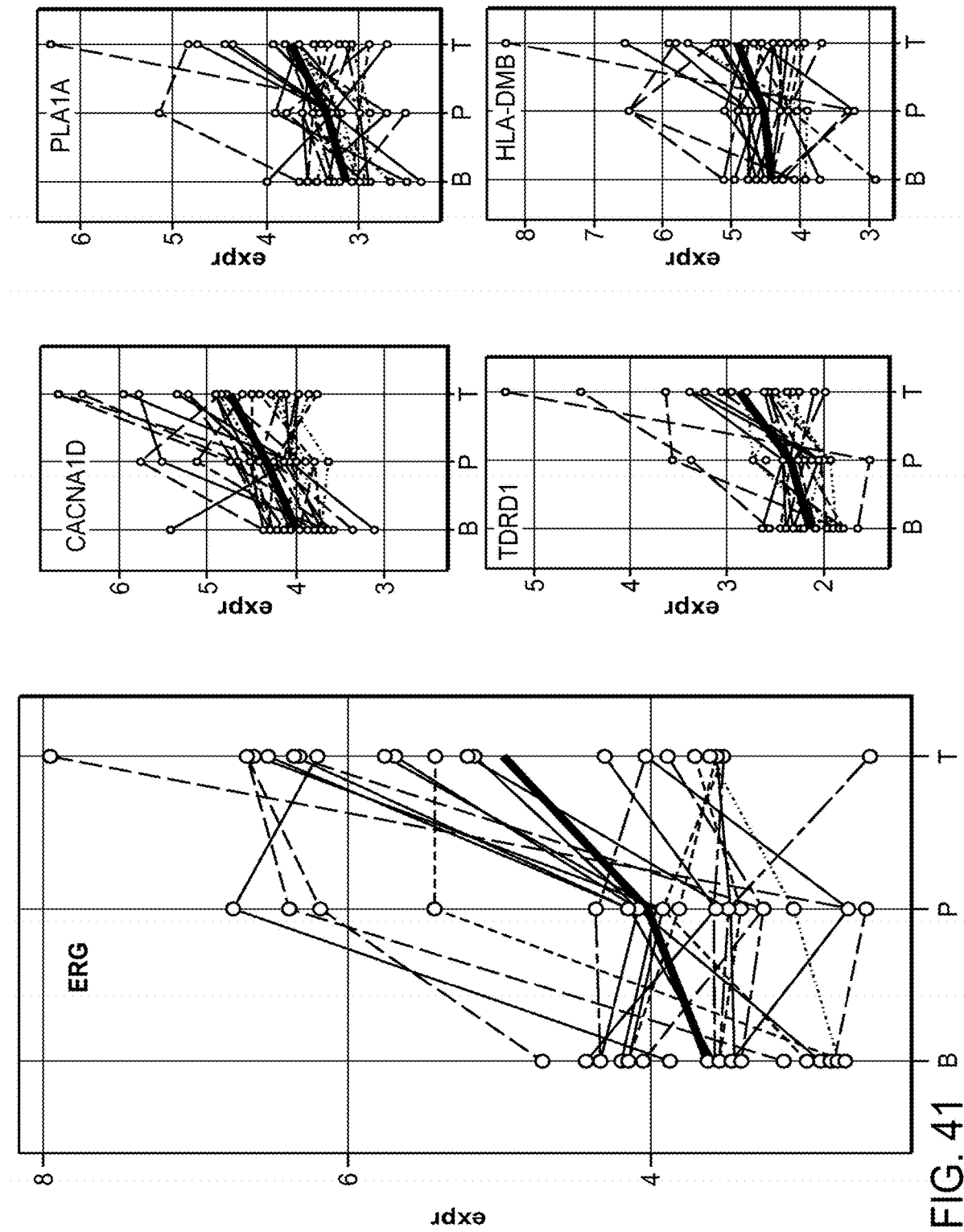

ERG is a prominent over-expressed prostate tumor gene that is frequently fused with the promoter region of the TMPRSS2 gene. A series of ERG regulated genes such as CACNA1D, PLA1A, TDRD1 and HLA-DMB follow the same trend (FIG. 41). THBS4 is a member of a family of extracellular glycoproteins and has been shown to be over-expressed in tumor associated stroma in breast cancer, indicating a strong interaction of invading tumor cells and stromal fibroblasts in the local microenvironment. IGF2 is related to loss of genomic imprinting associated with NFkB activity in prostate tumorigenesis. Well characterized prostate-specific genes were found to be significant. P63 and KRT5, markers of normal basal cells of the prostate gland were upregulated in benign microdissected samples, and AMACR, KLK2, KLK3, ERG and a subset of its regulated genes such as CACNA1D, PLA1A, TDRD1 and HLA-DMB were all upregulated in the tumor microdissected samples. Representative plots of prostate-related gene epithelial and stromal trends are shown in FIG. 6B and FIG. 6C, respectively.

Figure 40:
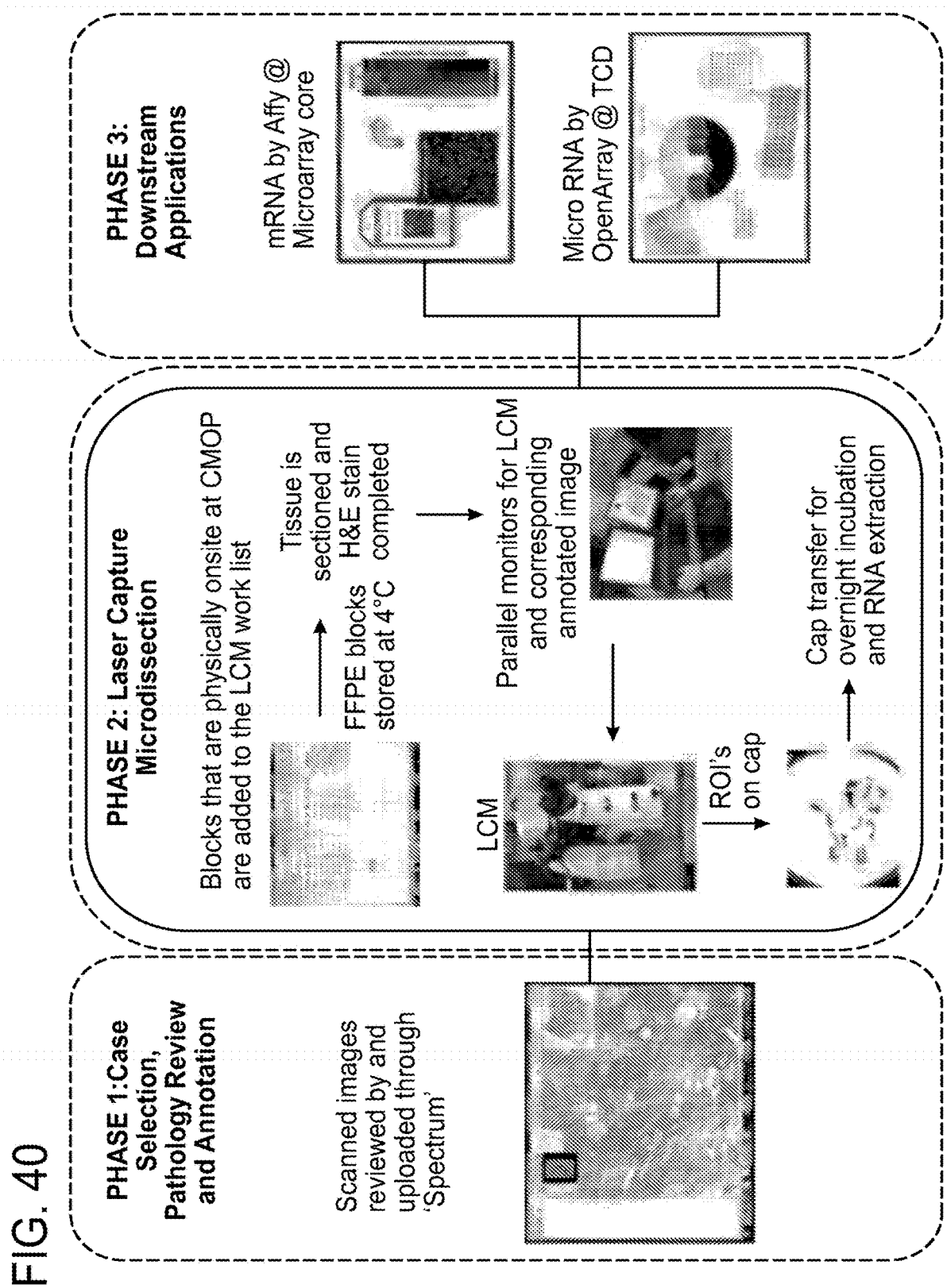

Example 5: High-Grade (HG) PIN Differs in an Inconsistent Manner from Both Benign and Invasive Components From the annotated, web accessible H&E's (FIG. 7A), the epithelial and adjacent stromal regions of interest (ROI) associated with benign, high-grade Prostatic Intraepithelial Neoplasia (PIN) and tumor morphological areas were microdissected for each case. The generation of highly pure cellular populations of sufficient yield and concentration for whole transcriptome gene expression analysis was vital. For each experiment, each stained LCM section was imaged pre- and post-microdissection and the microdissected cells transferred to the polymer membrane cap, as shown in FIG. 40.

Figure 7B:
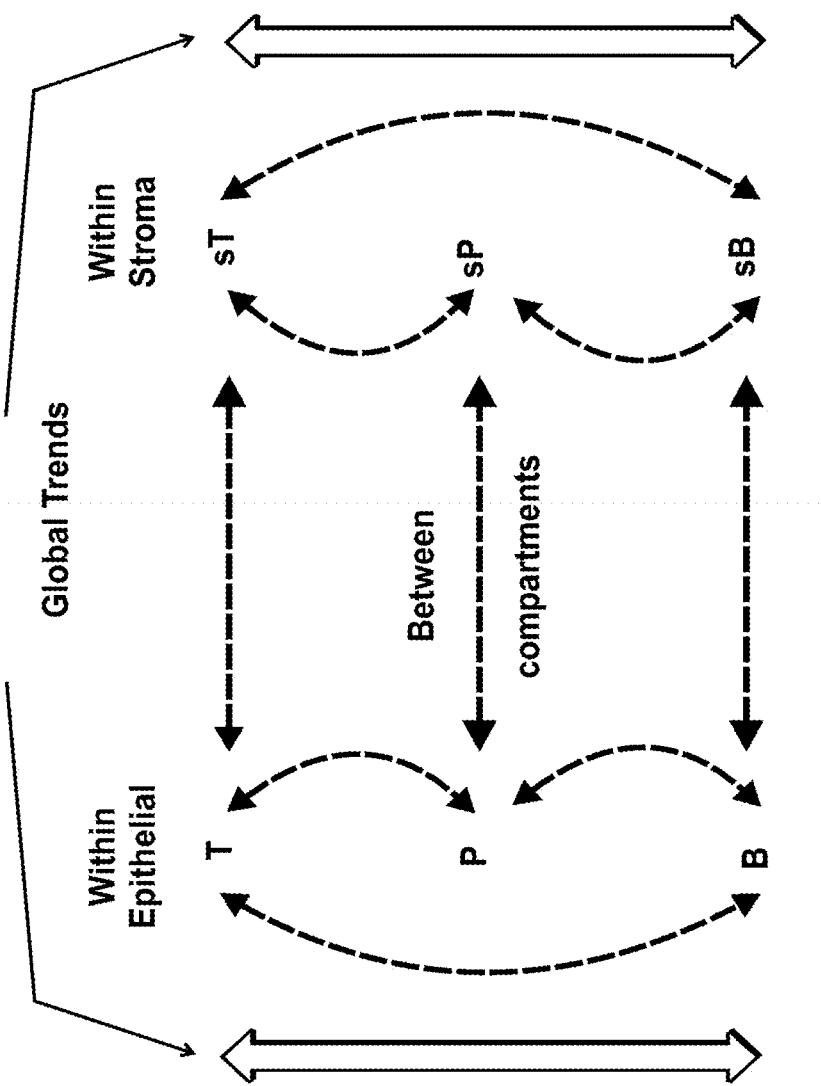
FIG. 7B is a diagram showing the schematic representation of epithelial-stromal comparisons.
Figure 7A:
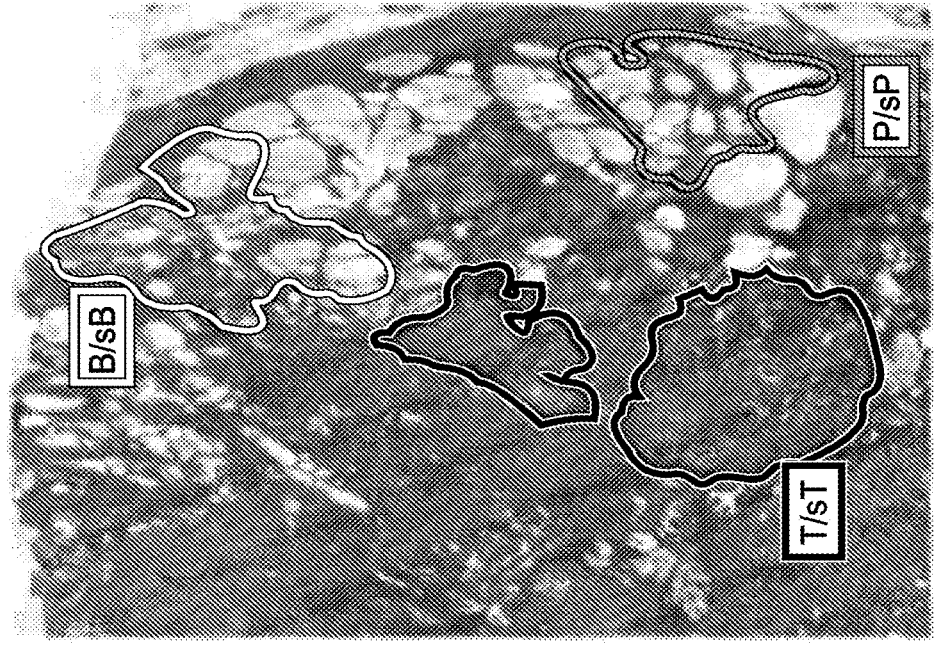
FIG. 7A is an image showing tissues stained for H&E, scanned by Aperio and annotated by pathologists, who identified tumor (green), high-grade PIN (blue) and benign (red) regions of interest for remote laser capture microdissection.
Figure 7D:
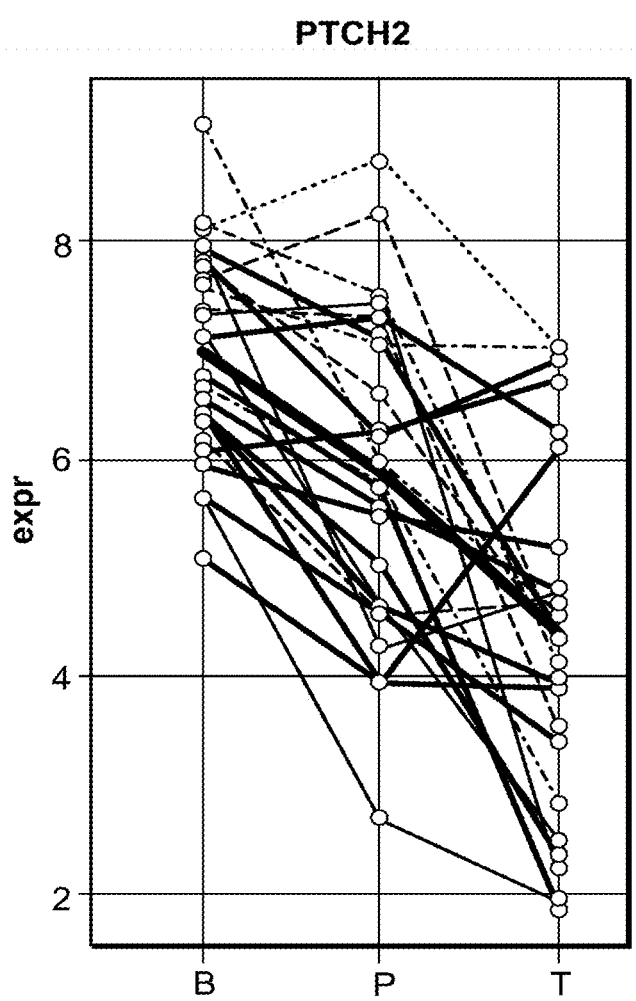
FIG. 7D is a plot showing the up and down regulation of the PTCH2 gene. Bracketed numbers indicate up- or down-regulation of the gene. The black line indicates the mean expression within a given region of interest across all 25 radical prostatectomy cases.

Differentially expressed genes within the epithelial and stromal compartments comparing T-P, T-B and P-B and then sT-sP, sT-sB and sP-sB were evaluated (FIG. 7B). FIG. 7C is a chart showing the number of differentially expressed genes for each of the comparisons within the epithelium and within the stroma. FIG. 7D is a plot showing the up and down regulation of the PTCH2 gene.

Figure 8A:
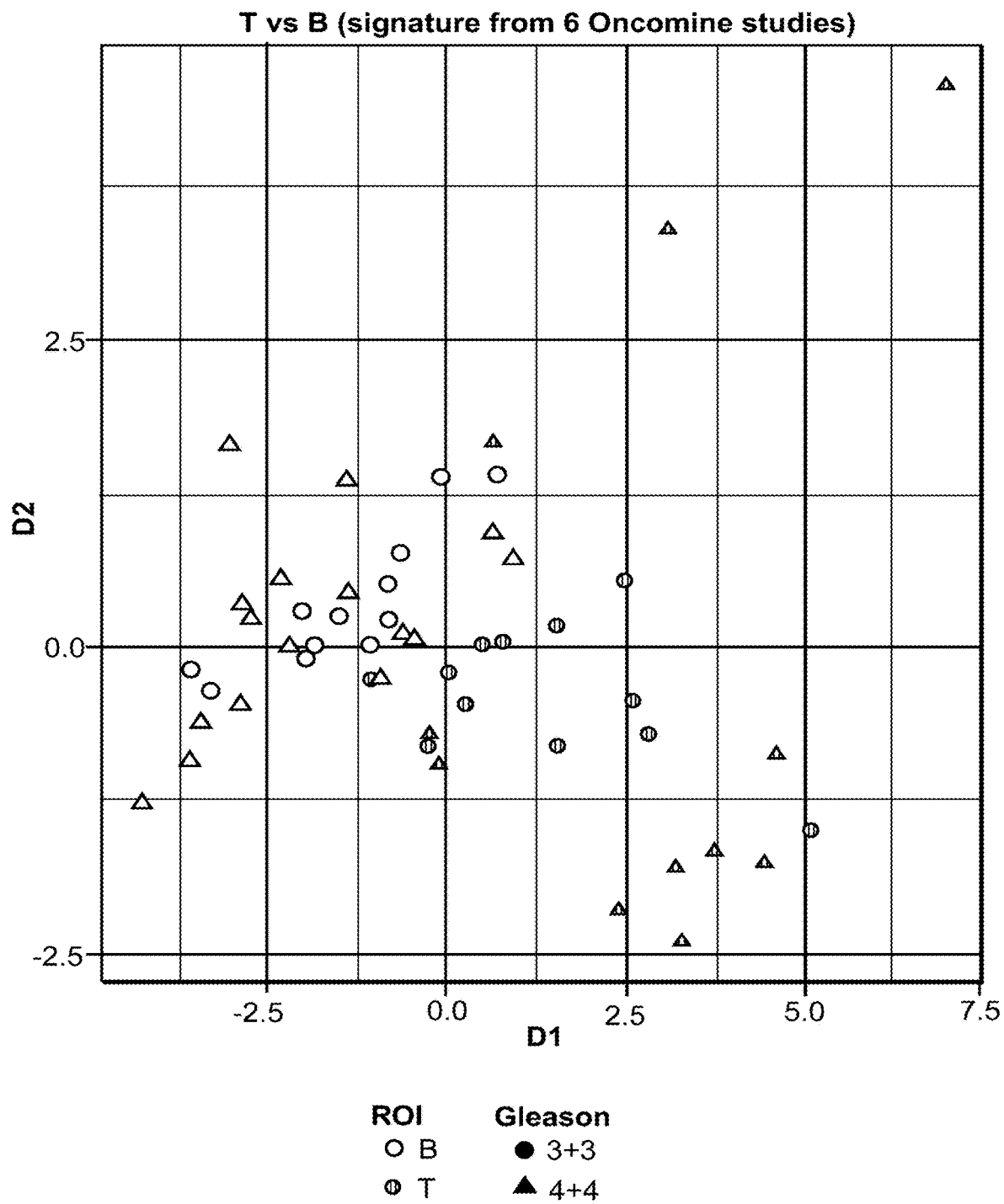
FIG. 8A is a plot showing a PCA of differentially expressed tumor and normal epithelial genes derived from Oncomine datasets.
Figure 8B:
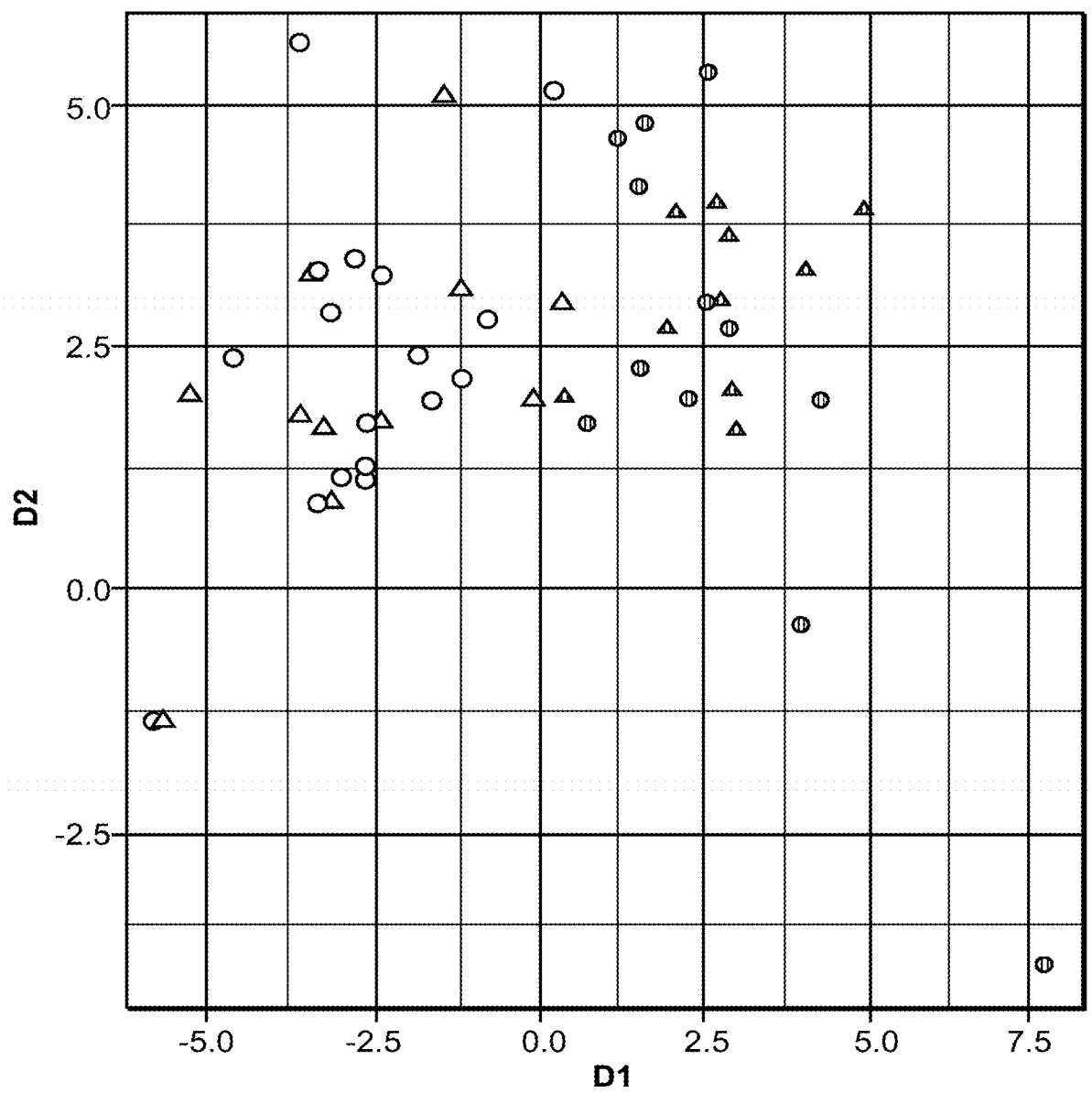
FIG. 8B is a plot showing a PCA of differentially expressed tumor and normal stroma genes derived from Oncomine datasets.

Prior to investigating differentially expressed genes in the T-B comparison in the microdissected tissues, known epithelial tumor and benign associated prostate cancer genes were evaluated utilizing an enriched Oncomine signature comprised of gene expression data from 6 prostate cancer studies (Singh D, et al., Cancer Cell. 1, 203-9 (2002), Lapointe J, et al., Proc Natl Acad Sci. 101, 811-16 (2004), Yu Y P, et al., J Clin Oncol. 22, 2790-9 (220040), Tomlins S A, Nat Genet. 39, 41-51 (2007), Wallace T A, et al., Cancer Res. 68, 927-36 (2008), and Penney K L, et al., J Clin Oncol. 29, 2391-6 (2011)) in the data. The results of which are shown in FIG. 8A and FIG. 8B with clear separation of the benign and tumor epithelial regions from each other by the 1st principle component. FIGS. 8A and 8B are plots showing a PCA of differentially expressed tumor and normal genes derived from Oncomine datasets (epithelial and stroma genes for FIG. 8A and FIG. 8B, respectively).

Within the epithelial compartment (Table 6), 176/234 genes were differentially expressed in the T-B comparison only, of which 79 were upregulated and 97 downregulated. 5/24 genes were differentially expressed in the T-P comparison only, of which all 5 were downregulated. 13/52 genes were differentially expressed in the P-B comparison only, of which 8 were upregulated and 5 downregulated. 22 genes were upregulated (all small nucleolar RNA's with the exception of HPN and TRIB1) and 14 genes downregulated in both the P-B and T-B comparisons. Prostate tumor-expressing genes, ERG, AMACR and OR51E1 were upregulated and 15 genes (mostly methallothioneins and keratins) downregulated in both the T-P and T-B comparisons. PTCH2, the tumor suppressor gene, was upregulated in the P-B, T-P and T-B comparisons and when plotted resulted in a decreasing expression associated with progression from B to P to T.

Within the stromal compartment (Table 7), 49 genes were differentially expressed in the sT-sB comparison of which 36 were upregulated and 13 downregulated. A number of prostate cancer associated genes were up-regulated, including NKX3-1, KLK2, KLK3, ERG, FOXA1 and EPCAM. For each of these genes, it was confirmed that the stroma mRNA expression level was lower than that of the tumor epithelium. IGF1 and IGF2 were 2/13 genes downregulated in the sT-sB comparison, where loss of imprinting (LOI) has long been associated with tumorigenesis. NELL2, a glycoprotein containing EGF-like domains with similarities to thrombospondin was found to be downregulated in both the sP-sB and sT-sB comparisons. BMP5, a member of the TGFβ superfamily, was upregulated in the sP-sB comparison only. The mean expression of hgPIN (high-grade PIN) tissues had a large variance, which made tracking prostate cancer progression trends somewhat challenging. It did open up the concept that hgPIN has benign and tumor characteristics, and perhaps even a subset of unique transcriptional programs that were not well defined prior to the invention described herein.

| PIN-Benign | | | | Tumor-PIN | | | | Tumor Benign | | | |
|---|---|---|---|---|---|---|---|---|---|---|---|
| Affymetrix ID | Gene | logFC | adj. P. Val | Affymetrix ID | Gene | logFC | adj. P.Val | Affymetrix ID | Gene | logFC | adj. P.Val |
| 7945997 | OR51C1P | 1.30223 | 0.01975 | 8111430 | AMACR | 1.297604 | 0.00028 | 8111430 | AMACR | 1.891429 | 1.40E-10 |
| 7922408 | SNORD78 | 1.14210 | 0.00113 | 7937952 | OR51E1 | 1.102829 | 0.00805 | 7945991 | OR51E2 | 1.591508 | 0.00093 |
| 8108420 | SNORD74A | 1.02036 | 0.00367 | 8070297 | ERG | 0.955177 | 0.02278 | 7922408 | SNORD78 | 1.457603 | 3.35E-07 |
| 8066258 | SNORA71A | 0.96265 | 0.00113 | 8015387 | KRT17 | -0.59095 | 0.00009 | 8108420 | SNORA74A | 1.411334 | 3.59E-07 |
| 8095585 | SLC4A4 | 0.95198 | 0.00256 | 8015016 | TNS4 | -0.61723 | 0.00087 | 8070297 | ERG | 1.3471 | 3.14E-06 |
| 8032749 | SNORD37 | 0.92851 | 0.00834 | 7919055 | HMGCS2 | -0.61887 | 0.01476 | 7937952 | OR51E1 | 1.268867 | 3.23E-05 |
| 8004508 | SNORA67 | 0.86282 | 0.00113 | 7952426 | VSIG2 | -0.6201 | 0.00005 | 8108629 | VTRNA1-2 | 1.196451 | 0.002178 |
| 8158998 | SNORD36C | 0.84612 | 0.00809 | 7995797 | MT1E | -0.6866 | 0.01692 | 8032749 | SNORD37 | 1.125583 | 4.61E-05 |
| 7981970 | SNORD116-11 | 0.81578 | 0.00139 | 8114797 | SPRY4 | -0.68666 | 0.03234 | 8162117 | GOLM1 | 1.113169 | 0.000138 |
| 8027266 | HOM1 | 0.80912 | 0.04509 | 7928882 | C10orf116 | -0.72929 | 0.00360 | 8158998 | SNORD36C | 1.086689 | 1.30E-05 |
| 8159006 | SNORD36B | 0.78059 | 0.01323 | 8013042 | KRT17 | -0.75252 | 0.00000 | 7922410 | SNORD44 | 1.060308 | 0.000215 |
| 7922418 | SNORD74 | 0.71468 | 0.01574 | 7963427 | KRT5 | -0.81033 | 0.00000 | 8159006 | SNORD36B | 1.059825 | 1.13E-05 |
| 7980080 | ENTPD5 | 0.69665 | 0.00635 | 8107474 | DMX11 | -0.81364 | 0.00278 | 8126905 | CRISP3 | 1.035895 | 0.010291 |
| 7982006 | SNORD116-29 | 0.68633 | 0.03096 | 8153334 | PSCA | -0.81781 | 0.03300 | 8057803 | TMEFF2 | 0.996799 | 0.013029 |
| 7922402 | SNORD47 | 0.68516 | 0.04540 | 8061564 | ID1 | -0.82266 | 0.00087 | 8027002 | GDF15 | 0.970189 | 0.000914 |
| 7899480 | SNORA73A | 0.67634 | 0.00767 | 8001531 | MT1G | -0.88092 | 0.01776 | 8148304 | TRIB1 | 0.962309 | 5.09E-05 |
| 7998722 | SNORD60 | 0.65601 | 0.03192 | 8008885 | MIR21 | -0.88457 | 0.02278 | 7999981 | ACSM1 | 0.953702 | 3.27E-06 |
| 8148304 | TRIB1 | 0.65454 | 0.04776 | 8015337 | KRT15 | -0.89051 | 0.00000 | 7922418 | SNORD74 | 0.946854 | 2.63E-05 |
| 8060501 | SN0RA51 | 0.65343 | 0.00019 | 8135015 | MUC3A | -0.89705 | 0.02278 | 7967127 | CAMKK2 | 0.941993 | 2.34E-08 |
| 7922400 | GASS | 0.65252 | 0.02448 | 8141661 | MUC3A | -1.03945 | 0.01425 | 8098459 | EPCAM | 0.935762 | 0.001166 |
| 8066262 | SN0RA71D | 0.62685 | 0.00443 | 7995838 | MT1X | -1.0787 | 0.00001 | 8005202 | SNORD49A | 0.909378 | 0.000987 |
| 7951032 | SNORA1 | 0.62256 | 0.02014 | 8096030 | SNORA75 | -1.20691 | 0.01222 | 7922404 | SNORD80 | 0.907681 | 0.000664 |
| 8027728 | HPN | 0.62078 | 0.00022 | 7915612 | PTCH2 | -1.47488 | 0.00117 | 8041853 | EPCAM | 0.872574 | 1.03E-05 |
| 8174715 | SNORA69 | 0.61963 | 0.00367 | 8096027 | GDEP | -1.8905 | 0.00196 | 8066258 | SNORA71A | 0.857728 | 0.000648 |
| 8005955 | SNORD42A | 0.61515 | 0.00797 | | | | | 7942592 | SNORD15A | 0.849386 | 5.09E-05 |
| 8122144 | SNORA33 | 0.60844 | 0.04540 | | | | | 8155930 | GCNT1 | 0.832637 | 4 20E-08 |
| 7998666 | SNORA64 | 0.60707 | 0.03428 | | | | | 8120783 | MYO6 | 0.82843 | 6.23E-07 |
| 8066260 | SNORA71C | 0.60517 | 0.00229 | | | | | 7922416 | SNORD75 | 0.818361 | 0.00028 |
| 8050253 | SNORA80B | 0.60335 | 0.01037 | | | | | 8126784 | PLA2G7 | 0.798904 | 0 001389 |
| 8025498 | SNORA70 | 0.59650 | 0.03628 | | | | | 8140840 | STEAP4 | 0.794254 | 0.00025 |
| 7941936 | GSTP1 | -0.58069 | 0.00742 | | | | | 7972297 | ABCC4 | 0.772376 | 0.003594 |
| 8133721 | HSPB1 | -0.58295 | 0.00916 | | | | | 8027728 | HPN | 0.764808 | 6.00E-08 |
| 8094240 | CD38 | -0.58416 | 0.01875 | | | | | 8080511 | CACNA1D | 0.763922 | 1.17E-05 |
| 7909422 | MIR205 | -0.58490 | 0.00103 | | | | | 8060S01 | SNORA51 | 0.756896 | 2.75E-07 |
| 8053417 | CAPG | -0.60423 | 0.00001 | | | | | 8139107 | TARP | 0.754585 | 0.002176 |
| 7898585 | NBL1 | -0.62802 | 0.00367 | | | | | 8118319 | SNORD48 | 0.753473 | 0.002728 |
| 8042439 | ANTXR1 | -0.63054 | 0.01457 | | | | | 7922414 | SNORD76 | 0.751575 | 0.001824 |
| 7898939 | NIPAL3 | -0.64822 | 0.00527 | | | | | 8150877 | SN0R054 | 0.749387 | 0.004946 |
| 8083494 | MMF | -0.66088 | 0.00750 | | | | | 8005951 | SNORD42B | 0.748969 | 0.015875 |
| 8018975 | LGALS3BP | -0.72265 | 0.00000 | | | | | 7930631 | TDRD1 | 0.742341 | 2.75E-07 |
| 8155849 | ANXA1 | -0.74043 | 0.01684 | | | | | 7951030 | SNORD6 | 0.738071 | 0.001986 |
| 8089714 | ISAMP | -0.74359 | 0.00035 | | | | | 8166243 | REPS2 | 0.720418 | 6.84E-08 |
| 7976816 | SNORD114-3 | -0.79994 | 0.04509 | | | | | 8122144 | SNORA33 | 0.712936 | 0.001769 |
| 8029280 | CD177 | -0.84105 | 0.00001 | | | | | 7998722 | SNORD60 | 0.710724 | 0.002621 |
| 7997642 | CRISPL02 | -0.84526 | 0.00113 | | | | | 8004508 | SNORA67 | 0.705729 | 0.002062 |
| 7980316 | TGFB3 | -0.85827 | 0.01694 | | | | | 7922402 | SNORD47 | 0.705222 | 0.007635 |
| 8167185 | TIMP1 | -0.87514 | 0.00870 | | | | | 7948904 | SNORD28 | 0.70119 | 0.006586 |
| 8021081 | SLC14A1 | -1.05168 | 0.00001 | | | | | 79488% | SNORD22 | 0.698303 | 0.00087 |
| 8037298 | C0177 | -1.08457 | 0 00009 | | | | | 8174715 | SNORA69 | 0.697389 | 4.70E-05 |
| 7915612 | PTCH2 | -1.12239 | 0.02000 | | | | | 8010082 | SNOROIA | 0.697369 | 2.60E-05 |
| 8072229 | NEFH | -1.42171 | 0.00385 | | | | | 8041170 | SNORD122 | 0.695112 | 0.014545 |
| | | | | | | | | 8030366 | SN0R035A | 0.69221 | 0.003405 |
| | | | | | | | | 8038624 | C19orf48 | 0.690775 | 0.000116 |
| | | | | | | | | 8148501 | PTP4A3 | 0.690657 | 3.23E-05 |
| | | | | | | | | 8063345 | SNORD12C | 0.687899 | 0.003733 |
| | | | | | | | | 8163185 | TXN | 0.684962 | 6.58E-07 |
| | | | | | | | | 7951036 | SNORD5 | 0.683477 | 0.000225 |
| | | | | | | | | 8062427 | VSTM2L | 0.679297 | 1.07E-06 |
| | | | | | | | | 7948420 | FABP5 | 0.664713 | 0.002275 |
| | | | | | | | | 8116649 | TUBB2A | 0.660089 | 1.17E05 |
| | | | | | | | | 8116653 | TUBB2A | 0.660089 | 1.17E-05 |
| | | | | | | | | 7899480 | SNORA73A | 0.659702 | 0.001336 |
| | | | | | | | | 8147049 | FABP5 | 0.65773 | 0 002045 |
| | | | | | | | | 8134030 | STEAP1 | 0.653061 | 0.029608 |
| | | | | | | | | 7901050 | SNORD38A | 0.650043 | 0.005223 |
| | | | | | | | | 8059712 | SNORD82 | 0.647384 | 0.009876 |
| | | | | | | | | 8065280 | RALGAPA2 | 0.64624 | 8.26E-06 |
| | | | | | | | | 7938687 | NUCB2 | 0 643379 | 0.002039 |
| | | | | | | | | 8148040 | MA12 | 0.641406 | 4.50E-05 |
| | | | | | | | | 8005200 | SNORD49B | 0.639298 | 9.97E-05 |
| | | | | | | | | 8052141 | snoRNA | 0.637S79 | 1.57E-05 |
| | | | | | | | | 8159004 | SNORD24 | 0.633898 | 0.002083 |
| | | | | | | | | 8177222 | C024 | 0.6338S9 | 0.012403 |
| | | | | | | | | 8076221 | SNORD83A | 0.633776 | 0.000755 |
| | | | | | | | | 8118322 | SNORD52 | 0.632169 | 0.014328 |

-continued

| PIN-Benign | | | | Tumor-PIN | | | | Tumor Benign | | | |
|---|---|---|---|---|---|---|---|---|---|---|---|
| Affymetrix ID | Gene | logFC | adj. P. Val | Affymetrix ID | Gene | logFC | adj. P.Val | Affymetrix ID | Gene | logFC | adj. P.Val |
| | | | | | | | | 7951032 | SNORA1 | 0.628148 | 0.003323 |
| | | | | | | | | 7981970 | SN0R0116-11 | 0.626384 | 0.004937 |
| | | | | | | | | 7901052 | SNORD38B | 0.620864 | 0.036107 |
| | | | | | | | | 8041168 | SNORD53 | 0.618859 | 0.010096 |
| | | | | | | | | 8124492 | HIST1H2BK | 0.615374 | 0.001492 |
| | | | | | | | | 8109750 | RPLPO | 0.6146 | 0.000397 |
| | | | | | | | | 7998666 | SNORA64 | 0.612453 | 0.00632 |
| | | | | | | | | 8098103 | FNIP2 | 0.611807 | 1.83E−06 |
| | | | | | | | | 8112469 | GUSBP3 | 0.610841 | 1.29E 05 |
| | | | | | | | | 8066262 | SN0RA710 | 0.610144 | 0.000733 |
| | | | | | | | | 8116651 | TUBB2BP1 | 0.609796 | 0.000785 |
| | | | | | | | | 7939642 | CREB3L1 | 0.607966 | 0.000106 |
| | | | | | | | | 8148317 | MYC | 0.607595 | 6.21E−05 |
| | | | | | | | | 7980S47 | SEL1L | 0.605765 | 3.14E−07 |
| | | | | | | | | 8112564 | GUSBP3 | 0.605211 | 1.48E 05 |
| | | | | | | | | 7948900 | SNORD30 | 0.604659 | 0.005083 |
| | | | | | | | | 7946807 | RPL36A | 0.601659 | 5.27E−05 |
| | | | | | | | | 8050240 | 0DC1 | 0.601655 | 0.005399 |
| | | | | | | | | 8139456 | SN0RA9 | 0.599248 | 0.002152 |
| | | | | | | | | 8081890 | PLA1A | 0.598233 | 0.00068 |
| | | | | | | | | 8050253 | SNORA80B | 0.598135 | 0.001697 |
| | | | | | | | | 8097957 | GUCY1A3 | 0.596386 | 0.00062 |
| | | | | | | | | 8133070 | snoRNA | 0.594422 | 0.006864 |
| | | | | | | | | 7998664 | SNORAIO | 0.59136 | 0.000849 |
| | | | | | | | | 8041204 | SNORAIO | 0.59136 | 0.000849 |
| | | | | | | | | 8174189 | TMSB15A | 0.591288 | 0.000206 |
| | | | | | | | | 7906863 | UAP1 | 0.589045 | 1.47E−08 |
| | | | | | | | | 8066260 | SN0RA71C | 0.586723 | 0.000362 |
| | | | | | | | | 7948906 | SNORD27 | 0.581236 | 0.015963 |
| | | | | | | | | 8103025 | 2NF827 | −0.58092 | 1.00E−05 |
| | | | | | | | | 7945371 | IFITM3 | −0.58568 | 0.001823 |
| | | | | | | | | 8048432 | CYP27A1 | −0.58585 | 9.34E−08 |
| | | | | | | | | 8177732 | HLA-A | −0.58596 | 0.000243 |
| | | | | | | | | 8075477 | RNF185 | −0.58683 | 0.00034 |
| | | | | | | | | 7979813 | ZFP36L1 | −0.58733 | 1.83E 06 |
| | | | | | | | | 7898957 | RCAN3 | −0.58776 | 0 000696 |
| | | | | | | | | 7986517 | C15orf51 | −0.58955 | 0.001102 |
| | | | | | | | | 7986522 | C15orf51 | −0.58955 | 0.001102 |
| | | | | | | | | 8005449 | KRT17 | −0.59101 | 2.28E−08 |
| | | | | | | | | 8175666 | 6ABRE | −0.59615 | 2.01E07 |
| | | | | | | | | 7986509 | C15orfSl | −0.59835 | 0.001993 |
| | | | | | | | | 7986512 | C15orf51 | −0.59835 | 0.001993 |
| | | | | | | | | 7921099 | CRABP2 | −0.5996 | 0.000422 |
| | | | | | | | | 7960529 | SCNN1A | −0.60505 | 0.000141 |
| | | | | | | | | 8021442 | ZNF532 | −0.60944 | 2.02E−07 |
| | | | | | | | | 8095362 | MT2A | −0.61153 | 7.02E−06 |
| | | | | | | | | 8046536 | HOXOIO | −0.61342 | 2.11E−08 |
| | | | | | | | | 8104601 | BASP1 | −0.61874 | 3.22E−06 |
| | | | | | | | | 8168892 | TCEAL2 | −0.61903 | 0.000778 |
| | | | | | | | | 8054872 | TFCP211 | −0.61945 | 1.25E−07 |
| | | | | | | | | 8051814 | ZFP36L2 | −0.62303 | 6.00E−08 |
| | | | | | | | | 8055222 | POTEE | −0.62319 | 0.041406 |
| | | | | | | | | 8015635 | PTRF | −0.62819 | 5.53E−05 |
| | | | | | | | | 8141094 | PDK4 | −0.62879 | 0.002728 |
| | | | | | | | | 8116848 | PAK1IP1 | −0.62889 | 0.002408 |
| | | | | | | | | 8174361 | TSa203 | −0.63026 | 4.67E−07 |
| | | | | | | | | 8150698 | SNAI2 | −0.63798 | 0.000122 |
| | | | | | | | | 8179041 | HLA-A | −0.64442 | 0.000674 |
| | | | | | | | | 7986520 | C15orf51 | −0.64496 | 0.000416 |
| | | | | | | | | 8117034 | GMPR | −0.65175 | 0.000115 |
| | | | | | | | | 8009334 | CACNG4 | −0.65342 | 4.46E−06 |
| | | | | | | | | 7977965 | SLC22A17 | −0.65385 | 3.05E−14 |
| | | | | | | | | 8015133 | KRT23 | −0.65524 | 4.09E−05 |
| | | | | | | | | 7952046 | MPZL2 | −0.65805 | 2.81E−07 |
| | | | | | | | | 8036133 | UPK1A | −0.65812 | 2.75E−07 |
| | | | | | | | | 8009951 | ITGB4 | −0.65843 | 9.15E−14 |
| | | | | | | | | 7903753 | GSTM2 | −0.65895 | 1.40E−05 |
| | | | | | | | | 8015349 | KRT19 | −0.66466 | 3.71E−05 |
| | | | | | | | | 7952426 | VSIG2 | −0.66567 | 3.35E−07 |
| | | | | | | | | 7977621 | NDRG2 | −0.67164 | 1.58E−08 |
| | | | | | | | | 8084766 | TP63 | −0.67343 | 2.63E−16 |
| | | | | | | | | 8063000 | WFDC2 | −0.67526 | 4.85E 08 |
| | | | | | | | | 7976812 | SNORD113-4 | −0.67611 | 0.019355 |

-continued

| PIN-Benign | | | | Tumor-PIN | | | | Tumor Benign | | | |
|---|---|---|---|---|---|---|---|---|---|---|---|
| Affymetrix ID | Gene | logFC | adj. P. Val | Affymetrix ID | Gene | logFC | adj. P.Val | Affymetrix ID | Gene | logFC | adj. P.Val |
| | | | | | | | | 8021614 | SERPINB11 | −0.67752 | 0.016975 |
| | | | | | | | | 8058869 | TNS1 | −0.67762 | 0.012945 |
| | | | | | | | | 8041781 | EPAS1 | −0.6781 | 2.27E−06 |
| | | | | | | | | 8082012 | SLC15A2 | −0.68054 | 8.16E−06 |
| | | | | | | | | 8155665 | PGM5 | −0.68299 | 0.016241 |
| | | | | | | | | 7899265 | SFN | −0.69041 | 9.96E−05 |
| | | | | | | | | 7981427 | CKB | −0.69467 | 6.566-07 |
| | | | | | | | | 8015387 | KRT17 | −0.69606 | 5.55E−08 |
| | | | | | | | | 8083494 | MME | −0.70353 | 0.000362 |
| | | | | | | | | 8055153 | POTEF | −0.70362 | 0.011109 |
| | | | | | | | | 8075635 | TIMP3 | −0.70961 | 0.015264 |
| | | | | | | | | 8003667 | SERPINF1 | −0.71261 | 0.002106 |
| | | | | | | | | 7969288 | OLFM4 | −0.71778 | 0.002557 |
| | | | | | | | | 7935180 | P0LIM1 | −0.7215 | 1.66E−06 |
| | | | | | | | | 7984908 | CPLX3 | −0.72254 | 1.35E−07 |
| | | | | | | | | 8045257 | POTEE | −0.72643 | 0.007241 |
| | | | | | | | | 7995825 | MT1F | −0.73176 | 2.18E−05 |
| | | | | | | | | 7995787 | MT1M | −0.7396 | 0.003733 |
| | | | | | | | | 8073068 | APOBEC3C | −0.74153 | 3.67E−09 |
| | | | | | | | | 80346% | MIR27A | −0.74401 | 0.005976 |
| | | | | | | | | 8153334 | PSCA | −0.74436 | 0.007752 |
| | | | | | | | | 7987385 | MEIS2 | −0.74451 | 8.17E−08 |
| | | | | | | | | 7958784 | ALOH2 | −0.74904 | 3.47E−08 |
| | | | | | | | | 7995793 | MT1L | −0.74992 | 2.92E−06 |
| | | | | | | | | 8018975 | LGALS3BP | −0.75016 | 5.03E−08 |
| | | | | | | | | 8052355 | EFEMP1 | −0.76511 | 0.002106 |
| | | | | | | | | 7935058 | MYOF | −0.78287 | 1.08E−12 |
| | | | | | | | | 7989335 | ANXA2 | −0.7968 | 1.66E−05 |
| | | | | | | | | 7961693 | IDHB | −0.81657 | 3.71E−05 |
| | | | | | | | | 8089714 | ISAMP | −0.81785 | 2.55E−06 |
| | | | | | | | | 8053417 | CAP6 | −0.83975 | 3.75E−12 |
| | | | | | | | | 8013042 | KRT17 | −0.84141 | 1.34E−09 |
| | | | | | | | | 8058927 | TMBIM1 | −0.843% | 0.000336 |
| | | | | | | | | 8095751 | PARM1 | −0.84657 | 2.39E−07 |
| | | | | | | | | 8094240 | C038 | −0.85164 | 6.18E−06 |
| | | | | | | | | 8042439 | ANTXR1 | −0.85236 | 1.41E−05 |
| | | | | | | | | 8155849 | ANXA1 | −0.86527 | 0.000315 |
| | | | | | | | | 8133721 | HSPB1 | −0.86629 | 5.67E−07 |
| | | | | | | | | 8101260 | ANTXR2 | −0.86649 | 2.27E−07 |
| | | | | | | | | 7913655 | 103 | −0.87604 | 1.96E−05 |
| | | | | | | | | 7976816 | SNORD114-3 | −0.87828 | 0.003787 |
| | | | | | | | | 8037298 | CD177 | −0.8806 | 0.000289 |
| | | | | | | | | 8167449 | PLP2 | −0.89267 | 2.16E−08 |
| | | | | | | | | 8149330 | CTSB | −0.90352 | 7.35E−09 |
| | | | | | | | | 8015016 | TNS4 | −0.9149 | 8.75E−10 |
| | | | | | | | | 7951662 | CRYAB | −0.91692 | 0.00162 |
| | | | | | | | | 8160670 | AQP3 | −0.92573 | 5.11E−06 |
| | | | | | | | | 8135015 | MUC3A | −0.93668 | 0.000867 |
| | | | | | | | | 7952290 | TRIM29 | −0.93671 | 2.03E 13 |
| | | | | | | | | 7898939 | NIPAL3 | −0.9537 | 1.53E−07 |
| | | | | | | | | 8074170 | POTEM | −0.96445 | 0.008176 |
| | | | | | | | | 7940565 | FADS2 | −0.96869 | 7.68E−0S |
| | | | | | | | | 7972983 | POTEM | 0.97099 | 0.009254 |
| | | | | | | | | 7995797 | MT1E | −0.97503 | 1.27E−06 |
| | | | | | | | | 7898585 | NBll | −0.99043 | 8.91E−09 |
| | | | | | | | | 8135031 | MUC12 | −0.9953 | 0.001606 |
| | | | | | | | | 7984914 | CPLX3 | −1.01161 | 6.33E−07 |
| | | | | | | | | 7940654 | SC6B1A1 | −1.0175 | 0.000256 |
| | | | | | | | | 7984892 | LMAN1L | −1.01922 | 3.70E−08 |
| | | | | | | | | 7977456 | P0TE6 | −1.02336 | 0.012404 |
| | | | | | | | | 7909422 | MIR205 | −1.02359 | 1.75E−12 |
| | | | | | | | | 8141374 | AZGP1 | −1.04663 | 0.001026 |
| | | | | | | | | 8061564 | 101 | −1.05896 | 9.62E−08 |
| | | | | | | | | 8029280 | CD177 | −1.08866 | 4.25E−11 |
| | | | | | | | | 8141661 | MUC3A | −1.0894 | 0.000373 |
| | | | | | | | | 7941936 | GSTP1 | −1.11514 | 3.83E−11 |
| | | | | | | | | 8082673 | ACPP | −1.12748 | 0.005312 |
| | | | | | | | | 8167185 | TIMP1 | −1.1283 | 1.46E−05 |
| | | | | | | | | 7997642 | CRISPID2 | −1.13938 | 8.07E−08 |
| | | | | | | | | 7928882 | C10orf16 | −1.15485 | 1.97E−09 |
| | | | | | | | | 8135033 | MUC12 | −1.18471 | 0 004946 |
| | | | | | | | | 7980316 | TGFB3 | −1.18768 | 1 39E−05 |
| | | | | | | | | 7963427 | KRT5 | −1.22502 | 1.20E−15 |

-continued

| PIN-Benign | | | | Tumor-PIN | | | | Tumor Benign | | | |
|---|---|---|---|---|---|---|---|---|---|---|---|
| Affymetrix ID | Gene | logFC | adj. P. Val | Affymetrix ID | Gene | logFC | adj. P.Val | Affymetrix ID | Gene | logFC | adj. P.Val |
| | | | | | | | | 8001531 | MT1G | −1.23538 | 2.03E−06 |
| | | | | | | | | 7995838 | MT1X | −1.25369 | 5.08E−09 |
| | | | | | | | | 8119898 | VEGFA | −1.27594 | 1.55E−08 |
| | | | | | | | | 7995783 | MT2A | −1.28084 | 2.41E−05 |
| | | | | | | | | 8015337 | KRT15 | −1.38255 | 2.26E−15 |
| | | | | | | | | 7991335 | ANPEP | −1.44607 | 0.000428 |
| | | | | | | | | 8096027 | GDEP | −1.59616 | 0.001443 |
| | | | | | | | | 8021081 | SLC14A1 | −1.69241 | 4.82E−15 |
| | | | | | | | | 8079279 | TGM4 | −2.01159 | 0.00078 |
| | | | | | | | | 8072229 | NEFH | −2.15455 | 3.70E−08 |
| | | | | | | | | 7927529 | MSMB | −2.36316 | 8.17E−06 |
| | | | | | | | | 7915612 | PTCH2 | −2.59727 | 1.08E−12 |

FC positive in Tumor-PIN samples: AMACR, OR5IE1, and ERG.
FC negative in Tumor-PIN samples: KRT17, TNS4, HMGCS2, VSIG2, MTIE, SPRY4, C10orf16, KRT17, KRT5, DMXL1 PSCA, ID1, MT1G, MIR21, KRT15, MUC3A, MTIX, SNORA75, PTCH2, and GDEP.
FC postitve in PIN-Benign samples: OR51CIP, SNORD78, SNORA74A, SNORA71 A, SLC4A4, SNORD37, SNORA67, SNORD36C, SNORD116-11, HOM1, SNORD36B, SNORD74, ENTPD5, SNORD116-29, SNORD47, SNORA73A, SNORD60, TRIB1, SNORA51, GAS5, SNORA71D, SNORA1, HPN, SNORA69, SNORD42A, SNORA33, SNORA64, SNORA71C, SNORA80B, SNORA70, and GSTP1.
FC negative in PIN-Benign samples: HSPB1, CD38, MIR205, CAPG, NBL1, ANTXR1, NIPAL3, MME, LGALS3BP, ANXA1, LSAMP, SNORD114-3, CD177, CRISPLD2, TGFB3, TIMP1, SLC14A1, CD177, PTCF12, and NEFH.
FC Postive in tumor benign samples: AMACR, OR51E2, SNORD78, SNORA74A, ERG, OR51E1, VTRNA1-2, SNORD37, GOLM1, SNORD36C, SNORD44, SNORD36B, CRISP3, TMEFF2, GDFI5, TRIB1, ACSM1, SNORD74, CAMKK2, EPCAM, SNORD49A, SNORD80, EPCAM, SNORA71 A, SNORD15A, GCNT1, MY06, SNORD75, PLA2G7, STEAP4, ABCC4, HPN, CACNA1D, SNORA51, TARP, SNORD48, SNORD76, SNORD54, SNORD42B, TDRD1, SNORD6, REPS2, SNORA33, SNORD60, SNORA67, NORD47, SNORD28, SNORD22, SNORA69, SNORD1A, SNORD122, SNORA35A, C19orf48, PTP4A3, SNORD12C, TXN, SNORD5, VSTM2L, FABP5, TUBB2A, TUBB2A, SNORA73A, FABP5, STEAP1, SNORD38A, SNORD82, RALGAPA2, NUCB2, MAL2, SNORD49B, snoRNA, SNORD24, CD24, SNORD83A, SNORD52, SNORA1, SNORD116-11, SNORD38B, SNORD53, HIST1H2BK, RPLP0, SNORA64, FNIP2, GUSBP3, SNORA71D, TUBB2BPI, CREB3L1, MYC, SEL1L, GUSBP3, SNORD30, RPL36A, ODCI, SNOR A9, PL AI A, SNORA80B, GUCY1 A3, SNORA10, TMSB15A, UAP1, SNORA71C, and SNORD27.
FC Negative in tumor benign samples: ZNF827, IFITM3, CYP27A1, HLA-A, RNF185, ZFP36L1, RCAN3, C15orf51, KRT17, GABRE, CRABP2, SCNN1A, ZNF532, MT2A, HOXDIO, BASP1, TCEAL2, TFCP2L1, ZFP36L2, POTEE, PTRF, PDK4, PAK1IPI, TSC22D3, SNAI2, HLA-A, C15orf51, GMPR, CACNG4, SLC22A17, KRT23, MPZL2, UPKI A, ITGB4, GSTM2, KRT19, VSIG2, NDRG2, TP63, WFDC2, SNORD113-4, SERPINB11, TNSI, EPAS1, SLC15A2, PGM5, SFN, CKB, KRT17, MME, POTEF, TIMP3, ERPINF1, OLFM4, PDLIM1, CPLX3, POTEE, MT1F, MTIM, APOBEC3C, MIR27A, PSCA, MEIS2, ALDH2, MT1L, LGALS3BP, EFEMP1, MYOF, ANXA2, LDHB, LSAMP, CAPG, KRT17, TMBIMI, PARM1, CD38, ANTXR1, ANXA1, HSPB1, ANTXR2, ID3, SNORD114-3, KRT17, TNS4, CRYAB, AQP3, MUC3A, TRIM29, NIPAL3, POTEM, FADS2, POTEM, MT1E, NBL1, MUCI2, CPLX3, SCGBIA1, LMAN1L, POTEG, MIR205, AZGP1, ID1, CD177, MUC3A, GSTP1, ACPP, TIMP1, CRISPLD2, C10orf116, MUCI2, TGFB3, KRT5, MTIG, MTIX, VEGFA, MT2A, KRT15, ANPEP, GDEP, SLC14A1, TGM4, NEFH, MSMB, PTCH2.

| Pin-Benign | Tumor-PIN | Tumor-Benign | # comparison | Comparison | Trend based on FC |
|---|---|---|---|---|---|
| PTCH | PTCH2 | PTCH | 3 | P-B, T-P, T-B | up in B |
| HPN | | HPN | 2 | P-B, T-B | down in B |
| SNORA1 | | SNORA1 | 2 | P-B, T-B | down in B |
| SNORA33 | | SNORA33 | 2 | P-B, T-B | down in B |
| SNORA51 | | SNORA51 | 2 | P-B, T-B | down in B |
| SNORA64 | | SNORA64 | 2 | P-B, T-B | down in B |
| SNORA67 | | SNORA67 | 2 | P-B, T-B | down in B |
| SNORA69 | | SNORA69 | 2 | P-B, T-B | down in B |
| SNORA71A | | SNORA71A | 2 | P-B, T-B | down in B |
| SNORA71C | | SNORA71C | 2 | P-B, T-B | down in B |
| SNORA71D | | SNORA71D | 2 | P-B, T-B | down in B |
| SNORA73A | | SNORA73A | 2 | P-B, T-B | down in B |
| SNORA74A | | SNORA74A | 2 | P-B, T-B | down in B |
| SNORA80B | | SNORA80B | 2 | P-B, T-B | down in B |
| SNORD116-11 | | SNORD116-11 | 2 | P-B, T-B | down in B |
| SNORD36B | | SNORD36B | 2 | P-B, T-B | down in B |
| SNORD36C | | SNORD36C2 | 2 | P-B, T-B | down in B |
| SNORD37 | | SNORD37 | 2 | P-B, T-B | down in B |
| SNORD47 | | SNORD47 | 2 | P-B, T-B | down in B |
| SNORD60 | | SNORD60 | 2 | P-B, T-B | down in B |
| SNORD74 | | SNORD74 | 2 | P-B, T-B | down in B |
| SNORD78 | | SNORD78 | 2 | P-B, T-B | down in B |
| TRIB1 | | TRIB1 | 2 | P-B, T-B | down in B |
| | C10orf116 | C10orf116 | 2 | T-P, T-B | down in T |
| | GDEP | GDEP | 2 | T-P, T-B | down in T |
| | ID1 | ID1 | 2 | T-P, T-B | down in T |
| | KRT15 | KRT15 | 2 | T-P, T-B | down in T |
| | KRT17 | KRT17 | 2 | T-P, T-B | down in T |
| | KRT17 | KRT17 | 2 | T-P, T-B | down in T |
| | KRT5 | KRT5 | 2 | T-P, T-B | down in T |
| | MT1E | MT1E | 2 | T-P, T-B | down in T |
| | MT1G | MT1G | 2 | T-P, T-B | down in T |
| | MT1X | MT1X | 2 | T-P, T-B | down in T |
| | MUC3A | MUC3A | 2 | T-P, T-B | down in T |
| | MUC3A | MUC3A | 2 | T-P, T-B | down in T |
| | PSCA | PSCA | 2 | T-P, T-B | down in T |
| | TNS4 | TNS4 | 2 | T-P, T-B | down in T |
| | VSIG2 | VSIG2 | 2 | T-P, T-B | down in T |

-continued

| Pin-Benign | Tumor-PIN | Tumor-Benign | # comparison | Comparison | Trend based on FC |
|---|---|---|---|---|---|
| GSTP1 | | | 2 | P-B, T-B | mixed? |
| HSPB1 | | | 2 | P-B, T-B | up in B |
| LSAMP | | | 2 | P-B, T-B | up in B |
| ANTXR1 | | | 2 | P-B, T-B | up in B |
| ANXA1 | | | 2 | P-B, T-B | up in B |
| LGALS3BP | | | 2 | P-B, T-B | up in B |
| MIR2005 | | | 2 | P-B, T-B | up in B |
| MME | | | 2 | P-B, T-B | up in B |
| MBL1NEFH | | | 2 | P-B, T-B | up in B |
| NIPAL3 | | | 2 | P-B, T-B | up in B |
| SLC14A1 | | | 2 | P-B, T-B | up in B |
| SNORD114-3 | | | 2 | P-B, T-B | up in B |
| TGFB3 | | TGFB3 | 2 | P-B, T-B | up in B |
| TIMP1 | | TIMP1 | 2 | P-B, T-B | up in B |
| | ERG | ERG | 2 | T-P, T-B | down in T |
| | AMACR | AMACR | 2 | T-P, T-B | down in T |
| | OR51E1 | OR51E1 | 2 | T-P, T-B | down in T |
| ENTPD5 | | | 1 | P-B | |
| GAS5 | | | 1 | P-B | |
| HOM1 | | | 1 | P-B | |
| OR51C1P | | | 1 | P-B | |
| SLC4A4 | | | 1 | P-B | |
| SNORA70 | | | 1 | P-B | |
| SNORD116-29 | | | 1 | P-B | |
| SNORD42A | | | 1 | P-B | |
| CAPG | | | 1 | P-B | |
| CD177 | | | 1 | P-B | |
| CD177 | | | 1 | P-B | |
| CD38 | | | 1 | P-B | |
| CRISPLD2 | | | 1 | P-B | |
| | | SNORD122 | 1 | T-B | |
| | | SNORD12C | 1 | T-B | |
| | | SNORD15A | 1 | T-B | |
| | | SNORD1A | 1 | T-B | |
| | | SNORD22 | 1 | T-B | |
| | | SNORD24 | 1 | T-B | |
| | | SNORD27 | 1 | T-B | |
| | | SNORD28 | 1 | T-B | |
| | | SNORD30 | 1 | T-B | |
| | | SNORD35A | 1 | T-B | |
| | | SNORD38A | 1 | T-B | |
| | | SNORD38B | 1 | T-B | |
| | | SNORD42B | 1 | T-B | |
| | | SNORD44 | 1 | T-B | |
| | | SNORD48 | 1 | T-B | |
| | | SNORD49A | 1 | T-B | |
| | | SNORD49B | 1 | T-B | |
| | | SNORD5 | 1 | T-B | |
| | | SNORD52 | 1 | T-B | |
| | | SNORD53 | 1 | T-B | |
| | | SNORD54 | 1 | T-B | |
| | | SNORD6 | 1 | T-B | |
| | | SNORD75 | 1 | T-B | |
| | | SNORD76 | 1 | T-B | |
| | | SNORD80 | 1 | T-B | |
| | | SNORD82 | 1 | T-B | |
| | | SNORD83A | 1 | T-B | |
| | | snoRNA | 1 | T-B | |
| | | snoRNA | 1 | T-B | |
| | | STEAP1 | 1 | T-B | |
| | | STEAP4 | 1 | T-B | |
| | | TARP | 1 | T-B | |
| | | TCEAL2 | 1 | T-B | |
| | | TDRD1 | 1 | T-B | |
| | | TFCP2L1 | 1 | T-B | |
| | | TGM4 | 1 | T-B | |
| | | TIMP3 | 1 | T-B | |
| | | TMBIM1 | 1 | T-B | |
| | | TMEFF2 | 1 | T-B | |
| | | TMSB15A | 1 | T-B | |
| | | TNS1 | 1 | T-B | |
| | | TP63 | 1 | T-B | |
| | | TRIM29 | 1 | T-B | |
| | | TSC22D3 | 1 | T-B | |
| | | TUBB2A | 1 | T-B | |
| | | TUBB2A | 1 | T-B | |
| | | TUBB2BP1 | 1 | T-B | |

| Pin-Benign | Tumor-PIN | Tumor-Benign | # comparison | Comparison | Trend based on FC |
|---|---|---|---|---|---|
| | | TXN | 1 | T-B | |
| | | UAP1 | 1 | T-B | |
| | | UPK1A | 1 | T-B | |
| | | VEGFA | 1 | T-B | |
| | | VSTM2L | 1 | T-B | |
| | | VTRNA1-2 | 1 | T-B | |
| | | WFDC2 | 1 | T-B | |
| | | ZFP36L1 | 1 | T-B | |
| | | ZFP36L2 | 1 | T-B | |
| | | ZNF532 | 1 | T-B | |
| | | ZNF827 | 1 | T-B | |
| | | SNORA9 | 1 | T-B | |
| | | SNORD113-4 | 1 | T-B | |
| | | ACPP | 1 | T-B | |
| | | ALDH2 | 1 | T-B | |
| | | ANPEP | 1 | T-B | |
| | | ANTXR2 | 1 | T-B | |
| | | ABCC4 | 1 | T-B | |
| | | ACSM1 | 1 | T-B | |
| | | ANXA2 | 1 | T-B | |
| | | APOBEC3C | 1 | T-B | |
| | | AQP3 | 1 | T-B | |
| | | AZGP1 | 1 | T-B | |
| | | BASP1 | 1 | T-B | |
| | | C15orf51 | 1 | T-B | |
| | | C15orf51 | 1 | T-B | |
| | | C15orf51 | 1 | T-B | |
| | | C15orf51 | 1 | T-B | |
| | | C19orf48 | 1 | T-B | |
| | | CACNA1D | 1 | T-B | |
| | | CACNG4 | 1 | T-B | |
| | | CAMKK2 | 1 | T-B | |
| | | CAPG | 1 | T-B | |
| | | CD177 | 1 | T-B | |
| | | CD177 | 1 | T-B | |
| | | CD24 | 1 | T-B | |
| | | CKB | 1 | T-B | |
| | | CPLX3 | 1 | T-B | |
| | | CPLX3 | 1 | T-B | |
| | | CRABP2 | 1 | T-B | |
| | | CREB3L1 | 1 | T-B | |
| | | CRISP3 | 1 | T-B | |
| | | CRISPLD2 | 1 | T-B | |
| | | CRYAB | 1 | T-B | |
| | | CTSB | 1 | T-B | |
| | | CYP27A1 | 1 | T-B | |
| | | EFEMP1 | 1 | T-B | |
| | | EPAS1 | 1 | T-B | |
| | | EPCAM | 1 | T-B | |
| | | EPCAM | 1 | T-B | |
| | | FABP5 | 1 | T-B | |
| | | FABP5 | 1 | T-B | |
| | | FADS2 | 1 | T-B | |
| | | FNIP2 | 1 | T-B | |
| | | GABRE | 1 | T-B | |
| | | GCNT1 | 1 | T-B | |
| | | GDF15 | 1 | T-B | |
| | | GMPR | 1 | T-B | |
| | | GOLM1 | 1 | T-B | |
| | | GSTM2 | 1 | T-B | |
| | | GUCY1A3 | 1 | T-B | |
| | | GUSBP3 | 1 | T-B | |
| | | GUSBP3 | 1 | T-B | |
| | | HIST1H2BK | 1 | T-B | |
| | | HLA-A | 1 | T-B | |
| | | HLA-A | 1 | T-B | |
| | | HOXD10 | 1 | T-B | |
| | | ID3 | 1 | T-B | |
| | | IFITM3 | 1 | T-B | |
| | | ITGB4 | 1 | T-B | |
| | | KRT19 | 1 | T-B | |
| | | KRT23 | 1 | T-B | |
| | | LDHB | 1 | T-B | |
| | | LMAN1L | 1 | T-B | |
| | | MAL2 | 1 | T-B | |
| | | MEIS2 | 1 | T-B | |
| | | MIR27A | 1 | T-B | |

| Pin-Benign | Tumor-PIN | Tumor-Benign | # comparison | Comparison | Trend based on FC |
|---|---|---|---|---|---|
| | | MPZL2 | 1 | T-B | |
| | | MSMB | 1 | T-B | |
| | | MT1F | 1 | T-B | |
| | | MT1L | 1 | T-B | |
| | | MT1M | 1 | T-B | |
| | | MT2A | 1 | T-B | |
| | | MT2A | 1 | T-B | |
| | | MUC12 | 1 | T-B | |
| | | MUC12 | 1 | T-B | |
| | | MYC | 1 | T-B | |
| | | MYO6 | 1 | T-B | |
| | | MYOF | 1 | T-B | |
| | | NDRG2 | 1 | T-B | |
| | | NUCB2 | 1 | T-B | |
| | | ODC1 | 1 | T-B | |
| | | OLFM4 | 1 | T-B | |
| | | OR51E2 | 1 | T-B | |
| | | PAK1IP1 | 1 | T-B | |
| | | PARM1 | 1 | T-B | |
| | | PDK4 | 1 | T-B | |
| | | PDLIM1 | 1 | T-B | |
| | | PGM5 | 1 | T-B | |
| | | PLA1A | 1 | T-B | |
| | | PLA2G7 | 1 | T-B | |
| | | PLP2 | 1 | T-B | |
| | | POTEE | 1 | T-B | |
| | | POTEE | 1 | T-B | |
| | | POTEF | 1 | T-B | |
| | | POTEG | 1 | T-B | |
| | | POTEM | 1 | T-B | |
| | | POTEM | 1 | T-B | |
| | | PTP4A3 | 1 | T-B | |
| | | PTRF | 1 | T-B | |
| | | RALGAPA2 | 1 | T-B | |
| | | RCAN3 | 1 | T-B | |
| | | REPS2 | 1 | T-B | |
| | | RNF185 | 1 | T-B | |
| | | RPL36A | 1 | T-B | |
| | | RPLP0 | 1 | T-B | |
| | | SCGB1A1 | 1 | T-B | |
| | | SCNN1A | 1 | T-B | |
| | | SEL1L | 1 | T-B | |
| | | SERPINB11 | 1 | T-B | |
| | | SERPINF1 | 1 | T-B | |
| | | SFN | 1 | T-B | |
| | | SLC15A2 | 1 | T-B | |
| | | SLC22A17 | 1 | T-B | |
| | | SNAI2 | 1 | T-B | |
| | | SNORA10 | 1 | T-B | |
| | | SNORA10 | 1 | T-B | |
| | HMGCS2 | | 1 | T-P | |
| | MIR21 | | 1 | T-P | |
| | SNORA75 | | 1 | T-P | |

-continued

| Pin-Benign | Tumor-PIN | Tumor-Benign | # comparison | Comparison | Trend based on FC |
|---|---|---|---|---|---|
| | SPRY4 | | 1 | T-P | |
| | DMXL1 | | 1 | T-P | |

FC positive in PIN-Benign samples: HPN, SNORA1, SNORA33, SNORA51, SNORA64, SNORA67, SNORA69, SNORA71A, SNORA71C, SNORA71D, SNORA73A, SNORA74A, SNORA80B, SNORD116-11, SNORD36B, SNORD36C, SNORD37, SNORD47, SNORD60, SNORD74, SNORD78, TRIB1, GSTP1, ENTPD5, GAS5, HOM1 OR51C1P, SLC4A4, SNORA70, SNORD116-29, and SNORD42A.
FC Negative in PIN-Benign samples: PTCH2, HSPB1, LSAMP, ANTXR1, ANXA1, LGALS3BP, MIR205, MME, NBL1, NEFH, N1PAL3, SLC14A1, SNORD114-3, TGFB3, TIMP1, CAPG, CD177, CD38, and CRISPLD2.
FC positive in Tumor-PIN samples: ERG, AMACR, and OR51EI.
FC negative in Tumor-PIN samples: PTCH2, C10orf116, GDEP, ID1, KRT15, KRT17, KRT5, MT1E, MT1G, MT1X, MUC3A, MUC3A, PSCA, TNS4, VSIG2, HMGCS2, MIR21, SNORA75, SPRY4, and DMXL1.
FC positive in Tumor-Benign samples: HPN, SNORA1, SNORA33, SNORA51, SNORA64, SNORA67, SNORA69, SNORA71A, SNORA71C, SNORA71D, SNORA73A, SNORA74A, SNORA80B, SNORD116-11, SNORD36B, SNORD36C, SNORD37, SNORD47, SNORD60, SNORD74, SNORD78, TRIB1, ERG, AMACR, OR51E1, SNORD122, SNORD12C, SNORD15A, SNORD1A, SNORD22, SNORD24, SNORD27, SNORD28, SNORD30, SNORD35A, SNORD38A, SNORD38B, SNORD42B, SNORD44, SNORD48, SNORD49A, SNORD49B, SNORD5, SNORD52, SNORD53, SNORD54, SNORD6, SNORD75, SNORD76, SNORD80, SNORD82, SNORD83A, snoRNA, STEAP1, STEAP4, TARP, TDRD1, TMEFF2, TMSB15A, TUBB2A, TUBB2BP1, TXN, UAP1, VSTM2L, VTRNA1-2, SNORA9, ABCC4, ACSM1, C19orf48, CACNA1D, CAMKK2, CD24, CREB3L1, CRISP3, EPCAM, FABP5, FNIP2, GCNT1, GDF15, GOLM1, GUCY1A3, GUSBP3, HIST1H2BK, MAL2, MYC, MYO6, NUCB2, ODC1, OR51E2, PLA1A, PLA2G7, PTP4A3, RALGAPA2, REPS2, RPL36A, RPLP0, SEL1L, and SNORA10.
FC negative in Tumor-Benign samples: PTCH2, C10orf116, GDEP, ID1, KRT15, KRT17, KRT5, MT1E, MT1G, MT1X, MUC3A, PSCA, TNS4, VSIG2, GSTP1, HSPB1, LSAMP, ANTXR1, ANXA1, LGALS3BP, MIR205, MME, NBL1, NEFH, NIPAL3, SLC14A1, SNORD114-3, TGFB3, TIMP1, TCEAL2, TFCP2L1, TGM4, TIMP3, TMBIM1, TNS1, TP63, TRIM29, TSC22D3, UPKIA, VEGFA, WFDC2, ZFP36L1, ZFP36L2, ZNF532, ZNF827, SNORD113-4, ACPP, ALDH2, ANPEP, ANTXR2, ANXA2, APOBEC3C, AQP3, AZGP1, BASP1, C15orf51, CACNG4, CAPG, CD177, CD38, CKB, CPLX3, CRABP2, CRISPLD2, CRYAB, CTSB, CYP27A1, EFEMP1, EPAS1, FADS2, GABRE, GMPR, GSTM2, HLA-A, HOXDIO, ID3, IFITM3, ITGB4, KRT19, KRT23, LDHB, LMANIL, MEIS2, MIR27A, MPZL2, MSMB, MT1F, MT1L, MTIM, MT2A, MUC12, MYOF, NDRG2, OLFM4, PAKI1P1, PARM1, PDK4, PDLIM1, PGM5, PLP2, POTEE, POTEF, POTEG, POTEM, PTRF, RCAN3, RNFI85, SCGB1A1, SCNN1A, SERPINB11, SERPINF1, SFN, SLC15A2, SLC22A17, and SNAI2.

Table 7. Within compartment differentially expressed genes of statistical significance for the epithelial T-P, T-B, P-B (A) and and stromal sT-sP, sT-sB and sP-sB comparison (B)

| Affymetrix ID | Gene | logFC | adj.P.Val |
|---|---|---|---|
| stroma PIN-stroma Benign | | | |
| 8127193 | BMP5 | −0.5849 | 0.04562 |
| 7962455 | NELL2 | −0.68577 | 0.035758 |
| stroma Tumor-stroma PIN | | | |
| NA | | | |
| stroma Tumor-stroma Benign | | | |
| 8030753 | KLK3 | 1.45558 | 0.000389 |
| 8030768 | KLK2 | 1.443873 | 0.000305 |
| 8180366 | NA | 1.347155 | 0.045557 |
| 8180367 | NA | 1.347155 | 0.045557 |
| 8098439 | EPCAM | 1.129716 | 0.001218 |
| 8108629 | VTRNA1-2 | 1.113824 | 0.033255 |
| 7901175 | TSPAN1 | 1.067972 | 0.002287 |
| 7983393 | SORD | 1.033584 | 0.002878 |
| 8027002 | GDF15 | 0.988487 | 0.009351 |
| 8108420 | SNORA74A | 0.980191 | 0.008986 |
| 8070467 | TMPRSS2 | 0.941364 | 0.032579 |
| 8162117 | GOLM1 | 0.899859 | 0.024102 |
| 8038655 | KLK4 | 0.861369 | 0.001428 |
| 8097056 | SNORA24 | 0.839021 | 0.013137 |
| 8125843 | SPDEF | 0.823875 | 0.001653 |
| 7978706 | FOXA1 | 0.799363 | 0.001218 |
| 7972297 | ABCC4 | 0.780219 | 0.02526 |
| 8125149 | SLC44A4 | 0.763406 | 0.020797 |
| 8178653 | SLC44A4 | 0.763406 | 0.020797 |
| 8179861 | SLC44A4 | 0.763406 | 0.020797 |
| 7916432 | DHCR24 | 0.762503 | 0.03123 |
| 8139087 | SFRP4 | 0.729489 | 0.00209 |
| 8019392 | FASN | 0.722887 | 0.013137 |
| 8019762 | P4HB | 0.721664 | 9.64E−05 |
| 8066258 | SNORA71A | 0.718002 | 0.039518 |
| 8016484 | PRAC | 0.701345 | 0.028525 |
| 8121489 | AMD1 | 0.693993 | 0.013137 |
| 8149811 | NKX3-1 | 0.686398 | 0.002878 |
| 8021376 | NEDD4L | 0.680371 | 0.028454 |
| 8050240 | ODC1 | 0.668529 | 0.013773 |
| 8106573 | THBS4 | 0.660172 | 0.001508 |
| 7996837 | CDH1 | 0.648023 | 0.033255 |
| 7963567 | KRT8 | 0.637383 | 0.020131 |
| 8019250 | P4HB | 0.63353 | 0.000129 |
| 8122279 | KIAA1244 | 0.608693 | 0.013958 |
| 7899480 | SNORA73A | 0.607363 | 0.027729 |
| 7916584 | TACSTD2 | 0.59779 | 0.00628 |
| 8075657 | NA | −0.59049 | 0.027792 |
| 8167592 | PAGE4 | −0.59668 | 0.013958 |
| 7922130 | DPT | −0.59876 | 0.013137 |
| 7951977 | FXYD6 | −0.67542 | 8.37E−05 |
| 7962455 | NELL2 | −0.71823 | 0.00146 |
| 7896623 | NA | −0.73692 | 0.027321 |
| 7987315 | ACTC1 | −0.76484 | 0.013137 |
| 8105084 | C7 | −0.77399 | 0.03154 |
| 7975390 | SMOC1 | −0.79155 | 0.00084 |
| 8024062 | CFD | −0.82366 | 0.000305 |
| 7937772 | IGF2 | −0.97934 | 0.008986 |
| 7965873 | IGF1 | −0.99699 | 0.005631 |

FC negative in stoma PIN-stroma Benign samples: BMP5 and NELL2.
FC positive in stroma Tumor-stroma Benign samples: KLK3, KLK2, EPCAM, VTRNA1-2, TSPAN1, SORD, GDF15, SNORA74A, TMPRSS2, GOLM1, KLK4, SNORA24, SPDEF, FOXA1, ABCC4, SLC44A4, DHCR24, SFRP4,FASN, P4HB,SNORA71A, PRAC,AMD1, NKX3-1, NEDD4L, ODC1, THBS4, CDH1, KRT8, KIAA1244, and SNORA73A.
FC negative in stroma Tumor-stroma Benign samples: TACSTD2, PAGE4, DPT, FXYD6, NELL2, ACTC1, C7, SMOC1, CFD, IGF2, and IGF1.

Figure 9A:
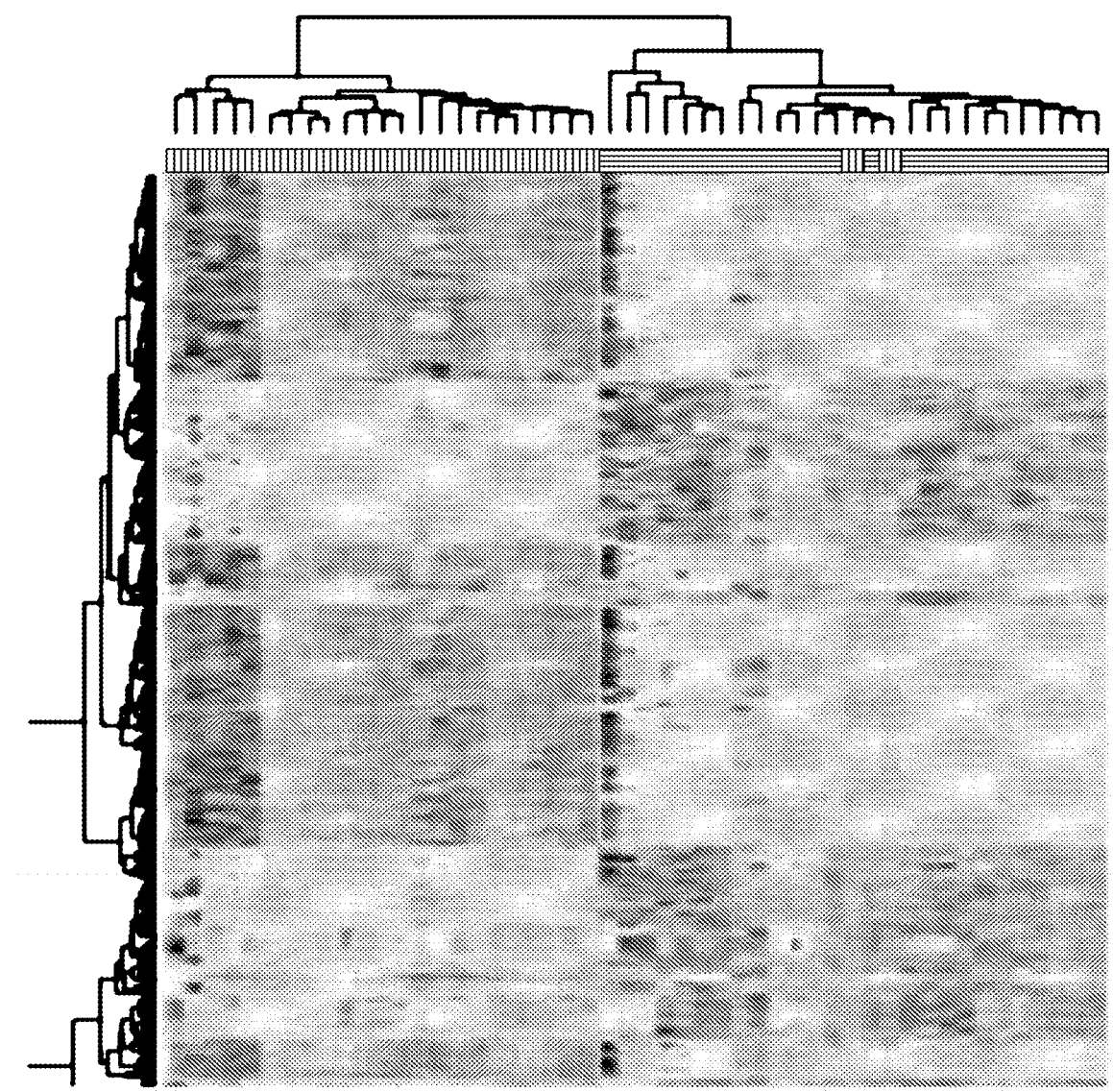
FIG. 9A is a heatmap showing the differentially expressed gene sets for the B-sB epithelial-stromal comparisons.
Figure 9B:
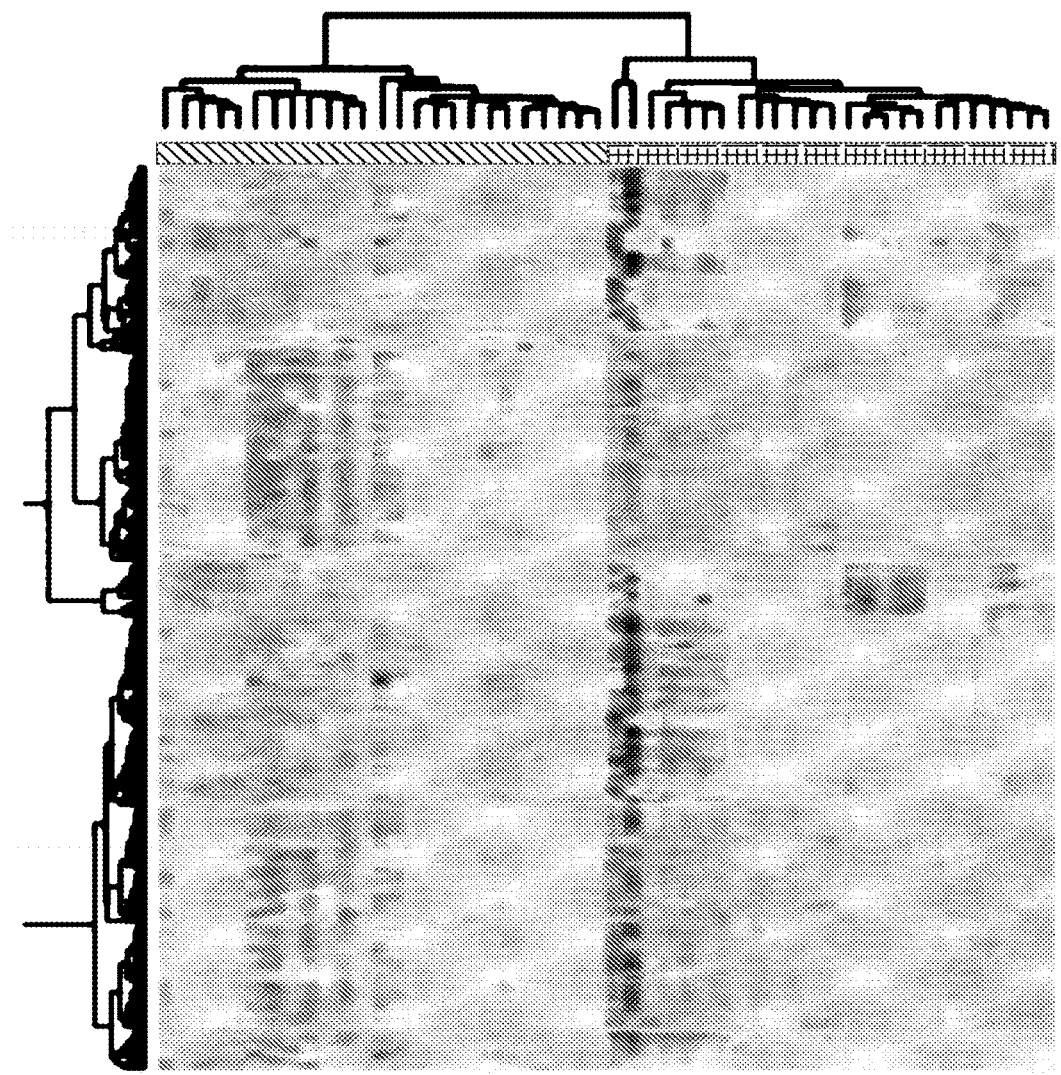
FIG. 9B is a heatmap showing the differentially expressed gene sets for the P-sP epithelial-stromal comparisons.
Figure 9C:
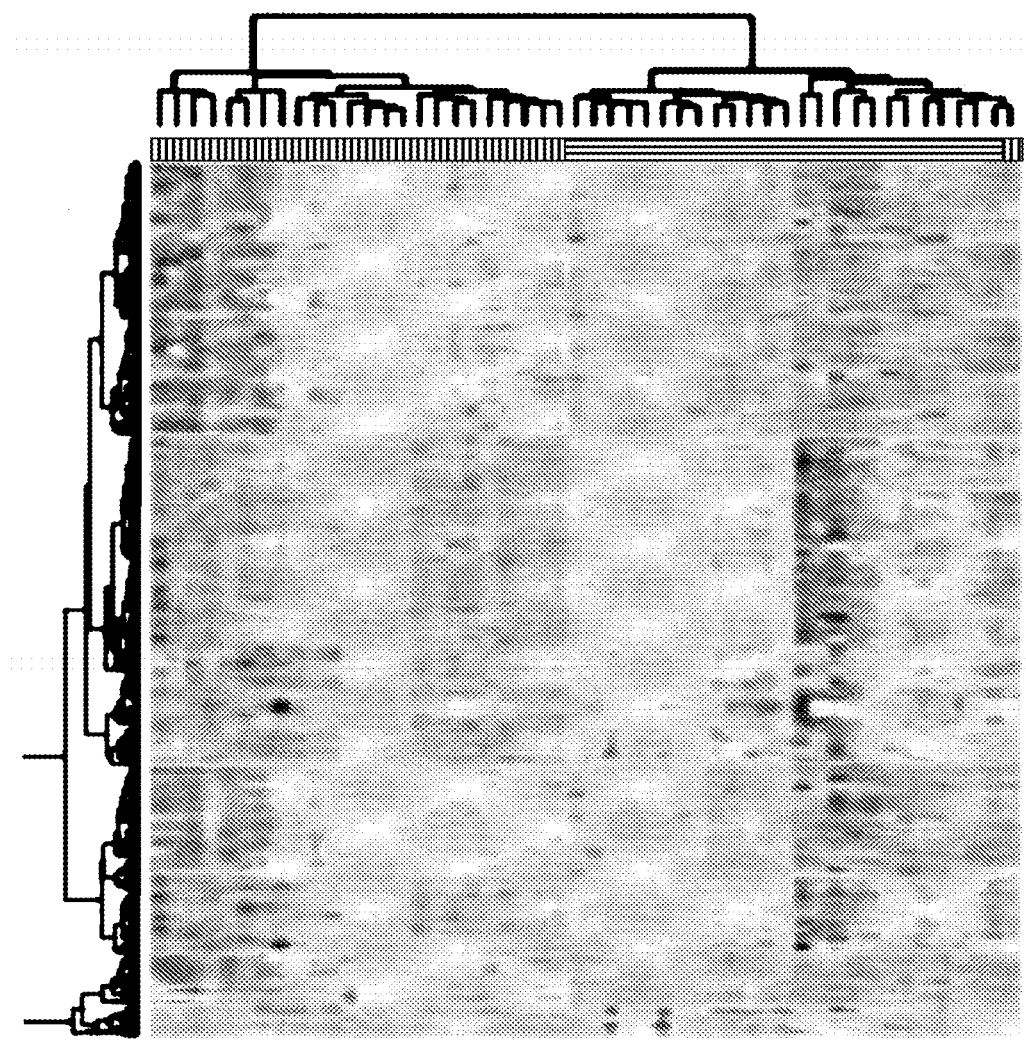
FIG. 9C is a heatmap showing the differentially expressed gene sets for the T-sT epithelial-stromal comparisons.

Example 6: Differentially Expressed Genes Between Epithelium and Stroma Exclusively Associated with Malignancy Comparisons across the epithelial and the stromal compartments (FIG. 7B) were performed, comparing B-sB, P-sP and T-sT and plotted the differentially expressed genes as heatmaps (FIG. 9A-9C). The number of differentially expressed genes (for each across compartment comparison) is tabulated in FIG. 9D. Approximately 20% of the differentially expressed genes were common to all comparisons. Tabulated gene lists for each compartment comparison are provided in Table 8.

Table 8. Across compartment differentialy expressed genes of statistical significance for the B-sB, P-sP and T-sT epithelial-stromal comparisons.

| epithelial Benign-stromal benign | | | | epithelial PIN-stromal PIN | | | | epithelial tumor-stromal tumor | | | |
|---|---|---|---|---|---|---|---|---|---|---|---|
| Affymetrix ID | Gene | LogFC | Adj. P.Val | Affymetrix ID | Gene | LogFC | Adj. P.Val | Affymetrix ID | Gene | LogFC | Adj. P.Val |
| 7927529 | MSMB | 3.183183 | 8.55E-11 | 8030753 | KLK3 | 2.235404 | 1.31E-12 | 8162117 | GOLM1 | 1.619828 | 1.51E-09 |
| 8082673 | ACPP | 2.97426 | 3.30E-16 | 8030768 | KLK2 | 2.227584 | 4.59E-13 | 8131919 | NPY | 1.593615 | 0.004129 |
| 8030753 | KLK3 | 2.900432 | 2.08E-18 | 7901175 | TSPAN1 | 2.103336 | 1.99E-15 | 8030753 | KLK3 | 1.588711 | 3.69E-07 |
| 8030768 | KLK2 | 2.890765 | 4.71E-19 | 8070467 | TMPRSS2 | 2.045628 | 2.63E-12 | 8030768 | KLK2 | 1.556662 | 3.03E-07 |
| 8070467 | TMPRSS2 | 2.516376 | 1.10E-16 | 8096027 | GDEP | 1.9719 | 7.01E-06 | 7901175 | TSPAN1 | 1.477351 | 9.91E-09 |
| 8141374 | AZGP1 | 2.512111 | 3.81E-17 | 8082673 | ACPP | 1.860907 | 7.30E-08 | 8180366 | NA | 1.406998 | 0.001545 |
| 8072229 | NEFH | 2.507563 | 6.99E-12 | 8095585 | SLC4A4 | 1.812609 | 4.39E-14 | 8180367 | NA | 1.406998 | 0.001545 |
| 7977456 | POTEG | 2.452374 | 2.18E-12 | 8162117 | GOLM1 | 1.761441 | 3.48E-11 | 7945991 | OR51E2 | 1.389187 | 0.001716 |
| 7983393 | SORD | 2.406299 | 3.83E-19 | 8097056 | SNORA24 | 1.74978 | 8.32E-14 | 8108420 | SNORA74A | 1.3829 | 9.04E-08 |
| 7923792 | SLC45A3 | 2.327968 | 5.10E-18 | 7948058 | FOLH1 | 1.749166 | 1.85E-07 | 8082673 | ACPP | 1.326955 | 0.000183 |
| 8096027 | GDEP | 2.28285 | 2.19E-07 | 7942998 | FOLH1B | 1.727296 | 2.00E-07 | 7948058 | FOLH1 | 1.322837 | 0.000119 |
| 7972983 | POTEM | 2.203038 | 6.27E-12 | 8066258 | SNORA71A | 1.706536 | 1.04E-13 | 8111430 | AMACR | 1.313653 | 1.58E-06 |
| 8074170 | POTEM | 2.158326 | 6.82E-12 | 7923792 | SLC45A3 | 1.705001 | 2.15E-11 | 7942998 | FOLH1B | 1.312567 | 0.000115 |
| 7901175 | TSPAN1 | 2.144819 | 7.46E-16 | 8180366 | NA | 1.681724 | 8.79E-05 | 8090690 | CPNE4 | 1.304445 | 2.57E-09 |
| 7996837 | CDH1 | 2.091999 | 1.37E-21 | 8180367 | NA | 1.681724 | 8.79E-05 | 8125149 | SLC44A4 | 1.242913 | 2.38E-08 |
| 7979743 | RDH11 | 2.049497 | 4.68E-15 | 8141374 | AZGP1 | 1.676429 | 2.66E-09 | 8178653 | SLC44A4 | 1.242913 | 2.38E-08 |
| 8149811 | NKX3-1 | 1.966383 | 3.19E-25 | 7977456 | POTEG | 1.661685 | 1.09E-06 | 8179861 | SLC44A4 | 1.242913 | 2.38E-08 |
| 7903592 | KIAA1324 | 1.954591 | 1.27E-16 | 8014755 | SNORA21 | 1.654881 | 1.80E-16 | 7923792 | SLC45A3 | 1.230318 | 1.35E-06 |
| 7991335 | ANPEP | 1.938454 | 1.26E-07 | 8180366 | NA | 1.639598 | 7.33E-10 | 8134030 | STEAP1 | 1.215929 | 7.14E-07 |
| 8131919 | NPY | 1.899959 | 0.000422 | 8049746 | TRPM8 | 1.639215 | 1.47E-09 | 8098439 | EPCAM | 1.203273 | 2.85E-06 |
| 8119898 | VEGFA | 1.867243 | 2.19E-17 | 8108420 | SNORA74A | 1.628411 | 2.45E-10 | 7945997 | NA | 1.201683 | 0.003046 |
| 7916432 | DHCR24 | 1.844476 | 1.43E-14 | 8125149 | SLC44A4 | 1.604303 | 8.76E-13 | 7937952 | OR51E1 | 1.18926 | 2.49E-05 |
| 8038655 | KLK4 | 1.843406 | 2.05E-18 | 8178653 | SLC44A4 | 1.604303 | 8.76E-13 | 8097056 | SNORA24 | 1.182483 | 2.82E-07 |
| 8125149 | SLC44A4 | 1.759316 | 1.17E-14 | 8179861 | SLC44A4 | 1.604303 | 8.76E-13 | 8014755 | SNORA21 | 1.180671 | 1.32E-09 |
| 8178653 | SLC44A4 | 1.759316 | 1.17E-14 | 8090690 | CPNE4 | 1.599123 | 4.17E-13 | 7972297 | ABCC4 | 1.180261 | 3.51E-07 |
| 8179861 | SLC44A4 | 1.759316 | 1.17E-14 | 7996837 | CDH1 | 1.586545 | 1.08E-14 | 8070467 | TMPRSS2 | 1.1793 | 5.43E-05 |
| 7913216 | PLA2G2A | 1.719272 | 2.39E-06 | 8138381 | AGR2 | 1.576126 | 7.39E-07 | 7979743 | RDH11 | 1.171357 | 4.07E-06 |
| 8055153 | POTEF | 1.687359 | 1.25E-12 | 7979743 | RDH11 | 1.550132 | 7.71E-10 | 8029489 | BCAM | 1.164914 | 1.79E-13 |
| 8125843 | SPDEF | 1.681152 | 1.00E-16 | 8125843 | SPDEF | 1.546042 | 7.68E-15 | 7922408 | SNORD78 | 1.16117 | 1.36E-05 |
| 7939314 | EHF | 1.670268 | 7.51E-21 | 8149811 | NKX3-1 | 1.539507 | 3.34E-18 | 8125843 | SPDEF | 1.148709 | 3.66E-09 |
| 8045257 | POTEE | 1.661108 | 1.58E-12 | 7903592 | KIAA1324 | 1.52934 | 1.45E-11 | 8177222 | CD24 | 1.133273 | 1.29E-07 |
| 8097056 | SNORA24 | 1.65439 | 1.17E-12 | 8170863 | SNORA70 | 1.528128 | 6.84E-15 | 8021376 | NEDD4L | 1.128677 | 4.44E-08 |
| 8135033 | MUC12 | 1.63522 | 6.74E-06 | 7972983 | POTEM | 1.519675 | 1.28E-06 | 8041853 | EPCAM | 1.12562 | 1.05E-09 |
| 8055222 | POTEE | 1.629 | 3.24E-11 | 8131919 | NPY | 1.518366 | 0.005782 | 8001007 | PRSS8 | 1.124871 | 1.65E-10 |
| 7948058 | FOLH1 | 1.619235 | 1.59E-06 | 8025498 | SNORA70 | 1.508335 | 1.80E-14 | 8066258 | SNORA71A | 1.110862 | 8.59E-07 |
| 7979473 | DHRS7 | 1.618291 | 5.71E-13 | 7983393 | SORD | 1.506125 | 1.67E-09 | 7979473 | DHRS7 | 1.108873 | 5.72E-07 |
| 8056222 | DPP4 | 1.613516 | 6.24E-11 | 8096030 | NA | 1.484517 | 1.98E-06 | 8134036 | STEAP2 | 1.108293 | 1.79E-09 |
| 8079279 | TGM4 | 1.60369 | 0.004084 | 8074170 | POTEM | 1.482422 | 1.49E-06 | 8138381 | AGR2 | 1.106629 | 0.000823 |
| 7978706 | FOXA1 | 1.596363 | 5.70E-17 | 8050253 | SNORA80B | 1.476784 | 5.48E-17 | 8149811 | NKX3-1 | 1.106053 | 7.69E-11 |
| 7942998 | FOLH1B | 1.577359 | 2.35E-06 | 7978706 | FOXA1 | 1.476504 | 3.27E-15 | 7983393 | SORD | 1.092517 | 1.56E-05 |
| 7984466 | NA | 1.57072 | 3.67E-09 | 7945982 | OR51E2 | 1.469755 | 0.000683 | 8038655 | KLK4 | 1.088055 | 4.46E-08 |
| 8180366 | NA | 1.535888 | 0.000446 | 8056222 | DPP4 | 1.466888 | 1.94E-09 | 7978706 | FOXA1 | 1.087758 | 2.76E-09 |
| 8180367 | NA | 1.535888 | 0.000446 | 7972297 | ABCC4 | 1.449664 | 3.19E-10 | 7988440 | NA | 1.085757 | 5.74E-05 |
| 7992732 | ZG16B | 1.520399 | 1.50E-19 | 7916432 | DHCR24 | 1.447122 | 4.84E-10 | 8122279 | KIAA1244 | 1.083512 | 3.81E-10 |
| 7916584 | TACSTD2 | 1.50207 | 6.10E-20 | 8098439 | EPCAM | 1.428038 | 1.78E-08 | 8080555 | C9orf152 | 1.08031 | 4.35E-11 |
| 8141661 | MUC3A | 1.501873 | 4.23E-08 | 7939314 | EHF | 1.41841 | 1.05E-16 | 7996837 | CDH1 | 1.077145 | 7.84E-08 |
| 7963567 | KRT8 | 1.498868 | 3.15E-15 | 7927529 | MSMB | 1.416688 | 0.005105 | 7922418 | SNORD74 | 1.072562 | 2.41E-07 |
| 8027748 | FXYD3 | 1.493936 | 2.38E-18 | 7980080 | ENTPD5 | 1.404564 | 8.30E-14 | 8025498 | SNORA70 | 1.069176 | 2.96E-08 |
| 8121489 | AMD1 | 1.466009 | 5.68E-14 | 8038655 | KLK4 | 1.387146 | 3.63E-12 | 7916432 | DHCR24 | 1.065858 | 5.36E-06 |
| 8030980 | ZNF525 | 1.460187 | 9.49E-10 | 7974027 | NA | 1.384554 | 2.55E-11 | 8170863 | SNORA70 | 1.06528 | 2.62E-09 |
| 8040292 | GREB1 | 1.445173 | 1.81E-13 | 7922408 | SNORD78 | 1.370346 | 1.74E-07 | 7922410 | SNORD44 | 1.060701 | 5.03E-05 |
| 8099967 | RBM47 | 1.430605 | 2.91E-20 | 8027002 | GDF15 | 1.365341 | 1.18E-07 | 8049487 | MLPH | 1.047683 | 6.04E-11 |
| 8159379 | TMEM141 | 1.420318 | 2.93E-22 | 8004508 | SNORA67 | 1.361515 | 1.77E-11 | 7905672 | CREB3L4 | 1.047445 | 1.06E-09 |
| 7984914 | CPLX3 | 1.412399 | 1.95E-13 | 8121489 | AMD1 | 1.355563 | 1.92E-12 | 7916112 | RAB3B | 1.039604 | 5.35E-09 |
| 8044804 | DBI | 1.40849 | 2.45E-13 | 8021376 | NEDD4L | 1.353215 | 4.57E-11 | 8019392 | FASN | 1.033775 | 1.87E-07 |
| 8162117 | GOLM1 | 1.406519 | 9.41E-08 | 8143499 | TRPV6 | 1.33702 | 4.48E-12 | 7922416 | SNORD75 | 1.022823 | 5.34E-07 |
| 7984892 | LMAN1L | 1.403187 | 2.72E-15 | 7998666 | SNORA64 | 1.333483 | 7.32E-12 | 8164215 | SNORA65 | 1.017228 | 1.88E-08 |
| 8098439 | EPCAM | 1.397227 | 3.96E-08 | 8164215 | SNORA65 | 1.333142 | 3.10E-13 | 8159006 | SNORD36B | 1.01451 | 5.60E-06 |
| 8154725 | KRT18 | 1.393888 | 3.99E-12 | 8049487 | MLPH | 1.316281 | 7.61E-16 | 8143499 | TRPV6 | 1.013525 | 1.38E-07 |
| 8160670 | AQP3 | 1.393635 | 2.61E-13 | 7979473 | OHRS7 | 1.311627 | 2.36E-09 | 8057803 | TMEFF2 | 1.013109 | 0.004247 |
| 8090690 | CPNE4 | 1.393389 | 1.47E-10 | 8107474 | DMXL1 | 1.305186 | 2.19E-11 | 8027002 | GDF15 | 1.011078 | 0.000129 |
| 8143499 | TRPV6 | 1.382983 | 1.09E-12 | 7945997 | NA | 1.304968 | 0.000937 | 7903592 | KIAA1324 | 1.007217 | 8.74E-06 |
| 8138381 | AGR2 | 1.368091 | 2.13E-05 | 8134030 | STEAP1 | 1.292389 | 9.04E-08 | 8016484 | PRAC | 1.004577 | 2.36E-06 |
| 8135015 | MUC3A | 1.367161 | 4.04E-08 | 8134036 | STEAP2 | 1.286959 | 2.79E-12 | 7916584 | TACSTD2 | 0.998743 | 1.17E-10 |
| 7969574 | MIR622 | 1.355819 | 2.79E-12 | 8154725 | KRT18 | 1.277931 | 1.33E-10 | 7980080 | ENTPD5 | 0.9981 | 7.03E-08 |
| 8153060 | NDRG1 | 1.351256 | 1.78E-15 | 7969574 | MIR622 | 1.277564 | 3.10E-11 | 8122144 | SNORA33 | 0.996286 | 7.89E-07 |
| 8049394 | TRPM8 | 1.351013 | 6.01E-07 | 7905677 | CREB3L4 | 1.269302 | 2.12E-13 | 8174715 | SNORA69 | 0.989876 | 4.93E-10 |
| 8049487 | MLPH | 1.35043 | 2.09E-16 | 8019392 | FASN | 1.25107 | 2.33E-10 | 7998666 | SNORA64 | 0.983901 | 3.92E-07 |
| 8021376 | NEDD4L | 1.342288 | 7.11E-11 | 8055153 | POTEF | 1.245654 | 7.91E-08 | 7975238 | PLEKHH1 | 0.977552 | 5.18E-10 |
| 7977452 | FLJ39632 | 1.333924 | 3.42E-11 | 8045257 | POTEE | 1.244101 | 6.09E-08 | 7939314 | EHF | 0.96898 | 4.12E-09 |
| 7952830 | NCAPD3 | 1.323004 | 3.86E-08 | 7920875 | SCARNA4 | 1.236284 | 6.53E-11 | 8109999 | ERGIC1 | 0.967921 | 5.85E-14 |
| 8074168 | FLJ39632 | 1.319443 | 8.52E-12 | 8016484 | PRAC | 1.234456 | 4.52E-09 | 8154725 | KRT18 | 0.966769 | 1.29E-06 |
| 7948588 | SYT7 | 1.31302 | 4.58E-20 | 7916584 | TACSTD2 | 1.232449 | 4.75E-15 | 7895405 | NA | 0.966367 | 4.88E-05 |
| 7988426 | SLC30A4 | 1.294676 | 4.38E-13 | 8066262 | SNORA71D | 1.228781 | 8.34E-14 | 8140840 | STEAP4 | 0.965006 | 9.36E-07 |
| 7953291 | C09 | 1.28937 | 1.50E-17 | 8141661 | MUC3A | 1.224728 | 7.19E-06 | 7905731 | NA | 0.963174 | 7.95E-07 |

-continued

| epithelial Benign-stromal benign | | | | epithelial PIN-stromal PIN | | | | epithelial tumor-stromal tumor | | | |
|---|---|---|---|---|---|---|---|---|---|---|---|
| Affymetrix ID | Gene | LogFC | Adj. P.Val | Affymetrix ID | Gene | LogFC | Adj. P.Val | Affymetrix ID | Gene | LogFC | Adj. P.Val |
| 8098204 | CPE | 1.289163 | 1.13E−10 | 8122279 | KIAA1244 | 1.217671 | 1.73E−12 | 8050253 | SNORA80B | 0.960237 | 1.43E−08 |
| 7974027 | NA | 1.285992 | 5.04E−10 | 7982028 | SNORD115-11 | 1.215324 | 6.66E−05 | 8067233 | PMEPA1 | 0.958461 | 1.41E−08 |
| 8147697 | GRHL2 | 1.283618 | 3.02E−17 | 7982064 | SNORD115-11 | 1.215324 | 6.66E−05 | 8019250 | P4HB | 0.93401 | 6.11E−13 |
| 8049799 | AN07 | 1.271174 | 1.78E−12 | 7982078 | SNORD115-11 | 1.215324 | 6.66E−05 | 7969574 | MIR622 | 0.93385 | 1.24E−06 |
| 7898939 | NIPAL3 | 1.268607 | 1.66E−13 | 7982092 | SNORD115-11 | 1.215324 | 6.66E−05 | 7940667 | SNORA57 | 0.931283 | 3.80E−11 |
| 8028311 | SPINT2 | 1.266029 | 1.37E−21 | 7922418 | SNORD74 | 1.21243 | 3.71E−09 | 7922404 | SNORD80 | 0.926538 | 0.000125 |
| 8135031 | MUC12 | 1.264651 | 5.15E−06 | 7922410 | SNORD44 | 1.211892 | 2.22E−06 | 8127145 | ELOVL5 | 0.924254 | 1.10E−08 |
| 7905677 | CREB3L4 | 1.263496 | 2.72E−13 | 7982050 | SNORD115-11 | 1.210827 | 0.000105 | 7982084 | SNORD115-11 | 0.92365 | 0.005287 |
| 8117034 | GMPR | 1.25899 | 2.66E−15 | 7982016 | SNORD115-12 | 1.208462 | 7.57E−05 | 8139456 | SNORA9 | 0.923394 | 8.64E−08 |
| 7894529 | NA | 1.249674 | 2.72E−08 | 7982024 | SNORD115-12 | 1.208462 | 7.57E−05 | 8004508 | SNORA67 | 0.919992 | 5.54E−06 |
| 8019250 | P4HB | 1.244696 | 5.87E−20 | 7982030 | SNORD115-12 | 1.208462 | 7.57E−05 | 7951032 | SNORA1 | 0.914084 | 1.06E−06 |
| 8134036 | STEAP2 | 1.239657 | 1.45E−11 | 7913216 | PLA2G2A | 1.206476 | 0.001205 | 7974027 | NA | 0.9114 | 1.18E−05 |
| 8089851 | HGD | 1.238056 | 9.05E−11 | 7899480 | SNORA73A | 1.205291 | 4.17E−11 | 7951038 | SNORA40 | 0.910346 | 5.48E−06 |
| 8093278 | HGD | 1.238056 | 9.05E−11 | 8139456 | SNORA9 | 1.202447 | 3.89E−12 | 8148040 | MAL2 | 0.909407 | 4.70E−10 |
| 8029489 | BCAM | 1.237749 | 5.04E−15 | 7951038 | SNORA40 | 1.201505 | 1.38E−09 | 8018982 | CANT1 | 0.905754 | 6.04E−12 |
| 7899265 | SFN | 1.221646 | 1.30E−13 | 7982058 | SNORD115-26 | 1.199843 | 7.79E−05 | 8038624 | C19orf48 | 0.905648 | 3.36E−08 |
| 7964927 | TSPAN8 | 1.219288 | 3.94E−08 | 8135033 | MUC12 | 1.197335 | 0.001252 | 8050240 | ODC1 | 0.904474 | 1.40E−06 |
| 8019392 | FASN | 1.207145 | 9.51E−10 | 8055222 | POTEE | 1.188737 | 8.29E−07 | 8016487 | HOX813 | 0.895435 | 1.73E−08 |
| 8075182 | XBP1 | 1.206333 | 8.98E−15 | 8001007 | PRSS8 | 1.187762 | 9.42E−12 | 8019762 | P4HB | 0.895384 | 3.64E−10 |
| 8107474 | DMXL1 | 1.194909 | 7.40E−11 | 7982084 | SNORD115-11 | 1.181122 | 0.000174 | 7982058 | SNORD115-26 | 0.894033 | 0.005335 |
| 8001007 | PRSS8 | 1.193693 | 8.25E−12 | 7915227 | SNORA55 | 1.18056 | 1.81E−12 | 7915227 | SNORA55 | 0.893404 | 7.93E−08 |
| 8019762 | P4HB | 1.191018 | 4.79E−16 | 7977452 | FU39632 | 1.179171 | 3.09E−09 | 7982028 | SNORD115-11 | 0.893252 | 0.005595 |
| 7972297 | ABCC4 | 1.188104 | 2.22E−07 | 7937483 | SNORA52 | 1.178462 | 3.21E−15 | 7982064 | SNORD115-11 | 0.893252 | 0.005595 |
| 7982084 | SNORD115-11 | 1.187321 | 0.000186 | 8049799 | ANo7 | 1.172747 | 4.85E−11 | 7982078 | SNORD115-11 | 0.893252 | 0.005595 |
| 7935776 | SCO | 1.182853 | 4.37E−07 | 8098328 | GALNT7 | 1.170714 | 1.41E−12 | 7982092 | SNORD115-11 | 0.893252 | 0.005595 |
| 8016484 | PRAC | 1.182401 | 2.06E−08 | 7982094 | SNORD115-44 | 1.170665 | 7.38E−05 | 7998664 | SNORA1O | 0.888536 | 2.26E−08 |
| 7923958 | C10rf116 | 1.179368 | 1.92E−16 | 8078916 | SNORA6 | 1.169407 | 6.25E−12 | 8041204 | SNORA1O | 0.888536 | 2.26E−08 |
| 8016487 | HOXB13 | 1.17806 | 2.40E−13 | 8099967 | RBM47 | 1.167175 | 3.04E−15 | 7982050 | SNORD115-11 | 0.886402 | 0.007461 |
| 8001531 | MT1G | 1.163673 | 1.14E−06 | 7998664 | SNORA10 | 1.163182 | 4.33E−13 | 7963567 | KRT8 | 0.885007 | 1.62E−06 |
| 7948912 | CHRM1 | 1.163596 | 1.25E−20 | 8041204 | SNORA10 | 1.163182 | 4.33E−13 | 7982016 | SNORD115-12 | 0.88444 | 0.006253 |
| 8014755 | SNORA21 | 1.15937 | 1.58E−09 | 7951032 | SNORA1 | 1.154971 | 5.31E−10 | 7982024 | SNORD115-12 | 0.88444 | 0.006253 |
| 8149590 | NA | 1.1554 | 8.26E−08 | 8177222 | CD24 | 1.150971 | 5.25E−08 | 7982030 | SNORD115-12 | 0.88444 | 0.006253 |
| 7982016 | SNORD115-12 | 1.144899 | 0.00022 | 8050240 | ODC1 | 1.150162 | 6.25E−10 | 7892661 | NA | 0.882681 | 3.65E−06 |
| 7982024 | SNORD115-12 | 1.144899 | 0.00022 | 7982046 | SNORD115-20 | 1.149591 | 0.000111 | 7894562 | NA | 0.878254 | 0.000182 |
| 7982030 | SNORD115-12 | 1.144899 | 0.00022 | 8030980 | ZNF525 | 1.143196 | 1.29E−06 | 7945204 | ST14 | 0.877902 | 6.55E−11 |
| 8095585 | SLC4A4 | 1.138125 | 1.06E−06 | 8048116 | NA | 1.143107 | 2.40E−10 | 8120783 | MY06 | 0.876764 | 1.63E−08 |
| 7982028 | SNORD115-11 | 1.137546 | 0.000237 | 8027748 | FXYD3 | 1.142761 | 2.05E−12 | 8141374 | AZGP1 | 0.873458 | 0.003128 |
| 7982064 | SNORD115-11 | 1.137546 | 0.000237 | 8019250 | P4HB | 1.1418 | 9.05E−18 | 7962827 | SNORA2A | 0.868487 | 5.99E−06 |
| 7982078 | SNORD115-11 | 1.137546 | 0.000237 | 7963567 | KRT8 | 1.141592 | 4.70E−10 | 7937483 | SNORA52 | 0.861796 | 3.54E−09 |
| 7982092 | SNORD115-11 | 1.137546 | 0.000237 | 8019762 | P4HB | 1.14103 | 4.40E−15 | 7920875 | SCARNA4 | 0.861416 | 5.76E−06 |
| 8122279 | KIAA1244 | 1.122862 | 5.75E−11 | 8147697 | GRHL2 | 1.13758 | 1.58E−14 | 8048116 | NA | 0.861225 | 2.07E−06 |
| 7982050 | SNORD115-11 | 1.122633 | 0.000414 | 8108629 | VTRNA1-2 | 1.135673 | 0.001123 | 8015460 | ACLY | 0.860831 | 1.81E−11 |
| 8058552 | IDH1 | 1.104052 | 2.85E−13 | 8122144 | SNORA33 | 1.133057 | 1.31E−08 | 8126784 | PLA2G7 | 0.859905 | 0.000126 |
| 7982058 | SNORD115-26 | 1.10387 | 0.00036 | 8098204 | CPE | 1.131458 | 1.05E−08 | 8030980 | ZNF525 | 0.858599 | 0.000441 |
| 7896714 | NA | 1.097176 | 9.32E−11 | 8040792 | GREB1 | 1.130491 | 3.40E−09 | 8005202 | SNORD49A | 0.854728 | 0.000692 |
| 8037298 | CD177 | 1.091864 | 5.39E−07 | 7992732 | ZG16B | 1.127881 | 1.04E−12 | 7982094 | SNORD115-44 | 0.85192 | 0.006508 |
| 8080714 | FLNB | 1.090102 | 8.99E−16 | 8163181 | C9orf152 | 1.122852 | 4.36E−12 | 7993638 | TMC5 | 0.851682 | 7.19E−07 |
| 8096030 | NA | 1.089166 | 0.000737 | 8118207 | SNORA38 | 1.122812 | 8.34E−14 | 7999981 | ACSM1 | 0.851617 | 7.67E−06 |
| 7975268 | ARG2 | 1.074633 | 2.15E−09 | 8074148 | FU39632 | 1.119752 | 4.00E−09 | 7967127 | CAMKK2 | 0.850323 | 6.13E−08 |
| 8067233 | PMEPA1 | 1.07286 | 1.74E−10 | 8066256 | SNORA71B | 1.118165 | 1.02E−12 | 7922414 | SNORD76 | 0.849869 | 7.55E−05 |
| 8029280 | CD177 | 1.070112 | 3.62E−12 | 8026875 | SNORA68 | 1.108401 | 2.77E−11 | 8129783 | MAP7 | 0.846894 | 1.90E−09 |
| 7983490 | C15orf21 | 1.06877 | 1.11E−09 | 8028311 | SPINT2 | 1.105367 | 5.19E−18 | 7977456 | POTEG | 0.846163 | 0.024583 |
| 7995895 | HERPUD1 | 1.065288 | 3.13E−12 | 7971386 | SNORA31 | 1.099638 | 1.12E−12 | 8066262 | SNORA71D | 0.845294 | 1.76E−07 |
| 8170863 | SNORA70 | 1.064529 | 1.89E−08 | 8112865 | SERINC5 | 1.097815 | 9.84E−11 | 8112865 | SERINC5 | 0.844207 | 7.08E−07 |
| 8025498 | SNORA70 | 1.0629 | 2.52E−08 | 7940667 | SNORA57 | 1.097325 | 1.13E−14 | 7992732 | ZG16B | 0.843778 | 7.72E−08 |
| 8094240 | CD38 | 1.06157 | 9.31E−10 | 8029489 | BCAM | 1.088087 | 2.06E−12 | 8095585 | SLC4A4 | 0.842204 | 0.000445 |
| 8030993 | ZNF761 | 1.060605 | 1.94E−09 | 7948858 | SYT7 | 1.085858 | 2.22E−15 | 8090688 | SNORA58 | 0.841172 | 1.03E−07 |
| 8074192 | NA | 1.057831 | 3.61E−08 | 8174715 | SNORA69 | 1.083528 | 7.31E−12 | 8078916 | SNORA6 | 0.841096 | 6.90E−07 |
| 7928367 | NA | 1.049239 | 3.15E−05 | 8059708 | SNORA75 | 1.07899 | 1.27E−08 | 7894416 | NA | 0.839548 | 1.48E−07 |
| 8163181 | C9orf152 | 1.04482 | 9.35E−11 | 7982070 | SNORD115-32 | 1.075986 | 0.001538 | 8021453 | SEC11C | 0.833711 | 6.59E−06 |
| 8112865 | SERINC5 | 1.044468 | 7.13E−10 | 7981947 | SNORD109A | 1.075833 | 2.04E−10 | 8060501 | SNORA51 | 0.833601 | 1.56E−09 |
| 8116848 | PAK1IP1 | 1.042726 | 8.60E−09 | 7982098 | SNORD109A | 1.075833 | 2.04E−10 | 7988426 | SLC30A4 | 0.829749 | 2.59E−06 |
| 7975238 | PLEKHH1 | 1.038708 | 2.93E−11 | 8078918 | SNORA62 | 1.074072 | 6.16E−10 | 8049394 | TRPM8 | 0.827942 | 0.003656 |
| 7898957 | RCAN3 | 1.036244 | 2.85E−11 | 7922402 | SNORD47 | 1.070698 | 1.72E−06 | 8075182 | XBP1 | 0.827458 | 4.86E−08 |
| 8021453 | SEC11C | 1.033379 | 1.71E−08 | 8015460 | ACLY | 1.06909 | 2.93E−16 | 8030993 | ZNF761 | 0.823617 | 3.71E−06 |
| 8109999 | ERGIC1 | 1.031737 | 1.30E−15 | 8119898 | VEGFA | 1.065875 | 2.31E−07 | 8066256 | SNORA71B | 0.823223 | 1.20E−07 |
| 7900792 | PTPRF | 1.029824 | 8.19E−22 | 7957966 | MYBPC1 | 1.064782 | 1.78E−07 | 8012126 | CLDN7 | 0.817911 | 2.57E−09 |
| 8027002 | GDF15 | 1.029377 | 8.59E−05 | 8135015 | MUC3A | 1.061611 | 1.94E−05 | 7893733 | NA | 0.816579 | 1.83E−06 |
| 8015460 | ACLY | 1.024407 | 2.96E−15 | 7981980 | SNORD116-16 | 1.061275 | 0.000127 | 8098328 | GALNT7 | 0.816197 | 6.31E−07 |
| 8082478 | COPG | 1.020944 | 2.38E−16 | 8075182 | XBP1 | 1.059972 | 3.39E−12 | 8103106 | LRBA | 0.814003 | 5.30E−08 |
| 8021081 | SLC14A1 | 1.018508 | 1.87E−07 | 8109999 | ERGIC1 | 1.057449 | 3.31E−16 | 8147351 | ESRP1 | 0.81359 | 1.37E−10 |
| 7991034 | HOMER2 | 1.016371 | 2.50E−12 | 8027266 | NA | 1.051963 | 7.55E−05 | 8099967 | RBM47 | 0.813439 | 1.64E−Q8 |
| 8151475 | TPD52 | 1.011612 | 1.156−11 | 7975238 | PLEKHH1 | 1.049187 | 1.76E−11 | 8118207 | SNORA38 | 0.809519 | 4.59E−08 |

-continued

| epithelial Benign-stromal benign | | | | epithelial PIN-stromal PIN | | | | epithelial tumor-stromal tumor | | | |
| --- | --- | --- | --- | --- | --- | --- | --- | --- | --- | --- | --- |
| Affymetrix ID | Gene | LogFC | Adj. P.Val | Affymetrix ID | Gene | LogFC | Adj. P.Val | Affymetrix ID | Gene | LogFC | Adj. P.Val |
| 8039144 | TMC4 | 1.010505 | 2.00E-16 | 7962827 | SNORA2A | 1.0464 | 3.13E-08 | 7982046 | SNORD115-20 | 0.809258 | 0.010888 |
| 7982046 | SNORD115-20 | 1.00944 | 0.000945 | 8022927 | SLC39A6 | 1.042809 | 1.99E-16 | 8121489 | AMD1 | 0.805272 | 2.73E-05 |
| 8039010 | ZNF765 | 1.004139 | 2.85E-13 | 8041853 | EPCAM | 1.041579 | 8.52E-09 | 8096511 | BMPR1B | 0.804331 | 1.99E-07 |
| 7945204 | ST14 | 0.998583 | 1.27E-13 | 8058552 | IDH1 | 1.038173 | 4.21E-12 | 8039144 | TMC4 | 0.797741 | 2.77E-11 |
| 7916112 | RA83B | 0.989703 | 1.82E-08 | 7971373 | NA | 1.034296 | 1.13E-06 | 8009241 | SNORD104 | 0.79706 | 3.99E-06 |
| 8017378 | CYB561 | 0.984299 | 7.46E-16 | 8159006 | SNORD36B | 1.033644 | 2.57E-06 | 8158998 | SNORD36C | 0.796498 | 0.00073 |
| 8009334 | CACNG4 | 0.983799 | 2.02E-13 | 8016487 | HOXB13 | 1.031105 | 6.80E-11 | 8065280 | RALGAPA2 | 0.796418 | 3.60E-09 |
| 8021727 | CNDP2 | 0.973391 | 2.94E-15 | 8018982 | CANT1 | 1.028204 | 8.53E-15 | 7939642 | CREB3L1 | 0.795824 | 2.96E-08 |
| 7982090 | SNORD115-42 | 0.972134 | 0.000194 | 7964927 | TSPAN8 | 1.025986 | 3.35E-06 | 7922402 | SNORD47 | 0.795343 | 0.000609 |
| 8015337 | KRT15 | 0.971518 | 7.51E-10 | 7988426 | SLC30A4 | 1.019828 | 5.12E-09 | 7901052 | SNORD38B | 0.794629 | 0.001225 |
| 8050240 | ODC1 | 0.971349 | 1.63E-07 | 7920873 | SNORA42 | 1.018134 | 5.29E-14 | 8151475 | TPD52 | 0.79437 | 9.02E-08 |
| 8134030 | STEAP1 | 0.971205 | 7.68E-05 | 7983490 | C15orf21 | 1.013009 | 6.43E-09 | 8166243 | REPS2 | 0.794018 | 2.62E-10 |
| 8066258 | SNORA71A | 0.971136 | 1.50E-05 | 8044804 | OBI | 1.007904 | 6.85E-08 | 7982070 | SNORD115-32 | 0.793197 | 0.030244 |
| 8018982 | CANT1 | 0.969573 | 1.51E-13 | 7923958 | C10rf116 | 1.004243 | 5.16E-13 | 7901229 | FAAH | 0.79234 | 1.26E-11 |
| 8145291 | SLC25A37 | 0.965418 | 7.60E-13 | 7993638 | TMCS | 1.002886 | 3.74E-09 | 7894974 | NA | 0.791649 | 0.041421 |
| 8104601 | BASP1 | 0.959923 | 2.61E-14 | 8049961 | F8X025 | 1.001534 | 0.000266 | 8082607 | ATP2C1 | 0.788653 | 3.48E-08 |
| 7937079 | BNIP3 | 0.955993 | 1.12E-15 | 7952830 | NCAPD3 | 1.001256 | 3.14E-05 | 7904881 | PDIA3P | 0.787429 | 1.34E-07 |
| 7986605 | POTEB | 0.953175 | 2.53E-08 | 8140840 | STEAP4 | 0.996924 | 2.65E-07 | 8124492 | HIST1H2BK | 0.786767 | 4.89E-06 |
| 7984908 | CPLX3 | 0.952063 | 2.08E-13 | 8103106 | LRBA | 0.996336 | 2.58E-11 | 7895011 | NA | 0.784651 | 0.000375 |
| 8108420 | SNORA74A | 0.951757 | 0.000263 | 7895405 | NA | 0.991307 | 2.25E-05 | 7938291 | SNORA3 | 0.777381 | 6.28E-07 |
| 7995362 | GPT2 | 0.950115 | 1.08E-13 | 8066260 | SNORA71C | 0.989496 | 2.80E-11 | 8022927 | SLC39A6 | 0.775782 | 3.13E-10 |
| 8023392 | SNORA37 | 0.949736 | 3.12E-08 | 8114287 | SPOCK1 | 0.988566 | 2.51E-09 | 7899480 | SNORA73A | 0.775506 | 2.43E-05 |
| 7982018 | SNORD115-6 | 0.939228 | 0.000257 | 7938291 | SNORA3 | 0.988289 | 2.02E-10 | 7920873 | SNORA42 | 0.76854 | 8.21E-09 |
| 8050253 | SNORA80B | 0.936818 | 2.16E-08 | 7982090 | SNORD115-42 | 0.984655 | 0.000135 | 8059953 | NA | 0.768319 | 4.83E-07 |
| 7893733 | NA | 0.933691 | 3.61E-08 | 7905731 | NA | 0.980763 | 3.30E-07 | 8070297 | ERG | 0.766697 | 0.006586 |
| 7996081 | GPR56 | 0.932824 | 4.59E-18 | 7906079 | RAB25 | 0.978115 | 2.84E-13 | 7983274 | PDIA3 | 0.76458 | 7.82E-08 |
| 7951038 | SNORA40 | 0.932753 | 2.53E-06 | 8129783 | MAP7 | 0.977714 | 3.84E-12 | 8108629 | VTRNA1-2 | 0.763167 | 0.046324 |
| 7892661 | NA | 0.931772 | 7.75E-07 | 7922404 | SNORA76 | 0.974768 | 3.31E-06 | 7982052 | PAR4 | 0.76307 | 0.00885 |
| 8004784 | ALOX15B | 0.931685 | 6.59E-18 | 7982018 | SNORD115-6 | 0.974368 | 0.000121 | 7982018 | SNORD115-6 | 0.760437 | 0.004279 |
| 8127145 | ELOVL5 | 0.930232 | 6.00E-09 | 7922404 | SNORD80 | 0.974205 | 3.94E-05 | 8049961 | FBX025 | 0.759834 | 0.009051 |
| 8149918 | CHRNA2 | 0.929796 | 3.99E-09 | 8039144 | TMC4 | 0.969666 | 1.63E-15 | 8112107 | PPAP2A | 0.759695 | 0.000266 |
| 8116780 | DSP | 0.929783 | 9.80E-14 | 8023392 | SNORA37 | 0.968148 | 1.59E-08 | 7923958 | C10rf116 | 0.759419 | 3.48E-06 |
| 8038735 | KLK11 | 0.925425 | 2.71E-06 | 7981958 | SNORD116-5 | 0.962969 | 2.44E-06 | 8109750 | RPLPO | 0.757978 | 1.33E-06 |
| 8082012 | SLC15A2 | 0.922421 | 6.59E-11 | 7981962 | SNORD116-5 | 0.962969 | 2.44E-06 | 8114287 | SPOCK1 | 0.756784 | 6.37E-06 |
| 7924058 | IRF6 | 0.919628 | 1.64E-13 | 8009241 | SNORD104 | 0.959923 | 1.78E-08 | 8107769 | SLC12A2 | 0.755579 | 1.67E-06 |
| 8103176 | LRBA | 0.919151 | 6.48E-10 | 8126135 | GLOl | 0.958878 | 1.15E-08 | 8026875 | SNORA68 | 0.752038 | 6.50E-06 |
| 8112107 | PPAP2A | 0.91878 | 6.52E-06 | 7982006 | SNORD116-29 | 0.955552 | 7.89E-06 | 7982090 | SNORD115-42 | 0.751347 | 0.005784 |
| 8140140 | CLDN3 | 0.917053 | 8.77E-10 | 7945204 | ST14 | 0.95465 | 9.45E-13 | 8147697 | GRHL2 | 0.750977 | 2.12E-07 |
| 8067125 | BCAS1 | 0.914236 | 1.45E-13 | 7982052 | PAR4 | 0.952081 | 0.000587 | 8082478 | COPG | 0.7491 | 5.39E-10 |
| 7906079 | RAB25 | 0.913962 | 6.09E-12 | 8140140 | CLDN3 | 0.948952 | 2.27E-10 | 7937971 | NA | 0.748367 | 5.21E-07 |
| 8022927 | SLC39A6 | 0.911754 | 1.88E-13 | 7922904 | SNORD75 | 0.94808 | 2.38E-06 | 8073585 | SERHL | 0.747707 | 1.66E-06 |
| 8164215 | SNORA65 | 0.909392 | 3.57E-07 | 8082607 | ATP2C1 | 0.945817 | 3.29E-11 | 8059708 | SNORA75 | 0.744574 | 0.000121 |
| 8067844 | POTED | 0.909044 | 2.90E-08 | 8004506 | SNORA48 | 0.942214 | 4.86E-10 | 7906079 | RAB25 | 0.74369 | 1.97E-08 |
| 8156761 | NANS | 0.90833 | 7.09E-13 | 8159379 | TMEM141 | 0.94186 | 2.07E-12 | 8098204 | CPE | 0.742828 | 0.00025 |
| 7977933 | SLC7A8 | 0.904355 | 2.91E-15 | 8093576 | SCARNA22 | 0.938166 | 4.44E-10 | 7980826 | CCDC88C | 0.74166 | 0.001757 |
| 7973002 | FU39632 | 0.90244 | 1.18E-09 | 8067233 | PMEPA1 | 0.93809 | 1.69E-08 | 7896561 | NA | 0.734419 | 5.52E-05 |
| 8043197 | VAMP8 | 0.902172 | 4.19E-16 | 7919193 | NUDT4P1 | 0.937052 | 6.77E-12 | 7895694 | NA | 0.733978 | 0.000108 |
| 7912347 | CASZ1 | 0.901709 | 1.30E-10 | 7982040 | SNORD115-17 | 0.936396 | 0.000185 | 7909877 | MOSC1 | 0.7329 | 1.65E-11 |
| 8129783 | MAP7 | 0.901072 | 1.21E-10 | 7982042 | SNORD115-17 | 0.936396 | 0.000185 | 8018264 | C17orf28 | 0.731937 | 2.02E-09 |
| 7971373 | NA | 0.896789 | 3.05E-05 | 7982044 | SNORD115-17 | 0.936396 | 0.000185 | 8056222 | DPP4 | 0.730632 | 0.004656 |
| 8114287 | SPOCK1 | 0.896412 | 6.39E-08 | 7956120 | ERBB3 | 0.93422 | 1.27E-17 | 8027748 | FXYD3 | 0.730366 | 6.15E-06 |
| 7982008 | SNORD115-1 | 0.892067 | 0.000242 | 7922400 | NA | 0.933327 | 2.30E-06 | 7922400 | NA | 0.730336 | 0.000338 |
| 7982032 | SNORD115-1 | 0.892067 | 0.000242 | 8060591 | SNORA51 | 0.933325 | 1.12E-11 | 8028311 | SPINT2 | 0.728423 | 2.32E-09 |
| 7982038 | SNORD115-1 | 0.892067 | 0.000242 | 8012126 | CLDN7 | 0.927302 | 1.23E-11 | 8159379 | TMEM141 | 0.728405 | 4.58E-08 |
| 8111101 | ANKH | 0.891728 | 5.80E-16 | 7982008 | SNORD115-1 | 0.921542 | 0.000122 | 7958375 | NA | 0.725751 | 5.16E-09 |
| 7901229 | FAAH | 0.884882 | 4.58E-14 | 7982032 | SNORD115-1 | 0.921542 | 0.000122 | 8044804 | DBI | 0.72548 | 0.000151 |
| 8117106 | RNF144B | 0.884571 | 1.45E-11 | 7982038 | SNORD115-1 | 0.921542 | 0.000122 | 8032749 | SNORD37 | 0.724233 | 0.00681 |
| 8153334 | PSCA | 0.879371 | 0.00029 | 8080714 | FINB | 0.919947 | 2.85E-12 | 8014487 | ACACA | 0.724193 | 2.76E-09 |
| 7998666 | SNORA64 | 0.877897 | 5.01E-06 | 8069985 | SNORA80 | 0.916239 | 5.47E-14 | 7972983 | POTEM | 0.7218 | 0.040819 |
| 8082607 | ATP2C1 | 0.875313 | 7.21E-10 | 8038624 | C19orf48 | 0.91331 | 1.60E-08 | 8080714 | FLNB | 0.719485 | 4.09E-08 |
| 7897745 | AGTRAP | 0.875182 | 4.23E-13 | 8090688 | SNORA58 | 0.913167 | 5.12E-09 | 8078918 | SNORA62 | 0.719389 | 4.30E-05 |
| 7909400 | CD46 | 0.874789 | 4.87E-14 | 8147153 | ESRP1 | 0.91084 | 6.04E-13 | 8090380 | SNORA38B | 0.718855 | 6.13E-06 |
| 7920971 | C10rf8S | 0.873073 | 8.72E-11 | 7982072 | SNORD115-33 | 0.910477 | 0.000533 | 7948588 | SYT7 | 0.716817 | 7.05E-08 |
| 8034084 | AP1M2 | 0.871086 | 6.11E-16 | 7916112 | RAB3B | 0.907082 | 2.06E-07 | 8010082 | SNORD1A | 0.715769 | 2.88E-06 |
| 7940654 | SCGB1A1 | 0.870098 | 0.000703 | 7989768 | NA | 0.901678 | 1.02E-08 | 7989768 | NA | 0.715206 | 7.32E-06 |
| 8103025 | ZNF827 | 0.868001 | 1.56E-12 | 7937079 | BNIP3 | 0.900292 | 1.61E-12 | 7951034 | SNORA8 | 0.714366 | 0.001822 |
| 7982040 | SNORD115-17 | 0.864709 | 0.000719 | 7893309 | NA | 0.89592 | 3.95E-08 | 7982008 | SNORD115-1 | 0.711008 | 0.004869 |
| 7982042 | SNORD115-17 | 0.864709 | 0.000719 | 8030993 | ZNF761 | 0.893996 | 3.26E-07 | 7982032 | SNORD115-1 | 0.711008 | 0.004869 |
| 7982044 | SNORD115-17 | 0.864709 | 0.000719 | 7900792 | PTPRF | 0.893007 | 4.76E-18 | 7982038 | SNORD115-1 | 0.711008 | 0.004869 |
| 8019357 | DCXR | 0.863678 | 1.47E-11 | 7892661 | NA | 0.88841 | 2.15E-06 | 8027728 | HPN | 0.709816 | 6.76E-08 |
| 7982070 | SNORD115-32 | 0.862853 | 0.016641 | 7896561 | NA | 0.88575 | 6.65E-07 | 7948896 | SNORD22 | 0.709025 | 0.000186 |
| 8177222 | CD24 | 0.858674 | 6.22E-05 | 8074192 | NA | 0.884393 | 3.63E-06 | 8089851 | HGD | 0.708532 | 0.000255 |
| 7929816 | SCO | 0.857913 | 4.11E-08 | 7991034 | HOMER2 | 0.884293 | 6.13E-10 | 8093278 | HGD | 0.708532 | 0.000255 |

-continued

| epitheliail Benign-stromal benign | | | | epithelial PIN-stromal PIN | | | | epithelial tumor-stromal tumor | | | |
|---|---|---|---|---|---|---|---|---|---|---|---|
| Affymetrix ID | Gene | LogFC | Adj. P.Val | Affymetrix ID | Gene | LogFC | Adj. P.Val | Affymetrix ID | Gene | LogFC | Adj. P.Val |
| 7923778 | ELK4 | 0.857597 | 3.91E-13 | 8135031 | MUC12 | 0.88421 | 0.001887 | 7948906 | SNORD27 | 0.705919 | 0.000639 |
| 7993638 | TMC5 | 0.856087 | 4.87E-07 | 8117034 | GMPR | 0.884075 | 6.93E-09 | 8140140 | CLDN3 | 0.704503 | 2.83E-06 |
| 8098328 | GALNT7 | 0.856031 | 1.32E-05 | 8027728 | HPN | 0.883757 | 1.78E-11 | 7975268 | ARG2 | 0.703381 | 0.000115 |
| 7995825 | MT1F | 0.854967 | 5.62E-08 | 7968234 | SNORA27 | 0.883014 | 1.66E-07 | 7948900 | SNORD30 | 0.702233 | 0.000214 |
| 7963427 | KRT5 | 0.854383 | 5.47E-10 | 8045210 | C2orf14 | 0.882886 | 1.25E-06 | 8116780 | DSP | 0.701088 | 1.21E-08 |
| 8126382 | C6orf132 | 0.851576 | 4.67E-14 | 7981949 | SNORD116-1 | 0.880728 | 7.82E-06 | 7949679 | SPTBN2 | 0.700975 | 2.05E-11 |
| 7982052 | PAR4 | 0.851244 | 0.002835 | 7901229 | FAAH | 0.878107 | 6.10E-14 | 7951030 | SNORD6 | 0.699466 | 0.001226 |
| 8103951 | ACSL1 | 0.848569 | 2.60E-11 | 8149590 | NA | 0.873474 | 1.50E-05 | 8019357 | DCXR | 0.697425 | 4.77E-08 |
| 7920875 | SCARNA4 | 0.844783 | 7.18E-06 | 7935776 | SCD | 0.872295 | 0.000217 | 8162147 | ZCCHC6 | 0.695328 | 1.24E-06 |
| 7899615 | SERINC2 | 0.843149 | 1.01E-16 | 7984914 | CPLX3 | 0.871794 | 2.87E-06 | 7989922 | SCARNA14 | 0.694841 | 6.83E-05 |
| 7895841 | NA | 0.84121 | 4.90E-07 | 7951034 | SNORA8 | 0.867089 | 8.47E-15 | 8088642 | LRIG1 | 0.692238 | 1.58E-08 |
| 7980080 | ENTPD5 | 0.837519 | 4.95E-06 | 7893733 | NA | 0.866719 | 2.65E-07 | 8074170 | POTEM | 0.690359 | 0.047373 |
| 8018264 | C17orf28 | 0.836341 | 6.99E-12 | 7981953 | SNORD116-3 | 0.86645 | 1.42E-05 | 8048733 | ACSL3 | 0.690113 | 1.06E-05 |
| 8149574 | CSGALNACT1 | 0.836028 | 1.58E-08 | 7981966 | SNORD116-3 | 0.86645 | 1.42E-05 | 8151890 | TP53INP1 | 0.689528 | 4.29E-09 |
| 7957966 | MYBPC1 | 0.835092 | 5.42E-05 | 7981998 | SNORD116-25 | 0.866133 | 0.000411 | 8106068 | MCCC2 | 0.687244 | 1.98E-06 |
| 8023855 | CYB5A | 0.834985 | 8.83E-11 | 7938329 | SNORA23 | 0.866016 | 1.96E-07 | 8177601 | MCCC2 | 0.687244 | 1.98E-06 |
| 8068684 | FAM3B | 0.834621 | 1.27E-06 | 7981970 | SNORD116-11 | 0.865692 | 5.68E-06 | 7955277 | TMBIM6 | 0.685878 | 1.06E-08 |
| 8092169 | TNFSF10 | 0.83132 | 8.11E-08 | 7948912 | CHRM1 | 0.865196 | 1.53E-13 | 7893309 | NA | 0.683378 | 3.93E-05 |
| 8021301 | RAB27B | 0.827201 | 9.24E-13 | 7981964 | SN0R0116-8 | 0.864907 | 1.13E-05 | 8066260 | SNORA71C | 0.682009 | 4.65E-06 |
| 7904254 | ATP1A1 | 0.826902 | 5.11E-13 | 7981996 | SNORD116-24 | 0.864478 | 0.000893 | 7971386 | SNORA31 | 0.679921 | 9.34E-06 |
| 8068810 | SLC37A1 | 0.825504 | 5.21E-13 | 8160295 | SCARNA8 | 0.863555 | 6.21E-09 | 7951036 | SNORD5 | 0.677825 | 6.23E-05 |
| 7894186 | NA | 0.824587 | 2.39E-09 | 7981976 | SNORD116-14 | 0.862224 | 0.000199 | 8063345 | SNORD12C | 0.67716 | 0.001493 |
| 8021614 | SERPINB11 | 0.822319 | 0.000666 | 8082478 | COPG | 0.860576 | 1.01E-12 | 7982056 | SNORD115-25 | 0.676087 | 0.005515 |
| 8167305 | EBP | 0.822275 | 1.20E-09 | 8073585 | SERHL | 0.858159 | 2.47E-08 | 8155930 | GCNT1 | 0.673286 | 1.85E-06 |
| 8116835 | GCNT2 | 0.820931 | 3.30E-08 | 8153334 | PSCA | 0.856963 | 0.000369 | 8052141 | NA | 0.670895 | 8.87E-07 |
| 7955637 | KRT18 | 0.820159 | 4.06E-14 | 7981994 | SNORD116-23 | 0.856919 | 0.0002 | 8150877 | SNORD54 | 0.667691 | 0.006096 |
| 7895405 | NA | 0.817402 | 0.000681 | 7939642 | CREB3L1 | 0.855104 | 1.71E-09 | 7991034 | HOMER2 | 0.666812 | 3.72E-06 |
| 7899821 | KIAA1522 | 0.81528 | 1.45E-17 | 7925182 | SNORA14B | 0.853891 | 4.88E-08 | 7952335 | SNORD14E | 0.663969 | 0.000797 |
| 8141206 | BAIAP2L1 | 0.809575 | 1.06E-12 | 7953291 | CD9 | 0.853779 | 1.97E-09 | 8034084 | AP1M2 | 0.663421 | 2.64E-10 |
| 7940565 | FADS2 | 0.808795 | 0.000366 | 7919055 | HMGCS2 | 0.849353 | 2.42E-07 | 7894316 | NA | 0.65995 | 1.62E-07 |
| 8052762 | GFPT1 | 0.807945 | 3.60E-12 | 8021453 | SEC11C | 0.847585 | 3.20E-06 | 8031825 | ZNF552 | 0.658757 | 0.000107 |
| 8094988 | CWH43 | 0.807619 | 1.17E-10 | 8145291 | SLC25A37 | 0.846844 | 1.68E-10 | 7900792 | PTPRF | 0.656942 | 3.79E-11 |
| 7982056 | SNORD115-25 | 0.807373 | 0.000615 | 8090565 | SNORA7B | 0.844661 | 9.94E-09 | 7894716 | NA | 0.656391 | 0.000962 |
| 7920873 | SNORA42 | 0.806989 | 9.86E-10 | 7952335 | SNORD14E | 0.843986 | 9.92E-06 | 7982040 | SNORD115-17 | 0.655936 | 0.014723 |
| 8096511 | BMPR1B | 0.80644 | 1.39E-07 | 8156761 | NANS | 0.84223 | 1.72E-11 | 7982042 | SNORD115-17 | 0.655936 | 0.014723 |
| 7909422 | MIR205 | 0.802305 | 1.95E-09 | 8127145 | ELOVL5 | 0.839999 | 1.23E-07 | 7982044 | SNORD115-17 | 0.655936 | 0.014723 |
| 7939897 | FOLH1 | 0.80051 | 0.00139 | 8116780 | DSP | 0.83884 | 8.99E-12 | 7939897 | FOLH1 | 0.654569 | 0.011839 |
| 7926679 | KIAA1217 | 0.798629 | 2.00E-16 | 8021727 | CNDP2 | 0.835881 | 3.59E-12 | 8010243 | SYNGR2 | 0.654133 | 1.74E-11 |
| 8163678 | ASTN2 | 0.793087 | 9.42E-19 | 8149918 | CHRNA2 | 0.83582 | 9.92E-08 | 7892882 | NA | 0.653054 | 0.000297 |
| 8104607 | NA | 0.791999 | 3.22E-05 | 7989922 | SCARNA14 | 0.833995 | 1.02E-06 | 7968029 | PCOTH | 0.652649 | 0.016911 |
| 8048733 | ACSL3 | 0.788985 | 3.47E-07 | 8089851 | HGD | 0.832923 | 9.90E-06 | 7980891 | TC2N | 0.652166 | 1.76E-07 |
| 8145532 | EPHX2 | 0.786492 | 2.53E-12 | 8093278 | HGD | 0.832923 | 9.90E-06 | 7968234 | SNORA27 | 0.651374 | 0.000168 |
| 7971386 | SNORA31 | 0.786388 | 2.14E-07 | 8158998 | SNORD36C | 0.832328 | 0.000308 | 7895317 | NA | 0.650545 | 1.14E-06 |
| 8147351 | ESRP1 | 0.785636 | 2.99E-10 | 7939897 | FOLH1 | 0.831912 | 0.00073 | 7998722 | SNORD60 | 0.650491 | 0.002514 |
| 8165575 | PNPLA7 | 0.784458 | 1.28E-13 | 8018264 | C17orf28 | 0.825637 | 1.14E-11 | 7893657 | NA | 0.650036 | 0.010825 |
| 8030991 | LOC147804 | 0.781779 | 5.57E-08 | 8055214 | C2orf14 | 0.825322 | 1.42E-06 | 7893641 | NA | 0.649875 | 4.10E-05 |
| 8156309 | GA0D45G | 0.781298 | 6.29E-07 | 8017378 | CYB561 | 0.82459 | 3.39E-12 | 7997381 | CENPN | 0.649838 | 6.75E-06 |
| 8123407 | MLLT4 | 0.780888 | 1.20E-13 | 7981992 | SNORD116-22 | 0.823556 | 0.003071 | 7983490 | C15orf21 | 0.648333 | 0.000293 |
| 8078916 | SNORA6 | 0.780358 | 3.39E-06 | 7955637 | KRT18 | 0.822093 | 3.39E-14 | 8143684 | PDIA4 | 0.647277 | 3.71E-09 |
| 8165406 | NPDC1 | 0.780307 | 1.14E-18 | 8112274 | ELOVL7 | 0.821845 | 5.28E-08 | 7913385 | RAP1GAP | 0.645585 | 2.79E-07 |
| 7971461 | LCP1 | 0.780281 | 8.85E-07 | 8010137 | SCARNA16 | 0.82027 | 3.71E-07 | 8035980 | RHPN2 | 0.645227 | 2.58E-07 |
| 8178676 | NEU1 | 0.778896 | 9.88E-15 | 8009380 | SNORA38B | 0.81781 | 1.72E-07 | 8041170 | NA | 0.644239 | 0.011352 |
| 7919193 | NUDT4P1 | 0.775959 | 9.01E-09 | 7984892 | LMAN1L | 0.816673 | 1.43E-06 | 7948898 | SNORD31 | 0.643117 | 0.004186 |
| 7980828 | CCDC88C | 0.775142 | 0.000953 | 7892817 | NA | 0.814192 | 1.30E-09 | 7894529 | NA | 0.642678 | 0.007222 |
| 8143307 | HIPK2 | 0.774196 | 1.47E-12 | 8170992 | SNORA56 | 0.81294 | 9.02E-09 | 7893592 | NA | 0.640789 | 2.56E-06 |
| 8084717 | ST6GAL1 | 0.772646 | 1.41E-05 | 7901052 | SNORD38B | 0.812534 | 0.000761 | 8110392 | TMED9 | 0.640741 | 1.42E-09 |
| 8107769 | SLC12A2 | 0.770994 | 7.90E-07 | 8160670 | AQP3 | 0.811924 | 1.18E-05 | 7956120 | ERBB3 | 0.639964 | 1.09E-09 |
| 7956120 | ERBB3 | 0.770555 | 3.00E-13 | 8038735 | KLK11 | 0.810374 | 3.95E-06 | 8068810 | SLC37A1 | 0.639466 | 1.65E-08 |
| 8045210 | C2orf14 | 0.763133 | 3.51E-05 | 8068684 | FAM3B | 0.807842 | 2.40E-06 | 8058552 | IOH1 | 0.63939 | 1.92E-05 |
| 8015349 | KRT19 | 0.762589 | 2.01E-07 | 7895317 | NA | 0.807544 | 1.13E-09 | 8080511 | CACNA1D | 0.638353 | 8.36E-05 |
| 7951032 | SNORA1 | 0.762324 | 4.54E-05 | 7977075 | SNORA28 | 0.805884 | 8.44E-06 | 8162502 | FBP1 | 0.636846 | 2.13E-07 |
| 8139456 | SNORA9 | 0.761711 | 8.37E-06 | 8023855 | CYB5A | 0.800662 | 3.99E-10 | 8141206 | BAIAP2L1 | 0.635985 | 1.71E-08 |
| 8133360 | CLDN4 | 0.759891 | 1.16E-10 | 7982056 | SNORD115-25 | 0.799945 | 0.000608 | 8010137 | SCARNA16 | 0.635744 | 0.000122 |
| 7919055 | HMGCS2 | 0.757915 | 4.76E-06 | 8107326 | SNORA13 | 0.798383 | 3.91E-06 | 7987869 | TMEM87A | 0.635526 | 4.05E-08 |
| 7908793 | ELF3 | 0.752238 | 3.43E-07 | 8096511 | BMPR1B | 0.797829 | 1.66E-07 | 8087830 | RPL29 | 0.635286 | 2.25E-10 |
| 8073585 | SERHL | 0.752064 | 1.13E-06 | 8019357 | OCXR | 0.794497 | 3.73E-10 | 7893821 | NA | 0.633857 | 3.91E-06 |
| 8038624 | C19orf48 | 0.751203 | 3.68E-06 | 7951030 | SN0RD6 | 0.792476 | 0.00016 | 8052762 | GFPT1 | 0.633378 | 4.36E-08 |
| 8140840 | STEAP4 | 0.750646 | 0.000147 | 8092169 | TNFSF10 | 0.786634 | 3.30E-07 | 7977452 | FU39632 | 0.633087 | 0.002335 |
| 7895011 | NA | 0.749022 | 0.000688 | 7998722 | SNORD60 | 0.784317 | 0.00015 | 8022711 | DSC2 | 0.632938 | 4.56E-08 |
| 7982094 | SNORD115-44 | 0.747978 | 0.020374 | 7894774 | NA | 0.783832 | 1.67E-11 | 8126135 | GLO1 | 0.632828 | 0.000241 |
| 8117382 | HIST1H2BD | 0.746349 | 1.18E-11 | 8030251 | TRPM4 | 0.781826 | 1.86E-14 | 7980547 | SEL1L | 0.631049 | 1.21E-08 |
| 8095986 | ANXA3 | 0.742875 | 2.88E-10 | 8107769 | SLC12A2 | 0.780919 | 4.86E-07 | 7894774 | NA | 0.630871 | 6.05 E-08 |
| 8049961 | FBX025 | 0.742845 | 0.01118 | 8001746 | SNORA46 | 0.780544 | 4.43E-07 | 8139482 | SNORA5A | 0.630059 | 0.001178 |

-continued

| epithelial Benign-stromal benign | | | | epithelial PIN-stromal PIN | | | | epithelial tumor-stromal tumor | | | |
|---|---|---|---|---|---|---|---|---|---|---|---|
| Affymetrix ID | Gene | LogFC | Adj. P.Val | Affymetrix ID | Gene | LogFC | Adj. P.Val | Affymetrix ID | Gene | LogFC | Adj. P.Val |
| 8054308 | TBC1D8 | 0.742084 | 1.11E-13 | 8039010 | ZNF765 | 0.7787 | 6.40E-09 | 8139107 | TARP | 0.62962 | 0.005786 |
| 8177867 | DDR1 | 0.741235 | 1.90E-14 | 7970595 | C1QTNF9B | 0.777856 | 0.002135 | 8055222 | POTEE | 0.628202 | 0.017039 |
| 8030251 | TRPM4 | 0.739931 | 2.78E-13 | 8128886 | NA | 0.776413 | 4.23E-07 | 8093576 | SCARNA22 | 0.628055 | 3.66E-05 |
| 8112274 | ELOVL7 | 0.739772 | 1.08E-06 | 8005953 | SNORD4A | 0.774244 | 7.89E-05 | 7925182 | SNORA14B | 0.628019 | 8.58E-05 |
| 8066262 | SNORA71D | 0.738146 | 4.21E-06 | 7975268 | ARG2 | 0.769833 | 1.62E-05 | 8144121 | PTPRN2 | 0.627959 | 1.40E-08 |
| 8105495 | PARTI | 0.737481 | 5.25E-07 | 8130578 | SNORD20 | 0.767111 | 3.30E-06 | 8010078 | SNORD1C | 0.627364 | 0.008672 |
| 7906146 | TMEM79 | 0.737236 | 3.34E-12 | 8133360 | CLON4 | 0.765558 | 7.73E-11 | 8074969 | DDT | 0.627181 | 0.00015 |
| 7908672 | PKP1 | 0.735312 | 1.27E-12 | 8001748 | SNORA50 | 0.764135 | 2.08E-05 | 8017378 | CYB561 | 0.626057 | 1.10E-07 |
| 7912316 | CASZ1 | 0.735238 | 4.01E-13 | 7894858 | NA | 0.76275 | 3.47E-14 | 7894858 | NA | 0.6258 | 3.37E-10 |
| 8148548 | PSCA | 0.731507 | 0.000223 | 7981978 | SNORD116-1S | 0.761116 | 0.002414 | 7892643 | NA | 0.625742 | 8.80E-07 |
| 8134680 | ZKSCAN1 | 0.731271 | 1.30E-11 | 7924058 | IRF6 | 0.760931 | 4.33E-10 | 8131600 | TSPAN13 | 0.622802 | 1.83E-08 |
| 7904881 | PDIA3P | 0.730598 | 7.68E-07 | 7894479 | NA | 0.760773 | 5.35E-06 | 8123407 | MLLT4 | 0.62275 | 2.18E-09 |
| 8066256 | SNORA71B | 0.727947 | 2.27E-06 | 7896596 | NA | 0.76069 | 0.0004 | 7912347 | CASZ1 | 0.622123 | 9.78E-06 |
| 7968035 | SPATA13 | 0.727777 | 2.28E-12 | 8162147 | ZCCHC6 | 0.759914 | 7.61E-08 | 8023392 | SNORA37 | 0.621981 | 0.000418 |
| 8143684 | P0IA4 | 0.725675 | 3.28E-11 | 7973002 | FIJ39632 | 0.758473 | 2.43E-07 | 8059712 | SNORD82 | 0.621901 | 0.005622 |
| 8035980 | RHPN2 | 0.725521 | 5.39E-09 | 8032749 | SNORD37 | 0.758216 | 0.003634 | 7896434 | NA | 0.620875 | 0.001966 |
| 8043995 | IL1R1 | 0.72446 | 2.15E-10 | 7893573 | NA | 0.758047 | 0.019896 | 8134680 | ZKSCAN1 | 0.620283 | 9.61E-09 |
| 8114068 | SHROOM1 | 0.724044 | 8.99E-06 | 8034084 | AP1M2 | 0.757866 | 5.51E-13 | 8160295 | SCARNA8 | 0.619783 | 4.06E-05 |
| 7899480 | SNORA73A | 0.723167 | 7.90E-05 | 8045319 | NA | 0.757665 | 2.90E-07 | 8116520 | GNB2L1 | 0.619146 | 8.48E-08 |
| 7998664 | SNORA10 | 0.722303 | 4.34E-06 | 8055234 | NA | 0.757665 | 2.90E-07 | 8143307 | HIPK2 | 0.618519 | 1.28E-08 |
| 8041204 | SNORA10 | 0.722303 | 4.34E-06 | 7971461 | LCP1 | 0.757579 | 1.58E-06 | 7985809 | ABHD2 | 0.617205 | 4.02E-06 |
| 7969288 | OLFM4 | 0.721327 | 0.000712 | 8068810 | SLC37A1 | 0.755507 | 2.25E-11 | 8166925 | MAOA | 0.617085 | 1.20E-05 |
| 8015412 | JUP | 0.720984 | 1.92E-16 | 8105495 | PARTI | 0.75541 | 2.38E-07 | 8005953 | SNORD4A | 0.616102 | 0.002612 |
| 8160138 | NFIB | 0.720023 | 1.07E-09 | 7995362 | GPT2 | 0.755399 | 1.29E-09 | 8047780 | SNORA41 | 0.613255 | 0.000209 |
| 8062349 | RPN2 | 0.720011 | 6.46E-12 | 8162502 | FBP1 | 0.755097 | 5.89E-10 | 7896140 | NA | 0.612685 | 0.000152 |
| 8004508 | SNORA67 | 0.718217 | 0.00046 | 7896439 | NA | 0.752082 | 1.66E-05 | 7953291 | CD9 | 0.612391 | 2.16E-05 |
| 7940667 | SNORA57 | 0.717139 | 1.75E-07 | 8148040 | MAL2 | 0.749202 | 1.45E-07 | 8000716 | SEZ612 | 0.612304 | 6.82E-08 |
| 8118613 | SLC39A7 | 0.716636 | 1.34E-14 | 8062490 | SNORA60 | 0.746313 | 6.18E-07 | 7894816 | NA | 0.612172 | 1.12E-05 |
| 8178225 | SLC39A7 | 0.716636 | 1.34E-14 | 7904881 | PDIA3P | 0.743874 | 4.08E-07 | 8074168 | FIJ39632 | 0.611435 | 0.002088 |
| 8179525 | SLC39A7 | 0.716636 | 1.34E-14 | 7928367 | NA | 0.74262 | 0.004323 | 7894978 | NA | 0.610499 | 8.32E-09 |
| 8072926 | H1F0 | 0.716568 | 3.12E-14 | 8010078 | SNORD1C | 0.742462 | 0.001171 | 7942592 | SNORD15A | 0.610153 | 0.002219 |
| 8144669 | FDFT1 | 0.716567 | 8.76E-06 | 8109350 | SLC36A1 | 0.741678 | 9.26E-07 | 7896439 | NA | 0.609439 | 0.000745 |
| 8012126 | CLDN7 | 0.712921 | 1.33E-07 | 8106068 | MCCC2 | 0.740606 | 1.94E-07 | 8126382 | C6orf132 | 0.607258 | 4.21E-06 |
| 8025255 | STXBP2 | 0.711624 | 2.71E-16 | 8177601 | MCCC2 | 0.740606 | 1.94E-07 | 8068422 | DOPEY2 | 0.606885 | 2.25E-10 |
| 7980891 | TC2N | 0.711094 | 9.39E-09 | 7899265 | SFN | 0.740526 | 3.54E-06 | 8109773 | WWC1 | 0.606404 | 1.95E-08 |
| 8121277 | AIM1 | 0.709885 | 9.64E-11 | 8114068 | SHROOM1 | 0.740052 | 4.90E-06 | 7894165 | NA | 0.606143 | 0.006081 |
| 7925250 | GNG4 | 0.70988 | 5.73E-11 | 7949679 | SPTBN2 | 0.739676 | 1.02E-12 | 7964927 | TSPAN8 | 0.60609 | 0.010905 |
| 7921713 | FUR | 0.709529 | 2.72E-13 | 7987869 | TMEM87A | 0.737267 | 1.52E-10 | 8091458 | SERP1 | 0.606021 | 2.98E-08 |
| 7950067 | DHCR7 | 0.70886 | 2.98E-12 | 7896423 | NA | 0.735708 | 2.89E-06 | 8138361 | RPL36A | 0.605964 | 0.000114 |
| 8048116 | NA | 0.708192 | 9.85E-05 | 7912347 | CASZ1 | 0.735009 | 1.10E-07 | 7938329 | SNORA23 | 0.6051 | 0.000437 |
| 8055214 | C2orf14 | 0.707801 | 4.52E-05 | 7977507 | RPPH1 | 0.73457 | 4.28E-12 | 8055153 | POTEF | 0.604892 | 0.016674 |
| 8069985 | SNORA80 | 0.706758 | 2.67E-09 | 8084708 | SNORA4 | 0.733682 | 5.74E-06 | 8080419 | GNL3 | 0.604392 | 3.02E-09 |
| 8022428 | POTEC | 0.705397 | 1.57E-07 | 7914212 | SNORA61 | 0.732045 | 1.99E-06 | 8063473 | RPL12 | 0.604133 | 9.38E-09 |
| 8000716 | SEZ6L2 | 0.704916 | 4.35E-10 | 8094988 | CWH43 | 0.731461 | 3.86E-09 | 7958130 | HSP90B1 | 0.602675 | 9.54E-06 |
| 7944656 | SC5DL | 0.703616 | 2.83E-09 | 8068422 | DOPEY2 | 0.730506 | 3.74E-14 | 8128886 | NA | 0.602437 | 0.000131 |
| 7989768 | NA | 0.703572 | 8.49E-06 | 7960052 | SNORA49 | 0.73023 | 1.32E-05 | 7982006 | SNORD116-29 | 0.602334 | 0.008636 |
| 7960730 | LPCAT3 | 0.702402 | 2.48E-09 | 8148548 | PSCA | 0.728922 | 0.000202 | 7924058 | IRF6 | 0.601448 | 9.40E-07 |
| 7952046 | MPZL2 | 0.700323 | 3.42E-09 | 7956031 | ORMDL2 | 0.726834 | 2.76E-11 | 8020779 | DSG2 | 0.601137 | 4.09E-08 |
| 7905929 | EFNA1 | 0.700035 | 5.81E-11 | 8144021 | PTPRN2 | 0.72655 | 4.24E-11 | 8004506 | SNORA48 | 0.600422 | 9.25E-05 |
| 8150276 | PPAPDC1B | 0.699837 | 4.76E-09 | 7899821 | KIAA1522 | 0.726064 | 6.85E-15 | 8002218 | ESRP2 | 0.600204 | 2.64E-10 |
| 7986359 | IGF1R | 0.69871 | 1.13E-08 | 7981988 | SNORD116-20 | 0.725577 | 0.000548 | 8159004 | SNORD24 | 0.59969 | 0.001336 |
| 8118207 | SNORA38 | 0.694345 | 2.13E-06 | 7983274 | PDIA3 | 0.725271 | 2.22E-07 | 8062490 | SNORA60 | 0.598821 | 9.39E-05 |
| 8079060 | VIPR1 | 0.692744 | 3.52E-12 | 7986708 | POTEB | 0.724945 | 2.15E-05 | 8174189 | TMSB15A | 0.597772 | 3.96E-05 |
| 8162147 | ZCCHC6 | 0.690919 | 1.14E-06 | 8151475 | TPD52 | 0.724286 | 7.21E-07 | 8030366 | SNORD35A | 0.597604 | 0.005928 |
| 8126135 | GLO1 | 0.689773 | 4.86E-05 | 8096682 | ARHGEF38 | 0.723425 | 1.14E-08 | 8061428 | ENTPD6 | 0.596144 | 9.41E-10 |
| 7977075 | SNORA28 | 0.689759 | 0.000186 | 7938293 | SNORA45 | 0.722966 | 4.83E-06 | 7935776 | SCD | 0.596026 | 0.019455 |
| 7952046 | VSIG2 | 0.689342 | 1.12E-08 | 7951036 | SNORD5 | 0.722723 | 1.35E-05 | 7981970 | SNORD116-11 | 0.595104 | 0.003085 |
| 7983274 | PDIA3 | 0.689327 | 9.85E-07 | 7980891 | TC2N | 0.722007 | 5.06E-09 | 8041168 | SNORD53 | 0.594698 | 0.005706 |
| 8043522 | PROM2 | 0.689037 | 1.31E-10 | 7981982 | SNORD116-17 | 0.721957 | 0.002121 | 8148304 | TRIB1 | 0.592557 | 0.010635 |
| 7893880 | NA | 0.688926 | 2.14E-07 | 7981986 | SNORD116-17 | 0.721957 | 0.002121 | 8097513 | MGST2 | 0.592449 | 5.33E-06 |
| 7947274 | MPPED2 | 0.688369 | 6.04E-10 | 7899615 | 5ERINC2 | 0.720112 | 2.74E-13 | 7896423 | NA | 0.591591 | 0.000258 |
| 8015016 | TN54 | 0.688084 | 4.60E-07 | 8112107 | PPAP2A | 0.719742 | 0.000482 | 7982072 | SNORD115-33 | 0.590178 | 0.04177 |
| 8120552 | FAM135A | 0.685697 | 1.10E-07 | 7908793 | ELF3 | 0.719483 | 9.34E-07 | 7892817 | NA | 0.590068 | 1.37E-05 |
| 8045319 | NA | 0.685648 | 4.06E-06 | 8045423 | SNORA40 | 0.716864 | 5.55E-05 | 7894744 | NA | 0.589853 | 5.60E-05 |
| 8055234 | NA | 0.685648 | 4.06E-06 | 8024323 | REEP6 | 0.71613 | 5.69E-15 | 8172154 | RPS2 | 0.586011 | 0.00014 |
| 8061428 | ENTPD6 | 0.68447 | 2.16E-12 | 8032789 | STAP2 | 0.716107 | 6.33E-14 | 7977075 | SNORA28 | 0.585758 | 0.00199 |
| 7920123 | S100A10 | 0.682884 | 7.77E-06 | 8061428 | ENTPD6 | 0.715507 | 2.81E-13 | 8050160 | MBOAT2 | 0.585305 | 6.03E-06 |
| 8032789 | STAP2 | 0.681001 | 7.09E-13 | 8101086 | NAAA | 0.713832 | 3.54E-09 | 8021727 | CNOP2 | 0.583472 | 1.07E-06 |
| 7982072 | SNORD115-33 | 0.680487 | 0.015587 | 8041170 | NA | 0.713073 | 0.003706 | 7892915 | NA | 0.58291 | 0.002019 |
| 8179184 | DDR1 | 0.679877 | 1.28E-14 | 8001531 | MT1G | 0.710684 | 0.00422 | 7948679 | EEF1G | 0.582891 | 2.89E-10 |
| 7955277 | TMBIM6 | 0.679083 | 1 OOE-08 | 7977933 | SLC7A8 | 0.703017 | 2.04E-10 | 7960730 | LPCAT3 | 0.582143 | 9.18E-07 |
| 8021418 | MALT1 | 0.678876 | 7.65E-08 | 7895693 | NA | 0.702652 | 1.97E-06 | 8103951 | ACSL1 | 0.5815% | 4.78E-06 |
| 8009241 | SN0RD104 | 0.678792 | 8.75E-05 | 8124492 | HIST1H28K | 0.702606 | 3.69E-05 | 7893097 | NA | 0.581492 | 6.56E-06 |

-continued

| epithelial Benign-stromal benign ||| | epithelial PIN-stromal PIN ||| | epithelial tumor-stromal tumor |||
|---|---|---|---|---|---|---|---|---|---|---|---|
| Affymetrix ID | Gene | LogFC | Adj. P.Val | Affymetrix ID | Gene | LogFC | Adj. P.Val | Affymetrix ID | Gene | LogFC | Adj. P.Val |
| 8007363 | WNK4 | 0.677873 | 5.56E−09 | 8062695 | SRSF6 | 0.70078 | 4.42E−13 | 8090565 | SNORA7B | 0.581382 | 0.000111 |
| 8062490 | SNORA60 | 0.677565 | 7.14E−06 | 8139482 | SNORA5A | 0.700401 | 0.000207 | 7893558 | NA | 0.581152 | 0.000291 |
| 8026587 | NWOl | 0.677361 | 7.05E−11 | 8030991 | LOC147804 | 0.699615 | 1.01E−06 | 7982082 | SNORD115-38 | 0.580306 | 0.013994 |
| 8023497 | ATP8B1 | 0.676609 | 1.81E−12 | 7968029 | PCOTH | 0.699485 | 0.008256 | 8180363 | NA | −0.5803 | 6.11E−13 |
| 8083494 | MME | 0.676044 | 0.000163 | 8165406 | NPDC1 | 0.697665 | 5.96E−16 | 7980044 | PNMA1 | −0.58045 | 3.64E−09 |
| 7986092 | FURIN | 0.675593 | 8.81E−12 | 8052762 | GFPT1 | 0.69755 | 1.12E−09 | 7922130 | DPT | −0.58149 | 0.000611 |
| 8054872 | TFCP2L1 | 0.675172 | 5.07E−10 | 7982066 | SNORD115-30 | 0.694733 | 0.000181 | 8179041 | HLA-A | −0.58208 | 0.000815 |
| 8155849 | ANXA1 | 0.672321 | 0.002818 | 8031837 | ZNF587 | 0.694562 | 4.82E−08 | 7896438 | NA | −0.58237 | 0.021982 |
| 8059708 | SNORA75 | 0.671736 | 0.000568 | 7948900 | SNORD30 | 0.693843 | 0.000204 | 8115814 | SH3PXD2B | −0.58275 | 1.05E−09 |
| 8149725 | PEBP4 | 0.671282 | 3.30E−08 | 8010243 | SYNGR2 | 0.692682 | 7.38E−13 | 8083429 | MBNl1 | −0.5829 | 1.68E−11 |
| 7982878 | CHP | 0.669213 | 1.11E−06 | 8005202 | SNORD49A | 0.691643 | 0.006833 | 7916747 | JAK1 | −0.58386 | 1.06E−08 |
| 8162744 | C0R02A | 0.668499 | 6.81E−10 | 8063345 | SNORD12C | 0.690817 | 0.000968 | 7948667 | AHNAK | −0.58394 | 1.06E−07 |
| 8162502 | FBP1 | 0.665472 | 4.38E−08 | 7952339 | SNORD14C | 0.689629 | 0.000178 | 7903777 | GSTM5 | −0.58476 | 2.59E−05 |
| 8021442 | ZNF532 | 0.664301 | 9.62E−10 | 7982082 | SNORD115-38 | 0.688133 | 0.002242 | 7921821 | ADAMTS4 | −0.58502 | 4.13E−05 |
| 8174715 | SNORA69 | 0.663974 | 2.30E−05 | 7948898 | SNORD31 | 0.686528 | 0.001676 | 8009040 | MRC2 | −0.58594 | 1.54E−09 |
| 8125139 | NEU1 | 0.663532 | 1.16E−13 | 8025255 | STXBP2 | 0.685081 | 1.96E−15 | 8103399 | PDGFC | −0.58767 | 2.03E−08 |
| 8179851 | NEU1 | 0.663532 | 1.16E−13 | 8126382 | C6orf132 | 0.684572 | 4.66E−10 | 8156759 | NA | −0.58797 | 4.41E−05 |
| 7895693 | NA | 0.662653 | 8.50E−06 | 8047780 | SNORA41 | 0.683606 | 2.30E−05 | 8043480 | NA | −0.58921 | 1.02E−05 |
| 7997593 | ATP2C2 | 0.66231 | 5.92E−10 | 7901050 | SNORD38A | 0.683589 | 0.000783 | 7931977 | ITIH5 | −0.58966 | 4.20E−09 |
| 8060134 | KIF1A | 0.66014 | 1.71E−09 | 8121277 | AIM1 | 0.681166 | 4.22E−10 | 8095854 | 11-Sep | −0.5912 | 8.65E−07 |
| 7912343 | CASZ1 | 0.659241 | 1.71E−09 | 8128867 | CDK19 | 0.6796 | 3.95E−07 | 7933194 | CXCL12 | −0.59256 | 1.02E−08 |
| 8144786 | SLC7A2 | 0.659006 | 5.28E−07 | 8156309 | GADD45G | 0.678368 | 1.45E−05 | 7934997 | PPP1R3C | −0.59438 | 0.000107 |
| 8075217 | AP1B1 | 0.658975 | 1.48E−12 | 8076219 | SNORD83B | 0.67591 | 2.01E−05 | 8024062 | CFD | −0.59464 | 0.000868 |
| 8006906 | ERBB2 | 0.658657 | 5.20E−13 | 8109750 | RPLPO | 0.675348 | 1.27E−05 | 8089785 | P0PDC2 | −0.59508 | 2.48E−05 |
| 7958726 | CUX2 | 0.657695 | 1.81E−13 | 7895937 | NA | 0.675162 | 5.93E−07 | 7896716 | NA | −0.59511 | 4.76E−05 |
| 8117900 | DDR1 | 0.657407 | 1.27E−14 | 8165575 | PNPLA7 | 0.674978 | 7.77E−11 | 8125289 | TNXA | −0.59544 | 4.35E−10 |
| 7913593 | TCEA3 | 0.655652 | 7.33E−12 | 8015412 | JUP | 0.674965 | 5.57E−15 | 8119712 | SRF | −0.59551 | 6.67E−10 |
| 7937483 | SNORA52 | 0.654132 | 5.54E−06 | 8127841 | PGM3 | 0.674701 | 6.00E−09 | 7958764 | ALDH2 | −0.59624 | 2.30E−06 |
| 8024323 | REEP6 | 0.652214 | 5.16E−13 | 7894861 | NA | 0.674537 | 9.11E−05 | 8115831 | DUSP1 | −0.59761 | 0.006586 |
| 7895881 | NA | 0.652205 | 2.25E−08 | 7893058 | NA | 0.674372 | 0.004549 | 7919568 | NA | −0.59804 | 5.95E−07 |
| 8090688 | SNORA58 | 0.650292 | 3.62E−05 | 8126324 | PGC | 0.673409 | 0.003398 | 8124848 | IER3 | −0.59914 | 6.39E−10 |
| 7960529 | SCNN1A | 0.649847 | 6.12E−06 | 8139507 | TARP | 0.67311 | 0.002383 | 8179704 | IER3 | −0.59914 | 6.39E−10 |
| 8030982 | ZNF765 | 0.649343 | 2.34E−08 | 7895518 | NA | 0.672022 | 1.45E−08 | 7989718 | RASL12 | −0.60058 | 1.14E−06 |
| 7956038 | MMP19 | 0.648383 | 8.52E−09 | 7892707 | NA | 0.671416 | 0.000257 | 8167763 | TSPYL2 | −0.60099 | 2.62E−10 |
| 8086607 | LTF | 0.64818 | 0.038636 | 8038919 | ZNF350 | 0.67128 | 5.46E−07 | 8018975 | LGALS3BP | −0.6022 | 2.53E−06 |
| 8041853 | EPCAM | 0.648089 | 0.000476 | 8079060 | VIPR1 | 0.671227 | 1.27E−11 | 7995806 | MT1A | −0.60359 | 0.000466 |
| 7894479 | NA | 0.647139 | 0.000147 | 8006865 | PPP1R1B | 0.671224 | 8.15E−07 | 7955663 | TENC1 | −0.60432 | 7.49E−11 |
| 7966690 | TBX3 | 0.646652 | 2.79E−12 | 8111101 | ANKH | 0.670189 | 2.30E−10 | 7908388 | RGS1 | −0.60439 | 0.000162 |
| 7905938 | RAG1AP1 | 0.645812 | 1.38E−09 | 8006906 | ERBB2 | 0.669022 | 2.47E−13 | 7990632 | SGK269 | −0.60447 | 0.000125 |
| 8070961 | LSS | 0.645032 | 2.79E−12 | 8063473 | RPL12 | 0.668105 | 1.54E−10 | 7974316 | FRMD6 | −0.60515 | 1.4CE−08 |
| 8037913 | NAPA | 0.644597 | 1.03E−14 | 7894416 | NA | 0.667463 | 2.35E−05 | 7917885 | CNN3 | −0.60552 | 3.60E−10 |
| 8064100 | PPDPF | 0.644284 | 1.51E−15 | 8000716 | SEZ6L2 | 0.667416 | 2.73E−09 | 7905116 | PLEKHO1 | −0.60633 | 3.64E−11 |
| 8150112 | GSR | 0.64333 | 5.46E−15 | 8055143 | LOC440905 | 0.667271 | 2.72E−06 | 8135587 | CAV2 | −0.60722 | 1.11E−06 |
| 7896423 | NA | 0.642633 | 5.64E−05 | 7981990 | SNORD116-21 | 0.666066 | 0.008461 | 8103166 | SH3D19 | −0.60874 | 9.74E−08 |
| 7949679 | SPTBN2 | 0.63919 | 4.43E−10 | 7914809 | KIAA0319L | 0.665982 | 1.43E−12 | 7932254 | ITGA8 | −0.6097 | 0.000227 |
| 7962827 | SNORA2A | 0.63912 | 0.001103 | 7994637 | MAZ | 0.665932 | 7.34E−13 | 7976200 | CALM1 | −0.60986 | 2.08E−07 |
| 8068422 | DOPEY2 | 0.63882 | 1.64E−11 | 8123407 | MLLT4 | 0.665158 | 1.10E−10 | 8034698 | MIR23A | −0.60997 | 7.93E−05 |
| 7893558 | NA | 0.638669 | 5.26E−05 | 7996081 | 6PR56 | 0.665076 | 5.87E−11 | 8150698 | SNAI2 | −0.61057 | 6.30E−05 |
| 7991886 | CIB1 | 0.635509 | 4.49E−16 | 7965460 | RPL41 | 0.664655 | 5.96E−07 | 8090193 | HEG1 | −0.61137 | 2.89E−09 |
| 8106068 | MCCC2 | 0.63465 | 9.51E−06 | 7982129 | RPL41 | 0.664655 | 5.96E−07 | 7995523 | NA | −0.61175 | 0.001503 |
| 8177601 | MCCC2 | 0.63465 | 9.51E−06 | 8030366 | SNOR035A | 0.664629 | 0.001546 | 7894171 | NA | −0.61195 | 0.021656 |
| 8075477 | RNF185 | 0.634191 | 1.66E−05 | 8172154 | RPS2 | 0.66389 | 1.00E−05 | 8059648 | NA | −0.61267 | 0.001089 |
| 7903092 | FNBP1L | 0.631612 | 2.30E−07 | 7995895 | HERPUOl | 0.66349 | 9.28E−06 | 8104901 | IL7R | −0.61339 | 2.07E−07 |
| 8031837 | 2NF587 | 0.630811 | 7.94E−07 | 7948904 | SNORD28 | 0.663475 | 0.003735 | 8169473 | PLS3 | −0.61411 | 2.92E−10 |
| 7956031 | ORMDL2 | 0.63037 | 5.99E−09 | 8031825 | ZNF552 | 0.663197 | 7.40E−05 | 8092970 | APOD | −0.61421 | 0.010405 |
| 7982066 | SNORD115-30 | 0.630047 | 0.000905 | 7903092 | FNBPl1 | 0.662583 | 5.13E−08 | 8129497 | EPB41L2 | −0.61546 | 8.59E−09 |
| 7912257 | CLSTN1 | 0.629458 | 2.96E−15 | 8097513 | MGST2 | 0.662011 | 2.33E−07 | 7982871 | GREM1 | −0.61589 | 1.66E−07 |
| 8134452 | BHLHA15 | 0.62802 | 4.32E−08 | 8030982 | ZNF765 | 0.661741 | 1.14E−06 | 8001457 | CES1 | −0.61603 | 3.16E−06 |
| 8010562 | BAIAP2 | 0.626687 | 8.99E−14 | 8150877 | SNORD54 | 0.661178 | 0.005759 | 7909789 | TGFB2 | −0.61865 | 1.34E−05 |
| 8101086 | NAAA | 0.626484 | 2.19E−07 | 8067844 | POTED | 0.660174 | 5.70E−05 | 7953040 | CACNA1C | −0.6187 | 1.83E−10 |
| 7915227 | SNORA55 | 0.625096 | 0.000186 | 8074969 | DDT | 0.658151 | 5.04E−05 | 8065403 | CST3 | −0.62129 | 2.71E−08 |
| 7982829 | SPINT1 | 0.624739 | 3.46E−12 | 8005471 | RPS28 | 0.658115 | 2.76E−08 | 8080344 | STAB1 | −0.62406 | 6.38E−14 |
| 8004506 | SNORA48 | 0.624299 | 4.00E−05 | 8129876 | PBOV1 | 0.657212 | 2.11E−08 | 8126760 | RCAN2 | −0.62513 | 1.51E−06 |
| 7951034 | SNORA8 | 0.622822 | 0.007945 | 8109773 | WWC1 | 0.657138 | 7.77E−10 | 7934690 | ZCCHC24 | −0.62761 | 7.14E−11 |
| 8060205 | PASK | 0.622811 | 1.79E−10 | 8095986 | ANXA3 | 0.656958 | 1.78E−08 | 7906085 | LMNA | −0.62948 | 3.49E−06 |
| 7894089 | NA | 0.620959 | 0.002275 | 8154620 | NA | 0.655823 | 3.25E−08 | 7947512 | PAMR1 | −0.63025 | 3.53E−11 |
| 7924636 | TMEM63A | 0.620436 | 3.43E−08 | 8120783 | MYO6 | 0.654169 | 1.90E−05 | 7942596 | SERPINH1 | −0.63068 | 2.36E−11 |
| 7905731 | NA | 0.619687 | 0.002051 | 8083978 | NAALADL2 | 0.650952 | 1.76E−06 | 8111772 | DAB2 | −0.63187 | 2.36E−10 |
| 7991453 | FAM174B | 0.618665 | 3.03E−14 | 7912343 | CASZ1 | 0.650847 | 2.42E−09 | 8089835 | FSTL1 | −0.63414 | 4.02E−06 |
| 8145281 | SLC25A37 | 0.618566 | 1.84E−14 | 7921713 | FUR | 0.650363 | 1.17E−11 | 7908841 | PPP1R12B | −0.63472 | 8.21E−10 |
| 8009380 | SNORA38B | 0.61855 | 0.000103 | 8038086 | RPL18 | 0.647984 | 2.63E−12 | 7954899 | CNTN1 | −0.63553 | 5.18E−06 |
| 8129880 | PERP | 0.618395 | 2.20E−08 | 7920082 | RORC | 0.647521 | 2.84E−11 | 8123744 | F13A1 | −0.63603 | 2.47E−10 |
| 8073743 | UPK3A | 0.616873 | 3.29E−09 | 8035980 | RHPN2 | 0.64668 | 1.62E−07 | 8027778 | FXYD5 | −0.63963 | 2.53E−10 |

-continued

| epitheliail Benign-stromal benign | | | | epithelial PIN-stromal PIN | | | | epithelial tumor-stromal tumor | | | |
|---|---|---|---|---|---|---|---|---|---|---|---|
| Affymetrix ID | Gene | LogFC | Adj. P.Val | Affymetrix ID | Gene | LogFC | Adj. P.Val | Affymetrix ID | Gene | LogFC | Adj. P.Val |
| 7893642 | NA | 0.616102 | 6.76E−05 | 7929816 | SCD | 0.646166 | 3.59E−05 | 8043476 | LOC652493 | −0.64022 | 0.000304 |
| 7896375 | NA | 0.616093 | 2.20E−08 | 8071737 | MIF | 0.645753 | 9.45E−13 | 8172022 | TMEM47 | −0.64025 | 3.44 E−08 |
| 7939642 | CREB3L1 | 0.61542 | 1.54E−05 | 8052141 | NA | 0.645601 | 1.56E−06 | 8115076 | CSF1R | −0.6407 | 3.99E−10 |
| 7905079 | HIST2H2AA3 | 0.614447 | 6.25E−10 | 8025395 | RPS28 | 0.644506 | 1.13E−08 | 7937802 | CD81 | −0.64095 | 1.21E−09 |
| 7919619 | HIST2H2AA3 | 0.614447 | 6.25E−10 | 7948906 | SNORD27 | 0.644333 | 0.001737 | 7903893 | CD53 | −0.64147 | 7.35E−10 |
| 8068833 | PDE9A | 0.614245 | 1.10E−08 | 7948896 | SNORD22 | 0.644021 | 0.000645 | 8127234 | DST | −0.64891 | 6.94E−11 |
| 8107326 | SNORA13 | 0.610822 | 0.000616 | 8170882 | ATP6AP1 | 0.642816 | 3.20E−10 | 7945262 | JAM 3 | −0.65012 | 3.77E−09 |
| 7944049 | SIDT2 | 0.610778 | 3.16E−09 | 8088642 | LRIG1 | 0.642715 | 9.19E−08 | 8038407 | RRAS | −0.65116 | 1.21E−09 |
| 7934852 | GLUD1 | 0.608475 | 1.14E−08 | 7940135 | GLYATL1 | 0.64253 | 1.28E−09 | 7996027 | CX3CL1 | −0.65118 | 1.51E−09 |
| 7896517 | NA | 0.608092 | 1.45E−07 | 7993756 | ACSM3 | 0.642492 | 5.24E−06 | 7969677 | MBNL2 | −0.65128 | 7.10E−10 |
| 8044584 | PSD4 | 0.608052 | 8.67E−12 | 7897745 | AGTRAP | 0.642193 | 4.63E−08 | 7981732 | IGHV4-59 | −0.65142 | 0.004361 |
| 8001746 | SNORA46 | 0.607511 | 0.000116 | 8021301 | RAB27B | 0.641681 | 1.42E−08 | 8170602 | ZNF185 | −0.65279 | 1.18E−06 |
| 8154620 | NA | 0.606259 | 3.56E−07 | 8047635 | RPL12 | 0.641473 | 4.77E−10 | 8014369 | CCL3 | −0.6529 | 4.02E−06 |
| 8090565 | SNORA7B | 0.605485 | 4.73E−05 | 8143307 | HIPK2 | 0.641281 | 2.31E−09 | 8178712 | TNXB | −0.65461 | 1.10E−10 |
| 8026875 | SNORA68 | 0.604535 | 0.00033 | 8145532 | EPHX2 | 0.640164 | 6.36E−09 | 8179935 | TNXB | −0.65461 | 1.10E−10 |
| 8126324 | PGC | 0.603107 | 0.011668 | 7892868 | NA | 0.640015 | 8.04E−06 | 7965767 | NA | −0.65471 | 0.013569 |
| 8020779 | DSG2 | 0.602811 | 2.67E−08 | 8002218 | ESRP2 | 0.639964 | 1.09E−11 | 8076185 | CBX7 | −0.65519 | 7.67E−12 |
| 7997381 | CENPN | 0.601877 | 2.78E−05 | 8131600 | TSPAN13 | 0.638598 | 5.03E−09 | 7980152 | LTBP2 | −0.65577 | 5.84E−12 |
| 7952290 | TRIM29 | 0.6014 | 2.30E−07 | 8014487 | ACACA | 0.63752 | 9.35E−08 | 8135734 | C7orf58 | −0.6563 | 4.15E−10 |
| 8030067 | SULT2B1 | 0.60007 | 1.12E−14 | 8123658 | SLC22A23 | 0.637211 | 1.48E−08 | 8159521 | PTGDS | −0.65748 | 9.55E−09 |
| 8061186 | SEC23B | 0.599974 | 1.12E−07 | 8159004 | SNORD24 | 0.636401 | 0.000491 | 8039084 | NA | −0.65796 | 0.002791 |
| 8070579 | TFF1 | 0.599783 | 0.000286 | 8144669 | FDFT1 | 0.635654 | 4.10E−08 | 7903742 | GSTM4 | −0.65872 | 1.59E−07 |
| 8122144 | SNORA33 | 0.599105 | 0.004445 | 7982829 | SPINT1 | 0.635637 | 1.55E−12 | 7926545 | PLXDC2 | −0.65961 | 2.02E−10 |
| 7896439 | NA | 0.598115 | 0.000906 | 7896349 | NA | 0.635102 | 8.78E−10 | 8114612 | CD14 | −0.6598 | 3.74E−12 |
| 8060225 | HDLBP | 0.597567 | 1.45E−14 | 8061186 | SEC23B | 0.634778 | 1.79E−08 | 8056860 | WIPF1 | −0.66009 | 1.60E−10 |
| 8023561 | LMAN1 | 0.597287 | 3.12E−08 | 7948908 | SNORD26 | 0.634252 | 0.001101 | 7942417 | ARHGEF17 | −0.66184 | 1.47E−12 |
| 7920128 | S100A11 | 0.596645 | 8.97E−05 | 8144786 | SLC7A2 | 0.632468 | 1.29E−06 | 8108631 | VTRNA1-3 | −0.66227 | 0.002028 |
| 7960514 | NA | 0.594548 | 0.000459 | 7894529 | NA | 0.631263 | 0.007379 | 8043465 | IGKC | −0.66258 | 0.000394 |
| 8109773 | WWC1 | 0.59434 | 2.58E−08 | 7948910 | SNORD25 | 0.630488 | 5.76E−08 | 7906720 | FCER1G | −0.66438 | 7.51E−10 |
| 8097513 | MGST2 | 0.594123 | 4.06E−06 | 8005547 | SNORD3A | 0.628846 | 2.29E−05 | 8028104 | HCST | −0.66504 | 2.24E−08 |
| 7914809 | KIAA0319L | 0.593168 | 1.86E−10 | 8005553 | SNORD3A | 0.628846 | 2.29E−05 | 7901788 | NFIA | −0.66545 | 3.20E−11 |
| 8045423 | SNORA40 | 0.592819 | 0.001234 | 8013323 | SNORD3A | 0.628846 | 2.29E−05 | 7973336 | MMP14 | −0.66585 | 2.85E−12 |
| 8170882 | ATP6AP1 | 0.591584 | 6.63E−09 | 8013325 | SNORD3A | 0.628846 | 2.29E−05 | 7903753 | GSTM2 | −0.66764 | 1.98E−06 |
| 7987815 | PLA2G4F | 0.591367 | 2.83E−09 | 8013329 | SNORD3A | 0.628846 | 2.29E−05 | 8020110 | RAB31 | −0.67035 | 1.70E−09 |
| 7989224 | ADAM 10 | 0.591241 | 2.34E−08 | 7942824 | RPS28 | 0.62808 | 1.16E−08 | 7963142 | FAIM2 | −0.67062 | 1.71E−08 |
| 8078918 | SNORA62 | 0.591097 | 0.000923 | 7995825 | MT1F | 0.627607 | 7.01E−05 | 8040792 | EMILIN1 | −0.67266 | 3.83E−13 |
| 8038653 | KIKP1 | 0.590525 | 1.97E−06 | 8082012 | SLC15A2 | 0.627439 | 6.60E−06 | 8027760 | FXYD1 | −0.6747 | 3.14E−06 |
| 7899323 | SYTL1 | 0.590102 | 7.72E−14 | 7968035 | SPATA13 | 0.627249 | 7.98E−10 | 7935180 | PDLIM1 | −0.67679 | 1.31E−06 |
| 7977507 | RPPH1 | 0.588148 | 1.89E−08 | 8055476 | YWHAE | 0.625884 | 1.89E−05 | 8095080 | PDGFRA | −0.67753 | 7.95E−10 |
| 8064388 | C20orf54 | 0.587921 | 2.52E−09 | 8084717 | ST6GAL1 | 0.625386 | 0.000507 | 8045088 | NA | −0.6813 | 0.000509 |
| 7919637 | HIST2H2BE | 0.587715 | 1.83E−06 | 7955277 | TMBIM6 | 0.625283 | 1.09E−07 | 7904158 | OLFML3 | −0.68133 | 5.28E−08 |
| 8038919 | ZNF350 | 0.587112 | 1.42E−05 | 7926679 | KIAA1217 | 0.625124 | 2.01E−11 | 8162531 | NA | −0.68538 | 0.004234 |
| 8004521 | MPDU1 | 0.587011 | 1.19E−10 | 7893558 | NA | 0.624275 | 6.92E−05 | 7961540 | RERG | −0.6854 | 2.73E−08 |
| 7894210 | NA | 0.585559 | 0.003676 | 8045182 | PTPN18 | 0.624271 | 1.94E−09 | 8107133 | PAM | −0.6857 | 3.64E−11 |
| 7949765 | PPP1CA | 0.585532 | 2.78E−15 | 8048733 | ACSL3 | 0.623908 | 5.76E−05 | 7896711 | NA | −0.68713 | 0.017553 |
| 7892830 | NA | 0.584316 | 3.29E−08 | 7960728 | SCARNA12 | 0.623744 | 1.60E−07 | 7896708 | NA | −0.68795 | 0.016559 |
| 8054254 | AFF3 | 0.584106 | 8.03E−06 | 8100026 | ATP8A1 | 0.621779 | 1.48E−09 | 8112855 | NA | −0.69027 | 0.005901 |
| 8036133 | UPK1A | 0.583847 | 7.59E−07 | 7901046 | SNORD55 | 0.621213 | 0.000486 | 8171921 | DMD | −0.69044 | 2.82E−07 |
| 8127841 | PGM3 | 0.582533 | 5.21E−07 | 7978707 | NA | 0.621199 | 4.42E−07 | 7932966 | ITGB1 | −0.69096 | 2.15E−10 |
| 8160295 | SCARNA8 | 0.58245 | 0.000111 | 7922095 | BRP44 | 0.620315 | 6.58E−12 | 8156848 | NR4A3 | −0.69137 | 1.67E−05 |
| 8063761 | CDH26 | 0.580436 | 4.22E−08 | 7912316 | CASZ1 | 0.620217 | 4.32E−10 | 8023415 | TCF4 | −0.6931 | 6.28E−12 |
| 8088642 | LRIG1 | 0.580109 | 1.61E−06 | 8038913 | ZNF649 | 0.619809 | 1.20E−07 | 8106573 | THBS4 | −0.69347 | 7.08E−06 |
| 7913237 | CAMK2N1 | −0.5801 | 1.17E−05 | 8039904 | ZNF577 | 0.619609 | 2.64E−06 | 7992181 | TPSAB1 | −0.69423 | 4.41E−10 |
| 8129497 | EPB41L2 | −0.58027 | 3.76E−08 | 8125750 | RPL12 | 0.617281 | 1.34E−08 | 7979813 | ZFP36L1 | −0.69605 | 1.49E−09 |
| 8004510 | CD68 | −0.58051 | 1.71E−05 | 7982088 | SNORD115-41 | 0.616601 | 0.001272 | 8149387 | FAM86B1 | −0.69625 | 3.53E−06 |
| 7916747 | JAK1 | −0.58161 | 8.18E−09 | 8139484 | SNORA5C | 0.61596 | 1.90E−05 | 8010978 | LOC100130876 | −0.70068 | 0.000287 |
| 8115261 | CCOC69 | −0.58213 | 3.30E−12 | 8135876 | SND1 | 0.6156 | 7.79E−12 | 8028652 | ZFP36 | −0.70105 | 0.008305 |
| 8175755 | CETN2 | −0.58238 | 2.29E−09 | 8118613 | SLC39A7 | 0.615082 | 1.35E−11 | 7938608 | SPON1 | −0.70126 | 2.60E−08 |
| 7978718 | SEC23A | −0.58422 | 6.36E−10 | 8178225 | SLC39A7 | 0.615082 | 1.35E−11 | 7987315 | ACTC1 | −0.70245 | 0.001141 |
| 8127563 | COL12A1 | −0.58474 | 0.000236 | 8179525 | SLC39A7 | 0.615082 | 1.35E−11 | 7939559 | TSPAN18 | −0.70498 | 5.28E−08 |
| 7946245 | DCHS1 | −0.58506 | 1.61E−11 | 8062349 | RPN2 | 0.615027 | 2.57E−09 | 7981722 | IGHA1 | −0.70624 | 0.000182 |
| 8078330 | RBMS3 | −0.58622 | 3.57E−07 | 8149525 | CSGALNACT1 | 0.613955 | 3.19E−05 | 7946401 | ST5 | −0.70912 | 2.03E−11 |
| 8045088 | NA | −0.58625 | 0.003308 | 8157270 | SLC31A1 | 0.613185 | 1.97E−06 | 8152703 | FBXO32 | −0.71277 | 1.48E−07 |
| 8938225 | OLFMll | −0.58691 | 5.05E−10 | 8141206 | BAIAP2L1 | 0.612025 | 3.46E−08 | 7917516 | GBP1 | −0.71429 | 1.19E−07 |
| 8145685 | NA | −0.58705 | 1.82E−07 | 7913385 | RAP1GAP | 0.611505 | 7.72E−07 | 7937335 | IFITM1 | −0.71488 | 5.47E−08 |
| 8011499 | P2RX1 | −0.58824 | 2.40E−07 | 8117382 | HIST1H2BD | 0.610276 | 1.72E−08 | 8048995 | ITM2C | −0.71637 | 5.07E−09 |
| 8029831 | CALM3 | −0.58837 | 8.55E−12 | 8076270 | RPL3 | 0.610112 | 3.42E−10 | 8154962 | DNAJB5 | −0.71777 | 2.18E−09 |
| 8127234 | DST | −0.58858 | 1.55E−09 | 8065280 | RALGAPA2 | 0.609723 | 4.01E−06 | 7989335 | ANXA2 | −0.71847 | 2.90E−05 |
| 7976795 | MEG3 | −0.58944 | 7.94E−06 | 7919761 | NA | 0.609688 | 0.002557 | 8105229 | PELO | −0.71886 | 5.37E−09 |
| 8030277 | CD37 | −0.58963 | 2.36E−10 | 8116520 | GNB2L1 | 0.607982 | 9.19E−08 | 8094134 | USP17L6P | −0.72036 | 6.24E−09 |
| 8109305 | SYNPO | −0.59032 | 1.98E−16 | 7923778 | ELK4 | 0.607881 | 1.21E−07 | 7946589 | MRVI1 | −0.72205 | 1.71E−12 |
| 8088476 | NA | −0.59069 | 0.003399 | 7934698 | SFTPA2 | 0.607336 | 8.58E−05 | 8006621 | CCL4L1 | −0.72205 | 4.18E−07 |
| 7958846 | PTPN11 | −0.59076 | 2.45E−10 | 7934708 | SFTPA2 | 0.607336 | 8.58E−05 | 8019651 | CCL4L1 | −0.72205 | 4.18E−07 |

-continued

| epitheliail Benign-stromal benign | | | | epithelial PIN-stromal PIN | | | | epithelial tumor-stromal tumor | | | |
|---|---|---|---|---|---|---|---|---|---|---|---|
| Affymetrix ID | Gene | LogFC | Adj. P.Val | Affymetrix ID | Gene | LogFC | Adj. P.Val | Affymetrix ID | Gene | LogFC | Adj. P.Val |
| 8090852 | AMOTL2 | −0.59112 | 2.74E−09 | 7960730 | LPCAT3 | 0.607232 | 2.01E−07 | 7906767 | FCGR2C | −0.72252 | 2.01E−09 |
| 7946142 | PRKCDBP | −0.5922 | 4.31E−09 | 8072926 | H1F0 | 0.606522 | 4.65E−11 | 8075310 | LIF | −0.72328 | 1.04E−05 |
| 8095080 | POGFRA | −0.59314 | 4.29E−08 | 7896253 | NA | 0.606271 | 0.000198 | 8163257 | LPAR1 | −0.72336 | 2.78E−07 |
| 7971077 | POSTN | −0.5938 | 0.002259 | 7952426 | VSIG2 | 0.606209 | 4.13E−07 | 8043449 | IGK@ | −0.72388 | 8.59E−05 |
| 8117045 | RBM24 | −0.59526 | 1.09E−09 | 7904254 | ATP1A1 | 0.606081 | 5.40E−08 | 8099340 | WDR1 | −0.7245 | 2.63E−13 |
| 8050548 | LAPTM4A | −0.59527 | 1.15E−06 | 8099912 | C4orf34 | 0.60466 | 3.06E−09 | 8132092 | INMT | −0.72592 | 7.32E−15 |
| 8083429 | MBNL1 | −0.5998 | 2.63E−12 | 7916343 | YIPF1 | 0.603897 | 4.38E−08 | 7998434 | TPSAB1 | −0.7262 | 8.54E−10 |
| 8073680 | NA | −0.60139 | 0.000149 | 8061364 | RPL41 | 0.602253 | 1.04E−05 | 8103544 | SPOCK3 | −0.72944 | 2.55E−06 |
| 8157650 | PTGS1 | −0.60236 | 3.91E−07 | 7895215 | NA | 0.602095 | 2.44E−07 | 8078330 | RBMS3 | −0.72993 | 5.04E−10 |
| 8133721 | HSPB1 | −0.60269 | 0.000206 | 7894188 | NA | 0.601985 | 0.004209 | 8112139 | IL6ST | −0.73131 | 1.31E−09 |
| 7914361 | COL16A1 | −0.60324 | 5.14E−11 | 7909400 | CD46 | 0.601504 | 7.99E−08 | 7929689 | MARVELD1 | −0.73136 | 1.37E−13 |
| 8083260 | CPA3 | −0.60329 | 3.51E−08 | 7896434 | NA | 0.601487 | 0.0024 | 7944302 | PHLDB1 | −0.7323 | 2.64E−11 |
| 8102938 | RNF150 | −0.60561 | 7.65E−10 | 8067125 | BCAS1 | 0.601373 | 5.06E−07 | 8118409 | C4A | −0.73245 | 0.000758 |
| 8121749 | GJA1 | −0.60564 | 0.000124 | 7894658 | NA | 0.600115 | 0.00544 | 8118455 | C4A | −0.73245 | 0.000758 |
| 7894581 | NA | −0.60613 | 0.003482 | 8092090 | TERC | 0.599919 | 3.09E−07 | 8179399 | C4A | −0.73245 | 0.000758 |
| 7974316 | FRMD6 | −0.60888 | 7.90E−09 | 7946201 | ARFIP2 | 0.59987 | 7.58E−13 | 7990545 | CSP64 | −0.73264 | 2.28E−09 |
| 8001656 | NA | −0.60913 | 3.20E−05 | 7956038 | MMP19 | 0.599775 | 8.25E−08 | 7957260 | GLIPR1 | −0.7335 | 5.26E−07 |
| 8170602 | ZNF185 | −0.61211 | 4.33E−06 | 8054308 | TBC1D8 | 0.599566 | 7.34E−10 | 8145470 | DPYSL2 | −0.73378 | 6.04E−13 |
| 8075462 | SEIM | −0.61244 | 3.84E−11 | 8082133 | PDIA5 | 0.598525 | 1.93E−09 | 8037005 | TGFB1 | −0.73457 | 2.79E−14 |
| 8053735 | NA | −0.61321 | 4.27E−07 | 7894700 | NA | 0.597852 | 0.000655 | 7954997 | ANO6 | −0.73552 | 2.60E−07 |
| 8112139 | IL6ST | −0.61394 | 2.17E−07 | 7896375 | NA | 0.597767 | 4.84E−08 | 7978586 | CFL2 | −0.73641 | 3.91E−06 |
| 7973709 | NFATC4 | −0.6146 | 1.00E−16 | 7967127 | CAMKK2 | 0.597656 | 0.000128 | 8047487 | FZD7 | −0.73681 | 9.36E−15 |
| 7917516 | GBP1 | −0.61533 | 4.16E−06 | 7896205 | NA | 0.597303 | 0.000429 | 7989670 | RBPMS2 | −0.73727 | 4.94E−09 |
| 7919815 | CTSK | −0.61571 | 8.54E−08 | 8013348 | RPS2 | 0.596266 | 1.53E−09 | 8121275 | NA | −0.73834 | 0.001481 |
| 7974902 | RHOJ | −0.61586 | 1.53E−09 | 7896044 | NA | 0.596106 | 0.005081 | 8131844 | GPNMB | −0.73944 | 1.26E−08 |
| 7961532 | ARHGDIB | −0.61675 | 6.48E−07 | 7926875 | BAMBI | 0.596009 | 3.57E−07 | 7981718 | IGHM | −0.74107 | 0.000224 |
| 8118409 | C4A | −0.61715 | 0.00567 | 7948679 | EEF16 | 0.595874 | 6.57E−11 | 8101673 | NA | −0.7446 | 0.010336 |
| 8118455 | C4A | −0.61715 | 0.00567 | 7895112 | NA | 0.59559 | 6.69E−07 | 7980316 | TGFB3 | −0.74462 | 0.004913 |
| 8179399 | C4A | −0.61715 | 0.00567 | 8134680 | ZKSCAN1 | 0.59556 | 2.08E−08 | 8151816 | GEM | −0.74464 | 1.02E−07 |
| 8049528 | LRRFIP1 | −0.61804 | 5.38E−06 | 7896140 | NA | 0.595356 | 0.000191 | 8102792 | PCDH18 | −0.74538 | 1.06E−06 |
| 7967702 | NA | −0.61822 | 6.94E−06 | 7913593 | TCEA3 | 0.595302 | 3.24E−10 | 8164607 | FNBP1 | −0.74774 | 1.26E−13 |
| 7938544 | TEA01 | −0.61954 | 7.11E−11 | 8119620 | GNMT | 0.593686 | 3.32E−06 | 8109157 | MIR143 | −0.74889 | 4.64E−07 |
| 8180377 | NA | −0.61954 | 1.33E−08 | 7892906 | NA | 0.592277 | 8.06 E−06 | 8174670 | KIAA1210 | −0.749 | 0.00017 |
| 7895619 | NA | −0.6196 | 0.001019 | 8162744 | CORO2A | 0.592089 | 3.47E−08 | 8029950 | EHD2 | −0.75468 | 1.08E−13 |
| 8078450 | CRTAP | −0.61996 | 8.46E−15 | 8059953 | NA | 0.591439 | 9.63E−05 | 8081686 | BOC | −0.75656 | 1.40E−10 |
| 8009040 | MRC2 | −0.6209 | 1.13E−10 | 8082408 | SEC61A1 | 0.589382 | 4.76E−09 | 8129573 | MOXD1 | −0.75797 | 2.29E−09 |
| 7962455 | NELL2 | −0.62116 | 0.000207 | 8092541 | LIPH | 0.588903 | 8.39E−08 | 7937772 | IGF2 | −0.75933 | 0.00503 |
| 8075310 | LIF | −0.62117 | 0.00016 | 7960635 | SCARNA11 | 0.588289 | 0.001074 | 7949412 | LTBP3 | −0.75936 | 4.77E−15 |
| 8094625 | KLHL5 | −0.62301 | 1.97E−07 | 8167305 | EBP | 0.587931 | 1.19E−05 | 7976795 | MEG3 | −0.76023 | 1.23E−08 |
| 8043114 | TCF7L1 | −0.62303 | 1.42E−09 | 8163328 | PTGR1 | 0.587208 | 3.31E−10 | 8043114 | TCF7L1 | −0.76183 | 7.03E−13 |
| 7944361 | NA | −0.62332 | 1.18E−07 | 7894148 | TM7SF2 | 0.586939 | 1.11E−11 | 8043363 | NCRNA00152 | −0.76184 | 5.88E−10 |
| 7908841 | PPP1R12B | −0.62688 | 8.03E−10 | 8105432 | RPL41 | 0.586902 | 1.91E−05 | 7906954 | PBX1 | −0.76387 | 6.17E−12 |
| 8180379 | NA | −0.62832 | 5.57E−10 | 8005951 | SNORD42B | 0.586175 | 0.038454 | 8095751 | PARM1 | −0.76452 | 5.34E−07 |
| 8091078 | RBP1 | −0.63034 | 9.83E−09 | 8116532 | SNORD95 | 0.586103 | 0.000341 | 7914282 | SDC3 | −0.76562 | 5.18E−15 |
| 8108217 | TGFBI | −0.63192 | 1.73E−07 | 8143684 | PDIA4 | 0.585285 | 5.46E−08 | 7908409 | RGS2 | −0.76774 | 0.000201 |
| 7894771 | NA | −0.63376 | 0.000525 | 7896142 | NA | 0.58523 | 0.00042 | 7902810 | LM04 | −0.76917 | 1.70E−12 |
| 7934997 | PPP1R3C | −0.63443 | 2.83E−05 | 8170859 | RPL10 | 0.585066 | 8.95E−05 | 8121729 | PIN | −0.77204 | 3.92E−06 |
| 7954293 | PDE3A | −0.63471 | 4.11E−07 | 7919637 | HIST2H2BE | 0.5849 | 1.78E−06 | 8132118 | AQP1 | −0.77321 | 1.13E−11 |
| 7918825 | CSOE1 | −0.63491 | 5.73E−11 | 8150276 | PPAPDC1B | 0.583828 | 8.37E−07 | 8045009 | GY PC | −0.77432 | 1.62E−14 |
| 8119357 | OAAM2 | −0.6352 | 2.99E−10 | 8044584 | PSD4 | 0.583728 | 4.26E−11 | 8075462 | SELM | −0.77442 | 1.26E−15 |
| 8147573 | OSR2 | −0.63616 | 3.49E−12 | 7917276 | LPAR3 | 0.583377 | 4.04E−07 | 8158627 | NCS1 | −0.77527 | 1.15E−09 |
| 8145954 | TACC1 | −0.63668 | 2.72E−09 | 7909877 | MOSC1 | 0.582911 | 3.24E−08 | 8043438 | IGKV1-5 | −0.77531 | 0.000828 |
| 8136159 | NA | −0.64013 | 0.000467 | 8126784 | PLA2G7 | 0.582902 | 0.012509 | 8033257 | C3 | −0.77534 | 3.74E−05 |
| 8020110 | RAB31 | −0.64062 | 5.24E−09 | 7917347 | DDAH1 | 0.582431 | 6.37E−10 | 8117054 | CAP2 | −0.7762 | 7.50E−09 |
| 8036252 | CLIP3 | −0.64211 | 2.06E−16 | 7896517 | NA | 0.582415 | 4.07E−07 | 8178435 | IER3 | −0.7772 | 5.88E−10 |
| 7950062 | NA | −0.64227 | 0.015309 | 8095834 | SHROOM3 | 0.581887 | 1.62E−09 | 8156783 | C0L15A1 | −0.77768 | 1.14E−12 |
| 8047738 | NRP2 | −0.64292 | 3.18E−10 | 8024801 | SERPINB11 | 0.58108 | 0.021932 | 7950005 | MRGPRF | −0.77875 | 1.10E−10 |
| 8015835 | 0USP3 | −0.64455 | 2.10E−11 | 7982002 | SNORD116-27 | 0.580833 | 2.06E−05 | 8087337 | LAMB2 | −0.78015 | 4.20E−14 |
| 8094134 | USP17L6P | −0.64616 | 1.25E−07 | 8030871 | ZNF613 | 0.580473 | 6.42E−09 | 7906501 | ATP1A2 | −0.78126 | 2.09E−09 |
| 8050089 | TMSB4XP2 | −0.64732 | 4.48E−12 | 7895334 | NA | 0.580214 | 0.000212 | 7921916 | RGS5 | −0.78213 | 1.11E−08 |
| 8135587 | CAV2 | −0.64776 | 1.52E−07 | 7958130 | HSP90B1 | 0.580176 | 1.55E−05 | 7984813 | ISLR | −0.78252 | 1.22E−11 |
| 7973797 | COCH | −0.64838 | 1.98E−12 | 8177807 | DDR1 | 0.580095 | 6.43E−10 | 8138789 | JAZF1 | −0.78643 | 2.32E−11 |
| 7942596 | SERPINH1 | −0.64983 | 8.48E−12 | 7954926 | PDZRN4 | −0.58093 | 1.77E−06 | 8108217 | TGFBI | −0.78672 | 1.95E−10 |
| 8172022 | TMEM47 | −0.65083 | 1.47E−08 | 8043363 | NCRNA00152 | −0.5818 | 1.24E−06 | 8145954 | TACC1 | −0.78866 | 9.18E−13 |
| 7896698 | NA | −0.65228 | 4.90E−10 | 8151993 | COX6C | −0.58202 | 0.001538 | 7981317 | NA | −0.79067 | 1.82E−09 |
| 8043468 | NA | −0.65229 | 8.83E−06 | 7903893 | CD53 | −0.58298 | 1.12E−08 | 8118594 | HLA-DPB1 | −0.79068 | 2.19E−09 |
| 8055038 | LIMS2 | −0.65278 | 9.07E−13 | 8178426 | HLA-DQB1 | −0.58317 | 0.000387 | 8043459 | IGKC | −0.79193 | 6.18E−05 |
| 7894919 | NA | −0.65361 | 0.007393 | 8180022 | HLA-DQB1 | −0.58317 | 0.000387 | 7949588 | CD248 | −0.79366 | 4.13E−06 |
| 8089785 | POPDC2 | −0.6538 | 2.66E−06 | 7999476 | NA | −0.58451 | 4.19E−05 | 7915229 | HEYL | −0.79622 | 1.82E−12 |
| 8129037 | NA | −0.659 | 1.95E−09 | 8048995 | ITM2C | −0.58497 | 1.11E−06 | 7956856 | MSRB3 | −0.79647 | 1.15E−07 |
| 7981720 | IGHV3-48 | −0.65984 | 2.03E−07 | 8066117 | SAMHD1 | −0.585 | 2.00E−08 | 7989491 | TPM1 | −0.79656 | 2.00E−14 |
| 7952268 | THY1 | −0.66004 | 1.32E−07 | 8016390 | COPZ2 | −0.58569 | 4.44E−09 | 7997582 | WFDC1 | −0.79662 | 4.80E−13 |
| 8099340 | WDR1 | −0.66034 | 8.84E−12 | 8161852 | NA | −0.58707 | 0.003307 | 8113504 | C5orf13 | −0.79771 | 9.68E−09 |

-continued

| epithelial Benign-stromal benign | | | | epithelial PIN-stromal PIN | | | | epithelial tumor-stromal tumor | | | |
|---|---|---|---|---|---|---|---|---|---|---|---|
| Affymetrix ID | Gene | LogFC | Adj. P.Val | Affymetrix ID | Gene | LogFC | Adj. P.Val | Affymetrix ID | Gene | LogFC | Adj. P.Val |
| 8126760 | RCAN2 | −0.6617 | 8.25E−12 | 7981720 | IGHV3-48 | −0.58723 | 3.35E−06 | 8168557 | SH3BGRL | −0.7989 | 5.93E−11 |
| 7922887 | NA | −0.66193 | 1.22E−05 | 8072705 | RASD2 | −0.58801 | 1.69E−11 | 8051762 | SLC8A1 | −0.7995 | 7.93E−09 |
| 7907368 | NA | −0.66287 | 6.51E−06 | 7933872 | EGR2 | −0.58915 | 1.11E−06 | 7899160 | CD52 | −0.80043 | 1.49E−07 |
| 7959361 | MLXIP | −0.66416 | 2.79E−13 | 7926916 | ZEB1 | −0.58934 | 1.57E−12 | 8055465 | CXCR4 | −0.80147 | 1.04E−08 |
| 8041781 | EPAS1 | −0.66578 | 4.38E−07 | 7961710 | ABCC9 | −0.58975 | 5.49E−12 | 7919815 | CTSK | −0.80148 | 6.52E−12 |
| 7925876 | PFKP | −0.66595 | 2.35E−11 | 8149387 | FAM86B1 | −0.5942 | 6.55E−05 | 7957023 | LYZ | −0.80244 | 6.82E−05 |
| 7894527 | NA | −0.66637 | 0.000201 | 8028652 | ZFP36 | −0.59456 | 0.027767 | 7995206 | TGFB1I1 | −0.80454 | 2.38E−15 |
| 7990632 | SGK269 | −0.66654 | 1.75E−05 | 7946142 | PRKCDBP | −0.59636 | 3.06E−09 | 8150318 | FGFR1 | −0.80494 | 2.74E−11 |
| 7971163 | NA | −0.66751 | 1.31E−07 | 8015835 | DUSP3 | −0.59667 | 3.99E−10 | 8030007 | EMP3 | −0.80701 | 6.25E−10 |
| 8151816 | GEM | −0.66869 | 1.35E−06 | 7942596 | SERPINH1 | −0.59693 | 2.36E−10 | 7995477 | NA | −0.80766 | 9.15E−06 |
| 8080685 | SLMAP | −0.66891 | 9.48E−11 | 8001656 | NA | −0.59703 | 4.13E−05 | 7951917 | FXYD6 | −0.80769 | 7.29E−10 |
| 8163257 | LPAR1 | −0.6697 | 1.59E−06 | 8050548 | LAPTM4A | −0.59783 | 8.91E−07 | 7965123 | PPP1R12A | −0.80895 | 6.81E−09 |
| 8056860 | WIPF1 | −0.67015 | 5.09E−11 | 8120402 | BAG2 | −0.59946 | 7.77E−08 | 8036473 | PPP1R14A | −0.80948 | 5.22E−12 |
| 7931977 | ITIH5 | −0.67098 | 2.04E−11 | 7974902 | RHOJ | −0.59961 | 3.51E−09 | 8090070 | ADCY5 | −0.81236 | 1.12E−10 |
| 8044143 | C2orf40 | −0.67191 | 8.21E−09 | 8043468 | NA | −0.60007 | 4.25E−05 | 8161755 | ALDH1A1 | −0.81238 | 1.40E−06 |
| 7946589 | MRVI1 | −0.67207 | 2.10E−11 | 8122150 | EYA4 | −0.60059 | 1.92E−08 | 8180349 | NA | −0.81367 | 1.83E−09 |
| 7929689 | MARVELD1 | −0.67501 | 2.91E−12 | 7895247 | NA | −0.60163 | 0.005498 | 8077441 | BHLHE40 | −0.81639 | 1.74E−05 |
| 7916304 | GLIS1 | −0.67645 | 4.18E−13 | 8023462 | NA | −0.60247 | 0.00946 | 7926037 | PFKFB3 | −0.81838 | 4.13E−13 |
| 8168892 | TCEAL2 | −0.67727 | 3.79E−05 | 8121275 | NA | −0.60336 | 0.010631 | 8014316 | CCL5 | −0.81855 | 1.31E−07 |
| 8040473 | RHOB | −0.6778 | 1.73E−05 | 7895588 | NA | −0.60336 | 0.001159 | 8055624 | ZEB2 | −0.81957 | 7.00E−11 |
| 7899627 | TINAGL1 | −0.67932 | 9.46E−13 | 8006621 | CCL4L1 | −0.60366 | 1.86E−05 | 8164269 | ENG | −0.82057 | 1.10E−12 |
| 8081686 | BOC | −0.68258 | 3.48E−09 | 8019651 | CCL4L1 | −0.60366 | 1.86E−05 | 8141094 | PDK4 | −0.82124 | 8.75E−06 |
| 7965048 | NAP1L1 | −0.68268 | 6.04E−10 | 7972946 | RASA3 | −0.60434 | 3.45E−12 | 8180379 | NA | −0.82228 | 7.87E−15 |
| 7896228 | NA | −0.6847 | 0.01359 | 8038038 | NA | −0.60525 | 6.93E−08 | 8069676 | ADAMTS1 | −0.82248 | 5.03E−05 |
| 7981740 | IGHA1 | −0.68474 | 1.15E−06 | 8141843 | RASA4 | −0.60693 | 0.000131 | 8150428 | SFRP1 | −0.82264 | 3.80E−15 |
| 8036284 | COX7A1 | −0.68517 | 2.79E−12 | 8017599 | PECAM1 | −0.60761 | 2.65E−12 | 8005048 | MYOCD | −0.82539 | 1.29E−06 |
| 8066393 | JPH2 | −0.68732 | 2.60E−11 | 7946033 | HBB | −0.61045 | 0.020016 | 8041048 | FOSL2 | −0.83073 | 1.49E−09 |
| 8041048 | FOSL2 | −0.69273 | 2.92E−07 | 8029040 | MRC2 | −0.61474 | 1.50E−10 | 8004510 | CD68 | −0.83084 | 1.28E−09 |
| 8152453 | TRPS1 | −0.69283 | 1.24E−08 | 8137264 | TMEM176A | −0.61648 | 1.67E−07 | 8143144 | PTN | −0.83547 | 0.000614 |
| 8040792 | EMILIN1 | −0.69295 | 5.08E−14 | 8167763 | TSPYL2 | −0.61655 | 5.09E−11 | 8130867 | THBS2 | −0.83616 | 2.25E−10 |
| 8038407 | RRAS | −0.69564 | 6.14E−11 | 7947423 | NA | −0.61681 | 0.000308 | 8179519 | HLA-DPB1 | −0.8383 | 8.12E−09 |
| 8101061 | NA | −0.69574 | 1.80E−08 | 8078450 | CRTAP | −0.61688 | 9.90E−15 | 8053713 | NA | −0.83939 | 0.000894 |
| 8090193 | HEG1 | −0.69662 | 1.22E−11 | 8126760 | RCAN2 | −0.62082 | 1.01E−10 | 8029693 | FOSB | −0.84467 | 0.015339 |
| 8158627 | NCS1 | −0.69675 | 2.65E−08 | 8055952 | NR4A2 | −0.62117 | 0.003048 | 7905147 | C10orf54 | −0.84621 | 5.06E−08 |
| 8048551 | SPEG | −0.69725 | 3.13E−17 | 8080344 | STAB1 | −0.62151 | 4.09E−14 | 8155327 | ALDH1B1 | −0.8497 | 9.89E−10 |
| 8164269 | ENG | −0.6976 | 5.04E−10 | 8018975 | LGALS3BP | −0.62154 | 7.90E−07 | 8178199 | HLA-DQA1 | −0.85061 | 7.74E−05 |
| 7896710 | NA | −0.70036 | 0.000456 | 8050089 | TMSB4XP2 | −0.62264 | 2.15E−11 | 8179489 | HLA-DQA1 | −0.85061 | 7.74E−05 |
| 8043480 | NA | −0.70066 | 1.10E−07 | 7950671 | GAB2 | −0.62472 | 1.02E−10 | 8122176 | TCF21 | −0.85065 | 9.45E−08 |
| 8145470 | DPYSL2 | −0.70193 | 2.42E−12 | 8152453 | TRPS1 | −0.62654 | 2.15E−07 | 7975390 | SMOC1 | −0.85403 | 1.18E−06 |
| 8101673 | NA | −0.70224 | 0.017289 | 7922229 | SELE | −0.62706 | 2.28E−05 | 8021181 | SCARNA17 | −0.85664 | 1.79E−09 |
| 7901784 | NFIA | −0.70405 | 1.55E−12 | 7945262 | JAM3 | −0.62714 | 7.50E−09 | 7902071 | S100A4 | −0.85769 | 1.95E−06 |
| 7981317 | NA | −0.70465 | 5.10E−08 | 7945680 | H19 | −0.62727 | 0.001052 | 7952205 | MCAM | −0.86089 | 1.49E−10 |
| 8103166 | SH3D19 | −0.7053 | 5.40E−10 | 8011499 | P2RX1 | −0.62908 | 3.02E−08 | 8143772 | RARRES2 | −0.86818 | 1.18E−13 |
| 8161852 | NA | −0.70537 | 0.00035 | 8124040 | ATXN1 | −0.62928 | 5.22E−09 | 7981730 | IGJ | −0.8725 | 1.74E−05 |
| 7896703 | NA | −0.70716 | 0.000889 | 8047738 | NRP2 | −0.62967 | 6.22E−10 | 8113039 | MEF2C | −0.87418 | 4.71E−12 |
| 8094301 | SLIT2 | −0.70821 | 3.70E−11 | 7896727 | NA | −0.63039 | 6.29E−07 | 7981514 | AHNAK2 | −0.87552 | 2.42E−11 |
| 8161884 | PRUNE2 | −0.70952 | 6.92E−07 | 8115814 | SH3PXD2B | −0.63097 | 2.69E−11 | 8054611 | NCRNA00152 | −0.87711 | 1.07E−10 |
| 7894518 | NA | −0.70992 | 0.004336 | 7902565 | LPHN2 | −0.63119 | 5.33E−09 | 7960865 | SLC2A3 | −0.87805 | 8.32E−07 |
| 7892894 | NA | −0.71099 | 0.001967 | 7916741 | JAK1 | −0.63238 | 3.92E−10 | 8108627 | VTRNA1-1 | −0.87945 | 9.82E−06 |
| 8120402 | BAG2 | −0.71293 | 2.69E−12 | 7944361 | NA | −0.63277 | 6.69E−08 | 7977270 | LOC388022 | −0.88083 | 3.25E−08 |
| 8164607 | FNBP1 | −0.71384 | 5.99E−13 | 8161884 | PRUNE2 | −0.63312 | 8.73E−06 | 8056201 | RBMS1 | −0.88139 | 2.17E−11 |
| 8055465 | CXCR4 | −0.71539 | 2.20E−07 | 7978718 | SEC23A | −0.63473 | 2.30E−11 | 8024111 | CNN2 | −0.88419 | 1.83E−10 |
| 7893991 | NA | −0.71825 | 0.001107 | 8018993 | FCER1G | −0.63534 | 1.77E−07 | 7934570 | KCNMA1 | −0.88434 | 5.93E−12 |
| 8001457 | CES1 | −0.71876 | 3.92E−08 | 8018993 | RBFOX3 | −0.63546 | 1.43E−09 | 8041995 | SPTBN1 | −0.88499 | 4.83E−15 |
| 8151927 | NA | −0.71996 | 7.95E−06 | 7979813 | ZFP36L1 | −0.63609 | 1.74E−08 | 8172204 | MAOB | −0.88624 | 1.59E−07 |
| 8028652 | ZFP36 | −0.72151 | 0.0063 | 7937802 | CD81 | −0.63829 | 7.77E−10 | 7952268 | THY1 | −0.89363 | 4.40E−12 |
| 8171291 | DMD | −0.72201 | 5.87E−08 | 8170009 | FAM127A | −0.64012 | 1.31E−08 | 8103254 | SFRP2 | −0.89467 | 5.70E−12 |
| 7955663 | TENC1 | −0.72423 | 1.19E−14 | 7899627 | TINAGL1 | −0.64044 | 1.14E−11 | 8180377 | NA | −0.89483 | 5.44E−15 |
| 7934690 | ZCCHC24 | −0.72593 | 6.46E−14 | 7981737 | NA | −0.6408 | 2.72E−09 | 7938528 | PARVA | −0.89582 | 2.82E−12 |
| 7953040 | CACNA1C | −0.7281 | 9.14E−14 | 8180349 | NA | −0.64196 | 1.24E−06 | 8040473 | RHOB | −0.89707 | 1.72E−08 |
| 7944302 | PHLDB1 | −0.73139 | 1.51E−11 | 7949124 | PYGM | −0.64217 | 1.68E−10 | 8097449 | PCDH10 | −0.89722 | 1.71E−10 |
| 8119573 | SRF | −0.73152 | 6.46E−14 | 8048551 | SPEG | −0.64236 | 2.39E−15 | 7956551 | ARHGEF25 | −0.89896 | 9.45E−11 |
| 8097717 | ARHGAP10 | −0.73216 | 2.32E−10 | 8119357 | DAAM2 | −0.64244 | 1.77E−10 | 7963880 | ITGA7 | −0.89949 | 5.04E−13 |
| 7946661 | DKK3 | −0.73308 | 1.35E−09 | 8080685 | SLMAP | −0.64362 | 3.75E−10 | 8162373 | OGN | −0.89976 | 2.85E−06 |
| 7939559 | TSPAN18 | −0.73601 | 9.79E−09 | 8178435 | IER3 | −0.64404 | 1.47E−07 | 7907222 | PRRX1 | −0.90263 | 1.74E−11 |
| 7952805 | LOC283174 | −0.73781 | 6.49E−11 | 8056206 | RBMS1 | −0.64501 | 3.72E−08 | 7946661 | DKK3 | −0.9048 | 4.51E−13 |
| 8151993 | COX6C | −0.73816 | 4.35E−05 | 8115076 | CSF1R | −0.64564 | 1.68E−10 | 8081081 | EPHA3 | −0.90837 | 8.32E−09 |
| 7916491 | NA | −0.73913 | 0.000342 | 8065403 | CST3 | −0.64572 | 4.87E−09 | 8026047 | JUNB | −0.90908 | 0.000157 |
| 7980044 | PNMA1 | −0.73919 | 1.17E−13 | 8008588 | HLF | −0.647 | 6.01E−11 | 7986517 | C15orf51 | −0.92263 | 1.16E−08 |
| 7915229 | HEYL | −0.73933 | 2.48E−11 | 7972557 | GPR183 | −0.64701 | 3.57E−08 | 7986522 | C15orf51 | −0.92263 | 1.16E−08 |
| 7921916 | RGS5 | −0.73945 | 4.37E−08 | 8023415 | TCF4 | −0.64804 | 5.18E−11 | 8121749 | GJA1 | −0.927 | 4.43E−09 |
| 8029693 | FOSB | −0.73983 | 0.041342 | 7894518 | NA | −0.64815 | 0.009223 | 7908917 | BTG2 | −0.92765 | 1.90E−05 |
| 7919568 | NA | −0.74107 | 5.32E−10 | 7958644 | ATP2A2 | −0.64887 | 6.04E−12 | 8168892 | TCEAL2 | −0.92892 | 1.92E−08 |

-continued

| epitheliail Benign-stromal benign | | | | epithelial PIN-stromal PIN | | | | epithelial tumor-stromal tumor | | | |
|---|---|---|---|---|---|---|---|---|---|---|---|
| Affymetrix ID | Gene | LogFC | Adj. P.Val | Affymetrix ID | Gene | LogFC | Adj. P.Val | Affymetrix ID | Gene | LogFC | Adj. P.Val |
| 8014316 | CCL5 | −0.7433 | 1.29E−06 | 8127234 | DST | −0.64966 | 3.30E−11 | 7939492 | C11orf96 | −0.93237 | 2.02E−09 |
| 7959482 | NA | −0.74335 | 0.002866 | 8083429 | MBNL1 | −0.64983 | 6.29E−14 | 7987385 | MEIS2 | −0.93438 | 1.52E−12 |
| 7895039 | NA | −0.7439 | 1.73E−07 | 8051361 | SRD5A2 | −0.65001 | 1.37E−10 | 7935228 | NA | −0.93713 | 6.57E−05 |
| 7949503 | EFEMP2 | −0.74437 | 5.09E−10 | 8176253 | NA | −0.65039 | 0.000415 | 7898988 | CLIC4 | −0.93721 | 2.51E−14 |
| 8156848 | NR4A3 | −0.74565 | 2.59E−06 | 8108627 | VTRNA1-1 | −0.65141 | 0.001202 | 8034696 | MIR27A | −0.93877 | 6.80E−05 |
| 7914282 | SDC3 | −0.74735 | 9.49E−15 | 8091243 | PCOLCE2 | −0.65167 | 6.09E−11 | 7895846 | NA | −0.94173 | 1.30E−06 |
| 8161444 | NA | −0.74804 | 0.005554 | 7931977 | ITIH5 | −0.6521 | 1.S5E−10 | 8051583 | CYP1B1 | −0.94182 | 0.000836 |
| 8135734 | C7orfS8 | −0.75079 | 9.17E−13 | 7905116 | PlEKHOl | −0.65235 | 8.18E−13 | 8055688 | RND3 | −0.944 | 2.28E−11 |
| 8138789 | JAZF1 | −0.75367 | 7.35E−11 | 8037005 | TGFB1 | −0.65401 | 3.10E−12 | 7975779 | FOS | −0.9441 | 0.01157 |
| 8168557 | SH3BGRL | −0.75508 | 2.99E−10 | 8043360 | IGK@ | −0.65907 | 1.25E−06 | 7988467 | FBN1 | −0.946 | 4.81E−13 |
| 7921821 | ADAMTS4 | −0.75851 | 6.72E−08 | 7932254 | ITGA8 | −0.65933 | 4.59E−05 | 8147165 | MATN2 | −0.95157 | 1.67E−10 |
| 8148156 | NA | −0.7587 | 0.000112 | 7942417 | ARHGEF17 | −0.66028 | 8.71E−13 | 7970329 | GAS6 | −0.95972 | 2.37E−14 |
| 8132092 | INMT | −0.75988 | 3.49E−16 | 7974316 | FRMD6 | −0.66056 | 4.09E−10 | 8128991 | LAMA4 | −0.96841 | 1.83E−10 |
| 7928489 | NA | −0.76208 | 0.001434 | 8001457 | CES1 | −0.66122 | 3.65E−07 | 8060758 | PRNP | −0.9708 | 4.20E−14 |
| 7893390 | NA | −0.76239 | 2.17E−05 | 8043443 | NA | −0.66123 | 2.03E−05 | 8145865 | GPR124 | −0.97302 | 1.32E−13 |
| 8113039 | MEF2C | −0.76379 | 5.94E−10 | 8125436 | HLA-DRB5 | −0.66131 | 2.40E−05 | 7916493 | PPAP2B | −0.97357 | 1.09E−12 |
| 7938608 | SPON1 | −0.76408 | 9.86E−10 | 7949412 | LTBP3 | −0.66328 | 1.50E−12 | 8115099 | PDGFRB | −0.97472 | 5.42E−13 |
| 8156783 | COL15A1 | −0.76714 | 1.17E−12 | 8156759 | NA | −0.66509 | 2.38E−06 | 8108370 | EGR1 | −0.97517 | 0.001557 |
| 7896138 | NA | −0.76909 | 0.000137 | 8111772 | DAB2 | −0.666 | 1.51E−11 | 8089112 | FILIP1L | −0.97829 | 4.42E−12 |
| 8043360 | IGK@ | −0.7708 | 1.82E−08 | 8118594 | HLA-DPB1 | −0.66694 | 2.52E−07 | 7958253 | C12orf75 | −0.97839 | 7.60E−06 |
| 7896708 | NA | −0.77147 | 0.006005 | 8083260 | CPA3 | −0.6676 | 1.09E−09 | 7986520 | C15orf51 | −0.98702 | 2.66E−09 |
| 8077376 | ITPR1 | −0.77154 | 6.24E−11 | 7948667 | AHNAK | −0.67351 | 6.26E−10 | 8151310 | EYA1 | −0.98712 | 4.70E−10 |
| 8056201 | RBMS1 | −0.77162 | 1.99E−09 | 7938608 | SPON1 | −0.67665 | 4.80E−08 | 7898805 | C1QB | −0.98739 | 1.74E−11 |
| 8112855 | NA | −0.77242 | 0.001618 | 8050766 | ADCY3 | −0.67929 | 6.14E−14 | 8139087 | SFRP4 | −0.99435 | 1.30E−08 |
| 7896716 | NA | −0.77246 | 8.16E−08 | 7933194 | CXCL12 | −0.68242 | 3.38E−11 | 8178220 | HLA-DPB1 | −0.99566 | 2.25E−08 |
| 8165911 | TBL1X | −0.77342 | 1.18E−11 | 8094301 | SLIT2 | −0.68244 | 1.47E−10 | 8041781 | EPAS1 | −1.00079 | 2.67E−13 |
| 8139212 | GLI3 | −0.77886 | 1.47E−14 | 8055038 | UMS2 | −0.68341 | 1.03E−13 | 8098263 | PALLD | −1.00227 | 6.67E−14 |
| 8043474 | NA | −0.7823 | 1.94E−05 | 7959361 | MLXIP | −0.68453 | 6.33E−14 | 8061114 | DSTN | −1.0044 | 1.17E−10 |
| 8121275 | NA | −0.78343 | 0.000638 | 7961540 | RERG | −0.68473 | 1.74E−08 | 7986509 | C15orf51 | −1.00487 | 4.91E−09 |
| 8095854 | 11-Sep | −0.78349 | 7.11E−11 | 8149330 | CTSB | −0.68604 | 1.38E−06 | 7986512 | CISorfSl | −1.00487 | 4.91E−09 |
| 7898805 | C1QB | −0.78478 | 3.95E−08 | 7934997 | PPP1R3C | −0.68689 | 4.59E−06 | 7986527 | NA | −1.00487 | 4.91E−09 |
| 7920258 | S100A6 | −0.78572 | 2.02E−07 | 8101061 | NA | −0.68718 | 2.29E−08 | 7906878 | DDR2 | −1.00531 | 1.76E−13 |
| 8043476 | LOC652493 | −0.78631 | 5.65E−06 | 7896708 | NA | −0.68871 | 0.014687 | 7979204 | FERMT2 | −1.00665 | 2.39E−09 |
| 7933194 | CXCL12 | −0.78826 | 6.46E−14 | 8095751 | PARM1 | −0.68901 | 4.55E−06 | 7949503 | EFEMP2 | −1.00701 | 1.22E−15 |
| 7986517 | C15orf51 | −0.78858 | 7.75E−07 | 8172022 | TMEM47 | −0.68975 | 1.86E−09 | 7920258 | S100A6 | −1.00715 | 7.75E−11 |
| 7986522 | C15orf51 | −0.78858 | 7.75E−07 | 7996072 | CX3CL1 | −0.69305 | 9.64E−11 | 8041383 | LTBP1 | −1.00989 | 6.77E−13 |
| 7976812 | SNORD113-4 | −0.79155 | 0.001339 | 7990632 | SGK269 | −0.69321 | 6.72E−06 | 8134869 | PCOLCE | −1.01039 | 2.05E−11 |
| 8029950 | EHD2 | −0.79246 | 5.42E−15 | 8130867 | THBS2 | −0.69554 | 6.18E−08 | 8167449 | PLP2 | −1.01549 | 1.6SE−11 |
| 8043433 | IGKC | −0.7956 | 7.81E−06 | 8107133 | PAM | −0.69599 | 1.00E−11 | 8043431 | IGKC | −1.01682 | 1.08E−07 |
| 8043470 | IGKV3D-11 | −0.79717 | 1.19E−06 | 7921821 | A0AMTS4 | −0.69639 | 6.16E−07 | 8115756 | KCNMB1 | −1.01989 | 8.82E−14 |
| 7938528 | PARVA | −0.79776 | 1.87E−10 | 8169617 | PGRMC1 | −0.69654 | 2.31E−11 | 8135576 | TES | −1.0207 | 1.28E−06 |
| 7984813 | ISLR | −0.80146 | 2.31E−12 | 8036284 | COX7A1 | −0.69678 | 1.26E−12 | 8101774 | TMSL3 | −1.02561 | 1.12E−12 |
| 7902810 | LMO4 | −0.80299 | 1.30E−13 | 7953040 | CACNA1C | −0.69863 | 5.85E−13 | 8158240 | TMSB4X | −1.02576 | 9.12E−11 |
| 7914270 | LAPTM5 | −0.80381 | 2.43E−06 | 7896721 | NA | −0.7007 | 0.000706 | 8137979 | ACTB | −1.03079 | 1.42E−19 |
| 8047487 | FZD7 | −0.80392 | 5.22E−17 | 8103166 | SH3D19 | −0.70091 | 6.10E−10 | 8091422 | WWTR1 | −1.03926 | 2.62E−13 |
| 7895247 | NA | −0.80626 | 0.000129 | 7903753 | GSTM2 | −0.70124 | 3.82E−07 | 7919324 | NA | −1.04122 | 0.000197 |
| 8102792 | PCDH18 | −0.80718 | 9.29E−08 | 8054611 | NCRNA00152 | −0.70222 | 1.06E−07 | 8042356 | MEIS1 | −1.04213 | 2.42E−11 |
| 7903777 | GSTM5 | −0.80769 | 4.11E−09 | 7954090 | EMP1 | −0.70231 | 0.000834 | 7938154 | ILK | −1.04354 | 5.75E−14 |
| 7898793 | C1QA | −0.80931 | 1.70E−10 | 8179519 | HLA-DPB1 | −0.70452 | 7.61E−07 | 8149330 | CTSB | −1.04834 | 1.27E−12 |
| 8143772 | RARRES2 | −0.80971 | 1.58E−12 | 8038407 | RRAS | −0.70715 | 2.80E−11 | 8178802 | HLA-DRB3 | −1.05418 | 8.78E−09 |
| 7965429 | NA | −0.81018 | 0.001832 | 8168557 | SH3BGRL | −0.70782 | 2.75E−09 | 8012896 | PMP22 | −1.06042 | 1.01E−14 |
| 8055688 | RND3 | −0.81047 | 4.06E−09 | 8078350 | TGFBR2 | −0.70858 | 8.83E−15 | 7965873 | IGF1 | −1.06245 | 2.97E−05 |
| 7932966 | ITGB1 | −0.81064 | 1.28E−13 | 8044143 | C2orf40 | −0.7093 | 1.14E−09 | 8163637 | TNC | −1.06411 | 1.05E−10 |
| 8113504 | C5orf13 | −0.81156 | 3.59E−09 | 7979133 | NID2 | −0.71095 | 6.90E−15 | 8148070 | COL14A1 | −1.06579 | 3.36E−12 |
| 8178802 | HLA-DRB3 | −0.81242 | 7.18E−06 | 8040792 | EMILIN1 | −0.71099 | 1.31E−14 | 8114920 | DPYSL3 | −1.06807 | 2.84E−14 |
| 8042439 | ANTXR1 | −0.8152 | 5.99E−06 | 7969677 | MBNL2 | −0.71453 | 1.03E−11 | 7914342 | FABP3 | −1.06884 | 2.18E−08 |
| 7989491 | TPM1 | −0.81641 | 3.08E−15 | 8150698 | SNAI2 | −0.71471 | 1.69E−06 | 7941936 | GSTP1 | −1.06886 | 1.74E−11 |
| 7954997 | ANO6 | −0.81759 | 8.09E−06 | 8135587 | CAV2 | −0.71705 | 6.06E−09 | 8066619 | PLTP | −1.06927 | 7.45E−11 |
| 8159521 | PTGDS | −0.8249 | 8.68E−13 | 7947512 | PAMR1 | −0.71799 | 5.38E−14 | 8067007 | TMSB4X | −1.06951 | 5.20E−13 |
| 7978586 | CFL2 | −0.82832 | 1.52E−07 | 7908841 | PPP1R12B | −0.72001 | 2.93E−12 | 8097692 | EONRA | −1.06974 | 9.50E−10 |
| 7990545 | CSPG4 | −0.82933 | 1.21E−11 | 8075462 | SELM | −0.72004 | 2.58E−14 | 7913655 | ID3 | −1.07475 | 1.57E−08 |
| 8045009 | GYPC | −0.82942 | 2.43E−16 | 8125289 | TNXA | −0.72018 | 6.89E−14 | 8053690 | IGK@ | −1.08583 | 3.07E−06 |
| 7989718 | RASL12 | −0.83002 | 1.98E−11 | 8094625 | KLHL5 | −0.72128 | 1.79E−09 | 8166072 | TMSB4X | −1.09724 | 1.10E−12 |
| 7963142 | FAIM2 | −0.8316 | 3.32E−12 | 7929689 | MARVELD1 | −0.72287 | 1.25E−13 | 7914270 | LAPTM5 | −1.10051 | 2.56E−10 |
| 7954899 | CNTN1 | −0.83202 | 1.84E−09 | 7954293 | PDE3A | −0.72526 | 6.93E−09 | 7971077 | POSTN | −1.10773 | 4.91E−09 |
| 7986520 | C15orf51 | −0.83224 | 3.47E−07 | 7976795 | MEG3 | −0.72528 | 3.26E−08 | 8018864 | SOCS3 | −1.10836 | 8.90E−08 |
| 8036473 | PPP1R14A | −0.84056 | 5.19E−13 | 7914282 | SDC3 | −0.72586 | 3.65E−14 | 7929026 | ACTA2 | −1.1102 | 2.09E−14 |
| 8026047 | JUNB | −0.84098 | 0.000489 | 7923978 | CD 34 | −0.72866 | 2.75E−13 | 7956211 | MYL6 | −1.11583 | 8.14E−13 |
| 8146863 | SULF1 | −0.84372 | 8.77E−10 | 7946401 | ST5 | −0.72929 | 3.09E−12 | 8046333 | CYBRD1 | −1.11987 | 9.88E−13 |
| 7932254 | IT6A8 | −0.84541 | 1.67E−07 | 8108217 | TGFBI | −0.72959 | 1.67E−09 | 8100827 | IGJ | −1.12045 | 0.000278 |
| 8103254 | SFRP2 | −0.84673 | 3.20E−11 | 8075310 | LIF | −0.73006 | 6.09E−06 | 7898793 | C1QA | −1.12841 | 4.18E−17 |
| 7904158 | OLFML3 | −0.85171 | 1.15E−11 | 7986517 | C15orf51 | −0.73048 | 4.20E−06 | 8072413 | SMTN | −1.13561 | 9.49E−16 |
| 8135576 | TES | −0.8535 | 4.99E−05 | 7986522 | C15orf51 | −0.73048 | 4.20E−06 | 7972750 | COL4A1 | −1.1369 | 2.36E−16 |

-continued

| epitheliail Benign-stromal benign | | | | epithelial PIN-stromal PIN | | | | epithelial tumor-stromal tumor | | | |
|---|---|---|---|---|---|---|---|---|---|---|---|
| Affymetrix ID | Gene | LogFC | Adj. P.Val | Affymetrix ID | Gene | LogFC | Adj. P.Val | Affymetrix ID | Gene | LogFC | Adj. P.Val |
| 7895846 | NA | −0.85371 | 9.72E−06 | 8161865 | PRUNE2 | −0.73077 | 3.61E−07 | 8066925 | PTGIS | −1.14735 | 4.78E−12 |
| 8161865 | PRUNE2 | −0.85929 | 3.02E−09 | 8076185 | CBX7 | −0.73098 | 2.58E−14 | 8146863 | SULF1 | −1.15089 | 1.68E−15 |
| 7950005 | MRGPRF | −0.86084 | 8.66E−13 | 7941936 | GSTP1 | −0.73189 | 1.92E−06 | 7961693 | LDHB | −1.15414 | 3.49E−10 |
| 7934570 | KCNMA1 | −0.86106 | 1.00E−11 | 7895039 | NA | −0.73334 | 2.23E−07 | 7956301 | LRP1 | −1.16191 | 9.80E−15 |
| 7956856 | MSRB3 | −0.86298 | 6.95E−09 | 8152703 | FBX032 | −0.73374 | 4.10E−08 | 7925320 | NID1 | −1.16922 | 1.23E−11 |
| 7997582 | WFDC1 | −0.86377 | 5.10E−15 | 7913237 | CAMK2N1 | −0.73422 | 2.36E−08 | 8115234 | ANXA6 | −1.17014 | 1.34E−17 |
| 7981718 | IGHM | −0.86592 | 1.08E−05 | 8132092 | INMT | −0.73465 | 1.99E−15 | 8104022 | PDUM3 | −1.17125 | 5.42E−09 |
| 7908917 | BTG2 | −0.86613 | 6.14E−05 | 8129037 | NA | −0.73501 | 2.80E−11 | 7981728 | NA | −1.17212 | 5.71E−05 |
| 8041995 | SPTBN1 | −0.86799 | 6.96E−15 | 7917516 | GBP1 | −0.73634 | 3.10E−08 | 8180003 | HLA-DRB3 | −1.17888 | 1.69E−09 |
| 7928838 | LDB3 | −0.86824 | 2.18E−14 | 8119712 | SRF | −0.73689 | 4.19E−14 | 8028872 | LTBP4 | −1.18117 | 5.23E−13 |
| 8043431 | IGKC | −0.86856 | 4.63E−06 | 7937335 | IFITM1 | −0.73748 | 1.32E−08 | 7927964 | SRGN | −1.1813 | 5.23E−12 |
| 7988467 | FBN1 | −0.87095 | 9.94E−12 | 8009301 | PRKCA | −0.73788 | 2.44E−08 | 7997642 | CRISPLD2 | −1.19133 | 2.03E−09 |
| 8180003 | HLA-DRB3 | −0.87981 | 5.00E−06 | 7926037 | PFKFB3 | −0.73833 | 1.86E−11 | 8135069 | SERPINE1 | −1.19254 | 1.63E−07 |
| 8105229 | PEIO | −0.88229 | 1.09E−12 | 8095854 | 11-Sep | −0.74028 | 5.53E−10 | 8069269 | COL6A1 | −1.20025 | 3.83E−18 |
| 8154962 | DNAJB5 | −0.88368 | 2.79E−13 | 8066393 | JPH2 | −0.74126 | 9.50E−13 | 8161056 | TLN1 | −1.20301 | 3.59E−20 |
| 8027760 | FXYD1 | −0.89041 | 6.26E−10 | 8129497 | EPB41L2 | −0.74191 | 4.09E−12 | 7966135 | CORO1C | −1.20362 | 4.73E−13 |
| 7922130 | DPT | −0.89305 | 5.68E−08 | 8097717 | ARHGAP10 | −0.74293 | 1.21E−10 | 7972803 | NA | −1.2124 | 1.27E−08 |
| 8097449 | PCDH10 | −0.89494 | 1.11E−10 | 8131844 | GPNMB | −0.74376 | 6.36E−09 | 8136918 | ZYX | −1.21452 | 1.82E−18 |
| 8069676 | ADAMTS1 | −0.89568 | 7.56E−06 | 7894171 | NA | −0.74428 | 0.003145 | 7980908 | FBLN5 | −1.21453 | 8.95E−12 |
| 7945680 | H19 | −0.89716 | 1.70E−06 | 7961521 | ARHGDIB | −0.74468 | 1.92E−09 | 7953200 | CCND2 | −1.2236 | 2.82E−12 |
| 7977270 | LOC388022 | −0.89841 | 1.24E−08 | 8151816 | GEM | −0.75013 | 5.20E−13 | 8163896 | STOM | −1.22479 | 2.60E−15 |
| 8178811 | HLA-DRB4 | −0.90569 | 8.29E−06 | 7899160 | CD52 | −0.75022 | 5.58E−07 | 8072626 | TIMP3 | −1.22952 | 2.38E−12 |
| 8174670 | KIAA1210 | −0.90623 | 3.47E−06 | 8043470 | IGKV3D-11 | −0.75042 | 4.31E−06 | 7977615 | RNASE1 | −1.2331 | 1.48E−15 |
| 8117054 | CAP2 | −0.90753 | 1.33E−11 | 8129573 | M0XD1 | −0.75103 | 1.86E−09 | 8051573 | CDC42EP3 | −1.24267 | 9.52E−13 |
| 8030007 | EMP3 | −0.90784 | 3.17E−12 | 7980044 | PNMA1 | −0.75183 | 4.85E−14 | 8084742 | LPP | −1.24296 | 1.85E−19 |
| 8155327 | ALDH1B1 | −0.90892 | 4.66E−11 | 8051583 | CYP1B1 | −0.75283 | 0.008787 | 7981724 | IGHD | −1.24328 | 3.66E−06 |
| 7995477 | NA | −0.90909 | 4.39E−07 | 7928838 | LDB3 | −0.7536 | 1.27E−11 | 7901535 | PODN | −1.24593 | 2.07E−17 |
| 7970329 | GAS6 | −0.91036 | 1.64E−13 | 8178712 | TNXB | −0.75361 | 1.27E−13 | 7970033 | COL4A2 | −1.24684 | 1.S6E−17 |
| 7906501 | ATP1A2 | −0.91544 | 2.45E−12 | 8179935 | TNXB | −0.75361 | 1.27E−13 | 8135594 | CAV1 | −1.25721 | 7.89E−12 |
| 8163637 | TNC | −0.91577 | 1.33E−08 | 8077376 | ITPR1 | −0.75371 | 1.42E−10 | 8178811 | HLA-DRB4 | −1.25817 | 1.10E−09 |
| 8021181 | SCARNA17 | −0.9161 | 9.23E−11 | 8024111 | CNN2 | −0.7538 | 2.46E−08 | 7963054 | TUBA1A | −1.26188 | 4.41E−10 |
| 8103544 | SPOCK3 | −0.91784 | 2.48E−09 | 7932956 | ITGB1 | −0.75615 | 2.80E−12 | 8133721 | HSPB1 | −1.26463 | 3.40E−14 |
| 7945371 | IFITM3 | −0.92229 | 2.14E−08 | 8139087 | SFRP4 | −0.75619 | 1.10E−05 | 7928444 | VCL | −1.26879 | 3.78E−13 |
| 8132118 | AQP1 | −0.92458 | 1.27E−15 | 7909789 | TGFB2 | −0.75623 | 6.25E−08 | 8069301 | COL6A2 | −1.27066 | 5.44E−18 |
| 8052581 | NA | −0.92623 | 0.000266 | 8090193 | HEG1 | −0.75664 | 3.11E−13 | 7913450 | HSPG2 | −1.28273 | 2.73E−18 |
| 7986509 | C15orf51 | −0.92659 | 4.36E−08 | 7946586 | MRVI1 | −0.75826 | 9.32E−14 | 8007100 | IGFBP4 | −1.28283 | 1.82E−18 |
| 7986512 | C1SorfS1 | −0.92659 | 4.36E−08 | 8020110 | RAB31 | −0.76429 | 5.72E−12 | 7976812 | SNORD113-4 | −1.298 | 7.45E−08 |
| 7986527 | NA | −0.92659 | 4.36E−08 | 8087337 | LAMB2 | −0.7666 | 5.14E−14 | 7945371 | IFITM3 | −1.30231 | 3.46E−14 |
| 7963880 | ITGA7 | −0.9292 | 6.02E−14 | 8173522 | NA | −0.76709 | 0.001624 | 7995783 | MT2A | −1.31309 | 2.71E−06 |
| 7909789 | TGFB2 | −0.92936 | 5.73E−11 | 7934690 | ZCCHC24 | −0.76884 | 3.54E−15 | 8001800 | CDH11 | −1.32441 | 2.40E−16 |
| 7894451 | NA | −0.92967 | 0.02894 | 7896698 | NA | −0.77059 | 4.63E−13 | 7991234 | MFGE8 | −1.34361 | 3.48E−19 |
| 7965767 | NA | −0.93223 | 0.000192 | 7976200 | CALM1 | −0.77131 | 4.77E−11 | 7979824 | ACTN1 | −1.35944 | 9.35E−20 |
| 8180100 | HLA-DPA1 | −0.9346 | 1.91E−05 | 8109157 | MIR143 | −0.77235 | 1.33E−07 | 7984079 | TPM1 | −1.37543 | 1.06E−16 |
| 8121729 | PLN | −0.93477 | 1.70E−08 | 8101673 | NA | −0.77366 | 0.006314 | 8118548 | HLA-DRA | −1.378 | 1.27E−08 |
| 8089112 | FILIP1L | −0.93843 | 1.39E−11 | 8121214 | NA | −0.77400 | 0.000182 | 8106923 | NR2F1 | −1.3815 | 3.84E−15 |
| 7914342 | FABP3 | −0.94059 | 6.14E−07 | 8034696 | MIR27A | −0.77442 | 0.001076 | 7932796 | SVIL | −1.3835 | 3.18E−13 |
| 8151310 | EYA1 | −0.94122 | 1.60E−09 | 7952805 | LOC283174 | −0.77519 | 7.76E−12 | 8052355 | EFEMP1 | −1.39155 | 3.64E−10 |
| 7992181 | TPSAB1 | −0.94332 | 2.23E−16 | 8146921 | RDH10 | −0.77581 | 5.05E−08 | 7937330 | IFITM2 | −1.39316 | 5.85E−14 |
| 7898988 | CLIC4 | −0.94451 | 9.17E−15 | 7901780 | NF1A | −0.77645 | 1.48E−14 | 7906900 | DDR2 | −1.3963 | 1.68E−10 |
| 7905147 | C10rf54 | −0.94546 | 8.97E−10 | 8014316 | CCL5 | −0.78012 | 3.18E−07 | 8034130 | KANK2 | −1.4054 | 4.24E−18 |
| 8143144 | PTN | −0.94892 | 7.21E−05 | 7997582 | WFDC1 | −0.78022 | 6.37E−13 | 8179481 | HLA-DRA | −1.41029 | 1.00E−08 |
| 8060758 | PRNP | −0.95226 | 6.06E−14 | 7919568 | NA | −0.78037 | 6.60E−11 | 8036151 | HSPB6 | −1.4304 | 4.32E−17 |
| 8092970 | APOD | −0.95401 | 2.17E−05 | 8153716 | ID3 | −0.78041 | 3.16E−05 | 8046922 | COL3A1 | −1.43799 | 2.84E−14 |
| 7995206 | TGFB1I1 | −0.95862 | 5.41E−20 | 8139212 | GLI3 | −0.78312 | 1.08E−14 | 7902495 | NEXN | −1.44297 | 6.58E−11 |
| 8001800 | CDH11 | −0.96127 | 3.50E−10 | 8055465 | CXCR4 | −0.78518 | 1.21E−08 | 8015635 | PTRF | −1.44613 | 2.21E−20 |
| 7916493 | PPAP2B | −0.96827 | 7.65E−13 | 8024062 | CFD | −0.78572 | 4.91E−06 | 8178193 | HLA-DRA | −1.45255 | 5.88E−09 |
| 8043465 | IGKC | −0.97273 | 9.10E−08 | 8133254 | SFRP2 | −0.78584 | 5.17E−10 | 8157605 | NA | −1.46372 | 1.06E−13 |
| 8134869 | PCOLCE | −0.9743 | 5.16E−11 | 8112139 | IL6ST | −0.78796 | 4.24E−11 | 8021183 | SCARNA17 | −1.46736 | 2.15E−13 |
| 7981722 | IGHA1 | −0.97598 | 1.25E−07 | 8170602 | ZNF185 | −0.7881 | 3.11E−09 | 7898799 | C1QC | −1.48149 | 5.46E−14 |
| 7998434 | TPSAB1 | −0.97661 | 9.63E−16 | 8039084 | NA | −0.78862 | 0.000191 | 8102532 | PDE5A | −1.50591 | 6.89E−14 |
| 8122176 | TCF21 | −0.97813 | 6.83E−10 | 8148156 | NA | −0.78905 | 4.77E−05 | 8105084 | C7 | −1.52244 | 2.45E−10 |
| 8167592 | PAGE4 | −0.9816 | 3.80E−09 | 8021181 | SCARNA17 | −0.79134 | 1.46E−08 | 8174515 | CHRDL1 | −1.5232 | 3.54E−10 |
| 8009301 | PRKCA | −0.98434 | 4.34E−13 | 7977270 | LOC388022 | −0.79204 | 4.19E−07 | 8180100 | HLA-DPA1 | −1.52401 | 1.01E−11 |
| 7939492 | C11orf96 | −0.98589 | 1.65E−10 | 7957023 | LYZ | −0.79287 | 6.57E−05 | 7963786 | ITGA5 | −1.52774 | 6.63E−13 |
| 8125556 | HLA-DPA1 | −0.9859 | 2.30E−05 | 8095080 | PDGFRA | −0.79312 | 7.24E−13 | 8031047 | MYADM | −1.53235 | 3.40E−14 |
| 8178891 | HLA-DPA1 | −0.9859 | 2.30E−05 | 8145470 | DPYSL2 | −0.79332 | 7.54E−15 | 8042439 | ANTXR1 | −1.53291 | 7.95E−16 |
| 7960865 | SLC2A3 | −0.99257 | 1.93E−08 | 7989718 | RASL12 | −0.79697 | 9.31E−13 | 8116070 | PDLIM7 | −1.55133 | 1.83E−19 |
| 8051762 | SLC8A1 | −0.99296 | 1.06E−12 | 8081686 | BOC | −0.79698 | 8.65E−12 | 8125556 | HLA-DPA1 | −1.56231 | 4.84E−11 |
| 8081081 | EPHA3 | −0.99308 | 2.28E−10 | 8180379 | NA | −0.79703 | 1.82E−14 | 8178891 | HLA-DPA1 | −1.56231 | 4.84E−11 |
| 8145865 | GPR124 | −0.99612 | 2.29E−14 | 7957260 | GLIPR1 | −0.79749 | 3.25E−08 | 7965403 | LUM | −1.56809 | 2.42E−09 |
| 8055624 | ZEB2 | −0.99771 | 5.04E−15 | 8043114 | TCF7L1 | −0.79823 | 4.12E−14 | 8003667 | SERPINF1 | −1.58139 | 6.89E−14 |
| 8043438 | IGKV1-5 | −1.00633 | 7.68E−06 | 7922130 | DPT | −0.79899 | 1.04E−06 | 7902687 | CYR61 | −1.58642 | 9.83E−11 |
| 8024062 | CFD | −1.00788 | 5.94E−09 | 7895846 | NA | −0.79905 | 3.33E−05 | 7976816 | SNORD114-3 | −1.60051 | 1.93E−09 |

-continued

| epithelial Benign-stromal benign | | | | epithelial PIN-stromal PIN | | | | epithelial tumor-stromal tumor | | | |
|---|---|---|---|---|---|---|---|---|---|---|---|
| Affymetrix ID | Gene | LogFC | Adj. P.Val | Affymetrix ID | Gene | LogFC | Adj. P.Val | Affymetrix ID | Gene | LogFC | Adj. P.Val |
| 7907222 | PRRX1 | −1.00906 | 6.42E−14 | 8004510 | CD68 | −0.79916 | 2.82E−09 | 8167965 | MSN | −1.62687 | 1.56E−17 |
| 8046333 | CYBRD1 | −1.01039 | 4.65E−11 | 7902810 | LM04 | −0.79964 | 1.51E−13 | 8089544 | CCDC80 | −1.62884 | 6.40E−13 |
| 7981514 | AHNAK2 | −1.02282 | 1.10E−14 | 8156848 | NR4A3 | −0.79983 | 3.85E−07 | 8115147 | CD74 | −1.63172 | 3.98E−12 |
| 8109157 | MIR143 | −1.02693 | 6.27E−12 | 8026047 | JUNB | −0.80324 | 0.000815 | 8106098 | MAP1B | −1.63678 | 8.11E−15 |
| 7976816 | SNORD114-3 | −1.02711 | 0.000111 | 7954899 | CNTN1 | −0.8039 | 5.43E−09 | 7995681 | MMP2 | −1.65344 | 7.79E−17 |
| 8098263 | PAILD | −1.02752 | 1.11E−14 | 8022310 | FAM38B | −0.80566 | 4.17E−11 | 8157582 | GSN | −1.6618 | 4.73E−17 |
| 8012896 | PMP22 | −1.03389 | 1.90E−14 | 7892901 | NA | −0.80817 | 0.000483 | 8100541 | IGFBP7 | −1.66381 | 4.23E−19 |
| 8150318 | FGFR1 | −1.03627 | 8.19E−17 | 8027760 | FXYD1 | −0.80865 | 1.49E−08 | 8161513 | PGM5P2 | −1.67969 | 1.38E−14 |
| 8115099 | PDGFRB | −1.03798 | 1.43E−14 | 8105229 | PELO | −0.80937 | 3.92E−11 | 8006433 | CCL2 | −1.68495 | 6.54E−08 |
| 8090070 | ADCY5 | −1.04133 | 6.42E−16 | 8135734 | C7orf58 | −0.80955 | 2.56E−14 | 7908924 | PRELP | −1.68753 | 1.49E−19 |
| 8018864 | SOCS3 | −1.04591 | 3.38E−07 | 8159521 | PTGDS | −0.81282 | 1.58E−12 | 8013341 | MFAP4 | −1.69064 | 5.04E−13 |
| 8015635 | PTRF | −1.05035 | 4.49E−13 | 8090070 | ADCY5 | −0.81304 | 5.56E−11 | 7960744 | C1R | −1.69863 | 3.78E−18 |
| 7981730 | IGU3 | −1.05216 | 1.52E−07 | 7975779 | FOS | −0.81782 | 0.031168 | 8149927 | CIU | −1.70421 | 3.88E−17 |
| 8007100 | IGFBP4 | −1.05414 | 4.13E−14 | 7981740 | IGHA1 | −0.82093 | 5.31E−09 | 7926368 | VIM | −1.72204 | 1.65E−15 |
| 7989670 | RBPMS2 | −1.05995 | 4.14E−16 | 8164269 | ENG | −0.821 | 5.72E−13 | 8170648 | BGN | −1.72988 | 2.36E−16 |
| 8135069 | SERPINE1 | −1.06152 | 2.53E−06 | 7971163 | NA | −0.82203 | 1.08E−10 | 8135990 | FLNC | −1.74084 | 1.25E−16 |
| 7981732 | IGHV4-59 | −1.06935 | 7.83E−07 | 7986520 | C15orf51 | −0.82593 | 3.63E−07 | 7959102 | HSPB8 | −1.7453 | 9.36E−15 |
| 8066619 | PITP | −1.07151 | 3.84E−11 | 8040473 | RHOB | −0.82687 | 1.24E−07 | 8167185 | TIMP1 | −1.75139 | 1.18E−12 |
| 8115234 | ANXA6 | −1.07167 | 1.02E−15 | 7989491 | TPM1 | −0.82691 | 1.53E−15 | 8016646 | COL1A1 | −1.75878 | 5.53E−15 |
| 8114920 | DPYSL3 | −1.07179 | 1.28E−14 | 8056201 | RBMS1 | −0.83265 | 1.09E−10 | 7908940 | ATP2B4 | −1.77056 | 1.32E−17 |
| 8091422 | WWTR1 | −1.07207 | 3.13E−14 | 8167449 | PLP2 | −0.8336 | 1.22E−08 | 8161520 | PGM5P2 | −1.78864 | 1.06E−14 |
| 7893777 | NA | −1.07319 | 3.09E−06 | 7955663 | TENC1 | −0.83399 | 5.19E−18 | 8129562 | CTGF | −1.80043 | 2.40E−16 |
| 8041383 | LTBP1 | −1.07469 | 1.90E−14 | 8163257 | LPAR1 | −0.83563 | 2.11E−09 | 8073775 | FBLN1 | −1.80501 | 4.42E−16 |
| 8053713 | NA | −1.07620 | 1.14E−05 | 7939559 | TSPAN18 | −0.8365 | 8.18E−11 | 8145669 | RBPMS | −1.81965 | 1.06E−16 |
| 7920271 | S100A4 | −1.07701 | 1.78E−09 | 8099340 | WDR1 | −0.83996 | 6.53E−17 | 8132557 | AEBP1 | −1.82112 | 4.78E−20 |
| 8128991 | LAMA4 | −1.07704 | 1.21E−12 | 7984813 | ISLR | −0.84226 | 2.38E−13 | 8072876 | LGALS1 | −1.83196 | 1.25E−16 |
| 8097692 | EDNRA | −1.07819 | 4.45E−10 | 8143144 | PTN | −0.84453 | 0.000422 | 7986385 | SYNM | −1.86519 | 1.58E−15 |
| 8173522 | NA | −1.08245 | 5.22E−06 | 8089785 | POPDC2 | −0.84467 | 1.34E−09 | 7953603 | CIS | −1.86561 | 2.42E−18 |
| 8147516 | MATN2 | −1.08987 | 2.79E−13 | 7896703 | NA | −0.84476 | 4.41E−05 | 8170119 | FHL1 | −1.88308 | 1.48E−15 |
| 7956551 | ARHGEF25 | −1.09048 | 8.98E−15 | 7908917 | BTG2 | −0.84769 | 7.84E−05 | 8058857 | IGFBP5 | −1.88458 | 1.10E−12 |
| 7972750 | COL4A1 | −1.0923 | 1.16E−15 | 7903777 | GSTM5 | −0.84804 | 6.66E−10 | 8007420 | AOC3 | −1.88751 | 2.49E−17 |
| 8118548 | HLA-DRA | −1.09368 | 4.91E−06 | 8029950 | EHD2 | −0.84872 | 1.35E−06 | 8075635 | TIMP3 | −1.91046 | 5.46E−14 |
| 7965123 | PPP1R12A | −1.09456 | 1.47E−14 | 7896438 | NA | −0.85037 | 0.00029 | 8059905 | COL6A3 | −1.93671 | 1.69E−17 |
| 8172204 | MAOB | −1.09712 | 8.55E−11 | 7944302 | PHLDB1 | −0.85112 | 1.44E−14 | 7940028 | SERPING1 | −1.9482 | 9.28E−17 |
| 8179481 | HLA-DRA | −1.09892 | 6.22E−06 | 7991762 | HBA2 | −0.85125 | 0.000987 | 8134263 | COL1A2 | −1.97138 | 8.16E−16 |
| 8042356 | MEIS1 | −1.09971 | 1.28E−12 | 7991765 | HBA1 | −0.85125 | 0.000987 | 7982597 | THBS1 | −1.98259 | 6.55E−12 |
| 7979204 | FERMT2 | −1.1002 | 5.66E−11 | 8045009 | GYPC | −0.85538 | 3.92E−17 | 8155665 | PGM5 | −2.02704 | 5.19E−16 |
| 7898799 | C1QC | −1.10246 | 5.72E−09 | 8094134 | USP17L6P | −0.85749 | 4.73E−12 | 7960947 | A2M | −2.04999 | 1.51E−14 |
| 7952205 | MCAM | −1.10272 | 9.65E−16 | 8145954 | TACC1 | −0.85758 | 8.89E−15 | 7951662 | CRYAB | −2.05194 | 1.72E−14 |
| 8043459 | IGKC | −1.10491 | 1.42E−08 | 7990545 | CSPG4 | −0.85841 | 2.63E−12 | 8109159 | MIR145 | −2.11963 | 8.44E−15 |
| 8108570 | EGR1 | −1.11081 | 0.000231 | 8150428 | SFRP1 | −0.86016 | 1.67E−16 | 8115327 | SPARC | −2.12452 | 5.24E−14 |
| 8178193 | HLA-DRA | −1.11177 | 6.50E−06 | 8158627 | NCS1 | −0.86109 | 1.07E−11 | 8058765 | FN1 | −2.1278 | 6.32E−18 |
| 8043449 | IGK(S> | −1.12333 | 6.91E−10 | 7919815 | CTSK | −0.86123 | 1.31E−13 | 8018966 | TIMP2 | −2.19971 | 2.26E−18 |
| 7949588 | CD248 | −1.13396 | 4.27E−16 | 8143772 | RARRES2 | −0.863 | 8.08E−14 | 7935188 | SORBS1 | −2.20637 | 1.65E−18 |
| 8148070 | COL14A1 | −1.13484 | 1.0SE−13 | 7965767 | NA | −0.86459 | 0.000529 | 7965410 | DCN | −2.23318 | 3.76E−13 |
| 7956211 | MYL6 | −1.13873 | 1.76E−13 | 7950005 | MRGPRF | −0.86557 | 6.46E−13 | 7923386 | LMOD1 | −2.29277 | 3.42E−18 |
| 8161755 | ALDH1A1 | −1.13953 | 1.48E−11 | 7906954 | PBX1 | −0.87098 | 7.07E−15 | 8097080 | SYNP02 | −2.36222 | 1.42E−19 |
| 7927964 | SRGN | −1.14324 | 1.15E−11 | 8112855 | NA | −0.874 | 0.000244 | 7896722 | NA | −2.4112 | 2.86E−14 |
| 7906878 | DDR2 | −1.15864 | 6.99E−17 | 8036472 | PPP1R14A | −0.87487 | 7.45E−14 | 8068651 | PCP4 | −2.4139 | 5.44E−15 |
| 7977615 | RNASE1 | −1.15942 | 1.81E−14 | 7952268 | THY1 | −0.87662 | 5.06E−12 | 7923378 | CSRP1 | −2.50682 | 3.73E−23 |
| 7935228 | NA | −1.16177 | 4.88E−07 | 8053735 | NA | −0.88243 | 9.62E−13 | 8090098 | MYLK | −2.52569 | 9.60E−19 |
| 7966135 | COROIC | −1.16243 | 1.21E−12 | 7986509 | C15orf51 | −0.88393 | 1.54E−07 | 8058869 | TNS1 | −2.58978 | 9.66E−24 |
| 8006433 | CCL2 | −1.1626 | 0.00021 | 7986512 | C15orf51 | −0.88393 | 1.54E−07 | 7915612 | PTCH2 | −2.67097 | 2.06E−14 |
| 8136918 | ZYX | −1.16317 | 1.32E−17 | 7986527 | NA | −0.88393 | 1.54E−07 | 8136347 | CALD1 | −2.71291 | 1.45E−22 |
| 7951977 | FXYD6 | −1.17048 | 1.31E−17 | 8178220 | HLA-DPB1 | −0.88409 | 4.26E−07 | 8175531 | CDR1 | −2.91785 | 1.44E−11 |
| 8137979 | ACTB | −1.17856 | 9.93E−24 | 8043474 | NA | −0.88522 | 1.04E−06 | 8101659 | SPARCL1 | −2.92796 | 1.10E−17 |
| 8005048 | MYOCD | −1.18005 | 5.83E−12 | 8043476 | LOC652493 | −0.88588 | 2.58E−07 | 8161044 | TPM2 | −3.07102 | 3.73E−23 |
| 8067007 | TMSB4X | −1.19064 | 1.46E−15 | 8164607 | FNBP1 | −0.88619 | 7.67E−18 | 7961514 | MGP | −3.08124 | 2.58E−18 |
| 7938154 | ILK | −1.19247 | 3.02E−17 | 8154962 | DNAJB5 | −0.88702 | 2.28E−13 | 8048541 | DES | −3.18091 | 6.06E−26 |
| 8101774 | TMSL3 | −1.19476 | 3.30E−16 | 7906501 | ATP1A2 | −0.88898 | 8.13E−12 | 8062312 | MYL9 | −3.23293 | 7.29E−27 |
| 8163896 | STOM | −1.19622 | 4.80E−15 | 7898805 | C1QB | −0.89109 | 5.03E−10 | 8025918 | CNN1 | −3.3425 | 6.55E−22 |
| 7979824 | ACTN1 | −1.19754 | 9.13E−17 | 8047487 | FZD7 | −0.89426 | 6.70E−20 | 8176026 | FLNA | −3.36254 | 7.29E−27 |
| 8162373 | OGN | −1.1977 | 3.93E−10 | 8178199 | HLA-DQA1 | −0.89499 | 2.27E−05 | 7944082 | TAGLN | −3.60901 | 7.29E−27 |
| 8158240 | TMSB4X | −1.19866 | 5.32E−14 | 8179489 | HLA-DQA1 | −0.89499 | 2.27E−05 | 7999674 | MYH11 | −3.79773 | 9.20E−26 |
| 7937330 | IFITM2 | −1.2011 | 2.53E−11 | 8030007 | EMP3 | −0.89499 | 5.55E−12 | 7934906 | ACTA2 | −3.84608 | 8.69E−24 |
| 7975390 | SMOC1 | −1.21427 | 6.37E−12 | 7898793 | C1QA | −0.89858 | 2.08E−12 | 8042788 | ACTG2 | −4.2539 | 3.73E−23 |
| 8066925 | PTGIS | −1.21483 | 1.93E−13 | 8056860 | WIPF1 | −0.90133 | 2.92E−17 | | | | |
| 8061114 | DSTN | −1.21762 | 1.19E−14 | 7956856 | MSRB3 | −0.90343 | 1.29E−09 | | | | |
| 8161056 | TLN1 | −1.21773 | 9.30E−21 | 7954997 | AN06 | −0.90628 | 1.87E−10 | | | | |
| 8084742 | IPP | −1.21923 | 3.60E−19 | 8155327 | ALDH1B1 | −0.9099 | 3.95E−11 | | | | |
| 7991234 | MFGE8 | −1.23496 | 3.02E−17 | 7904158 | OLFML3 | −0.91136 | 5.79E−13 | | | | |
| 8052355 | EFEMP1 | −1.24752 | 1.04E−08 | 7946661 | DKK3 | −0.9117 | 1.60E−13 | | | | |
| 8166072 | TMSB4X | −1.25169 | 9.65E−16 | 7915229 | HEYL | −0.91304 | 1.28E−1S | | | | |

-continued

| epitheliail Benign-stromal benign | | | | epithelial PIN-stromal PIN | | | | epithelial tumor-stromal tumor | | | |
|---|---|---|---|---|---|---|---|---|---|---|---|
| Affymetrix ID | Gene | LogFC | Adj. P.Val | Affymetrix ID | Gene | LogFC | Adj. P.Val | Affymetrix ID | Gene | LogFC | Adj. P.Val |
| 7980908 | FBLN5 | −1.25817 | 1.03E−12 | 8113039 | MEF2C | −0.9154 | 3.06E−13 | | | | |
| 8072413 | SMTN | −1.25884 | 1.54E−18 | 8121749 | GJA1 | −0.91609 | 3.92E−09 | | | | |
| 7956301 | LRP1 | −1.2595 | 7.91E−17 | 8029693 | FOSB | −0.91635 | 0.006553 | | | | |
| 8115756 | KCNMB1 | −1.26761 | 3.60E−19 | 7978586 | CFL2 | −0.91966 | 5.46E−09 | | | | |
| 7953200 | CCND2 | −1.26801 | 2.99E−13 | 8041383 | LTBP1 | −0.91969 | 2.05E−11 | | | | |
| 8003667 | SERPINF1 | −1.29012 | 2.60E−10 | 8138789 | JAZF1 | −0.919971 | 9.11E−15 | | | | |
| 8069301 | COL6A2 | −1.30077 | 8.30E−19 | 7981317 | NA | −0.92015 | 2.62E−12 | | | | |
| 8069269 | COL6A1 | −1.30219 | 1.59E−20 | 7921916 | RGS5 | −0.92286 | 1.42E−11 | | | | |
| 7926368 | VIM | −1.30252 | 2.71E−10 | 8171921 | DMD | −0.92427 | 7.53E−12 | | | | |
| 8167965 | MSN | −1.30447 | 7.65E−13 | 8081081 | EPHA3 | −0.92452 | 2.73E−09 | | | | |
| 8028872 | LTBP4 | −1.30738 | 2.02E−15 | 8180377 | NA | −0.92576 | 4.52E−16 | | | | |
| 8157605 | NA | −1.30792 | 9.21E−12 | 8156783 | COL15A1 | −0.93248 | 6.22E−17 | | | | |
| 8170648 | BGN | −1.31218 | 6.22E−11 | 7995206 | TGFB1I1 | −0.93407 | 2.12E−19 | | | | |
| 8115147 | CD74 | −1.31681 | 8.28E−09 | 7905147 | C10orf54 | −0.93461 | 1.23E−09 | | | | |
| 8021183 | SCARNA17 | −1.31871 | 1.33E−11 | 7989670 | RBPMS2 | −0.93616 | 1.97E−13 | | | | |
| 8058857 | IGFBP5 | −1.3276 | 2.16E−07 | 8167592 | PAGE4 | −0.93921 | 1.45E−08 | | | | |
| 7987315 | ACTC1 | −1.32961 | 2.41E−10 | 8108370 | EGR1 | −0.93932 | 0.002054 | | | | |
| 7963786 | ITGA5 | −1.35085 | 7.34E−11 | 8102792 | PCDH18 | −0.9397 | 5.74E−10 | | | | |
| 7970033 | COL4A2 | −1.35451 | 6.10E−20 | 7963142 | FAIM2 | −0.94355 | 8.89E−15 | | | | |
| 7901526 | PODN | −1.36484 | 5.41E−20 | 8041048 | FOSL2 | −0.94499 | 5.37E−12 | | | | |
| 8106923 | NR2F1 | −1.37195 | 2.92E−15 | 7919324 | NA | −0.94559 | 0.000679 | | | | |
| 7908409 | RGS2 | −1.37327 | 1.90E−11 | 8168892 | TCEAL2 | −0.94561 | 6.71E−09 | | | | |
| 8046922 | COL3A1 | −1.3735 | 1.43E−13 | 8078330 | RBMS3 | −0.94919 | 2.40E−15 | | | | |
| 7995681 | MMP2 | −1.37353 | 5.37E−13 | 7992181 | TPSAB1 | −0.95314 | 1.14E−16 | | | | |
| 7919324 | NA | −1.37994 | 4.58E−07 | 7987385 | MEIS2 | −0.95379 | 3.16E−13 | | | | |
| 8072626 | TIMP3 | −1.3841 | 4.76E−15 | 8010978 | LOC100130876 | −0.95723 | 3.28E−07 | | | | |
| 7925320 | NID1 | −1.40199 | 1.22E−15 | 8043449 | IGK@ | −0.96092 | 9.85E−08 | | | | |
| 8053690 | IGK@ | −1.40246 | 1.30E−09 | 8117054 | CAP2 | −0.96302 | 9.75E−13 | | | | |
| 7906900 | DDR2 | −1.41022 | 6.59E−11 | 8055624 | ZEB2 | −0.96318 | 2.70E−14 | | | | |
| 7960744 | C1R | −1.4159 | 4.03E−14 | 8077441 | BHLHE40 | −0.96702 | 2.18E−07 | | | | |
| 7929026 | ACTA2 | −1.42008 | 9.64E−21 | 7971077 | POSTN | −0.97057 | 1.72E−07 | | | | |
| 8034130 | KANK2 | −1.42352 | 1.22E−18 | 8055688 | RND3 | −0.97221 | 3.31E−12 | | | | |
| 7958253 | C12orf75 | −1.43172 | 5.72E−11 | 8089112 | FILIP1L | −0.97455 | 2.63E−12 | | | | |
| 8135594 | CAV1 | −1.43839 | 8.46E−15 | 8012896 | PMP22 | −0.97894 | 2.55E−13 | | | | |
| 8051573 | CDC42EP3 | −1.44693 | 2.72E−16 | 8043465 | IGKC | −0.98132 | 6.14E−08 | | | | |
| 7981724 | IGHD | −1.46856 | 3.29E−08 | 8043480 | NA | −0.98195 | 3.56E−13 | | | | |
| 7913450 | HSPG2 | −1.47041 | 2.93E−22 | 8150318 | FGFR1 | −0.98302 | 1.26E−15 | | | | |
| 8102532 | PDE5A | −1.48048 | 8.99E−14 | 7998434 | TPSAB1 | −0.98543 | 5.56E−16 | | | | |
| 7982597 | THBS1 | −1.52378 | 5.51E−08 | 7934570 | KCNMA1 | −0.99112 | 1.49E−14 | | | | |
| 7963054 | TUBA1A | −1.524 | 8.26E−14 | 7963880 | ITGA7 | −0.99139 | 2.22E−15 | | | | |
| 7981728 | NA | −1.53068 | 9.27E−08 | 7920271 | S100A4 | −0.99177 | 2.41E−08 | | | | |
| 7972803 | NA | −1.53504 | 8.71E−13 | 7898988 | CLIC4 | −0.99344 | 6.51E−16 | | | | |
| 8157582 | GSN | −1.53556 | 2.12E−15 | 8113504 | C5orf13 | −0.99395 | 1.14E−12 | | | | |
| 7928444 | VCL | −1.53898 | 9.07E−18 | 8097449 | PCDH10 | −0.99483 | 1.20E−12 | | | | |
| 7984079 | TPM1 | −1.54632 | 5.88E−20 | 8052581 | NA | −0.99967 | 6.29E−05 | | | | |
| 8016646 | COL1A1 | −1.54732 | 1.34E−12 | 8132118 | AQP1 | −1.00489 | 1.13E−17 | | | | |
| 7937772 | IGF2 | −1.56005 | 1.24E−09 | 7970329 | GAS6 | −1.00739 | 1.05E−15 | | | | |
| 8116070 | PDLIM7 | −1.57264 | 4.58E−20 | 7949503 | EFEMP2 | −1.01338 | 4.39E−16 | | | | |
| 7932796 | SVIL | −1.58024 | 2.11E−16 | 8043433 | IGKC | −1.01375 | 1.09E−08 | | | | |
| 8100541 | IGFBP7 | −1.58026 | 5.41E−18 | 7956551 | ARHGEF25 | −1.01441 | 2.73E−13 | | | | |
| 8104022 | PDLIM3 | −1.58429 | 1.13E−14 | 8103544 | SPOCK3 | −1.01856 | 4.57E−11 | | | | |
| 7902495 | NEXN | −1.61417 | 2.76E−13 | 8041995 | SPTBN1 | −1.01907 | 7.95E−19 | | | | |
| 8132557 | AEBP1 | −1.6266 | 2.40E−17 | 8178802 | HLA-DRB3 | −1.02164 | 1.43E−08 | | | | |
| 8036151 | HSPB6 | −1.64186 | 7.50E−21 | 7995477 | NA | −1.02532 | 1.14E−08 | | | | |
| 7908924 | PRELP | −1.64449 | 3.89E−19 | 8134869 | PCOLCE | −1.03722 | 3.39E−12 | | | | |
| 8100827 | IGJ | −1.64828 | 4.29E−08 | 7988467 | FBN1 | −1.03732 | 2.75E−15 | | | | |
| 7951662 | CRYAB | −1.66164 | 1.13E−10 | 7938528 | PARVA | −1.03911 | 1.14E−15 | | | | |
| 7965403 | LUM | −1.67434 | 1.40E−10 | 7981514 | AHNAK2 | −1.04708 | 3.17E−15 | | | | |
| 8129562 | CTGF | −1.69136 | 3.95E−15 | 8172204 | MAOB | −1.05059 | 4.04E−10 | | | | |
| 8031047 | MYADM | −1.69873 | 9.13E−17 | 8121729 | PLN | −1.052 | 2.49E−10 | | | | |
| 7953603 | C1S | −1.70129 | 2.59E−16 | 8041781 | EPAS1 | −1.05535 | 1.04E−14 | | | | |
| 8072876 | LGALS1 | −1.71668 | 2.51E−15 | 8146863 | SULF1 | −1.05681 | 6.26E−14 | | | | |
| 8161513 | PGM5P2 | −1.7452 | 1.02E−15 | 7907222 | PRRX1 | −1.05953 | 5.57E−15 | | | | |
| 8106098 | MAP1B | −1.75931 | 9.95E−17 | 7949588 | CD248 | −1.06146 | 1.21E−14 | | | | |
| 8058765 | FN1 | −1.76725 | 7.52E−14 | 8018864 | SOCS3 | −1.06797 | 1.66E−07 | | | | |
| 7908940 | ATP2B4 | −1.77039 | 8.22E−18 | 7981732 | IGHV4-59 | −1.07284 | 6.14E−07 | | | | |
| 7940028 | SERPING1 | −1.78973 | 5.04E−15 | 7961693 | LDHB | −1.08908 | 1.57E−09 | | | | |
| 8073775 | FBLN1 | −1.80823 | 2.28E−16 | 8133721 | HSPB1 | −1.09177 | 1.36E−11 | | | | |
| 7965873 | IGF1 | −1.80913 | 1.49E−12 | 8141094 | PDK4 | −1.09375 | 2.14E−09 | | | | |
| 8013341 | MFAP4 | −1.81151 | 1.01E−14 | 7952205 | MCAM | −1.09596 | 1.28E−15 | | | | |
| 8089544 | CCDC80 | −1.8157 | 1.77E−15 | 8091422 | WWTR1 | −1.09638 | 9.90E−15 | | | | |
| 8105084 | C7 | −1.81621 | 6.92E−14 | 8148070 | COL14A1 | −1.09873 | 4.42E−13 | | | | |
| 8145669 | RBPMS | −1.81823 | 7.13E−17 | 7920258 | S100A6 | −1.10251 | 8.70E−13 | | | | |

-continued

| epitheliail Benign-stromal benign | | | | epithelial PIN-stromal PIN | | | | epithelial tumor-stromal tumor | | | |
|---|---|---|---|---|---|---|---|---|---|---|---|
| Affymetrix ID | Gene | LogFC | Adj. P.Val | Affymetrix ID | Gene | LogFC | Adj. P.Val | Affymetrix ID | Gene | LogFC | Adj. P.Val |
| 8149927 | CLU | −1.83868 | 2.66E−19 | 7938154 | ILK | −1.10302 | 1.90E−15 | | | | |
| 8075635 | TIMP3 | −1.83899 | 1.82E−13 | 8061114 | DSTN | −1.10313 | 1.18E−12 | | | | |
| 7902687 | CYR61 | −1.84837 | 6.69E−14 | 8122176 | TCF21 | −1.1038 | 5.20E−12 | | | | |
| 8161520 | PGM5P2 | −1.85153 | 9.65E−16 | 7951977 | FXY06 | −1.10677 | 2.53E−16 | | | | |
| 7960947 | A2M | −1.86675 | 7.02E−13 | 7916493 | PPAP2B | −1.11307 | 8.12E−16 | | | | |
| 8174513 | CHRDL1 | −1.91659 | 8.46E−15 | 8174670 | KIAA1210 | −1.11429 | 1.05E−08 | | | | |
| 8007420 | AOC3 | −1.94919 | 2.38E−14 | 7965123 | PPP1R12A | −1.11527 | 5.86E−15 | | | | |
| 7959102 | HSPB8 | −1.97055 | 7.10E−18 | 7981718 | IGHM | −1.11683 | 1.18E−08 | | | | |
| 8135990 | FLNC | −1.98254 | 3.62E−20 | 7939492 | C11orf96 | −1.1175 | 8.23E−13 | | | | |
| 7986385 | SYNM | −1.98983 | 2.70E−17 | 7975390 | SMOC1 | −1.11783 | 1.68E−10 | | | | |
| 8134263 | COL1A2 | −1.99053 | 2.64E−16 | 8145865 | GPR124 | −1.11922 | 4.67E−17 | | | | |
| 8170119 | FHL1 | −2.00495 | 2.74E−17 | 7914270 | LAPTMS | −1.13163 | 4.54E−11 | | | | |
| 8059905 | COL6A3 | −2.03889 | 4.79E−19 | 7960865 | SLC2A3 | −1.1352 | 1.59E−10 | | | | |
| 8155665 | PGM5 | −2.04207 | 2.03E−16 | 8180003 | HLA-DRB3 | −1.13526 | 3.61E−09 | | | | |
| 8068651 | PCP4 | −2.08792 | 2.79E−12 | 8115099 | PDGFRB | −1.13572 | 1.23E−16 | | | | |
| 8018966 | TIMP2 | −2.16261 | 3.52E−18 | 8051762 | SLC8A1 | −1.13667 | 1.48E−15 | | | | |
| 8058869 | TNS1 | −2.21943 | 2.18E−19 | 8114920 | DPYSL3 | −1.13686 | 5.96E−16 | | | | |
| 7965410 | DCN | −2.27984 | 7.56E−14 | 8005048 | MYOCO | −1.14379 | 1.99E−11 | | | | |
| 8115327 | SPARC | −2.30772 | 4.16E−16 | 7997642 | CRISPLD2 | −1.14681 | 4.44E−09 | | | | |
| 7935188 | SORBS1 | −2.3827 | 8.01E−21 | 8046333 | CYBRD1 | −1.15017 | 1.51E−13 | | | | |
| 7923386 | LMOD1 | −2.38549 | 1.85E−19 | 7981722 | IGHA1 | −1.1522 | 5.01E−10 | | | | |
| 8136347 | CALD1 | −2.39375 | 3.89E−19 | 8060758 | PRNP | −1.15344 | 1.76E−18 | | | | |
| 8109159 | MIR145 | −2.40156 | 5.10E−18 | 8084742 | LPP | −1.1674 | 4.20E−18 | | | | |
| 8097080 | SYNP02 | −2.43512 | 1.13E−20 | 7893777 | NA | −1.16917 | 3.11E−07 | | | | |
| 7923378 | CSRP1 | −2.44753 | 2.08E−22 | 7945371 | IFITM3 | −1.17363 | 2.28E−12 | | | | |
| 7896722 | NA | −2.68296 | 6.30E−17 | 7937772 | IGF2 | −1.17496 | 3.89E−06 | | | | |
| 8101659 | SPARCL1 | −2.69521 | 6.42E−16 | 8092970 | APOD | −1.17534 | 1.28E−07 | | | | |
| 8090098 | MYLK | −2.73373 | 4.19E−21 | 8098263 | PALLD | −1.17647 | 6.25E−18 | | | | |
| 7961514 | MGP | −2.9717 | 1.31E−17 | 8178811 | HLA-DRB4 | −1.17968 | 5.84E−09 | | | | |
| 8161044 | TPM2 | −3.06333 | 4.48E−23 | 7976812 | SNORD113-4 | −1.18253 | 6.14E−07 | | | | |
| 8175531 | CDR1 | −3.07244 | 8.02E−13 | 8069676 | ADAMTS1 | −1.18418 | 3.03E−09 | | | | |
| 8176026 | FLNA | −3.21755 | 2.02E−25 | 8097692 | EDNRA | −1.18871 | 8.36E−12 | | | | |
| 8062312 | MYL9 | −3.23274 | 5.12E−27 | 8067007 | TMSB4X | −1.19783 | 1.04E−15 | | | | |
| 8048541 | DES | −3.38358 | 1.01E−27 | 8066619 | PLTP | −1.20285 | 2.38E−13 | | | | |
| 8025918 | CNN1 | −3.39946 | 1.91E−22 | 8135576 | TES | −1.20432 | 7.46E−09 | | | | |
| 7944082 | TAGLN | −3.60123 | 8.08E−27 | 7979204 | FERMT2 | −1.20551 | 1.06E−12 | | | | |
| 7934906 | ACTA2 | −3.86287 | 5.21E−24 | 7906878 | DDR2 | −1.20579 | 5.76E−18 | | | | |
| 7999674 | MYH11 | −3.87157 | 2.17E−26 | 8128991 | LAMA4 | −1.21022 | 4.59E−15 | | | | |
| 8042788 | ACTG2 | −4.34933 | 6.69E−24 | 8001800 | CDH11 | −1.21504 | 1.18E−14 | | | | |
| | | | | 8137979 | ACTB | −1.21685 | 4.90E−25 | | | | |
| | | | | 8147516 | MATN2 | −1.21689 | 1.21E−15 | | | | |
| | | | | 7987315 | ACTC1 | −1.21692 | 5.14E−09 | | | | |
| | | | | 8021183 | SCARNA17 | −1.22025 | 2.72E−10 | | | | |
| | | | | 8115234 | ANXA6 | −1.22715 | 3.75E−19 | | | | |
| | | | | 7972750 | COL4A1 | −1.22784 | 1.40E−18 | | | | |
| | | | | 8042356 | MEIS1 | −1.2295 | 6.42E−15 | | | | |
| | | | | 7956211 | MYL6 | −1.23285 | 3.47E−15 | | | | |
| | | | | 7980908 | FBLN5 | −1.23772 | 2.01E−12 | | | | |
| | | | | 8101774 | TMSL3 | −1.23942 | 3.92E−17 | | | | |
| | | | | 8151310 | EYA1 | −1.24305 | 1.08E−14 | | | | |
| | | | | 7908409 | RGS2 | −1.24615 | 7.46E−10 | | | | |
| | | | | 8052355 | EFEMP1 | −1.24981 | 8.73E−09 | | | | |
| | | | | 8136918 | ZYX | −1.25336 | 1.1SE−19 | | | | |
| | | | | 7966135 | COROIC | −1.25578 | 3.19E−14 | | | | |
| | | | | 8163637 | TNC | −1.25656 | 3.55E−14 | | | | |
| | | | | 8161056 | TLN1 | −1.26949 | 3.64E−22 | | | | |
| | | | | 8066925 | PTGIS | −1.27714 | 1.62E−14 | | | | |
| | | | | 8158240 | TMSB4X | −1.27844 | 1.99E−15 | | | | |
| | | | | 7953200 | CCN02 | −1.27887 | 1.98E−13 | | | | |
| | | | | 8006433 | CCL2 | −1.27888 | 3.35E−05 | | | | |
| | | | | 8043459 | IGKC | −1.28119 | 6.28E−11 | | | | |
| | | | | 8162373 | OGN | −1.28425 | 2.30E−11 | | | | |
| | | | | 7981730 | IGU3 | −1.28998 | 1.58E−10 | | | | |
| | | | | 8135069 | SERPINE1 | −1.29171 | 9.49E−09 | | | | |
| | | | | 7977615 | RNASE1 | −1.29339 | 5.38E−17 | | | | |
| | | | | 8166072 | TMSB4X | −1.30982 | 7.40E−17 | | | | |
| | | | | 7927964 | SRGN | −1.31044 | 2.16E−14 | | | | |
| | | | | 7979824 | ACTN1 | −1.31153 | 3.40E−19 | | | | |
| | | | | 8043431 | IGKC | −1.32196 | 5.74E−12 | | | | |
| | | | | 8042439 | ANTXR1 | −1.32785 | 4.93E−13 | | | | |
| | | | | 8161755 | ALDH1A1 | −1.32866 | 1.26E−14 | | | | |
| | | | | 8115756 | KCNMB1 | −1.33214 | 1.06E−20 | | | | |
| | | | | 7901535 | PODN | −1.33633 | 1.59E−19 | | | | |

| epithelial Benign-stromal benign | | | | epithelial PIN-stromal PIN | | | | epithelial tumor-stromal tumor | | | |
|---|---|---|---|---|---|---|---|---|---|---|---|
| Affymetrix ID | Gene | LogFC | Adj. P.Val | Affymetrix ID | Gene | LogFC | Adj. P.Val | Affymetrix ID | Gene | LogFC | Adj. P.Val |
| | | | | 7991234 | MFGE8 | −1.34133 | 1.73E−19 | | | | |
| | | | | 7958253 | C12orf75 | −1.36313 | 3.41E−10 | | | | |
| | | | | 8069269 | COL6A1 | −1.36577 | 4.58E−22 | | | | |
| | | | | 8028872 | LTBP4 | −1.374 | 1.28E−16 | | | | |
| | | | | 8007100 | IGFBP4 | −1.37899 | 7.52E−21 | | | | |
| | | | | 8163896 | STOM | −1.39237 | 8.60E−19 | | | | |
| | | | | 7937330 | IFITM2 | −1.39352 | 3.05E−14 | | | | |
| | | | | 7965873 | IGF1 | −1.39547 | 2.38E−08 | | | | |
| | | | | 7914342 | FABP3 | −1.39899 | 4.16E−13 | | | | |
| | | | | 7898799 | C1QC | −1.40009 | 4.20E−13 | | | | |
| | | | | 8069301 | COL6A2 | −1.40135 | 5.37E−21 | | | | |
| | | | | 8015635 | PTRF | −1.40361 | 5.60E−20 | | | | |
| | | | | 7935228 | NA | −1.40412 | 1.28E−09 | | | | |
| | | | | 8043438 | IGKV1-5 | −1.40457 | 4.58E−10 | | | | |
| | | | | 8072413 | SMTN | −1.40854 | 8.04E−22 | | | | |
| | | | | 8167185 | TIMP1 | −1.41561 | 2.89E−09 | | | | |
| | | | | 8072626 | TIMP3 | −1.42414 | 1.04E−15 | | | | |
| | | | | 7906900 | DDR2 | −1.42787 | 3.54E−11 | | | | |
| | | | | 7929026 | ACTA2 | −1.43255 | 3.73E−21 | | | | |
| | | | | 8046922 | COL3A1 | −1.44227 | 1.26E−14 | | | | |
| | | | | 7970033 | COL4A2 | −1.44672 | 6.34E−22 | | | | |
| | | | | 7925320 | NID1 | −1.46148 | 1.22E−16 | | | | |
| | | | | 7915612 | PTCH2 | −1.47133 | 9.62E−06 | | | | |
| | | | | 7982597 | THBS1 | −1.49245 | 8.99 E−08 | | | | |
| | | | | 8106923 | NR2F1 | −1.49288 | 2.67E−17 | | | | |
| | | | | 7963054 | TUBA1A | −1.495 | 1.94E−13 | | | | |
| | | | | 8053713 | NA | −1.49619 | 1.01E−09 | | | | |
| | | | | 8180100 | HLA-DPA1 | −1.50299 | 9.21E−12 | | | | |
| | | | | 8118548 | HLA-DRA | −1.50493 | 3.60E−10 | | | | |
| | | | | 8053690 | IGK@ | −1.50882 | 7.68E−11 | | | | |
| | | | | 8104022 | PDLIM3 | −1.51638 | 8.81E−14 | | | | |
| | | | | 8179481 | HLA-DRA | −1.53815 | 2.83E−10 | | | | |
| | | | | 7960744 | C1R | −1.54409 | 4.52E−16 | | | | |
| | | | | 8051573 | CDC42EP3 | −1.54432 | 6.00E−18 | | | | |
| | | | | 7928444 | VCL | −1.54473 | 5.89E−18 | | | | |
| | | | | 8034130 | KANK2 | −1.55154 | 4.12E−21 | | | | |
| | | | | 7956301 | LRP1 | −1.55255 | 1.12E−22 | | | | |
| | | | | 8031047 | MYADM | −1.55635 | 8.40E−15 | | | | |
| | | | | 8003667 | SERPINF1 | −1.58204 | 3.59E−14 | | | | |
| | | | | 8178193 | HLA-DRA | −1.586 | 1.49E−10 | | | | |
| | | | | 7913450 | HSPG2 | −1.59626 | 4.26E−25 | | | | |
| | | | | 7984079 | TPM1 | −1.60125 | 4.67E−21 | | | | |
| | | | | 8125556 | HLA-DPA1 | −1.60457 | 8.13E−12 | | | | |
| | | | | 8178891 | HLA-DPA1 | −1.60457 | 8.13E−12 | | | | |
| | | | | 8135594 | CAV1 | −1.618 | 1.26E−17 | | | | |
| | | | | 7932796 | SVIL | −1.62191 | 4.38E−17 | | | | |
| | | | | 8167965 | MSN | −1.62291 | 9.16E−18 | | | | |
| | | | | 7976816 | SNORD114-3 | −1.62453 | 6.46E−10 | | | | |
| | | | | 8157605 | NA | −1.62726 | 2.44E−16 | | | | |
| | | | | 8036151 | HSP86 | −1.63649 | 5.20E−21 | | | | |
| | | | | 7965403 | LUM | −1.63672 | 3.03E−10 | | | | |
| | | | | 7972803 | NA | −1.64536 | 3.24E−14 | | | | |
| | | | | 7902687 | CYR61 | −1.65761 | 8.32E−12 | | | | |
| | | | | 7908924 | PRELP | −1.66947 | 1.26E−19 | | | | |
| | | | | 7902495 | NEXN | −1.67373 | 4.73E−14 | | | | |
| | | | | 8102532 | PDE5A | −1.67999 | 1.26E−16 | | | | |
| | | | | 7981724 | IGHD | −1.7033 | 1.79E−10 | | | | |
| | | | | 7963786 | ITGA5 | −1.71007 | 1.42E−15 | | | | |
| | | | | 8115147 | CD74 | −1.71431 | 2.20E−13 | | | | |
| | | | | 7995681 | MMP2 | −1.72027 | 4.20E−18 | | | | |
| | | | | 8106098 | MAP1B | −1.74514 | 1.30E−16 | | | | |
| | | | | 7926368 | VIM | −1.75542 | 3.02E−16 | | | | |
| | | | | 8170648 | BGN | −1.77259 | 3.05E−17 | | | | |
| | | | | 7953603 | C1S | −1.78766 | 1.37E−17 | | | | |
| | | | | 8116070 | PDUM7 | −1.79827 | 2.92E−24 | | | | |
| | | | | 8129562 | CTGF | −1.8205 | 6.87E−17 | | | | |
| | | | | 8149927 | CLU | −1.83525 | 2.29E−19 | | | | |
| | | | | 8016646 | COL1A1 | −1.85761 | 1.47E−16 | | | | |
| | | | | 8089544 | CCDC80 | −1.86146 | 4.46E−16 | | | | |
| | | | | 7981728 | NA | −1.86753 | 9.70E−11 | | | | |
| | | | | 8161513 | PGM5P2 | −1.88183 | 1.37E−17 | | | | |
| | | | | 8100541 | IGFBP7 | −1.88341 | 5.05E−23 | | | | |
| | | | | 8105084 | C7 | −1.88819 | 9.77E−15 | | | | |

-continued

| epitheliail Benign-stromal benign | | | | epithelial PIN-stromal PIN | | | | epithelial tumor-stromal tumor | | | |
|---|---|---|---|---|---|---|---|---|---|---|---|
| Affymetrix ID | Gene | LogFC | Adj. P.Val | Affymetrix ID | Gene | LogFC | Adj. P.Val | Affymetrix ID | Gene | LogFC | Adj. P.Val |
| | | | | 8174513 | CHRDL1 | −1.89689 | 1.26E−14 | | | | |
| | | | | 8132557 | AEBP1 | −1.90951 | 7.70E−22 | | | | |
| | | | | 8013341 | MFAP4 | −1.92033 | 4.52E−16 | | | | |
| | | | | 7959102 | HSPB8 | −1.92614 | 2.17E−17 | | | | |
| | | | | 7908940 | ATP2B4 | −1.93154 | 2.90E−20 | | | | |
| | | | | 8072876 | L6ALS1 | −1.9357 | 2.89E−18 | | | | |
| | | | | 8157582 | GSN | −1.95792 | 7.81E−22 | | | | |
| | | | | 8135990 | FLNC | −1.96413 | 4.51E−20 | | | | |
| | | | | 8100827 | IGJ | −1.96538 | 8.69E−11 | | | | |
| | | | | 7940028 | SERPING1 | −1.99741 | 1.13E−17 | | | | |
| | | | | 8075635 | TIMP3 | −2.00836 | 2.32E−15 | | | | |
| | | | | 8007420 | AOC3 | −2.00876 | 3.11E−19 | | | | |
| | | | | 8161520 | PGM5P2 | −2.02444 | 5.89E−18 | | | | |
| | | | | 8073775 | FBLN1 | −2.03025 | 2.21E−19 | | | | |
| | | | | 8170119 | FHL1 | −2.05546 | 5.31E−18 | | | | |
| | | | | 7951662 | CRYAB | −2.05803 | 7.68E−15 | | | | |
| | | | | 8145669 | RBPMS | −2.08142 | 1.39E−20 | | | | |
| | | | | 7960947 | A2M | −2.17222 | 3.74E−16 | | | | |
| | | | | 8134263 | COL1A2 | −2.20599 | 6.02E−19 | | | | |
| | | | | 8059905 | COL6A3 | −2.24192 | 7.81E−22 | | | | |
| | | | | 7986385 | SYNM | −2.26114 | 7.52E−21 | | | | |
| | | | | 8058765 | FN1 | −2.35914 | 4.67E−21 | | | | |
| | | | | 8155665 | PGM5 | −2.38492 | 1.37E−20 | | | | |
| | | | | 8058857 | IGFBP5 | −2.41062 | 1.35E−18 | | | | |
| | | | | 7923386 | LMOD1 | −2.48679 | 8.99E−21 | | | | |
| | | | | 8109159 | MIR145 | −2.50516 | 3.13E−19 | | | | |
| | | | | 7935188 | S0RBS1 | −2.52153 | 1.05E−22 | | | | |
| | | | | 8115327 | SPARC | −2.57104 | 7.38E−19 | | | | |
| | | | | 8018966 | TIMP2 | −2.61841 | 8.30E−24 | | | | |
| | | | | 7965410 | DCN | −2.67815 | 1.37E−17 | | | | |
| | | | | 8097080 | SYNPO2 | −2.69907 | 5.70E−24 | | | | |
| | | | | 8068651 | PCP4 | −2.7169 | 3.94E−18 | | | | |
| | | | | 7923378 | CSRP1 | −2.72564 | 3.20E−26 | | | | |
| | | | | 8058869 | TNS1 | −2.76306 | 2.92E−26 | | | | |
| | | | | 7896722 | NA | −2.86904 | 9.90E−19 | | | | |
| | | | | 8136347 | CALD1 | −2.87214 | 1.13E−24 | | | | |
| | | | | 8090098 | MYLK | −2.89108 | 5.26E−23 | | | | |
| | | | | 8175531 | CDR1 | −3.0189 | 1.65E−12 | | | | |
| | | | | 8101659 | SPARCL1 | −3.43137 | 1.96E−22 | | | | |
| | | | | 8161044 | TPM2 | −3.48291 | 1.07E−27 | | | | |
| | | | | 7961514 | MGP | −3.55742 | 1.02E−22 | | | | |
| | | | | 8062312 | MY19 | −3.64445 | 7.16E−32 | | | | |
| | | | | 8176026 | FLNA | −3.66801 | 1.53E−30 | | | | |
| | | | | 8048541 | DES | −3.67446 | 1.11E−31 | | | | |
| | | | | 8025918 | CNN1 | −3.89607 | 2.64E−27 | | | | |
| | | | | 7944082 | TAGLN | −4.22234 | 7.86E−33 | | | | |
| | | | | 7999674 | MYH11 | −4.43624 | 1.03E−31 | | | | |
| | | | | 7934906 | ACTA2 | −4.48002 | 1.40E−29 | | | | |
| | | | | 8042788 | ACTG2 | −5.00704 | 3.66E−29 | | | | |

FC positive in epitheliail Benign-stromal benign samples: MSMB, ACPP, KLK3, KLK2, TMPRSS2, AZGP1, NEFH, POTEG, SORD, SLC45A3, GDEP, POTEM, TSPAN1, CDH1, RDH11, NKX3-1, KIAA1324, ANPEP, NPY, VEGFA, DHCR24, KLK4, SLC44A4, PLA2G2A, POTEF, SPDEF, EHF, POTEE, SNORA24, MUC12 POTEE FOLH1B, DHRS7, DPP4, TGM4, FOXA1, FOLH1B, ZG16B, TACSTD2, MUC3A, KRT8, FXYD3, AMD1, ZNF525, GREB1, RBM47, TMEM141, CPLX3, DBI, GOLM1, LMAN1L, PCAM, RT18, AQP3, CPNE4, TRPV6, AGR2, MUC3A, MIR622, NDRG1, TRPM8, MLPH, NEDD4L, FLJ39632, NCAPD3, FLJ39632, SYT7, SLC30A4, CD9, CPE, GRHL2, AN07, N1PAL3, SPINT2, MUC12, CREB3L4, GMPR, P4HB, STEAP2, HGD, BCAM, SFN, TSPAN8, FASN, XBP1, DMXL1, PRSS8, P4HB, ABCC4, SNORD115-11, SCD, PRAC, C10rf1 16, HOXB13, MT1G, CHRM1, SNORA21, SNORD115-12, SLC4A4 SNORD115-11, KlAAI244, SNORD115-11, IDH1, SNORD115-26, CD177, FLNB, ARG2, MEPA1, D177, C15orf21, HERPUD1, SNORA70, CD38, ZNF761 , C9orf152, SERINC5, PAKIIP1, PLEKHH1, RCAN3, SEC11C, ERGIC1, PTPRF, GDF15, ACLY, COPG, SLCl4A1, HOMER2, TPD52, TMC4, SNORD115-20, ZNF765, STM, RAB3B, CYB561, CACNG4, CNDP2, SNORD115-42, KRT15, ODC1, STEAP1, SNORA71 A, CANT1, SLC25A37, BASP1, BN1P3, POTEB, CPLX3, SNORA74A, GPT2, SNORA37, SNORD115-6, SNORA80B, GPR56, SNORA40, ALOX15B, ELOVL5, CHRNA2, DSP, KLK11, SLC15A2,IRF6, LRBA, PPAP2A, CLDN3, BCAS1, RAB25, SLC39A6, SNORA65, POTED, NANS, SLC7A8, FLJ39632, VAMP8, CASZ1, MAP7, SPOCK1, SNORD115-1, ANKH, FAAH, RNF144B, PSCA, SNORA64, ATP2C1, AGTRAP, CD46, C10rf85, API M2, SCGB1A1, ZNF827, SNORD115-17, DCXR, SNORD115-32, CD24, SCD, ELK4, TMC5, GALNT7, MT1F, KRT5, C6orf132, PAR4, ACSL1, SCARNA4, SER1NC2, ENTPD5, C17orf28, CSGALNACT1, MYBPC1, CYB5A, FAM3B, TNFSF10, RAB27B, ATPI 1, SLC37A1, SERPINBI1, EBP, GCNT2, KRT18, KIAA1522, BAIAP2L1, FADS2, GFPT1, CWH43, SNORD115-25, SNORA42, BMPR1B, MIR205, FOLH1, KIAA12I7, ASTN2, ACSL3, EPHX2, SNORA3I, ESRP1, PNPLA7, LOC147804, GADD45G, MLLT4, SNORA6 NPDC1 LCP1, NEU1, NUDT4P1, CCDC88C, HIPK2, ST6GAL1, SLC12A2, ERBB3, C2orf14, KRT19, SNORA1, SNORA9, CLDN4, HMGCS2, ELF3, SERHL, C19orf48, STEAP4, SNORD115-44, H1ST1H2BD, ANXA3, FBX025, TBC1D8, DDR1, RPM4, ELOVL7, SNORA71D, PART1, TMEM79 PKP1 CASZ1, PSCA, ZKSCAN1, PDIA3P, SNORA71B, SPATA13, PD1A4, RHPN2, IL1R1, SHROOM1, SNORA73A, SNORAIO, OLFM4, JUP, NFIB, RPN2, SNORA67, SNORA57, SLC39A7, SLC39A7, HIF0, FDFT1, CLDN7, STXBP2, TC2N, A1M1, GNG4, FUR, DHCR7, C2orf14, SNORA80 POTEC, SEZ6L2, SC5DL, LPCAT3, MPZL2, EFNA1, PPAPDC1B, IGF1R, SNORA38, VIPR1, ZCCHC6, GLO1, SNORA28, VSIG2, PDIA3, PROM2, MPPED2, TNS4, AMI35A, ENTPD6, S100A10, STAP2, SNORD115-33, DDR1, TMBIM6, MALT 1SNORD104, WNK4, SNORA60, NWD1, ATP8B1, MME, FURIN, TFCP2L1, ANXA1, SNORA75, PEBP4, CHP, CORO2A, FBP1, ZNF532, SNORA69, NEU1, ATP2C2, K1F1 A, CASZ1, SLC7A2, APIB1, ERBB2, CUX2, DDR1, TCEA3, SNORA52, REEP6, SNORA58, SCNN1 A, ZNF765, MMP19, LTF, EPCAM, TBX3, RAG1AP1, LSS, NAPA, PPDPF, GSR, SPTBN2, SNORA2A, DOPEY2, CIB1, MCCC2, RNF185, FNBP1L, ZNF587, RMDL2, SNORD115-30, CLSTN1, BHLHAI5, BAIAP2, NAAA, SNORA55, SPINT1, SNORA48 SNORA8 PASK , TMEM63A, FAM174B, SLC25A37, SNORA38B, PERP, UPK3A, CREB3L1, H1ST2H2AA3, PDE9A, SNORA 13, SIDT2, GLUD1 PSD4, SNORA46, SNORA7B, SNOR A68, PGC, DSG2, CENPN, TRIM29, SULT2B1, SEC23B, TFF1, SNORA33, HDLBP, LMAN1, S100A11, WWC1, MGST1, KIAA0319L, SNORA40, ATP6AP1, PLA2G4F, ADAM10, SNORA62, KLKP1, SYTL1, RPPH1, C20orf54, IST2H2BE, ZNF350, MPDU1, PPP1CA, AFF3, UPK1A, PGM3, SCARNA8, CDH26, and LR1G1.

| epitheliail Benign-stromal benign | | | | epithelial PIN-stromal PIN | | | | epithelial tumor-stromal tumor | | | |
|---|---|---|---|---|---|---|---|---|---|---|---|
| Affymetrix ID | Gene | LogFC | Adj. P.Val | Affymetrix ID | Gene | LogFC | Adj. P.Val | Affymetrix ID | Gene | LogFC | Adj. P.Val |

FC negative in epitheliail Benign-stromal benign samples: CAMK2NI, EPB4IL2, CD68, JAK1, CCDC69, CETN2, SEC23A, COL12A1, DCHS1, RBMS3, OLFMLI P2RXI CALM3, DST, MEG3, CD37, SYNPO, PTPN11, AMOTL2, PRKCDBP, PDGFRA, POSTN, RBM24, LAPTM4A, MBNLI, PTGS1, HSPB1, COL16A1 CPA3, RNF150, GJA1, FRMD6, ZNFI85, SELM, IL6ST, NFATC4, GBP I, CTSK RHOJ, ARHGDIB, C4A, LRRFIPI, TEAD1, CRTAP, MRC2, NELL2, LIF, KLHL5, TCF7L1, PPP1R12B, RBP1, TGFBI, PP1R3C, PDE3A,CSDE1, DAAM2, OSR2, TACC1, RAB31, CLIP3, NRP2, DUSP3, USP17L6P, TMSB4XP2 CAV2 COCH, SERPINHI, TMEM47, LIMS2, POPDC2, IGHV3-48, TFIY1, WDRI, RCAN2, MLXIP, EPASI, PFKP, SGK269, GEM, SLMAP, LPARI WIPF1 ITIH5, C2orf40, MRVI1, MARVELD1, GLIS1, TCEAL2, RHOB, TINAGLI, BOC, NAP 1 LI, IGHA1, COX7AI, JPH2, FOSL2, TRPS1, EMILINI, RRAS, HEG1, NCS1, SPEG, ENG, DPYSL2, NFIA, SH3DI9, SLIT2, PRUNE2, BAG2, FNBPI, CXCR4, CESI, FP36, DMD, TENC1, ZCCHC24, CACNAIC, PFILDBI, SRF, ARHGAP10, DKK3, TSPAN18, LOC283174,COX6C, PNMAI, HEYL, RGS5, FOSB, CCL5, EFEMP2, NR4A3, SDC3, C7orf58, JAZFI, SH3BGRL, ADAMTS4, INMT, MEF2C, SPONI,COLI5AI, IGK, ITPRI, RBMS1, TBL1X, GLI3, 11-Sep, CIQB, SI00A6, LOC652493, CXCLI2, C15orf51, SNORD113-4, EHD2, IGKC, IGKV3D-11, PARVA, ISLR, LM04, LAPTM5, FZD7, PCDFI18, GSTM5, CIQA, RARRES2, RND3, ITGBI, C5orf13, HLA-DRi33 ANTXRI, PM1, AN06, PTGDS, CFL2, CSPG4, GYPC, RASL12, FAIM2, CNTN1, PPPIRI4A, JUNB, SULFI, ITGA8, SFRP2, OLFML3, TES, PRUNE2 MRGPRF KCNMAI, MSRB3, WFDC1, IGHM, BTG2, SPTBNI, LDB3, IGKC, FBN1, HLA-DRB3, PELO, DNAJB5, FXYD1, DPT, PCDHIO, ADAMTS1 HI9 LOC388022, HLA-DRB4, KIAA12I0, CAP2, EMP3, ALDH1BI, GAS6, ATP1A2, TNC, SCARNAI7, SPOCK3,1FITM3, AQP1, C15orfl5l, ITGA7 TGFB2 HLA-DPA1, PLN, FILIP1L, FABP3, EYAl, TPSAB1, CLIC4, C10rf54, TN, PRNP, APOD, TGFB1II, CDHI1, PPAP2B, IGKC, PCOLCE, IGHAI TPSAB1, TCF2I, PAGE4, PRKCA, C1 lorf96, HLA-DPA1, SLC2A3, SLC8AI, EPHA3, GPRI24, ZEB2, IGKVI-5, CFD, PRRXI, CYBRDI, AHNAK2, MIR143, SNORD 114-3, PALLD, PMP22, FGFR1, PDGFRB, ADCY5, SOCS3, PTRF, IGLJ3,1GFBP4, RBPMS2, SERPINE1,1GHV4-59, PLTP, ANXA6, DPYSL3, WWTR1, LTBPI, SI00A4, LAMA4, EDNRA, MATN2, ARFIGEF25, COL4AI, HLA-DRA, PPPIRI2A, MAOB, HLA-DRA, MEIS1, ERMT2, C1QC, MCAM IGKC EGR1 HLA-DRA, IGK, CD248, COLI4AI, MYL6, ALDH1 Al, SRGN, DDR2, RNASE1, COROIC, CCL2, ZYX, FXYD6, ACTB, MYOCD, TMSB4X ILK' TMSL3 STOM, ACTN1, OGN, IFITM2, SMOC1, PTGIS, DSTN, TLN1, LPP, MFGE8, EFEMPI, FBLN5, SMTN, LRP1, KCNMBI,CCND2, SERPINFI COL6A2, COL6A1, VIM, MSN, LTBP4, BGN, CD74, SCARNA17, IGFBP5, ACTCI, ITGA5, COL4A2, PODN, NR2FI, RGS2, COL3AI, MMP2, TIMP3, NIDI, DDR2, CIR, ACTA2, ANK2, C12orf75, CAV1, CDC42EP3, IGHD, HSPG2, PDE5A, THBS1, TUB AI A, GSN, VCL, TPM 1, COL1AI, IGF2, PDLIM7 SVIL IGFBP7 PDLIM3, NEXN, AEBPI, HSPB6, PRELP, IGJ, CRYAB, LUM, CTGF, MYADM, CIS, LGALSI, PGM5P2, MAPIB, FNI, ATP2B4, SERPING1, FBLNI, IGF1, MFAP4, CCDC80, C7, RBPMS, CLU, TIMP3, CYR61, PGM5P2, A2M, CHRDL1, AOC3, HSPB8, FLNC, SYNM, COLIA2, FHLI, COL6A3, PGM5, PCP4, TIMP2, TNS1, DCN, SPARC, SORBS1,LMOD1, CALD1, IR145, SYNP02, CSRPI, SPARCL1, MYLK, MGP, TPM2, CDR1, FLNA, MYL9, DFS, CNN1, TAGLN, ACTA2, MYHI I, and ACTG2.

FC positive in epithelial PIN-stromal PIN samples: KLK3, KLK2, TSPAN1, TMPRSS2, GDEP, ACPP, SLC4A4, GOLMI SNORA24, FOLH1, FOLH1B, SNORA71 A, SLC45A3, AZGPI, POTEG, SNORA21, TRPM8, SNORA74A, SLC44A4, CPNE4, CDHI, AGR2, RDH11, SPDEF, NKX3-1, KIA A1324, SNORA70, POTEM, NPY, SNORA70, SORD, POTEM, SNORA80B, FOXA1, OR51E2, DPP4, ABCC4, DHCR24, EPCAM, EHF, MSMB, ENTPD5, KLK4, SNORD78, GDF15, SNORA67, AMD1, NEDD4L, TRPV6, NORA64, SNORA65, MLPH, DHRS7, DMXLI, STEAPI, STEAP2, KRT18, MIR622, CREB3L4, FASN, POTEF, POTEE, SCARNA4, PRAC, TACSTD2, SNORA71D, MUC3A, KIAAI244, SNORD115-11, SNORD74, SNORD44, SNORD115-12 PLA2G2A, SNORA73A, SNORA9, SNORA40, SNORD115-26, MUC12,' POTEE, PRSS8, SNORA55, FLJ39632, SNORA52, AN07, GALNT7, SNORD115-44 SNORA6, RBM47, SNORAIO, SNORA1, CD24, ODC1, SNORD115-20, ZNF525, FXYD3, P4HB, KRT8, P4HB, RHL2, TRNA1-2, SNORA33, CPE, GREB1, ZG16B, C9orfl52, SNORA38, FLJ39632, SNORA71B, SNORA68, SPINT2, SNORA31, SERINC5, SNORA57, BCAM, SYT7, SNORA69, SNORA75, SNORD115-32, SNORD109A, SNORA62, SNORD47, ACLY, VEGFA, MYBPC1, MUC3A, SNORD116-16, XBPI, ERGICI, PLEKHHI, SNORA2A, SLC39A6, EPCAM, IDHI, SNORD36B, HOXB13, CANTI, TSPAN8, SLC30A4, SNORA42, C15orf21, DBI, C10rfl 16, TMC5, FBX025, NCAPD3, STEAP4, LRBA, SNORA71C, POCK1, SNORA3, SNORD115-42, RAB25, MAP7, SNORD76, SNORD115-6, SNORD80, TMC4, SNORA37, SNORD116-5, SNORD104, GLOI, SNORD116-29, ST 14, PAR4, CLDN3, SNORD75, ATP2C1, SNORA48, TMEMI41, SCARNA22, PMEPA1, NUDT4P1, SNORD115-17, ERBB3, SNORA51, CLDN7, SNORD115-1, FLNB, SNORA80, C19orf48, SNORA58, ESRPI, SNORD115-33, RAB3B, BNIP3, ZNF761, PTPRF, HOMER2, MUC12, GMPR, HPN, SNORA27, C2orfl4, SNORD116-1, FAAH, SCD, CPLX3, NORA8, SNORD116-3, SNORD116-25, SNORA23, SNORD116- 11 CHRMI, SNORD116-8, SNORD116-4, SCARNA8, SNORD115-44 COPG, SERHL, PSCA, SNORD115-38, SNORD31, STXBP2, C6orfl32, CD9, HMGCS2, SECI1C, SLC25A37, SNORA7B, SNORD14E, NANS, ELOVL5, DSP, CNDP2, CHRNA2, SCARNA14, HGD, SNORD36C, FOLH1, C17orf28, C2orfl4, CYB561, SNORD116-22, KRT18, ELOVL7, SCARNA16, SNORA38B, LMANIL, SNORA56, AQP3, KLK11, TAM3B, SNORA 28, CYB5A, SNORD115-25, SNORA13, BMPRIB, DCXR, SNORD6, TNFSF10, SNORD60, TRPM4, SLC12A2, SNORA46, ZNF765, C1QTNF9B, SNORD4A, ARG2, SNORA20, CLDN4, SNORA50, SNORD116-15,IRF6, ZCCHC6, FLJ39632, SNORD37, AP1M2, LCP1, SLC37A1, PARTI, GPT2, FBP1, MAL2, SNORA60, PDIA3P, SNORDIC, SLC36A1, MCCC2, SFN, SHROOM1, SPTBN2, TMEM87A, CASZ1, RPPHI, SNORA4, SNORA61, CWH43, DOPEY2, SNORA49, PSCA, ORMDL2, PTPRN2, KIAA1522, SNORD116-20, DIA3, POTEB, TPD52, ARHGEF38, SNORA45, SNORD5, TC2N, SNORD116-17, SNORD116-17, SERINC2, PPAP2A, ELF3, SNORA40, REEP6, STAP2, ENTPD6, NAAA, MT1G, SLC7A8, H1ST1H2BK, SRSF6, SNORA5A, LOC147804, PCOTH, NPDC1, GFPT1, SNORD115-30, ZNF587, SNORD30, SYNGR2, SNORD49A, SNORD12C, SNORD14C, SNORD115-38, SNORD31, STXBP2, C6orfl32, SNORA41, SNORD38A, AIM I, CDKI9, GADD45G, SNORD83B, RPLPO, PNPLA7JUP, PGM3, PGC, TARP, NF350, IPRI, PPP1R1B, ANKH, ERBB2, RPL12, SEZ6L2, LOC440905, SNORD116-21, KIAA0319L, MAZ, MLLT4, GPR56, RPL41, SNORD35A, RPS2, HERPUDJ, SNORD28, ZNF552, FNBP1L, MGST2, ZNF765, SNORD54, POTED DDT RPS28 PBOV1, WWC1, ANXA3, MY06, NAALADL2, CASZ1, FI IR, RPL18, RORC, RHPN2, SCD, MIF, RPS28, SNORD27, SNORD22, ATP6AP1, LRIGI, GLYATL1, ACSM3, AGTRAP, RAB27B, RPL12, H1PK2, EPHX2, ESRP2, TSPAN 13, ACACA, SLC22A23, SNORD24, FDFT1, PINTI, SEC23B, SNORD26, SLC7A2, SNORD25, SNORD3A, RPS28, MT1F, SLC15A2, SPATA13, YWHAE, ST6GAL1, TMBIM6, KIAA1217, PTPN18, ACSL3, SCARN A12 ATP8AI SNORD55, BRPA4, CASZ1, ZNF649, ZNF577, RPL12, SNORD115-41, SNORA5C, SNDI, SLC39A7, RPN2, CSGALNACT1, SLC31A1, BAIAP2L1, RAP1GAP, HIST1H2BD, RPL3, RALGAPA2, GNB2L1, ELK4, SFTPA2, LPCAT3, H1F0, VSIG2, ATP1A1, C4orf34, YIPF1, RPL4I, CD46, BCASI, TERC, ARFIP2, MMPI9, TBC1D8, DIA5, CAMKK2, RPS2, BAMBI, EEF1G, ZKSCAN1, TCEA3, GNMT, C0R02A, SEC61 Al, LIPH, SCARNA11, EBP, PTGRI, TM7SF2, RPL41, SNORD42B, SNORD95, PD1A4, RPL 10, HIST2H2BE, PPAPDC1B, PSD4, LPAR3, MOSCI, PLA2G7, DDAH1, SHROOM3, SERPINB11, SNORD 116-27, ZNF613, HSP90BI, and DDR1.

FC negative in epithelial PIN-stromal PIN samples: PDZRN4, NCRNA00152, COX6C, CD53, HLA-DQBI, ITM2C, SAMHD1, COPZ2, IGHV3-48, RASD2, EGR2 ZEB1 ABCC9 FAM86BI, ZFP36, PRKCDBP, DUSP3, SERPINHI, LAPTM4A, BAG2, RHOJ, EYA4, CCL4LI, RASA3, RASA4, PECAMI, HBB,,. MRC2 TMEM176A, TSPYL2, CRTAP, RCAN2, NR4A2, STAB 1, LGALS3BP, TMSB4XP2, GAB2, TRPSI, SELE, IAM3, H19, P2RX1, ATXNI, NRP2, SH3PXD2B, LPHN2, JAK1, PRUNE2, SEC23A, FCERIG, BFOX3, ZFP36L1, CD8I, FAMI27A, T1NAGLI, PYGM, SPEG, DAAM2, SLMAP, 1ER3, RBMS1, CSF1R, CST3 HLF, GPR183, TCF4, ATP2A2, DST,MBNLI, SRD5A2,VTRNA1-1, ITIH5, PCOLCE2, PLEKHOI, TGFBI,1GK, ITGA8, ARHGEF17, FRMD6, CESI HLA-DRB5, LTBP3, DAB2, HLA-DPBI, CPA3, AHNAK, SPONI, ADCY3, CXCLI2, SLIT2, LIMS2, MLXIP, RERG, CTSB, PPP1R3C, PARMI, TMEM47, CX3CL1, SGK269, THBS2, PAM, ADAMTS4, PGRMCI, COX7AI, CACNAIC, SH3DI9, GSTM2, CRNA00152, EMP1, FILA-DPB1, RRAS, SH3BGRL TGFBR2, C2orf40, NID2, EMILIN1, MBNL2, SNAI2, CAV2, PAMR1, PPP1R12B, SELM, TNXA, KLHL5, MARVELD1, PDE3A, MEG3, SDC3, CD34, ST5, TGFBI, LIF, C15orf51, PRUNE2, CBX7, GSTP1, FBX032, CAMK2N1, INMT, GBP1, SRF, IFITMI, PRKCA, PFKFB3, 11-Sep, JPH2, EPB4IL2, ARHGAP10, GPNMB, ARHGDIB, GEM, CD52, IGKV3D-I1, MOXD1, PNMA1, CYP1BI, LDB3, TNXB, ITPRI, CNN2, ITGBI, SFRP4, TGFB2, HEGI, MRVI1, AB31, LAMB2, ZCCHC24, CALM I, M1R143, MIR27A, LOC283174, RDH10, NF1A, CCL5, WFDC1,1D3, GLI3, CXCR4, CPD, SFRPP2, CD.149, PDGFRA, DPYSL2, RASL12, BOC, GLIPR1, TCF7L1, DPT, CD68, LM04, NR4A3, JUNB, CNTNI, FAM38B, FXYDI 'PELO, C7orf58, PTGDS, ADCY5, FOS, IGHA1, ENG, C15orf51, RHOB, TPM1, RBMS1, PLP2, TENCI, LPARI, TSPAN18, WDR1, ISLR, PTN, POPDC2, DEG2, GSTM5, EHD2, PHLDB1, HBA2, HBA1, GYPC, SP17L6P, TACC1,CSPG4, SFRPI, NCS1, CTSK, RARRES2, MRGPRF, PBX1, PPP1R14A, THY1 C15orf51, HLA-DPBI, LOC652493, FNBPI, DNAJB5, ATP1A2, C1QB, FZD7, HLA-DQA1, EMP3, CIQA, WIPF1, MSRB3, AN06, ALDH1B1, OLFML3 DKK3, HEYL, MEF2C, GJA1, FOSB, CFL2, LTBPI, JAZFI, RGS5, DMD, EPHA3, COL15A1, TGFBIII,C10rf54, RBPMS2, PAGE4, EGR1, PCDH18, FAIM2, FOSL2, TCEAL2, RBMS3, TPSAB1, MEIS2, LOC1 00130876, CAP2, ZEB2, BHLHE40, POSTN, KNDI, NUDT4PI, PTGS, FHL I, PMP222, IGKC, FGFRI, TPSAB1 KCNMA1, ITGA7, S100A4, CLIC4, C5orf1 3, PCDH10, AQP1, GAS6, EFEMP2, IGKC, ARHGEF25, SPOCK3, SPTBN1, HLA-DRB3, PCOLCE, FBN1 PARVA, AHNAK2, MAOB, PLN, EPASI, SULF1, PRRXI, CD248, SOCS3, IGHV4-59, ILDHB, HSPB1, PDK4, MCAM, WWTR1, COLI4AI, IGHA1, ILK DSTN, 5CF21, FXYD6, PPAP2B, KIAA1210, PPP1R12A, IGHM, C11orf96, SMOC1, GPR124, LAPTM5, SLC2A3, HLA-DRB3, PDGFRB, SLC8A1, DPYSL5, MYOCD, RISPLD2, CYBRDI, IGHA1, PRNP, LPP, 1FITM3, IGF2, APOD, PALLD, HLA-DRB4, SNORD113-4, ADAMTS1, EDNRA, TMSB4X, PLTP TES, FERMT2, DDR2, LAMA4, CDH11, ACTB, MATN2, ACTCI, SCARNA17, ANXA6, COL4A1, MEIS1, MYL6, FBLN5, TMSL3, EYA1, RGS2, EFEMPI ZYX CORO 1C, TNC, TLN1, PTGIS, TMSB4X, CCND2, CCL2, IGKC, OGN, IGU3, SERPINEI, RNASE1, TMSB4X, SRGN, ACTN1, IGKC, ANTXRI ALDHIA1 NCMAI, PODN, MFGE8, C12orf75, COL6A1, TBP4,1GFBP4, STOM, IFITM2, IGF1, FABP3, C1QC, COL6A2, PTRF, IGKV1-5, SMTNTIMP1, TIMP3, DDR2, ACTA2, COL3A1, COL4A2, NIDI, PTCH2, THBS1, NR2F1, TUBA1 A, HLA-DPAI, HLA-DRA, PDLIM3, C1R, CDC42EP3, VCL KANK2 LRPI MYADM SERPINFI, HSPG2, TPMI, CAV1, SVIL, MSN, SNORD114-3, HSPB6, LUM, CYR61, PRELP, NEXN, PDE5A, IGHD, ITGA5, CD74, MMP2, MAP 1BV1M, BGN, CIS, PDLIM7, CTGF, CLU, COL I AI, CCDC80, PGM5P2, IGFBP7, C7, CHRDLI, EBP1, MFAP4, HSPB8 ATP2B4 LG A LSI GSN, FLNC, IGJ, SERPING1, TIMP3, AOC3, PGM5P2, FBLN1, FHL1, CRY AB, RBPMS, A2M, COLIA2, COL6A3, SYNM, FN1, PGM5, IGFBP5, LMODI, MIR145, SORBS1, SPARC, TIMP2, DCN, SYNP02, PCP4, CSRPI, TNSI, CALDI, MYLK, CDRI, SPARCL1, TPM2, MGP, MYL9, FLNA, DES, CNNL TAGLN, MYH11, ACTA 2, and ACTG2.

FC positive in epithelial tumor-stromal tumor samples: GOLMI, NPY, KLK3, KLK2, TSPAN1, OR51E2, SNORA74A, ACPP, FOLH1, AMACR, FOLH1B, CPNE4, SLC44A4, SLC45A3, STEAPI, EPCAM, OR51E1, SNORA24, SNORA21, ABCC4, TMPRSS2, RDH11, BCAM, SNORD78, SPDEF, CD24, NEDD4L, EPCAM PRSS8, SNORA71 A, DHRS7, STEAP2, AGR2, NKX3-1, SORD, KLK4, FOXA1, KIAA1244, C9orfl52, CDHI, SNORD74, SNORA70, DHCR24, SNORA70 SNORD44, MLPH, CREB3L4, ASN, SNORD75, SNORA65, SNORD36B, TRPV6, TMEFF2, GDF15, KIAA1324, PRAC, TACSTD2, ENTPD5, SNORA33, SNORA69, SNORA64, PLEK,HH1, EHF, ERGICI, KRT18, STEAP4, SNORA80B, PMEPA1, P4HB, MIR622, SNORA4, SNORD80, ELOVL5 SNORD115-11, SNORA9, SNORA40, MAL2, CANTI, C19orf48, ODCI, HOXB13, P4HB, SNORD115-26, SNORA55, SNORD115-11, SNORD115-11, SNORD115-11, SNORAIO, SNORAIO, SNORD115-11, RT8SNORD115-12, ST14, MY06, AZGPI, SNORA2A, SNORA52, SCARNA4, ACLY, PLA2G7, ZNF525, SNORD49A, SNORD115-44, TMC5, ACSM1, CAMKK2, SNORD76, MAP7, POTEG, SNORA71D, SERINC5, ZG16B, SLC4A4, SNORA58, SNORA6, SECI1C, SNORA51, SLC30A4, TRPM8, XBP1, ZNF761, SNORA71B, CLDN7, GALNT7, LRBA, ESRPI, RBM47, SNORA38, SNORD115-20, AMD1, BMPR1B, TMC4, SNORD104, SNORD36C, RALGAPA2, CREB3L1, SNORD47, SNORD38B, TPD52, REPS2, NORD115-32, FAAH, ATP2C1, PDIA3P, HIST1H2BK, SNORA3, SLC39A6, SNORA73A, SNORA42, ERG, PDIA3, VTRNA1-2, PAR4, SNORD115-6, FBX025, PPAP2A, C10rf1 16, RPLPO, SPOCK1, SLC12A2, SNORA68, SNORD115-42, GRHL2, COPG, SERHL, SNORA75, RAB25, CPE, CCDC88C, MOSCI, C17orf28, DPP4, FXYD5, SP1NT2, TMEM141, DB1, SNORD37, ACACA, POTEM, FLNB, SNQRA62, SNORD115-17, SNORD1A, SNORA8, SNORD115-1, HPN, SNORD22, SNORD27, CLDN3, ARG2, NORD30, DSP, SPTBN2, SNORD6, SNORD9, ZCCHC6, SCARNA14, LRIGI, POTEM, ACSL3, TP53INP1, MCCC2, TMBIM6, SNORA7IC, SNORA31, SNORD5, SNORD12C, SNORD115-25, GCNTI, SNORD54, HOMER2, SNORD14E, AP1M2, ZNF552, PTPRF, SNORD115-17, FOLH1, SYNGR2, PCOTH, TC2N, SNORD60, CNPEN, C15orf21, PDIA4, RAP I GAP, RHPN2, SNORD31, TMED9 ERBB3, SLC37A1, IDH1, CACNAID, FBPI, BAIAP2L1, SCARNA16, TMEM87A, RPL29, GFPT1, FLJ39632, SC2, GLOI, SELIL, SNORA5A, TARP, POTEE, SCARNA22, SNORA14B, PTPRN2, SNORDIC, DDT, CYB561, TSPAN13, MLLT4, CASZ1, SNORA37, SNORD82, ZKSCAN1, SCARNA8, GNB2L1 HIPK2 ABHD2 MAOA, SNORD4A, SNORA4I, CD9, SEZ6L2, FLJ39632, SNORD15A, C6orfl32, DOPEY2, WWC1, TSPAN8, SERPI, RPL36A, SNORA23, POTEF, GNL3, RPL12, HSP90B1, SNORD116-29, IRF6, DSG2, SNORA48, ESRP2, SNORD24, SNORA60, TMSB15A, SNORD35A, ENTPD6, SCD, SNORD116-1, NORD53, TRIB1, MGST2, SNORD115-33, RPS2, SNORA28, MBOAT2, CNDP2, EEF1G, LPCAT3, ACSL1, SNORA7B, and SNORD115-38.

-continued

| epitheliail Benign-stromal benign | | | | epithelial PIN-stromal PIN | | | | epithelial tumor-stromal tumor | | | |
|---|---|---|---|---|---|---|---|---|---|---|---|
| Affymetrix ID | Gene | LogFC | Adj. P.Val | Affymetrix ID | Gene | LogFC | Adj. P.Val | Affymetrix ID | Gene | LogFC | Adj. P.Val |

FC negative in epithelial tumor-stromal tumor samples: PNMA1, DPT, HLA-A, SH3PXD2B, MBNLI, JAK1, AHNAK, GSTM5, ADAMTS4, MRC2, PDGFC, ITIH5, 11-Sep, CXCL12, PPPIR3C, CFD, POPDC2, TNXA, SRF, ALDH2, DUSPI, IER3, RASLI2, TSPYL2, LGALS3BP, MT1A, TENC1, RGS1,SGK269, FRMD6 CNN3, PLEKHOI, CAV2, SH3D19, ITGA8, CALM 1, MIR23A, SNAI2, HEGI, IL7R, PLS3, APOD, EPB41L2, GREMI, CES1, TGFB2, CACNAIC, CST3 STAB I RCAN2 ZCCHC24, LMNA, PAMR1, ERPINHI, DAB2, FSTLI, PPPIR12B, CNTNI, F13A1, FXYD5, LOC652493, TMEM47, CSF1R, CD8I, CD53', DST, JAM3, RRAS, CX3CL1, MBNL2, IGHV4-59, ZNF185, CCL3, TNXB, CBX7, LTBP2, C7orf58, PTGDS, GSTM4, PLXDC2, CDI4, WIPFI, ARHGEFI7, VTRNAI-3, IGKC, FCERIG, HCST, NFIA, MMPI4, GSTM2, RAB31, FAIM2, EMIL1NI, FXYDI, PDLIM1, PDGFRA, OLFML3, RERG, PAM, DMD ITGBI, NR4A3, TCF4, THBS4, TPSAB1, ZFP36LI, FAM86B1, LOC100130876, ZFP36, SPON1,ACTCI, SPAN18, 1GHA1, STS, FBX032, GBP 1, IFITM1 ITM2C DNAJB5, ANXA2, PELO, USP17L6P, MRVII,CCL4LI, FCGR2C, LIF, LPAR1, WDRI, INMT, TPSAB 1, SPOCK3, RBMS3, IL6ST, MARVELD1 PHLDBI, C4A, CSPG4, GLIPR1, DPYSL2, TGFB1, ANO6, CFL2, FZD7, RBPMS2, GPNMB, 1GHM, TGFB3, GEM, PCDHI8, FNBPI, MIR143, KIAA1210, EHD2, BOC, MOXDI, IGF2, LTBP3, MEG3, TCF7LI, NCRNA00152, PBX1, PARM1, SDC3, RGS2, LM04, PLN, AQP1, GYPC, SELM, NCS1, IGKVI-5 C3 AP2 ER3, COL15A1, MRGPRF, LAMB2, ATP1A2, RGS5,1SLR, JAZF1, TGFBI, TACC1,, HLA-DPB1, IGKC, CD248, HEYL, MSRB3, TPM1 WFDCI C5orf13, SH3BGRL, SLC8A1, CD52, CXCR4, CTSK, LYZ, TGFBI II, FGFR1, EMP3, FXYD6, PPP1R12A, PPP1R14A, ADCY5, ALDH1A I, BHLHE40 PFKFB3 CCL5 ZEB2, ENG, PDK4, ADAMTS1, SFRP1, MYOCD, FOSL2,CD68, PTN, THBS2, HLA-DPB1, FOSB, C10rf54, ALDHIBI, HLA- DQA1 TCF2I SMOCI, SCARNAI7, SIOOA4, MCAM, RARRES2, IGLJ3, EF2C, AHNAK2, NCRNA00I52, SLC2A3, VTRNAI-I, LOC388022, RBMS1, CNN2'KCNMAI, SPTBN1, MAOB, THY I, SFRP2, PARVA, RHOB, PCDHIO, ARHGEF25,1TGA7, OGN, PRRX1, DKK3, EPHA3, JUNB, CI5orf5l, GJA1, BTG2, TCEAL2, C11 orf96, MEIS,, CLIC4, M1R27A, CYP1B1, RND3, FOS, FBN1, MATN2, GAS6, LAMA4, PRNP, GPR124, PPAP2B, PDGFRB, EGRI, FILIPiL C12orf75 C15orf5l, EYAI, C1QB, SFRP4, HLA-DPB1, EPASI, PALLD, DSTN, DDR2, FERMT2, EFEMP2, S100A6, LTBP1, COLCE, PLP2, 1GKCKCNMBI, TES, TMSL3, TMSB4X, ACTB, WWTRI, MEIS I, ILK, CTSB, HLA-DRB3, PMP22, IGF I, TNC, COLI4AI, DPYSL3, FABP3, GSTPI, PLTP, TMSB4X EDNRA, 1D3, TMSB4X, LAPTM5, POSTN, SOCS3, ACTA2, MYL6, CYBRD1, IGJ, C1QA, SMTN, COL4A1, PTGIS, SULFI, LDHB, LRP1, NIDI, ANXA6 PDLIM3, HLA-DRB3, LTBP4, SRGN, CRISPLD2, SERPINEI, COL6A1, TLNI, CORO 1C, ZYX, FBLN5, CCND2, STOM, TIMP3, RNASEI, CDC42EP3, LPP, IGHD, PODN, OL4A2, CAV1, HLA-DRB4, TUBA 1 A, HSPBI, VCL, COL6A2, HSPG2, IGFBP4, SNORD113-4, IFITM3, MT2A, CDH11, MFGE8 ACTNI, TPM1, HLA-DRA, NR2F1, SVIL, EFEMP1, IFITM2, DDR2, KANK2, HLA-DRA, HSPB6, COL3AI,NEXN, PTRF, HLA-DRA, SCARNA17, C1QC PDE5A, C7, CHRDL1, HLA-DPA1, ITGA5, MY ADM, ANTXR1, PDLIM7, HLA-DPAI, HLA-DPAI, LUM, SERPINFI, CYR61, SNORD 114-3, MSN, CCDC80, CD74, MAP IB, MMP2, GSN, IGFBP7, PGM5P2, CCL2, PRELP, FAP4, 1R, CLU, VIM, BGN, FLNC, HSPB8, T1MP1, COL I AI, ATP2B4, PGM5P2, CTGF, FBLNI, RBPMS, AEBP1, LGALSI, SYNM, CIS, FHL1, IGFBP5, AOC3, TIMP3,COL6A3, SERPING1, COLIA2, THBS1, PGM5, A2M, CRYAB, MIRI45, SPARC, FNI, TIMP2, SORBS1, DCN, LMODI, SYNP02, PCP4, CSRP1, MYLK, TNS1, PTCH2, CALDI, CDRI, SPARCLI, TPM2, MGP, DES, MYL9, CNN1, FLNA, TAGLN, MYH11, ACTA2, and ACTG2.

Figure 2A:
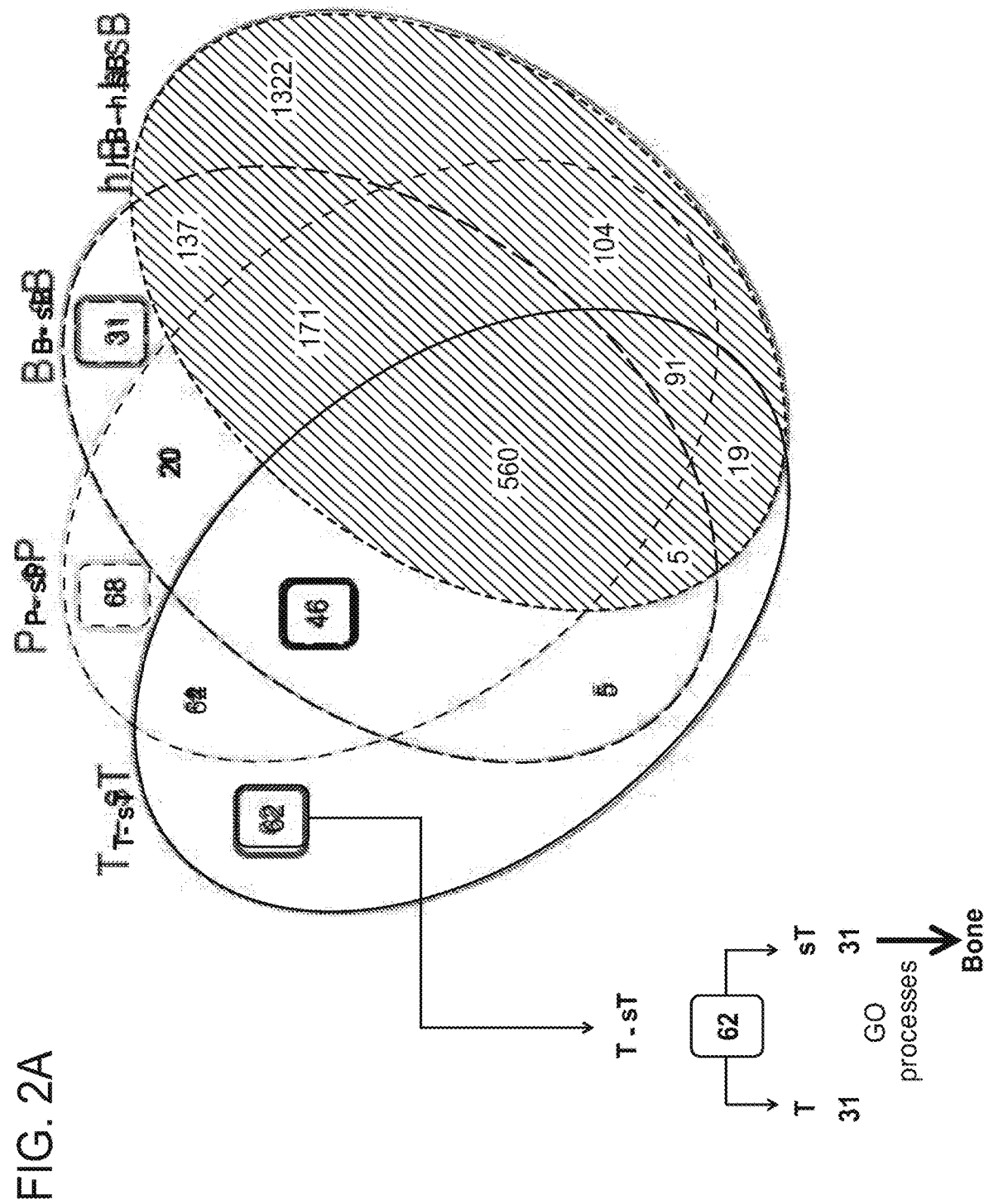
FIG. 2A is a four-set Venn diagram showing the relation of differentially expressed genes between the epithelial-stromal compartment for the 4 comparisons T-sT, P-sP, B-sB and HB-HsB. The gray shaded area represents all differently expressed genes that were found in the HB-HsB. T: Tumor; s: Stroma; P: PIN; B: benign

This was expanded across compartment analysis to include the cystoprostatectomy H-HsB comparison, the results of which are represented by Venn diagram in FIG. 2A. Enrichment ontology analysis of the genes was differentially expressed in all four epithelial-stromal comparisons is provided in Table 9 showing the most statistically significant pathways, networks and GO processes. Pathways and network processes coalesced around cell adhesion, cytoskeleton remodeling, epithelial-to-mesenchymal transition (EMT), with TGFβ and/or Wnt signaling in relation to cytoskeletal remodeling and/or EMT induction featured in the top enriched pathway maps. GO processes involved multicellular development and extracellular organization. Table 9. Enrichment analysis uusing the GeneGo database, to determine pathways, networks and cellular processes, for the genes found to be differentially expressed in the B-sB, P-sP, T-sB and HB-HsB epithelial-stromal comparisons, where H indicates healthy.

TABLE 9

Enrichment analysis using the GeneGo database, lo determine pathways, networks and cellular processes, for Ihe genes found to be differentially expressed in the B-sB. P-sP. T-sB and HB-HsB cpilhclial-slromal comparisons, where H indicalcs hcallhv.

| # | Maps Enrichment analysis report Enrichment by Pathway Maps | Total | pValue | Min FDR | p-value | FDR | In Data | all.4.commonGeneGo_genelist Network Objects from Active Data |
|---|---|---|---|---|---|---|---|---|
| 1 | Cell adhesion_ECM remodeling | 52 | 1.626E-16 | 8.812E-14 | 1.626E-16 | 8.812E-14 | 18 | IBP4, TIMP2, IGF-1, MSN (moesin), Fibronectin, Kallikrein 1, Nidogen, Osteonectin, alpha-5/beta-1 integrin, LAMA4, IGF-2, Kallikrein 2, TIMP3, Collagen I, MMP-2, Kallikrein 3 (PSA), Collagen III, Collagen IV |
| 2 | Cell adhesion_Integrin-mediated cell adhesion and migration | 48 | 7.405E-16 | 2.007E-13 | 7.405E-16 | 2.007E-13 | 17 | Talin, MLCP (reg), MELC, Vinculin, Fibronectin, MyHC, MYLK1, alpha-5/beta-1 integrin, Actin cytoskeletal, Alpha-actinin, Zyxin, MLCK, MRLC, Collagen I, Cofilin, alpha-7/beta-1 integrin, Collagen IV |

TABLE 9-continued

Enrichment analysis using the GeneGo database, to determine pathways, networks and cellular processes, for the genes found to be differentially expressed in the B-sB. P-sP. T-sB and HB-HsB epithelial-stromal comparisons, where H indicates healthy.

| 3 | Cytoskeleton remodeling_Cytoskeleton remodeling | 102 | 4.689E−15 | 8.472E−13 | 4.689E−15 | 8.472E−13 | 22 | Talin, MLCP (reg), MELC, Vinculin, C1 inhibitor, Fibronectin, MyHC, MYLK1, Tcf(Lef), Actin cytoskeletal, Alpha-actinin, Zyxin, Destrin, Filamin A, MLCK, ILK, MRLC, Collagen I, Cofilin, Alpha-actinin 1, Caveolin-1, Collagen IV |
|---|---|---|---|---|---|---|---|---|
| 4 | Cell adhesion_Chemokines and adhesion | 100 | 3.560E−14 | 4.824E−12 | 3.560E−14 | 4.824E−12 | 21 | Talin, Caveolin-2, Vinculin, alpha-8/beta-1 integrin, Thrombospondin 1, MSN (moesin), Fibronectin, Tcf(Lef), Actin cytoskeletal, Actin, Alpha-actinin, LAMA4, Zyxin, Filamin A, ILK, Collagen I, Cofilin, Alpha-actinin 1, MMP-2, Caveolin-1, Collagen IV |
| 5 | Development_Regulation of epithelial-to-mesenchymal transition (EMT) | 64 | 1.684E−13 | 1.826E−11 | 1.684E−13 | 1.826E−11 | 17 | E-cadherin, TGF-beta 2, HGF receptor (Met), Fibronectin, Caldesmon, ACTA2, Vimentin, Tropomyosin-1, SRF, Frizzled, EDNRA, FGFR1, ACTB, PDGF-R-alpha, SIP1 (ZFHX1B), PDGF-R-beta, MMP-2 |
| 6 | Cytoskeleton remodeling_TGF, WNT and cytoskeletal remodeling | 111 | 3.097E−12 | 2.797E−10 | 3.097E−12 | 2.797E−10 | 20 | Talin, MLCP (reg), MELC, Vinculin, C1 inhibitor, Fibronectin, MYLK1, Tcf(Lef), Actin cytoskeletal, Actin, Alpha-actinin, |

TABLE 9-continued

Enrichment analysis using the GeneGo database, to determine pathways, networks and cellular processes, for the genes found to be differentially expressed in the B-sB, P-sP, T-sB and HB-HsB epithelial-stromal comparisons, where H indicates healthy.

| | | | | | | | | |
|---|---|---|---|---|---|---|---|---|
| 7 | Cell adhesion_Histamine H1 receptor signaling in the interruption of cell barrier integrity | 45 | 4.023E−11 | 3.115E−09 | 4.023E−11 | 3.115E−09 | 13 | Destrin, MLCK, ILK, MRLC, Frizzled, Cofilin, Alpha-actinin 1, Caveolin-1, Collagen IV Talin, MLCP (reg), MELC, Vinculin, E-cadherin, Myosin II, GEFT, Actin cytoskeletal, Alpha-actinin, MLCK, MRLC, CPI-17, Cofilin |
| 8 | Development_TGF-beta-dependent induction of EMT via RhoA, PI3K and ILK. | 46 | 5.485E−11 | 3.716E−09 | 5.485E−11 | 3.716E−09 | 13 | Hic-5/ARA55, E-cadherin, TGF-beta 2, Fibronectin, Caldesmon, ACTA2, Vimentin, Actin, Tropomyosin-1, SRF, ILK, ACTB, Cofilin |
| 9 | Cytoskeleton remodeling_Regulation of actin cytoskeleton by Rho GTPases | 23 | 7.026E−11 | 4.231E−09 | 7.026E−11 | 4.231E−09 | 10 | MLCP (reg), MELC, Myosin II, MyHC, Actin cytoskeletal, Actin, Filamin A, MLCK, MRLC, Cofilin |
| 10 | Cytoskeleton remodeling_Integrin outside-in signaling | 49 | 1.324E−10 | 7.175E−09 | 1.324E−10 | 7.175E−09 | 13 | Talin, Vinculin, alpha-8/beta-1 integrin, Fibronectin, Tcf(Lef), alpha-5/beta-1 integrin, Actin cytoskeletal, Alpha-parvin, Alpha-actinin, Filamin A, ILK, Collagen I, Collagen IV |

| | | | | | all.4.commonGeneGo_genelist | | | |
|---|---|---|---|---|---|---|---|---|
| # | Networks | Total | pValue | Min FDR | p-value | FDR | In Data | Network Objects from Active Data |
| | Enrichment by Process Networks | | | | | | | |
| 1 | Cell adhesion_Integrin-mediated cell-matrix adhesion | 214 | 1.043E−24 | 1.503E−22 | 1.043E−24 | 1.503E−22 | 52 | Tubulin alpha 1A, Tensin, OSF-2, Talin, Hic-5/ARA55, Caveolin-2, Galectin-1, MELC, Vinculin, alpha-8/beta-1 integrin, |

TABLE 9-continued

Enrichment analysis using the GeneGo database, lo determine pathways, networks and cellular processes, for Ihe genes found to be differentially expressed in the B-sB. P-sP. T-sB and HB-HsB cpilhclial-slromal comparisons, where H indicalcs hcallhv.

| # | Pathway | Count | p-val | p-val | p-val | p-val | N | Genes |
|---|---|---|---|---|---|---|---|---|
| | | | | | | | | Collagen XIV, Fibrillin 1, ITGA5, MSN (moesin), Fibronectin, Tenascin-C, ITGB1, RhoB, ERM proteins, Kindlin-2, Osteonectin, MyHC, Tcf(Lef), alpha-5/beta-1 integrin, Filamin B (TABP), Actin cytoskeletal, Alpha-parvin, Actin, Alpha-actinin, LAMA4, Zyxin, Tubulin alpha, Filamin A, MLCK, ILK, MRLC, ITGA8, Collagen I, ACTB, Cofilin, Filamin C, Cyr61, Alpha-actinin 1, alpha-7/beta-1 integrin, CD9, RhoE, Caveolin-1, Tetraspanin-8, Collagen III, Collagen IV, ITGA7, Decorin |
| 2 | Cytoskeleton_Actin filaments | 176 | 1.004E−19 | 7.232E−18 | 1.004E−19 | 7.232E−18 | 42 | MYH11, Dystrophin, Tensin, Talin, MELC, Transgelin, Annexin VI, Vinculin, Thymosin beta-4, Myosin II, SPTBN(spectrin1-4), MSN (moesin), ERM proteins, ACTC, Kindlin-2, SVIL, MyHC, MYLK1, Filamin B (TABP), Actin cytoskeletal, Actin, Tropomyosin-1, Alpha-actinin, BPAG1, Beta-fodrin, Calponin-1, Gelsolin, Zyxin, Destrin, SDF-1, Filamin A, MLCK, MRLC, ACTB, Cofilin, Filamin C, Actin muscle, SPTBN2, Tropomyosin, WaspIP, Tropomyosin-2, Alpha-actinin 1 |
| 3 | Development_Skeletal muscle development | 144 | 7.613E−17 | 3.654E−15 | 7.613E−17 | 3.654E−15 | 35 | Alpha crystallin B, MYH11, Dystrophin, Smooth muscle myosin, L-type Ca(II) channel, alpha 1C subunit, MELC, |

TABLE 9-continued

Enrichment analysis using the GeneGo database, to determine pathways, networks and cellular processes, for the genes found to be differentially expressed in the B-sB. P-sP. T-sB and HB-HsB epithelial-stromal comparisons, where H indicates heallhy.

| | | | | | | | |
|---|---|---|---|---|---|---|---|
| 4 | Cell adhesion_Cell-matrix interactions | 211 | 7.496E−16 | 2.699E−14 | 7.496E−16 | 2.699E−14 | 41 |
| 5 | Cytoskeleton_Regulation of cytoskeleton rearrangement | 183 | 3.362E−14 | 9.684E−13 | 3.362E−14 | 9.684E−13 | 36 |

Row 4 genes: Transgelin, Desmin, IGF-1, HGF receptor (Met), CRP3 (MLP), Myosin II, ITGB1, Caldesmon, ACTA2, SVIL, MyHC, Smoothelin, Filamin B (TABP), Actin, Tropomyosin-1, SRF, MEF2, MAP-1B, MRLC, MYRL2, Filamin C, Actin muscle, Tropomyosin, MEF2C, Tropomyosin-2, ACTG2, alpha-7/beta-1 integrin, Collagen IV, ITGA7 COL1A1, Fibulin-3, TIMP2, Galectin-1, alpha-8/beta-1 integrin, Collagen XIV, Thrombospondin 1, Biglycan, Fibrillin 1, ITGA5, Fibulin-5, Lumican, Fibronectin, Tenascin-C, BETA-IG-H3, ITGB1, Nidogen, Collagen VI, alpha-5/beta-1 integrin, Fibrillin, COL4A2, SPOCK, LAMA4, COL6A1, COL4A1, Fibulin-1, BCAM, COL1A2, ITGA8, CSPG4 (NG2), EMILIN-1, TIMP3, Collagen I, Connexin 43, MFAP4, MMP-2, alpha-7/beta-1 integrin, Perlecan, Collagen III, Collagen IV, Decorin Row 5 genes: Tubulin alpha 1A, Talin, MELC, Vinculin, Thymosin beta-4, Desmin, Myosin II, SPTBN(spectrin1-4), MSN (moesin), ERM proteins, ACTC, Vimentin, SVIL, MyHC, Filamin B (TABP), Actin cytoskeletal, Actin, Alpha-actinin, BPAG1, Beta-fodrin, Calponin-1, Gelsolin, TABLE 9-continued Enrichment analysis using the GeneGo database, to determine pathways, networks and cellular processes, for the genes found to be differentially expressed in the B-sB, P-sP, T-sB and HB-HsB epithelial-stromal comparisons, where H indicates healthy.

| | | | | | | | | |
|---|---|---|---|---|---|---|---|---|
| 6 | Muscle contraction | 173 | 1.878E−13 | 4.506E−12 | 1.878E−13 | 4.506E−12 | 34 | Zyxin, Destrin, Tubulin alpha, SDF-1, Filamin A, MLCK, MRLC, ACTB, Cofilin, Filamin C, Actin muscle, SPTBN2, WaspIP, Alpha-actinin 1 Alpha crystallin B, MYH11, Dystrophin, Smooth muscle myosin, MLCP (reg), MELC, Annexin VI, Phospholamban, Desmin, Thrombospondin 1, Myosin II, Caldesmon, ACTA2, ACTC, MyHC, Smoothelin, alpha-5/beta-1 integrin, MaxiK alpha subunit, Troponin C, cardiac, Actin, Tropomyosin-1, Alpha-actinin, NCX1, Calponin-1, Phospholemman, SRF, Galpha(q)-specific peptide GPCRs, MLCK, MRLC, EDNRA, MYRL2, Connexin 43, Actin muscle, Tropomyosin |
| 7 | Development_EMT_Regulation of epithelial-to-mesenchymal transition | 225 | 2.114E−11 | 4.348E−10 | 2.114E−11 | 4.348E−10 | 36 | PDGF receptor, Hic-5/ARA55, Desmin, E-cadherin, TGF-beta 2, HGF receptor (Met), Fibronectin, Keratin 8, ITGB1, Caldesmon, ACTA2, EGR1, Vimentin, Keratin 18, TGF-beta, Actin, Tropomyosin-1, AP-1, IGF-2, SRF, MTS1 (S100A4), COL1A2, ILK, Frizzled, EDNRA, FGFR1, Collagen I, ACTB, Cofilin, CTGF, PDGF-R-alpha, SIP1 (ZFHX1B), PDGF-R-beta, MMP-2, Collagen III, Desmoplakin |
| 8 | Proteolysis_ECM remodeling | 85 | 7.609E−10 | 1.370E−08 | 7.609E−10 | 1.370E−08 | 20 | TIMP2, Collagen XIV, Lumican, Fibronectin, Tenascin-C, Nidogen, Osteonectin, SPOCK, SPOCK3, |

TABLE 9-continued

Enrichment analysis using the GeneGo database, to determine pathways, networks and cellular processes, for the genes found to be differentially expressed in the B-sB. P-sP. T-sB and HB-HsB epilhclial-slromal comparisons, where H indicates hcallhv.

| # | | Total | pValue | Min FDR | | | | |
|---|---|---|---|---|---|---|---|---|
| | | | | | | | | Kallikrein 4, A2M receptor, Kallikrein 2, TIMP3, Collagen I, CTGF, MMP-2, Kallikrein 3 (PSA), Clusterin, Collagen III, Collagen IV |
| 9 | Cell adhesion_Platelet-endothelium-leucocyte interactions | 174 | 6.401E−08 | 1.024E−06 | 6.401E−08 | 1.024E−06 | 26 | CCL5, PDGF receptor, Plasma kallikrein, Endoglin, Thrombospondin 1, TGF-beta 2, HGF receptor (Met), C1 inhibitor, Fibronectin, ITGB1, IGFBP7, TGF-beta, DDR2, gp130, ILK, A2M receptor, Collagen I, CTGF, PDGF-R-alpha, PDGF-R-beta, Cyr61, MMP-2, CD9, Collagen III, Collagen IV, IGFBP7/8 |
| 10 | Proteolysis_Connective tissue degradation | 119 | 3.225E−07 | 4.644E−06 | 3.225E−07 | 4.644E−06 | 20 | TIMP2, Lumican, Fibronectin, Kallikrein 1, Tenascin-C, Nidogen, SPOCK, Matriptase, SPOCK3, Kallikrein 4, DPP4, Tissue kallikreins, A2M receptor, Kallikrein 2, TIMP3, Collagen I, MMP-2, Kallikrein 3 (PSA), Collagen III, Collagen IV |

| | | | | all.4.commonGeneGo_genelist | | | |
|---|---|---|---|---|---|---|---|
| # | Processes | Total | pValue | Min FDR | p-value | FDR | In Data | Network Objects from Active Data |
| | Enrichment by GO Processes | | | | | | | |
| 1 | tissue development | 2280 | 2.223E−51 | 1.353E−47 | 2.223E−51 | 1.353E−47 | 185 | ESE3, COL1A1, HSP47, MYH11, Dystrophin, PDGF receptor, IRF6, Smooth muscle myosin, JunB, ARG2, ATP2C1, OSF-2, IBP5, Hic-5/ARA55, Caveolin-2, Homer, CDH1, MELC, Transgelin, Endoglin, Vinculin, CD24, APOD, MYL6, Willin, Palladin, alpha-8/beta-1 integrin, Phospholamban, |

TABLE 9-continued

Enrichment analysis using the GeneGo database, to determine pathways, networks and cellular processes, for the genes found to be differentially expressed in the B-sB, P-sP, T-sB and HB-HsB epithelial-stromal comparisons, where H indicates healthy.

|  |  |  |  | microRNA 143, Collagen XIV, IGF-1, PDE, Decorin proteoglycan, Thrombospondin 1, E-cadherin, TGF-beta 2, ITGA5, COUP-TF, HGF receptor (Met), CRP3 (MLP), TCF21, HIPK2, Myosin II, MSN (moesin), Lumican, CACNA1 L-type, POPDC2, Fibronectin, Tenascin-C, BETA-IG-H3, Ephrin-A receptor 3, ITGB1, COUP-TFII, ACTA2, EGR1, ERM proteins, ACTC, Ep-CAM, RNP24, Collagen VI, HOXB13, Rab-25, HNF3-alpha, Vimentin, AF-6, HEYL, CBFB/MYH11 fusion protein, SVIL, Claudin-3, Nelin, MyHC, MYLK1, Tcf(Lef), MGP, SFRP2, MLPH, alpha-5/beta-1 integrin, TGF-beta, Filamin B (TABP), Actin cytoskeletal, DDR2, FZD7, MaxiK alpha subunit, CES1, XBP1, TCF7L1 (TCF3), COL4A2, Troponin C, cardiac, TAZ, Thy-1, Actin, IFITM3, Tropomyosin-1, AP-1, Ephrin-A receptors, NK31, Myocardin, DBI, NCX1, PEDF (serpinF1), PTGIS, Pleiotrophin (OSF1), HEG1, COL6A1, Gelsolin, EYA1, MYADM, Fatty acid-binding protein, COL4A1, Matriptase, PDEF, SULF1, |

TABLE 9-continued

Enrichment analysis using the GeneGo database, to determine pathways, networks and cellular processes, for the genes found to be differentially expressed in the B-sB. P-sP. T-sB and HB-HsB epithelial-stromal comparisons, where H indicates heallhy.

| | | | | | | | | |
|---|---|---|---|---|---|---|---|---|
| | | | | | | | | MEG3, MAP7(EMAP115), Telokin, SRF, BMPR1B, Galpha(q)-specific peptide GPCRs, DHC24, EDNRB, SDF-1, Prostasin, MEF2, XK, MTS1 (S100A4), HNF3, IBP, Gas6, ATF/CREB, Filamin A, MLCK, DSPP, ILK, MRLC, Tissue kallikreins, ITGA8, BTG2, Kallikrein 2, Frizzled, EDNRA, NKCC1, TIMP3, FGFR1, FosB/JunB, Collagen I, ACTB, Cofilin, Connexin 43, Aquaporin 1, Actin muscle, Phox1 (PRRX1), CLIC4, CTGF, Serglycin, Galpha(i)-specific EDG GPCRs, Tropomyosin, PDGF-R-alpha, SIP1 (ZFHX1B), MEF2C, AL1A1, PDGF-R-beta, Cyr61, PDLIM3, SelM, FA2H, Cyclin D, PMCA4, ANO6, microRNA 145, GRHL2, MMP-2, alpha-7/beta-1 integrin, LMO4, Perlecan, Kallikrein 3 (PSA), Caveolin-1, NF-1, Collagen III, Collagen IV, ITGA7, ErbB3, IGFBP7/8, TACSTD2 (TROP2), Desmoplakin, Decorin |
| 2 | system development | | 5451 | 7.601E−51 | 2.312E−47 | 7.601E−51 | 2.312E−47 | 297 | NPY, MHC class II alpha chain, COL1A1, IBP4, CCL5, HSP47, Alpha crystallin B, AEBP1, |

TABLE 9-continued

Enrichment analysis using the GeneGo database, to determine pathways, networks and cellular processes, for the genes found to be differentially expressed in the B-sB. P-sP. T-sB and HB-HsB epithelial-stromal comparisons, where H indicates heallhv.

MYH11, Dystrophin, PDGF receptor, IRF6, Smooth muscle myosin, JunB, Cyclin D2, LPA1 receptor, C1qb, ARG2, ATP2C1, Plasma kallikrein, OSF-2, IBP5, L-type Ca(II) channel, alpha 1C subunit. MFGE8, Talin, MHC class II beta chain, R-Ras, Cofilin, muscle, DCOR, Prolargin, TIMP2, Caveolin-2, Homer, CDH1, Galectin-1, MELC, Transgelin, EPAS1, Endoglin, Vinculin, CD24, APOD, MYL6, PEP-19, PTPRF (LAR), Palladin, alpha-8/beta-1 integrin, Phospholamban, microRNA 143, Collagen XIV, CNTN1 (F3), Desmin, WDR1, IGF-1, PDE, Decorin proteoglycan, Thrombospondin 1, E-cadherin, ZnT4, DKK3, TGF-beta 2, COL6A2, Fibrillin 1, ITGA5, COUP-TF, Geminin, SEZ6L2, HGF receptor (Met), TEM5, CRP3 (MLP), TCF21, HIPK2, Myosin II, C1q, SPTBN(spectrin1-4), Lumican, CACNA1 L-type, POPDC2, Carboxypeptidase H, Fibronectin, Keratin 8, Tenascin-C, BETA-IG-H3, Ephrin-A receptor 3, ITGB1, COUP-TFII, RhoB, TABLE 9-continued Enrichment analysis using the GeneGo database, to determine pathways, networks and cellular processes, for the genes found to be differentially expressed in the B-sB. P-sP. T-sB and HB-HsB epithelial-stromal comparisons, where H indicates healthy.

ACTA2, EGR1, ERM proteins, ACTC, Ep-CAM, Nidogen, RNP24, Collagen VI, HOXB13, HNF3-alpha, Rab-3, Vimentin, Osteonectin, HEYL, NCS-1, CBFB/MYH11 fusion protein, SVIL, IDH1, Dynamin-1, Nelin, MyHC, MYLK1, TACC1, Tcf(Lef), MGP, Smoothelin, Tensin 2, IGFBP7, SFRP2, alpha-5/beta-1 integrin, TGF-beta, Filamin B (TABP), Actin cytoskeletal, Rbm47, DDR2, Fibrillin, FZD7, MaxiK alpha subunit, Chordin-like 1, Matrilin-2, Alpha-parvin, CAP2, XBP1, BOC, TCF7L1 (TCF3), COL4A2, Troponin C, cardiac, gp130, TAZ, MHC class II, MCAM, Thy-1, Actin, IFITM3, FNBP1, Tropomyosin-1, Galpha(q)-specific EDG GPCRs, SPOCK, P311, PDE5A, AP-1, LAMA4, Ephrin-A receptors, NK31, Myocardin, DBI, BPAG1, FAIM2, NCX1, PEDF (serpinF1), CRMP2, PTGIS, Pleiotrophin (OSF1), HEG1, Beta-fodrin, IGF-2, COL6A1, Talin-1, IFITM2, Gelsolin, EYA1, Fatty acid-binding protein, TABLE 9-continued Enrichment analysis using the GeneGo database, to determine pathways, networks and cellular processes, for the genes found to be differentially expressed in the B-sB, P-sP, T-sB and HB-HsB epithelial-stromal comparisons, where H indicates healthy.

COL4A1, MEIS1, Matriptase, D52, CRP1, COUP-TFI, Adenylate cyclase, Phospholemman, PDEF, SULF1, NFIA, LPP3, MEG3, MAP7(EMAP115), 15), Kallikrein 4, Telokin, SRF, BMPR1B, FHL1 (SLIM1), Glyoxalase 1, Galpha(q)-specific peptide GPCRs, C1s, PIP5KIII, COL6A3, DHC24, EDNRB, PBR, MAOB, SDF-1, CD248, Prostasin, Adenylate cyclase type V, MEF2, XK, MTS1 (S100A4), HNF3, IBP, Gas6, ATF/CREB, Filamin A, COL1A2, MLCK, DSPP, MAP-1B, Acyl-CoA synthetase, SERINC5, ILK, C1, MRLC, Tissue kallikreins, A2M receptor, ITGA8, ZCCHC24, CD74, BTG2, Kallikrein 2, Frizzled, PRNP, COL15A1, CSPG4 (NG2), EDNRA, PMP22, NKCC1, TIMP3, ACSL3, FGFR1, FosB/JunB, Collagen I, ACTB, MYRL2, Cofilin, Keratin 8/18, Connexin 43, Aquaporin 1, Actin muscle, Phox1 (PRRX1), CLIC4, Calcyclin, Phosphatase regulator (inhibitor), CTGF, Serglycin, TABLE 9-continued Enrichment analysis using the GeneGo database, to determine pathways, networks and cellular processes, for the genes found to be differentially expressed in the B-sB. P-sP. T-sB and HB-HsB epithelial-stromal comparisons, where H indicates healthy.

| | | | | | | | | |
|---|---|---|---|---|---|---|---|---|
| | | | | | | | | SPTBN2, BCAT2, Galpha(i)-specific EDG GPCRs, Tropomyosin, PDGF-R-alpha, PPAP2, SMOC1, Bl-1, CRMP4, SIP1 (ZFHX1B), MEF2C, AL1A1, PDGF-R-beta, Cyr61, PDLIM3, SelM, IP10, FA2H, HSPC117, Cyclin D, Cadherin 11, PMCA4, ANO6, microRNA 145, GRHL2, MMP-2, alpha-7/beta-1 integrin, LMO4, CD9, TIG2, Perlecan, Protocadherin 18, Kallikrein 3 (PSA), MAO, Caveolin-1, NF-I, Clusterin, Collagen III, Collagen IV, ITGA7, A26C1A, ErbB3, IGFBP7/8, TACSTD2 (TROP2), Desmoplakin, Dynamin, Decorin |
| 3 | single-organism developmental process | 6923 | 5.373E−48 | 1.090E−44 | 5.373E−48 | 1.090E−44 | 335 | NPY, MHC class II alpha chain, ESE3, COL1A1, IBP4, CCL5, HSP47, Alpha crystallin B, Leiomodin, AEBP1, ATR/TEM8, MYH11, Dystrophin, PDGF receptor, IRF6, Smooth muscle myosin, JunB, Cyclin D2, LPA1 receptor, PCOLCE, C1qb, ARG2, RGS2, ATP2C1, Plasma kallikrein, OSF-2, IBP5, L-type Ca(II) channel, alpha 1C subunit, MFGE8, AMD1, Talin, MHC |

TABLE 9-continued

Enrichment analysis using the GeneGo database, to determine pathways, networks and cellular processes, for the genes found to be differentially expressed in the B-sB, P-sP, T-sB and HB-HsB epithelial-stromal comparisons, where H indicates healthy.

class II beta chain, R-Ras, Cofilin, muscle, DCOR, Hic-5/ARA55, Prolargin, ENIGMA, TIMP2, Caveolin-2, Homer, CDH1, Galectin-1, MELC, Transgelin, EPAS1, Endoglin, Vinculin, CD24, APOD, MYL6, Willin, PEP-19, PTPRF (LAR), Palladin, alpha-8/beta-1 integrin, Phospholamban, microRNA 143, Collagen XIV, CNTN1 (F3), Desmin, WDR1, IGF-1, PDE, Decorin proteoglycan, Thrombospondin 1, E-cadherin, ZnT4, DKK3, hnRNP C, TGF-beta 2, SCD, COL6A2, Fibrillin 1, ITGA5, COUP-TF, Geminin, SEZ6L2, HGF receptor (Met), TEM5, CRP3 (MLP), TCF21, HIPK2, Myosin II, C1q, SPTBN(spectrin1-4), STEAP4, MSN (moesin), C1 inhibitor, FASN, Lumican, CACNA1 L-type, POPDC2, Carboxpeptidase, H, Fibronectin, A2M, PDF, Keratin 8, Tenascin-C, BETA-IG-H3, Ephrin-A receptor 3, CASZ1, ITGB1, COUP-TFII, RhoB, ACTA2, EGR1, ERM proteins, ACTC, ENDO180, Ep-CAM, Nidogen, RNP24, Collagen VI, TABLE 9-continued Enrichment analysis using the GeneGo database, to determine pathways, networks and cellular processes, for the genes found to be differentially expressed in the B-sB. P-sP. T-sB and HB-HsB epithelial-stromal comparisons, where H indicates heallhv.

HOXB13, Rab-25, HNF3-alpha, Kindlin-2, Rab-3, Vimentin, Osteonectin, AF-6, HEYL, NCS-1, CBFB/MYH11 fusion protein, SVIL, Claudin-3, IDH1, Dynamin-1, Nelin, MyHC, MYLK1, TACC1, Tcf(Lef), MGP, Smoothelin, Tensin 2, IGFBP7, SFRP2, MLPH, alpha-5/beta-1 integrin, TGF-beta, Filamin B (TABP), Actin cytoskeletal, Rbm47, DDR2, Fibrillin, FZD7, MaxiK alpha subunit, Chordin-like 1, TMSB4X, Matrilin-2, Alpha-parvin, CES1, CAP2, XBP1, BOC, DOPEY2, TCF7L1 (TCF3), COL4A2, Troponin C, cardiac, gp130, TAZ, MHC class II, MCAM, Thy-1, Actin, IFITM3, FNBP1, Tropomyosin-1, CREB4, Galpha(q)-specific EDG GPCRs, SPOCK, P311, SGK269, PDE5A, AP-1, LAMA4, Ephrin-A receptors, NK31, Myocardin, DBI, BPAG1, FAIM2, NCX1, PEDF (serpinF1), CRMP2, PTGIS, Pleiotrophin (OSF1), HEG1, Beta-fodrin, IGF-2, COL6A1, Talin-1, IFITM2, Gelsolin, EYA1, MYADM, Fatty acid-binding TABLE 9-continued Enrichment analysis using the GeneGo database, to determine pathways, networks and cellular processes, for the genes found to be differentially expressed in the B-sB, P-sP, T-sB and HB-HsB epithelial-stromal comparisons, where H indicates healthy.

protein, COL4A1, MEIS1, Matriptase, Fibulin-1, D52, CRP1, LTBP4, COUP-TFI, Adenylate cyclase, Phospholemman, PDEF, SULF1, NFIA, LPP3, MEG3, MAP7(EMAP115), 15), Kallikrein 4, Telokin, SRF, BMPR1B, FHL1 (SLIM1), Glyoxalase 1, Galpha(q)-specific peptide GPCRs, C1s, PIP5KIII, COL6A3, DHC24, EDNRB, PBR, MAOB, SDF-1, CD248, Prostasin, Adenylate cyclase type V, MEF2, XK, MTS1 (S100A4), HNF3, IBP, Gas6, ATF/CREB, Filamin A, COL1A2, TMPRSS2/ERG fusion protein, MLCK, DSPP, MAP-1B, Acyl-CoA synthetase, SERINC5, ILK, C1, MRLC, Tissue kallikreins, OLFML3, A2M receptor, ITGA8, ZCCHC24, CD74, BTG2, Kallikrein 2, Frizzled, PRNP, COL15A1, CSPG4 (NG2), EDNRA, PMP22, NKCC1, TIMP3, ACSL3, FGFR1, FosB/JunB, Collagen I, ACTB, MYRL2, AP-1 mu subunits, Cofilin, Keratin 8/18, Filamin C, Connexin 43, PLA2R1, Aquaporin 1, Actin muscle, TABLE 9-continued Enrichment analysis using the GeneGo database, to determine pathways, networks and cellular processes, for the genes found to be differentially expressed in the B-sB. P-sP. T-sB and HB-HsB epithelial-stromal comparisons, where H indicates healthy.

| | | | | | | | | |
|---|---|---|---|---|---|---|---|---|
| | | | | | | | | Phox1 (PRRX1), CLIC4, Calcyclin, Phosphatase regulator (inhibitor), CTGF, Serglycin, SPTBN2, BCAT2, Galpha(i)-specific EDG GPCRs, Tropomyosin, PDGF-R-alpha, PPAP2, SMOC1, BI-1, CRMP4, SIP1 (ZFHX1B), MEF2C, AL1A1, PDGF-R-beta, Cyr61, PDLIM3, SelM, IP10, FA2H, HSPC117, Cyclin D, Cadherin 11, PMCA4, ANO6, microRNA 145, GRHL2, MMP-2, alpha-7/beta-1 integrin. LMO4, CD9, TIG2, Perlecan, Protocadherin 18, Kallikrein 3 (PSA), MAO, Caveolin-1, NF-I, Clusterin, Collagen III, Collagen IV, ITGA7, A26C1A, ErbB3, IGFBP7/8, TACSTD2 (TROP2), Desmoplakin, AOC3, Dynamin, Decorin |
| 4 | anatomical structure development | 6236 | 9.599E-48 | 1.329E-44 | 9.599E-48 | 1.329E-44 | 315 | NPY, MHC class II alpha chain, ESE3, COL1A1, IBP4, CCL5, HSP47, Alpha crystallin B, Leiomodin, AEBP1, ATR/TEM8, MYH11, Dystrophin, PDGF receptor, IRF6, Smooth muscle myosin, JunB, Cyclin D2, LPA1 receptor, C1qb, ARG2, |

TABLE 9-continued

Enrichment analysis using the GeneGo database, to determine pathways, networks and cellular processes, for the genes found to be differentially expressed in the B-sB. P-sP. T-sB and HB-HsB epithelial-stromal comparisons, where H indicates healthy.

ATP2C1, Plasma kallikrein, OSF-2, IBP5, L-type Ca(II) channel, alpha 1C subunit, MFGE8, AMD1, Talin, MHC class II beta chain, R-Ras, Cofilin, muscle, DCOR, Hic-5/ARA55, Prolargin, TIMP2, Caveolin-2, Homer, CDH1, Galectin-1, MELC, Transgelin, EPAS1, Endoglin, Vinculin, CD24, APOD, MYL6, Willin, PEP-19, PTPRF (LAR), Palladin, alpha-8/beta-1 integrin, Phospholamban, microRNA 143, Collagen XIV, CNTN1 (F3), Desmin, WDR1, IGF-1, PDE, Decorin proteoglycan, Thrombospondin 1, E-cadherin, ZnT4, DKK3, TGF-beta 2, COL6A2, Fibrillin 1, ITGA5, COUP-TF, Geminin, SEZ6L2, HGF receptor (Met), TEM5, CRP3 (MLP), TCF21, HIPK2, Myosin II, C1q, SPTBN(spectrin1-4), MSN (moesin), Lumican, CACNA1 L-type, POPDC2, Carboxpeptidase, H, Fibronectin, PDF, Keratin 8, Tenascin-C, BETA-IG-H3, Ephrin-A receptor 3, ITGB1, COUP-TFII, RhoB, ACTA2, EGR1, ERM proteins, ACTC, Ep-CAM, Nidogen, RNP24, TABLE 9-continued Enrichment analysis using the GeneGo database, to determine pathways, networks and cellular processes, for the genes found to be differentially expressed in the B-sB. P-sP. T-sB and HB-HsB epithelial-stromal comparisons, where H indicates healthy.

Collagen VI, HOXB13, Rab-25, HNF3-alpha, Kindlin-2, Rab-3, Vimentin, Osteonectin, AF-6, HEYL, NCS-1, CBFB/MYH11 fusion protein, SVIL, Claudin-3, IDH1, Dynamin-1, Nelin, MyHC, MYLK1, TACC1, Tcf(Lef), Keratin 18, MGP, Smoothelin, Tensin 2, IGFBP7, SFRP2, MLPH, alpha-5/beta-1 integrin, TGF-beta, Filamin B (TABP), Actin cytoskeletal, Rbm47, DDR2, Fibrillin, FZD7, MaxiK alpha subunit, Chordin-like 1, Matrilin-2, Alpha-parvin, CES1, CAP2, XBP1, BOC, TCF7L1 (TCF3), COL4A2, Troponin C, cardiac, gp130, TAZ, MHC class II, MCAM, Thy-1, Actin, IFITM3, FNBP1, Tropomyosin-1, Galpha(q)-specific EDG GPCRs, SPOCK, P311, SGK269, PDE5A, AP-1, LAMA4, Ephrin-A receptors, NK31, Myocardin, DBI, BPAG1, FAIM2, NCX1, PEDF (serpinF1), CRMP2, PTGIS, Pleiotrophin (OSF1), HEG1, Beta-fodrin, IGF-2, COL6A1, Talin-1, IFITM2, Gelsolin, EYA1, MYADM, Fatty acid-binding TABLE 9-continued Enrichment analysis using the GeneGo database, to determine pathways, networks and cellular processes, for the genes found to be differentially expressed in the B-sB. P-sP. T-sB and HB-HsB epithelial-stromal comparisons, where H indicates healthy.

protein, COL4A1, MEIS1, Matriptase, D52, CRP1, COUP-TFI, Adenylate cyclase, Phospholemman, PDEF, SULF1, NFIA, LPP3, MEG3, MAP7(EMAP115), Kallikrein 4, Telokin, SRF, BMPR1B, FHL1 (SLIM1), Glyoxalase 1, Galpha(q)-specific peptide GPCRs, C1s, PIP5KIII, COL6A3, DHC24, EDNRB, PBR, MAOB, SDF-1, CD248, Prostasin, Adenylate cyclase type V, MEF2, XK, MTS1 (S100A4), HNF3, IBP, Gas6, ATF/CREB, Filamin A, COL1A2, MLCK, DSPP, MAP-1B, Acyl-CoA synthetase, SERINC5, ILK, C1, MRLC, Tissue kallikreins, A2M receptor, ITGA8, ZCCHC24, CD74, BTG2, Kallikrein 2, Frizzled, PRNP, COL15A1, CSPG4 (NG2), EDNRA, PMP22, NKCC1, TIMP3, ACSL3, FGFR1, FosB/JunB, Collagen I, ACTB, MYRL2, Cofilin, Keratin 8/18, Filamin C, Connexin 43, Aquaporin 1, Actin muscle, Phox1 (PRRX1), CLIC4, Calcyclin, Phosphatase regulator (inhibitor), TABLE 9-continued Enrichment analysis using the GeneGo database, to determine pathways, networks and cellular processes, for the genes found to be differentially expressed in the B-sB. P-sP. T-sB and HB-HsB epithelial-stromal comparisons, where H indicates healthy.

| | | | | | | | | |
|---|---|---|---|---|---|---|---|---|
| | | | | | | | | CTGF, Serglycin, SPTBN2, BCAT2, Galpha(i)-specific EDG GPCRs, Tropomyosin, PDGF-R-alpha, PPAP2, SMOC1, BI-1, CRMP4, SIP1 (ZFHX1B), MEF2C, AL1A1, PDGF-R-beta, Cyr61, PDLIM3, SelM, IPI0, FA2H, HSPC117, Cyclin D, Cadherin 11, PMCA4, ANO6, microRNA 145, GRHL2, MMP-2, alpha-7/beta-1 integrin, LMO4, CD9, TIG2, Perlecan, Protocadherin 18, Kallikrein 3 (PSA), MAO, Caveolin-1, NF-I, Clusterin, Collagen III, Collagen IV, ITGA7, A26C1A, ErbB3, IGFBP7/8, TACSTD2 (TROP2), Desmoplakin, Dynamin, Decorin |
| 5 | developmental process | 6979 | 1.093E−47 | 1.329E−44 | 1.093E−47 | 1.329E−44 | 336 | NPY, MHC class II alpha chain, ESE3, COL1A1, IBP4, CCL5, HSP47, Alpha crystallin B, Leiomodin, AEBP1, ATR/TEM8, MYH11, Dystrophin, PDGF receptor, IRF6, Smooth muscle myosin, JunB, Cyclin D2, LPA1 receptor, PCOLCE, C1qb, ARG2, RGS2, ATP2C1, Plasma kallikrein, OSF-2, IBP5, L-type Ca(II) channel, alpha 1C subunit, MFGE8, AMD1, Talin, MHC class II beta chain, R-Ras, Cofilin, |

TABLE 9-continued

Enrichment analysis using the GeneGo database, to determine pathways, networks and cellular processes, for the genes found to be differentially expressed in the B-sB. P-sP. T-sB and HB-HsB epithelial-stromal comparisons, where H indicates healthy.

muscle, DCOR, Hic-5/ARA55, Prolargin, ENIGMA, TIMP2, Caveolin-2, Homer, CDH1, Galectin-1, MELC, Transgelin, EPAS1, Endoglin, Vinculin, CD24, APOD, MYL6, Willin, PEP-19, PTPRF (LAR), Palladin, alpha-8/beta-1 integrin, Phospholamban, microRNA 143, Collagen XIV, CNTN1 (F3), Desmin, WDR1, IGF-1, PDE, Decorin proteoglycan, Thrombospondin 1, E-cadherin, ZnT4, DKK3, hnRNP C, TGF-beta 2, SCD, COL6A2, Fibrillin 1, ITGA5, COUP-TF, Geminin, SEZ6L2, HGF receptor (Met), TEM5, CRP3 (MLP), TCF21, HIPK2, Myosin II, C1q, SPTBN(spectrin1-4), STEAP4, MSN (moesin), C1 inhibitor, FASN, Lumican, CACNA1 L-type, POPDC2, Carboxpeptidase, H, Fibronectin, A2M, PDF, Keratin 8, Tenascin-C, BETA-IG-H3, Ephrin-A receptor 3, CASZ1, ITGB1, COUP-TFII, RhoB, ACTA2, EGR1, ERM proteins, ACTC, ENDO180, Ep-CAM, Nidogen, RNP24, Collagen VI, HOXB13, Rab-25, HNF3-alpha, Kindlin- TABLE 9-continued Enrichment analysis using the GeneGo database, to determine pathways, networks and cellular processes, for the genes found to be differentially expressed in the B-sB, P-sP, T-sB and HB-HsB epithelial-stromal comparisons, where H indicates healthy.

2, Rab-3, Vimentin, Osteonectin, AF-6, HEYL, NCS-1, CBFB/MYH11 fusion protein, SVIL, Claudin-3, IDH1, Dynamin-1, Nelin, MyHC, MYLK1, TACC1, Tcf(Lef), Keratin 18, MGP, Smoothelin, Tensin 2, IGFBP7, SFRP2, MLPH, alpha-5/beta-1 integrin, TGF-beta, Filamin B (TABP), Actin cytoskeletal, Rbm47, DDR2, Fibrillin, FZD7, MaxiK alpha subunit, Chordin-like 1, TMSB4X, Matrilin-2, Alpha-parvin, CES1, CAP2, XBP1, BOC, DOPEY2, TCF7L1 (TCF3), COL4A2, Troponin C, cardiac, gp130, TAZ, MHC class II, MCAM, Thy-1, Actin, IFITM3, FNBP1, Tropomyosin-1, CREB4, Galpha(q)-specific EDG GPCRs, SPOCK, P311, SGK269, PDE5A, AP-1, LAMA4, Ephrin-A receptors, NK31, Myocardin, DBI, BPAG1, FAIM2, NCX1, PEDF (serpinF1), CRMP2, PTGIS, Pleiotrophin (OSF1), HEG1, Beta-fodrin, IGF-2, COL6A1, Talin-1, IFITM2, Gelsolin, EYA1, MYADM, Fatty acid-binding protein, TABLE 9-continued Enrichment analysis using the GeneGo database, to determine pathways, networks and cellular processes, for the genes found to be differentially expressed in the B-sB, P-sP, T-sB and HB-HsB epithelial-stromal comparisons, where H indicates healthy.

COL4A1, MEIS1, Matriptase, Fibulin-1, D52, CRP1, LTBP4, COUP-TFI, Adenylate cyclase, Phospholemman, PDEF, SULF1, NFIA, LPP3, MEG3, MAP7(EMAP115), Kallikrein 4, Telokin, SRF, BMPR1B, FHL1 (SLIM1), Glyoxalase 1, Galpha(q)-specific peptide GPCRs, C1s, PIP5KIII, COL6A3, DHC24, EDNRB, PBR, MAOB, SDF-1, CD248, Prostasin, Adenylate cyclase type V, MEF2, XK, MTS1 (S100A4), HNF3, IBP, Gas6, ATF/CREB, Filamin A, COL1A2, TMPRSS2/ERG fusion protein, MLCK, DSPP, MAP-1B, Acyl-CoA synthetase, SERINC5, ILK, C1, MRLC, Tissue kallikreins, OLFML3, A2M receptor, ITGA8, ZCCHC24, CD74, BTG2, Kallikrein 2, Frizzled, PRNP, COL15A1, CSPG4 (NG2), EDNRA, PMP22, NKCC1, TIMP3, ACSL3, FGFR1, FosB/JunB, Collagen I, ACTB, MYRL2, AP-1 mu subunits, Cofilin, Keratin 8/18, Filamin C, Connexin 43, PLA2R1, Aquaporin 1, Actin muscle, Phox1

TABLE 9-continued

Enrichment analysis using the GeneGo database, to determine pathways, networks and cellular processes, for the genes found to be differentially expressed in the B-sB. P-sP. T-sB and HB-HsB epithelial-stromal comparisons, where H indicates healthy.

| | | | | | | | | |
|---|---|---|---|---|---|---|---|---|
| 6 | extracellular matrix organization | 489 | 4.383E−46 | 4.444E−43 | 4.383E−46 | 4.444E−43 | 84 | (PRRX1), CLIC4, Calcyclin, Phosphatase regulator (inhibitor), CTGF, Serglycin, SPTBN2, BCAT2, Galpha(i)-specific EDG GPCRs, Tropomyosin, PDGF-R-alpha, PPAP2, SMOC1, BI-1, CRMP4, SIP1 (ZFHX1B), MEF2C, AL1A1, PDGF-R-beta, Cyr61, PDLIM3, SelM, IP10, FA2H, HSPC117, Cyclin D, Cadherin 11, PMCA4, ANO6, microRNA 145, GRHL2, MMP-2, alpha-7/beta-1 integrin, LMO4, CD9, TIG2, Perlecan, Protocadherin 18, Kallikrein 3 (PSA), MAO, Caveolin-1, NF-I, Clusterin, Collagen III, Collagen IV, ITGA7, A26C1A, ErbB3, IGFBP7/8, TACSTD2 (TROP2), Desmoplakin, AOC3, Dynamin, Decorin Tryptase, COL1A1, HSP47, MYH11, Dystrophin, PDGF receptor, Fibulin-3, Smooth muscle myosin, Plasma kallikrein. OSF-2, TIMP2, Endoglin, P4HB, alpha-8/beta-1 integrin, Collagen XIV, Decorin proteoglycan, Thrombospondin |

TABLE 9-continued

Enrichment analysis using the GeneGo database, to determine pathways, networks and cellular processes, for the genes found to be differentially expressed in the B-sB. P-sP. T-sB and HB-HsB epithelial-stromal comparisons, where H indicates healthy.

| | | | | | | | | |
|---|---|---|---|---|---|---|---|---|
| | | | | | | | | 1, E-cadherin, Biglycan, TGF-beta 2, COL6A2, Fibrillin 1, ITGA5, Myosin II, Fibulin-5, Lumican, Fibronectin, A2M, Tenascin-C, BETA-IG-H3, ITGB1, Nidogen, Collagen VI, Beta-tryptase 1, Osteonectin, CBFB/MYH11 fusion protein, LTBP1, MyHC, SFRP2, alpha-S/beta-1 integrin, TGF-beta, DDR2, Fibrillin, COL4A2, CCDC80, Alpha-actinin, LAMA4, BPAG1, Biglycan proteoglycan, COL6A1, COL4A1, Fibulin-1, LTBP4, SULF1, Cathepsin K, Kallikrein 4, COL6A3, Gas6, COL1A2, DSPP, ILK, Tissue kallikreins, ITGA8, EFEMP2, Kallikrein 2, COL15A1, EMILIN-1, Collagen I, CTGF, MFAP4, PDGF-R-alpha, SMOC1, Cyr61, Alpha-actinin 1, MMP-2, alpha-7/beta-1 integrin, Perlecan, Collagen III, Collagen IV, ITGA7, Syndecan-3, IGFBP7/8, Beta-tryptase 2, Decorin |
| 7 | extracellular structure organization | 490 | 5.178E−46 | 4.500E−43 | 5.178E−46 | 4.500E−43 | 84 | Tryptase, COL1A1, HSP47, MYH11, Dystrophin, PDGF |

TABLE 9-continued

Enrichment analysis using the GeneGo database, to determine pathways, networks and cellular processes, for the genes found to be differentially expressed in the B-sB, P-sP, T-sB and HB-HsB epithelial-stromal comparisons, where H indicates heallhy.

receptor, Fibulin-3, Smooth muscle myosin, Plasma kallikrein, OSF-2, TIMP2, Endoglin, P4HB, alpha-8/beta-1 integrin, Collagen XIV, Decorin proteoglycan, Thrombospondin 1, E-cadherin, Biglycan, TGF-beta 2, COL6A2, Fibrillin 1, ITGA5, Myosin II, Fibulin-5, Lumican, Fibronectin, A2M, Tenascin-C, BETA-IG-H3, ITGB1, Nidogen, Collagen VI, Beta-tryptase 1, Osteonectin, CBFB/MYH11 fusion protein, LTBP1, MyHC, SFRP2, alpha-5/beta-1 integrin, TGF-beta, DDR2, Fibrillin, COL4A2, CCDC80, Alpha-actinin, LAMA4, BPAG1, Biglycan proteoglycan, COL6A1, COL4A1, Fibulin-1, LTBP4, SULF1, Cathepsin K, Kallikrein 4, COL6A3, Gas6, COL1A2, DSPP, ILK, Tissue kallikreins, ITGA8, EFEMP2, Kallikrein 2, COL15A1, EMILIN-1, Collagen I, CTGF, MFAP4, PDGF-R-alpha, SMOC1, Cyr61, Alpha-actinin 1, MMP-2, alpha-7/beta-1 integrin, Perlecan, Collagen III, Collagen IV, TABLE 9-continued Enrichment analysis using the GeneGo database, to determine pathways, networks and cellular processes, for the genes found to be differentially expressed in the B-sB, P-sP, T-sB and HB-HsB epithelial-stromal comparisons, where H indicates healthy.

| | | | | | | | |
|---|---|---|---|---|---|---|---|
| 8 | multicellular organismal development | 6179 | 2.289E−45 | 1.741E−42 | 2.289E−45 | 1.741E−42 | 309 | ITGA7, Syndecan-3, IGFBP7/8, Beta-tryptase 2, Decorin NPY, MHC class II alpha chain, ESE3, COL1A1, IBP4, CCL5, HSP47, Alpha crystallin B, AEBP1, MYH11, Dystrophin, PDGF receptor, IRF6, Smooth muscle myosin, JunB, Cyclin D2, LPA1 receptor, PCOLCE, C1qb, ARG2, ATP2C1, Plasma kallikrein, OSF-2, IBP5, L-type Ca(II) channel, alpha 1C subunit, MFGE8, AMD1, Talin, MHC class II beta chain, R-Ras, Cofilin, muscle, DCOR, Hic-5/ARA55, Prolargin, ENIGMA, TIMP2, Caveolin-2, Homer, CDH1, Galectin-1, MELC, Transgelin, EPAS1, Endoglin, Vinculin, CD24, APOD, MYL6, PEP-19, PTPRF (LAR), alpha-8/beta-1 integrin, Phospholamban, microRNA 143, Collagen XIV, CNTN1 (F3), Desmin, WDR1, IGF-1, PDE, Decorin proteoglycan, Thrombospondin 1, E-cadherin, ZnT4, DKK3, TGF-beta 2, COL6A2, Fibrillin 1, |

TABLE 9-continued

Enrichment analysis using the GeneGo database, to determine pathways, networks and cellular processes, for the genes found to be differentially expressed in the B-sB. P-sP. T-sB and HB-HsB epithelial-stromal comparisons, where H indicates heallhv.

ITGA5, COUP-TF, Geminin, SEZ6L2, HGF receptor (Met), TEM5, CRP3 (MLP), TCF21, HIPK2, Myosin II, C1q, SPTBN(spectrin1-4), Lumican, CACNA1 L-type, POPDC2, Carboxpeptidase H, Fibronectin, Keratin 8, Tenascin-C, BETA-IG-H3, Ephrin-A receptor 3, CASZ1, ITGB1, COUP-TFII, RhoB, ACTA2, EGR1, ERM proteins, ACTC, Ep-CAM, Nidogen, RNP24, Collagen VI, HOXB13, HNF3-alpha, Rab-3, Vimentin, Osteonectin, HEYL, NCS-1, CBFB/MYH11 fusion protein, SVIL, IDH1, Dynamin-1, Nelin, MyHC, MYLK1, TACC1, Tcf(Lef), MGP, Smoothelin, Tensin 2, IGFBP7, SFRP2, alpha-5/beta-1 integrin, TGF-beta, Filamin B (TABP), Actin cytoskeletal, Rbm47, DDR2, Fibrillin, FZD7, MaxiK alpha subunit, Chordin-like 1, Matrilin-2, Alpha-parvin, CAP2, XBP1, BOC, DOPEY2, TCF7L1 (TCF3), COL4A2, Troponin C, cardiac, gp130, TAZ, MHC class II, MCAM, Thy-1, Actin, IFITM3, FNBP1, Tropomyosin-1, CREB4, TABLE 9-continued Enrichment analysis using the GeneGo database, lo determine pathways, networks and cellular processes, for Ihe genes found to be differentially expressed in the B-sB. P-sP. T-sB and HB-HsB cpilhclial-slromal comparisons, where H indicalcs hcallhv.

Galpha(q)-specific EDG GPCRs, SPOCK, P311, PDE5A, AP-1, LAMA4, Ephrin-A receptors, NK31, Myocardin, DBI, BPAG1, FAIM2, NCX1, PEDF (serpinF1), CRMP2, PTGIS, Pleiotrophin (OSF1), HEG1, Beta-fodrin, IGF-2, COL6A1, Talin-1, IFITM2, Gelsolin, EYA1, Fatty acid-binding protein, COL4A1, MEIS1, Matriptase, Fibulin-1, D52, CRP1, LTBP4, COUP-TFI, Adenylate cyclase, Phospholemman, PDEF, SULF1, NFIA, LPP3, MEG3, MAP7(EMAP115), Kallikrein 4, Telokin, SRF, BMPR1B, FHL1 (SLIM1), Glyoxalase 1, Galpha(q)-specific peptide GPCRs, C1s, PIP5KIII, COL6A3, DHC24, EDNRB, PBR, MAOB, SDF-1, CD248, Prostasin, Adenylate cyclase type V, MEF2, XK, MTS1 (S100A4), HNF3, IBP, Gas6, ATF/CREB, Filamin A, COL1A2, TMPRSS2/ERG fusion protein, MLCK, DSPP, MAP-1B, Acyl-CoA synthetase, SERINC5, ILK, Cl, MRLC, Tissue kallikreins, OLFML3, A2M receptor, ITGA8, TABLE 9-continued Enrichment analysis using the GeneGo database, to determine pathways, networks and cellular processes, for the genes found to be differentially expressed in the B-sB, P-sP, T-sB and HB-HsB epithelial-stromal comparisons, where H indicates healthy.

ZCCHC24, CD74, BTG2, Kallikrein 2, Frizzled, PRNP, COL15A1, CSPG4 (NG2), EDNRA, PMP22, NKCC1, TIMP3, ACSL3 FGFR1, FosB/JunB, Collagen I, ACTB, MYRL2, Cofilin, Keratin 8/18, Connexin 43, Aquaporin 1, Actin muscle, Phox1 (PRRX1), CLIC4, Calcyclin, Phosphatase regulator (inhibitor), CTGF, Serglycin, SPTBN2, BCAT2, Galpha(i)-specific EDG GPCRs, Tropomyosin, PDGF-R-alpha, PPAP2, SMOC1, BI-1, CRMP4, SIP1 (ZFHX1B), MEF2C, AL1A1, PDGF-R-beta, Cyr61, PDLIM3, SelM, IP10, FA2H, HSPC117, Cyclin D, Cadherin 11, PMCA4, ANO6, microRNA 145, GRHL2, MMP-2, alpha-7/beta-1 integrin, LMO4, CD9, TIG2, Perlecan, Protocadherin 18, Kallikrein 3 (PSA), MAO, Caveolin-1, NF-I, Clusterin, Collagen III, Collagen IV, ITGA7, A26C1A, ErbB3, IGFBP7/8, TACSTD2 (TROP2), Desmoplakin, Dynamin, Decorin TABLE 9-continued Enrichment analysis using the GeneGo database, to determine pathways, networks and cellular processes, for the genes found to be differentially expressed in the B-sB, P-sP, T-sB and HB-HsB epithelial-stromal comparisons, where H indicates healthy.

| 9 | anatomical structure morphogenesis | 2888 | 1.101E−44 | 7.440E−42 | 1.101E−44 | 7.440E−42 | 199 | COL1A1, HSP47, Alpha crystallin B, Leiomodin, ATR/TEM8, MYH11, Dystrophin, PDGF receptor, Smooth muscle myosin, JunB, IBP5, L-type Ca(II) channel, alpha 1C subunit, MFGE8, Talin, R-Ras, Cofilin, muscle, Hic-5/ARA55, MELC, EPAS1, Endoglin, Vinculin, CD24, APOD, MYL6, Willin, Palladin, alpha-8/beta-1 integrin, microRNA 143, CNTN1 (F3), IGF-1, PDE, Decorin proteoglycan, Thrombospondin 1, E-cadherin, DKK3, TGF-beta 2, COL6A2, ITGA5, COUP-TF, Geminin, HGF receptor (Met),TEM5, CRP3 (MLP), TCF21, HIPK2, Myosin II, SPTBN(spectrin l-4), CACNA1 L-type, Carboxpeptidase H, Fibronectin, Keratin 8, Tenascin-C, BETA-IG-H3, Ephrin-A receptor 3, ITGB1, COUP-TFII, RhoB, ERM proteins, ACTC, RNP24, Collagen VI, HOXB13, Rab-25, HNF3-alpha, Kindlin-2, Rab-3, HEYL, CBFB/MYH11 fusion protein, Claudin-3, Dynamin-1, MyHC, MYLK1, Tcf(Lef), Keratin 18, MGP, SFRP2, |

TABLE 9-continued

Enrichment analysis using the GeneGo database, lo determine pathways, networks and cellular processes, for Ihe genes found to be differentially expressed in the B-sB. P-sP. T-sB and HB-HsB cpilhclial-slromal comparisons, where H indicalcs hcallhv.

alpha-5/beta-1 integrin, TGF-beta, Filamin B (TABP), Actin cytoskeletal, DDR2, Fibrillin, FZD7, Matrilin-2, Alpha-parvin, CAP2, XBP1, BOC, TCF7L1 (TCF3), COL4A2, Troponin C, cardiac, TAZ, MCAM, Thy-1, Actin, Tropomyosin-1, Galpha(q)-specific EDG GPCRs, SGK269, AP-1, Ephrin-A receptors, NK31, Myocardin, BPAG1, FAIM2, NCX1, CRMP2, HEG1, Beta-fodrin, IGF-2, COL6A1, Talin-1, Gelsolin, EYA1, COL4A1, MEIS1, D52, Adenylate cyclase, SULF1, LPP3, MAP7(EMAP115, 15), Kallikrein 4, Telokin, SRF, BMPR1B, FHL1 (SLIM1), Galpha(q)-specific peptide GPCRs, PIP5KIII, COL6A3, SDF-1, CD248, MEF2, MTS1 (S100A4), HNF3, IBP, ATF/CREB, Filamin A, COL1A2, MLCK, DSPP, MAP-1B, ILK, MRLC, Tissue kallikreins, A2M receptor, ITGA8, Kallikrein 2, Frizzled, PRNP, COL15A1, CSPG4 (NG2), EDNRA, PMP22, NKCC1, FGFR1, FosB/JunB, Collagen I, ACTB, MYRL2, Cofilin, TABLE 9-continued Enrichment analysis using the GeneGo database, to determine pathways, networks and cellular processes, for the genes found to be differentially expressed in the B-sB, P-sP, T-sB and HB-HsB epithelial-stromal comparisons, where H indicates healthy.

| | | | | | | | | |
|---|---|---|---|---|---|---|---|---|
| | | | | | | | | Keratin 8/18, Connexin 43, Aquaporin 1, Actin muscle, Phox1 (PRRX1), CLIC4, Calcyclin, CTGF, SPTBN2, Galpha(i)-specific EDG GPCRs, Tropomyosin, PDGF-R-alpha, PPAP2, CRMP4, SIP1 (ZFHX1B), MEF2C, AL1A1, PDGF-R-beta, Cyr61, Cadherin 11, microRNA 145, GRHL2, MMP-2, alpha-7/beta-1 integrin, LMO4, CD9, Perlecan, Kallikrein 3 (PSA), Caveolin-1, NF-I, Clusterin, Collagen III, Collagen IV, ITGA7, ErbB3, IGFBP7/8, TACSTD2 (TROP2), Desmoplakin, Dynamin, Decorin |
| 10 | muscle structure development | 705 | 8.901E−43 | 5.415E−40 | 8.901E−43 | 5.415E−40 | 95 | Alpha crystallin B, Leiomodin, AEBP1, MYH11, Dystrophin, PDGF receptor, Smooth muscle myosin, IBP5, Cofilin, muscle, Caveolin-2, Homer, Galectin-1, MELC, Transgelin, EPAS1, MYL6, alpha-8/beta-1 integrin, microRNA 143, Desmin, IGF-1, Decorin proteoglycan, TGF-beta 2, COUP-TF, HGF receptor (Met), CRP3 (MLP), TCF21, Myosin II, CACNA1 L- |

TABLE 9-continued

Figure 2B:
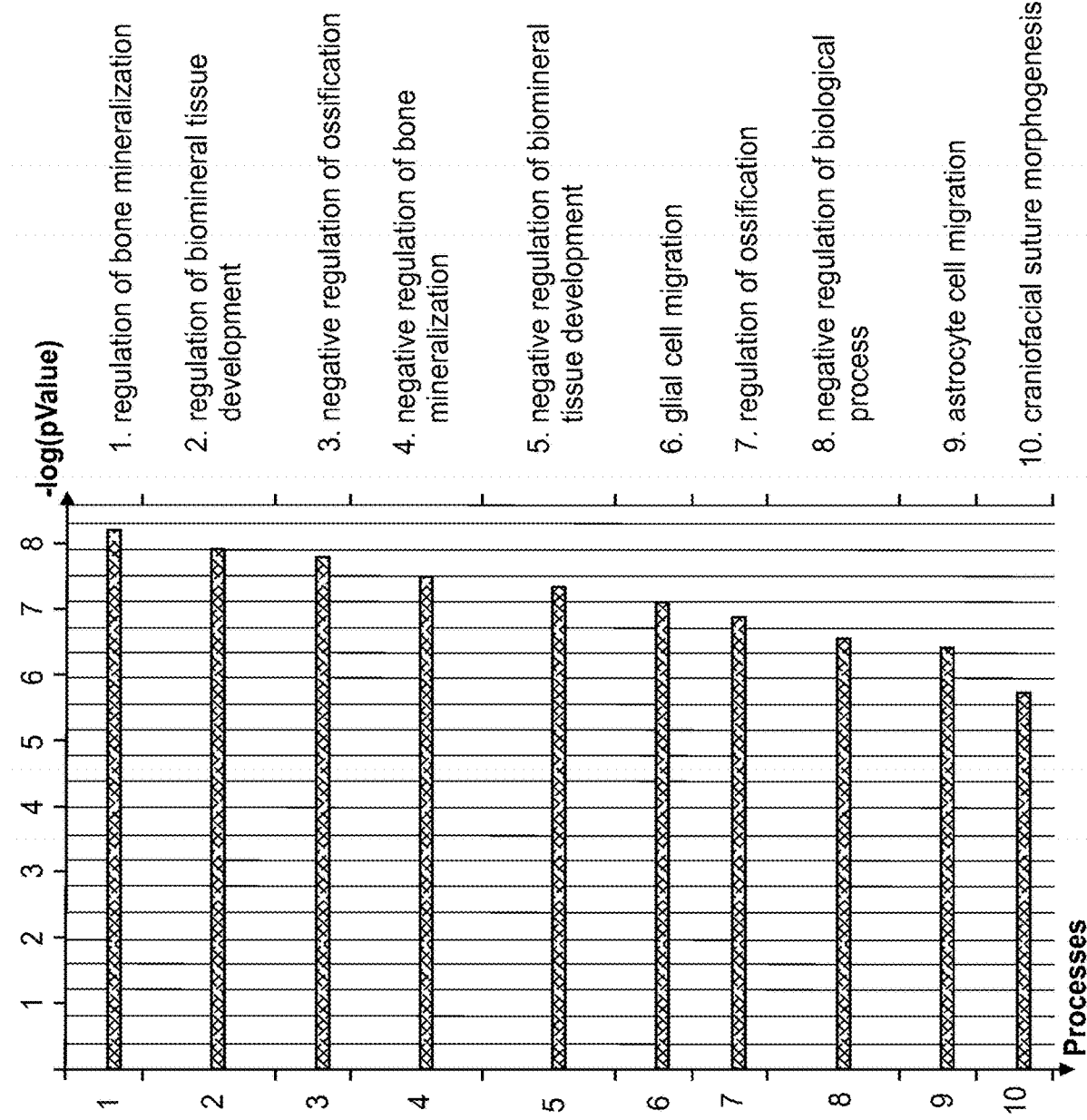
FIG. 2B is a plot showing the GeneGO enrichment analysis of the stromal genes exclusive to the T-sT comparison (31/62 were upregulated in the stroma). The plotted log(p-value) of the statistically significant GO cellular processes is shown.

Enrichment analysis using the GeneGo database, to determine pathways, networks and cellular processes, for the genes found to be differentially expressed in the B-sB. P-sP. T-sB and HB-HsB epithelial-stromal comparisons, where H indicates healthy.

type, POPDC2, Keratin 8, ITGB1, COUP-TFII, EGR1, ACTC, Collagen VI, HEYL, CBFB/MYH11 fusion protein, SVIL, Nelin, MyHC, MYLK1, Tcf(Lef), Smoothelin, alpha-5/beta-1 integrin, TGF-beta, Filamin B (TABP), Actin cytoskeletal, BOC, Troponin C, cardiac, Actin, IFITM3, Tropomyosin-1, AP-1, Myocardin, NCX1, HEG1, IGF-2, MEG3, Telokin, SRF, FHL1 (SLIM1), Galpha(q)-specific peptide GPCRs, COL6A3, EDNRB, MEF2, XK, IBP, ATF/CREB, MLCK, MRLC, Tissue kallikreins, ITGA8, BTG2, Kallikrein 2, Frizzled, Cofilin, Keratin 8/18, Filamin C, Actin muscle, Galpha(i)-specific EDG GPCRs, Tropomyosin, PDGF-R-alpha, MEF2C, PDGF-R-beta, PDLIM3, IP10, microRNA 145, alpha-7/beta-1 integrin, Kallikrein 3 (PSA), Caveolin-1, Collagen III, ITGA7, ErbB3, Desmoplakin, Decorin By filtering out the cystoprostatectomy associated differentially expressed genes between the healthy benign and its adjacent stroma (represented as the shaded HB-HsB area on the Venn diagram), genes that were exclusively associated with prostate malignancy were evaluated. 46 genes were identified as differentially expressed in the B-sB, P-sP and T-sT comparisons, exclusive of HB-HsB. Only 4 genes, FOHL1 (PSMA), FBXO25, CLDN7 and AGR2, were upregulated, indicating that stromal associated expression is prevalent and influential on prostate carcinogenesis. These stromal expressing genes, such as IL-2RB, CCL2 and CXCR4, LIF, HLA-DPA1 were predominantly associated with inflammation and the immune response (Table 10). 62 genes were exclusively differentially expressed in the T-sT comparison (blue box in Venn diagram, FIG. 2A), of which 31 were upregulated in the stromal compartment. Enrichment ontology analysis of the genes was found to be differentially expressed in the stroma is provided in Table 11, showing the most statistically significant pathways, networks and GO processes. Immunological and TGFβ related EMT pathways, inflammatory; cell adhesion and cell cycle process networks were featured. GO processes were dominated by ossification, bone mineralization, and biomineral development. This result indicated the stromal environment adjacent to tumor glands was altered and could provide a favorable environment for infiltrating tumor cells to home to the bone (FIG. 2B).

Figure 2C:
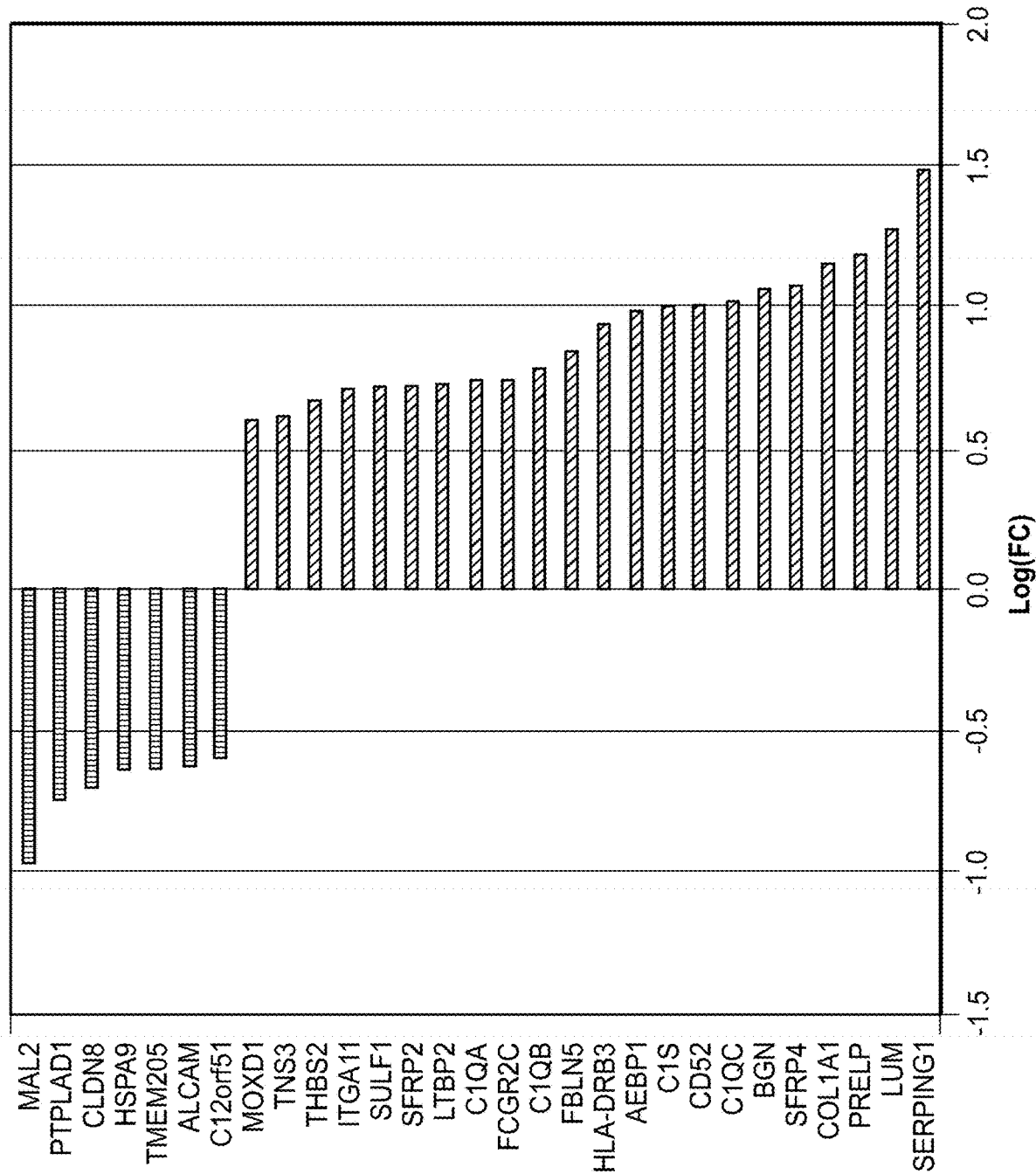
FIG. 2C is a graph showing that distinct stromal changes and genes involved in the tumor-stromal interaction were involved with Gleason.

An enrichment analysis was conducted of the DE genes that were found in a single comparison, namely, P-sP only (68 genes). The GO cellular processes for all three comparisons are shown in FIG. 2C. Immune response, cytokine secretion and inflammation were common amongst the P-sP and T-sT DE genes. In P-sP DE genes the focus was on MHC-II complex assemblies, indicating an impact on T cell protection and recognition, whereas in T-sT DE genes, leukocyte chemotaxis was found indicating stem cell-like activities. Genes differentially expressed between tumor and adjacent stroma were all associated with bone regulation, differentiation and growth. For these DE genes, a network map was constructed based on canonical pathways. The network had several nodes including stem cell markers, BMP's and SMAD. The DE genes most closely associated with OCT3/4, SOX and NANOG indicating uncontrolled self-renewal is an important carcinogenic mechanism at play.

Table 10. 46 genes differentially expressed in malignant tissue comparisons, B-sB, P-sP and T-sT, exclusive of healthy, HB-HsB comparison

| Affymetrix ID | B-sB. logFC | B-sB. P.Value | B-sB.adj. P.Val | P-sP. logFC | P-sP. P.Value | P-sP.adj. P.Val | T-sT. logFC | T-sT. P.Value | T-sT.adj. P.Val | Gene | entrezgene | ensembl_gene_id |
|---|---|---|---|---|---|---|---|---|---|---|---|---|
| 8138381 | 1.36809126 | 1.24E-06 | 2.13E-05 | 1.576126 | 3.41E-08 | 7.39E-07 | 1.10663 | 7.03E-05 | 0.00082272 | AGR2 | 8138381 | AGR2 |
| 7939897 | 0.80051026 | 0.0001365 | 0.00139041 | 0.831912 | 7.61E-05 | 0.0007305 | 0.65457 | 0.001666 | 0.0118382 | FOLH1 | 7939897 | FOLH1, TRIM51GP, TRIM51FP, RP11-163O10.1, TRIM51DP, FOLH1B |
| 8049961 | 0.7428448 | 0.00152 | 0.0118014 | 1.001534 | 2.46E-05 | 0.0002658 | 0.75983 | 0.001192 | 0.00905131 | FBXO25 | 8049961 | FBXO25, AC093642.5 |
| 8012126 | 0.71292118 | 4.31E-09 | 1.33E-07 | 0.927302 | 1.68E-13 | 1.23E-11 | 0.81791 | 3.47E-11 | 2.57E-09 | CLDN7 | 8012126 | CLDN7 |
| 8133721 | -0.6026905 | 1.55E-05 | 0.00020559 | -1.09177 | 1.92E-13 | 1.36E-11 | 1.26463 | 1.09E-16 | 3.40E-14 | HSPB1 | 8133721 | HSPB1 |
| 8075310 | -0.6211701 | 1.17E-05 | 0.00016045 | -0.73006 | 3.56E-07 | 6.09E-06 | 0.72328 | 4.47E-07 | 1.04E-05 | LIF | 8075310 | LIF |
| 7908841 | 0.62687586 | 1.53E-11 | 8.03E-10 | -0.72001 | 3.41E-14 | 2.93E-12 | 0.63472 | 9.30E-12 | 8.21E-10 | PPP1R12B | 7908841 | PPP1R12B |
| 8041048 | 0.69272807 | 1.02E-08 | 2.92E-07 | -0.94499 | 6.67E-14 | 5.37E-12 | 0.83073 | 1.82E-11 | 1.49E-09 | FOSL2 | 8041048 | FOSL2 |
| 8043480 | 0.70065953 | 3.46E-09 | 1.10E-07 | -0.98195 | 3.14E-15 | 3.56E-13 | 0.58921 | 4.40E-07 | 1.02E-05 | NA | 8043480 | IGKV1OR9-1, IGKV1OR-3, IGKV1OR10-1, IGKV1OR9-2, IGKV1OR2-2, IGKV1OR22-5, IGKV1OR1-1, IGKV1OR-2, IGKV1OR2-118, IGKV1OR2-1 |
| 8101673 | -0.7022444 | 0.0025448 | 0.01728914 | -0.77366 | 0.000919 | 0.0063142 | -0.7446 | 0.001403 | 0.01033618 | NA | 8101673 | Y-RNA |
| 8055465 | 0.71539479 | 7.48E-09 | 2.20E-07 | -0.78518 | 3.46E-10 | 1.21E-08 | 0.80147 | 1.65E-10 | 1.04E-08 | CXCR4 | 8055465 | CXCR4 |
| 7919568 | 0.74107177 | 9.66E-12 | 5.32E-10 | -0.78037 | 1.09E-12 | 6.60E-11 | 0.59804 | 1.69E-08 | 5.95E-07 | NA | 7919568 | NA |
| 8156848 | 0.74565026 | 1.17E-07 | 2.59E-06 | -0.79983 | 1.65E-08 | 3.85E-07 | 0.69137 | 7.66E-07 | 1.67E-05 | NR4A3 | 8156848 | NR4A3 |
| 7921821 | -0.7585124 | 2.03E-09 | 6.72E-08 | -0.69639 | 2.79E-08 | 6.16E-07 | 0.58502 | 2.19E-06 | 4.13E-05 | ADAMTS4 | 7921821 | ADAMTS4 |
| 7896708 | 0.77147093 | 0.0007303 | 0.0060054 | -0.68871 | 0.002468 | 0.014687 | 0.68795 | 0.002495 | 0.01655868 | NA | 7896708 | IL2RB |
| 8112855 | 0.77242141 | 0.0001623 | 0.00161836 | -0.874 | 2.24E-05 | 0.0002443 | 0.69027 | 0.000708 | 0.00590146 | NA | 8112855 | Y_RNA |
| 8121275 | 0.78343442 | 5.57E-05 | 0.00063783 | -0.60336 | 0.0017 | 0.0106312 | 0.73834 | 0.000139 | 0.00148128 | NA | 8121275 | Y_RNA |
| 8043476 | 0.78630822 | 2.80E-07 | 5.65E-06 | -0.88588 | 1.05E-08 | 2.58E-07 | 0.64022 | 2.20E-05 | 0.00030412 | LOC652493 | 8043476 | IGKV1-9, IGKV1D-43 |
| 7976812 | 0.79155061 | 0.0001308 | 0.00133893 | -1.18253 | 2.78E-08 | 6.14E-07 | -1.298 | 1.56E-09 | 7.45E-08 | SNORD113-4 | 7976812 | SNORD113-4, MEG8 |
| 8178802 | 0.81241794 | 3.69E-07 | 7.18E-06 | -1.02164 | 4.19E-10 | 1.43E-08 | 1.05418 | 1.36E-10 | 8.78E-09 | NA | 8178802 | NA |
| 7981718 | 0.86591738 | 5.86E-07 | 1.08E-05 | -1.11683 | 3.36E-10 | 1.18E-08 | 0.74107 | 1.54E-05 | 0.00022424 | HLA-DRB3 | 7981718 | IGHV3-30, IGHV3-33 |
| 8043431 | 0.86686149 | 2.23E-07 | 4.63E-06 | -1.32196 | 7.21E-14 | 5.74E-12 | 1.01682 | 2.38E-09 | 1.08E-07 | IGHM | 8043431 | IGKV1-33, IGKV1D-33 |
| 8069676 | 0.89567657 | 3.93E-07 | 7.56E-06 | -1.18418 | 7.43E-11 | 3.03E-09 | 0.82248 | 2.76E-06 | 5.03E-05 | IGKC | 8069676 | ADAMTS1 |
| 7995477 | 0.90908522 | 1.60E-08 | 4.39E-07 | -1.02532 | 3.22E-10 | 1.14E-08 | 0.80766 | 3.88E-07 | 9.15E-06 | ADAMTS1 | 7995477 | ADAMTS1 |
| 7965767 | 0.93223231 | 1.43E-05 | 0.00019161 | -0.86459 | 5.31E-05 | 0.0005291 | 0.65471 | 0.00196 | 0.01356861 | NA | 7965767 | Y_RNA |
| 8043465 | 0.97232883 | 2.82E-09 | 9.10E-08 | -0.98132 | 2.09E-09 | 6.14E-08 | 0.66258 | 2.95E-05 | 0.000394 | IGKC | 8043465 | IGKV1-13, IGKV1D-13 |
| 7981722 | 0.97598211 | 3.99E-09 | 1.25E-07 | -1.1522 | 1.01E-11 | 5.01E-10 | 0.70624 | 1.21E-05 | 0.00018188 | IGHA1 | 7981722 | AC136616.2, IGHM, |

-continued

| Affymetrix ID | B-sB. logFC | B-sB. P.Value | B-sB.adj. P.VAl | P-sP. logFC | P-sP. P.Value | P-sP.adj. P.VAl | T-sT. logFC | T-sT. P.Value | T-sT.adj. P.Val | Gene | entrezgene | ensembl_gene_id |
|---|---|---|---|---|---|---|---|---|---|---|---|---|
| | | | | | | | | | | | | IGHV3-38, |
| | | | | | | | | | | | | IGHV3-16, |
| | | | | | | | | | | | | IGHV3-48, |
| | | | | | | | | | | | | IGHV3-13, |
| | | | | | | | | | | | | IGHV3-23, |
| | | | | | | | | | | | | IGHV3-21, |
| | | | | | | | | | | | | IGHV3-22, |
| | | | | | | | | | | | | OGHV3-35, |
| | | | | | | | | | | | | IGHV3-64, |
| | | | | | | | | | | | | IGHV3-52, |
| | | | | | | | | | | | | IGHV3 66, |
| | | | | | | | | | | | | IGHV3-53, |
| | | | | | | | | | | | | IGHV3-60, |
| | | | | | | | | | | | | IGHV3-65, |
| | | | | | | | | | | | | IGHV3-62, |
| | | | | | | | | | | | | RP11-170L3.7, |
| | | | | | | | | | | | | IGHV3-15, |
| | | | | | | | | | | | | IGHV3OR16-13, |
| | | | | | | | | | | | | IGHV3-41, |
| | | | | | | | | | | | | IGHV3-11, |
| | | | | | | | | | | | | IGHV3-7, |
| | | | | | | | | | | | | IGHG1, |
| | | | | | | | | | | | | IGHV3OR16-6, |
| | | | | | | | | | | | | IGHV3OR16-7, |
| | | | | | | | | | | | | IGHV3-71, |
| | | | | | | | | | | | | IGHV3-72, |
| | | | | | | | | | | | | IGHV3-74 |
| 7939492 | -0.985889 | 2.66E-12 | 1.65E-10 | -1.1175 | 8.04E-15 | 8.23E-13 | 0.93237 | 2.60E-11 | 2.02E-09 | C11orf96 | 7939492 | C11orf96 |
| 8125556 | 0.98589844 | 1.35E-06 | 2.30E-05 | -1.60457 | 1.06E-13 | 8.13E-12 | 1.56231 | 3.62E-13 | 4.84E-11 | HLA-DPA1 | 8125556 | HLA-DPA1 |
| 8178891 | 0.98589844 | 1.35E-06 | 2.30E-05 | -1.60457 | 1.06E-13 | 8.13E-12 | 1.56231 | 3.62E-13 | 4.84E-11 | HLA-DPA1 | 8178891 | HLADPA1 |
| 7960865 | 0.99256725 | 5.01E-10 | 1.93E-08 | -1.1352 | 2.84E-12 | 1.59E-10 | 0.87805 | 2.47E-08 | 8.32E-07 | SLC2A3 | 7960865 | SLC2A3 |
| 8043438 | 1.00632694 | 4.00E-07 | 7.68E-06 | -1.40457 | 9.13E-12 | 4.58E-10 | 0.77531 | 7.09E-05 | 0.00082844 | IGKV1-5 | 8043438 | IGKV2D-40, |
| | | | | | | | | | | | | IGKV2-29, |
| | | | | | | | | | | | | IGKV2-30, |
| | | | | | | | | | | | | IGKC, |
| | | | | | | | | | | | | IGKV2-28, |
| | | | | | | | | | | | | K3KV2OR22-4, |
| | | | | | | | | | | | | IGKV2OR22-3, |
| | | | | | | | | | | | | IGKV2D-30, |
| | | | | | | | | | | | | IGKV2D-29, |
| | | | | | | | | | | | | IGKV2D-28, |
| | | | | | | | | | | | | IGKV2D-10, |
| | | | | | | | | | | | | IGKV2-19, |
| | | | | | | | | | | | | IGKV2-4 |
| 7976816 | 1.02710768 | 7.72E-06 | 0.00011133 | -1.62453 | 1.37E-11 | 6.46E-10 | 1.60051 | 2.47E-11 | 1.93E-09 | SNORD114-3 | 7976816 | SNORD114-3, SNHG23 |
| 8018864 | 1.04591057 | 1.19E-08 | 3.38E-07 | -1.06797 | 6.31E-09 | 1.66E-07 | 1.10836 | 1.93E-09 | 8.90E-08 | SOCS3 | 8018864 | SOCS3 |
| 7981730 | 1.05215949 | 4.96E-09 | 1.52E-07 | -1.28998 | 2.82E-12 | 1.58E-10 | -0.8725 | 8.04E-07 | 1.74E-05 | IGIJ3 | 7981730 | AC136616.2, IGHM, IGHV3-38, |

| Affymetrix ID | B-sB. logFC | B-sB. P.Value | B-sB.adj. P.Val | P-sP. logFC | P-sP. P.Value | P-sP.adj. P.Val | T-sT. logFC | T-sT. P.Value | T-sT.adj. P.Val | Gene | entrezgene | ensembl_gene_id |
|---|---|---|---|---|---|---|---|---|---|---|---|---|
| | | | | | | | | | | | | IGHV3-48, IGHV3-13, IGHV3-23, IGHV3-21, IGHV3-64, IGHV3-66, IGHV3-53, IGHV3-62, IGHV3-41, IGHV3-7, IGHV3-71, IGHV3-72, IGHV3-74 |
| 8135069 | 1.06151702 | 1.14E-07 | 2.53E-06 | -1.29171 | 2.61E-10 | 9.49E-09 | 1.19254 | 3.88E-09 | 1.63E-07 | SERPINE1 | 8135069 | SERPINE1 |
| 7981732 | 1.06934936 | 3.05E-08 | 7.83E-07 | -1.07284 | 2.78E-08 | 6.14E-07 | 0.65142 | 0.000493 | 0.00436133 | IGHV4-59 | 7981732 | AC233755.1, IGHV4-28, IGHV4-34, IGHV4-39, IGHV4-59, IGHV4-61, IGHV4-55, RP11-294C11.2, IGHV4OR15-8, IGHV44 |
| 8053713 | 1.07602211 | 6.22E-07 | 1.14E-05 | -1.49619 | 2.21E-11 | 1.01E-09 | 0.83939 | 7.78E-05 | 0.00089429 | NA | 8053713 | IGKV2D-40, IGKV2-29, IGKV2-30, IGKC, IGKV2-28, IGKV2OR22-4, IGKV2D-30, IGKV2D-29, IGKV2D-28, IGKV2D-10, IGKV2-10, IGKV2-4 |
| 8043459 | 1.10490685 | 3.56E-10 | 1.42E-08 | -1.28119 | 1.03E-12 | 6.28E-11 | 0.79193 | 3.51E-06 | 6.18E-05 | IGKC | 8043459 | IGKVD-16 |
| 8043449 | 1.12332526 | 1.30E-11 | 6.91E-10 | -0.96092 | 3.55E-09 | 9.85E-08 | 0.72388 | 5.16E-06 | 8.59E-05 | IGK@ | 8043449 | IGKV3-15, IGKC, IGKV3OR2-268, IGKV3D-15, IGKV3D-20 |
| 8006433 | 1.16260245 | 1.58E-05 | 0.00021009 | -1.27888 | 2.37E-06 | 3.35E-05 | 1.68495 | 1.35E-09 | 6.54E-08 | CCL2 | 8006433 | CCL2 |
| 7919324 | 1.37993797 | 1.68E-08 | 4.58E-07 | -0.94559 | 7.01E-05 | 0.0006787 | 1.04122 | 1.34E-05 | 0.00019708 | NA | 7919324 | Y-RNA |
| 8053690 | 1.40246399 | 2.64E-11 | 1.30E-09 | -1.50882 | 1.29E-12 | 7.68E-11 | 1.08583 | 1.09E-07 | 3.07E-06 | IGK@ | 8053690 | NA |
| 7981724 | 1.46855941 | 9.06E-10 | 3.29E-08 | -1.7033 | 3.25E-12 | 1.79E-10 | 1.24328 | 1.33E-07 | 3.66E-06 | IGHD | 7981724 | AC141272.1, AC233755.2, IGHM, IGHV3-16, |

| Affymetrix ID | B-sB. logFC | B-sB. P.Value | B-sB.adj. P.VAl | P-sP. logFC | P-sP. P.Value | P-sP.adj. P.VAl | T-sT. logFC | T-sT. P.Value | T-sT.adj. P.Val | Gene | entrezgene | ensembl_gene_id |
|---|---|---|---|---|---|---|---|---|---|---|---|---|
| | | | | | | | | | | | | IGHV3-43, |
| | | | | | | | | | | | | IGHV3-48, |
| | | | | | | | | | | | | IGHV3-13, |
| | | | | | | | | | | | | IGHV3-23, |
| | | | | | | | | | | | | IGHV3-21, |
| | | | | | | | | | | | | IGHV3-22, |
| | | | | | | | | | | | | IGHV3-19, |
| | | | | | | | | | | | | IGHV3-64, |
| | | | | | | | | | | | | IGHV3-66, |
| | | | | | | | | | | | | IGHV3-53, |
| | | | | | | | | | | | | IGHV3-65, |
| | | | | | | | | | | | | IGHV3-62, |
| | | | | | | | | | | | | IGHV3OR16-9, |
| | | | | | | | | | | | | RP11-1166P10.8, |
| | | | | | | | | | | | | RP11-170L3.7, |
| | | | | | | | | | | | | IGHV3-30, |
| | | | | | | | | | | | | IGHV3-11, |
| | | | | | | | | | | | | IGHV3-7, |
| | | | | | | | | | | | | IGHG1, |
| | | | | | | | | | | | | IGHV3OR16-10, |
| | | | | | | | | | | | | IGHV3-71, |
| | | | | | | | | | | | | IGHV3-74 |
| 7981728 | 1.53067984 | 2.88E−09 | 9.27E−08 | −1.86753 | 1.67E−12 | 9.70E−11 | 1.17212 | 3.21E−06 | 5.71E−05 | NA | 7981728 | AC141272.1, |
| | | | | | | | | | | | | AC233755.2, |
| | | | | | | | | | | | | IGHV3-6, |
| | | | | | | | | | | | | IGHM, |
| | | | | | | | | | | | | IGHV3-38, |
| | | | | | | | | | | | | IGHV3-16, |
| | | | | | | | | | | | | IGHV3-43, |
| | | | | | | | | | | | | IGHV3-48, |
| | | | | | | | | | | | | IGHV3-13, |
| | | | | | | | | | | | | IGHV3-23, |
| | | | | | | | | | | | | IGHV3-21, |
| | | | | | | | | | | | | IGHV3-22, |
| | | | | | | | | | | | | IGHV3-19, |
| | | | | | | | | | | | | IGHV3-35, |
| | | | | | | | | | | | | IGHV3-64, |
| | | | | | | | | | | | | IGHV3-52, |
| | | | | | | | | | | | | IGHV3-60, |
| | | | | | | | | | | | | IGHV3-65, |
| | | | | | | | | | | | | IGHV3-62, |
| | | | | | | | | | | | | IGHV3-OR16-9, |
| | | | | | | | | | | | | RP11-170L3.7, |
| | | | | | | | | | | | | IGHV3OR16-13, |
| | | | | | | | | | | | | IGHV3-30, |
| | | | | | | | | | | | | IGHV3-11, |
| | | | | | | | | | | | | IGHV3-7, |
| | | | | | | | | | | | | IGHG1, |

-continued

| Affymetrix ID | B-sB. logFC | B-sB. PValue | B-sB.adj. P.VAl | P-sP. logFC | P-sP. PValue | P-sP.adj. P.VAl | T-sT. logFC | T-sT. PValue | T-sT.adj. P.Val | Gene | entrezgene | ensembl_gene_id |
|---|---|---|---|---|---|---|---|---|---|---|---|---|
| 8100827 | −1.6482815 | 1.24E-09 | 4.29E-08 | −1.96538 | 1.48E-12 | 8.69E-11 | 1.12045 | 1.98E-05 | 0.00027782 | IGJ | 8100827 | IGHV3-71, IGHV3-72, IGHV3-74 IGJ |

FC positive: AGR2, FOLH1, TRIM51GP, TRIM51FP, RP11, 163O19.1, TRIM51DP, FOLH1B, FBXO25, AC093642.5, and CLDN7.
FC negative: HSPB1, LIF, PPP1R12B, FOSL2, IGKV1OR9-1, IGKV1OR-3, IGKV1OR10-1, IGKV1OR9-2, IGKV1OR22-5, IGKV1OR1-1, IGKV1OR2-1, Y_RNA, CXCR4, NR4A3, ADAMTS4, IL2RB, IGKV1-9, IGKV1D-43, SNORD113-4, MEG8, IGHV3-30, IGKV3-33, IGKV1-33, ADAMTS1, RNY4P3, IGKV1-13, AC136616.2, IGHM, IGHV3-38, IGHV3-16, IGHV3-23, IGHV3-21, IGHV3-35, IGHV3-64, SNORD113-4, IGHV3-66, IGHV3-53, IGHV3-60, IGHV3-65, RP11-170L3.7, IGHV3-15 IGHV3OR16-13, RP11-170L3.7, IGHG1, IGHV3OR16-6, IGHV3OR16-7, IGHV3-71, IGHV3-72, IGHV3-74, C11orf96, HLA-DPA1, SLC2A3, IGKV2D-40, IGKV2-29 IGKV2-30 IGKC, IGKV2-28 IGKV2OR22-4, IGKV2OR22-3, IGKV2D-29, IGKV2D-30, IGKV2D-10, IGKV2-4, SNORD114-3, SNHG23, SOCS3, AC136616.2, IGHM, IGHV3-38, IGHV3-48, IGHV3-13, IGKC, IGKV2D-40, IGHV4-4, IGKV2-29, IGKV2-30, IGKC, IGKV2D-28, IGKV2D-29, IGKC, IGKV2D-10, IGKV2-4 IGKV1D-16, IGKC, IGKV3-15, IGKC, IGKV3OR2-268, IGKV3D-15, RP11-294C11.2, AC141272.1, AC233755.2, IGHM, IGHV3-16, IGHV3-43, IGHV3-48, IGHV3-16, IGHV3-23, IGHV3-19, IGHV3-64, IGHV3-65, IGHV3-53, IGHV3-66, RP11-1166P10.8, RP11-170L3.7, IGKV3D-20, CCL2, AC141272.1, IGHG1, IGHV3OR16-10, IGHV3OR16-9, IGHV3-7, IGHV3-74, AC141272.1, AC233755.2, IGHM, IGHV3-6, IGHM, IGHV3-38, IGHV3-43, IGHV3-48, IGHV3-22, IGHV3-21, IGHV3-19, IGHV3-35, IGHV3-64, IGHV3-52, IGHV3-60, IGHV3-65, IGHV3OR16-13, IGHV3-30, IGHV3OR16-13, IGHV3OR16-9, RP11-170L3.7, IGHV3OR16-13, IGHV3-30, IGHV3-11, IGHG1, IGHV3-7, IGHG1, IGHV3-71, IGHV3-72, IGHV3-74, and IGJ.

Table 11. Enrichment analysis using the GeneGo database, to determine pathways, networks and cellular processes, for the genes found to be upregulated in the stroma, found exclusively in the T-sT comparison in malignant tissue

| | | | | | Enrichment analysis report | | | |
|---|---|---|---|---|---|---|---|---|
| Enrichment by Pathway Maps | | | | | | t.only.stromaGeneGo(1)_genelist | | |
| # | Maps | Total | pValue | Min FDR | p-value | FDR | In Data | Network Objects from Active Data |
| 1 | Immune response_Alternative complement pathway | 39 | 2.354E−10 | 2.283E−08 | 2.354E−10 | 2.283E−08 | 6 | C3c, C3, C3dg, C3b, iC3b, C3a |
| 2 | Immune response_Lectin induced complement pathway | 49 | 9.943E−10 | 4.660E−08 | 9.943E−10 | 4.660E−08 | 6 | C3c, C3, C3dg, C3b, iC3b, C3a |
| 3 | Immune response_Classical complement pathway | 52 | 1.441E−09 | 4.660E−08 | 1.441E−09 | 4.660E−08 | 6 | C3c, C3, C3dg, C3b, iC3b, C3a |
| 4 | Complement pathway disruption in thrombotic microangiopathy | 37 | 8.092E−05 | 1.962E−03 | 8.092E−05 | 1.962E−03 | 3 | C3, C3b, C3a |
| 5 | Immune response_T cell subsets: secreted signals | 25 | 1.504E−03 | 2.917E−02 | 1.504E−03 | 2.917E−02 | 2 | TGF-beta, MIP-1- alpha |
| 6 | Histamine metabolism | 28 | 1.887E−03 | 3.050E−02 | 1.887E−03 | 3.050E−02 | 2 | AL1A1, ALDH2 |
| 7 | Development_TGF-beta-dependent induction of EMT via SMADs | 35 | 2.940E−03 | 4.075E−02 | 2.940E−03 | 4.075E−02 | 2 | TGF-beta, TGF-beta 3 |
| 8 | Substance P-mediated inflammation and pain in Sickle cell disease | 38 | 3.459E−03 | 4.195E−02 | 3.459E−03 | 4.195E−02 | 2 | MIP-1-alpha, CD14 |
| 9 | Role of cell adhesion in vaso-occlusion in Sickle cell disease | 43 | 4.412E−03 | 4.756E−02 | 4.412E−03 | 4.756E−02 | 2 | iC3b, CD14 |
| 10 | Development_TGF-beta-dependent induction of EMT via MAPK | 47 | 5.253E−03 | 4.826E−02 | 5.253E−03 | 4.826E−02 | 2 | TGF-beta, TGF-beta 3 |
| Enrichment by Process Networks | | | | | | t.only.stromaGeneGo(1)_genelist | | |
| # | Networks | Total | pValue | Min FDR | p-value | FDR | In Data | Network Objects from Active Data |
| 1 | Inflammation_Complement system | 73 | 3.542E−06 | 1.983E−04 | 3.542 E−06 | 1.983E−04 | 5 | C3, C3dg, C3b, iC3b, C3a |
| 2 | Inflammation_Innate inflammatory response | 181 | 2.836E−04 | 7.941E−03 | 2.836E−04 | 7.941E−03 | 5 | sCD14, C3, C3b, C3a, CD 14 |
| 3 | Immune response_Phagocytosis | 222 | 7.255E−04 | 1.354E−02 | 7.255E−04 | 1.354E−02 | 5 | C3, C3dg, C3b, iC3b, CD14 |
| 4 | Cell adhesion_Platelet-endothelium-leucocyte interactions | 174 | 2.466E−03 | 3.452E−02 | 2.466E−03 | 3.452E−02 | 4 | Thrombospondin 4, TGF-beta, TGF-beta 3, MIP-1-alpha |
| 5 | Immune response_Phagosome in antigen presentation | 243 | 8.111E−03 | 9.084E−02 | 8.111E−03 | 9.084E−02 | 4 | C3, C3dg, iC3b, CD14 |
| 6 | Proliferation_Negative regulation of cell proliferation | 184 | 2.285E−02 | 1.860E−01 | 2.285E−02 | 1.860E−01 | 3 | CCL3L1, TGF-beta, TGF-beta 3 |
| 7 | Inflammation_Jak-STAT Pathway | 186 | 2.350E−02 | 1.860E−01 | 2.350E−02 | 1.860E−01 | 3 | CCL3L1, IL7RA, MIP-1-alpha |
| 8 | Cell cycle_G1-S Growth factor regulation | 195 | 2.657E−02 | 1.860E−01 | 2.657E−02 | 1.860E−01 | 3 | TGF-beta, TGF-beta 3, LTBP3 |
| 9 | Chemotaxis | 137 | 7.656E−02 | 3.951E−01 | 7.656E−02 | 3.951E−01 | 2 | CCL3L1, MIP-1-alpha |
| 10 | Apoptosis_Apoptosis stimulation by external signals | 144 | 8.344E−02 | 3.951E−01 | 8.344E−02 | 3.951E−01 | 2 | TGF-beta, TGF-beta 3 |
| Enrichment by GO Processes | | | | | | t.only.stromaGeneGo(1)_genelist | | |
| # | Processes | Total | pValue | Min FDR | p-value | FDR | In Data | Network Objects from Active Data |
| 1 | regulation of bone mineralization | 95 | 6.716E−09 | 1.029E−05 | 6.716E−09 | 1.029E−05 | 6 | Gremlin, CCL3L1, TGF-beta, TGF-beta 3, MIP-1-alpha, LTBP3 |
| 2 | regulation of biomineral tissue development | 106 | 1.302E−08 | 1.029E−05 | 1.302E−08 | 1.029E−05 | 6 | Gremlin, CCL3L1, TGF-beta, TGF-beta 3, MIP-1-alpha, LTBP3 |
| 3 | negative regulation of ossification | 109 | 1.541E−08 | 1.029E−05 | 1.541E−08 | 1.029E−05 | 6 | Gremlin, CCL3L1, TGF-beta, microRNA 23a, MIP-1-alpha, LTBP3 |
| 4 | negative regulation of bone mineralization | 22 | 3.401E−08 | 1.704E−05 | 3.401E−08 | 1.704E−05 | 4 | Gremlin, CCL3L1, MIP-1-alpha, LTBP3 |
| 5 | negative regulation of biomineral tissue development | 24 | 4.929E−08 | 1.976E−05 | 4.929E−08 | 1.976E−05 | 4 | Gremlin, CCL3L1, MIP-1-alpha, LTBP3 |
| 6 | glial cell migration | 27 | 8.115E−08 | 2.710E−05 | 8.115E−08 | 2.710E−05 | 4 | CCL3L1, MMP-14, TGF-beta, MIP-1- alpha |
| 7 | regulation of ossification | 272 | 1.647E−07 | 4.714E−05 | 1.647E−07 | 4.714E−05 | 7 | Gremlin, CCL3L1, TGF-beta, TGF-beta 3, microRNA 23a, MIP-1-alpha, LTBP3 |
| 8 | negative regulation of biological process | 5615 | 2.919E−07 | 7.313E−05 | 2.919E−07 | 7.313E−05 | 23 | IEX1, Annexin II, Lamin A/C, C3, Calponin-3, Gremlin, RGS1, Thrombospondin 4, Metallothionein-ll, CCL3L1, MMP-14, TGF-beta, RPB7.0, TGF-beta 3, |

-continued

Enrichment analysis report

| | | | | | | | |
|---|---|---|---|---|---|---|---|
| 9 | astrocyte cell migration | 10 | 4.010E−07 | 8.929E−05 | 4.010E−07 | 8.929E−05 | 3 | CCL3L1, MMP-14, MIP-1-alpha |
| 10 | craniofacial suture morphogenesis | 17 | 2.256E−06 | 4.468E−04 | 2.256E−06 | 4.468E−04 | 3 | MMP-14, TGF-beta, TGF-beta 3 |

(Row 8 continued from previous page, column 8): microRNA 23a, IL7RA, MIP-1-alpha, MKP-1, FXYD5, ALDH2, Metallothionein-IA, LTBP3, Metallothionein-I Bone related: regulation of bone mineralization, regulation of biomineral tissue developoment, negative regulation of ossification, negative regulation of bone mineralization, negative regulation of biomineral tissue development, regulation of ossification, and craniofacial suture morphogenesis.

Example 7: Distinct Stromal Changes and Genes Involved in the Tumor-Stromal Interaction are Associated with the Gleason Score Gleason grade is one of the strongest clinical predictors of prostate cancer progression and outcomes (Penney K L, et al., J Clin Oncol. 29, 2391-6 (2011)). Men with low-grade Gleason ≤6 tumors, have a low metastatic potential, even in the absence of therapy; in contrast, men with high-grade Gleason 8 to 10 tumors have a high likelihood of progression, even with curative therapies. Genes were identified that were associated with low and high Gleason scores in the different compartments. Three comparisons were performed to identify differentially expressed genes that were associated with a Gleason score. The first compared the Gleason 6 and Gleason 8 tumors within the epithelium, T8-T6. The second compared the Gleason 6 and Gleason 8 within the stroma, sT8-sT6. Third, the magnitude of the differential expression between the compartments, (sT8-T8)-(sT6-T6) associated with Gleason score were assessed. A TGF-β-responsive marker and functional regulator of prostate cancer metastasis to bone, ALCAM (Hansen A G, et al., Cancer Res. 74, 1404-15 (2014)) was identified as the only significantly differentially expressed gene in the epithelium comparison. 16 differentially expressed genes were associated with Gleason within the stromal compartment, (sT8-sT6). 22 genes (including 9 of the 16 above) were significant in the (sT8-T8)-(sT6-T6) comparison. The interaction gene set also contained ALCAM and an additional 6 epithelial genes that further augment the ability to elucidate the influence and processes associated with the epithelium and stroma independently and in conjunction with each other. A total of 29 genes were inspected graphically and assigned to the epithelial or stromal compartment based on which compartment contributed more to the observed difference between the low and high grade.

Next, the compartment of origin of the discriminating genes was assessed by classifying them as stromal or epithelial based on the direction of their fold-changes in the global comparisons of epithelium versus stroma. Overall a 29-gene signature was defined (7 epithelial and 22 stromal genes), which distinguishes Gleason 6 from Gleason 8 (Table 1), which comprise a "bone homing signature".

In FIG. 42, representative interaction plots showing 4 distinct trends and color-tabulated gene list assigning whether the gene is associated with the tumor or its adjacent stroma based on these trends is provided. Stromal cells aid tumor cell growth by secreting cytokines into the microenvironment through the extracellular matrix. Lumican is a small leucine-rich proteoglycan (SLRP's), biologically active in the ECM that is over expressed in the stroma surrounding prostate tumor cells (Coulson-Thomas ref). BGN and Col1A1 are also glycoproteins that have been shown to be over expressed in stroma adjacent to prostate tumor glands. Along with Lumican, these 3 genes form the stromal component of the recently FDA approved OncoDX 17-gene signature of prostate cancer aggressiveness regardless of multifocality, heterogeneity with clinical applicability to biopsied tissue specimens. Cumulative higher expression of all 3 stromal genes was shown to be associated with worse outcome (Klein E A, et al., Eur Urol, 2011. 66: p. 672-84). Col1A1 is an osteoblastic differentiation marker (Nakajima K, Neoplasia. 16, 939-49 (2014)) and BGN modulates angiogenesis and bone formation during fracture healing (Berendsen A D, et al., Matrix Biol. 35, 223-31 (2014)). Bone metastasis is a clinically devastating development of progressive cancers including prostate carcinoma, breast carcinoma and multiple myeloma. Bone metastases are typically painful, lead to adverse skeletal related events, such as fracture, and are highly resistant to therapy (Sottnik J L, et al., Clin Exp Metastasis., 2013. 30: p. 569-78). SFRP2 and SFRP4 are frizzled proteins that are part of the Wnt signaling pathway, comprised of secreting glycoproteins that mediate bone development. These genes keep the bone formation and remodeling mechanisms in check. Wnt dysregulation has been widely associated with osteosarcoma (Li C, et al., Front Biosci (Landmark Ed). 2013 Jun. 1; 18:1384-91). The Wnt pathway has been investigated extensively for potential therapeutic nodes, suitable for patients with bone metastasis who are highly resistant to treatment (Hall C L, et al., Cancer Metastasis Rev. 2006, 25, 551-8). SFRP2 and SFRP4 are osteoblastic genes (osteomimicry) that contribute to homing and growth of cells metastatic to bone (Hassan M Q, M. Y., et al., J Biol Chem. 287, 42084-92 (2012)). They have both been shown to be associated with aberrant methylation in carcinogenesis, including prostate cancer (Perry A S, et al., Int J Cancer. 132, 1771-80 (2013); Pohl S, Scott R, et al., Tumour Biol. 36, 143-52 (2015)). C1S is secreted by fibroblast cells in the stroma microenvironment. SerpinG1 encodes a highly glycosylated plasma protein involved in the regulation of the complement cascade. Its protein inhibits and regulates complement activation. The C1q family of proteins has in recent times been implicated in apoptosis of prostate cancer cells (Ghebrehiwet B. et al., Front Immunol. 3, 52 (2012)). C1q is structurally and functionally related to TNF-α-like family of proteins and shares some of their cytokine-like properties. C1q has been gaining recognition as a bridge between innate and adaptive immunity (Nayak A, et al., Immunol Lett. 131, 139-50 (2010)) and has been shown to be involved in the function of many types of immune cells. C1q subunits, C1qB and C1qC have been implicated in bone marrow macrophage regulation (Luo Y et al., *PLoS One.* 6, e20971 (2011)) and enhancement of the homing-related response of hematopoietic stem/progenitor cells (mesenchymal stromal cells) to inflammation sites and tissue injury (Teo B H, et al., *Biochem J,* 2012. 447: p. 229-37), respectively. AEBP1 is a proinflammatory macrophage mediator, which has been implicated in tumor cell growth and survival by aberrant sonic hedgehog in breast cancer (Holloway R W, et al. *J Biol Chem.* 287, 39171-81 (2012)). AEBP1 has also been shown to be associated with increased methylation in rat prostates (Yamashita S, et al., *Cancer Res.* 68, 2112-21 (2008)) and TGF-beta signaling associated with metastasis and poor outcome in ovarian cancer patients (Cheon D J, et al., *Clin Cancer Res.* 20, 711-23 (2014)). HLA-DRB3 has been shown to play a role in T-cell immune response and FCGR2C in B-cell immune response (Li X, W. J. et al., *Sci Transl Med.* 5, 216 (2013)). CD52 has also been associated with immune T-cell response in multiple myeloma (Gupta R. et al., *Am J Clin Pathol,* 132, 728-32 (2009)), which also has a prevalence of myeloma bone disease (Hameed A. et al., *Cancer Growth Metastasis.* 7, 33-42 (2014)). FBLN5 (Bing Z, et al., *Mol Biol Rep.* 39, 6077-85 (2012)), ITGA11 (Kaltz N. et al., *Exp Cell Res.* 316, 2609-17 (2010)) and SULF1 have been to varying degrees associated with bone-marrow mesenchymal stem cell (BM-MSC's) differentiation. FBLN5 has a role in metastatic organ colonization (Moller, *Mol Cancer Res,* 2011, 9, 553-63). Alterations in glycobiology might play an important role in the aging of human bmMSC. Aging is associated with bone loss and tissue degeneration. SULF1 is implicated in the pathology of osteoporosis and osteoarthritis in aging with increasing altered immunology (Jiang S S, et al., *Aging.* 3, 672-84 (2011)). SULF1 has also been implicated in hematopoeitic mulitlineage development (Buono M, et al., *J Exp Med.* 207, 1647-60 (2011)). PRELP and LTBP2 are associated with osteoblastic mesenchymal stromal cell expression. PRELP is a glycosaminoglycan (GAG)- and collagen-binding anchor protein highly expressed in cartilage, basement membranes, and developing bone with a role in osteoclastogenesis and of pathological important in cytoskeletal remodeling (Rucci N, R. A. et al., *J Cell Biol.* 187, 669-83 (2009)). LTBP2 is associated with osteopenia and osteoblastic transdifferentiation and has been identified as a candidate gene in chromosome 14q QTL for BMD variation and fracture (Cheung CL. et al., *J Clin Endocrinol Metab.* 93, 4448-55 (2008)). TNS3 is involved in normal bone development and has been implicated in breast cancer metastasis but not bone metastasis of prostate origin (Qian X. et al., *Cancer Cell.* 16, 246-58 (2009)). THBS2 is stromally expressed in prostate cancer and has been implicated in cancer associated fibroblastic suppression via ERa functioning through a CAF-epithelial interaction where thrombospondin 2 is selectively upregulated (Slavin S, et al., *Carcinogenesis.* 35, 1301-9 (2014)). C12orf51, TMEM205 and PTPLAD1 have no reported role of function in prostate cancer or carcinogeneisis. PTPLAD1 is a cell cycle regulatory gene. C12orf51 is a metabolic syndrome and inflammation marker (Kraja A T. et al. *Mol Genet Metab.* 2014, 112, 317-38). TMEM205 is a transmembrane protein has been shown to be over-expressed in resistance to cisplatin. HSPA9, CLDN8 and MAL2 have more interesting biological associations that have applicability in the prostate tumor microenvironment. HSPA9 is a small, nucleolar ribonucleoprotein involved in telomere length maintenance. This ability could provide insight into a potential mechanism contributing to multiple myeloma tumor cells expanding into the bone marrow (Diaz de la Guardia R1, et al., *J Cell Mol Med.* 2012, 16, 3009-21). CLDN8 is a cell adhesion molecule that is a marker of spermatogonial stem cells (McMillan M. et al., *Reprod Fertil Dev.* 26, 633-44 (2014)). Somatic cells within the SSC niche are able to secrete growth factors that stimulate self-renewal (GDNF, FGF2) and differentiation (activin A, BMP4, and SCF) (de Rooij D G. *Microsc Res Tech.* 2009, 72, 580-5). MAL2 is a raft-associated integral membrane protein. Prostate epithelial cells contain vesicular organelles enriched in raft components named prostasomes that are secreted in the prostate fluid (Eguchi D, et al. *Surgery.* 2013, 154, 573-82).

A stromal microenvironment surrounding Gleason 8 tumors that is altered is described. This altered state is bone-like, featuring wound healing and metastasis markers (ALCAM, SFRP2, SFRP4, THBS2), stem cell and hematopoietic bone marrow markers (ITGA11, LTBP2, SULF1, FBLN5, COL1A1) and immune cell markers (C1S, C1Q, Serping1, HLA-DRB3, FCGR2C, HSPA9). A full description of the 29-gene signature is provided in Table 12, where genes are categorized into 1 or more of bone, metastasis, immune, stemness and metabolism with supporting literature citations. Immune response dominates the top 10 enriched pathways, network and processes shown to be statistically significant. The next most prevalent characteristics determined from the enrichment analysis is association to bone-related pathways (Hedgehog associated bone development and osteoporosis) and inflammation, cartilage development and bone remodeling networks. These in conjunction with the wealth of literature support for each gene or subset of genes within the 29-gene Gleason signature describe a stromal microenvironment surrounding Gleason 8 tumors that is altered and this alteration looks remarkably bone-like harboring bone-specific markers, stem cell and hematopoetic associated bone marrow associated markers and immune cell markers. Plots showing trends across benign to PIN to tumor samples for each gene within the 29-gene signature are shown in FIGS. 45-73, e.g., C12orf51 (FIG. 45), PTPLAD (FIG. 46), TMEM205 (FIG. 47), CLDN8 (FIG. 48), ALCAM (FIG. 49), HSPA9 (FIG. 50), MAL2 (FIG. 51), C1QA (FIG. 52), C1QC (FIG. 53), C1QB (FIG. 54), CD52 (FIG. 55), FCGR2C (FIG. 56), PRELP (FIG. 57), SERPING1 (FIG. 58), C1S (FIG. 59), LUM (FIG. 60), LTBP2 (FIG. 61), FBLN5 (FIG. 62), ITGA11 (FIG. 63), COL1A1 (FIG. 64), SFRP2 (FIG. 65), MOXD1 (FIG. 66), THBS2 (FIG. 67), AEBP1 (FIG. 68), SFRP4 (FIG. 69), TNS3 (FIG. 70), SULF1 (FIG. 71), BGN (FIG. 72), HLA-DRB3 (FIG. 73), and a summary plot in FIG. 74.

TABLE 12

29-gene signature, role and implications in cancer and metastasis

| Gene | Role in Cancer | Family | Other Functional Details | Ref | Biological role |
|---|---|---|---|---|---|
| ALCAM | Regulates metastasis to bone met in PrCa | Immunoglobulin | Cell adhesion molecule that binds to CD6, role in the binding of T- and B-cells to activated leukocytes | Hansen | Bone-related, metastasis |

TABLE 12-continued

29-gene signature, role and implications in cancer and metastasis

| Gene | Role in Cancer | Family | Other Functional Details | Ref | Biological role |
|------|----------------|--------|--------------------------|-----|-----------------|
| LUM | Increase in lumican expression was observed in the reactive stroma surrounding prostate primary tumors with fibrotic deposition surrounding the acinar glands. | ECM - Proteoglycan SLRP | Extracellular, Golgi, Lysosome, regulation of collagen assembly into fibrils in various connective tissue | Klein, Coulson-Thomas | Stromal |
| COL1A1 | Osteoblast differentiation marker | Collagens | Extracellular, Endoplasmic Reticulum, fibril forming, putative downregulated c-Myc target gene | Klein, Nakajima | Bone-related |
| BGN | Biglycan modulates angiogenesis and bone formation during fracture healing, downregulated in response to reduced bioavailability of insulin | ECM - Proteoglycan SLRP | Extracellular, Golgi, Lysosome, involved in collagen fiber assembly | Klein, Berendsen | Bone-related |
| C1QC | enhances the homing-related response of hematopoietic stem/progenitor cells (mesenchymal stromal cells) to inflammation sites and tissue injury | Complement - Collagen-like regions | Extracellular | Nayak, Teo | N/A |
| C1S | upregulated C1s inflammatory response in bone marrow-derived macrophages | Complement - Collagen-like regions | Extracellular, Enzyme regualtion through inhibition by SERPING1 | Ghebrehiwet | Bone-related, immune response |
| C1QB | regulators of bone marrow macrophages | Complement - Collagen-like regions | Extracellular | Nayak, Luo | Bone-related |
| HLA-DRB3 | Central to immune response, DRB bone marrow polymorphisms | MHC class II family | All cellular compartments, Binds peptides derived from antigens that access the endocytic route of antigen presenting cells (APC) and presents them on the cell surface for recognition by the CD4 T-cells. | Li | Immune response |
| AEBP1 | TGFb signaling gene signature poor outcome and met in ovarian cancer, mammory hyperplasia to tumorigenesis, hdhg sig and inflammation, methylation siliencing in rat prostates | peptidase M14 family | Extracellular and Nucleus, positively regulate MAP-kinase activity in adipocytes, positively regulate NF-kappa-B activity in positive regualtion of NFkB leading to enhanced macrophage inflammatory responsiveness | Holloway, Yamashita, Cheon | Metastasis, stromal |
| SFRP4 | mets in ovarian, cervical, pancreatic, Overexpressed inhibits cancer progression, aggressiveness and metastatic potential in prca, more epitheliod cell type, osteoblastogenesis of human multipotent mesenchymal stromal cells, wnt beta catenin signaling | Secreted frizzled-related | Extracellular and Nucleus, directly modulates of Wnt signaling | Hassan, Pohl | Bone-related, metastasis, stemness |
| FBLN5 | dowregulated in prostate cancer, BM-MSC differentiation | Fibulin - EGF-like domains | Extracellular, Promotes adhesion of endothelial cells through interaction of integrins, vascular development and remodeling | Bing, Moller | Bone-related |
| FCGR2C | B cells immune response | immunoreceptor tyrosine-based activator motif (ITAM) | plasma membrane primarily expressed by cells of the myeloid lineage (bone marrow and stemness), myeloid plasticity after AR depravation | Li | Immune response |
| C1QA | CRPC survival and poor outcome | Complement - Collagen-like regions | Extracellular | Nayak | Metastasis, immune response |
| SFRP2 | MicroRNAs (miRNAs) negatively and post-transcriptionally regulate expression of multiple target genes to support anabolic pathways for bone formation, osteoblastic genes (osteomimicry) that contribute to homing and growth of cells metastatic to bone | secreted frizzled-related | Extracellular and plasma membrane, directly modulates of Wnt signaling | Hassan, Perry | Bone-related, metastasis |
| SULF1 | low expression in prostate stromal, in particular BPH, regulated fgf and wnt signaling bm-msc age-related skeletal diseases | Sulfatase | Extracellular, Endoplasmic Reticulum, highly specific endoglucosamine-6-sulfatase activity, diminishes proliferation, and facilitates | Jiang, Buono | Bone-related, stromal |

TABLE 12-continued 29-gene signature, role and implications in cancer and metastasis

| Gene | Role in Cancer | Family | Other Functional Details | Ref | Biological role |
|---|---|---|---|---|---|
| THBS2 | Era signaling in CAF modulated by THBS2 suppressing prostate cancer development, regulate MMP2and9, intrevertebel emt proteins, associated with increased bone density and thickness, | Thrombospondin - EGF-like domains | apoptosis in response to exogenous stimulation Extracellular, Adhesive glycoprotein that mediates cell-to-cell and cell-to-matrix interactions. Ligand for CD36 mediating antiangiogenic properties | Slavin | Bone-related |
| MOXD1 | downregulated in response to reduced bioavailability of insulin | copper type II ascorbate-dependent | Endoplasmic Reticulum | | Insulin-reated |
| SERPING1 | C1 inhibitor, angioedema, kallikrein assoc in melanoma | Serpin (Kallikrein) | Extracellular, play a potentially crucial role in regulating important physiological pathways including complement activation, blood coagulation, fibrinolysis and the generation of kinins | Kiflemariam | Immune response |
| PRELP | stromal cell expression, Synovial fluid MSC, than normal of OS-MSC, also SFRP4, synovial cysts | SLRP class | Extracellular, Golgi, Lysosome, matrix protein of articular cartilage | Rucci | Bone-related, stromal |
| CD52 | multiple myeloma ass, immune response, t-cells | CAMPATH | plasma membrane | Gupta Hameed | Immune response |
| LTBP2 | Bone Mineral Density (Osteopenia), osteoblastic transdifferentiation | TGFB-binding | Extracellular, Most similar to fibrilins, cell adhesion, | Cheung | Bone-related |
| ITGA11 | osteogenic differentiation in BM-MSC, expressed in bone, cartilage, cardiac muscle, and skeletal muscle | Integrin alpha chain | Plasma membrane, Involved in attaching muscle tissue to the extracellular matrix | Kaltz | Bone-related |
| TNS3 | important for normal development of bone, tumorigenesis and metastasis in breast, not prostate yet, phosphorylation ass with src | SH2 domain | Nucleus, May be involved in cell migration and bone development, downregulated by EGF | Qian | N/A |
| C12orf51 | MetS candidate gene, high-density lipoprotein metabolism | HECT domain (Ubiquitin-protein ligase) | important paralog of this gene is HERC1 | Heo, Kraja | Metabolism |
| TMEM205 | Cisplatin resistance, transmembrane protein on Yomics panel | | Extracellular | Shen, Gottesman | N/A |
| HSPA9 | knockdown of HSPA9 in human cells significantly delayed the maturation of erythroid precursors, but not myeloid or megakaryocytic precursors, and suppressed cell growth by 6-fold secondary to an increase in apoptosis and a decrease in the cycling of cells compared with control cells. Erythroid precursors, B lymphocytes, and the bone marrow progenitors c-kit(+)/lineage(−)/Sca-1(+) (KLS) and megakaryocyte/erythrocyte progenitor (MEP) were significantly reduced in a murine Hspa9-knockdown model. | heat shock protein 70 | cell proliferation and cellular aging. May also act as a chaperone. role in cell proliferation, stress response and maintenance of the mitochondria | Walter | Stemness, immune response |
| CLDN8 | Cell Adhesion molecule, testes spermatogonial stem-cell niche, ER association in high-grade breast cancer | Claudin | Endoplasmic Reticulum, tight junction-specific obliteration of the intercellular space | McMillian | Stemness |
| PTPLAD1 | BIND1, Human buterate-induced transcript 1, B-ind1 as a novel component of Rac1-signaling pathways leading to the modulation of its gene expression | long-chain fatty acids dehydratase HACD | Endoplasmic reticulum | Courilleau | N/A |
| MAL2 | Secretory cell clusters endocrine glands in prostate, mast cells of peritumoral stroma, MAL based trafficking pathways | Mal | Plasma membrane, polarised transport, raft-associated integral membrane proteins of the MAL family of proteins involved in membrane trafficking processes | Marazuela, Llorente | N/A |

The 29-gene signature is heavily comprised of stromal expressing genes, where increasing expression from healthy to benign to PIN to tumor was observed in Gleason 8 samples, for a subset of 13 genes, including C1QA, C1QB, C1QC, CD52, FCGR2C, LTBP2, ITGA11, MAXD1, THBS2, SFRP4, TNS3, BGN and HLA-DRB3. In Gleason 6 samples, expression levels in stroma were predominantly unchanged, with the exception being a subset of 4 genes with a decreasing trend from healthy to benign to PIN to tumor, PRELP, SerpinG1, FBLN5 and SULF1. Of the 7 epithelial expression genes, ALCAM, MAL2, CLDN8 and C12orf51 have increasing expression from healthy to benign to PIN to tumor in Gleason 8 samples. HSPA9 and PTP-LAD1 were only increased in the Gleason 8 tumor epithelial samples. No trends were observed in Gleason 8 samples (FIG. 3A-3H).

Genes were identified for which expression levels within the different compartments (T8 vsT6 and sT8 vs sT6) or the magnitude of the differential expression between the compartments (sT8-T8) vs (sT6-T6) (an interaction term in the linear model) were associated with low and high Gleason scores. The stromal or epithelial compartment of origin of these 22 genes was assigned based on the direction of their fold-changes in the comparisons of all epithelial versus all stromal ROIs. The assigned compartment contributed more to the observed difference between the low and high grade by visually inspecting interaction plots.

The compartment of origin of the discriminating genes was confirmed by classifying them as contingently stromal or epithelial based on the direction of their fold-changes in the global comparisons of epithelium vs stroma (T+B+S)/3−(sT+sB+sP)/3, and in comparisons within benign and malignant tissue (B-sB and T-sT respectively) (Table 20). Genes that were significant with fold-changes of 1.5 and above were classified as 'strongly' epithelial or stromal, genes with fold-changes below 1.5 were called 'weakly' epithelial or stromal, and genes that were not statistically significant in these comparisons were classified as 'unclear'. The Protein Atlas database was used as a benchmark for compartmental expression by standard chromogenic IHC in prostate tumor tissue cores (Uhlen M, et al. Tissue-based map of the human proteome, Science, 2015, 347, 6220. DOI: 10.1126/science.1260419). The cancer tissue atlas contains a multitude of human cancer specimens representing the 20 most common forms of cancer, including breast-, colon-, prostate-, lung-, urothelial-, skin-, endometrial- and cervical cancer. Altogether, 216 different cancer samples are used to generate protein expression profiles for all proteins using immunohistochemistry. The data is presented as pathology-based annotation of protein expression levels in tumor cells, along with the images underlying the annotation. This enables the identification of a potential protein signature for each given type of cancer. This provides a starting point for further analyses of cancer type-specific proteins. Because the cancer atlas contains a large number of cancer samples the protein profiles provide a starting point for further analysis and identification of new potential cancer biomarkers.

TABLE 20

The compartment of origin of the discriminating genes

| Gene | Significant comparison | Origin of difference between grades | Global comparisons status | Malignant comparisons status | Benign comparisons status | Protein atlas Malignant |
|---|---|---|---|---|---|---|
| AEBP1 | S, I | S | strongly stromal | strongly stromal | strongly stromal | Stromal |
| ALCAM | E, I | E | weakly epithelial | weakly epithelial | weakly epithelial | Strongly epithelial |
| BGN | S | S | strongly stromal | strongly stromal | strongly stromal | stromal |
| C12orf51 | I | E | weakly epithelial | weakly epithelial | weakly epithelial | epithelial |
| C1QA | S, I | S | strongly stromal | strongly stromal | strongly weakly | Weakly stroma, epithelial |
| C1QB | S | S | strongly stromal | strongly stromal | strongly stromal | Negative |
| C1QC | S | S | strongly stromal | strongly stromal | strongly stromal | Weakly stromal |
| C1S | S | S | strongly stromal | strongly stromal | strongly | Negative |
| CD52 | I | S | strongly stromal | strongly stromal | weakly stromal | No IHC available |
| CLDN8 | I | E | weakly epithelial | weakly epithelial | unclear | Strongly epithelial |
| COL1A1 | S | S | strongly stromal | strongly stromal | strongly stromal | Stromal |
| FBLN5 | S, I | S | strongly stromal | strongly stromal | strongly stromal | Stromal |
| FCGR2C | S, I | S | weakly stromal | strongly stromal | weakly stromal | No IHC available |
| HLA-DRB3 | S | S | strongly stromal | strongly stromal | strongly stromal | No IHC available |
| HSPA9 | I | E | weakly epithelial | weakly epithelial | weakly epithelial | Strongly epithelial, weakly stroma |
| ITGA11 | I | S | weakly stromal | weakly stromal | weakly stromal | Strongly epithelial, weakly stromal |
| LTBP2 | I | S | weakly stromal | strongly stromal | weakly stromal | Stromal |
| LUM | S | S | strongly stromal | strongly stromal | strongly stromal | Stromal |

TABLE 20-continued

The compartment of origin of the discriminating genes

| Gene | Significant comparison | Origin of difference between grades | Global comparisons status | Malignant comparisons status | Benign comparisons status | Protein atlas Malignant |
|---|---|---|---|---|---|---|
| MAL2 | I | E | strongly epithelial | strongly epithelial | weakly epithelial | Negative |
| MOXD1 | S, I | S | strongly stromal | strongly stromal | weakly stromal | Weakly stromal |
| PRELP | I | S | strongly stromal | strongly stromal | strongly stromal | Strongly stromal |
| PTPLAD1 | I | E | weakly epithelial | weakly epithelial | unclear weakly | Strongly epithelial, stromal |
| SERPING1 | I | S | strongly stromal | strongly stromal | strongly stromal | Stromal |
| SFRP2 | S, I | S | strongly stromal | strongly stromal | strongly stromal | Weakly stromal |
| SFRP4 | S, I | S | strongly stromal | strongly stromal | unclear | Negative |
| SULF1 | S, I | S | strongly stromal | strongly stromal | strongly stromal | Strongly stromal |
| THBS2 | S, I | S | strongly stromal | strongly stromal | weakly stromal | Strongly stromal |
| TMEM205 | I | E | weakly epithelial | weakly epithelial | weakly epithelial | Strongly epithelial |
| TNS3 | I | S | weakly stromal | weakly stromal | weakly stromal | stromal |

Example 8: Crosstalk Analysis Reveals Tumor-Stromal Interactions that Distinguish Gleason 6 from Gleason 8

Figure 3A:
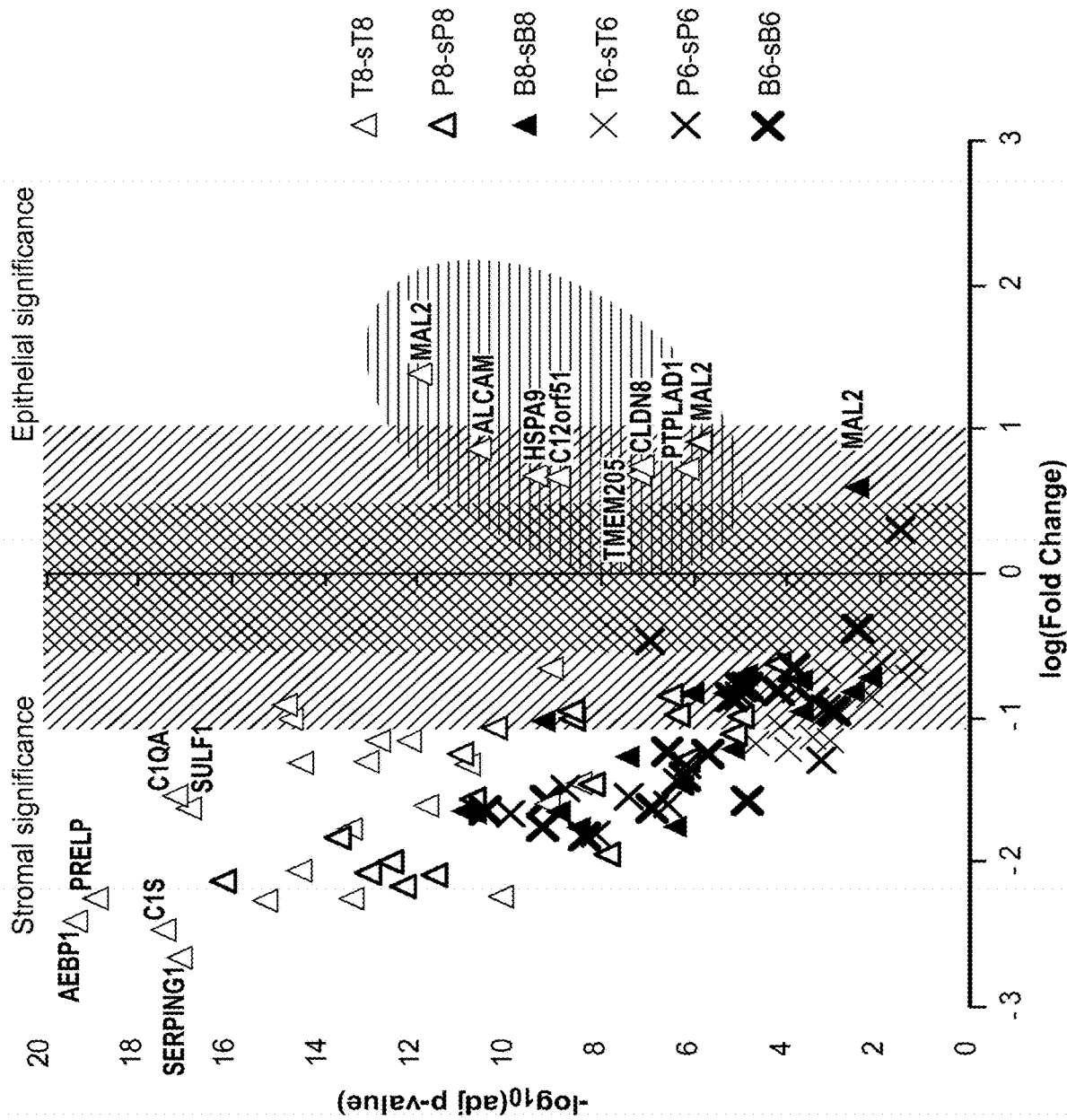
FIG. 3A is a volcano plot for Gleason comparisons of epithelium (B, P, T) and stroma (sB, SP, sT) showing FDR value [$-\log_{10}$)] versus fold change [$\log_2$].
Figure 3B:
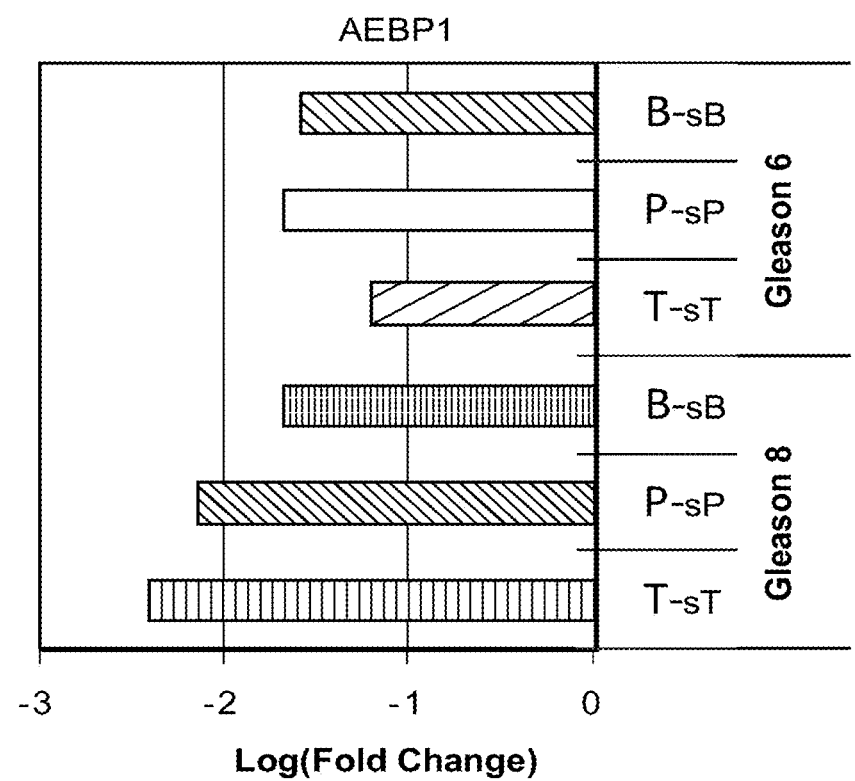
FIG. 3B is a bar chart showing the stromal over-expressing gene, AEBP1, plotted in relation to Gleason score and progression trend.
Figure 3C:
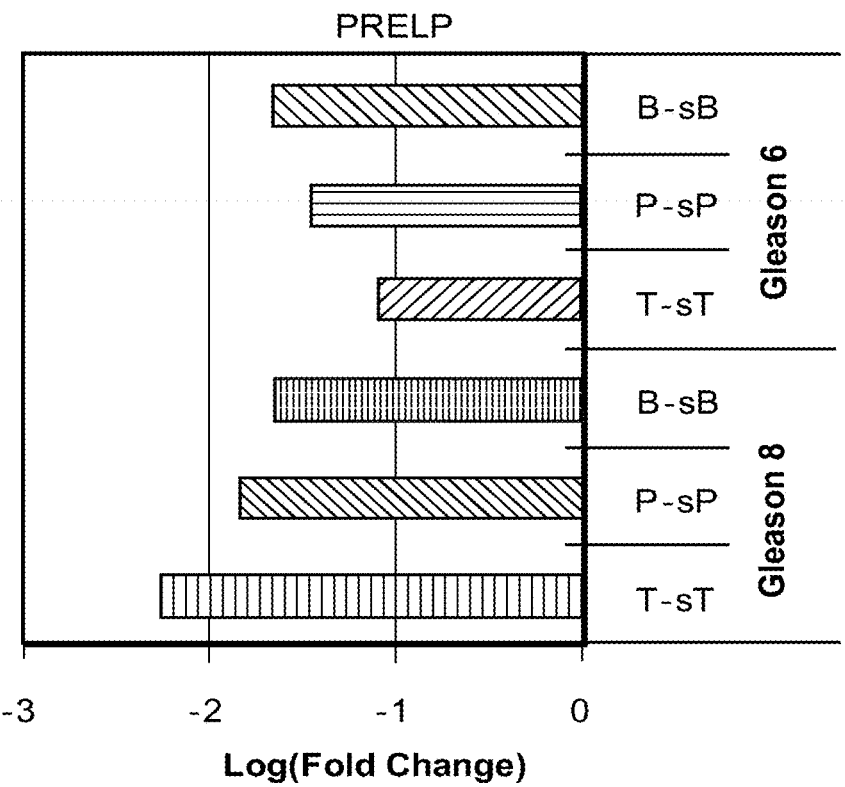
FIG. 3C is a bar chart showing the stromal over-expressing gene, PRELP, plotted in relation to Gleason score and progression trend.
Figure 3D:
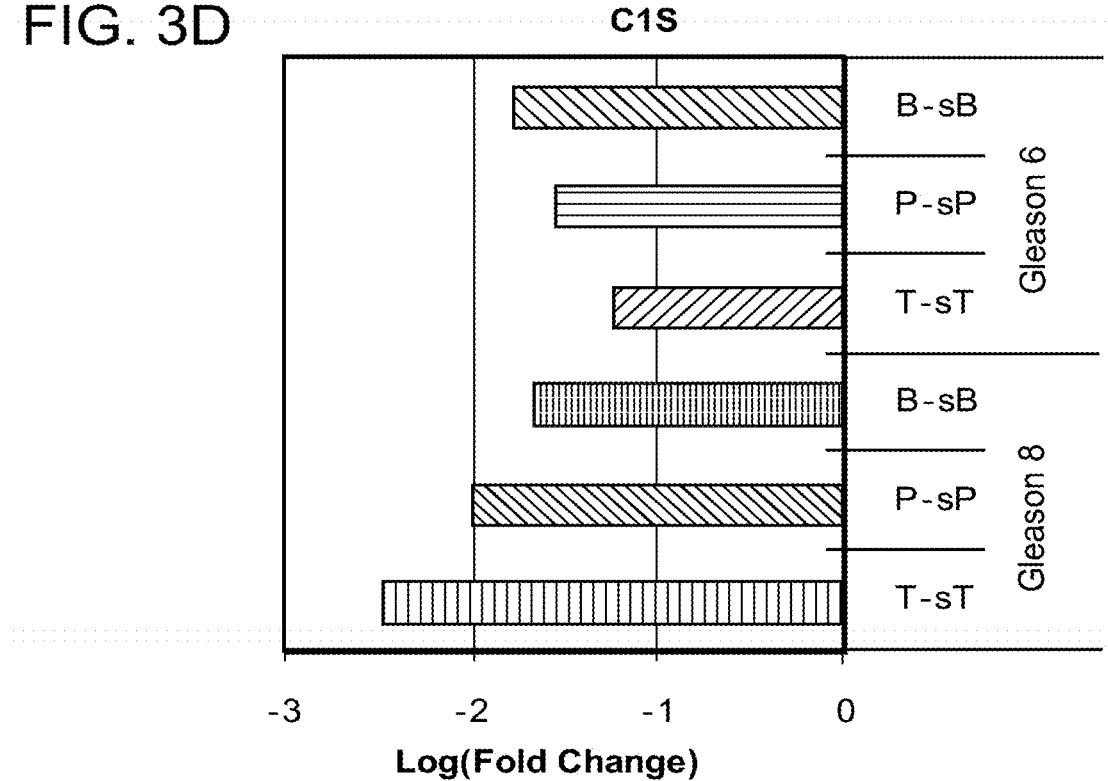
FIG. 3D is a bar chart showing the stromal over-expressing gene, C1S, plotted in relation to Gleason score and progression trend.
Figure 3E:
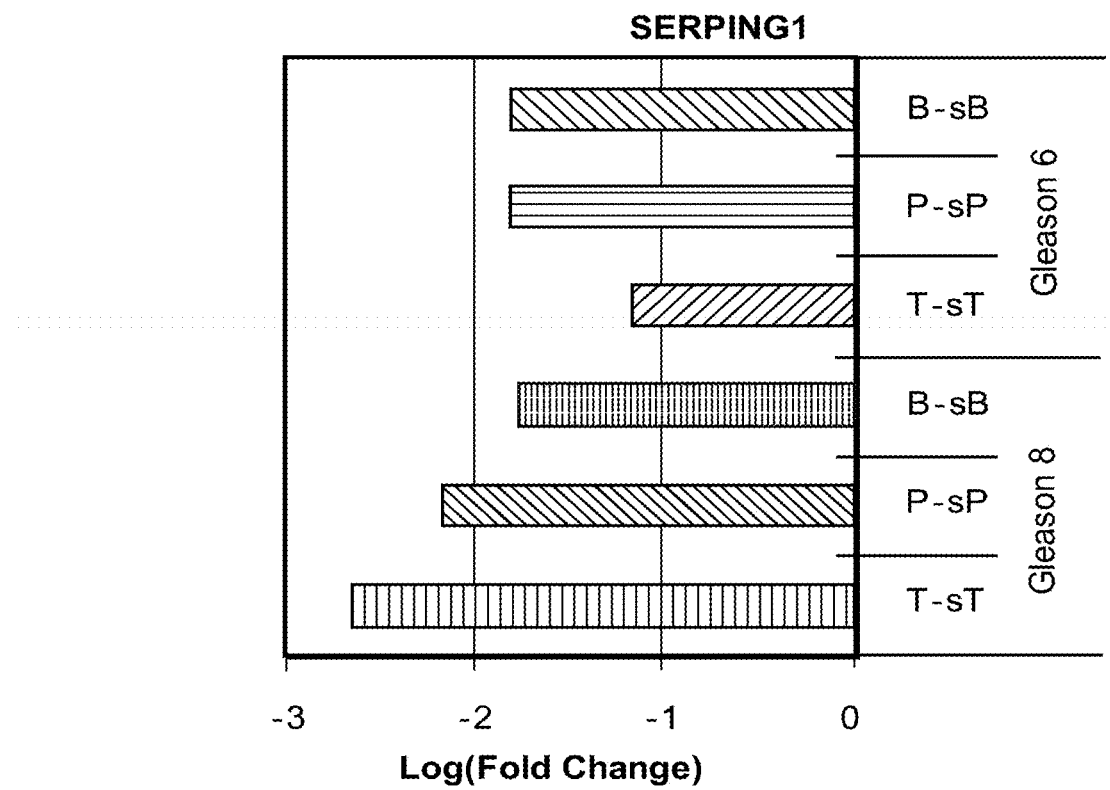
FIG. 3E is a bar chart showing the stromal over-expressing gene, SERPING1, plotted in relation to Gleason score and progression trend.
Figure 3F:
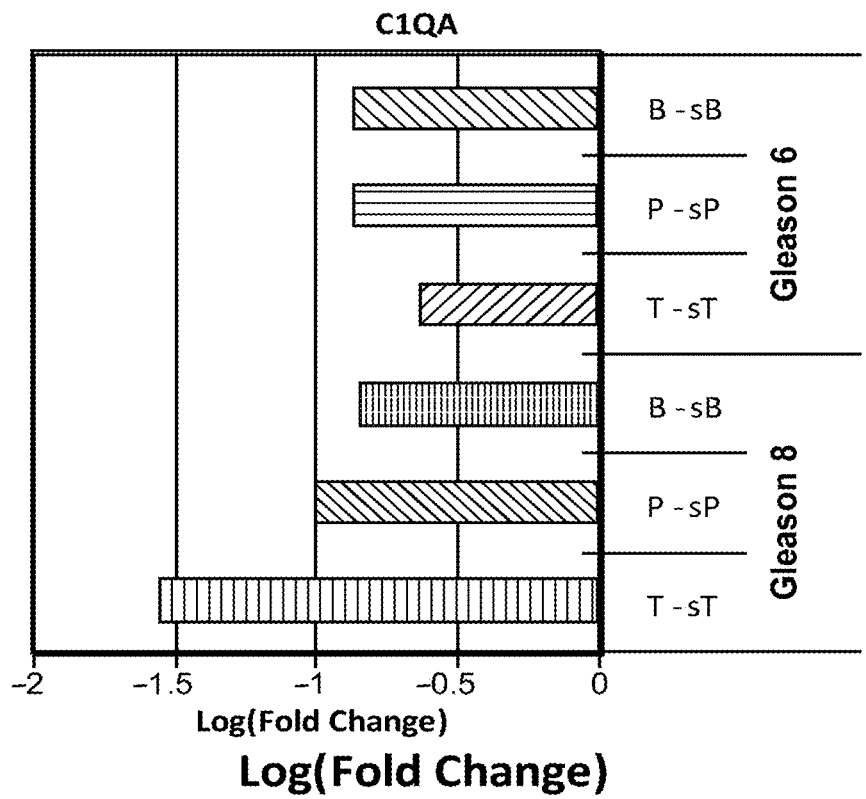
FIG. 3F is a bar chart showing the stromal over-expressing gene, C1QA, plotted in relation to Gleason score and progression trend.
Figure 3G:
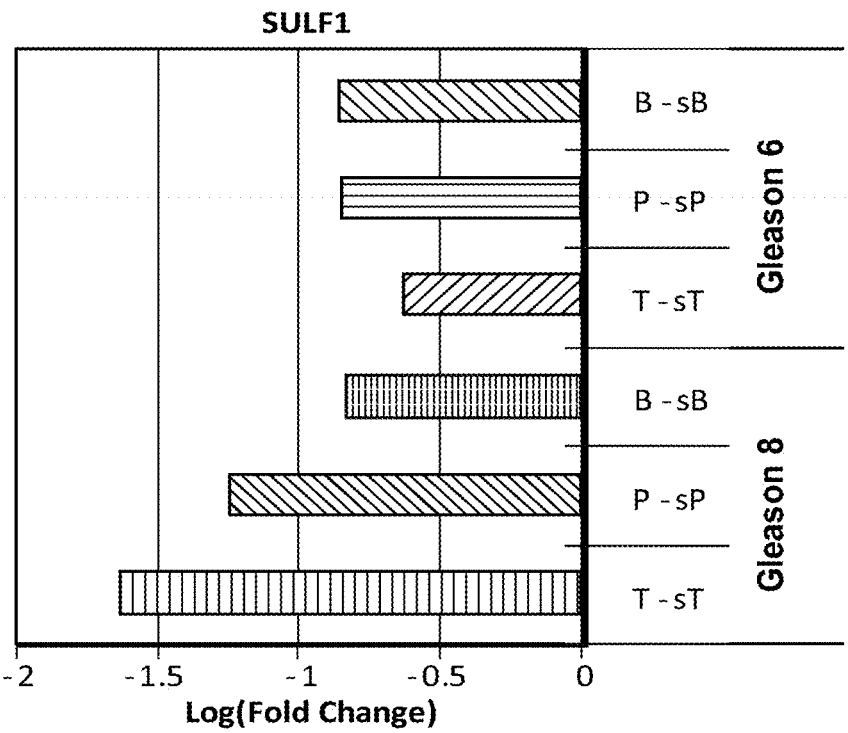
FIG. 3G is a bar chart showing the stromal over-expressing gene, SULF1, plotted in relation to Gleason score and progression trend.
Figure 3H:
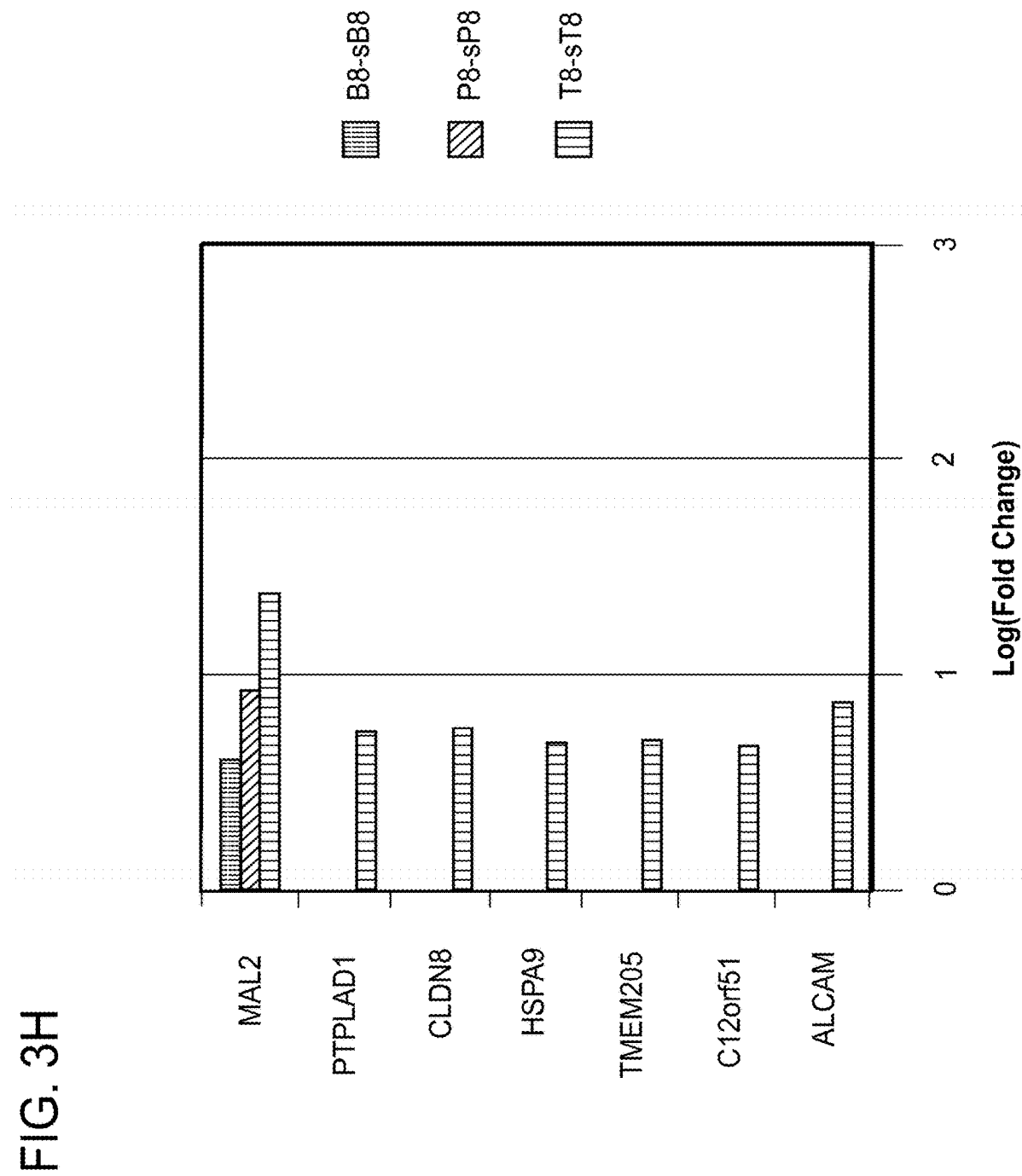
FIG. 3H is a bar chart plotted as log(fold change), showing Gleason 8 epithelial expression genes, where MAL2 was the only gene observed to be over-expressed in the [B8-sB8] and [P8-sP8] comparisons. MAL2 shows an increasing trend associated with progression.

The GAB-SUB crosstalk model facilitated the discovery of tumor-stroma gene associations that separate Gleason 8 from Gleason 6 cases that were not found by standard comparative analysis of differentially expressed genes. 22% of the crosstalk interactions represented the top 10 stroma-expressed genes, whereas 55% of all crosstalk interactions were associated with the top 10 tumor-expressing genes. The most prominent stroma-expressed gene was NPNT, found in 13 crosstalk interactions. The most prominent tumor-expressed gene was ST6GAL1, found in 61 crosstalk interactions as shown in FIGS. 4A and 4B. The top 10 gene pair lists were tabulated with cross-correlation coefficients and associated p-value provided in Table 13. A number of the 29-gene signature were represented in the correct compartment within the top 10 interactions, therefore the crosstalk model to the 29-gene signature was applied and 10/29 genes were found to be represented in many statistically significant interactions, accounting for 10% of all tumor-stromal associations that differentiate Gleason 8 from Gleason 6 (n=500 gene pairs, cross-correlation >0.76). These 10 stromal genes (C1QB, C1QC, SERPING1, C1S, PRELP, FBLN5, C1QA, AEBP1, BGN, and COL1A1) interacted with 22 "tumor-expressing" genes (FIG. 4C). PRELP was the most prominent gene of the 29-gene signature interacting with 11/22 "tumor-expressing" genes. The 22 genes comprised 8 of the top 10 most frequently found genes representing the tumor-expressing component of the crosstalk. On the flip side MAL2 was the most prominent epithelial gene from the 29-gene signature interacting with 28 "stromal-expressing" genes (FIG. 4D). The cross-correlation coefficients and p-value significance are tabulated in Table 14. The results of enrichment analysis showing associated GO processes and MSigDB hallmarks of cancer both gene sets are provided in Table 15 and Table 16, respectively. For the 22 tumor-expressing genes, there was predominant fatty acid metabolism enrichment with estrogen response featuring significantly in the hallmark gene sets. For the 28 stroma-expressing genes, there was a mix of GO processes involving the G-protein coupled acetylcholine receptor signaling pathway and calcium signaling with androgen responsiveness identified in the hallmark data sets. The two most prominently identified stromal-expressing and epithelial-expressing genes that differentiate Gleason 6 from Gleason 8 tumors via the crosstalk model were also highly significant from the volcano plot (FIG. 3A). Also unsurprisingly, PRELP and MAL2 were a stromal-tumor crosstalk pair of statistical significance (Cross-correlation coefficient: 0.82510, p=$8.38E^{-06}$).

Table 13. Top 10 "tumor-expressing" and "stroma-expressing" genes in the cross-correlation GAPSUB model

| Stroma | Tumor | cross-correlation coefficient | p-value |
|---|---|---|---|
| ANTXR1 | GSTT1 | 0.950544456 | 2.09E–06 |
| ANTXR1 | MAL2 | 0.886398601 | 4.19E–06 |
| ANTXR1 | ANO7 | 0.884275724 | 4.19E–06 |
| ANTXR1 | H19 | 0.847272727 | 8.38E–06 |
| ANTXR1 | unknown | 0.834160839 | 8.38E–06 |
| ANTXR1 | SNORA28 | 0.831468531 | 8.38E–06 |
| ANTXR1 | ST6GAL1 | 0.780364635 | 3.98E–05 |
| ANTXR1 | NCAPD3 | 0.772672328 | 4.40E–05 |
| ANTXR1 | UBAP2L | 0.763761239 | 5.24E–05 |
| ANTXR1 | SNORA58 | 0.763431568 | 5.24E–05 |
| CSGALNACT1 | MT1M | 0.917427572 | 4.19E–06 |
| CSGALNACT1 | MUC3A | 0.90018981 | 4.19E–06 |
| CSGALNACT1 | CCL5 | 0.886478521 | 4.19E–06 |
| CSGALNACT1 | SNAI2 | 0.866703297 | 6.28E–06 |
| CSGALNACT1 | C8orf4 | 0.859240759 | 6.28E–06 |
| CSGALNACT1 | ID1 | 0.855829171 | 6.28E–06 |
| CSGALNACT1 | MT1A | 0.853271728 | 8.38E–06 |
| CSGALNACT1 | MT1H | 0.831148851 | 8.38E–06 |
| CSGALNACT1 | MT1L | 0.784045954 | 3.35E–05 |
| CSGALNACT1 | LAPTM5 | 0.774460539 | 4.19E–05 |
| CSGALNACT1 | SOD2 | 0.768926074 | 4.82E–05 |
| CYB561 | ACSL1 | 0.921783217 | 4.19E–06 |
| CYB561 | ORMDL2 | 0.850704296 | 8.38E–06 |
| CYB561 | ST6GAL1 | 0.838081918 | 8.38E–06 |

| Stroma | Tumor | cross-correlation coefficient | p-value |
|---|---|---|---|
| CYB561 | IRF6 | 0.816568432 | 1.26E−05 |
| CYB561 | SNORA28 | 0.807442557 | 1.88E−05 |
| CYB561 | RGS2 | 0.804025974 | 1.88E−05 |
| CYB561 | GSTT1 | 0.802167832 | 2.09E−05 |
| CYB561 | DSP | 0.782857143 | 3.56E−05 |
| CYB561 | MAL2 | 0.768721279 | 4.82E−05 |
| HIST1H4C | CSGALNACT1 | 1.11011988 | 0 |
| HIST1H4C | NCAPD3 | 1.077417582 | 0 |
| HIST1H4C | ANO7 | 0.988201798 | 0 |
| HIST1H4C | ST6GAL1 | 0.947782218 | 2.09E−06 |
| HIST1H4C | MSMB | 0.887292707 | 4.19E−06 |
| H1ST1H4C | MT1L | 0.88492008 | 4.19E−06 |
| HIST1H4C | CDH1 | 0.873091908 | 6.28E−06 |
| HIST1H4C | CHRNA2 | 0.8498002 | 8.38E−06 |
| HIST1H4C | HERPUD1 | 0.826793207 | 8.38E−06 |
| HIST1H4C | FKBP5 | 0.821168831 | 1.05E−05 |
| HIST1H4C | K1AA1324 | 0.795114885 | 2.72E−05 |
| NPNT | TRPS1 | 1.011933067 | 0 |
| NPNT | ST6GAL1 | 0.96958042 | 2.09E−06 |
| NPNT | STEAP4 | 0.868391608 | 6.28E−06 |
| NPNT | CACNA1D | 0.85532967 | 6.28E−06 |
| NPNT | LRIG1 | 0.838246753 | 8.38E−06 |
| NPNT | IGFBP7 | 0.797697303 | 2.51E−05 |
| NPNT | ZNF587 | 0.792692308 | 2.72E−05 |
| NPNT | TNC | 0.792347652 | 2.72E−05 |
| NPNT | IFITM3 | 0.783776224 | 3.35E−05 |
| NPNT | KCNN4 | 0.776128871 | 4.19E−05 |
| NPNT | Y_RNA.1-530 | 0.771638362 | 4.61E−05 |
| NPNT | MLPH | 0.763971029 | 5.24E−05 |
| NPNT | TAGLN | 0.763756244 | 5.24E−05 |
| PRELP | ST6GAL1 | 0.921408591 | 4.19E−06 |
| PRELP | ERG | 0.92032967 | 4.19E−06 |
| PRELP | GSTT1 | 0.908156843 | 4.19E−06 |
| PRELP | ANO7 | 0.871303696 | 6.28E−06 |
| PRELP | SNORA28 | 0.870859141 | 6.28E−06 |
| PRELP | APOD | 0.861288711 | 6.28E−06 |
| PRELP | SNORA58 | 0.847627373 | 8.38E−06 |
| PRELP | MAL2 | 0.825104895 | 8.38E−06 |
| PRELP | TRPS1 | 0.822617383 | 8.38E−06 |
| PRELP | K1AA1324 | 0.8149001 | 1.26E−05 |
| PRELP | WWC1 | 0.768126873 | 4.82E−05 |
| RCAN3 | SERPINA3 | 1.117957043 | 0 |
| RCAN3 | SOD2 | 0.931023976 | 4.19E−06 |
| RCAN3 | MT1A | 0.918976024 | 4.19E−06 |
| RCAN3 | ST6GAL1 | 0.914235764 | 4.19E−06 |
| RCAN3 | ELOVL5 | 0.822907093 | 8.38E−06 |
| RCAN3 | YRNA.1-850 | 0.811928072 | 1.47E−05 |
| RCAN3 | PRDX6 | 0.811793607 | 1.47E−05 |
| RCAN3 | PMEPA1 | 0.77491009 | 4.19E−05 |
| RCAN3 | RNU4-7P | 0.762727273 | 5.24E−05 |
| RCAN3 | IRF6 | 0.762692308 | 5.24E−05 |
| SGK269 | ST6GAL1 | 1.020434565 | 0 |
| SGK269 | RGS2 | 0.943351648 | 4.19E−06 |
| SGK269 | SOD2 | 0.934365634 | 4.19E−06 |
| SGK269 | HSD17B4 | 0.914605395 | 4.19E−06 |
| 8GK269 | SLC14A1 | 0.839360639 | 8.38E−06 |
| SGK269 | SERPINA3 | 0.815604396 | 1.26E−05 |
| SGK269 | Y_RNA.1-850 | 0.813601399 | 1.47E−05 |
| SGK269 | LRP1 | 0.79994006 | 2.09E−05 |
| SGK269 | Y_RNA.1-353 | 0.797927073 | 2.51E−05 |
| SGK269 | GDF15 | 0.787502498 | 2.72E−05 |
| 8GK269 | MT1A | 0.770729271 | 4.61E−05 |
| SOAT1 | ST6GAL1 | 1.159180819 | 0 |
| SOAT1 | ANO7 | 0.988621379 | 0 |
| SOAT1 | TRPS1 | 0.94488012 | 2.09E−06 |
| SOAT1 | IRF6 | 0.928446553 | 4.19E−06 |
| SOAT1 | MAL2 | 0.901238761 | 4.19E−06 |
| SOAT1 | RGS2 | 0.802912088 | 2.09E−05 |
| SOAT1 | FASN | 0.788851149 | 2.72E−05 |
| SOAT1 | ACSL1 | 0.783921079 | 3.35E−05 |
| SOAT1 | STEAP4 | 0.768601399 | 4.82E−05 |
| ZNF577 | ANO7 | 1.28008991 | 0 |
| ZNF577 | VEGFA | 1.279495504 | 0 |
| ZNF577 | MT1L | 0.978386613 | 0 |
| ZNF577 | ACSL1 | 0.955834166 | 2.09E−06 |
| ZNF577 | NCAPD3 | 0.893131868 | 4.19E−06 |
| ZNF577 | AZGP1 | 0.879665335 | 4.19E−06 |
| ZNF577 | CHRNA2 | 0.84543956 | 8.38E−06 |
| ZNF577 | UPK1A | 0.843781219 | 8.38E−06 |
| ZNF577 | IGF1R | 0.837982018 | 8.38E−06 |
| ZNF577 | ID2 | 0.808566434 | 1.88E−05 |
| C1QB | ACSL1 | 0.867377622 | 6.28E−06 |
| C1QC | ACSL1 | 0.862767233 | 6.28E−06 |
| C1R | ACSL1 | 0.794150849 | 2.72E−05 |
| CPLX3 | ACSL1 | 0.848311688 | 8.38E−06 |
| FGFR1 | ACSL1 | 0.784000999 | 3.35E−05 |
| GJA1 | ACSL1 | 0.827652348 | 8.38E−06 |
| H19 | ACSL1 | 0.800909091 | 2.09E−05 |
| MT1F | ACSL1 | 0.810864136 | 1.68E−05 |
| NANS | ACSL1 | 1.109515485 | 0 |
| PRRX1 | ACSL1 | 0.786743257 | 2.93E−05 |
| RHOJ | ACSL1 | 0.777012987 | 4.19E−05 |
| SAR1B | ACSL1 | 0.873006993 | 6.28E−06 |
| SCARNA17 | ACSL1 | 0.918256743 | 4.19E−06 |
| SEC11C | ACSL1 | 0.794120879 | 2.72E−05 |
| SERPING1 | ACSL1 | 0.864515485 | 6.28E−06 |
| SPATA13 | ACSL1 | 0.956008991 | 2.09E−06 |
| AHNAK2 | ANO7 | 0.855929071 | 6.28E−06 |
| BAIAP2L1 | ANO7 | 0.969010989 | 2.09E−06 |
| C15orf21 | ANO7 | 0.914545455 | 4.19E−06 |
| C1S | ANO7 | 0.777427572 | 3.98E−05 |
| CCDC80 | ANO7 | 1.133826174 | 0 |
| CD248 | ANO7 | 0.831638362 | 8.38E−06 |
| COL6A3 | ANO7 | 0.787707293 | 2.72E−05 |
| CRYAB | ANO7 | 0.961118881 | 2.09E−06 |
| CYBRD1 | ANO7 | 0.777442557 | 3.98E−05 |
| DCN | ANO7 | 0.865539461 | 6.28E−06 |
| ENTPD5 | ANO7 | 0.964170829 | 2.09E−06 |
| FGFR1 | ANO7 | 0.816098901 | 1.26E−05 |
| IRF6 | ANO7 | 0.774745255 | 4.19E−05 |
| ISLR | ANO7 | 0.845919081 | 8.38E−06 |
| K1F5C | ANO7 | 0.776893107 | 4.19E−05 |
| LTBP1 | ANO7 | 0.84496004 | 8.38E−06 |
| MFAP4 | ANO7 | 0.77523976 | 4.19E−05 |
| MMP2 | ANO7 | 0.851713287 | 8.38E−06 |
| ORMDL2 | ANO7 | 0.937547453 | 4.19E−06 |
| PCOLCE | ANO7 | 0.873056943 | 6.28E−06 |
| PHLDB1 | ANO7 | 0.817702298 | 1.26E−05 |
| PLEKHH1 | ANO7 | 0.866048951 | 6.28E−06 |
| PODN | ANO7 | 0.962167832 | 2.09E−06 |
| PPP1R14A | ANO7 | 0.825114895 | 8.38E−06 |
| PRAC | ANO7 | 0.814310689 | 1.47E−05 |
| PRNP | ANO7 | 0.856878122 | 6.28E−06 |
| RNU6-1089P-201 | ANO7 | 0.84954046 | 8.38E−06 |
| S100A6 | ANO7 | 0.827227772 | 8.38E−06 |
| SAR1B | ANO7 | 0.763686314 | 5.24E−05 |
| SERPING1 | ANO7 | 0.812402597 | 1.47E−05 |
| SLC30A4 | ANO7 | 0.841468531 | 8.38E−06 |
| SNORD102 | ANO7 | 0.797492507 | 2.51E−05 |
| SPARCL1 | ANO7 | 0.801198801 | 2.09E−05 |
| SPTBN2 | ANO7 | 0.799015984 | 2.30E−05 |
| TBC1D4 | ANO7 | 0.911488511 | 4.19E−06 |
| TIMP2 | ANO7 | 0.81475025 | 1.26E−05 |
| TIMP3 | ANO7 | 0.958051948 | 2.09E−06 |
| TIMP3 | ANO7 | 0.927767233 | 4.19E−06 |
| TSPAN18 | ANO7 | 0.768906094 | 4.82E−05 |
| WWTR1 | ANO7 | 0.866718282 | 6.28E−06 |
| AEBP1 | GSTT1 | 0.873971029 | 6.28E−06 |
| AQP1 | GSTT1 | 0.949180819 | 2.09E−06 |
| BGN | GSTT1 | 0.780559441 | 3.98E−05 |
| C1R | GSTT1 | 0.835849151 | 8.38E−06 |
| C1S | GSTT1 | 0.812297702 | 1.47E−05 |
| CAP2 | GSTT1 | 0.832387612 | 8.38E−06 |
| CCDC80 | GSTT1 | 0.765784216 | 5.03E−05 |
| COL6A3 | GSTT1 | 0.771873127 | 4.61E−05 |
| CYBRD1 | GSTT1 | 0.881098901 | 4.19E−06 |
| DCN | GSTT1 | 0.871093906 | 6.28E−06 |
| EFEMP2 | GSTT1 | 0.903211788 | 4.19E−06 |
| HCST | GSTT1 | 1.025689311 | 0 |
| HMGCS2 | GSTT1 | 0.828186813 | 8.38E−06 |
| IGFBP7 | GSTT1 | 0.872517483 | 6.28E−06 |

| Stroma | Tumor | cross-correlation coefficient | p-value |
|---|---|---|---|
| LAPTM5 | GSTT1 | 0.844775225 | 8.38E−06 |
| LGALS1 | GSTT1 | 0.868936064 | 6.28E−06 |
| LTBP1 | GSTT1 | 0.811473526 | 1.68E−05 |
| MATN2 | GSTT1 | 0.813006993 | 1.47E−05 |
| MGP | GSTT1 | 1.040534466 | 0 |
| MSN | GSTT1 | 0.859125874 | 6.28E−06 |
| PDGFRB | GSTT1 | 0.839000999 | 8.38E−06 |
| PEBP4 | GSTT1 | 0.806203796 | 1.88E−05 |
| PRRX1 | GSTT1 | 0.793741259 | 2.72E−05 |
| TCF21 | GSTT1 | 0.835274725 | 8.38E−06 |
| TMEM141 | GSTT1 | 0.799490509 | 2.09E−05 |
| ACSL1 | IRF6 | 0.859095904 | 6.28E−06 |
| DHRS7 | IRF6 | 0.770709291 | 4.61E−05 |
| FLNB | IRF6 | 0.803241758 | 1.88E−05 |
| GJA1 | IRF6 | 0.987847153 | 0 |
| HOMER2 | IRF6 | 0.838906094 | 8.38E−06 |
| HOXB13 | IRF6 | 0.930324675 | 4.19E−06 |
| IGF2 | IRF6 | 0.907017982 | 4.19E−06 |
| KLK4 | IRF6 | 0.7795005 | 3.98E−05 |
| NANS | IRF6 | 0.834440559 | 8.38E−06 |
| ODC1 | IRF6 | 0.762662338 | 5.24E−05 |
| PRSS8 | IRF6 | 0.809180819 | 1.88E−05 |
| SAT1 | IRF6 | 0.859390609 | 6.28E−06 |
| srn | IRF6 | 0.783011988 | 3.35E−05 |
| SLC30A4 | IRF6 | 0.960984016 | 2.09E−06 |
| SYT7 | IRF6 | 0.977172827 | 0 |
| ABHD2 | MAL2 | 0.91487013 | 4.19E−06 |
| AHNAK2 | MAL2 | 0.773731269 | 4.19E−05 |
| CAMKK2 | MAL2 | 0.783431568 | 3.35E−05 |
| CHRM1 | MAL2 | 0.932227772 | 4.19E−06 |
| DHCR24 | MAL2 | 0.76976024 | 4.61E−05 |
| DHRS7 | MAL2 | 0.798386613 | 2.51E−05 |
| FAAH | MAL2 | 0.838416583 | 8.38E−06 |
| GSTT1 | MAL2 | 1.087812188 | 0 |
| HOMER2 | MAL2 | 0.896083916 | 4.19E−06 |
| HOXB13 | MAL2 | 0.897002997 | 4.19E−06 |
| IRF6 | MAL2 | 1.042782218 | 0 |
| LRIG1 | MAL2 | 0.869435564 | 6.28E−06 |
| MON1B | MAL2 | 0.777677323 | 3.98E−05 |
| NDUFA2 | MAL2 | 0.865384615 | 6.28E−06 |
| NR2F1 | MAL2 | 0.767647353 | 4.82E−05 |
| ODC1 | MAL2 | 0.898081918 | 4.19E−06 |
| SLC30A4 | MAL2 | 1.041303696 | 0 |
| SPINT2 | MAL2 | 0.770654346 | 4.61E−05 |
| SPOCK1 | MAL2 | 0.787767233 | 2.72E−05 |
| SPTBN2 | MAL2 | 0.796323676 | 2.51E−05 |
| SYT7 | MAL2 | 0.950659341 | 2.09E−06 |
| TBC1D4 | MAL2 | 0.859310689 | 6.28E−06 |
| ZG16B | MAL2 | 0.852617383 | 8.38E−06 |
| AHNAK2 | MT1A | 0.781478521 | 3.77E−05 |
| C15orf21 | MT1A | 0.775174825 | 4.19E−05 |
| CD68 | MT1A | 0.816303696 | 1.26E−05 |
| DPYSL2 | MT1A | 0.944180819 | 2.09E−06 |
| HCST | MT1A | 0.782977023 | 3.35E−05 |
| HOMER2 | MT1A | 0.767627373 | 4.82E−05 |
| HOXB13 | MT1A | 0.827212787 | 8.38E−06 |
| MAP7 | MT1A | 0.866418581 | 6.28E−06 |
| MLPH | MT1A | 0.780989011 | 3.98E−05 |
| MOSC1 | MT1A | 0.775334665 | 4.19E−05 |
| SPTBN2 | MT1A | 0.879460539 | 4.19E−06 |
| TBC1D4 | MT1A | 0.808831169 | 1.88E−05 |
| TMC5 | MT1A | 0.996693307 | 0 |
| AP1M2 | RGS2 | 0.871203796 | 6.28E−06 |
| AQP1 | RGS2 | 0.923446553 | 4.19E−06 |
| C1QA | RGS2 | 0.815929071 | 1.26E−05 |
| C1QB | RGS2 | 0.802097902 | 2.09E−05 |
| C1QC | RGS2 | 0.90028971 | 4.19E−06 |
| CD46 | RGS2 | 0.796988012 | 2.51E−05 |
| CD74 | RGS2 | 0.769130869 | 4.82E−05 |
| CDR1 | RGS2 | 0.782767233 | 3.56E−05 |
| CNDP2 | RGS2 | 0.770984016 | 4.61E−05 |
| COL1A1 | RGS2 | 0.82018981 | 1.05E−05 |
| COL1A2 | RGS2 | 0.792272727 | 2.72E−05 |
| DPYSL2 | RGS2 | 0.815644356 | 1.26E−05 |
| FGFR1 | RGS2 | 0.78972028 | 2.72E−05 |
| HCST | RGS2 | 0.846933067 | 8.38E−06 |
| KANK2 | RGS2 | 0.763146853 | 5.24E−05 |
| MMP2 | RGS2 | 0.787747253 | 2.72E−05 |
| PLTP | RGS2 | 0.782547453 | 3.56E−05 |
| PODN | RGS2 | 0.771703297 | 4.61E−05 |
| PPAP2A | RGS2 | 0.875424575 | 4.19E−06 |
| RNASE1 | RGS2 | 1.036083916 | 0 |
| SEC11C | RGS2 | 0.904080919 | 4.19E−06 |
| SERPING1 | RGS2 | 0.83002997 | 8.38E−06 |
| SLC30A4 | RGS2 | 0.785094905 | 3.35E−05 |
| SPATA13 | RGS2 | 0.771843157 | 4.61E−05 |
| WWTR1 | RGS2 | 0.793926074 | 2.72E−05 |
| C12orf75 | SOD2 | 0.785769231 | 3.14E−05 |
| C1S | SOD2 | 0.918836164 | 4.19E−06 |
| CD68 | SOD2 | 0.787957043 | 2.72E−05 |
| CHRM1 | SOD2 | 0.768061938 | 4.82E−05 |
| CTSB | SOD2 | 0.915784216 | 4.19E−06 |
| CYR61 | SOD2 | 0.780679321 | 3.98E−05 |
| DCN | SOD2 | 0.794815185 | 2.72E−05 |
| PLEKHH1 | SOD2 | 0.78473027 | 3.35E−05 |
| PTCH2 | SOD2 | 0.787147852 | 2.93E−05 |
| S100A6 | SOD2 | 0.782707293 | 3.56E−05 |
| SERPING1 | SOD2 | 0.789285714 | 2.72E−05 |
| TBC1D4 | SOD2 | 0.823686314 | 8.38E−06 |
| TIMP2 | SOD2 | 0.822647353 | 8.38E−06 |
| VIM | SOD2 | 0.868651349 | 6.28E−06 |
| A2M | ST6GAL1 | 1.078536464 | 0 |
| ACLY | ST6GAL1 | 0.855604396 | 6.28E−06 |
| ADAM10 | ST6GAL1 | 0.766913087 | 4.82E−05 |
| ALOX15B | ST6GAL1 | 0.856553447 | 6.28E−06 |
| AP1M2 | ST6GAL1 | 0.875689311 | 4.19E−06 |
| AQP1 | ST6GAL1 | 0.772427572 | 4.40E−05 |
| ARHGDIB | ST6GAL1 | 0.942372627 | 4.19E−06 |
| BGN | ST6GAL1 | 0.966558442 | 2.09E−06 |
| C1QB | ST6GAL1 | 1.000054945 | 0 |
| C1QC | ST6GAL1 | 1.137177822 | 0 |
| C1R | ST6GAL1 | 0.917412587 | 4.19E−06 |
| C8orf4 | ST6GAL1 | 0.806623377 | 1.88E−05 |
| CAMKK2 | ST6GAL1 | 0.831073926 | 8.38E−06 |
| CCDC80 | ST6GAL1 | 0.870004995 | 6.28E−06 |
| CCL5 | ST6GAL1 | 0.809210789 | 1.88E−05 |
| CD177 | ST6GAL1 | 0.81530969 | 1.26E−05 |
| CD68 | ST6GAL1 | 0.810814186 | 1.68E−05 |
| CD74 | ST6GAL1 | 0.976558442 | 0 |
| CFD | ST6GAL1 | 0.898291708 | 4.19E−06 |
| CXCR4 | ST6GAL1 | 0.799385614 | 2.30E−05 |
| CYBRD1 | ST6GAL1 | 0.832132867 | 8.38E−06 |
| DCN | ST6GAL1 | 1.171108891 | 0 |
| DPYSL2 | ST6GAL1 | 0.805609391 | 1.88E−05 |
| EBP | ST6GAL1 | 0.786843157 | 2.93E−05 |
| FBLN5 | ST6GAL1 | 1.012557443 | 0 |
| FLNB | ST6GAL1 | 0.989050949 | 0 |
| GPT2 | ST6GAL1 | 0.840724276 | 8.38E−06 |
| GSTT1 | ST6GAL1 | 0.799270729 | 2.30E−05 |
| HCST | ST6GAL1 | 0.950314685 | 2.09E−06 |
| IGF2 | ST6GAL1 | 0.797012987 | 2.51E−05 |
| IGFBP7 | ST6GAL1 | 0.981528472 | 0 |
| IRF6 | ST6GAL1 | 0.813936064 | 1.47E−05 |
| LAPTM5 | ST6GAL1 | 0.919535465 | 4.19E−06 |
| LTBP1 | ST6GAL1 | 0.771723277 | 4.61E−05 |
| MAOA | ST6GAL1 | 0.778406593 | 3.98E−05 |
| MFAP4 | ST6GAL1 | 0.823091908 | 8.38E−06 |
| MGP | ST6GAL1 | 0.893701299 | 4.19E−06 |
| MMP2 | ST6GAL1 | 0.780824176 | 3.98E−05 |
| MON1B | ST6GAL1 | 0.998161838 | 0 |
| MT1F | ST6GAL1 | 0.782967033 | 3.35E−05 |
| PODN | ST6GAL1 | 0.864425574 | 6.28E−06 |
| PPP1R14A | ST6GAL1 | 0.911358641 | 4.19E−06 |
| RNASE1 | ST6GAL1 | 0.837042957 | 8.38E−06 |
| S100A6 | ST6GAL1 | 0.821843157 | 1.05E−05 |
| SEC11C | ST6GAL1 | 0.793586414 | 2.72E−05 |
| SERPING1 | ST6GAL1 | 0.845454545 | 8.38E−06 |
| SLC30A4 | ST6GAL1 | 0.783401598 | 3.35E−05 |
| SPARCL1 | ST6GAL1 | 0.775624376 | 4.19E−05 |
| SYT7 | ST6GAL1 | 0.842347652 | 8.38E−06 |
| TGFB1 | ST6GAL1 | 0.852162837 | 8.38E−06 |
| TIMP2 | ST6GAL1 | 0.854325674 | 8.38E−06 |

-continued

| Stroma | Tumor | cross-correlation coefficient | p-value |
|---|---|---|---|
| VIM | ST6GAL1 | 0.851358641 | 8.38E−06 |
| WWTR1 | ST6GAL1 | 0.849425574 | 8.38E−06 |
| ALOX15B | TRPS1 | 0.826568432 | 8.38E−06 |
| AQP1 | TRPS1 | 0.765814186 | 5.03E−05 |
| C1QA | TRPS1 | 0.942172827 | 4.19E−06 |
| C1QB | TRPS1 | 0.901668332 | 4.19E−06 |
| C1QC | TRPS1 | 1.052432567 | 0 |
| COL6A3 | TRPS1 | 0.789285714 | 2.72E−05 |
| GMPR | TRPS1 | 0.913881119 | 4.19E−06 |
| IRF6 | TRPS1 | 0.804280719 | 1.88E−05 |
| LGALS1 | TRPS1 | 0.788856144 | 2.72E−05 |
| MGP | TRPS1 | 0.926608392 | 4.19E−06 |
| PPP1R14A | TRPS1 | 0.830534466 | 8.38E−06 |
| RNASE1 | TRPS1 | 1.050264735 | 0 |
| SLC30A4 | TRPS1 | 0.821293706 | 1.05E−05 |
| SPARC | TRPS1 | 0.805154845 | 1.88E−05 |
| SPARCL1 | TRPS1 | 0.763871129 | 5.24E−05 |

The top 10 most represented "tumor-expressing" genes in cross-correlation analysis: ANTXR1, CSGALNACT1, CYB561, HIST1H4C, NPNT, PRELP, RCAN3, SGK269, SOAT1 and ZNF577.
The top 10 most represented "stroma-expressing" genes in cross-correlation analysis: ACSL1, ANO7, GSTT1, IRF6, MAL2, MT1A, RGS2, SOD2, ST6GAL1, and TRPS1.
Genes of the 29-gene bone signature associated with Gleason tumor differential expression in tumor samples: MAL2.
Genes of the 29-gene bone signature associated with Gleason tumor differential expression in stoma samples: PRELP, C1QA, C1QB, C1QC, SERPING1, C1S, AEBP1, BGN, COL1A1, and FBLN5.

Table 14. 29-gene signature representation in the cross-correlation GAPSUB model

| Stroma | Tumor | cross-correlation coefficient | p-value |
|---|---|---|---|
| AEBP1 | ERG | 0.79536963 | 2.51E−05 |
| AEBP1 | GSTT1* | 0.873971029 | 6.28E−06 |
| AEBP1 | NCAPD3 | 0.802752248 | 2.09E−-05 |
| AEBP1 | ORMDL2 | 0.791693307 | 2.72E−-05 |
| AEBP1 | SERPINA3 | 0.777407592 | 3.98E−-05 |
| AEBP1 | SNORA28 | 0.806938062 | 1.88E−-05 |
| BGN | GSTT1* | 0.780559441 | 3.98E−-05 |
| BGN | NCAPD3 | 0.788916084 | 2.72E−-05 |
| BGN | ST6GAL1* | 0.966558442 | 2.09E−-06 |
| C1QA | CSPG4 | 0.840074925 | 8.38E−06 |
| C1QA | RGS2* | 0.815929071 | 1.26E−05 |
| C1QA | SNORA58 | 0.800454545 | 2.09E−05 |
| C1QA | TRPS1* | 0.942172827 | 4.19E−06 |
| C1QB | ACSL1* | 0.867377622 | 6.28E−06 |
| C1QB | RGS2* | 0.802097902 | 2.09E−05 |
| C1QB | ST6GAL1* | 1.000054945 | 0 |
| C1QB | TRPS1 | 0.901668332 | 4.19E−06 |
| C1QC | ACSL1* | 0.862767233 | 6.28E−06 |
| C1QC | ELOVL5 | 0.833911089 | 8.38E−06 |
| C1QC | LRIG1 | 0.770699301 | 4.61E−05 |
| C1QC | RGS2* | 0.90028971 | 4.19E−06 |
| C1QC | ST6GAL1* | 1.137177822 | 0 |
| C1QC | TRPS1* | 1.052432567 | 0 |
| C1S | ANO7* | 0.777427572 | 3.98E−05 |
| C1S | ELF3 | 0.787567433 | 2.72E−05 |
| C1S | GSTT1* | 0.812297702 | 1.47E−05 |
| C1S | SNORA28 | 0.811263736 | 1.68E−05 |
| C1S | SNORA58 | 0.808301698 | 1.88E−05 |
| C1S | SOD2* | 0.918836164 | 4.19E−06 |
| COL1A1 | ORMDL2 | 0.78047952 | 3.98E−05 |
| COL1A1 | RGS2* | 0.82018981 | 1.05E−05 |
| FBLN5 | APOD | 0.829445554 | 8.38E−06 |
| FBLN5 | ST6GAL1* | 1.012557443 | 0 |
| PRELP | ANO7* | 0.871303696 | 6.28E−06 |
| PRELP | APOD | 0.861288711 | 6.28E−06 |
| PRELP | ERG | 0.92032967 | 4.19E−06 |
| PRELP | GSTT1* | 0.908156843 | 4.19E−06 |
| PRELP | K1AA1324 | 0.8149001 | 1.26E−05 |
| PRELP | SNORA28 | 0.870859141 | 6.28E−06 |
| PRELP | SNORA58 | 0.847627373 | 8.38E−06 |
| PRELP | ST6GAL1* | 0.921408591 | 4.19E−06 |
| PRELP | TRPS1* | 0.822617383 | 8.38E−06 |
| PRELP | WWC1 | 0.768126873 | 4.82E−05 |
| PRELPA | MAL2* | 0.825104895 | 8.38E−06 |
| SERPING1 | ACSL1* | 0.864515485 | 6.28E−06 |
| SERPING1 | ANO7* | 0.812402597 | 1.47E−05 |
| SERPING1 | C8orf4* | 0.838696304 | 8.38E−06 |
| SERPING1 | RGS2* | 0.83002997 | 8.38E−06 |
| SERPING1 | SOD2* | 0.789285714 | 2.72E−05 |
| SERPING1 | ST6GAL1* | 0.845454545 | 8.38E−06 |
| ABHD2 | MAL2 | 0.91487013 | 4.19E−06 |
| AHNAK2 | MAL2 | 0.773731269 | 4.19E−05 |
| ANTXR1A | MAL2 | 0.886398601 | 4.19E−06 |
| CAMKK2 | MAL2 | 0.783431568 | 3.35E−05 |
| CHRM1 | MAL2 | 0.932227772 | 4.19E−06 |
| CYB561 | MAL2 | 0.768721279 | 4.82E−05 |
| DHCR24 | MAL2 | 0.76976024 | 4.61E−05 |
| DHRS7 | MAL2 | 0.798386613 | 2.51E−05 |
| FAAH | MAL2 | 0.838416583 | 8.38E−06 |
| GSTT1 | MAL2 | 1.087812188 | 0 |
| HOMER2 | MAL2 | 0.896083916 | 4.19E−06 |
| HOXB13 | MAL2 | 0.897002997 | 4.19E−06 |
| IRF6 | MAL2 | 1.042782218 | 0 |
| LRIG1 | MAL2 | 0.869435564 | 6.28E−06 |
| MON1B | MAL2 | 0.777677323 | 3.98E−05 |
| NDUFA2 | MAL2 | 0.865384615 | 6.28E−06 |
| NR2F1 | MAL2 | 0.767647353 | 4.82E−05 |
| ODC1 | MAL2 | 0.898081918 | 4.19E−06 |
| SLC30A4 | MAL2 | 1.041303696 | 0 |
| SOAT1A | MAL2 | 0.901238761 | 4.19E−06 |
| SPINT2 | MAL2 | 0.770654346 | 4.61E−05 |
| SPOCK1 | MAL2 | 0.787767233 | 2.72E−05 |
| SPTBN2 | MAL2 | 0.796323676 | 2.51E−05 |
| SYT7 | MAL2 | 0.950659341 | 2.09E−06 |
| TBC1D4 | MAL2 | 0.859310689 | 6.28E−06 |
| ZG16B | MAL2 | 0.852617383 | 8.38E−06 |
| CALM1 | THBS2 | 0.777727273 | 3.98E−05 |
| TBC1D4 | THBS2 | 1.051033966 | 0 |

Stroma: Genes of the 29-gene bone signature associated with Gleason stromal differential expression: AEBP1, BGN, C1QA, C1QB, C1QC, C1S, COL1A1, FBLN5, PRELP, and SERPING1.

Tumor: Gene of the 29-gene bone signature associated with Gleason tumor differential expression: MAL2.

Tumor: Comprises 22 tumor genes associated with the 10 stromal genes of the 29-gene bone signature that differentiate Gleason: ERG, NCAPD3, ORMDL21, SERPINA3, SNORA28, GSTT1*, NCAPD3, ST6GAL1*, CSPG4, SNORA58, ACSL1*, RGS2*, ELOVL5, LRIG1, ANO7*, ELF3, SOD2*, ORMDL2, APOD, KIAA1324, TRPS1*, WWC1, MAL2*, and C8orf4*.

Stroma: Comprises 28 stroma genes associated with the 2 tumor genes of the 29-gene bone signature that differentiate Gleason: ABHD2, AHNAK2, ANTXR1^, CAMKK2, CHRM1, CYB561^, DHCR24, DHRS7, FAAH, GSTT1, HOMER2, HOXB13, IRF6, LRIG1, MON1B, NDUFA2, NR2F1, ODC1, SLC30A4, SOAT1^, SPINT2, SPOCK1, SPTBN2, SYT7, TBC1D4, ZG16B, CALM1, and TBC1D4.

*Top 10 most represented "tumor-expressing" genes in cross-correlation analysis

^Top 10 most represented "stroma-expressing" genes in cross-correlation analysis Table 15. Enrichment analysis using the GeneGo database, to determine pathways, networks and cellular processes, for the genes found to be differentially expressed in 29-gene signature in the cross-correlation GAP-SUB model Enrichment analysis report Enrichment GO Processes

| # | Processes | Total | pValue | Min FDR | p-value | FDR | In Data | Network Objects from Active Data |
|---|---|---|---|---|---|---|---|---|
| | | | | | 22_TumorGenes_10BoneSigGenes_StromaCrossTalk_genelist | | | |
| 1 | alpha-linolenic acid metabolic process | 12 | 4.079E-07 | 5.099E-04 | 4.079E-07 | 5.099E-04 | 3 | ELOVL5, ACSL1, Acyl-CoA synthetase |
| 2 | long-chain fatty-acyl-CoA | 18 | 1.505E-06 | 8.747E-04 | 1.505E-06 | 8.747E-04 | 3 | ELOVL5, ACSL1, Acyl-CoA synthetase |
| 3 | fatty-acyl-CoA biosynthetic process | 20 | 2.099E-06 | 8.747E-04 | 2.099E-06 | 8.747E-04 | 3 | ELOVL5, ACSL1, Acyl-CoA synthetase |
| 4 | linoleic acid metabolic process | 23 | 3.253E-06 | 1.017E-03 | 3.253E-06 | 1.017E-03 | 3 | ELOVL5, ACSL1, Acyl-CoA synthetase |
| 5 | long-chain fatty-acyl-CoA metabolic process | 26 | 4.764E-06 | 1.191E-03 | 4.764E-06 | 1.191E-03 | 3 | ELOVL5, ACSL1, Acyl-CoA synthetase |
| 6 | acyl-CoA biosynthetic process | 35 | 1.190E-05 | 1.859E-03 | 1.190E-05 | 1.859E-03 | 3 | ELOVL5, ACSL1, Acyl-CoA synthetase |
| 7 | thioester biosynthetic process | 35 | 1.190E-05 | 1.859E-03 | 1.190E-05 | 1.859E-03 | 3 | ELOVL5, ACSL1, Acyl-CoA synthetase |
| 8 | fatty-acyl-CoA metabolic process | 35 | 1.190E-05 | 1.859E-03 | 1.190E-05 | 1.859E-03 | 3 | ELOVL5, ACSL1, Acyl-CoA synthetase |
| 9 | sulfur compound metabolic process | 440 | 1.641E-05 | 2.279E-03 | 1 641E-05 | 2.279E-03 | 6 | ELOVL5, CSPG4 (NG2), ACSL1, GSTT1, Acyl-CoA synthetase, SOD2 |
| 10 | triglyceride biosynthetic process | 47 | 2.918E-05 | 2.918E-03 | 2.918E-05 | 2.918E-03 | 3 | ELOVL5, ACSL1, Acyl-CoA synthetase |
| | | | | | 28_StromaGenes_2BoneSigGenes_TumorCrossTalk_genelist | | | |
| 1 | phospholipase C-activating G-protein coupled acetylcholine receptor signaling pathway | 7 | 2.986E-10 | 5 755E-07 | 2.986E-10 | 5.755E-07 | 4 | Galpha(q)-specific amine GPCRs, Galpha(i)-specific amine GPCRs, ACM1, CHRM |
| 2 | saliva secretion | 10 | 1 785E-09 | 1 720E-06 | 1.785E-09 | 1 720E-06 | 4 | Galpha(q)-specific amine GPCRs, Galpha(i)-specific amine GPCRs, ACM1, CHRM |
| 3 | regulation of phosphatidylinositol dephosphorylation | 4 | 2.083E-08 | 1 338E-05 | 2.083E-08 | 1 338E-05 | 3 | Galpha(q)-specific amine GPCRs, Galpha(i)-specific amine GPCRs, CHRM |
| 4 | behavioral response to cocaine | 19 | 3.257E-08 | 1 431 E-05 | 3.257E-08 | 1.431E-05 | 4 | Homer 2, Homer, Galpha(q)-specific amine GPCRs, Galpha(i)-specific amine GPCRs |
| 5 | regulation of calcium ion-dependent exocytosis | 54 | 4 062E-08 | 1.431E-05 | 4.062E-08 | 1 431 E-05 | 5 | Synaptotagmin, Synaptotagmin VII, SPTBN2, Galpha(i)-specific amine GPCRs, SPTBN(spectrin1-4) |
| 6 | calcium-mediated signaling | 115 | 5 190E-08 | 1 431E-05 | 5.190E-08 | 1 431E-05 | 6 | CaMKK2, Homer 2, Homer, Galpha(q)-specific amine GPCRs, CaMKK, Calmodulin |
| 7 | adenylate cyclase-inhibiting G-protein coupled acetylcholine receptor signaling pathway | 5 | 5.200E-08 | 1.431E-05 | 5.200E-08 | 1.431 E-05 | 3 | Galpha(q)-specific amine GPCRs, Galpha(i)-specific amine GPCRs, CHRM |
| 8 | second-messenger-mediated signaling | 220 | 1 094E-07 | 2 636E-05 | 1 094E-07 | 2.636E-05 | 7 | CaMKK2. Homer 2, Homer, Galpha(q)-specific amine GPCRs, CaMKK, Galpha(i)-specific amine GPCRs, Calmodulin |
| 9 | G-protein coupled acetylcholine receptor signaling pathway | 26 | 1 245E-07 | 2.666E-05 | 1.245E-07 | 2.666E-05 | 4 | Galpha(q)-specific amine GPCRs, Galpha(i)-specific amine GPCRs, ACM1, CHRM |
| 10 | regulation of vascular smooth muscle contraction | 8 | 2.901 E-07 | I 5.591 E-05 | 2.901 E-07 | 5.591 E-05 | 3 | Galpha(q)-specific amine GPCRs, Galpha(i)-specific amine GPCRs, CHRM |

Table 16. Utilization of the MSigDB Hallmark gene sets to compute overlaps in the 29-gene signature in the cross-correlation GAP-SUB model

| Gene Set Name | # Genes in Gene Set (K) | Description | # Genes in Overlap (k) | k/K | p-value | FDR q-value | Genes |
|---|---|---|---|---|---|---|---|
| HALLMARK_ESTROGEN_RESPONSE_EARLY | 200 | Genes defining early response to estrogen. | 4 | 0.02 | 2.39E−06 | 1.20E−04 | ELOVL5, ELF3, LRIG1, WWC1 |
| HALLMARK_PEROXISOME | 104 | Genes encoding components of peroxisome. | 3 | 0.0288 | 1.68E−05 | 4.20E−04 | ELOV5, ACSL1, SOD2 |
| HALLMARK_KRAS_SIGNALING_UP | 200 | Genes up-regulated by KRAS activation. | 3 | 0.015 | 1.18E−04 | 1.96E−04 | SERPINA3, APOD, ST6GAL1 |
| HALLMARK_FATTY_ACID_METABOLISM | 158 | Genes encoding proteins involved in metabolism of fatty acids. | 2 | 0.0127 | 2.59E−03 | 3.24E−04 | ELOVL5, ASCL1 |
| HALLMARK_ESTROGEN_RESPONSE_LATE | 200 | Genes defining late response to estrogen. | 2 | 0.01 | 4.11E−03 | 3.43E−04 | ELOVL5, SERPINA3 |
| HALMARK_MYOGENESIS | 200 | Genes involved in development of skeletal muscle (myogenesis). | 2 | 0.01 | 4.11E−03 | 3.43E−04 | SOD2 ST6GAL1 |
| HALLMARK_ANDROGEN_RESPONSE | 101 | Genes defining response to androgens. | 4 | 0.0396 | 4.32E−07 | 2.16E−05 | DHCR24, ABHD2, HOMER2, CAMKK2 |
| HALLMARK_IL2_STAT5_SIGNALING | 200 | Genes up-regulated by STAT5 in response to IL2 stimulation. | 3 | 0.015 | 2.45E−04 | 6.14E−03 | ODC1, LRIG1, IRF6 |

Figure 5D:
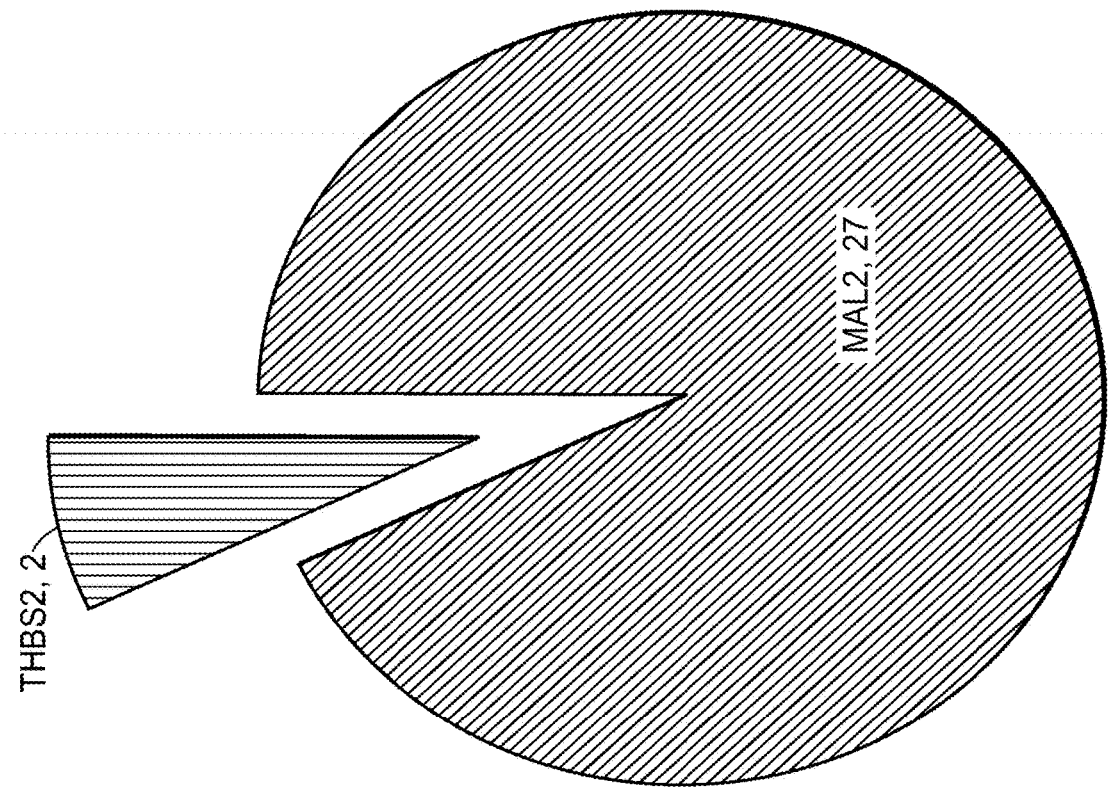
FIG. 5D is a pie chart showing the representation of the 29-gene signature in the GAP-SUB crosstalk model in the epithelial compartment.

22_TumorGenes_10BoneSigGenes_StromaCrossTalk_genelist collective impact of the 29-gene signature whereby the metastatic score was higher than that associated with the primary tumors (FIG. 5D).

Figure 5C:
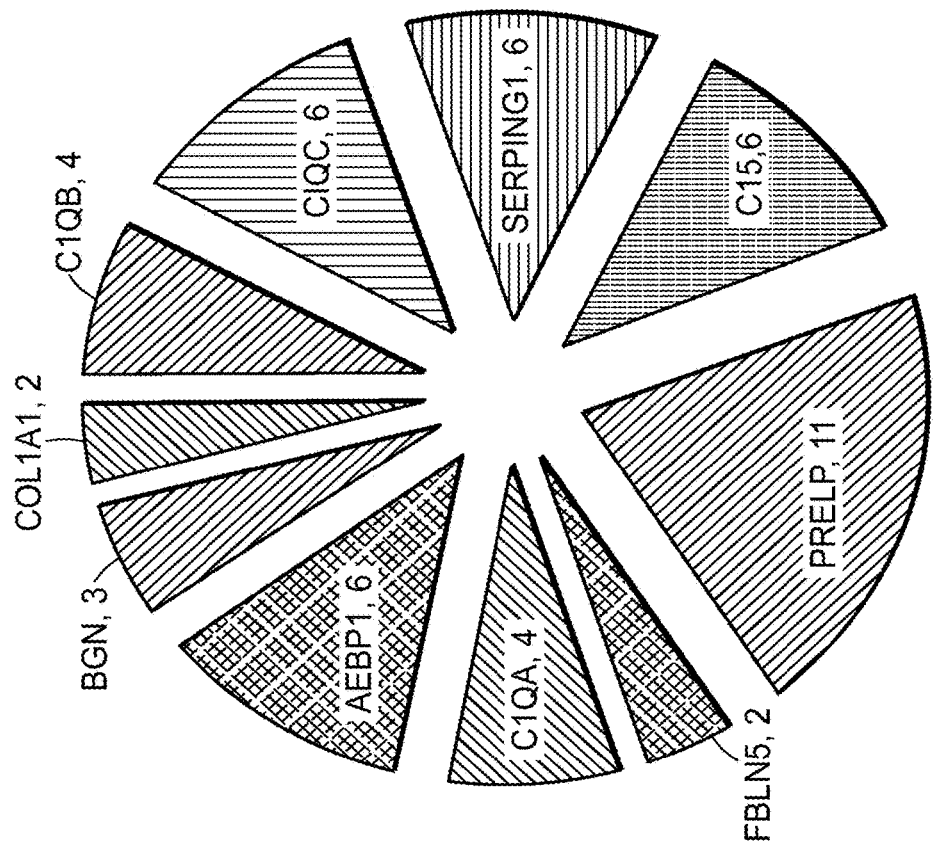
FIG. 5C is a pie chart showing the representation of the 29-gene signature in the GAP-SUB crosstalk model in the stromal compartment.

Example 9: The Stroma Associated with Gleason 8 Tumors Harbors a Bone Formation-Like Signature To establish whether the 29-gene signature could be associated with metastasis to the bone, two clinical studies were assessed that looked at the transcriptional landscape of breast and prostate bone metastatic tissues and/or biopsies, respectively. The first study (GEO Data Set: GSE 14776) was described by Clemons et al. in Clin Exp Metastasis in 2014 (Cawthorn T R, Clin Exp Metastasis. 26, 935-40 (2009)). Bone metastatic and disseminated tumor cells from breast cancer patient biopsies were obtained and gene expression profiles were compared. In FIG. 5A, a heat map for the genes in the 29-gene signature that were identified in the Clemons gene expression dataset were plotted. The signature clearly separates the metastatic tumor samples from the disseminated tumor cells by principle component analysis, whereby the 1st principal component explains 84% of the variance (FIG. 5B). Single-sample Gene Set Enrichment Analysis (ssGSEA) showed the over-expression for the majority of genes from the signature in the metastatic bone biopsies relative to the disseminated tumor cells (FIG. 5B). The second study (GEO dataset GSE 32269) was described by Balk et al. in J Clin Invest in 2013 (Cai C, et al., J Clin Invest. 123, 1109-22 (2013)). 22 hormone-dependent primary prostate cancer specimens were compared to 29 metastatic prostate cancer biopsies (CRPC). In FIG. 5C, a heat map for the genes from the 29-gene signature that were identified in the Balk gene expression dataset were plotted. Predominantly, the bone metastatic biopsy specimens had a higher expression level for the 29-gene signature than the primary prostate cancer specimens. ssGSEA showed the The 29-gene signature has also been recapitulated in osteosarcoma gene expression studies, as shown in FIG. 43A and FIG. 43B. Taken collectively, the results presented herein demonstrate that the 29-gene signature identified in Gleason comparisons in the stroma (sT8-sT6) and at the stromal tumor interface [(sT8-T8)-(sT6-T6)] form the basis of a signature associated with potential to metastasize to the bone, where the immune response plays a key role in the cytoskeletal development/modification, as influenced by cellular changes in the stromal compartment.

Example 10: Protein Atlas of 29-Gene Signature

The Human Protein Atlas (HPA) program is a scientific research program to explore the whole human proteome using an antibody-based approach. The project has a gene-centric approach with the effort to map and characterize a representative protein for each protein-coding human gene (approximately 20,000 genes). Antibodies, both in-house produced and external (commercial and from collaborators), are validated in the HPA workflow and used for protein characterization.

Figure 10C:
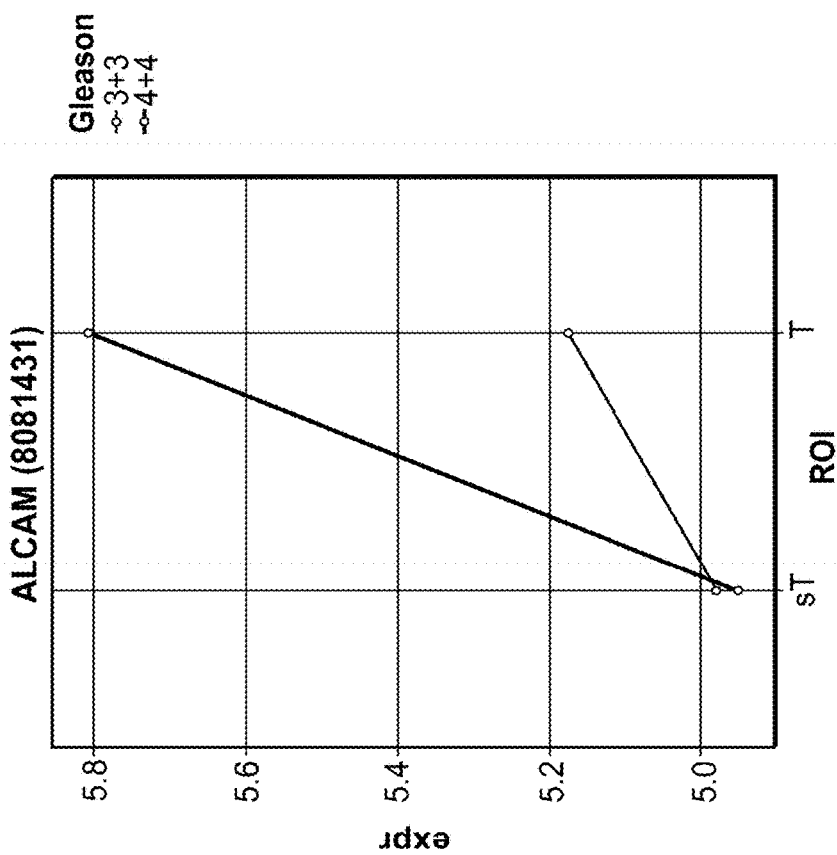
FIG. 10C is a graph showing the ROI versus ALCAM expression in a Gleason 3+3 and Gleason 4+4 patient.
Figure 10A:
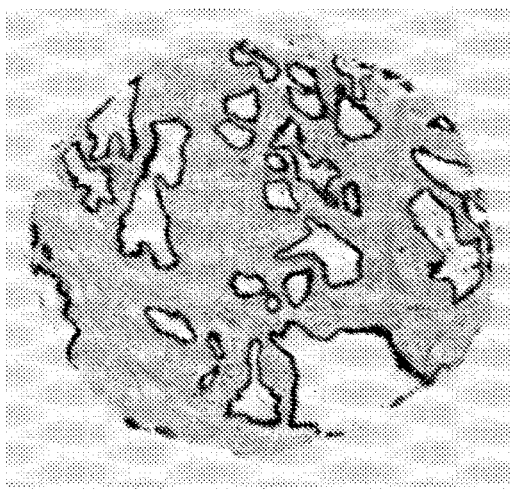
FIG. 10A is an immunohistochemistry (IHC) image showing of ALCAM (activated leucocyte cell adhesion molecule) expression in normal tissue ([T8-T6]). Moderate cytoplasmic/membranous staining was observed in epithelium stroma.
Figure 10B:
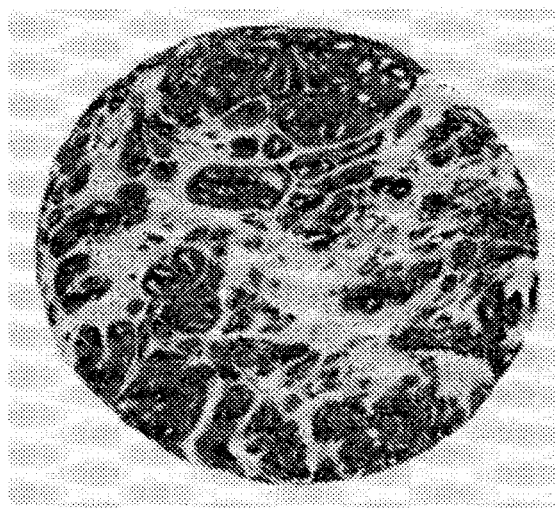
FIG. 10B is an IHC image showing of ALCAM expression in a tumor. Strong, cytoplasmic/membranous staining in epithelium stroma was observed.
Figure 11C:
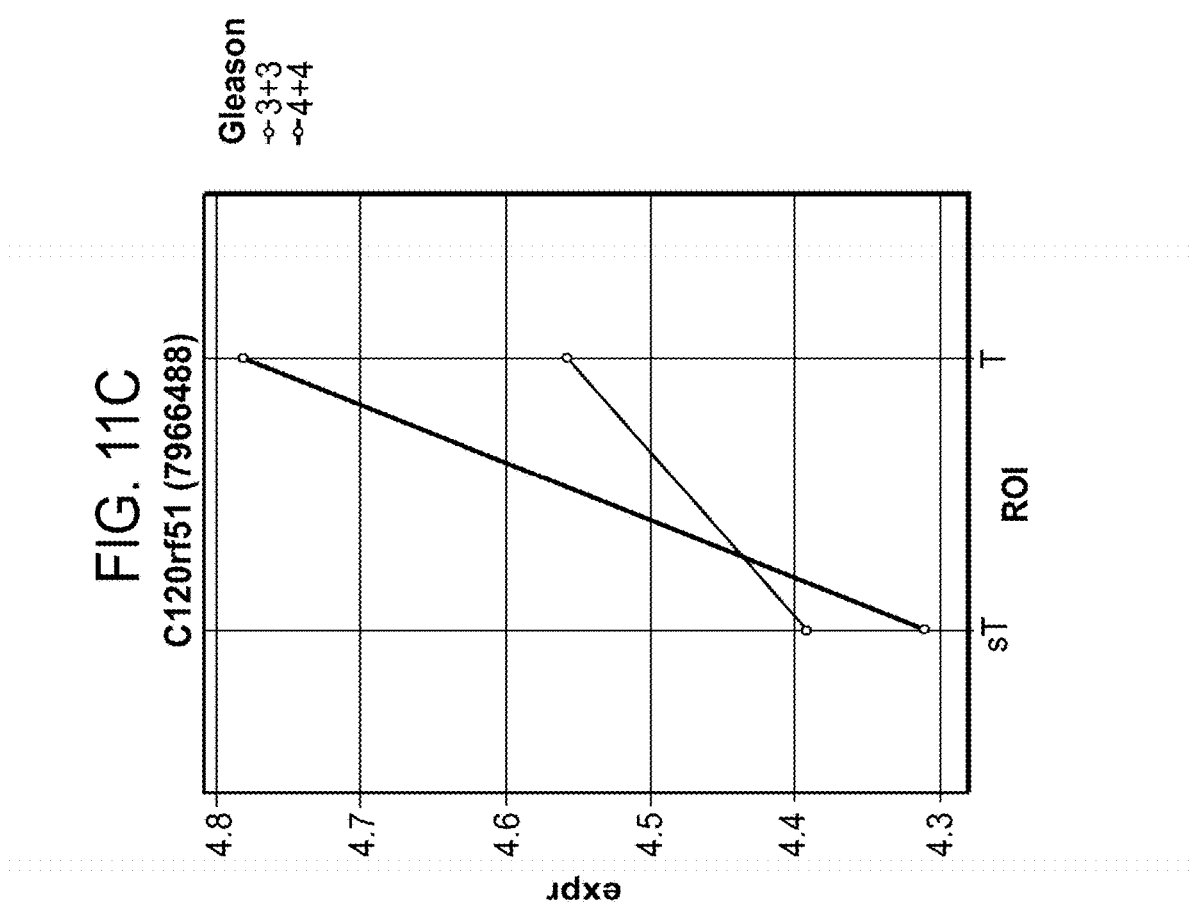
FIG. 11C is a graph showing the ROI versus C12orf51 (7966488) expression in a Gleason 3+3 and Gleason 4+4 patient.
Figure 11A:
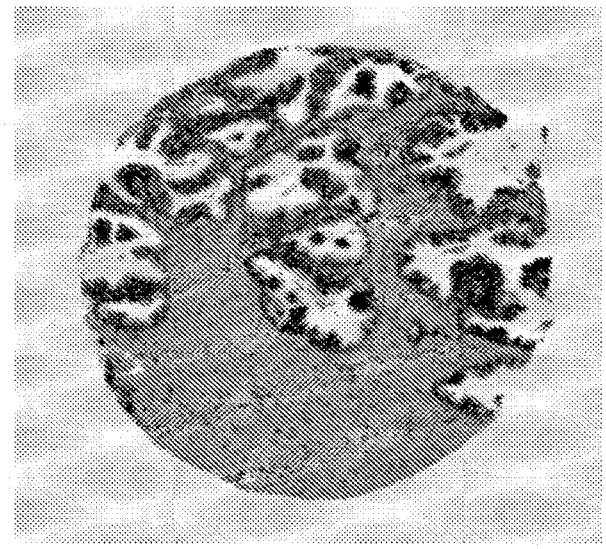
FIG. 11A is an IHC image showing of C12orf51 (HECT4) expression in normal tissue ([sT8-T8]-[sT6-T6]). Moderate, nuclear staining in the epithelium stroma was observed.
Figure 11B:
FIG. 11B is an IHC image showing IHC of C12orf51 (HECT4) (HECT Domain Containing E3 Ubiquitin Protein Ligase 4) expression in a tumor. Strong nuclear staining in epithelium stroma was observed.
Figure 12C:
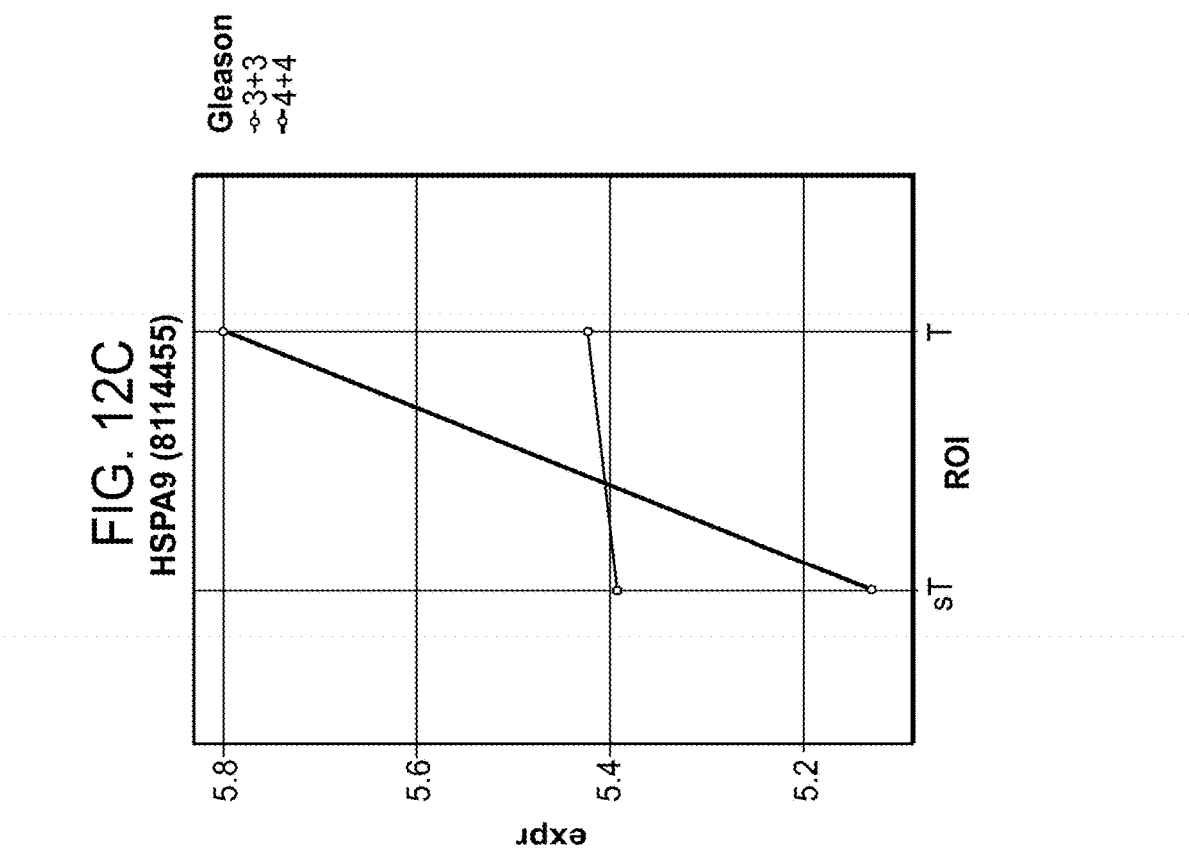
FIG. 12C is a graph showing the ROI versus HSPA9 (8114455) expression in a Gleason 3+3 and Gleason 4+4 patient.
Figure 12A:
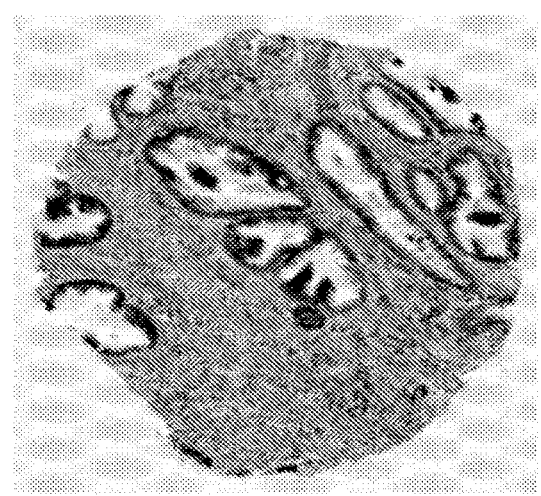
FIG. 12A is an IHC image showing of HSPA9 (Heat shock 70 kDa protein 9 (mortalin)) expression in normal tissue. Moderate cytoplasmic/membranous staining in the epithelium was observed ([sT8-T8]-[sT6-T6]).
Figure 12B:
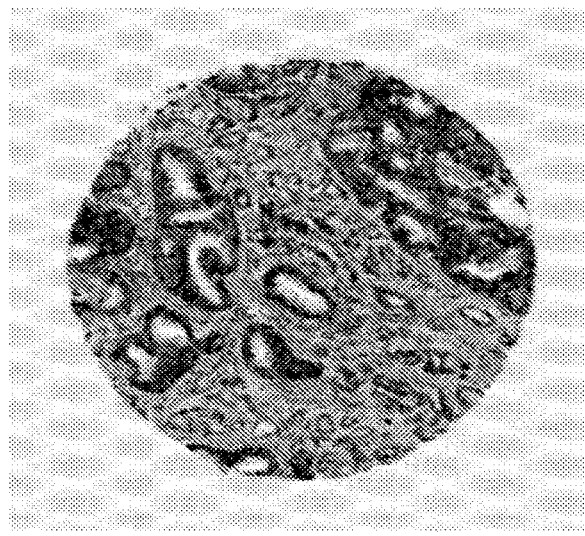
FIG. 12B is an IHC image showing of HSPA9 expression in a tumor. Strong cytoplasmic/membranous staining in the epithelium stroma was observed.
Figure 15C:
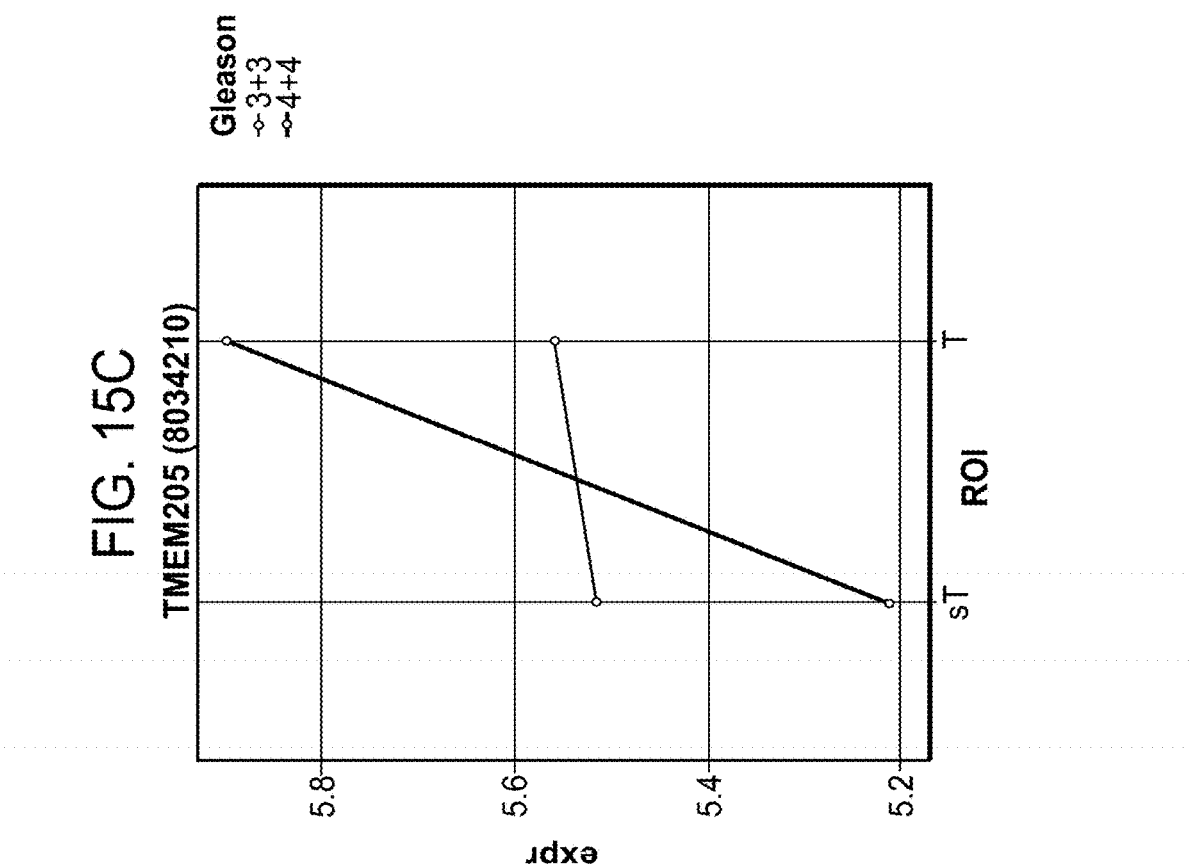
FIG. 15C is a graph showing the ROI versus TMEM205 (8034210) expression in a Gleason 3+3 and Gleason 4+4 patient.
Figure 15A:
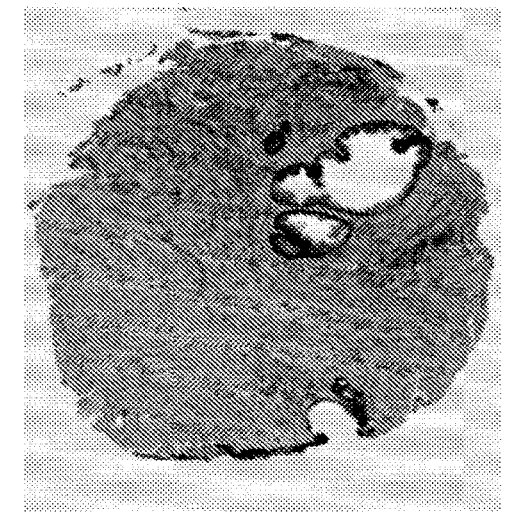
FIG. 15A is an IHC image showing of TMEM205 (transmembrane protein 205) expression in normal tissue ([sT8-T8]-[sT6-T6]). Strong cytoplasmic/membranous staining was observed in epithelium stroma.
Figure 15B:
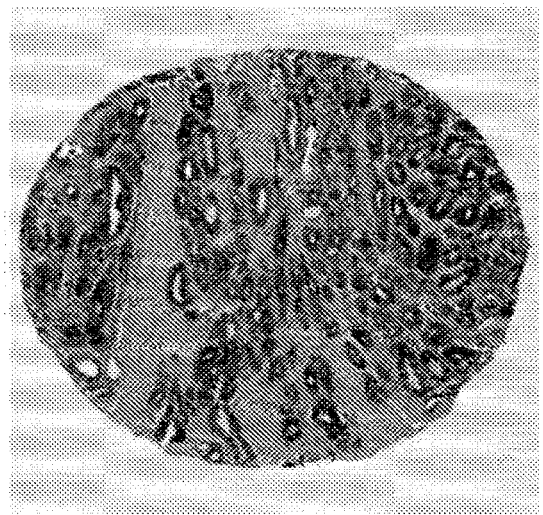
FIG. 15B is an IHC image showing of TMEM205 expression in a tumor. Strong cytoplasmic/membranous staining was observed in epithelium stroma.
Figure 16C:
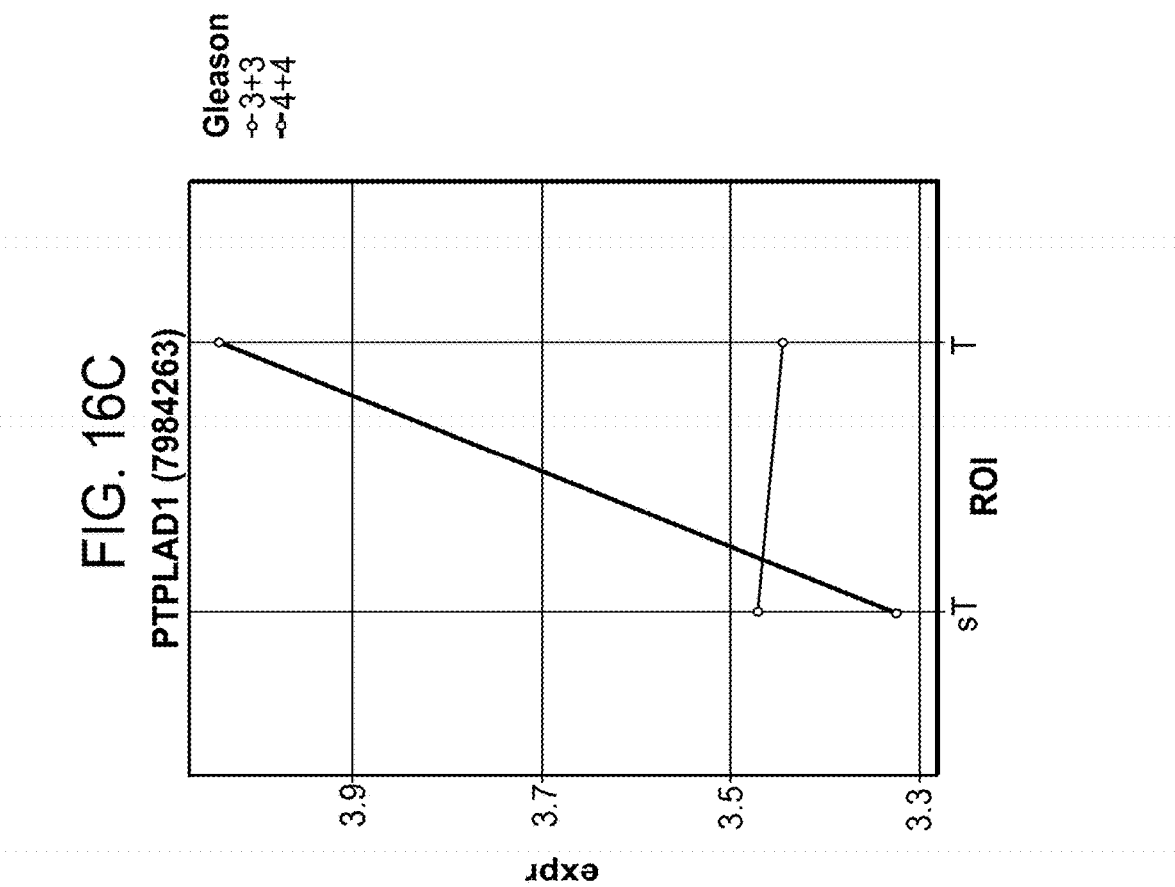
FIG. 16C is a graph showing the ROI versus PTPLAD1 (7984263) expression in a Gleason 3+3 and Gleason 4+4 patient.
Figure 16A:
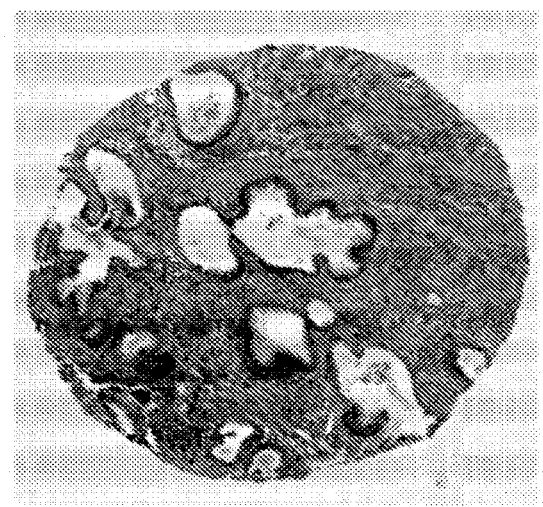
FIG. 16A is an IHC image showing of PTPLAD1 (protein tyrosine phosphatase-like A domain containing 1) expression in normal tissue ([sT8-T8]-[sT6-T6]). Mild cytoplasmic/membranous staining was observed in epithelium stroma.
Figure 16B:
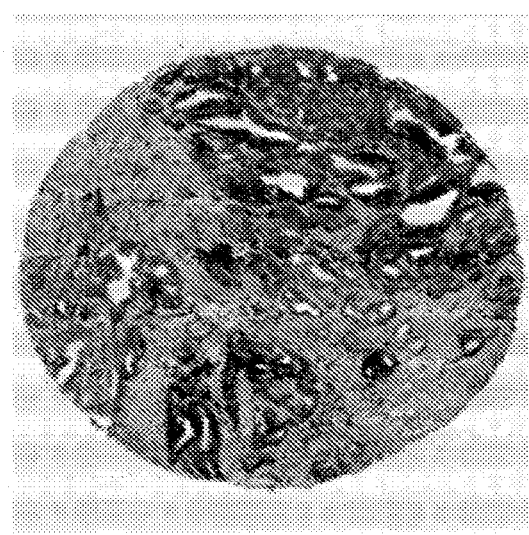
FIG. 16B is an IHC image showing of PTPLAD1 expression in a tumor. Strong cytoplasmic/membranous staining was observed in epithelium stroma.
Figure 18C:
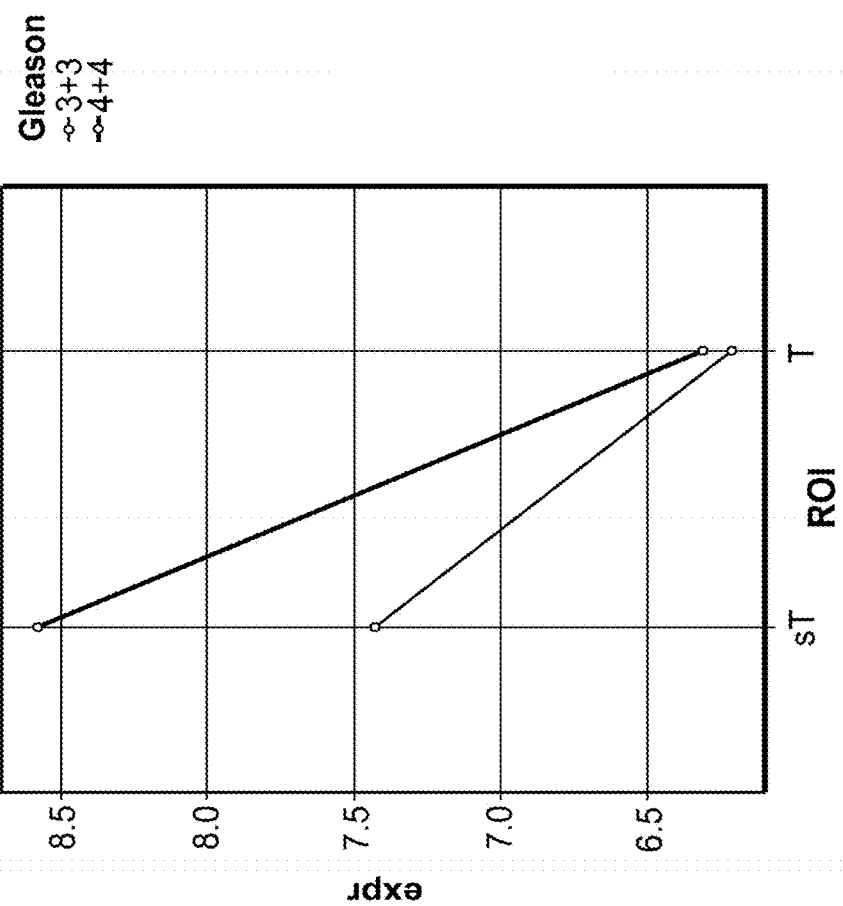
FIG. 18C is a graph showing the ROI versus COL1A1 (8016646) expression in a Gleason 3+3 and Gleason 4+4 patient.
Figure 18A:
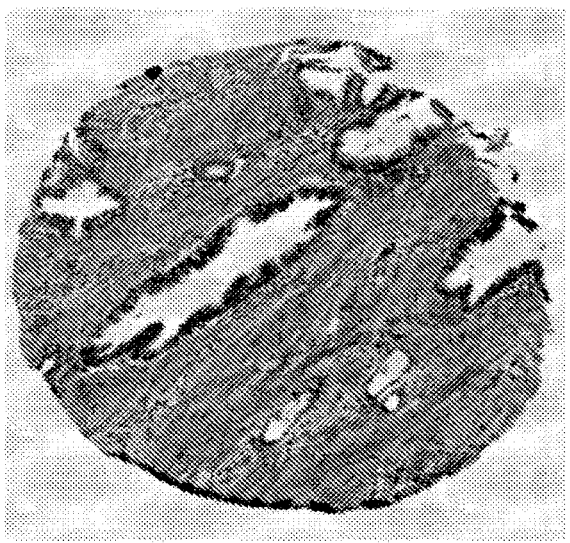
FIG. 18A is an IHC image showing of COL1A1 (collagen type 1) expression in normal tissue ([sT8-sT6]). Negative staining was observed in epithelium stroma.
Figure 18B:
FIG. 18B is an IHC image showing of COL1A1 expression in a tumor. Weak staining was observed in epithelium stroma.
Figure 20A:
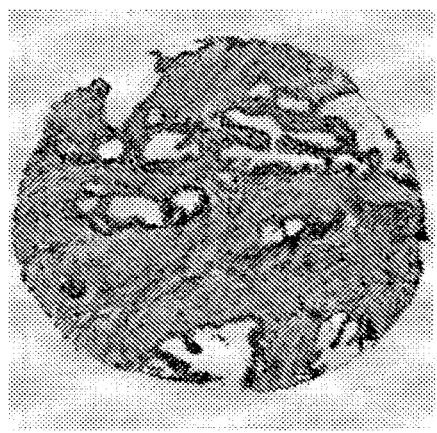
FIG. 20A is an IHC image showing of BGN (byglycan) expression in normal tissue ([sT8-sT6]). Negative staining was observed in epithelium stroma.
Figure 20B:
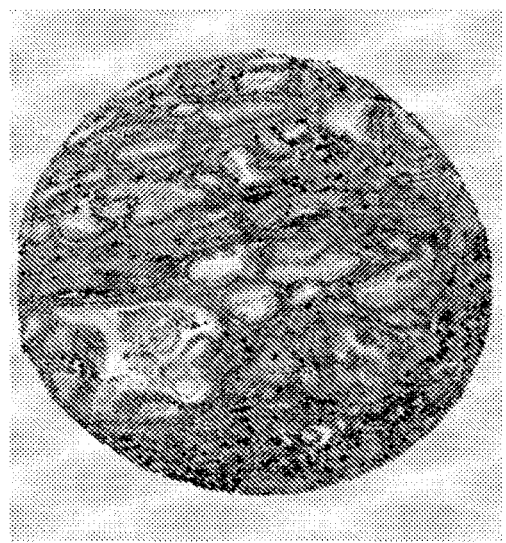
FIG. 20B is an IHC image showing of BGN expression in a tumor. Negative staining was observed in epithelium stroma.
Figure 20C:
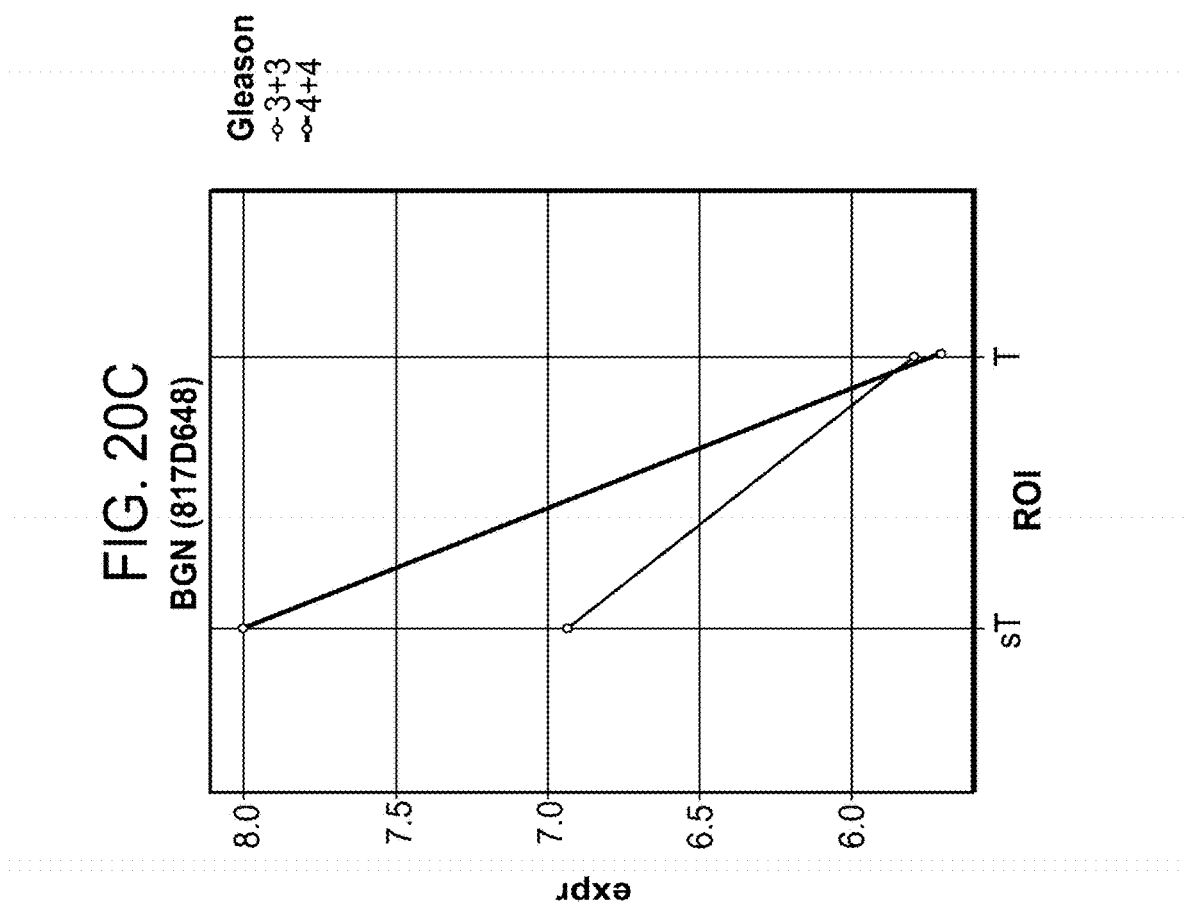
FIG. 20C is a graph showing the ROI versus BGN (8170648) expression in a Gleason 3+3 and Gleason 4+4 patient.
Figure 22A:
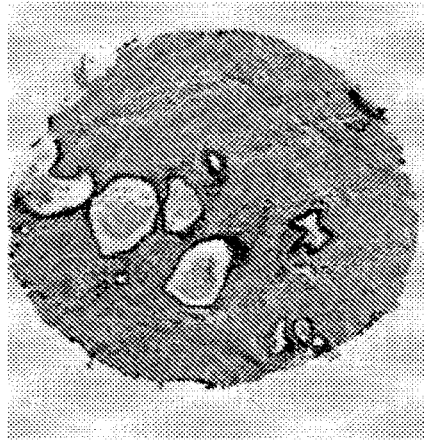
FIG. 22A is an IHC image showing of C1S (complement component 1, s subcomponent) expression in normal tissue ([sT8-sT6]). Negative staining was observed in epithelium stroma.
Figure 22B:
FIG. 22B is an IHC image showing of C1S expression in a tumor. Negative staining was observed in epithelium stroma.
Figure 22C:
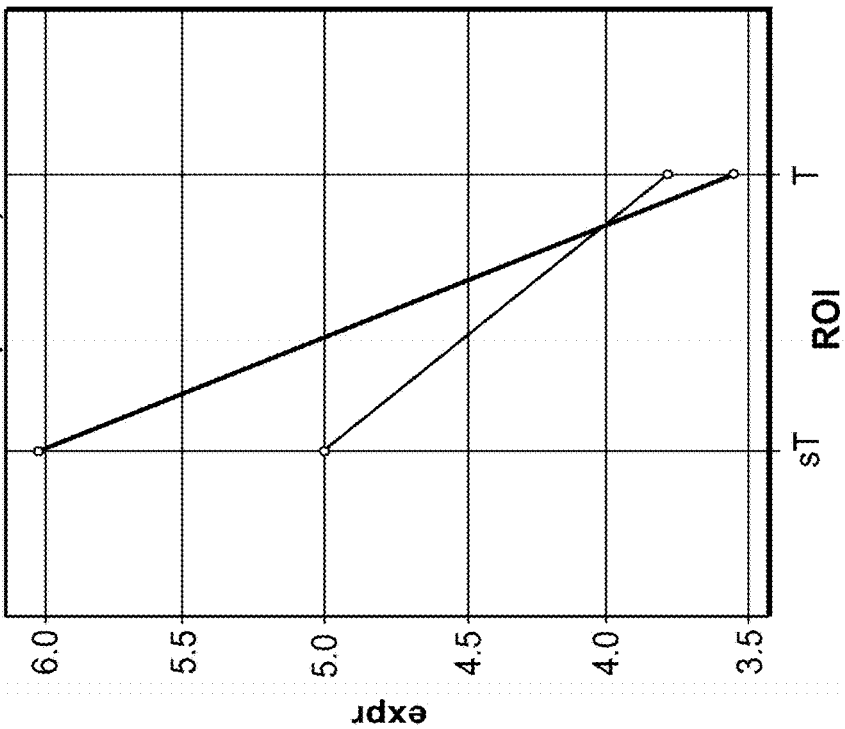
FIG. 22C is a graph showing the ROI versus C1S (7953603) expression in a Gleason 3+3 and Gleason 4+4 patient.
Figure 23C:
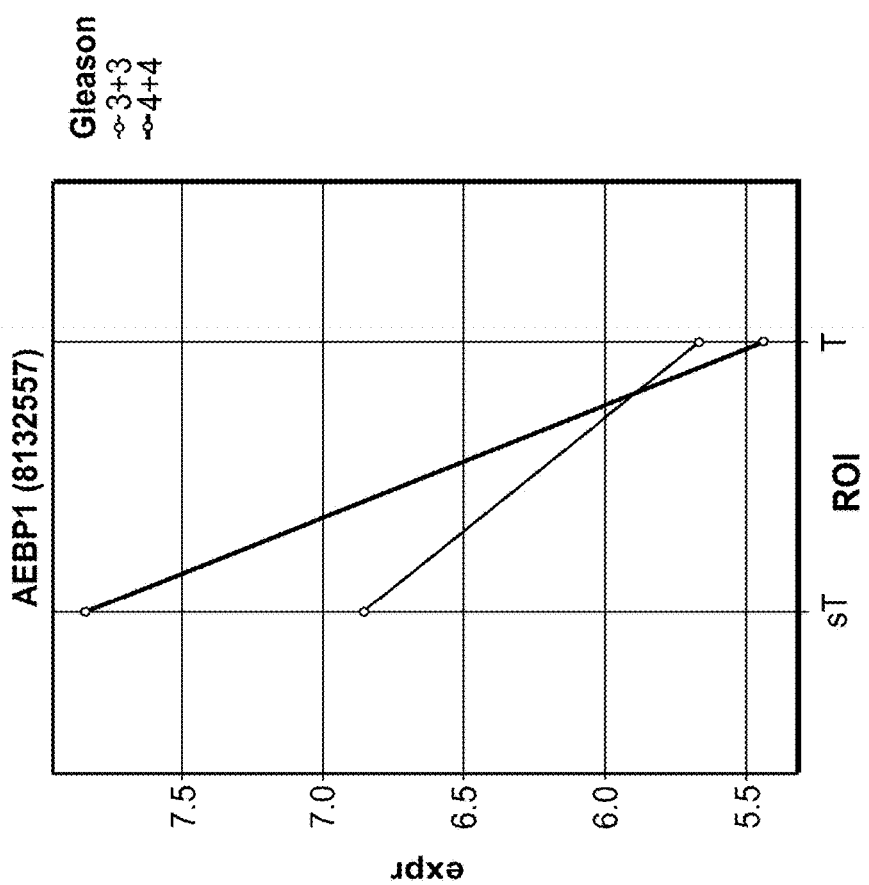
FIG. 23C is a graph showing the ROI versus AEBP1 (8132557) expression in a Gleason 3+3 and Gleason 4+4 patient.
Figure 23A:
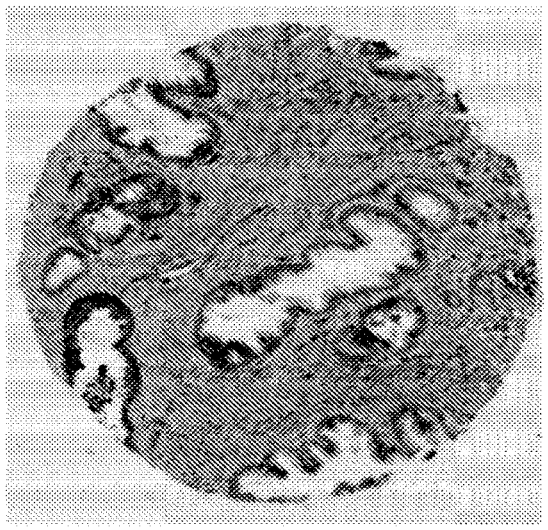
FIG. 23A is an IHC image showing of AEBP1 (stromal adipocyte enhancer-binding protein) expression in normal tissue ([sT8-sT6]). Moderate staining was observed in epithelium stroma.
Figure 23B:
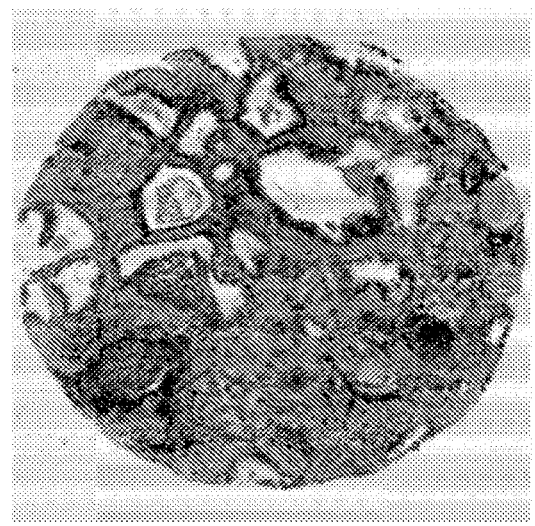
FIG. 23B is an IHC image showing of AEBP1 expression in a tumor. Negative staining was observed in epithelium stroma.
Figure 26C:
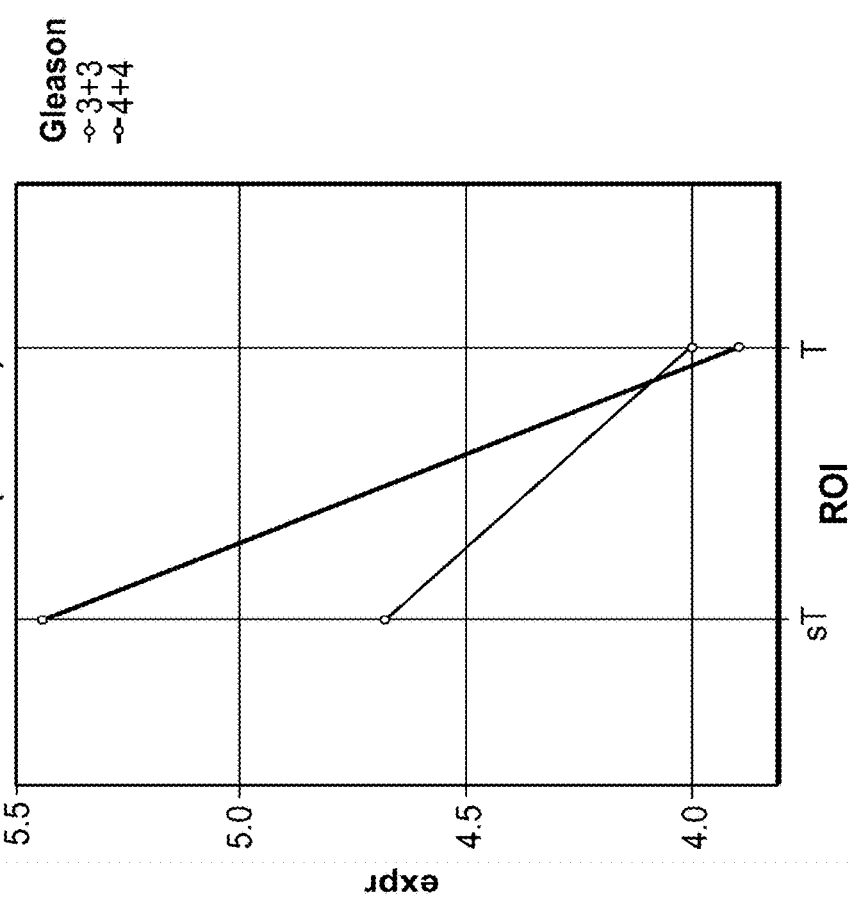
FIG. 26C is a graph showing the ROI versus C1QA (7898793) expression in a Gleason 3+3 and Gleason 4+4 patient.
Figure 26A:
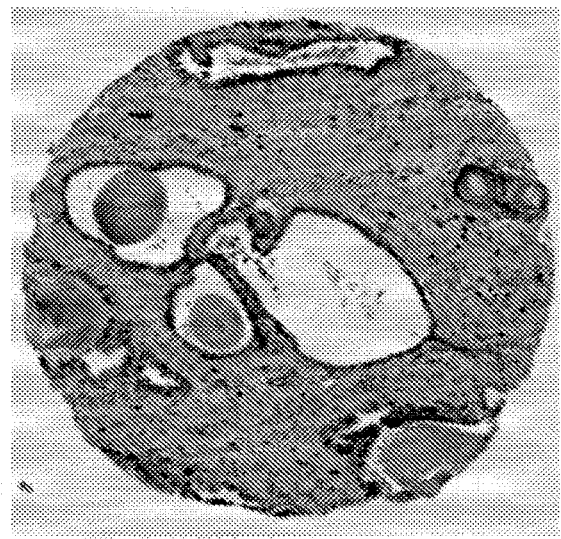
FIG. 26A is an IHC image showing of C1QA (complement component 1, q subcomponent, A chain) expression in normal tissue ([sT8-sT6]). Negative staining was observed in epithelium stroma.
Figure 26B:
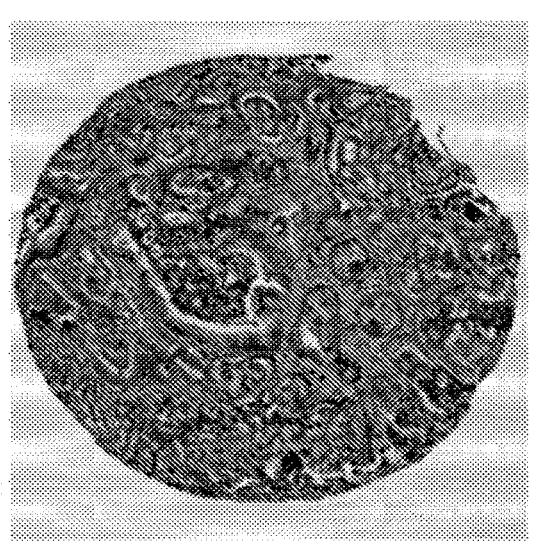
FIG. 26B is an IHC image showing of C1QA expression in a tumor. Weak staining was observed in epithelium stroma.
Figure 27C:
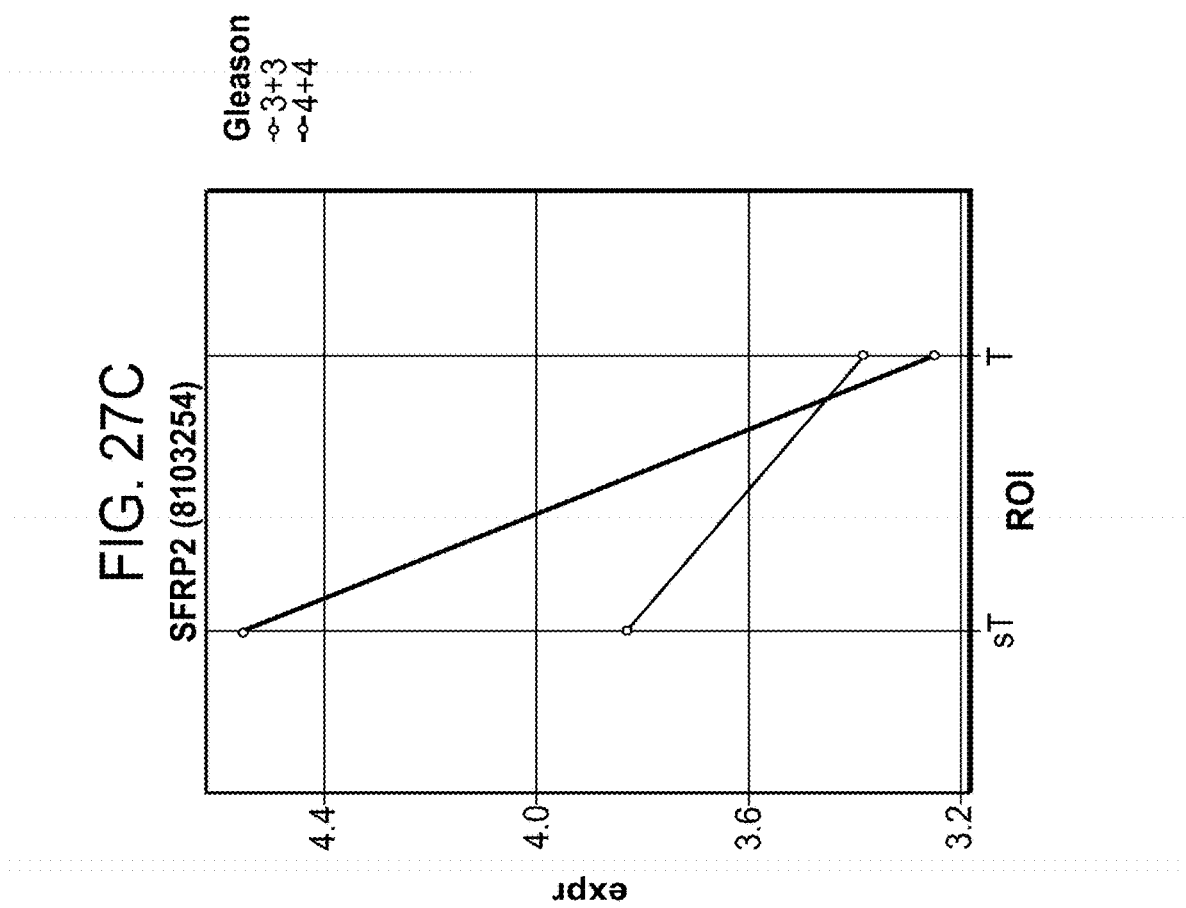
FIG. 27C is a graph showing the ROI versus SFRP2 (8103254) expression in a Gleason 3+3 and Gleason 4+4 patient.
Figure 27A:
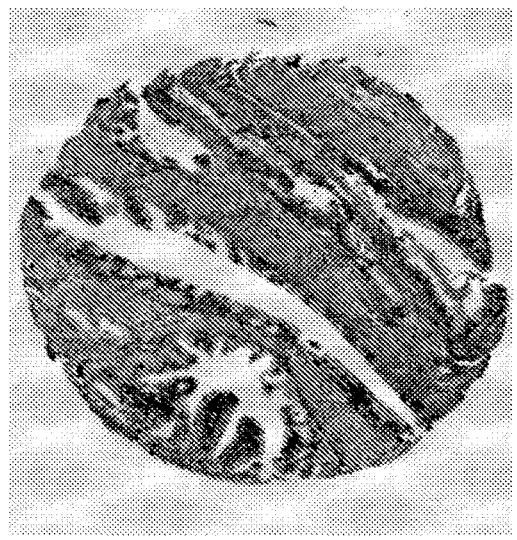
FIG. 27A is an IHC image showing of SFRP2 (secreted frizzled related protein 2) expression in normal tissue ([sT8-sT6]). Weak staining was observed in epithelium stroma.
Figure 27B:
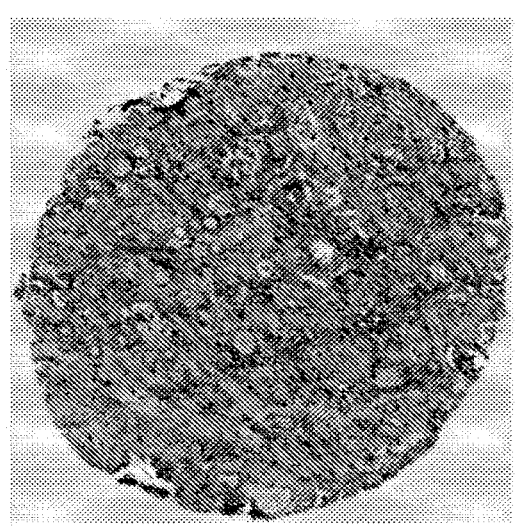
FIG. 27B is an IHC image showing of SFRP2 expression in a tumor. Weak staining was observed in epithelium stroma.
Figure 28C:
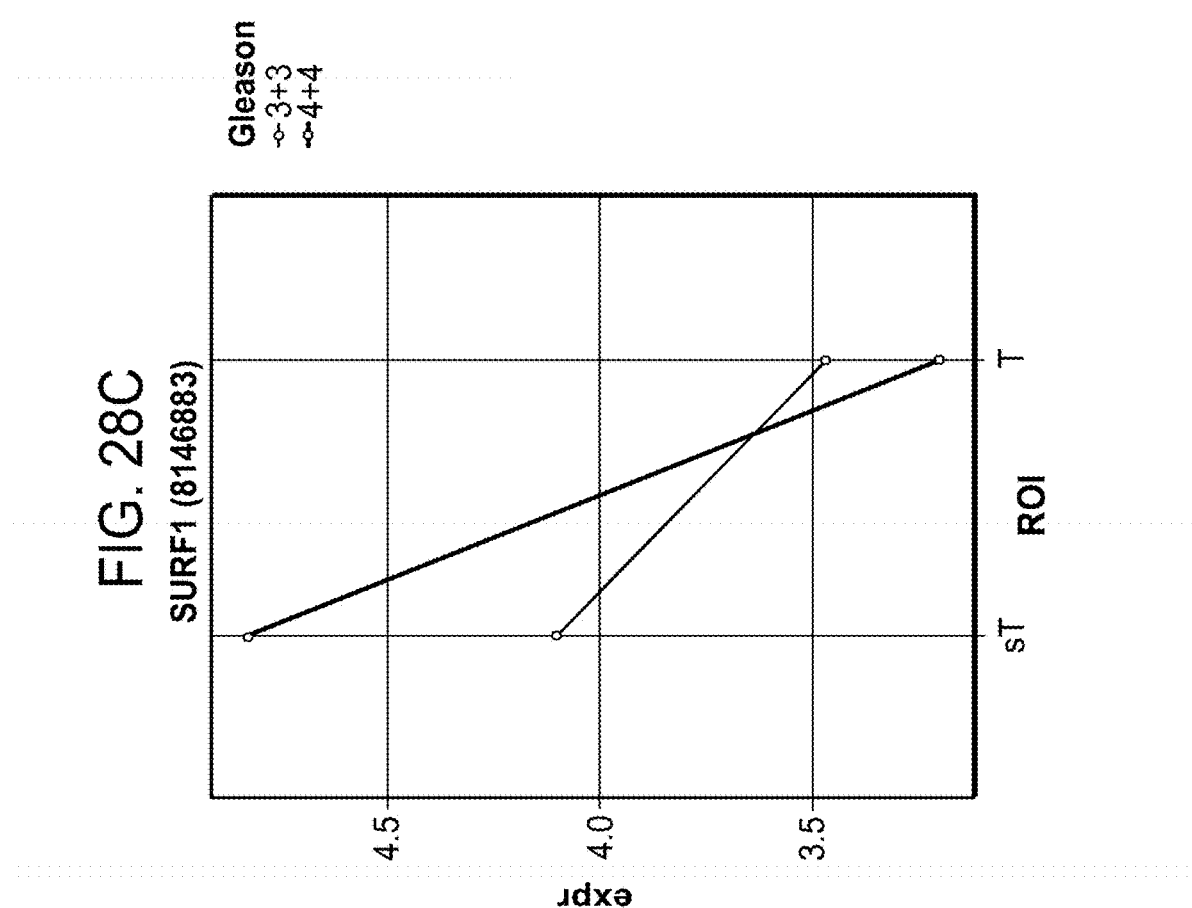
FIG. 28C is a graph showing the ROI versus SULF1 (8146863) expression in a Gleason 3+3 and Gleason 4+4 patient.
Figure 28A:
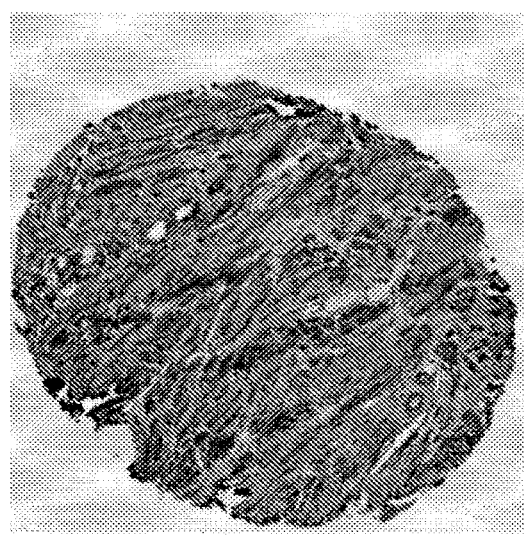
FIG. 28A is an IHC image showing of SULF1 (sulfatase 1) expression in normal tissue ([sT8-sT6]). Moderate staining was observed in epithelium stroma.
Figure 28B:
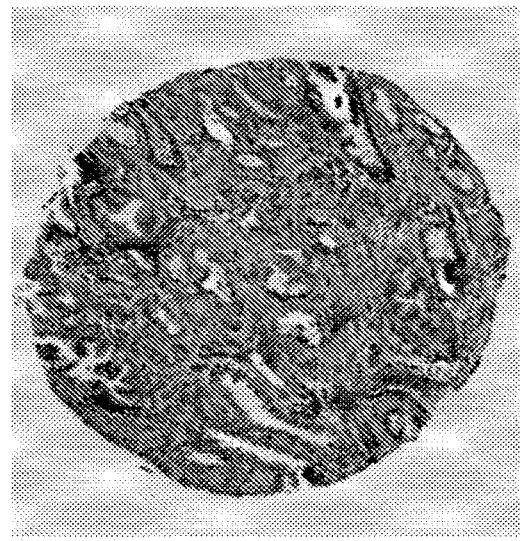
FIG. 28B is an IHC image showing of SULF1 expression in a tumor. Negative staining was observed in epithelium stroma.
Figure 29C:
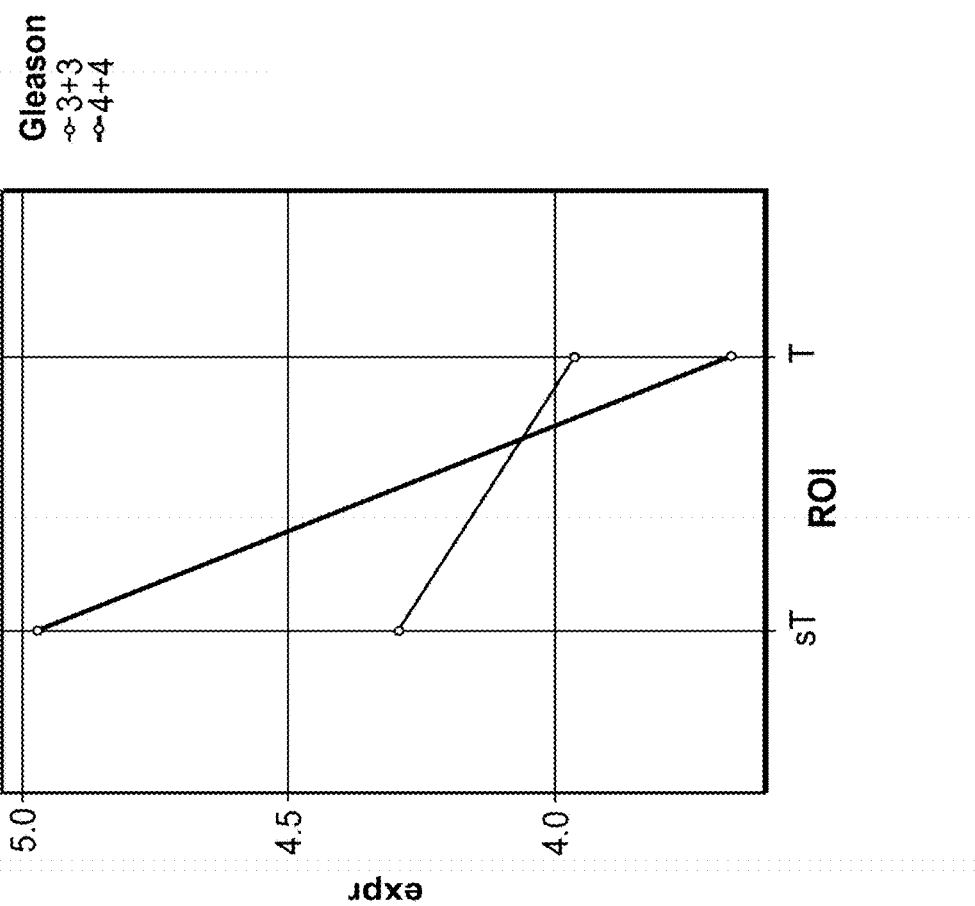
FIG. 29C is a graph showing the ROI versus THBS2 (8130867) expression in a Gleason 3+3 and Gleason 4+4 patient.
Figure 29A:
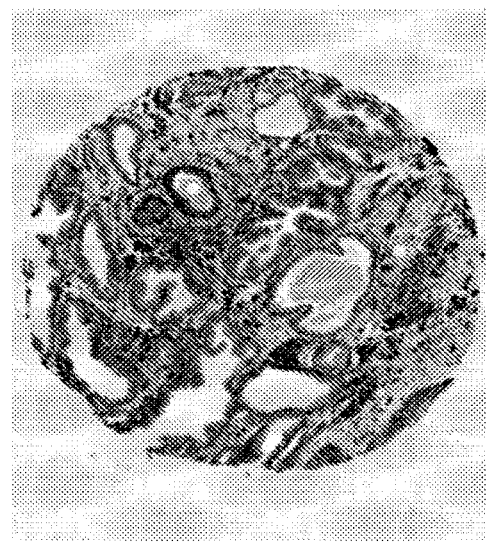
FIG. 29A is an IHC image showing of THBS2 (thrombospondin 2) expression in normal tissue ([sT8-sT6]). Weak staining was observed in epithelium stroma.
Figure 29B:
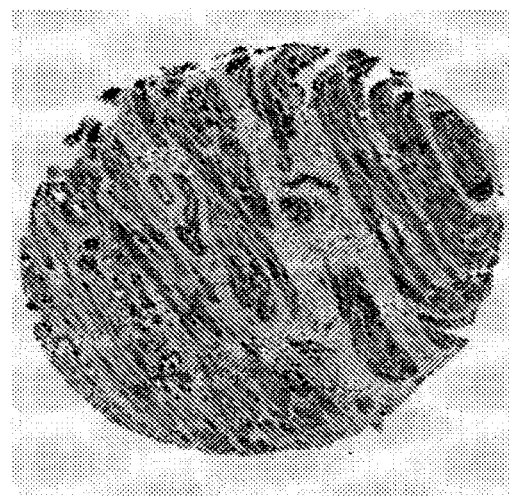
FIG. 29B is an IHC image showing of THBS2 expression in a tumor. Weak staining was observed in epithelium stroma.
Figure 30C:
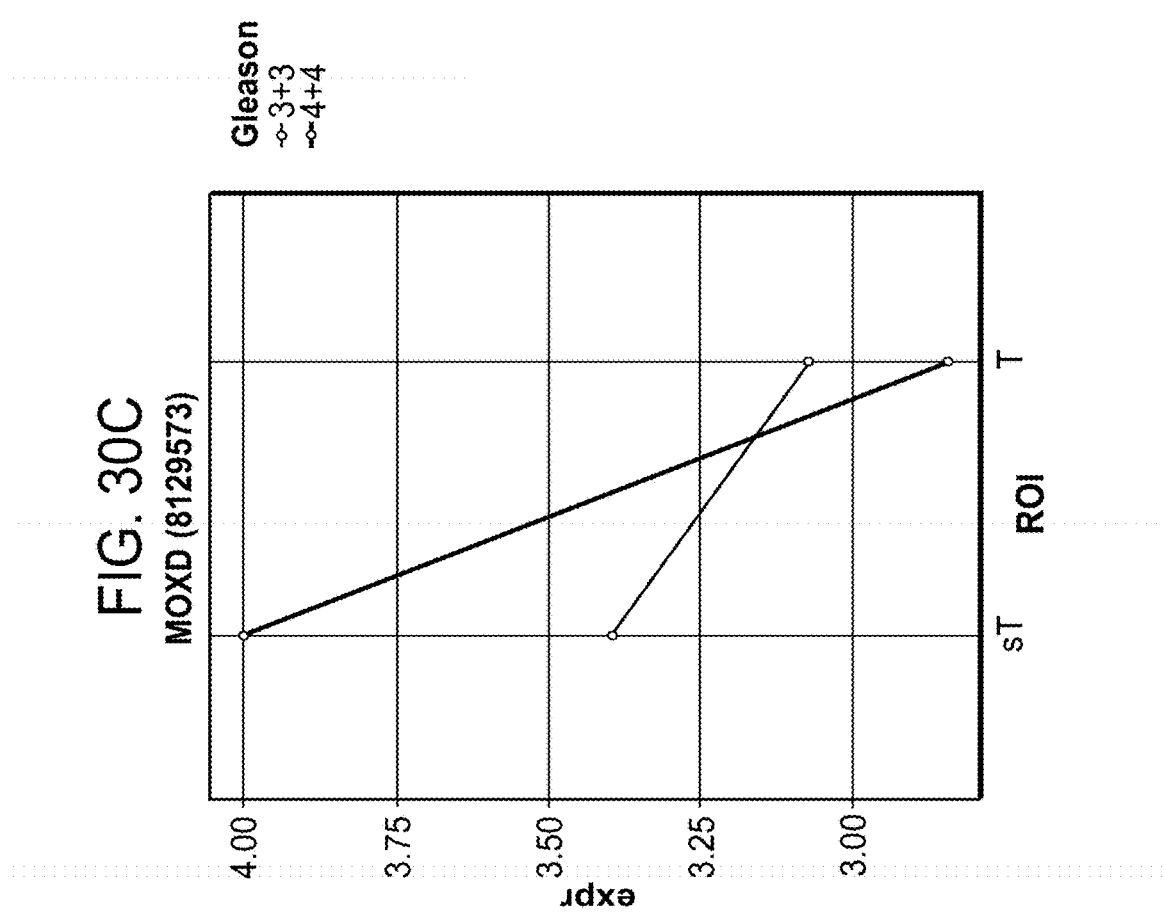
FIG. 30C is a graph showing the ROI versus MOXD1 (8129573) expression in a Gleason 3+3 and Gleason 4+4 patient.
Figure 30A:
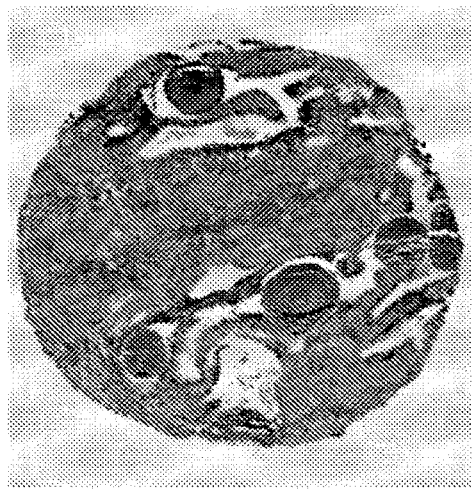
FIG. 30A is an IHC image showing of MOXD1 (monoxygenase, DBH-like 1) expression in normal tissue ([sT8-sT6]). Negative staining was observed in epithelium stroma.
Figure 30B:
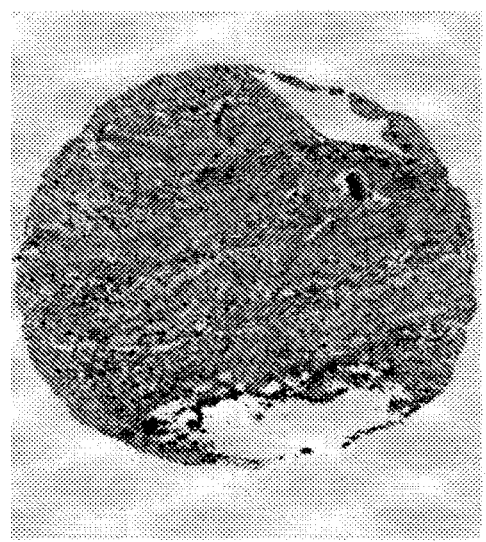
FIG. 30B is an IHC image showing of MOXD1 expression in a tumor. Negative staining was observed in epithelium stroma.
Figure 32C:
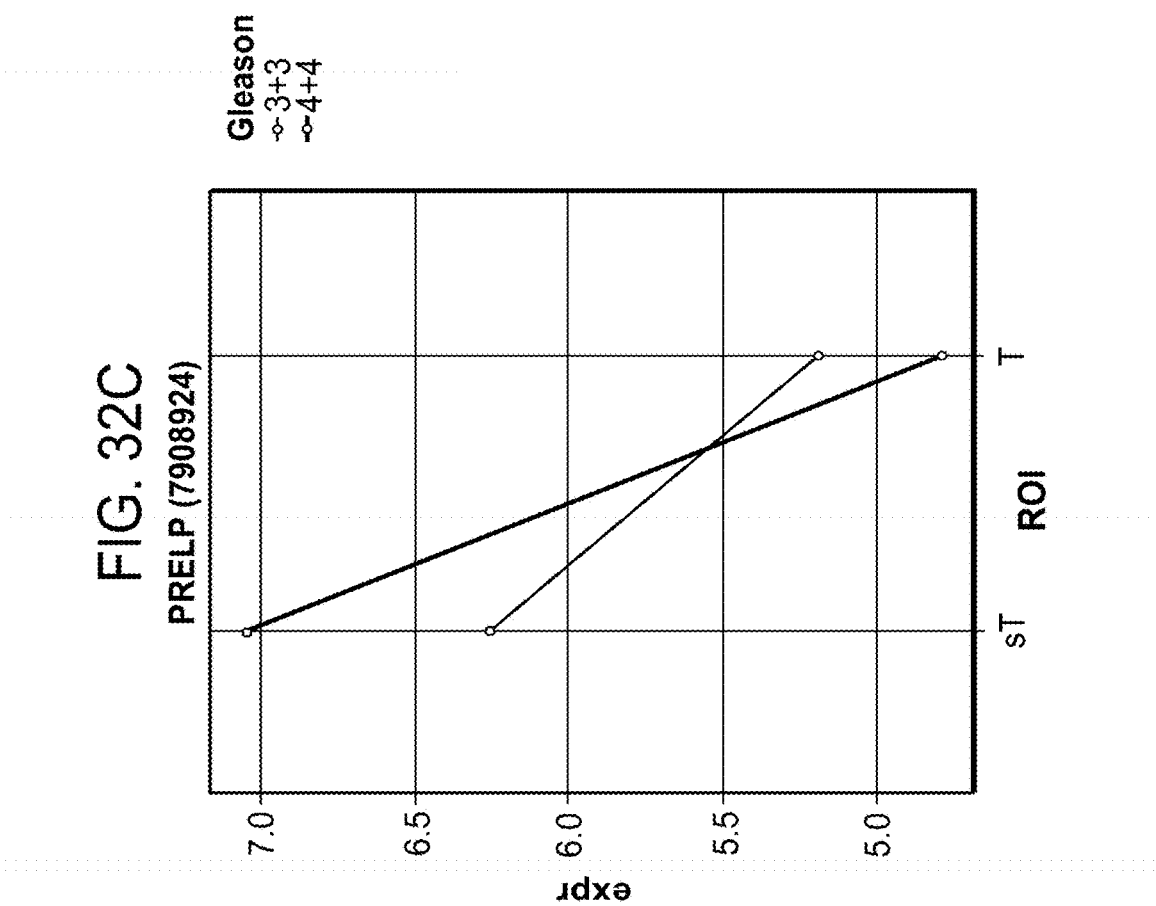
FIG. 32C is a graph showing the ROI versus PRELP (7908924) expression in a Gleason 3+3 and Gleason 4+4 patient.
Figure 32A:
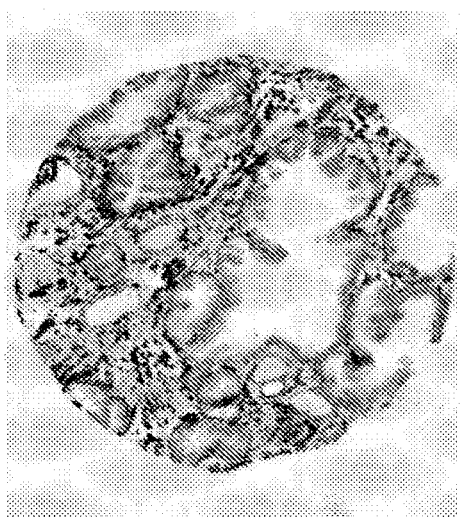
FIG. 32A is an IHC image showing of PRELP (proline/arginine-rich end leucine-rich repeat protein) expression in normal tissue ([sT8-T8]-[sT6-T6]). Negative staining was observed in epithelium stroma.
Figure 32B:
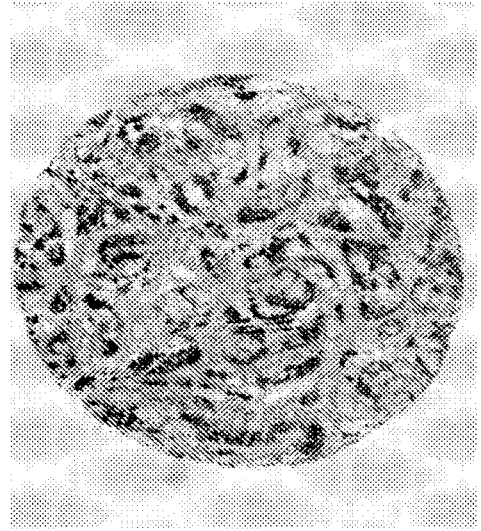
FIG. 32B is an IHC image showing of PRELP expression in a tumor. Negative staining was observed in epithelium stroma.
Figure 35C:
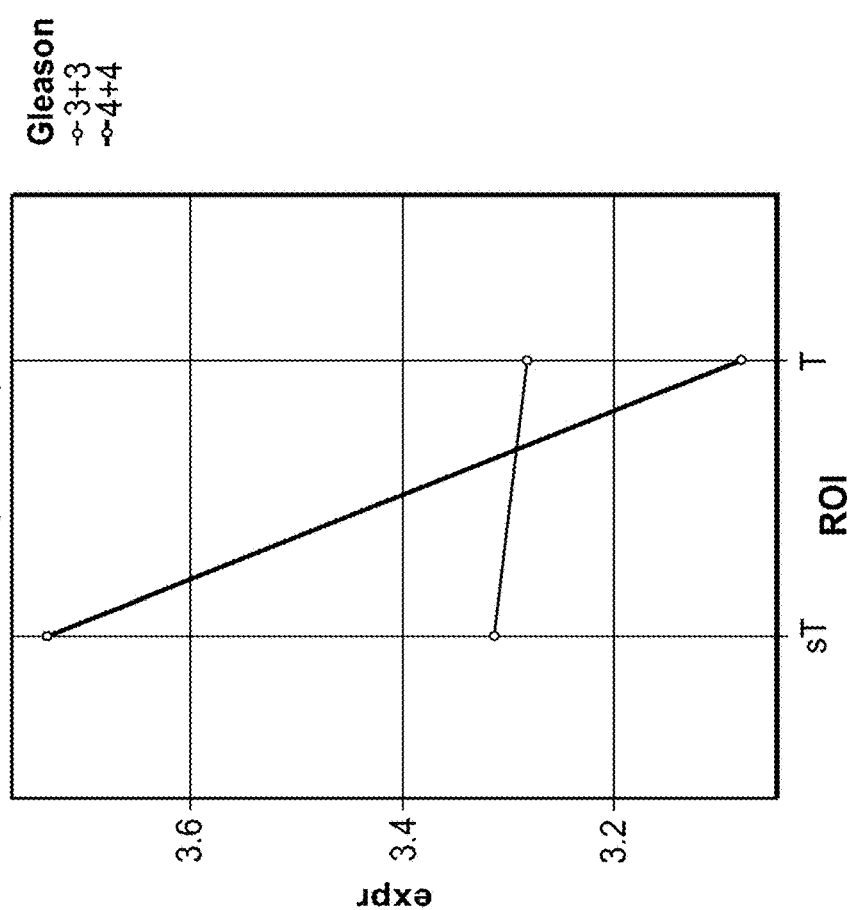
FIG. 35C is a graph showing the ROI versus TNS3 (8139500) expression in a Gleason 3+3 and Gleason 4+4 patient.
Figure 35A:
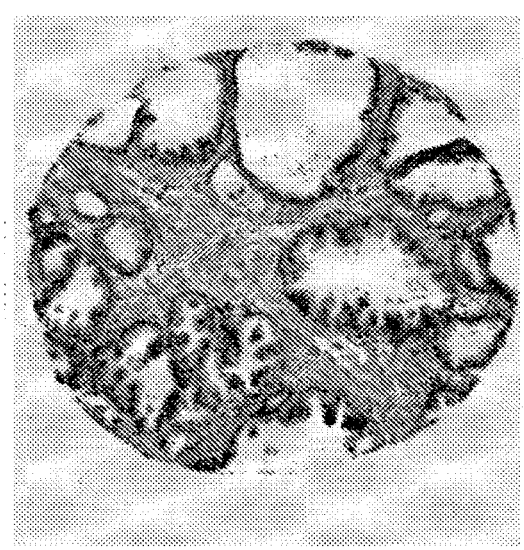
FIG. 35A is an IHC image showing of TNS3 (tensin 3) expression in normal tissue ([sT8-T8]-[sT6-T6]). Negative staining was observed in epithelium stroma.
Figure 35B:
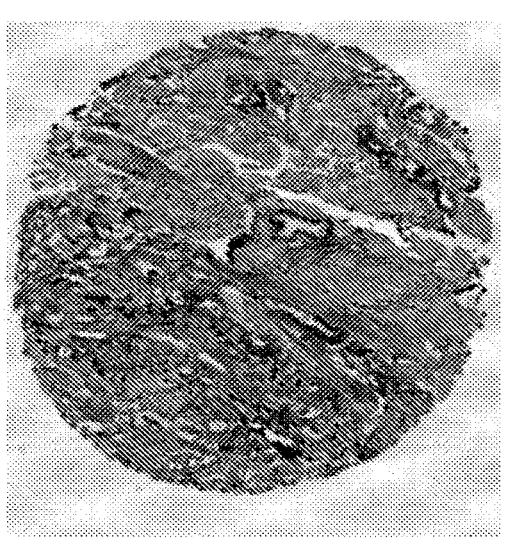
FIG. 35B is an IHC image showing of TNS3 expression in a tumor. Weak staining was observed in epithelium stroma.
Figure 36A:
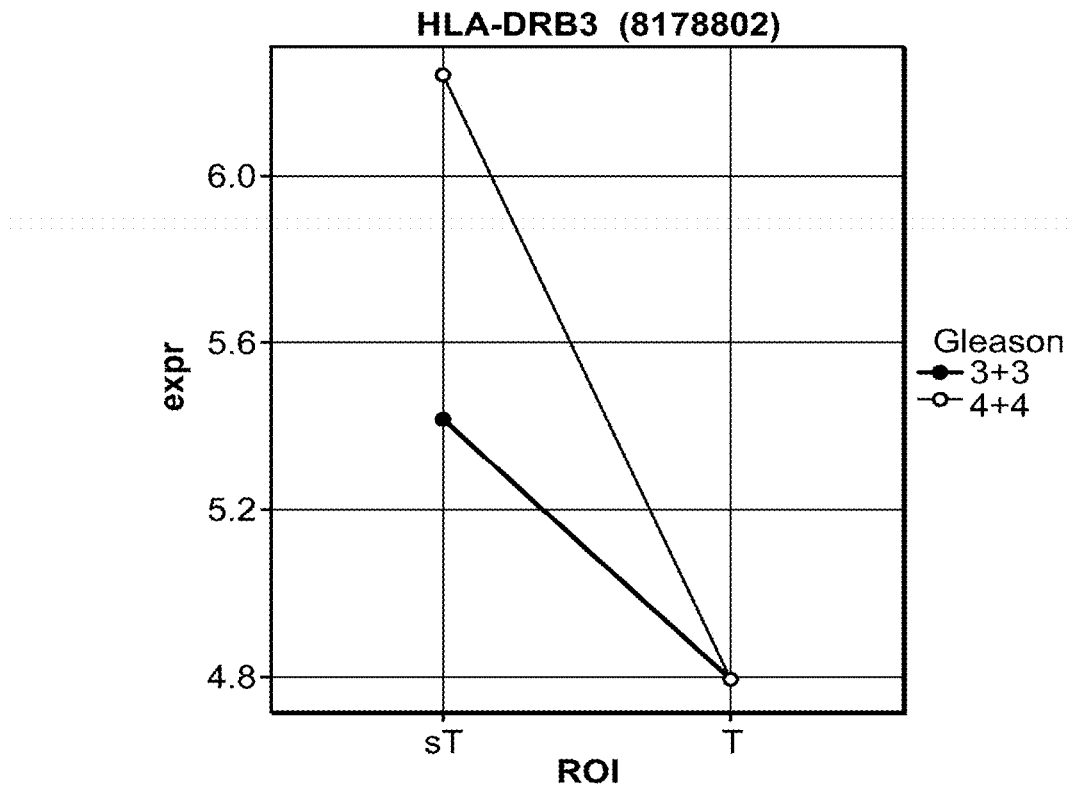
FIG. 36A is a graph showing the ROI versus HLA-DRB3 (major histocompatibility complex, class II, DR beta 3) (8178802) expression in a Gleason 3+3 and Gleason 4+4 patient.
Figure 36B:
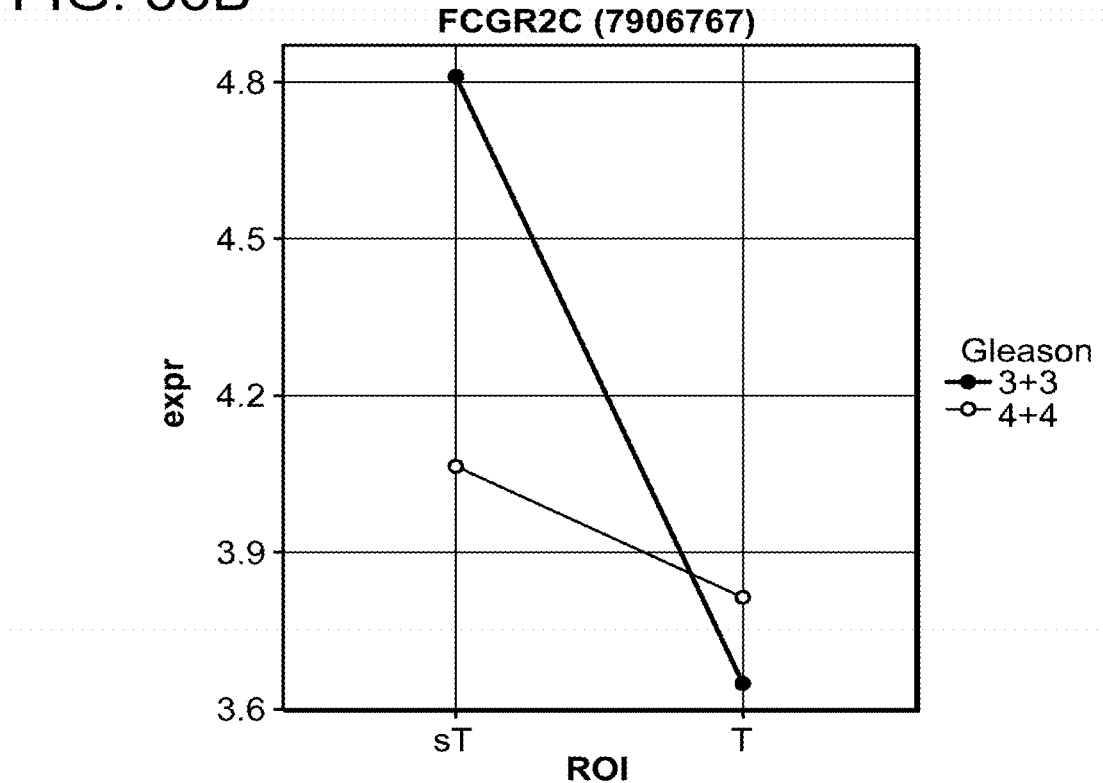
FIG. 36B is a graph showing the ROI versus FCGR2C (Fc fragment of IgG, low affinity llc, receptor for (CD32) (gene/pseudogene) (7906767) expression in a Gleason 3+3 and Gleason 4+4 patient.
Figure 36C:
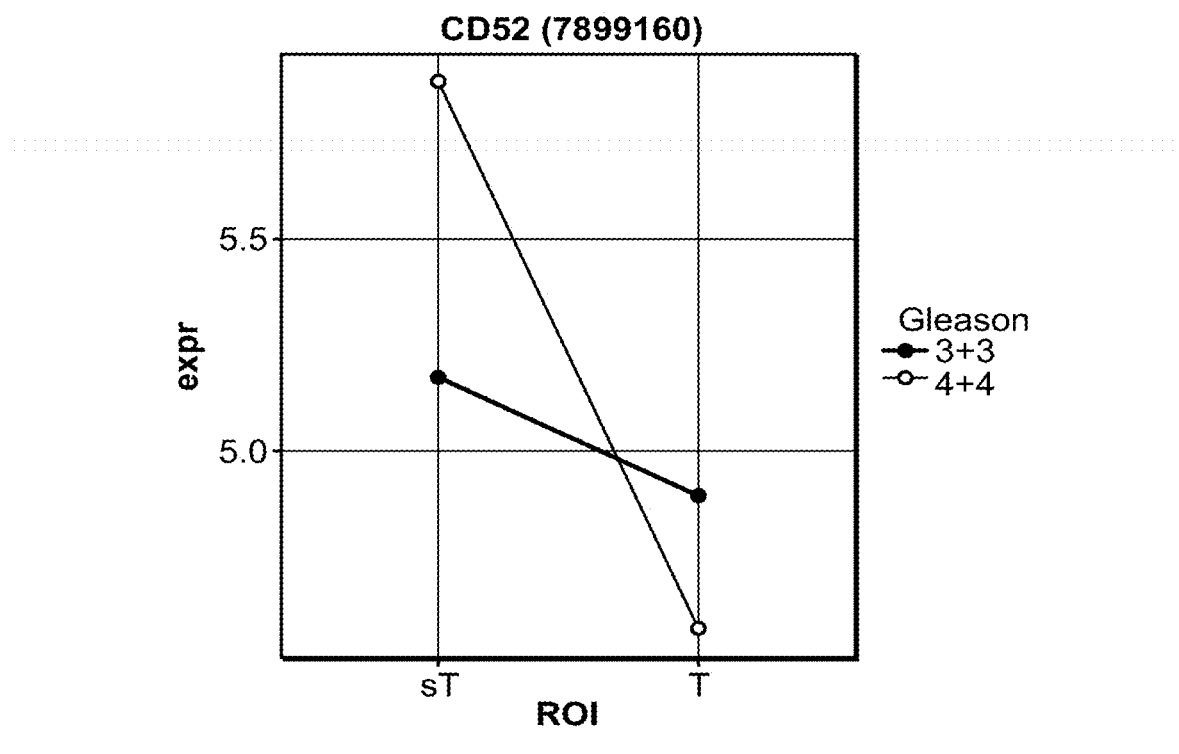
FIG. 36C is a graph showing the ROI versus CD52 (cluster of differentiation 52) (7899160) expression in a Gleason 3+3 and Gleason 4+4 patient.
Figure 37:
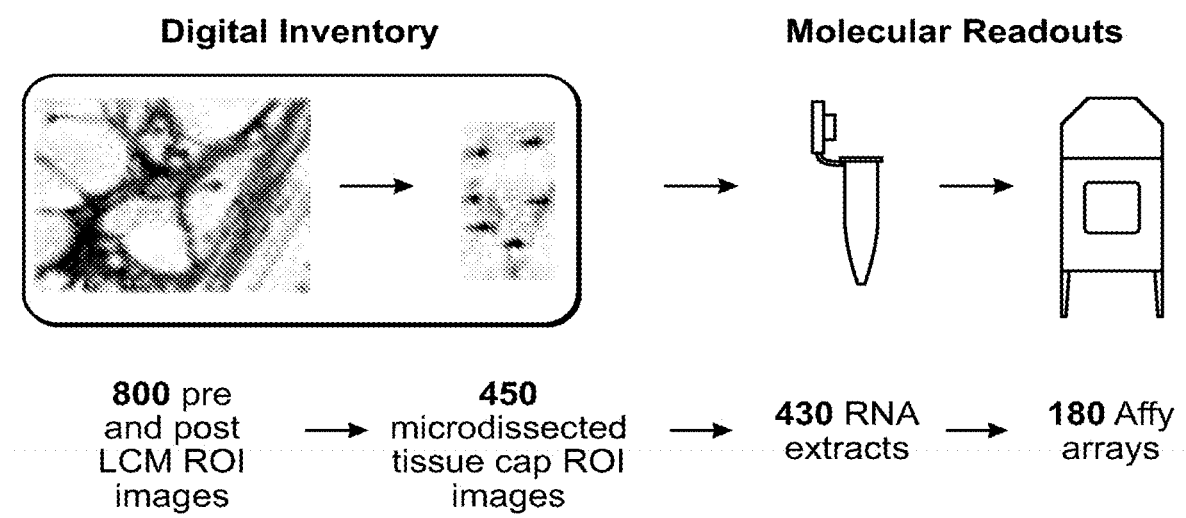
FIG. 37 is a schematic showing a matched LCM image and RNA inventories that were created.
Figure 38A:
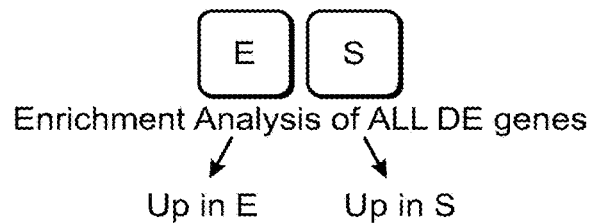
FIG. 38A is a schematic representation of the comparison and subsequent enrichment analysis performed to compare epithelial and stromal differentially expressed genes.
Figure 38B:
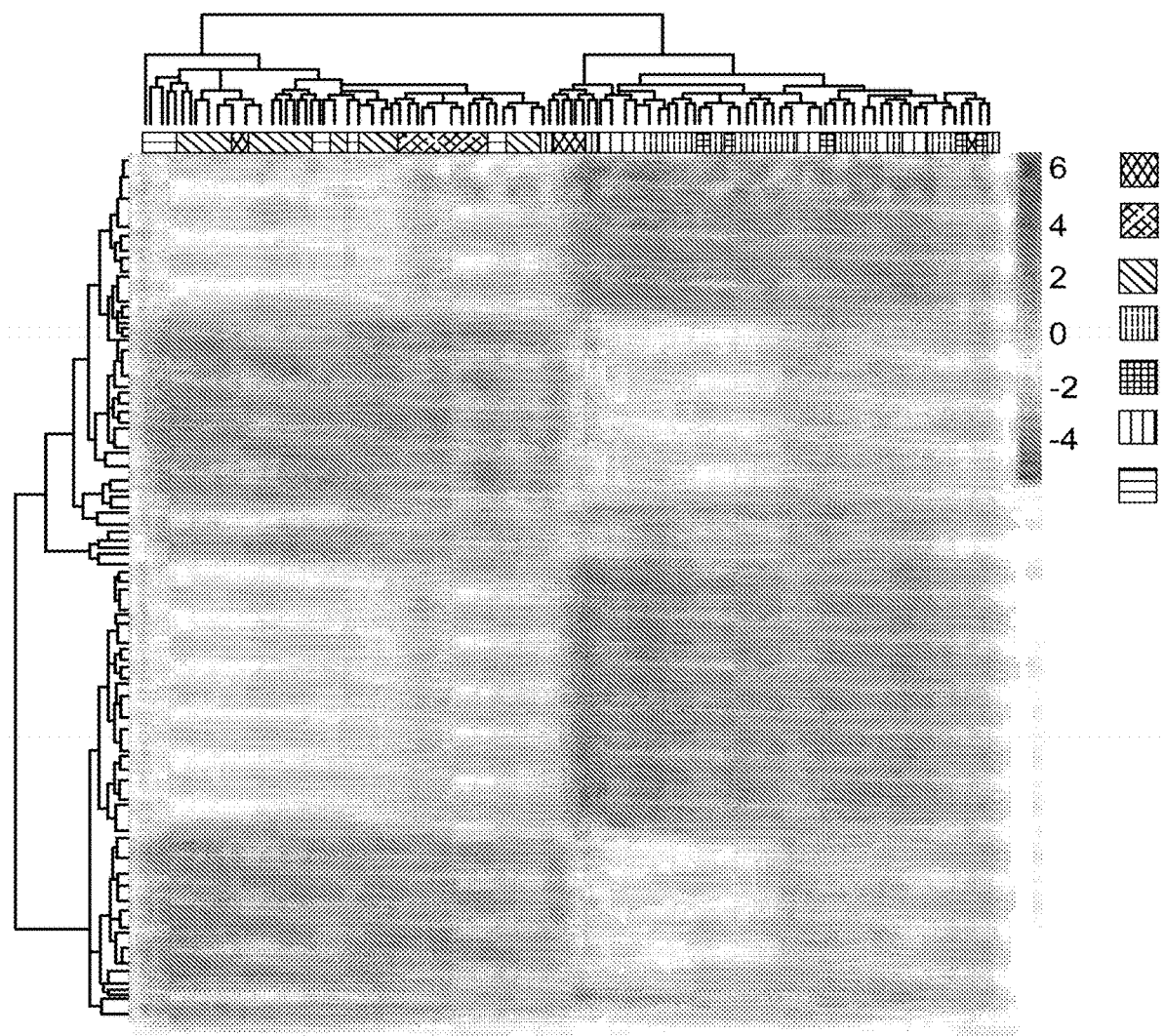
FIG. 38B is a heatmap of the global gene expression of the E-s comparison using the filtered data sets horizontal barcode shows sample clustering (T is turquoise, sT is pink, B is red, sB is blue and P is green and sP is yellow, with clear separation of the epithelial (T,P,B) and stromal (sT,sP,sB) regions of interest (ROI's) across the entire sample set, vertical barcode shows genes clustering, from the 1000 genes found in the E-S comparison.
Figure 39A:
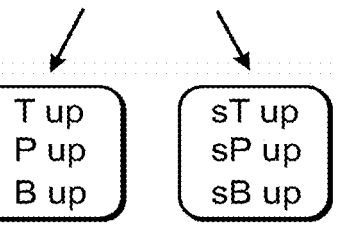
FIG. 39A is a schematic representation of the "between compartment" comparisons and subsequent enrichment analysis performed.
Figure 39B:
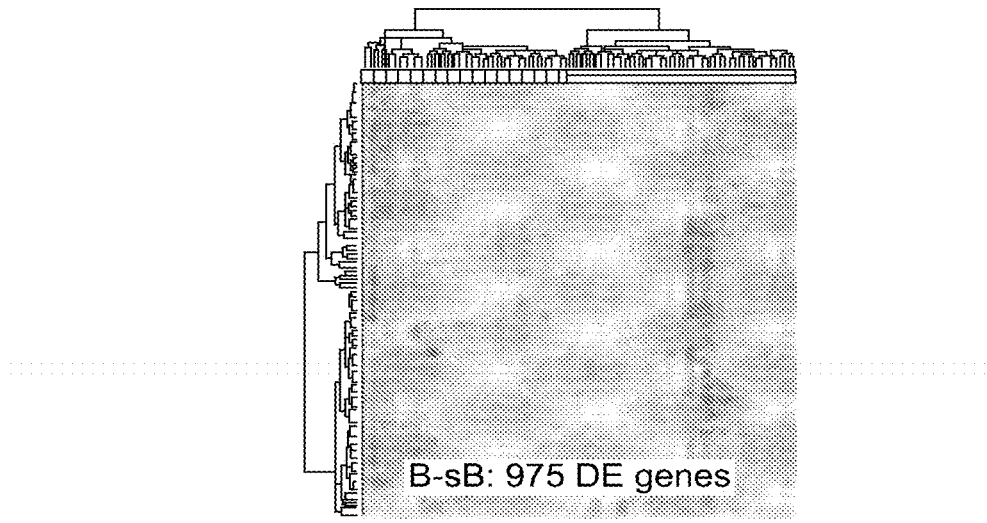
FIG. 39B is a heatmap of each epithelial ROI relative to its associated adjacent stromal ROI, namely B-s. Upregulated genes are shown in red and downregulated genes in blue, where expression levels are plotted as Log(Fold Change).
Figure 39C:
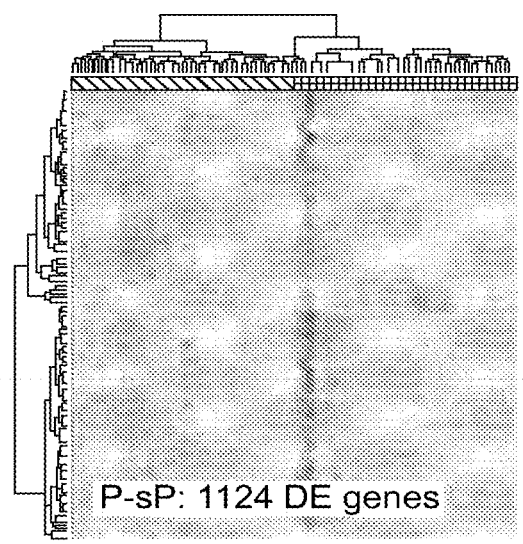

Representative normal included by way of reference point. Only high grade tumor cases were used for staining assessment. In the Protein Atlas analysis of the 29-gene signature, ALCAM (FIGS. 10A-10C), C12orf51 (HECT4) (FIGS. 11A-11C), HSPA9 (FIGS. 12A-12C), CLDN8 (FIGS. 14A-14C), TMEM205 (FIGS. 15A-15C), and PTPLAD1 (FIGS. 16A-16C), were epithelial driven genes based on IHC and mRNA data. LUM (FIGS. 17A-17C), COL1A1 (FIGS. 18A-18C), BGN (FIGS. 20A-20C), C1QC (FIGS. 21A-21C), AEP1 (FIGS. 23A-23C), FBLN5 (FIGS. 24A-24C), C1QA (FIGS. 26A-26C), SULF1 (FIGS. 28A-28C), THBS2 (FIGS. 29A-29C), MOXD1 (FIGS. 30A-30C), SERPING1 (FIGS. 31A-31C), PRELP (FIGS. 32A-32C), ITGA11 (FIGS. 34A-34C), and TNS3 (FIGS. 35A-35C) were stroma driven genes in the gene signature based on IHC and mRNA data. MAL2 (FIGS. 13A-13C) and SFRP4 (FIGS. 19A-19C) were negative by IHC, and C1S (FIGS. 22A-22C), C1QB (FIGS. 25A-25C), SFRP2 (FIGS. 27A-27C), LTBP2 (FIGS. 33A-33C), HLA-DRB3 (FIGS. 36A-36C), FCGR2C, and CD52 were unknown by IHC.

Example 11: A Stromal-Epithelial Transcriptional Map of Initiation, Progression, and Metastatic Potential of Prostate Cancer While progression from normal prostatic epithelium to invasive cancer is driven by molecular alterations, tumor cells and cells in the cancer microenvironment are co-dependent and co-evolve. As described herein, gene expression profiling of laser capture microdissected normal non-neoplastic prostate (cystoprostatectomies) epithelial tissue was performed and compared to non-transformed and neoplastic low and high grade prostate epithelial tissue from radical prostatectomies, each with its immediately surrounding stroma. Whereas benign epithelium in prostates with and without tumor were similar in gene expression space, stroma away from tumor was significantly different from that in prostates without cancer. A stromal gene signature reflecting bone remodeling and immune-related pathways was upregulated in high compared to low Gleason score cases. In validation data, the signature discriminated cases that developed metastasis from those that did not. These data suggest that the microenvironment may influence prostate cancer initiation, maintenance, and metastatic progression.

The prostate consists of the glandular epithelium and supporting stroma. This connective stroma is comprised of fibroblasts, myofibroblasts, smooth muscle cells, vascular endothelial cells, nerve cells, and inflammatory cells. While prostate cancer arises from the epithelial component of the gland, the surrounding stroma is increasingly recognized as an important contributor in the process of carcinogenesis and a driver of cancer progression (Bhowmick, N. A., et al. *Science* 303, 848-851 (2004); Olumi, A. F., et al. *Cancer research* 59, 5002-5011 (1999)). Experimental models demonstrate that altered stromal cells can induce tumor formation in non-cancerous prostate epithelial cells and in cell lines derived from prostate cancer (Olumi, A. F., et al. *Cancer research* 59, 5002-5011 (1999)). Benign prostate epithelial cells proliferate more and ultimately undergo transformation when combined with prostate cancer-derived fibroblasts (Olumi, A. F., et al. *Cancer research* 59, 5002-5011 (1999); Hayward, S. W., et al. *Cancer Res* 61, 8135-8142 (2001)). It is also clear that the stroma can morphologically and functionally change in the presence of cancer and other insults. Compared to normal stroma, there is a switching of the cellular phenotype, remodeling of the extracellular matrix (Morrison, C., Thornhill, J. & Gaffney, E. *Urol Res* 28, 304-307 (2000)), increases in expression of growth factors and proteases (Giri, D., Ropiquet, F. & Ittmann, M. *Clin Cancer Res* 5, 1063-1071 (1999)) increased angiogenesis (Rowley, D. R. *Cancer Metastasis Rev* 17, 411-419 (1998)), and change in inflammatory cells (Shimura, S., et al. *Cancer Res* 60, 5857-5861 (2000)). The bidirectional signaling between epithelial cells and stromal constituents during normal prostate homeostasis is disrupted early in tumorigenesis (Barron, D. A. & Rowley, D. R. *Endocr Relat Cancer* 19, R187-204 (2012)). The consequences are diverse and range from deposition of extracellular matrix, to recruitment of inflammatory cells, production of miRNA, promotion of tissue regeneration and angiogenesis, ultimately resulting in stimulation of growth and survival of tumor cells (Hanahan D, W. R. *Cell*, 646-674 (2011); Josson et al., *Clin Cancer Res* (2014)). When the stromal compartment becomes reactive normal fibroblasts are replaced by cancer-associated fibroblasts (CAFs). The increase of CAFs, which begins around in situ lesions, evolves during prostate tumorigenesis and is inversely proportional to tumor differentiation (Tuxhorn, et al., *J Urol* 166, 2472-2483 (2001)).

Signaling factors from the microenvironment influence epithelial cells to acquire properties such as increased motility, proliferation or migratory and invasive behavior. To this end, TGFbeta and Wnt signaling pathways have been shown to play important regulatory roles in stromal-epithelial interactions in both prostate development and tumorigenesis (Barron, D. A. & Rowley, D. R. The reactive stroma microenvironment and prostate cancer progression. *Endocr Relat Cancer* 19, R187-204 (2012); Carstens J L, S. P., Van Tsang S, Smith B, Creighton C J, Zhang Y, Seamans A, Seethammagari M, Vedula I, Levitt J M, Ittmann M M, Rowley D R, Spencer D M. FGFR1-WNT-TGF-β signaling in prostate cancer mouse models recapitulates human reactive stroma. *Cancer Res* (2014); Smith B N, B. N. Role of EMT in Metastasis and Therapy Resistance. *J Clin Med* (2016). A variety of additional growth factors produced by stromal cells have been shown to affect tumor cell survival (Shiao S L, C. G., Chung L W. Regulation of prostate cancer progression by the tumor microenvironment. *Cancer Lett* (2016)). In addition, soluble cytokine and chemokines influence the interaction between the epithelial and stromal compartment during prostate cancer progression. For example, peri-prostatic adipose tissue can affect migration of prostate cancer cells via secretion of CCL7 by adipocytes (Laurent V, G. A., Mazerolles C, Le Gonidec S, Toulet A, Nieto L, Zaidi F, Majed B, Garandeau D, Socrier Y, Golzio M, Cadoudal T, Chaoui K, Dray C, Monsarrat B, Schiltz O, Wang Y Y, Couderc B, Valet P, Malavaud B, Muller C. Periprostatic adipocytes act as a driving force for prostate cancer progression in obesity. *Nat Commun* (2016). Finally, androgen receptor, expressed by a subset of myofibroblasts in the prostate stroma, may regulate the expression of growth factors secreted by these cells. Thus, tumor growth and biologic behavior is strongly regulated by the extracellular milieu.

Mutational landscapes have been measured in an attempt to predict biologic behavior of human prostate tumors (Network, C.G.A.R. *Cell* (2015); Robinson et al., *Cell* (2015)). In addition, epigenetic and transcriptional signatures are associated with the degree of differentiation and are an important adjunct in predicting aggressive and indolent behavior (Penney, K. L., et al. *J Clin Oncol* 29, 2391-2396 (2011); Sinnott, J. A., et al. *Clin Cancer Res* (2016); Zhao et al., *Clin Cancer Res* (2016)). These are turning out to be invaluable tools to guide therapeutic options in prostate cancer patients but could be further improved by knowledge of the contribution of stromal elements. While it has been recently shown that stroma adjacent to prostate cancer epithelium does not harbor clonal DNA alterations and appears to be genetically stable (Bianchi-Frias, D., et al. *Mol Cancer Res* 14, 374-384 (2016)), biological behavior of the epithelial component of the tumor, may be affected by variability of gene expression in the stroma. In turn, epithelial alterations may condition stromal behavior. For instance, hyperactivated focal adhesion kinase (FAK) activity has been shown to be an important regulator of the fibrotic and immunosuppressive stromal microenvironment in pancreatic cancer (Jiang et al., *Nat Med* (2016)). Additionally, it has previously been shown that stromal gene expression signatures predict outcome in breast (Finak, G., et al. *Nat Med* 14, 518-527 (2008); Roman-Perez, E., et al. *Breast Cancer Res* 14, R51 (2012); Winslow, S. *Breast Cancer Res* 17, 23 (2015) and colorectal (Calon, A., et al. *Nat Genet* 47, 320-329 (2015)) cancer patients.

Laser-capture microdissection (LCM) has facilitated the isolation and study of specific cellular populations within the prostate tumor microenvironment. This labor-intensive technology, however, limits large-scale efforts. Prior to the invention described herein, differences between the tumor and its adjacent stroma in prostate cancer (Gregg et al., *BMC Cancer.* (2010)) between normal and reactive stroma (Dakhova, O., et al. *Clin Cancer Res* 15, 3979-3989 (2009)), and differences between benign and tumor epithelium (Dakhova, O., et al. *Clin Cancer Res* 15, 3979-3989 (2009); Furusato et al., *Prostate Cancer Prostatic Dis* (2008); Tomlins, S. A., et al. *Nat Genet* 39, 41-51 (2007)) have been addressed utilizing LCM, albeit on a small scale. Analyses were centered predominantly on the epithelial compartment. Limited studies of stromal gene expression using high-throughput assays exist for prostate cancer aggressiveness. One such study showed alterations in neurogenesis, axonogenesis, and DNA damage/repair pathway to be associated with grade 3 reactive stroma (Dakhova, O., et al. *Clin Cancer Res* 15, 3979-3989 (2009)).

Here, it was hypothesized that progression of normal prostate to PIN to invasive cancer is driven by molecular alterations in both epithelium and stroma, and that changes in the microenvironment can potentially contribute to tumor initiation, maintenance and progression. Thus, it was asked whether gene expression of non-transformed epithelial and stromal tissues differ in prostates with and without tumor, and how the stromal genes are associated with prostate cancer progression and aggressiveness (Gleason score).

The results from this example are described in detail below.

Gene expression profiling was performed on laser capture microdissected tissue specimens from 25 radical prostatecomy (RP) and 5 'healthy' cystoprostatectomy cases. For each RP case, 6 regions of interest were examined: tumor (T), PIN (P) and benign (B) epithelium each with the adjacent stroma (sT, sP, sB). For cystoprostatectomy, benign epithelium and adjacent stroma (H.B and H.sB) was examined. Cystoprostatectomies were confirmed not to harbor prostate cancer foci through review of the entire submitted specimen. Clinicopathological features of the cohort are described in Table 23.

TABLE 23

Clinical characteristics of the LCM cohort

| Clinical Stage | |
| --- | --- |
| T1 | 4 |
| T1c | 1 |
| T2 | 12 |
| T2a | 2 |
| T3 | 1 |
| M1 | 1 |
| NA | 7 |
| Pathological Stage | |
| pT1 | 2 |
| pT2 | 4 |
| pT2a | 2 |

TABLE 23-continued

Clinical characteristics of the LCM cohort

| pT2b | 1 |
| --- | --- |
| pT2c | 7 |
| pT3a | 4 |
| pT3b | 4 |
| M1 | 1 |
| NA | 5 |
| Gleason score | |
| 3 + 3 | 12 |
| >= 8 | 13 |
| Tissue Type | |
| RP | 25 |
| Cystoprostatectomy | 5 |

Total number of cases 30
Mean (sd) Age at Diagnosis 63.7 (7.7)

Gene Expression Differences Between Compartments Across Progression

As expected from the experimental design, the major share of variability in gene expression was explained by differences between epithelial and stromal tissue compartments (FIG. 79A). Many of the differentially expressed genes as well as pathways were shared across the H.B-H.sB, B-sB, P-sP and T-sT comparisons (FIG. 79B and FIG. 75A-FIG. 75B). The GO biological processes commonly upregulated in the epithelium and maintained through "progression" to invasive tumors, included amino acid metabolism, RNA processing, protein translation and post-translational modification. (FIG. 75A). Common processes upregulated in stroma were mostly comprised of muscle development as well as changes in cytoskeletal structure (FIG. 75B). Among processes upregulated in all stromal components of the RP specimens, increasing occurrence of immune-related pathways, such as lymphocyte differentiation and activation, is identified. Interestingly, the bone remodeling pathway was upregulated only in the stroma adjacent to the tumors.

Gene Expression Differences within Compartments Across Progression

As proof of principle examples, P63, a marker of normal basal cells of the prostate gland was upregulated in benign microdissected epithelial samples compared to invasive cancer, while AMACR and ERG were all upregulated in the tumor microdissected epithelial samples compared to benign epithelium and, to a lesser extent, PIN.

Gene set analysis in tumor epithelium showed pathways associated with nucleotide metabolism, translation, and RNA processing (FIG. 76A). Translation, protein folding, as well as negative regulation of apoptosis were upregulated in the tumor-adjacent stroma (FIG. 76B). Muscle development GO biological process decreased in tumor-associated stroma, potentially indicating transformation of stromal composition from mainly muscle cells to myofibroblasts and fibroblasts.

Gene Expression Differences Between RP and Cystoprostatectomy Cases

The benign epithelial glands from the cystoprostatectomy and RP (B-H.B) were compared and 15 differentially-expressed probesets (FDR<0.05, FC>=1.5; FIG. 77A) were identified. In the comparisons of the adjacent stroma from the cystoprostatectomy and RP tissues (sB-HsB), a larger number of probesets (n=130; FIG. 77B-FIG. 77C) were significant. Forty two of them were small nucleolar mRNAs (almost all C/D box), all overexpressed in normal stroma from RP specimens. The GO biological processes associated with the sB-HsB differentially expressed genes included N-linked glycosylation, membrane and Golgi transport, and the unfolded protein response (FIG. 75D). Genes comprising these pathways generally had higher expression in the benign stroma of RP cases.

Interestingly, the hierarchical clustering revealed greater similarity in the expression of stromal genes between stroma adjacent to benign epithelium in the prostates with no tumor (cystoprostatectomies) and the benign stroma from prostates with high grade tumors, even though the physical distance between sB regions selected for analysis and the closest tumor focus, on average was smaller for high grade cases (t-test; p=0.04). This might suggest, that stroma surrounding Gleason 3+3 cases is inherently different. In the direct comparisons of the sB from high and low grade cases no genes reached statistical significance.

Gene Expression Differences Between High and Low Grade Tumors.

Gleason grade is one of the strongest clinical predictors of prostate cancer progression and outcomes. As described herein, genes differentially expressed between high and low grade epithelium (T.high–T.low) and in adjacent stroma (sT.high–sT.low) were identified. A TGF-β-responsive marker and functional regulator of prostate cancer metastasis to bone, ALCAM (FDR=0.005) (Hansen A G, A. S., Jiang M, Palmer T D, Ketova T, Merkel A, Pickup M, Samaras S, Shyr Y, Moses H L, Hayward S W, Sterling J A, Zijlstra A. ALCAM/CD166 Is a TGF-β Responsive Marker and Functional Regulator of Prostate Cancer Metastasis to Bone. Cancer Res (2014)) was identified as the only significantly differentially expressed gene in the epithelium comparison. Differences between gene expression in the sT.high–sT.low comparison, however, were more striking. 27 transcript clusters corresponding to 24 unique gene symbols were differentially expressed in stroma (Table 24). All genes were upregulated in high Gleason grade cases. The genes comprising this stromal signature include a group of genes overexpressed in osteoblasts and osteoblast-like cells, as well as some gene overexpressed in macrophages, T and B cells. Immune response as well as complement activation GO biological processes were significantly enriched in the signature (all corresponding FDR values $<10^{-5}$). This signature features wound healing and metastasis markers (SFRP2, SFRP4, THBS2), hematopoietic bone marrow markers (SULF1, COL1A1), immune cell markers (C1S, HLA-DRB1, FCGR2C), and complement cascade genes (C1QA, C1QB, C1QC).

The single sample gene set enrichment (ssGSEA) score was calculated for the genes in the tumor-associated stroma, comparing the high and low Gleason score cases, and the difference in the score was highly statistically significant (FIG. 78A; $p<=10^{-3}$). Interestingly, while none of the individual genes from the signature reached statistical significance when stroma surrounding benign glands in the prostates bearing high and low Gleason cancers was compared, the difference in ssGSEA scores computed in the benign stroma was marginally significant (FIG. 78B; p=0.08).

TABLE 24

Genes differentially expressed between stroma adjacent to high and low Gleason grade tumors in LCM data and publically available studies used for validation

| | | | LCM | | TCGA | | GSE46691 | | | |
|---|---|---|---|---|---|---|---|---|---|---|
| | | | | | | | Gleason | | Outcome | |
| Affy ID | Gene symbol | logFC | P-value | FDR | P-value | FDR | P-value | FDR | P-value | value |
| 8132557 | AEBP1 | 0.987 | $<10^{-4}$ | 0.011 | 0.004 | 0.015 | 0.009 | 0.019 | 0.024 | 0.041 |
| 8042439 | ANTXR1 | 0.841 | $<10^{-4}$ | 0.042 | 0.015 | 0.032 | 0.002 | 0.005 | 0.003 | 0.013 |
| 8170648 | BGN | 1.059 | $<10^{-4}$ | 0.012 | 0.009 | 0.024 | $<10^{-4}$ | $<10^{-4}$ | 0.004 | 0.015 |
| 7898793 | C1QA | 0.747 | $<10^{-4}$ | 0.007 | 0.115 | 0.132 | 0.159 | 0.190 | 0.087 | 0.105 |
| 7898805 | C1QB | 0.786 | $<10^{-4}$ | 0.012 | 0.180 | 0.197 | 0.084 | 0.106 | 0.046 | 0.065 |
| 7898799 | C1QC | 1.014 | $<10^{-4}$ | 0.012 | 0.103 | 0.131 | 0.002 | 0.005 | 0.001 | 0.007 |
| 7960744 | C1R | 0.865 | $<10^{-4}$ | 0.042 | 0.076 | 0.117 | 0.061 | 0.081 | 0.067 | 0.084 |
| 7953603 | C1S | 1.005 | $<10^{-4}$ | 0.026 | 0.099 | 0.131 | 0.029 | 0.044 | 0.017 | 0.032 |
| 8001800 | CDH11 | 0.711 | $<10^{-4}$ | 0.046 | 0.017 | 0.033 | $<10^{-4}$ | 0.002 | 0.002 | 0.010 |
| 8016646 | COL1A1 | 1.149 | $<10^{-4}$ | 0.012 | 0.001 | 0.003 | 0.001 | 0.003 | 0.006 | 0.015 |
| 8046922 | COL3A1 | 0.867 | $<10^{-4}$ | 0.043 | 0.004 | 0.015 | 0.001 | 0.003 | 0.012 | 0.024 |
| 7980908 | FBLN5 | 0.849 | $<10^{-4}$ | 0.026 | 0.047 | 0.084 | 0.058 | 0.081 | 0.033 | 0.050 |
| 7906767 | FCGR2B | 0.747 | $<10^{-4}$ | 0.002 | 0.082 | 0.118 | 0.352 | 0.384 | 0.056 | 0.075 |
| 8178811 | HLA-DRB1 | 0.973 | $<10^{-4}$ | 0.047 | 0.246 | 0.257 | 0.483 | 0.504 | 0.129 | 0.141 |
| 8180003 | HLA-DRB1 | 0.944 | $<10^{-4}$ | 0.043 | 0.246 | 0.257 | 0.483 | 0.504 | 0.129 | 0.141 |
| 7965403 | LUM | 1.274 | $<10^{-4}$ | 0.043 | 0.113 | 0.132 | 0.003 | 0.008 | 0.005 | 0.015 |
| 8129573 | MOXD1 | 0.607 | $<10^{-4}$ | 0.016 | 0.009 | 0.024 | 0.013 | 0.024 | 0.371 | 0.387 |
| 7908924 | PRELP | 0.788 | $<10^{-4}$ | 0.046 | 0.076 | 0.117 | 0.023 | 0.036 | 0.032 | 0.050 |
| 7977615 | RNASE1 | 0.714 | $<10^{-4}$ | 0.042 | 0.283 | 0.283 | 0.278 | 0.318 | 0.126 | 0.141 |
| 8103254 | SFRP2 | 0.727 | $<10^{-4}$ | 0.008 | 0.001 | 0.003 | $<10^{-4}$ | 0.001 | 0.009 | 0.022 |
| 8139087 | SFRP4 | 1.074 | $<10^{-4}$ | 0.002 | $<10^{-4}$ | 0.001 | $<10^{-4}$ | $<10^{-4}$ | 0.001 | 0.007 |
| 8146863 | SULF1 | 0.721 | $<10^{-4}$ | 0.012 | 0.011 | 0.024 | $<10^{-4}$ | $<10^{-4}$ | 0.001 | 0.007 |
| 8130867 | THBS2 | 0.678 | $<10^{-4}$ | 0.012 | $<10^{-4}$ | 0.001 | 0.005 | 0.010 | 0.001 | 0.007 |
| 7952268 | THY1 | 0.589 | $<10^{-4}$ | 0.043 | 0.006 | 0.019 | 0.015 | 0.025 | 0.012 | 0.024 |
| 8101774 | TMSB4X | 0.657 | $<10^{-4}$ | 0.042 | NA | NA | 0.728 | 0.728 | 0.817 | 0.817 |
| 8067007 | TMSB4X | 0.664 | $<10^{-4}$ | 0.043 | | | | | | |
| 8166072 | TMSB4X | 0.675 | $<10^{-4}$ | 0.049 | | | | | | |

Signature Validation in External Data.

Next the stromal signature (Table 24) was applied to the prostate data from The Cancer Genome Atlas (Network, C.G.A.R. The Molecular Taxonomy of Primary Prostate Cancer. Cell (2015)). TCGA prostate samples were comprehensively re-reviewed by a group of GU pathologists. A large variation in tumor purity was reported for 333 TCGA samples. Specimens with low purity contain a lot of stroma, which made them good candidates for preliminary validation of this stromal signature associated with Gleason grade. Cases were grouped into those with relatively high stromal content (tumor cellularity ≤40%) and cases enriched for tumor epithelium (tumor cellularity ≥80%). ssGSEA score of the stromal gene signature was calculated. Interestingly, a significant difference of the ssGSEA signature score between 3+3 and 8+ Gleason in both low (FIG. 78C; t-test, p=0.006) and high (FIG. 78D; t-test, p=0.02) cellularity subsets was found, but the difference is smaller and less significant in high cellularity samples, despite the larger sample size. This demonstrates that while it is possible to observe signal from the stromal genes in specimens with low stromal content, it might be significantly diluted. Therefore, it is important to interpret prostate expression data as a function of stromal content.

Similarly, the signature was applied to stromally enriched samples from the publicly available gene expression data from the Mayo clinic cohort (GSE46691). The signature was significantly different between high and low Gleason grade samples (t-test, p<$2*10^{-10}$), and between cases that did or did not develop metastasis (FIG. 78D). The AUC of the score alone for predicting metastatic events using logistic regression model was 0.67, and together with Gleason score 0.74. In this cohort, Gleason score alone predicted outcome with ROC of 0.72.

Validation Using Immunohistochemistry

Protein expression of selected genes in the signature was tested by immunohistochemistry (IHC) to verify cell of origin. Only genes with IHC-validated antibodies were tested. As examples, the only significant gene in the epithelial compartment, ALCAM was overexpressed in the epithelial component of Gleason 8 tumors (FIG. 78F-FIG. 78G), while the stromal gene SULF1 was highly expressed in stroma adjacent to high-grade but not low-grade tumor (FIG. 78H-FIG. 78I).

The traditional consensus is that tumorigenesis is caused by mutations exclusive to epithelial cells that promote increased growth and invasive capacity, eventually resulting in metastasis. For some time, compelling data primarily derived from pre-clinical models have suggested that the microenvironment within which the cancer cells reside plays a pivotal role in cancer initiation and progression. Further, altered microenvironment may even precede genetic alterations in epithelial cells. The results presented herein show that changes in the microenvironment are important contributors to tumor initiation and may affect progression.

It was observed that stromal, but not the epithelial gene expression, obtained from benign areas (away from invasive tumors) in RP specimen differs significantly from that of prostates without cancer. Pathways such as N-glycosylation and the unfolded protein response (UPR) were upregulated in RP benign stroma compared to cystoprostatectomy specimens. These pathways are important in a variety of biological processes such as nutrient sensing or control of lipogenesis and are commonly altered in cancer. For instance, UPR can be an androgen responsive process in prostate cells and an aberrant UPR can lead to suppression of apoptosis, increased protein expression, and survival of prostate cancer cells. Metabolic challenges such as fluctuations in nutrient availability, hypoxia and increased demand on protein synthesis, can lead to perturbation of endoplasmic reticulum (ER) function, accumulation of misfolded proteins, and ER stress. In an attempt to restore ER homeostasis, the cell mounts a response called the UPR, a set of intracellular signaling pathways that aim to adjust the protein folding capacity of the cell (Storm M, S. X., Arnoldussen Y J, Saatcioglu F. Prostate cancer and the unfolded protein response. Oncotarget (2016)). Translational control of protein synthesis is therefore important for prostate cancer cell proliferation and survival, but the role of stromal cells in this regard is new, perhaps suggesting that a stromal environment exists in some individuals that is permissive for survival and proliferation of transformed epithelial cells.

Gleason grade is one of the strongest clinical predictors of prostate cancer progression and outcomes. An mRNA signature associated with Gleason grade improves risk stratification (Sinnott, J. A., et al. Prognostic Utility of a New mRNA Expression Signature of Gleason Score. *Clin Cancer Res* (2016)). Only one gene was identified as differentially expressed between high and low grade tumor epithelium, ALCAM, a TGF beta responsive gene, previously shown to be associated with metastasis (Hansen A G, A. S., Jiang M, Palmer T D, Ketova T, Merkel A, Pickup M, Samaras S, Shyr Y, Moses H L, Hayward S W, Sterling J A, Zijlstra A. ALCAM/CD166 Is a TGF-βResponsive Marker and Functional Regulator of Prostate Cancer Metastasis to Bone. *Cancer Res* (2014)). It is well known that TGF beta signaling has been shown to play important regulatory roles in stromal-epithelial interactions in both prostate development and tumorigenesis. Differences between gene expression in stroma adjacent to high and low grade cancer were much more striking: 25 genes were differentially expressed. All genes comprising this stromal signature of Gleason were more highly expressed in stroma from high Gleason cases than those from low grade. The fact that gene expression from stroma across Gleason grades is more different than epithelial tumor confirms the importance of the microenvironment and suggests that more work to develop drugs that specifically target the stroma is warranted.

Interestingly, among the 25 stromal genes differentially expressed across high and low grade were genes expressed by the immune system including complement, as well as many genes that are expressed in osteoblasts and osteoblast-like cells. The complement cascade is known to be an effector arm of innate immunity, playing a role in clearance of pathogens as well as in tumor immune surveillance. The complement system also plays a role in cartilage and bone development, as well as in regenerative pathways in injured tissue (Rutkowski M J, S. M., Kane A J, Ahn B J, Fang S, Parsa A T. The complement cascade as a mediator of tissue growth and regeneration. *Inflamm Res.* (2010)). Of note, some complement proteins are distributed throughout immature, developing bone and appear to be important in osteogenesis. Uncontrolled complement activation can also promote inflammation. Consistent with these findings, bone remodeling pathways were upregulated only in stroma adjacent to malignant epithelium, and not in benign or PIN adjacent stroma. The stromal genes lumican (LUM), COL1A1 and BGN, belonging to both the signature reported here and comprising all stromal genes in the commercial OncoDx kit (Klein et al., *European urology* 66, e117-118 (2014)), are also interesting in terms of the theme of bone remodelling. COL1A1 is an osteoblastic differentiation marker and BGN modulates angiogenesis and bone formation during fracture healing. As prostate cancer most commonly metastasizes to bone, and Gleason 8 tumors are more likely to metastasize than Gleason 6, the finding of the overexpression of bone remodeling pathways in high grade stroma is particularly interesting. The interaction of prostate cancer with the bone microenvironment contributes to selfperpetuating progression of cancer in bone and the osteoclast-targeted agents zoledronic acid and denosumab decrease metastases to bone in metastatic castration-resistant prostate cancer (Gartrell et al., European Urology 68 (2015) 850-858). This prostate stromal environment may prepare cells from high grade tumors to thrive in bone.

Next, the association of this Gleason signature was validated with Gleason score in TCGA data. Not surprisingly, the signature was more strongly associated with Gleason in tumors with lower purity that have a higher percentage of stromal tissue. The signature was also significantly associated with lethal disease in expression data from the Mayo clinic cohort, although its prognostic power is likely to be suboptimal in this patient dataset because the Mayo clinic data was designed to be enriched for epithelium. As the analysis of TCGA data suggests, it was expected that stronger performance of the signature for prostate cancer prognosis would be identified in the stroma enriched specimens.

Interestingly, this Gleason signature was also borderline significantly different in stroma from benign areas of the prostates with high and low grade tumors. Additionally, when examining all gene expression data, it was observed that benign stroma from men with high grade tumors was more similar to cystoprostatectomy stroma than low grade benign stroma, despite the fact that in the samples benign stroma from high grade cases was physically closer to a tumor focus than in low grade cases. This could suggest that there is a "prostate-wide" difference in the stroma of men who develop low grade disease that allows for the development of well differentiated cancer with low malignant potential. Additional larger scale studies with benign stroma from healthy individuals and prostate cancer patients' samples taken repeatedly at different distances from tumor foci would validate these findings. However, this provides convincing evidence that it might be possible to identify a prognostic signature from stroma from biopsies that do not contain malignant epithelial cells. In prostate cancer, negative biopsies are a common occurrence and a significant clinical problem that results from random sampling in a PSA screened population. After a man has had an elevated PSA, but a negative biopsy, the normal stroma could be used to determine if he seems at risk only for low grade disease. This could help determine if and when he should return for a follow-up biopsy. In addition, a stromal signature in biopsies without neoplastic tissue may be of importance in the context of active surveillance.

While the results presented herein focused on comparing patients with Gleason scores 6 and 8+, many men are diagnosed with Gleason score 7 disease. The data from this study do not permit comment on how the stroma behaves in these patients, but from the Mayo cohort data and TCGA data, it appears that the stromal signature in Gleason score 7 tumors falls in between Gleason score 6 and 8, suggesting an intermediate state of Gleason 7 stroma. A further investigation of the stroma in Gleason score 7 cases would confirm the contributions of the low and high grade patterns within Gleason 7.

This study is the first to comprehensively assess gene expression from microdissected prostate tissue specimens, focusing on epithelial and stromal compartments across progression.

The following methods were utilized in this example.

Clinical Specimens 25 patients were selected with either pure low grade (Gleason ≤6) or pure high grade (Gleason ≥8) prostate cancer in the whole prostate who underwent radical prostatectomy from the following Institutions' cohorts: Harvard School of Public Health, Boston, USA; King's College London, UK; Prostate Cancer Research Consortium, Ireland; Orebro University Hospital, Sweden; S.Orsola-Malpighi Hospital Bologna, Italy. Each case had enough material for micro-dissection and nucleic acid extraction in the epithelial and stromal compartments, and areas of prostate cancer, PIN and normal or hyperplastic prostate tissue, all surrounded by significant intervening stroma were present in the same histological block. 5 prostates from cysto-prostatectomy cases, included in the PROPP-Study, collected from patients with bladder cancer were included in the study as normal controls for prostate. Cystoprostatectomy patients were not treated with BCG and none of the cases had incidental prostate cancer or excessive inflammation in the stromal component or atrophy in the epithelial component. All patients were consented and approved by each local IRB and research ethics committees.

A pathology review of all the histological slides was centralized in Italy. The slides selected for microdis section were scanned with an Aperio instrument in Bologna and put on a dedicated proprietary website protected by regulated access. Circling of the epithelial and stromal counterparts in cancer, PIN and normal tissue areas was performed on digitized H&Es by MF. Annotated pathological scans were remotely accessed for the laser capture microdissection.

Laser Capture Microdissection and Gene Expression Profiling

The LCM workflow comprised preliminary ROI review by digital annotation, tissue block sectioning and staining, 2 hr of microdissection on the Arcturus platform (Life Technologies), overnight incubation in lysis buffer/Proteinase K and subsequent RNA extraction by AllPrep (Qiagen) and quantification by RiboGreen assay (Life Technology). To accommodate the low RNA concentration and yields associated with microdissected tissues, the SensationPlus FFPE method was adopted as a suitable labeling technique. 20 ng total RNA at a concentration of 2.5 ng/ul, was used to measure RNA expression across the whole transcriptome on the Affymetrix Gene Array STA 1.0.

Normalization and Differential Gene Expression Analysis

Preprocessing of the microarray data consisted of adjusting raw data at the probe level for technical variables, such as batches, overall median of the fluorescence intensities in each array and fraction of the probes with intensity higher than background levels. Adjusted values were normalized using RMA (robust multichip average) method 40. There were no extreme outliers or failing samples, therefore all assayed samples and ROIs were retained for further analysis. For the analysis we retained transcript clusters from the 'main' category with log-median intensity of 3 in at least one of the ROIs.

Random effects linear models approach was utilized to account for correlations between compartments within cases using Bioconductor package limma 41. Multiple comparisons was adjusted for using the Benjamini-Hochberg False Discovery Rate (FDR) method. A FDR≤0.05 was considered significant. Significantly differentially expressed genes with the fold-changes not exceeding 1.5 were not reported.

Pathway Analysis

For pathway analysis a Wilcoxon test implemented in geneSetTest function in limma was used, signed and unsigned moderated t-statistics from linear model fits were used to rank the genes. Gene Ontology Biological Processes annotations were downloaded from MSigDb42 and Enrichment Map Gene Sets collections (download.baderlab.org/EM_Genesets/). For analysis, only gene sets with less than 200 and more than 20 genes were considered. Benjamini-Hocheberg FDR method was used to correct for multiple comparisons.

ssGSEA Signature Score ssGSEA scores were computed using GSVA Bioconductor package. The genes that were significantly upregulated in sT vs T comparison were used as a reference set (log FC thresholding was not applied here). For the TCGA and GSE46697 data sets both signature genes and reference set were subsetted to the genes measured in each study.

Publicly Available Data

Annotations for 333 TCGA prostate cancer samples were downloaded from cBioPortal (cbioportal.org/study?id=prad_tcga_pub #summary) and corresponding RSEM normalized gene expression values from FireHose portal (firebrowse.org/?cohort=PRAD&download_dialog=true). Mayo clinic cohort data were downloaded from Gene Expression Omnibus, accession number GSE46691.

Selection of Stromally Enriched Samples

In order to identify stromally enriched GSE46691 samples ssGSEA scores of the genes found to be significantly different with negative log FC in T-sT comparison (3000 genes) in the LCM data were computed using all measured genes as reference set. The scores computed on this set of genes had high correlations 0.34 and 0.82 with 1-Tumor Cellularity values inferred by pathologist and RNA-Seq-based computational estimates in TCGA data. Stromally enriched samples were defined as those having score above the median of the distribution of the score across all samples.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of determining whether prostate cancer in a human subject will metastasize comprising:
   obtaining a prostate tissue test sample from a human subject having or at risk of developing prostate cancer;
   determining the expression level of at least one prostate cancer-associated gene in the test sample, wherein the at least one prostate cancer-associated gene comprises proline/arginine-rich end leucine-rich repeat protein (PRELP);
   comparing the expression level of the prostate cancer-associated gene in the test sample with the expression level of the prostate cancer-associated gene in a reference sample;
   detecting a higher expression level of the prostate cancer-associated gene in the test sample as compared to the expression level of the prostate cancer-associated gene in a reference sample;
   determining that the prostate cancer in the subject will metastasize; and
   performing a radical prostatectomy on the subject or treating the subject with a chemotherapeutic agent, radiation therapy, cryotherapy, or hormone therapy.

2. The method of claim 1, wherein the prostate cancer metastasizes to bone.

3. The method of claim 1, wherein the subject is identified as having Gleason 6 grade prostate cancer or Gleason 8 or higher grade prostate cancer.

4. The method of claim 1, wherein the sample is obtained from prostate stromal tissue, prostate tumor tissue, or prostate stromal-tumor interface tissue.

5. The method of claim 1, wherein said sample comprises ribonucleic acid (RNA).

6. The method of claim 1, wherein the reference sample is obtained from healthy normal control prostate stromal tissue, benign prostate stromal tissue, prostatic intraepithelial neoplasia (PIN) stromal tissue, or cancerous prostate stromal tissue.

7. The method of claim 1, wherein the subject has relapsed with prostate cancer or is at risk of relapsing with prostate cancer.

8. The method of claim 1, wherein the expression level of the prostate cancer-associated gene is detected via a Gene Hybridization Array, or a real time reverse transcriptase polymerase chain reaction (real time RT-PCR) assay.

9. The method of claim 1, wherein the subject has undergone a radical prostatectomy.

10. The method of claim 1, wherein the method comprises performing a radical prostatectomy on the subject.

11. The method of claim 1, wherein the method comprises treating the subject with a chemotherapeutic agent, radiation therapy, cryotherapy, or hormone therapy.

12. The method of claim 11, wherein the chemotherapeutic agent comprises doceaxel, cabazitaxel, mitoxantrone, estramustine, doxorubicin, etoposide or paclitaxel.

13. The method of claim 1, further comprising repeating the method over time, wherein an alteration in the level of the prostate cancer-associated gene over time indicates a corresponding alteration in the aggressiveness of the prostate cancer.

14. The method of claim 1, further comprising administering an inhibitor of the prostate cancer gene with a higher level of expression compared to the level of the prostate cancer-associated gene in the reference sample, thereby treating the prostate cancer.

15. The method of claim 14, wherein the inhibitor comprises a small molecule inhibitor, RNA interference (RNAi), an antibody, or any combination thereof.

16. The method of claim 1, further comprising administering an agonist of the prostate cancer gene with a lower level of expression compared to the level of the prostate cancer-associated gene in the reference sample, thereby treating the prostate cancer.

* * * * *